(12) United States Patent
Jiang et al.

(10) Patent No.: US 12,195,443 B2
(45) Date of Patent: *Jan. 14, 2025

(54) PYRIMIDINE TRICYCLIC ENONE DERIVATIVES FOR INHIBITION OF ROR-GAMMA AND OTHER USES

(71) Applicant: REATA PHARMACEUTICALS, INC., Irving, TX (US)

(72) Inventors: Xin Jiang, Coppell, TX (US); Christopher F. Bender, Garland, TX (US); Melean Visnick, Irving, TX (US); Martha R. Hotema, Hurst, TX (US); Zachary S. Sheldon, Dallas, TX (US); Chitase Lee, Ann Arbor, MI (US); Bradley William Caprathe, Livonia, MI (US); Gary Bolton, Ann Arbor, MI (US); Brian Kornberg, Ann Arbor, MI (US)

(73) Assignee: REATA PHARMACEUTICALS, INC., Irving, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/577,456

(22) Filed: Jan. 18, 2022

(65) Prior Publication Data
US 2022/0135534 A1 May 5, 2022

Related U.S. Application Data

(63) Continuation of application No. 16/468,054, filed as application No. PCT/US2017/000094 on Dec. 16, 2017, now Pat. No. 11,292,781.

(60) Provisional application No. 62/435,588, filed on Dec. 16, 2016.

(51) Int. Cl.
| | | |
|---|---|---|
| C07D 401/04 | (2006.01) |
| A61K 31/517 | (2006.01) |
| A61P 29/00 | (2006.01) |
| A61P 35/00 | (2006.01) |
| A61P 37/00 | (2006.01) |
| C07D 221/04 | (2006.01) |
| C07D 239/70 | (2006.01) |
| C07D 401/12 | (2006.01) |
| C07D 401/14 | (2006.01) |
| C07D 403/04 | (2006.01) |
| C07D 405/14 | (2006.01) |
| C07D 413/04 | (2006.01) |
| C07D 413/14 | (2006.01) |
| C07D 417/14 | (2006.01) |
| C07D 471/04 | (2006.01) |

(52) U.S. Cl.
CPC ......... *C07D 401/04* (2013.01); *C07D 239/70* (2013.01); *C07D 401/12* (2013.01); *C07D 401/14* (2013.01); *C07D 403/04* (2013.01); *C07D 413/04* (2013.01); *C07D 413/14* (2013.01); *C07D 417/14* (2013.01)

(58) Field of Classification Search
CPC .. C07D 401/04; C07D 239/70; C07D 401/12; C07D 401/14; C07D 403/04; C07D 413/04; C07D 413/14; C07D 417/14; C07D 221/04; C07D 405/14; C07D 471/04; Y02A 50/30; A61P 29/00; A61P 35/00; A61P 37/00; A61K 31/517
See application file for complete search history.

(56) References Cited

U.S. PATENT DOCUMENTS

| | | |
|---|---|---|
| 6,326,507 B1 | 12/2001 | Gribble et al. |
| 6,552,075 B2 | 4/2003 | Gribble et al. |
| 6,974,801 B2 | 12/2005 | Honda et al. |

(Continued)

FOREIGN PATENT DOCUMENTS

| | | |
|---|---|---|
| WO | WO 1999/065478 | 12/1999 |
| WO | WO 2002/047611 | 6/2002 |

(Continued)

OTHER PUBLICATIONS

Abstract of WO 2015112792, 2023.*

(Continued)

*Primary Examiner* — Sun Jae Yoo
(74) *Attorney, Agent, or Firm* — Parker Highlander PLLC

(57) ABSTRACT

Disclosed herein are compounds of the formulas:

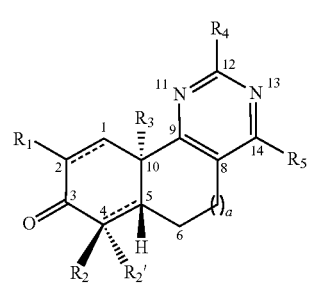

(I)

as well as analogs thereof, wherein the variables are defined herein. Also provided are pharmaceutical compositions thereof. In some aspects, the compounds and compositions provided herein may be used to inhibit RORγ and/or reduce the expression of IL-17. Also provided are methods of administering compounds and composition provided herein to a patient in need thereof, for example, for the treatment or prevention of diseases or disorders associated with inflammation or autoimmune disorders.

35 Claims, No Drawings

(56) References Cited

U.S. PATENT DOCUMENTS

| | | |
|---|---|---|
| 7,176,237 B2 | 2/2007 | Honda et al. |
| 7,288,568 B2 | 10/2007 | Gribble et al. |
| 7,435,755 B2 | 10/2008 | Konopleva et al. |
| 7,678,830 B2 | 3/2010 | Honda et al. |
| 7,714,012 B2 | 5/2010 | Honda et al. |
| 7,795,305 B2 | 9/2010 | Konopleva et al. |
| 7,863,327 B2 | 1/2011 | Gribble et al. |
| 7,915,402 B2 | 3/2011 | Anderson et al. |
| 7,943,778 B2 | 5/2011 | Jiang et al. |
| 8,034,955 B2 | 10/2011 | Gribble et al. |
| 8,067,394 B2 | 11/2011 | Honda et al. |
| 8,067,465 B2 | 11/2011 | Honda et al. |
| 8,071,632 B2 | 12/2011 | Jiang et al. |
| 8,088,824 B2 | 1/2012 | Walling et al. |
| 8,124,656 B2 | 2/2012 | Anderson et al. |
| 8,124,799 B2 | 2/2012 | Anderson et al. |
| 8,129,429 B2 | 3/2012 | Sporn et al. |
| 8,258,329 B2 | 9/2012 | Anderson et al. |
| 8,299,046 B2 | 10/2012 | Sporn et al. |
| 8,309,601 B2 | 11/2012 | Walling et al. |
| 8,314,137 B2 | 11/2012 | Honda et al. |
| 8,338,618 B2 | 12/2012 | Jiang et al. |
| 8,394,967 B2 | 3/2013 | Jiang et al. |
| 8,440,820 B2 | 5/2013 | Anderson et al. |
| 8,440,854 B2 | 5/2013 | Anderson et al. |
| 8,455,544 B2 | 6/2013 | Sporn et al. |
| 8,513,436 B2 | 8/2013 | Anderson et al. |
| 8,586,775 B2 | 11/2013 | Gribble et al. |
| RE45,288 E | 12/2014 | Anderson et al. |
| 8,921,340 B2 | 12/2014 | Sporn et al. |
| RE45,325 E | 1/2015 | Anderson et al. |
| 8,993,640 B2 | 3/2015 | Anderson et al. |
| 9,000,188 B2 | 4/2015 | Honda et al. |
| 9,090,574 B2 | 7/2015 | Anderson et al. |
| 9,102,681 B2 | 8/2015 | Anderson et al. |
| 9,174,941 B2 | 11/2015 | Anderson et al. |
| 9,233,998 B2 | 1/2016 | Anderson et al. |
| 9,249,089 B2 | 2/2016 | Jiang et al. |
| 9,278,912 B2 | 3/2016 | Jiang et al. |
| 9,290,536 B2 | 3/2016 | Anderson et al. |
| 9,464,082 B2 | 10/2016 | Donner et al. |
| 9,796,668 B2 | 10/2017 | Anderson et al. |
| 9,884,809 B2 | 2/2018 | Anderson et al. |
| 11,059,792 B2 | 7/2021 | Jiang et al. |
| 11,192,852 B2 | 12/2021 | Anderson et al. |
| 11,292,781 B2 * | 4/2022 | Jiang .................. C07D 403/04 |
| 2002/0042535 A1 | 4/2002 | Gribble et al. |
| 2002/0115856 A1 | 8/2002 | Sakya |
| 2003/0119732 A1 | 1/2003 | Konopleva et al. |
| 2003/0125361 A1 | 7/2003 | Clare et al. |
| 2003/0232786 A1 | 12/2003 | Honda et al. |
| 2003/0236303 A1 | 12/2003 | Gribble et al. |
| 2004/0002463 A1 | 1/2004 | Honda et al. |
| 2005/0288363 A1 | 12/2005 | Gribble et al. |
| 2007/0155742 A1 | 7/2007 | Honda et al. |
| 2008/0220057 A1 | 9/2008 | Gribble et al. |
| 2008/0233195 A1 | 9/2008 | Sporn et al. |
| 2008/0261985 A1 | 10/2008 | Honda et al. |
| 2009/0048204 A1 | 2/2009 | Walling et al. |
| 2009/0048205 A1 | 2/2009 | Meyer et al. |
| 2009/0060873 A1 | 3/2009 | Sporn et al. |
| 2009/0093447 A1 | 4/2009 | Konopleva et al. |
| 2009/0270364 A1 | 10/2009 | Liu et al. |
| 2009/0326063 A1 | 12/2009 | Sporn et al. |
| 2010/0041904 A1 | 2/2010 | Jiang et al. |
| 2010/0048887 A1 | 2/2010 | Anderson et al. |
| 2010/0048892 A1 | 2/2010 | Anderson et al. |
| 2010/0048911 A1 | 2/2010 | Jiang et al. |
| 2010/0056777 A1 | 3/2010 | Anderson et al. |
| 2010/0261930 A1 | 10/2010 | Honda et al. |
| 2011/0009363 A1 | 1/2011 | Honda et al. |
| 2011/0196007 A1 | 8/2011 | Honda et al. |
| 2011/0245206 A1 | 10/2011 | Jiang et al. |
| 2011/0245233 A1 | 10/2011 | Anderson et al. |
| 2011/0281955 A1 | 11/2011 | Meyer et al. |
| 2012/0071684 A1 | 3/2012 | Walling et al. |
| 2012/0101149 A1 | 4/2012 | Honda et al. |
| 2012/0196880 A1 | 8/2012 | Anderson et al. |
| 2012/0214814 A1 | 8/2012 | Anderson et al. |
| 2012/0220652 A1 | 8/2012 | Sporn et al. |
| 2012/0238767 A1 | 9/2012 | Jiang et al. |
| 2012/0245374 A1 | 9/2012 | Anderson et al. |
| 2012/0252776 A1 | 10/2012 | Anderson et al. |
| 2012/0283450 A1 | 11/2012 | Anderson et al. |
| 2013/0089526 A1 | 4/2013 | Sporn et al. |
| 2013/0122053 A1 | 5/2013 | Sporn et al. |
| 2013/0237721 A1 | 9/2013 | Gribble et al. |
| 2013/0274480 A1 | 10/2013 | Honda et al. |
| 2013/0317007 A1 | 11/2013 | Anderson et al. |
| 2013/0324599 A1 | 12/2013 | Anderson et al. |
| 2013/0345276 A1 | 12/2013 | Sporn et al. |
| 2014/0051739 A1 | 2/2014 | Anderson et al. |
| 2014/0066408 A1 | 3/2014 | Jiang et al. |
| 2014/0088163 A1 | 3/2014 | Jiang et al. |
| 2014/0088188 A1 | 3/2014 | Jiang et al. |
| 2014/0100227 A1 | 4/2014 | Bender et al. |
| 2014/0179928 A1 | 6/2014 | Anderson et al. |
| 2014/0275618 A1 | 9/2014 | Gribble et al. |
| 2014/0377235 A1 | 12/2014 | Sporn et al. |
| 2015/0080465 A1 | 3/2015 | Chin et al. |
| 2015/0148384 A1 | 5/2015 | Anderson et al. |
| 2015/0152071 A1 | 6/2015 | Jiang et al. |
| 2015/0225397 A1 | 8/2015 | Donner et al. |
| 2015/0259377 A1 | 9/2015 | Anderson et al. |
| 2016/0130220 A1 | 5/2016 | Anderson et al. |
| 2016/0145200 A1 | 5/2016 | Anderson et al. |
| 2018/0111931 A1 | 4/2018 | Barlaam et al. |
| 2018/0127380 A1 | 5/2018 | Jiang et al. |
| 2018/0170908 A1 | 6/2018 | Aspnes et al. |
| 2018/0170931 A1 | 6/2018 | Koudriakova et al. |
| 2018/0265455 A1 | 9/2018 | Anderson et al. |
| 2019/0322665 A1 | 10/2019 | Bacani et al. |
| 2020/0077658 A1 | 3/2020 | Sambasivan et al. |
| 2020/0207706 A1 | 7/2020 | Anderson et al. |
| 2021/0292281 A1 | 9/2021 | Jiang et al. |

FOREIGN PATENT DOCUMENTS

| | | |
|---|---|---|
| WO | WO 2003/059339 | 7/2003 |
| WO | WO 2004/064723 | 8/2004 |
| WO | WO 2006/089406 | 8/2006 |
| WO | WO 2008/064132 | 5/2008 |
| WO | WO 2008/064133 | 5/2008 |
| WO | WO 2008/136838 | 11/2008 |
| WO | WO 2009/023232 | 2/2009 |
| WO | WO 2009/023845 | 2/2009 |
| WO | WO 2009/089545 | 7/2009 |
| WO | WO 2009/129545 | 10/2009 |
| WO | WO 2009/129546 | 10/2009 |
| WO | WO 2009/129548 | 10/2009 |
| WO | WO 2009/146216 | 12/2009 |
| WO | WO 2009/146218 | 12/2009 |
| WO | WO 2010/011782 | 1/2010 |
| WO | WO 2010/053817 | 5/2010 |
| WO | WO 2010/093944 | 8/2010 |
| WO | WO 2011/130302 | 10/2011 |
| WO | WO 2012/083306 | 6/2012 |
| WO | WO 2012/125488 | 9/2012 |
| WO | WO 2013/163344 | 10/2013 |
| WO | WO 2013/188818 | 12/2013 |
| WO | WO 2014/040056 | 3/2014 |
| WO | WO 2014/040060 | 3/2014 |
| WO | WO 2014/040073 | 3/2014 |
| WO | WO 2015/027206 | 2/2015 |
| WO | WO 2015/112792 | 7/2015 |
| WO | WO 2016/130927 | 8/2016 |

(56) References Cited

FOREIGN PATENT DOCUMENTS

| WO | WO 2019/241796 | 12/2019 |
|---|---|---|
| WO | WO 2019/246461 | 12/2019 |

OTHER PUBLICATIONS

Albini and Sporn, "Opinion: the tumour microenvironment as a target for chemoprevention," *Nature Reviews Cancer*, 7: 139-147, 2007.
Andresen and Margaretha, "Preparation of Dialkyl 2-Cyanocycloalk-2-en-1-ones," *J. Chem. Research (S)*, 332, 1994.
Caron et al., "Versatile Strategy to access tricycles related to quassinoids and triterpenes," *Org. Letters*, 12(3) 508-511, 2010.
Chadalapaka, et al., "Structure-dependent inhibition of bladder and pancreatic cancer cell growth by 2-substituted glycyrrhetinic and ursolic acid derivatives," *Bioorganic & Medicinal Chemistry Letters*, 18:2633-2639, 2008.
Chintharlapalli et al., "Structure-dependent activity of glycyrrhetinic acid derivatives as peroxisome proliferator-activated receptor γ agonists in colon cancer cells," *Molecular Cancer Therapeutics*, 6 (5): 1588-1598, 2007.
Clinton et al., "Steroidal [3,2-c]pyrazoles. II. Androstanes, 19-norandrostanes and their unsaturated analogs," *J. Am Chem Soc.*, 83:1478-1491, 1961.
Connolly et al., "Grandiofolione: a novel tetranortriterpenoid," *Chemical Communications*, 23:867-568, 1966.
De Ruggieri et al., "Deidrogenazione e bromurazione di beta-chetonitrili steroidali," *II Farmaco*, 20: 358-388, 1964. (English summary).
Dinkova-Kostova et al., "Extremely potent triterpenoid inducers of the phase 2 response: correlations of protection against oxidant and inflammatory stress," *Proc. Natl. Acad. Sci.*, 102(12): 4584-4589, 2005.
Duan et al., "Immunosuppressive terpenoids from extracts of *Tripterygium wilfordii*," *Tetrahedron*, 57 (40): 8413-8424, 2001.
Favaloro et al., "Design and synthesis of tricyclic compounds with enone functionalities in rings A and C: a novel class of highly active inhibitors of nitric oxide production in mouse macrophages," *J. Med. Chem.*, 45:4801-4805, 2002.
Ferreira et al., "Phytochemistry of the mopane, *Colophosperum mopane*," *Phytochemistry*, 64 (1): 31-51, 2003.
Finlay et al., "Novel A-ring cleaved analogs of oleanolic and ursolic acids which affect growth regulation in NRP.152 prostate cells," *Biorg. Med. Chem. Lett.*, 7(13): 1769-1772, 1997.
Finlay et al., "The Effects of A and C Ring Modification of Oleanolic and Ursolic Acid on the Inhibition of Nitric Oxide Formation in Mouse Macrophages," 213th American Chemical Society National Meeting, Abstract: 084, 1997.
Hatcher et al., "Curcumin: from ancient medicine to current clinical trials," *CMLS Cellular and Molecular Life Sciences*, 65 (11): 1631-1652, 2008.
Honda et al., "A novel dicyanotriterpenoid, 2-cyano-3,12-dioxooleana-1,9(11)-dien-28-onitrile, active at picomolar concentrations for inhibition of nitric oxide production," *Bioorg. Med. Chem. Lett.*, 12:1027-1030, 2002.
Honda et al., "An efficient synthesis of tricyclic compounds (+)-(4aβ, 8aβ, 10aα)-1,2,3,4,4a,6,7,8,8a,9,10,10a-Dodecahydro-1,1,4a-Trimethyl-2-Oxophenanthrene-8a-Carboxolic acid, its methyl ester, and (+)-(4aβ,8aβ,10aα)-3,4,4a,6,7,8,8a,9,10,10a-Decahydro-8a-hydroxymethyl-1,1,4a-trimethylphenanthren-2(1H)-one," *Org. Prep. Proced. Int.*, 37(6): 546-550, 2005.
Honda et al., "Design and synthesis of 23, 24-dinoroleanolic acid derivatives, novel triterpenoid-steroid hybrid molecules," *J. Org. Chem.*, 63:4846-4849, 1998.
Honda et al., "Design and synthesis of 2-cyano-3,12-dioxoolean-1,9-dien-28-oic acid, a novel and highly active inhibitor of nitric oxide production in mouse macrophages," *Bioorg Med Chem Lett.*, 8(19):2711-2714, 1998.
Honda et al., "Design, synthesis, and biological evaluation of biotin conjugates of 2-cyano-3,12-dioxooleana-1,9(11)-dien-28-oic acid for the isolation of the protein targets," *J. Med. Chem.*, 47 (20): 4923-4932, 2004.
Honda et al., "Efficient synthesis of (–)- and (+)-tricyclic compounds with enome functionalities in rings A and C. A novel class of orally active anti-inflammatory and cancer chemopreventive agents," *Org Biomol Chem.*, 1:4384-4391, 2003.
Honda et al., "New enone derivatives of oleanolic acid and ursolic acid as inhibitors of nitric oxide production in mouse macrophages," *Bioorg. Med. Chem. Lett.*, 7:1623-1628, 1997.
Honda et al., "New synthetic oleanane and ursane triterpenoids as inhibitors of nitric oxide production in mouse macrophages," The Fifth Chemical Congress of North America, Cancun, Mexico, Abstract 552 and slides for oral presentation, Nov. 1997.
Honda et al., "Novel synthetic oleanane and ursane triterpenoids with various enone functionalities in ring A as inhibitors of nitric oxide production in mouse macrophages," *J. Med. Chem.*, 43:1866-1877, 2000.
Honda et al., "Novel synthetic oleanane triterpenoids: a series of highly active inhibitors of nitric oxide production in mouse macrophages," *Bioorg Med Chem Lett*, 9(24):3429-3434, 1999.
Honda et al., "Novel tricyclic compounds having acetylene groups at C-8a and cyano enones in rings A and C: highly potent anti-inflammatory and cytoprotective agents," *J. Med. Chem.*, 50:1731-1734, 2007.
Honda et al., "Revision and confirmation of the regiochemistry of isoxazoles derived from methyl oleanonate and lanost-8-en-3-one. Synthesis of a new lanostane triterpenoid with a cyano-enone functionality in ring A," *J. Org. Chem.*, 68:4991-4993, 2003.
Honda et al., "Synthesis of (±)-3,3-ethylenedioxy-14α-hydroxy-5-picrasene-11,16-dione, a 14αH-picrasane derivative," *Chem. Lett.*, 299-302, 1981.
Honda et al., "Synthesis of a novel dicyano abietane analogue: a potential antiinflammatory agent," *J. Org. Chem.*, 71:3314-3316, 2006.
Honda et al., "Synthetic oleanane and ursane triterpenoids with modified rings A and C: A series of highly active inhibitors of nitric oxide production in mouse macrophages," *J. Med. Chem.*, 43:4233-4246, 2000.
Honda et al., "Tricyclic Compounds Containing Nonenolizable Cyano Enones. A Novel Class of Highly Potent Anti-Inflammatory and Cytoprotective Agents," *J. Med. Chem.*, 54(6):1762-1778, 2011.
Huerta et al., "Characterization of novel small-molecule NRF2 activators: Structural and biochemical validation of stereospecific KEAP1 binding", *Biochem. Biophys. Acta*, 1860(11):2537-2552, 2016.
Hybertson, et al., "Oxidative stress in health and disease: The therapeutic potential of Nrf2 activation", *Molecular Aspects of Medicine*, 2011, 32:234-246.
International Preliminary Report on Patentability issued in corresponding PCT Application No. PCT/US2015/012579, mailed on Jul. 26, 2016.
International Preliminary Report on Patentability issued in corresponding PCT Application No. PCT/US2017/000094, mailed on Jun. 27, 2019.
International Preliminary Report on Patentability issued in corresponding PCT Application No. PCT/US2016/017769, mailed on Aug. 15, 2017.
International Preliminary Report on Patentability issued in corresponding PCT Application No. PCT/US2011/065897, mailed on Jun. 27, 2013.
International Search Report and Written Opinion issued in corresponding PCT Application No. PCT/US2015/012579, mailed on Mar. 19, 2015.
International Search Report and Written Opinion issued in corresponding PCT Application No. PCT/US2017/000094, mailed on Mar. 26, 2018.
International Search Report and Written Opinion issued in corresponding PCT Application No. PCT/US2016/017769, mailed on Apr. 15, 2016.

(56) References Cited

OTHER PUBLICATIONS

International Search Report and Written Opinion issued in corresponding PCT Application No. PCT/US2011/065897, mailed on Jul. 27, 2012.
Kato, Research Flow of Optical Heterogeneous Drugs, Yakuji, Yakuji Jihou, Limited, 29(10):2039-42, 1987.
Kato, Research Flow of Optical Heterogeneous Drugs, Yakuji, Yakuji Jihou, Limited, 29(10):2039-42, 1987. (Partial English Translation).
Kincl et al., "Pituitary gonadotropin inhibitory action of neutral steroids," *Acta. Endocrinologica*, 46: 300-306, 1964.
Kobayashi et al., "The antioxidant defense system Keap1-Nrf2 comprises a multiple sensing mechanism for responding to a wide range of chemical compounds," *Mol. Cell Biol.*, 29(2):493-502, 2009.
Konopleva et al., "Activation of nuclear transcription factor PPARγ by the novel triterpenoid CDDO as targeted therapy in breast cancer," 2002 Keystone Symposium, Abstract No. 539, 2002.
Konopleva et al., "Mechanisms and Activity of PPARγ-Active Triterpenoids CDDO and CDDO-Me in Leukemias," *Blood*, 106:2460, 2005.
Konopleva et al., "Novel synthetic triterpenoid CDDO-Me: potent antiproliferative, proapoptotic and differentiating agent in AML," *Blood*, 96(11), Part 1: 121A, abstract # 522, 2000.
Konopleva et al., "Novel synthetic triterpenoid, CDDO, and its methyl ester: Potent antiproliferative, proapoptotic and differentiating agents in AML," *Blood*, 94(Suppl 1):479a, Abstract #2140, 1999.
Konopleva et al., "Novel triterpenoid CDDO-Me is a potent inducer of apoptosis and differentiation in acute myelogenous leukemia," *Blood*, 99(1):326-335, 2002.
Konopleva et al., "Peroxisome proliferator-activated receptor gamma and retinoid X receptor ligands are potent inducers of differentiation and apoptosis in leukemias," *Mol. Cancer Ther.*, 3:1249-1262, 2004.
Konopleva et al., "PPARγ Ligand CDDO Induces Apoptosis in Leukemias Via Multiple Apoptosis Pathways," Abstracts of the 44th Annual Meeting of the American Society of Hematology, Abstract No. 2209, 2002.
Konopleva et al., "PPARγ Ligands Are Potent Inducers of Apoptosis in Leukemias and Lymphomas," American Society of Hematology 43rd Annual Meeting and Exposition, Abstract No. 501, 2001.
Konopleva et al., "PPARγ Nuclear Receptor as a Novel Molecular Target in Leukemia Therapy," *Proc. Amer. Assoc. Cancer Res.*, 43:4730, 2002.
Konopleva et al., "PPARγ nuclear receptor as a novel therapeutic target in AML," *Blood*, 96(11):460a, Abstract #1982, 2000.
Konopleva et al., "PPARγ nuclear receptor as a novel therapeutic target in AML," *Proc. of the AACR*, 42, Abstract #4458, 2001.
Konopleva et al., "Suppression of ERK Activation is Required for Triterpenoid Methyl-CDDO-Induced Apoptosis in AML," *Blood*, 102(11):1404, 2003.
Konopleva et al., "Synthetic triterpenoid 2-cyano-3,12-dioxooleana-1,9-dien-28-oic acid induces growth arrest in HER2-overexpressing breast cancer cells," *Mol. Cancer Ther.*, 5:317-328, 2006.
Konopleva et al., "Synthetic triterpenoid CDDO as a novel therapy for resistant breast cancer," *Proc. Amer. Assoc. Cancer Res.*, 44:2726, 2003.
Konopleva et al., "The novel triterpenoid CDDO-Me suppresses MAPK pathways and promotes p38 activation in acute myeloid leukemia cells," *Leukemia*, 19:1350-1354, 2005.
Konopleva et al., "The synthetic triterpenoid 2-cyano-3,12-dioxooleana-1,9-dien-28-oic acid induces caspase-dependent and -independent apoptosis in acute myelogenous leukemia," *Cancer Res.*, 64:7927-7935, 2004.
Liby et al., "A novel acetylenic tricyclic bis-(cyano enone) potently induces phase 2 cytoprotective pathways and blocks liver carcinogenesis induced by aflatoxin," *Cancer Res.*, 68:6727-6733, 2008.
Liby et al., "Novel semisynthetic analogues of betulinic acid with diverse cytoprotective, antiproliferative, and proapoptotic activities," *Mol. Cancer. Ther.*, 6(7): 2113-2119, 2007.
Liby et al., "The rexinoid LG100268 and the synthetic triterpenoid CDDO-methyl amide are more potent than erlotinib for prevention of mouse lung carcinogenesis," *Mol. Cancer Ther.*, 7:1251-1257, 2008.
Liby et al., "The synthetic triterpenoid CDDO-Imidazolide suppresses STAT phosphorylation and induces apoptosis in myeloma and lung cancer cells," *Clinical Cancer Research*, 12 (14 Part 1): 4288-4293, 2006.
Liby et al., "The synthetic triterpenoids CDDO-Methyl ester and CDDO-ethyl amide prevent lung cancer induced by vinyl carbamate in A/J mice," *Cancer Research*, 67 (6): 1-7, 2007.
Liby et al., "The synthetic triterpenoids, CDDO and CDDO-imidazolide, are potent inducers of heme oxygenase-1 and Nrf2/ARE signaling," *Cancer Res.*, 65:4789-4798, 2005.
Liby et al., "Triterpenoids and rexinoids as multifunctional agents for the prevention and treatment of cancer," *Nat. Rev. Cancer*, 7 (5): 357-369, 2007.
Nohira, Optically Active Substance, Organic Industrial Chemistry thereof, Asakura Shoten Co., Ltd., 20-21, 1989.
Nohira, Optically Active Substance, Organic Industrial Chemistry thereof, Asakura Shoten Co., Ltd., 20-21, 1989. (Partial English Translation).
Orr et al., "Steroids. CCLXV. Studies in cyano steroids. 3. Unsaturated 2-cyano steroids," *J. Org. Chem.*, 29(11): 3300-3303, 1964.
Ribo et al., "Synthesis of methyl 1,11-dioxooleanan-2,12-dien-30-oate and its 24-nor derivative," *Afinidad*, 38(373): 197-200, 1981.
Satoh et al., "Activation of the Keap1/Nrf2 pathway for neuroprotection by electrophilic phase II inducers," *PNAS*, 103 (3): 768-773, 2006.
Shin et al., "Inhibitory roles of NRF2 and an oleanolic triterpenoid on adipocyte differentiation and obesity," dissertation submitted to John Hopkins University in conformity with the requirements for the degree of Doctor of Philosophy, Mar. 2009.
Shin et al., "NRF2 modulates aryl hydrocarbon receptor signaling: influence on adipogenesis," *Molecular and Cellular Biology*, 27 (20): 7188-7197, 2007.
Soufli et al., "Overview of cytokines and nitric oxide involvement in immuno-pathogenesis of inflammatory bowel diseases", *World J. Gastrointest. Pharmacol. Ther.*, 7(3):353-360, 2016.
Sporn et al., "New Synthetic Triterpenoids: Potent Agents for Prevention and Treatment of Tissue Injury Caused by Inflammatory and Oxidative Stress," *J. Nat. Prod.*, 74(3):537-545, 2011.
Subba Rao, et al., "Chemical modifications of natural triterpenes—glycyrrhetinic and boswellic acids: evaluation of their biological activity," *Tetrahedron*, 64(51): 11541-11548, 2008.
Suh et al., "A novel synthetic oleanane triterpenoid, 2-cyano-3,12-dioxoolean-1,9-dien-28-oic acid (CDDO), induces cell differentiation in human myeloid leukemias," Proceedings of the American Association for Cancer Research Annual Meeting, 40:300, abstract 1988, 1999.
Suh et al., "A novel synthetic oleanane triterpenoid, 2-cyano-3,12-dioxoolean-1,9-dien-28-oic acid, with potent differentiating, antiproliferative, and anti-inflammatory activity," *Cancer Res.*, 59(2):336-341, 1999.
Suh et al., "New triterpenoids as cancer preventive and anti-inflammatory agents," Proceedings of the American Association for Cancer Research, Abstract No. 1457, 38: 216, 1997.
Suh et al., "Novel triterpenoids suppress inducible nitric oxide synthase (iNOS) and inducible cyclooxygenase (COX-2) in mouse macrophages," *Cancer Res.*, 58:717-723, 1998.
Suh et al., "Novel triterpenoids suppress inducible nitric oxide synthase (iNOS) and inducible cyclooxygenase (COX-2)," Proceedings of the American Association for Cancer Research Annual Meeting, 39: Abstract No. 1821, 1998.
Suh et al., "Synthetic triterpenoids activate a pathway for apoptosis in AML cells involving downregulation of FLIP and sensitization to TRAIL," *Leukemia*, 17:2122-2129, 2003.
Suh et al., "Synthetic triterpenoids enhance transforming growth factor β/Smad signaling," *Cancer Res.*, 63:1371-1376, 2003.

(56) References Cited

OTHER PUBLICATIONS

Suh et al., "Triterpenoids CDDO and CDDO-Me Down-Regulate FLIP Expression and Sensitize AML Cells to Trail-Induced Apoptosis," American Society of Hematology 43rd Annual Meeting and Exposition, Abstract No. 498, 2001.
Sun et al., "Structure-activity relationships of oleanan- and ursane-type triterpenoids," Botanical Studies, 47:339-368, 2006.
Xu et al., "The role of nitric oxide in cancer", *Cell Res.*, 12:311-320, 2002.
Yamanaka et al., Quarterly Chemical Review, Separation of Optically Isomers, Academic Society Publishing Center, Inc., 6:8-10, 124, 212-213, 1999.
Yamanaka et al., Quarterly Chemical Review, Separation of Optically Isomers, Academic Society Publishing Center, Inc., 6:8-10, 124, 212-213, 1999. (Partial English Translation).
Yates et al., "Potent protection against aflatoxin-induced tumorigenesis through induction of Nrf2-regulated pathways by the triterpenoid 1-[2-cyano-3-, 12-dioxooleana-1,9(11)-dien-28-oyl]imidazole," *Cancer Res.*, 66 (4): 2488-2494, 2007.
You et al., "Synthesis and cytotoxic activity of a-ring modified betulinic acid derivatives," *Bioorganic and Medicinal Chemistry Letters*, 13 (19): 3137-3140, 2003.

\* cited by examiner

PYRIMIDINE TRICYCLIC ENONE DERIVATIVES FOR INHIBITION OF ROR-GAMMA AND OTHER USES

This application is a continuation of U.S. patent application Ser. No. 16/468,054, filed Jun. 10, 2019, which is a national phase application under 35 U.S.C. § 371 of International Application No. PCT/US2017/000094, filed Dec. 16, 2017, which claims the benefit of priority to U.S. Provisional Application No. 62/435,588, filed on Dec. 16, 201, the entire contents of each of which are hereby incorporated by reference.

BACKGROUND OF THE INVENTION

I. Field of the Invention

The present invention relates generally to the fields of biology and medicine. More particularly, it concerns compounds, compositions, and methods for the treatment and prevention of diseases such as those associated with RAR-related orphan receptor γ (RORγ) and excess production of IL-17.

II. Description of Related Art

Inflammatory diseases, particularly autoimmune diseases, such as rheumatoid arthritis, osteoarthritis, psoriasis, and multiple sclerosis, frequently have severe and long-term adverse effects on a patient's physical well-being and quality of life. In many patients these diseases cause significant disability, and in some cases (e.g., lupus and multiple sclerosis), they may be life-threatening. Recent advances in therapeutic options, such as the development of therapeutic antibodies against tumor necrosis factor (TNF), have improved outcomes and quality of life for many patients. However, significant numbers of patients do not achieve adequate relief of symptoms from these therapies or cannot tolerate them. Even in patients who do respond, side effects can be significant and may be life-threatening due to immune suppression or other complications.

Recent research on chronic inflammation and autoimmunity has revealed an important role played by a subpopulation of T lymphocytes known as Th17 cells. These cells produce the inflammatory cytokine interleukin 17 (IL-17). Excessive levels of IL-17 have been reported in a variety of autoimmune diseases including multiple sclerosis, rheumatoid arthritis, psoriasis, inflammatory bowel diseases, vitiligo, Sjögren syndrome, and ankylosing spondylitis (Miossec and Kolls, 2012; Yang et al., 2014; Gaffen et al., 2014). Evidence suggests that IL-17 also plays a significant role in the pathology of vasculitis, atherosclerosis, and inflammatory lung diseases, such as cystic fibrosis and chronic obstructive pulmonary disease (COPD). IL-17 is also implicated in the pathophysiology of epilepsy and neurodegenerative diseases including Alzheimer's disease, Parkinson's disease, and ALS. Elevated levels of IL-17 or Th17 cells have been reported in patients with psychiatric and neuro-psychiatric conditions including schizophrenia, obsessive-compulsive disorder, bipolar disorder, post-traumatic stress disorder, major depression, and autism. Elevations in IL-17 have been implicated in other conditions involving dysregulated inflammatory signaling, including obesity, insulin resistance, and fatty liver disease.

Although Th17 cells are not the only source of IL-17, it has been reported that these cells are a major source of this cytokine in tissues undergoing damage from autoimmune disease, such as arthritic joints. And elevated levels of IL-17 have been reported to promote tissue degradation, e.g., by stimulating the production of matrix metalloproteinases (a source of damage to connective tissue and cartilage) and increasing the expression of receptor activator of NF-κB ligand (RANKL), which stimulates osteoclast activity and promotes bone damage.

Inappropriate activity of Th17 cells, including overproduction of IL-17, has also been implicated in the pathologies associated with certain viral and parasitic infections. For example, IL-17 has been implicated in the development of severe neuroinflammation associated with *Toxoplasma gondii* infection and increased severity of lesions associated with *Leishmania* infection. In these and other cases, IL-17 appears to play a role in perpetuating the infection, promoting an excessive inflammatory response, and inhibiting clearance of the infectious agent (Waite and Skokos, 2011). Accordingly, therapies that prevent or inhibit excess production of IL-17, or otherwise reduce circulating levels of IL-17, would have significant potential in a wide range of diseases or disorders, including those with inflammatory and autoimmune-related components.

Both the differentiation of Th17 cells and their production of IL-17 are regulated to a significant degree by the RAR-related orphan receptor RORγt, a member of the nuclear hormone receptor family. Expression of RORγt is common to all types of Th17 cells and plays a significant role in their differentiation as well as their activity. RORγ also regulates the production of IL-17 in other cell types, including gamma delta T cells, innate lymphoid cells, and lymphoid tissue inducer cells (Bronner et al., 2016). Inhibition of RORγt activity has been shown to result in reduced expression of IL-17. As such, the identification and synthesis of small molecule inhibitors of RORγt is of great interest.

SUMMARY OF THE INVENTION

The present disclosure provides novel compounds, including pyrimidinyl tricyclic enone derivatives with anti-inflammatory and/or antioxidant properties, pharmaceutical compositions thereof, methods for their manufacture, and methods for their use, including for the inhibition of RORγ nuclear receptor the prevention and treatment of diseases or disorders associated with and/or IL-17 overproduction of IL-17.

In some aspects, the present disclosure provides compounds of the formula:

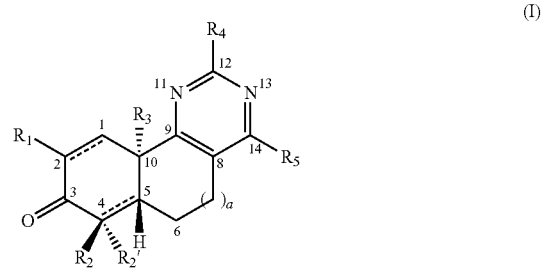

wherein:
  the bond between carbon atoms 1 and 2 is a single bond, an epoxidized double bond, or a double bond;
  the bond between carbon atoms 4 and 5 is a single bond or a double bond;
  a is 0, 1, or 2;

$R_1$ is cyano, heteroaryl$_{(C\leq 8)}$, substituted heteroaryl$_{(C\leq 8)}$, —CF$_3$, or —C(O)R$_a$; wherein:
  $R_a$ is hydroxy, amino, or alkoxy$_{(C\leq 8)}$, alkylamino$_{(C\leq 8)}$, dialkylamino$_{(C\leq 8)}$, alkylsulfonylamino$_{(C\leq 8)}$, or a substituted version of any of these groups;
$R_2$ is hydrogen or alkyl$_{(C\leq 12)}$, cycloalkyl$_{(C\leq 12)}$, alkenyl$_{(C\leq 12)}$, alkynyl$_{(C\leq 12)}$, aryl$_{(C\leq 12)}$, aralkyl$_{(C\leq 12)}$, heteroaryl$_{(C\leq 12)}$, heteroaralkyl$_{(C\leq 12)}$, acyl$_{(C\leq 12)}$, or a substituted version of any of these groups, or -alkanediyl$_{(C\leq 8)}$-cycloalkyl$_{(C\leq 12)}$ or a substituted version of this group;
$R_2'$ is absent, hydrogen, or alkyl$_{(C\leq 12)}$, cycloalkyl$_{(C\leq 12)}$, alkenyl$_{(C\leq 12)}$, alkynyl$_{(C\leq 12)}$, aryl$_{(C\leq 12)}$, aralkyl$_{(C\leq 12)}$, heteroaryl$_{(C\leq 12)}$, heteroaralkyl$_{(C\leq 12)}$, acyl$_{(C\leq 12)}$, or a substituted version of these groups; provided that when the bond between carbon atoms 4 and 5 is a double bond then $R_2'$ is absent;
$R_3$ is alkyl$_{(C\leq 12)}$, alkenyl$_{(C\leq 12)}$, aryl$_{(C\leq 12)}$, aralkyl$_{(C\leq 12)}$, or a substituted version of any of these groups;
$R_4$ is hydrogen, amino, alkyl$_{(C\leq 18)}$, substituted alkyl$_{(C\leq 18)}$, cycloalkyl$_{(C\leq 18)}$, substituted cycloalkyl$_{(C\leq 18)}$, aryl$_{(C\leq 18)}$, substituted aryl$_{(C\leq 18)}$, aralkyl$_{(C\leq 18)}$, substituted aralkyl$_{(C\leq 18)}$, heteroaryl$_{(C\leq 18)}$, substituted heteroaryl$_{(C\leq 18)}$, heteroaralkyl$_{(C\leq 18)}$, substituted heteroaralkyl$_{(C\leq 18)}$, heterocycloalkyl$_{(C\leq 18)}$, substituted heterocycloalkyl$_{(C\leq 18)}$, amido$_{(C\leq 18)}$, substituted amido$_{(C\leq 18)}$, or —X$_1$—(CH$_2$)$_m$—R$_4'$;

wherein:
  X$_1$ is NR$_b$, O, or S; wherein:
    R$_b$ is hydrogen, alkyl$_{(C\leq 6)}$, or substituted alkyl$_{(C\leq 6)}$;
  m is 0, 1, 2, 3, or 4; and
  R$_4'$ is alkyl$_{(C\leq 12)}$, cycloalkyl$_{(C\leq 12)}$, aryl$_{(C\leq 18)}$, aralkyl$_{(C\leq 8)}$, heteroaryl$_{(C\leq 18)}$, heteroaralkyl$_{(C\leq 18)}$, heterocycloalkyl$_{(C\leq 18)}$, or a substituted version of any of these groups; or

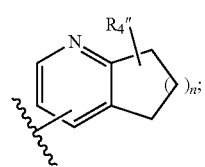

wherein:
  n is 0, 1, 2, 3, or 4; and
  R$_4''$ is —H, —OH, —F, —Cl, —Br, —I, —NH$_2$, —NO$_2$, —CN, —SH, —S(O)$_2$OH, or —S(O)$_2$NH$_2$, or alkyl$_{(C\leq 8)}$, cycloalkyl$_{(C\leq 8)}$, aryl$_{(C\leq 8)}$, heteroaryl$_{(C\leq 8)}$, heterocycloalkyl$_{(C\leq 8)}$, acyl$_{(C\leq 8)}$, amido$_{(C\leq 8)}$, alkoxy$_{(C\leq 8)}$, acyloxy$_{(C\leq 8)}$, alkylamino$_{(C\leq 8)}$, dialkylamino$_{(C\leq 8)}$, —C(O)-alkoxy$_{(C\leq 8)}$, —C(O)-alkylamino$_{(C\leq 8)}$, —C(O)-dialkylamino$_{(C\leq 8)}$, alkylsulfonyl$_{(C\leq 8)}$, arylsulfonyl$_{(C\leq 8)}$, alkoxysulfonyl$_{(C\leq 8)}$, or a substituted version of any of these groups; or —X$_2$—(CH$_2$)$_p$—R$_4'''$;

wherein:
  X$_2$ is arenediyl$_{(C\leq 12)}$, substituted arenediyl$_{(C\leq 12)}$, heterocycloalkanediyl$_{(C\leq 12)}$, substituted heterocycloalkanediyl$_{(C\leq 12)}$, heteroarenediyl$_{(C\leq 12)}$, or substituted heteroarenediyl$_{(C\leq 12)}$;
  p is 0, 1, 2, 3, or 4; and R$_4'''$ is alkyl$_{(C\leq 8)}$, cycloalkyl$_{(C\leq 8)}$, aryl$_{(C\leq 8)}$, heteroaryl$_{(C\leq 8)}$, heterocycloalkyl$_{(C\leq 8)}$, acyl$_{(C\leq 8)}$, amido$_{(C\leq 8)}$, alkoxy$_{(C\leq 8)}$, acyloxy$_{(C\leq 8)}$, —C(O)-alkoxy$_{(C\leq 8)}$, —C(O)-alkylamino$_{(C\leq 8)}$, —C(O)-dialkyl-amino$_{(C\leq 8)}$, alkylsulfonyl$_{(C\leq 8)}$, arylsulfonyl$_{(C\leq 8)}$, alkoxysulfonyl$_{(C\leq 8)}$, or a substituted version of any of these groups; and
$R_5$ is amino, hydroxy, —OS(O)$_2$C$_6$H$_4$CH$_3$, alkyl$_{(C\leq 12)}$, alkoxy$_{(C\leq 12)}$, cycloalkyl$_{(C\leq 12)}$, cycloalkoxy$_{(C\leq 12)}$, aryl$_{(C\leq 12)}$, aralkyl$_{(C\leq 12)}$, heteroaryl$_{(C\leq 12)}$, heteroaralkyl$_{(C\leq 12)}$, heterocycloalkyl$_{(C\leq 12)}$, acyl$_{(C\leq 12)}$, acyloxy$_{(C\leq 12)}$, alkylamino$_{(C\leq 12)}$, dialkylamino$_{(C\leq 12)}$, alkylsulfonylamino$_{(C\leq 12)}$, or a substituted version of any of the last fourteen groups, or

—OY$_1$—A$_1$;

wherein:
  Y$_1$ is alkanediyl$_{(C\leq 8)}$ or substituted alkanediyl$_{(C\leq 8)}$; and
  A$_1$ is cycloalkyl$_{(C\leq 8)}$ or substituted cycloalkyl$_{(C\leq 8)}$; or —Y$_2$—C(O)NR$_c$—A$_2$;

wherein:
  Y$_2$ is arenediyl$_{(C\leq 8)}$ or substituted arenediyl$_{(C\leq 8)}$;
  R$_c$ is hydrogen, alkyl$_{(C\leq 6)}$, or substituted alkyl$_{(C\leq 6)}$; and
  A$_2$ is aralkyl$_{(C\leq 12)}$ or substituted aralkyl$_{(C\leq 12)}$; or —A$_3$R$_d$;

wherein:
  A$_3$ is —O— or —NR$_c$—, wherein
    R$_c$ is hydrogen, alkyl$_{(C\leq 6)}$, or substituted alkyl$_{(C\leq 6)}$; and
  R$_d$ is acyl$_{(C\leq 12)}$, or substituted acyl$_{(C\leq 12)}$;
provided that when carbon atoms 4 and 5 are joined by a double bond, then R$_2'$ and the hydrogen atom at carbon atom 5 are absent;
or a pharmaceutically acceptable salt thereof.

In some embodiments, the present disclosure provides compounds of the formula:

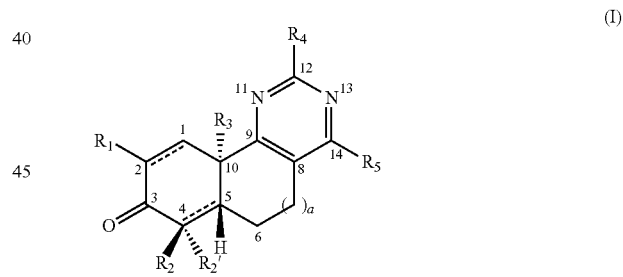

(I)

wherein:
  the bond between carbon atoms 1 and 2 is a single bond, an epoxidized double bond, or a double bond;
  the bond between carbon atoms 4 and 5 is a single bond or a double bond;
  a is 0, 1, or 2;
  $R_1$ is cyano, heteroaryl$_{(C\leq 8)}$, substituted heteroaryl$_{(C\leq 8)}$, —CF$_3$, or —C(O)R$_a$; wherein:
    R$_a$ is hydroxy, amino, or alkoxy$_{(C\leq 8)}$, alkylamino$_{(C\leq 8)}$, dialkylamino$_{(C\leq 8)}$, alkylsulfonylamino$_{(C\leq 8)}$, or a substituted version of any of these groups;
  $R_2$ is hydrogen or alkyl$_{(C\leq 12)}$, cycloalkyl$_{(C\leq 12)}$, alkenyl$_{(C\leq 12)}$, alkynyl$_{(C\leq 12)}$, aryl$_{(C\leq 12)}$, aralkyl$_{(C\leq 12)}$, heteroaryl$_{(C\leq 12)}$, heteroaralkyl$_{(C\leq 12)}$, acyl$_{(C\leq 12)}$, or a substituted version of any of these groups, or -alkanediyl$_{(C\leq 8)}$-cycloalkyl$_{(C\leq 12)}$ or a substituted version of this group;

$R_2'$ is absent, hydrogen, or alkyl$_{(C≤12)}$, cycloalkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heteroaralkyl$_{(C≤12)}$, acyl$_{(C≤12)}$, or a substituted version of these groups; provided that when the bond between carbon atoms 4 and 5 is a double bond then $R_2'$ is absent;

$R_3$ is alkyl$_{(C≤12)}$, alkenyl$_{(C≤12)}$, aryl$_{(C≤12)}$, aralkyl$_{(C≤12)}$, or a substituted version of any of these groups;

$R_4$ is hydrogen, amino, alkyl$_{(C≤18)}$, substituted alkyl$_{(C≤18)}$, cycloalkyl$_{(C≤18)}$, substituted cycloalkyl$_{(C≤18)}$, aryl$_{(C≤18)}$, substituted aryl$_{(C≤18)}$, aralkyl$_{(C≤18)}$, substituted aralkyl$_{(C≤18)}$, heteroaryl$_{(C≤18)}$, substituted heteroaryl$_{(C≤18)}$, heteroaralkyl$_{(C≤18)}$, substituted heteroaralkyl$_{(C≤18)}$, heterocycloalkyl$_{(C≤18)}$, substituted heterocycloalkyl$_{(C≤18)}$, amido$_{(C≤18)}$, substituted amido$_{(C≤18)}$, or —$X_1$—(CH$_2$)$_m$—$R_4'$;

wherein:
$X_1$ is NR$_b$, O, or S; wherein:
$R_b$ is hydrogen, alkyl$_{(C≤6)}$, or substituted alkyl$_{(C≤6)}$;
m is 0, 1, 2, 3, or 4; and
$R_4'$ is alkyl$_{(C≤12)}$, cycloalkyl$_{(C≤12)}$, aryl$_{(C≤18)}$, aralkyl$_{(C≤8)}$, heteroaryl$_{(C≤18)}$, heteroaralkyl$_{(C≤18)}$, heterocycloalkyl$_{(C≤18)}$, or a substituted version of any of these groups; or

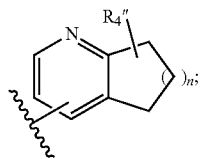

wherein:
n is 0, 1, 2, 3, or 4; and
$R_4''$ is —OH, —F, —Cl, —Br, —I, —NH$_2$, —NO$_2$, —CN, —SH, —S(O)$_2$OH, or —S(O)$_2$NH$_2$, or alkyl$_{(C≤8)}$, cycloalkyl$_{(C≤8)}$, aryl$_{(C≤8)}$, heteroaryl$_{(C≤8)}$, heterocycloalkyl$_{(C≤8)}$, acyl$_{(C≤8)}$, amido$_{(C≤8)}$, alkoxy$_{(C≤8)}$, acyloxy$_{(C≤8)}$, alkylamino$_{(C≤8)}$, dialkylamino$_{(C≤8)}$, —C(O)-alkoxy$_{(C≤8)}$, —C(O)-alkylamino$_{(C≤8)}$, —C(O)-dialkyl-amino$_{(C≤8)}$, alkylsulfonyl$_{(C≤8)}$, arylsulfonyl$_{(C≤8)}$, alkoxysulfonyl$_{(C≤8)}$, or a substituted version of any of these groups; or —$X_2$—(CH$_2$)$_p$—$R_4'''$;

wherein:
$X_2$ is heterocycloalkanediyl$_{(C≤12)}$, substituted heterocycloalkanediyl$_{(C≤12)}$, heteroarenediyl$_{(C≤12)}$, or substituted heteroarenediyl$_{(C≤12)}$;
p is 0, 1, 2, 3, or 4; and
$R_4'''$ is alkyl$_{(C≤8)}$, cycloalkyl$_{(C≤8)}$, aryl$_{(C≤8)}$, heteroaryl$_{(C≤8)}$, heterocycloalkyl$_{(C≤8)}$, acyl$_{(C≤8)}$, alkoxy$_{(C≤8)}$, acyloxy$_{(C≤8)}$, —C(O)-alkoxy$_{(C≤8)}$, —C(O)-alkylamino$_{(C≤8)}$, —C(O)-dialkyl-amino$_{(C≤8)}$, alkylsulfonyl$_{(C≤8)}$, arylsulfonyl$_{(C≤8)}$, alkoxysulfonyl$_{(C≤8)}$, or a substituted version of any of these groups; and $R_5$ is hydroxy, —OS(O)$_2$C$_6$H$_4$CH$_3$, alkyl$_{(C≤12)}$, alkoxy$_{(C≤12)}$, cycloalkyl$_{(C≤12)}$, cycloalkoxy$_{(C≤12)}$, aryl$_{(C≤12)}$, aralkyl$_{(C≤12)}$, heteroaryl$_{(C≤12)}$, heteroaralkyl$_{(C≤12)}$, heterocycloalkyl$_{(C≤12)}$, alkylamino$_{(C≤12)}$, dialkylamino$_{(C≤12)}$, alkylsulfonylamino$_{(C≤12)}$, or a substituted version of any of the last eleven groups, or

—OY$_1$—A$_1$;

wherein:
$Y_1$ is alkanediyl$_{(C≤8)}$ or substituted alkanediyl$_{(C≤8)}$; and
$A_1$ is cycloalkyl$_{(C≤8)}$ or substituted cycloalkyl$_{(C≤8)}$; or
—$Y_2$—C(O)NR$_c$—A$_2$;

wherein:
$Y_2$ is arenediyl$_{(C≤8)}$ or substituted arenediyl$_{(C≤8)}$;
$R_c$ is hydrogen, alkyl$_{(C≤6)}$, or substituted alkyl$_{(C≤6)}$; and
$A_2$ is aralkyl$_{(C≤12)}$ or substituted aralkyl$_{(C≤12)}$; or
provided that when carbon atoms 4 and 5 are joined by a double bond, then $R_2'$ and the hydrogen atom at carbon atom 5 are absent;
or a pharmaceutically acceptable salt thereof.

In some embodiments, the compounds are further defined as:

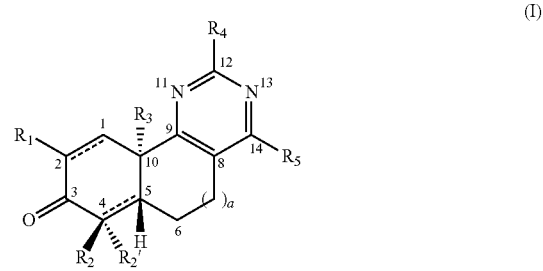

(I)

wherein:
the bond between carbon atoms 1 and 2 is a single bond, an epoxidized double bond, or a double bond;
the bond between carbon atoms 4 and 5 is a single bond or a double bond;
a is 0, 1, or 2;
$R_1$ is cyano, heteroaryl$_{(C≤8)}$, substituted heteroaryl$_{(C≤8)}$, —CF$_3$, or —C(O)R$_a$; wherein:
$R_a$ is hydroxy, amino, or alkoxy$_{(C≤8)}$, alkylamino$_{(C≤8)}$, dialkylamino$_{(C≤8)}$, alkylsulfonylamino$_{(C≤8)}$, or a substituted version of any of these groups;

$R_2$ is hydrogen or alkyl$_{(C≤12)}$, cycloalkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heteroaralkyl$_{(C≤12)}$, acyl$_{(C≤12)}$, or a substituted version of any of these groups, or -alkanediyl$_{(C≤8)}$-cycloalkyl$_{(C≤12)}$ or a substituted version of this group;

$R_2'$ is absent, hydrogen, or alkyl$_{(C≤12)}$, cycloalkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heteroaralkyl$_{(C≤12)}$, acyl$_{(C≤12)}$, or a substituted version of these groups; provided that when the bond between carbon atoms 4 and 5 is a double bond then $R_2'$ is absent;

$R_3$ is alkyl$_{(C≤12)}$, alkenyl$_{(C≤12)}$, aryl$_{(C≤12)}$, aralkyl$_{(C≤12)}$, or a substituted version of any of these groups;

$R_4$ is hydrogen, amino, alkyl$_{(C2-18)}$, substituted alkyl$_{(C≤18)}$, cycloalkyl$_{(C≤18)}$, substituted cycloalkyl$_{(C≤18)}$, aryl$_{(C≤18)}$, substituted aryl$_{(C≤18)}$, aralkyl$_{(C≤18)}$, substituted aralkyl$_{(C≤18)}$, heteroaryl$_{(C≤18)}$, substituted heteroaryl$_{(C≤18)}$, heteroaralkyl$_{(C≤18)}$, substituted heteroaralkyl$_{(C≤18)}$, heterocycloalkyl$_{(C≤18)}$, substituted heterocycloalkyl$_{(C≤18)}$, amido$_{(C≤18)}$, substituted amido$_{(C≤18)}$, or —$X_1$—(CH$_2$)$_m$—$R_4'$;

wherein:
$X_1$ is NR$_b$, O, or S; wherein:
$R_b$ is hydrogen, alkyl$_{(C≤6)}$, or substituted alkyl$_{(C≤6)}$;
m is 0, 1, 2, 3, or 4; and R$_4$' is alkyl$_{(C≤12)}$, cycloalkyl$_{(C≤18)}$, aryl$_{(C≤18)}$, aralkyl$_{(C≤18)}$, heteroaryl$_{(C≤18)}$, heteroaralkyl$_{(C≤18)}$, heterocycloalkyl$_{(C≤18)}$, or a substituted version of any of these groups, provided that when X$_1$ is O, then R$_4$' is not methyl; or

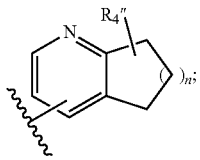

wherein:
n is 0, 1, 2, 3, or 4; and
R$_4$" is —H, —OH, —F, —Cl, —Br, —I, —NH$_2$, —NO$_2$, —CN, —SH, —S(O)$_2$OH, or —S(O)$_2$NH$_2$, or alkyl$_{(C≤8)}$, cycloalkyl$_{(C≤8)}$, aryl$_{(C≤8)}$, heteroaryl$_{(C≤8)}$, heterocycloalkyl$_{(C≤8)}$, acyl$_{(C≤8)}$, amido$_{(C≤8)}$, alkoxy$_{(C≤8)}$, acyloxy$_{(C≤8)}$, alkylamino$_{(C≤8)}$, dialkylamino$_{(C≤8)}$, —C(O)-alkoxy$_{(C≤8)}$, —C(O)-alkylamino$_{(C≤8)}$, —C(O)-dialkylamino$_{(C≤8)}$, alkylsulfonyl$_{(C≤8)}$, arylsulfonyl$_{(C≤8)}$, alkoxysulfonyl$_{(C≤8)}$, or a substituted version of any of these groups; or —X$_2$—(CH$_2$)$_p$—R$_4$'";

wherein:
X$_2$ is arenediyl$_{(C≤12)}$, substituted arenediyl$_{(C≤12)}$, heterocycloalkanediyl$_{(C≤12)}$, substituted heterocycloalkanediyl$_{(C≤12)}$, heteroarenediyl$_{(C≤12)}$, or substituted heteroarenediyl$_{(C≤12)}$;
p is 0, 1, 2, 3, or 4; and
R$_4$'" is alkyl$_{(C≤8)}$, cycloalkyl$_{(C≤8)}$, aryl$_{(C≤8)}$, heteroaryl$_{(C≤8)}$, heterocycloalkyl$_{(C≤8)}$, acyl$_{(C≤8)}$, amido$_{(C≤8)}$, alkoxy$_{(C≤8)}$, acyloxy$_{(C≤8)}$, —C(O)-alkoxy$_{(C≤8)}$, —C(O)-alkylamino$_{(C≤8)}$, —C(O)-dialkyl-amino$_{(C≤8)}$, alkylsulfonyl$_{(C≤8)}$, arylsulfonyl$_{(C≤8)}$, alkoxysulfonyl$_{(C≤8)}$, or a substituted version of any of these groups; and
R$_5$ is amino, hydroxy, —OS(O)$_2$C$_6$H$_4$CH$_3$, alkyl$_{(C≤12)}$, alkoxy$_{(C≤12)}$, cycloalkyl$_{(C≤12)}$, cycloalkoxy$_{(C≤12)}$, aryl$_{(C≤12)}$, aralkyl$_{(C≤12)}$, heteroaryl$_{(C≤12)}$, heteroaralkyl$_{(C≤12)}$, heterocycloalkyl$_{(C≤12)}$, acyl$_{(C≤12)}$, acyloxy$_{(C≤12)}$, alkylamino$_{(C≤12)}$, dialkylamino$_{(C≤12)}$, alkylsulfonylamino$_{(C≤12)}$, or a substituted version of any of the last fourteen groups, or

—OY$_1$—A$_1$;

wherein:
Y$_1$ is alkanediyl$_{(C≤8)}$ or substituted alkanediyl$_{(C≤8)}$; and
A$_1$ is cycloalkyl$_{(C≤8)}$ or substituted cycloalkyl$_{(C≤8)}$; or —Y$_2$—C(O)NR$_c$—A$_2$;

wherein:
Y$_2$ is arenediyl$_{(C≤8)}$ or substituted arenediyl$_{(C≤8)}$;
R$_c$ is hydrogen, alkyl$_{(C≤6)}$, or substituted alkyl$_{(C≤6)}$; and
A$_2$ is aralkyl$_{(C≤12)}$ or substituted aralkyl$_{(C≤12)}$; or —A$_3$R$_d$;

wherein:
A$_3$ is O or NR$_e$, wherein
R$_e$ is hydrogen, alkyl$_{(C≤6)}$, or substituted alkyl$_{(C≤6)}$; and R$_d$ is acyl$_{(C≤12)}$, or substituted acyl$_{(C≤12)}$;
provided that when carbon atoms 4 and 5 are joined by a double bond, then R$_2$' and the hydrogen atom at carbon atom 5 are absent;
or a pharmaceutically acceptable salt thereof.

In other embodiments, the compounds are further defined as:

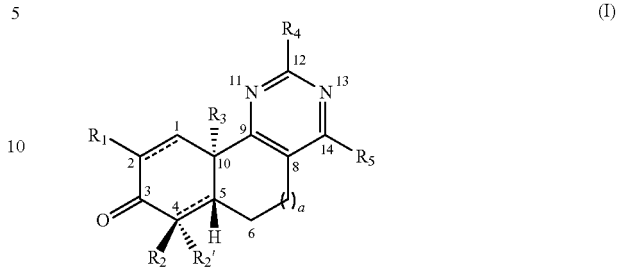

(I)

wherein:
the bond between carbon atoms 1 and 2 is a single bond, an epoxidized double bond, or a double bond;
the bond between carbon atoms 4 and 5 is a single bond or a double bond;
a is 0, 1, or 2;
R$_1$ is cyano, heteroaryl$_{(C≤8)}$, substituted heteroaryl$_{(C≤8)}$, —CF$_3$, or —C(O)R$_a$; wherein:
R$_a$ is hydroxy, amino, or alkoxy$_{(C≤8)}$, alkylamino$_{(C≤8)}$, dialkylamino$_{(C≤8)}$, alkylsulfonylamino$_{(C≤8)}$, or a substituted version of any of these groups;
R$_2$ is hydrogen or alkyl$_{(C≤12)}$, cycloalkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heteroaralkyl$_{(C≤12)}$, acyl$_{(C≤12)}$, or a substituted version of any of these groups, or -alkanediyl$_{(C≤8)}$-cycloalkyl$_{(C≤12)}$ or a substituted version of this group;
R$_2$' is absent, hydrogen, or alkyl$_{(C≤12)}$, cycloalkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heteroaralkyl$_{(C≤12)}$, acyl$_{(C≤12)}$, or a substituted version of these groups; provided that when the bond between carbon atoms 4 and 5 is a double bond then R$_2$' is absent;
R$_3$ is alkyl$_{(C≤12)}$, alkenyl$_{(C≤12)}$, aryl$_{(C≤12)}$, aralkyl$_{(C≤12)}$, or a substituted version of any of these groups;
R$_4$ is hydrogen, amino, cycloalkyl$_{(C≤18)}$, substituted cycloalkyl$_{(C≤18)}$, aryl$_{(C≤18)}$, substituted aryl$_{(C≤18)}$, aralkyl$_{(C≤18)}$, substituted aralkyl$_{(C≤18)}$, heteroaryl$_{(C≤18)}$, substituted heteroaryl$_{(C≤18)}$, heteroaralkyl$_{(C≤18)}$, substituted heteroaralkyl$_{(C≤18)}$, heterocycloalkyl$_{(C≤18)}$, substituted heterocycloalkyl$_{(C≤18)}$, amido$_{(C≤18)}$, substituted amido$_{(C≤18)}$, or —X$_1$—(CH$_2$)$_m$—R$_4$';

wherein:
X$_1$ is NR$_b$, O, or S; wherein:
R$_b$ is hydrogen, alkyl$_{(C≤6)}$, or substituted alkyl$_{(C≤6)}$;
m is 0, 1, 2, 3, or 4; and
R$_4$' is cycloalkyl$_{(C≤18)}$, aryl$_{(C≤18)}$, aralkyl$_{(C≤18)}$, heteroaryl$_{(C≤18)}$, heteroaralkyl$_{(C≤18)}$, heterocycloalkyl$_{(C≤18)}$, or a substituted version of any of these groups; or

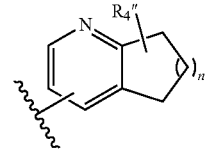

wherein:

n is 0, 1, 2, 3, or 4; and $R_4''$ is —H, —OH, —F, —Cl, —Br, —I, —NH$_2$, —NO$_2$, —CN, —SH, —S(O)$_2$OH, or —S(O)$_2$NH$_2$, or alkyl$_{(C \le 8)}$, cycloalkyl$_{(C \le 8)}$, aryl$_{(C \le 8)}$, heteroaryl$_{(C \le 8)}$, heterocycloalkyl$_{(C \le 8)}$, acyl$_{(C \le 8)}$, amido$_{(C \le 8)}$, alkoxy$_{(C \le 8)}$, acyloxy$_{(C \le 8)}$, alkylamino$_{(C \le 8)}$, dialkylamino$_{(C \le 8)}$, —C(O)-alkoxy$_{(C \le 8)}$, —C(O)-alkylamino$_{(C \le 8)}$, —C(O)-dialkylamino$_{(C \le 8)}$, alkylsulfonyl$_{(C \le 8)}$, arylsulfonyl$_{(C \le 8)}$, alkoxysulfonyl$_{(C \le 8)}$, or a substituted version of any of these groups; or —X$_2$—(CH$_2$)$_p$—R$_4'''$;

wherein:

X$_2$ is arenediyl$_{(C \le 12)}$, substituted arenediyl$_{(C \le 12)}$, heterocycloalkanediyl$_{(C \le 12)}$, substituted heterocycloalkanediyl$_{(C \le 12)}$, heteroarenediyl$_{(C \le 12)}$, or substituted heteroarenediyl$_{(C \le 12)}$;

p is 0, 1, 2, 3, or 4; and $R_4'''$ is alkyl$_{(C \le 8)}$, cycloalkyl$_{(C \le 8)}$, aryl$_{(C \le 8)}$, heteroaryl$_{(C \le 8)}$, heterocycloalkyl$_{(C \le 8)}$, acyl$_{(C \le 8)}$, amido$_{(C \le 8)}$, alkoxy$_{(C \le 8)}$, acyloxy$_{(C \le 8)}$, —C(O)-alkoxy$_{(C \le 8)}$, —C(O)-alkylamino$_{(C \le 8)}$, —C(O)-dialkyl-amino$_{(C \le 8)}$, alkylsulfonyl$_{(C \le 8)}$, arylsulfonyl$_{(C \le 8)}$, alkoxysulfonyl$_{(C \le 8)}$, or a substituted version of any of these groups; and R$_5$ is amino, hydroxy, —OS(O)$_2$C$_6$H$_4$CH$_3$, alkyl$_{(C \le 12)}$, alkoxy$_{(C \le 12)}$, cycloalkyl$_{(C \le 12)}$, cycloalkoxy$_{(C \le 12)}$, aryl$_{(C \le 12)}$, aralkyl$_{(C \le 12)}$, heteroaryl$_{(C \le 12)}$, heteroaralkyl$_{(C \le 12)}$, heterocycloalkyl$_{(C \le 12)}$, acyl$_{(C \le 12)}$, acyloxy$_{(C \le 12)}$, alkylamino$_{(C \le 12)}$, dialkylamino$_{(C \le 12)}$, alkylsulfonylamino$_{(C \le 12)}$, or a substituted version of any of the last fourteen groups, or

—OY$_1$—A$_1$;

wherein:

Y$_1$ is alkanediyl$_{(C \le 8)}$ or substituted alkanediyl$_{(C \le 8)}$; and

A$_1$ is cycloalkyl$_{(C \le 8)}$ or substituted cycloalkyl$_{(C \le 8)}$; or

—Y$_2$—C(O)NR$_c$—A$_2$;

wherein:

Y$_2$ is arenediyl$_{(C \le 8)}$ or substituted arenediyl$_{(C \le 8)}$;

R$_c$ is hydrogen, alkyl$_{(C \le 6)}$, or substituted alkyl$_{(C \le 6)}$; and

A$_2$ is aralkyl$_{(C \le 12)}$ or substituted aralkyl$_{(C \le 12)}$; or

—A$_3$R$_d$;

wherein:

A$_3$ is —O— or —NR$_c$—, wherein

R$_c$ is hydrogen, alkyl$_{(C \le 6)}$, or substituted alkyl$_{(C \le 6)}$; and

R$_d$ is acyl$_{(C \le 12)}$, or substituted acyl$_{(C \le 12)}$;

provided that when carbon atoms 4 and 5 are joined by a double bond, then R$_2'$ and the hydrogen atom at carbon atom 5 are absent;

or a pharmaceutically acceptable salt thereof.

In some embodiments, the compounds are further defined as:

(II)

wherein:

the bond between carbon atoms 1 and 2 is a single bond, an epoxidized double bond, or a double bond;

the bond between carbon atoms 4 and 5 is a single bond or a double bond;

R$_1$ is cyano, heteroaryl$_{(C \le 8)}$, substituted heteroaryl$_{(C \le 8)}$, —CF$_3$, or —C(O)R$_a$; wherein:

R$_a$ is hydroxy, amino, or alkoxy$_{(C \le 8)}$, alkylamino$_{(C \le 8)}$, dialkylamino$_{(C \le 8)}$, alkylsulfonylamino$_{(C \le 8)}$, or a substituted version of any of these groups;

R$_2$ is hydrogen or alkyl$_{(C \le 12)}$, cycloalkyl$_{(C \le 12)}$, alkenyl$_{(C \le 12)}$, alkynyl$_{(C \le 12)}$, aryl$_{(C \le 12)}$, aralkyl$_{(C \le 12)}$, heteroaryl$_{(C \le 12)}$, heteroaralkyl$_{(C \le 12)}$, acyl$_{(C \le 12)}$, or a substituted version of any of these groups, or -alkanediyl$_{(C \le 8)}$-cycloalkyl$_{(C \le 12)}$ or a substituted version of this group;

R$_2'$ is absent, hydrogen, alkyl$_{(C \le 12)}$, cycloalkyl$_{(C \le 12)}$, alkenyl$_{(C \le 12)}$, alkynyl$_{(C \le 12)}$, or a substituted version of the last four groups; provided that when the bond between carbon atoms 4 and 5 is a double bond then R$_2'$ is absent;

R$_3$ is alkyl$_{(C \le 12)}$, alkenyl$_{(C \le 12)}$, aryl$_{(C \le 12)}$, aralkyl$_{(C \le 12)}$, or a substituted version of any of these groups;

R$_4$ is hydrogen, amino, alkyl$_{(C2-18)}$, substituted alkyl$_{(C \le 18)}$, cycloalkyl$_{(C \le 18)}$, substituted cycloalkyl$_{(C \le 18)}$, aryl$_{(C \le 18)}$, substituted aryl$_{(C \le 18)}$, aralkyl$_{(C \le 18)}$, substituted aralkyl$_{(C \le 18)}$, heteroaryl$_{(C \le 18)}$, substituted heteroaryl$_{(C \le 18)}$, heteroaralkyl$_{(C \le 18)}$, substituted heteroaralkyl$_{(C \le 18)}$, heterocycloalkyl$_{(C \le 18)}$, substituted heterocycloalkyl$_{(C \le 18)}$, alkylamino$_{(C \le 18)}$, substituted alkylamino$_{(C \le 18)}$, dialkylamino$_{(C \le 18)}$, substituted dialkylamino$_{(C \le 18)}$, alkylthio$_{(C \le 18)}$, substituted alkylthio$_{(C \le 18)}$, amido$_{(C \le 18)}$, substituted amido$_{(C \le 18)}$, or —X$_1$—(CH$_2$)$_m$—R$_4'$;

wherein:

X$_1$ is NR$_b$, O, or S; wherein:

R$_b$ is hydrogen, alkyl$_{(C \le 6)}$, or substituted alkyl$_{(C \le 6)}$;

m is 0, 1, 2, 3, or 4; and

R$_4'$ is alkyl$_{(C \le 12)}$, cycloalkyl$_{(C \le 18)}$, aryl$_{(C \le 18)}$, aralkyl$_{(C \le 18)}$, heteroaryl$_{(C \le 18)}$, heteroaralkyl$_{(C \le 18)}$, heterocycloalkyl$_{(C \le 18)}$, or a substituted version of any of these groups, provided that when X$_1$ is O, then R$_4'$ is not methyl; or

;

wherein:

n is 0, 1, 2, 3, or 4; and $R_4''$ is —H, —OH, —F, —Cl, —Br, —I, —$NH_2$, —$NO_2$, —CN, —SH, —$S(O)_2OH$, or —$S(O)_2NH_2$, or $alkyl_{(C≤8)}$, $cycloalkyl_{(C≤8)}$, $aryl_{(C≤8)}$, $heteroaryl_{(C≤8)}$, $heterocycloalkyl_{(C≤8)}$, $acyl_{(C≤8)}$, $amido_{(C≤8)}$, $alkoxy_{(C≤8)}$, $acyloxy_{(C≤8)}$, $alkylamino_{(C≤8)}$, $dialkylamino_{(C≤8)}$, —$C(O)$-$alkoxy_{(C≤8)}$, —$C(O)$-$alkylamino_{(C≤8)}$, —$C(O)$-$dialkylamino_{(C≤8)}$, $alkylsulfonyl_{(C≤8)}$, $arylsulfonyl_{(C≤8)}$, $alkoxysulfonyl_{(C≤8)}$, or a substituted version of any of these groups; or —$X_2$—$(CH_2)_p$—$R_4'$;

wherein:

$X_2$ is $arenediyl_{(C≤12)}$, substituted $arenediyl_{(C≤12)}$, $heterocycloalkanediyl_{(C≤12)}$, substituted $heterocycloalkanediyl_{(C≤12)}$, $heteroarenediyl_{(C≤12)}$, or substituted $heteroarenediyl_{(C≤12)}$;

p is 0, 1, 2, 3, or 4; and $R_4'''$ is $alkyl_{(C≤8)}$, $cycloalkyl_{(C≤8)}$, $aryl_{(C≤8)}$, $heteroaryl_{(C≤8)}$, $heterocycloalkyl_{(C≤8)}$, $acyl_{(C≤8)}$, $amido_{(C≤8)}$, $alkoxy_{(C≤8)}$, $acyloxy_{(C≤8)}$, —$C(O)$-$alkoxy_{(C≤8)}$, —$C(O)$-$alkylamino_{(C≤8)}$, —$C(O)$-$dialkyl$-$amino_{(C≤8)}$, $alkylsulfonyl_{(C≤8)}$, $arylsulfonyl_{(C≤8)}$, $alkoxysulfonyl_{(C≤8)}$, or a substituted version of any of these groups; and $R_5$ is amino, hydroxy, —$OS(O)_2C_6H_4CH_3$, $alkyl_{(C≤12)}$, $alkoxy_{(C≤12)}$, $cycloalkyl_{(C≤12)}$, $cycloalkoxy_{(C≤12)}$, $aryl_{(C≤12)}$, $aralkyl_{(C≤12)}$, $heteroaryl_{(C≤12)}$, $heteroaralkyl_{(C≤12)}$, $heterocycloalkyl_{(C≤12)}$, $acyl_{(C≤12)}$, $acyloxy_{(C≤12)}$, $alkylamino_{(C≤12)}$, $dialkylamino_{(C≤12)}$, $alkylsulfonylamino_{(C≤12)}$, or a substituted version of any of the last fourteen groups, or

—$OY_1$—$A_1$;

wherein:

$Y_1$ is $alkanediyl_{(C≤8)}$ or substituted $alkanediyl_{(C≤8)}$; and $A_1$ is $cycloalkyl_{(C≤8)}$ or substituted $cycloalkyl_{(C≤8)}$; or —$Y_2$—$C(O)NR_c$—$A_2$;

wherein:

$Y_2$ is $arenediyl_{(C≤8)}$ or substituted $arenediyl_{(C≤8)}$;

$R_c$ is hydrogen, $alkyl_{(C≤6)}$, or substituted $alkyl_{(C≤6)}$; and $A_2$ is $aralkyl_{(C≤12)}$ or substituted $aralkyl_{(C≤12)}$; or —$A_3R_d$;

wherein:

$A_3$ is —O— or —$NR_c$—, wherein $R_c$ is hydrogen, $alkyl_{(C≤6)}$, or substituted $alkyl_{(C≤6)}$; and $R_d$ is $acyl_{(C≤12)}$, or substituted $acyl_{(C≤12)}$;

provided that when carbon atoms 4 and 5 are joined by a double bond, then $R_2'$ and the hydrogen atom at carbon atom 5 are absent;

or a pharmaceutically acceptable salt thereof.

In some embodiments, the compounds are further defined as:

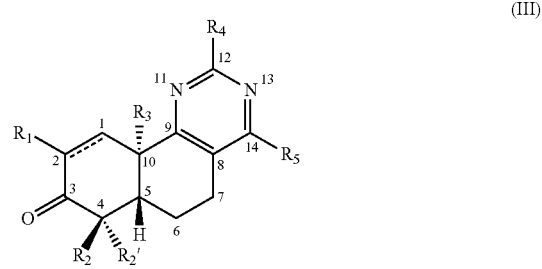

(III)

wherein:

the bond between carbon atoms 1 and 2 is a single bond, an epoxidized double bond, or a double bond;

$R_1$ is cyano, $heteroaryl_{(C≤8)}$, substituted $heteroaryl_{(C≤8)}$, —$CF_3$, or —$C(O)R_a$; wherein:

$R_a$ is hydroxy, amino, or $alkoxy_{(C≤8)}$, $alkylamino_{(C≤8)}$, $dialkylamino_{(C≤8)}$, $alkylsulfonylamino_{(C≤8)}$, or a substituted version of any of these groups;

$R_2$ is hydrogen or $alkyl_{(C≤12)}$, $cycloalkyl_{(C≤12)}$, $alkenyl_{(C≤12)}$, $alkynyl_{(C≤12)}$, $aryl_{(C≤12)}$, $aralkyl_{(C≤12)}$, $heteroaryl_{(C≤12)}$, $heteroaralkyl_{(C≤12)}$, $acyl_{(C≤12)}$, or a substituted version of any of these groups, or -$alkanediyl_{(C≤8)}$-$cycloalkyl_{(C≤12)}$ or a substituted version of this group;

$R_2'$ is hydrogen, $alkyl_{(C≤12)}$, $cycloalkyl_{(C≤12)}$, $alkenyl_{(C≤12)}$, $alkynyl_{(C≤12)}$, or a substituted version of the last four groups;

$R_3$ is $alkyl_{(C≤12)}$, $aryl_{(C≤12)}$, $aralkyl_{(C≤12)}$, or a substituted version of any of these groups; $R_4$ is hydrogen, amino, $alkyl_{(C2-18)}$, substituted $alkyl_{(C≤18)}$, $cycloalkyl_{(C≤18)}$, substituted $cycloalkyl_{(C≤18)}$, $aryl_{(C≤18)}$, substituted $aryl_{(C≤18)}$, $aralkyl_{(C≤18)}$, substituted $aralkyl_{(C≤18)}$, $heteroaryl_{(C≤18)}$, substituted $heteroaryl_{(C≤18)}$, $heteroaralkyl_{(C≤18)}$, substituted $heteroaralkyl_{(C≤18)}$, $heterocycloalkyl_{(C≤18)}$, substituted $heterocycloalkyl_{(C≤18)}$, $alkylamino_{(C≤18)}$, substituted $alkylamino_{(C≤18)}$, $dialkylamino_{(C≤18)}$, substituted $dialkylamino_{(C≤18)}$, $alkylthio_{(C≤18)}$, substituted $alkylthio_{(C≤18)}$, $amido_{(C≤18)}$, substituted $amido_{(C≤18)}$, or wherein:

$X_1$ is $NR_b$, O, or S; wherein:

$R_b$ is hydrogen, $alkyl_{(C≤6)}$, or substituted $alkyl_{(C≤6)}$;

m is 0, 1, 2, 3, or 4; and $R_4'$ is $alkyl_{(C≤12)}$, $cycloalkyl_{(C≤18)}$, $aryl_{(C≤18)}$, $aralkyl_{(C≤18)}$, $heteroaryl_{(C≤18)}$, $heteroaralkyl_{(C≤18)}$, $heterocycloalkyl_{(C≤18)}$, or a substituted version of any of these groups, provided that when $X_1$ is O, then $R_4'$ is not methyl; or

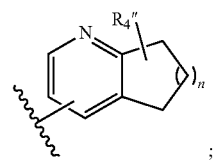

;

wherein:

n is 0, 1, 2, 3, or 4; and $R_4''$ is —H, —OH, —F, —Cl, —Br, —I, —$NH_2$, —$NO_2$, —CN, —SH, —$S(O)_2OH$, or —$S(O)_2NH_2$, or $alkyl_{(C≤8)}$, $cycloalkyl_{(C≤8)}$, $aryl_{(C≤8)}$, $heteroaryl_{(C≤8)}$, $heterocycloalkyl_{(C≤8)}$, $acyl_{(C≤8)}$, $amido_{(C≤8)}$, $alkoxy_{(C≤8)}$, $acyloxy_{(C≤8)}$, alkylamino$_{(C≤8)}$, dialkylamino$_{(C≤8)}$, —C(O)-alkoxy$_{(C≤8)}$, —C(O)-alkylamino$_{(C≤8)}$, —C(O)-dialkylamino$_{(C≤8)}$, alkylsulfonyl$_{(C≤8)}$, arylsulfonyl$_{(C≤8)}$, alkoxysulfonyl$_{(C≤8)}$, or a substituted version of any of these groups; or —X$_2$—(CH$_2$)$_p$—R$_4$''';

wherein:
  X$_2$ is arenediyl$_{(C≤12)}$, substituted arenediyl$_{(C≤12)}$, heterocycloalkanediyl$_{(C≤12)}$, substituted heterocycloalkanediyl$_{(C≤12)}$, heteroarenediyl$_{(C≤12)}$, or substituted heteroarenediyl$_{(C≤12)}$;
  p is 0, 1, 2, 3, or 4; and
  R$_4$''' is alkyl$_{(C≤8)}$, cycloalkyl$_{(C≤8)}$, aryl$_{(C≤8)}$, heteroaryl$_{(C≤8)}$, heterocycloalkyl$_{(C≤8)}$, acyl$_{(C≤8)}$, amido$_{(C≤8)}$, alkoxy$_{(C≤8)}$, acyloxy$_{(C≤8)}$, —C(O)-alkoxy$_{(C≤8)}$, —C(O)-alkylamino$_{(C≤8)}$, —C(O)-dialkyl-amino$_{(C≤8)}$, alkylsulfonyl$_{(C≤8)}$, arylsulfonyl$_{(C≤8)}$, alkoxysulfonyl$_{(C≤8)}$, or a substituted version of any of these groups; and R$_5$ is amino, hydroxy, —OS(O)$_2$C$_6$H$_4$CH$_3$, alkyl$_{(C≤12)}$, alkoxy$_{(C≤12)}$, cycloalkyl$_{(C≤12)}$, cycloalkoxy$_{(C≤12)}$, aryl$_{(C≤12)}$, aralkyl$_{(C≤12)}$, heteroaryl$_{(C≤12)}$, heteroaralkyl$_{(C≤12)}$, heterocycloalkyl$_{(C≤12)}$, acyl$_{(C≤12)}$, acyloxy$_{(C≤12)}$, alkylamino$_{(C≤12)}$, dialkylamino$_{(C≤12)}$, alkylsulfonylamino$_{(C≤12)}$, or a substituted version of any of the last fourteen groups, or

—OY$_1$—A$_1$;

wherein:
  Y$_1$ is alkanediyl$_{(C≤8)}$ or substituted alkanediyl$_{(C≤8)}$; and
  A$_1$ is cycloalkyl$_{(C≤8)}$ or substituted cycloalkyl$_{(C≤8)}$; or —Y$_2$—C(O)NR$_b$—A$_2$;

wherein:
  Y$_2$ is arenediyl$_{(C≤8)}$ or substituted arenediyl$_{(C≤8)}$;
  R$_b$ is hydrogen, alkyl$_{(C≤6)}$, or substituted alkyl$_{(C≤6)}$; and
  A$_2$ is aralkyl$_{(C≤12)}$ or substituted aralkyl$_{(C≤12)}$; or —A$_3$R$_d$;

wherein:
  A$_3$ is —O— or —NR$_c$—, wherein
    R$_c$ is hydrogen, alkyl$_{(C≤6)}$, or substituted alkyl$_{(C≤6)}$; and
  R$_d$ is acyl$_{(C≤12)}$, or substituted acyl$_{(C≤12)}$;

or a pharmaceutically acceptable salt thereof.

In other embodiments, the compounds are further defined as:

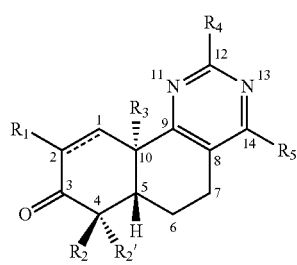

(III)

wherein:
  the bond between carbon atoms 1 and 2 is a single bond, an epoxidized double bond, or a double bond;
  R$_1$ is cyano, heteroaryl$_{(C≤8)}$, substituted heteroaryl$_{(C≤8)}$, —CF$_3$, or —C(O)R$_a$; wherein:

R$_a$ is hydroxy, amino, or alkoxy$_{(C≤8)}$, alkylamino$_{(C≤8)}$, dialkylamino$_{(C≤8)}$, alkylsulfonylamino$_{(C≤8)}$, or a substituted version of any of these groups;
  R$_2$ is hydrogen or alkyl$_{(C≤12)}$, cycloalkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heteroaralkyl$_{(C≤12)}$, acyl$_{(C≤12)}$, or a substituted version of any of these groups, or -alkanediyl$_{(C≤8)}$-cycloalkyl$_{(C≤12)}$ or a substituted version of this group;
  R$_2$' is hydrogen, alkyl$_{(C≤12)}$, cycloalkyl$_{(C≤12)}$, alkenyl$_{(C≤12)}$, alkynyl$_{(C≤12)}$, or a substituted version of the last four groups;
  R$_3$ is alkyl$_{(C≤12)}$, aryl$_{(C≤12)}$, aralkyl$_{(C≤12)}$, or a substituted version of any of these groups;
  R$_4$ is hydrogen, amino, cycloalkyl$_{(C≤18)}$, substituted cycloalkyl$_{(C≤18)}$, aryl$_{(C≤18)}$, substituted aryl$_{(C≤18)}$, aralkyl$_{(C≤18)}$, substituted aralkyl$_{(C≤18)}$, heteroaryl$_{(C≤18)}$, substituted heteroaryl$_{(C≤18)}$, heteroaralkyl$_{(C≤18)}$, substituted heteroaralkyl$_{(C≤18)}$, heterocycloalkyl$_{(C≤18)}$, substituted heterocycloalkyl$_{(C≤18)}$, alkylamino$_{(C≤18)}$, substituted alkylamino$_{(C≤18)}$, dialkylamino$_{(C≤18)}$, substituted dialkylamino$_{(C≤18)}$, alkylthio$_{(C≤18)}$, substituted alkylthio$_{(C≤18)}$, amido$_{(C≤18)}$, substituted amido$_{(C≤18)}$, or —X$_1$—(CH$_2$)$_m$—R$_4$';

wherein:
  X$_1$ is NR$_b$, O, or S; wherein:
    R$_b$ is hydrogen, alkyl$_{(C≤6)}$, or substituted alkyl$_{(C≤6)}$;
  m is 0, 1, 2, 3, or 4; and
  R$_4$' is cycloalkyl$_{(C≤18)}$, aryl$_{(C≤18)}$, aralkyl$_{(C≤18)}$, heteroaryl$_{(C≤18)}$, heteroaralkyl$_{(C≤18)}$, heterocycloalkyl$_{(C≤18)}$, or a substituted version of any of these groups, provided that when X$_1$ is O, then R$_4$' is not methyl; or

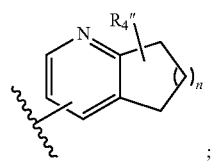

;

wherein:
  n is 0, 1, 2, 3, or 4; and
  R$_4$" is —H, —OH, —F, —Cl, —Br, —I, —NH$_2$, —NO$_2$, —CN, —SH, —S(O)$_2$OH, or —S(O)$_2$NH$_2$, or alkyl$_{(C≤8)}$, cycloalkyl$_{(C≤8)}$, aryl$_{(C≤8)}$, heteroaryl$_{(C≤8)}$, heterocycloalkyl$_{(C≤8)}$, acyl$_{(C≤8)}$, amido$_{(C≤8)}$, alkoxy$_{(C≤8)}$, acyloxy$_{(C≤8)}$, alkylamino$_{(C≤8)}$, dialkylamino$_{(C≤8)}$, —C(O)-alkoxy$_{(C≤8)}$, —C(O)-alkylamino$_{(C≤8)}$, —C(O)-dialkylamino$_{(C≤8)}$, alkylsulfonyl$_{(C≤8)}$, arylsulfonyl$_{(C≤8)}$, alkoxysulfonyl$_{(C≤8)}$, or a substituted version of any of these groups; or —X$_2$—(CH$_2$)$_p$—R$_4$''';

wherein:
  X$_2$ is arenediyl$_{(C≤12)}$, substituted arenediyl$_{(C≤12)}$, heterocycloalkanediyl$_{(C≤12)}$, substituted heterocycloalkanediyl$_{(C≤12)}$, heteroarenediyl$_{(C≤12)}$, or substituted heteroarenediyl$_{(C≤12)}$;
  p is 0, 1, 2, 3, or 4; and
  R$_4$''' is alkyl$_{(C≤8)}$, cycloalkyl$_{(C≤8)}$, aryl$_{(C≤8)}$, heteroaryl$_{(C≤8)}$, heterocycloalkyl$_{(C≤8)}$, acyl$_{(C≤8)}$, amido$_{(C≤8)}$, alkoxy$_{(C≤8)}$, acyloxy$_{(C≤8)}$, —C(O)- alkoxy$_{(C≤8)}$, —C(O)-alkylamino$_{(C≤8)}$, —C(O)-dialkyl-amino$_{(C≤8)}$, alkylsulfonyl$_{(C≤8)}$, arylsulfonyl$_{(C≤8)}$, alkoxysulfonyl$_{(C≤8)}$, or a substituted version of any of these groups; and $R_5$ is amino, hydroxy, —OS(O)$_2$C$_6$H$_4$CH$_3$, alkyl$_{(C≤12)}$, alkoxy$_{(C≤12)}$, cycloalkyl$_{(C≤12)}$, cycloalkoxy$_{(C≤12)}$, aryl$_{(C≤12)}$, aralkyl$_{(C≤12)}$, heteroaryl$_{(C≤12)}$, heteroaralkyl$_{(C≤12)}$, heterocycloalkyl$_{(C≤12)}$, acyl$_{(C≤12)}$, acyloxy$_{(C≤12)}$, alkylamino$_{(C≤12)}$, dialkylamino$_{(C≤12)}$, alkylsulfonylamino$_{(C≤12)}$, or a substituted version of any of the last fourteen groups, or

—OY$_1$—A$_1$;

wherein:
  Y$_1$ is alkanediyl$_{(C≤8)}$ or substituted alkanediyl$_{(C≤8)}$; and
  A$_1$ is cycloalkyl$_{(C≤8)}$ or substituted cycloalkyl$_{(C≤8)}$; or —Y$_2$—C(O)NR$_b$—A$_2$;

wherein:
  Y$_2$ is arenediyl$_{(C≤8)}$ or substituted arenediyl$_{(C≤8)}$;
  R$_b$ is hydrogen, alkyl$_{(C≤6)}$, or substituted alkyl$_{(C≤6)}$; and
  A$_2$ is aralkyl$_{(C≤12)}$ or substituted aralkyl$_{(C≤12)}$; or —A$_3$R$_d$;

wherein:
  A$_3$ is —O— or —NR$_c$—, wherein
    R$_c$ is hydrogen, alkyl$_{(C≤6)}$, or substituted alkyl$_{(C≤6)}$; and
  R$_d$ is acyl$_{(C≤12)}$, or substituted acyl$_{(C≤12)}$;
or a pharmaceutically acceptable salt thereof.

In some embodiments, the compounds are further defined as:

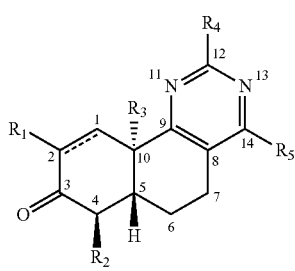
(IV)

wherein:
  the bond between carbon atoms 1 and 2 is a single bond, an epoxidized double bond, or a double bond;
  $R_1$ is cyano, heteroaryl$_{(C≤8)}$, substituted heteroaryl$_{(C≤8)}$, —CF$_3$, or —C(O)R$_a$; wherein:
    R$_a$ is hydroxy, amino, or alkoxy$_{(C≤8)}$, alkylamino$_{(C≤8)}$, dialkylamino$_{(C≤8)}$, alkylsulfonylamino$_{(C≤8)}$, or a substituted version of any of these groups;
  $R_2$ is hydrogen or alkyl$_{(C≤12)}$, cycloalkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heteroaralkyl$_{(C≤12)}$, acyl$_{(C≤12)}$, or a substituted version of any of these groups, or -alkanediyl$_{(C≤8)}$-cycloalkyl$_{(C≤12)}$ or a substituted version of this group;
  $R_3$ is alkyl$_{(C≤12)}$, aryl$_{(C≤12)}$, aralkyl$_{(C≤12)}$, or a substituted version of any of these groups;
  $R_4$ is hydrogen, amino, alkyl$_{(C2-18)}$, substituted alkyl$_{(C≤18)}$, cycloalkyl$_{(C≤18)}$, substituted cycloalkyl$_{(C≤18)}$, aryl$_{(C≤18)}$, substituted aryl$_{(C≤18)}$, aralkyl$_{(C≤18)}$, substituted aralkyl$_{(C≤18)}$, heteroaryl$_{(C≤18)}$, substituted heteroaryl$_{(C≤18)}$, heteroaralkyl$_{(C≤18)}$, substituted heteroaralkyl$_{(C≤18)}$, heterocycloalkyl$_{(C≤18)}$, substituted heterocycloalkyl$_{(C≤18)}$, alkylamino$_{(C≤18)}$, substituted alkylamino$_{(C≤18)}$, dialkylamino$_{(C≤18)}$, substituted dialkylamino$_{(C≤18)}$, alkylthio$_{(C≤18)}$, substituted alkylthio$_{(C≤18)}$, amido$_{(C≤18)}$, substituted amido$_{(C≤18)}$, or —X$_1$—(CH$_2$)$_m$—R$_4$';

wherein:
  X$_1$ is NR$_b$, O, or S; wherein:
    R$_b$ is hydrogen, alkyl$_{(C≤6)}$, or substituted alkyl$_{(C≤6)}$;
  m is 0, 1, 2, 3, or 4; and
  R$_4$' is alkyl$_{(C≤12)}$, cycloalkyl$_{(C≤18)}$, aryl$_{(C≤18)}$, aralkyl$_{(C≤18)}$, heteroaryl$_{(C≤18)}$, heteroaralkyl$_{(C≤18)}$, heterocycloalkyl$_{(C≤18)}$, or a substituted version of any of these groups, provided that when X$_1$ is O, then R$_4$' is not methyl; or

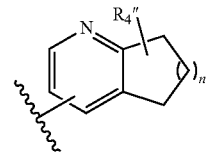
;

wherein:
  n is 0, 1, 2, 3, or 4; and
  R$_4$" is —H, —OH, —F, —Cl, —Br, —I, —NH$_2$, —NO$_2$, —CN, —SH, —S(O)$_2$OH, or —S(O)$_2$NH$_2$, or alkyl$_{(C≤8)}$, cycloalkyl$_{(C≤8)}$, aryl$_{(C≤8)}$, heteroaryl$_{(C≤8)}$, heterocycloalkyl$_{(C≤8)}$, acyl$_{(C≤8)}$, amido$_{(C≤8)}$, alkoxy$_{(C≤8)}$, acyloxy$_{(C≤8)}$, alkylamino$_{(C≤8)}$, dialkylamino$_{(C≤8)}$, —C(O)-alkoxy$_{(C≤8)}$, —C(O)-alkylamino$_{(C≤8)}$, —C(O)-dialkyl-amino$_{(C≤8)}$, alkylsulfonyl$_{(C≤8)}$, arylsulfonyl$_{(C≤8)}$, alkoxysulfonyl$_{(C≤8)}$, or a substituted version of any of these groups; or —X$_2$—(CH$_2$)$_p$—R$_4$'";

wherein:
  X$_2$ is arenediyl$_{(C≤12)}$, substituted arenediyl$_{(C≤12)}$, heterocycloalkanediyl$_{(C≤12)}$, substituted heterocycloalkanediyl$_{(C≤12)}$, heteroarenediyl$_{(C≤12)}$, or substituted heteroarenediyl$_{(C≤12)}$;
  p is 0, 1, 2, 3, or 4; and
  R$_4$'" is alkyl$_{(C≤8)}$, cycloalkyl$_{(C≤8)}$, aryl$_{(C≤8)}$, heteroaryl$_{(C≤8)}$, heterocycloalkyl$_{(C≤8)}$, acyl$_{(C≤8)}$, amido$_{(C≤8)}$, alkoxy$_{(C≤8)}$, acyloxy$_{(C≤8)}$, —C(O)-alkoxy$_{(C≤8)}$, —C(O)-alkylamino$_{(C≤8)}$, —C(O)-dialkyl-amino$_{(C≤8)}$, alkylsulfonyl$_{(C≤8)}$, arylsulfonyl$_{(C≤8)}$, alkoxysulfonyl$_{(C≤8)}$, or a substituted version of any of these groups; and $R_5$ is amino, hydroxy, —OS(O)$_2$C$_6$H$_4$CH$_3$, alkyl$_{(C≤12)}$, alkoxy$_{(C≤12)}$, cycloalkyl$_{(C≤12)}$, cycloalkoxy$_{(C≤12)}$, aryl$_{(C≤12)}$, aralkyl$_{(C≤12)}$, heteroaryl$_{(C≤12)}$, heteroaralkyl$_{(C≤12)}$, heterocycloalkyl$_{(C≤12)}$, acyl$_{(C≤12)}$, acyloxy$_{(C≤12)}$, alkylamino$_{(C≤12)}$, dialkylamino$_{(C≤12)}$, alkylsulfonylamino$_{(C≤12)}$, or a substituted version of any of the last fourteen groups, or

—OY$_1$—A$_1$;

wherein:
  Y$_1$ is alkanediyl$_{(C≤8)}$ or substituted alkanediyl$_{(C≤8)}$; and
  A$_1$ is cycloalkyl$_{(C≤8)}$ or substituted cycloalkyl$_{(C≤8)}$; or —Y$_2$—C(O)NR$_b$—A$_2$;

wherein:
- $Y_2$ is arenediyl$_{(C \leq 8)}$ or substituted arenediyl$_{(C \leq 8)}$;
- $R_b$ is hydrogen, alkyl$_{(C \leq 6)}$, or substituted alkyl$_{(C \leq 6)}$; and
- $A_2$ is aralkyl$_{(C \leq 12)}$ or substituted aralkyl$_{(C \leq 12)}$; or
  —$A_3R_d$;

wherein:
- $A_3$ is —O— or —NR$_c$—, wherein
  - $R_c$ is hydrogen, alkyl$_{(C \leq 6)}$, or substituted alkyl$_{(C \leq 6)}$; and
- $R_d$ is acyl$_{(C \leq 12)}$, or substituted acyl$_{(C \leq 12)}$;

or a pharmaceutically acceptable salt thereof.

In other embodiments, the compounds are further defined as:

(IV)

[Chemical structure]

wherein:
- the bond between carbon atoms 1 and 2 is a single bond, an epoxidized double bond, or a double bond;
- $R_1$ is cyano, heteroaryl$_{(C \leq 8)}$, substituted heteroaryl$_{(C \leq 8)}$, —CF$_3$, or —C(O)R$_a$; wherein:
  - $R_a$ is hydroxy, amino, or alkoxy$_{(C \leq 8)}$, alkylamino$_{(C \leq 8)}$, dialkylamino$_{(C \leq 8)}$, alkylsulfonylamino$_{(C \leq 8)}$, or a substituted version of any of these groups;
- $R_2$ is hydrogen or alkyl$_{(C \leq 12)}$, cycloalkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, acyl$_{(C \leq 12)}$, or a substituted version of any of these groups, or -alkanediyl$_{(C \leq 8)}$-cycloalkyl$_{(C \leq 12)}$ or a substituted version of this group;
- $R_3$ is alkyl$_{(C \leq 12)}$, aryl$_{(C \leq 12)}$, aralkyl$_{(C \leq 12)}$, or a substituted version of any of these groups;
- $R_4$ is hydrogen, amino, cycloalkyl$_{(C \leq 18)}$, substituted cycloalkyl$_{(C \leq 18)}$, aryl$_{(C \leq 18)}$, substituted aryl$_{(C \leq 18)}$, aralkyl$_{(C \leq 18)}$, substituted aralkyl$_{(C \leq 18)}$, heteroaryl$_{(C \leq 18)}$, substituted heteroaryl$_{(C \leq 18)}$, heteroaralkyl$_{(C \leq 18)}$, substituted heteroaralkyl$_{(C \leq 18)}$, heterocycloalkyl$_{(C \leq 18)}$, substituted heterocycloalkyl$_{(C \leq 18)}$, alkylamino$_{(C \leq 18)}$, substituted alkylamino$_{(C \leq 18)}$, dialkylamino$_{(C \leq 18)}$, substituted dialkylamino$_{(C \leq 18)}$, alkylthio$_{(C \leq 18)}$, substituted alkylthio$_{(C \leq 18)}$, amido$_{(C \leq 18)}$, substituted amido$_{(C \leq 18)}$, or —$X_1$—(CH$_2$)$_m$—$R_4'$;

wherein:
- $X_1$ is NR$_b$, O, or S; wherein:
  - $R_b$ is hydrogen, alkyl$_{(C \leq 6)}$, or substituted alkyl$_{(C \leq 6)}$;
- m is 0, 1, 2, 3, or 4; and
- $R_4'$ is cycloalkyl$_{(C \leq 18)}$, aryl$_{(C \leq 18)}$, aralkyl$_{(C \leq 18)}$, heteroaryl$_{(C \leq 18)}$, heteroaralkyl$_{(C \leq 18)}$, heterocycloalkyl$_{(C \leq 18)}$, or a substituted version of any of these groups, provided that when $X_1$ is O, then $R_4'$ is not methyl; or

[Chemical structure]

wherein:
- n is 0, 1, 2, 3, or 4; and
- $R_4''$ is —H, —OH, —F, —Cl, —Br, —I, —NH$_2$, —NO$_2$, —CN, —SH, —S(O)$_2$OH, or —S(O)$_2$NH$_2$, or alkyl$_{(C \leq 8)}$, cycloalkyl$_{(C \leq 8)}$, aryl$_{(C \leq 8)}$, heteroaryl$_{(C \leq 8)}$, heterocycloalkyl$_{(C \leq 8)}$, acyl$_{(C \leq 8)}$, amido$_{(C \leq 8)}$, alkoxy$_{(C \leq 8)}$, acyloxy$_{(C \leq 8)}$, alkylamino$_{(C \leq 8)}$, dialkylamino$_{(C \leq 8)}$, —C(O)-alkoxy$_{(C \leq 8)}$, —C(O)-alkylamino$_{(C \leq 8)}$, —C(O)-dialkylamino$_{(C \leq 8)}$, alkylsulfonyl$_{(C \leq 8)}$, arylsulfonyl$_{(C \leq 8)}$, alkoxysulfonyl$_{(C \leq 8)}$, or a substituted version of any of these groups; or —$X_2$—(CH$_2$)$_p$—$R_4'''$;

wherein:
- $X_2$ is arenediyl$_{(C \leq 12)}$, substituted arenediyl$_{(C \leq 12)}$, heterocycloalkanediyl$_{(C \leq 12)}$, substituted heterocycloalkanediyl$_{(C \leq 12)}$, heteroarenediyl$_{(C \leq 12)}$, or substituted heteroarenediyl$_{(C \leq 12)}$;
- p is 0, 1, 2, 3, or 4; and
- $R_4'''$ is alkyl$_{(C \leq 8)}$, cycloalkyl$_{(C \leq 8)}$, aryl$_{(C \leq 8)}$, heteroaryl$_{(C \leq 8)}$, heterocycloalkyl$_{(C \leq 8)}$, acyl$_{(C \leq 8)}$, amido$_{(C \leq 8)}$, alkoxy$_{(C \leq 8)}$, acyloxy$_{(C \leq 8)}$, —C(O)-alkoxy$_{(C \leq 8)}$, —C(O)-alkylamino$_{(C \leq 8)}$, —C(O)-dialkyl-amino$_{(C \leq 8)}$, alkylsulfonyl$_{(C \leq 8)}$, arylsulfonyl$_{(C \leq 8)}$, alkoxysulfonyl$_{(C \leq 8)}$, or a substituted version of any of these groups; and
- $R_5$ is amino, hydroxy, —OS(O)$_2$C$_6$H$_4$CH$_3$, alkyl$_{(C \leq 12)}$, alkoxy$_{(C \leq 12)}$, cycloalkyl$_{(C \leq 12)}$, cycloalkoxy$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, heterocycloalkyl$_{(C \leq 12)}$, acyl$_{(C \leq 12)}$, acyloxy$_{(C \leq 12)}$, alkylamino$_{(C \leq 12)}$, dialkylamino$_{(C \leq 12)}$, alkylsulfonylamino$_{(C \leq 12)}$, or a substituted version of any of the last fourteen groups, or

—OY$_1$—A$_1$;

wherein:
- $Y_1$ is alkanediyl$_{(C \leq 8)}$ or substituted alkanediyl$_{(C \leq 8)}$; and
- $A_1$ is cycloalkyl$_{(C \leq 8)}$ or substituted cycloalkyl$_{(C \leq 8)}$; or —Y$_2$—C(O)NR$_b$—A$_2$;

wherein:
- $Y_2$ is arenediyl$_{(C \leq 8)}$ or substituted arenediyl$_{(C \leq 8)}$;
- $R_b$ is hydrogen, alkyl$_{(C \leq 6)}$, or substituted alkyl$_{(C \leq 6)}$; and
- $A_2$ is aralkyl$_{(C \leq 12)}$ or substituted aralkyl$_{(C \leq 12)}$; or —A$_3$R$_d$;

wherein:
- $A_3$ is —O— or —NR$_c$—, wherein
  - $R_c$ is hydrogen, alkyl$_{(C \leq 6)}$, or substituted alkyl$_{(C \leq 6)}$; and
- $R_d$ is acyl$_{(C \leq 12)}$, or substituted acyl$_{(C \leq 12)}$;

or a pharmaceutically acceptable salt thereof.

In some embodiments, the compounds are further defined as:

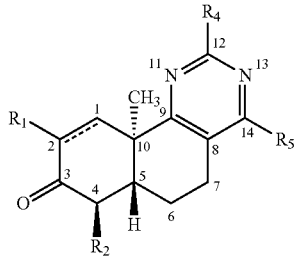

(V)

wherein:
the bond between carbon atoms 1 and 2 is a single bond, an epoxidized double bond, or a double bond;
$R_1$ is cyano, heteroaryl$_{(C≤8)}$, substituted heteroaryl$_{(C≤8)}$, —CF$_3$, or —C(O)R$_a$; wherein:
  $R_a$ is hydroxy, amino, or alkoxy$_{(C≤8)}$, alkylamino$_{(C≤8)}$, dialkylamino$_{(C≤8)}$, alkylsulfonylamino$_{(C≤8)}$, or a substituted version of any of these groups;
$R_2$ is hydrogen or alkyl$_{(C≤12)}$, cycloalkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heteroaralkyl$_{(C≤12)}$, acyl$_{(C≤12)}$, or a substituted version of any of these groups, or -alkanediyl$_{(C≤8)}$-cycloalkyl$_{(C≤12)}$ or a substituted version of this group;
$R_4$ is hydrogen, amino, alkyl$_{(C2-18)}$, substituted alkyl$_{(C≤18)}$, cycloalkyl$_{(C≤18)}$, substituted cycloalkyl$_{(C≤18)}$, aryl$_{(C≤18)}$, substituted aryl$_{(C≤18)}$, aralkyl$_{(C≤18)}$, substituted aralkyl$_{(C≤18)}$, heteroaryl$_{(C≤18)}$, substituted heteroaryl$_{(C≤18)}$, heteroaralkyl$_{(C≤18)}$, substituted heteroaralkyl$_{(C≤18)}$, heterocycloalkyl$_{(C≤18)}$, substituted heterocycloalkyl$_{(C≤18)}$, alkylamino$_{(C≤18)}$, substituted alkylamino$_{(C≤18)}$, dialkylamino$_{(C≤18)}$, substituted dialkylamino$_{(C≤18)}$, alkylthio$_{(C≤18)}$, substituted alkylthio$_{(C≤18)}$, amido$_{(C≤18)}$, substituted amido$_{(C≤18)}$, or —X$_1$—(CH$_2$)$_m$—R$_4$';

wherein:
$X_1$ is NR$_b$, O, or S; wherein:
  $R_b$ is hydrogen, alkyl$_{(C≤6)}$, or substituted alkyl$_{(C≤6)}$;
m is 0, 1, 2, 3, or 4; and
$R_4$' is alkyl$_{(C≤12)}$, cycloalkyl$_{(C≤18)}$, aryl$_{(C≤18)}$, aralkyl$_{(C≤18)}$, heteroaryl$_{(C≤18)}$, heteroaralkyl$_{(C≤18)}$, heterocycloalkyl$_{(C≤18)}$, or a substituted version of any of these groups, provided that when $X_1$ is O, then $R_4$' is not methyl; or

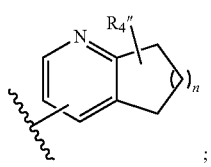

;

wherein:
n is 0, 1, 2, 3, or 4; and
$R_4$" is —H, —OH, —F, —Cl, —Br, —I, —NH$_2$, —NO$_2$, —CN, —SH, —S(O)$_2$OH, or —S(O)$_2$NH$_2$, or alkyl$_{(C≤8)}$, cycloalkyl$_{(C≤8)}$, aryl$_{(C≤8)}$, heteroaryl$_{(C≤8)}$, heterocycloalkyl$_{(C≤8)}$, acyl$_{(C≤8)}$, amido$_{(C≤8)}$, alkoxy$_{(C≤8)}$, acyloxy$_{(C≤8)}$, alkylamino$_{(C≤8)}$, dialkylamino$_{(C≤8)}$, —C(O)-alkoxy$_{(C≤8)}$, —C(O)-alkylamino$_{(C≤8)}$, —C(O)-dialkylamino$_{(C≤8)}$, alkylsulfonyl$_{(C≤8)}$, arylsulfonyl$_{(C≤8)}$, alkoxysulfonyl$_{(C≤8)}$, or a substituted version of any of these groups; or —X$_2$—(CH$_2$)$_p$—R$_4$'";

wherein:
$X_2$ is arenediyl$_{(C≤12)}$, substituted arenediyl$_{(C≤12)}$, heterocycloalkanediyl$_{(C≤12)}$, substituted heterocycloalkanediyl$_{(C≤12)}$, heteroarenediyl$_{(C≤12)}$, or substituted heteroarenediyl$_{(C≤12)}$;
p is 0, 1, 2, 3, or 4; and
$R_4$'" is alkyl$_{(C≤8)}$, cycloalkyl$_{(C≤8)}$, aryl$_{(C≤8)}$, heteroaryl$_{(C≤8)}$, heterocycloalkyl$_{(C≤8)}$, acyl$_{(C≤8)}$, amido$_{(C≤8)}$, alkoxy$_{(C≤8)}$, acyloxy$_{(C≤8)}$, —C(O)-alkoxy$_{(C≤8)}$, —C(O)-alkylamino$_{(C≤8)}$, —C(O)-dialkyl-amino$_{(C≤8)}$, alkylsulfonyl$_{(C≤8)}$, arylsulfonyl$_{(C≤8)}$, alkoxysulfonyl$_{(C≤8)}$, or a substituted version of any of these groups; and
$R_5$ is amino, hydroxy, —OS(O)$_2$C$_6$H$_4$CH$_3$, alkyl$_{(C≤12)}$, alkoxy$_{(C≤12)}$, cycloalkyl$_{(C≤12)}$, cycloalkoxy$_{(C≤12)}$, aryl$_{(C≤12)}$, aralkyl$_{(C≤12)}$, heteroaryl$_{(C≤12)}$, heteroaralkyl$_{(C≤12)}$, heterocycloalkyl$_{(C≤12)}$, acyl$_{(C≤12)}$, acyloxy$_{(C≤12)}$, alkylamino$_{(C≤12)}$, dialkylamino$_{(C≤12)}$, alkylsulfonylamino$_{(C≤12)}$, or a substituted version of any of the last fourteen groups, or

—OY$_1$—A$_1$;

wherein:
$Y_1$ is alkanediyl$_{(C≤8)}$ or substituted alkanediyl$_{(C≤8)}$; and
$A_1$ is cycloalkyl$_{(C≤8)}$ or substituted cycloalkyl$_{(C≤8)}$; or —Y$_2$—C(O)NR$_b$—A$_2$;

wherein:
$Y_2$ is arenediyl$_{(C≤8)}$ or substituted arenediyl$_{(C≤8)}$;
$R_b$ is hydrogen, alkyl$_{(C≤6)}$, or substituted alkyl$_{(C≤6)}$; and
$A_2$ is aralkyl$_{(C≤12)}$ or substituted aralkyl$_{(C≤12)}$; or —A$_3$R$_d$;

wherein:
$A_3$ is —O— or —NR$_c$—, wherein
  $R_c$ is hydrogen, alkyl$_{(C≤6)}$, or substituted alkyl$_{(C≤6)}$; and
$R_d$ is acyl$_{(C≤12)}$, or substituted acyl$_{(C≤12)}$;
or a pharmaceutically acceptable salt thereof.

In other embodiments, the compounds are further defined as:

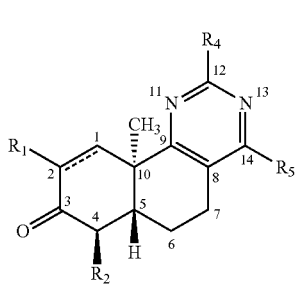

(V)

wherein:
the bond between carbon atoms 1 and 2 is a single bond, an epoxidized double bond, or a double bond;
$R_1$ is cyano, heteroaryl$_{(C≤8)}$, substituted heteroaryl$_{(C≤8)}$, —CF$_3$, or —C(O)R$_a$; wherein:

R$_a$ is hydroxy, amino, or alkoxy$_{(C\leq 8)}$, alkylamino$_{(C\leq 8)}$, dialkylamino$_{(C\leq 8)}$, alkylsulfonylamino$_{(C\leq 8)}$, or a substituted version of any of these groups;

R$_2$ is hydrogen or alkyl$_{(C\leq 12)}$, cycloalkyl$_{(C\leq 12)}$, alkenyl$_{(C\leq 12)}$, alkynyl$_{(C\leq 12)}$, aryl$_{(C\leq 12)}$, aralkyl$_{(C\leq 12)}$, heteroaryl$_{(C\leq 12)}$, heteroaralkyl$_{(C\leq 12)}$, acyl$_{(C\leq 12)}$, or a substituted version of any of these groups, or -alkanediyl$_{(C\leq 8)}$-cycloalkyl$_{(C\leq 12)}$ or a substituted version of this group;

R$_4$ is hydrogen, amino, cycloalkyl$_{(C\leq 18)}$, substituted cycloalkyl$_{(C\leq 18)}$, aryl$_{(C\leq 18)}$, substituted aryl$_{(C\leq 18)}$, aralkyl$_{(C\leq 18)}$, substituted aralkyl$_{(C\leq 18)}$, heteroaryl$_{(C\leq 18)}$, substituted heteroaryl$_{(C\leq 18)}$, heteroaralkyl$_{(C\leq 18)}$, substituted heteroaralkyl$_{(C\leq 18)}$, heterocycloalkyl$_{(C\leq 18)}$, substituted heterocycloalkyl$_{(C\leq 18)}$, alkylamino$_{(C\leq 18)}$, substituted alkylamino$_{(C\leq 18)}$, dialkylamino$_{(C\leq 18)}$, substituted dialkylamino$_{(C\leq 18)}$, alkylthio$_{(C\leq 18)}$, substituted alkylthio$_{(C\leq 18)}$, amido$_{(C\leq 18)}$, substituted amido$_{(C\leq 18)}$, or —X$_1$—(CH$_2$)$_m$—R$_4$';

wherein:
X$_1$ is NR$_b$, O, or S; wherein:
R$_b$ is hydrogen, alkyl$_{(C\leq 6)}$, or substituted alkyl$_{(C\leq 6)}$; m is 0, 1, 2, 3, or 4; and
R$_4$' is cycloalkyl$_{(C\leq 18)}$, aryl$_{(C\leq 18)}$, aralkyl$_{(C\leq 18)}$, heteroaryl$_{(C\leq 18)}$, heteroaralkyl$_{(C\leq 18)}$, heterocycloalkyl$_{(C\leq 18)}$, or a substituted version of any of these groups, provided that when X$_1$ is O, then R$_4$' is not methyl; or

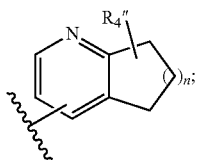

wherein:
n is 0, 1, 2, 3, or 4; and
R$_4$" is —H, —OH, —F, —Cl, —Br, —I, —NH$_2$, —NO$_2$, —CN, —SH, —S(O)$_2$OH, or —S(O)$_2$NH$_2$, or alkyl$_{(C\leq 8)}$, cycloalkyl$_{(C\leq 8)}$, aryl$_{(C\leq 8)}$, heteroaryl$_{(C\leq 8)}$, heterocycloalkyl$_{(C\leq 8)}$, acyl$_{(C\leq 8)}$, amido$_{(C\leq 8)}$, alkoxy$_{(C\leq 8)}$, acyloxy$_{(C\leq 8)}$, alkylamino$_{(C\leq 8)}$, dialkylamino$_{(C\leq 8)}$, —C(O)-alkoxy$_{(C\leq 8)}$, —C(O)-alkylamino$_{(C\leq 8)}$, —C(O)-dialkylamino$_{(C\leq 8)}$, alkylsulfonyl$_{(C\leq 8)}$, arylsulfonyl$_{(C\leq 8)}$, alkoxysulfonyl$_{(C\leq 8)}$, or a substituted version of any of these groups; or —X$_2$—(CH$_2$)$_p$—R$_4$''';

wherein:
X$_2$ is arenediyl$_{(C\leq 12)}$, substituted arenediyl$_{(C\leq 12)}$, heterocycloalkanediyl$_{(C\leq 12)}$, substituted heterocycloalkanediyl$_{(C\leq 12)}$, heteroarenediyl$_{(C\leq 12)}$, or substituted heteroarenediyl$_{(C\leq 12)}$;
p is 0, 1, 2, 3, or 4; and
R$_4$''' is alkyl$_{(C\leq 8)}$, cycloalkyl$_{(C\leq 8)}$, aryl$_{(C\leq 8)}$, heteroaryl$_{(C\leq 8)}$, heterocycloalkyl$_{(C\leq 8)}$, acyl$_{(C\leq 8)}$, amido$_{(C\leq 8)}$, alkoxy$_{(C\leq 8)}$, acyloxy$_{(C\leq 8)}$, —C(O)-alkoxy$_{(C\leq 8)}$, —C(O)-alkylamino$_{(C\leq 8)}$, —C(O)-dialkyl-amino$_{(C\leq 8)}$, alkylsulfonyl$_{(C\leq 8)}$, arylsulfonyl$_{(C\leq 8)}$, alkoxysulfonyl$_{(C\leq 8)}$, or a substituted version of any of these groups; and R$_5$ is amino, hydroxy, —OS(O)$_2$C$_6$H$_4$CH$_3$, alkyl$_{(C\leq 12)}$, alkoxy$_{(C\leq 12)}$, cycloalkyl$_{(C\leq 12)}$, cycloalkoxy$_{(C\leq 12)}$, aryl$_{(C\leq 12)}$, aralkyl$_{(C\leq 12)}$, heteroaryl$_{(C\leq 12)}$, heterocycloalkyl$_{(C\leq 12)}$, acyl$_{(C\leq 12)}$, acyloxy$_{(C\leq 12)}$, alkylamino$_{(C\leq 12)}$, dialkylamino$_{(C\leq 12)}$, alkylsulfonylamino$_{(C\leq 12)}$, or a substituted version of any of the last fourteen groups, or

—OY$_1$—A$_1$;

wherein:
Y$_1$ is alkanediyl$_{(C\leq 8)}$ or substituted alkanediyl$_{(C\leq 8)}$; and
A$_1$ is cycloalkyl$_{(C\leq 8)}$ or substituted cycloalkyl$_{(C\leq 8)}$; or —Y$_2$—C(O)NR$_b$—A$_2$;

wherein:
Y$_2$ is arenediyl$_{(C\leq 8)}$ or substituted arenediyl$_{(C\leq 8)}$;
R$_b$ is hydrogen, alkyl$_{(C\leq 6)}$, or substituted alkyl$_{(C\leq 6)}$; and
A$_2$ is aralkyl$_{(C\leq 12)}$ or substituted aralkyl$_{(C\leq 12)}$; or —A$_3$R$_d$;

wherein:
A$_3$ is —O— or —NR$_c$—, wherein
R$_c$ is hydrogen, alkyl$_{(C\leq 6)}$, or substituted alkyl$_{(C\leq 6)}$; and
R$_d$ is acyl$_{(C\leq 12)}$, or substituted acyl$_{(C\leq 12)}$;

or a pharmaceutically acceptable salt thereof.

In some embodiments, the compounds are further defined as:

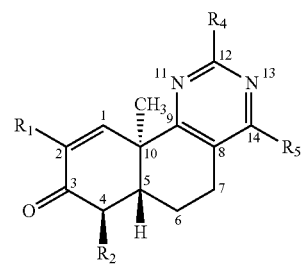

(VI)

wherein:
R$_1$ is cyano, heteroaryl$_{(C\leq 8)}$, substituted heteroaryl$_{(C\leq 8)}$, —CF$_3$, or —C(O)R$_a$; wherein:
R$_a$ is hydroxy, amino, or alkoxy$_{(C\leq 8)}$, alkylamino$_{(C\leq 8)}$, dialkylamino$_{(C\leq 8)}$, alkylsulfonylamino$_{(C\leq 8)}$, or a substituted version of any of these groups;

R$_2$ is hydrogen or alkyl$_{(C\leq 12)}$, cycloalkyl$_{(C\leq 12)}$, alkenyl$_{(C\leq 12)}$, alkynyl$_{(C\leq 12)}$, aryl$_{(C\leq 12)}$, aralkyl$_{(C\leq 12)}$, heteroaryl$_{(C\leq 12)}$, heteroaralkyl$_{(C\leq 12)}$, acyl$_{(C\leq 12)}$, or a substituted version of any of these groups, or -alkanediyl$_{(C\leq 8)}$-cycloalkyl$_{(C\leq 12)}$ or a substituted version of this group;

R$_4$ is hydrogen, amino, alkyl$_{(C2-18)}$, substituted alkyl$_{(C\leq 18)}$, cycloalkyl$_{(C\leq 18)}$, substituted cycloalkyl$_{(C\leq 18)}$, aryl$_{(C\leq 18)}$, substituted aryl$_{(C\leq 18)}$, aralkyl$_{(C\leq 18)}$, substituted aralkyl$_{(C\leq 18)}$, heteroaryl$_{(C\leq 18)}$, substituted heteroaryl$_{(C\leq 18)}$, heteroaralkyl$_{(C\leq 18)}$, substituted heteroaralkyl$_{(C\leq 18)}$, heterocycloalkyl$_{(C\leq 18)}$, substituted heterocycloalkyl$_{(C\leq 18)}$, alkylamino$_{(C\leq 18)}$, substituted alkylamino$_{(C\leq 18)}$, dialkylamino$_{(C\leq 18)}$, substituted dialkylamino$_{(C\leq 18)}$, alkylthio$_{(C\leq 18)}$, substituted alkylthio$_{(C\leq 18)}$, amido$_{(C\leq 18)}$, substituted amido$_{(C\leq 18)}$, or —X$_1$—(CH$_2$)$_m$—R$_4$';

wherein:
X$_1$ is NR$_b$, O, or S; wherein:
R$_b$ is hydrogen, alkyl$_{(C\leq 6)}$, or substituted alkyl$_{(C\leq 6)}$; m is 0, 1, 2, 3, or 4; and $R_4'$ is alkyl$_{(C≤12)}$, cycloalkyl$_{(C≤18)}$, aryl$_{(C≤18)}$, aralkyl$_{(C≤18)}$, heteroaryl$_{(C≤18)}$, heteroaralkyl$_{(C≤18)}$, heterocycloalkyl$_{(C≤18)}$, or a substituted version of any of these groups, provided that when $X_1$ is O, then $R_4'$ is not methyl; or

[Structure: bicyclic pyridine-cyclopentane with $R_4''$ substituent and $(\text{})_n$ ring size indicator]

wherein:
n is 0, 1, 2, 3, or 4; and
$R_4''$ is —H, —OH, —F, —Cl, —Br, —I, —NH$_2$, —NO$_2$, —CN, —SH, —S(O)$_2$OH, or —S(O)$_2$NH$_2$, or alkyl$_{(C≤8)}$, cycloalkyl$_{(C≤8)}$, aryl$_{(C≤8)}$, heteroaryl$_{(C≤8)}$, heterocycloalkyl$_{(C≤8)}$, acyl$_{(C≤8)}$, amido$_{(C≤8)}$, alkoxy$_{(C≤8)}$, acyloxy$_{(C≤8)}$, alkylamino$_{(C≤8)}$, dialkylamino$_{(C≤8)}$, —C(O)-alkoxy$_{(C≤8)}$, —C(O)-alkylamino$_{(C≤8)}$, —C(O)-dialkylamino$_{(C≤8)}$, alkylsulfonyl$_{(C≤8)}$, arylsulfonyl$_{(C≤8)}$, alkoxysulfonyl$_{(C≤8)}$, or a substituted version of any of these groups; or —X$_2$—(CH$_2$)$_p$—R$_4'''$;

wherein:
X$_2$ is arenediyl$_{(C≤12)}$, substituted arenediyl$_{(C≤12)}$, heterocycloalkanediyl$_{(C≤12)}$, substituted heterocycloalkanediyl$_{(C≤12)}$, heteroarenediyl$_{(C≤12)}$, or substituted heteroarenediyl$_{(C≤12)}$;
p is 0, 1, 2, 3, or 4; and
$R_4'''$ is alkyl$_{(C≤8)}$, cycloalkyl$_{(C≤8)}$, aryl$_{(C≤8)}$, heteroaryl$_{(C≤8)}$, heterocycloalkyl$_{(C≤8)}$, acyl$_{(C≤8)}$, amido$_{(C≤8)}$, alkoxy$_{(C≤8)}$, acyloxy$_{(C≤8)}$, —C(O)-alkoxy$_{(C≤8)}$, —C(O)-alkylamino$_{(C≤8)}$, —C(O)-dialkyl-amino$_{(C≤8)}$, alkylsulfonyl$_{(C≤8)}$, arylsulfonyl$_{(C≤8)}$, alkoxysulfonyl$_{(C≤8)}$, or a substituted version of any of these groups; and
$R_5$ is amino, hydroxy, —OS(O)$_2$C$_6$H$_4$CH$_3$, alkyl$_{(C≤12)}$, alkoxy$_{(C≤12)}$, cycloalkyl$_{(C≤12)}$, cycloalkoxy$_{(C≤12)}$, aryl$_{(C≤12)}$, aralkyl$_{(C≤12)}$, heteroaryl$_{(C≤12)}$, heterocycloalkyl$_{(C≤12)}$, acyl$_{(C≤12)}$, acyloxy$_{(C≤12)}$, alkylamino$_{(C≤12)}$, dialkylamino$_{(C≤12)}$, alkylsulfonylamino$_{(C≤12)}$, or a substituted version of any of the last fourteen groups, or

—OY$_1$—A$_1$;

wherein:
Y$_1$ is alkanediyl$_{(C≤8)}$ or substituted alkanediyl$_{(C≤8)}$; and
A$_1$ is cycloalkyl$_{(C≤8)}$ or substituted cycloalkyl$_{(C≤8)}$; or —Y$_2$—C(O)NR$_b$—A$_2$;

wherein:
Y$_2$ is arenediyl$_{(C≤8)}$ or substituted arenediyl$_{(C≤8)}$;
R$_b$ is hydrogen, alkyl$_{(C≤6)}$, or substituted alkyl$_{(C≤6)}$; and
A$_2$ is aralkyl$_{(C≤12)}$ or substituted aralkyl$_{(C≤12)}$; or —A$_3$R$_d$;

wherein:
A$_3$ is —O— or —NR$_c$—, wherein
R$_c$ is hydrogen, alkyl$_{(C≤6)}$, or substituted alkyl$_{(C≤6)}$; and
R$_d$ is acyl$_{(C≤12)}$, or substituted acyl$_{(C≤12)}$;
or a pharmaceutically acceptable salt thereof.

In other embodiments, the compounds are further defined as:

[Structure (VI): tetracyclic compound with positions labeled 1-14, substituents $R_1$, $R_2$, $R_4$, $R_5$, CH$_3$ at position 9, O at position 3, H at position 6]

(VI)

wherein:
$R_1$ is cyano, heteroaryl$_{(C≤8)}$, substituted heteroaryl$_{(C≤8)}$, —CF$_3$, or —C(O)R$_a$; wherein:
R$_a$ is hydroxy, amino, or alkoxy$_{(C≤8)}$, alkylamino$_{(C≤8)}$, dialkylamino$_{(C≤8)}$, alkylsulfonylamino$_{(C≤8)}$, or a substituted version of any of these groups;
$R_2$ is hydrogen or alkyl$_{(C≤12)}$, cycloalkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heteroaralkyl$_{(C≤12)}$, acyl$_{(C≤12)}$, or a substituted version of any of these groups, or -alkanediyl$_{(C≤8)}$-cycloalkyl$_{(C≤12)}$ or a substituted version of this group;
$R_4$ is hydrogen, amino, cycloalkyl$_{(C≤18)}$, substituted cycloalkyl$_{(C≤18)}$, aryl$_{(C≤18)}$, substituted aryl$_{(C≤18)}$, aralkyl$_{(C≤18)}$, substituted aralkyl$_{(C≤18)}$, heteroaryl$_{(C≤18)}$, substituted heteroaryl$_{(C≤18)}$, heteroaralkyl$_{(C≤18)}$, substituted heteroaralkyl$_{(C≤18)}$, heterocycloalkyl$_{(C≤18)}$, substituted heterocycloalkyl$_{(C≤18)}$, alkylamino$_{(C≤18)}$, substituted alkylamino$_{(C≤18)}$, dialkylamino$_{(C≤18)}$, substituted dialkylamino$_{(C≤18)}$, alkylthio$_{(C≤18)}$, substituted alkylthio$_{(C≤18)}$, amido$_{(C≤18)}$, substituted amido$_{(C≤18)}$, or —X$_1$—(CH$_2$)$_m$—R$_4'$;

wherein:
X$_1$ is NR$_b$, O, or S; wherein:
R$_b$ is hydrogen, alkyl$_{(C≤6)}$, or substituted alkyl$_{(C≤6)}$;
m is 0, 1, 2, 3, or 4; and
$R_4'$ is cycloalkyl$_{(C≤18)}$, aryl$_{(C≤18)}$, aralkyl$_{(C≤18)}$, heteroaryl$_{(C≤18)}$, heteroaralkyl$_{(C≤18)}$, heterocycloalkyl$_{(C≤18)}$, or a substituted version of any of these groups; or

[Structure: bicyclic pyridine-cyclopentane with $R_4''$ substituent and $(\text{})_n$]

wherein:
n is 0, 1, 2, 3, or 4; and
$R_4''$ is —H, —OH, —F, —Cl, —Br, —I, —NH$_2$, —NO$_2$, —CN, —SH, —S(O)$_2$OH, or —S(O)$_2$NH$_2$, or alkyl$_{(C≤8)}$, cycloalkyl$_{(C≤8)}$, aryl$_{(C≤8)}$, heteroaryl$_{(C≤8)}$, heterocycloalkyl$_{(C≤8)}$, acyl$_{(C≤8)}$, amido$_{(C≤8)}$, alkoxy$_{(C≤8)}$, acyloxy$_{(C≤8)}$, alkylamino$_{(C≤8)}$, dialkylamino$_{(C≤8)}$, —C(O)-alkoxy$_{(C≤8)}$, —C(O)-alkylamino$_{(C≤8)}$, —C(O)-dialkylamino$_{(C≤8)}$, alkylsulfonyl$_{(C≤8)}$, arylsulfonyl$_{(C≤8)}$, alkoxysulfonyl$_{(C≤8)}$, or a substituted version of any of these groups; or —X$_2$—(CH$_2$)$_p$—R$_4'''$, wherein:
- $X_2$ is arenediyl$_{(C \leq 12)}$, substituted arenediyl$_{(C \leq 12)}$, heterocycloalkanediyl$_{(C \leq 12)}$, substituted heterocycloalkanediyl$_{(C \leq 12)}$, heteroarenediyl$_{(C \leq 12)}$, or substituted heteroarenediyl$_{(C \leq 12)}$;
- p is 0, 1, 2, 3, or 4; and
- $R_4'''$ is alkyl$_{(C \leq 8)}$, cycloalkyl$_{(C \leq 8)}$, aryl$_{(C \leq 8)}$, heteroaryl$_{(C \leq 8)}$, heterocycloalkyl$_{(C \leq 8)}$, acyl$_{(C \leq 8)}$, amido$_{(C \leq 8)}$, alkoxy$_{(C \leq 8)}$, acyloxy$_{(C \leq 8)}$, —C(O)-alkoxy$_{(C \leq 8)}$, —C(O)-alkylamino$_{(C \leq 8)}$, —C(O)-dialkyl-amino$_{(C \leq 8)}$, alkylsulfonyl$_{(C \leq 8)}$, arylsulfonyl$_{(C \leq 8)}$, alkoxysulfonyl$_{(C \leq 8)}$, or a substituted version of any of these groups; and
- $R_5$ is amino, hydroxy, —OS(O)$_2$C$_6$H$_4$CH$_3$, alkyl$_{(C \leq 12)}$, alkoxy$_{(C \leq 12)}$, cycloalkyl$_{(C \leq 12)}$, cycloalkoxy$_{(C \leq 12)}$, aryl$_{(C \leq 12)}$, aralkyl$_{(C \leq 12)}$, heteroaryl$_{(C \leq 12)}$, heterocycloalkyl$_{(C \leq 12)}$, acyl$_{(C \leq 12)}$, acyloxy$_{(C \leq 12)}$, alkylamino$_{(C \leq 12)}$, dialkylamino$_{(C \leq 12)}$, alkylsulfonylamino$_{(C \leq 12)}$, or a substituted version of any of the last fourteen groups, or

—OY$_1$—A$_1$;

wherein:
- $Y_1$ is alkanediyl$_{(C \leq 8)}$ or substituted alkanediyl$_{(C \leq 8)}$; and
- $A_1$ is cycloalkyl$_{(C \leq 8)}$ or substituted cycloalkyl$_{(C \leq 8)}$; or —Y$_2$—C(O)NR$_b$—A$_2$;

wherein:
- $Y_2$ is arenediyl$_{(C \leq 8)}$ or substituted arenediyl$_{(C \leq 8)}$;
- $R_b$ is hydrogen, alkyl$_{(C \leq 6)}$, or substituted alkyl$_{(C \leq 6)}$; and
- $A_2$ is aralkyl$_{(C \leq 12)}$ or substituted aralkyl$_{(C \leq 12)}$; or —A$_3$R$_d$, wherein:
- $A_3$ is —O— or —NR$_c$—, wherein
  - $R_c$ is hydrogen, alkyl$_{(C \leq 6)}$, or substituted alkyl$_{(C \leq 6)}$; and
- $R_d$ is acyl$_{(C \leq 12)}$, or substituted acyl$_{(C \leq 12)}$;

or a pharmaceutically acceptable salt thereof.

In some embodiments, the compounds are further defined as:

(VII)

wherein:
- $R_2$ is hydrogen or alkyl$_{(C \leq 12)}$, cycloalkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, acyl$_{(C \leq 12)}$, or a substituted version of any of these groups, or -alkanediyl$_{(C \leq 8)}$cycloalkyl$_{(C \leq 12)}$ or a substituted version of this group;
- $R_4$ is hydrogen, amino, alkyl$_{(C2-18)}$, substituted alkyl$_{(C \leq 18)}$, cycloalkyl$_{(C \leq 18)}$, substituted cycloalkyl$_{(C \leq 18)}$, aryl$_{(C \leq 18)}$, substituted aryl$_{(C \leq 18)}$, aralkyl$_{(C \leq 18)}$, substituted aralkyl$_{(C \leq 18)}$, heteroaryl$_{(C \leq 18)}$, substituted heteroaryl$_{(C \leq 18)}$, heteroaralkyl$_{(C \leq 18)}$, substituted heteroaralkyl$_{(C \leq 18)}$, heterocycloalkyl$_{(C \leq 18)}$, substituted heterocycloalkyl$_{(C \leq 18)}$, alkylamino$_{(C \leq 18)}$, substituted alkylamino$_{(C \leq 18)}$, dialkylamino$_{(C \leq 18)}$, substituted dialkylamino$_{(C \leq 18)}$, alkylthio$_{(C \leq 18)}$, substituted alkylthio$_{(C \leq 18)}$, amido$_{(C \leq 18)}$, substituted amido$_{(C \leq 18)}$, or —X$_1$—(CH$_2$)$_m$—R$_4'$;

wherein:
- $X_1$ is NR$_b$, O, or S; wherein:
  - $R_b$ is hydrogen, alkyl$_{(C \leq 6)}$, or substituted alkyl$_{(C \leq 6)}$;
- m is 0, 1, 2, 3, or 4; and
- $R_4'$ is alkyl$_{(C \leq 12)}$, cycloalkyl$_{(C \leq 18)}$, aryl$_{(C \leq 18)}$, aralkyl$_{(C \leq 18)}$, heteroaryl$_{(C \leq 18)}$, heteroaralkyl$_{(C \leq 18)}$, heterocycloalkyl$_{(C \leq 18)}$, or a substituted version of any of these groups, provided that when $X_1$ is O, then $R_4'$ is not methyl; or wherein:
- n is 0, 1, 2, 3, or 4; and
- $R_4''$ is —H, —OH, —F, —Cl, —Br, —I, —NH$_2$, —NO$_2$, —CN, —SH, —S(O)$_2$OH, or —S(O)$_2$NH$_2$, or alkyl$_{(C \leq 8)}$, cycloalkyl$_{(C \leq 8)}$, aryl$_{(C \leq 8)}$, heteroaryl$_{(C \leq 8)}$, heterocycloalkyl$_{(C \leq 8)}$, acyl$_{(C \leq 8)}$, amido$_{(C \leq 8)}$, alkoxy$_{(C \leq 8)}$, acyloxy$_{(C \leq 8)}$, alkylamino$_{(C \leq 8)}$, dialkylamino$_{(C \leq 8)}$, —C(O)-alkoxy$_{(C \leq 8)}$, —C(O)-alkylamino$_{(C \leq 8)}$, —C(O)-dialkyl-amino$_{(C \leq 8)}$, alkylsulfonyl$_{(C \leq 8)}$, arylsulfonyl$_{(C \leq 8)}$, alkoxysulfonyl$_{(C \leq 8)}$, or a substituted version of any of these groups; or —X$_2$—(CH$_2$)$_p$—R$_4'''$;

wherein:
- $X_2$ is arenediyl$_{(C \leq 12)}$, substituted arenediyl$_{(C \leq 12)}$, heterocycloalkanediyl$_{(C \leq 12)}$, substituted heterocycloalkanediyl$_{(C \leq 12)}$, heteroarenediyl$_{(C \leq 12)}$, or substituted heteroarenediyl$_{(C \leq 12)}$;
- p is 0, 1, 2, 3, or 4; and
- $R_4'''$ is alkyl$_{(C \leq 8)}$, cycloalkyl$_{(C \leq 8)}$, aryl$_{(C \leq 8)}$, heteroaryl$_{(C \leq 8)}$, heterocycloalkyl$_{(C \leq 8)}$, acyl$_{(C \leq 8)}$, amido$_{(C \leq 8)}$, alkoxy$_{(C \leq 8)}$, acyloxy$_{(C \leq 8)}$, —C(O)-alkoxy$_{(C \leq 8)}$, —C(O)-alkylamino$_{(C \leq 8)}$, —C(O)-dialkyl-amino$_{(C \leq 8)}$, alkylsulfonyl$_{(C \leq 8)}$, arylsulfonyl$_{(C \leq 8)}$, alkoxysulfonyl$_{(C \leq 8)}$, or a substituted version of any of these groups; and
- $R_5$ is amino, hydroxy, —OS(O)$_2$C$_6$H$_4$CH$_3$, alkyl$_{(C \leq 12)}$, alkoxy$_{(C \leq 12)}$, cycloalkyl$_{(C \leq 12)}$, cycloalkoxy$_{(C \leq 12)}$, aryl$_{(C \leq 12)}$, aralkyl$_{(C \leq 12)}$, heteroaryl$_{(C \leq 12)}$, heterocycloalkyl$_{(C \leq 12)}$, acyl$_{(C \leq 12)}$, acyloxy$_{(C \leq 12)}$, alkylamino$_{(C \leq 12)}$, dialkylamino$_{(C \leq 12)}$, alkylsulfonylamino$_{(C \leq 12)}$, or a substituted version of any of the last fourteen groups, or

—OY$_1$—A$_1$;

wherein:
- $Y_1$ is alkanediyl$_{(C \leq 8)}$ or substituted alkanediyl$_{(C \leq 8)}$; and
- $A_1$ is cycloalkyl$_{(C \leq 8)}$ or substituted cycloalkyl$_{(C \leq 8)}$; or —Y$_2$—C(O)NR$_b$—A$_2$;

wherein:
- $Y_2$ is arenediyl$_{(C \leq 8)}$ or substituted arenediyl$_{(C \leq 8)}$;
- $R_b$ is hydrogen, alkyl$_{(C \leq 6)}$, or substituted alkyl$_{(C \leq 6)}$; and $A_2$ is aralkyl$_{(C \leq 12)}$ or substituted aralkyl$_{(C \leq 12)}$; or
—$A_3R_d$;
wherein:
$A_3$ is —O— or —NR$_c$—, wherein
$R_c$ is hydrogen, alkyl$_{(C \leq 6)}$, or substituted alkyl$_{(C \leq 6)}$; and
$R_d$ is acyl$_{(C \leq 12)}$, or substituted acyl$_{(C \leq 12)}$;
or a pharmaceutically acceptable salt thereof.

In other embodiments, the compounds are further defined as:

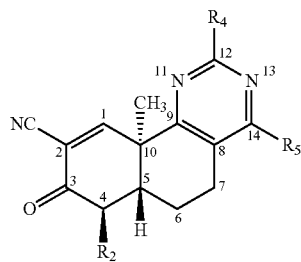

(VII)

wherein:
$R_2$ is hydrogen or alkyl$_{(C \leq 12)}$, cycloalkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, acyl$_{(C \leq 12)}$, or a substituted version of any of these groups, or -alkanediyl$_{(C \leq 8)}$-cycloalkyl$_{(C \leq 12)}$ or a substituted version of this group;
$R_4$ is hydrogen, amino, cycloalkyl$_{(C \leq 18)}$, substituted cycloalkyl$_{(C \leq 18)}$, aryl$_{(C \leq 18)}$, substituted aryl$_{(C \leq 18)}$, aralkyl$_{(C \leq 18)}$, substituted aralkyl$_{(C \leq 18)}$, heteroaryl$_{(C \leq 18)}$, substituted heteroaryl$_{(C \leq 18)}$, heteroaralkyl$_{(C \leq 18)}$, substituted heteroaralkyl$_{(C \leq 18)}$, heterocycloalkyl$_{(C \leq 18)}$, substituted heterocycloalkyl$_{(C \leq 18)}$, alkylamino$_{(C \leq 18)}$, substituted alkylamino$_{(C \leq 18)}$, dialkylamino$_{(C \leq 18)}$, substituted dialkylamino$_{(C \leq 18)}$, alkylthio$_{(C \leq 18)}$, substituted alkylthio$_{(C \leq 18)}$, amido$_{(C \leq 18)}$, substituted amido$_{(C \leq 18)}$, or —$X_1$—(CH$_2$)$_m$—$R_4'$;

wherein:
$X_1$ is NR$_b$, O, or S; wherein:
$R_b$ is hydrogen, alkyl$_{(C \leq 6)}$, or substituted alkyl$_{(C \leq 6)}$;
m is 0, 1, 2, 3, or 4; and
$R_4'$ is cycloalkyl$_{(C \leq 18)}$, aryl$_{(C \leq 18)}$, aralkyl$_{(C \leq 18)}$, heteroaryl$_{(C \leq 18)}$, heteroaralkyl$_{(C \leq 18)}$, heterocycloalkyl$_{(C \leq 18)}$, or a substituted version of any of these groups; or

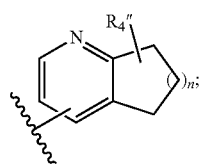

wherein:
n is 0, 1, 2, 3, or 4; and
$R_4''$ is —H, —OH, —F, —Cl, —Br, —I, —NH$_2$, —NO$_2$, —CN, —SH, —S(O)$_2$OH, or —S(O)$_2$NH$_2$, or alkyl$_{(C \leq 8)}$, cycloalkyl$_{(C \leq 8)}$, aryl$_{(C \leq 8)}$, heteroaryl$_{(C \leq 8)}$, heterocycloalkyl$_{(C \leq 8)}$, acyl$_{(C \leq 8)}$, amido$_{(C \leq 8)}$, alkoxy$_{(C \leq 8)}$, acyloxy$_{(C \leq 8)}$, alkylamino$_{(C \leq 8)}$, dialkylamino$_{(C \leq 8)}$, —C(O)-alkoxy$_{(C \leq 8)}$, —C(O)-alkylamino$_{(C \leq 8)}$, —C(O)-dialkylamino$_{(C \leq 8)}$, alkylsulfonyl$_{(C \leq 8)}$, arylsulfonyl$_{(C \leq 8)}$, alkoxysulfonyl$_{(C \leq 8)}$, or a substituted version of any of these groups; or —$X_2$—(CH$_2$)$_p$—$R_4'''$;

wherein:
$X_2$ is arenediyl$_{(C \leq 12)}$, substituted arenediyl$_{(C \leq 12)}$, heterocycloalkanediyl$_{(C \leq 12)}$, substituted heterocycloalkanediyl$_{(C \leq 12)}$, heteroarenediyl$_{(C \leq 12)}$, or substituted heteroarenediyl$_{(C \leq 12)}$;
p is 0, 1, 2, 3, or 4; and
$R_4'''$ is alkyl$_{(C \leq 8)}$, cycloalkyl$_{(C \leq 8)}$, aryl$_{(C \leq 8)}$, heteroaryl$_{(C \leq 8)}$, heterocycloalkyl$_{(C \leq 8)}$, acyl$_{(C \leq 8)}$, alkoxy$_{(C \leq 8)}$, acyloxy$_{(C \leq 8)}$, —C(O)-alkoxy$_{(C \leq 8)}$, —C(O)-alkylamino$_{(C \leq 8)}$, —C(O)-dialkylamino$_{(C \leq 8)}$, alkylsulfonyl$_{(C \leq 8)}$, arylsulfonyl$_{(C \leq 8)}$, alkoxysulfonyl$_{(C \leq 8)}$, or a substituted version of any of these groups; and
$R_5$ is amino, hydroxy, —OS(O)$_2$C$_6$H$_4$CH$_3$, alkyl$_{(C \leq 12)}$, alkoxy$_{(C \leq 12)}$, cycloalkyl$_{(C \leq 12)}$, cycloalkoxy$_{(C \leq 12)}$, aryl$_{(C \leq 12)}$, aralkyl$_{(C \leq 12)}$, heteroaryl$_{(C \leq 12)}$, heterocycloalkyl$_{(C \leq 12)}$, acyl$_{(C \leq 12)}$, acyloxy$_{(C \leq 12)}$, alkylamino$_{(C \leq 12)}$, dialkylamino$_{(C \leq 12)}$, alkylsulfonylamino$_{(C \leq 12)}$, or a substituted version of any of the last fourteen groups, or

—OY$_1$—A$_1$;

wherein:
$Y_1$ is alkanediyl$_{(C \leq 8)}$ or substituted alkanediyl$_{(C \leq 8)}$; and
$A_1$ is cycloalkyl$_{(C \leq 8)}$ or substituted cycloalkyl$_{(C \leq 8)}$; or —$Y_2$—C(O)NR$_b$—$A_2$;

wherein:
$Y_2$ is arenediyl$_{(C \leq 8)}$ or substituted arenediyl$_{(C \leq 8)}$;
$R_b$ is hydrogen, alkyl$_{(C \leq 6)}$, or substituted alkyl$_{(C \leq 6)}$; and
$A_2$ is aralkyl$_{(C \leq 12)}$ or substituted aralkyl$_{(C \leq 12)}$; or —$A_3R_d$;

wherein:
$A_3$ is —O— or —NR$_c$—, wherein
$R_c$ is hydrogen, alkyl$_{(C \leq 6)}$, or substituted alkyl$_{(C \leq 6)}$; and
$R_d$ is acyl$_{(C \leq 12)}$, or substituted acyl$_{(C \leq 12)}$;
or a pharmaceutically acceptable salt thereof.

In some embodiments, the compounds are further defined as:

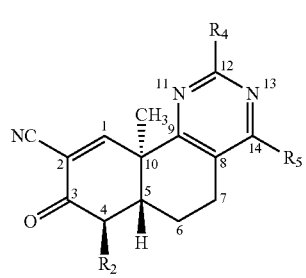

(VII)

wherein:
$R_2$ is hydrogen, alkyl$_{(C \leq 12)}$, or substituted alkyl$_{(C \leq 12)}$;
$R_4$ is heteroaryl$_{(C \leq 18)}$ or substituted heteroaryl$_{(C \leq 18)}$; and
$R_5$ is aryl$_{(C \leq 12)}$ or substituted aryl$_{(C \leq 12)}$;
or a pharmaceutically acceptable salt thereof.

In some embodiments, the compounds are further defined as:

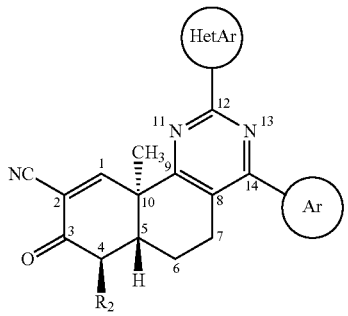

(VIII)

wherein:
R$_2$ is alkyl$_{(C\leq12)}$ or substituted alkyl$_{(C\leq12)}$;
HetAr is heteroaryl$_{(C\leq18)}$ or substituted heteroaryl$_{(C\leq18)}$; and
Ar is aryl$_{(C\leq12)}$ or substituted aryl$_{(C\leq12)}$;
or a pharmaceutically acceptable salt thereof.

In some embodiments, the compounds are further defined as:

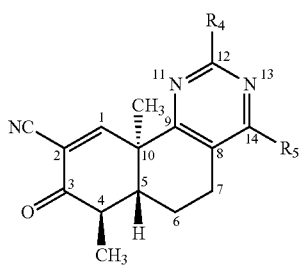

(IX)

wherein:
R$_4$ is heteroaryl$_{(C\leq18)}$ or substituted heteroaryl$_{(C\leq18)}$; and
R$_5$ is aryl$_{(C\leq12)}$ or substituted aryl$_{(C\leq12)}$;
or a pharmaceutically acceptable salt thereof.

In other embodiments, the present disclosure provides compounds of the formula:

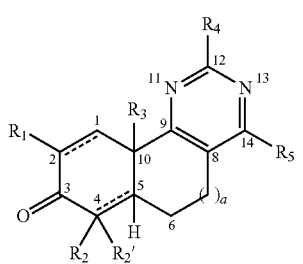

(X)

wherein:
the bond between carbon atoms 1 and 2 is a single bond, an epoxidized double bond, or a double bond;
the bond between carbon atoms 4 and 5 is a single bond or a double bond;
a is 0, 1, or 2;
R$_1$ is cyano, heteroaryl$_{(C\leq8)}$, substituted heteroaryl$_{(C\leq8)}$, CF$_3$, or C(O)R$_a$; wherein:

R$_a$ is hydroxy, amino, or alkoxy$_{(C\leq8)}$, alkylamino$_{(C\leq8)}$, dialkylamino$_{(C\leq8)}$, alkylsulfonylamino$_{(C\leq8)}$, or a substituted version of any of these groups;
R$_2$ is hydrogen, alkyl$_{(C\leq12)}$, cycloalkyl$_{(C\leq12)}$, alkenyl$_{(C\leq12)}$, alkynyl$_{(C\leq12)}$, or a substituted version of the last four groups, or alkanediyl$_{(C\leq8)}$cycloalkyl$_{(C\leq12)}$ or a substituted version of this group;
R$_2$' is absent, hydrogen, alkyl$_{(C\leq12)}$, cycloalkyl$_{(C\leq12)}$, alkenyl$_{(C\leq12)}$, alkynyl$_{(C\leq12)}$, or a substituted version of the last four groups, provided that when the bond between carbon atoms 4 and 5 is a double bond then R$_2$' is absent;
R$_3$ is alkyl$_{(C\leq12)}$, aryl$_{(C\leq12)}$, aralkyl$_{(C\leq12)}$, or a substituted version of any of these groups;
R$_4$ is cycloalkyl$_{(C\leq18)}$, substituted cycloalkyl$_{(C\leq18)}$, heteroaryl$_{(C\leq18)}$, substituted heteroaryl$_{(C\leq18)}$, heterocycloalkyl$_{(C\leq18)}$, substituted heterocycloalkyl$_{(C\leq18)}$, or
—X$_1$—(CH$_2$)$_m$—R$_4$';

wherein:
X$_1$ is NR$_b$, O, or S; wherein:
R$_b$ is hydrogen, alkyl$_{(C\leq6)}$, or substituted alkyl$_{(C\leq6)}$;
m is 0, 1, 2, 3, or 4; and
R$_4$' is cycloalkyl$_{(C\leq18)}$, aryl$_{(C\leq18)}$, aralkyl$_{(C\leq18)}$, heteroaryl$_{(C\leq18)}$, heteroaralkyl$_{(C\leq18)}$, heterocycloalkyl$_{(C\leq18)}$, or a substituted version of any of these groups; or

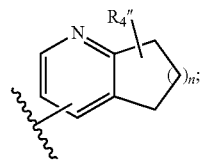

wherein:
n is 0, 1, 2, 3, or 4; and
R$_4$" is —H, —OH, —F, —Cl, —Br, —I, —NH$_2$, —NO$_2$, —CN, —SH, —S(O)$_2$OH, or —S(O)$_2$NH$_2$, or alkyl$_{(C\leq8)}$, cycloalkyl$_{(C\leq8)}$, aryl$_{(C\leq8)}$, heteroaryl$_{(C\leq8)}$, heterocycloalkyl$_{(C\leq8)}$, acyl$_{(C\leq8)}$, amido$_{(C\leq8)}$, alkoxy$_{(C\leq8)}$, acyloxy$_{(C\leq8)}$, alkylamino$_{(C\leq8)}$, dialkylamino$_{(C\leq8)}$, —C(O)-alkoxy$_{(C\leq8)}$, —C(O)-alkylamino$_{(C\leq8)}$, —C(O)-dialkylamino$_{(C\leq8)}$, alkylsulfonyl$_{(C\leq8)}$, arylsulfonyl$_{(C\leq8)}$, alkoxysulfonyl$_{(C\leq8)}$, or a substituted version of any of these groups; or
—X$_2$—(CH$_2$)$_p$—R$_4$''';

wherein:
X$_2$ is arenediyl$_{(C\leq12)}$, substituted arenediyl$_{(C\leq12)}$, heterocycloalkanediyl$_{(C\leq12)}$, substituted heterocycloalkanediyl$_{(C\leq12)}$, heteroarenediyl$_{(C\leq12)}$, or substituted heteroarenediyl$_{(C\leq12)}$;
p is 0, 1, 2, 3, or 4; and
R$_4$''' is alkyl$_{(C\leq8)}$, cycloalkyl$_{(C\leq8)}$, aryl$_{(C\leq8)}$, heteroaryl$_{(C\leq8)}$, heterocycloalkyl$_{(C\leq8)}$, acyl$_{(C\leq8)}$, alkoxy$_{(C\leq8)}$, acyloxy$_{(C\leq8)}$, —C(O)-alkoxy$_{(C\leq8)}$, —C(O)-alkylamino$_{(C\leq8)}$, —C(O)-dialkylamino$_{(C\leq8)}$, alkylsulfonyl$_{(C\leq8)}$, arylsulfonyl$_{(C\leq8)}$, alkoxysulfonyl$_{(C\leq8)}$, or a substituted version of any of these groups; and
R$_5$ is cycloalkoxy$_{(C\leq12)}$, aryl$_{(C\leq12)}$, heteroaryl$_{(C\leq12)}$, or a substituted version of any of the last three groups, or
—OY$_1$—A$_1$;

wherein:
Y$_1$ is alkanediyl$_{(C\leq8)}$ or substituted alkanediyl$_{(C\leq8)}$; and
A$_1$ is cycloalkyl$_{(C\leq8)}$ or substituted cycloalkyl$_{(C\leq8)}$; or provided that when carbon atoms 4 and 5 are joined by a double bond, then $R_2'$ and the hydrogen atom at carbon atom 5 are absent;

or a pharmaceutically acceptable salt thereof.

In some embodiments, the bond between carbon atom 1 and carbon atom 2 is an epoxidized double bond. In other embodiments, the bond between carbon atom 1 and carbon atom 2 is a double bond. In some embodiments, the bond between carbon atom 4 and carbon atom 5 is a single bond. In other embodiments, the bond between carbon atom 4 and carbon atom 5 is a double bond. In some embodiments, a is 1. In some embodiments, $R_1$ is cyano.

In some embodiments, $R_2$ is alkyl$_{(C \leq 12)}$ or substituted alkyl$_{(C \leq 12)}$. In some embodiments, $R_2$ is alkyl$_{(C \leq 12)}$ such as methyl, ethyl, or propyl. In some embodiments, $R_2$ is methyl. In some embodiments, $R_2$ is substituted alkyl$_{(C \leq 12)}$ such as 3-hydroxypropyl. In other embodiments, $R_2$ is alkenyl$_{(C \leq 12)}$ or substituted alkenyl$_{(C \leq 12)}$. In some embodiments, $R_2$ is alkenyl$_{(C \leq 12)}$ such as 2-propenyl. In some embodiments, $R_2'$ is hydrogen. In other embodiments, $R_2'$ is alkyl$_{(C \leq 12)}$ or substituted alkyl$_{(C \leq 12)}$. In some embodiments, $R_2'$ is alkyl$_{(C \leq 12)}$ such as methyl.

In some embodiments, $R_3$ is alkyl$_{(C \leq 12)}$ or substituted alkyl$_{(C \leq 12)}$. In some embodiments, $R_3$ is alkyl$_{(C \leq 12)}$ such as methyl, propyl, or isopentyl. In some embodiments, $R_3$ is methyl. In other embodiments, $R_3$ is aryl$_{(C \leq 12)}$ or substituted aryl$_{(C \leq 12)}$. In some embodiments, $R_3$ is aryl$_{(C \leq 12)}$ such as phenyl.

In some embodiments, $R_4$ is alkyl$_{(C2-18)}$ or substituted alkyl$_{(C2-18)}$. In other embodiments, $R_4$ is heteroaryl$_{(C \leq 18)}$ or substituted heteroaryl$_{(C \leq 18)}$. In some embodiments, $R_4$ is a heteroaryl$_{(C \leq 12)}$ or a substituted heteroaryl$_{(C \leq 12)}$ group wherein at least one of the heteroatoms in the aromatic ring is a nitrogen atom. In some embodiments, $R_4$ is heteroaryl$_{(C \leq 18)}$ such as 3-pyridinyl, 4-pyridinyl, 4-(2-cyclopropyl)-pyridinyl, 5-(2-cyclopropyl)-pyridinyl, 4-(2-morpholino)-pyridinyl, 4-(2-phenyl)-pyridinyl, 3-(5-methyl)-pyridinyl, 3-(6-methyl)-pyridinyl, 4-(2-methyl)-pyridinyl, 4-(3-methyl)-pyridinyl, 3-pyrazolo[1,5-a] pyridinyl, 3-(N-methyl)-pyrrolo[2,3-b]pyridinyl, 5-iso quinlinyl, 2-isoquinolinyl, 1-iso quinolinyl, 4-(2-phenyl)-pyridinyl, 5-(2-phenyl)-pyridinyl, 3-(5-methyl)-pyridinyl, 4-(3-methyl)-pyridinyl, 4-(3,5-dimethyl)-isoxazolyl, 4-(2-methyl)-pyridinyl, 4-(3-methyl)-pyridinyl, 3-(4-methyl)-pyridinyl, 4-(6-methyl)-pyrimidinyl, 6-(4-methyl)-pyrimidinyl, 4-pyridazinyl, 2-quinazolinyl, 4-quinazolinyl, 2-quinolinyl, 3-quinolinyl, 4-quinolinyl, 5-quinolinyl, 6-quinolinyl, 8-quinolinyl, 4-isoquinolinyl, 3-(8-methyl)-quinolinyl, 3-(1-methyl)-quinolinyl, 4-(2-methyl)-quinolinyl, 4-(2-isopropyl)-quinolinyl, 4-(6-methyl)-quinolinyl, 4-(7-methyl)-quinolinyl, 4-(8-methyl)-quinolinyl, 2-(N-methyl)-indolyl, 5-(2,4-dimethyl)-thiazolyl, or 5-(3-methyl)-oxadiazolyl. In other embodiments, $R_4$ is substituted heteroaryl$_{(C \leq 18)}$ such as 4-(2-trifluoromethyl)-pyridinyl, 4-(3-fluoro)-pyridinyl, 4-(2-methoxy)-pyridinyl, 4-(2-hydroxymethyl)-pyridinyl, 4-(2-acetylamino)-pyridinyl, 4-(2-fluoromethyl)-pyridinyl, 4-(2-acetamidylethyl)-pyridinyl, 4-(2-fluoromethyl)-quinolinyl, 4-(2-acetoxymethyl)-quinolinyl, 4-(2-formyl)-quinolinyl, 4-(6-fluoro)-quinolinyl, 4-(7-fluoro)-quinolinyl, 4-(8-fluoro)-quinolinyl, 4-(6,8-difluoro)-quinolinyl, 4-(6-fluoro-2-methyl)-quinolinyl, or 4-(8-fluoro-2-methyl)-quinolinyl.

In other embodiments, $R_4$ is aryl$_{(C \leq 12)}$ or substituted aryl$_{(C \leq 12)}$. In some embodiments, $R_4$ is aryl$_{(C \leq 12)}$ such as phenyl. In other embodiments, $R_4$ is substituted aryl$_{(C \leq 12)}$ such as 2-fluorophenyl or 4-trifluoromethylphenyl. In other embodiments, $R_4$ is cycloalkyl$_{(C \leq 12)}$ or substituted cycloalkyl$_{(C \leq 12)}$. In some embodiments, $R_4$ is cycloalkyl$_{(C \leq 12)}$ such as cyclohexyl.

In other embodiments, $R_4$ is:

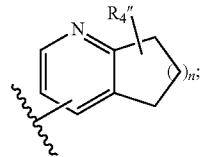

wherein:
n is 0, 1, 2, 3, or 4; and
$R_4''$ is —OH, —F, —Cl, —Br, —I, —NH$_2$, —NO$_2$, —CN, —SH, —S(O)$_2$OH, or —S(O)$_2$NH$_2$, or alkyl$_{(C \leq 8)}$, cycloalkyl$_{(C \leq 8)}$, aryl$_{(C \leq 8)}$, heteroaryl$_{(C \leq 8)}$, heterocycloalkyl$_{(C \leq 8)}$, acyl$_{(C \leq 8)}$, amido$_{(C \leq 8)}$, alkoxy$_{(C \leq 8)}$, acyloxy$_{(C \leq 8)}$, alkylamino$_{(C \leq 8)}$, dialkylamino$_{(C \leq 8)}$, —C(O)-alkoxy$_{(C \leq 8)}$, —C(O)-alkylamino$_{(C \leq 8)}$, —C(O)-dialkyl-amino$_{(C \leq 8)}$, alkylsulfonyl$_{(C \leq 8)}$, arylsulfonyl$_{(C \leq 8)}$, alkoxysulfonyl$_{(C \leq 8)}$, or a substituted version of any of these groups.

In other embodiments, $R_4$ is:

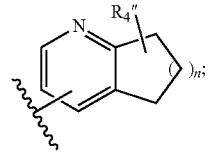

wherein:
n is 0, 1, 2, 3, or 4; and
$R_4''$ is —H, —OH, —F, —Cl, —Br, —I, —NH$_2$, —NO$_2$, —CN, —SH, —S(O)$_2$OH, or —S(O)$_2$NH$_2$, or alkyl$_{(C \leq 8)}$, cycloalkyl$_{(C \leq 8)}$, aryl$_{(C \leq 8)}$, heteroaryl$_{(C \leq 8)}$, heterocycloalkyl$_{(C \leq 8)}$, acyl$_{(C \leq 8)}$, amido$_{(C \leq 8)}$, alkoxy$_{(C \leq 8)}$, acyloxy$_{(C \leq 8)}$, alkylamino$_{(C \leq 8)}$, dialkylamino$_{(C \leq 8)}$, —C(O)-alkoxy$_{(C \leq 8)}$, —C(O)-alkylamino$_{(C \leq 8)}$, —C(O)-dialkyl-amino$_{(C \leq 8)}$, alkylsulfonyl$_{(C \leq 8)}$, arylsulfonyl$_{(C \leq 8)}$, alkoxysulfonyl$_{(C \leq 8)}$, or a substituted version of any of these groups.

In some embodiments, $R_4$ is:

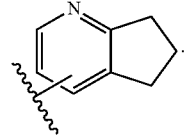

In some embodiments, $R_4$ is:

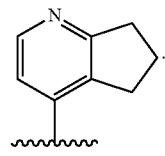

In other embodiments, $R_4$ is heterocycloalkyl$_{(C \leq 18)}$ or substituted heterocycloalkyl$_{(C \leq 18)}$. In some embodiments, $R_4$ is heterocycloalkyl$_{(C \leq 12)}$ such as morpholinyl, 4-piperidinyl, 3-(5-methyl-)1,2,3,6-tetrahydropyridinyl, or 4-N-methylpiperazinyl. In other embodiments, $R_4$ is substituted heterocycloalkyl$_{(C \leq 12)}$ such as N-t-butyloxycarbonyl-4-piperidinyl, N-acetyl-4-piperidinyl, N-t-butyloxycarbonyl-5-methyl-1,2,3,6-tetrahydropyridinyl, N-acetyl-5-methyl-1,2,3,6-tetrahydropyridinyl, or 4-N-acetylpiperazinyl. In other embodiments, $R_4$ is hydrogen.

In other embodiments, $R_4$ is —$X_1$—(CH$_2$)$_m$—$R_4'$; wherein:
   $X_1$ is NR$_b$, O, or S; wherein:
      $R_b$ is hydrogen, alkyl$_{(C \leq 6)}$, or substituted alkyl$_{(C \leq 6)}$;
   m is 0, 1, 2, 3, or 4; and
   $R_4'$ is alkyl$_{(C \leq 12)}$, cycloalkyl$_{(C \leq 18)}$, aryl$_{(C \leq 18)}$, aralkyl$_{(C \leq 18)}$, heteroaryl$_{(C \leq 18)}$, heteroaralkyl$_{(C \leq 18)}$, heterocycloalkyl$_{(C \leq 18)}$, or a substituted version of any of these groups, provided that when $X_1$ is O, then $R_4'$ is not methyl.

In other embodiments, $R_4$ is —$X_1$—(CH$_2$)$_m$—$R_4'$; wherein:
   $X_1$ is NR$_b$, O, or S; wherein:
      $R_b$ is hydrogen, alkyl$_{(C \leq 6)}$, or substituted alkyl$_{(C \leq 6)}$;
   m is 0, 1, 2, 3, or 4; and
   $R_4'$ is alkyl$_{(C \leq 12)}$, cycloalkyl$_{(C \leq 18)}$, aryl$_{(C \leq 18)}$, aralkyl$_{(C \leq 18)}$, heteroaryl$_{(C \leq 18)}$, heteroaralkyl$_{(C \leq 18)}$, heterocycloalkyl$_{(C \leq 18)}$, or a substituted version of any of these groups.

In some embodiments, $X_1$ is NR$_b$, wherein: $R_b$ is hydrogen, alkyl$_{(C \leq 6)}$, or substituted alkyl$_{(C \leq 6)}$. In some embodiments, $R_b$ is hydrogen. In some embodiments, m is 0 or 1. In some embodiments, m is 0. In some embodiments, $R_4'$ is cycloalkyl$_{(C \leq 18)}$, aryl$_{(C \leq 18)}$, aralkyl$_{(C \leq 18)}$, heteroaryl$_{(C \leq 18)}$, heteroaralkyl$_{(C \leq 18)}$, heterocycloalkyl$_{(C \leq 18)}$, or a substituted version of any of these groups. In some embodiments, $R_4'$ is heteroaryl$_{(C \leq 12)}$ or substituted heteroaryl$_{(C \leq 12)}$. In some embodiments, $R_4'$ is heteroaryl$_{(C \leq 12)}$ such as 4-pyridinyl.

In other embodiments, $R_4$ is amino. In other embodiments, $R_4$ is amido$_{(C \leq 12)}$ or substituted amido$_{(C \leq 12)}$. In some embodiments, $R_4$ is amido$_{(C \leq 12)}$ such as:

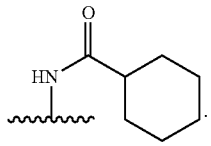 [SMILES: *NC(=O)C1CCCCC1]

In other embodiment, $R_4$ is —$X_2$—(CH$_2$)$_p$—$R_4'''$; wherein:
   $X_2$ is arenediyl$_{(C \leq 12)}$, substituted arenediyl$_{(C \leq 12)}$, heterocycloalkanediyl$_{(C \leq 12)}$, substituted heterocycloalkanediyl$_{(C \leq 12)}$, heteroarenediyl$_{(C \leq 12)}$, or substituted heteroarenediyl$_{(C \leq 12)}$;
   p is 0, 1, 2, 3, or 4; and
   $R_4'''$ is alkyl$_{(C \leq 8)}$, cycloalkyl$_{(C \leq 8)}$, aryl$_{(C \leq 8)}$, heteroaryl$_{(C \leq 8)}$, heterocycloalkyl$_{(C \leq 8)}$, acyl$_{(C \leq 8)}$, amido$_{(C \leq 8)}$, alkoxy$_{(C \leq 8)}$, acyloxy$_{(C \leq 8)}$, —C(O)-alkoxy$_{(C \leq 8)}$, —C(O)-alkylamino$_{(C \leq 8)}$, —C(O)-dialkylamino$_{(C \leq 8)}$, alkylsulfonyl$_{(C \leq 8)}$, arylsulfonyl$_{(C \leq 8)}$, alkoxysulfonyl$_{(C \leq 8)}$, or a substituted version of any of these groups.

In other embodiments, —$X_2$—(CH$_2$)$_p$—$R_4'''$; wherein:
   $X_2$ is heterocycloalkanediyl$_{(C \leq 12)}$, substituted heterocycloalkanediyl$_{(C \leq 12)}$, heteroarenediyl$_{(C \leq 12)}$, or substituted heteroarenediyl$_{(C \leq 12)}$;
   p is 0, 1, 2, 3, or 4; and
   $R_4'''$ is alkyl$_{(C \leq 8)}$, cycloalkyl$_{(C \leq 8)}$, aryl$_{(C \leq 8)}$, heteroaryl$_{(C \leq 8)}$, heterocycloalkyl$_{(C \leq 8)}$, acyl$_{(C \leq 8)}$, alkoxy$_{(C \leq 8)}$, acyloxy$_{(C \leq 8)}$, —C(O)-alkoxy$_{(C \leq 8)}$, —C(O)-alkylamino$_{(C \leq 8)}$, —C(O)-dialkylamino$_{(C \leq 8)}$, alkylsulfonyl$_{(C \leq 8)}$, arylsulfonyl$_{(C \leq 8)}$, alkoxysulfonyl$_{(C \leq 8)}$, or a substituted version of any of these groups.

In some embodiments, $X_2$ is heteroarenediyl$_{(C \leq 12)}$ or substituted heteroarenediyl$_{(C \leq 12)}$. In some embodiments, $X_2$ is heteroarenediyl$_{(C \leq 12)}$ such as pyridin-2,4-diyl or pyridine-2,5-diyl. In other embodiments, $X_2$ is heterocycloalkanediyl$_{(C \leq 12)}$ or substituted heterocycloalkanediyl$_{(C \leq 12)}$. In some embodiments, $X_2$ is heterocycloalkanediyl$_{(C \leq 12)}$ such as piperidin-1,4-diyl, piperazin-1,4-diyl, or 1,2,3,6-tetrahydropiperidin-1,5-diyl. In some embodiments, p is 0, 1, or 2. In some embodiments, p is 0. In other embodiments, p is 1. In other embodiments, p is 2.

In some embodiments, $R_4'''$ is acyl$_{(C \leq 8)}$ or substituted acyl$_{(C \leq 8)}$. In some embodiments, $R_4'''$ is acyl$_{(C \leq 8)}$ such as acetyl. In other embodiments, $R_4'''$ is amido$_{(C \leq 8)}$ or substituted amido$_{(C \leq 8)}$. In some embodiments, $R_4'''$ is amido$_{(C \leq 8)}$ such as acetamidyl. In other embodiments, $R_4'''$ is substituted acyl$_{(C \leq 8)}$ such as carboxy. In other embodiments, $R_4'''$ is cycloalkyl$_{(C \leq 8)}$ or substituted cycloalkyl$_{(C \leq 8)}$. In some embodiments, $R_4'''$ is cycloalkyl$_{(C \leq 8)}$ such as cyclopropyl. In other embodiments, $R_4'''$ is alkylsulfonyl$_{(C \leq 8)}$ or substituted alkylsulfonyl$_{(C \leq 8)}$. In some embodiments, $R_4'''$ is alkylsulfonyl$_{(C \leq 8)}$ such as —S(O)$_2$CH$_3$ or —S(O)$_2$CH$_2$CH$_3$. In other embodiments, $R_4'''$ is —C(O)-alkoxy$_{(C \leq 8)}$ such as —C(O)OEt. In other embodiments, $R_4'''$ is —C(O)-dialkylamino$_{(C \leq 8)}$ such as —C(O)NMe$_2$.

In some embodiments, $R_5$ is aryl$_{(C \leq 12)}$ or substituted aryl$_{(C \leq 12)}$. In some embodiments, $R_5$ is aryl$_{(C \leq 12)}$ such as phenyl, 4-methylphenyl, 3-isopropylphenyl, 4-isopropylphenyl, 1,3-biphenyl, or 1,4-biphenyl. In other embodiments, $R_5$ further comprises one or more fluorine atoms. In some embodiments, $R_5$ is substituted aryl$_{(C \leq 12)}$ such as 2-fluorophenyl, 3-fluorophenyl, 4-fluorophenyl, 2,4-difluorophenyl, 4-hydroxymethylphenyl, 3-trifluoromethylphenyl, 4-trifluoromethylphenyl, 4-methoxyphenyl, 4-chlorophenyl, or 3,4-dichlorophenyl. In other embodiments, $R_5$ is cycloalkyl$_{(C \leq 12)}$ or substituted cycloalkyl$_{(C \leq 12)}$ such as cyclopropyl. In other embodiments, $R_5$ is cycloalkoxy$_{(C \leq 12)}$ or substituted cycloalkoxy$_{(C \leq 12)}$ such as cyclobutyloxy, cyclopentyloxy, or cyclohexyloxy. In other embodiments, $R_5$ is alkylamino$_{(C \leq 12)}$, dialkylamino$_{(C \leq 12)}$, or a substituted version of either of these groups. In some embodiments, $R_5$ is dialkylamino$_{(C \leq 12)}$ or substituted dialkylamino$_{(C \leq 12)}$. In some embodiments, $R_5$ is dialkylamino$_{(C \leq 8)}$ or substituted dialkylamino$_{(C \leq 8)}$ such as dimethylamino. In other embodiments, $R_5$ is alkylsulfonylamino$_{(C \leq 12)}$ or substituted alkylsulfonylamino$_{(C \leq 12)}$ such as methylsulfonylamino. In other embodiments, $R_5$ is —OY$_1$—A$_1$; wherein:
   $Y_1$ is alkanediyl$_{(C \leq 8)}$ or substituted alkanediyl$_{(C \leq 8)}$; and
   $A_1$ is cycloalkyl$_{(C \leq 8)}$ or substituted cycloalkyl$_{(C \leq 8)}$.

In some embodiments, $Y_1$ is methylene. In some embodiments, $A_1$ is cyclobutyl. In some embodiments, $R_5$ is:

In other embodiments, $R_5$ is —$Y_2$—C(O)NR$_c$A$_2$; wherein:
   $Y_2$ is arenediyl$_{(C \leq 8)}$ or substituted arenediyl$_{(C \leq 8)}$;
   $R_c$ is hydrogen, alkyl$_{(C \leq 6)}$, or substituted alkyl$_{(C \leq 6)}$; and
   $A_2$ is aralkyl$_{(C \leq 12)}$ or substituted aralkyl$_{(C \leq 12)}$.

In some embodiments, $Y_2$ is arenediyl$_{(C \leq 8)}$ such as benzenediyl. In some embodiments, $R_c$ is alkyl$_{(C \leq 6)}$ such as methyl. In some embodiments, $A_2$ is aralkyl$_{(C \leq 12)}$ such as benzyl.

In other embodiments, $R_5$ is heteroaryl$_{(C≤12)}$ or substituted heteroaryl$_{(C≤12)}$. In some embodiments, $R_5$ is heteroaryl$_{(C≤12)}$ such as 5-(3-methyl)-oxadiazolyl, 4-(3,5-dimethyl)-isoxazolyl, furanyl, benzofuranyl, 2-thiazolyl, 5-(2-methyl)-furanyl, 3-pyridinyl, or 4-pyridinyl. In other embodiments, $R_5$ is hydroxy. In other embodiments, $R_5$ is $OS(O)_2C_6H_4CH_3$. In other embodiments, $R_5$ is heterocycloalkyl$_{(C≤12)}$ or substituted heterocycloalkyl$_{(C≤12)}$. In some embodiments, $R_5$ is heterocycloalkyl$_{(C≤12)}$ such as pyrrolidinyl. In other embodiments, $R_5$ is alkoxy$_{(C≤12)}$ or substituted alkoxy$_{(C≤12)}$. In some embodiments, $R_5$ is alkoxy$_{(C≤12)}$ such as methoxy or isopropoxy. In other embodiments, $R_5$ is aralkyl$_{(C≤12)}$ or substituted aralkyl$_{(C≤12)}$. In some embodiments, $R_5$ is aralkyl$_{(C≤12)}$ such as benzyl.

In some embodiments, the compounds are further defined as:

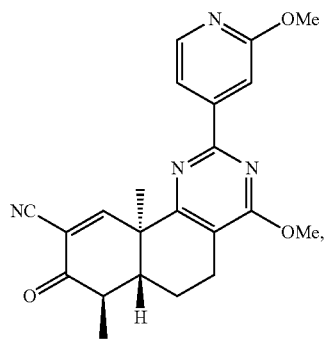

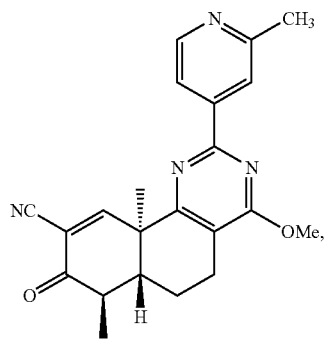

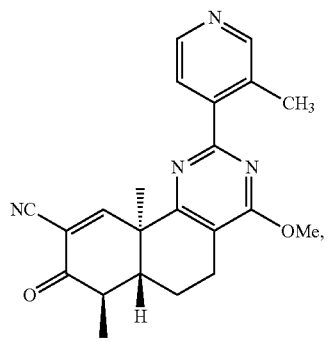

-continued

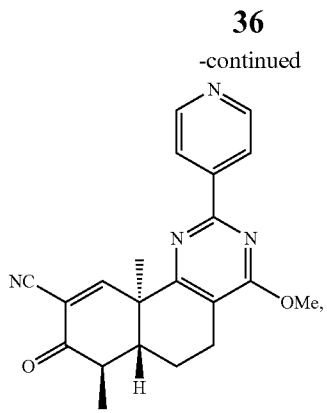

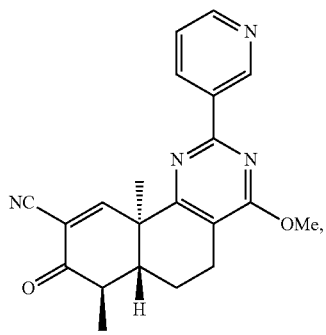

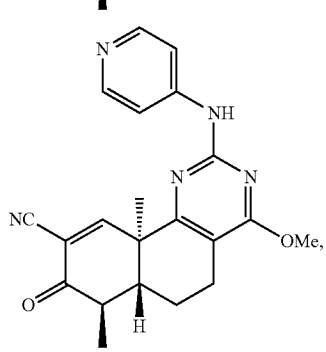

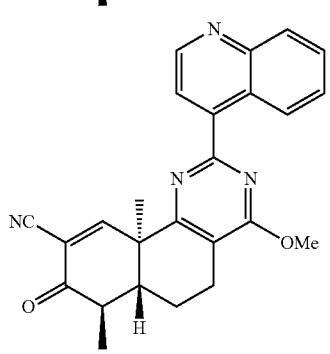

-continued
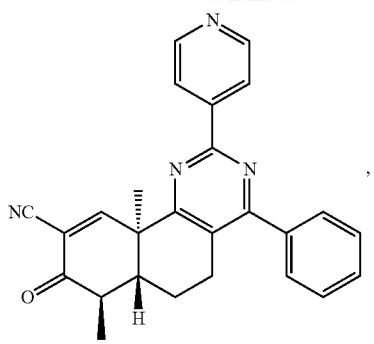
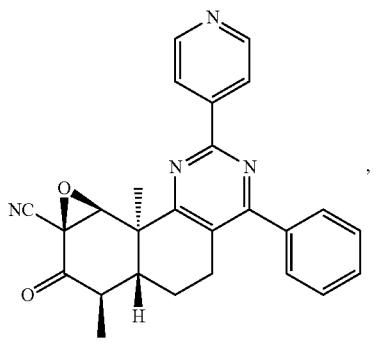
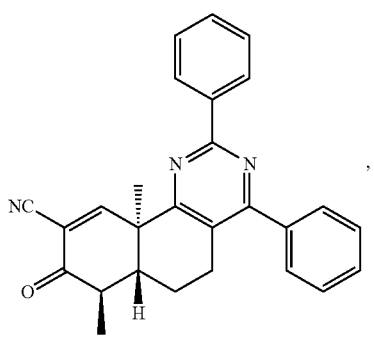
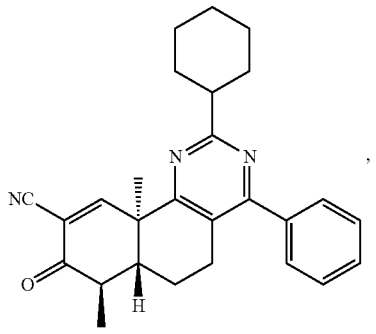
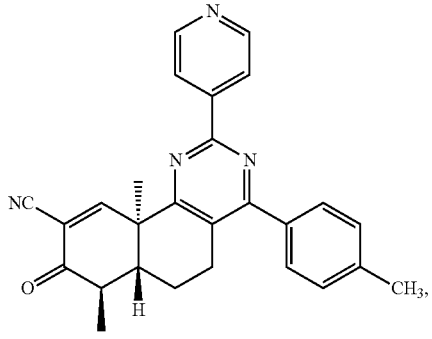
-continued
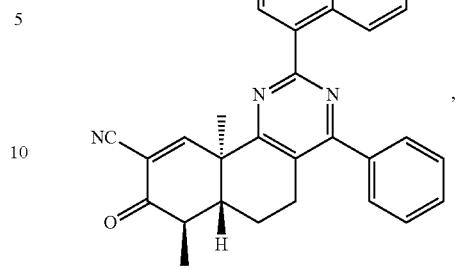
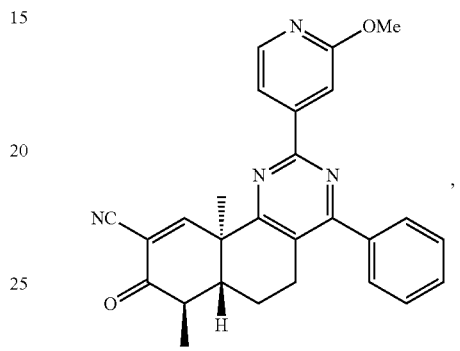
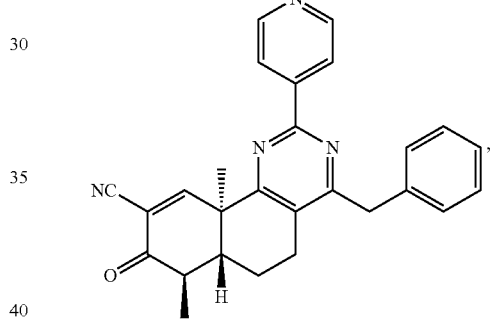
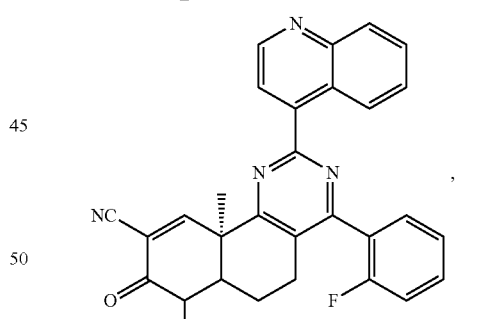
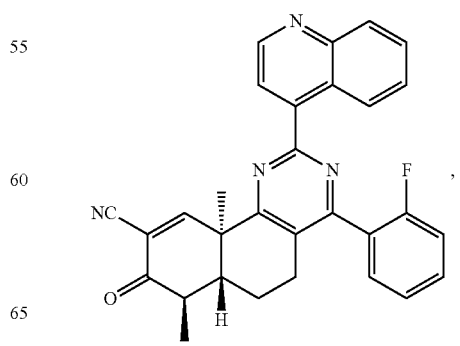

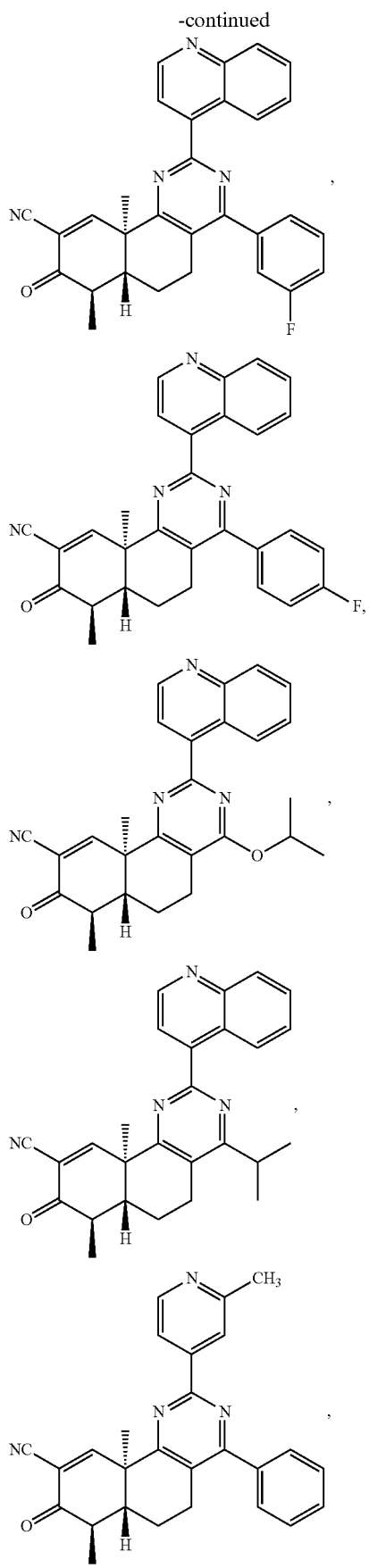
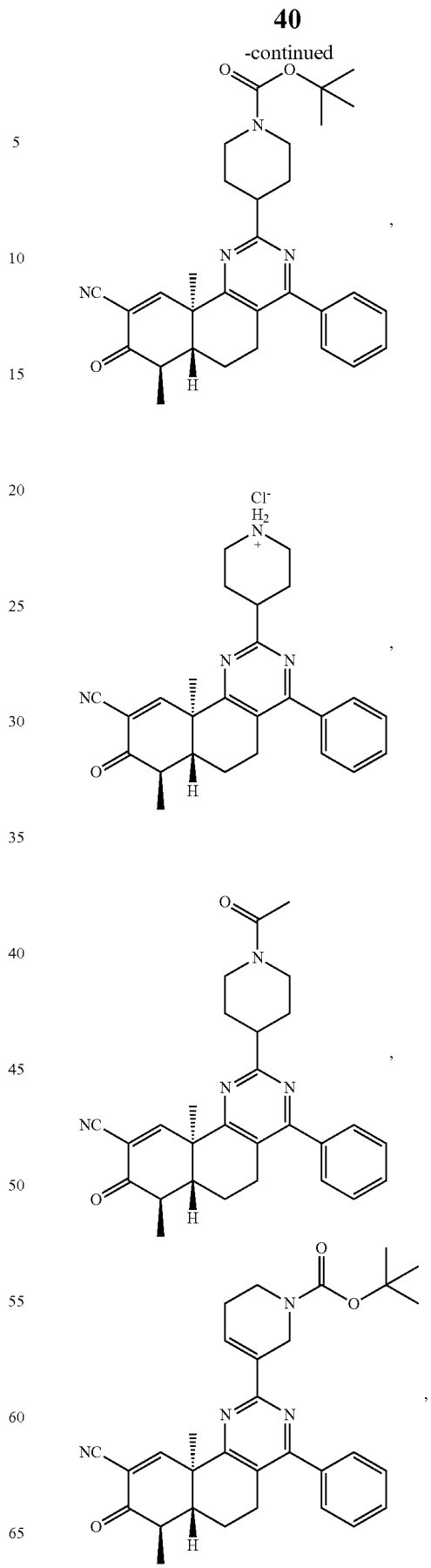

41
-continued
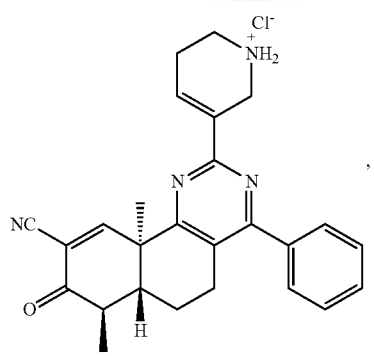
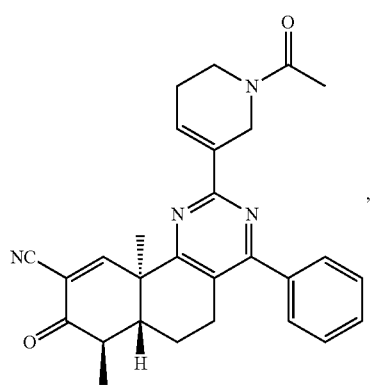
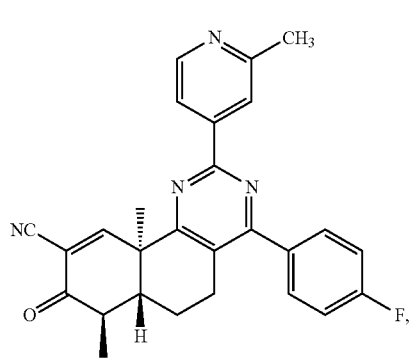
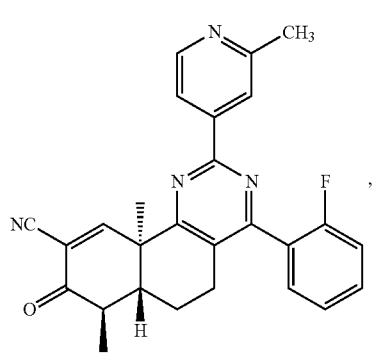
42
-continued
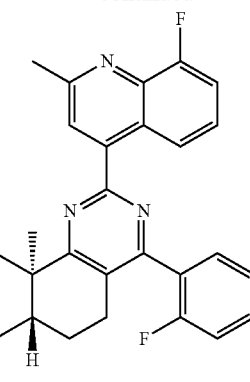
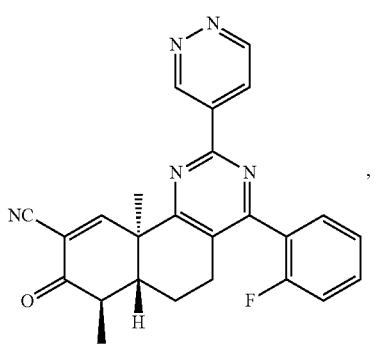
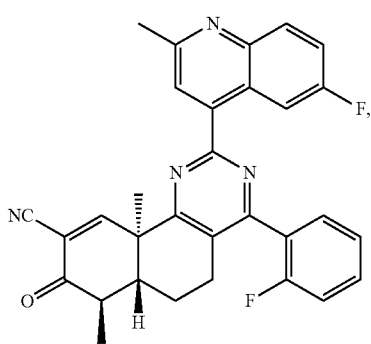
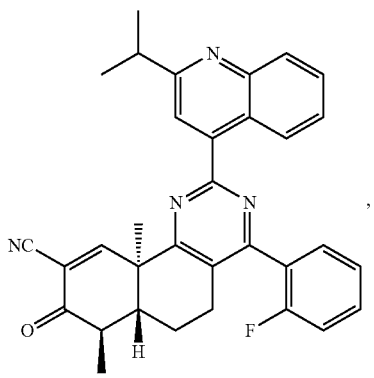

43
-continued
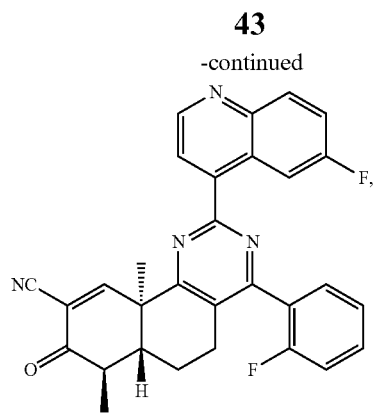
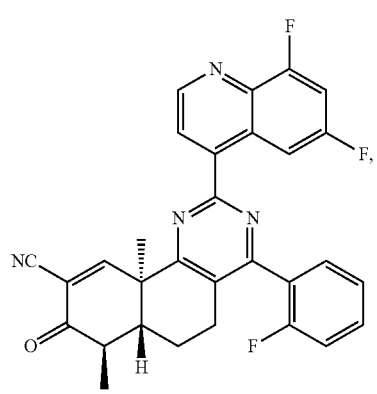
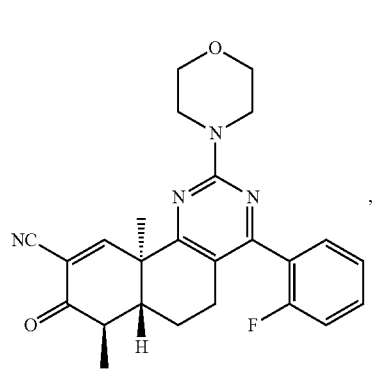
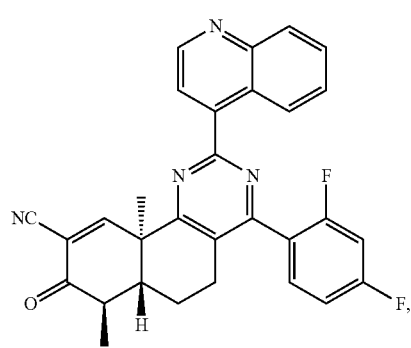
44
-continued
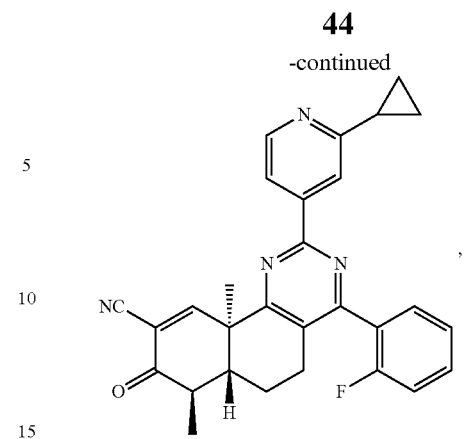
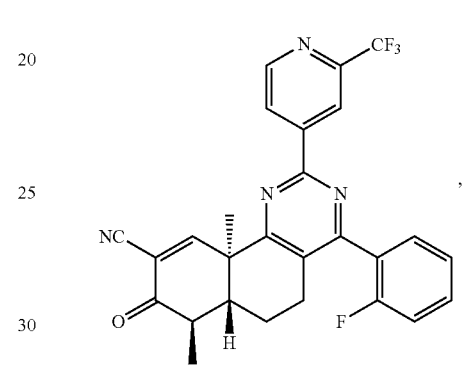
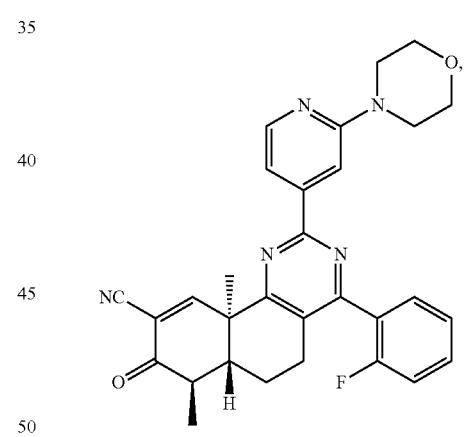
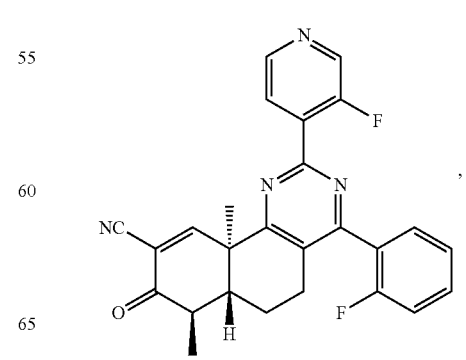

45
-continued
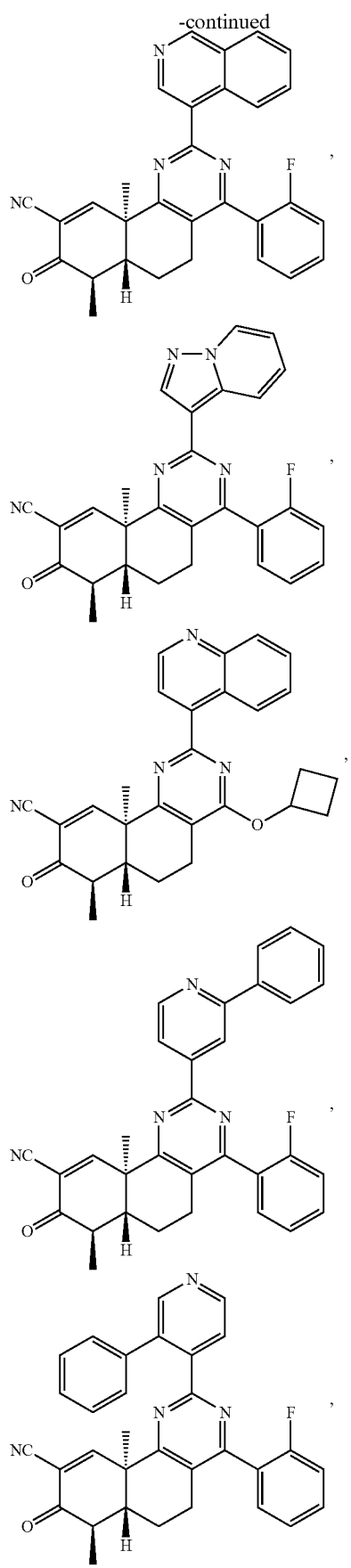
46
-continued
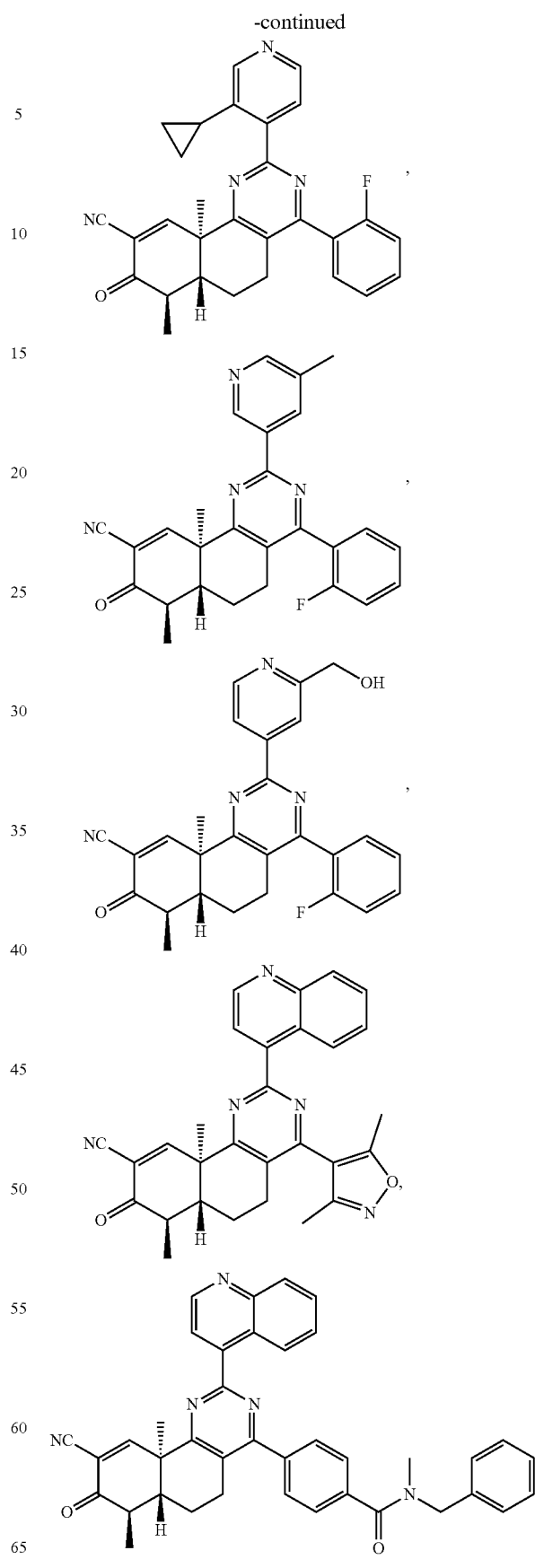

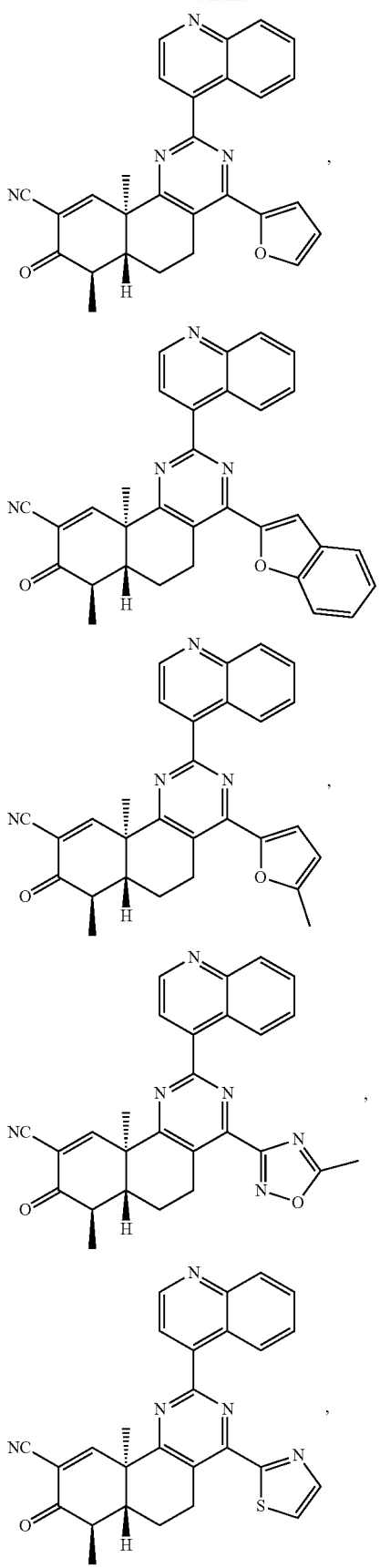
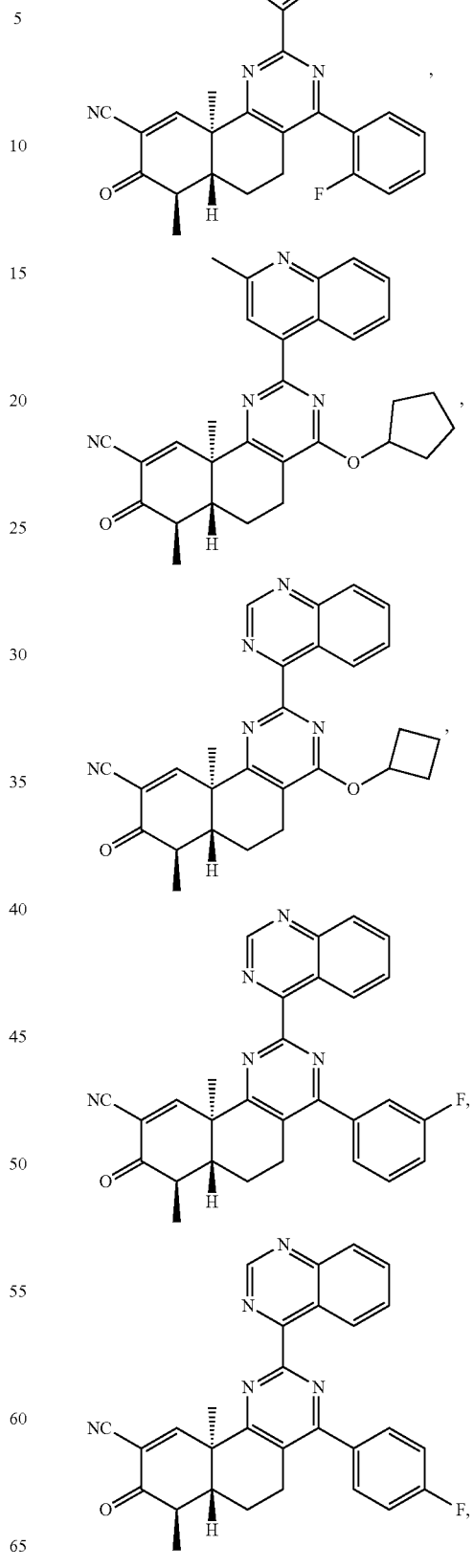

49
-continued
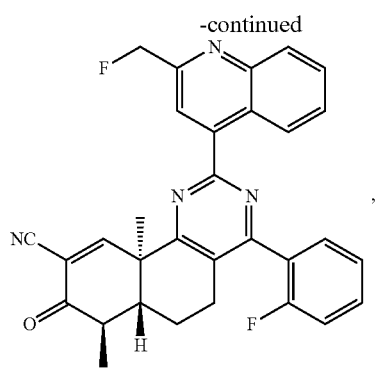
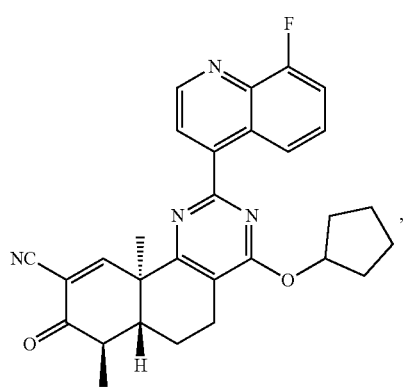
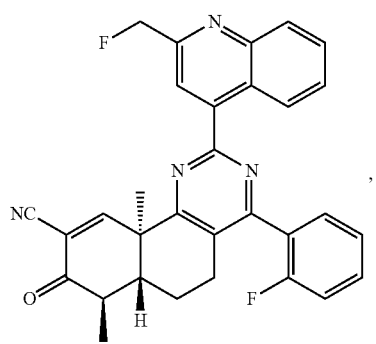
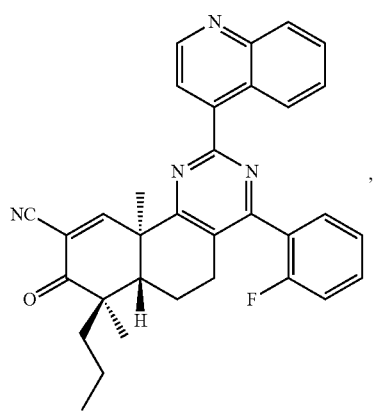
50
-continued
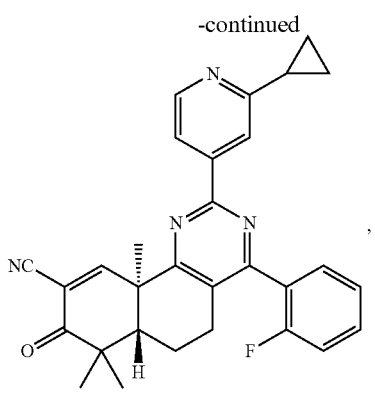
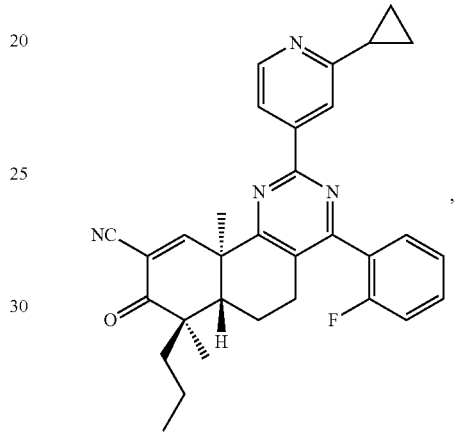
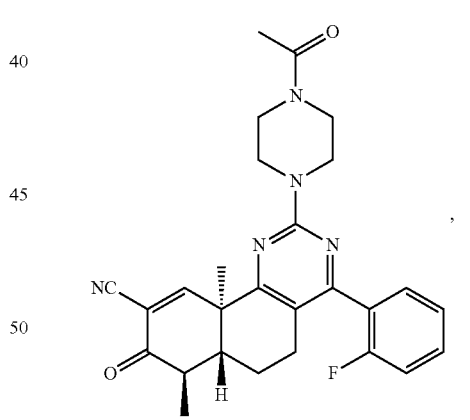
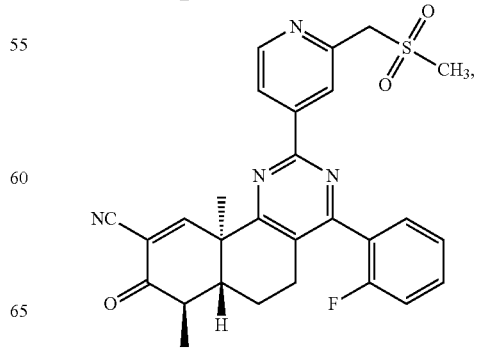

51
-continued
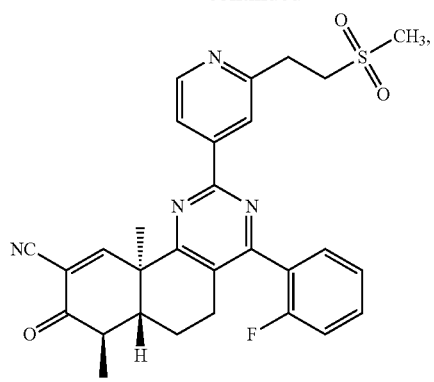
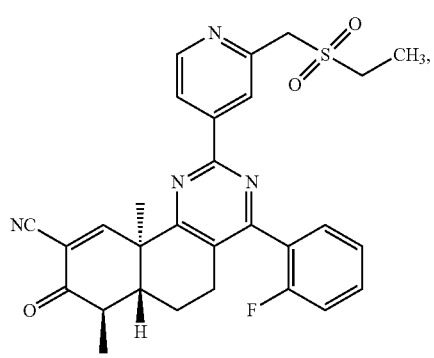
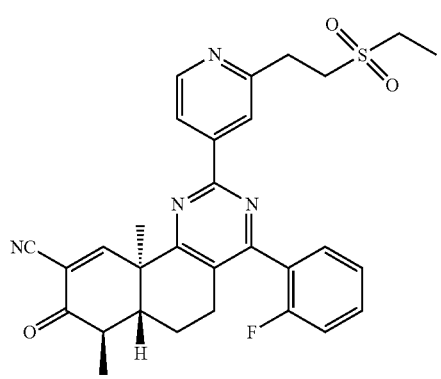
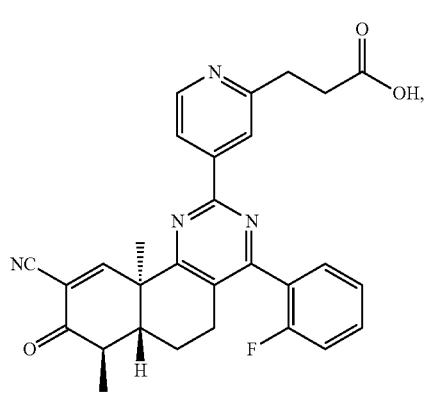
52
-continued
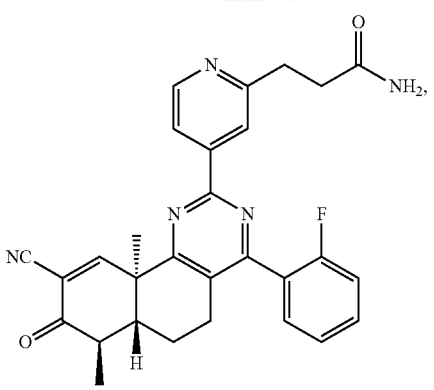
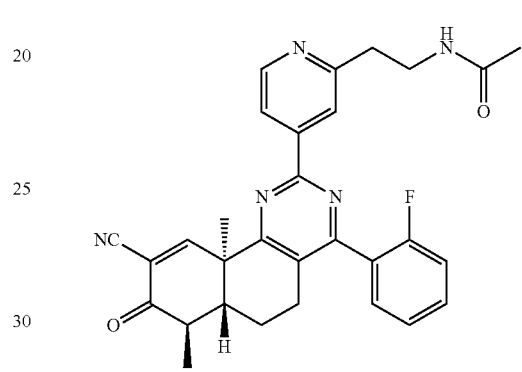
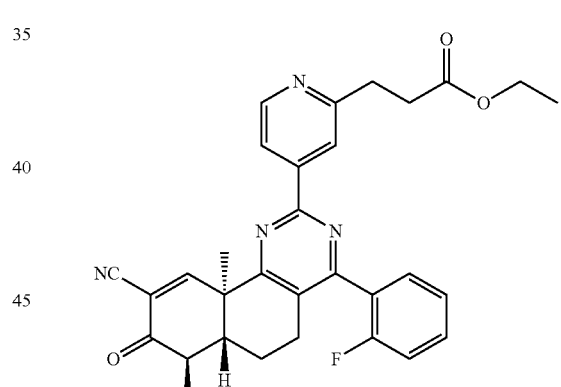
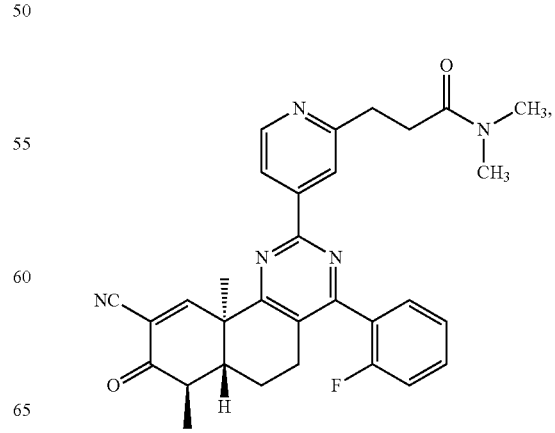

53
-continued
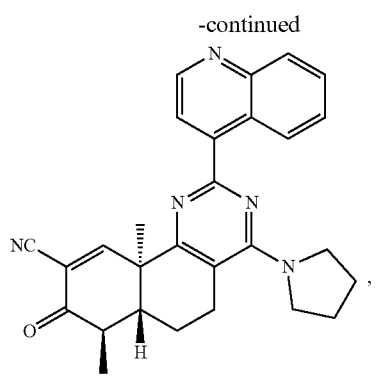
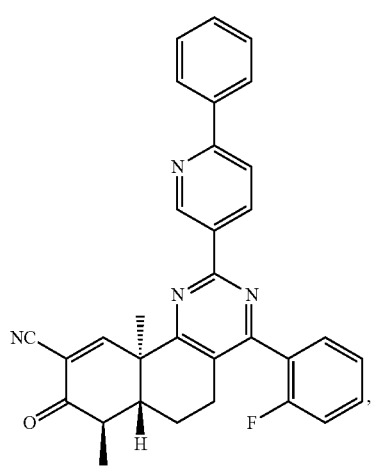
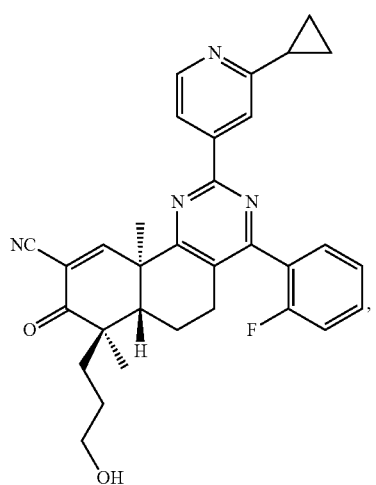
54
-continued
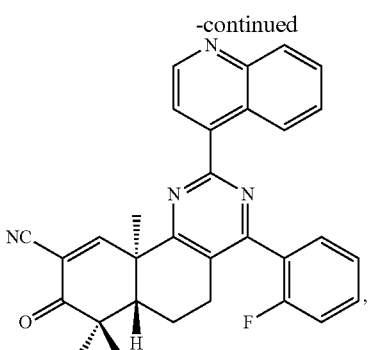
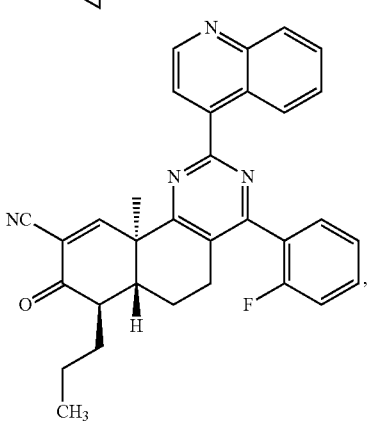
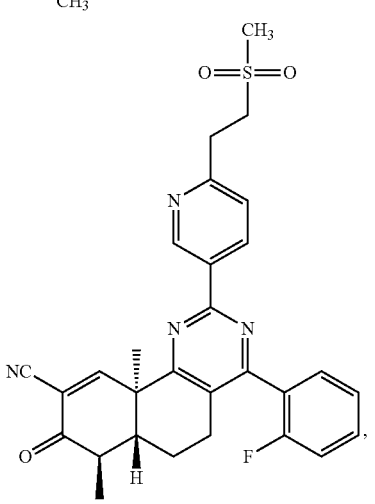

55
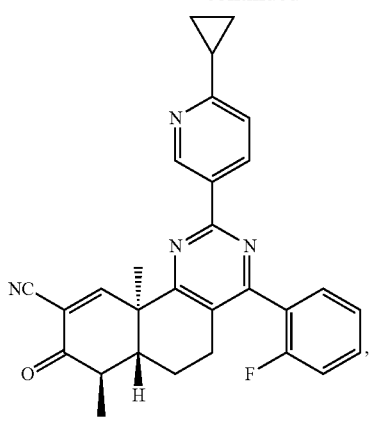
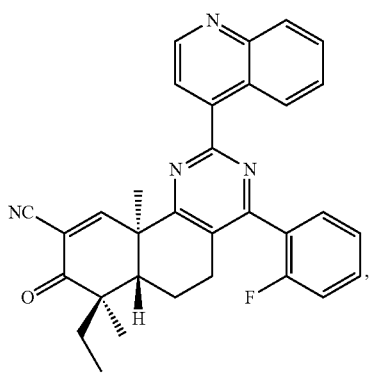
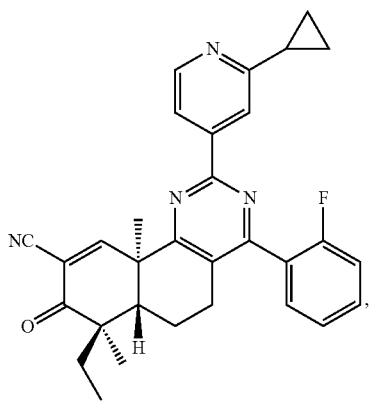
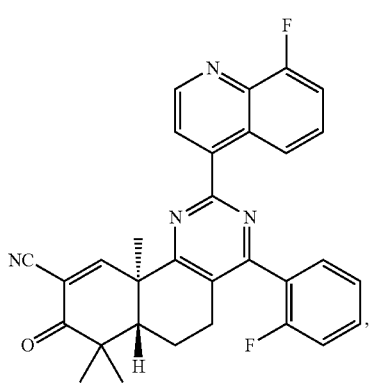
56
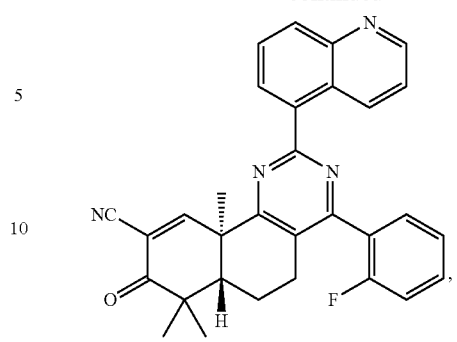
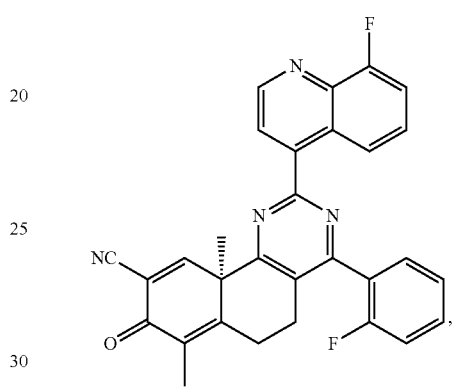
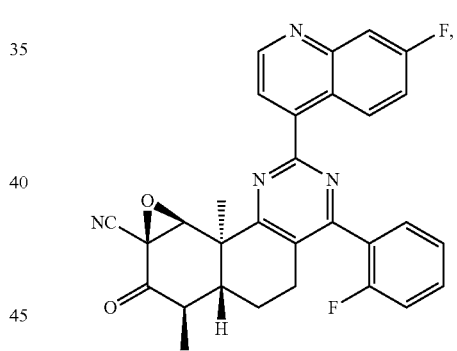
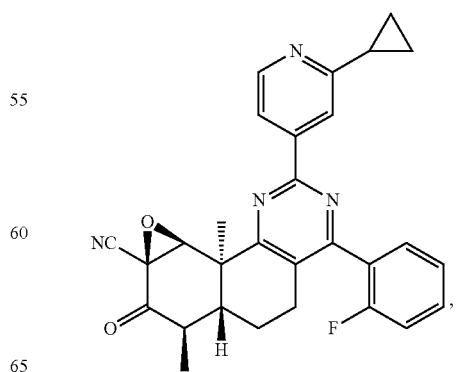

57
-continued
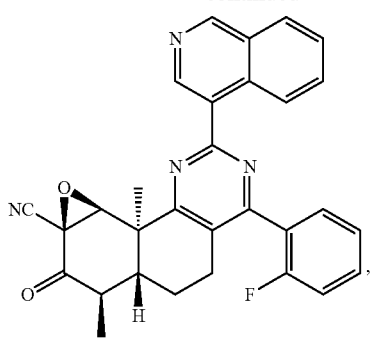
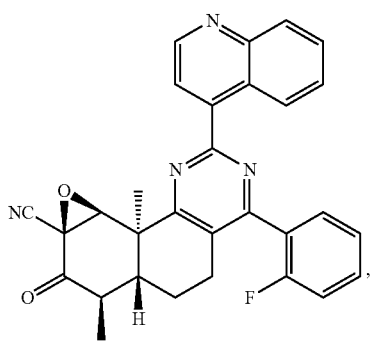
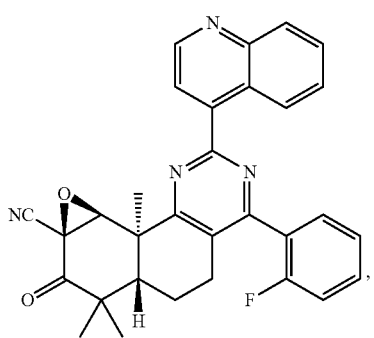
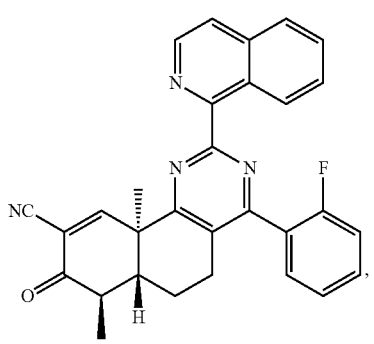
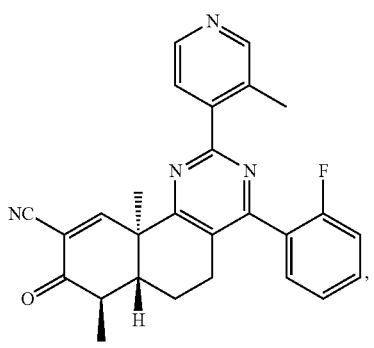
58
-continued
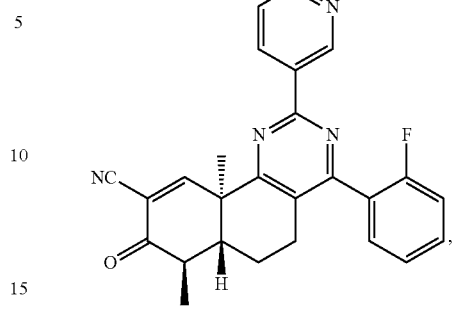
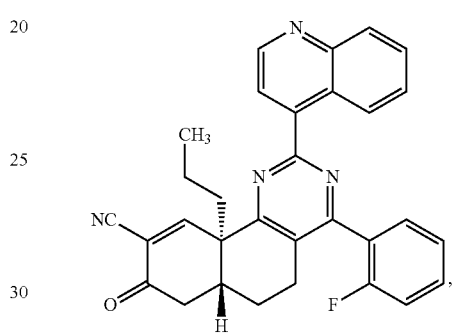
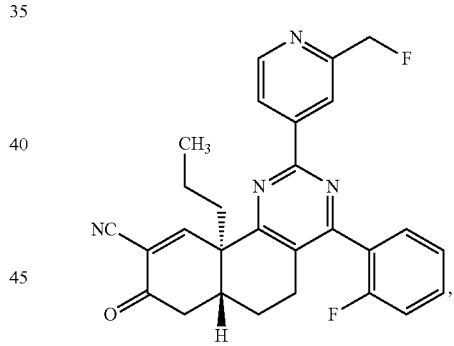
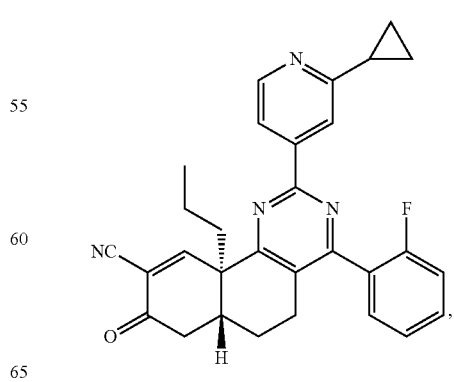

59
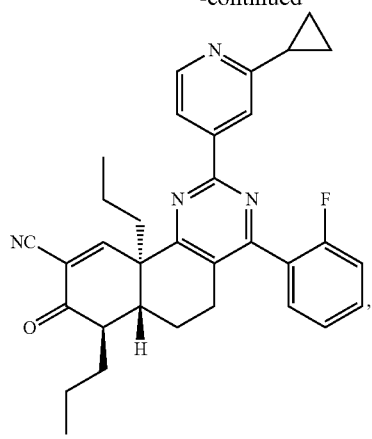
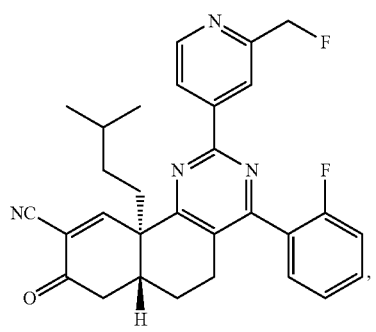
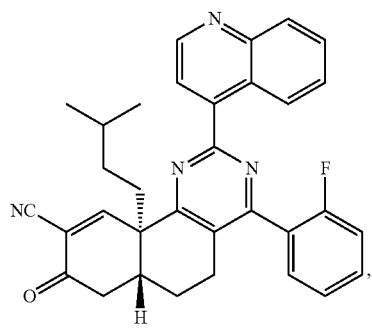
60
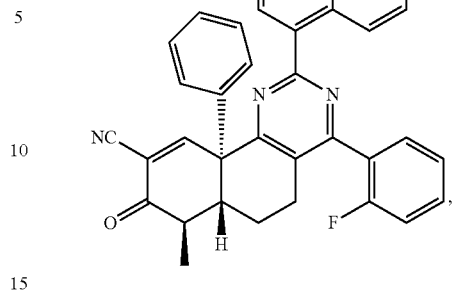
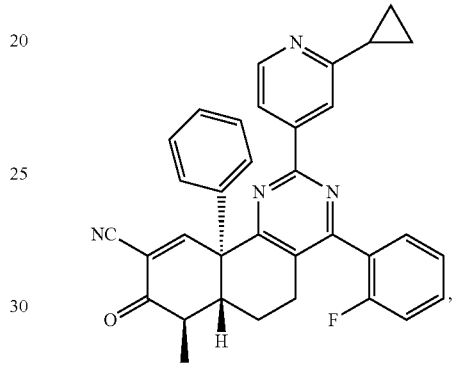
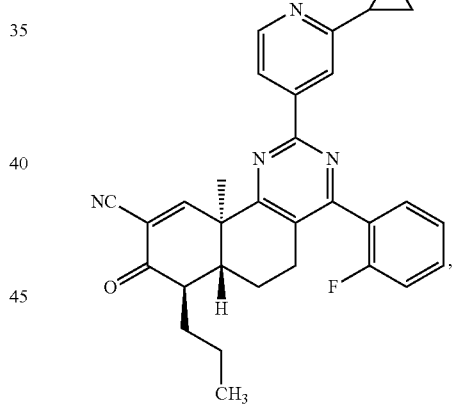
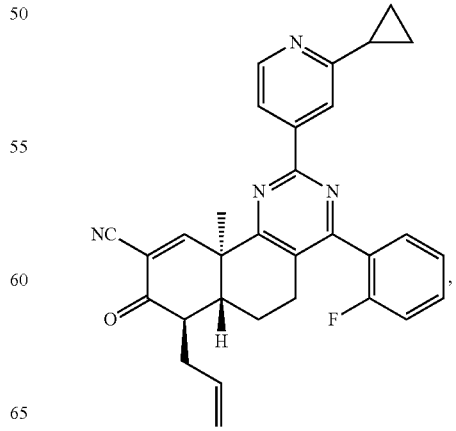

61
-continued
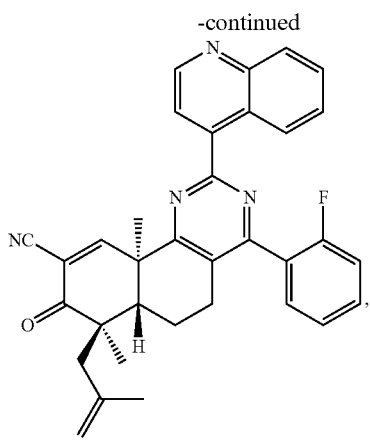
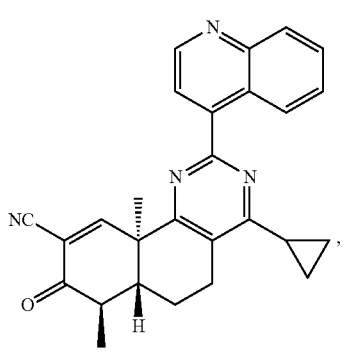
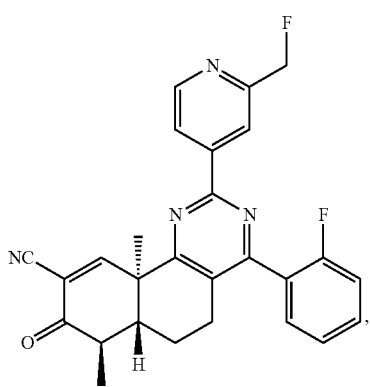
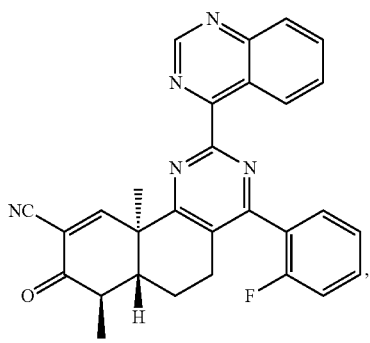
62
-continued
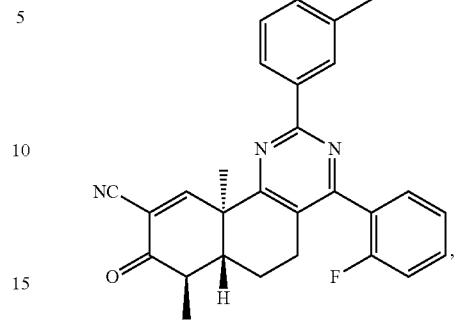
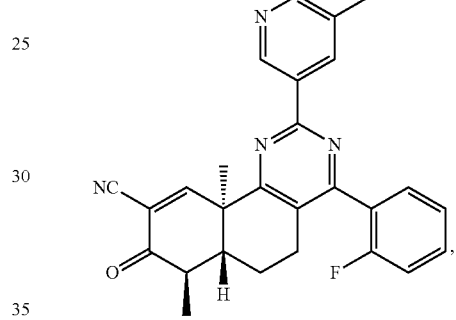
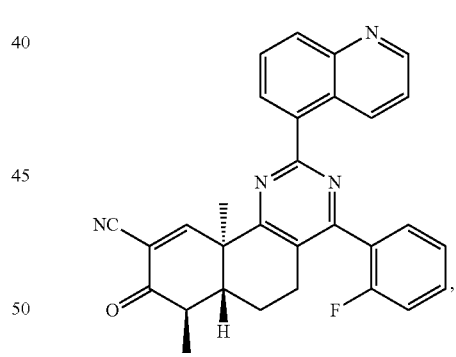
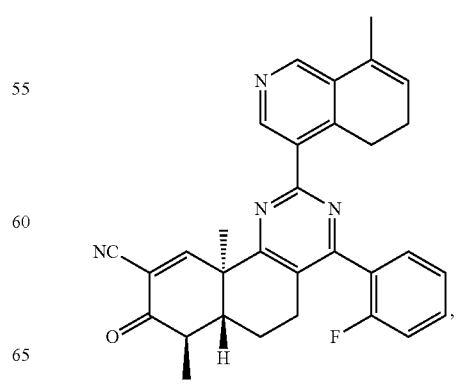

63
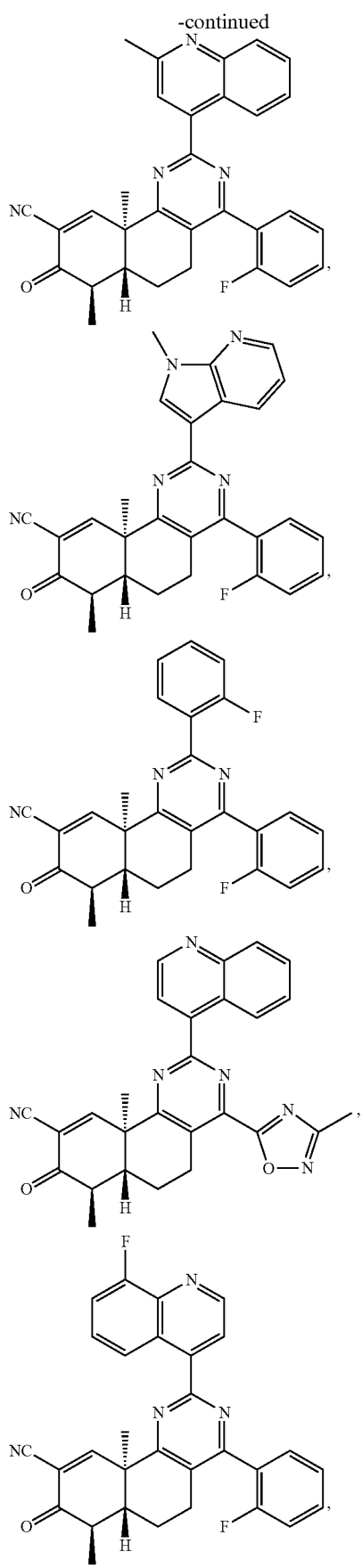
64
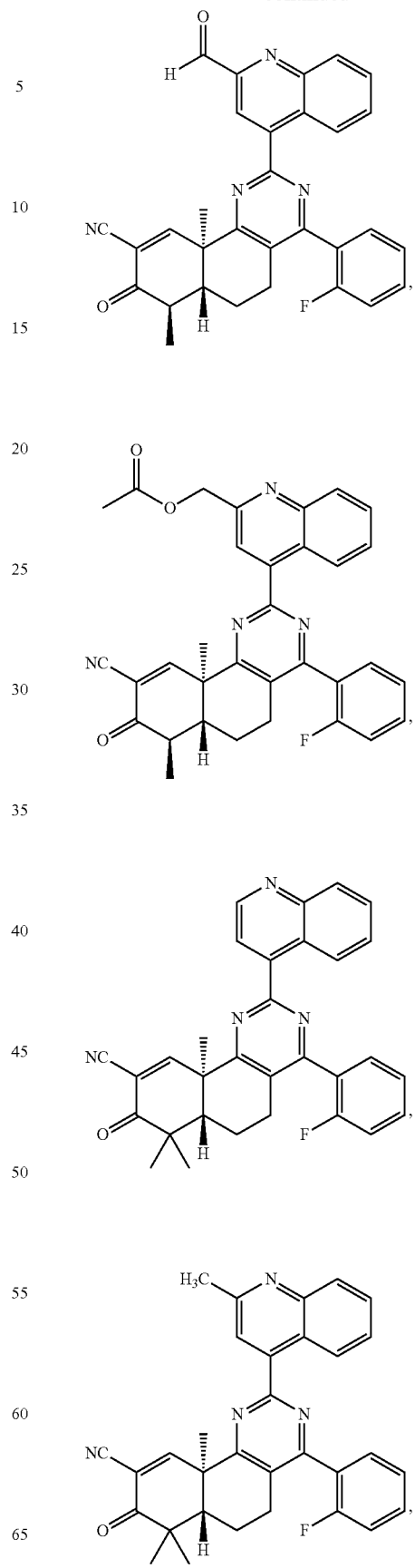

65
-continued
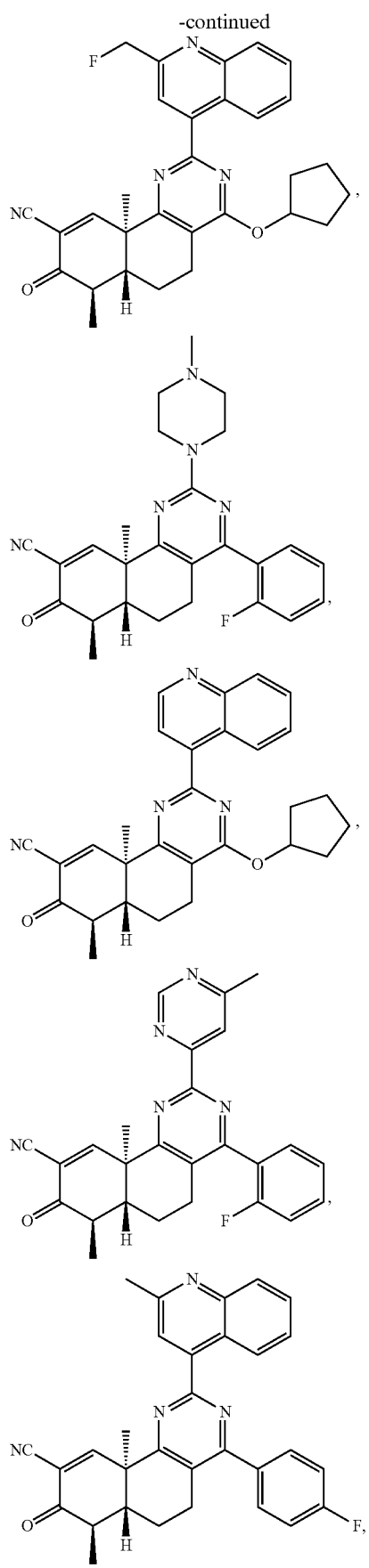
66
-continued
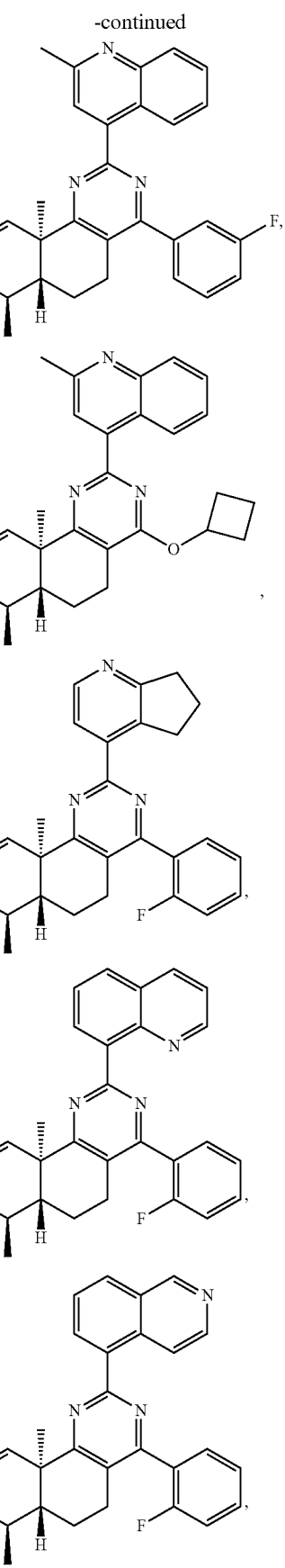

-continued
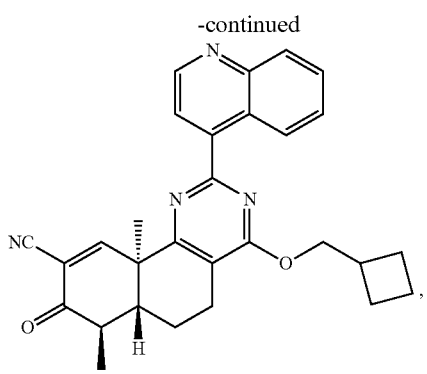
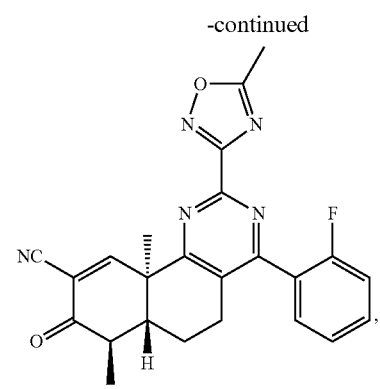
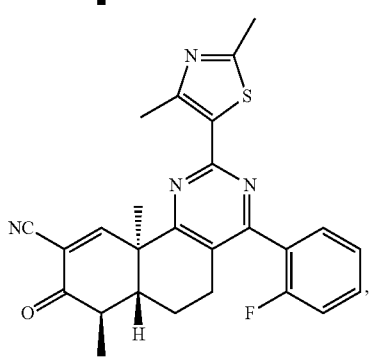
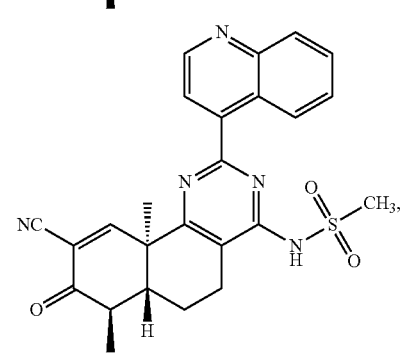
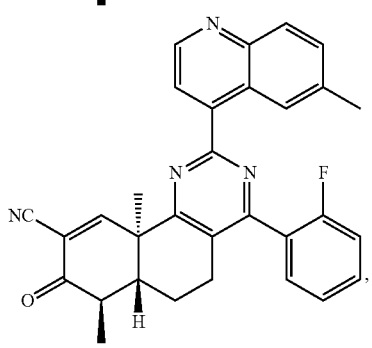
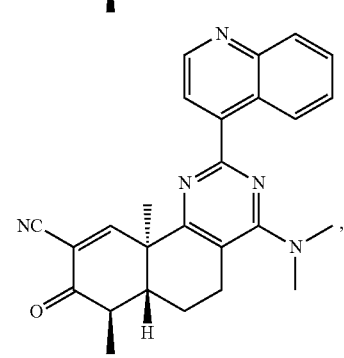
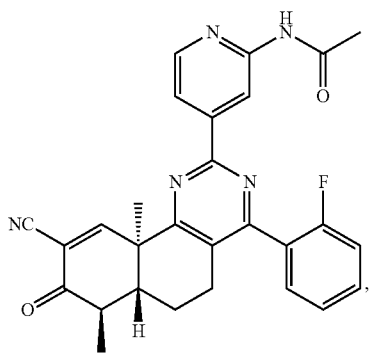
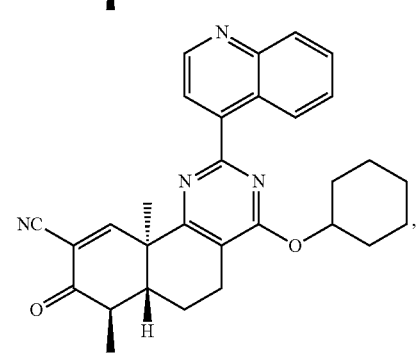
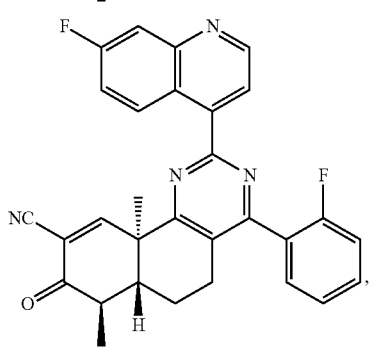
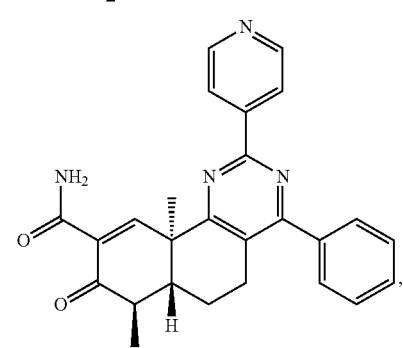

-continued
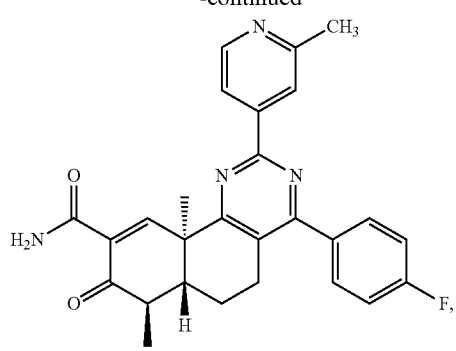
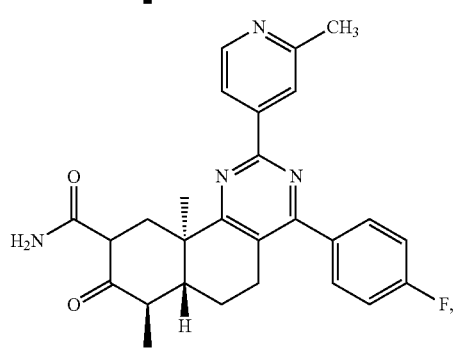
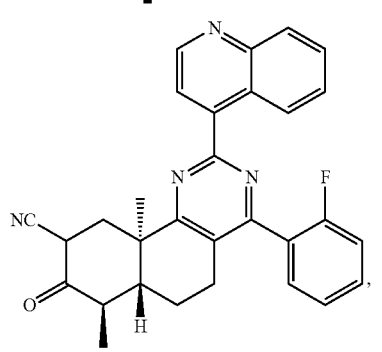
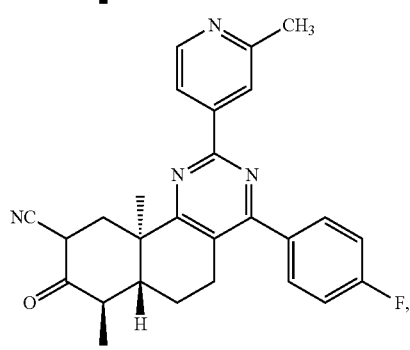
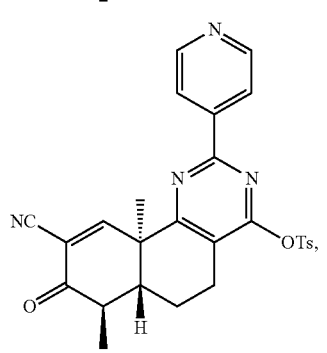
-continued
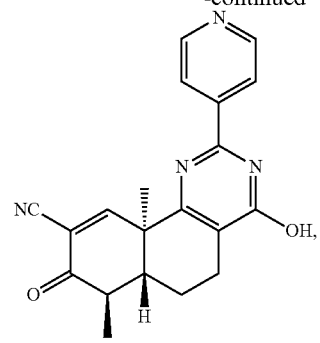
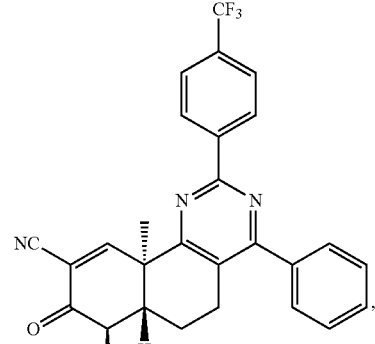
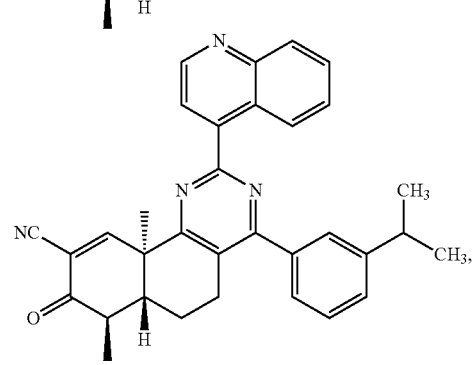
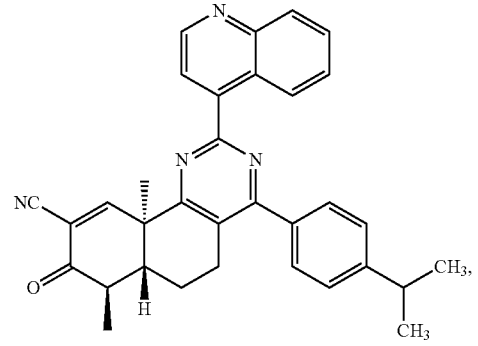
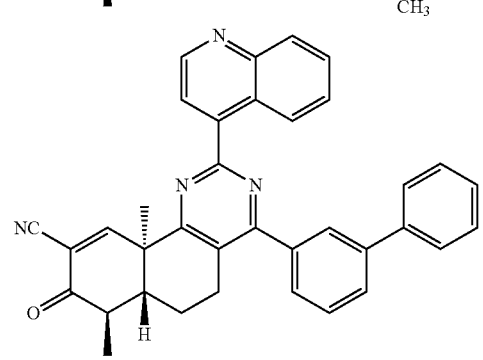

71
-continued
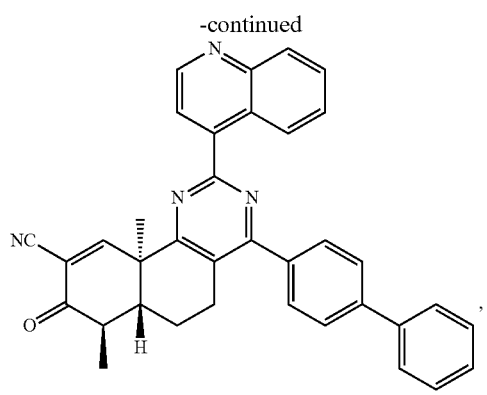
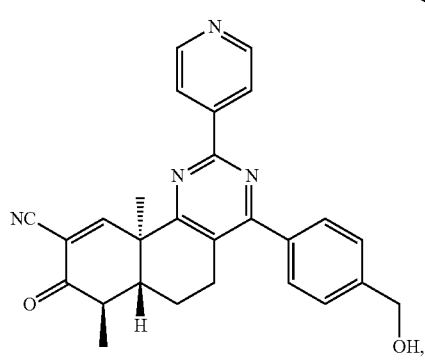
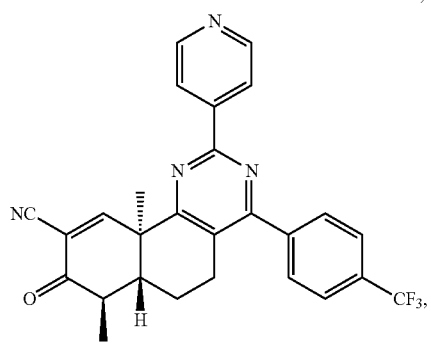
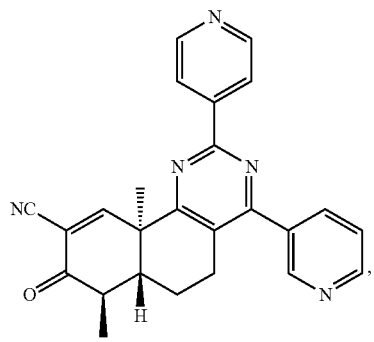
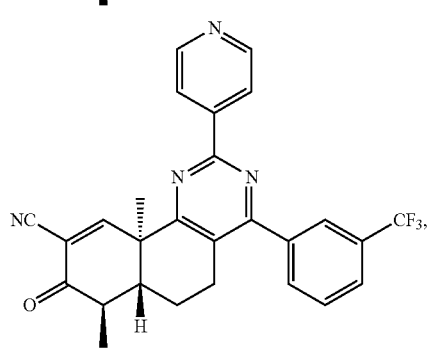
72
-continued
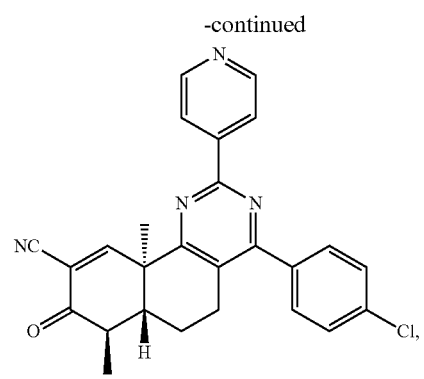
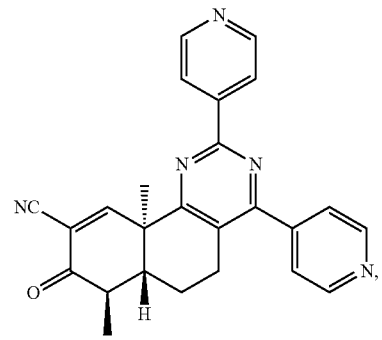
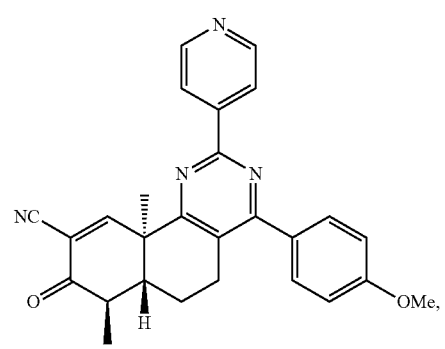
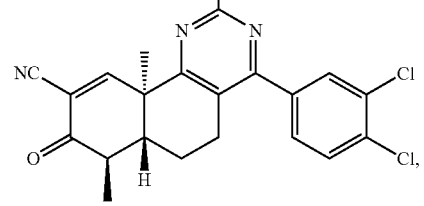
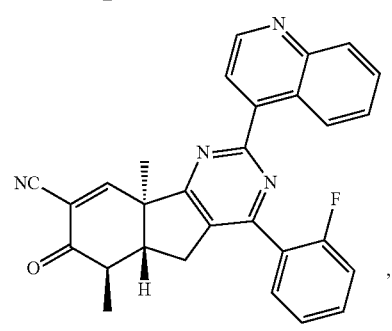

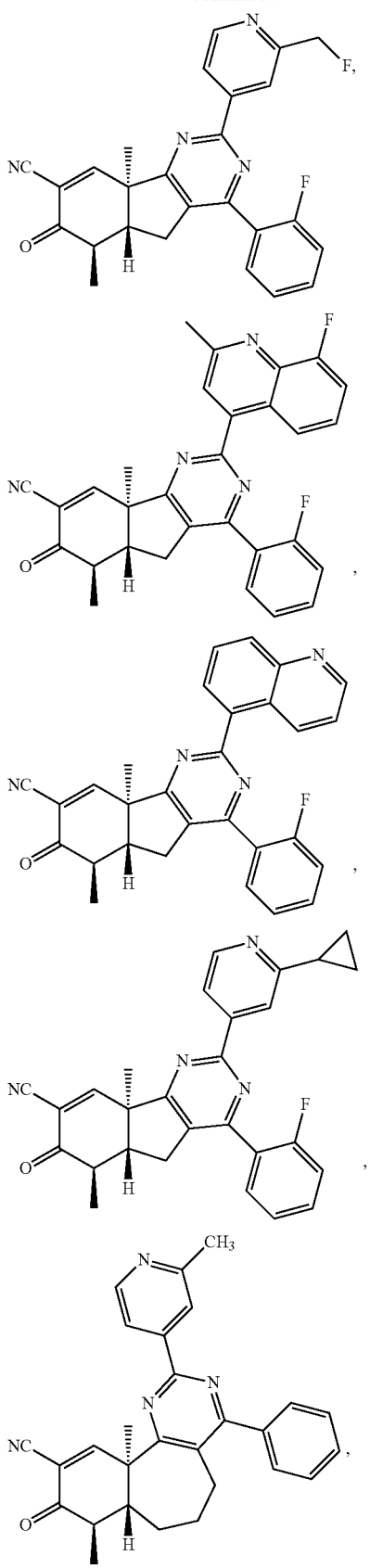
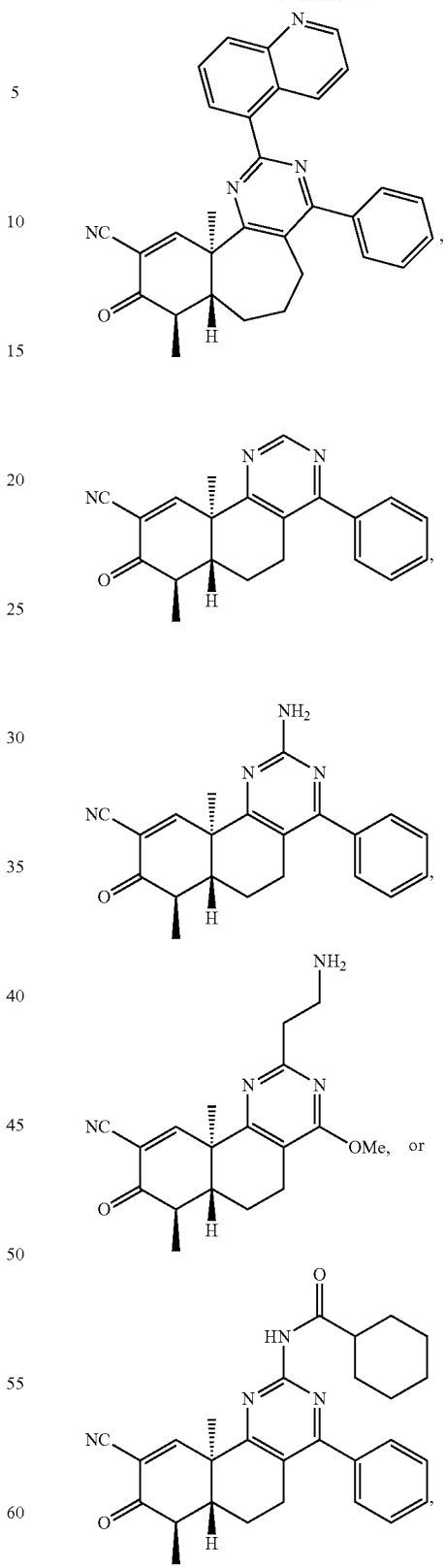
or a pharmaceutically acceptable salt thereof.
In still another aspect, the present disclosure provides compounds of the formula:

75
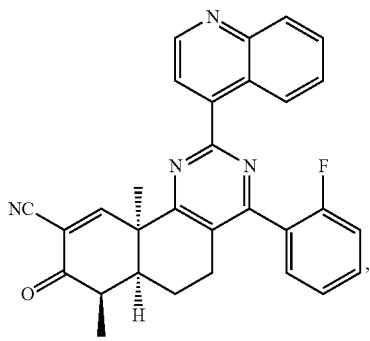
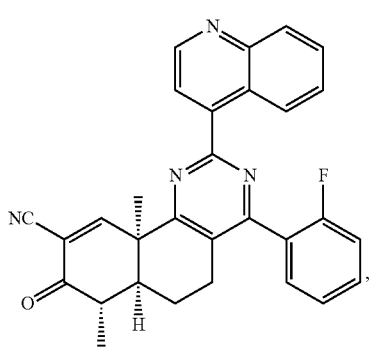
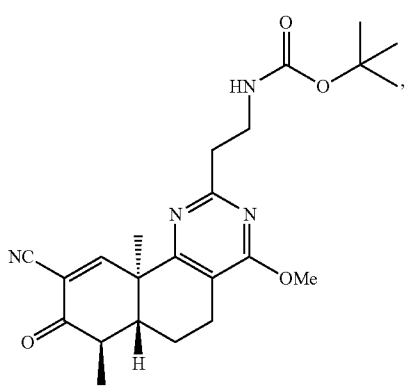
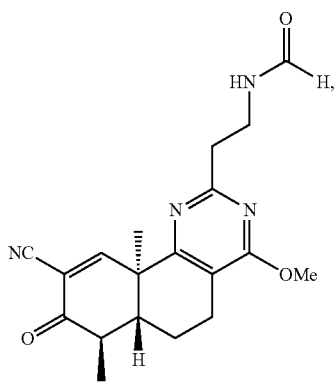
76
-continued
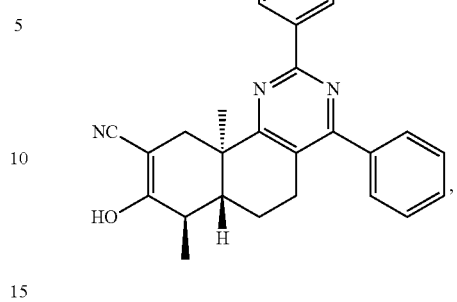
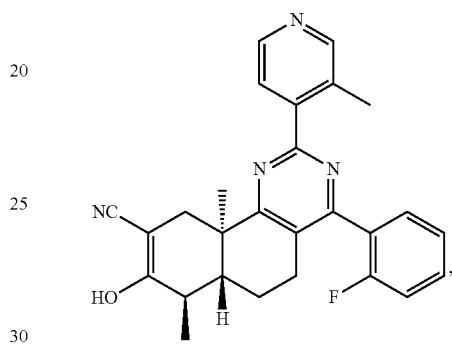
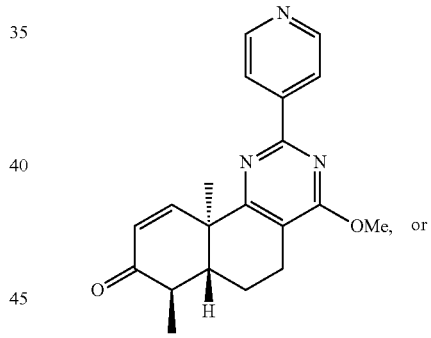
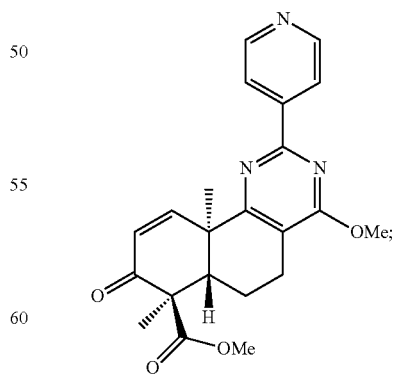
or a pharmaceutically acceptable salt thereof.
In yet another aspect, the present disclosure provides compounds of the formula:

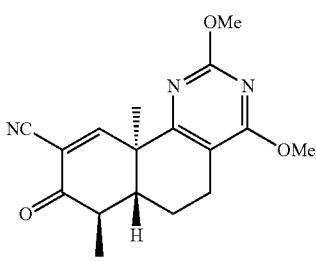 [SMILES: COc1nc(OC)c2c(n1)[C@]1(C)C=C(C#N)C(=O)[C@H](C)[C@H]1CC2]

or a pharmaceutically acceptable salt thereof.

In still yet another aspect, the present disclosure provides compounds further defined as:

(6aR,7R,10aS)-9-cyano-2,4-dimethoxy-7,10a-dimethyl-5,6a,7,10a-tetrahydrobenzo[h]quinazolin-8(6H)-one;

(6aR,7R,10aS)-9-cyano-4-methoxy-2-(2-methoxypyridin-4-yl)-7,10a-dimethyl-5,6a,7,10a-tetrahydrobenzo[h]quinazolin-8(6H)-one;

(6aR,7R,10aS)-9-cyano-4-methoxy-7,10a-dimethyl-2-(2-methylpyridin-4-yl)-5,6a,7,10a-tetrahydrobenzo[h]quinazolin-8(6H)-one;

(6aR,7R,10aS)-9-cyano-4-methoxy-7,10a-dimethyl-2-(3-methylpyridin-4-yl)-5,6a,7,10a-tetrahydrobenzo[h]quinazolin-8(6H)-one;

(6aR,7R,10aS)-9-cyano-4-methoxy-7,10a-dimethyl-2-(pyridin-4-yl)-5,6a,7,10a-tetrahydrobenzo[h]quinazolin-8(6H)-one;

(6aR,7R,10aS)-2-(2-fluoropyridin-4-yl)-9-cyano-4-methoxy-7,10a-dimethyl-5,6a,7,10a-tetrahydrobenzo[h]quinazolin-8(6H)-one;

(6aR,7R,10aS)-9-cyano-4-methoxy-7,10a-dimethyl-2-(pyridin-3-yl)-5,6a,7,10a-tetrahydrobenzo[h]quinazolin-8(6H)-one;

(6aR,7R,10aS)-9-cyano-4-methoxy-7,10a-dimethyl-2-(pyridin-4-ylamino)-5,6a,7,10a-tetrahydrobenzo[h]quinazolin-8(6H)-one;

(6aR,7R,10aS)-9-cyano-4-methoxy-7,10a-dimethyl-2-(quinolin-4-yl)-5,6a,7,10a-tetrahydrobenzo[h]quinazolin-8(6H)-one;

tert-butyl (2-((6aR,7R,10aS)-9-cyano-4-methoxy-7,10a-dimethyl-8-oxo-5,6,6a,7,8,10a-hexahydrobenzo[h]quinazolin-2-yl)ethyl)carbamate;

N-(2-((6aR,7R,10aS)-9-cyano-4-methoxy-7,10a-dimethyl-8-oxo-5,6,6a,7,8,10a-hexahydrobenzo[h]quinazolin-2-yl)ethyl)formamide;

(6aR,7R,10aS)-2-(2-aminoethyl)-9-cyano-4-methoxy-7,10a-dimethyl-5,6a,7,10a-tetrahydrobenzo[h]quinazolin-8(6H)-one;

(6aR,7R,10aR)-8-hydroxy-7,10a-dimethyl-4-phenyl-2-(pyridin-4-yl)-5,6,6a,7,10,10a-hexahydrobenzo[h]quinazoline-9-carbonitrile;

(6aR,7R,10aS)-7,10a-dimethyl-8-oxo-4-phenyl-2-(pyridin-4-yl)-5,6,6a,7,8,10a-hexahydrobenzo[h]quinazoline-9-carbonitrile;

(6aR,7R,8aS,9aS,9bR)-7,9b-dimethyl-8-oxo-4-phenyl-2-(pyridin-4-yl)-6,6a,7,8,9a,9b-hexahydrooxireno[2',3':3,4]benzo[1,2-h]quinazoline-8a(5H)-carbonitrile;

(6aR,7R,10aS)-7,10a-dimethyl-8-oxo-4-phenyl-2-(pyridin-4-yl)-5,6,6a,7,8,10a-hexahydrobenzo[h]quinazoline-9-carboxamide;

(6aR,7R,10aS)-4-hydroxy-7,10a-dimethyl-8-oxo-2-(pyridin-4-yl)-5,6,6a,7,8,10a-hexahydrobenzo[h]quinazoline-9-carbonitrile;

(6aR,7R,10aS)-9-cyano-7,10a-dimethyl-8-oxo-2-(pyridin-4-yl)-5,6,6a,7,8,10a-hexahydrobenzo[h]quinazolin-4-yl 4-methylbenzenesulfonate;

(6aR,7R,10aS)-7,10a-dimethyl-8-oxo-2,4-diphenyl-5,6,6a,7,8,10a-hexahydrobenzo[h]quinazoline-9-carbonitrile;

(6aR,7R,10aS)-7,10a-dimethyl-8-oxo-4-phenyl-2-(4-(trifluoromethyl)phenyl)-5,6,6a,7,8,10a-hexahydrobenzo[h]quinazoline-9-carbonitrile;

(6aR,7R,10aS)-4-(4-(hydroxymethyl)phenyl)-7,10a-dimethyl-8-oxo-2-(pyridin-4-yl)-5,6,6a,7,8,10a-hexahydrobenzo[h]quinazoline-9-carbonitrile;

(6aR,7R,10aS)-7,10a-dimethyl-8-oxo-4-phenyl-5,6,6a,7,8,10a-hexahydrobenzo[h]quinazoline-9-carbonitrile;

(6aR,7R,10aS)-2-cyclohexyl-7,10a-dimethyl-8-oxo-4-phenyl-5,6,6a,7,8,10a-hexahydrobenzo[h]quinazoline-9-carbonitrile;

(6aR,7R,10aS)-7,10a-dimethyl-8-oxo-2-(pyridin-4-yl)-4-(4-(trifluoromethyl)phenyl)-5,6,6a,7,8,10a-hexahydrobenzo[h]quinazoline-9-carbonitrile;

(6aR,7R,10aS)-7,10a-dimethyl-8-oxo-4-(pyridin-3-yl)-2-(pyridin-4-yl)-5,6,6a,7,8,10a-hexahydrobenzo[h]quinazoline-9-carbonitrile;

(6aR,7R,10aS)-7,10a-dimethyl-8-oxo-2-(pyridin-4-yl)-4-(3-(trifluoromethyl)phenyl)-5,6,6a,7,8,10a-hexahydrobenzo[h]quinazoline-9-carbonitrile;

(6aR,7R,10aS)-7,10a-dimethyl-8-oxo-2-(pyridin-4-yl)-4-(p-tolyl)-5,6,6a,7,8,10a-hexahydrobenzo[h]quinazoline-9-carbonitrile;

(6aR,7R,10aS)-4-(4-chlorophenyl)-7,10a-dimethyl-8-oxo-2-(pyridin-4-yl)-5,6,6a,7,8,10a-hexahydrobenzo[h]quinazoline-9-carbonitrile;

(6aR,7R,10aS))-7,10a-dimethyl-8-oxo-2,4-di(pyridin-4-yl)-5,6,6a,7,8,10a-hexahydrobenzo[h]quinazoline-9-carbonitrile;

(6aR,7R,10aS)-4-(4-methoxyphenyl)-7,10a-dimethyl-8-oxo-2-(pyridin-4-yl)-5,6,6a,7,8,10a-hexahydrobenzo[h]quinazoline-9-carbonitrile;

(6aR,7R,10aS)-4-(3,4-dichlorophenyl)-7,10a-dimethyl-8-oxo-2-(pyridin-4-yl)-5,6,6a,7,8,10a-hexahydrobenzo[h]quinazoline-9-carbonitrile;

(6aR,7R,10aS)-7,10a-dimethyl-8-oxo-4-phenyl-2-(quinolin-4-yl)-5,6,6a,7,8,10a-hexahydrobenzo[h]quinazoline-9-carbonitrile;

(6aR,7R,10aS)-2-(2-methoxypyridin-4-yl)-7,10a-dimethyl-8-oxo-4-phenyl-5,6,6a,7,8,10a-hexahydrobenzo[h]quinazoline-9-carbonitrile;

(6aR,7R,10aS)-2-amino-7,10a-dimethyl-8-oxo-4-phenyl-5,6,6a,7,8,10a-hexahydrobenzo[h]quinazoline-9-carbonitrile;

N-((6aR,7R,10aS)-9-cyano-7,10a-dimethyl-8-oxo-4-phenyl-5,6,6a,7,8,10a-hexahydrobenzo[h]quinazolin-2-yl)cyclohexanecarboxamide;

(6aR,7R,10aS)-4-benzyl-7,10a-dimethyl-8-oxo-2-(pyridin-4-yl)-5,6,6a,7,8,10a-hexahydrobenzo[h]quinazoline-9-carbonitrile;

(6aR,7R,10aS)-4-(2-fluorophenyl)-7,10a-dimethyl-8-oxo-2-(quinolin-4-yl)-5,6,6a,7,8,10a-hexahydrobenzo[h]quinazoline-9-carbonitrile;

(R)-4-(2-fluorophenyl)-7,10a-dimethyl-8-oxo-2-(quinolin-4-yl)-5,6,8,10a-tetrahydrobenzo[h]quinazoline-9-carbonitrile;

(6aR,7R,10aS)-4-(3-fluorophenyl)-7,10a-dimethyl-8-oxo-2-(quinolin-4-yl)-5,6,6a,7,8,10a-hexahydrobenzo[h]quinazoline-9-carbonitrile;

(6aR,7R,10aS)-4-(4-fluorophenyl)-7,10a-dimethyl-8-oxo-2-(quinolin-4-yl)-5,6,6a,7,8,10a-hexahydrobenzo[h]quinazoline-9-carbonitrile;

(6aR,7R,10aS)-9-cyano-4-isopropoxy-7,10a-dimethyl-2-(quinolin-4-yl)-5,6a,7,10a-tetrahydrobenzo[h]quinazolin-8(6H)-one;

(6aR,7R,10aS)-9-cyano-4-isopropyl-7,10a-dimethyl-2-(quinolin-4-yl)-5,6a,7,10a-tetrahydrobenzo[h]quinazolin-8(6H)-one;

(6aR,7R,10aS)-7,10a-dimethyl-2-(2-methylpyridin-4-yl)-8-oxo-4-phenyl-5,6,6a,7,8,10a-hexahydrobenzo[h]quinazoline-9-carbonitrile;

tert-butyl 4-((6aR,7R,10aS)-9-cyano-7,10a-dimethyl-8-oxo-4-phenyl-5,6,6a,7,8,10a-hexahydrobenzo[h]quinazolin-2-yl)piperidine-1-carboxylate;

4-((6aR,7R,10aS)-9-cyano-7,10a-dimethyl-8-oxo-4-phenyl-5,6,6a,7,8,10a-hexahydrobenzo[h]quinazolin-2-yl)piperidin-1-ium chloride;

(6aR,7R,10aS)-2-(1-acetylpiperidin-4-yl)-7,10a-dimethyl-8-oxo-4-phenyl-5,6,6a,7,8,10a-hexahydrobenzo[h]quinazoline-9-carbonitrile;

tert-butyl 5-((6aR,7R,10aS)-9-cyano-7,10a-dimethyl-8-oxo-4-phenyl-5,6,6a,7,8,10a-hexahydrobenzo[h]quinazolin-2-yl)-3,6-dihydropyridine-1(2H)-carboxylate;

5-((6aR,7R,10aS)-9-cyano-7,10a-dimethyl-8-oxo-4-phenyl-5,6,6a,7,8,10a-hexahydrobenzo[h]quinazolin-2-yl)-1,2,3,6-tetrahydropyridin-1-ium chloride;

(6aR,7R,10aS)-2-(1-acetyl-1,2,5,6-tetrahydropyridin-3-yl)-7,10a-dimethyl-8-oxo-4-phenyl-5,6,6a,7,8,10a-hexahydrobenzo[h]quinazoline-9-carbonitrile;

(6aR,7R,10aS)-4-(4-fluorophenyl)-7,10a-dimethyl-2-(2-methylpyridin-4-yl)-8-oxo-5,6,6a,7,8,10a-hexahydrobenzo[h]quinazoline-9-carbonitrile;

(6aR,7R,10aS)-4-(2-fluorophenyl)-7,10a-dimethyl-2-(2-methylpyridin-4-yl)-8-oxo-5,6,6a,7,8,10a-hexahydrobenzo[h]quinazoline-9-carbonitrile;

(6aR,7R,10aS)-4-(2,4-difluorophenyl)-7,10a-dimethyl-8-oxo-2-(quinolin-4-yl)-5,6,6a,7,8,10a-hexahydrobenzo[h]quinazoline-9-carbonitrile;

(6aR,7R,10aS)-2-(2-cyclopropylpyridin-4-yl)-4-(2-fluorophenyl)-7,10a-dimethyl-8-oxo-5,6,6a,7,8,10a-hexahydrobenzo[h]quinazoline-9-carbonitrile;

(6aR,7R,10aS)-4-(2-fluorophenyl)-7,10a-dimethyl-8-oxo-2-(2-(trifluoromethyl)pyridin-4-yl)-5,6,6a,7,8,10a-hexahydrobenzo[h]quinazoline-9-carbonitrile;

(6aR,7R,10aR)-4-(2-fluorophenyl)-8-hydroxy-7,10a-dimethyl-2-(3-methylpyridin-4-yl)-5,6,6a,7,10,10a-hexahydrobenzo[h]quinazoline-9-carbonitrile;

(6aR,7R,10aS)-4-(2-fluorophenyl)-7,10a-dimethyl-2-(3-methylpyridin-4-yl)-8-oxo-5,6,6a,7,8,10a-hexahydrobenzo[h]quinazoline-9-carbonitrile;

(6aR,7R,10aS)-4-(2-fluorophenyl)-2-(3-fluoropyridin-4-yl)-7,10a-dimethyl-8-oxo-5,6,6a,7,8,10a-hexahydrobenzo[h]quinazoline-9-carbonitrile;

(6aR,7R,10aS)-4-(2-fluorophenyl)-7,10a-dimethyl-2-(5-methylpyridin-3-yl)-8-oxo-5,6,6a,7,8,10a-hexahydrobenzo[h]quinazoline-9-carbonitrile;

(6aR,7R,10aS)-4-(2-fluorophenyl)-7,10a-dimethyl-8-oxo-2-(quinolin-3-yl)-5,6,6a,7,8,10a-hexahydrobenzo[h]quinazoline-9-carbonitrile;

(6aR,7R,10aS)-4-(2-fluorophenyl)-7,10a-dimethyl-8-oxo-2-(quinolin-6-yl)-5,6,6a,7,8,10a-hexahydrobenzo[h]quinazoline-9-carbonitrile;

N-(4-((6aR,7R,10aS)-9-cyano-4-(2-fluorophenyl)-7,10a-dimethyl-8-oxo-5,6,6a,7,8,10a-hexahydrobenzo[h]quinazolin-2-yl)pyridin-2-yl)acetamide;

(6aR,7R,10aS)-4-(2-fluorophenyl)-7,10a-dimethyl-8-oxo-2-(quinolin-8-yl)-5,6,6a,7,8,10a-hexahydrobenzo[h]quinazoline-9-carbonitrile;

(6aR,7R,10aS)-2-(8-fluoro-2-methylquinolin-4-yl)-4-(2-fluorophenyl)-7,10a-dimethyl-8-oxo-5,6,6a,7,8,10a-hexahydrobenzo[h]quinazoline-9-carbonitrile;

(6aR,7R,10aS)-4-(2-fluorophenyl)-7,10a-dimethyl-2-(2-morpholinopyridin-4-yl)-8-oxo-5,6,6a,7,8,10a-hexahydrobenzo[h]quinazoline-9-carbonitrile;

(6aR,7R,10aS)-4-(2-fluorophenyl)-7,10a-dimethyl-8-oxo-2-(2-phenylpyridin-4-yl)-5,6,6a,7,8,10a-hexahydrobenzo[h]quinazoline-9-carbonitrile;

(6aR,7R,10aS)-4-(2-fluorophenyl)-2-(isoquinolin-4-yl)-7,10a-dimethyl-8-oxo-5,6,6a,7,8,10a-hexahydrobenzo[h]quinazoline-9-carbonitrile;

(6aR,7R,10aS)-4-(2-fluorophenyl)-7,10a-dimethyl-8-oxo-2-(pyrazolo pyridin-3-yl)-5,6,6a,7,8,10a-hexahydrobenzo[h]quinazoline-9-carbonitrile;

(6aR,7R,10aS)-4-(2-fluorophenyl)-7,10a-dimethyl-2-(8-methylquinolin-4-yl)-8-oxo-5,6,6a,7,8,10a-hexahydrobenzo[h]quinazoline-9-carbonitrile;

(6aR,7R,10aS)-4-(2-fluorophenyl)-7,10a-dimethyl-2-(2-methylquinolin-4-yl)-8-oxo-5,6,6a,7,8,10a-hexahydrobenzo[h]quinazoline-9-carbonitrile;

(6aR,7R,10aS)-2-(2,4-dimethylthiazol-5-yl)-4-(2-fluorophenyl)-7,10a-dimethyl-8-oxo-5,6,6a,7,8,10a-hexahydrobenzo[h]quinazoline-9-carbonitrile;

(6aR,7R,10aS)-4-(2-fluorophenyl)-7,10a-dimethyl-2-(5-methyl-1,2,4-oxadiazol-3-yl)-8-oxo-5,6,6a,7,8,10a-hexahydrobenzo[h]quinazoline-9-carbonitrile;

(6aR,7R,10aS)-4-(2-fluorophenyl)-7,10a-dimethyl-2-(1-methyl-/H-pyrrolo[2,3-b]pyridin-3-yl)-8-oxo-5,6,6a,7,8,10a-hexahydrobenzo[h]quinazoline-9-carbonitrile;

(6aR,7R,10aS)-4-(2-fluorophenyl)-7,10a-dimethyl-2-(6-methylquinolin-4-yl)-8-oxo-5,6,6a,7,8,10a-hexahydrobenzo[h]quinazoline-9-carbonitrile;

(6aR,7R,10aS)-4-(2-fluorophenyl)-7,10a-dimethyl-8-oxo-2-(quinazolin-4-yl)-5,6,6a,7,8,10a-hexahydrobenzo[h]quinazoline-9-carbonitrile;

(6aR,7R,10aS)-4-(2-fluorophenyl)-2-(isoquinolin-1-yl)-7,10a-dimethyl-8-oxo-5,6,6a,7,8,10a-hexahydrobenzo[h]quinazoline-9-carbonitrile;

(6aR,7R,10aS)-4-(2-fluorophenyl)-2-(7-fluoroquinolin-4-yl)-7,10a-dimethyl-8-oxo-5,6,6a,7,8,10a-hexahydrobenzo[h]quinazoline-9-carbonitrile;

(6aR,7R,10aS)-4-(2-fluorophenyl)-2-(8-fluoroquinolin-4-yl)-7,10a-dimethyl-8-oxo-5,6,6a,7,8,10a-hexahydrobenzo[h]quinazoline-9-carbonitrile;

(6aR,7R,10aS)-4-(2-fluorophenyl)-7,10a-dimethyl-2-(6-methylpyrimidin-4-yl)-8-oxo-5,6,6a,7,8,10a-hexahydrobenzo[h]quinazoline-9-carbonitrile;

(6aR,7R,10aS)-4-(2-fluorophenyl)-7,10a-dimethyl-8-oxo-2-(pyridazin-4-yl)-5,6,6a,7,8,10a-hexahydrobenzo[h]quinazoline-9-carbonitrile;

(6aR,7R,10aS)-2-(6,7-dihydro-5H-cyclopenta[b]pyridin-4-yl)-4-(2-fluorophenyl)-7,10a-dimethyl-8-oxo-5,6,6a,7,8,10a-hexahydrobenzo[h]quinazoline-9-carbonitrile;

(6aR,7R,10aS)-2,4-bis(2-fluorophenyl)-7,10a-dimethyl-8-oxo-5,6,6a,7,8,10a-hexahydrobenzo[h]quinazoline-9-carbonitrile;

(6aR,7R,10aS)-4-(2-fluorophenyl)-2-(2-(hydroxymethyl)pyridin-4-yl)-7,10a-dimethyl-8-oxo-5,6,6a,7,8,10a-hexahydrobenzo[h]quinazoline-9-carbonitrile;

(6aR,7R,10aS)-2-(2-(fluoromethyl)pyridin-4-yl)-4-(2-fluorophenyl)-7,10a-dimethyl-8-oxo-5,6,6a,7,8,10a-hexahydrobenzo[h]quinazoline-9-carbonitrile;

(6aR,7R,10aS)-4-(2-fluorophenyl)-7,10a-dimethyl-8-oxo-2-(quinolin-5-yl)-5,6,6a,7,8,10a-hexahydrobenzo[h]quinazoline-9-carbonitrile;

(6aR,7R,10aS)-2-(6-fluoro-2-methylquinolin-4-yl)-4-(2-fluorophenyl)-7,10a-dimethyl-8-oxo-5,6,6a,7,8,10a-hexahydrobenzo[h]quinazoline-9-carbonitrile;

(6aR,7R,10aS)-4-(2-fluorophenyl)-2-(isoquinolin-5-yl)-7,10a-dimethyl-8-oxo-5,6,6a,7,8,10a-hexahydrobenzo[h]quinazoline-9-carbonitrile;

(6aR,7R,10aS)-2-(3,5-dimethylisoxazol-4-yl)-4-(2-fluorophenyl)-7,10a-dimethyl-8-oxo-5,6,6a,7,8,10a-hexahydrobenzo[h]quinazoline-9-carbonitrile;

(6aR,7R,10aS)-4-(2-fluorophenyl)-7,10a-dimethyl-2-(6-methylpyridin-3-yl)-8-oxo-5,6,6a,7,8,10a-hexahydrobenzo[h]quinazoline-9-carbonitrile;

(6aR,7R,10aS)-4-(2-fluorophenyl)-2-(6-fluoroquinolin-4-yl)-7,10a-dimethyl-8-oxo-5,6,6a,7,8,10a-hexahydrobenzo[h]quinazoline-9-carbonitrile;

(6aR,7R,10aS)-2-(6,8-difluoroquinolin-4-yl)-4-(2-fluorophenyl)-7,10a-dimethyl-8-oxo-5,6,6a,7,8,10a-hexahydrobenzo[h]quinazoline-9-carbonitrile;

(6aR,7R,10aS)-4-(2-fluorophenyl)-7,10a-dimethyl-2-(4-methylpiperazin-1-yl)-8-oxo-5,6,6a,7,8,10a-hexahydrobenzo[h]quinazoline-9-carbonitrile;

(6aR,7R,10aS)-4-(2-fluorophenyl)-7,10a-dimethyl-2-morpholino-8-oxo-5,6,6a,7,8,10a-hexahydrobenzo[h]quinazoline-9-carbonitrile;

(6aR,7R,10aS)-4-cyclopropyl-7,10a-dimethyl-8-oxo-2-(quinolin-4-yl)-5,6,6a,7,8,10a-hexahydrobenzo[h]quinazoline-9-carbonitrile;

(6aR,7R,10aS)-4-cyclobutoxy-7,10a-dimethyl-8-oxo-2-(quinolin-4-yl)-5,6,6a,7,8,10a-hexahydrobenzo[h]quinazoline-9-carbonitrile;

(6aR,7R,10aS)-4-(cyclobutylmethoxy)-7,10a-dimethyl-8-oxo-2-(quinolin-4-yl)-5,6,6a,7,8,10a-hexahydrobenzo[h]quinazoline-9-carbonitrile;

(6aR,7R,10aS)-4-(cyclohexyloxy)-7,10a-dimethyl-8-oxo-2-(quinolin-4-yl)-5,6,6a,7,8,10a-hexahydrobenzo[h]quinazoline-9-carbonitrile;

(6aR,7R,10aS)-4-(cyclopentyloxy)-7,10a-dimethyl-8-oxo-2-(quinolin-4-yl)-5,6,6a,7,8,10a-hexahydrobenzo[h]quinazoline-9-carbonitrile;

N-((6aR,7R,10aS)-9-cyano-7,10a-dimethyl-8-oxo-2-(quinolin-4-yl)-5,6,6a,7,8,10a-hexahydrobenzo[h]quinazolin-4-yl)methane sulfonamide;

(6aR,7R,10aS)-4-(dimethylamino)-7,10a-dimethyl-8-oxo-2-(quinolin-4-yl)-5,6,6a,7,8,10a-hexahydrobenzo[h]quinazoline-9-carbonitrile;

(6aR,7R,10aS)-4-(3,5-dimethylisoxazol-4-yl)-7,10a-dimethyl-8-oxo-2-(quinolin-4-yl)-5,6,6a,7,8,10a-hexahydrobenzo[h]quinazoline-9-carbonitrile;

N-benzyl-4-((6aR,7R,10aS)-9-cyano-7,10a-dimethyl-8-oxo-2-(quinolin-4-yl)-5,6,6a,7,8,10a-hexahydrobenzo[h]quinazolin-4-yl)-N-methylbenzamide;

(6aR,7R,10aS)-4-(furan-2-yl)-7,10a-dimethyl-8-oxo-2-(quinolin-4-yl)-5,6,6a,7,8,10a-hexahydrobenzo[h]quinazoline-9-carbonitrile;

(6aR,7R,10aS)-4-(benzofuran-2-yl)-7,10a-dimethyl-8-oxo-2-(quinolin-4-yl)-5,6,6a,7,8,10a-hexahydrobenzo[h]quinazoline-9-carbonitrile;

(6aR,7R,10aS)-7,10a-dimethyl-4-(5-methylfuran-2-yl)-8-oxo-2-(quinolin-4-yl)-5,6,6a,7,8,10a-hexahydrobenzo[h]quinazoline-9-carbonitrile;

(6aR,7R,10aS)-7,10a-dimethyl-4-(3-methyl-1,2,4-oxadiazol-5-yl)-8-oxo-2-(quinolin-4-yl)-5,6,6a,7,8,10a-hexahydrobenzo[h]quinazoline-9-carbonitrile;

(6aR,7R,10aS)-7,10a-dimethyl-4-(5-methyl-1,2,4-oxadiazol-3-yl)-8-oxo-2-(quinolin-4-yl)-5,6,6a,7,8,10a-hexahydrobenzo[h]quinazoline-9-carbonitrile;

(6aR,7R,10aS)-7,10a-dimethyl-8-oxo-2-(quinolin-4-yl)-4-(thiazol-2-yl)-5,6,6a,7,8,10a-hexahydrobenzo[h]quinazoline-9-carbonitrile;

(6aR,7R,10aS)-4-(3-fluorophenyl)-7,10a-dimethyl-2-(2-methylquinolin-4-yl)-8-oxo-5,6,6a,7,8,10a-hexahydrobenzo[h]quinazoline-9-carbonitrile;

(6aR,7R,10aS)-4-(4-fluorophenyl)-7,10a-dimethyl-2-(2-methylquinolin-4-yl)-8-oxo-5,6,6a,7,8,10a-hexahydrobenzo[h]quinazoline-9-carbonitrile;

(6aR,7R,10aS)-4-cyclobutoxy-7,10a-dimethyl-2-(2-methylquinolin-4-yl)-8-oxo-5,6,6a,7,8,10a-hexahydrobenzo[h]quinazoline-9-carbonitrile;

(6aR,7R,10aS)-4-(cyclopentyloxy)-7,10a-dimethyl-2-(2-methylquinolin-4-yl)-8-oxo-5,6,6a,7,8,10a-hexahydrobenzo[h]quinazoline-9-carbonitrile;

(6aR,7R,10aS)-4-cyclobutoxy-7,10a-dimethyl-8-oxo-2-(quinazolin-4-yl)-5,6,6a,7,8,10a-hexahydrobenzo[h]quinazoline-9-carbonitrile;

(6aR,7R,10aS)-4-(3-fluorophenyl)-7,10a-dimethyl-8-oxo-2-(quinazolin-4-yl)-5,6,6a,7,8,10a-hexahydrobenzo[h]quinazoline-9-carbonitrile;

(6aR,7R,10aS)-4-(4-fluorophenyl)-7,10a-dimethyl-8-oxo-2-(quinazolin-4-yl)-5,6,6a,7,8,10a-hexahydrobenzo[h]quinazoline-9-carbonitrile;

(6aR,7R,10aS)-2-(2-(fluoromethyl)quinolin-4-yl)-4-(2-fluorophenyl)-7,10a-dimethyl-8-oxo-5,6,6a,7,8,10a-hexahydrobenzo[h]quinazoline-9-carbonitrile;

(6aR,7R,10aS)-4-(2-fluorophenyl)-2-(2-formylquinolin-4-yl)-7,10a-dimethyl-8-oxo-5,6,6a,7,8,10a-hexahydrobenzo[h]quinazoline-9-carbonitrile;

(4-((6aR,7R,10aS)-9-cyano-4-(2-fluorophenyl)-7,10a-dimethyl-8-oxo-5,6,6a,7,8,10a-hexahydrobenzo[h]quinazolin-2-yl)quinolin-2-yl)methyl acetate;

(6aS,10aR)-4-(2-fluorophenyl)-7,7,10a-trimethyl-8-oxo-2-(quinolin-4-yl)-5,6,6a,7,8,10a-hexahydrobenzo[h]quinazoline-9-carbonitrile;

(6aS,10aR)-4-(2-fluorophenyl)-7,7,10a-trimethyl-2-(2-methylquinolin-4-yl)-8-oxo-5,6,6a,7,8,10a-hexahydrobenzo[h]quinazoline-9-carbonitrile;

(6aR,7R,10aS)-4-(cyclopentyloxy)-2-(2-(fluoromethyl)quinolin-4-yl)-7,10a-dimethyl-8-oxo-5,6,6a,7,8,10a-hexahydrobenzo[h]quinazoline-9-carbonitrile;

(6aR,7R,10aS)-4-(cyclopentyloxy)-2-(8-fluoroquinolin-4-yl)-7,10a-dimethyl-8-oxo-5,6,6a,7,8,10a-hexahydrobenzo[h]quinazoline-9-carbonitrile;

(6aS,10aR)-2-(2-(fluoromethyl)quinolin-4-yl)-4-(2-fluorophenyl)-7,7,10a-trimethyl-8-oxo-5,6,6a,7,8,10a-hexahydrobenzo[h]quinazoline-9-carbonitrile;

(6aR,7R,10aS)-4-(2-fluorophenyl)-2-(2-isopropylquinolin-4-yl)-7,10a-dimethyl-8-oxo-5,6,6a,7,8,10a-hexahydrobenzo[h]quinazoline-9-carbonitrile;

(6aS,7R,10aR)-4-(2-fluorophenyl)-7,10a-dimethyl-8-oxo-7-propyl-2-(quinolin-4-yl)-5,6,6a,7,8,10a-hexahydrobenzo[h]quinazoline-9-carbonitrile;

(6aS,10aR)-2-(2-cyclopropylpyridin-4-yl)-4-(2-fluorophenyl)-7,7,10a-trimethyl-8-oxo-5,6,6a,7,8,10a-hexahydrobenzo[h]quinazoline-9-carbonitrile;

(6aS,7R,10aR)-7-ethyl-4-(2-fluorophenyl)-7,10a-dimethyl-8-oxo-2-(quinolin-4-yl)-5,6,6a,7,8,10a-hexahydrobenzo[h]quinazoline-9-carbonitrile;

(6aS,10aR)-4-(2-fluorophenyl)-2-(8-fluoroquinolin-4-yl)-7,7,10a-trimethyl-8-oxo-5,6,6a,7,8,10a-hexahydrobenzo[h]quinazoline-9-carbonitrile;

(R)-4-(2-fluorophenyl)-2-(8-fluoroquinolin-4-yl)-7,10a-dimethyl-8-oxo-5,6,8,10a-tetrahydrobenzo[h]quinazoline-9-carbonitrile;

(6aR,7R,8aS,9aS,9bR)-4-(2-fluorophenyl)-2-(7-fluoroquinolin-4-yl)-7,9b-dimethyl-8-oxo-6,6a,7,8,9a,9b-hexahydrooxireno[2$^1$,3':3,4]benzo[1,2-h]quinazoline-8a(5H)-carbonitrile;

(6aR,7R,8aS,9aS,9bR)-2-(2-cyclopropylpyridin-4-yl)-4-(2-fluorophenyl)-7,9b-dimethyl-8-oxo-6,6a,7,8,9a,9b-hexahydrooxireno[2',3':3,4]benzo[1,2-h]quinazoline-8a(5H)-carbonitrile;

(6aR,7R,8aS,9aS,9bR)-4-(2-fluorophenyl)-2-(iso quinolin-4-yl)-7,9b-dimethyl-8-oxo-6,6a,7,8,9a,9b-hexahydrooxireno[2',3':3,4]benzo[1,2-h]quinazoline-8a(5H)-carbonitrile;

(6aR,7R,8aS,9aS,9bR)-4-(2-fluorophenyl)-7,9b-dimethyl-8-oxo-2-(quinolin-4-yl)-6,6a,7,8,9a,9b-hexahydrooxireno[2',3':3,4]benzo[1,2-h]quinazoline-8a(5H)-carbonitrile;

(6aS,8aS,9aS,9bR)-4-(2-fluorophenyl)-7,7,9b-trimethyl-8-oxo-2-(quinolin-4-yl)-6,6a,7,8,9a,9b-hexahydrooxireno[2',3':3,4]benzo[1,2-h]quinazoline-8a(5H)-carbonitrile;

(6aR,7R,10aR)-4-methoxy-7,10a-dimethyl-2-(pyridin-4-yl)-5,6a,7,10a-tetrahydrobenzo[h]quinazolin-8(6H)-one;

methyl (6aS,7R,10aR)-4-methoxy-7,10a-dimethyl-8-oxo-2-(pyridin-4-yl)-5,6,6a,7,8,10a-hexahydrobenzo[h]quinazoline-7-carboxy late;

(6aS,7R,10aR)-2-(2-cyclopropylpyridin-4-yl)-4-(2-fluorophenyl)-7-(3-hydroxypropyl)-7,10a-dimethyl-8-oxo-5,6,6a,7,8,10a-hexahydrobenzo[h]quinazoline-9-carbonitrile;

(6aS,7R,10aR)-2-(2-cyclopropylpyridin-4-yl)-4-(2-fluorophenyl)-7,10a-dimethyl-8-oxo-7-propyl-5,6,6a,7,8,10a-hexahydrobenzo[h]quinazoline-9-carbonitrile;

(6aR,7R,10aS)-7,10a-dimethyl-8-oxo-4-(pyrrolidin-1-yl)-2-(quinolin-4-yl)-5,6,6a,7,8,10a-hexahydrobenzo[h]quinazoline-9-carbonitrile;

(6aR,7R,10aS)-2-(4-acetylpiperazin-1-yl)-4-(2-fluorophenyl)-7,10a-dimethyl-8-oxo-5,6,6a,7,8,10a-hexahydrobenzo[h]quinazoline-9-carbonitrile;

(6aR,7R,10aS)-2-(6-cyclopropylpyridin-3-yl)-4-(2-fluorophenyl)-7,10a-dimethyl-8-oxo-5,6,6a,7,8,10a-hexahydrobenzo[h]quinazoline-9-carbonitrile;

(6aR,7R,10aS)-4-(2-fluorophenyl)-7,10a-dimethyl-8-oxo-2-(6-phenylpyridin-3-yl)-5,6,6a,7,8,10a-hexahydrobenzo[h]quinazoline-9-carbonitrile;

(6aR,7R,10aS)-4-(2-fluorophenyl)-7,10a-dimethyl-2-(6-(2-(methylsulfonyl)ethyl)pyridin-3-yl)-8-oxo-5,6,6a,7,8,10a-hexahydrobenzo[h]quinazoline-9-carbonitrile;

(6aR,7R,10aS)-4-(2-fluorophenyl)-7,10a-dimethyl-2-(2-((methylsulfonyl)methyl)pyridin-4-yl)-8-oxo-5,6,6a,7,8,10a-hexahydrobenzo[h]quinazoline-9-carbonitrile;

(6aR,7R,10aS)-4-(2-fluorophenyl)-7,10a-dimethyl-2-(2-(2-(methylsulfonyl)ethyl)pyridin-4-yl)-8-oxo-5,6,6a,7,8,10a-hexahydrobenzo[h]quinazoline-9-carbonitrile;

(6aR,7R,10aS)-7-allyl-2-(2-cyclopropylpyridin-4-yl)-4-(2-fluorophenyl)-10a-methyl-8-oxo-5,6,6a,7,8,10a-hexahydrobenzo[h]quinazoline-9-carbonitrile;

(6aR,7R,10aS)-2-(2-cyclopropylpyridin-4-yl)-4-(2-fluorophenyl)-10a-methyl-8-oxo-7-propyl-5,6,6a,7,8,10a-hexahydrobenzo[h]quinazoline-9-carbonitrile;

(6aR,7R,10aS)-2-(2-cyclopropylpyridin-4-yl)-4-(2-fluorophenyl)-7-methyl-8-oxo-10a-phenyl-5,6,6a,7,8,10a-hexahydrobenzo[h]quinazoline-9-carbonitrile;

(6aR,7R,10aS)-4-(2-fluorophenyl)-7-methyl-8-oxo-10a-phenyl-2-(quinolin-4-yl)-5,6,6a,7,8,10a-hexahydrobenzo[h]quinazoline-9-carbonitrile;

(6aS,10aS)-4-(2-fluorophenyl)-7,7,10a-trimethyl-8-oxo-2-(quinolin-5-yl)-5,6,6a,7,8,10a-hexahydrobenzo[h]quinazoline-9-carbonitrile;

3-(4-((6aR,7R,10aS)-9-cyano-4-(2-fluorophenyl)-7,10a-dimethyl-8-oxo-5,6,6a,7,8,10a-hexahydrobenzo[h]quinazolin-2-yl)pyridin-2-yl)propanoic acid;

ethyl 3-(4-((6aR,7R,10aS)-9-cyano-4-(2-fluorophenyl)-7,10a-dimethyl-8-oxo-5,6,6a,7,8,10a-hexahydrobenzo[h]quinazolin-2-yl)pyridin-2-yl)propanoate;

3-(4-((6aR,7R,10aS)-9-cyano-4-(2-fluorophenyl)-7,10a-dimethyl-8-oxo-5,6,6a,7,8,10a-hexahydrobenzo[h]quinazolin-2-yl)pyridin-2-yl)-N,N-dimethylpropanamide;

(6aR,7R,10aS)-2-(2-(2-(ethylsulfonyl)ethyl)pyridin-4-yl)-4-(2-fluorophenyl)-7,10a-dimethyl-8-oxo-5,6,6a,7,8,10a-hexahydrobenzo[h]quinazoline-9-carbonitrile;

(6aR,7R,10aS)-2-(2-((ethylsulfonyl)methyl)pyridin-4-yl)-4-(2-fluorophenyl)-7,10a-dimethyl-8-oxo-5,6,6a,7,8,10a-hexahydrobenzo[h]quinazoline-9-carbonitrile;

(6aR,10aS)-2-(2-(fluoromethyl)pyridin-4-yl)-4-(2-fluorophenyl)-8-oxo-10a-propyl-5,6,6a,7,8,10a-hexahydrobenzo[h]quinazoline-9-carbonitrile;

(6aR,10aS)-4-(2-fluorophenyl)-8-oxo-10a-propyl-2-(quinolin-4-yl)-5,6,6a,7,8,10a-hexahydrobenzo[h]quinazoline-9-carbonitrile;

(6aS,10aR)-7-(cyclopropylmethyl)-4-(2-fluorophenyl)-7,10a-dimethyl-8-oxo-2-(quinolin-4-yl)-5,6,6a,7,8,10a-hexahydrobenzo[h]quinazoline-9-carbonitrile;

(6aR,7R,10aS)-4-(2-fluorophenyl)-10a-methyl-8-oxo-7-propyl-2-(quinolin-4-yl)-5,6,6a,7,8,10a-hexahydrobenzo[h]quinazoline-9-carbonitrile;

(6aR,7R,10aS)-4-(2-fluorophenyl)-10a-methyl-8-oxo-7-propyl-2-(quinolin-5-yl)-5,6,6a,7,8,10a-hexahydrobenzo[h]quinazoline-9-carbonitrile;

(6aR,7R,10aS)-4-(3-isopropylphenyl)-7,10a-dimethyl-8-oxo-2-(quinolin-4-yl)-5,6,6a,7,8,10a-hexahydrobenzo[h]quinazoline-9-carbonitrile;

(6aR,7R,10aS)-4-(4-isopropylphenyl)-7,10a-dimethyl-8-oxo-2-(quinolin-4-yl)-5,6,6a,7,8,10a-hexahydrobenzo[h]quinazoline-9-carbonitrile;

(6aR,7R,10aS)-4-([1,1'-biphenyl]-3-yl)-7,10a-dimethyl-8-oxo-2-(quinolin-4-yl)-5,6,6a,7,8,10a-hexahydrobenzo[h]quinazoline-9-carbonitrile;

(6aR,7R,10aS)-4-([1,1'-biphenyl]-4-yl)-7,10a-dimethyl-8-oxo-2-(quinolin-4-yl)-5,6,6a,7,8,10a-hexahydrobenzo[h]quinazoline-9-carbonitrile;

(6aR,10aS)-4-(2-fluorophenyl)-10a-isopentyl-8-oxo-2-(quinolin-4-yl)-5,6,6a,7,8,10a-hexahydrobenzo[h]quinazoline-9-carbonitrile;

(6aR,10aS)-2-(2-(fluoromethyl)pyridin-4-yl)-4-(2-fluorophenyl)-10a-isopentyl-8-oxo-5,6,6a,7,8,10a-hexahydrobenzo[h]quinazoline-9-carbonitrile;

(6aS,7R,10aR)-4-(2-fluorophenyl)-7,10a-dimethyl-7-(2-methylallyl)-8-oxo-2-(quinolin-4-yl)-5,6,6a,7,8,10a-hexahydrobenzo[h]quinazoline-9-carbonitrile;

(6aR,10aS)-2-(2-cyclopropylpyridin-4-yl)-4-(2-fluorophenyl)-8-oxo-10a-propyl-5,6,6a,7,8,10a-hexahydrobenzo[h]quinazoline-9-carbonitrile;

(6aR,7R,10aS)-2-(2-cyclopropylpyridin-4-yl)-4-(2-fluorophenyl)-8-oxo-7,10a-dipropyl-5,6,6a,7,8,10a-hexahydrobenzo[h]quinazoline-9-carbonitrile;

(6aR,7R,10aS)-2-(2-cyclopropylpyridin-4-yl)-4-(2-fluorophenyl)-7-methyl-8-oxo-10a-propyl-5,6,6a,7,8,10a-hexahydrobenzo[h]quinazoline-9-carbonitrile;

(5aR,6R,9aS)-4-(2-fluorophenyl)-6,9a-dimethyl-7-oxo-2-(quinolin-4-yl)-5a,6,7,9a-tetrahydro-5H-indeno[1,2-d]pyrimidine-8-carbonitrile;

(5aR,6R,9aS)-2-(2-(fluoromethyl)pyridin-4-yl)-4-(2-fluorophenyl)-6,9a-dimethyl-7-oxo-5a,6,7,9a-tetrahydro-5H-indeno[1,2-d]pyrimidine-8-carbonitrile;

(5aR,6R,9aS)-2-(8-fluoro-2-methylquinolin-4-yl)-4-(2-fluorophenyl)-6,9a-dimethyl-7-oxo-5a,6,7,9a-tetrahydro-5H-indeno[1,2-d]pyrimidine-8-carbonitrile;

(5aR,6R,9aS)-4-(2-fluorophenyl)-6,9a-dimethyl-7-oxo-2-(quinolin-5-yl)-5a,6,7,9a-tetrahydro-5H-indeno[1,2-d]pyrimidine-8-carbonitrile;

(5aR,6R,9aS)-2-(2-cyclopropylpyridin-4-yl)-4-(2-fluorophenyl)-6,9a-dimethyl-7-oxo-5a,6,7,9a-tetrahydro-5H-indeno[1,2-d]pyrimidine-8-carbonitrile;

(6aS,7S,10aS)-4-(2-fluorophenyl)-7,10a-dimethyl-8-oxo-2-(quinolin-4-yl)-5,6,6a,7,8,10a-hexahydrobenzo[h]quinazoline-9-carbonitrile;

(6aS,7R,10aS)-4-(2-fluorophenyl)-7,10a-dimethyl-8-oxo-2-(quinolin-4-yl)-5,6,6a,7,8,10a-hexahydrobenzo[h]quinazoline-9-carbonitrile;

3-(4-((6aR,7R,10aS)-9-cyano-4-(2-fluorophenyl)-7,10a-dimethyl-8-oxo-5,6,6a,7,8,10a-hexahydrobenzo[h]quinazolin-2-yl)pyridin-2-yl)propanamide;

N-(2-(4-((6aR,7R,10aS)-9-cyano-4-(2-fluorophenyl)-7,10a-dimethyl-8-oxo-5,6,6a,7,8,10a-hexahydrobenzo[h]quinazolin-2-yl)pyridin-2-yl)ethyl)acetamide;

(6aR,7R,10aS)-4-(2-fluorophenyl)-7,10a-dimethyl-8-oxo-2-(3-phenylpyridin-4-yl)-5,6,6a,7,8,10a-hexahydrobenzo[h]quinazoline-9-carbonitrile;

(6aR,7R,10aS)-2-(3-cyclopropylpyridin-4-yl)-4-(2-fluorophenyl)-7,10a-dimethyl-8-oxo-5,6,6a,7,8,10a-hexahydrobenzo[h]quinazoline-9-carbonitrile;

(6aS,7R,10aR)-2-(2-cyclopropylpyridin-4-yl)-7-ethyl-4-(2-fluorophenyl)-7,10a-dimethyl-8-oxo-5,6,6a,7,8,10a-hexahydrobenzo[h]quinazoline-9-carbonitrile;

(7aR,8R,11aS)-8,11a-dimethyl-2-(2-methylpyridin-4-yl)-9-oxo-4-phenyl-6,7,7a,8,9,11a-hexahydro-5H-benzo[6,7]cyclohepta[1,2-d]pyrimidine-10-carbonitrile;

(7aR,8R,11aS)-8,11a-dimethyl-9-oxo-4-phenyl-2-(quinolin-5-yl)-6,7,7a,8,9,11a-hexahydro-5H-benzo[6,7]cyclohepta[1,2-d]pyrimidine-10-carbonitrile;

(6aR,7R,10aS)-4-(4-fluorophenyl)-7,10a-dimethyl-2-(2-methylpyridin-4-yl)-8-oxo-5,6,6a,7,8,10a-hexahydrobenzo[h]quinazoline-9-carboxamide;

(6aR,7R,10aR)-4-(4-fluorophenyl)-7,10a-dimethyl-2-(2-methylpyridin-4-yl)-8-oxo-5,6,6a,7,8,9,10,10a-octahydrobenzo[h]quinazoline-9-carboxamide; and (6aR,7R,10aR)-4-(4-fluorophenyl)-7,10a-dimethyl-2-(2-methylpyridin-4-yl)-8-oxo-5,6,6a,7,8,9,10,10a-octahydrobenzo[h]quinazoline-9-carbonitrile;

or a pharmaceutically acceptable salt thereof.

In still another aspect, the present disclosure provides pharmaceutical compositions comprising:

(A) a compound described herein; and (B) an excipient.

In some embodiments, the pharmaceutical compositions are formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in crémes, in lipid compositions, via a catheter, via a lavage, via continuous infusion, via infusion, via inhalation, via injection, via local delivery, or via localized perfusion. In some embodiments, the pharmaceutical compositions are formulated for oral administration. In other embodiments, the pharmaceutical compositions are formulated for administration via injection. In other embodiments, the pharmaceutical compositions are formulated for intraarterial administration, intramuscular administration, intraperitoneal administration, or intravenous administration. In other embodiments, the pharmaceutical compositions are formulated for administration topically such as for topical administration to the skin or to the eye. In other embodiments, the pharmaceutical compositions are formulated as a unit dose.

In yet another aspect, the present disclosure provides methods of treating or preventing a disease or disorder in a patient in need thereof comprising administering to the patient a pharmaceutically effective amount of a compound or composition described herein. In some embodiments, the patient is a mammal such as a human. In some embodiments, the disease or disorder is associated with increased production of cytokine IL-17. In some embodiments, the disease or disorder is associated with dysregulated angiogenesis.

In some embodiments, the disease or disorder is an autoimmune disease, organ rejection, asthma, cancer, a neurological disorder, a psychiatric disorder, a neuropsychiatric disorder, chronic pain syndrome, an inflammatory condition, a retinal disorder, or a cardiovascular disease. In some embodiments, the disease or disorder is cancer In some embodiments, the disease or disorder is an autoimmune disease such as psoriasis, multiple sclerosis, scleroderma, rheumatoid arthritis, lupus, psoriatic arthritis, ankylosing spondylitis, Sjögren syndrome, vitiligo, uveitis, dry eye syndrome, systemic sclerosis, type 1 diabetes, myasthenia gravis, and inflammatory bowel disease. In other embodiments, the disease or disorder is a cardiovascular disease such as vasculitis, atherosclerosis, myocardial infarction, myocarditis, heart failure, pulmonary hypertension, or stroke. In other embodiments, the disease or disorder is a neurological disorder such as epilepsy, multiple sclerosis, spinal cord injury, Guillain-Barre syndrome, or another neurological disorder involving dysregulated inflammatory signaling. In other embodiments, the disease or disorder is a neurodegenerative disorder such as Alzheimer's disease, Parkinson's disease, amyotrophic lateral sclerosis, or Huntington's disease. In other embodiments, the disease or disorder is an inflammatory condition such as pancreatitis, hepatitis, pulmonary fibrosis, cystic fibrosis, chronic obstructive pulmonary disease, asthma, dermatitis, gastritis, esophagitis, irritable bowel syndrome, inflammatory bowel disease, nephritis, muscle wasting, or osteoarthritis. In other embodiments, the disease or disorder is a chronic pain syndrome such as fibromyalgia or neuropathic pain. In other embodiments, the disease or disorder is a severe inflammatory response to a pathogen such as from encephalitis, meningitis, *H. pylori*, *Toxoplasma gondii*, or *Leishmania* spp. In other embodiments, the disease or disorder is obesity or a condition associated with obesity. In some embodiments, the condition associated with obesity is insulin resistance or fatty liver disease. In some embodiments, the retinal disorder is macular degeneration or another disorder of the retina.

In some embodiments, the disease or disorder is associated with inflammation. In some embodiments, the disease or disorder associated with inflammation is obesity, Type 2 diabetes, or a complication of Type 1 or Type 2 diabetes. In some embodiments, the complication of Type 1 or Type 2 diabetes is neuropathy, reduced kidney function or chronic kidney disease, retinopathy, diabetic ulcers, or cardiovascular disease. In other embodiments, the disease or disorder associated with inflammation is chronic kidney disease. In some embodiments, the chronic kidney disease is hereditary. In other embodiments, the chronic kidney disease is due to a non-hereditary cause.

In some embodiments, the methods comprise administering the compound once. In other embodiments, the methods comprise administering the compound two or more times.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

DESCRIPTION OF ILLUSTRATIVE EMBODIMENTS

Disclosed herein are new compounds and compositions that may be used to inhibit the activity of the RORγ nuclear receptor and/or IL-17 and are thus useful in the treatment of a wide variety of different indications such as autoimmune disease, metabolic diseases, cancer, and infections. In some embodiments, these compounds may be used to modulate the expression of one or more downstream compound such as interleukin-17 (IL-17), prevent or inhibit excessive production of IL-17, reduce circulating levels of IL-17, and/or prevent or treat wide range of diseases or disorders, including those with inflammatory and autoimmune-related components.

I. COMPOUNDS AND SYNTHETIC METHODS

The compounds of the present invention (also referred to as "compounds of the present disclosure") are shown, for example, above, in the summary of the invention section, and in the claims below. They may be made using the synthetic methods outlined in the Examples section. These methods can be further modified and optimized using the principles and techniques of organic chemistry as applied by a person skilled in the art. Such principles and techniques are taught, for example, in Smith, *March's Advanced Organic Chemistry: Reactions, Mechanisms, and Structure*, (2013), which is incorporated by reference herein. In addition, the synthetic methods may be further modified and optimized for preparative, pilot- or large-scale production, either batch or continuous, using the principles and techniques of process chemistry as applied by a person skilled in the art. Such principles and techniques are taught, for example, in Anderson, *Practical Process Research & Development A Guide for Organic Chemists* (2012), which is incorporated by reference herein.

All of the compounds of the present invention may be useful for the prevention and treatment of one or more diseases or disorders discussed herein or otherwise. In some embodiments, one or more of the compounds characterized or exemplified herein as an intermediate, a metabolite, and/or prodrug, may nevertheless also be useful for the prevention and treatment of one or more diseases or disorders. As such unless explicitly stated to the contrary, all of the compounds of the present invention are deemed "active compounds" and "therapeutic compounds" that are contemplated for use as active pharmaceutical ingredients (APIs). Actual suitability for human or veterinary use is typically determined using a combination of clinical trial protocols and regulatory procedures, such as those administered by the Food and Drug Administration (FDA). In the United States, the FDA is responsible for protecting the public health by assuring the safety, effectiveness, quality, and security of human and veterinary drugs, vaccines and other biological products, and medical devices.

In some embodiments, the compounds of the present invention have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

Compounds of the present invention may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration. In some embodiments, the present compounds may contain two or more atoms which have a defined stereochemical orientation.

In one aspect, the compounds of the present invention contain at least one stereogenic centers at carbon atoms 4, 5, and 10. In some embodiments, carbon atom 10 is in the S configuration. In some embodiments, the compounds of the present invention contain a stereogenic center at carbon atom 5, provided that carbon atom 5 is not part of a double bond. In some of these embodiments carbon atom 5 is in the R configuration. In some embodiments, the compounds of the present invention contain a stereogenic center at carbon atom 4, provided that carbon atom 4 is not a part of a double bond. In some of these embodiments, carbon atom 4 is in the R configuration.

Without being bound by theory, in some embodiments, the compounds provided herein which exhibit a specific stereochemical orientation at carbon atoms 4, 5, and/or 10 exhibit retained inhibition of hIL17 while exhibiting reduced NRF2 activation relative to compound with a different stereochemical orientation at carbon atoms 4, 5, and/or 10. In some embodiments, the present disclosure provides compounds exhibiting a lower $IC_{50}$ for inhibition of hIL17 as measure by determining the concentration required to inhibit using fluorescently tagged anti-IL17 antibodies, for example, as described in Example 2 when compared to the two fold activation of NRF2. In some embodiments, the present disclosure provides compounds exhibiting an increase in hIL17 inhibition when compared to the two fold NRF2 activation value when the 2-fold NRF2 activation is measured by determining the concentration requirement to increase GST ARE Luciferase reporter activity by 2-fold in AREc32 cells relative to DMSO treated cells, for example, as described in Example 2.

Chemical formulas used to represent compounds of the present invention will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

Compounds of the present invention may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It will appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof are within the scope of the present invention.

II. DISEASES ASSOCIATED WITH INFLAMMATORY CYTOKINE IL-17

Various reports have implicated the inflammatory cytokine IL-17 in the pathogenesis of many autoimmune diseases, including rheumatoid arthritis, psoriasis and psoriatic arthritis, inflammatory bowel diseases (including but not limited to Crohn's disease), multiple sclerosis, autoimmune nephritis, autoimmune uveitis, Type 1 diabetes, and ankylosing spondylitis. In some embodiments, the compounds provided herein may be administered to a patient in order to treat or prevent one or more of these diseases or disorders. A type of T lymphocyte known as a Th17 cell is a primary source of IL-17. There are multiple members of the IL-17 family. The first identified member, IL-17A, is commonly referred to as IL-17. IL-17 is composed of two monomers linked by disulfide bonds to form a homodimer (Miossec and Kolls, 2012). Aside from IL-17A, the other principal family member is IL-17F. Some evidence suggests that IL-17F and IL-17A, though they have many effects in common, may have different effects in certain settings such as lung inflammation. The IL-17 cytokines bind to IL-17 receptors (IL-17R) located in the membrane of select cell types. Although there are multiple subtypes of the IL-17 receptor, the IL-17RA/IL-17RC complex is required for the activity of IL-17A and IL-17F. IL-17RA has the unusual property of signaling through a pathway that involves an adaptor protein (ACT1) rather than the Janus kinase/signal transducer and activator of transcription (JAK/STAT) pathway employed by most interleukin receptors. Binding of IL-17A to IL-17RA activates the pro-inflammatory nuclear factor-kappa B (NF-κB) pathway and pro-inflammatory elements of the mitogen-activated protein kinase (MAPK) pathway such as JUN N-terminal kinase (JNK), p38 and extracellular signal-related kinase (ERK). IL-17 activity stimulates secretion of IL-6 and IL-8 from mesenchymal cells and leads to fever along with the accumulation of neutrophils in blood and tissue. In some embodiments, the compounds provided herein may be used to inhibit the secretion of IL-6 and IL-8 from mesenchymal cells. In some embodiments, the compounds provided herein may be administered to a patient in order to prevent or inhibit fever in a patient. In some embodiments, the compounds provided herein may be administered to a patient in order to prevent the accumulation of neutrophils in the blood or tissue of the patient.

Aside from its contribution to acute inflammation, IL-17 also contributes to chronic inflammation (Miossec and Kolls, 2012). In some embodiments, the compounds provided herein may be administered to a patient in order to prevent or treat chronic inflammation. IL-17 stimulates the production of matrix metalloproteinases (MMPs), which among other effects can degrade cartilage in joints. In some embodiments, the compounds provided herein may be administered to a patient in order to prevent or treat degradation of the patient's cartilage. IL-17 also increases the expression of receptor activator of NF-κB ligand (RANKL) in osteoblasts, leading to differentiation and activation of osteoclasts and bone degradation. In some embodiments, the compounds provided herein may be administered to a patient in order to prevent or treat degradation of the patient's bone. Depending on the target cell that is exposed to it, IL-17 may stimulate the production of IL-6, IL-8, IL-1, tumor necrosis factor (TNF), MMPs, nitric oxide, or several other proteins that are implicated in inflammatory conditions (e.g., tissue factor, CCL20, G-CSF and GM-CSF). In some embodiments, the compounds provided herein may be administered to a patient in order to inhibit the production of IL-6, IL-8, IL-1, tumor necrosis factor (TNF), MMPs, nitric oxide, or several other proteins that are implicated in inflammatory conditions (e.g., tissue factor, CCL20, G-CSF and GM-CSF).

Although IL-17 plays a role in the immune response to invading pathogens, excessive IL-17 activity has been implicated in pathologies associated with an excessive immune response to an infection. In some embodiments, the compounds provided herein may be administered to a patient in order to prevent or treat excessive immune response to an infection. For example, IL-17 has been implicated in the severe neuroinflammation associated with *Toxoplasma gondii* infection and increased severity of lesions associated with *Leishmania* infection. In some embodiments, the compounds provided herein may be administered to a patient in order to treat or prevent neuroinflammation, for example, neuroinflammation associated with *Toxoplasma gondii* infection. In some embodiments, the compounds provided herein may be administered to a patient in order to treat or prevent lesions associated with *Leishmania* infection. In these and other cases, IL-17 appears to play a role in perpetuating the infection, promoting an excessive inflammatory response, and inhibiting clearance of the infectious agent (Waite and Skokos, 2012). In some embodiments, the compounds provided herein may be administered to a patient in order to prevent an excessive inflammatory response and/or promote the clearance of an infectious agent.

Drugs targeting IL-17 have entered clinical trials for a wide variety of inflammatory conditions, including psoriasis, rheumatoid arthritis, ankylosing spondylitis, uveitis, Behcet's disease, psoriatic arthritis, Crohn's disease, polymyalgia rheumatica, dry eye syndrome, multiple sclerosis, graft-versus-host disease, and asthma. In some embodiments, the compounds provided herein may be administered to a patient in order to treat or prevent one or more of these diseases or disorders. Preclinical evidence also implicates IL-17 in the pathology of type 1 diabetes, and Th17 cells are elevated in patients with adult onset Still's disorder, another autoimmune disease. In some embodiments, the compounds provided herein may be administered to a patient in order to treat type 1 diabetes. In some embodiments, the compounds provided herein may be administered to a patient in order to treat or prevent adult onset Still's disorder. Activity of Th17 cells has been implicated in the development of graft-versus-host disease following allogeneic stem cell (e.g., bone marrow) transplantation (Fujiwara, et al., 2014). In some embodiments, the compounds provided herein may be administered to a patient in order to treat or prevent graft-versus-host disease, for example, following allogeneic stem cell (e.g., bone marrow) transplantation. Given the large body of evidence to date, it is likely that therapies reducing the expression of IL-17 or otherwise reducing its levels in circulation or target tissues (e.g., anti-IL17 monoclonal antibodies) could have broad applications in the treatment of autoimmune diseases and other inflammatory conditions. In some embodiments, the compounds provided herein may be administered to a patient in order to reduce the expression of IL-17 or its levels in circulation or target tissues (e.g., anti-IL17 monoclonal antibodies). In some embodiments, the compounds provided herein may be administered to a patient in order to treat autoimmune diseases or other inflammatory conditions.

Overproduction of IL-17 or elevated numbers of Th17 cells have been reported in patient studies or animal models of a large number of conditions, including autoimmune diseases, neurological disorders, cardiovascular diseases, cancer, psychiatric and neuropsychiatric disorders, acute and chronic inflammatory conditions, chronic pain syndromes, organ rejection or graft-versus-host disease, or asthma and other allergic conditions. In some embodiments, the compounds provided herein may be administered to a patient in order to treat or prevent one or more of these diseases or disorders.

Both the differentiation of Th17 cells and their production of IL-17 are regulated to a significant degree by the RAR-related orphan receptor RORγt, a member of the nuclear hormone receptor family. Expression of RORγt is common to all types of Th17 cells. RORγ also regulates the production of IL-17 in other cell types, including γδ T cells, innate lymphoid cells, and lymphoid tissue inducer cells (Bronner et al., 2016). Inhibition of RORγt activity results in reduced expression of IL-17. In some embodiments, the compounds provided herein may be administered to a patient in order to inhibit RORγt activity.

Compounds and compositions provided herein may be used to suppress IL-17 production in cultures of human T cells that are exposed to a mixture of cytokines known to induce differentiation into Th17 cells. In some embodiments, the ability to act as inverse agonists of RORγt is also demonstrated. Without wishing to be bound by any theory, it is believed that, for example, RORγt-independent mechanisms appear to contribute to the suppression of IL-17 production. Thus, the compounds and compositions provided herein may be used for inhibiting differentiation of T cells into Th17 cells, as well as inhibiting production of IL-17 by mature Th17 cells. In some of these embodiments, the net result is a reduction in IL-17 levels. In some embodiments, the compounds provided herein may be administered to a patient in order to suppress IL-17 production in one or more of the patient's tissues or organs.

III. PHARMACEUTICAL FORMULATIONS AND ROUTES OF ADMINISTRATION

For the purpose of administration to a patient in need of such treatment, pharmaceutical formulations (also referred to as a pharmaceutical preparations, pharmaceutical compositions, pharmaceutical products, medicinal products, medicines, medications, or medicaments) comprise a therapeutically effective amount of a compound of the present invention formulated with one or more excipients and/or drug carriers appropriate to the indicated route of administration. In some embodiments, the compounds of the present invention are formulated in a manner amenable for the treatment of human and/or veterinary patients. In some embodiments, formulation comprises admixing or combining one or more of the compounds of the present invention with one or more of the following excipients: lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol. In some embodiments, e.g., for oral administration, the pharmaceutical formulation may be tableted or encapsulated. In some embodiments, the compounds may be dissolved or slurried in water, polyethylene glycol, propylene glycol, ethanol, corn oil, cottonseed oil, peanut oil, sesame oil, benzyl alcohol, sodium chloride, and/or various buffers. Pharmaceutical formulations may be subjected to conventional pharmaceutical operations, such as sterilization and/or may contain drug carriers and/or excipients such as preservatives, stabilizers, wetting agents, emulsifiers, encapsulating agents such as lipids, dendrimers, polymers, proteins such as albumin, or nucleic acids, and buffers, etc.

Pharmaceutical formulations may be administered by a variety of methods, e.g., orally or by injection (e.g. subcutaneous, intravenous, intraperitoneal, etc.). Depending on the route of administration, the compounds of the present invention may be coated in a material to protect the compound from the action of acids and other natural conditions which may inactivate the compound. To administer the active compound by other than parenteral administration, it may be necessary to coat the compound with, or co-administer the compound with, a material to prevent its inactivation. For example, the active compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes.

The compounds of the present invention may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

The compounds of the present invention can be administered orally, for example, with an inert diluent or an assimilable edible carrier. The compounds and other ingredients may also be enclosed in a hard or soft shell gelatin capsule, compressed into tablets, or incorporated directly into the subject's diet. For oral therapeutic administration, the compounds of the present invention may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such pharmaceutical formulations is such that a suitable dosage will be obtained.

The therapeutic compound may also be administered topically to the skin, eye, ear, or mucosal membranes. Administration of the therapeutic compound topically may include formulations of the compounds as a topical solution, lotion, cream, ointment, gel, foam, transdermal patch, or tincture. When the therapeutic compound is formulated for topical administration, the compound may be combined with one or more agents that increase the permeability of the compound through the tissue to which it is administered. In other embodiments, it is contemplated that the topical administration is administered to the eye. Such administration may be applied to the surface of the cornea, conjunctiva, or sclera. Without wishing to be bound by any theory, it is believed that administration to the surface of the eye allows the therapeutic compound to reach the posterior portion of the eye. Ophthalmic topical administration can be formulated as a solution, suspension, ointment, gel, or emulsion. Finally, topical administration may also include administration to the mucosa membranes such as the inside of the mouth. Such administration can be directly to a particular location within the mucosal membrane such as a tooth, a sore, or an ulcer. Alternatively, if local delivery to the lungs is desired the therapeutic compound may be administered by inhalation in a dry-powder or aerosol formulation.

In some embodiments, it may be advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. In some embodiments, the specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient. In some embodiments, active compounds are administered at a therapeutically effective dosage sufficient to treat a condition associated with a condition in a patient. For example, the efficacy of a compound can be evaluated in an animal model system that may be predictive of efficacy in treating the disease in a human or another animal.

In some embodiments, the effective dose range for the therapeutic compound can be extrapolated from effective doses determined in animal studies for a variety of different animals. In general a human equivalent dose (HED) in mg/kg can be calculated in accordance with the following formula (see, e.g., Reagan-Shaw et al., *FASEB J.*, 22(3): 659-661, 2008, which is incorporated herein by reference):

$$\text{HED(mg/kg)} = \text{Animal dose(mg/kg)} \times (\text{Animal } K_m / \text{Human } K_m)$$

Use of the $K_m$ factors in conversion results in more accurate HED values, which are based on body surface area (BSA) rather than only on body mass. $K_m$ values for humans and various animals are well known. For example, the $K_m$ for an average 60 kg human (with a BSA of 1.6 m$^2$) is 37, whereas a 20 kg child (BSA 0.8 m$^2$) would have a $K_m$ of 25. $K_m$ for some relevant animal models are also well known, including: mice $K_m$ of 3 (given a weight of 0.02 kg and BSA of 0.007); hamster $K_m$ of 5 (given a weight of 0.08 kg and BSA of 0.02); rat $K_m$ of 6 (given a weight of 0.15 kg and BSA of 0.025) and monkey $K_m$ of 12 (given a weight of 3 kg and BSA of 0.24).

Precise amounts of the therapeutic composition depend on the judgment of the practitioner and are peculiar to each individual. Nonetheless, a calculated HED dose provides a general guide. Other factors affecting the dose include the physical and clinical state of the patient, the route of administration, the intended goal of treatment and the potency, stability and toxicity of the particular therapeutic formulation.

The actual dosage amount of a compound of the present disclosure or composition comprising a compound of the present disclosure administered to a subject may be determined by physical and physiological factors such as type of animal treated, age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

In some embodiments, the therapeutically effective amount typically will vary from about 0.001 mg/kg to about 1000 mg/kg, from about 0.01 mg/kg to about 750 mg/kg, from about 100 mg/kg to about 500 mg/kg, from about 1 mg/kg to about 250 mg/kg, from about 10 mg/kg to about 150 mg/kg in one or more dose administrations daily, for one or several days (depending of course of the mode of administration and the factors discussed above). Other suitable dose ranges include 1 mg to 10,000 mg per day, 100 mg to 10,000 mg per day, 500 mg to 10,000 mg per day, and 500 mg to 1,000 mg per day. In some particular embodiments, the amount is less than 10,000 mg per day with a range of 750 mg to 9,000 mg per day.

In some embodiments, the amount of the active compound in the pharmaceutical formulation is from about 2 to about 75 weight percent. In some of these embodiments, the amount if from about 25 to about 60 weight percent.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may taken orally and that the timing of which is or is not dependent upon food intake. Thus, for example, the agent can be taken every morning and/or every evening, regardless of when the subject has eaten or will eat.

IV. COMBINATION THERAPY

In addition to being used as a monotherapy, the compounds of the present invention may also find use in combination therapies. Effective combination therapy may be achieved with a single composition or pharmacological formulation that includes both agents, or with two distinct compositions or formulations, administered at the same time, wherein one composition includes a compound of this invention, and the other includes the second agent(s). Alternatively, the therapy may precede or follow the other agent treatment by intervals ranging from minutes to months.

Non-limiting examples of such combination therapy include combination of one or more compounds of the invention with another anti-inflammatory agent, a chemotherapeutic agent, radiation therapy, an antidepressant, an antipsychotic agent, an anticonvulsant, a mood stabilizer, an anti-infective agent, an antihypertensive agent, a cholesterol-lowering agent or other modulator of blood lipids, an agent for promoting weight loss, an antithrombotic agent, an agent for treating or preventing cardiovascular events such as myocardial infarction or stroke, an antidiabetic agent, an agent for reducing transplant rejection or graft-versus-host disease, an anti-arthritic agent, an analgesic agent, an anti-asthmatic agent or other treatment for respiratory diseases, or an agent for treatment or prevention of skin disorders. Compounds of the invention may be combined with agents designed to improve a patient's immune response to cancer, including (but not limited to) cancer vaccines. See Lu et al. (2011), which is incorporated herein by reference.

V. DEFINITIONS

When used in the context of a chemical group: "hydrogen" means H; "hydroxy" means —OH; "oxo" means =O; "carbonyl" means —C(=O)—; "carboxy" means —C(=O) OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "⚌" represents a single bond or a double bond. Thus, the formula

covers, for example,

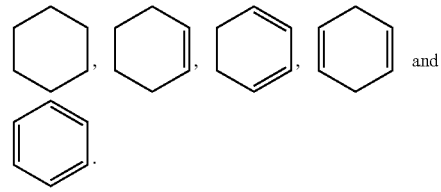

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "⁓", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◂▬" means a single bond where the group attached to the thick end of the wedge is "out of the page." The symbol "▦" means a single bond where the group attached to the thick end of the wedge is "into the page". The symbol "⁓" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a variable is depicted as a "floating group" on a ring system, for example, the group "R" in the formula:

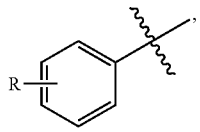

then the variable may replace any hydrogen atom attached to any of the ring atoms, including a depicted, implied, or expressly defined hydrogen, so long as a stable structure is formed. When a variable is depicted as a "floating group" on a fused ring system, as for example the group "R" in the formula:

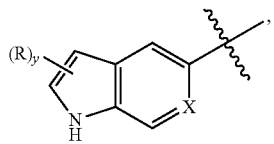

then the variable may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals CH), so long as a stable structure is formed. In the example depicted, R may reside on either the 5-membered or the 6-membered ring of the fused ring system. In the formula above, the subscript letter "y" immediately following the R enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "Cn" defines the maximum number (n) of carbon atoms that can be in the group/class, with the minimum number as small as possible for the group/class in question. For example, it is understood that the minimum number of carbon atoms in the groups "alkyl$_{(C \leq 8)}$", "alkanediyl$_{(C \leq 8)}$", "heteroaryl$_{(C \leq 8)}$", "acyl$_{(C \leq 8)}$", and "heterocycloalkyl$_{(C \leq 8)}$" is one, the minimum number of carbon atoms in the groups "alkenyl$_{(C \leq 8)}$", "alkenediyl$_{(C \leq 8)}$", and "alkynyl$_{(C \leq 8)}$", is two, the minimum number of carbon atoms in the group "cycloalkyl$_{(C \leq 8)}$" and "cycloalkanediyl$_{(C \leq 8)}$" is three, and the minimum number of carbon atoms in the groups "aryl$_{(C \leq 8)}$" and "arenediyl$_{(C \leq 8)}$" is six. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous. When any of the chemical groups or compound classes defined herein is modified by the term "substituted", any carbon atom in the moiety replacing the hydrogen atom is not counted. Thus methoxyhexyl, which has a total of seven carbon atoms, is an example of a substituted alkyl$_{(C1-6)}$. Unless specified otherwise, any chemical group or compound class listed in a claim set without a carbon atom limit has a carbon atom limit of less than or equal to twelve.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" signifies that the compound or chemical group so modified is an acyclic or cyclic, but non-aromatic compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" signifies that the compound or chemical group so modified has a planar unsaturated ring of atoms with 4n+2 electrons in a fully conjugated cyclic 7E system.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, Tr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula H—R, wherein R is alkyl as this term is defined above. When any of these terms is used with the "substituted" modifier, one or more hydrogen atom has been independently replaced by —OH, —F, —Cl, —Br, —I, —NH₂, —NO₂, —CO₂H, —C(O)H, —CO₂CH₃, —CN, —SH, —OCH₃, —OCH₂CH₃, —C(O) CH₃, —NHCH₃, —NHCH₂CH₃, —N(CH₃)₂, —C(O)NH₂, —C(O)NHCH₃, —C(O)N(CH₃)₂, —OC(O)CH₃, —NHC (O)CH₃, —S(O)₂CH₃, —S(O)₂OH, or —S(O)₂NH₂. The following groups are non-limiting examples of substituted alkyl groups: —CH₂OH, —CH₂Cl, —CF₃, —CH₂CN, —CH₂C(O)OH, —CH₂C(O)OCH₃, —CH₂C(O)NH₂, —CH₂C(O)CH₃, —CH₂OCH₃, —CH₂OC(O)CH₃, —CH₂NH₂, —CH₂N(CH₃)₂, and —CH₂CH₂Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH₂Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH₂F, —CF₃, and —CH₂CF₃ are non-limiting examples of fluoroalkyl groups.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH₂)₂ (cyclopropyl), cyclobutyl, cyclopentyl, or cyclohexyl (Cy). As used herein, the term does not preclude the presence of one or more alkyl groups (carbon number limitation permitting) attached to a carbon atom of the non-aromatic ring structure. The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

is a non-limiting example of cycloalkanediyl group. A "cycloalkane" refers to the class of compounds having the formula H—R, wherein R is cycloalkyl as this term is defined above. When any of these terms is used with the "substituted" modifier, one or more hydrogen atom has been independently replaced by —OH, —F, —Cl, —Br, —I, —NH₂, —NO₂, —CO₂H, —C(O)H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O) ₂CH₃, —S(O)₂OH, or —S(O)₂NH₂.

The term "alkenyl" when used without the "substituted" modifier refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH₂ (vinyl), —CH=CHCH₃, —CH=CHCH₂CH₃, —CH₂CH=CH₂ (allyl), —CH₂CH=CHCH₃, and —CH=CHCH=CH₂. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH=CH—, —CH=C(CH₃)CH₂—, —CH=CHCH₂—, and —CH₂CH=CHCH₂— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly, the terms "terminal alkene" and "α-olefin" are synonymous and refer to an alkene having just one carbon-carbon double bond, wherein that bond is part of a vinyl group at an end of the molecule. When any of these terms are used with the "substituted" modifier one or more hydrogen atom has been independently replaced by —OH, —F, —Cl, —Br, —I, —NH₂, —NO₂, —CO₂H, —C(O)H, —CO₂CH₃, —CN, —SH, —OCH₃, —OCH₂CH₃, —C(O) CH₃, —NHCH₃, —NHCH₂CH₃, —N(CH₃)₂, —C(O)NH₂, —C(O)NHCH₃, —C(O)N(CH₃)₂, —OC(O)CH₃, —NHC (O)CH₃, —S(O)₂CH₃, —S(O)₂O H, or —S(O)₂NH₂. The groups —CH=CHF, —CH=CHCl and —CH=CHBr are non-limiting examples of substituted alkenyl groups.

The term "alkynyl" when used without the "substituted" modifier refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH₃, and —CH₂C≡CCH₃ are non-limiting examples of alkynyl groups. An "alkyne" refers to the class of compounds having the formula H—R, wherein R is alkynyl. When any of these terms are used with the "substituted" modifier one or more hydrogen atom has been independently replaced by —OH, —F, —Cl, —Br, —I, —NH₂, —NO₂, —CO₂H, —C(O)H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂ CH₃, —S(O)₂OH, or —S(O)₂NH₂.

The term "aryl" when used without the "substituted" modifier refers to a monovalent unsaturated aromatic group with an aromatic carbon atom as the point of attachment, said carbon atom forming part of a one or more aromatic ring structures, each with six ring atoms that are all carbon, and wherein the group consists of no atoms other than carbon and hydrogen. If more than one ring is present, the rings may be fused or unfused. Unfused rings are connected with a covalent bond. As used herein, the term aryl does not preclude the presence of one or more alkyl groups (carbon number limitation permitting) attached to the first aromatic ring or any additional aromatic ring present. Non-limiting examples of aryl groups include phenyl (Ph), methylphenyl, (dimethyl)phenyl, —C₆H₄CH₂CH₃ (ethylphenyl), naphthyl, and a monovalent group derived from biphenyl (e.g., 4-phenylphenyl). The term "arenediyl" when used without the "substituted" modifier refers to a divalent aromatic group with two aromatic carbon atoms as points of attachment, said carbon atoms forming part of one or more six-membered aromatic ring structures, each with six ring atoms that are all carbon, and wherein the divalent group consists of no atoms other than carbon and hydrogen. As used herein, the term arenediyl does not preclude the presence of one or more alkyl, aryl, and/or aralkyl groups (carbon number limitation permitting) attached to the first aromatic ring or any additional aromatic ring present. If more than one ring is present, the rings may be fused or unfused. Unfused rings are connected with a covalent bond. Non-limiting examples of arenediyl groups include:

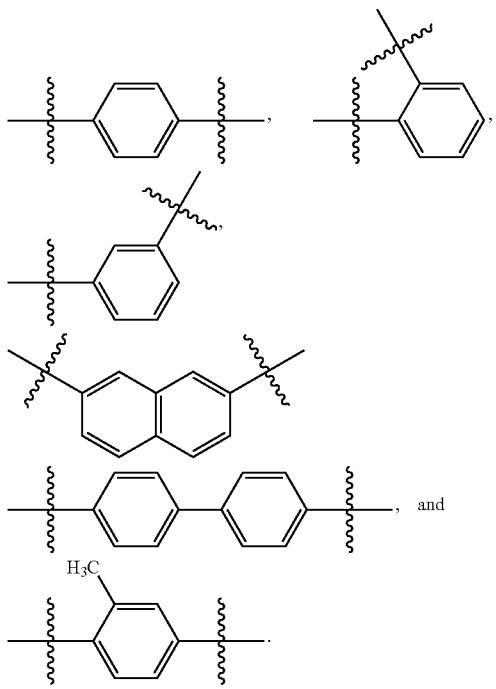

An "arene" refers to the class of compounds having the formula H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —C(O)H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$CH$_3$, —S(O)$_2$OH, or —S(O)$_2$NH$_2$.

The term "aralkyl" when used without the "substituted" modifier refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —C(O)H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$CH$_3$, —S(O)$_2$OH, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures, each ring structure having three to eight ring atoms, wherein at least one of the ring atoms of the aromatic ring structure(s) is nitrogen, oxygen or sulfur, and wherein the heteroaryl group consists of no atoms other than carbon, hydrogen, aromatic nitrogen, aromatic oxygen and aromatic sulfur. If more than one ring is present, the rings are fused; however, the term heteroaryl does not preclude the presence of one or more alkyl, cycloalkyl, heterocycloalkyl, aryl, and/or aralkyl groups (carbon number limitation permitting) attached to one or more ring atoms. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "heteroarenediyl" when used without the "substituted" modifier refers to a divalent aromatic group, with two aromatic carbon atoms, two aromatic nitrogen atoms, or one aromatic carbon atom and one aromatic nitrogen atom as the two points of attachment, said atoms forming part of one or more aromatic ring structures, each with three to eight ring atoms, wherein at least one of the ring atoms of the aromatic ring structure(s) is nitrogen, oxygen or sulfur, and wherein the divalent group consists of no atoms other than carbon, hydrogen, aromatic nitrogen, aromatic oxygen and aromatic sulfur. If more than one ring is present, the rings are be fused; however, the term heteroarenediyl does not preclude the presence of one or more alkyl or aryl groups (carbon number limitation permitting) attached to one or more ring atoms. Non-limiting examples of heteroarenediyl groups include:

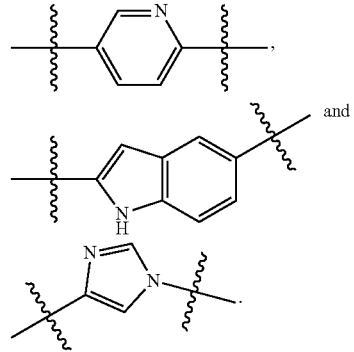

The term "N-heteroaryl" refers to a heteroaryl group with a nitrogen atom as the point of attachment. A "heteroarene" refers to the class of compounds having the formula H—R, wherein R is heteroaryl. Pyridine and quinoline are non-limiting examples of heteroarenes. When these terms are used with the "substituted" modifier one or more hydrogen atom on either the heteroaryl ring or any alkyl, cycloalkyl, heterocycloalkyl, aryl, and/or aralkyl groups attached thereto has been independently replaced by —OH, —F, —Cl, —Br, —I, —NH$_2$, —NO$_2$, —CO$_2$H, —C(O)H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$CH$_3$, —S(O)$_2$OH, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures, each ring structure having three to eight ring atoms, wherein at least one of the ring atoms of the non-aromatic ring structure(s) is nitrogen, oxygen or sulfur, and wherein the heterocycloalkyl group consists of no atoms other than carbon, hydrogen, nitrogen, oxygen and sulfur. If more than one ring is present, the rings are fused. As used herein, the term does not preclude the presence of one or more alkyl or cycloalkyl groups (carbon number limitation permitting) attached to one or more ring atoms. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "heterocycloalkanediyl" when used without the "substituted" modifier refers to a divalent cyclic group, with two carbon atoms, two nitrogen atoms, or one carbon atom and one nitrogen atom as the two points of attachment, said atoms forming part of one or more ring structure(s) wherein at least one of the ring atoms of the non-aromatic ring structure(s) is nitrogen, oxygen or sulfur, and wherein the divalent group consists of no atoms other than carbon, hydrogen, nitrogen, oxygen and sulfur. If more than one ring is present, the rings are fused. As used herein, the term heterocycloalkanediyl does not preclude the presence of one or more alkyl groups (carbon number limitation permitting) attached to one or more ring atoms. Also, the term does not preclude the presence of one or more double bonds in the ring or ring system, provided that the resulting group remains non-aromatic. Non-limiting examples of heterocycloalkanediyl groups include:

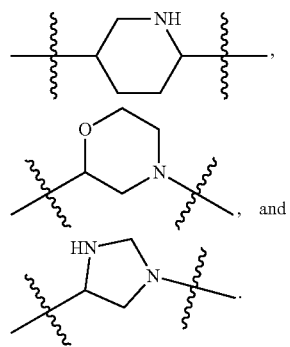

The term "N-heterocycloalkyl" refers to a heterocycloalkyl group with a nitrogen atom as the point of attachment. N-pyrrolidinyl is an example of such a group. When these terms are used with the "substituted" modifier one or more hydrogen atom on either the heterocycloalkyl ring or any alkyl and/or cycloalkyl groups attached thereto has been independently replaced by —OH, —F, —Cl, —Br, —I, —NH$_2$, —NO$_2$, —CO$_2$H, —C(O)H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$CH$_3$, —S(O)$_2$OH, or —S(O)$_2$NH$_2$.

The term "acyl" when used without the "substituted" modifier refers to the group —C(O)R, in which R is a hydrogen, alkyl, cycloalkyl, or aryl as those terms are defined above. The groups, —CHO, —C(O)CH$_3$ (acetyl, Ac), —C(O)CH$_2$CH$_3$, —C(O)CH(CH$_3$)$_2$, —C(O)CH(CH$_2$)$_2$, —C(O)C$_6$H$_5$, and —C(O)C$_6$H$_4$CH$_3$ are non-limiting examples of acyl groups. A "thioacyl" is defined in an analogous manner, except that the oxygen atom of the group C(O)R has been replaced with a sulfur atom, C(S)R. The term "aldehyde" corresponds to an alkyl group, as defined above, attached to a CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH$_2$, —NO$_2$, —CO$_2$H, —C(O)H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$CH$_3$, —S(O)$_2$OH, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), or —OC(CH$_3$)$_3$ (tert-butoxy). The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier, one or more hydrogen atom has been independently replaced by —OH, —F, —Cl, —Br, —I, —NH$_2$, —NO$_2$, —CO$_2$H, —C(O)H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$CH$_3$, —S(O)$_2$OH, or —S(O)$_2$NH$_2$.

The term "alkylamino" when used without the "substituted" modifier refers to the group —NHR, in which R is an alkyl, as that term is defined above. Non-limiting examples include: —NHCH$_3$ and —NHCH$_2$CH$_3$. The term "dialkylamino" when used without the "substituted" modifier refers to the group —NRR', in which R and R' can be the same or different alkyl groups. Non-limiting examples of dialkylamino groups include: —N(CH$_3$)$_2$ and —N(CH$_3$)(CH$_2$CH$_3$). The terms "cycloalkylamino", "alkenylamino", "alkynylamino", "arylamino", "aralkylamino", "heteroarylamino", "heterocycloalkylamino", and "alkoxyamino" when used without the "substituted" modifier, refers to groups, defined as —NHR, in which R is cycloalkyl, alkenyl, alkynyl, aryl, aralkyl, heteroaryl, heterocycloalkyl, and alkoxy, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. When any of these terms is used with the "substituted" modifier, one or more hydrogen atom attached to a carbon atom has been independently replaced by —OH, —F, —Cl, —Br, —I, —NH$_2$, —NO$_2$, —CO$_2$H, —C(O)H, —CO$_2$CH$_3$, —CN, —SH, —OCH$_3$, —OCH$_2$CH$_3$, —C(O)

$CH_3$, —$NHCH_3$, —$NHCH_2CH_3$, —$N(CH_3)_2$, —$C(O)NH_2$, —$C(O)NHCH_3$, —$C(O)N(CH_3)_2$, —$OC(O)CH_3$, —$NHC(O)CH_3$, —$S(O)_2CH_3$, —$S(O)_2OH$, or —$S(O)_2NH_2$. The groups —$NHC(O)OCH_3$ and —$NHC(O)NHCH_3$ are non-limiting examples of substituted amido groups.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

An "active ingredient" (AI) (also referred to as an active compound, active substance, active agent, pharmaceutical agent, agent, biologically active molecule, or a therapeutic compound) is the ingredient in a pharmaceutical drug or a pesticide that is biologically active. The similar terms active pharmaceutical ingredient (API) and bulk active are also used in medicine, and the term active substance may be used for pesticide formulations.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating or preventing a disease, is an amount sufficient to effect such treatment or prevention of the disease.

An "excipient" is a pharmaceutically acceptable substance formulated along with the active ingredient(s) of a medication, pharmaceutical composition, formulation, or drug delivery system. Excipients may be used, for example, to stabilize the composition, to bulk up the composition (thus often referred to as "bulking agents," "fillers," or "diluents" when used for this purpose), or to confer a therapeutic enhancement on the active ingredient in the final dosage form, such as facilitating drug absorption, reducing viscosity, or enhancing solubility. Excipients include pharmaceutically acceptable versions of antiadherents, binders, coatings, colors, disintegrants, flavors, glidants, lubricants, preservatives, sorbents, sweeteners, and vehicles. The main excipient that serves as a medium for conveying the active ingredient is usually called the vehicle. Excipients may also be used in the manufacturing process, for example, to aid in the handling of the active substance, such as by facilitating powder flowability or non-stick properties, in addition to aiding in vitro stability such as prevention of denaturation or aggregation over the expected shelf life. The suitability of an excipient will typically vary depending on the route of administration, the dosage form, the active ingredient, as well as other factors.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "$IC_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

A "pharmaceutically acceptable carrier," "drug carrier," or simply "carrier" is a pharmaceutically acceptable substance formulated along with the active ingredient medication that is involved in carrying, delivering and/or transporting a chemical agent. Drug carriers may be used to improve the delivery and the effectiveness of drugs, including for example, controlled-release technology to modulate drug bioavailability, decrease drug metabolism, and/or reduce drug toxicity. Some drug carriers may increase the effectiveness of drug delivery to the specific target sites. Examples of carriers include: liposomes, microspheres (e.g., made of polylactic-co-glycolic) acid), albumin microspheres, synthetic polymers, nanofibers, protein-DNA complexes, protein conjugates, erythrocytes, virosomes, and dendrimers.

A "pharmaceutical drug" (also referred to as a pharmaceutical, pharmaceutical preparation, pharmaceutical composition, pharmaceutical formulation, pharmaceutical product, medicinal product, medicine, medication, medicament, or simply a drug) is a compound or composition used to diagnose, cure, treat, or prevent disease. An active ingredient (AI) (defined above) is the ingredient in a pharmaceutical drug or a pesticide that is biologically active. The similar terms active pharmaceutical ingredient (API) and bulk active are also used in medicine, and the term active substance may be used for pesticide formulations. Some medications and pesticide products may contain more than one active ingredient. In contrast with the active ingredients, the inactive ingredients are usually called excipients (defined above) in pharmaceutical contexts.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease or symptom(s) in a subject or patient that is experiencing or displaying the pathology or symptomatology of the disease.

The term "unit dose" refers to a formulation of the compound or composition such that the formulation is prepared in a manner sufficient to provide a single therapeutically effective dose of the active ingredient to a patient in a single administration. Such unit dose formulations that may be used include but are not limited to a single tablet, capsule, or other oral formulations, or a single vial with a syringable liquid or other injectable formulations.

Other abbreviations used herein are as follows: NO, nitric oxide; iNOS, inducible nitric oxide synthase; COX-2, cyclooxygenase-2; FBS, fetal bovine serum; IFNγ or IFN-γ, interferon-γ; TNFα or TNF-α, tumor necrosis factor-α; interleukin-1β; IL17 or IL-17, interleukin 17; RORγ, retinoic acid receptor-related orphan receptor γ; HO-1, inducible heme oxygenase; Me, methyl; Bn, benzyl; Et, ethyl; Pr, propyl; iPr, isopropyl; Bu, butyl; i-Bu, isobutyl; tBu or Bu$^t$, tert-butyl; Ph, phenyl; Ac, acetyl; Bz, benzoyl; Ts, tosyl; Boc, t-butyloxycarbonyl; quant., quantitative; aq., aqueous; w/w, weight per weight; ° C., degrees Celsius, N, normal or normality; h or hr, hours; atm, atmosphere; rt, room temperature; TLC, thin layer chromatography; DMSO, dimethyl sulfoxide; EtOAc, ethyl acetate; DMF, NA-dimethylformamide; DMA, dimethylacetamide; MeCN, acetonitrile; MTBE, methyl t-butylether; Et$_2$O, diethyl ether; THF, tetrahydrofuran; MeOH, methanol; EtOH, ethanol; iPrOH, isopropanol; HMPA, hexamethylphosphoramide; DME, dimethoxy ethane; Pd/C, palladium on carbon; Pd$_2$(dba)$_3$, tris (dibenzylideneacetone)dipalladium (O); Pd(dppf)Cl$_2$, [1,1'-bis (diphenylphosphino)ferrocene]dichloro-palladium (II); Ac$_2$O, acetic anhydride; Tf$_2$O, trifluoromethanesulfonic anhydride; MsCl, mesyl choloride; TFA, trifluoroacetic acid; TFAA, trifluoroacetic anhydride; TsOH or p-TsOH, p-toluenesulfonic acid; Py, pyridine; Et$_3$N, triethylamine; LDA, lithium diisopropylamide; DIPEA, diisopropylethylamine;

LHMDS, lithium bis(trimethylsilyl)amide; DMAP, dimethylaminopyridine; NMP, N-methyl-2-pyrrolidone; mCPBA or m-CPBA, m-chloroperoxybenzoic acid; MOMCl, methoxymethyl chloride; TBSCl, t-butyldimethylsilyl chloride; SEMCl, 2-(trimethylsilyl)ethoxymethyl chloride; TBAF, tetra-n-butylammonium fluoride; PDC, pyridinium dichromate; DMP, Dess Martin periodinane; IBX, 2-iodoxybenzoic acid; T$_3$P®, propylphosphonic anhydride; DPPA, diphenylphosphoryl azide; Ph$_3$P or PPh$_3$, triphenyl phosphine; HATU, 1-[Bis(dimethylamino)methylene]-1H-1,2,3-triazolo[4,5-b]pyridinium 3-oxid hexafluorophosphate; NMO, N-methylmorpholine N-oxide; Xphos, 2-Dicyclohexylphosphino-2',4',6'-triisopropylbiphenyl; Xantphos, 4,5-Bis (diphenylphosphino)-9,9-dimethylxanthene; PPT S, pyridinium p-toluenesulfonate; DDQ, 2,3-dichloro-5,6-dicyano-1,4-benzoquinone; DAST, diethylaminosulfur trifluoride; TMSCHN$_2$, trimethylsilyldiazomethane; 9-BBN, 9-borabicyclo-[3.3.1]nonane; DBDMH, 1,3-dibromo-5,5-dimethylhydantoin.

The above definitions supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Synthesis and Characterization i. Synthesis

Scheme 1

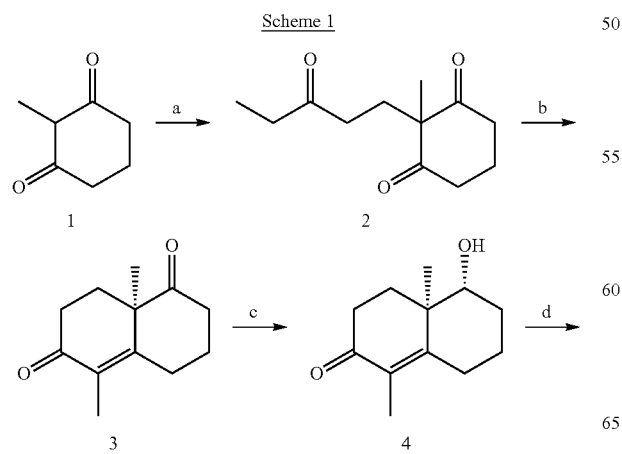

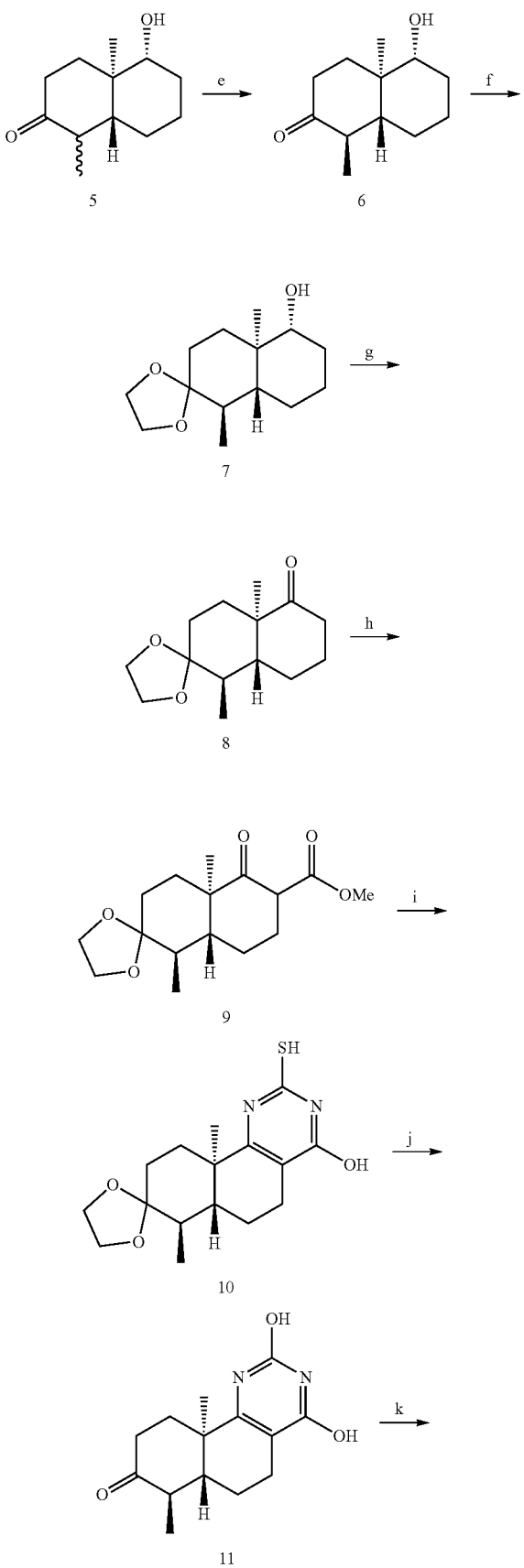

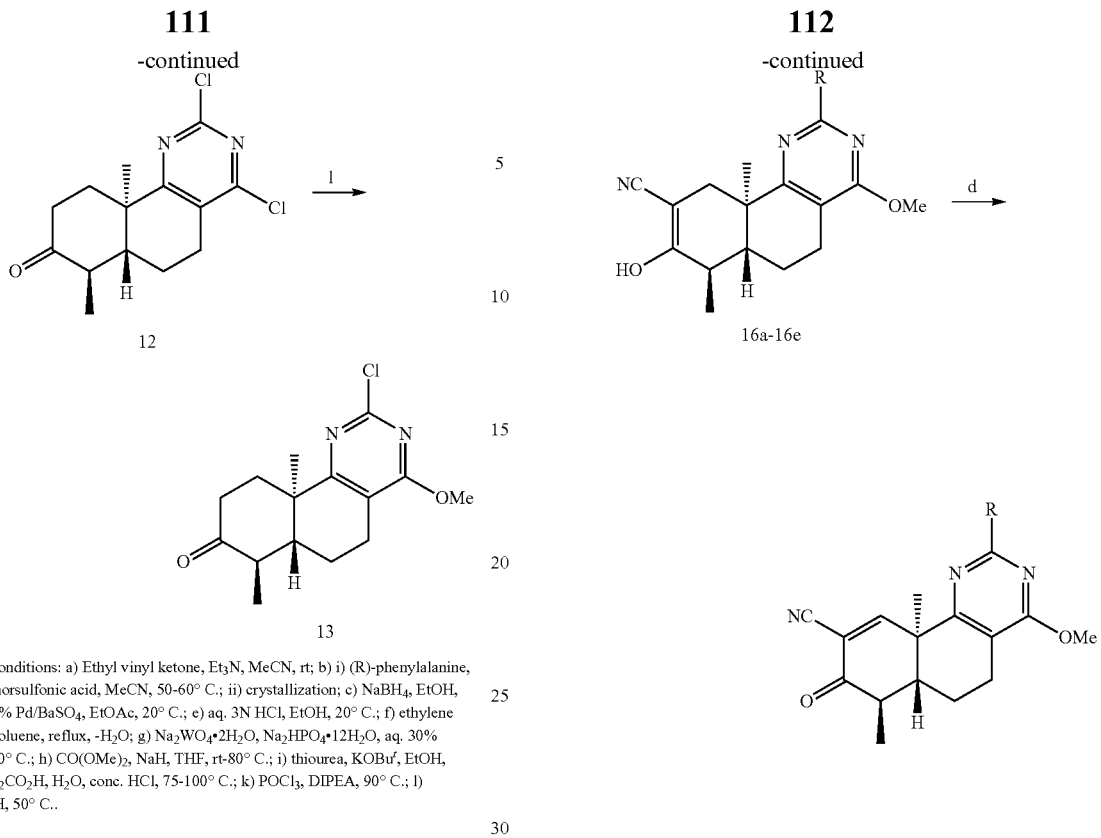

Reagents and conditions: a) Ethyl vinyl ketone, Et₃N, MeCN, rt; b) i) (R)-phenylalanine, (1S)-(+)-camphorsulfonic acid, MeCN, 50-60° C.; ii) crystallization; c) NaBH₄, EtOH, -5° C.; d) H₂, 5% Pd/BaSO₄, EtOAc, 20° C.; e) aq. 3N HCl, EtOH, 20° C.; f) ethylene glycol, PPTS, toluene, reflux, -H₂O; g) Na₂WO₄•2H₂O, Na₂HPO₄•12H₂O, aq. 30% H₂O₂, DMA, 90° C.; h) CO(OMe)₂, NaH, THF, rt-80° C.; i) thiourea, KOBuᵗ, EtOH, reflux; j) ClCH₂CO₂H, H₂O, conc. HCl, 75-100° C.; k) POCl₃, DIPEA, 90° C.; l) NaOMe, MeOH, 50° C..

Scheme 2

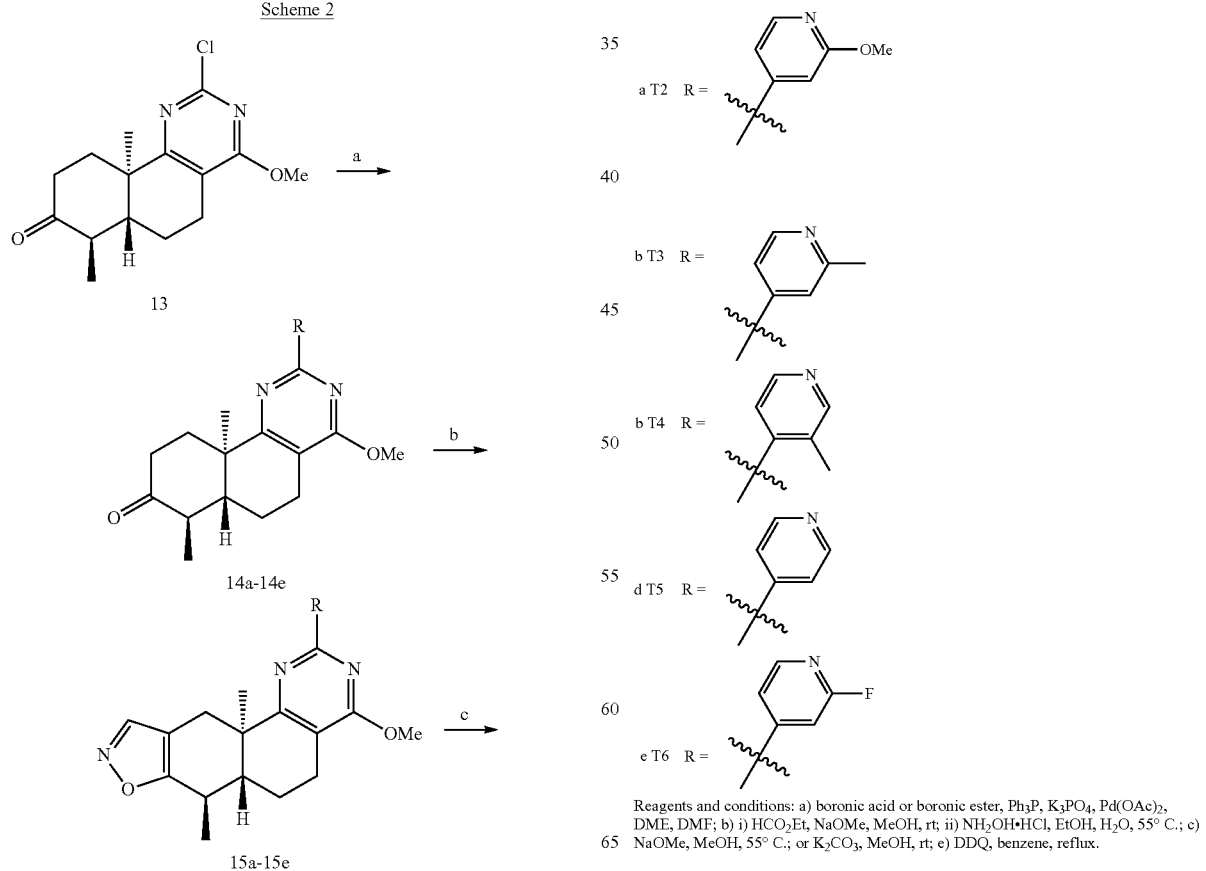

Reagents and conditions: a) boronic acid or boronic ester, Ph₃P, K₃PO₄, Pd(OAc)₂, DME, DMF; b) i) HCO₂Et, NaOMe, MeOH, rt; ii) NH₂OH•HCl, EtOH, H₂O, 55° C.; c) NaOMe, MeOH, 55° C.; or K₂CO₃, MeOH, rt; e) DDQ, benzene, reflux.

Scheme 3
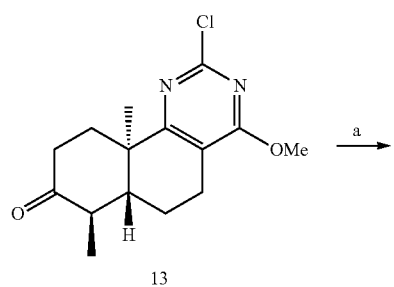
13
a →
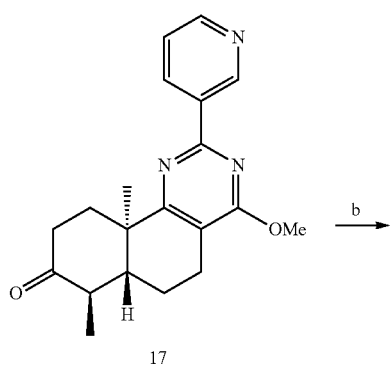
17
b →
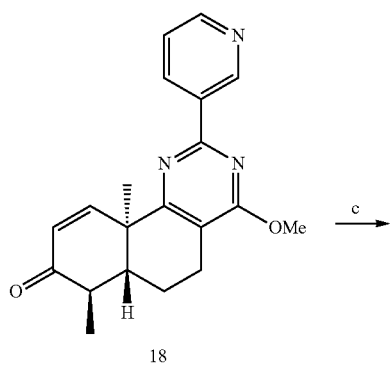
18
c →
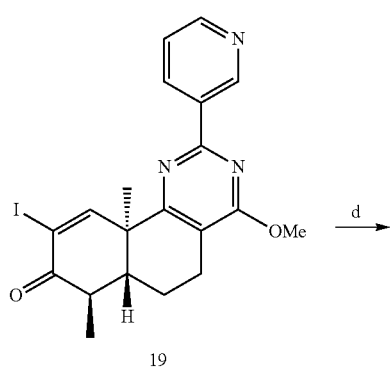
19
d →
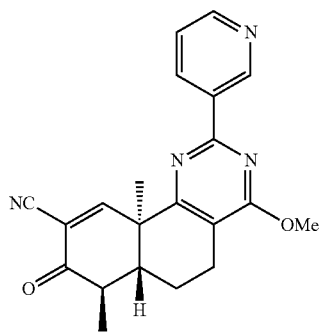 [SMILES: COc1nc(-c2cccnc2)nc2c1CC[C@@H]1[C@@H](C)C(=O)C(C#N)=C[C@@]21C]
T7
Reagents and conditions: a) pyridine-3-boronic acid, Ph₃P, K₃PO₄, Pd(OAc)₂, DME, DMF, microwave, 100° C.; b) i) LHMDS, PhSeCl, THF, −78° C.; ii) 30% aq. H₂O₂, EtOAc, THF, rt; c) I₂, pyridine, 80° C.; d) Zn(CN)₂, Pd(PPh₃)₄, DMF, 80° C.
Scheme 4
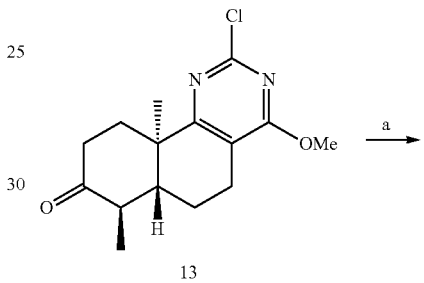
13
a →
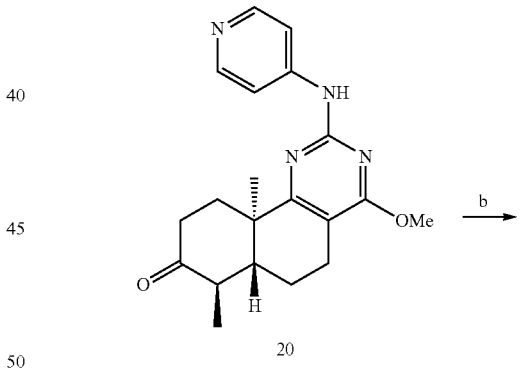
20
b →
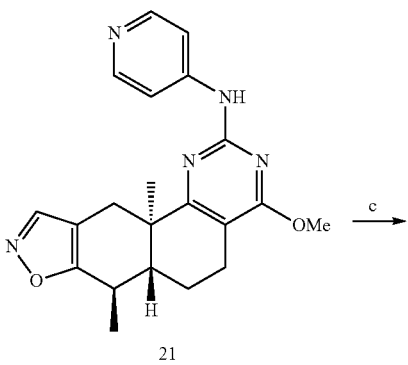
21
c →

115
-continued
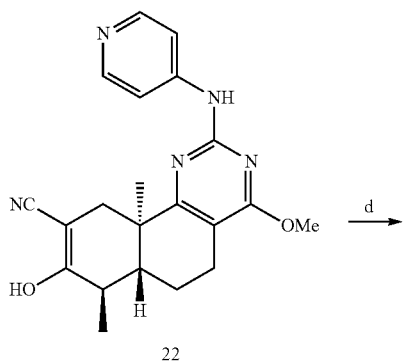
22
116
-continued
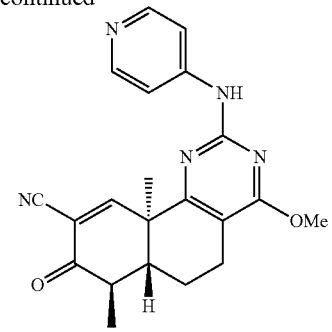
T8
Reagents and conditions: a) 4-pyridinamine, Cs₂CO₃, Xantphos, Pd₂(dba)₃, 1,4-dioxane, 100° C.; b) i) HCO₂Et, NaOMe, MeOH, 0° C. to rt; ii) 6N HCl, NH₂OH•HCl, EtOH, H₂O, 55° C.; c) NaOMe, MeOH, 55° C.; d) DDQ, benzene, 85° C.
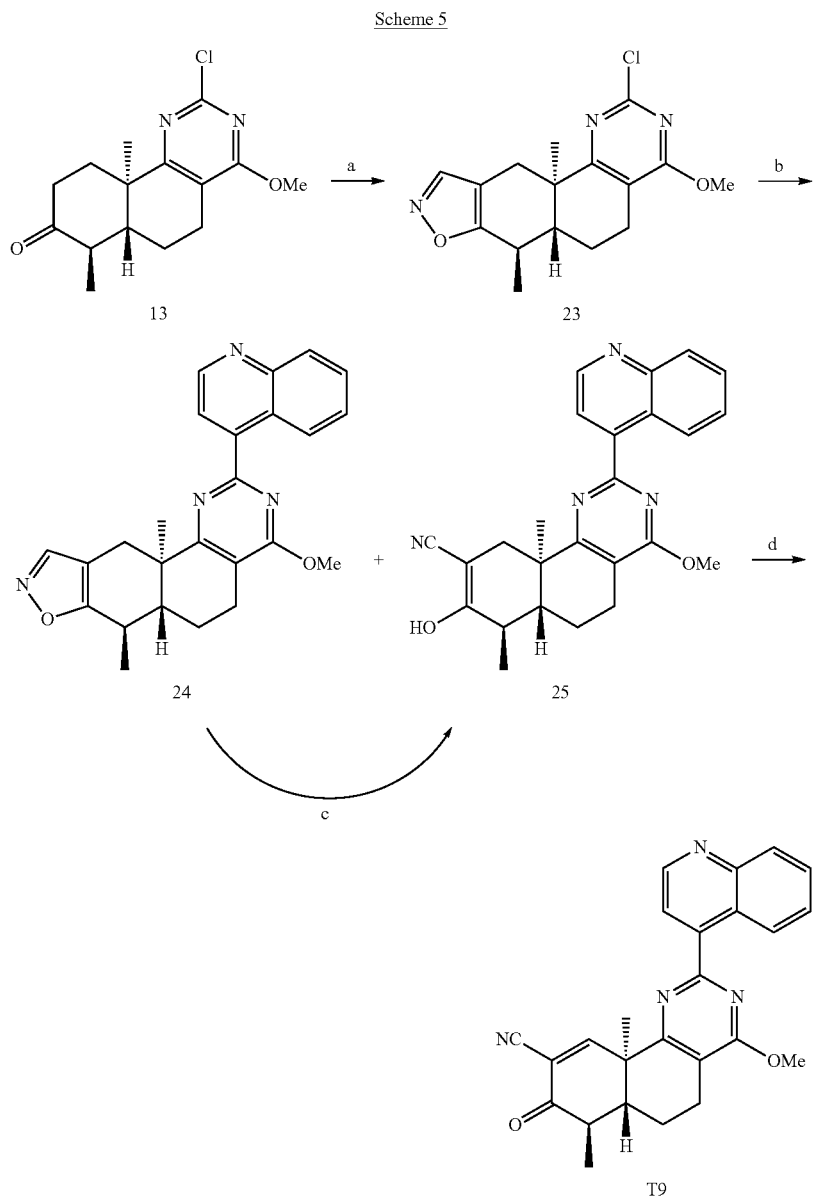

-continued

Reagents and conditions: a) i) HCO$_2$Et, NaOMe, MeOH, 0° C. to rt; ii) 6N HCl, NH$_2$OH•HCl, EtOH, H$_2$O, 55° C.; b) quinoline-4-boronic acid, Ph$_3$P, K$_3$PO$_4$, Pd(OAc)$_2$, DME, DMF, microwave, 110° C.; c) NaOMe, MeOH, 55° C.; d) DDQ, benzene, 85° C.

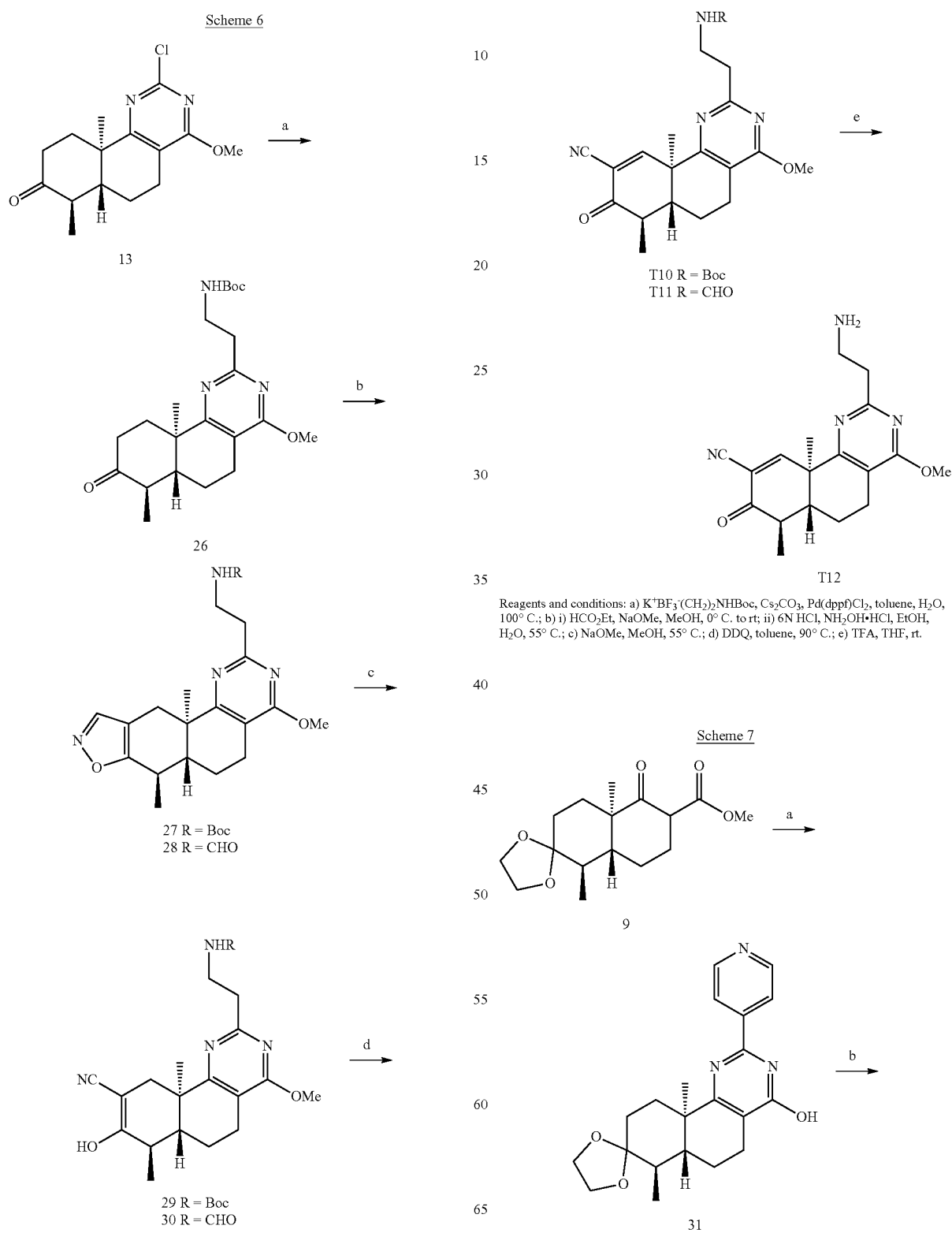

Reagents and conditions: a) K$^+$BF$_3^-$(CH$_2$)$_2$NHBoc, Cs$_2$CO$_3$, Pd(dppf)Cl$_2$, toluene, H$_2$O, 100° C.; b) i) HCO$_2$Et, NaOMe, MeOH, 0° C. to rt; ii) 6N HCl, NH$_2$OH•HCl, EtOH, H$_2$O, 55° C.; c) NaOMe, MeOH, 55° C.; d) DDQ, toluene, 90° C.; e) TFA, THF, rt.

-continued

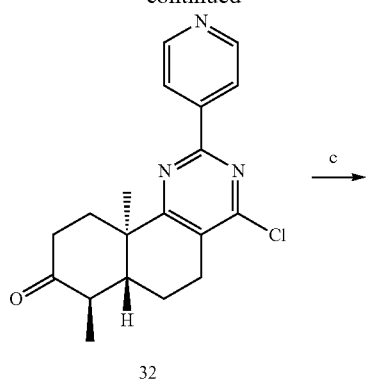

32

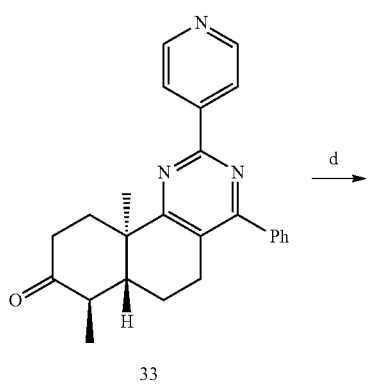

33

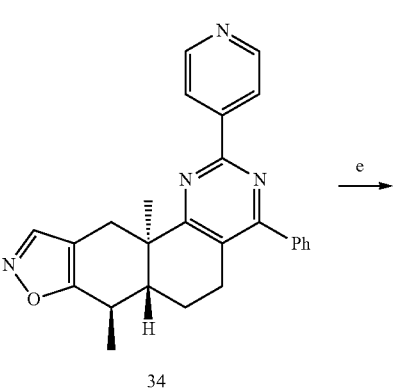

34

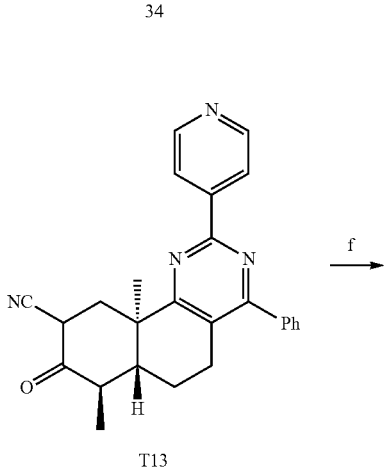

T13

-continued

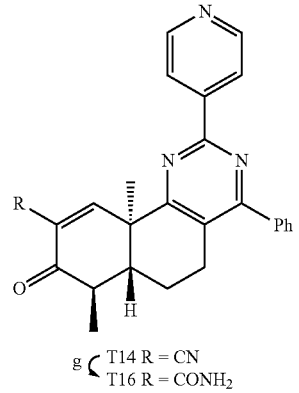

g ⌠ T14 R = CN
  ⌡ T16 R = CONH₂

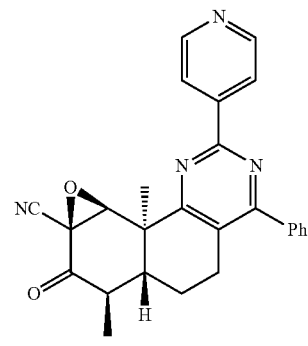

T15

Reagents and conditions: a) 4-amidinopyridine hydrochloride, K₂CO₃, EtOH, rt; b) POCl₃, toluene, 100° C.; c) PhB(OH)₂, Na₂CO₃, Pd(dppf)Cl₂, 1,4-dioxane, H₂O, microwave, 100° C.; d) i) HCO₂Et, NaOMe, MeOH, 0° C. to rt; ii) 6N HCl, NH₂OH·HCl, EtOH, H₂O, 55° C.; e) NaOMe, MeOH, 55° C.; f) i) DBDMH, DMF, 0° C.; ii) pyridine, 55° C.; g) hydrido(dimethylphosphinous acid-kP)[hydrogen bis(dimethylphosphinito-kP)]platinum(II), EtOH, H₂O, reflux.

Scheme 8

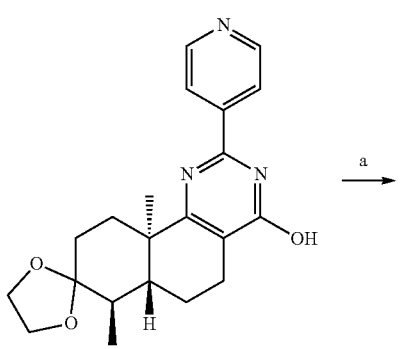

31

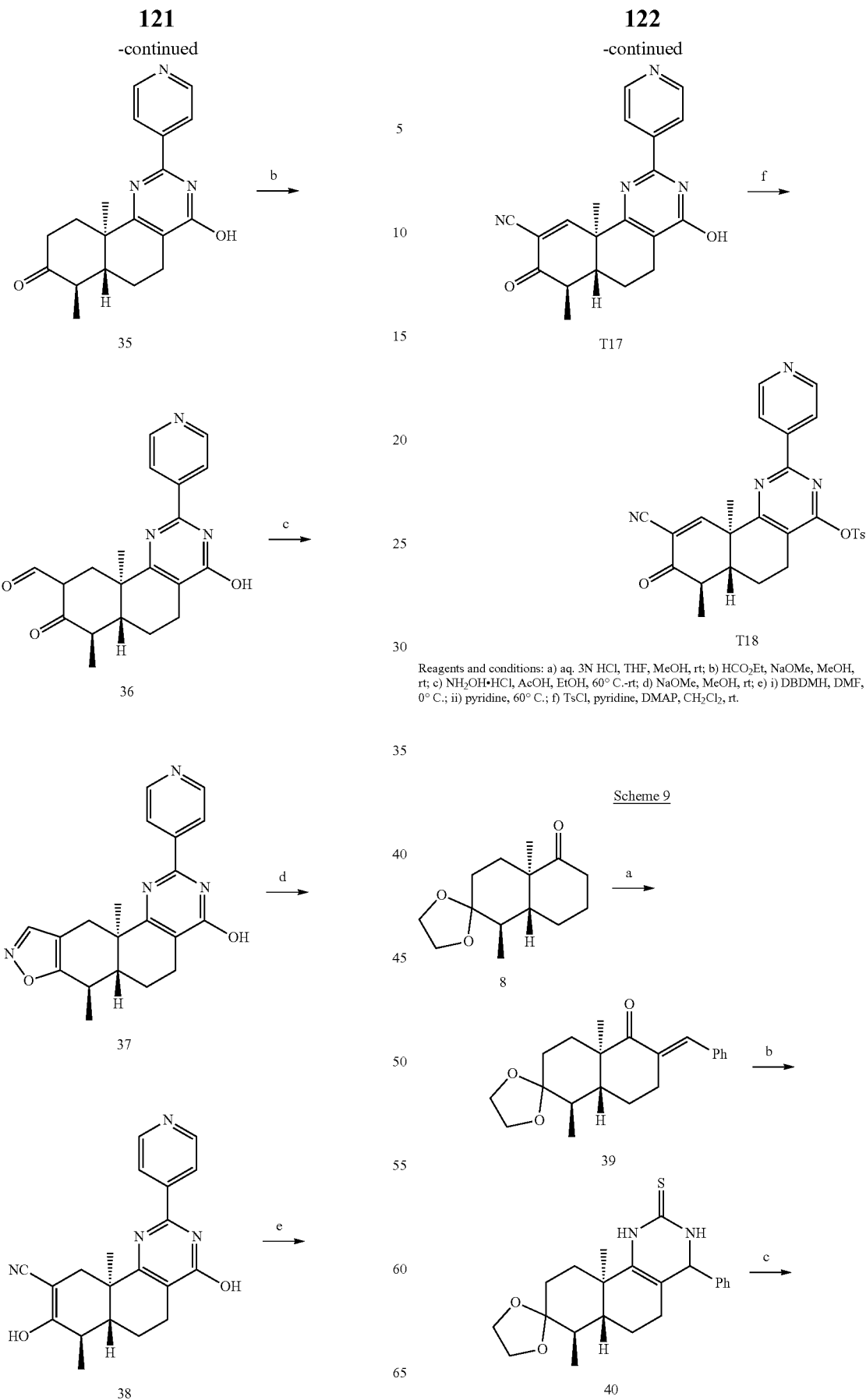
Reagents and conditions: a) aq. 3N HCl, THF, MeOH, rt; b) HCO₂Et, NaOMe, MeOH, rt; c) NH₂OH·HCl, AcOH, EtOH, 60° C.-rt; d) NaOMe, MeOH, rt; e) i) DBDMH, DMF, 0° C.; ii) pyridine, 60° C.; f) TsCl, pyridine, DMAP, CH₂Cl₂, rt.
Scheme 9

-continued

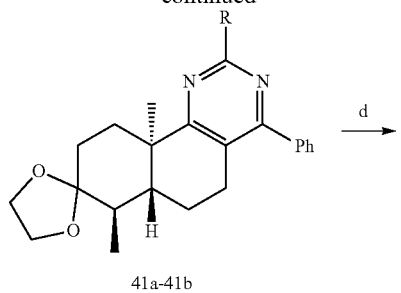

41a-41b

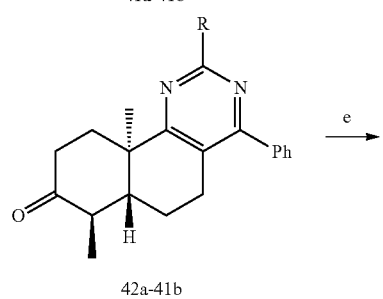

42a-41b

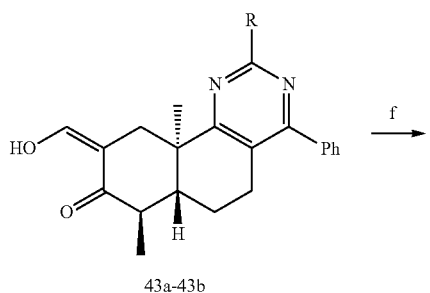

43a-43b

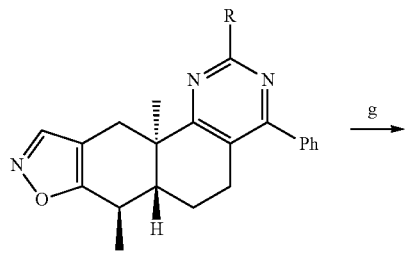

44a-44b

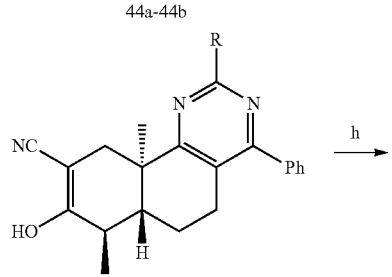

45a-45b

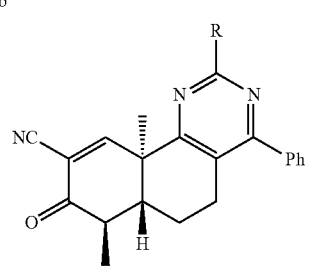

-continued

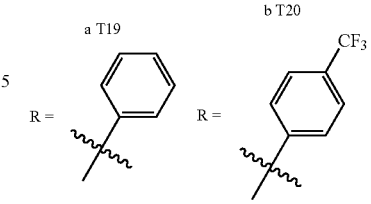

Reagents and conditions: a) PhCHO, NaOMe, THF, rt; b) thiourea, KOBu$^t$, EtOH, reflux; c) RB(OH)$_2$, copper(I) thiophene-2-carboxylate, Pd(PPh$_3$)$_4$, 1,4-dioxane, 100° C.; d) aq. 3N HCl, THF, rt; e) HCO$_2$Et, NaOMe, MeOH, rt; f) NH$_2$OH•HCl, EtOH, 50° C.; g) NaOMe, MeOH, THF, rt; h) i) Br$_2$, DMF/CH$_2$Cl$_2$, 0° C.; ii) pyridine, 50° C.

Scheme 10

T17

46

T21

Reagents and conditions: a) Tf$_2$O, Et$_3$N, CH$_2$Cl$_2$, 0° C.; b) 4-CH$_2$OH—PhB(OH)$_2$, K$_2$CO$_3$, Pd(dppf)Cl$_2$, 1,4-dioxane, 90° C.

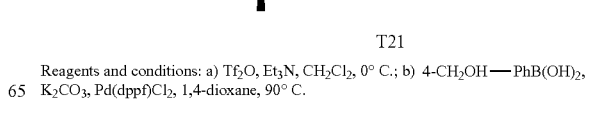

Scheme 11
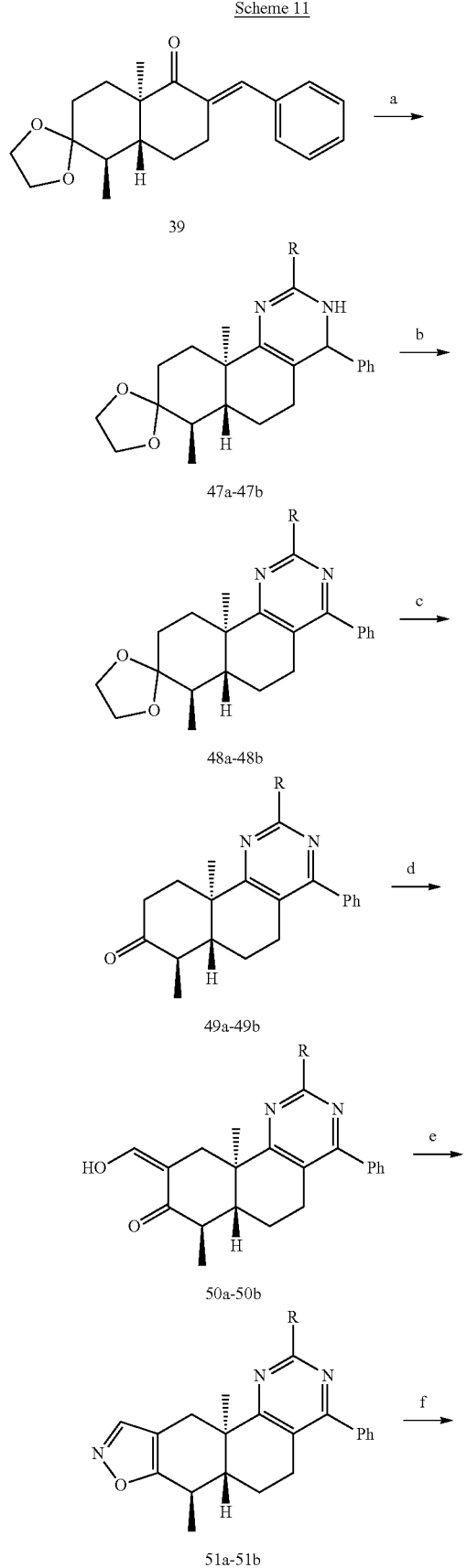
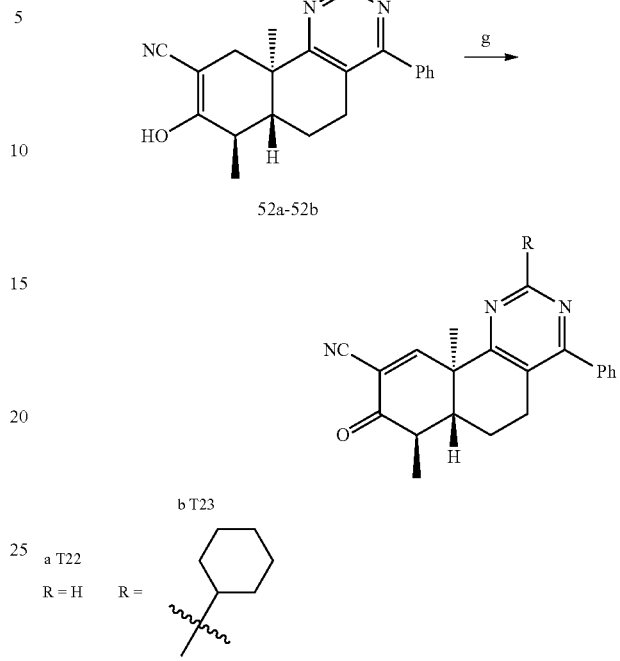
a T22  R = H
b T23  R = <image cyclohexyl>
Reagents and conditions: a) RC(NH)NH$_2$, KOBu$^t$, EtOH, reflux; b) MnO$_2$, CH$_2$Cl$_2$, rt; c) aq. 3N HCl, THF, rt; d) HCO$_2$Et, NaOMe, MeOH, rt; e) NH$_2$OH·HCl, EtOH, 50° C.; f) NaOMe, MeOH, THF, rt; g) i) Br$_2$, DMF, CH$_2$Cl$_2$, 0° C.; ii) pyridine, 50° C.
Scheme 12
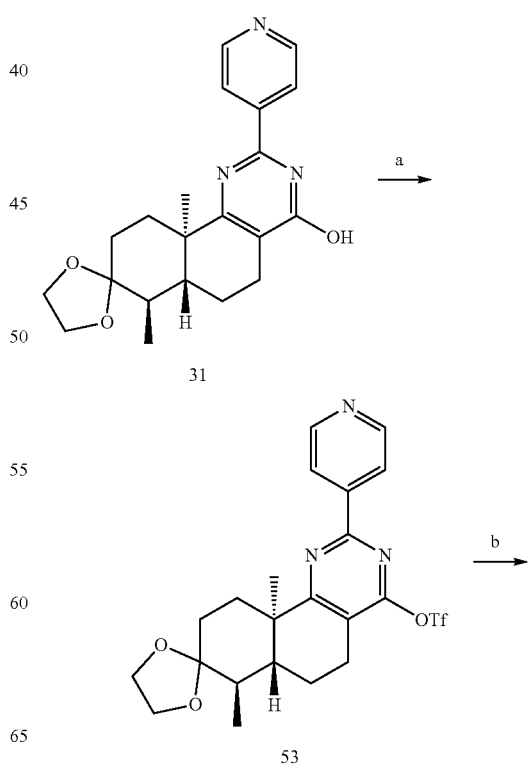

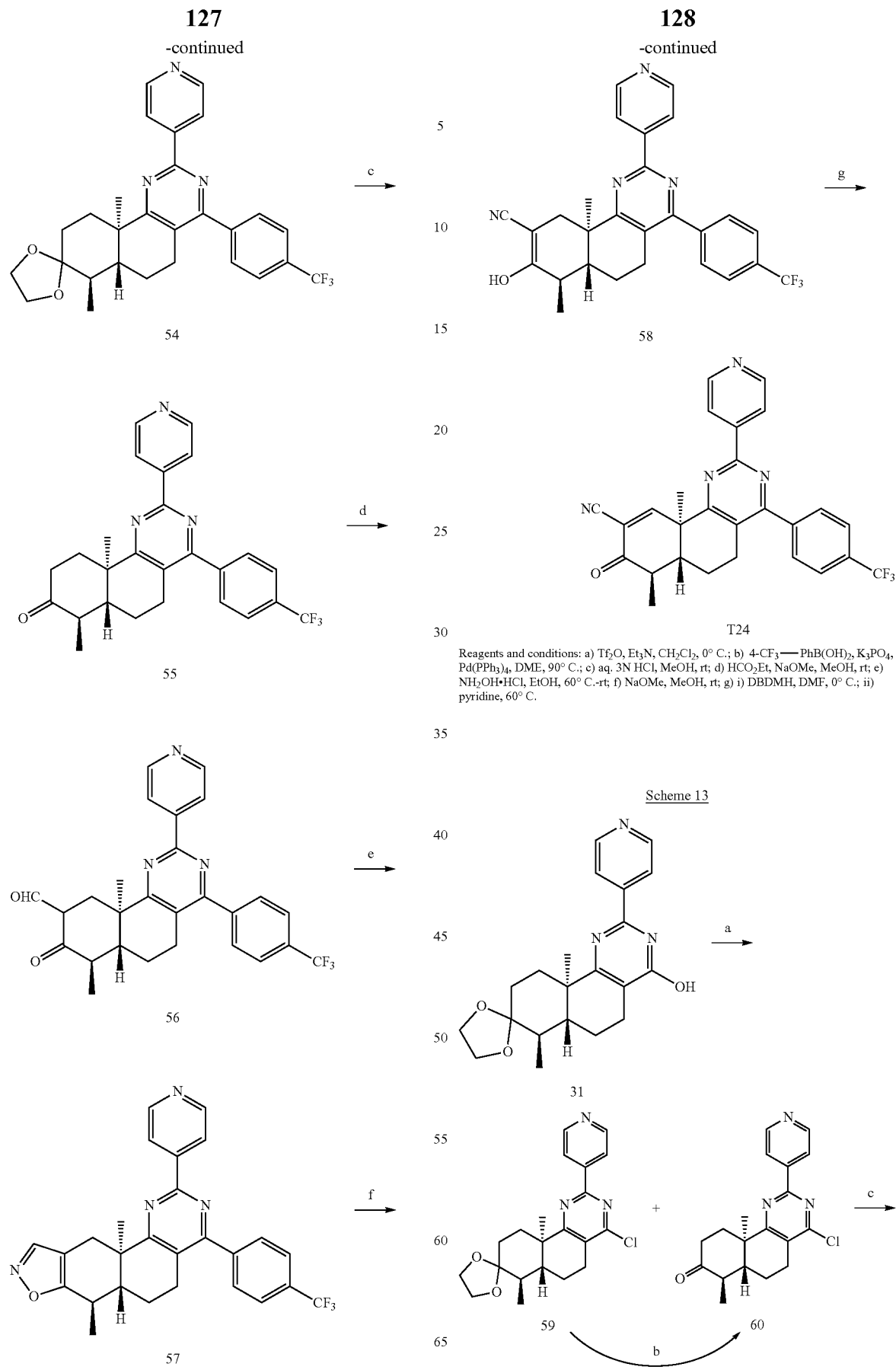

129
-continued
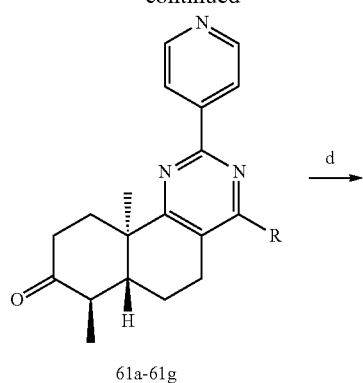
61a-61g
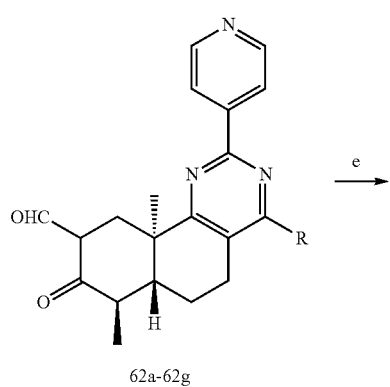
62a-62g
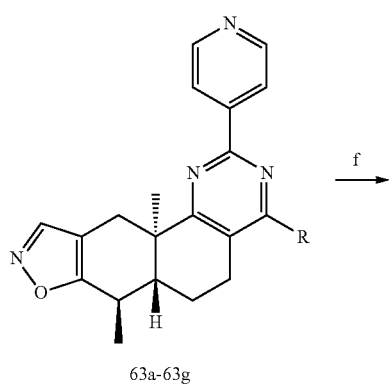
63a-63g
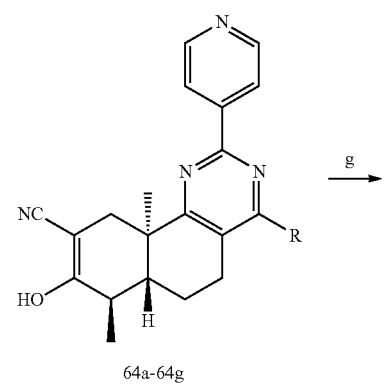
64a-64g
d →
e →
f →
g →
130
-continued
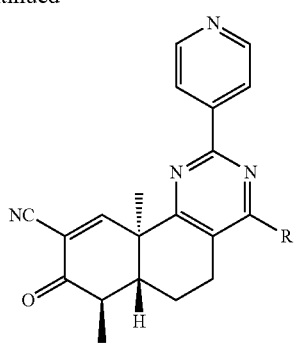
a T25  R = 3-pyridyl
b T26  R = 3-(trifluoromethyl)phenyl
c T27  R = 4-methylphenyl
d T28  R = 4-chlorophenyl
e T29  R = 4-pyridyl
f T30  R = 4-methoxyphenyl
g T31  R = 3,4-dichlorophenyl
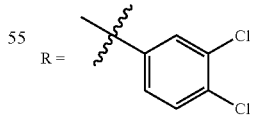
Reagents and conditions: a) POCl₃, toluene, 100° C.; b) aq. 3N HCl, MeOH, THF, rt; c) RB(OH)₂, K₃PO₄, Pd(PPh₃)₄, solvent, 90° C.; d) HCO₂Et, NaOMe, MeOH, rt; e) NH₂OH·HCl, EtOH, 60° C.-rt; f) NaOMe, MeOH, rt; g) i) DBDMH, DMF, 0° C.; ii) pyridine, 60° C.

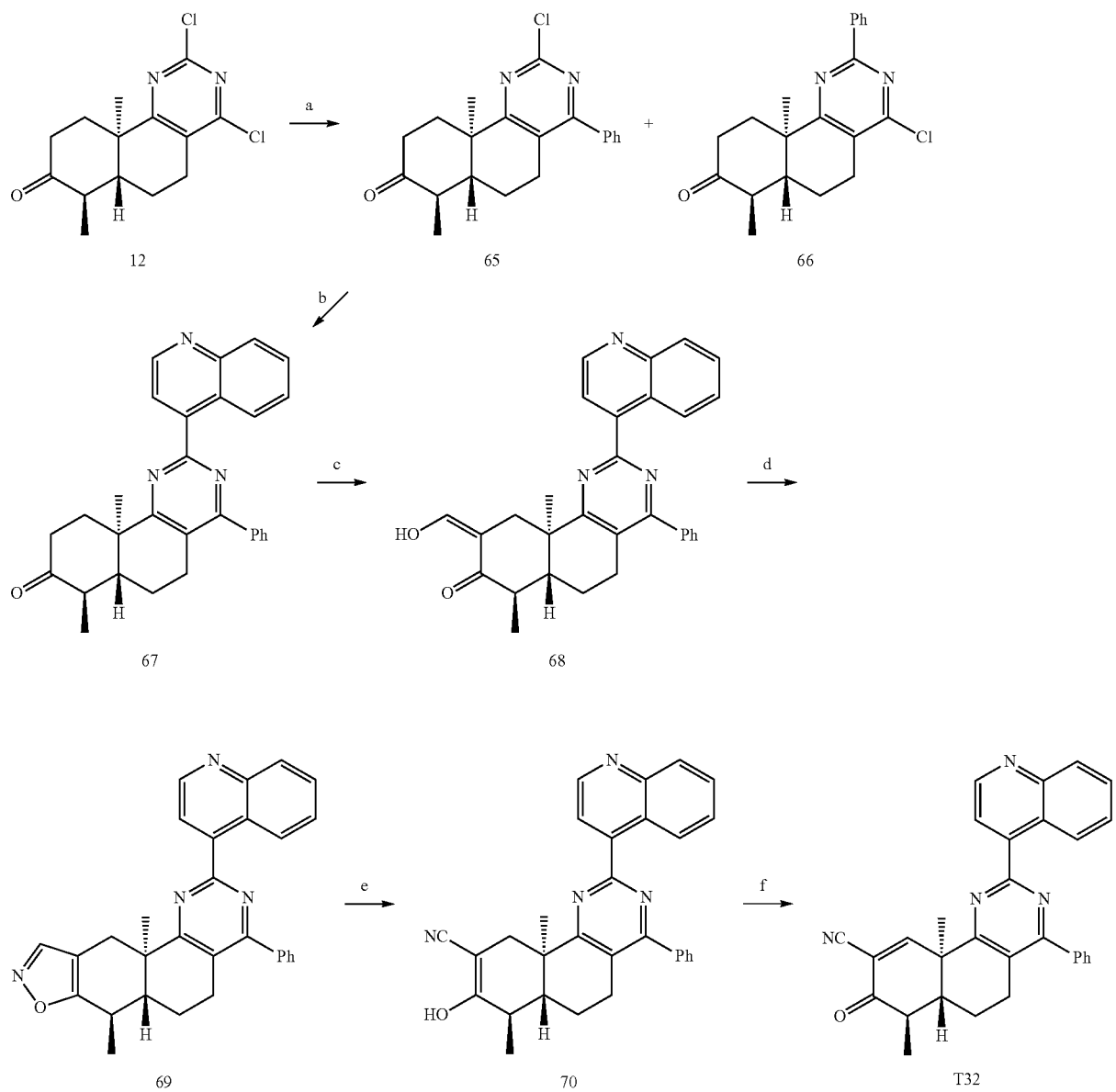
Scheme 14
Reagents and conditions: a) PhB(OH)$_2$, K$_2$CO$_3$, Pd(dppf)Cl$_2$, 1,4-dioxane, 90° C.; b) quinolin-4-ylboronic acid, K$_2$CO$_3$, Pd(dppf)Cl$_2$, 1,4-dioxane, DMF, 100° C.; c) HCO$_2$Et, NaOMe, MeOH, rt; d) NH$_2$OH•HCl, EtOH, 50° C.; e) NaOMe, MeOH, THF, rt; f) i) Br$_2$, DMF, CH$_2$Cl$_2$, 0° C.; ii) pyridine, 50° C.
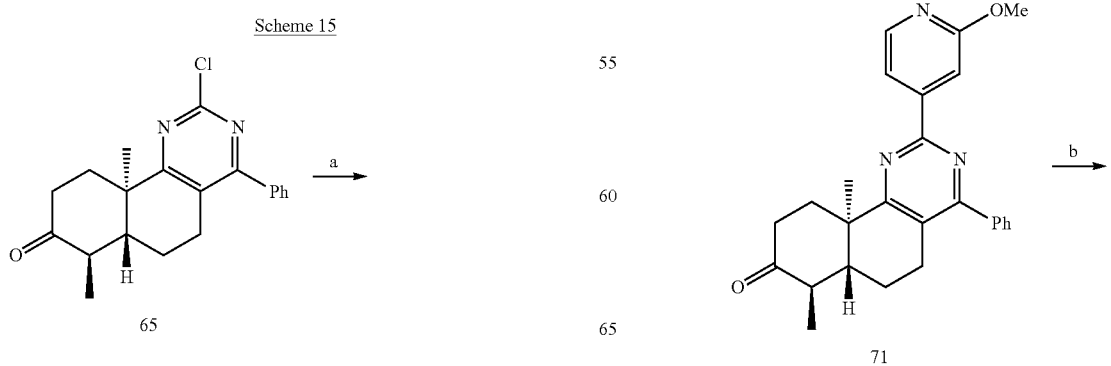
Scheme 15

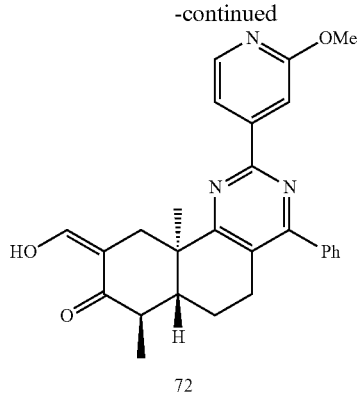
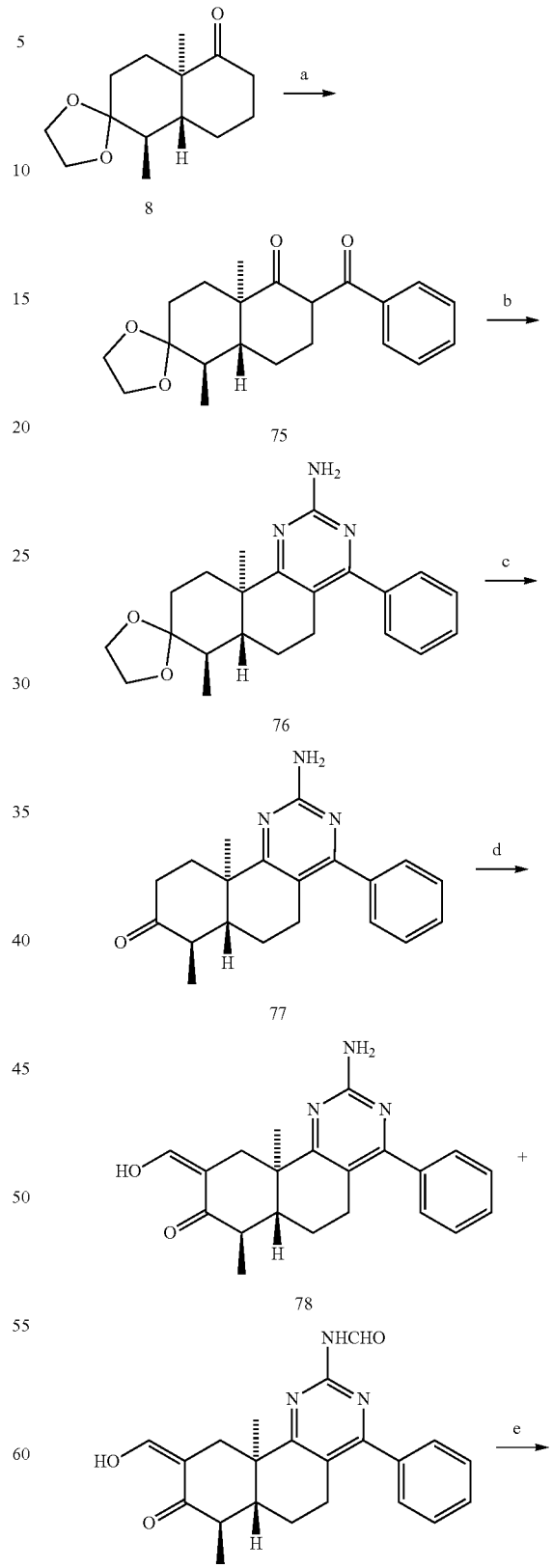
Scheme 16
Reagents and conditions: a) 2-methoxypyridine-4-boronic acid, K₂CO₃, Pd(dppf)Cl₂, 1,4-dioxane, DMF, 100° C.; b) HCO₂Et, NaOMe, MeOH, rt; c) NH₂OH·HCl, EtOH, 50° C.; d) NaOMe, MeOH, THF, rt; e) i) Br₂, DMF, CH₂Cl₂, 0° C.; ii) pyridine, 50° C.

135
-continued
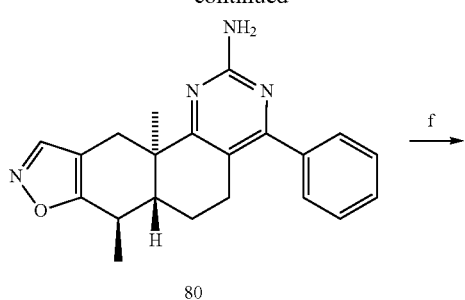 80
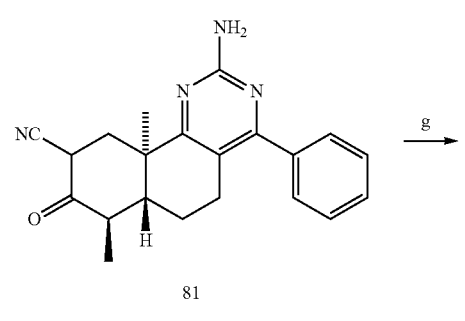 81
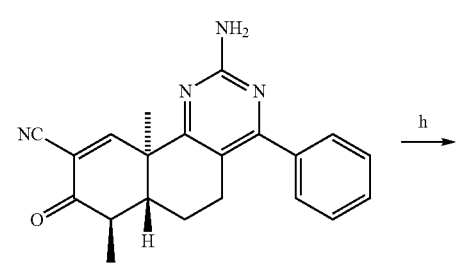 T34
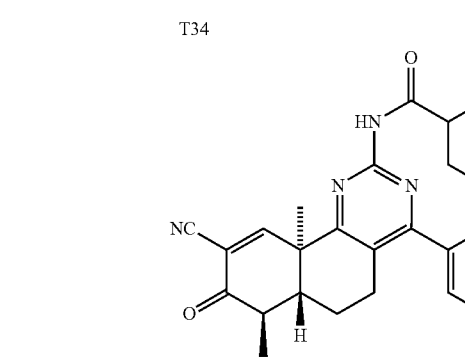 T35
Reagents and conditions: a) MgBr₂•OEt₂, DIPEA, PhCOCl, CH₂Cl₂, rt; b) guanidine carbonate, NaOMe, EtOH, reflux; c) aq. 1N HCl, MeOH, rt; d) HCO₂Et, NaOMe, MeOH, rt; e) NH₂OH•HCl, EtOH, H₂O, rt; f) NaOMe, MeOH, THF, rt; g) i) DBDMH, DMF, 0° C.; ii) pyridine, 65° C.; h) cyclohexanecarbonyl chloride, pyridine, CH₂Cl₂, rt.
Scheme 17
 8
136
-continued
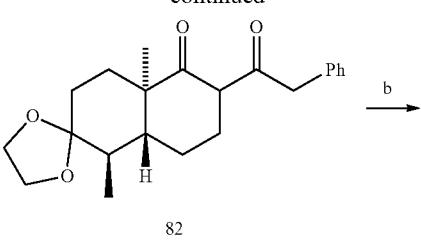 82
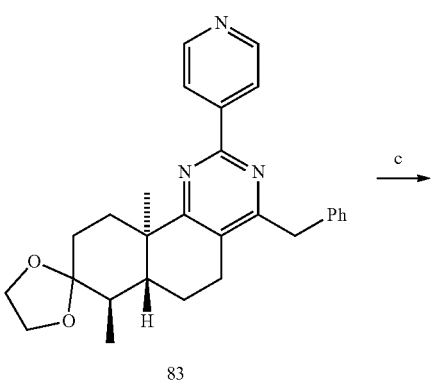 83
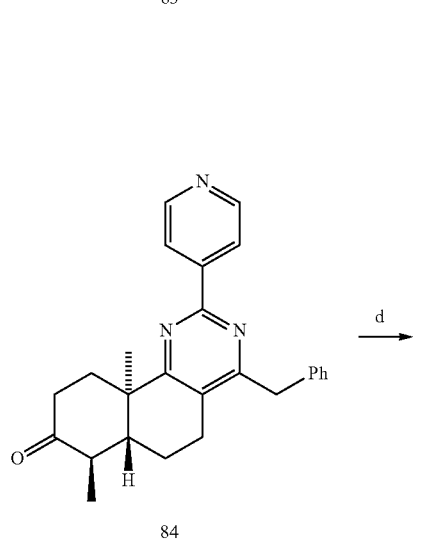 84
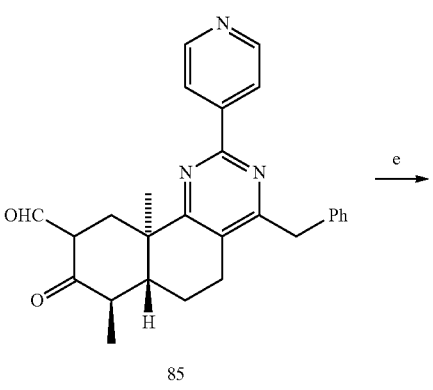 85

137
-continued
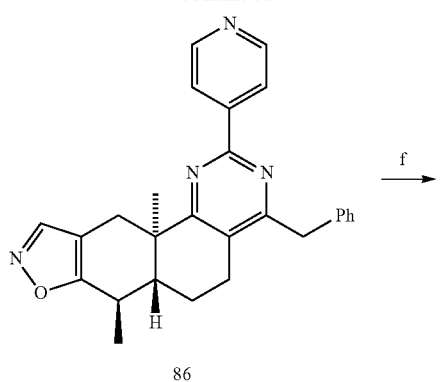
86
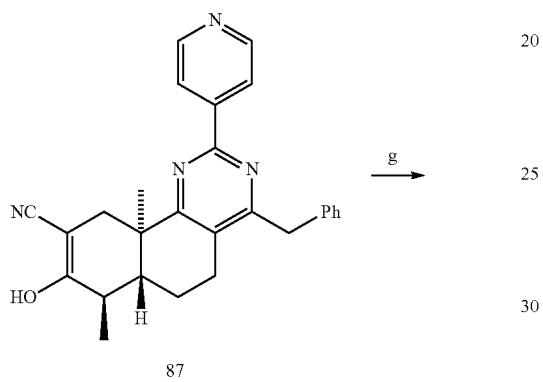
87
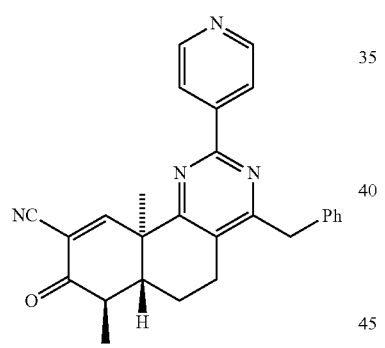
T36
Reagents and conditions: a) MgBr₂·OEt₂, DIPEA, PhCH₂COCl, CH₂Cl₂, rt; b) amidinopyridine hydrochloride, K₂CO₃, EtOH, rt; c) aq. 3N HCl, MeOH, rt; d) HCO₂Et, NaOMe, MeOH, rt; e) NH₂OH·HCl, EtOH, 60° C.-rt; f) NaOMe, MeOH, rt; g) i) DBDMH, DMF, 0° C.; ii) pyridine, 60° C.
Scheme 18
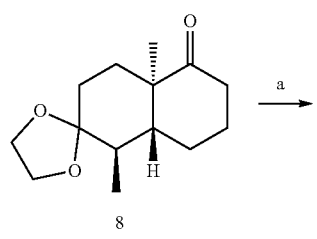
8
138
-continued
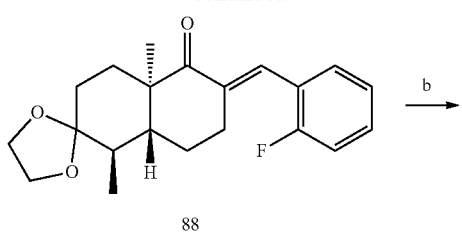
88
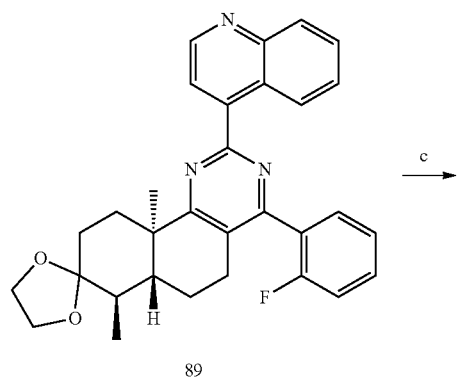
89
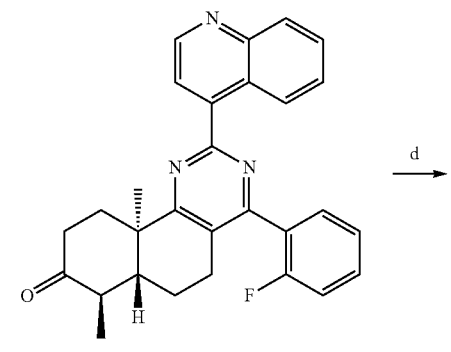
90
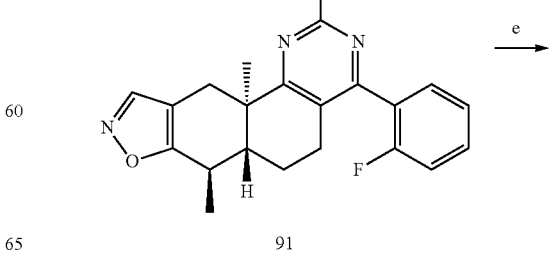
91

139
-continued

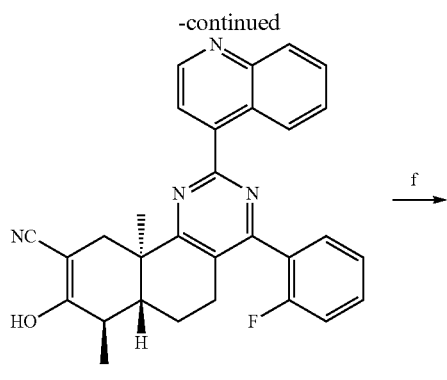

92

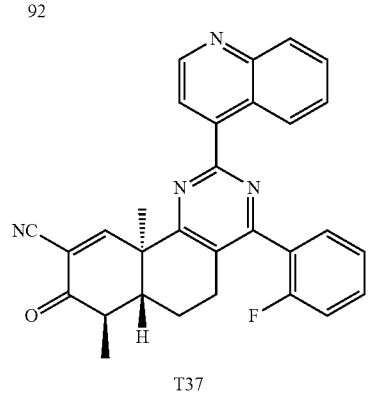

T37

Reagents and conditions: a) 2-fluorobenzaldehyde, KF/Al₂O₃, EtOH, rt; b) i) 4-quinolinecarboximidamide hydrochloride, K₂CO₃, EtOH, reflux; ii) MnO₂, CH₂Cl₂, rt; or ii) DDQ, CH₂Cl₂, rt; c) aq. 3N HCl, THF, rt; d) i) HCO₂Et, NaOMe, 0° C. to rt; ii) 6N HCl, NH₂OH·HCl, EtOH, 55° C.; e) NaOMe, MeOH, 55° C.; f) i) DBDMH, DMF, 0° C.; ii) pyridine, 55° C.

Scheme 19

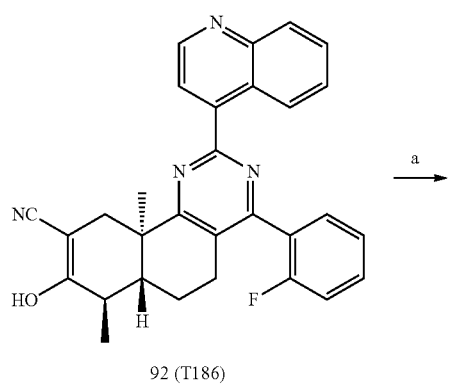

92 (T186)

T37

140
-continued

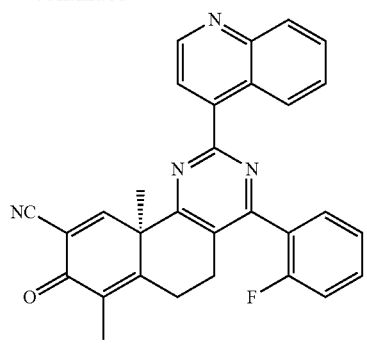

T38

Reagents and conditions: a) i) Br₂, DMF, CH₂Cl₂, 0° C.; ii) pyridine, 50° C.

Scheme 20

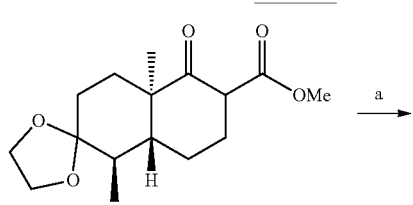

9

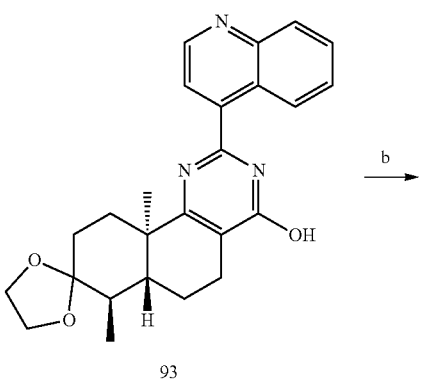

93

94

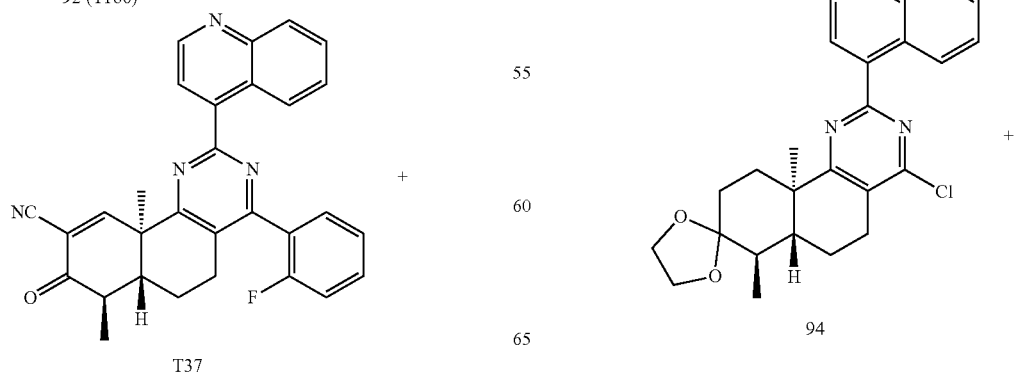

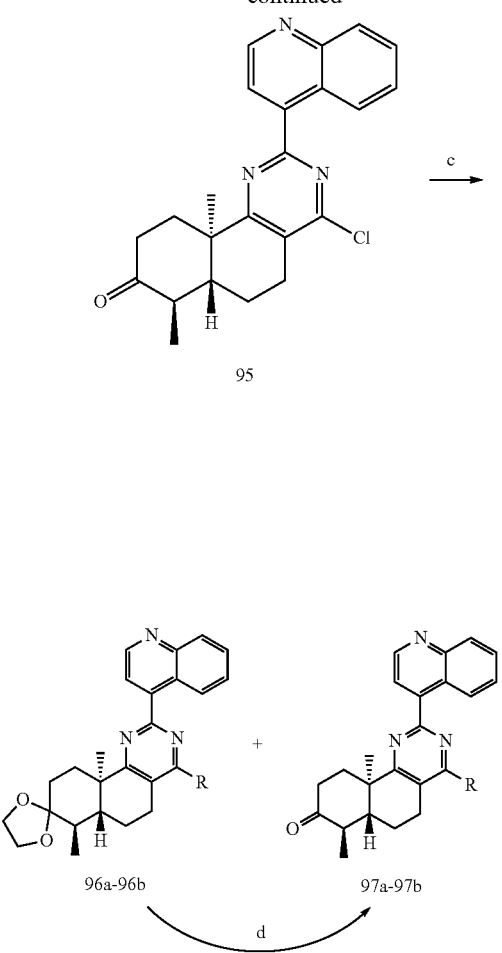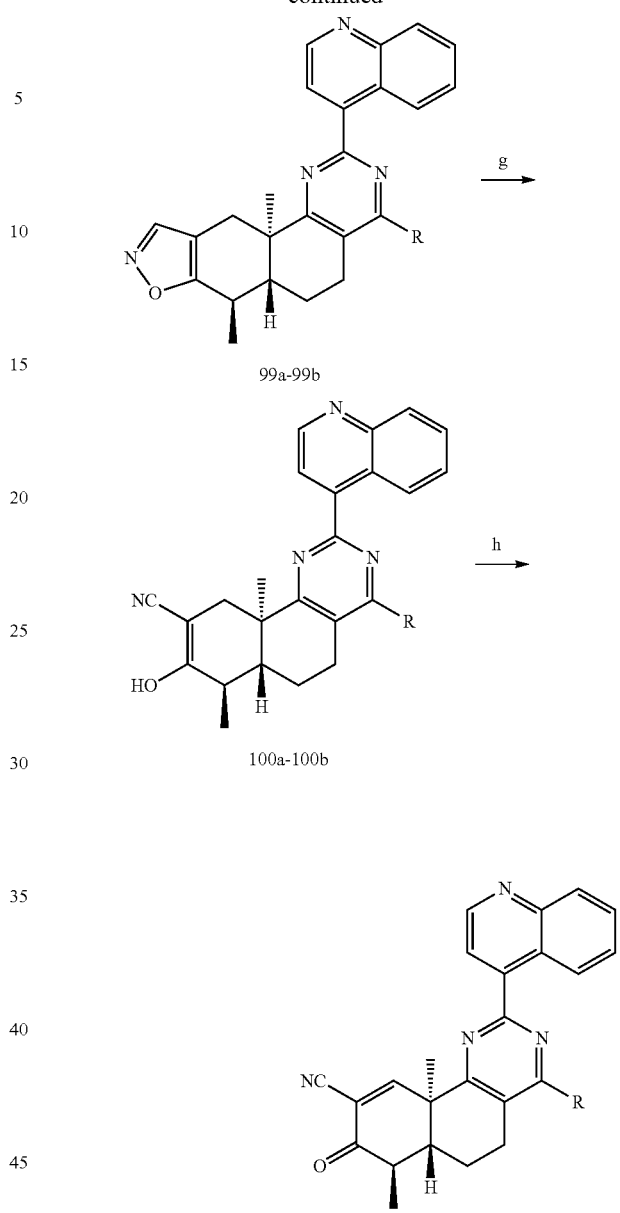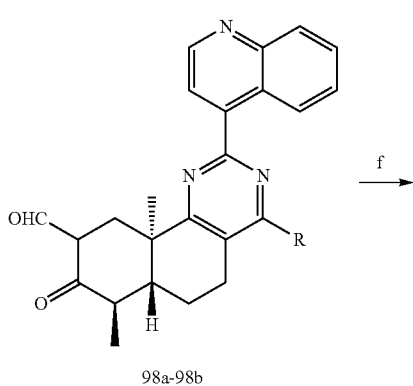
Reagents and conditions: a) quinoline-4-carboximidamide hydrochloride, $K_2CO_3$, EtOH, rt; b) $POCl_3$, toluene, microwave, 100° C.; c) $RB(OH)_2$, $Pd(dppf)Cl_2$, $K_2CO_3$, 1,4-dioxane, 90° C.; d) aq. 3N HCl, THF, rt; e) $HCO_2Et$, NaOMe, MeOH, rt; f) $NH_2OH \cdot HCl$, EtOH, 50° C.; g) NaOMe, MeOH, THF, rt; h) i) $Br_2$, DMF, $CH_2Cl_2$, 0° C.; ii) pyridine, 50° C.

Scheme 21
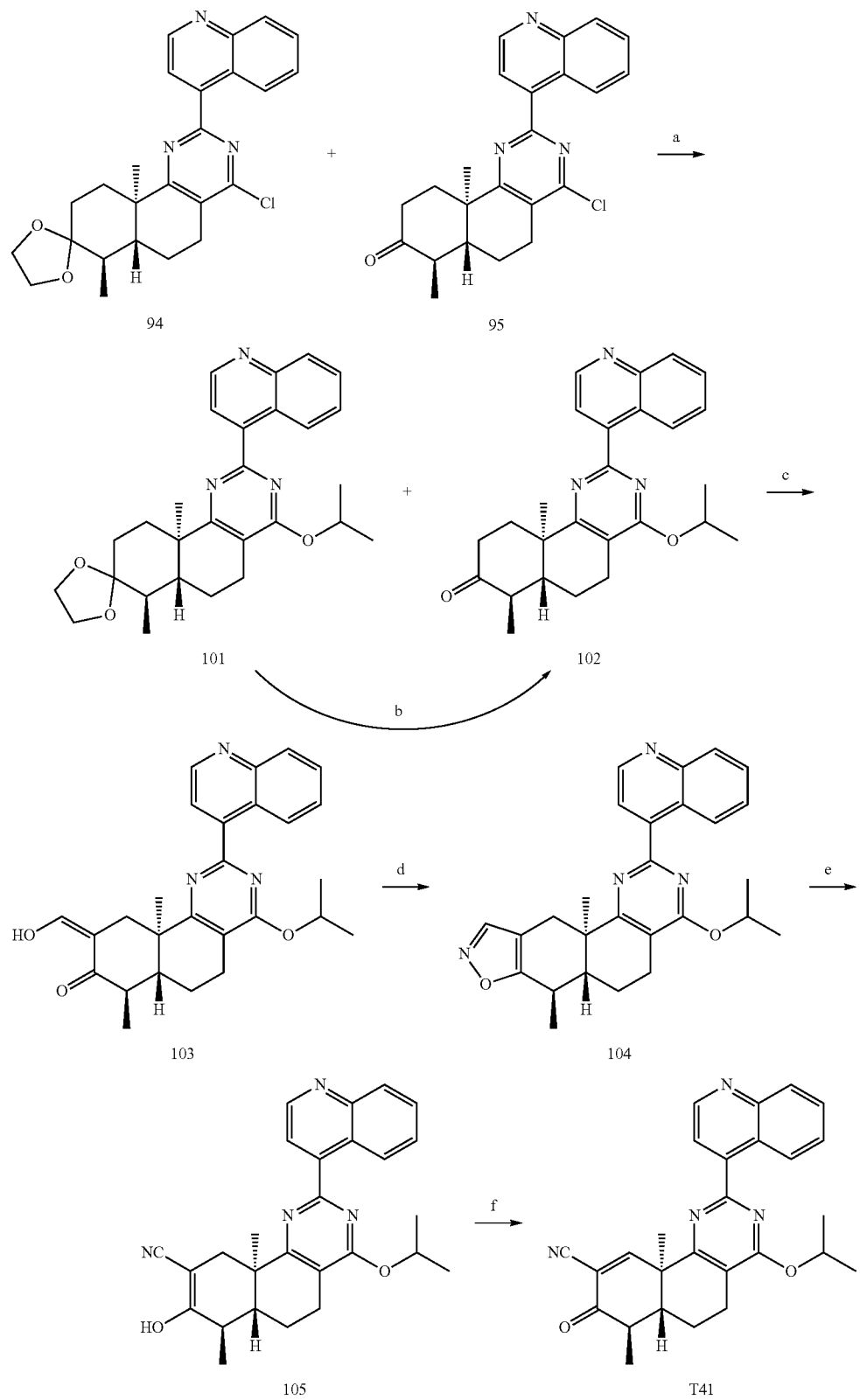
Reagents and conditions: a) 2-propanol, NaH, THF, rt; b) aq. 3N HCl, THF, rt; c) HCO$_2$Et, NaOMe, MeOH, rt; d) NH$_2$OH•HCl, EtOH, 50° C.; e) NaOMe, MeOH, THF, rt; f) i) Br$_2$. DMF, CH$_2$Cl$_2$, 0° C.; ii) pyridine, 50° C.

Scheme 22
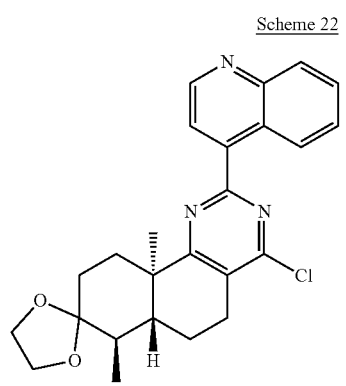
94
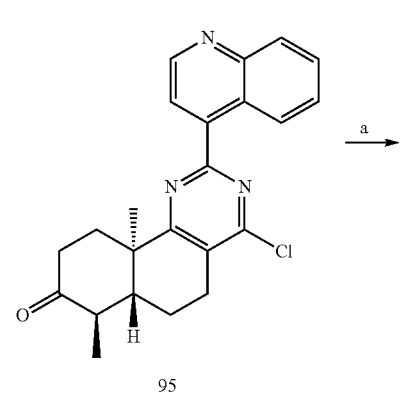
95
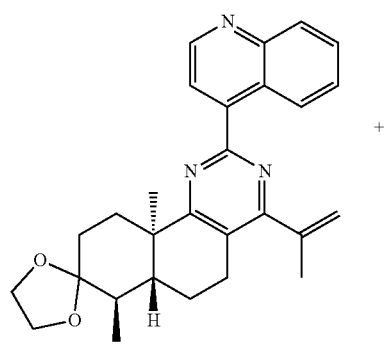
106
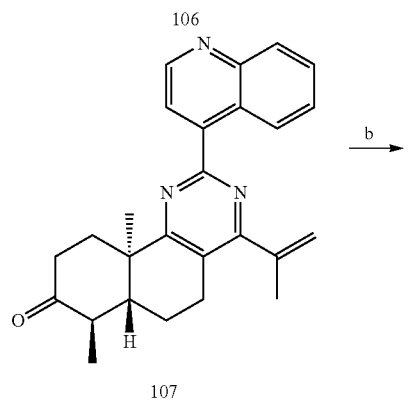
107
-continued
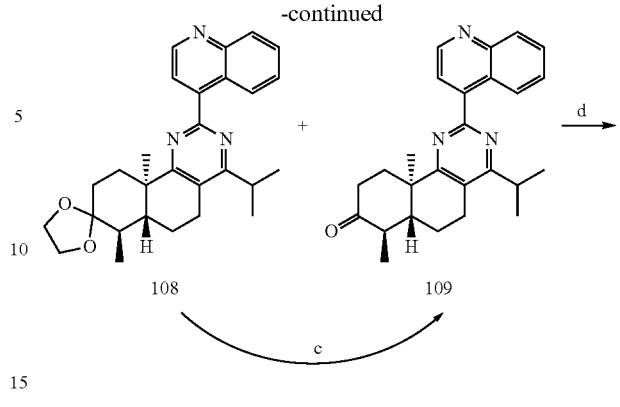
108    109
110
111
112

147
-continued

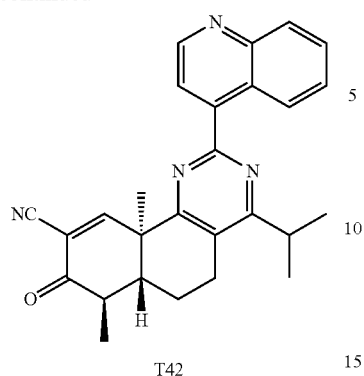

Reagents and conditions: a) 4,4,5,5-tetramethyl-2-(prop-1-en-2-yl)-1,3,2-dioxaborolane, Pd(dppf)Cl₂, K₂CO₃, 1,4-dioxane, 90° C.; b) H₂, 10% Pd/C, THF, rt; c) aq. 3N HCl, THF, rt; d) HCO₂Et, NaOMe, MeOH, rt; e) NH₂OH•HCl, EtOH, 50° C.; f) NaOMe, MeOH, THF, rt; g) i) Br₂, DMF, CH₂Cl₂, 0° C.; ii) pyridine, 50° C.

148
-continued

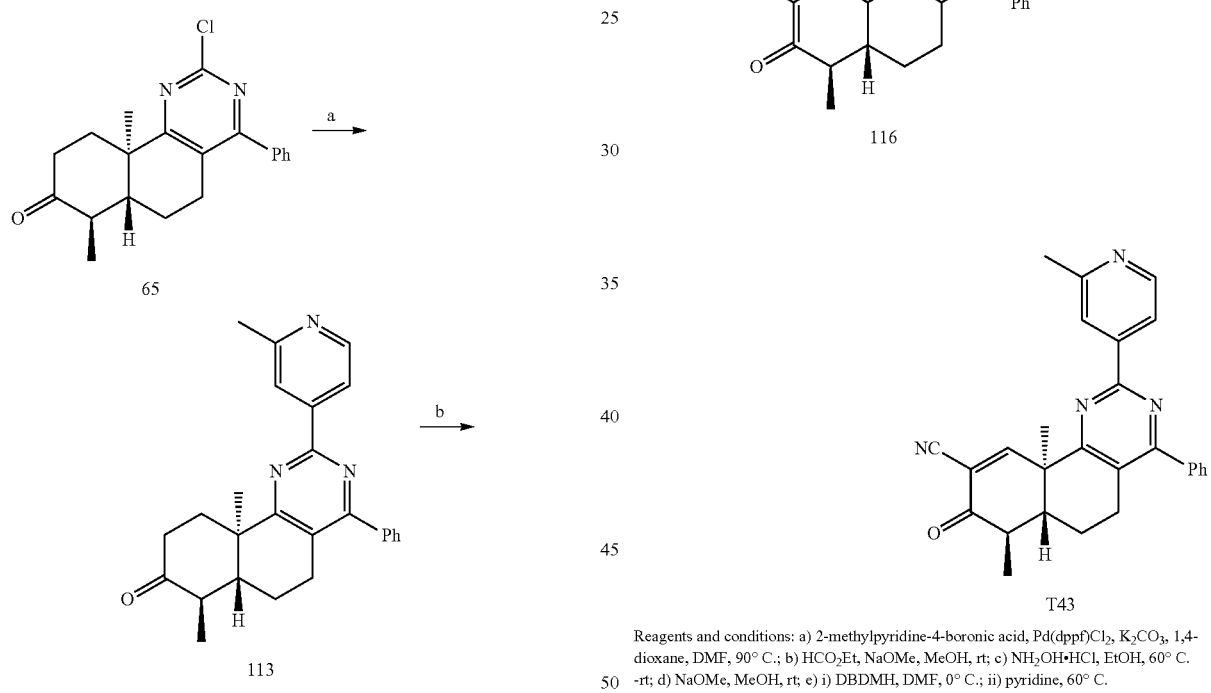

Reagents and conditions: a) 2-methylpyridine-4-boronic acid, Pd(dppf)Cl₂, K₂CO₃, 1,4-dioxane, DMF, 90° C.; b) HCO₂Et, NaOMe, MeOH, rt; c) NH₂OH•HCl, EtOH, 60° C. -rt; d) NaOMe, MeOH, rt; e) i) DBDMH, DMF, 0° C.; ii) pyridine, 60° C.

Scheme 24

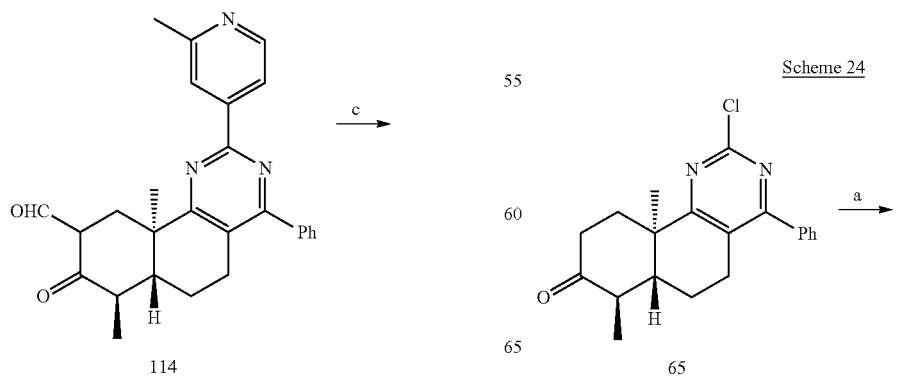

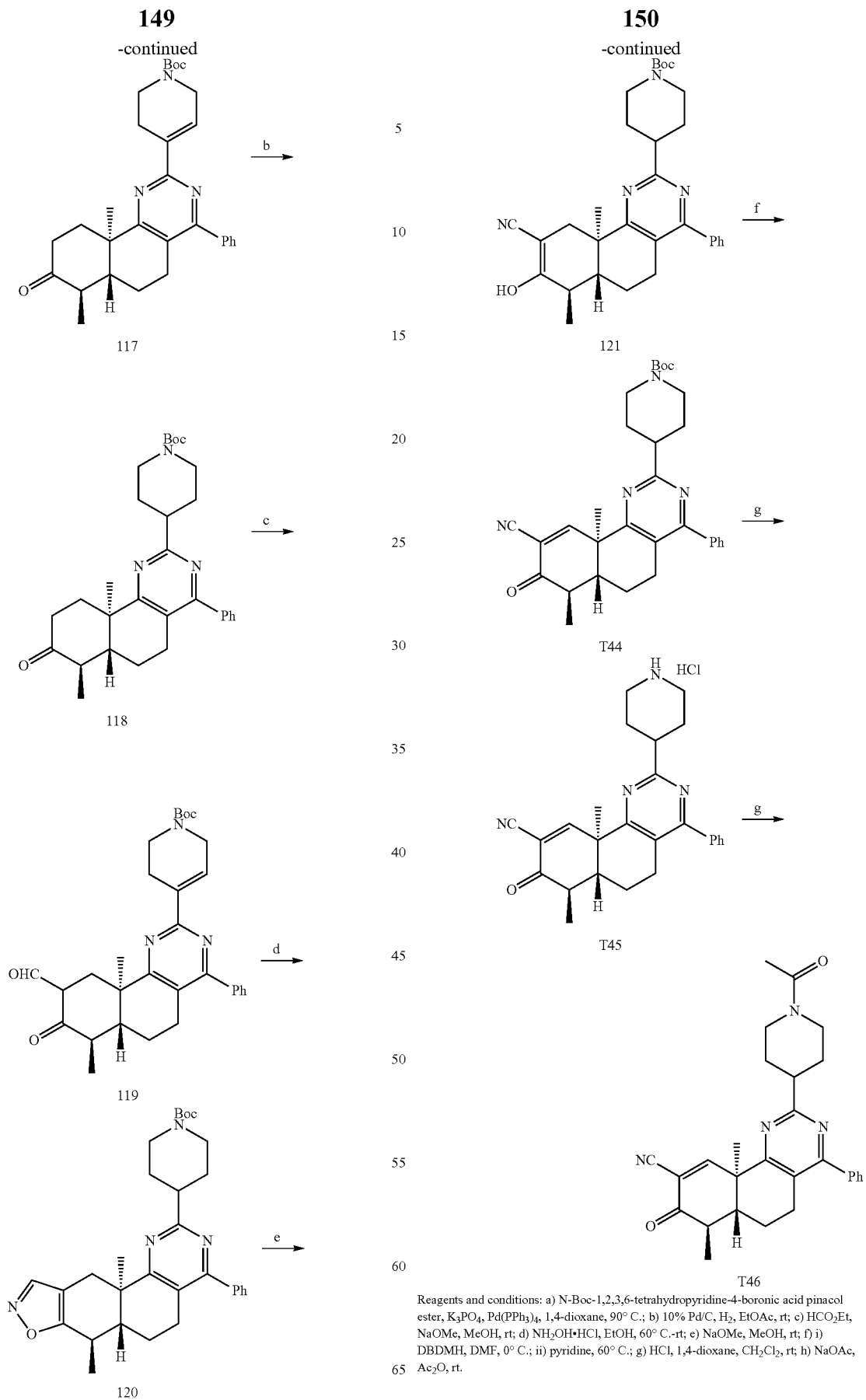
Reagents and conditions: a) N-Boc-1,2,3,6-tetrahydropyridine-4-boronic acid pinacol ester, K₃PO₄, Pd(PPh₃)₄, 1,4-dioxane, 90° C.; b) 10% Pd/C, H₂, EtOAc, rt; c) HCO₂Et, NaOMe, MeOH, rt; d) NH₂OH•HCl, EtOH, 60° C.-rt; e) NaOMe, MeOH, rt; f) i) DBDMH, DMF, 0° C.; ii) pyridine, 60° C.; g) HCl, 1,4-dioxane, CH₂Cl₂, rt; h) NaOAc, Ac₂O, rt.

Scheme 25
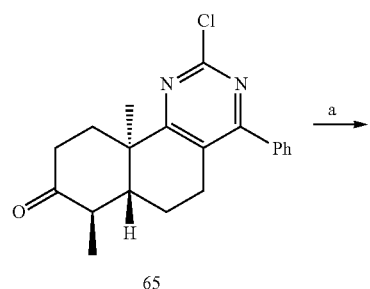
65
a →
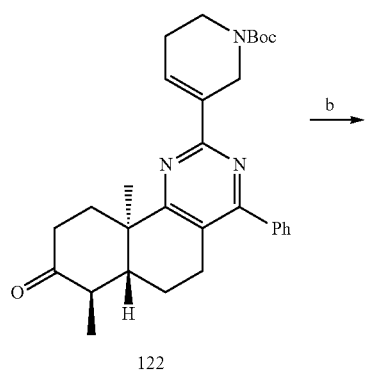
122
b →
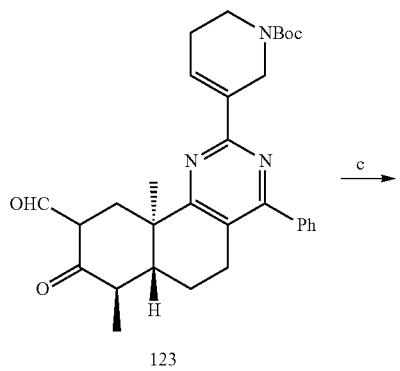
123
c →
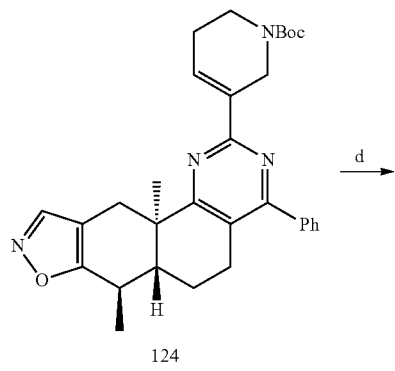
124
d →
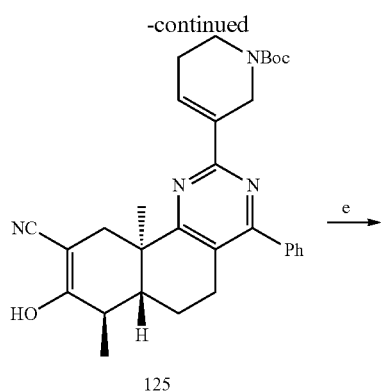
125
e →
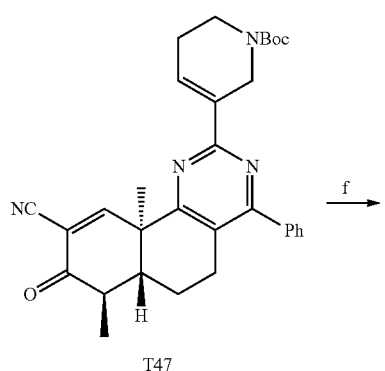
T47
f →
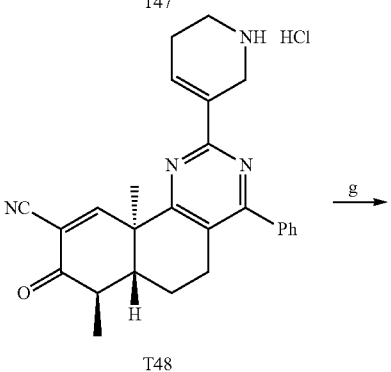
T48
g →
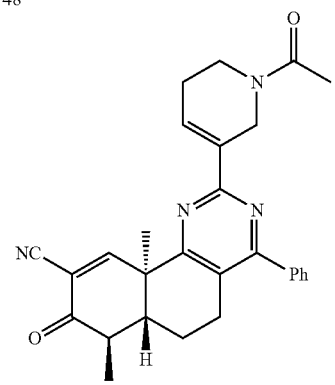
T49
Reagents and conditions: a) tert-butyl 3-(4,4,5,5-tetramethyl-1,3,2-dioxaborolan-2-yl)-5,6-dihydropyridine-1(2H)-carboxylate, $K_3PO_4$, Pd(PPh$_3$)$_4$, 1,4-dioxane, 90° C.; b) HCO$_2$Et, NaOMe, MeOH, rt; c) NH$_2$OH•HCl, EtOH, 60° C.-rt; d) NaOMe, MeOH, rt; e) i) DBDMH, DMF, 0° C.; ii) pyridine, 60° C.; f) HCl, 1,4-dioxane, CH$_2$Cl$_2$, rt; g) NaOAc, Ac$_2$O, rt.

Scheme 26
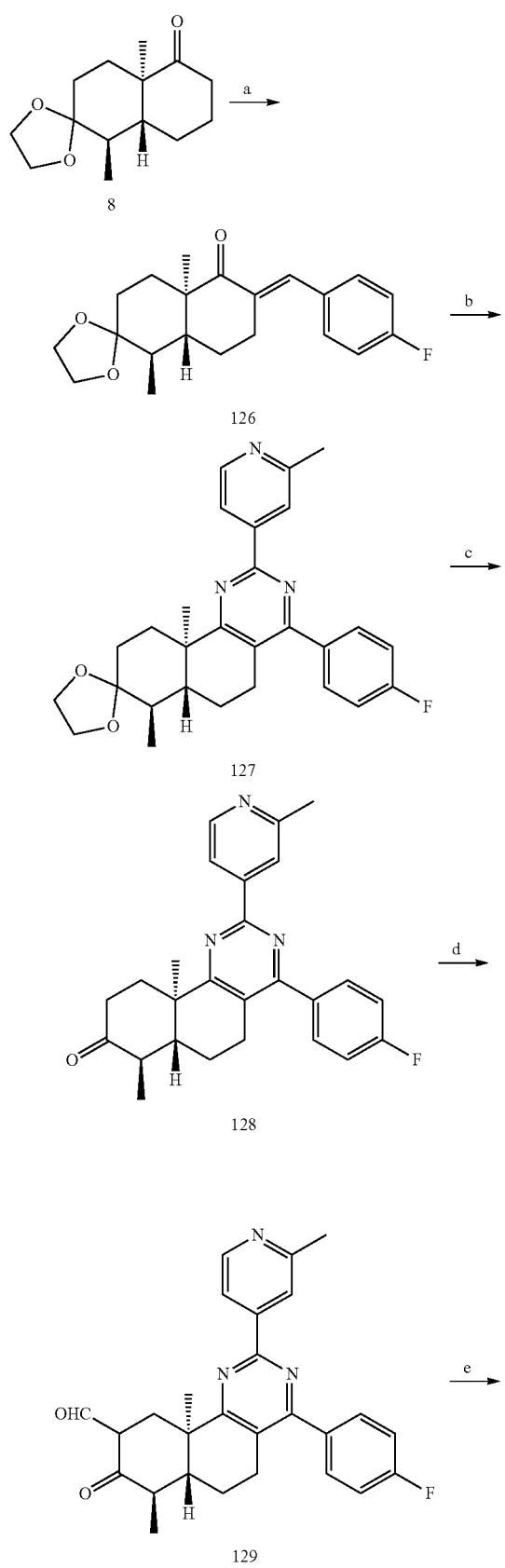
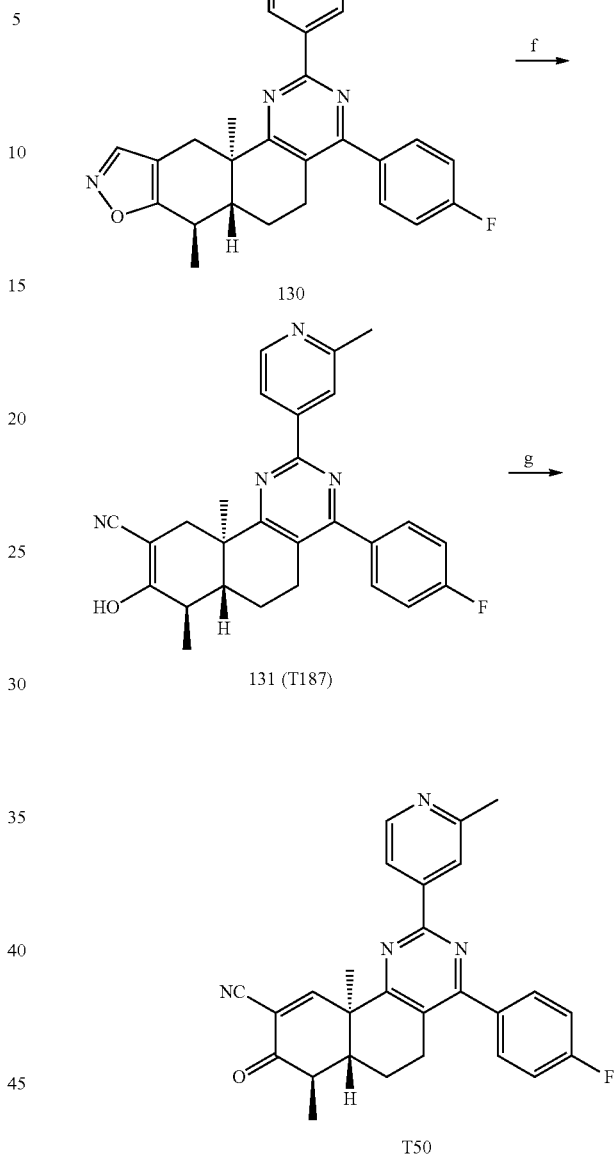
Reagents and conditions: a) 4-fluorobenzaldehyde, KF/Al₂O₃, 2-PrOH, 60° C.-rt; b) i) 2-methyl-4-pyridinecaroximidamide hydrochloride, K₂CO₃, EtOH, reflux; ii) MnO₂, CH₂Cl₂, rt; c) aq. 3N HCl, MeOH, rt; d) HCO₂Et, NaOMe, 0° C. to rt; e) NH₂OH•HCl, AcOH, EtOH, 60° C.-rt; f) K₂CO₃, MeOH, rt; g) i) DBDMH, DMF, 0° C.; ii) pyridine, 60° C.
Scheme 27
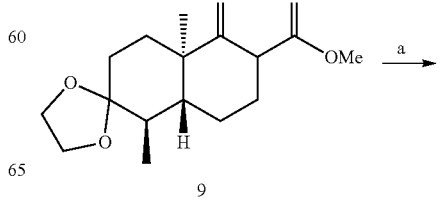

155
-continued
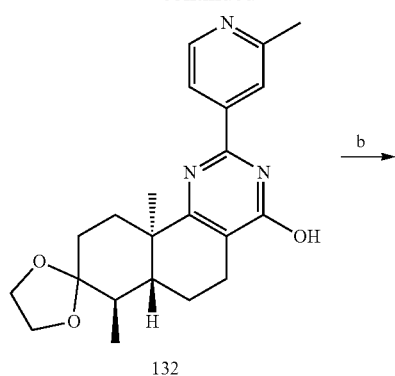
132
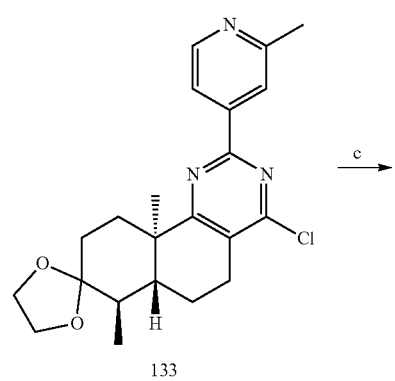
133
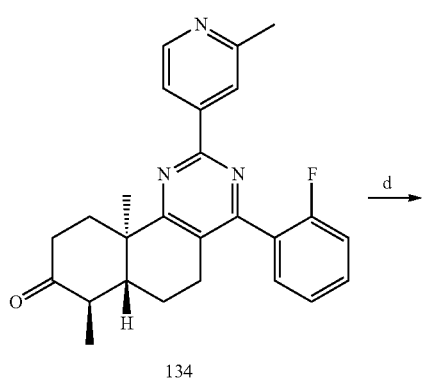
134
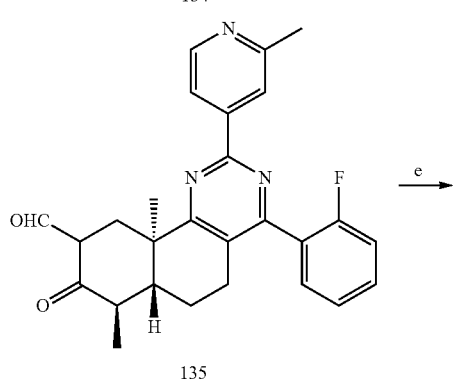
135
156
-continued
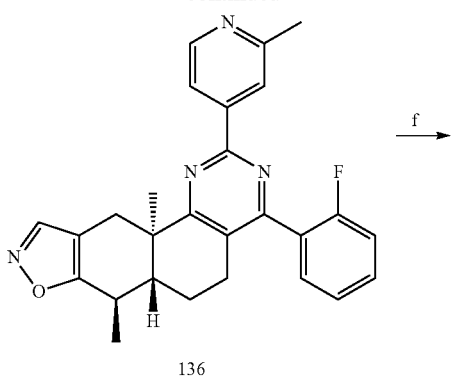
136
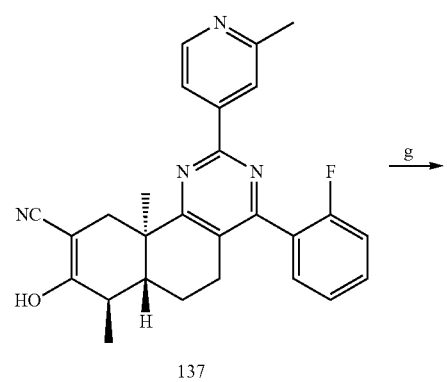
137
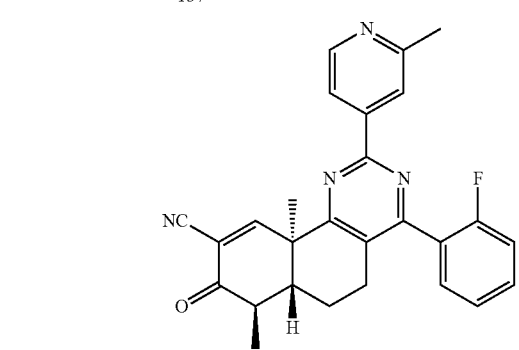
T51
Reagents and conditions: a) 2-methyl-4-pyridinecarboximidamide hydrochloride, K₂CO₃, EtOH, rt; b) i) POCl₃, toluene, microwave, 100° C.; ii) aq. 3N HCl, MeOH, rt; c) 2-F-PhB(OH)₂, K₂CO₃, Pd(PPh₃)₄, 1,4-dioxane, microwave, 100° C.; d) HCO₂Et, NaOMe, MeOH, rt; e) NH₂OH·HCl, AcOH, EtOH, 60° C.-rt; f) NaOMe, MeOH, rt; g) i) DBDMH, DMF, 0° C.; ii) pyridine, 60° C.
Scheme 28
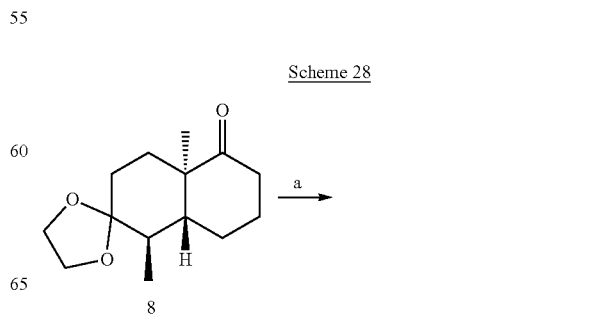
8

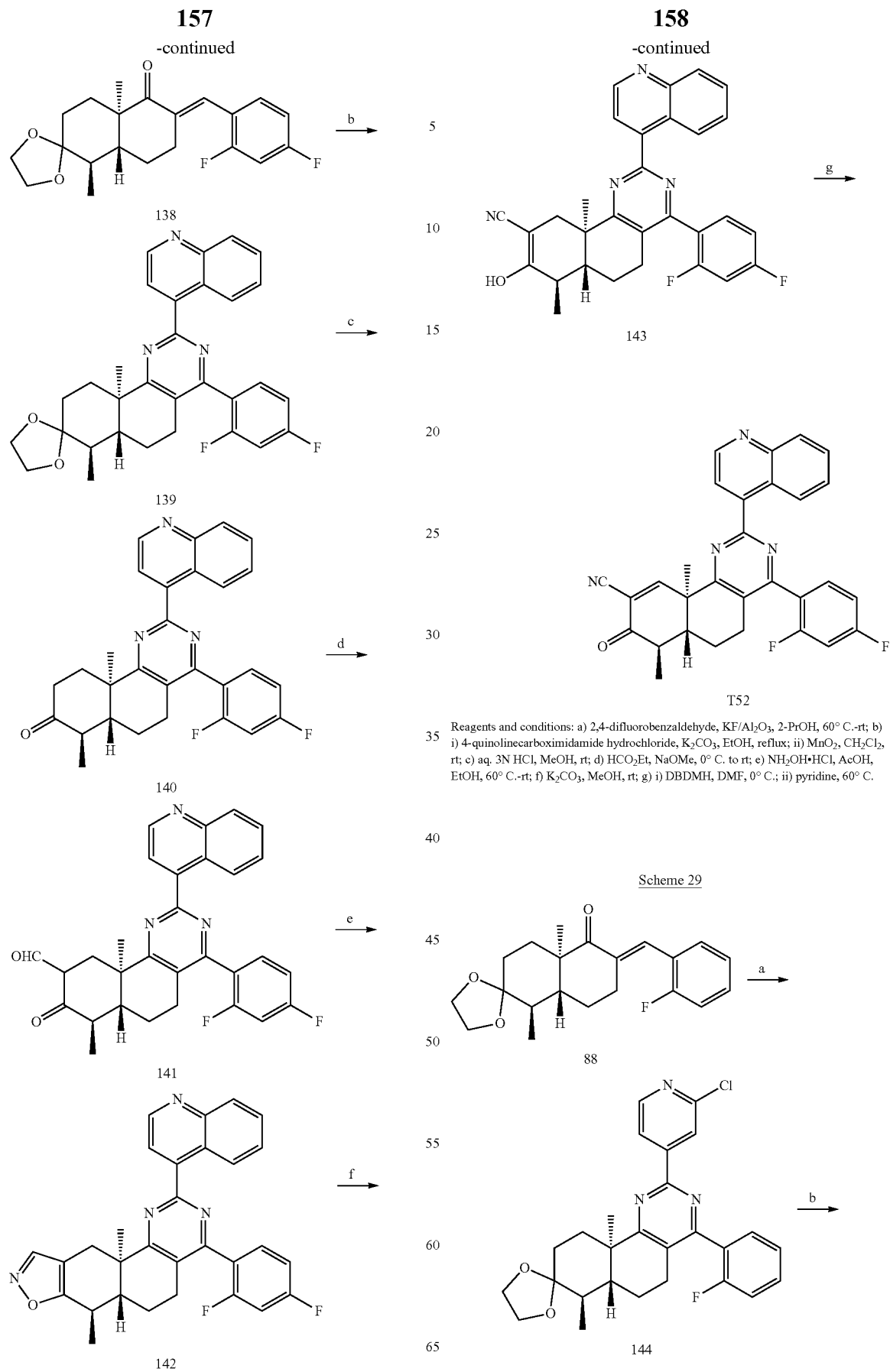

159
-continued

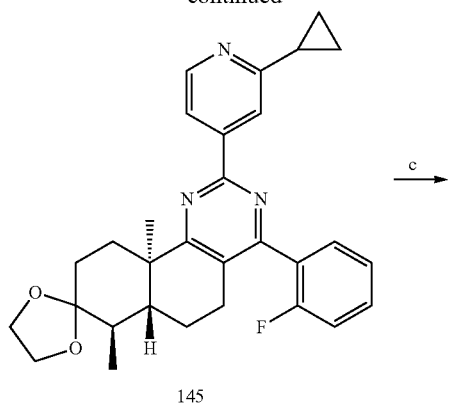
145

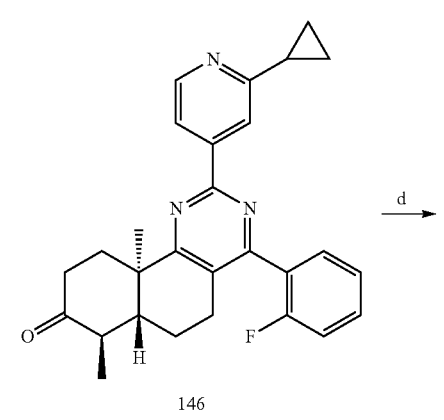
146

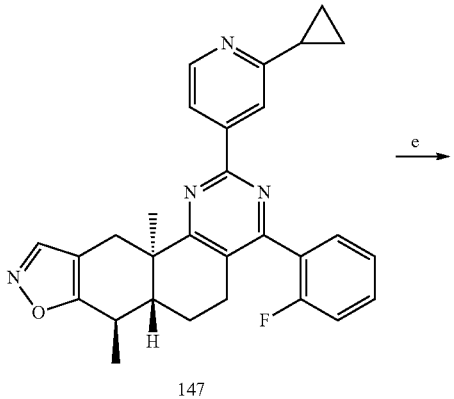
147

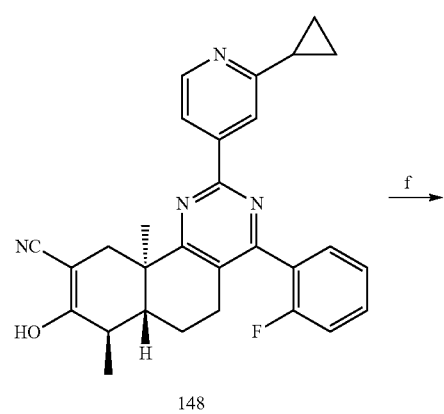
148 c → d → e → f →

160
-continued

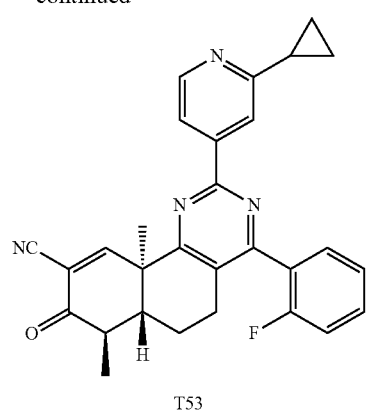
T53

Reagents and conditions: a) i) 2-chloropyridine-4-carboximidamide hydrochloride, K₂CO₃, EtOH, microwave, 120° C.; ii) DDQ, CH₂Cl₂, rt; b) cyclopropylboronic acid, K₃PO₄, Pd(OAc)₂, tricyclohexylphosphine, toluene, H₂O, microwave, 130° C.; c) aq. 3N HCl, THF, MeOH, rt; d) i) HCO₂Et, NaOMe, MeOH, 0° C. to rt; ii) 6N HCl, NH₂OH·HCl, EtOH, 55° C.; e) NaOMe, MeOH, 55° C.; f) i) DBDMH, DMF, 0° C.; ii) pyridine, 55° C.

Scheme 30

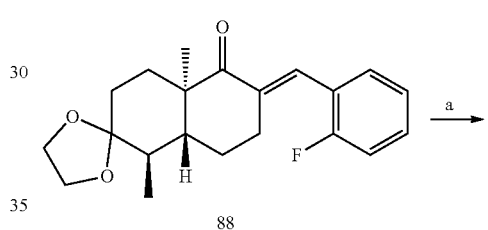
88 a →

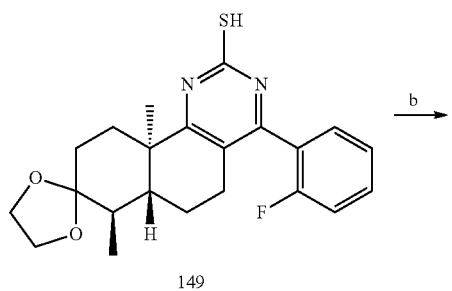
149 b →

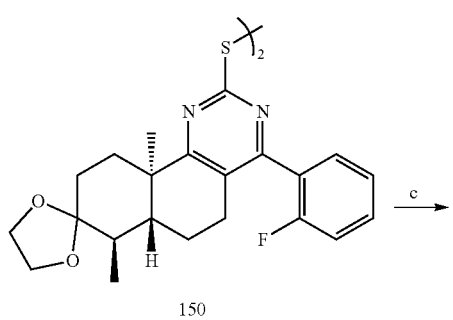
150 c →

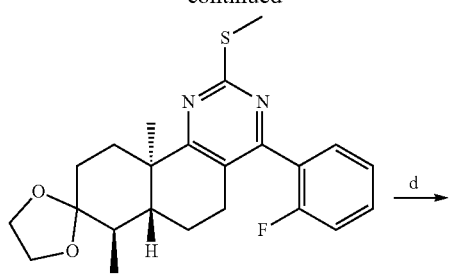

151

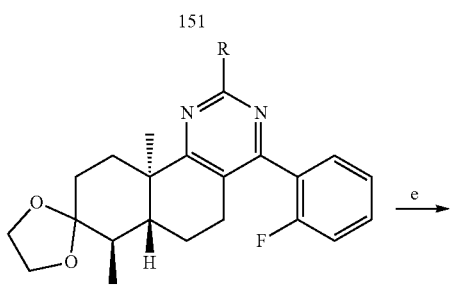

152a-152h

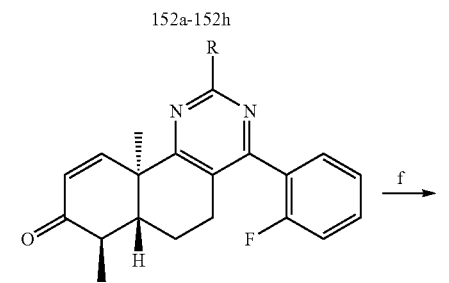

153a-153h

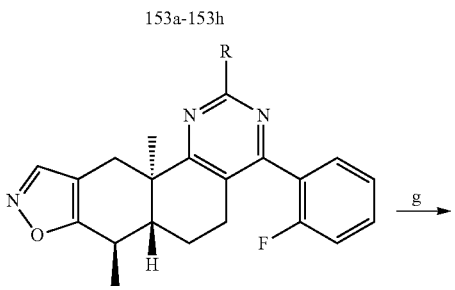

154a-154h

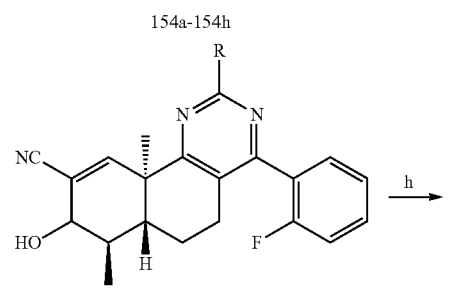

155a-155h

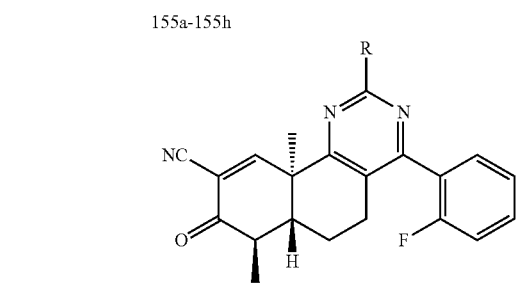

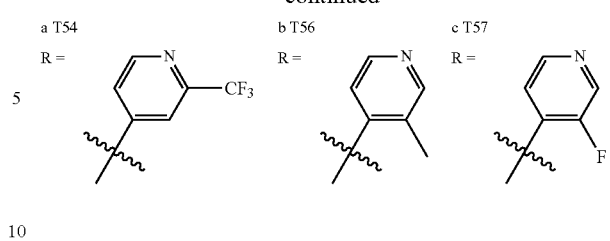

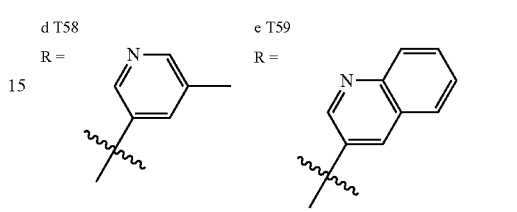

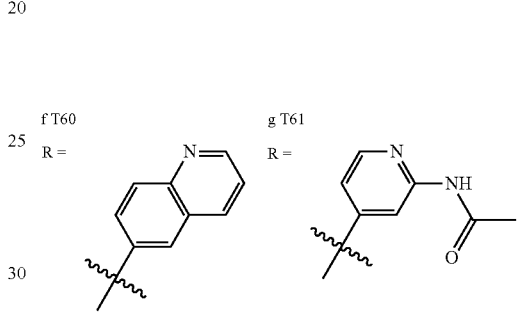

Reagents and conditions: a) thiourea, t-BuOK, EtOH, microwave, 120° C.; b) DDQ, CH$_2$Cl$_2$, rt; c) NaBH$_4$, MeI, EtOH, THF, 0° C.-rt; d) boronic acid or boronic ester, copper(I) thiophene-2-carboxylate, Pd(PPh$_3$)$_4$, THF, 100° C.; e) aq. 3N HCl, THF, MeOH, rt; f) i) HCO$_2$Et, NaOMe, MeOH, 0° C. to rt; ii) 6N HCl, NH$_2$OH•HCl, EtOH, 55° C.; g) NaOMe, MeOH, rt or 55° C.; h) i) DBDMH, DMF, 0° C.; ii) pyridine, 55° C.

Scheme 31

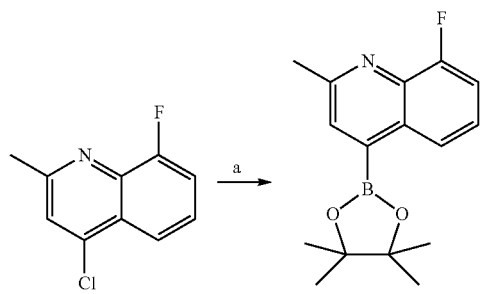

Reagents and conditions: a) bis(pinacolato)diboron, KOAc, Pd(dppf)Cl$_2$, 1,4-dioxane, 125° C.

Scheme 32
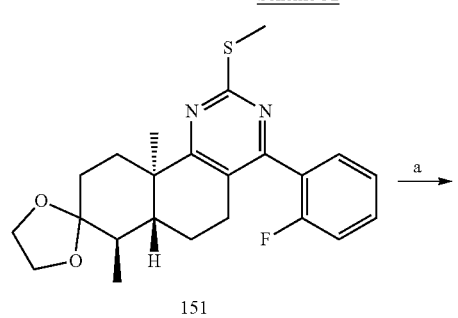
151
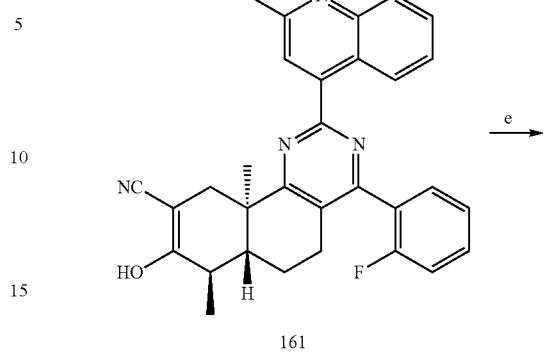
161
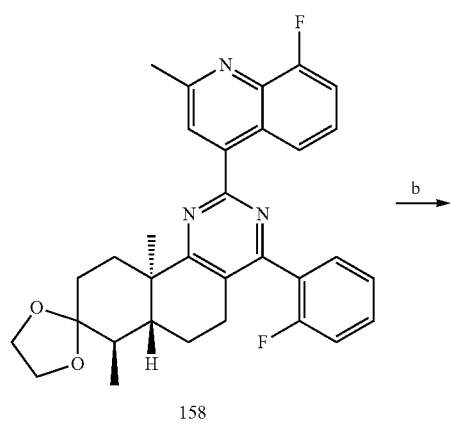
158
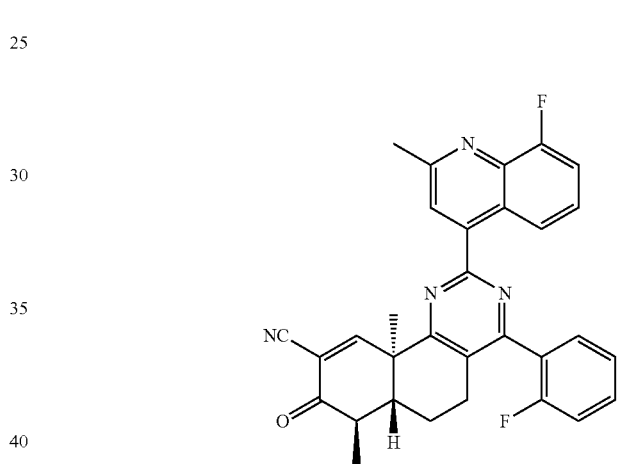
T63
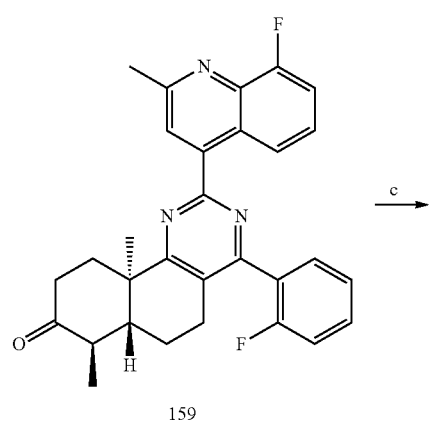
159
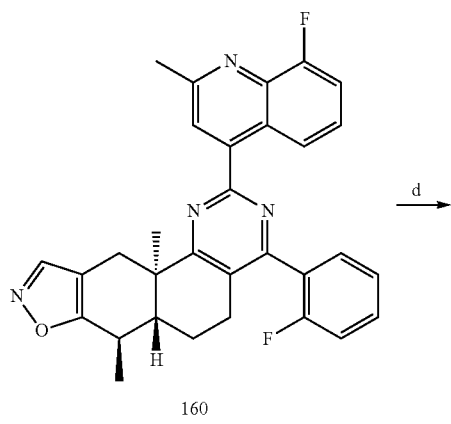
160
Reagents and conditions: a) 157, copper(I) thiophene-2-carboxylate, Pd(PPh₃)₄, THF, 100° C.; b) aq. 3N HCl, THF, MeOH, rt; c) i) HCO₂Et, NaOMe, MeOH, 0° C. to rt; ii) 6N HCl, NH₂OH·HCl, EtOH, 55° C.; d) K₂CO₃, MeOH, rt; e) DDQ, benzene, 85° C.
Scheme 33
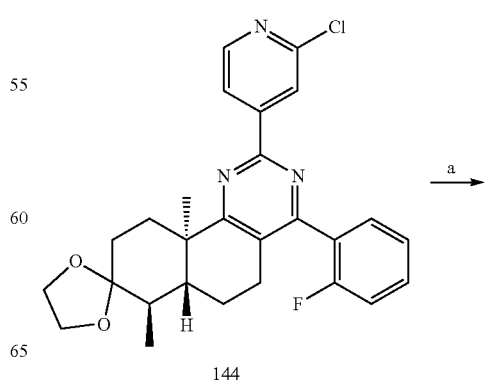
144

165
-continued
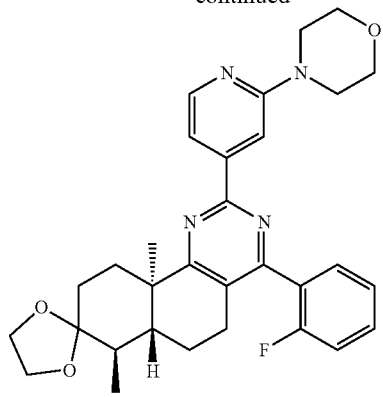
162
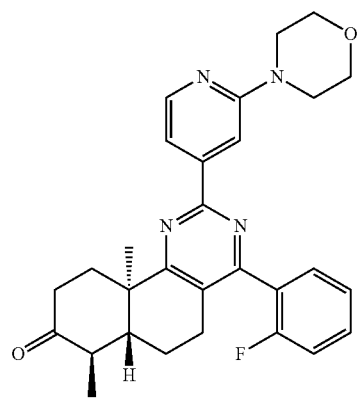
163
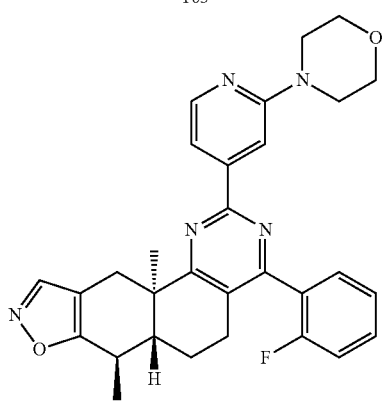
164
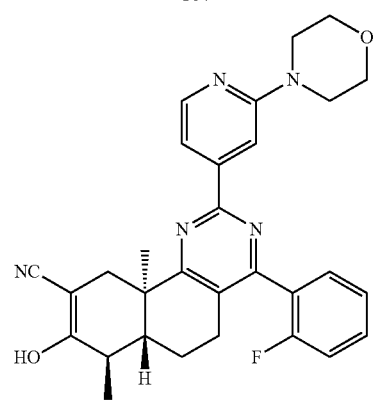
165
166
-continued
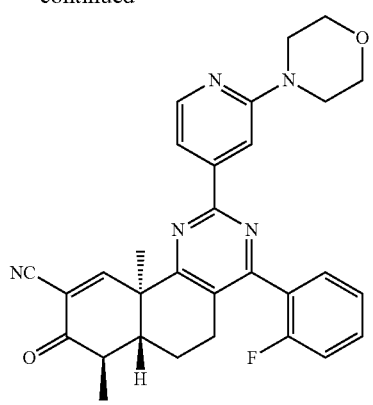
T64
Reagents and conditions: a) morpholine, t-BuONa, Xphos, Pd$_2$(dba)$_3$, toluene, microwave, 100° C.; b) aq. 3N HCl, THF, MeOH, rt; c) i) HCO$_2$Et, NaOMe, MeOH, 0° C. to rt; ii) 6N HCl, NH$_2$OH•HCl, EtOH, 55° C.; d) NaOMe, MeOH, 55° C.; e) DDQ, benzene, reflux.
Scheme 34
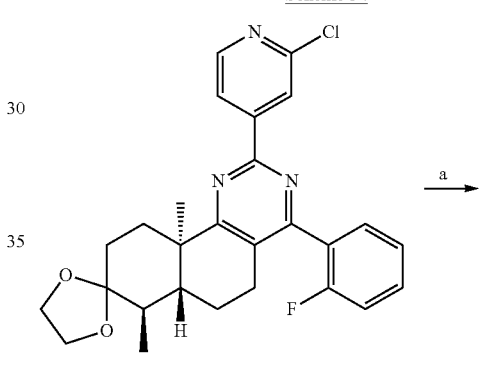
144
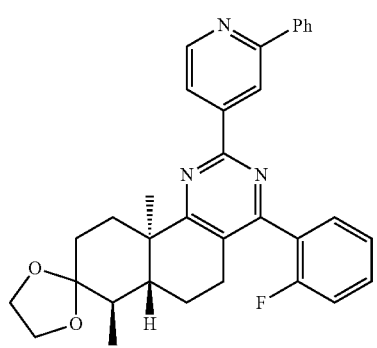
166

167
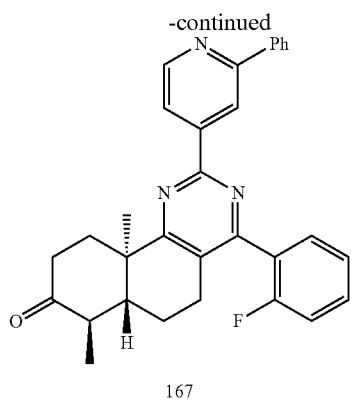
167
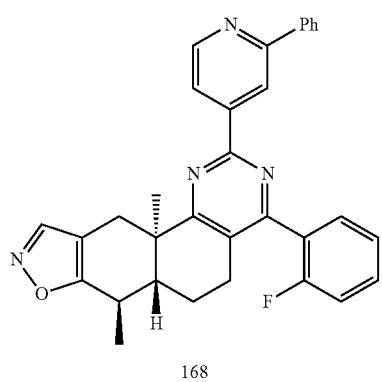
168
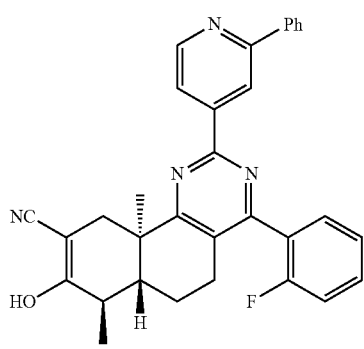
169
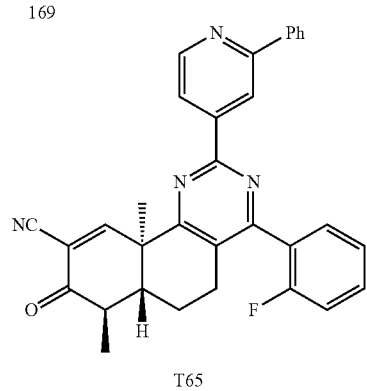
T65
Reagents and conditions: a) PhB(OH)$_2$, K$_2$CO$_3$, Pd(PPh$_3$)$_4$, toluene, EtOH, H$_2$O, microwave, 100° C.; b) aq 3N HCl, THF, MeOH, rt; c) i) HCO$_2$Et, NaOMe, MeOH, 0° C. to rt; ii) 6N HCl, NH$_2$OH·HCl, EtOH, 55° C.; d) NaOMe, MeOH, 55° C.; e) i)DBDMH, DMF, 0° C.; ii) pyridine, 55° C.
168
Scheme 35
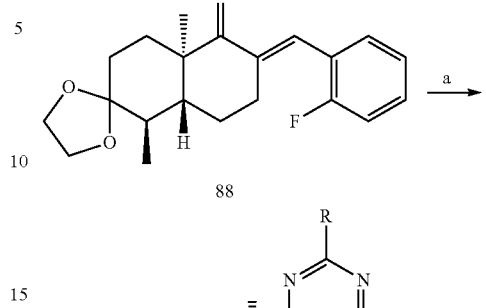
88
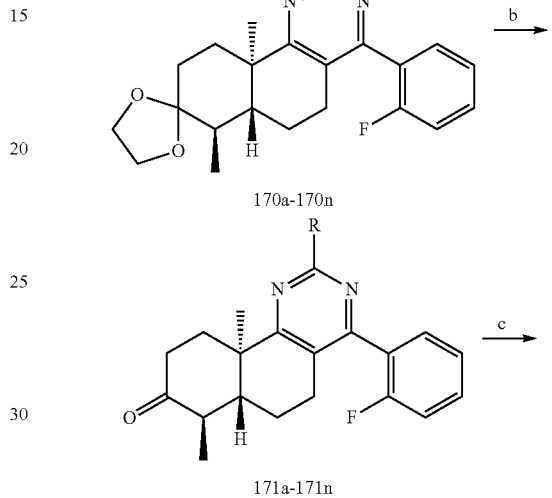
170a-170n
171a-171n
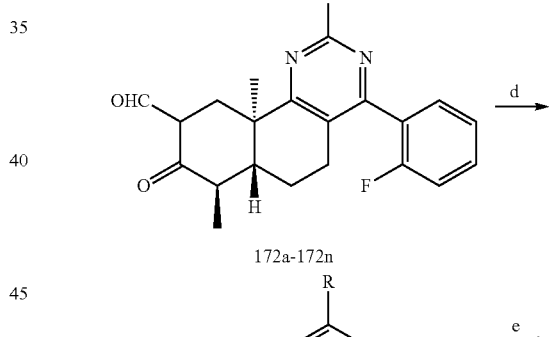
172a-172n
173a-173n
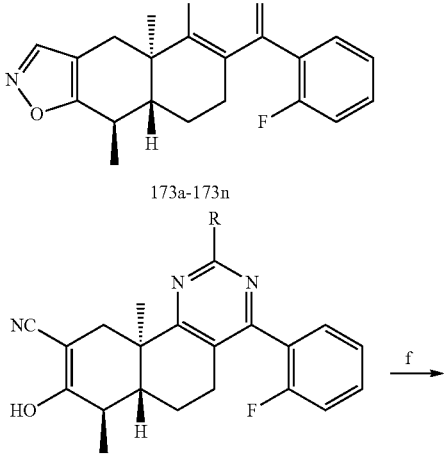
174a-174n 169
-continued
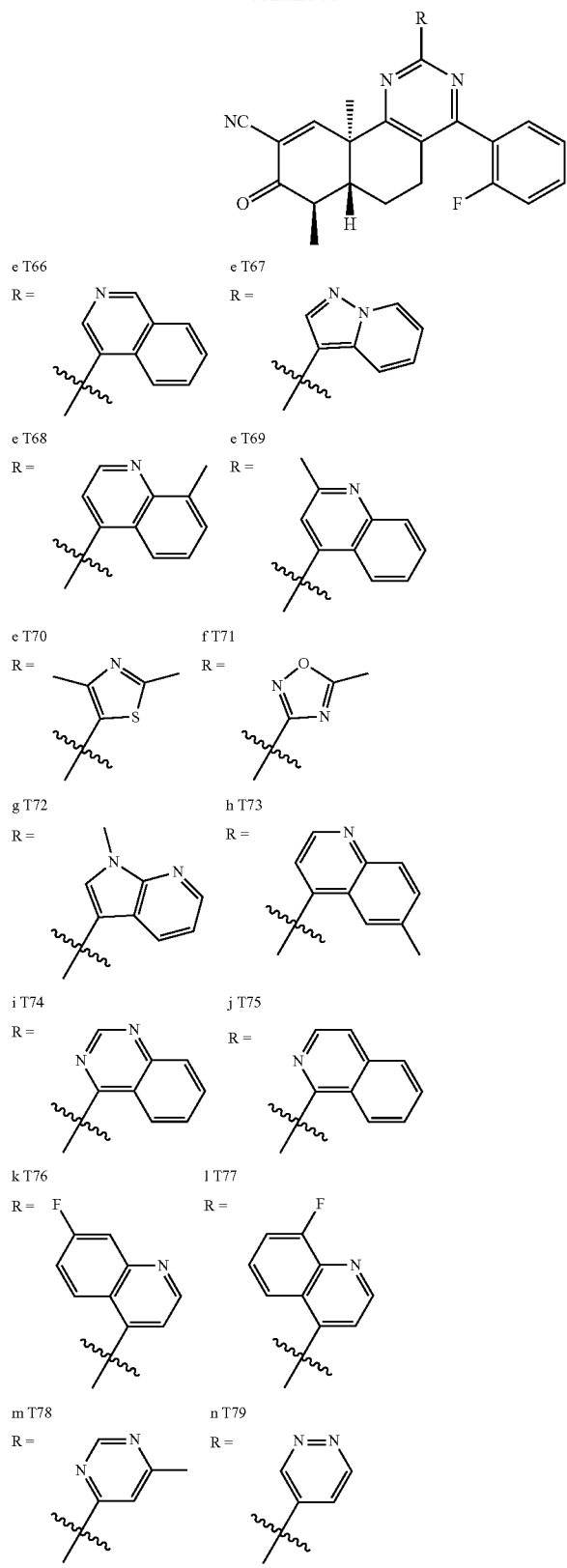
Reagents and conditions: a) i) amidine hydrochloride, K₂CO₃, EtOH, reflux, ii) MnO₂, CH₂Cl₂, rt; b) aq. 3N HCl, MeOH, rt; c) HCO₂Et, NaOMe, rt; d) NH₂OH•HCl, AcOH, EtOH, heat; e) K₂CO₃, MeOH, rt; f) i) DBDMH, DMF, 0° C.; ii) pyridine, 60° C.
170
Scheme 36
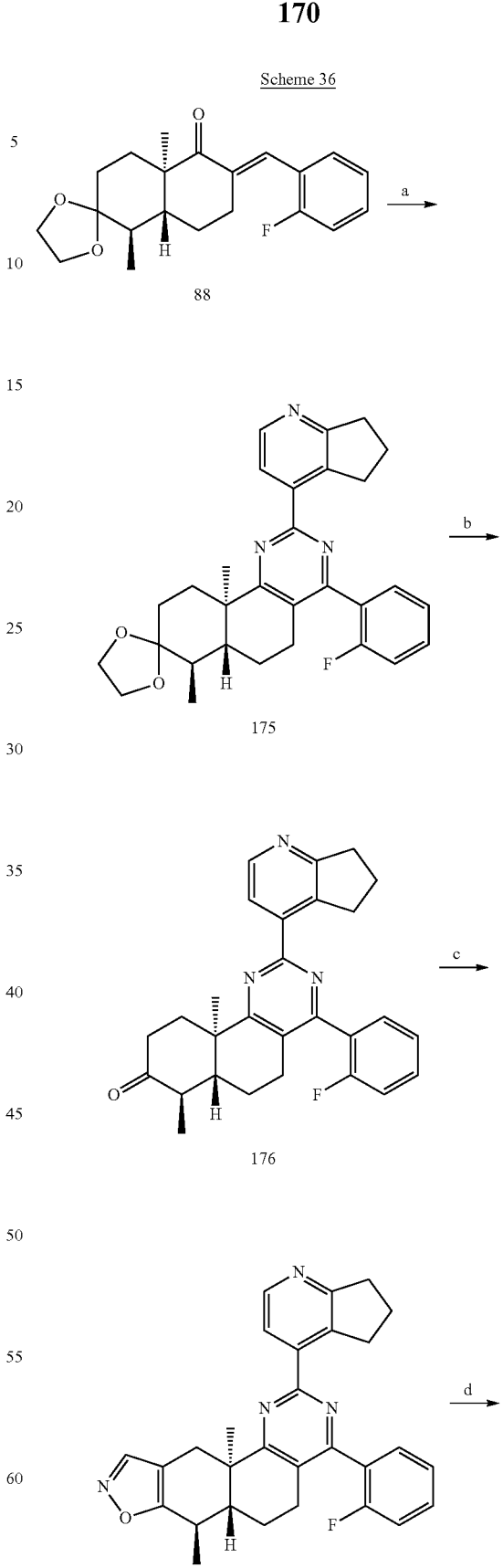

171
-continued

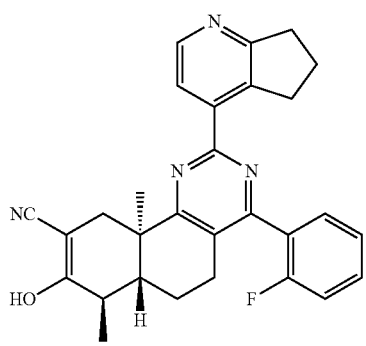

178

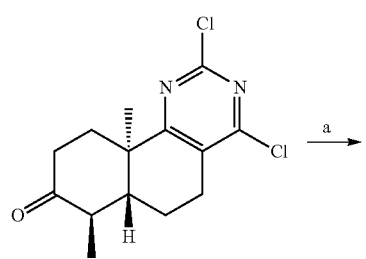

T80

Reagents and conditions: a) i) 6,7-dihydro-5H-cyclopenta[b]pyridine-4-carboximidamide hydrochloride, $K_2CO_3$, EtOH, microwave, 120° C.; ii) DDQ, $CH_2Cl_2$, rt; b) aq. 3N HCl, THF, MeOH, rt; c) i) $HCO_2Et$, NaOMe, MeOH, 0° C. to rt; ii) 6N HCl, $NH_2OH \cdot HCl$, EtOH, 55° C.; d) $K_2CO_3$, MeOH, rt; e) i) DBDMH, DMF, 0° C.; ii) pyridine, 55° C.

Scheme 37

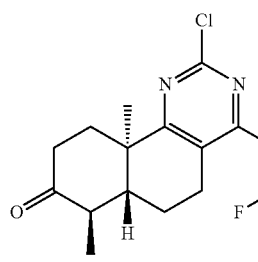

12

172
-continued

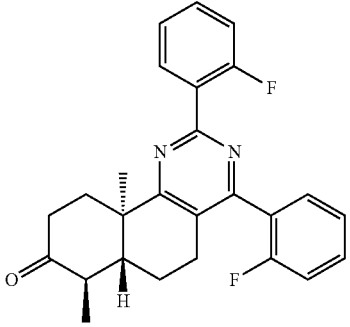

180

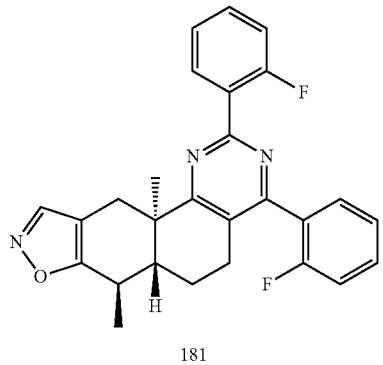

181

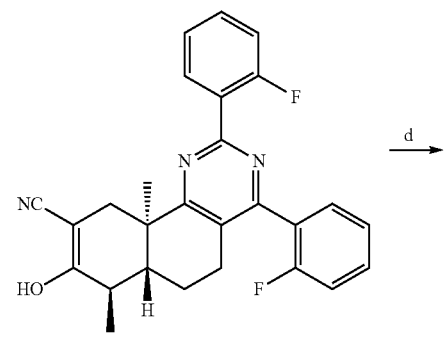

182

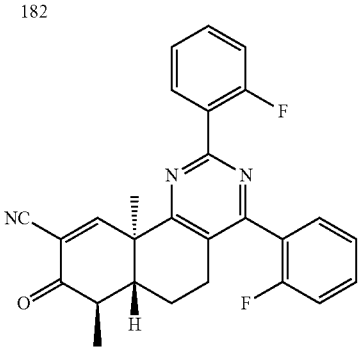

T81

Reagents and conditions: a) 2-F-PhB(OH)$_2$, $Na_2CO_3$, Pd(dppf)Cl$_2$, 1,4-dioxane, $H_2O$, 100° C.; b) i) $HCO_2Et$, NaOMe, MeOH, THF, 0° C. to rt; ii) 6N HCl, $NH_2OH \cdot HCl$, EtOH, 55° C.; c) $K_2CO_3$, MeOH, rt; d) i) DBDMH, DMF, 0° C.; ii) pyridine, 55° C.

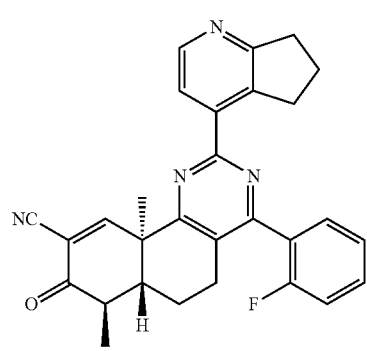

179

173
Scheme 38
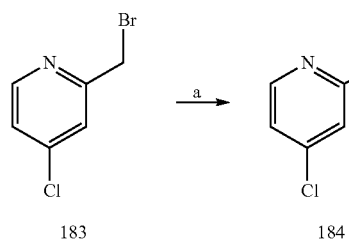
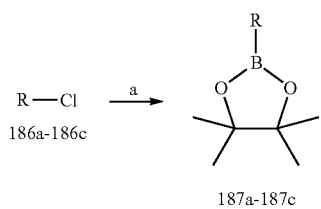
185
Reagents and conditions:
a) TBAF•3H₂O, MeCN, rt;
b) bis(pinacolate)diboron, KOAc, Pd(dppf)Cl₂, 1,4-dioxane, 130° C.
Scheme 39
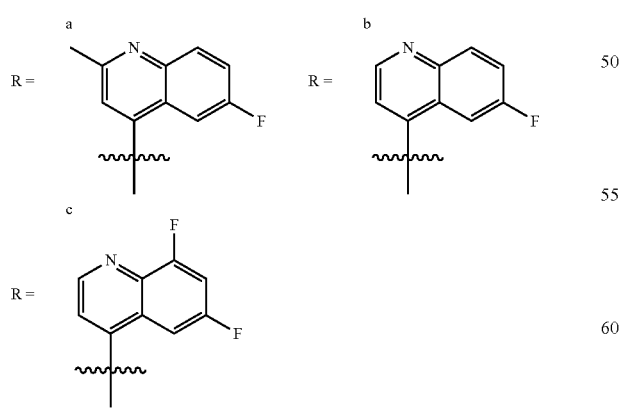
Reagents and conditions:
a) bis(pinacolato)diboron, KOAc, Pd(dppf)Cl₂, 1,4-dioxane, 125° C.
174
Scheme 40
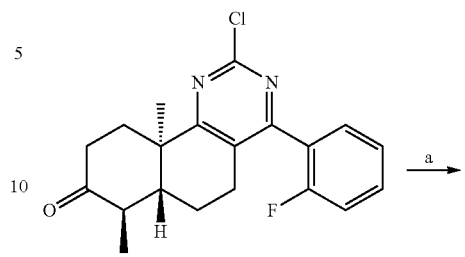
179
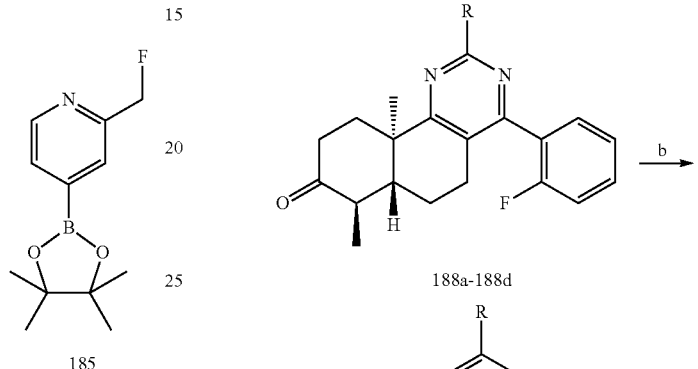
188a-188d
189a-189d
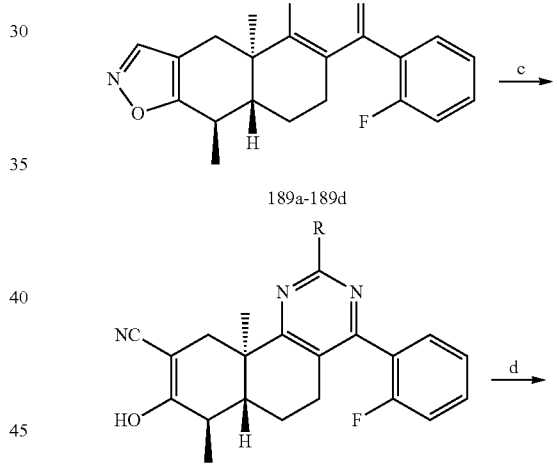
190a-190d
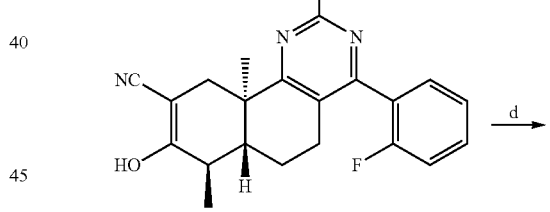
a T82    b T83
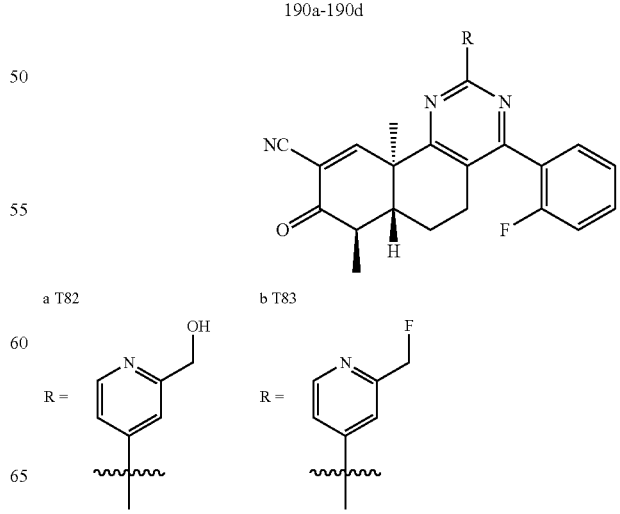

175
-continued c T84 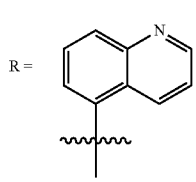  d T85 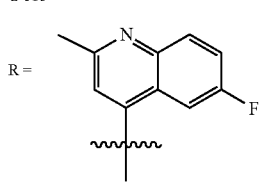

Reagents and conditions:
a) boronic acid or boronic ester, Na₂CO₃, Pd(dppf)Cl₂, 1,4-dioxane, H₂O, microwave heat;
b) i) HCO₂Et, NaOMe, MeOH, 0° C. to rt; ii) 6N HCl, NH₂OH•HCl, EtOH, 55° C.;
c) NaOMe, MeOH, 55° C.;
d) DDQ, benzene, reflux.

Scheme 41

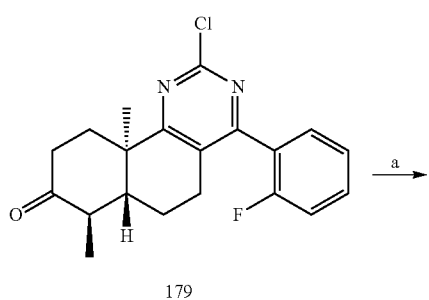

179

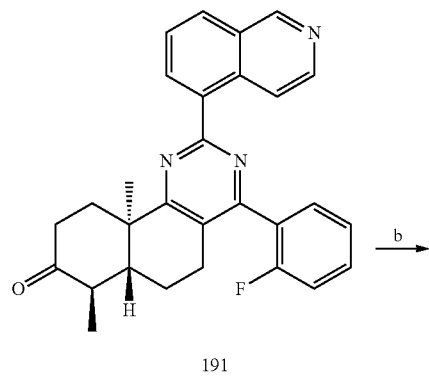

191

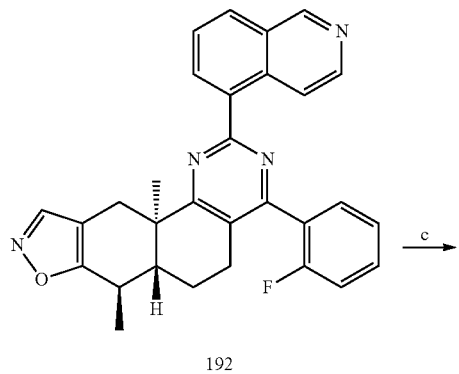

192

176
-continued

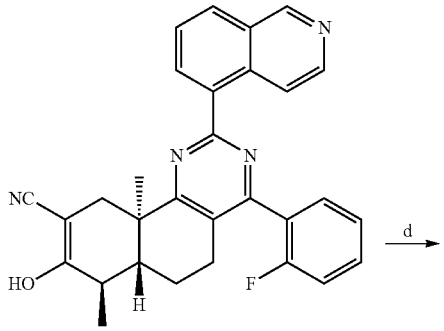

193

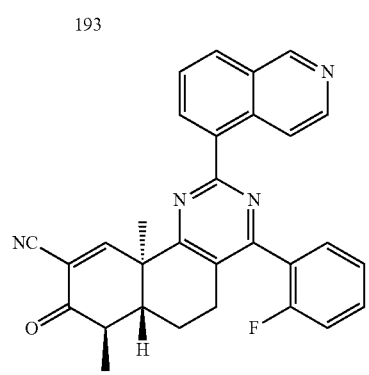

T86

Reagents and conditions:
a) isoquinoline-5-boronic acid, Na₂CO₃, Pd(dppf)Cl₂, 1,4-dioxane, H₂O, microwave, 110° C.;
b) i) HCO₂Et, NaOMe, MeOH, THF, 0° C. to rt; ii) 6N HCl, NH₂OH•HCl, EtOH, 55° C.;
c) K₂CO₃, MeOH, rt;
d) DDQ, benzene, 85° C.

Scheme 42

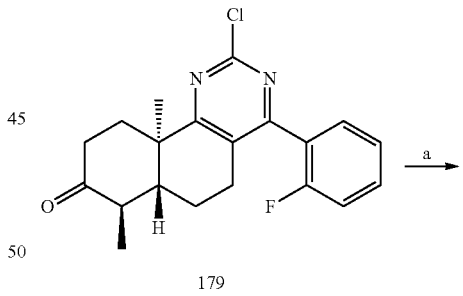

179

194a-194d

177
-continued
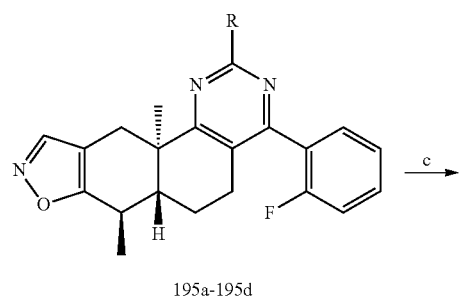
195a-195d
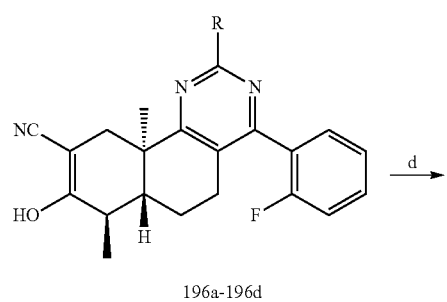
196a-196d
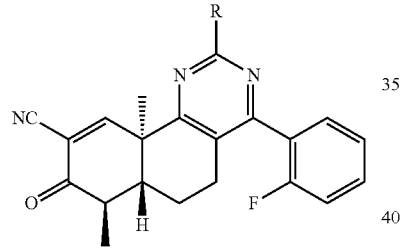
a T87
R = 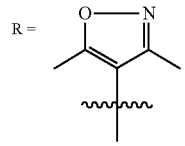
b T88
R = 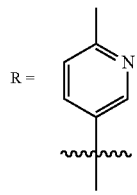
c T89
R = 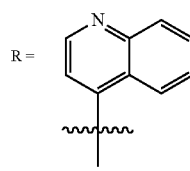
d T90
R = 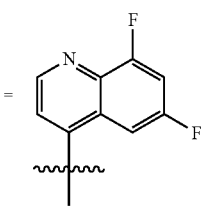
Reagents and conditions:
a) boronic acid or boronic ester, Na$_2$CO$_3$, Pd(dppf)Cl$_2$, 1,4-dioxane, H$_2$O, microwave, 110° C.;
b) i) HCO$_2$Et, NaOMe, MeOH, 0° C. to rt; ii) 6N HCl, NH$_2$OH·HCl, EtOH, 55° C.;
c) NaOMe, MeOH, 55° C.;
d) i) DBDMB, DMF, 0° C.; ii) pyridine, 55° C.
178
Scheme 43
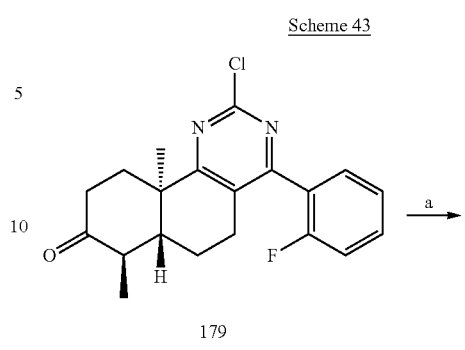
179
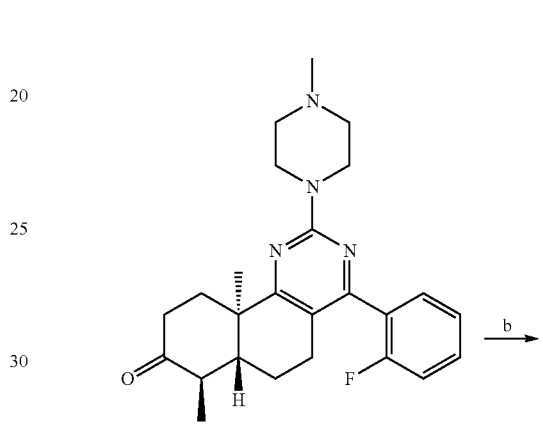
197
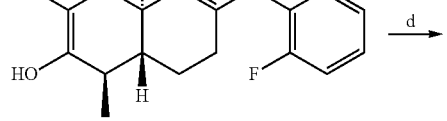
198
199

179

-continued

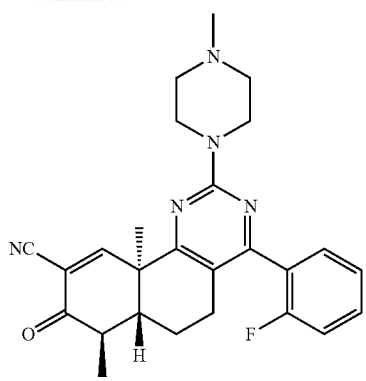

T91

Reagents and conditions:
a) 1-methylpiperazine, NMP, 100° C.;
b) i) HCO₂Et, NaOMe, MeOH, THF, 0° C. to rt; ii) 6N HCl, NH₂OH•HCl, EtOH, 55° C.;
c) K₂CO₃, MeOH, rt;
d) DDQ, benzene, 85° C.

Scheme 44

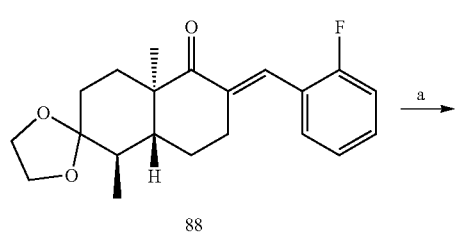

88

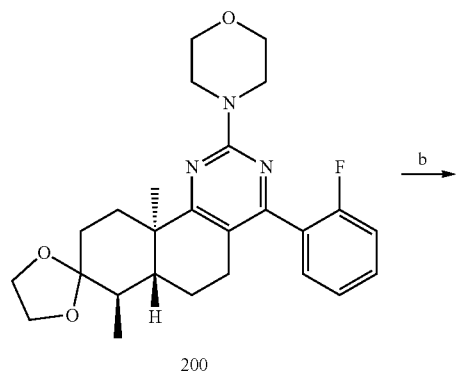

200

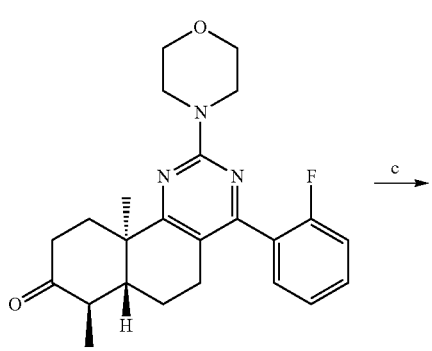

201

180

-continued

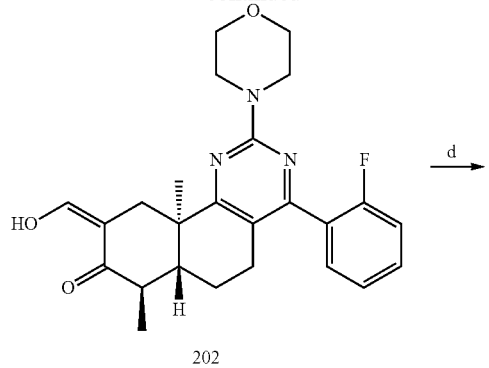

202

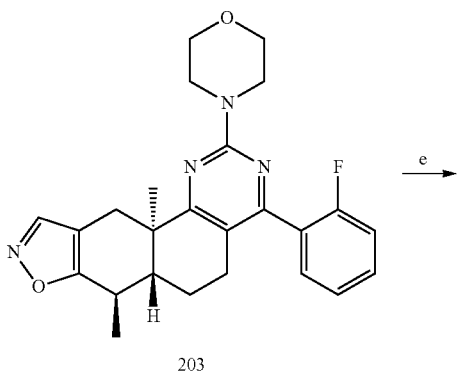

203

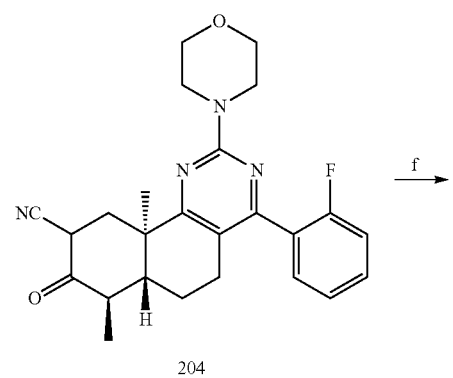

204

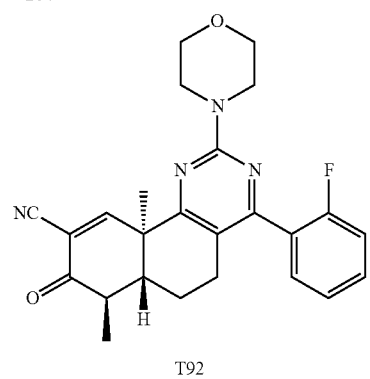

T92

Reagents and conditions: a) i) N-amidinomorpholine hydrobromide, K₂CO₃, EtOH, reflux; ii) MnO₂, CH₂Cl₂, rt; b) aq. 3N HCl, THF, rt; c) HCO₂Et, NaOMe, MeOH, rt; d) NH₂OH•HCl, HOAc, EtOH, 60° C.-rt; e) K₂CO₃, MeOH, rt; f) i) DBDMH, DMF, 0° C.; ii) pyridine, DMF, 60° C.

Scheme 45
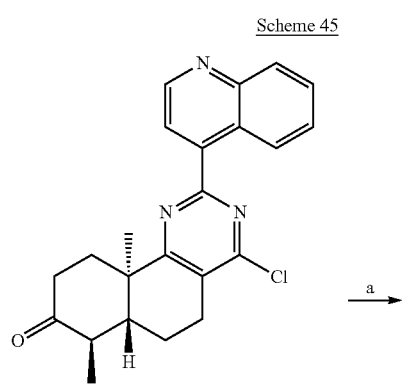
95
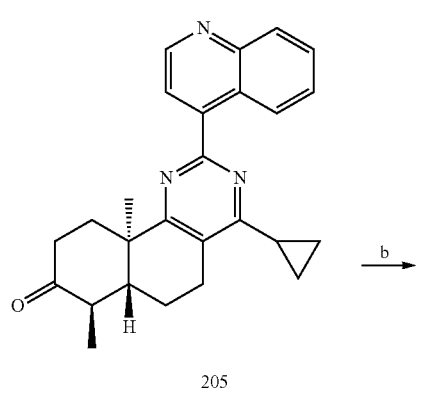
205
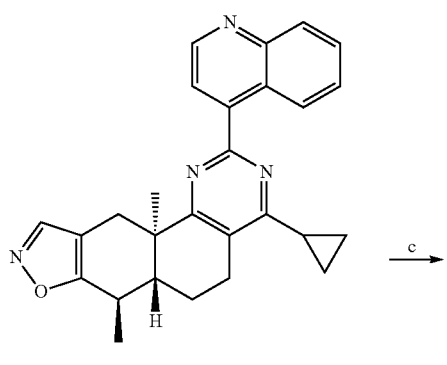
206
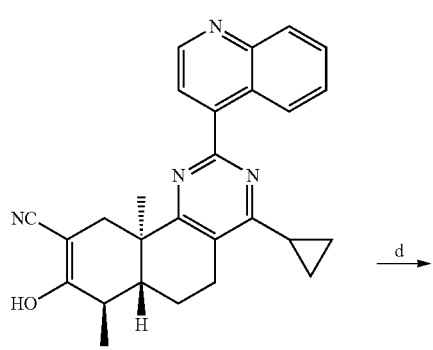
207
-continued
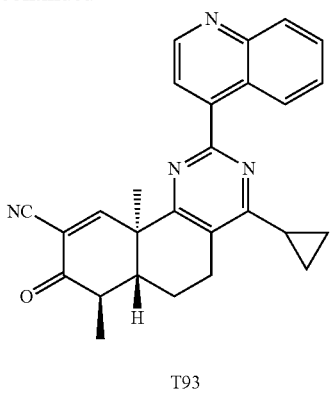
T93
Reagents and conditions:
a) cyclopropylboronic acid, $K_3PO_4$, $Pd(OAc)_2$, tricyclohexylphosphine, toluene, $H_2O$, microwave, 130° C.;
b) i) $HCO_2Et$, NaOMe, MeOH, 0° C. to rt; ii) 6N HCl, $NH_2OH \cdot HCl$, EtOH, 55° C.;
c) NaOMe, MeOH, 55° C.;
d) i) DBDMH, DMF, 0° C.; ii) pyridine, 55° C.
Scheme 46
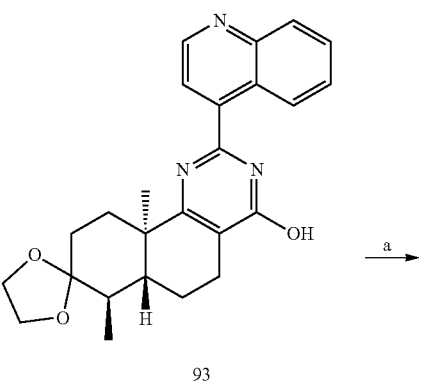
93
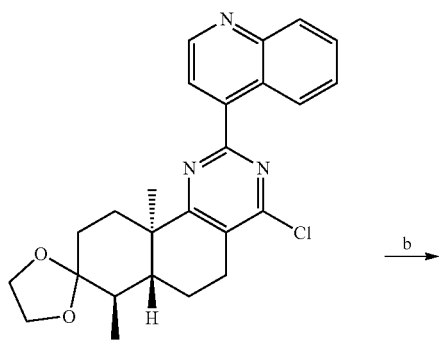
94

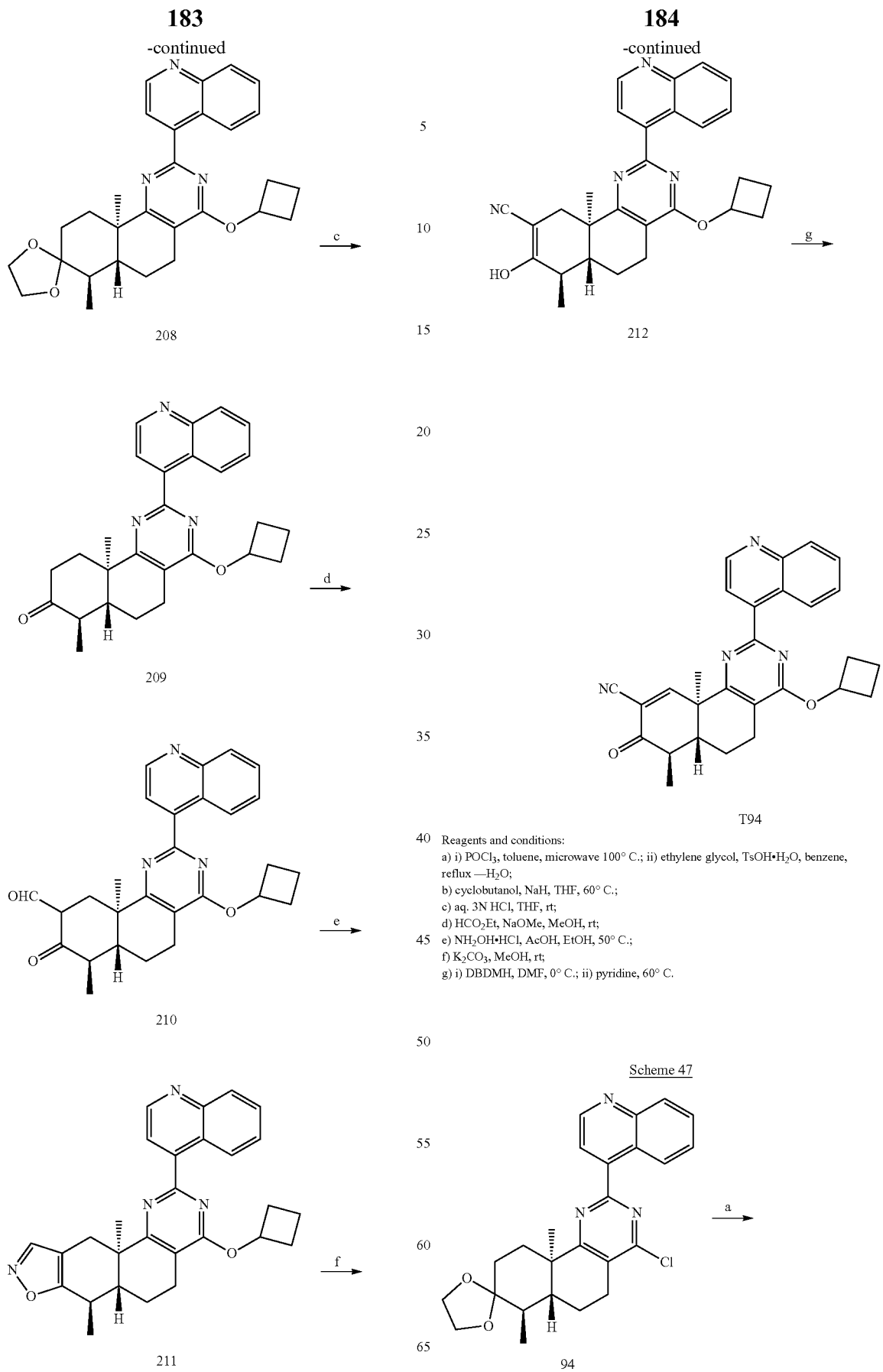
Reagents and conditions:
a) i) POCl₃, toluene, microwave 100° C.; ii) ethylene glycol, TsOH·H₂O, benzene, reflux —H₂O;
b) cyclobutanol, NaH, THF, 60° C.;
c) aq. 3N HCl, THF, rt;
d) HCO₂Et, NaOMe, MeOH, rt;
e) NH₂OH·HCl, AcOH, EtOH, 50° C.;
f) K₂CO₃, MeOH, rt;
g) i) DBDMH, DMF, 0° C.; ii) pyridine, 60° C.
Scheme 47

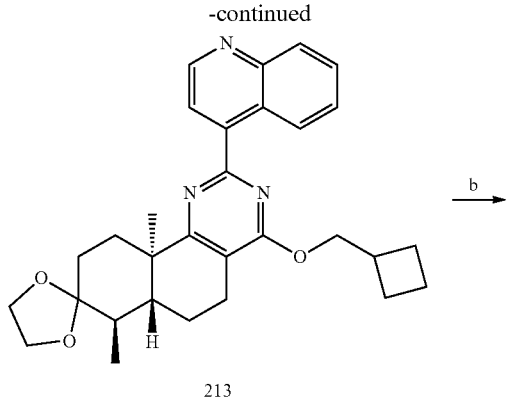
213
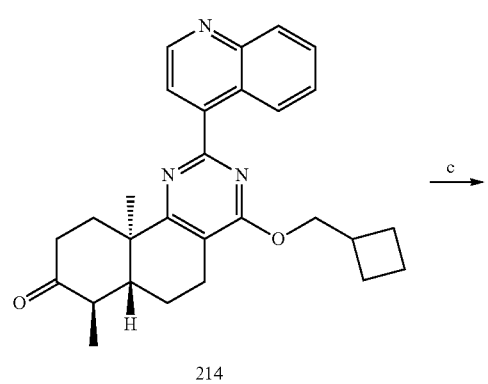
214
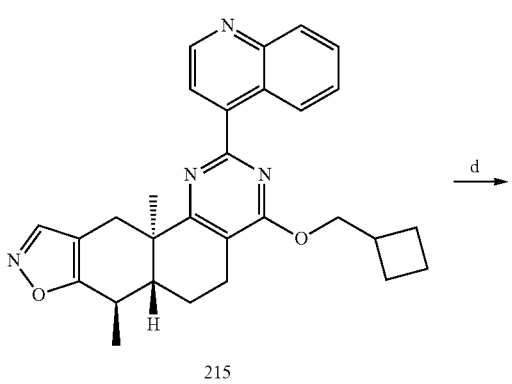
215
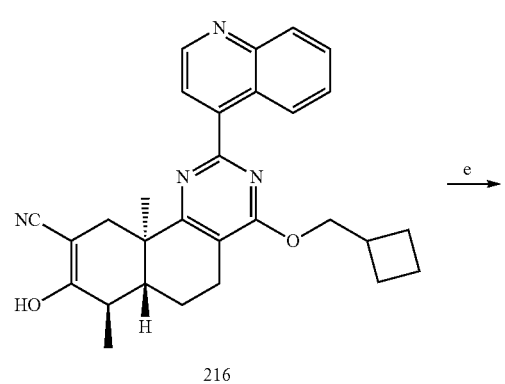
216
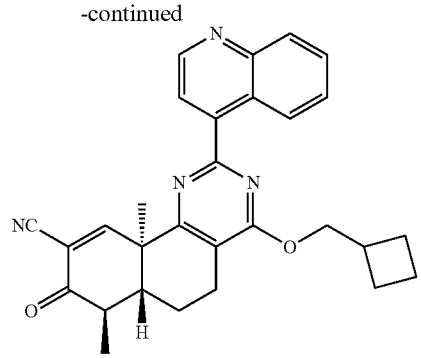
T95
Reagents and conditions: a) cyclobutanemethanol, NaH, THF, rt to 50° C.; b) aq. 3N HCl, THF, MeOH, rt; c) i) HCO₂Et, NaOMe, MeOH, THF, 0° C. to rt; ii) 6N HCl, NH₂OH•HCl, EtOH, 55° C.; d) K₂CO₃, MeOH, rt; e) i) DBDMH, DMF, 0° C.; ii) pyridine, 55° C.
Scheme 48
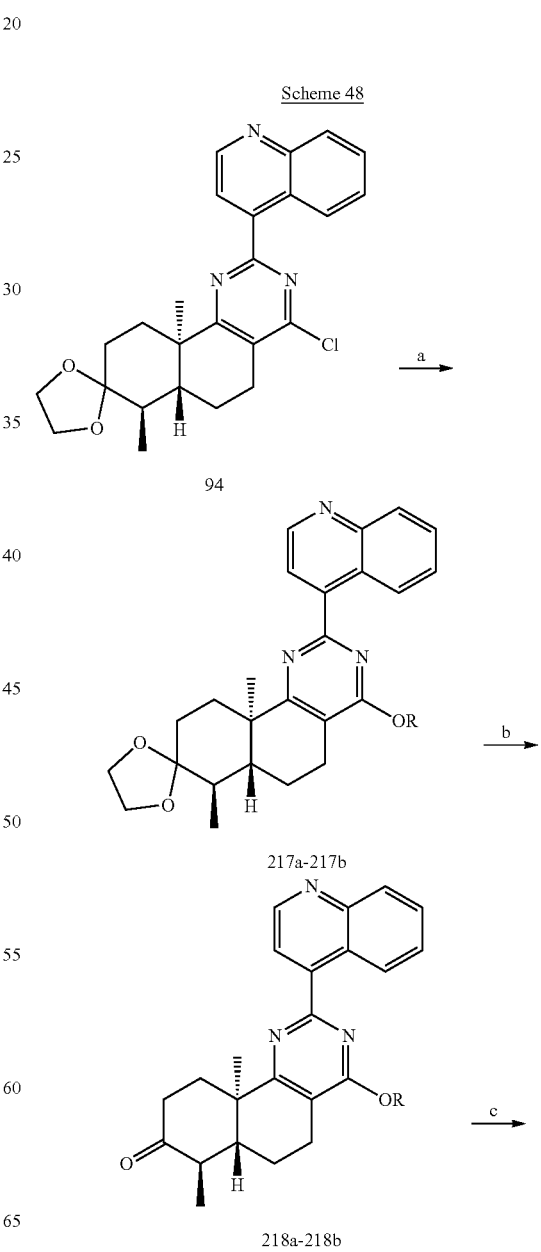
94
217a-217b
218a-218b Scheme 49
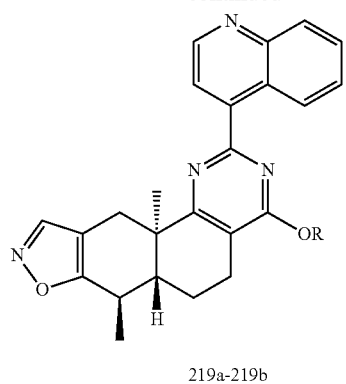
219a-219b
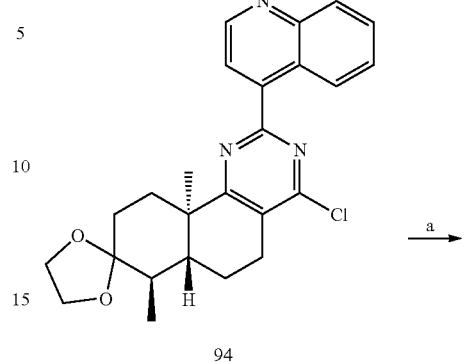
94
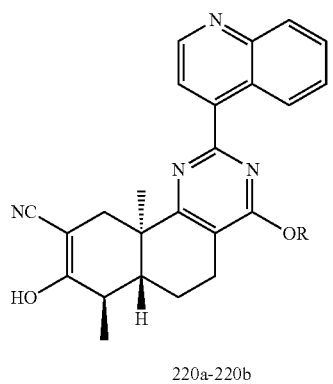
220a-220b
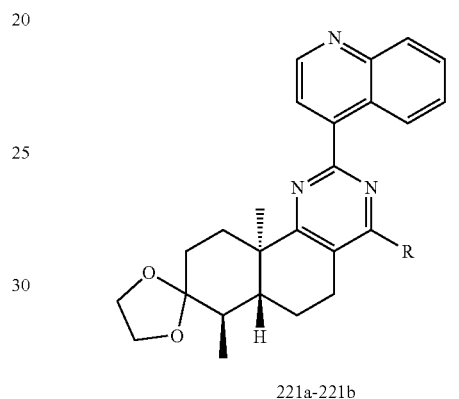
221a-221b
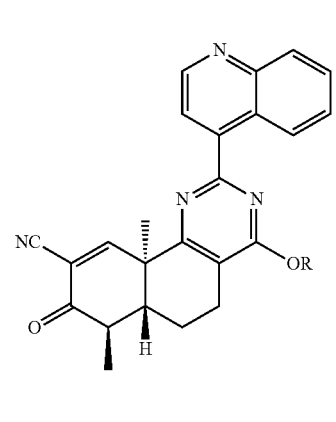 [SMILES: COc1nc(-c2ccnc3ccccc23)nc2c1CC[C@@H]1[C@@H](C)C(=O)C(C#N)=C[C@@]21C]
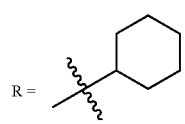 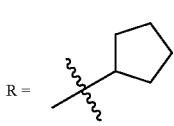
a T96    b T97
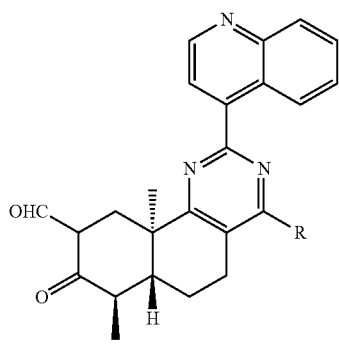
222a-222b
223a-223b
Reagents and conditions:
a) ROH, NaH, THF, rt to 50° C.;
b) aq. 3N HCl, THF, MeOH, rt;
c) i) HCO₂Et, NaOMe, MeOH, THF, 0° C. to rt; ii) 6N HCl, NH₂OH·HCl, EtOH, 55° C.;
d) NaOMe, MeOH, 55° C.;
e) i) DBDMH, DMF, 0° C.; ii) pyridine, 55° C.

189 -continued
190
Scheme 50
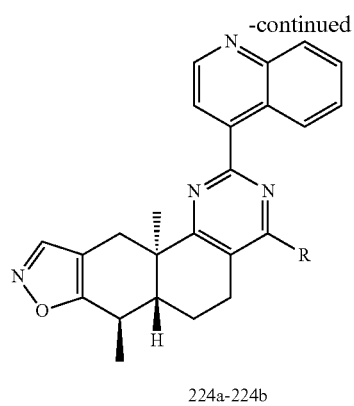
224a-224b
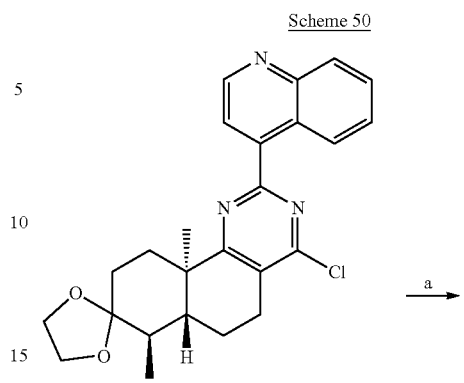
94
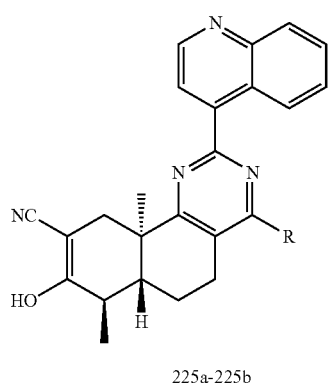
225a-225b
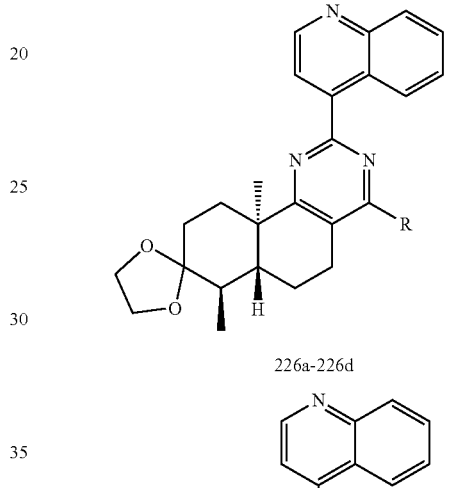
226a-226d
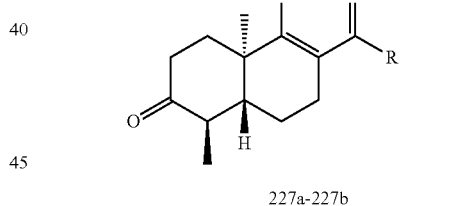
227a-227b
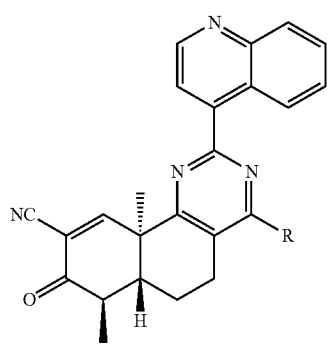
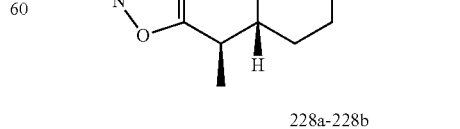
228a-228b
a T98
R = NHSO₂Me
b T99
R = NMe₂
Reagents and conditions:
a) MeSO₂NH₂, NaH, DMF, 80° C.;
b) aq. 3N HCl, THF, rt;
c) HCO₂Et, NaOMe, MeOH, rt;
d) NH₂•HCl, EtOH, AcOH, 50° C.;
e) K₂CO₃, MeOH, rt;
f) i) DBDMH, DMF, 0° C.; ii) pyridine, 60° C.

Scheme 51
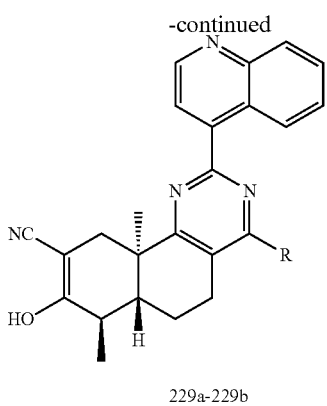
229a-229b
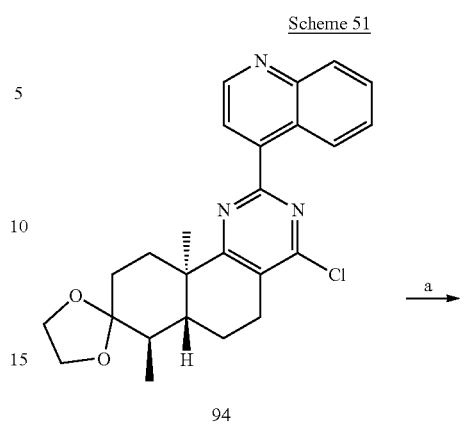
94
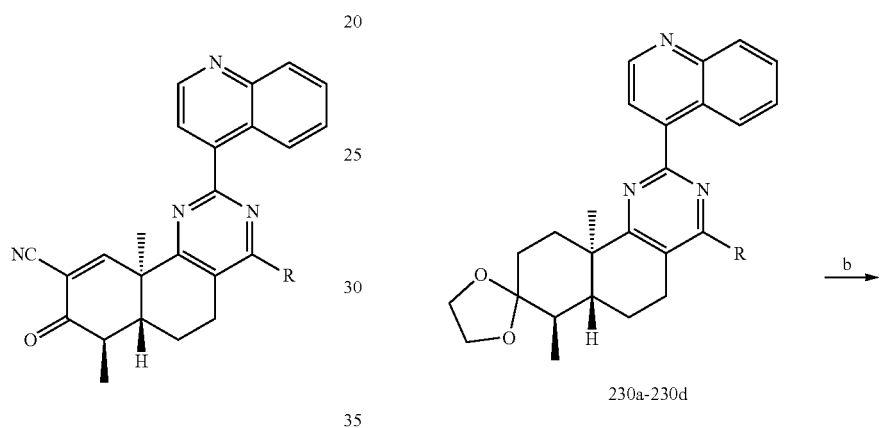
230a-230d
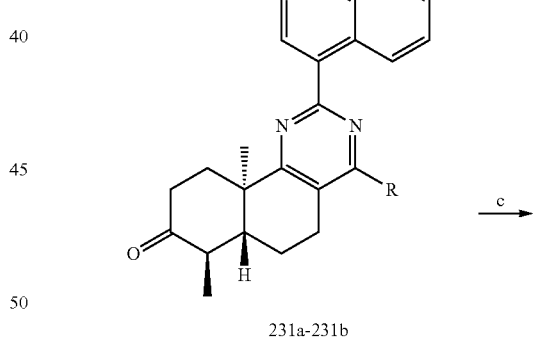
231a-231b
a T100
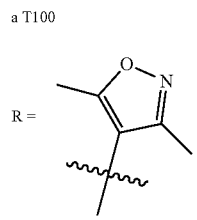
R =
b T101
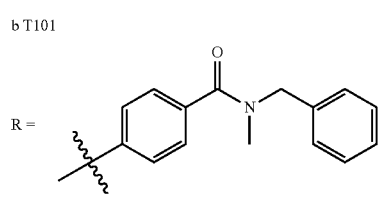
R =
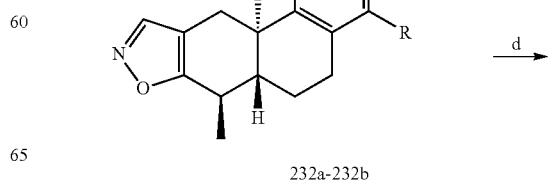
232a-232b
Reagents and conditions:
a) boronic acid or boronic ester, Pd(dppf)Cl₂, Na₂CO₃, 1,4-dioxane, H₂O, 110° C., microwave;
b) aq. 3N HCl, THF, MeOH, THF, rt;
c) i) HCO₂Et, NaOMe, MeOH, rt; ii) aq. 6N HCl, NH₂OH·HCl, EtOH, 55° C.;
d) NaOMe, MeOH, 55° C.;
e) i) DBDMH, DMF, 0° C.; ii) pyridine, 55° C.

-continued
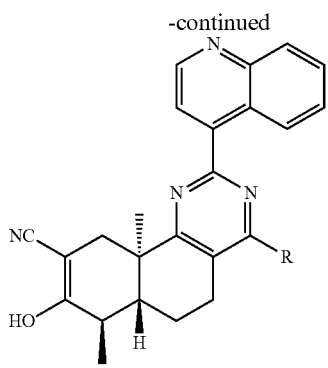
233a-233b
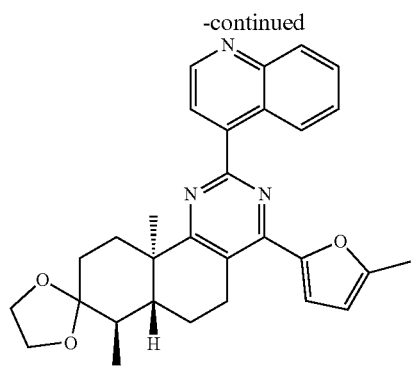
234
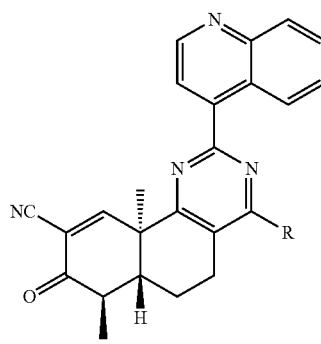
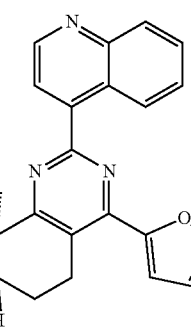
a T102    b T103
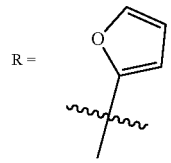
R =
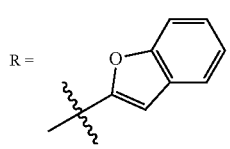
R =
Reagents and conditions:
a) boronic acid, Pd(dppf)Cl₂, Na₂CO₃, 1,4-dioxane, H₂O, 110° C., microwave;
b) aq. 3N HCl, THF, MeOH, THF, rt;
c) i) HCO₂Et, NaOMe, MeOH, rt; ii) aq. 6N HCl, NH₂OH·HCl, EtOH, 55° C.;
d) NaOMe, MeOH, 55° C.;
e) DDQ, benzene, reflux.
Scheme 52
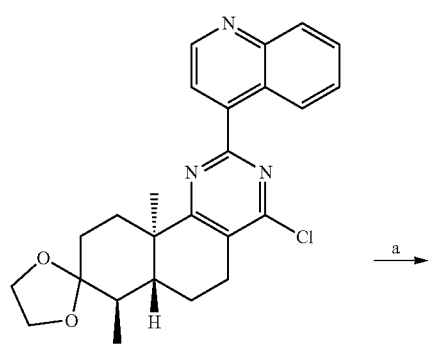
94
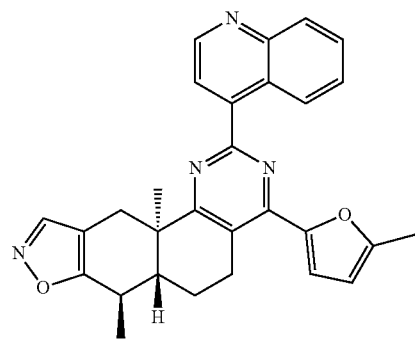
235
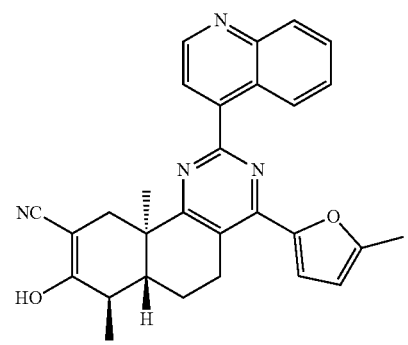
236
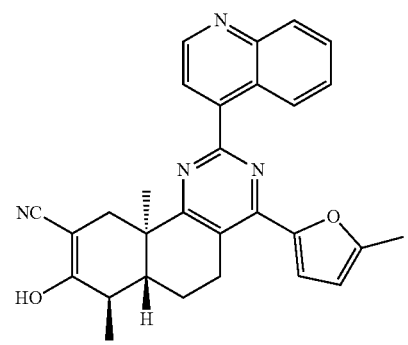
237

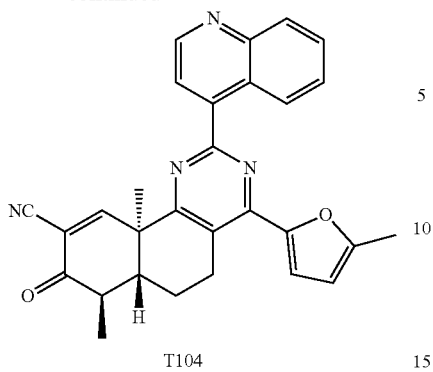
T104
Reagents and conditions:
a) 5-methyl-2-foranboronic acid pinacol ester, Pd(dppf)Cl₂, Na₂CO₃, 110° C., microwave;
b) aq. 3N HCl, THF, MeOH, THF, rt;
c) i) HCO₂Et, NaOMe, MeOH, rt; ii) aq. 6N HCl, NH₂OH·HCl, EtOH, 55° C.;
d) NaOMe, MeOH, 55° C.;
e) i) DBDMH, DMF, 0° C.; ii) pyridine, 55° C.
Scheme 53
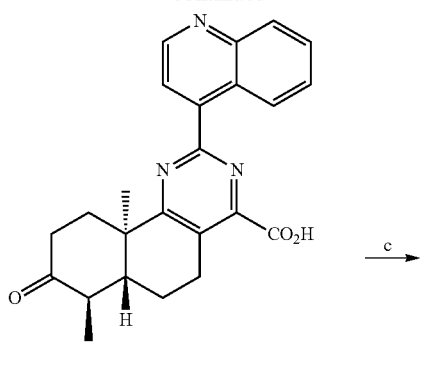
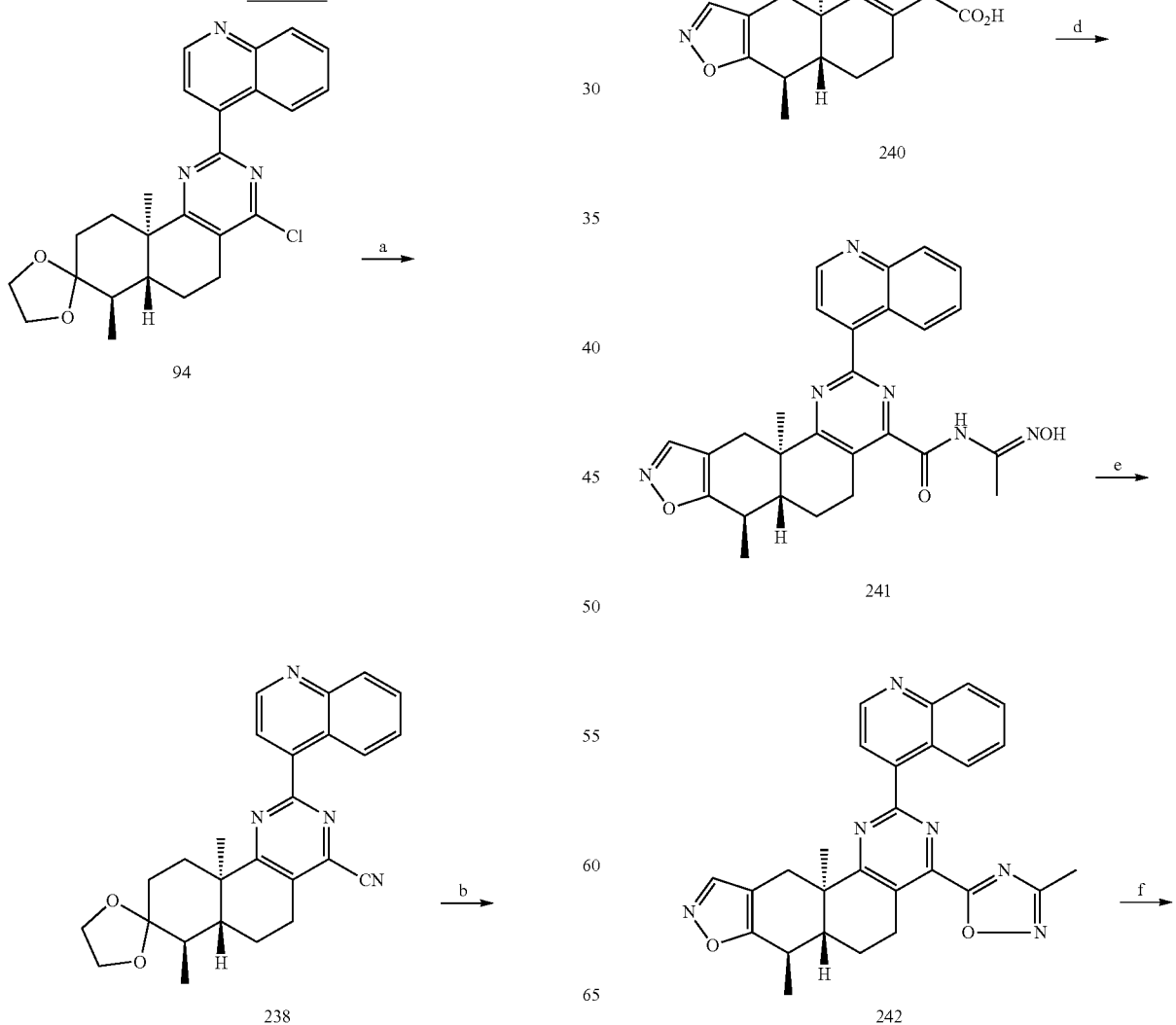

197
-continued
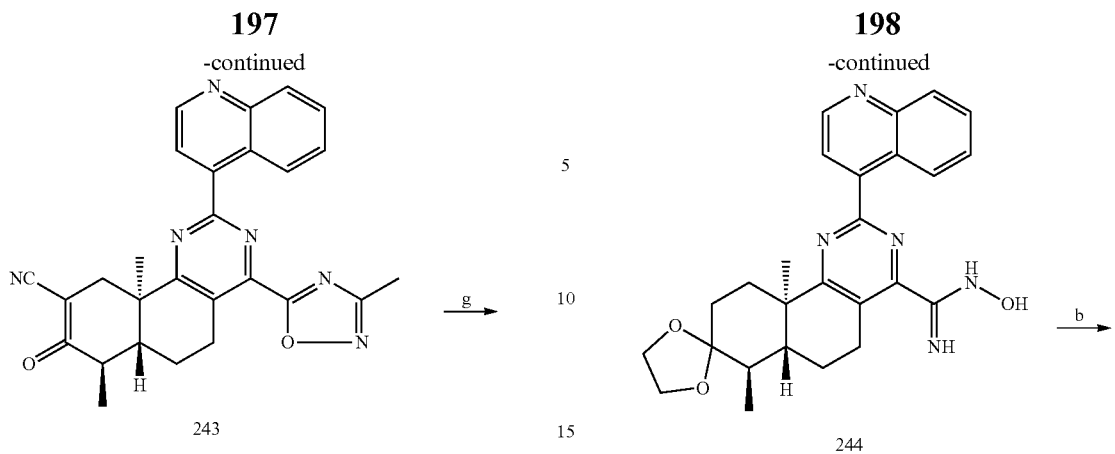
243
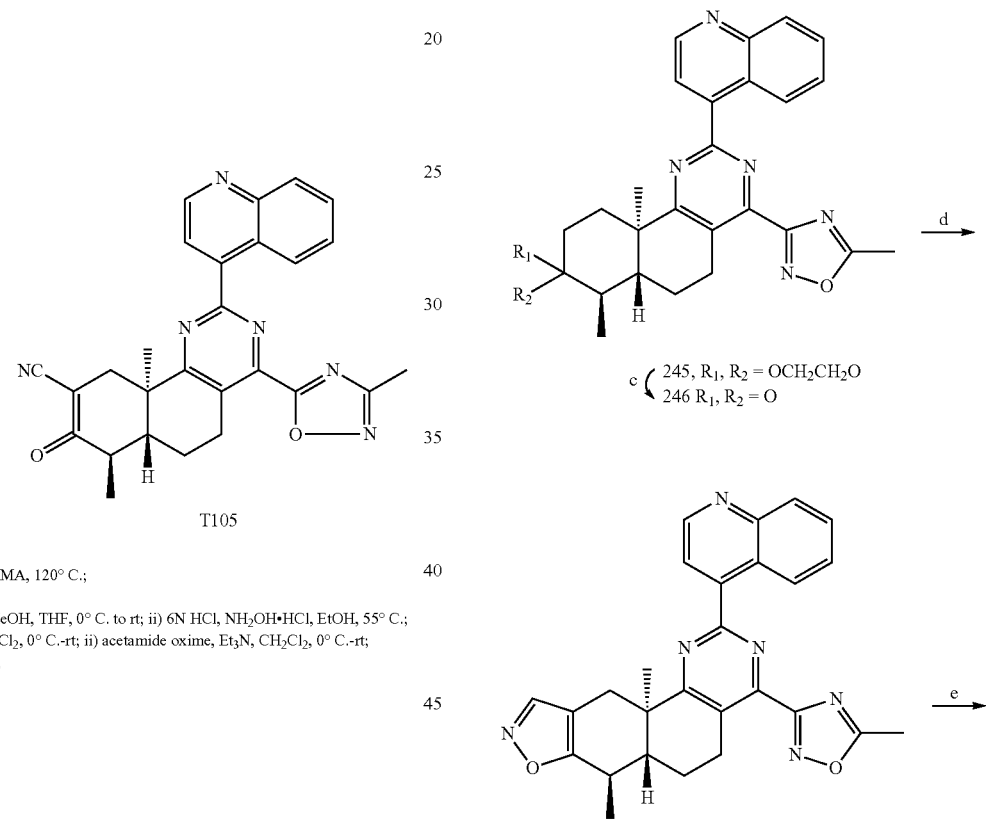
T105
Reagents and conditions:
a) Zn(CN)₂, Pd(PPh₃)₄, DMA, 120° C.;
b) aq. H₂SO₄, 100° C.;
c) i) HCO₂Et, NaOMe, MeOH, THF, 0° C. to rt; ii) 6N HCl, NH₂OH•HCl, EtOH, 55° C.;
d) i) (COCl)₂, DMF, CH₂Cl₂, 0° C.-rt; ii) acetamide oxime, Et₃N, CH₂Cl₂, 0° C.-rt;
e) toluene, reflux, —H₂O;
f) K₂CO₃, MeOH, rt;
g) DDQ, benzene, 85° C.
Scheme 54
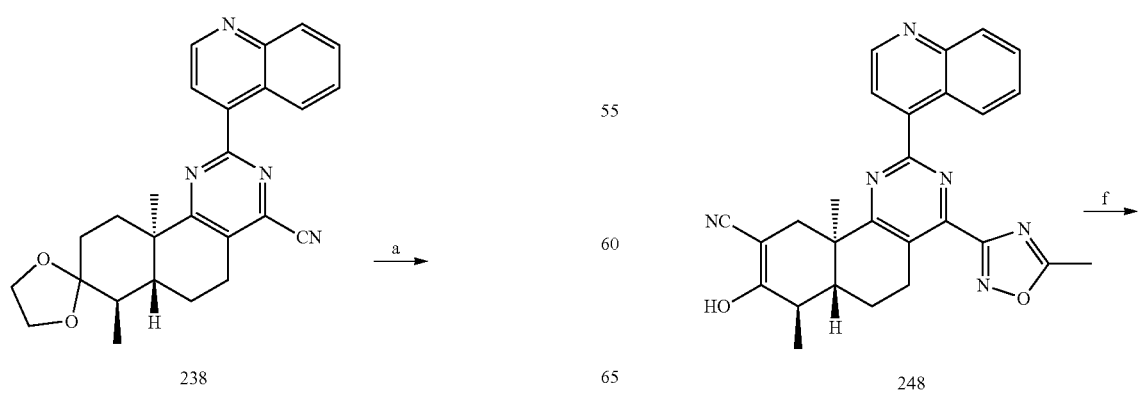
238
198
-continued
244
245, R₁, R₂ = OCH₂CH₂O
246 R₁, R₂ = O
247
248

199
-continued

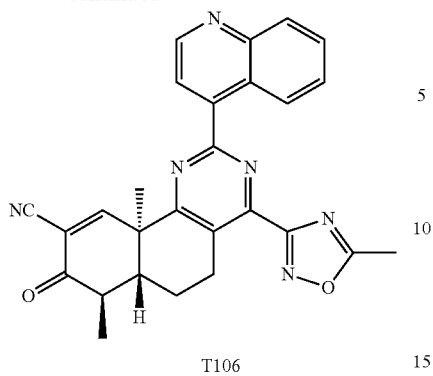

T106

Reagents and conditions:
a) NH₂OH•HCl, NaHCO₃, EtOH, reflux to rt;
b) Ac₂O, AcOH, rt to 100° C.;
c) aq. 3N HCl, MeOH, rt;
d) i) HCO₂Et, NaOMe, MeOH, THF, 0° C. to rt; ii) 6N HCl, NH₂OH•HCl, EtOH, 55° C.;
e) K₂CO₃, MeOH;
f) DDQ, benzene, 85° C.

Scheme 55

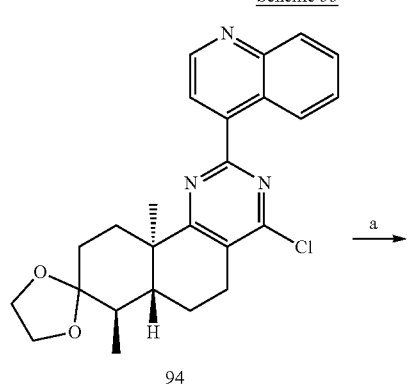

94 b

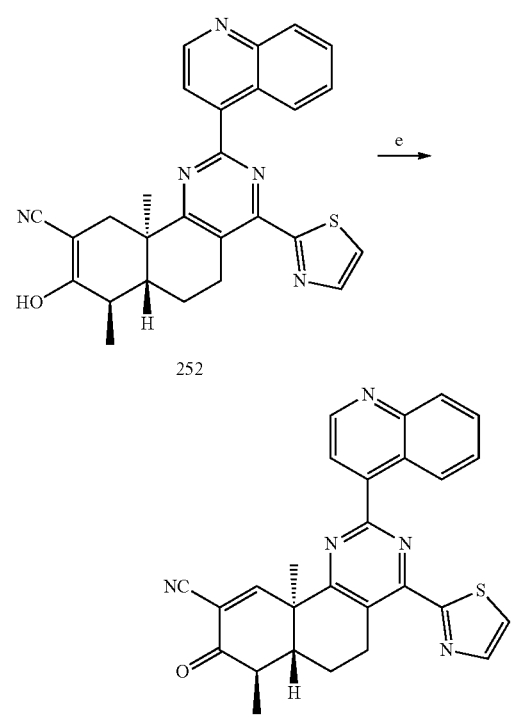

249

200
-continued

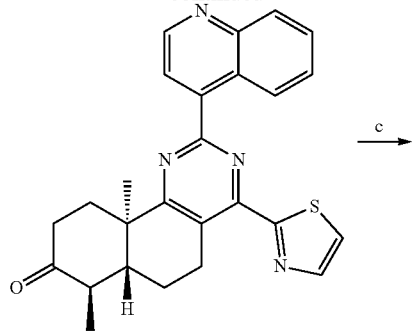

250 c

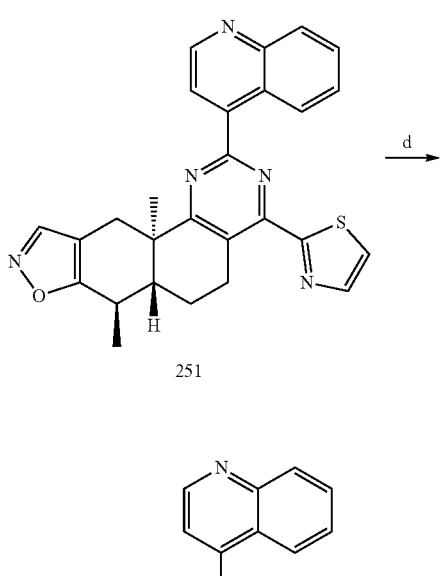

251 d

252 e

T107

Reagents and conditions: a) 2-(tri-n-butylstannyl)thiazole, Pd(PPh₃)₄, 1,4-dioxane, reflux; b) aq. 3N HCl, MeOH, THF, rt; c) i) HCO₂Et, NaOMe, MeOH, 0° C.-rt; ii) aq. 6N HCl, NH₂OH•HCl, EtOH, 55° C.; d) K₂CO₃, MeOH, rt; e) DDQ, benzene, reflux.

Scheme 56
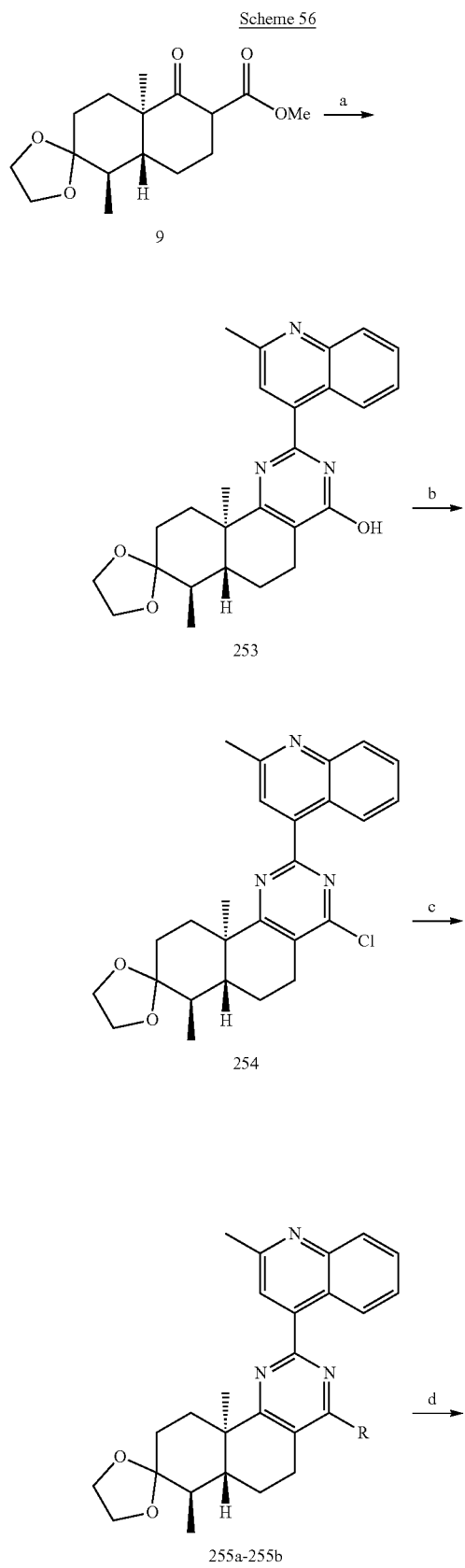
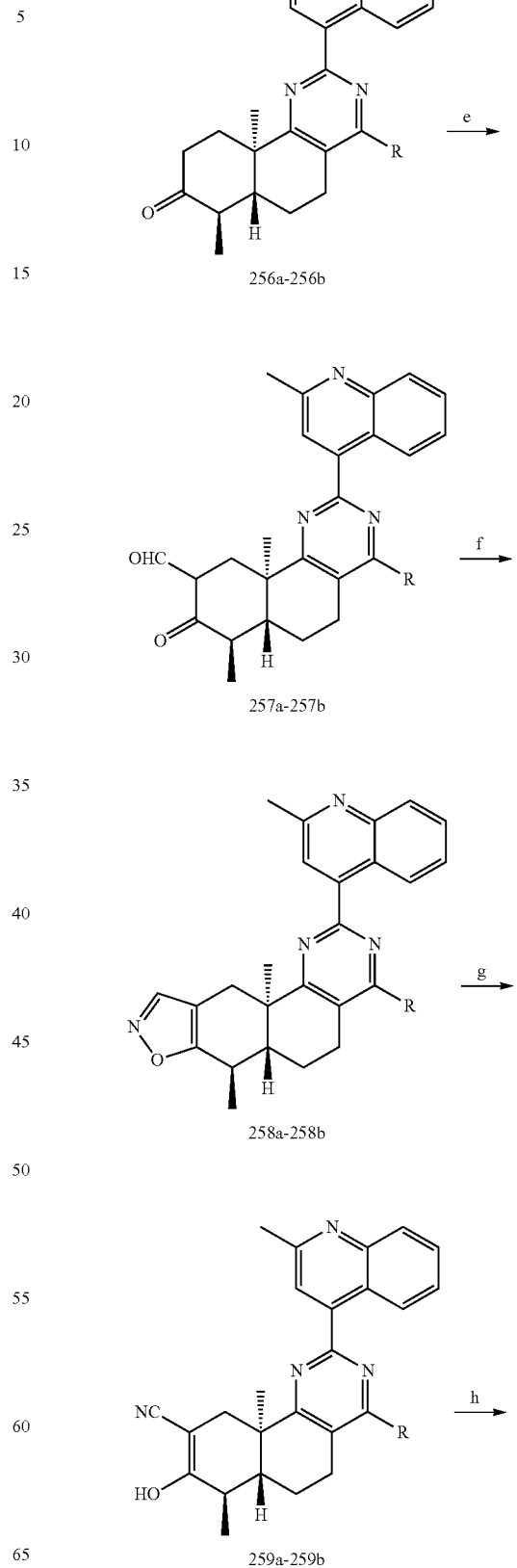

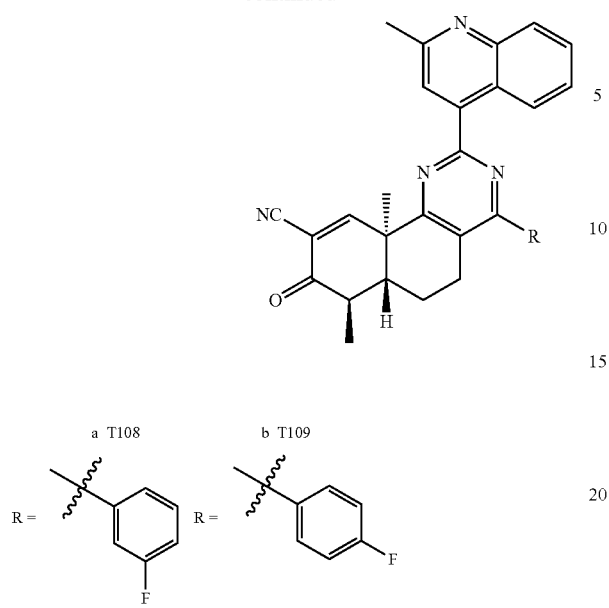
Reagents and conditions: a) 2-methyl-4-quinolinecarboximidamide hydrochloride, K₂CO₃, EtOH, 40° C.; b) i) POCl₃, toluene, microwave, 100° C.; ii) ethylene glycol, TsOH•H₂O, benzene, reflux, —H₂O; c) RB(OH)₂, K₃PO₄, Pd(PPh₃)₄, 1,4-dioxane, 90° C.; d) aq. 3N HCl, MeOH, rt; e) HCO₂Et, NaOMe, MeOH, rt; f) NH₂OH•HCl, EtOH, 60° C.-rt; g) K₂CO₃, MeOH, rt; i) DBDMH, DMF, 0° C.; ii) pyridine, 60° C.
Scheme 57
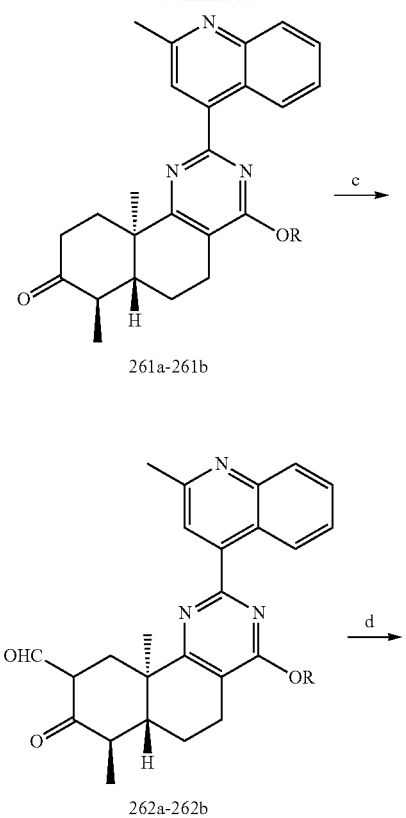
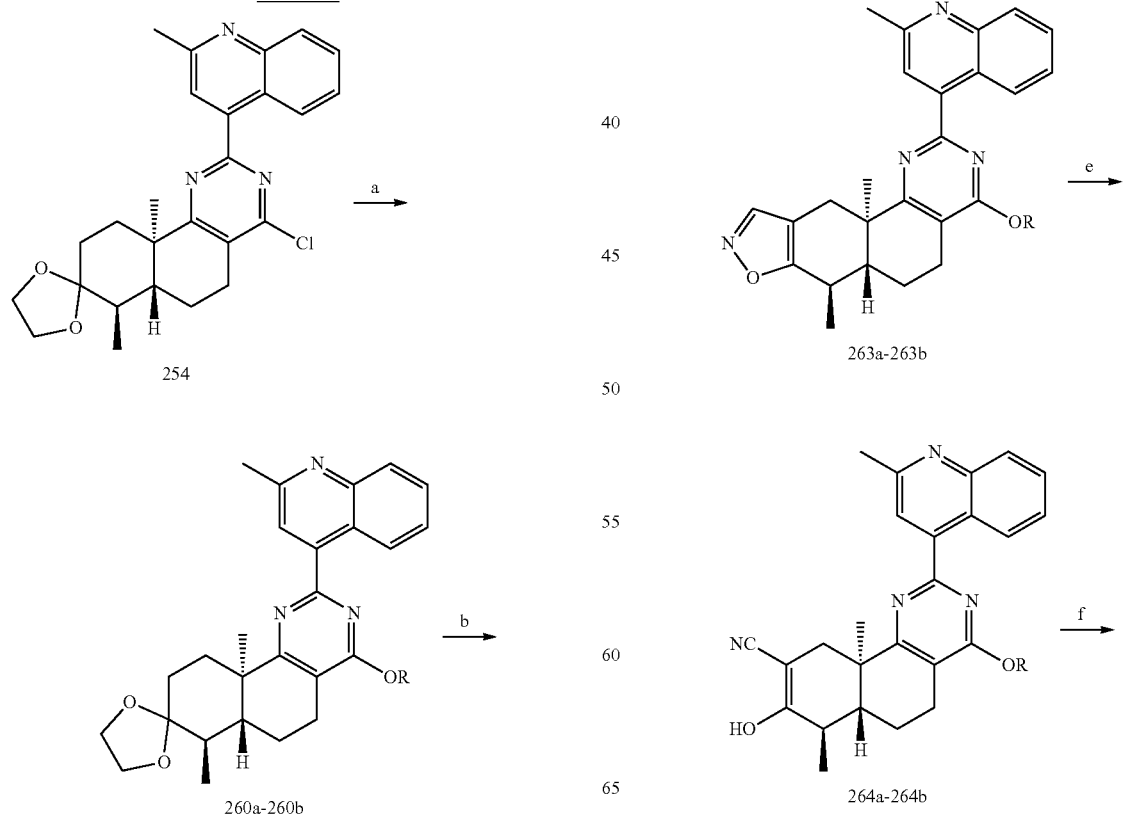

205
-continued
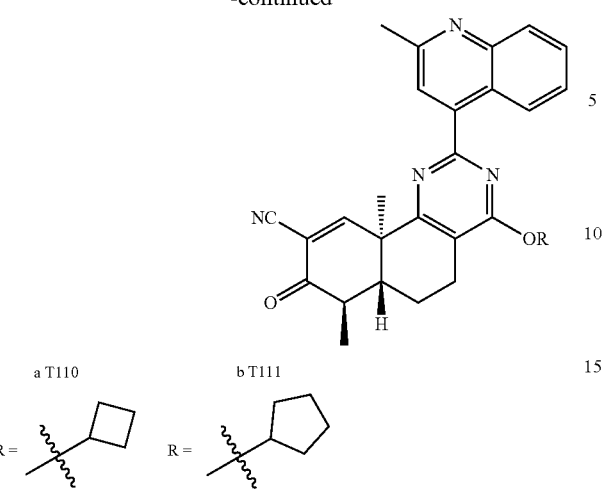
Reagents and conditions: a) ROH, NaH, THF, 60° C.; b) aq. 3N HCl, MeOH, rt; c) HCO₂Et, NaOMe, MeOH, rt; d) NH₂OH·HCl, AcOH, EtOH, heat; e) K₂CO₃, MeOH, rt; f) i) DBDMH, DMF, 0° C.; or Br₂, CH₂Cl₂, DMF, 0° C.; ii) pyridine, 60° C.
Scheme 58
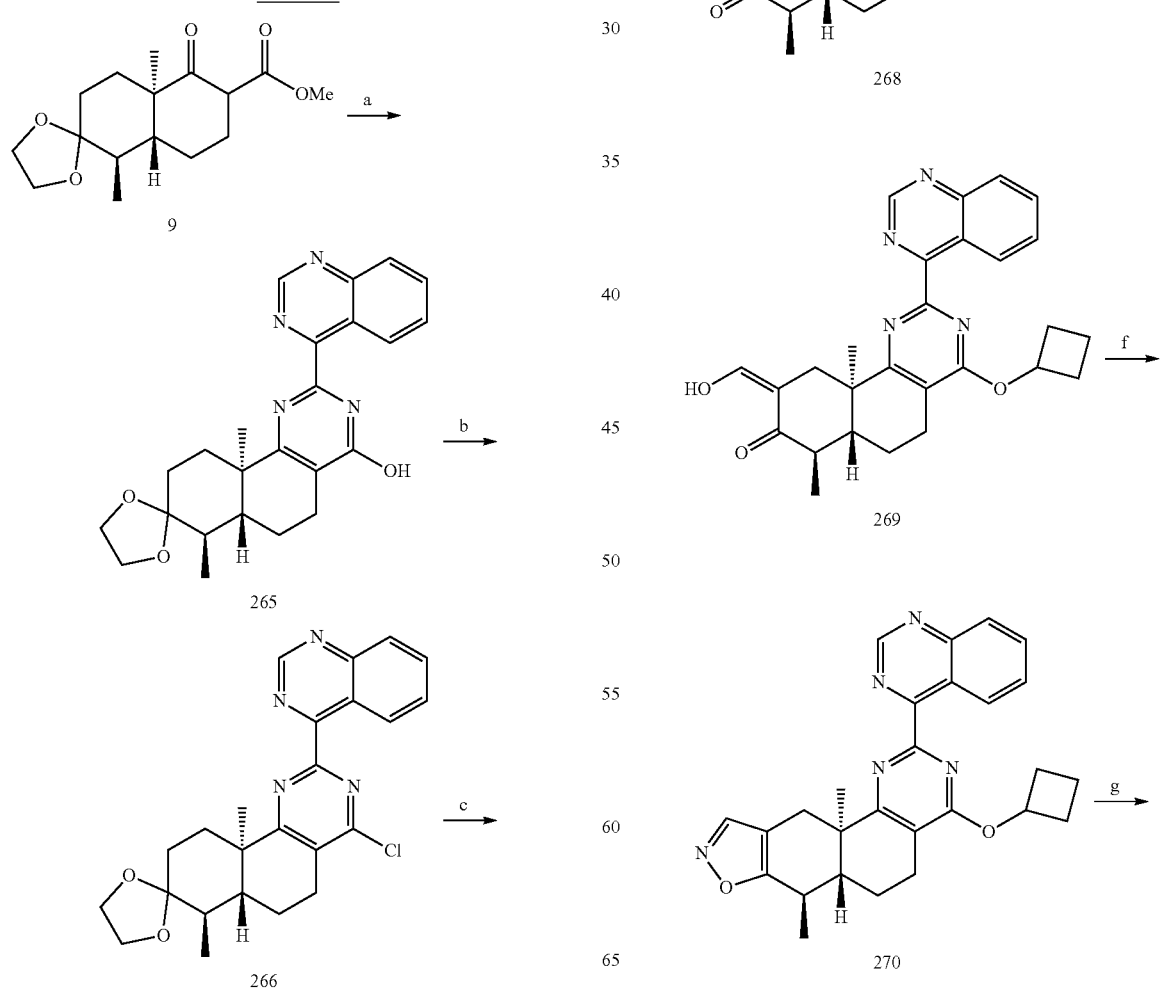
206
-continued
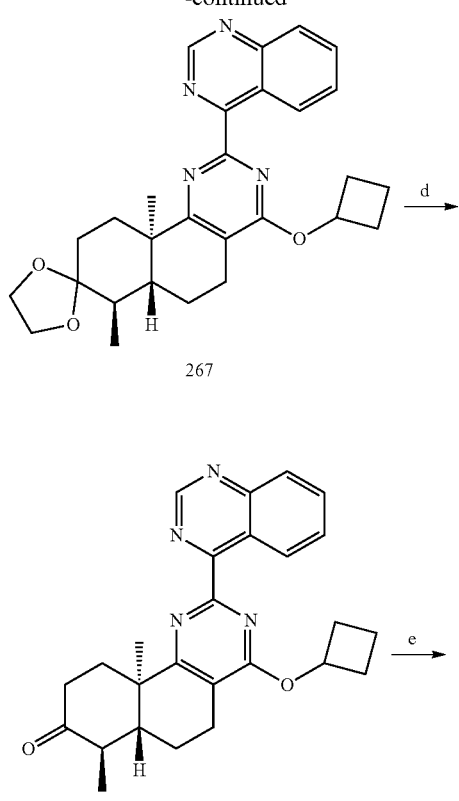

-continued
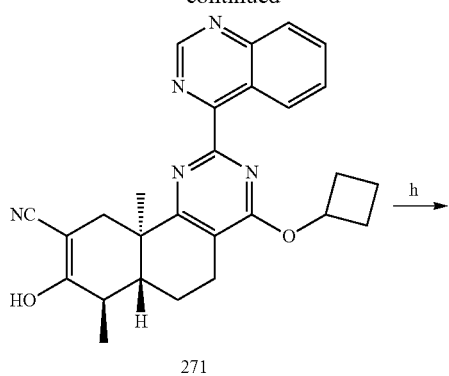
271
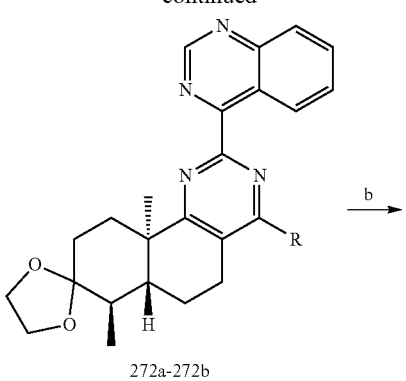
272a-272b
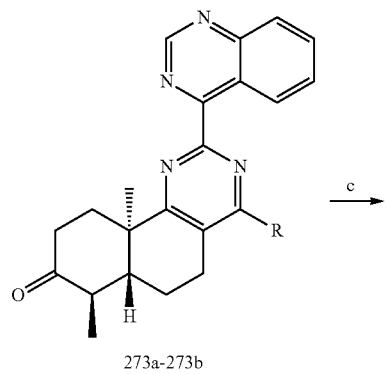
273a-273b
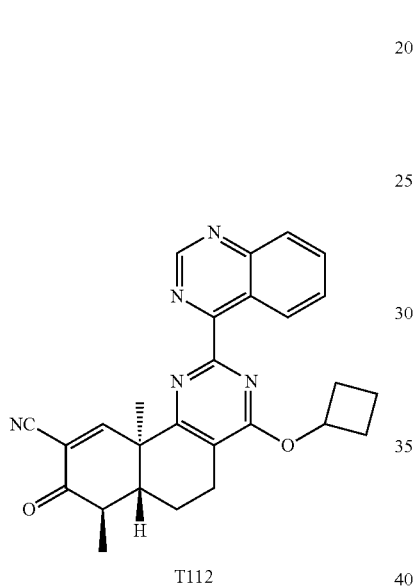
T112
Reagents and conditions: a) Quinazoline-4-carboximidamide hydrochloride, $K_2CO_3$, EtOH, 40° C.; b) i) $POCl_3$, toluene, microwave, 100° C.; ii) ethylene glycol, TsOH•$H_2O$, benzene, reflux, —$H_2O$; c) cyclobutanol, NaH, THF, 60° C.; d) aq. 3N HCl, THF, rt; e) $HCO_2Et$, NaOMe, MeOH, rt; f) $NH_2OH$•HCl, AcOH, EtOH, 50° C.; g) $K_2CO_3$, MeOH, rt; h) i) DBDMH, DMF, 0° C.; ii) pyridine, 60° C.
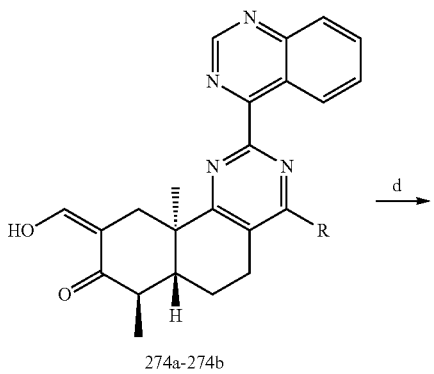
274a-274b
Scheme 59
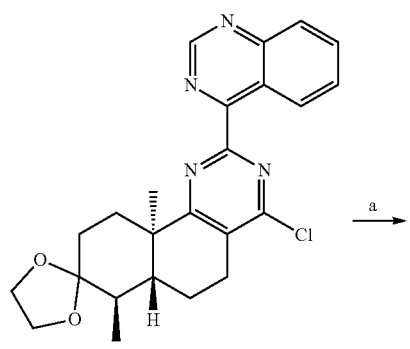
266
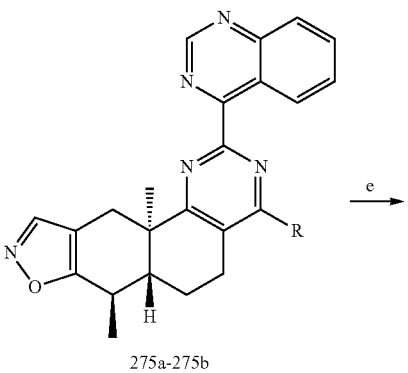
275a-275b 209
-continued
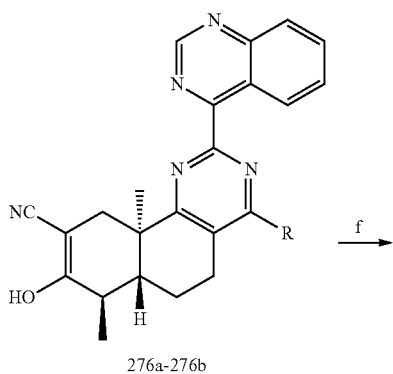
276a-276b
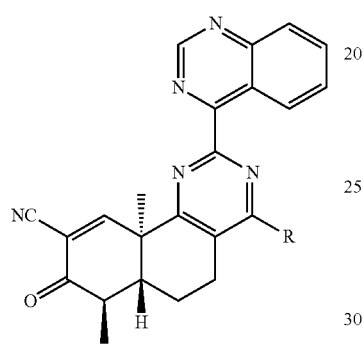
a T113  b T114
Reagents and conditions: a) RB(OH)₂, K₂CO₃, Pd(dppf)₂Cl₂, 1,4-dioxane, 90° C.; b) aq. 3N HCl, THF, rt; c) HCO₂Et, MeOH, rt; d) NH₂OH·HCl, AcOH, EtOH, 50° C.; e) K₂CO₃, MeOH, rt; f) i) DBDMH, DMF, 0° C.; ii) pyridine, 60° C.
Scheme 60
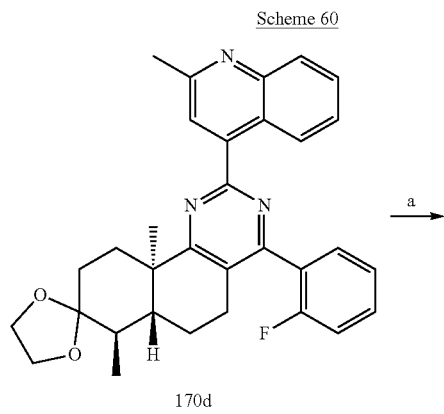
170d
210
-continued
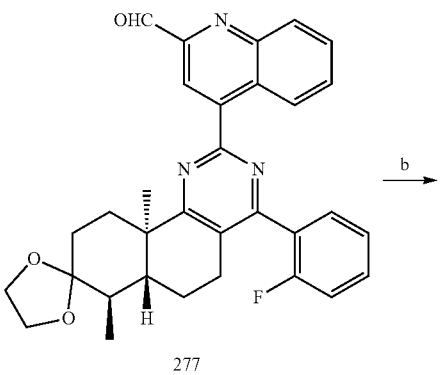
277
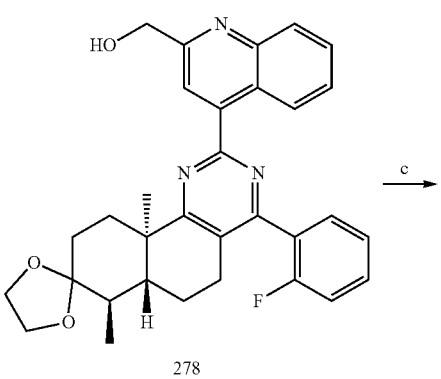
278
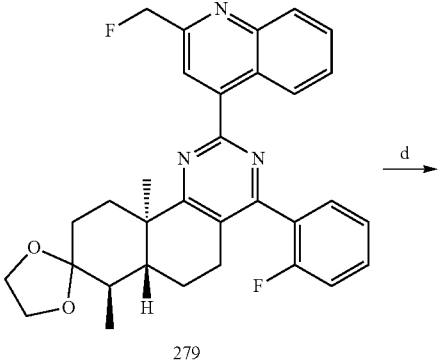
279
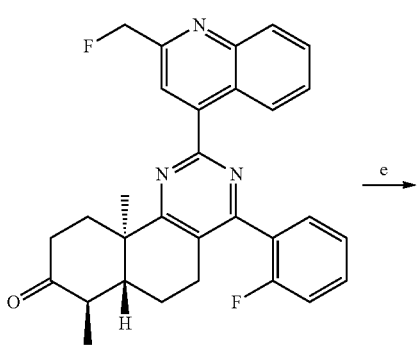
280

Scheme 61
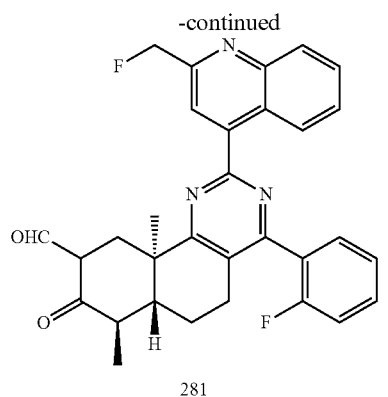
281
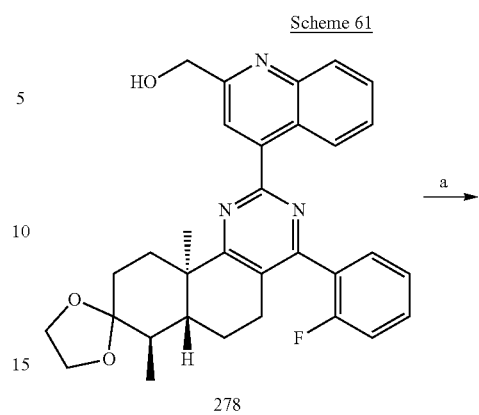
278
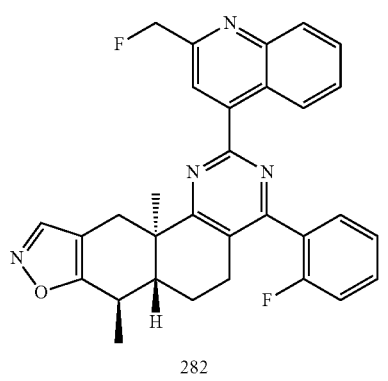
282
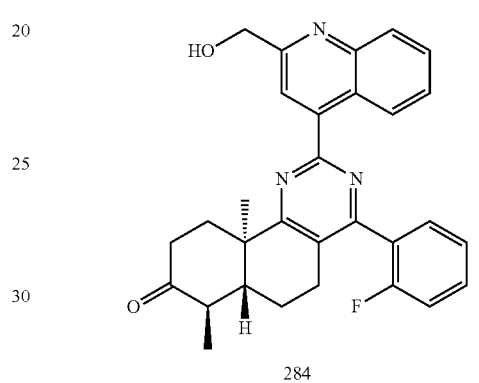
284
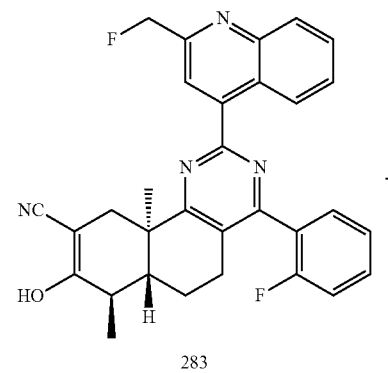
283
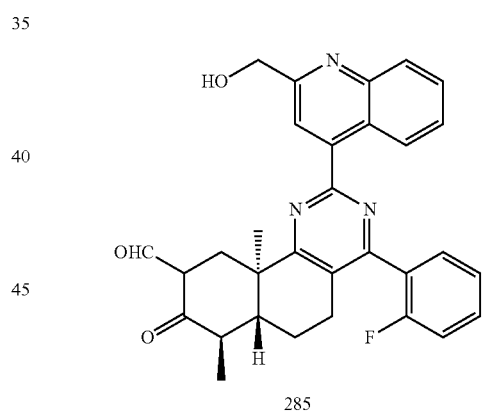
285
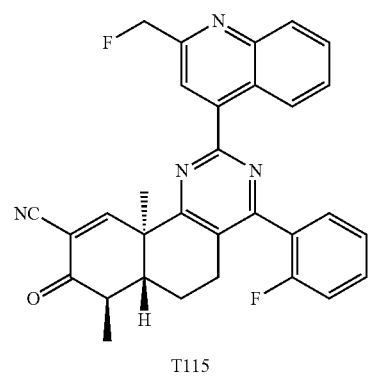
T115
Reagents and conditions: a) SeO₂, 1,4-dioxane, 100° C.; b) NaBH₄, EtOH, rt; c) DAST, CH₂Cl₂, 0° C.; d) aq. 3N HCl, MeOH, rt; e) HCO₂Et, NaOMe, MeOH, rt; f) NH₂OH·HCl, HOAc, EtOH, 60° C.-rt; g) K₂CO₃, MeOH, rt; h) i) DBDMH, DMF, 0° C.; ii) pyridine, DMF, 60° C.
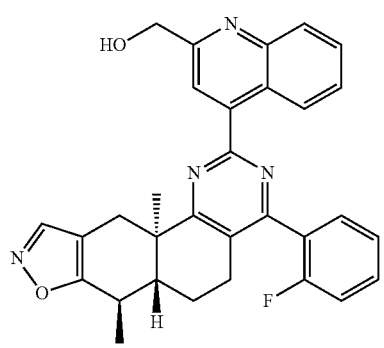
286

213

-continued

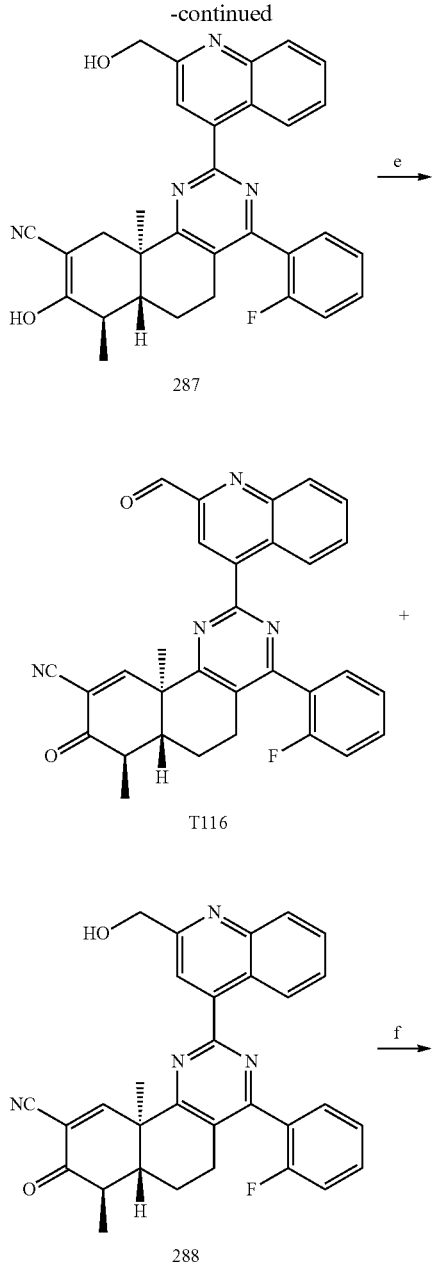

T116

T117

Reagents and conditions: a) aq. 3N HCl, MeOH, rt; b) HCO₂Et, NaOMe,
MeOH, rt; c) NH₂OH•HCl, HOAc, EtOH, 60° C. to rt; d) K₂CO₃, MeOH,
rt; e) DDQ, benzene, 80° C.; f) NaOAc, Ac₂O, rt.

214

Scheme 62

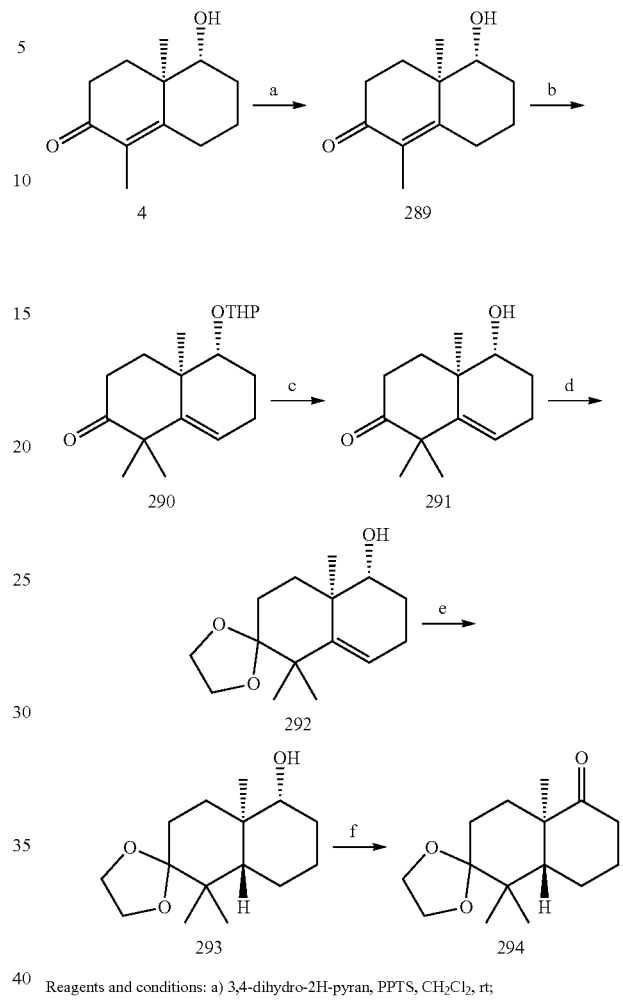

Reagents and conditions: a) 3,4-dihydro-2H-pyran, PPTS, CH₂Cl₂, rt;
b) i) t-BuOK, benzene, rt-60° C.; ii) MeI, 0° C.-rt; c) PPTS, EtOH, reflux;
d) ethylene glycol, p-TsOH, benzene, reflux, ——H₂O; e) i) H₂, Pd(OH)₂ on C,
MeOH, rt; ii) ethylene glycol, p-TsOH, benzene, reflux, ——H₂O;
f) PDC, MgSO₄, CH₂Cl₂, rt.

Scheme 63

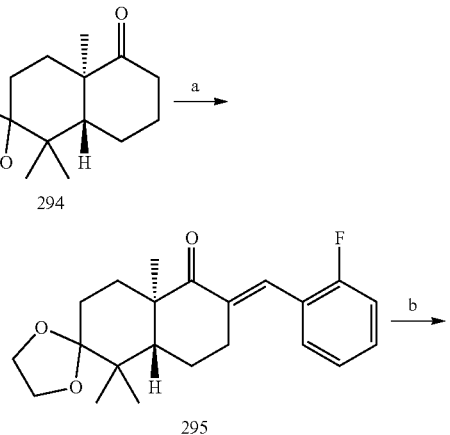

215
-continued
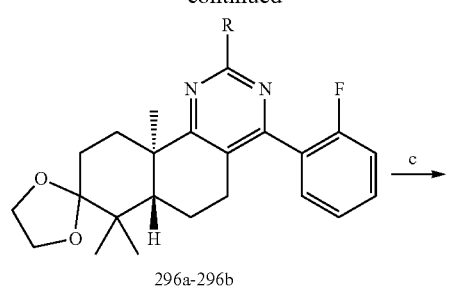
296a-296b
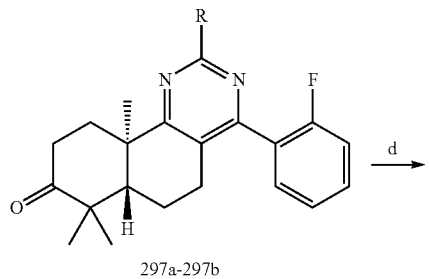
297a-297b
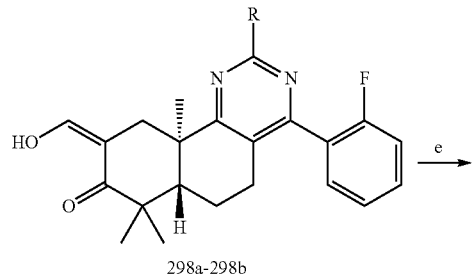
298a-298b
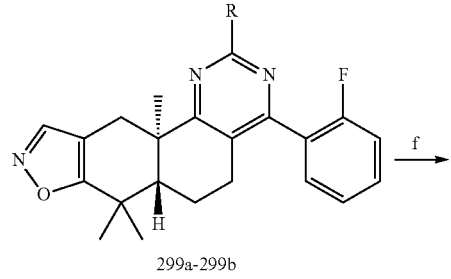
299a-299b
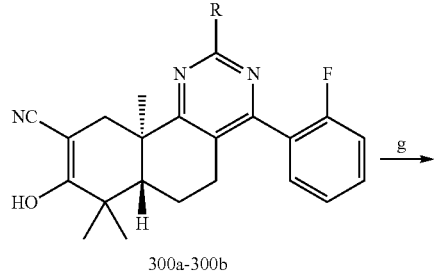
300a-300b
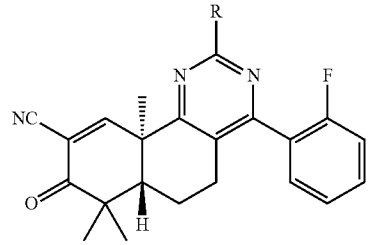
216
-continued
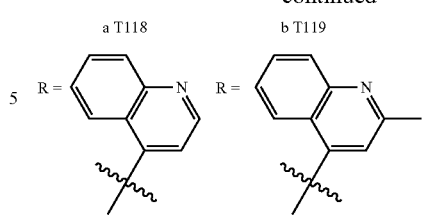
a T118  b T119
Reagents and conditions: a) 2-fluorobenzaldehyde, KF/Al$_2$O$_3$, EtOH, rt; b) i) RC(NH)NH$_2$•HCl, K$_2$CO$_3$, EtOH, reflux; ii) MnO$_2$, CH$_2$Cl$_2$, rt; c) aq•HCl, MeOH, rt; d) HCO$_2$Et, NaOMe, rt; e) NH$_2$OH•HCl, AcOH, EtOH, 60° C.-rt; f) K$_2$CO$_3$, MeOH, rt; g) i) DBDMH, DMF, 0° C.; ii) pyridine, 60° C.
Scheme 64
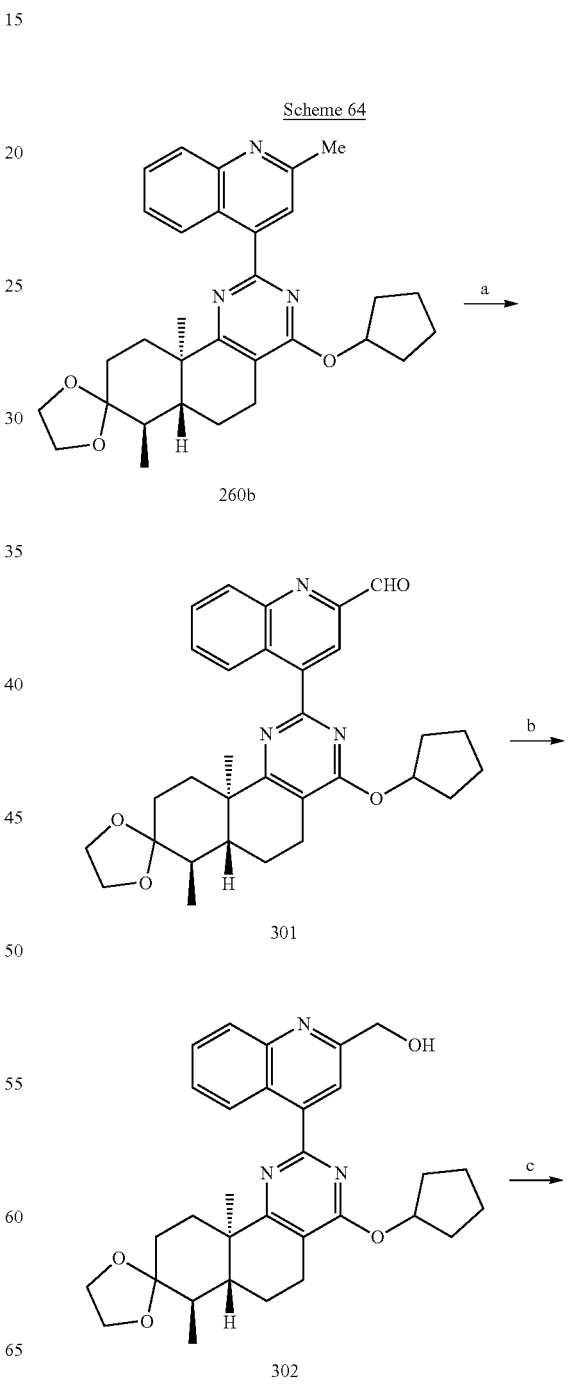
260b
301
302

217
-continued
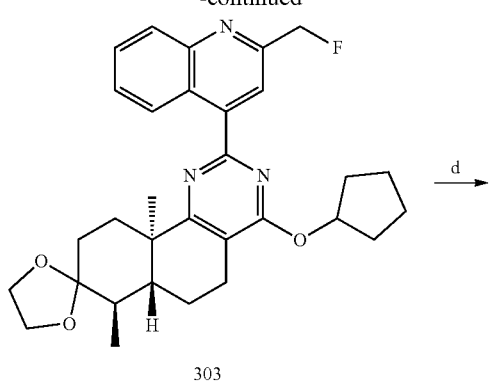
303
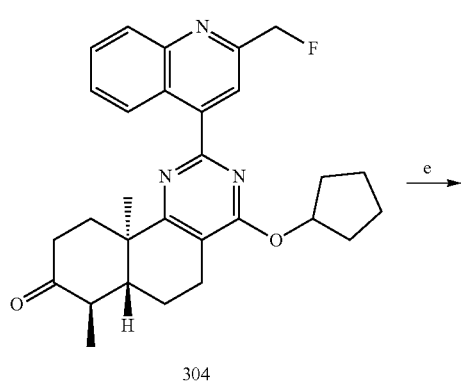
304
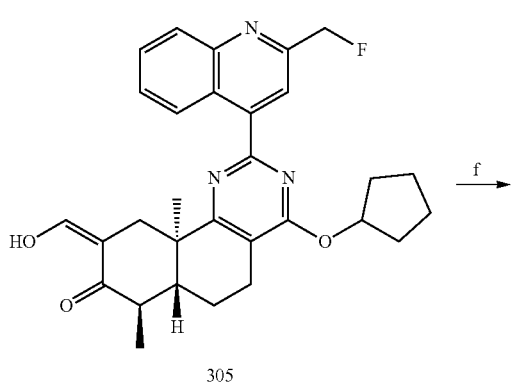
305
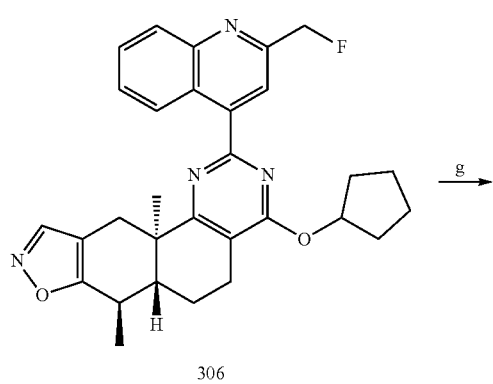
306
218
-continued
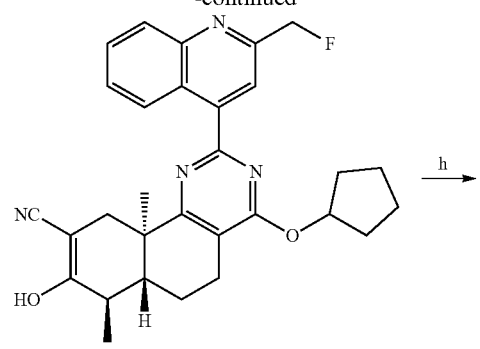
307
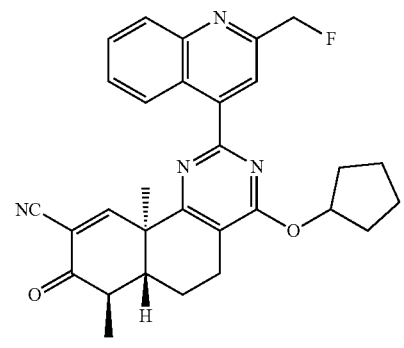
T120
Reagents and conditions: a) SeO$_2$, 1,4-dioxane, 100° C.; b) NaBH$_4$, EtOH, rt; c) DAST, CH$_2$Cl$_2$, 0° C.; d) aq. 3N HCl, MeOH, rt; e) HCO$_2$Et, NaOMe, MeOH, rt; f) NH$_2$OH•HCl, HOAc, EtOH, 60° C.-rt; g) K$_2$CO$_3$, MeOH, rt; h) i) DBDMH, DMF, 0° C.; ii) pyridine, DMF, 60° C.
Scheme 65
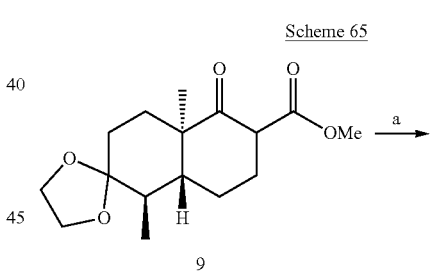
9
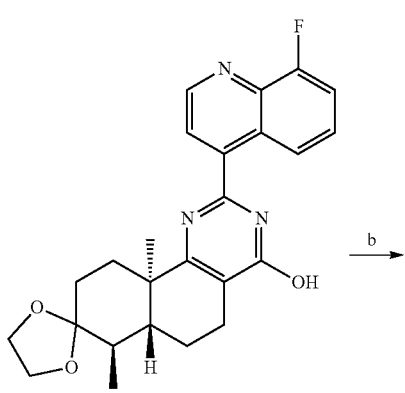
308

219
-continued
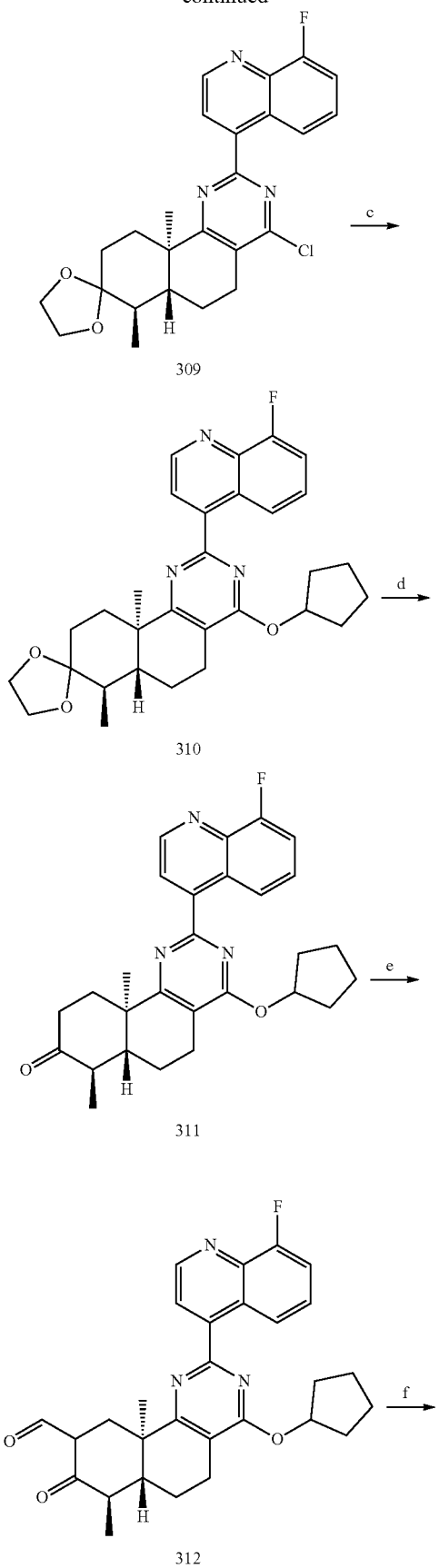
220
-continued
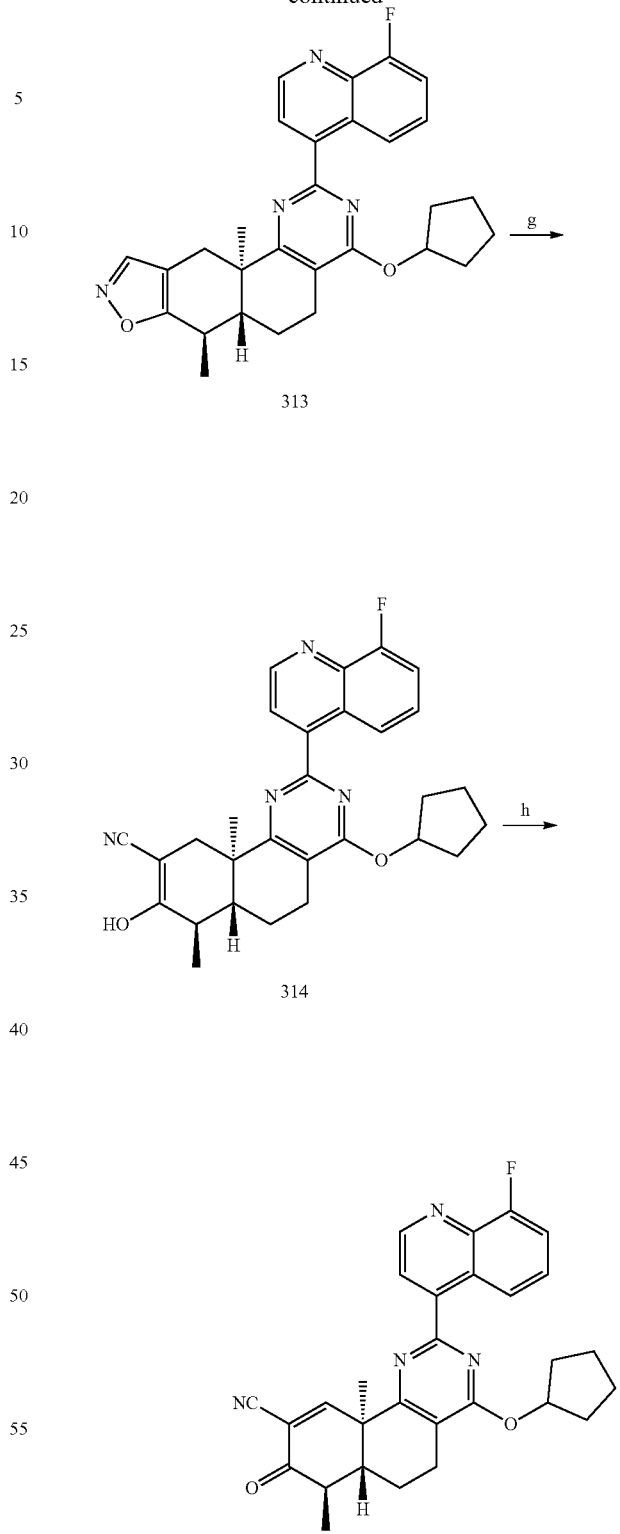
Reagents and conditions: a) 8-fluoro-4-quinolinecarboximidamide hydrochloride, K₂CO₃, EtOH, 40° C.; b) i) POCl₃, toluene, microwave, 100° C.; ii) ethylene glycol, TsOH·H₂O, benzene, reflux, —H₂O; c) NaH, cyclopentanol, THF; d) aq. 3N HCl, THF, rt; e) HCO₂Et, NaOMe, MeOH, rt; f) NH₂OH·HCl, AcOH, EtOH, 50° C.; g) K₂CO₃, MeOH, rt; h) i) Br₂, DMF, 0° C.; ii) pyridine, 60° C.

Scheme 66
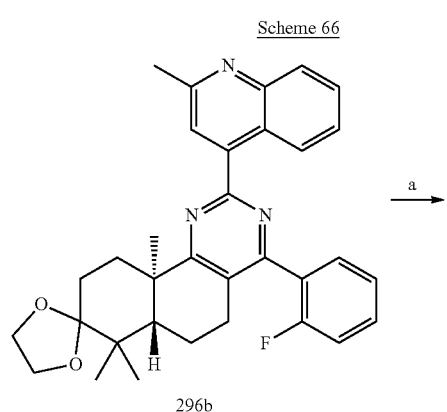# 296b
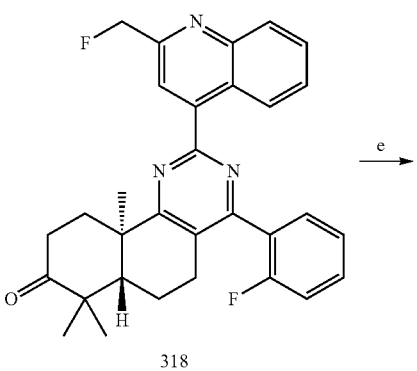# 318
a →
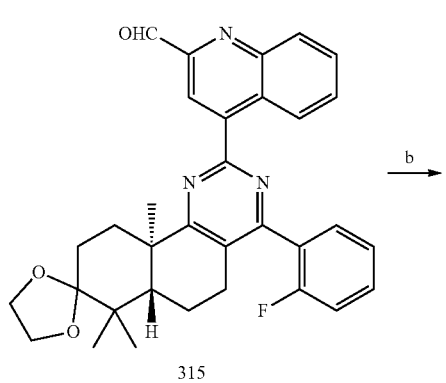# 315
e →
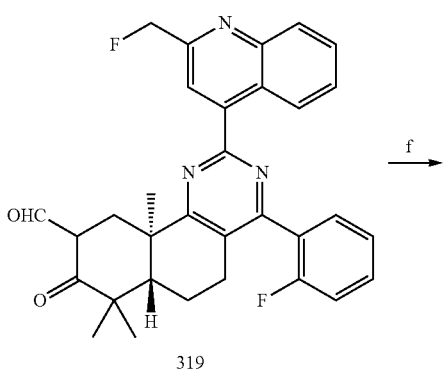# 319
b →
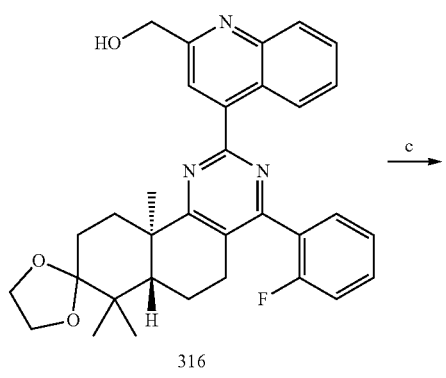# 316
f →
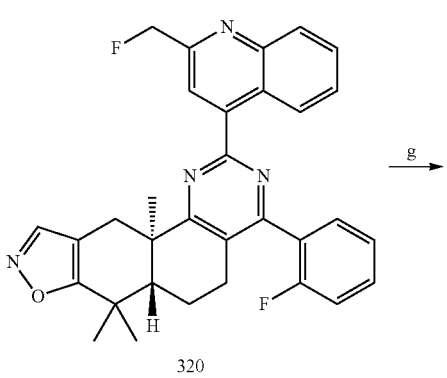# 320
c →
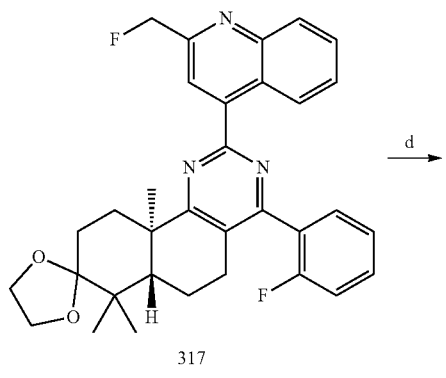# 317
g →
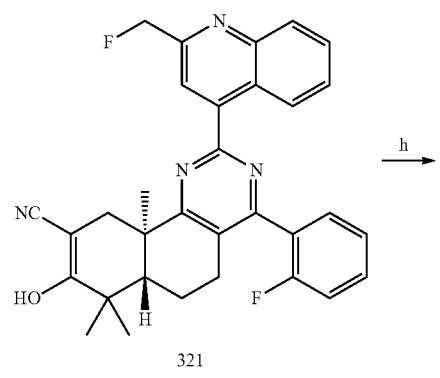# 321
d →
h →

223
-continued
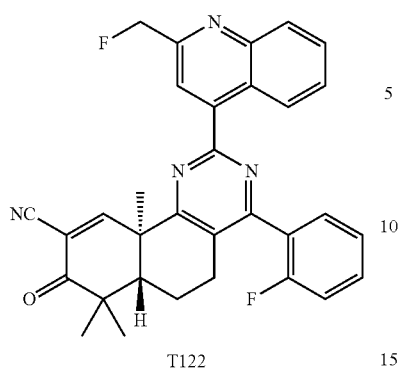
T122
Reagents and conditions; a) SeO₂, 1,4-dioxane, 100° C.; b) NaBH₄, EtOH, rt; c) DAST, CH₂Cl₂, 0° C.; d) aq. 3N HCl, MeOH, rt; e) HCO₂Et, NaOMe, MeOH, rt; f) NH₂OH•HCl, HOAc, EtOH, 60° C.-rt; g) K₂CO₃, MeOH, rt; h) i) DBDMH, DMF, 0° C.; ii) pyridine, DMF, 60° C.
Scheme 67
224
-continued
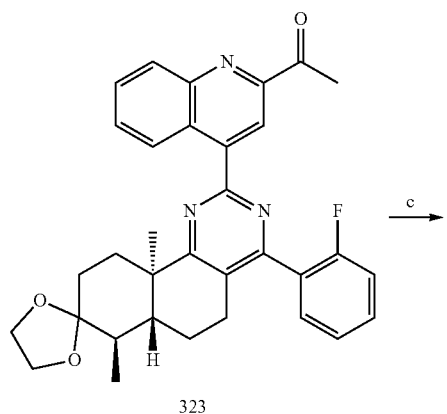
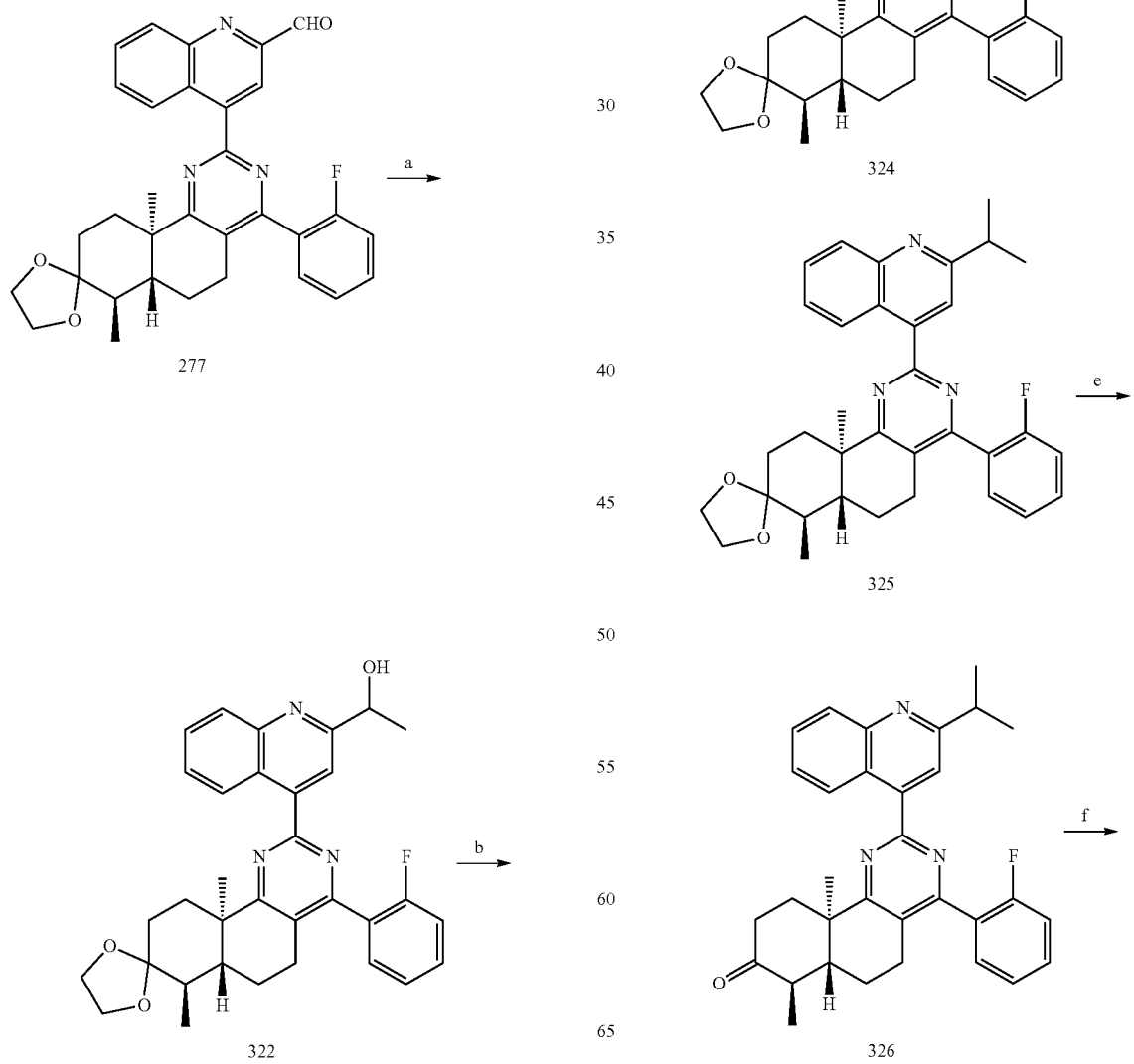

225
-continued
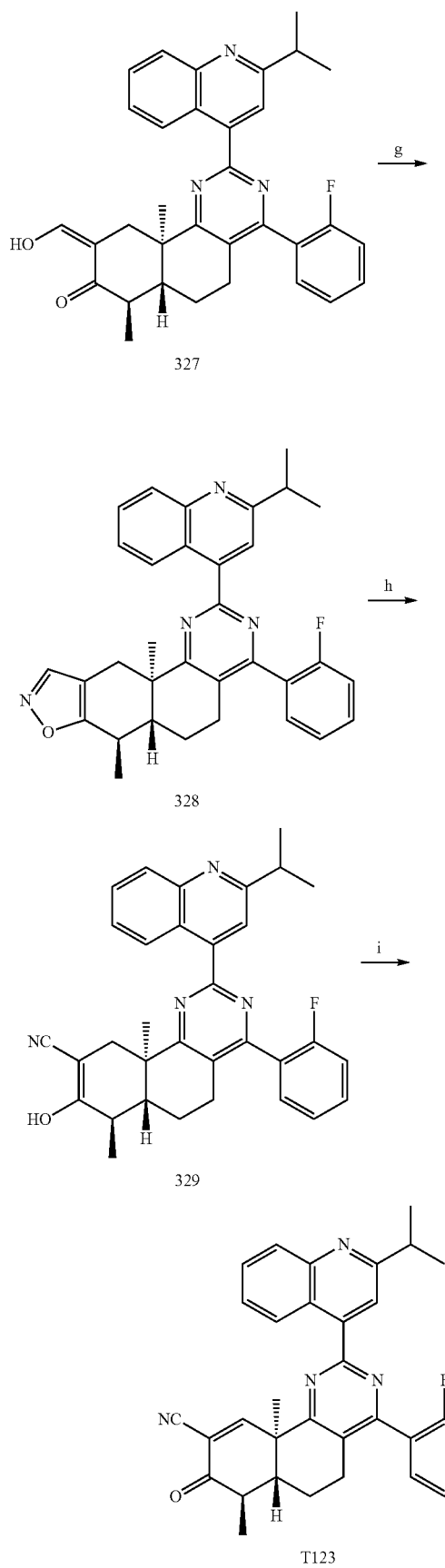
226
-continued
Reagents and conditions: a) MeMgBr, THF, 0° C.-rt; b) MnO$_2$, CH$_2$Cl$_2$, rt; c) Me(Ph$_3$P)Br, t-BuOK, THF, 0° C.-rt; d) H$_2$, Pd/C, MeOH, EtOAc, rt; e) aq. 3N HCl, THF, rt; f) HCO$_2$Et, NaOMe, MeOH, 0° C.-rt; g) NH$_2$OH•HCl, HOAc, EtOH, 60° C.-rt; h) K$_2$CO$_3$, MeOH, rt-50° C.; i) 1) DBDMH, DMF, 0° C.; 2) pyridine, 60° C.
Scheme 68
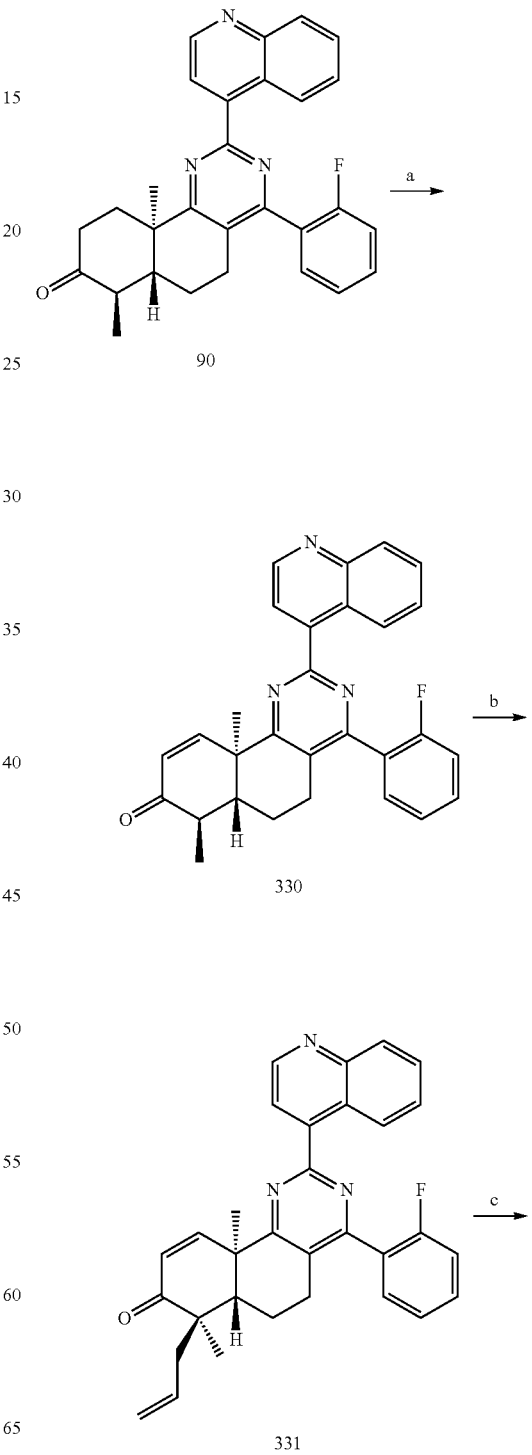

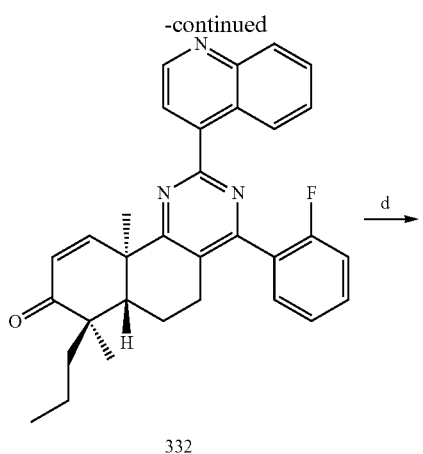
332
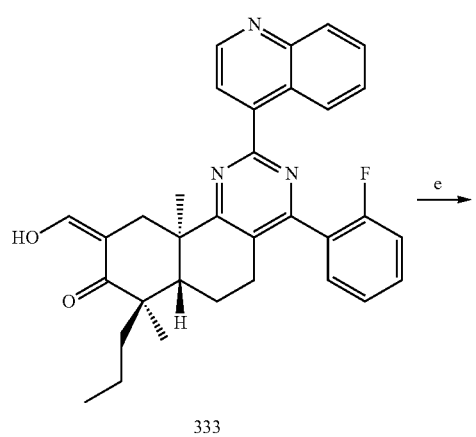
333
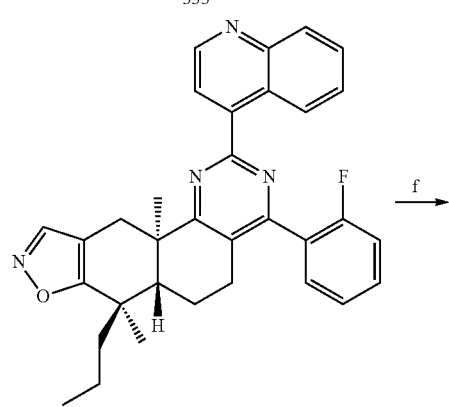
334
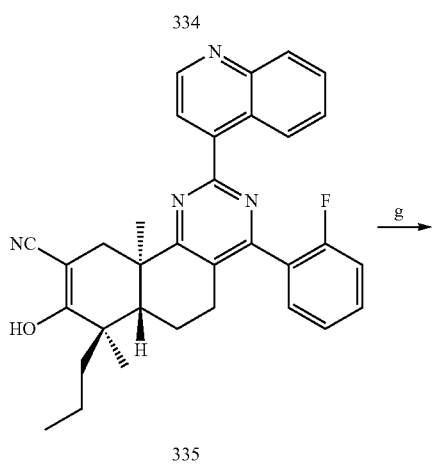
335
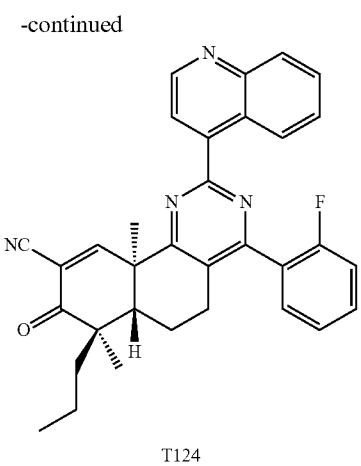
T124
Reagents and conditions: a) IBX, DMSO, 65° C.; b) KH, allyl bromide, THF, 0° C.; c) H₂, 10% Pd/C, MeOH, rt; d) HCO₂Et, NaOMe, MeOH, 0° C. to rt; e) NH₂OH•HCl, HOAc, EtOH, 60° C.; f) K₂CO₃, MeOH, rt to 50° C.; g) i) DBDMH, DMF, 0° C; ii) pyridine, 60° C.
Scheme 69
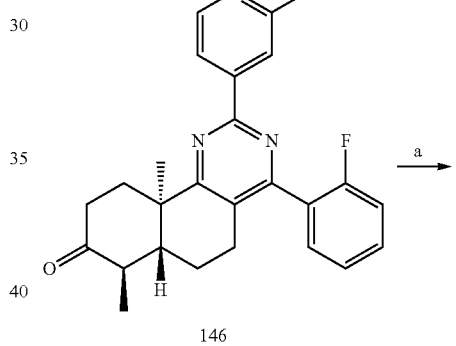
146
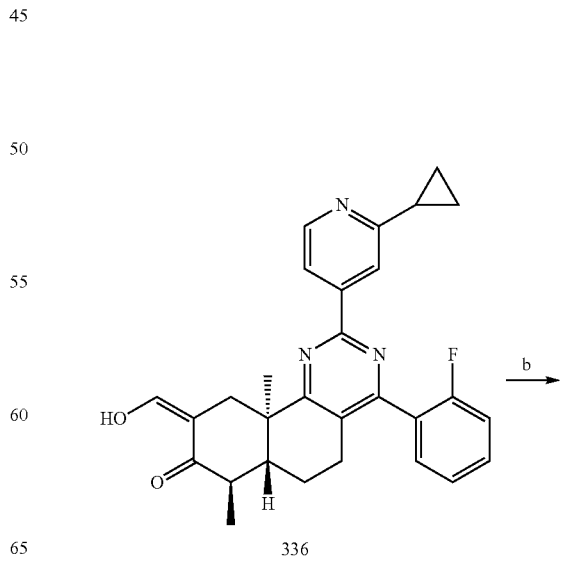
336

229
-continued
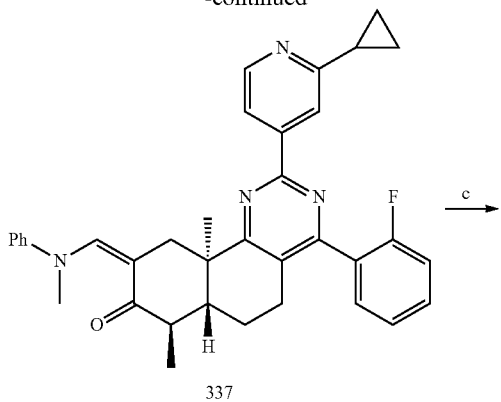
337
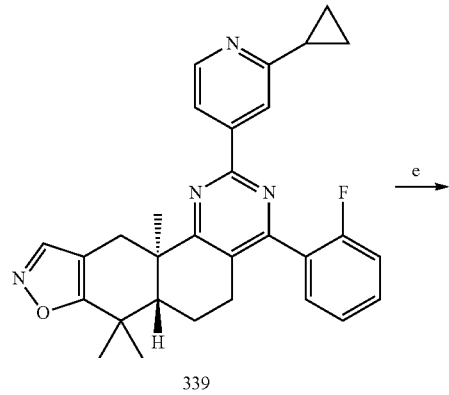
338
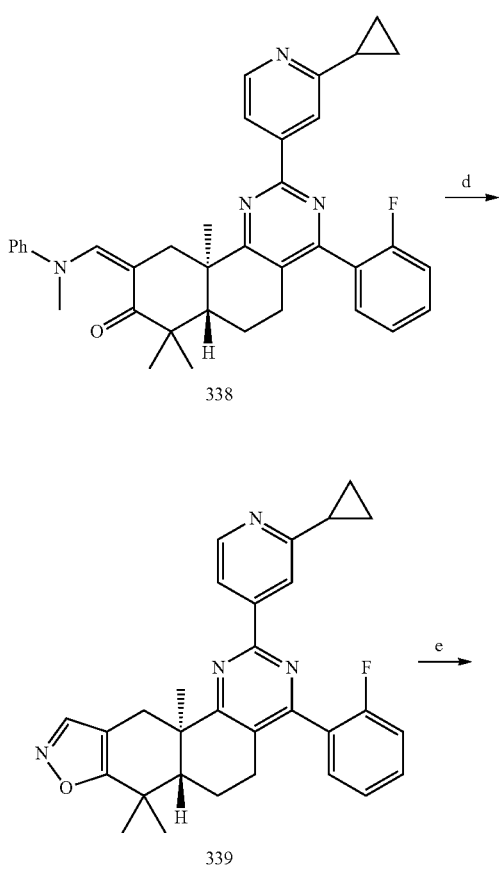
339
340
230
-continued
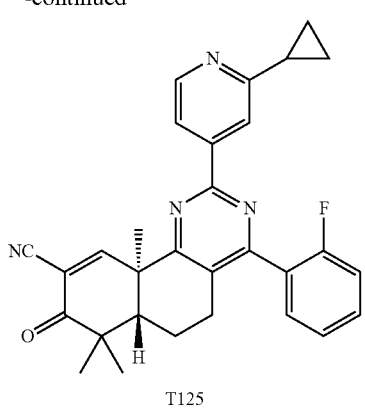
T125
Reagents and condtions: a) HCO₂Et, NaOMe, 0° C. to rt; b) PhNHCH₃, MgSO₄, p-TsOH•H₂O, CH₂Cl₂, rt; c) t-BuOK, MeI, THF, 0° C; d) NH₂OH•HCl, aq. 1N HCl, EtOH, 55° C.; e) NaOMe, MeOH, 55° C.; f) i) DBDMH, DMF, 0° C.; ii) pyridine, 55° C.
Scheme 70
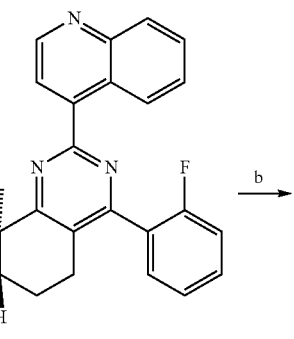
90

341

-continued
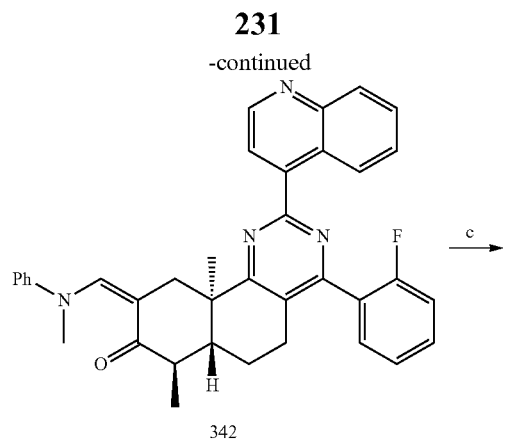
342
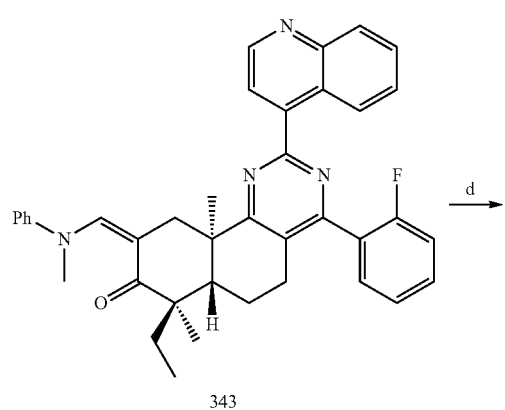
343
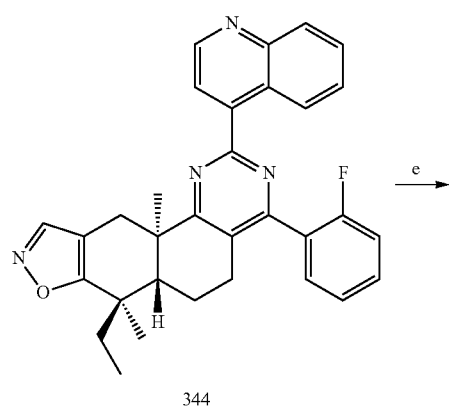
344
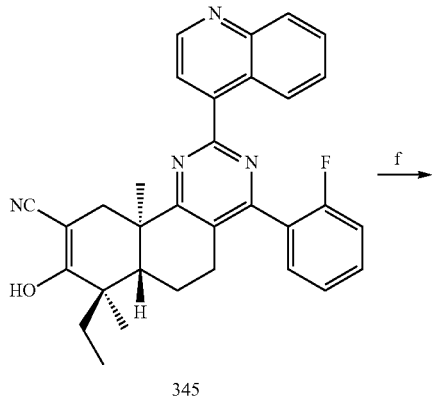
345
-continued
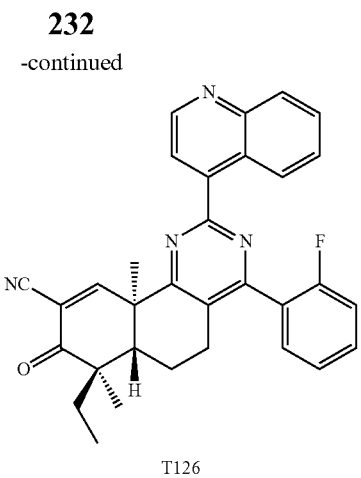
T126
Reagents and condtions: a) HCO₂Et, NaOMe, 0° C to rt; b) PhNHCH₃, benzene, reflux, —H₂O, rt; c) t-BuOK, EtI, THF, 0° C.; d) NH₂OH•HCl, aq. 1N HCl, EtOH, 55° C.; e) NaOMe, MeOH, 55° C.; f) i) DBDMH, DMF, 0° C.; ii) pyridine, 55° C.
Scheme 71
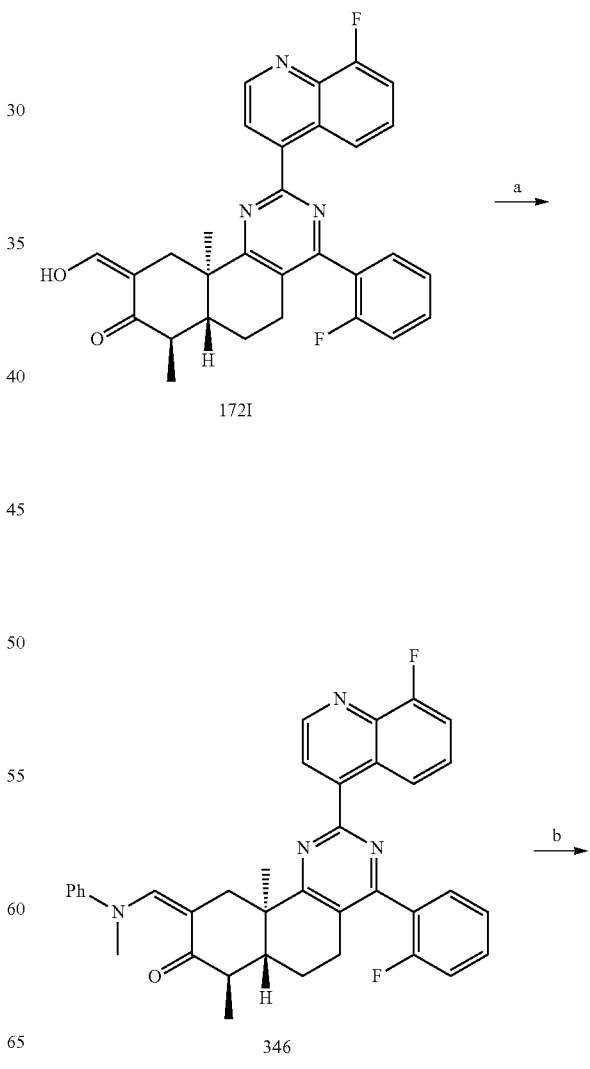

233
-continued
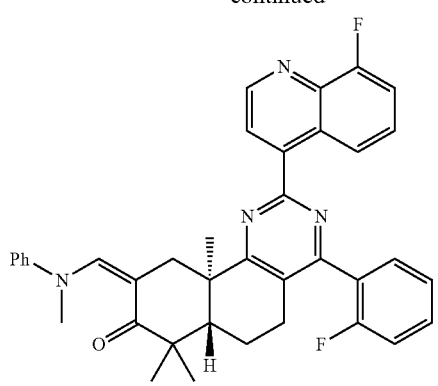
347
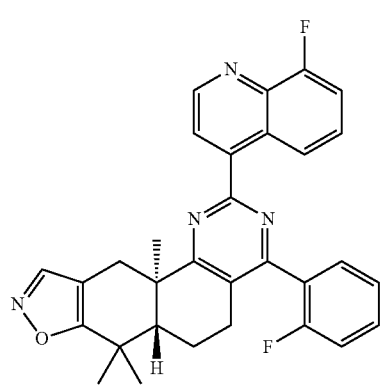
348
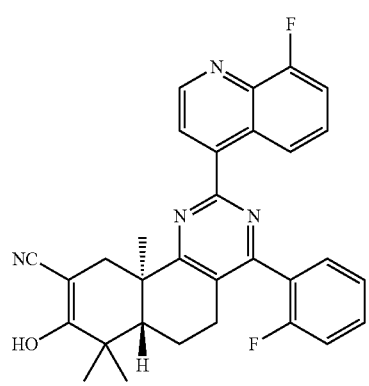
349
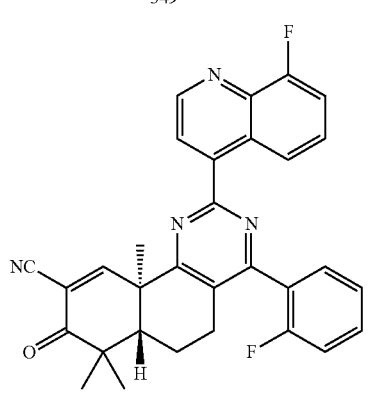
T127
+
234
-continued
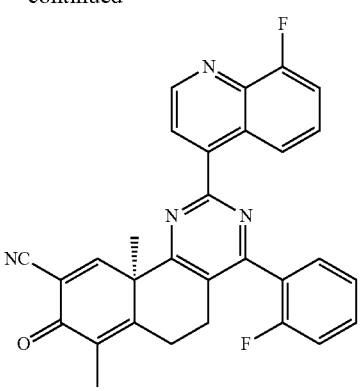
T128
Reagents and conditions: a) N-methylaniline, molecular sieve, CH₂Cl₂, rt; b) t-BuOK, MeI, THF, 0° C.; c) NH₂OH•HCl, EtOH, aq. 1N HCl, 50° C.; d) K₂CO₃, MeOH, rt; e) i) DBDMH, DMF, 0° C.; ii) pyridine, 60° C.
Scheme 72
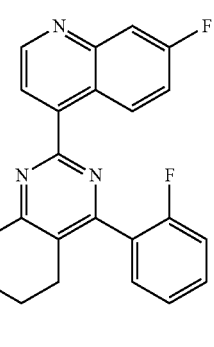
T76
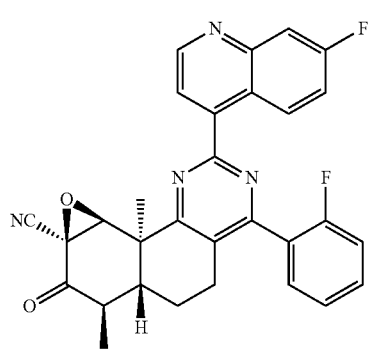
T129
Reagents and conditions: a) aq. 30% H₂O₂, MeCN, rt.

Scheme 73
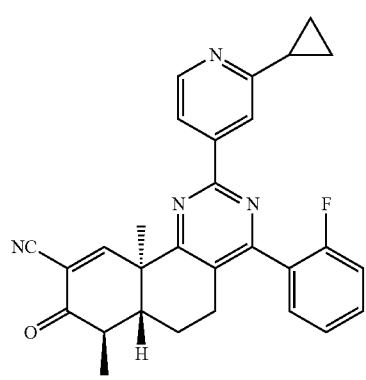
T53
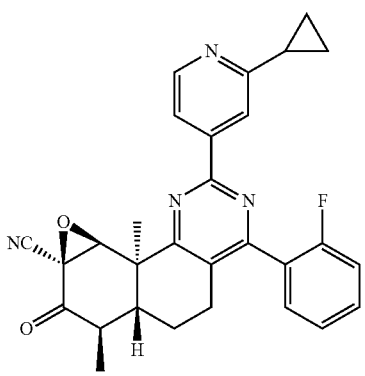
T130
Reagents and conditions: a) aq. 30% H₂O₂, MeCN, rt.
Scheme 74
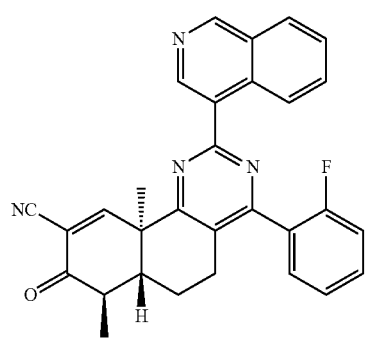
T66
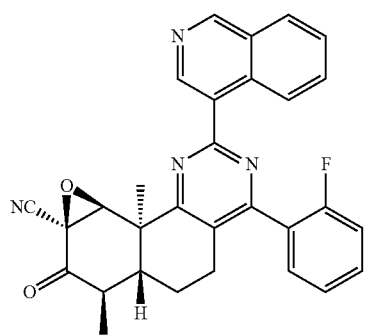
T131
Reagents and conditions: a) aq. 30% H₂O₂, MeCN, rt.
Scheme 75
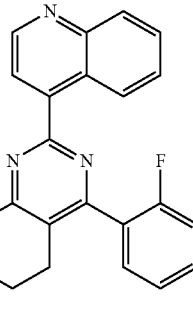
T37
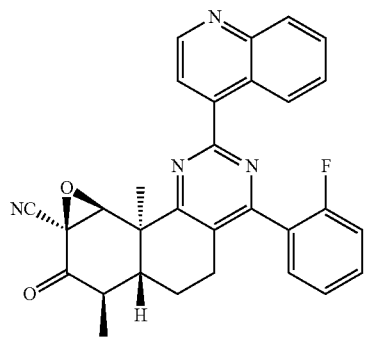
T132
Reagents and conditions: a) aq. 30% H₂O₂, MeCN, rt.

Scheme 76
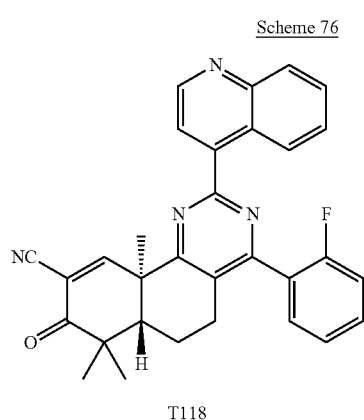
T118
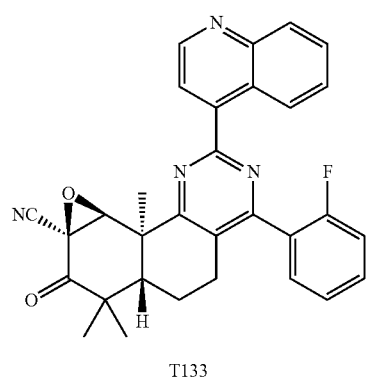
T133
Reagents and conditions: a) aq. 30% H₂O₂, MeCN, rt.
Scheme 77
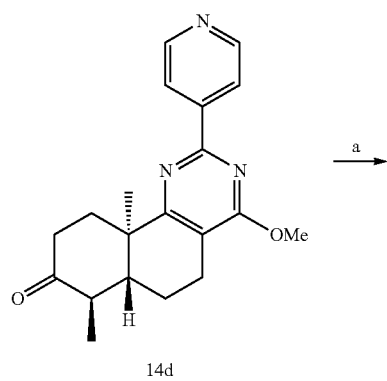
14d
T134
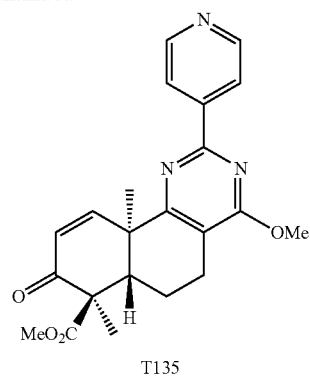
T135
Reagents and conditions: a) i) LHMDS, PhSeCl, THF, -78° C.; ii) 30% aq. H₂O₂, EtOAc, THF, rt; b) LDA, THF, -78° C. to 0° C.; HMPA, CNCO₂Me, THF, -78° C.
Scheme 78
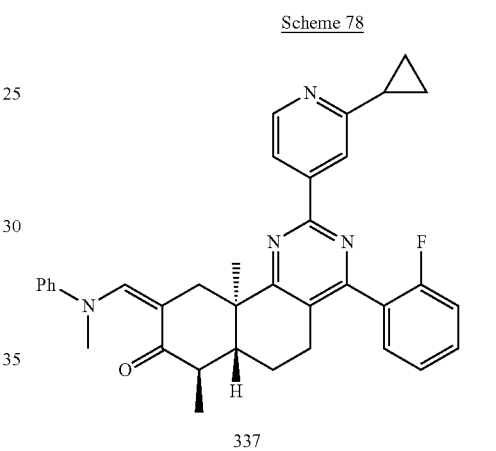
337
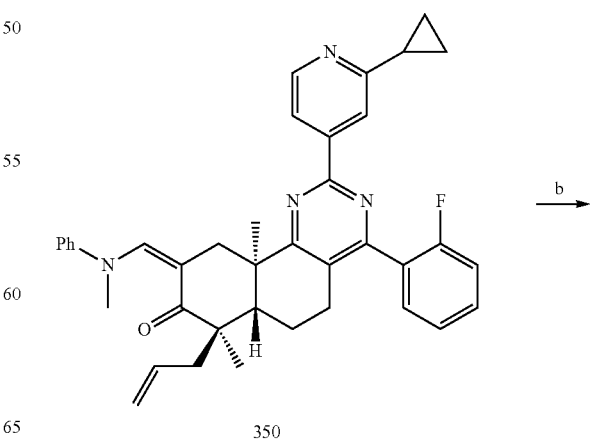
350

239
-continued
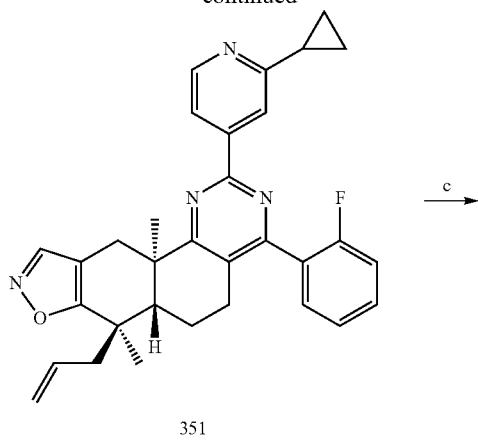
351
240
-continued
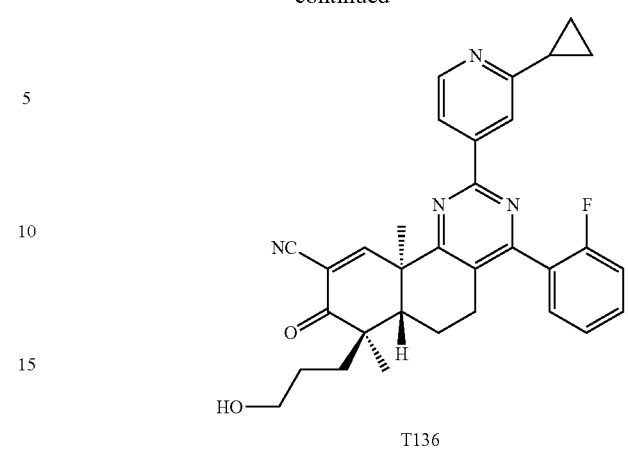
T136
Reagents and conditions: a) t-BuOk, allyl bromide, THF, 0° C.; b) NH₂OH•HCl, aq. 1N HCl, EtOH, 55° C.; c) i) 9-BBN, THF, rt; ii) H₂O aq. 3N NaOH, 30% H₂O₂, 0° C. to rt; d) NaOMe, MeOH, 55° C.; e) DDQ, benzene, reflux.
Scheme 79
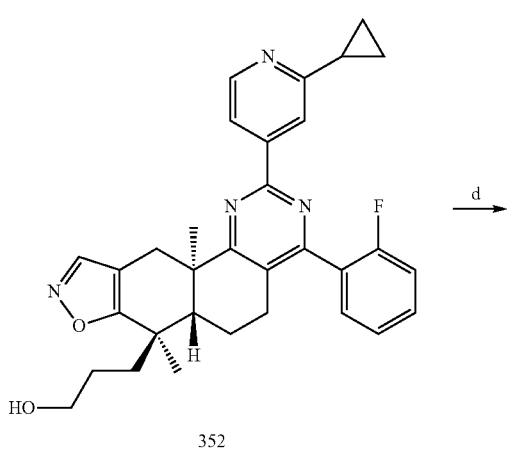
352
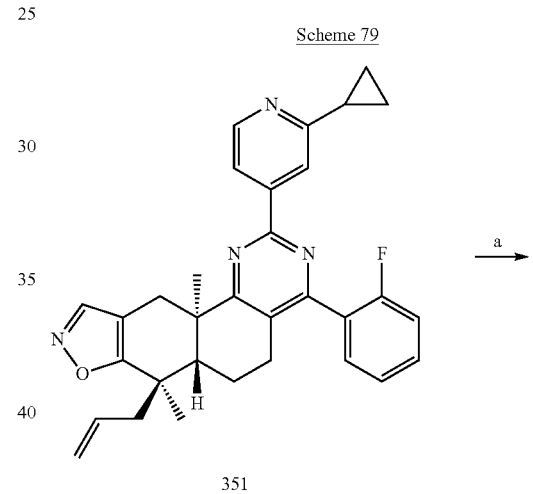
351
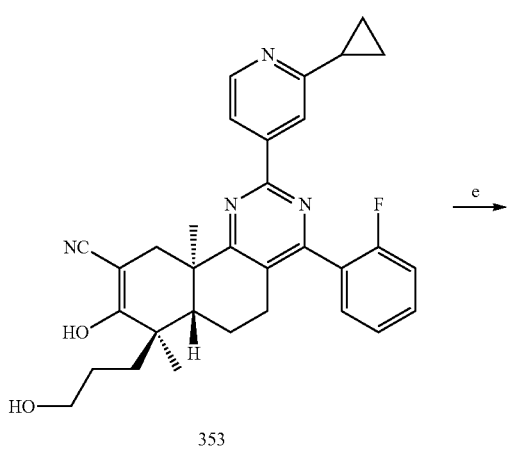
353
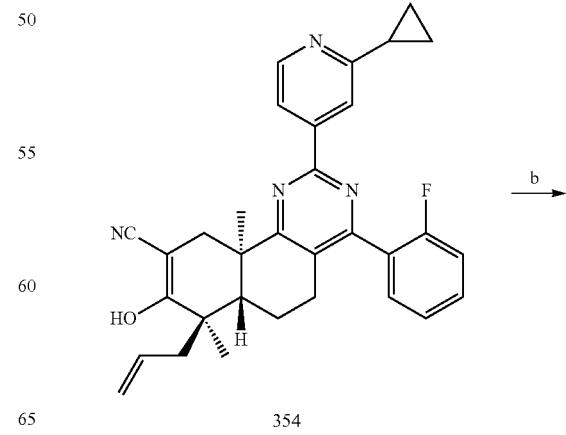
354

241
-continued
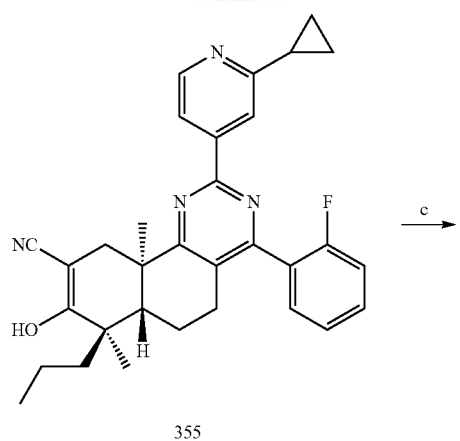
355
T137
Reagents and conditions: a) K₂CO₃, MeOH, rt; b) 10% Pd/C, H₂, EtOAc, rt; c) i) DBDMH, DMF, 0° C.; ii) pyridine, 55° C.
Scheme 80
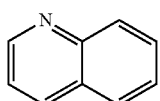
94
242
-continued
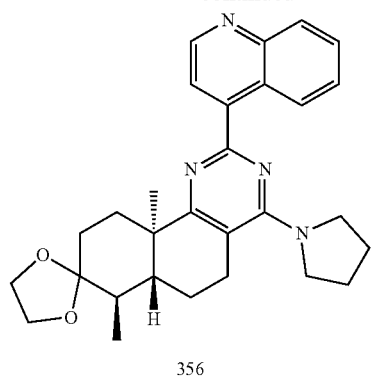
356
357
358
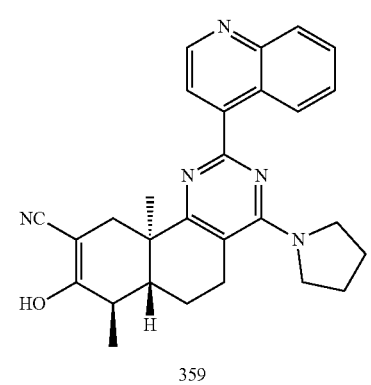
359

243
-continued
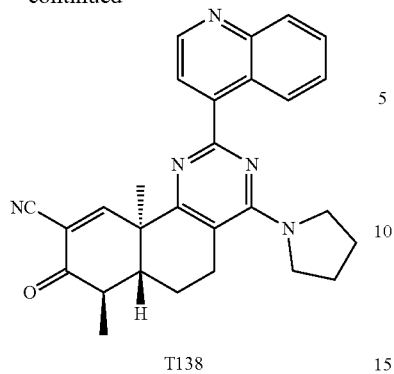
T138
Reagents and conditions: a) pyrrolidine, reflux; b) aq. 3N HCl, THF, MeOH, rt; c) i) HCO₂Et, NaOMe, MeOH, rt; ii) NH₂OH•HCl, aq. 6N HCl, EtOH, 55° C.; d) NaOMe, MeOH, 55° C.; e) i) DBDMH, DMF, 0° C.; ii) pyridine, 55° C.
Scheme 81
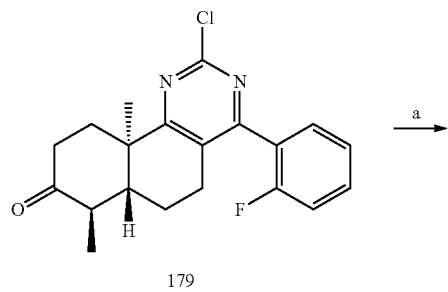
179
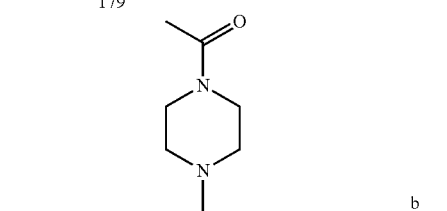
360
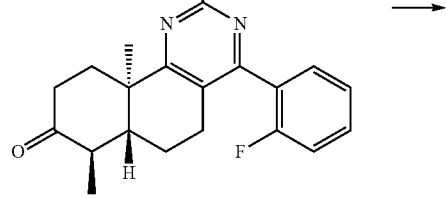
361
244
-continued
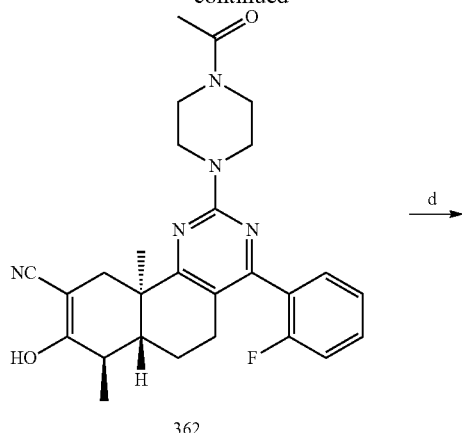
362
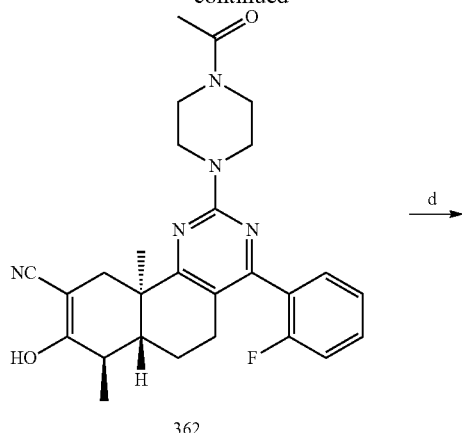
T139
Reagents and conditions: a) 1-acetylpiperazine, NMP, 100° C.; b) i) HCO₂Et, NaOMe, MeOH, THF, 0° C. to rt; ii) 6N HCl, NH₂OH•HCl, EtOH, 55° C.; c) NaOMe, MeOH, 55° C.; d) i) DBDMH, DMF, 0° C.; ii) pyridine, 55° C.
Scheme 82
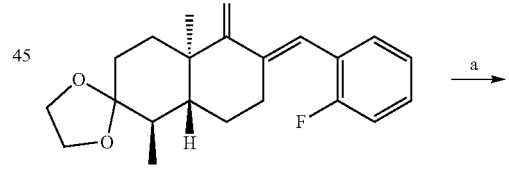
88
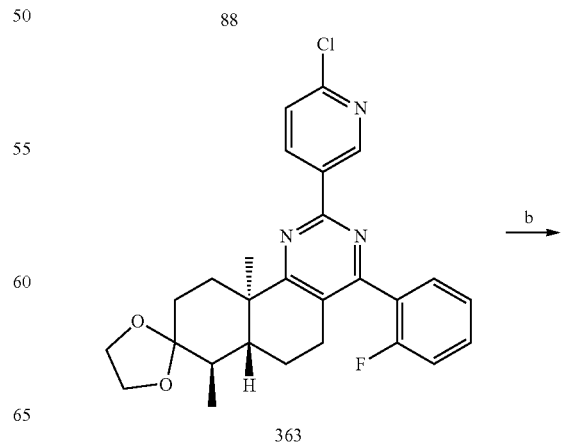
363

245
-continued
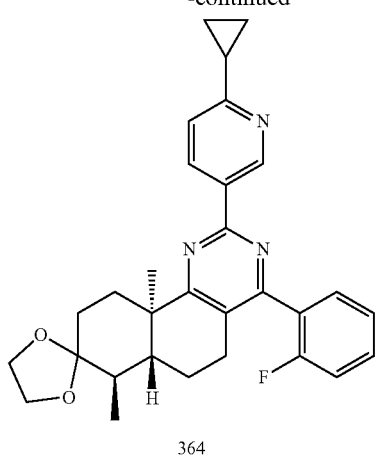
364
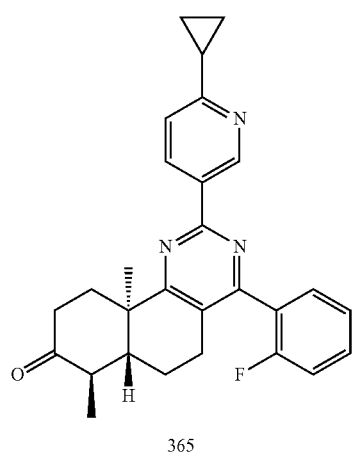
365
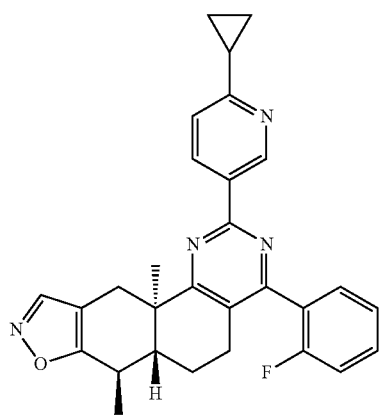
366
246
-continued
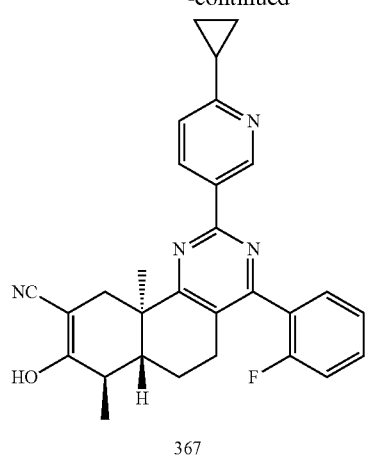
367
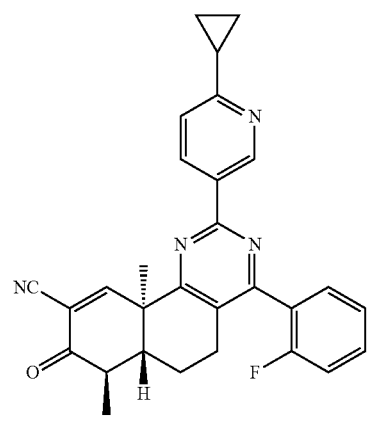
T140
Reagents and conditions: a) i) 6-chloropyridine-3-carboximidamide, hydrochloride, K₂CO₃, EtOH, microwave 120° C.; ii) DDQ, CH₂Cl₂, rt; b) cyclopropylboronic acid, K₃PO₄, Pd(OAc)₂, tricylcohexylphosphine, toluene, H₂O, microwave, 130° C.; c) aq. 3N HCl, MeOH, rt; d) i) HCO₂Et, NaOMe, MeOH, 0° C. to rt; ii) 6N HCl, NH₂OH·HCl, EtOH, 55° C.; e) NaOMe, MeOH, 55° C.; f) i) DBDMH, DMF, 0° C.; ii) pyridine, 55° C.
Scheme 83
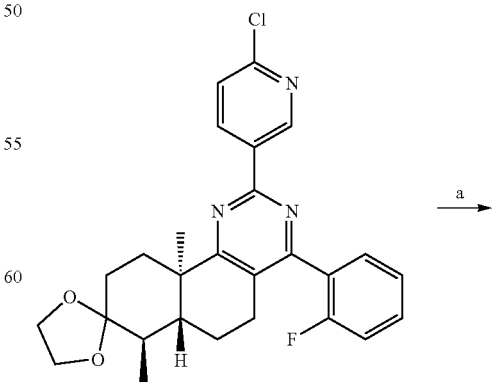
363

247
-continued
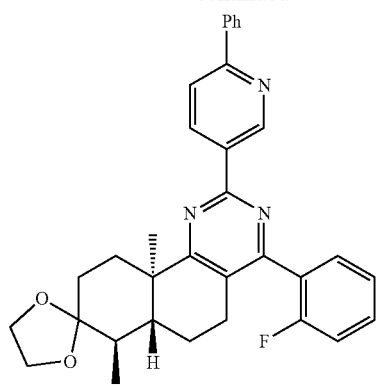
368
b →
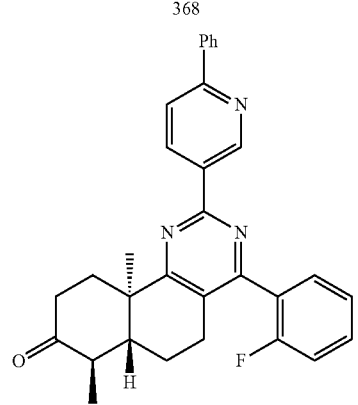
369
c →
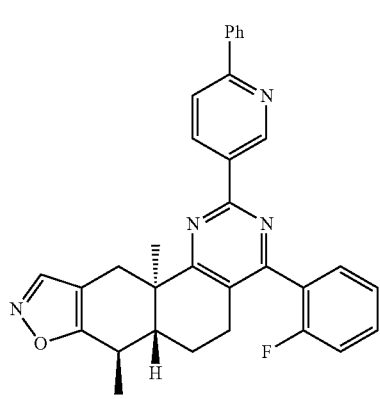
370
d →
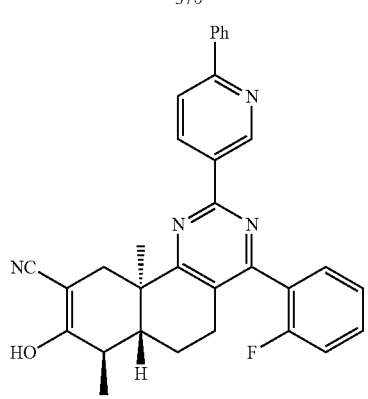
371
e →
248
-continued
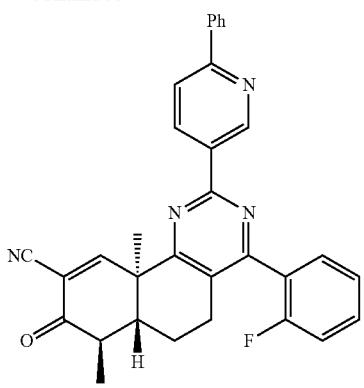
T141
Reagents and conditions: a) PhB(OH)$_2$, K$_2$CO$_3$, Pd(PPh$_3$)$_4$, toluene, EtOH, H$_2$O, microwave, 110° C.; b) aq. 3N HCl, MeOH, rt; c) i) HCO$_2$Et, NaOMe, MeOH, 0° C. to rt; ii) 6N HCl, NH$_2$OH·HCl, EtOH, 55° C.; d) NaOMe, MeOH, 55° C.; e) i) DBDMH, DMF, 0° C.; ii) pyridine, 55° C.
Scheme 84
363
a →
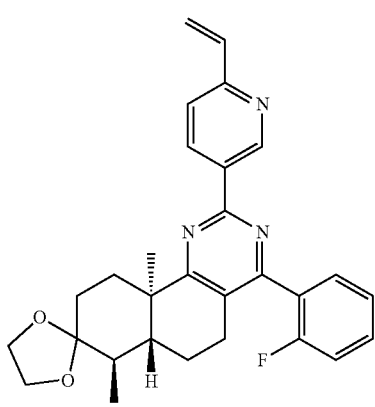
372
b →

249
-continued
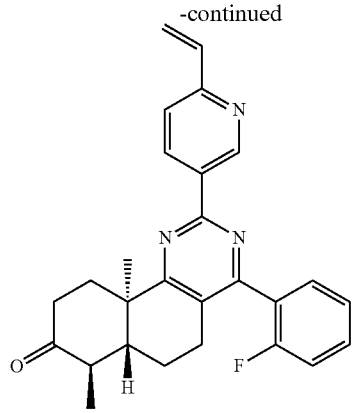
373
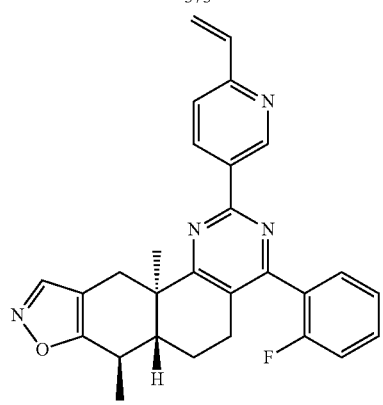
374
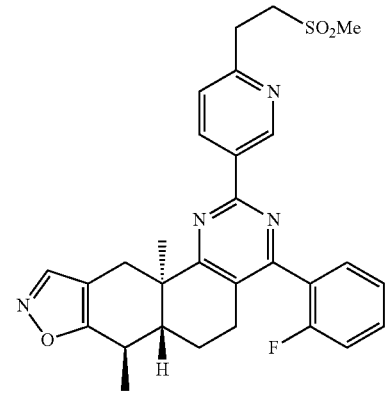
375
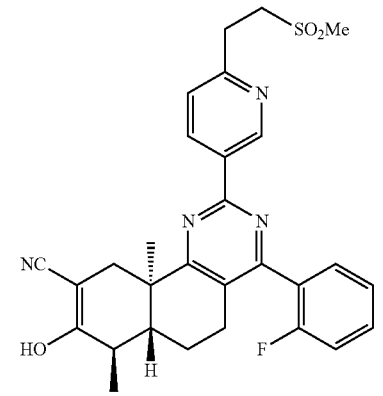
376
250
-continued
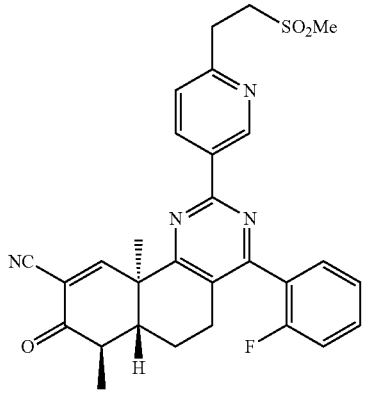
T142
Reagents and conditions: a) potassium vinyltrifluoroborate, $K_3PO_4$, $Pd_2(dba)_3$, tricyclohexylphosphine, 1,4-dioxane, $H_2O$, microwave, 140° C.; b) aq. 3N HCl, MeOH, THF, rt; c) i) $HCO_2Et$, NaOMe, MeOH, 0° C. to rt; ii) 6N HCl, $NH_2OH \cdot HCl$, EtOH, 55° C.; d) $MeSO_2Na$, AcOH, EtOH, 60° C.; e) $K_2CO_3$, MeOH, rt; f) i) DBDMH, DMF, 0° C.; ii) pyridine, 55° C.
Scheme 85
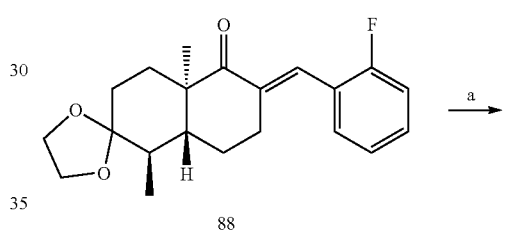
88
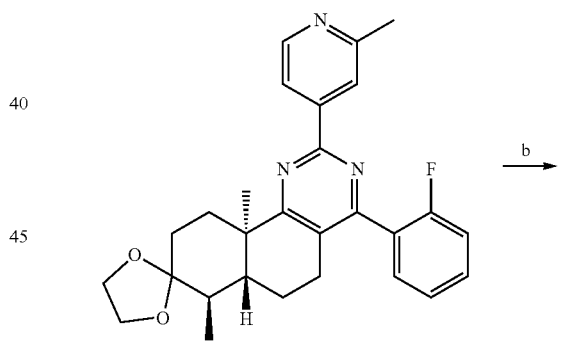
377
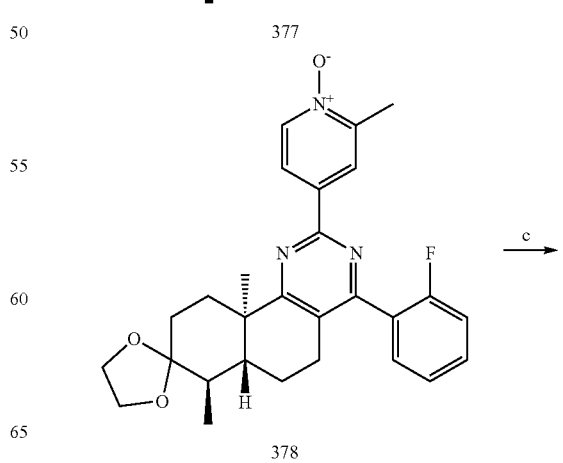
378

251
-continued
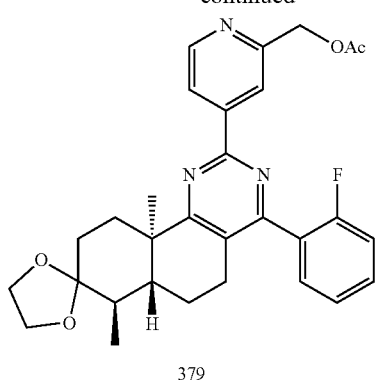
379
d →
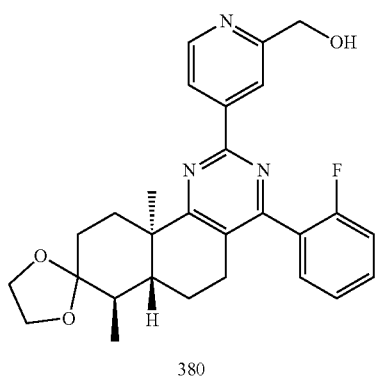
380
e →
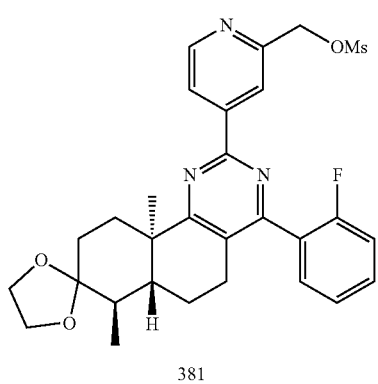
381
f →
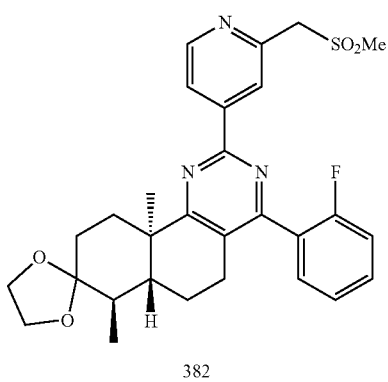
382
g →
252
-continued
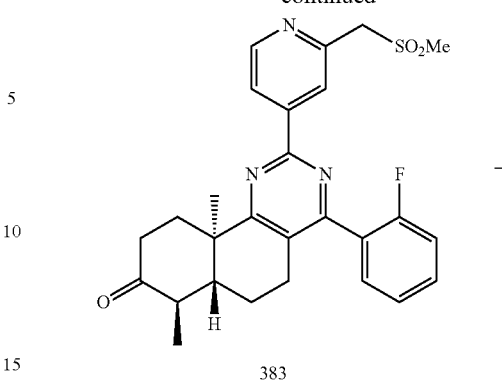
383
h →
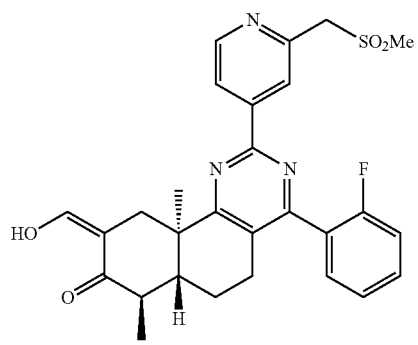
384
i →
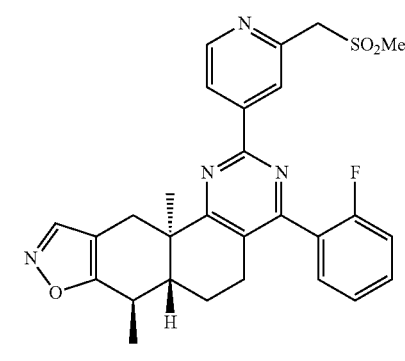
385
j →
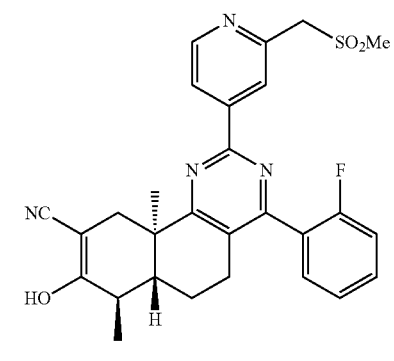
386
k →

253
-continued
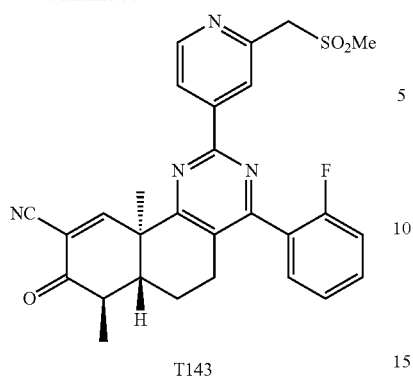
T143
Reagents and conditions: a) 2-methyl-4-pyridinecarboximidamide hydrochloride, K₂CO₃, EtOH, 80° C.; b) m-CPBA, CH₂Cl₂, rt; c) Ac₂O, 80° C.; d) K₂CO₃, MeOH, rt; e) MsCl, Et₃N, DMAP, CH₂Cl₂, 0° C.; f) MeSO₂Na, DMF, rt; g) aq. 3N HCl, MeOH, rt; h) HCO₂Et, NaOMe, MeOH, 0° C. to rt; i) NH₂OH·HCl, AcOH, EtOH, 60° C.; j) K₂CO₃, MeOH, rt; k) i) DBDMH, DMF, 0° C.; ii) pyridine, 60° C.
Scheme 86
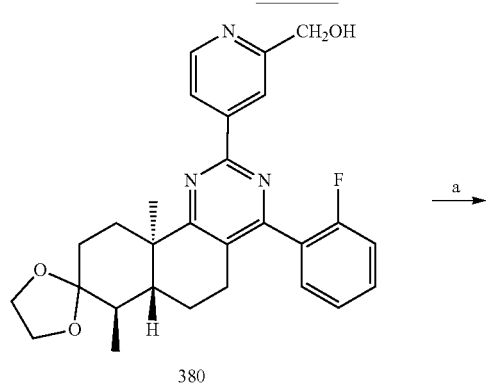
380
a →
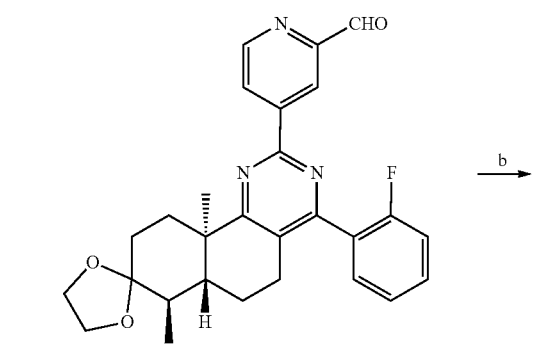
387
b →
254
-continued
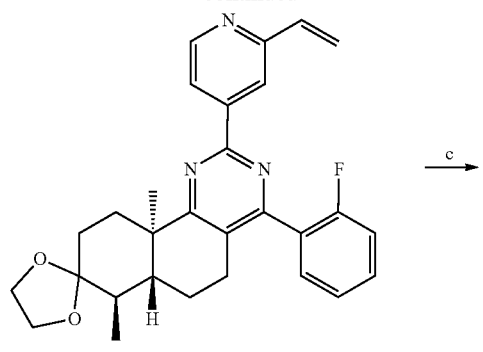
388
c →
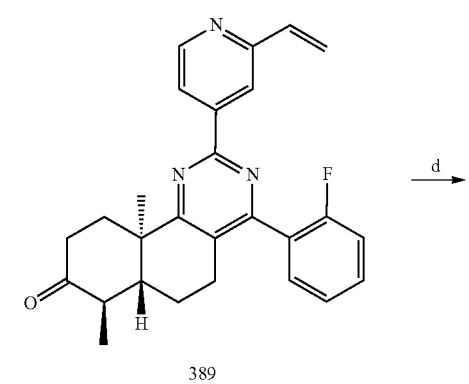
389
d →
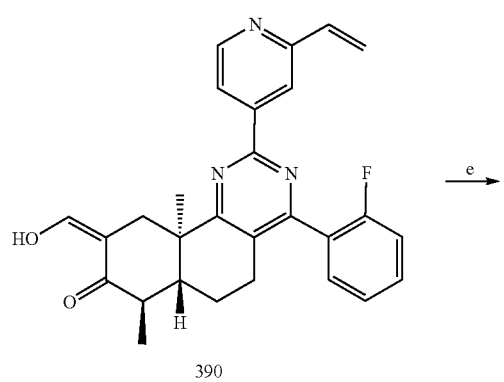
390
e →
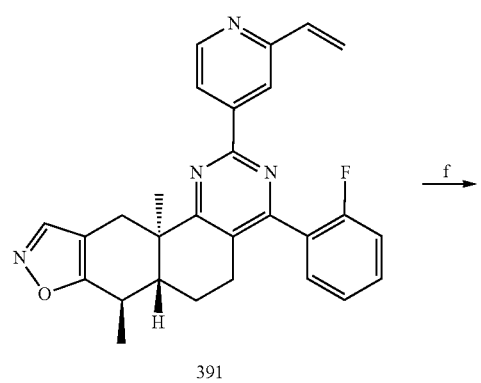
391
f →

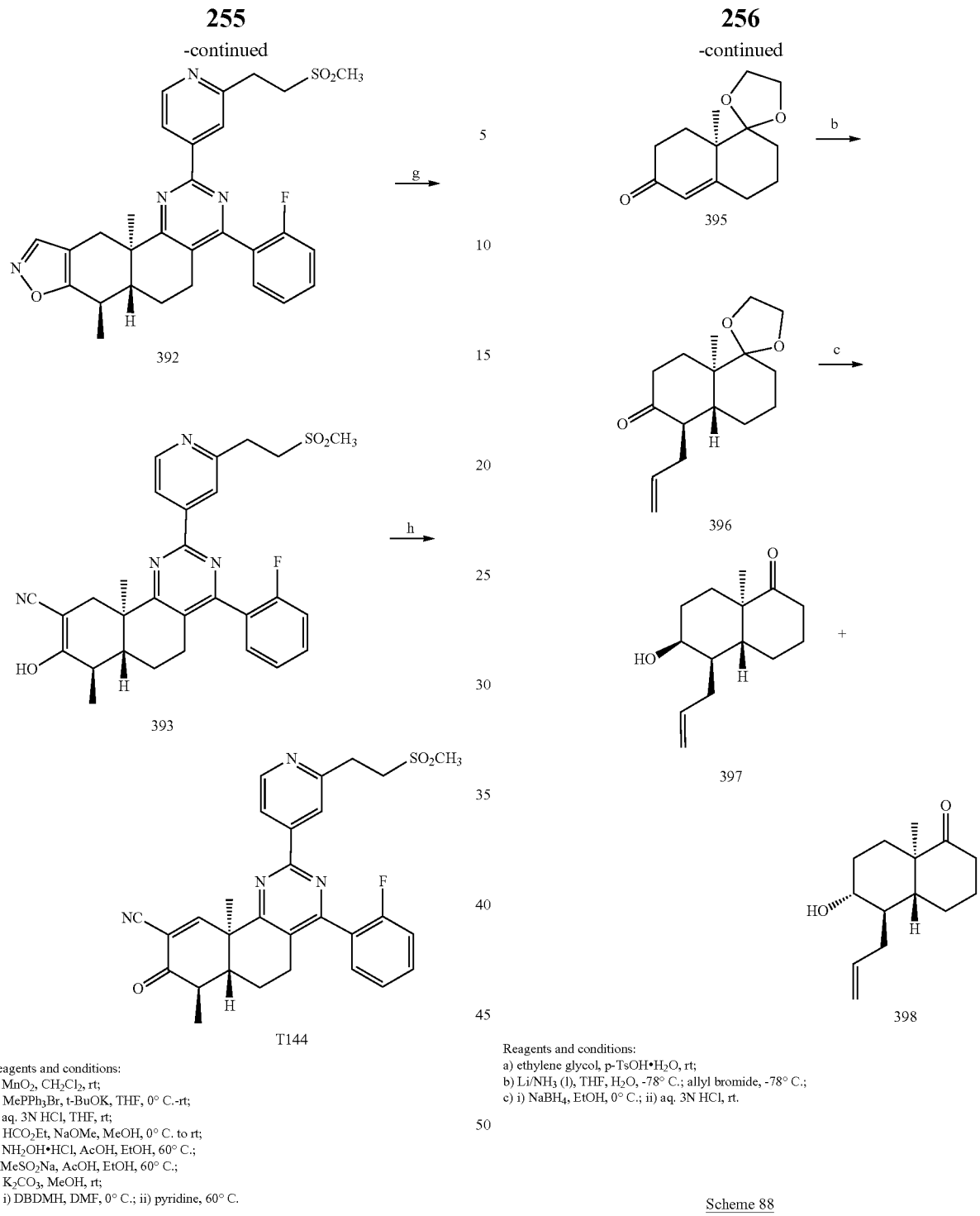
Reagents and conditions:
a) MnO₂, CH₂Cl₂, rt;
b) MePPh₃Br, t-BuOK, THF, 0° C.-rt;
c) aq. 3N HCl, THF, rt;
d) HCO₂Et, NaOMe, MeOH, 0° C. to rt;
e) NH₂OH•HCl, AcOH, EtOH, 60° C.;
f) MeSO₂Na, AcOH, EtOH, 60° C.;
g) K₂CO₃, MeOH, rt;
h) i) DBDMH, DMF, 0° C.; ii) pyridine, 60° C.
Reagents and conditions:
a) ethylene glycol, p-TsOH•H₂O, rt;
b) Li/NH₃ (l), THF, H₂O, -78° C.; allyl bromide, -78° C.;
c) i) NaBH₄, EtOH, 0° C.; ii) aq. 3N HCl, rt.
Scheme 88
Scheme 87
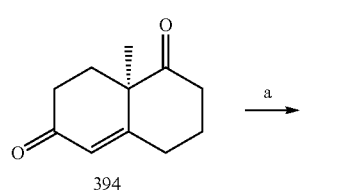
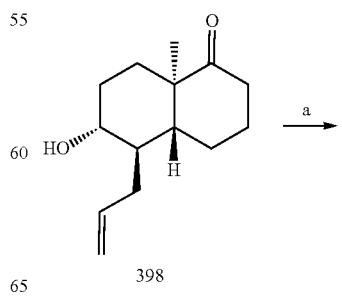

257
-continued
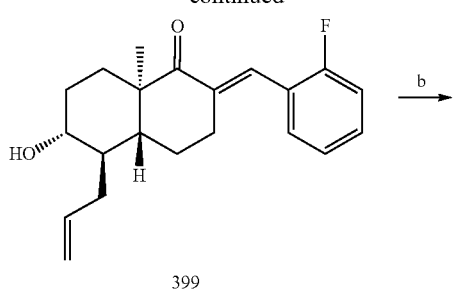
399
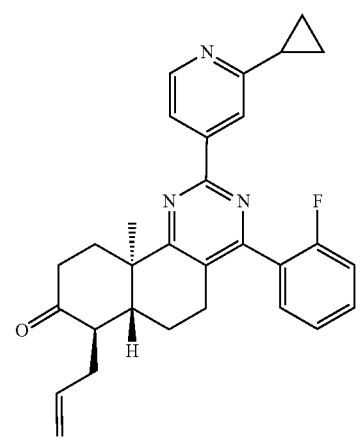
400
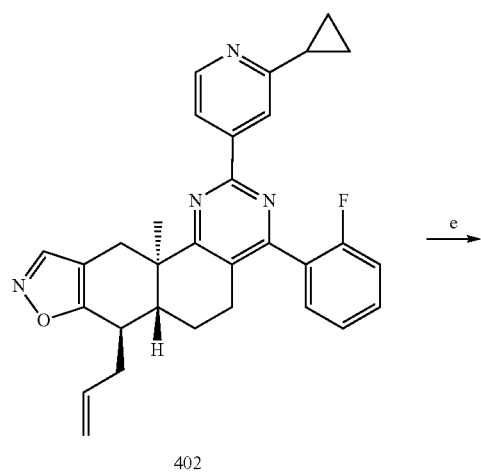
401
402
258
-continued
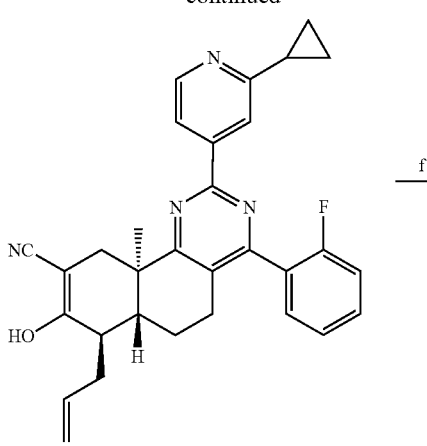
403
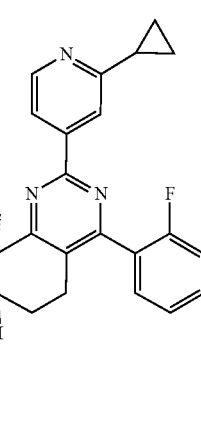
T145
Reagents and conditions:
a) 2-fluorobenzaldehyde, KF/Al₂O₃, EtOH, rt;
b) i) 2-cyclopropyl-4-carboximidamide pyridine hydrochloride, K₂CO₃, EtOH, reflux; ii) MnO₂, CH₂Cl₂, rt;
c) Dess-Martin periodinane, CH₂Cl₂, rt;
d) i) HCO₂Et, NaOMe, MeOH, 0° C.-rt; ii) NH₂OH • HCl, EtOH, H₂O, 55° C.;
e) NaOMe, MeOH, 55° C.;
f) DDQ, toluene, 85° C.
Scheme 89
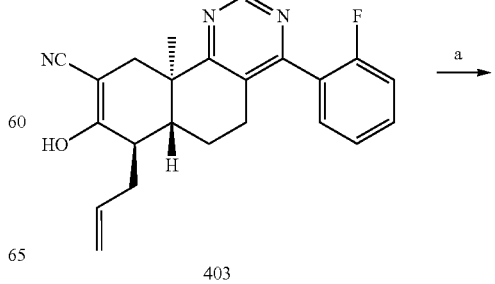
403

259
-continued
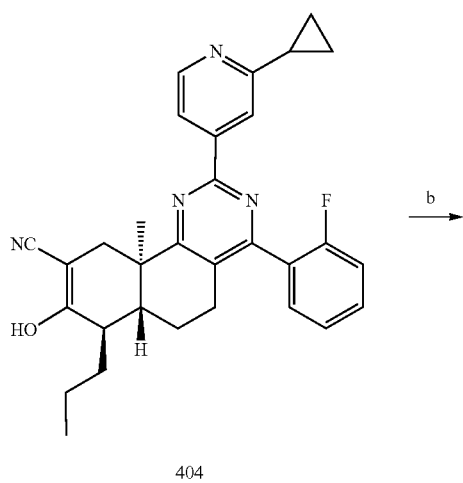
404
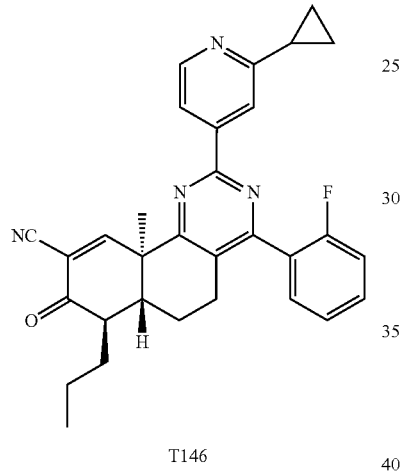
T146
Reagents and conditions:
a) H₂, 10% Pd/C, EtOAc, rt;
b) i) DBDMH, DMF, 0° C.; ii) pyridine, 55° C.
Scheme 90
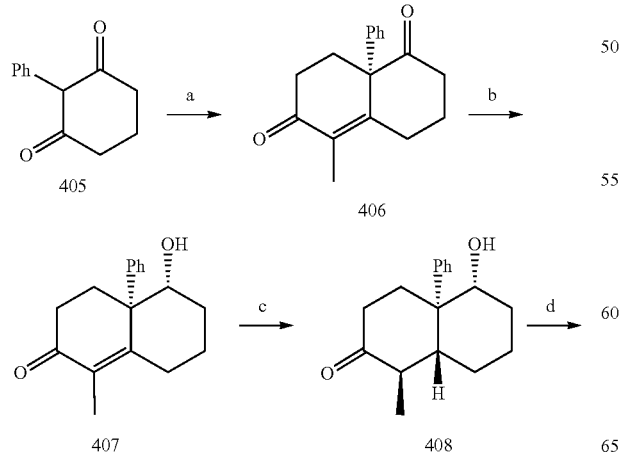
260
-continued
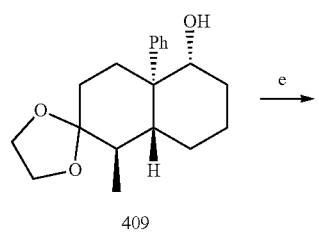
409
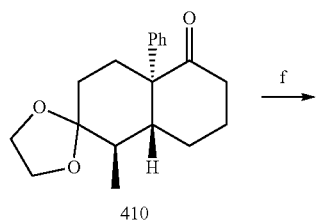
410
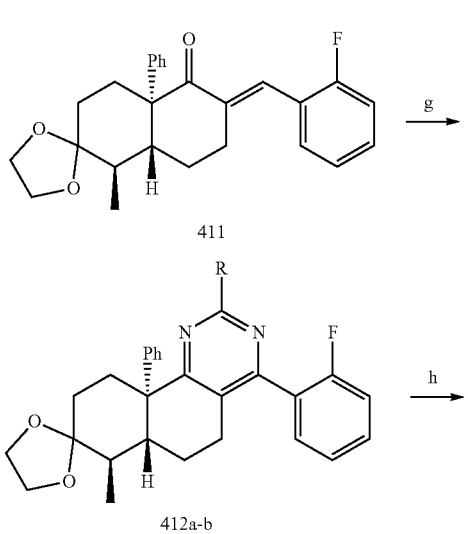
411
412a-b
413a-b
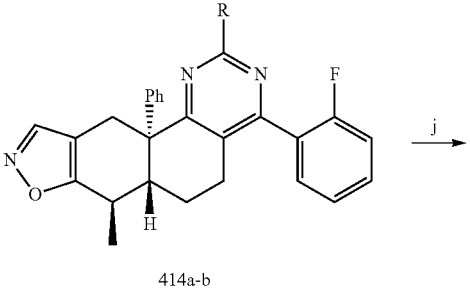
414a-b 261
-continued

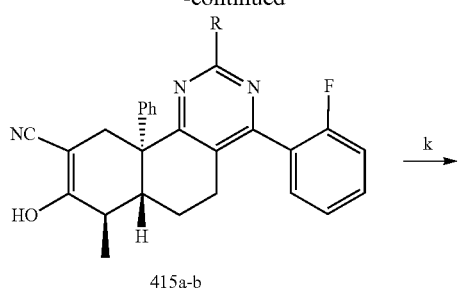
415a-b

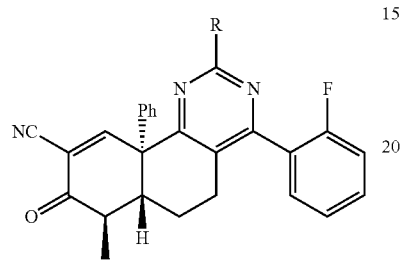

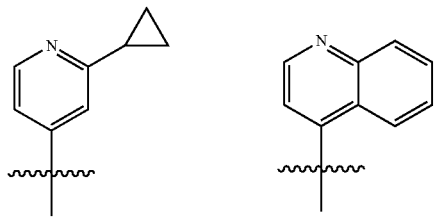

R = a T147  R = b T148

Reagents and conditions:
a) i) Ethyl vinyl ketone, Et₃N, MeCN, 75° C.; ii) D-phenylalanine, PPTS, DMSO, 45° C.;
b) i) NaBH₄, EtOH, 0° C.; ii) crystallization;
c) i) H₂, 10% Pd-C, pyridine, THF, rt; ii) aq. 3N HCl, EtOH, rt;
d) ethylene glycol, p-TsOH•H₂O, tolunene, reflux, —H₂O;
e) Na₂WO₄•2H₂O, Na₂HPO₄•2 H₂O, aq. 30% H₂O₂, DMA, 90° C.;
f) 2-fluorobenzaldehyde, KF/Al₂O₃, EtOH, THF, rt;
g) i) amidine hydrochloride, K₂CO₃, EtOH, reflux; ii) DDW, CH₂Cl₂, rt;
h) aq. 3N, HCl, MeOH, THF, rt;
i) 1) HCO₂Et, NaOMe, MeOH, 0° C.-rt; 2) aq. 6N HCl, NH₂OH•HCl, EtOH, H₂O, 55° C.;
j) NaOMe, MeOH, 55° C.;
k) i) DBDMH, DMF, 0° C.; ii) pyridine, 55° C.

Scheme 91

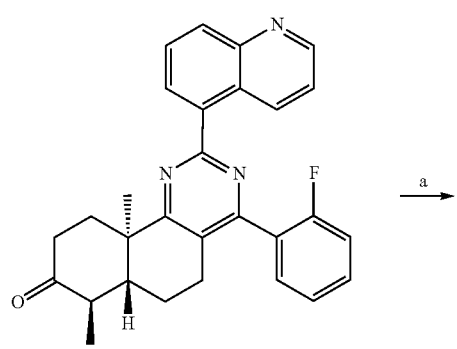
188c

262
-continued

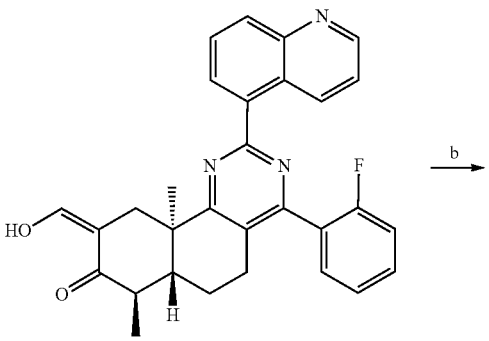
416

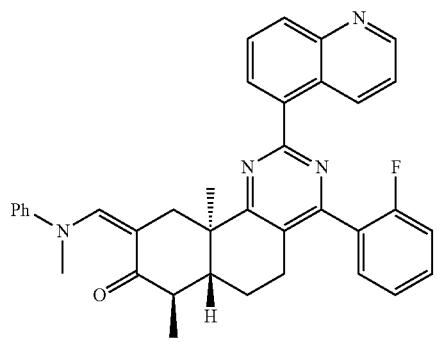
417

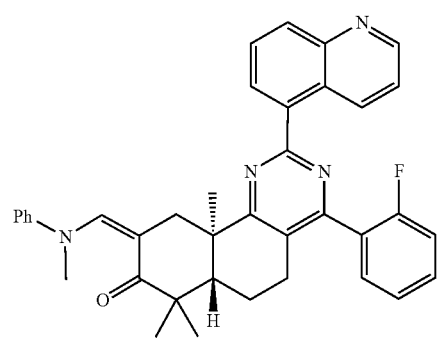
418

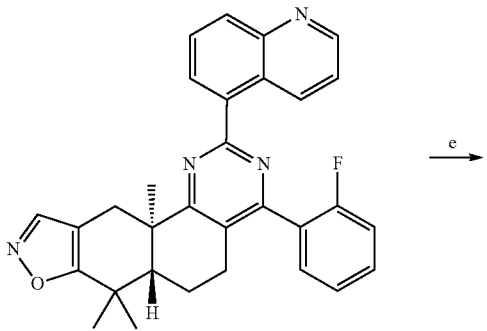
419

263
-continued
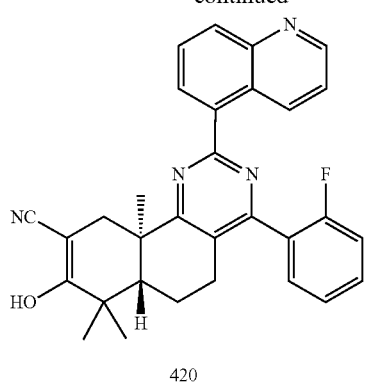
420
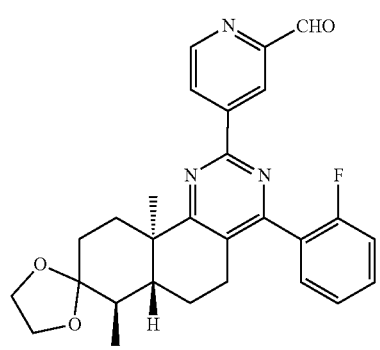
T149
Reagents and conditions:
a) HCO₂Et, NaOMe, MeOH, rt;
b) N-methylaniline, p-TsOH•H₂O, MgSO₄, CH₂Cl₂, rt;
c) t-BuOK, MeI, THF, 0° C.;
d) NH₂OH•HCl, aq. 1N HCl, EtOH, 55° C.;
e) NaOMe, MeOH, 55° C.;
f) i) DBDMH, DMF, 0° C.; ii) pyridine, 55° C.
Scheme 92
387
264
-continued
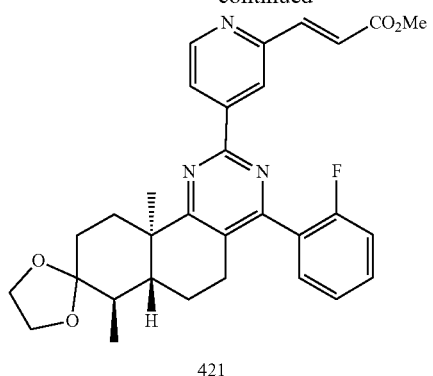
421
422
423
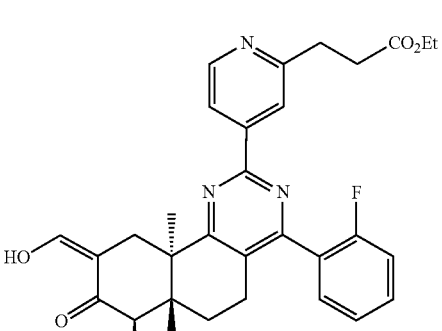
424

-continued
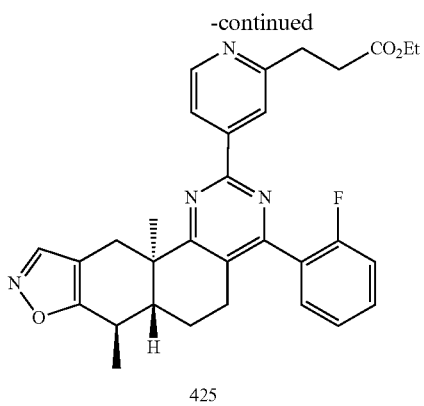
425
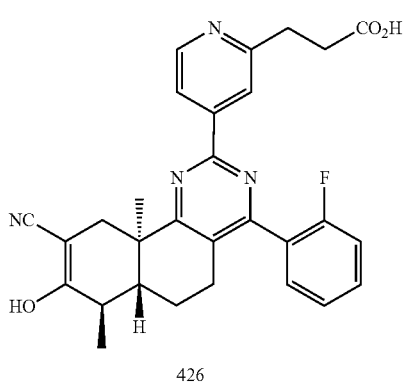
426
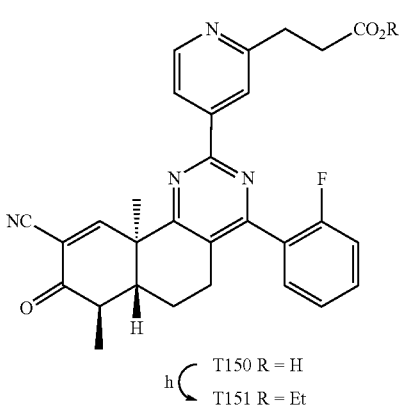
T150 R = H
T151 R = Et
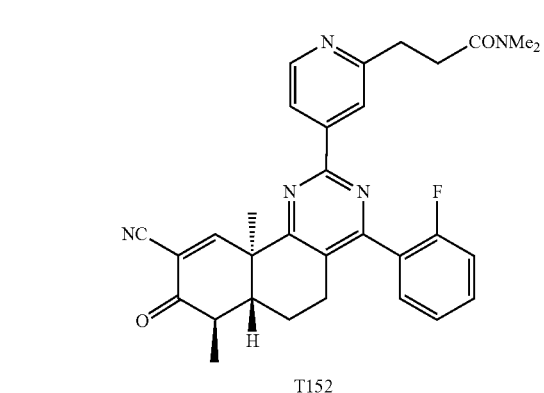
T152
-continued
Reagents and conditions:
a) methyl (triphenylphosphoranylidene)acetate, benzene, 80° C.;
b) H$_2$, 10% Pd/C, EtOAc, rt;
c) aq. 3N HCl, MeOH, rt;
d) HCO$_2$Et, NaOMe, MeOH, rt;
e) NH$_2$OH•HCl, AcOH, EtOH, 60° C.;
f) K$_2$CO$_3$, MeOH, rt;
g) i) DBDMH, DMF, 0° C.; ii) pyridine, 60° C.;
h) aq. 1N HCl, EtOH, 50° C.;
i) Me$_2$NH•HCl, HATU, DIPEA, CH$_2$Cl$_2$, 0° C. to rt.
Scheme 93
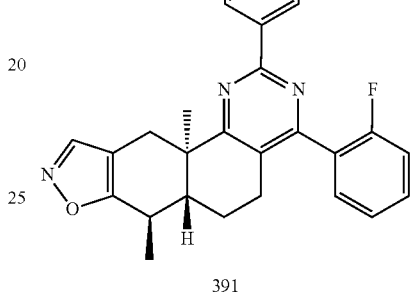
391
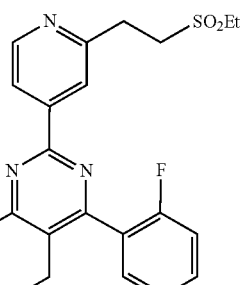
427
428

267
-continued
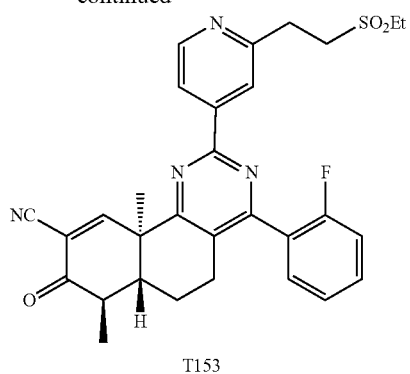
T153
Reagents and conditions:
a) EtSO₂Na, AcOH, EtOH, 60° C.;
b) K₂CO₃, MeOH, rt;
c) i) DBDMH, DMF, 0° C.; ii) pyridine, 60° C.
Scheme 94
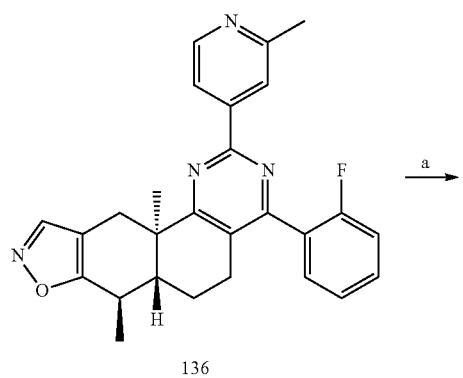
136
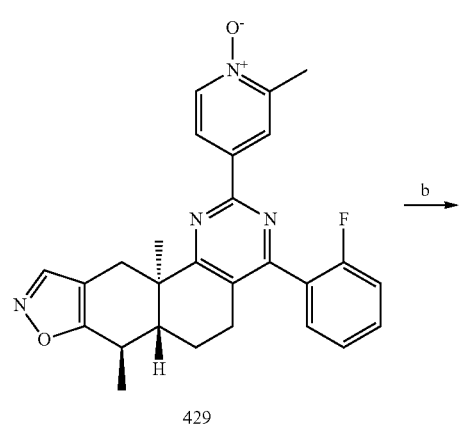
429
268
-continued
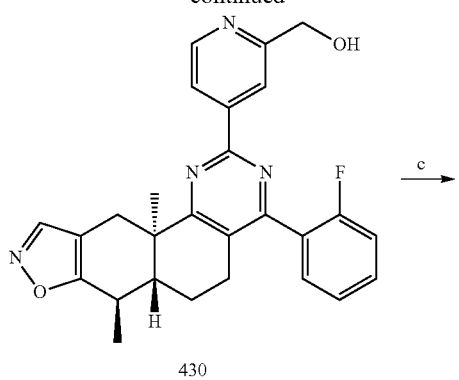
430
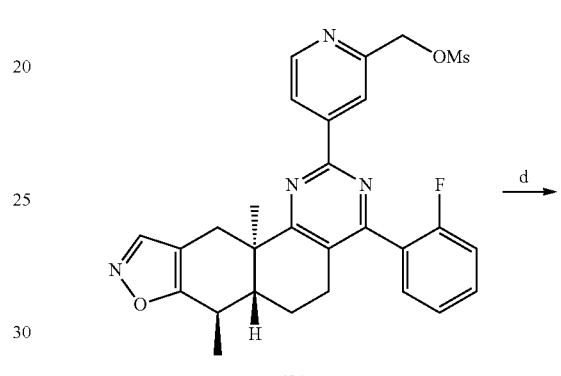
431
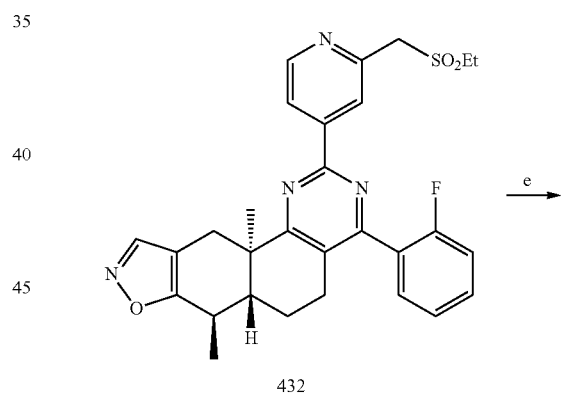
432
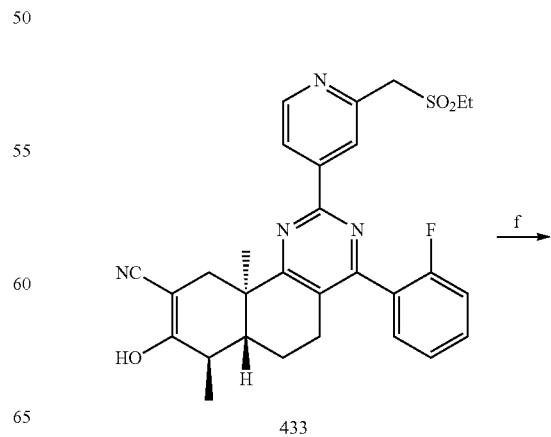
433

269
-continued
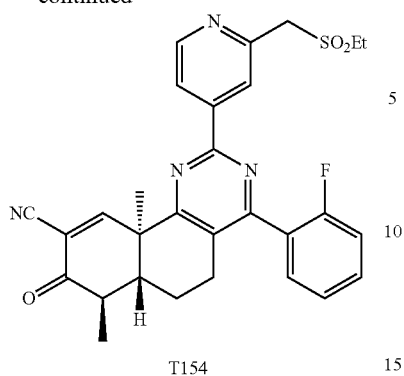
T154
Reagents and conditions: a) m-CPBA, CH₂Cl₂, rt; b) i) TFAA, CH₂Cl₂, rt, ii) sat. aq. NaHCO₃, EtOAc, rt; c) MsCl, Et₃N, DMAP, CH₂Cl₂, 0° C.; d) EtSO₂Na, DMF, rt; e) K₂CO₃, MeOH, rt; f) i) DBDMH, DMF, 0° C.; ii) pyridine, 60° C.
Scheme 95
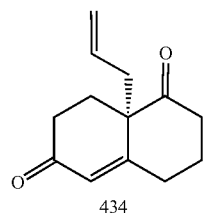
434
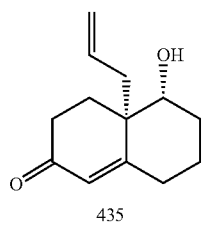
435
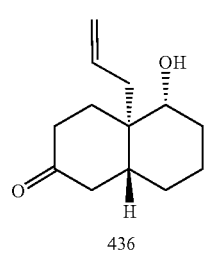
436
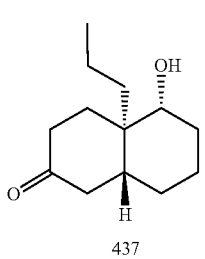
437
270
-continued
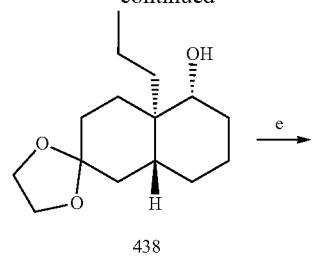
438
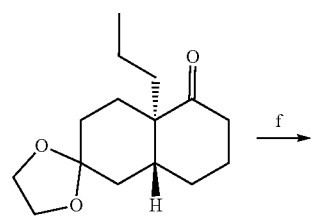
439
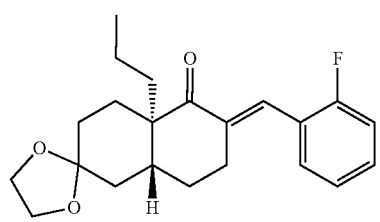
440
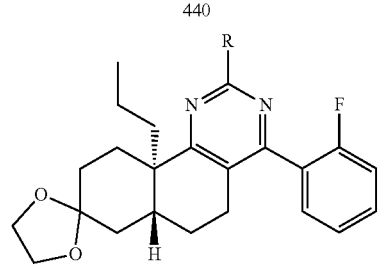
441a-441b
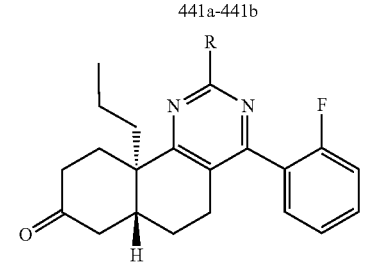
442a-442b
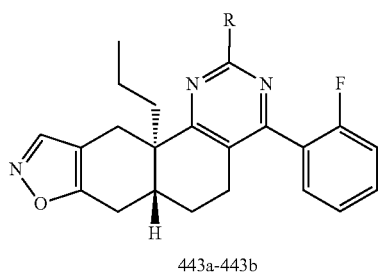
443a-443b

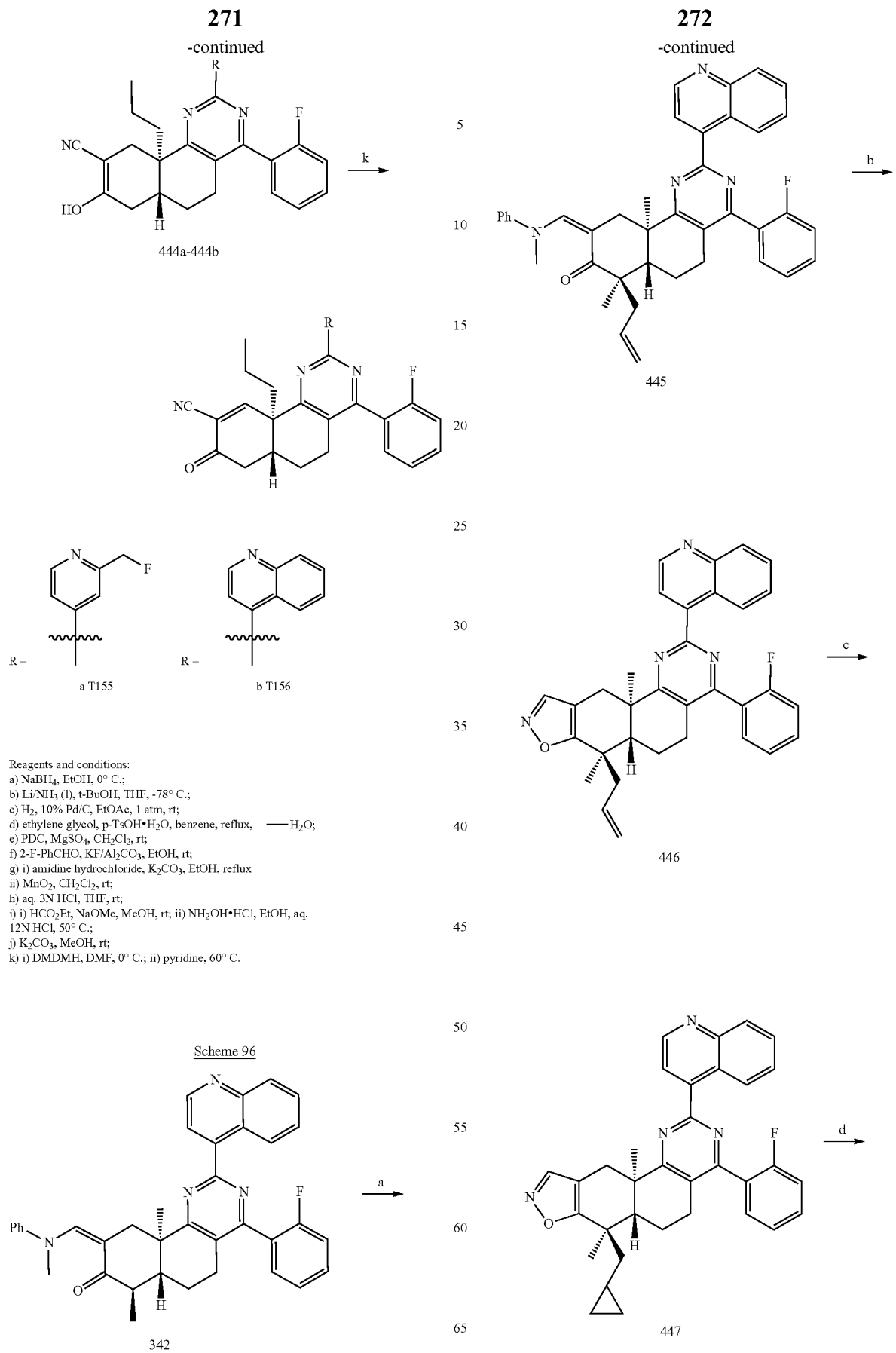
Reagents and conditions:
a) NaBH₄, EtOH, 0° C.;
b) Li/NH₃ (l), t-BuOH, THF, -78° C.;
c) H₂, 10% Pd/C, EtOAc, 1 atm, rt;
d) ethylene glycol, p-TsOH•H₂O, benzene, reflux, —H₂O;
e) PDC, MgSO₄, CH₂Cl₂, rt;
f) 2-F-PhCHO, KF/Al₂CO₃, EtOH, rt;
g) i) amidine hydrochloride, K₂CO₃, EtOH, reflux
ii) MnO₂, CH₂Cl₂, rt;
h) aq. 3N HCl, THF, rt;
i) i) HCO₂Et, NaOMe, MeOH, rt; ii) NH₂OH•HCl, EtOH, aq. 12N HCl, 50° C.;
j) K₂CO₃, MeOH, rt;
k) i) DMDMH, DMF, 0° C.; ii) pyridine, 60° C.
Scheme 96

273
-continued
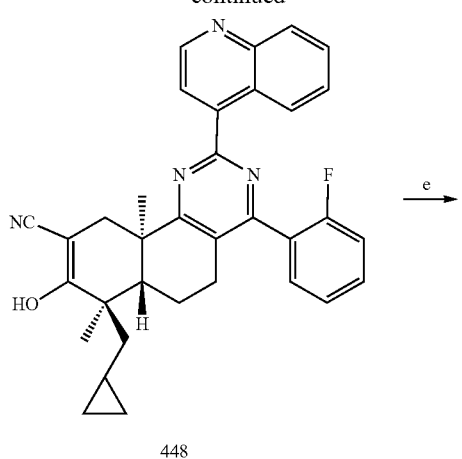
448
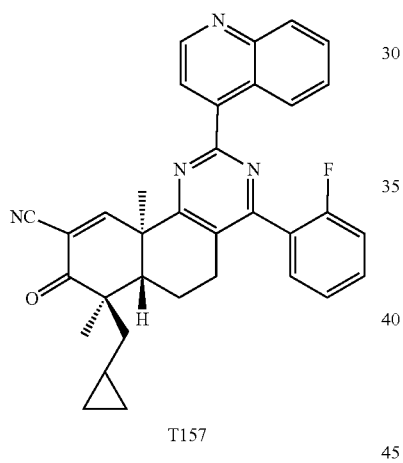
T157
Reagents and conditions:
a) t-BuOK, allyl bromide, THF, 0° C.;
b) NH$_2$OH•HCl, aq. 1N HCl, EtOH, 55° C.;
c) i) i-Bu$_3$Al, CH$_2$I$_2$, CH$_2$Cl$_2$, rt; ii) NMO, OsO$_4$, acetone, H$_2$O, 0° C. to rt;
d) NaOMe, MeOH, 55° C.;
e) i) DBDMH, DMF, 0° C.; ii) pyridine, 55° C.
Scheme 97
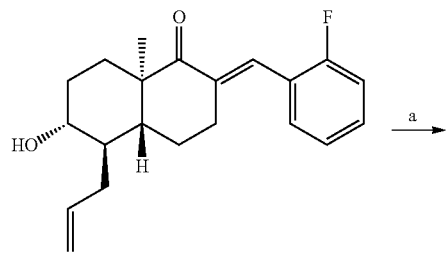
399
274
-continued
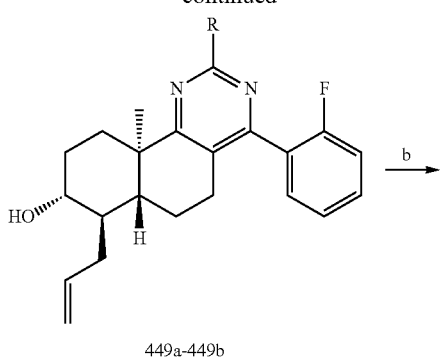
449a-449b
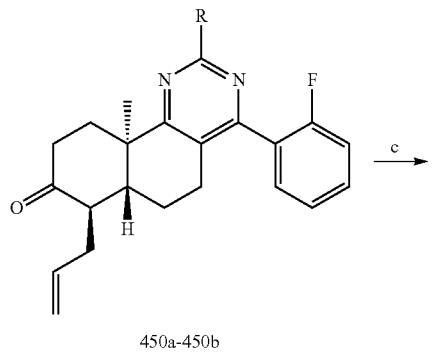
450a-450b
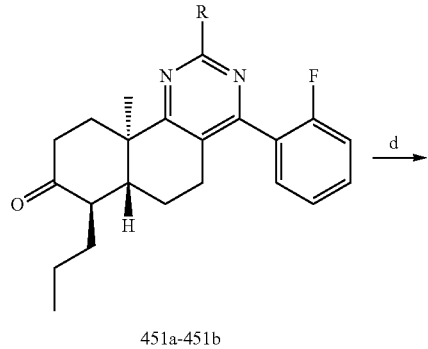
451a-451b 275
-continued
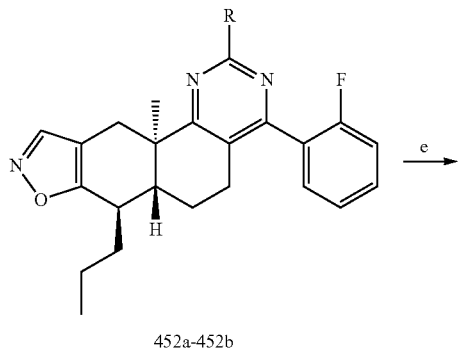
452a-452b
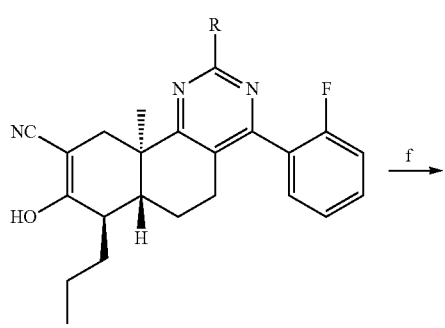
453a-453b
276
-continued
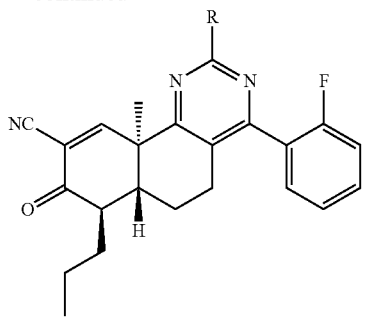
R = a T158 (4-quinolinyl)  R = b T159 (5-quinolinyl)
Reagents and conditions: a) i) amidine hydrochloride, K₂CO₃, EtOH, reflux; ii) MnO₂, CH₂Cl₂, rt; b) Dess-Martin periodinane, CH₂Cl₂, rt; c) H₂, 10% Pd/C, EtOAc, rt; d) i) HCO₂Et, NaOMe, MeOH, 0° C.-rt; ii) aq. 6N HCl, NH₂OH•HCl, EtOH, 55° C.; e) NaOMe, MeOH, 55° C.; f) i) DBDMH, DMF, 0° C.; ii) pyridine, 55° C.
Scheme 98
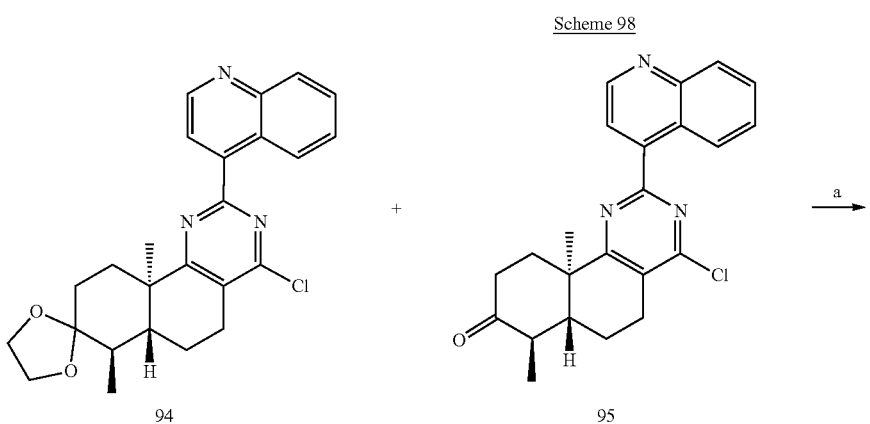
94   95

-continued
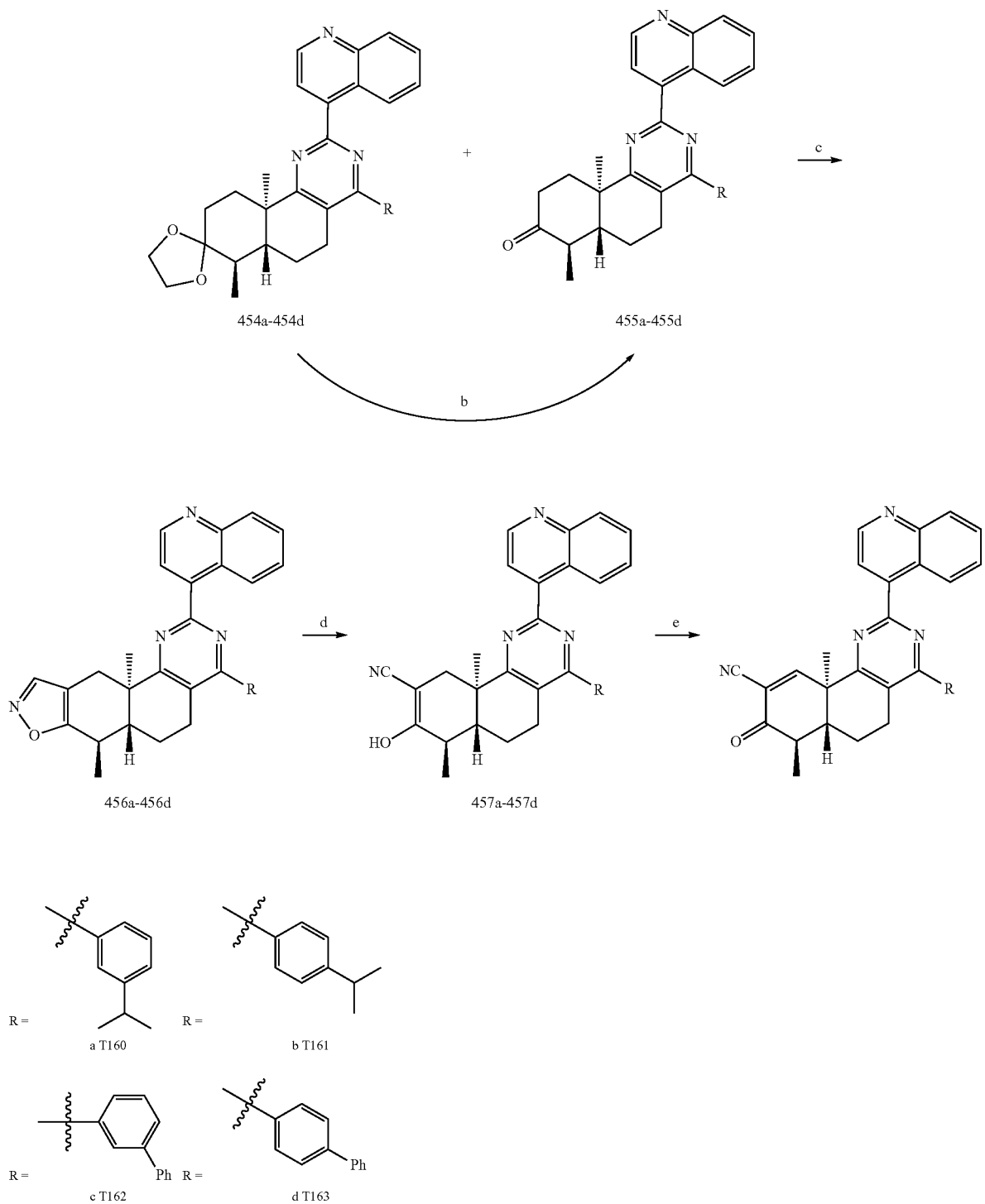
Reagents and conditions:
a) arylboronic acid, Pd(dppf)Cl$_2$, K$_2$CO$_3$, 1,4-dioxane, 90° C.;
b) aq. 3N HCl, THF, rt;
c) i) HCO$_2$Et, NaOMe, rt; ii) aq. 12N HCl, NH$_2$OH•HCl, EtOH, 55° C.;
d) K$_2$CO$_3$, MeOH, rt;
e) i) DBDMH, DMF, 0° C., 2 h; ii) pyridine, 60° C.

Scheme 99
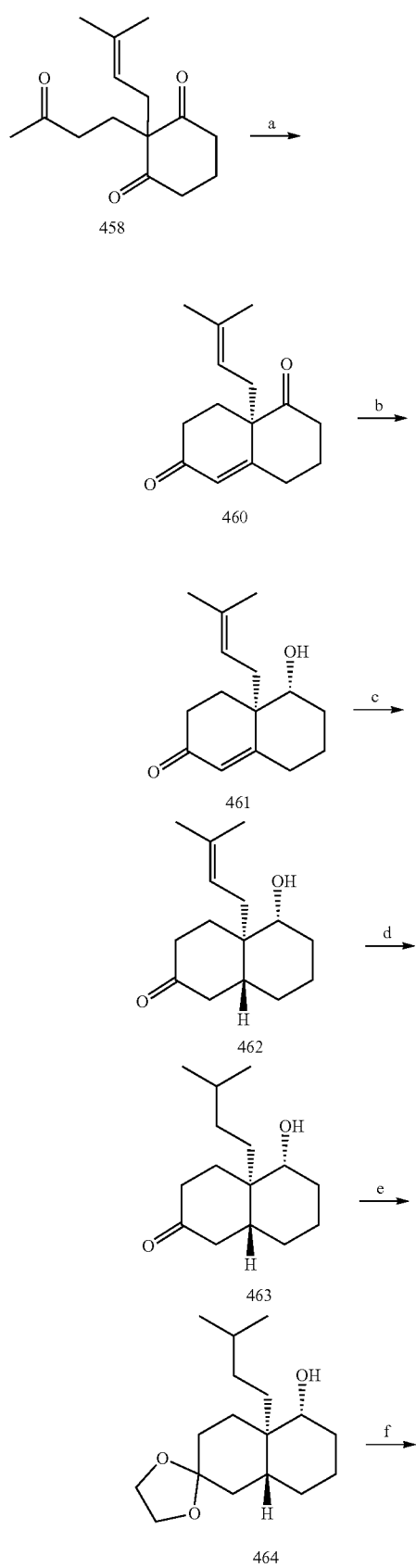
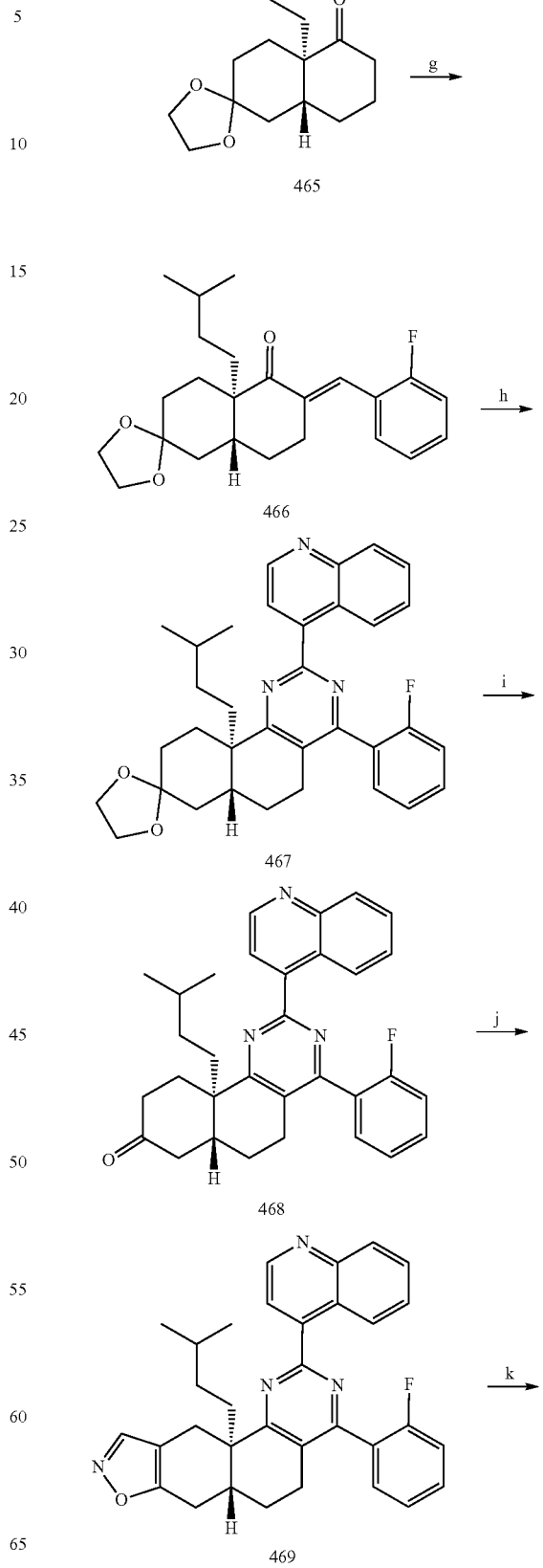

281
-continued

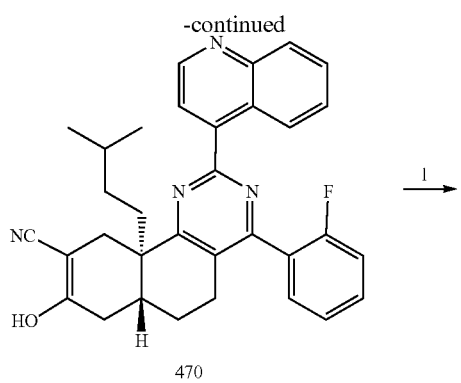
470

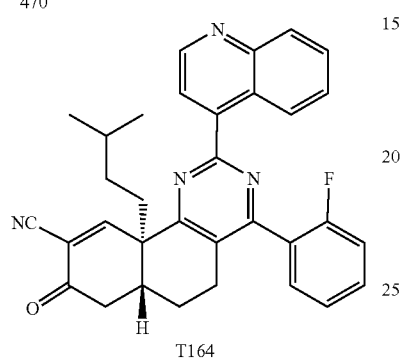
T164

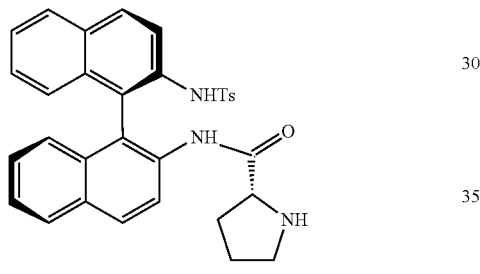
459

Reagents and conditions:
a) 459, benzoic acid, rt;
b) NaBH₄, EtOH, 0° C.;
c) Li/NH₃ (l), t-BuOH, THF, −78° C.;
d) H₂, 10% Pd/C, EtOAc, 1 atm, rt;
e) ethylene glycol, p-TsOH·H₂O, benzene, reflux, —H₂O;
f) PDC, MgSO₄, CH₂Cl₂, rt;
g) 2-F-PhCHO, KF/Al₂O₃, i-PrOH, rt;
h) i) 4-quinolinecarboximidamide hydrochloride, K₂CO₃, EtOH, reflux;
ii) MnO₂, CH₂Cl₂, rt;
i) aq. 3N HCl, THF, rt to 50° C.;
j) i) HCO₂Et, NaOMe, MeOH, rt;
ii) NH₂OH·HCl, EtOH, aq. 6N HCl, 55° C.;
k) K₂CO₃, MeOH, rt;
l) i) DBDMH, DMF, 0° C.; ii) pyridine, 60° C.

Scheme 100

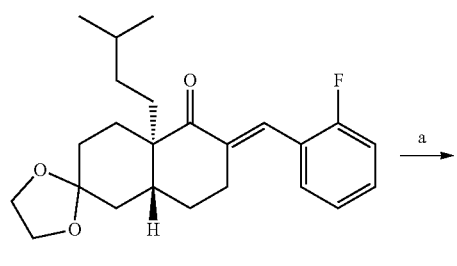
466

282
-continued

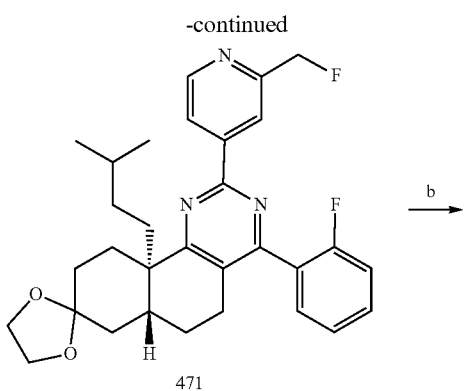
471

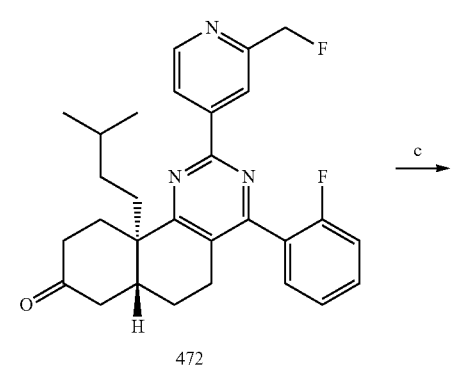
472

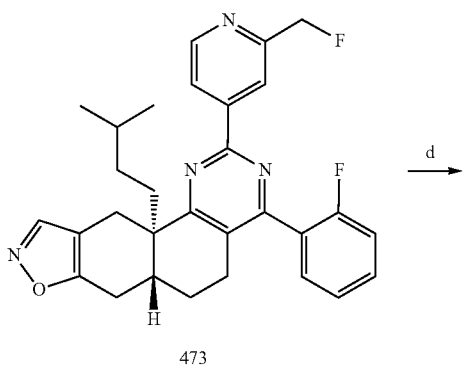
473

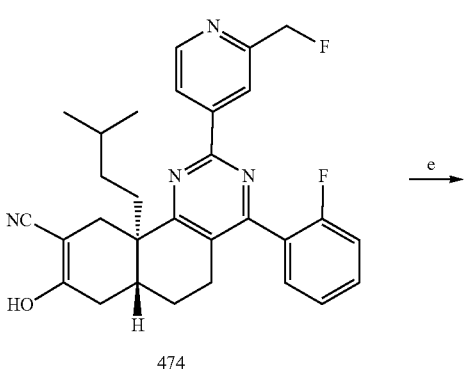
474

283
-continued
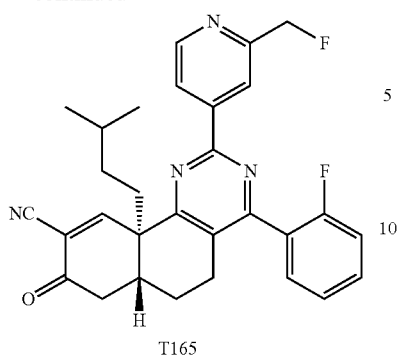
T165
Reagents and conditions:
a) i) amidine HCl, K₂CO₃, EtOH, reflux; ii) MnO₂, CH₂Cl₂, rt;
b) aq. HCl, THF, rt to 50° C.;
c) i) HCO₂Et, NaOMe, MeOH, 0° C. to rt; ii) aq. HCl, H₂NOH•HCl, EtOH, 55° C.;
d) K₂CO₃, MeOH, rt;
e) i) DBDMH, DMF, 0° C.; ii) pyridine, 60° C.
Scheme 101
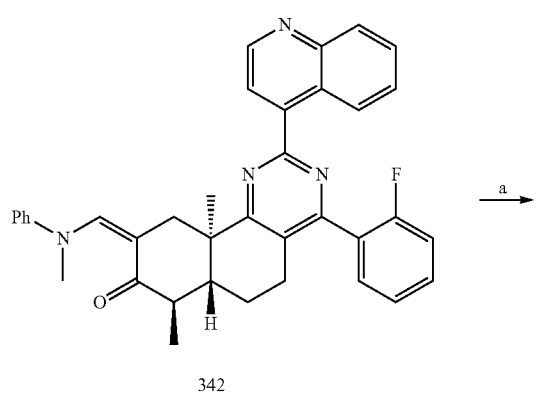
342
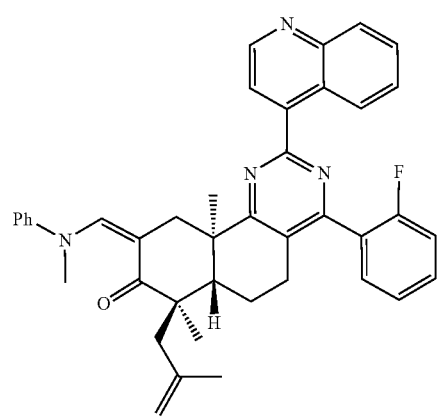
475
284
-continued
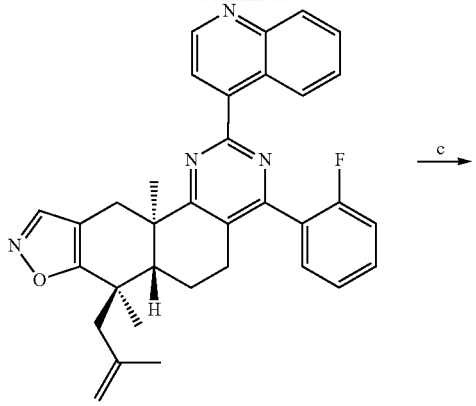
476
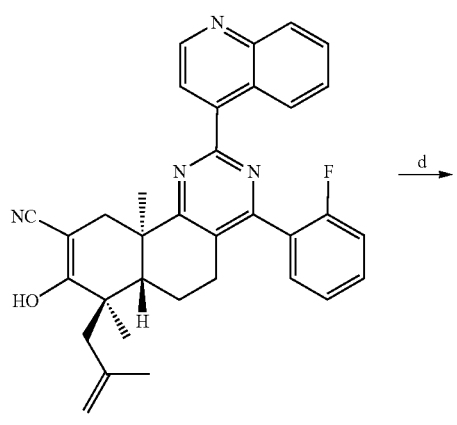
477
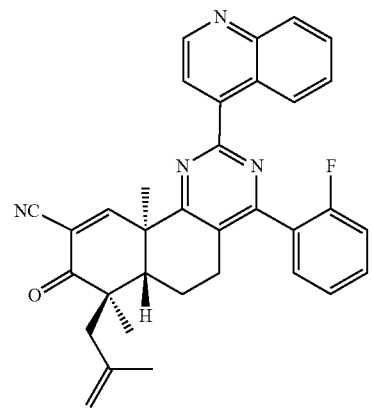
T166
Reagents and conditions:
a) t-BuOK, 3-chloro-2-methylpropene, THF, 0° C. to rt;
b) H₂NOH•HCl, aq. HCl, EtOH, 60° C. to rt;
c) K₂CO₃, MeOH, rt;
d) DDQ, toluene, rt.

Scheme 102
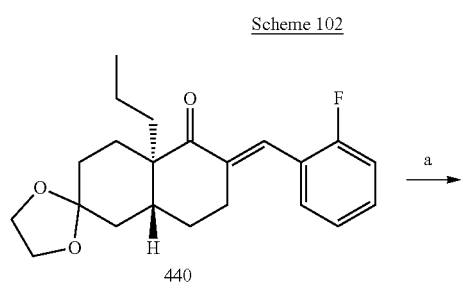
440
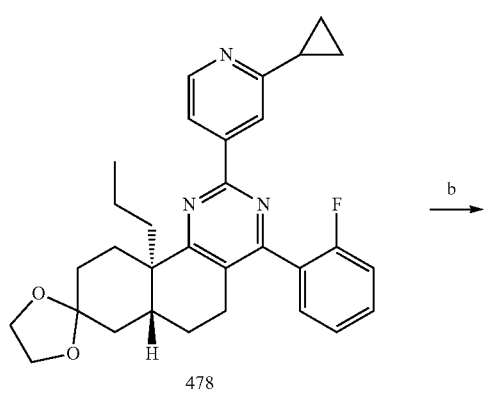
478
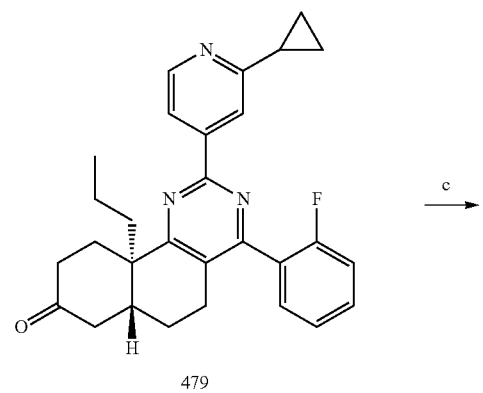
479
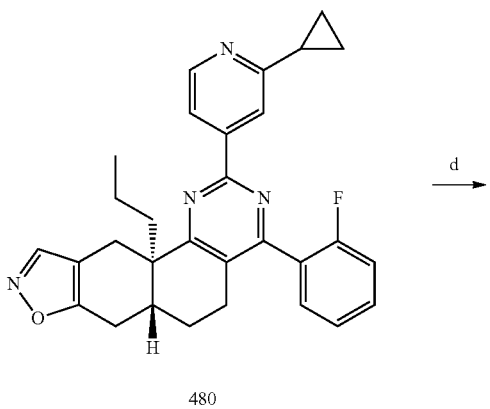
480
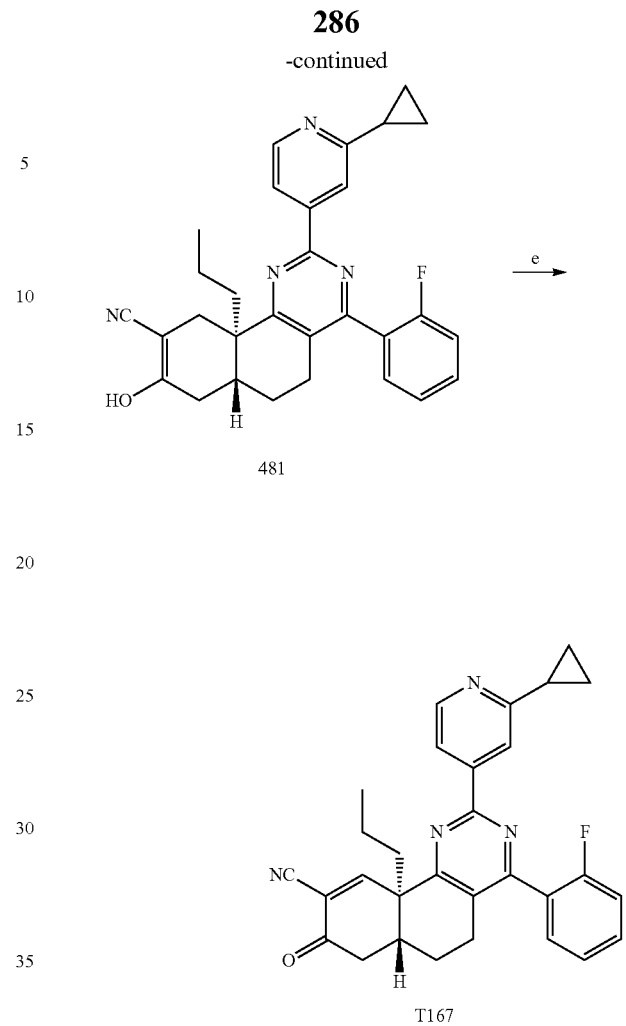
481
T167
Reagents and conditions:
a) i) 2-cyclopropylisonicotinimidamide hydrochloride, K$_2$CO$_3$, EtOH, reflux; ii) MnO$_2$, CH$_2$Cl$_2$, rt;
b) aq. 3N HCl, THF, rt;
c) i) HCO$_2$Et, NaOMe, MeOH, rt; ii) NH$_2$OH·HCl, EtOH, aq. 12N HCl, 50° C.;
d) K$_2$CO$_3$, MeOH, rt;
e) i) DBDMH, DMF, 0° C.; ii) pyridine, 60° C.
Scheme 103
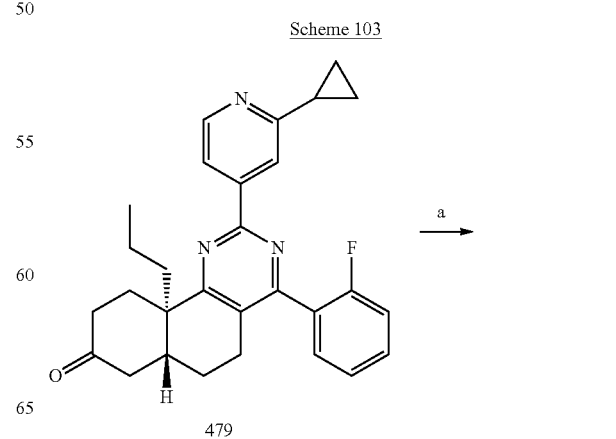
479

287
-continued
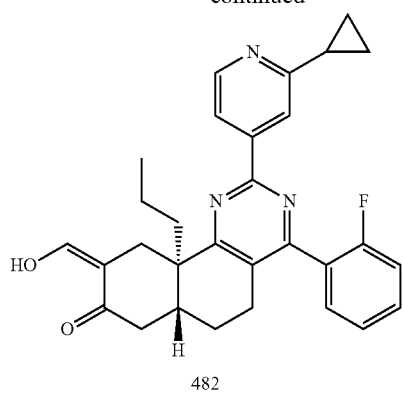
482
b →
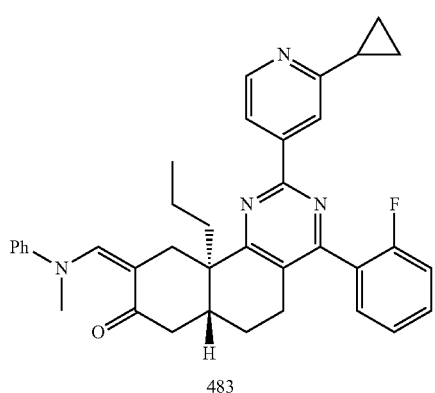
483
c →
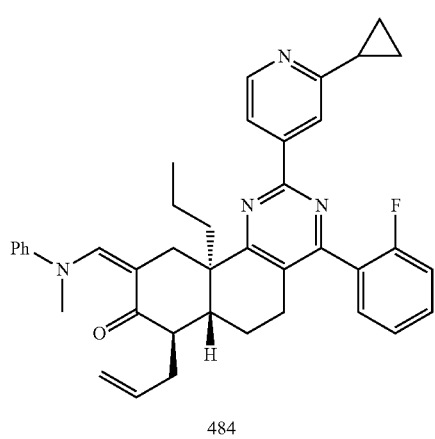
484
d →
485
e →
288
-continued
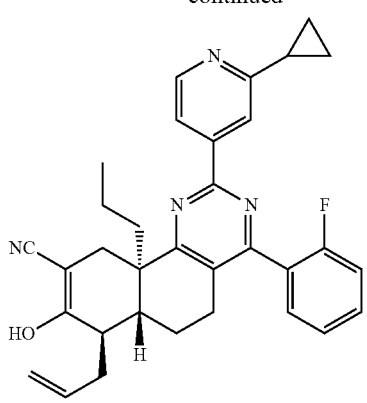
486
f →
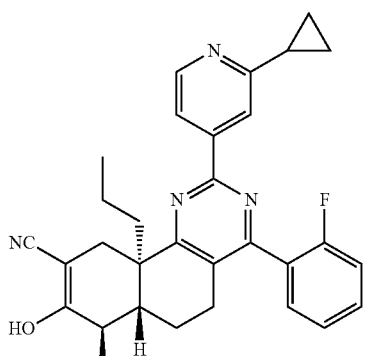
487
g →
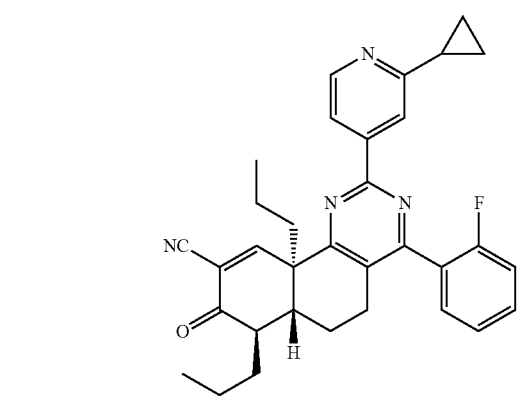
T168
Reagents and conditions: a) HCO₂Et, NaOMe, MeOH, rt; b) N-methylaniline, 3 Å molecular sieves, p-TsOH, CH₂Cl₂, rt; c) i) LDA, cyclohexane, THF, 0° C.; ii) allyl bromide, 0° C.; d) NH₂OH•HCl, 1N aq. HCl, EtOH, 55° C.; e) K₂CO₃, MeOH, rt; f) 10% Pd/C, H₂ (1 atm), EtOAc, rt; g) i) DBDMH, DMF, 0° C.; ii) pyridine, 60° C.
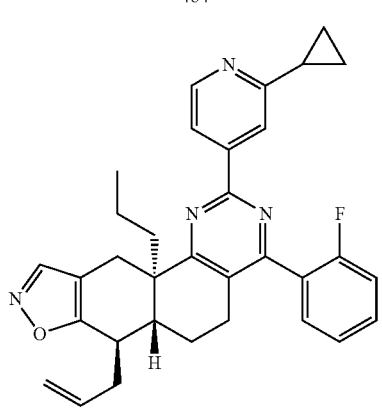

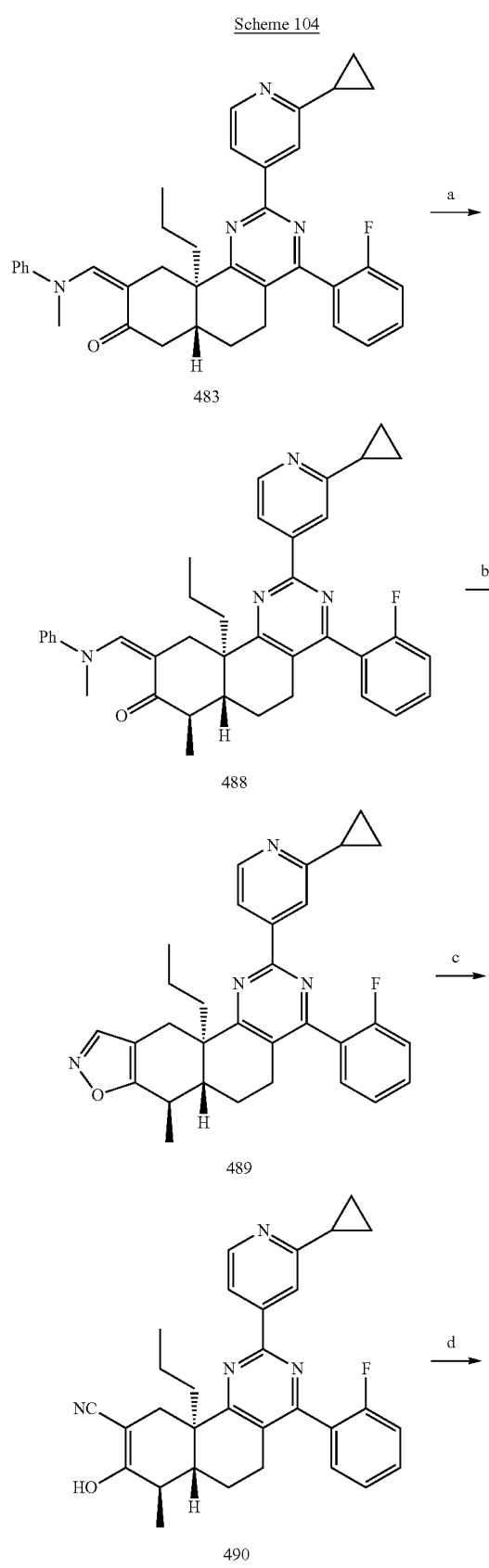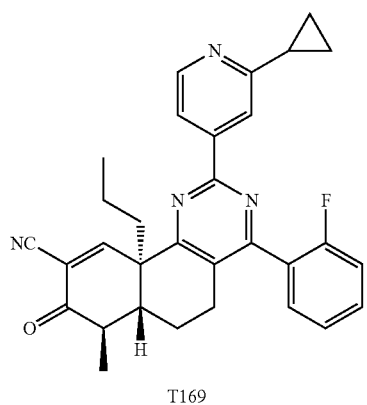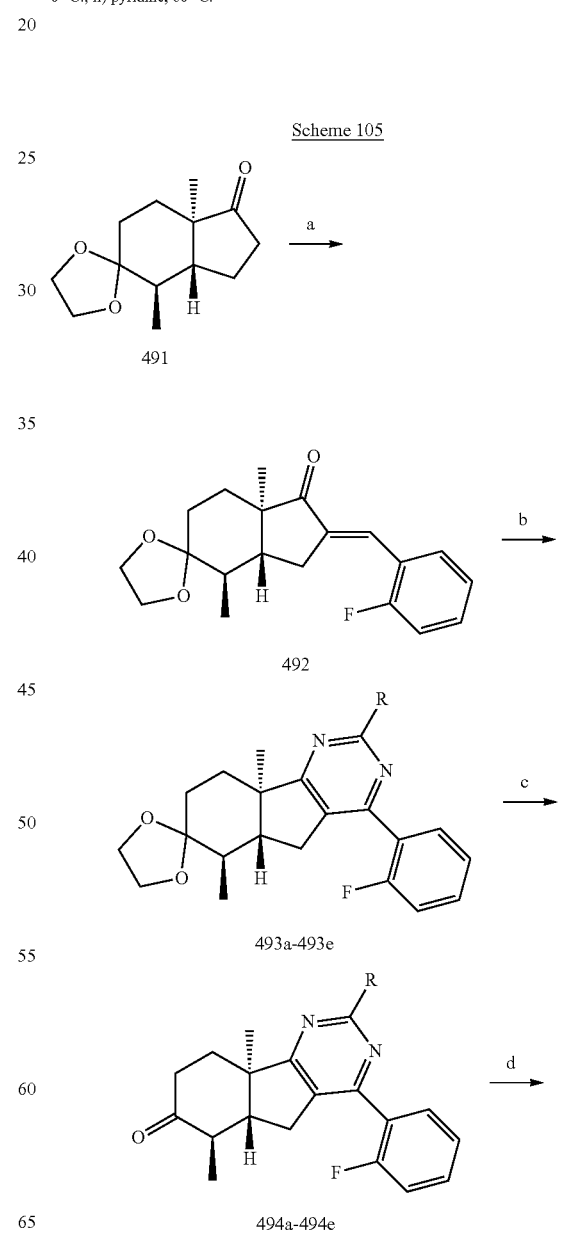
Scheme 104
Reagents and conditions: a) i) LDA, cyclohexane, THF, 0° C.; ii) MeI, 0° C.; b) NH₂OH•HCl, EtOH, 1N aq. HCl, 55° C.; c) K₂CO₃, MeOH, rt; d) i) DBDMH, DMF, 0° C.; ii) pyridine, 60° C.
Scheme 105

291
-continued
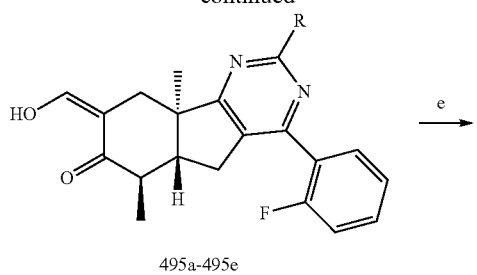
495a-495e
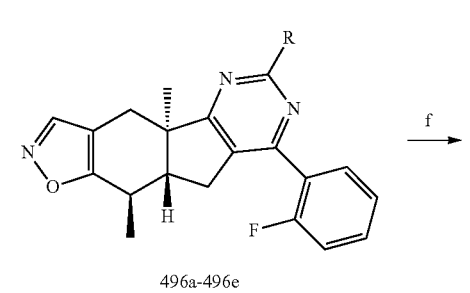
496a-496e
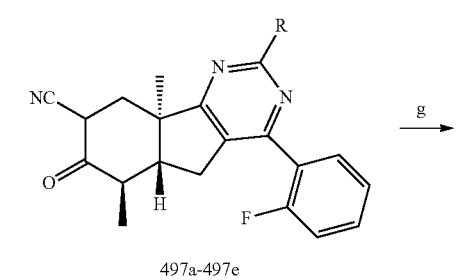
497a-497e
292
-continued
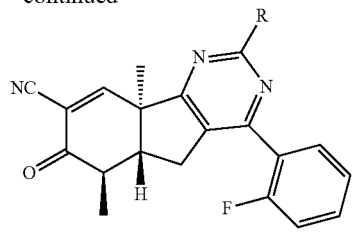
a T170
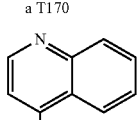
R =
c T172
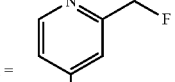
R =
d T173
R = 
e T174
R =
Reagents and conditions: a) 2-F-benzaldehyde, KF/Al$_2$O$_3$, EtOH, rt; b) i) amidine HCl, K$_2$CO$_3$, EtOH, reflux; ii) MnO$_2$, CH$_2$Cl$_2$, rt; c) aq. HCl, THF, rt; d) HCO$_2$Et, NaOMe, MeOH, rt; e) NH$_2$OH·HCl, 12N aq. HCl, EtOH, 55° C.; f) K$_2$CO$_3$, MeOH, rt; g) i) DBDMH, DMF, 0° C.; ii) pyridine, 60° C.
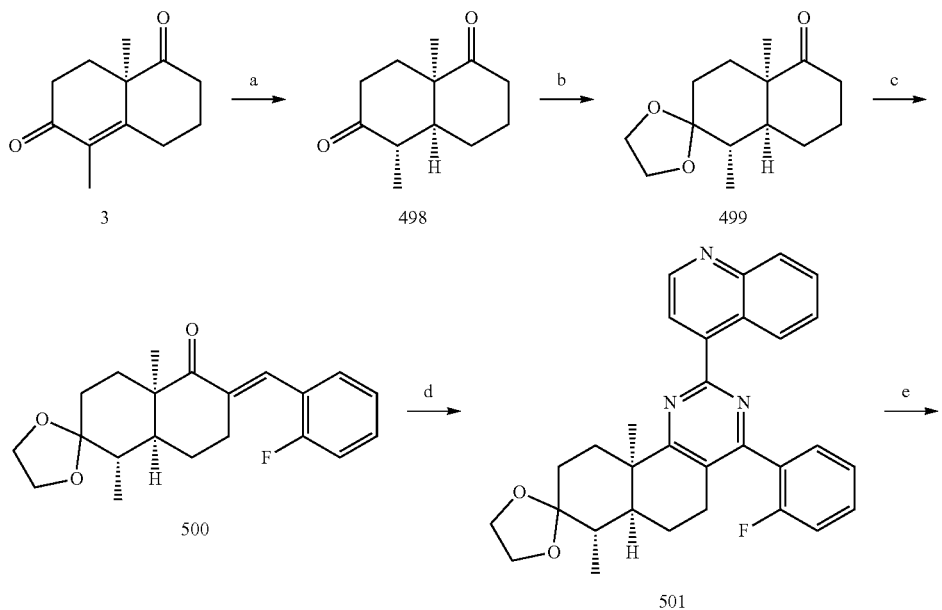
Scheme 106

-continued
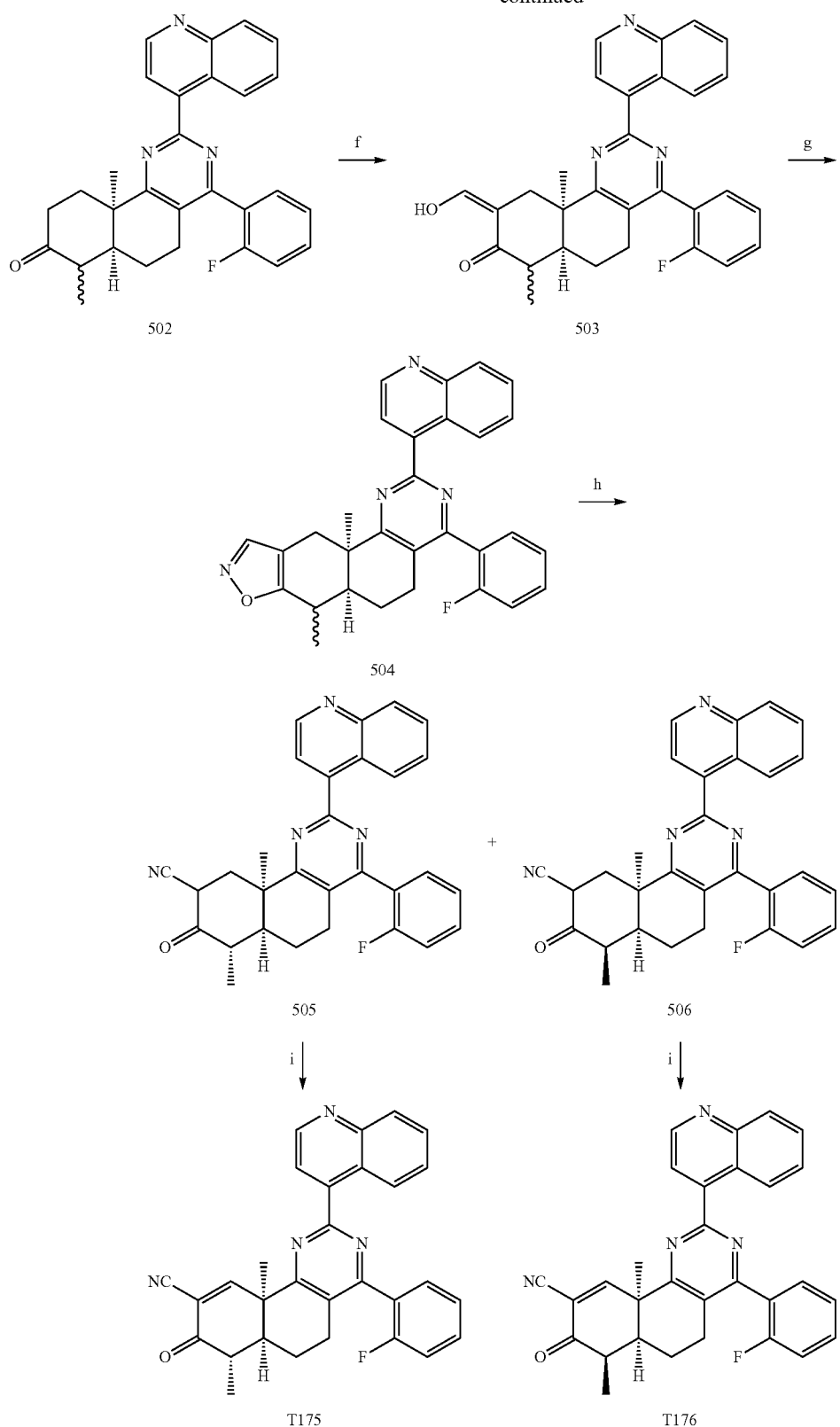
Reagents and conditions: a) H₂ (1 atm), 5% Pd/C, 95% aq. EtOH, rt; b) 2-ethyl-2-methyl-1,3-dioxolane, p-TsOH, ethylene glycol, 15° C.; c) 2-F-benzaldehyde, KF/Al₂O₃, EtOH, rt; d) i) amidine HCl, K₂CO₃, EtOH, reflux; ii) MnO₂, CH₂Cl₂, rt; e) aq. HCl, THF, rt; f) HCO₂Et, NaOMe, MeOH, rt; g) NH₂OH·HCl, 12N aq. HCl, EtOH, 55° C.; h) K₂CO₃, MeOH, rt; i) 1) DBDMH, DMF, 0° C.; 2) pyridine, 60° C.

Scheme 107
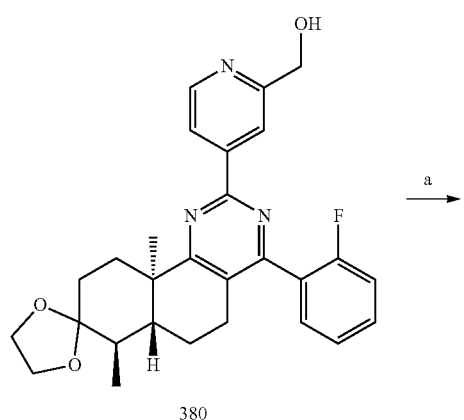
380
a →
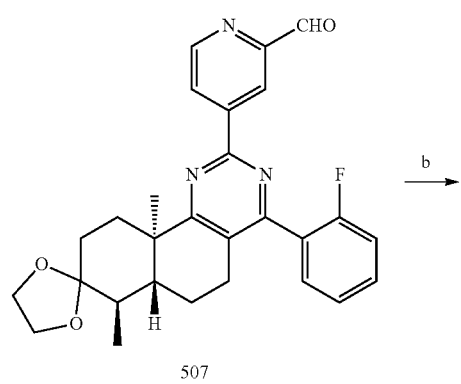
507
b →
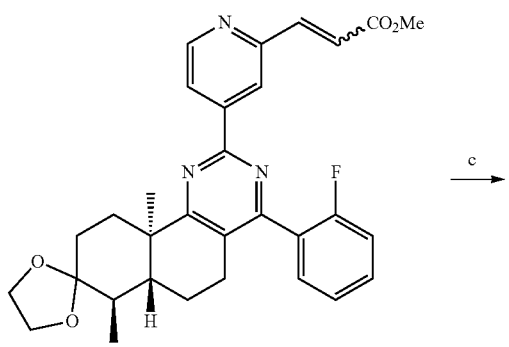
508
c →
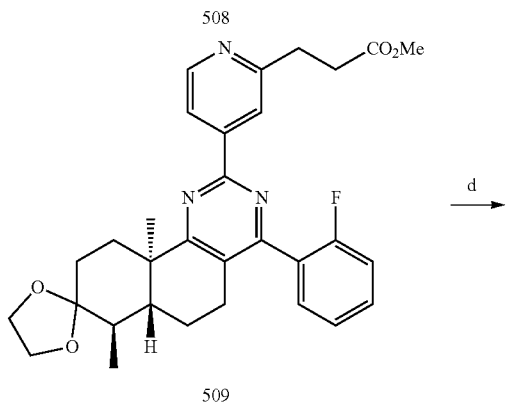
509
d →
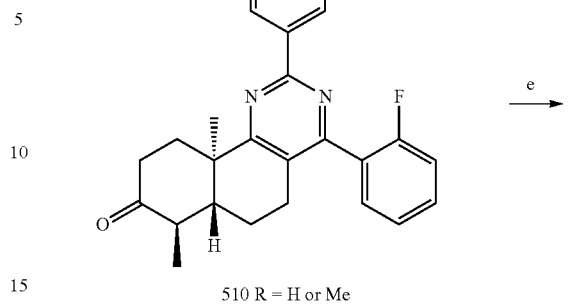
510 R = H or Me
e →
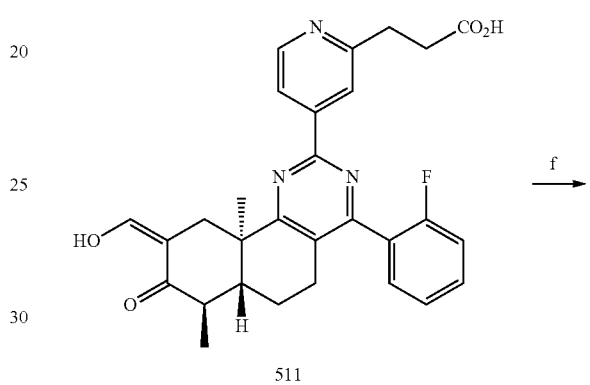
511
f →
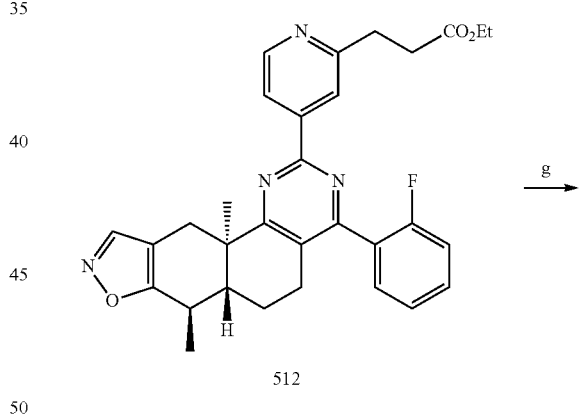
512
g →
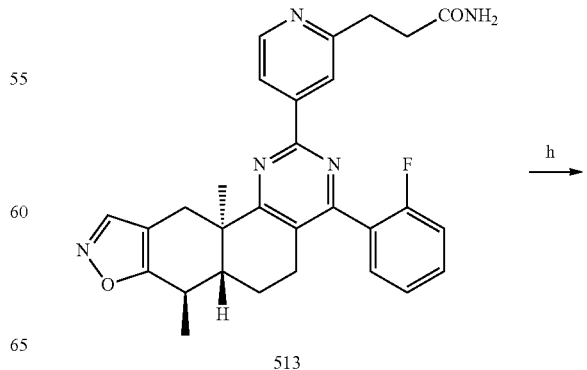
513
h →

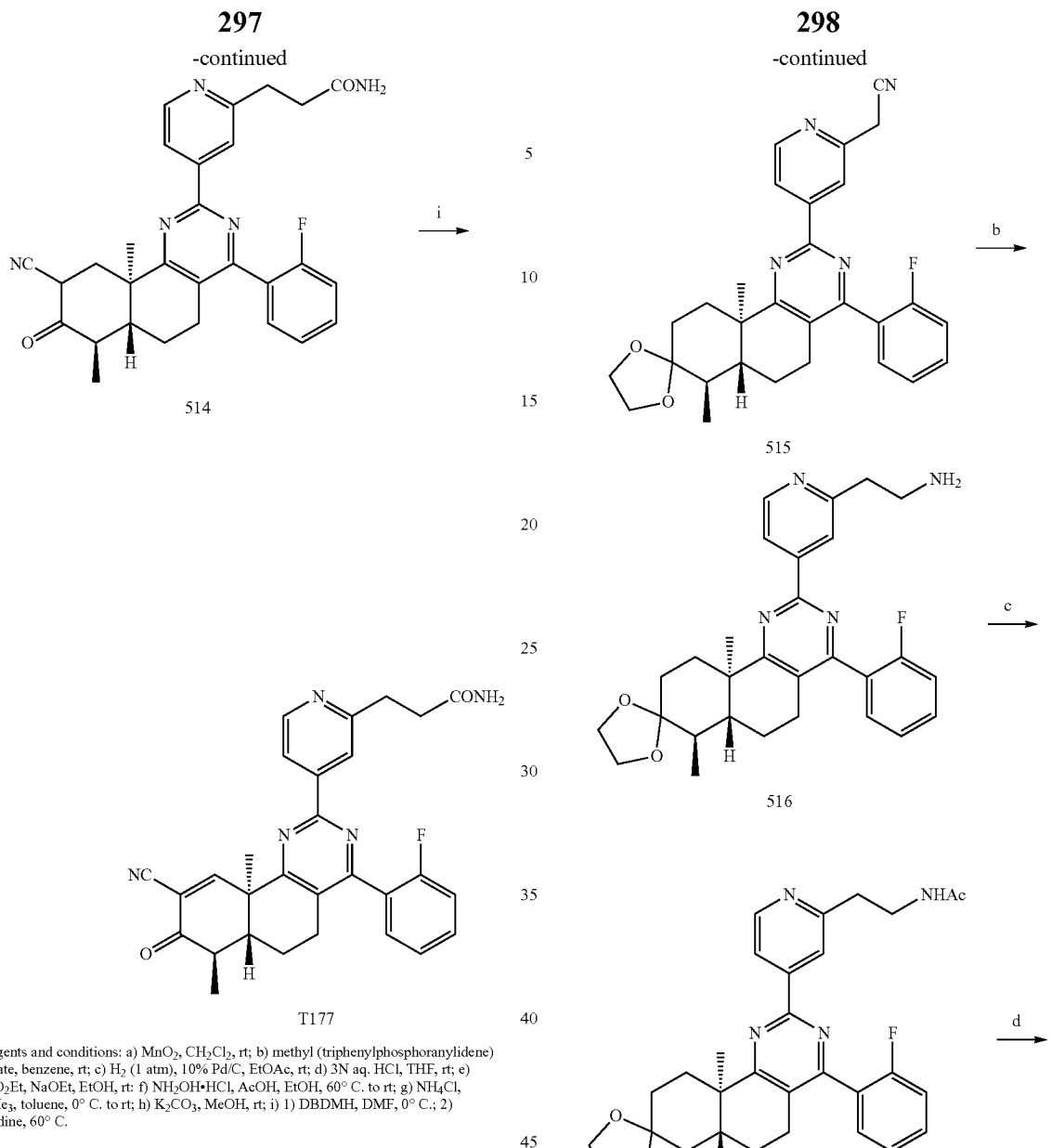
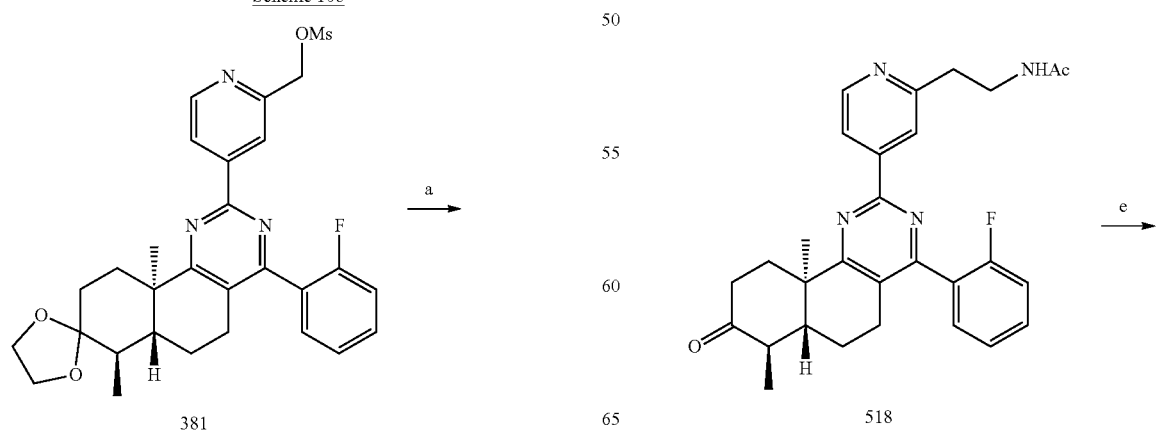
Reagents and conditions: a) MnO₂, CH₂Cl₂, rt; b) methyl (triphenylphosphoranylidene) acetate, benzene, rt; c) H₂ (1 atm), 10% Pd/C, EtOAc, rt; d) 3N aq. HCl, THF, rt; e) HCO₂Et, NaOEt, EtOH, rt: f) NH₂OH·HCl, AcOH, EtOH, 60° C. to rt; g) NH₄Cl, AlMe₃, toluene, 0° C. to rt; h) K₂CO₃, MeOH, rt; i) 1) DBDMH, DMF, 0° C.; 2) pyridine, 60° C.
Scheme 108

Scheme 109
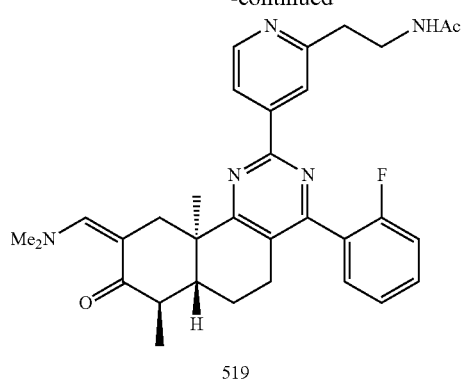
519
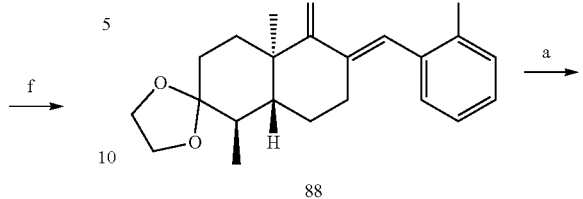
88
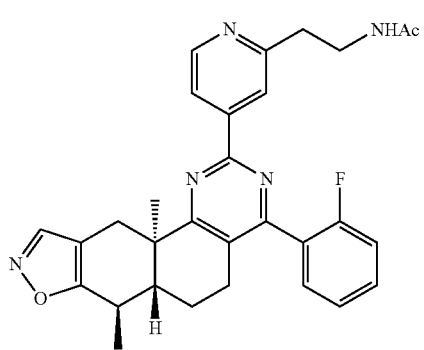
520
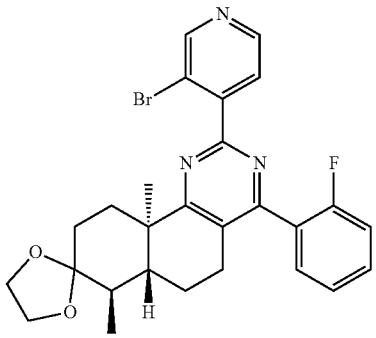
522
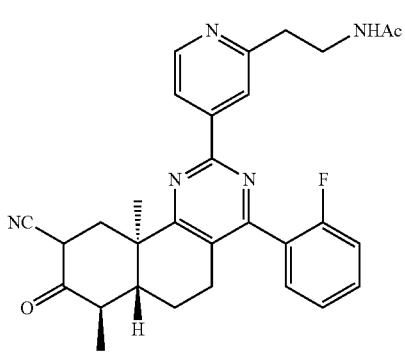
521
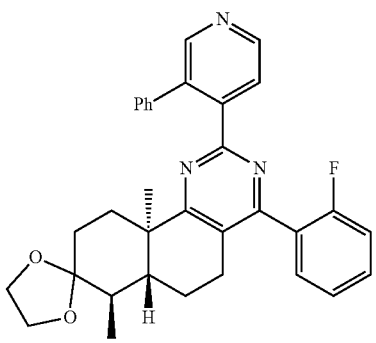
523
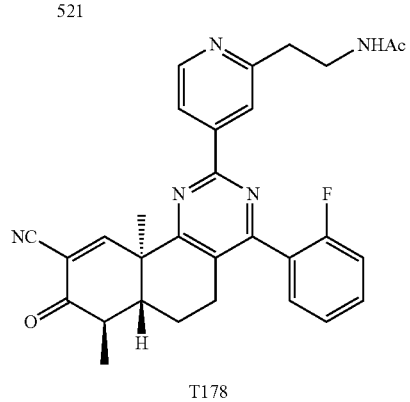
T178
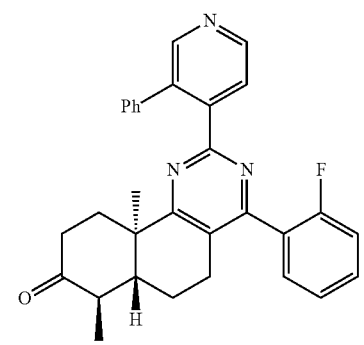
524
Reagents and conditions: a) KCN, 18-crown-6, MeCN, 50° C.; b) H₂ (1 atm), W2 Raney nickel, MeOH, rt; c) NaOAc, Ac₂O, rt; d) 3N aq. HCl, THF, rt; e) N,N-dimethylformamide dimethylacetal, 100° C.; f) NH₂OH·HCl, AcOH, EtOH, 60° C. to rt; g) K₂CO₃, MeOH, rt; h) 1) DBDMH, DMF, 0° C.; 2) pyridine, 60° C.

Scheme 110
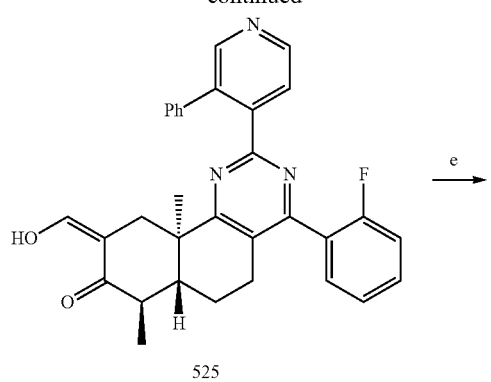
525
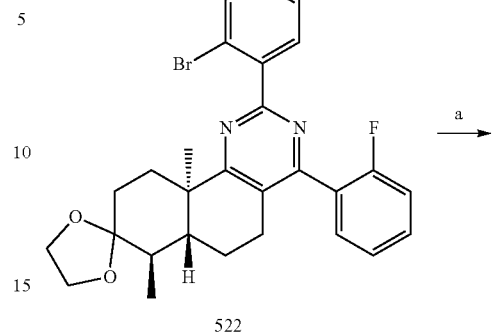
522
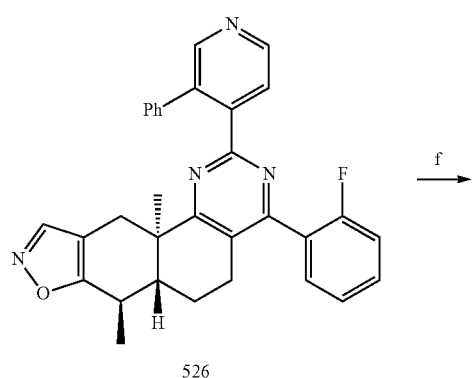
526
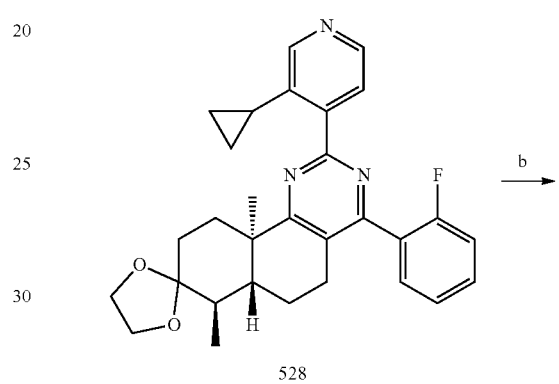
528
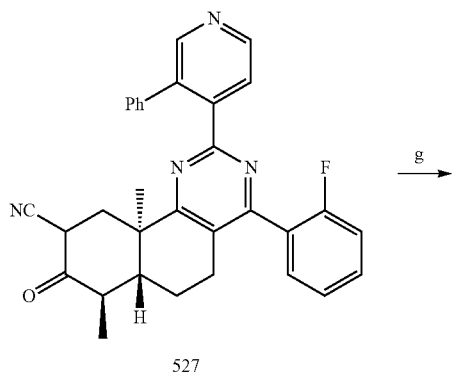
527
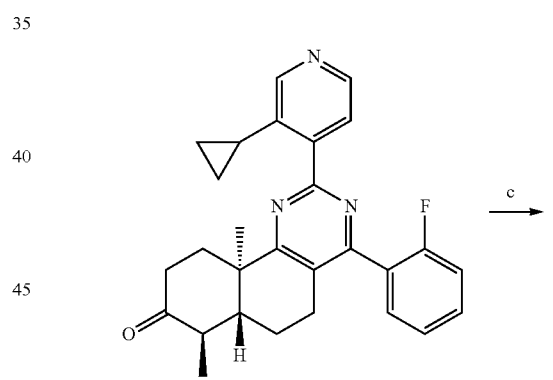
529
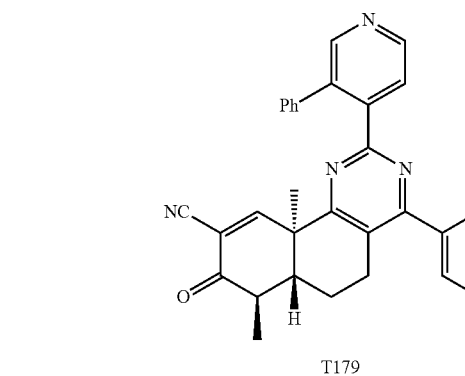
T179
Reagents and conditions: a) i) 3-bromoisonicotinimidamide hydrochloride, $K_2CO_3$, EtOH, rt to 80° C.; ii) $MnO_2$, $CH_2Cl_2$, rt; b) $PhB(OH)_2$, $K_3PO_4$, $Pd(PPh_3)_4$, 1,4-dioxane, DMF, 100° C.; c) aq. 3N HCl, MeOH, rt; d) $HCO_2Et$, NaOMe, MeOH, rt; e) $NH_2OH \cdot HCl$, AcOH, EtOH, 60° C. to rt; f) $K_2CO_3$, MeOH, rt; g) i) DBDMH, DMF, 0° C.; ii) pyridine, 60° C.
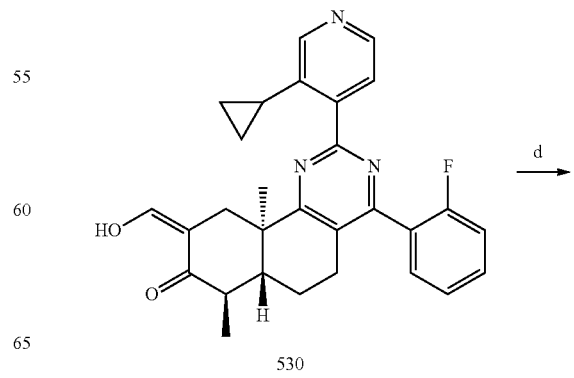
530

303
-continued
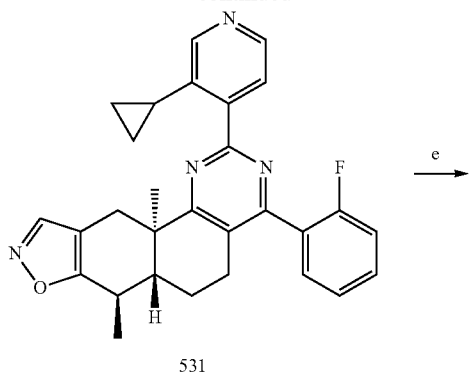
531
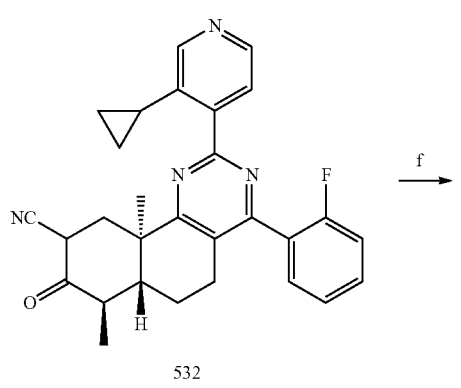
532
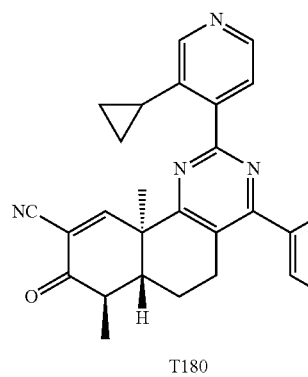
T180
Reagents and conditions: a) potassium cyclopropyltrifluoroborate, $K_3PO_4$, Pd(OAc)$_2$, RuPhos, toluene, water, 100° C.; b) aq. 3N HCl, MeOH, rt; c) HCO$_2$Et, NaOMe, MeOH, rt; d) NH$_2$OH•HCl, AcOH, EtOH, 60° C. to rt; e) $K_2CO_3$, MeOH, rt; f) i) DBDMH, DMF, 0° C.; ii) pyridine, 60° C.
304
Scheme 111
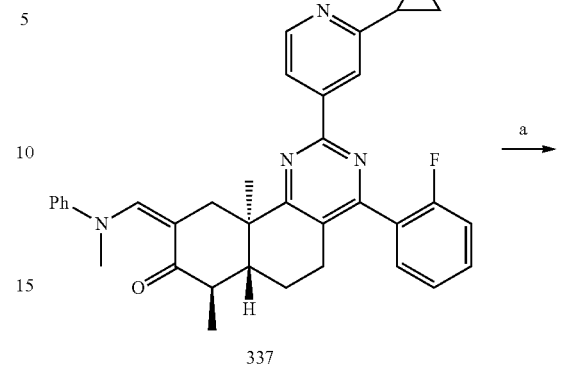
337
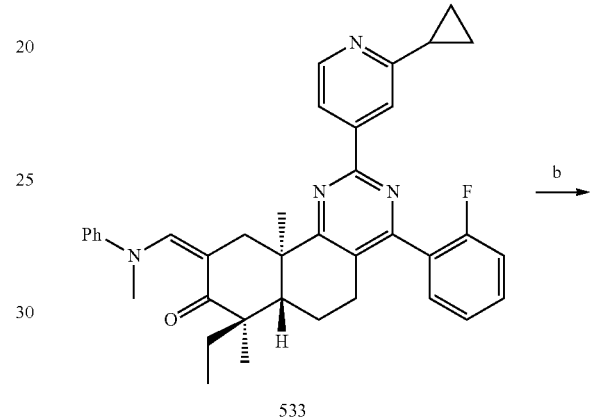
533
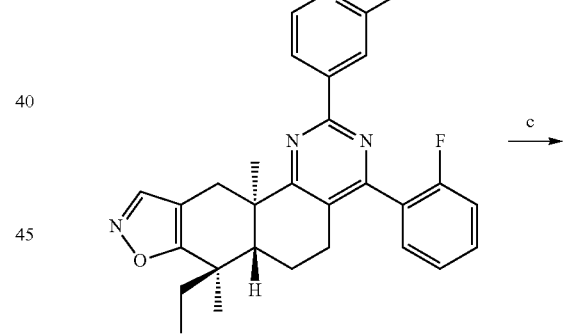
534
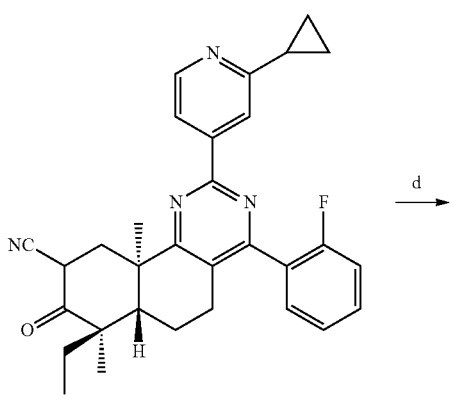
535

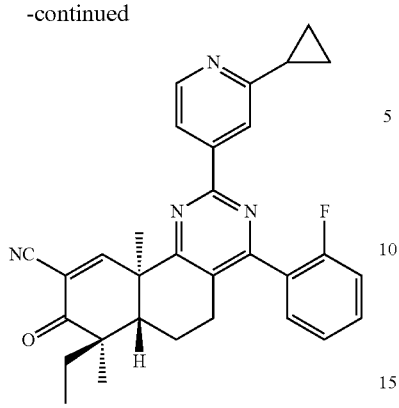
T181
Reagents and conditions: a) t-BuOK, EtI, THF, 0° C.; b) NH$_2$OH•HCl, 1N aq. HCl, EtOH, 60° C.; c) K$_2$CO$_3$, MeOH, rt; d) i) DBDMH, DMF, 0° C.; ii) pyridine, DMF, 55° C.
Scheme 112
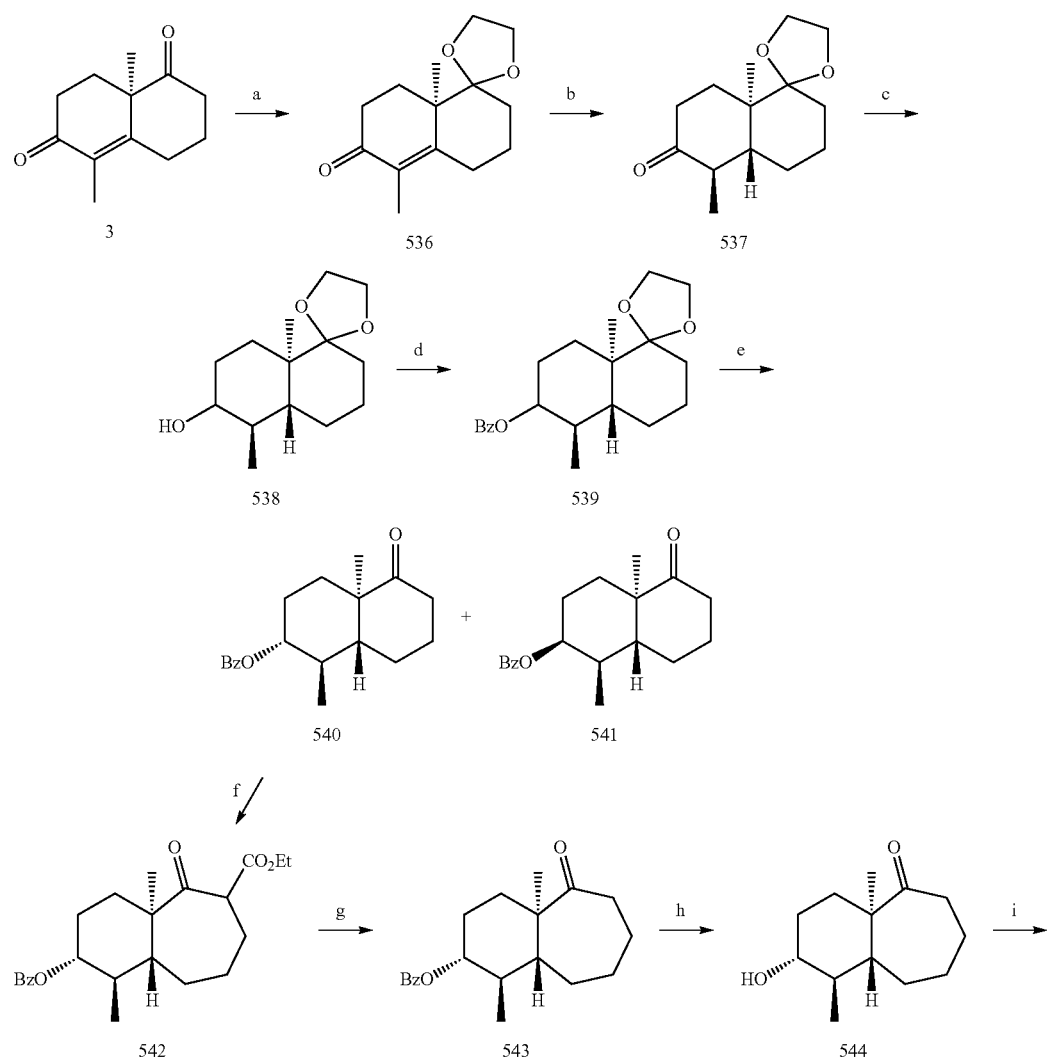

-continued

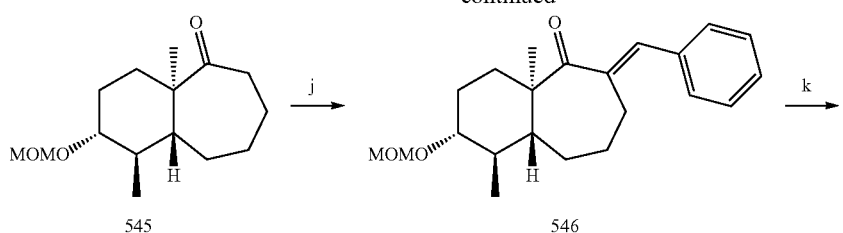

545 → 546

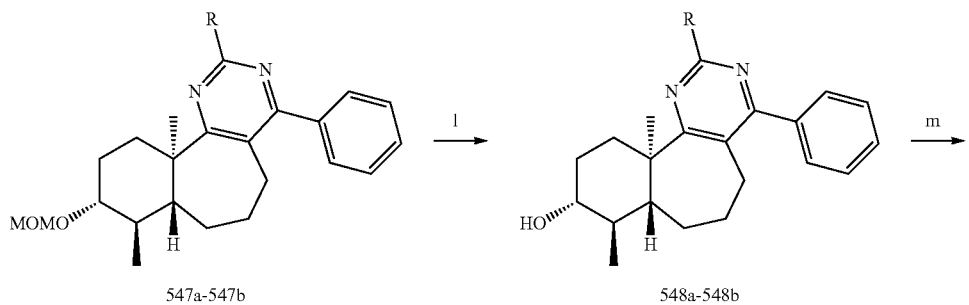

547a-547b → 548a-548b

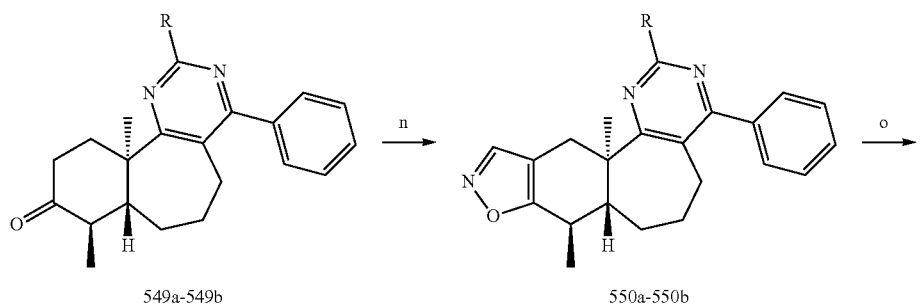

549a-549b → 550a-550b

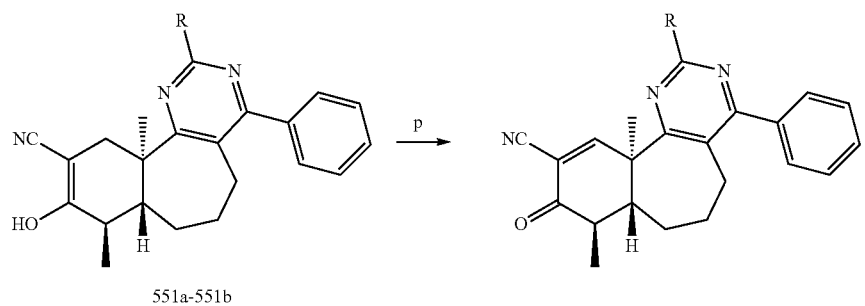

551a-551b

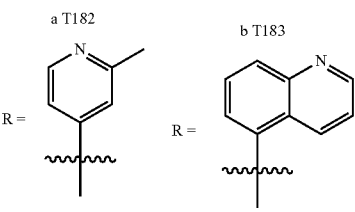

a T182  R =
b T183  R =

Reagents and conditions: a) ethylene glycol, p-TsOH•H₂O, 15° C.; b) Li, NH₃ (liq.), H₂O, THF, -78° C. to -30° C.; c) LiAlH₄, Et₂O, -78° C.; d) PhCOCl, pyridine, CH₂Cl₂, 15° C.; e) 3N aq. HCl, EtOH, 20° C.; f) ethyl diazoacetate, BF₃•OEt₂, Et₂O, 0° C. to 25° C.; g) LiI, H₂O, 2,4,6-collidine, 150° C.; h) 2M aq. NaOH, EtOH, 15° C.; i) MOMCl, (i-Pr)₂EtN, CH₂Cl₂, rt; j) PhCHO, t-BuOK, t-BuOH, reflux; k) 2-methylisonicotinimidamide hydrochloride, t-BuOK, 1,4-dioxane, 200° C., microwave; l) 12N aq. HCl, THF, H₂O, rt; m) Dess-Martin periodinane, CH₂Cl₂, rt; n) i) HCO₂Et, NaOMe, MeOH, 0° C. to rt; ii) 12N aq. HCl, NH₂OH•HCl, EtOH, 55° C.; o) NaOMe, MeOH, 55° C.; p) i) DBDMH, DMF, 0° C.; ii) pyridine, 55° C.

Scheme 113

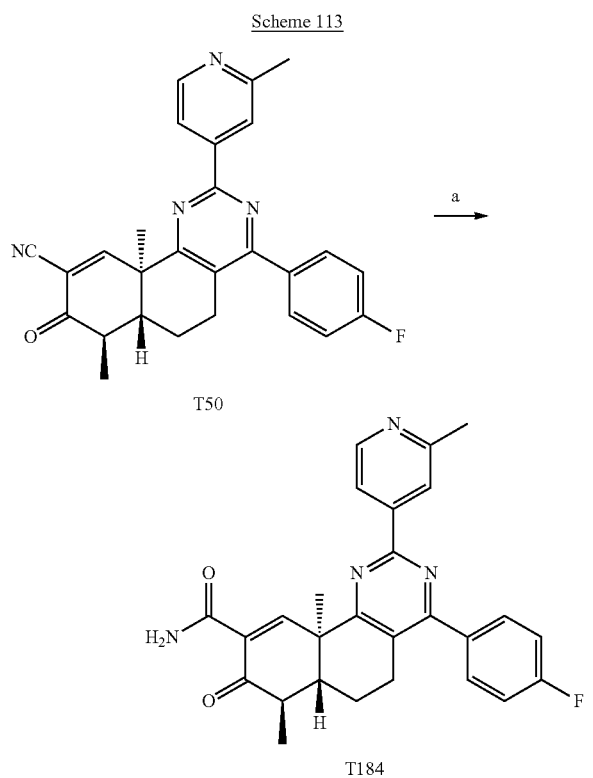

Reagents and conditions: a) hydrido(dimethylphosphinous acid-kP)[hydrogen bis(dimethylphosphinito-kP)]platinum(II), EtOH, H₂O, reflux.

Scheme 114

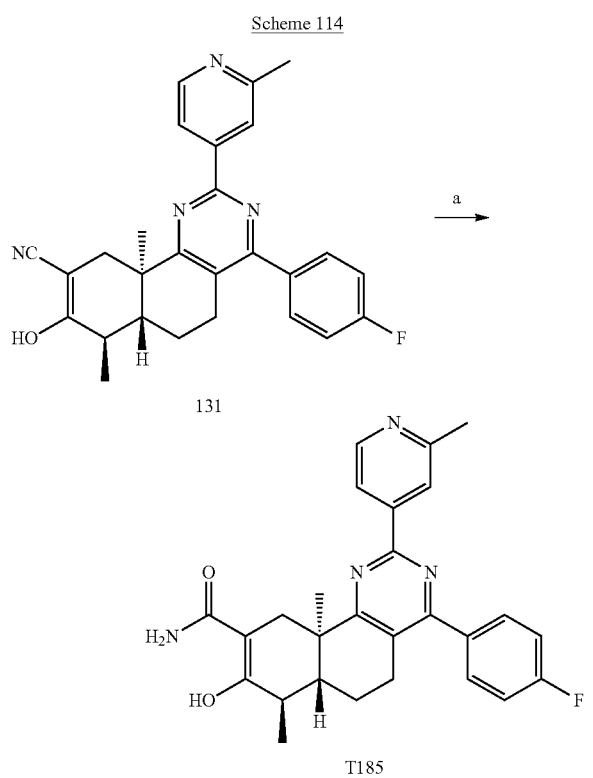

Reagents and conditions: a) hydrido(dimethylphosphinous acid-kP)[hydrogen bis(dimethylphosphinito-kP)]platinum(II), EtOH, H₂O, reflux.

ii. Characterization

I. General Information

Unless otherwise stated, commercially reagents were used as received, and all reactions were run under nitrogen atmosphere. Unless otherwise stated, the carboximidamides were prepared from the corresponding nitriles or carboxylic esters using the literature reported procedure (Garigipati, 1990). All solvents were of HPLC or ACS grade. Nuclear magnetic resonance (NMR) spectra were recorded on a Varian Inova-400 spectrometer at operating frequencies of 400 MHz ($^1$H NMR) or 100 MHz ($^{13}$C NMR). Chemical shifts (δ) are given in ppm relative to residual solvent (usually chloroform δ 7.26 ppm for $^1$H NMR), and coupling constants (J) in Hz. Multiplicity is tabulated as s for singlet, d for doublet, t for triplet, q for quadruplet, and m for multiplet. Mass spectra were recorded on Waters Micromass ZQ or Agilent 6120 mass spectrometer.

II. Compound Characterization

Compound 2: Compound 1 (750.00 g, 5.95 mol) was dissolved in MeCN (8 L). Ethyl vinyl ketone (625.15 g, 7.43 mol) and uinolonemine (962.57 g, 9.51 mol) were added dropwise at 10° C. The mixture was stirred for about 4 h, during which the temperature was kept below 25° C. TLC (silica gel, petroleum ether/EtOAc=3/1) indicated the starting material was consumed completely. MeCN was removed on a rotary evaporator, and the residue was diluted with ethyl acetate (8 L). The mixture was washed with aq. sat. KH₂PO₄ (8 L), and brine (5 L). The organic extract was dried over Na₂SO₄, and filtered. The filter cake was washed with MeCN (1 L). The combined filtrate was concentrated to give compound 2 (1.20 kg, 96% yield) as a yellow oil. m/z=211.1 (M+1).

Compound 3: A suspension of compound 2 (425.00 g, 2.02 mol), R-phenylalanine (267.11 g, 1.62 mol), (1S)-(+)-camphorsulfonic acid (281.72 g, 1.21 mol) in MeCN (2.1 L) was heated at 50° C. for 24 h, then at 60° C. for 48 h. The mixture was cooled to room temperature, and partitioned between EtOAc (3 L) and aq. sat. NaHCO₃ (3 L). The organic extract was washed with brine (3 L), dried over Na₂SO₄, filtered and concentrated. The residue was filtered through a silica gel pad, and eluted with 8/1 to 6/1 petroleum ether/EtOAc. The filtrate was concentrated to give crude compound 3 (388 g, quantitative yield).

Crude compound 3 (1.55 kg, 8.06 mol) was dissolved in MTBE (1.55 L). The mixture was cooled to 0° C., and seeded with purified compound 3. The mixture was kept at 0° C. for 2 h, then cooled to −10° C. and kept at the same temperature for 24 h. The precipitates were collected by filtration, and washed with cold MTBE (300 mL) to give compound 3 (792 g, 51% yield) as a white solid. m/z=193.1 (M+1).

Compound 4: Compound 3 (200.00 g, 1.04 mol) was dissolved in EtOH (2.80 L) and cooled to −5° C. (internal temperature). Sodium borohydride (11.02 g, 291.30 mmol) was added portion wise over 30 min. The mixture was stirred for 2 h, during which the internal reaction temperature was controlled below 0° C. TLC (silica gel, petroleum ether/EtOAc≤1/1) showed the start material was completely consumed. Acetic acid (96 mL, 1.68 mol) was added dropwise. After stirring for 30 min, the reaction mixture was concentrated on a rotary evaporator. EtOAc (1.5 L) was added and the mixture cooled to 0° C. Aq. NaOH [made from NaOH (80 g, 2 mol) and ice-water (1 L)] was added to adjust pH to~8. The solution was extracted with EtOAc (500 mL×3). The combined organic extracts were washed with water (1 L), dried over Na$_2$SO$_4$, filtered through a silica gel pad and concentrated in vacuo to give compound 4 (204.20 g, quantitative yield) as a viscous colorless oil, which was used in the next step without further purification. m/z=195.1 (M+1)

Compound 5: To a solution of compound 4 (204.20 g, 1.04 mol) in EtOAc (2.00 L) was added 5% palladium on barium sulfate (25.00 g). The mixture was stirred under hydrogen (15 psi) at 20° C. for 96 h. The catalyst was filtered off, and was washed with EtOAc (500 mL). The combined filtrate and wash was concentrated to give compound 5 (207 g, quantitative yield) as an oil, which was used in the next step without further purification.

Compound 6: A solution of compound 5 (207.00 g, 1.04 mol) in EtOH (2.00 L) was treated with aq. 3 N HCl (738.4 mL, 2.22 mol) at 20° C. The mixture was stirred for 2 h, and concentrated. The residue was diluted with EtOAc (2.5 L), and washed with brine (2×1 L). The organic extract was concentrated, and the residue was filtered through a pad of silica gel (eluting with 10/1 to 8/1 petroleum ether/EtOAc) to give the crude product as a light yellow solid (203.25 g). The solid was dissolved in MTBE (1.22 L) at 40° C., and n-pentane (1.22 mL) was added. The solution was cooled to room temperature, seeded with purified compound 6, and kept at −20° C. for 16 h. The precipitates was collected by filtration, washed with cold (−20° C.) mixture of MTBE and n-pentane (1/1, 100 mL) and dried under vacuum to give compound 6 (98 g, 48% yield) as a white solid. m/z=197.2 (M+1)

Compound 7: To a solution of compound 6 (118.00 g, 601.15 mmol) in toluene (2.60 L) was added pyridinium p-toluenesulfonate (15.11 g, 60.13 mmol) and ethylene glycol (373.13 g, 6.01 mol) sequentially. The reaction was heated to reflux with Dean-Stark trap for 3 h. TLC (silica gel, petroleum ether/EtOAc=3/1) showed the reaction was completed. The mixture was cooled to room temperature, and washed with water (2×1 L). The aqueous washes were extracted with toluene (2×1 L). The combined organic extracts were dried over Na$_2$SO$_4$, filtered and concentrated to give compound 7 (158.00 g, quantitative yield) as a glassy solid, which was used in the next step without further purification. m/z=241.1 (M+1).

Compound 8: Sodium phosphate dibasic dodecahydrate (18.5 g, 51.66 mmol) and sodium tungstate uinolone (4.26 g, 12.90 mmol) were dissolved in aq. 30% H$_2$O$_2$ (175.49 g, 1.55 mol) to give a yellow solution. The solution was added dropwise to a solution of compound 7 (311.00 g, 1.29 mol) in N,N-dimethylacetamide (2.60 L) at 60° C. over 15 min. The mixture was heated at 90° C. for 3 h. TLC (silica gel, petroleum ether/EtOAc=3:1) showed the reaction was completed. The mixture was cooled to room temperature, and diluted with EtOAc (5 L). The mixture was washed with aq. 10% Na$_2$SO$_3$ (2.5 L) and water (4×2 L) sequentially. The aqueous washes were extracted with EtOAc (2×1 L). The combined organic extracts were washed with water (2×1 L), dried over Na$_2$SO$_4$, filtered and concentrated. The crude product was dissolved in heptane (880 mL) at 40° C. The solution was cooled at 4° C. for 1 h, seeded with purified compound 8, and then kept at −20° C. for 20 h. The precipitates were collected by filtration, washed with cold (−20° C.) heptanes (300 mL), and dried under vacuum to give compound 8 (198.2 g, 64% yield) as a white solid. m/z=239.2 (M+1).

Compound 9: To a stirring solution of compound 8 (10 g, 42.0 mmol) in THF (63 mL) was added dimethyl carbonate (35.3 mL, 419.3 mmol) and sodium hydride (60% dispersion in mineral oil, 5.1 g, 127.5 mmol) sequentially at room temperature under nitrogen. After addition, the mixture was heated at 80° C. for 16 h, and cooled to 0° C. The reaction was quenched by dropwise addition of aq. sat. KH$_2$PO$_4$ and the mixture was extracted with EtOAc. The combined organic extract was washed with water, dried with Na$_2$SO$_4$, filtered and concentrated. The residue was purified by flash chromatography (silica gel, eluting with 0% to 10% acetone in hexanes) to give compound 9 (11.1 g, 89% yield) as a white solid. m/z=297 (M+1).

Compound 10: Compound 9 (5.47 g, 18.47 mmol) was taken up in EtOH (65 mL). Thiourea (14 g, 183.9 mmol) and potassium t-butoxide (2.1 g, 18.71 mmol) were added. After heated at reflux for 16 h, the reaction mixture was concentrated, mixed with water (50 mL), and neutralized with aq. 3 N HCl. The precipitate was collected by filtration, washed with water, and dried under vacuum to give compound 10 (5.95 g, quantitative yield) as an off-white solid. m/z=323 (M+1).

Compound 11: Compound 10 (5.95 g, 18.47 mmol) in chloroacetic acid (17.5 g, 185.2 mmol) was heated at 75° C. for 1 h. Water (15 mL) was added, and the mixture was heated at 100° C. for 4 h. Aq. conc. HCl (1.5 mL, 18 mmol) was added. The mixture was heated at 100° C. for another 16 h, cooled, and diluted with ice water (50 mL). The precipitate was collected by filtration, and dried under vacuum to give compound 11 (4.8 g, 99% yield) as an off-white solid. m/z=263 (M+1).

Compound 12: Compound 11 (4.8 g, 18.30 mmol) was taken up in POCl$_3$ (25 mL). N,N-Diisopropylethylamine (2.6 g, 20.12 mmol) was added. The mixture was heated at 90° C. for 16 h, cooled, and poured into ice. The precipitate was collected by filtration, washed with water, and dried under vacuum to give compound 12 (2.3 g, 42% yield) as a brown solid. m/z=299 (M+1).

Compound 13: To a solution of compound 12 (100 mg, 0.33 mmol) in MeOH (3.3 mL) was added sodium methoxide (25 wt. % in MeOH, 0.10 mL, 0.43 mmol). The mixture was stirred at 50° C. for 1 h, and cooled to room temperature. Aq. 1 N HCl (0.5 mL, 0.5 mmol) was added, and the mixture was concentrated. The residue was partitioned between EtOAc and water, and the organic extract was washed with water, dried over Na$_2$SO$_4$, filtered and concentrated. The residue was purified by chromatography (silica gel, eluting with 0% to 20% EtOAc in hexanes) to give compound 13 (82 mg, 83% yield) as a white solid. m/z=295 (M+1).

Compound 14a: A mixture of compound 13 (150 mg, 0.509 mmol), 2-methoxypyridine-4-boronic acid (111 mg, 0.726 mmol), triphenylphosphine (50.8 mg, 0.194 mmol), potassium phosphate (324 mg, 1.528 mmol) in 1,2-dimethoxyethane (2.1 mL) and DMF (4.2 mL) was sparged with N$_2$ for 30 min. Palladium(II) acetate (22.9 mg, 0.102 mmol) was added and the nitrogen sparging was continued for another 10 min. The reaction mixture was heated at 95° C. for 2 h, cooled to room temperature, and filtered. The filtrate was concentrated, and the residue was purified by flash chromatography (silica gel, eluting with 0% to 30% EtOAc in hexanes) to give compound 14a (136 mg, 73% yield) as a white solid. m/z=368 (M+1).

Compound 15a: To a stirring solution of compound 14a (130 mg, 0.354 mmol) in ethyl formate (3 mL, 37.3 mmol) was added sodium methoxide (25 wt. % solution in MeOH, 0.81 mL, 3.51 mmol) at room temperature. The reaction mixture was stirred overnight at room temperature, and partitioned between aq. KH$_2$PO$_4$ and EtOAc. The organic extract was washed with brine, dried over Na$_2$SO$_4$, filtered and concentrated. The residue was dissolved in EtOH (3 mL) and water (0.3 mL), and treated with hydroxylamine hydrochloride (32 mg, 0.46 mmol). The mixture was heated overnight at 55° C., cooled to room temperature, and concentrated. The residue was partitioned between water and EtOAc. The organic extract was dried with MgSO$_4$, filtered and concentrated to give compound 15a (95 mg, 68% yield) as a white solid. m/z=393 (M+1).

Compound 16a: To a solution of compound 15a (86.9 mg, 0.221 mmol) in a MeOH (2 mL) was added sodium methoxide (25 wt. % solution in MeOH, 0.3 mL, 1.30 mmol). The reaction mixture was stirred at 55° C. for 3 h, cooled and concentrated. The residue was partitioned between aq. KH$_2$PO$_4$ and EtOAc, and the organic extract was washed with brine, dried with MgSO$_4$, filtered and concentrated to give compound 16a (58 mg, 67% yield) as a solid. m/z=393 (M+1).

T2: To a solution of compound 16a (56 mg, 0.143 mmol) in benzene (14 mL) was added DDQ (42 mg, 0.186 mmol) at room temperature. The reaction mixture was refluxed for 3 h, cooled to room temperature and concentrated. The residue was purified by flash chromatography (silica gel, eluting with 0% to 40% EtOAc in hexanes) to give compound T2 (28 mg, 50% yield) as a white solid. $^1$H NMR (400 MHz, CDCl$_3$) δ 8.94 (s, 1H), 8.32 (m, 1H), 7.89 (m, 1H), 7.77 (m, 1H), 4.11 (s, 3H), 4.03 (s, 3H), 2.89 (dd, J=6.7, 18.7 Hz, 1H), 2.62 (m, 2H), 2.15 (m, 2H), 1.78 (m, 1H), 1.46 (s, 3H), 1.33 (d, J=6.8 Hz, 3H); m/z=391 (M+1).

Compound 14b: A mixture of Compound 13 (150 mg, 0.509 mmol), 2-methylpyridine-4-boronic acid pinacol ester (168 mg, 0.767 mmol), triphenylphosphine (50.8 mg, 0.194 mmol), potassium phosphate (324 mg, 1.53 mmol) in 1,2-dimethoxyethane (2.1 mL) and DMF (4.2 mL) was sparged with nitrogen for 30 min. Palladium(II) acetate (22.9 mg, 0.102 mmol) was added and the nitrogen sparging was continued for another 10 min. The reaction mixture was heated at 95° C. for 16 h, cooled to room temperature, and filtered. The filtrate was concentrated, and the residue was purified by flash chromatography (silica gel, eluting with 0% to 40% EtOAc in hexanes) to give compound 14b (140 mg, 78% yield) as a white solid. m/z=352 (M+1).

Compound 15b: To a stirring solution of compound 14b (130 mg, 0.370 mmol) in ethyl formate (3 mL, 37.3 mmol) was added sodium methoxide (25 wt. % solution in MeOH, 0.85 mL, 3.68 mmol) at room temperature. The reaction mixture was stirred overnight at room temperature, and partitioned between aq. KH$_2$PO$_4$ and EtOAc. The organic extract was washed with brine, dried over Na$_2$SO$_4$, filtered and concentrated. The residue was dissolved in EtOH (4 mL) and water (0.4 mL), and treated with hydroxylamine hydrochloride (33.5 mg, 0.482 mmol). The mixture was heated overnight at 55° C., cooled to room temperature, and concentrated. The residue was partitioned between water and EtOAc. The organic extract was dried with MgSO$_4$, filtered and concentrated to give compound 15b (98 mg, 70% yield) as a white solid. m/z=377 (M+1).

Compound 16b: To a solution of compound 15b (90 mg, 0.239 mmol) in a MeOH (2 mL) was added sodium methoxide (25 wt. % solution in MeOH, 0.33 mL, 1.43 mmol). The reaction mixture was stirred at 55° C. for 3 h, cooled and concentrated. The residue was partitioned between aq. KH$_2$PO$_4$ and EtOAc, and the organic extract was washed with brine, dried with MgSO$_4$, filtered and concentrated to give compound 16b (66 mg, 73% yield) as a pale yellow solid. m/z=377 (M+1).

Compound T3: To a solution of compound 16b (60 mg, 0.159 mmol) in benzene (14 mL) was added DDQ (47 mg, 0.207 mmol) at room temperature. The reaction mixture was refluxed for 3 h, cooled to room temperature and concentrated. The residue was purified by flash chromatography (silica gel, eluting with 0% to 60% EtOAc in hexanes) to give compound T3 (22 mg, 37% yield) as a white solid. $^1$H NMR (400 MHz, CDCl$_3$) δ 8.96 (s, 1H), 8.66 (d, J=5.2 Hz, 1H), 8.14 (s, 1H), 8.10 (d, J=5.1 Hz, 1H), 4.13 (s, 3H), 2.89 (dd, J=6.7, 18.8 Hz, 1H), 2.71 (s, 3H), 2.61 (m, 2H), 2.16 (m, 2H), 1.77 (m, 1H), 1.47 (s, 3H), 1.33 (d, J=6.7 Hz, 3H); m/z=375 (M+1).

Compound 14c: Compound 13 (50 mg, 0.17 mmol), 3-picoline-4-boronic acid (35 mg, 0.26 mmol), triphenylphosphine (17 mg, 0.065 mmol), potassium phosphate (108 mg, 0.51 mmol) and palladium acetate (7.6 mg, 0.034 mmol) in 1,2-dimethoxyethane (1.4 mL) and DMF (0.7 mL) in a microwave vial were sparged with nitrogen for 5 min. The vial was sealed, and heated in Biotage® microwave synthesizer at 100° C. for 5 h. The mixture was cooled to room temperature, filtered through a silica gel plug, and eluted with EtOAc. The filtrate was washed with water. The organic extract was dried with Na$_2$SO$_4$, and concentrated. The residue was purified by flash chromatography (silica gel, eluting with 0% to 50% EtOAc in hexanes) to give compound 14c (58 mg, 97% yield) as a yellow foamy solid. m/z=352 (M+1).

Compound 15c: To a stirred solution of compound 14c (80 mg, 0.23 mmol) in ethyl formate (0.55 mL) was added sodium methoxide (25 wt. % in methanol, 0.78 mL, 3.38 mmol) at 0° C. The mixture was stirred at room temperature for 1 h, and cooled to 0° C. Aq. 6 N HCl (0.57 mL, 3.42 mmol), EtOH (2.3 mL), and hydroxylamine hydrochloride (24 mg, 0.35 mmol) were added sequentially. The mixture was heated at 55° C. for 4 h. EtOAc was added. The mixture was washed with aq. sat. NaHCO$_3$. The organic extract was dried with Na$_2$SO$_4$, filtered and concentrated. The residue was purified by flash chromatography (silica gel, eluting with 0% to 50% EtOAc in hexanes) to give compound 15c (63 mg, 74% yield) as a white foamy solid. m/z=377 (M+1).

Compound 16c: Compound 15c (55 mg, 0.15 mmol) was dissolved in MeOH (1.5 mL). Sodium methoxide (25 wt. % in methanol, 50 μL, 0.22 mmol) was added. The reaction mixture was stirred at 55° C. for 1 h, and cooled to rt. EtOAc was added. The mixture was washed with aq. 10% KH$_2$PO$_4$. The organic extract was dried with Na$_2$SO$_4$ and concentrated. The residue was purified by flash chromatography (silica gel, eluting with 0% to 35% acetone in hexanes) to give compound 16c (48 mg, 87% yield) as a white solid. m/z=377 (M+1).

T4: Compound 16c (38 mg, 0.10 mmol) was dissolved in toluene (2 mL) and benzene (1 mL). DDQ (25 mg, 0.11 mmol) was added. The mixture was heated at 85° C. for 1 h, and was cooled to room temperature. CH$_2$Cl$_2$ was added. The mixture was washed with aq. sat. NaHCO$_3$. The organic extract was dried with Na$_2$SO$_4$, and concentrated. The residue was purified by flash chromatography (silica gel, eluting with 0% to 35% acetone in hexanes) to give compound T4 (22 mg, 58% yield) as an off-white foamy solid. $^1$H NMR (400 MHz, CDCl$_3$) δ 8.84 (s, 1H), 8.60 (m, 2H), 7.91 (d, J=5.0 Hz, 1H), 4.08 (s, 3H), 2.90 (dd, J=6.0, 18.8 Hz, 1H), 2.67 (s, 3H), 2.65 (m, 2H), 2.16 (m, 2H), 1.78 (m, 1H), 1.47 (s, 3H), 1.33 (d, J=6.7 Hz, 3H); m/z=375 (M+1).

Compound 14d: Compound 13 (150 mg, 0.51 mmol), pyridine-4-boronic acid (93 mg, 0.76 mmol), triphenylphosphine (51 mg, 0.19 mmol), potassium phosphate (324 mg, 1.52 mmol) and palladium acetate (22 mg, 0.10 mmol) in 1,2-dimethoxyethane (2.1 mL) and DMF (1.1 mL) in a microwave vial were sparged with nitrogen for 5 min. The vial was sealed, and heated in Biotage® microwave synthesizer at 100° C. for 5 h. The mixture was cooled to room temperature, filtered through a silica gel plug, and eluted with EtOAc. The filtrate was washed with water. The organic extract was dried with $Na_2SO_4$, and concentrated. The residue was purified by flash chromatography (silica gel, eluting with 0% to 50% EtOAc in hexanes) to give compound 14d (155 mg, 90% yield) as a white foamy solid. m/z=338 (M+1).

Compound 15d: To a stirred solution of compound 14d (90 mg, 0.27 mmol) in ethyl formate (0.64 mL) was added sodium methoxide (25 wt. % in methanol, 0.93 mL, 4.03 mmol) at 0° C. The mixture was stirred at room temperature for 1 h, and cooled to 0° C. Aq. 6 N HCl (0.67 mL, 4.02 mmol), EtOH (2.5 mL), and hydroxylamine hydrochloride (28 mg, 0.40 mmol) were added sequentially. The mixture was heated at 55° C. for 3 h. EtOAc was added. The mixture was washed with aq. sat. $NaHCO_3$. The organic extract was dried with $Na_2SO_4$, filtered and concentrated. The residue was purified by flash chromatography (silica gel, eluting with 0% to 50% EtOAc in hexanes) to give compound 15d (63 mg, 65% yield). m/z=363 (M+1).

Compound 16d: Compound 15d (63 mg, 0.17 mmol) was dissolved in MeOH (1.7 mL). Sodium methoxide (25 wt. % in methanol, 60 µL, 0.26 mmol) was added. The reaction mixture was stirred at 55° C. for 1 h, and cooled to rt. EtOAc was added. The mixture was washed with aq. 10% $KH_2PO_4$. The organic extract was dried with $Na_2SO_4$ and concentrated. The residue was purified by flash chromatography (silica gel, eluting with 0% to 35% acetone in hexanes) to give compound 16d (68 mg, quantitative yield) as a white solid. m/z=363 (M+1).

T5: Compound 16d (60 mg, 0.17 mmol) was dissolved in benzene (3.3 mL). DDQ (41 mg, 0.18 mmol) was added. The mixture was heated at 85° C. for 40 min, and was cooled to room temperature. $CH_2Cl_2$ was added. The mixture was washed with aq. sat. $NaHCO_3$. The organic extract was dried with $Na_2SO_4$, and concentrated. The residue was purified by flash chromatography (silica gel, eluting with 0% to 35% acetone in hexanes) to give compound T5 (30 mg, 50% yield) as a white solid. $^1$H NMR (400 MHz, $CDCl_3$) δ 8.96 (s, 1H), 8.79 (m, 2H), 8.30 (m, 2H), 4.14 (s, 3H), 2.90 (dd, J=5.9, 19.1 Hz, 1H), 2.63 (m, 2H), 2.15 (m, 2H), 1.77 (dq, J=6.8, 13.5 Hz, 1H), 1.47 (s, 3H), 1.33 (d, J=6.8 Hz, 3H); m/z=361 (M+1).

Compound 14e: Compound 13 (50 mg, 0.17 mmol), 2-fluoropyridine-4-boronic acid (36 mg, 0.26 mmol), triphenylphosphine (17 mg, 0.065 mmol), potassium phosphate (108 mg, 0.51 mmol) and palladium acetate (8 mg, 0.036 mmol) were weighed in a vial, and kept under vacuum. 1,2-dimethoxyethane (0.73 mL) and DMF (0.37 mL) (sparged with nitrogen for 5 min) were added. The vial was filled with nitrogen, and was heated in Biotage® microwave synthesizer at 100° C. for 100 min. The mixture was cooled to room temperature, filtered through a silica gel plug, and eluted with EtOAc. The filtrate was washed with water. The organic extract was dried with $Na_2SO_4$, and concentrated. The residue was purified by flash chromatography (silica gel, eluting with 0% to 20% EtOAc in hexanes) to give compound 14e (58 mg, 96% yield) as a white solid. m/z=356 (M+1).

Compound 15e: To a stirred solution of compound 14e (53 mg, 0.15 mmol) in ethyl formate (0.36 mL) was added sodium methoxide (25 wt. % in methanol, 0.52 mL, 2.25 mmol) at 0° C. The mixture was stirred at room temperature for 1 h, and cooled to 0° C. Aq. 6 N HCl (0.37 mL, 2.22 mmol), EtOH (1.5 mL), and hydroxylamine hydrochloride (16 mg, 0.23 mmol) were added sequentially. The mixture was heated at 55° C. for 16 h. EtOAc was added. The mixture was washed with aq. sat. $NaHCO_3$. The organic extract was dried with $Na_2SO_4$, filtered and concentrated. The residue was purified by flash chromatography (silica gel, eluting with 0% to 5% EtOAc in $CH_2Cl_2$) to give compound 15e (37 mg, 65% yield) as a white solid. m/z=381 (M+1).

Compound 16e: Compound 15e (37 mg, 0.097 mmol) was dissolved in MeOH (2 mL). Potassium carbonate (68 mg, 0.49 mmol) was added. The reaction mixture was stirred at room temperature for 16 h. EtOAc and aq. 1 N HCl (1 mL) were added. The mixture was extracted with EtOAc. The organic extract was washed with water, dried with $Na_2SO_4$ and concentrated. The residue was purified by flash chromatography (silica gel, eluting with 0% to 5% EtOAc in $CH_2Cl_2$) to give compound 16e (32 mg, 86% yield) as a white foamy solid. m/z=381 (M+1).

T6: Compound 16e (27 mg, 0.071 mmol) was dissolved in benzene (1.5 mL). DDQ (18 mg, 0.079 mmol) was added. The mixture was heated at 85° C. for 2 h, and was cooled to room temperature. The reaction mixture was purified by flash chromatography (silica gel, eluting with 0% to 15% acetone in hexanes) to give compound T6 (8 mg, 30% yield) as a yellow foamy solid. $^1$H NMR (400 MHz, $CDCl_3$) δ 8.91 (s, 1H), 8.38 (d, J=5.2 Hz, 1H), 8.21 (td, J=1.6, 5.2 Hz, 1H), 7.93 (s, 1H), 4.14 (s, 3H), 2.91 (dd, J=6.2, 18.9 Hz, 1H), 2.64 (m, 2H), 2.16 (m, 2H), 1.79 (m, 1H), 1.47 (s, 3H), 1.33 (d, J=6.7 Hz, 3H); m/z=379 (M+1).

Compound 17: Compound 13 (100 mg, 0.34 mmol), pyridine-3-boronic acid (62 mg, 0.50 mmol), triphenylphosphine (34 mg, 0.13 mmol), potassium phosphate (216 mg, 1.02 mmol) and palladium acetate (15 mg, 0.067 mmol) in 1,2-dimethoxyethane (1.4 mL) and DMF (0.7 mL) in a microwave vial were sparged with nitrogen for 5 min. The vial was sealed, and heated in Biotage® microwave synthesizer at 100° C. for 5 h. The mixture was cooled to room temperature, filtered through a silica gel plug, and eluted with EtOAc. The filtrate was washed with water. The organic extract was dried with $Na_2SO_4$, and concentrated. The residue was purified by flash chromatography to give compound 17 (106 mg, 92% yield) as a white foamy solid. m/z=338 (M+1).

Compound 18: To a solution of compound 17 (95 mg, 0.28 mmol) in THF (1.4 mL) was added lithium bis(trimethylsilyl)amide solution (1 M in THF, 0.42 mL, 0.42 mmol) at −78° C. After the mixture was stirred at −78° C. for 10 min, phenylselenyl chloride (82 mg, 0.43 mmol) in THF (1.4 mL) was added. The mixture was stirred at −78° C. for an additional 1.5 h. Aq. sat. $NH_4Cl$ was added. The mixture was extracted with EtOAc. The organic extract was dried with $Na_2SO_4$, and concentrated. The residue was purified by flash chromatography to give partially purified product. The product was dissolved in EtOAc (4 mL) and THF (1.2 mL). Hydrogen peroxide (30 wt. % solution in water, 0.14 mL, 1.37 mmol) was added at room temperature. The reaction was stirred for 1 h. Aq. 10% $Na_2SO_3$ was added. The mixture was extracted with EtOAc. The organic extract was washed with water, dried with $Na_2SO_4$, and concentrated. The residue was purified by flash chromatography to give compound 18 (46 mg, 48% yield) as a white solid. m/z=336 (M+1).

Compound 19: A solution of compound 18 (36 mg, 0.11 mmol) and iodine (27 mg, 0.11 mmol) in pyridine (0.5 mL) was heated at 80° C. for 16 h, and was cooled to rt. EtOAc was added. The mixture was washed with aq. 10% $Na_2SO_3$, aq. 1 N HCl and water. The organic extract was dried with $Na_2SO_4$, and concentrated. The residue was purified by flash chromatography (silica gel, eluting with 0% to 40% EtOAc in hexanes) to give compound 19 (23 mg, 46% yield) as a yellow solid. m/z=462 (M+1).

T7: A mixture of compound 19 (21 mg, 0.046 mmol), zinc cyanide (17 mg, 0.14 mmol) in DMF (0.5 mL) was sparged with nitrogen for 2 min. Tetrakis(triphenylphosphine)palladium(0) (6 mg, 0.005 mmol) was added. The nitrogen sparging was continued for another 2 min. The reaction was heated at 80° C. under nitrogen for 1 h, and was cooled to room temperature. EtOAc was added. The mixture was filtered through a pad of Celite®, and eluted with EtOAc. The filtrate was washed with water. The organic extract was dried with $Na_2SO_4$, and concentrated. The residue was purified by flash chromatography (silica gel, eluting with 0% to 30% acetone in hexanes to give compound T7 (2.1 mg, 13% yield) as a foamy solid. $^1$H NMR (400 MHz, CDCl$_3$) δ 9.66 (d, J=2.0 Hz, 1H), 8.96 (s, 1H), 8.72 (m, 2H), 7.44 (m, 1H), 4.12 (s, 3H), 2.88 (dd, J=6.0, 18.8 Hz, 1H), 2.62 (m, 2H), 2.15 (m, 2H), 1.77 (m, 1H), 1.47 (s, 3H), 1.33 (d, J=6.7 Hz, 3H); m/z=361 (M+1).

Compound 20: Compound 13 (60 mg, 0.20 mmol), 4-pyridinamine (38 mg, 0.40 mmol), cesium carbonate (100 mg, 0.31 mmol), Xantphos (8 mg, 0.014 mmol), tris(dibenzylideneacetone)dipalladium(0) (4 mg, 0.004 mmol) were weighed in a vial. The vial was sealed, and kept under vacuum. 1,4-dioxane (1 mL, sparged with nitrogen for 10 min) was added. The vial was filled with nitrogen, heated at 100° C. for 16 h, and cooled to room temperature. Acetone was added. The mixture was filtered through a silica gel pad, and eluted with acetone. The filtrate was concentrated. The residue was purified by flash chromatography (silica gel, eluting with 0% to 100% acetone in hexanes) to give compound 20 (70 mg, 97% yield) as a light yellow solid. m/z=353 (M+1).

Compound 21: To a stirred solution of compound 20 (60 mg, 0.17 mmol) in ethyl formate (0.41 mL) was added sodium methoxide (25 wt. % in methanol, 0.58 mL, 2.51 mmol) at 0° C. The mixture was stirred at room temperature for 1 h, and cooled to 0° C. Aq. 6 N HCl (0.42 mL, 2.52 mmol), EtOH (2 mL), and hydroxylamine hydrochloride (18 mg, 0.26 mmol) were added sequentially. The mixture was heated at 55° C. for 2.5 h. Aq. sat. NaHCO$_3$ was added. The mixture was extracted with EtOAc. The organic extract was dried with $Na_2SO_4$, filtered and concentrated. The residue was purified by flash chromatography (silica gel, eluting with 0% to 70% acetone in hexanes) to give compound 21 (52 mg, 81% yield). m/z=378 (M+1).

Compound 22: Compound 21 (45 mg, 0.12 mmol) was dissolved in MeOH (1.2 mL). Sodium methoxide (25 wt. % in methanol, 42 µL, 0.18 mmol) was added. The reaction mixture was stirred at 55° C. for 2 h, and cooled to rt. EtOAc was added. The mixture was washed with aq. 10% NaH$_2$PO$_4$. The aqueous wash was extracted with EtOAc. The combined organic extract was dried with $Na_2SO_4$ and concentrated to give compound 22 as a light brown foamy solid, which was used in the next step without further purification. m/z=378 (M+1).

T8: Compound 22 (all from above) was dissolved in benzene (2.4 mL). DDQ (30 mg, 0.13 mmol) was added. The mixture was heated at 85° C. for 40 min, and was cooled to room temperature. CH$_2$Cl$_2$ and aq. sat. NaHCO$_3$ were added, and the mixture was stirred at room temperature for 10 min. The mixture was extracted with CH$_2$Cl$_2$. The combined organic extract was dried with $Na_2SO_4$, and concentrated. The residue was purified by flash chromatography (silica gel, eluting with 0% to 100% acetone in CH$_2$Cl$_2$) to give partially purified product, which was purified again by flash chromatography (silica gel, eluting with 0% to 20% MeOH in CH$_2$Cl$_2$) to give compound T8 (11 mg, 25% yield from compound 21) as a yellow foamy solid. $^1$H NMR (400 MHz, CDCl$_3$) δ 8.74 (s, 1H), 8.49 (m, 2H), 7.58 (m, 2H), 7.15 (br s, 1H), 4.04 (s, 3H), 2.77 (ddd, J=1.2, 7.3, 17.8 Hz, 1H), 2.54 (m, 2H), 2.10 (m, 2H), 1.73 (m, 1H), 1.44 (s, 3H), 1.31 (d, J=6.8 Hz, 3H); m/z=376.2 (M+1).

Compound 23: To a stirred solution of compound 13 (117 mg, 0.40 mmol) in ethyl formate (0.96 mL) was added sodium methoxide (25 wt. % in methanol, 0.92 mL, 3.98 mmol) at 0° C. The mixture was stirred at room temperature for 1 h, and cooled to 0° C. Aq. 6 N HCl (0.67 mL, 4.02 mmol), EtOH (4 mL), and hydroxylamine hydrochloride (42 mg, 0.60 mmol) were added sequentially. The mixture was heated at 55° C. for 2 h. The solvent was removed. EtOAc was added. The mixture was washed with water. The organic extract was dried with $Na_2SO_4$, filtered and concentrated. The residue was purified by flash chromatography (silica gel, eluting with 0% to 20% EtOAc in hexanes) to give compound 23 (93 mg, 73% yield). m/z=320 (M+1).

Compound 25: Compound 23 (50 mg, 0.16 mmol), uinolone-4-boronic acid (45 mg, 0.26 mmol), triphenylphosphine (17 mg, 0.065 mmol), potassium phosphate (108 mg, 0.51 mmol) and palladium acetate (7.6 mg, 0.034 mmol) were weighed in a vial, and kept under vacuum. 1,2-dimethoxyethane (0.7 mL) and DMF (0.35 mL) (sparged with nitrogen for 5 min) were added. The vial was filled with nitrogen, and was heated in Biotage® microwave synthesizer at 110° C. for 5 h. The mixture was cooled to room temperature, filtered through a silica gel plug, and eluted with EtOAc. The filtrate was washed with water. The organic extract was dried with $Na_2SO_4$, and concentrated. The residue was purified by flash chromatography (silica gel, eluting with 0% to 50% EtOAc in hexanes) to give partially purified product, which was purified again by flash chromatography (silica gel, eluting with 0% to 10% acetone in CH$_2$Cl$_2$) to give a mixture of compound 24 and 25 (15 mg, 23% yield) as a glassy solid. The mixture was dissolved in MeOH (0.72 mL). Sodium methoxide (25 wt. % in methanol, 13 µL, 0.056 mmol) was added. The reaction mixture was stirred at 55° C. for 1.5 h, and cooled to rt. EtOAc was added. The mixture was washed with aq. 10% KH$_2$PO$_4$. The organic extract was dried with $Na_2SO_4$ and concentrated to give compound 25. m/z=413 (M+1).

T9: Compound 25 (all from above) was dissolved in benzene (0.7 mL). DDQ (9 mg, 0.040 mmol) was added. The mixture was heated at 85° C. for 20 min, and was cooled to room temperature. CH$_2$Cl$_2$ was added. The mixture was washed with aq. sat. NaHCO$_3$. The organic extract was dried with $Na_2SO_4$, and concentrated. The residue was purified by flash chromatography (silica gel, eluting with 0% to 10% acetone in CH$_2$Cl$_2$) to give compound T9 (6 mg, 40% yield) as a white solid. $^1$H NMR (400 MHz, CDCl$_3$) δ 9.08 (d, J=4.8 Hz, 1H), 8.88 (s, 1H), 8.77 (dd, J=0.8, 8.8 Hz, 1H), 8.21 (d, J=8.4 Hz, 1H), 8.00 (d, J=4.4 Hz, 1H), 7.77 (ddd, J=1.4, 6.8, 8.4 Hz, 1H), 7.63 (ddd, J=1.3, 6.8, 8.3 Hz, 1H), 4.12 (s, 3H), 2.95 (dd, J=6.0, 18.8 Hz, 1H), 2.71 (m, 1H), 2.60 (m, 1H), 2.18 (m, 2H), 1.81 (m, 1H), 1.51 (s, 3H), 1.34 (d, J=6.8 Hz, 3H); m/z=411 (M+1).

Compound 26: Compound 13 (100 mg, 0.34 mmol), cesium carbonate (333 mg, 1.02 mmol), potassium t-butyl N-[2-(trifluoroboranuidyl)ethyl]carbamate (85 mg, 0.34 mmol) and [1,1'-bis(diphenylphosphino)ferrocene]dichloropalladium(II) (14 mg, 0.019 mmol) were weighed in a vial. The vial was kept under vacuum. Toluene (3 mL) and water (0.5 mL) (both solvents purged with nitrogen for 5 min) were added. The vial was filled with nitrogen, heated at 100° C. for 16 h, and cooled to room temperature. The mixture was filtered through a pad of Celite®, and eluted with EtOAc. The filtrate was washed with water. The organic extract was dried with $Na_2SO_4$, filtered and concentrated. The residue was purified by flash chromatography (silica gel, eluting with 0% to 30% EtOAc in hexanes) to give compound 26 (105 mg, 77% yield). m/z=404 (M+1).

Compound 27 and 28: To a stirred solution of compound 26 (105 mg, 0.26 mmol) in ethyl formate (0.63 mL) was added sodium methoxide (25 wt. % in methanol, 0.90 mL, 3.90 mmol) at 0° C. The mixture was stirred at room temperature for 1 h, and cooled to 0° C. Aq. 6 N HCl (0.65 mL, 3.90 mmol), EtOH (2.6 mL), and hydroxylamine hydrochloride (28 mg, 0.40 mmol) were added sequentially. The mixture was heated at 55° C. for 2 h. Aq. sat. $NaHCO_3$ was added. The mixture was extracted with EtOAc. The organic extract was dried with $Na_2SO_4$, filtered and concentrated. The residue was purified by flash chromatography (silica gel, eluting with 0% to 100% EtOAc in hexanes) to give compound 27 (28 mg, 25% yield) and compound 28 (42 mg, 45% yield) as white foamy solid. Compound 27: m/z=429 (M+1). Compound 28: m/z=357 (M+1).

Compound 29: Compound 27 (28 mg, 0.065 mmol) was dissolved in MeOH (0.65 mL). Sodium methoxide (25 wt. % in methanol, 23 µL, 0.10 mmol) was added. The reaction mixture was stirred at 55° C. for 1.5 h, and cooled to rt. EtOAc was added. The mixture was washed with aq. 10% $NaH_2PO_4$. The aqueous wash was extracted with EtOAc. The combined organic extract was dried with $Na_2SO_4$ and concentrated to give compound 29, which was used in the next step without further purification. m/z=429 (M+1).

T10: Compound 29 (all from above) was dissolved in toluene (0.65 mL). DDQ (17 mg, 0.075 mmol) was added. The mixture was heated at 90° C. for 50 min, and was cooled to room temperature. $CH_2Cl_2$ and aq. sat. $NaHCO_3$ were added, and the mixture was stirred at room temperature for 10 min. The mixture was extracted with $CH_2Cl_2$. The combined organic extract was dried with $Na_2SO_4$, and concentrated. The residue was purified by flash chromatography (silica gel, eluting with 0% to 15% acetone in hexanes) to give compound T10 (19 mg, 68% yield from compound 27) as an off-white foamy solid. $^1$H NMR (400 MHz, $CDCl_3$) δ 8.82 (s, 1H), 5.17 (br s, 1H), 3.99 (s, 3H), 3.61 (m, 2H), 3.03 (t, J=6.5 Hz, 2H), 2.79 (dd, J=6.7, 18.4 Hz, 1H), 2.54 (m, 2H), 2.09 (m, 2H), 1.71 (m, 1H), 1.44 (s, 9H), 1.39 (s, 3H), 1.30 (d, J=6.7 Hz, 3H); m/z=427 (M+1).

Compound 30: Compound 28 (40 mg, 0.11 mmol) was dissolved in MeOH (1.1 mL). Sodium methoxide (25 wt. % in methanol, 39 µL, 0.17 mmol) was added. The reaction mixture was stirred at 55° C. for 1.5 h, and cooled to rt. EtOAc was added. The mixture was washed with aq. 10% $NaH_2PO_4$. The aqueous wash was extracted with EtOAc. The combined organic extract was dried with $Na_2SO_4$ and concentrated to give compound 30, which was used in the next step without further purification. m/z=357 (M+1).

T11: Compound 30 (all from above) was dissolved in toluene (1.1 mL). DDQ (28 mg, 0.12 mmol) was added. The mixture was heated at 90° C. for 40 min, and was cooled to room temperature. $CH_2Cl_2$ and aq. sat. $NaHCO_3$ were added, and the mixture was stirred at room temperature for 10 min. The mixture was extracted with $CH_2Cl_2$. The combined organic extract was dried with $Na_2SO_4$, and concentrated. The residue was purified by flash chromatography (silica gel, eluting with 0% to 40% acetone in hexanes) to give compound T11 (20 mg, 50% yield from compound 28) as an off-white foamy solid. T11 is 3:1 ratio of formamide tautomers. NMR (400 MHz, $CDCl_3$) δ [8.80 (s), 8.79 (s), 3:1, 1H], [8.19 (br s), 8.09 (d, J=12.1 Hz), 3:1, 1H], [6.15 (br s), 6.00 (br s), 3:1, 1H], 3.99 (s, 3H), 3.80 (m, 2H), 3.08 (t, J=6.4 Hz, 2H), 2.80 (dd, J=6.7, 18.4 Hz, 1H), 2.55 (m, 2H), 2.09 (m, 2H), 1.71 (m, 1H), 1.39 (s, 3H), 1.30 (d, J=6.7 Hz, 3H); m/z=355 (M+1).

T12: To a solution of compound T10 (9 mg, 0.021 mmol) in $CH_2Cl_2$ (0.2 mL) was added TFA (50 µL). The reaction was stirred at room temperature for 1 h, and concentrated. The residue was dissolved in $CH_2Cl_2$, treated with $Et_3N$ (2 drops), and purified by flash chromatography (silica gel, eluting with 0% to 20% MeOH in $CH_2Cl_2$) to give compound T12 (10 mg, quantitative yield) as an off-white foamy solid. $^1$H NMR (400 MHz, $CDCl_3$) δ 8.76 (s, 1H), 8.17 (br s, 2H), 3.95 (s, 3H), 3.49 (m, 2H), 3.22 (t, J=5.9 Hz, 2H), 2.78 (dd, J=6.5, 18.4 Hz, 1H), 2.54 (m, 2H), 2.07 (m, 2H), 1.69 (m, 1H), 1.37 (s, 3H), 1.27 (d, J=6.7 Hz, 3H); m/z=327 (M+1).

Compound 31: To a mixture of 4-amidinopyridine hydrochloride (318 mg, 2.02 mmol) in EtOH (1 mL) was added potassium carbonate (560 mg, 4.06 mmol) and a solution of compound 9 (500 mg, 1.69 mmol) in EtOH (4 mL) sequentially. The reaction was stirred at room temperature for 16 h, and was concentrated. EtOAc (20 mL) and water (2 mL) were added. The mixture was stirred at 65° C. for 10 min, and was cooled to room temperature. Aq. 10% $NaH_2PO_4$ (10 mL) was added, and the mixture was stirred at room temperature for another 5 min. The mixture was extracted with EtOAc. The combined organic extract was dried with $Na_2SO_4$, and concentrated. The residue was purified by flash chromatography (silica gel, eluting with 0% to 20% MeOH in $CH_2Cl_2$) to give compound 31 (400 mg, 65% yield) as a white foamy solid. m/z=368 (M+1).

Compound 32: To a solution of compound 31 (938 mg, 2.56 mmol) in toluene (5 mL) was added phosphorus (V) oxychloride (2.36 mL, 25.6 mmol) at room temperature. The mixture was heated at 100° C. for 1 h, and cooled to room temperature. Aq. sat. $NaHCO_3$ was added slowly to adjust the pH to 7. The mixture was extracted with EtOAc. The combined organic extract was washed with aq. sat. $NaHCO_3$, dried with $Na_2SO_4$, and concentrated. The residue was purified by flash chromatography (silica gel, eluting with 0% to 100% acetone in hexanes) to give compound 32 (618 mg, 71% yield) as an off-white solid. m/z=342 (M+1).

Compound 33: A mixture of compound 32 (618 mg, 1.81 mmol), phenylboronic acid (331 mg, 2.71 mmol), sodium carbonate (575 mg, 5.42 mmol) in 1,4-dioxane (14 mL) and water (5 mL) were sparged with nitrogen for 5 min. [1,1'-bis(diphenylphosphino)-ferrocene]-dichloropalladium(II) (265 mg, 0.36 mmol) was added. The mixture was sparged with nitrogen for another 5 min, heated in Biotage® microwave synthesizer at 100° C. for 1 h, and cooled to room temperature. EtOAc and water were added. The mixture was filtered through a plug of Celite®, and eluted with EtOAc. The filtrate was washed with water. The organic extract was dried with $Na_2SO_4$, filtered and concentrated. The residue was purified by flash chromatography (silica gel, eluting with 0% to 100% EtOAc in hexanes) to give compound 33 (640 mg, 92% yield) as a white foamy solid. m/z=384 (M+1).

Compound 34: To a stirred solution of compound 33 (3.01 g, 7.87 mmol) in ethyl formate (19 mL) was added sodium methoxide (25 wt. % in methanol, 27 mL, 116.9 mmol) at 0° C. The mixture was stirred at room temperature for 1 h, and cooled to 0° C. Aq. 6 N HCl (20 mL, 120 mmol), EtOH (79 mL), and hydroxylamine hydrochloride (830 mg, 11.9 mmol) were added sequentially. The mixture was heated at 55° C. for 4 h, and was concentrated. Aq. sat. NaHCO$_3$ was added. The mixture was extracted with EtOAc. The organic extract was dried with Na$_2$SO$_4$, filtered and concentrated. The residue was purified by flash chromatography (silica gel, eluting with 0% to 100% EtOAc in hexanes) to give compound 34 (2.62 g, 82% yield) as a white foamy solid. m/z=409 (M+1).

T13: Compound 34 (2.617 g, 6.41 mmol) was dissolved in MeOH (32 mL). Sodium methoxide (25 wt. % in methanol, 2.3 mL, 9.96 mmol) was added. The reaction mixture was stirred at 55° C. for 2 h, and cooled to rt. MTBE and aq. 10% NaH$_2$PO$_4$ were added. The mixture was extracted with EtOAc. The combined organic extract was dried with Na$_2$SO$_4$ and concentrated. The residue was purified by flash chromatography (silica gel, eluting with 0% to 50% acetone in hexanes) to give compound T13 (2.363 g, 90% yield) as a light yellow foamy solid. $^1$H NMR (400 MHz, CDCl$_3$) δ 8.76 (m, 2H), 8.34 (m, 2H), 7.60 (m, 2H), 7.51 (m, 3H), 3.92 (dd, J=5.7, 13.8 Hz, 1H), 3.59 (dd, J=5.7, 13.7 Hz, 1H), 2.95 (m, 2H), 2.60 (qd, J=6.5, 12.9 Hz, 1H), 2.28 (t, J=13.8 Hz, 1H), 2.05 (m, 1H), 1.90 (dt, J=2.7, 12.4 Hz, 1H), 1.69 (m, 1H), 1.54 (s, 3H), 1.20 (d, J=6.4 Hz, 3H); m/z=409 (M+1).

T14 and T15: Compound T13 (2.363 g, 5.79 mmol) was dissolved in anhydrous DMF (14 mL), and the solution was cooled to 0° C. 1,3-dibromo-5,5-dimethylhydantoin (828 mg, 2.90 mmol) in DMF (14 mL) was added. The reaction was stirred at 0° C. for 1 h. Pyridine (1.4 mL, 17.3 mmol) was added. The reaction was heated at 55° C. for 3 h, and cooled to room temperature. EtOAc was added. The mixture was washed with water, aq. 10% Na$_2$SO$_3$ and aq. 10% NaH$_2$PO$_4$. The organic extract was dried with Na$_2$SO$_4$, and concentrated. The residual pyridine was removed by azeotropic evaporation with toluene on rotary evaporator. The residue was purified by flash chromatography (silica gel, eluting with 0% to 50% acetone in hexanes) to give compound T14 (1.515 g, 64% yield) as a white foamy solid. $^1$H NMR (400 MHz, CDCl$_3$) δ 9.02 (s, 1H), 8.80 (m, 2H), 8.37 (m, 2H), 7.60 (m, 2H), 7.53 (m, 3H), 2.99 (m, 2H), 2.62 (m, 1H), 2.27 (dt, J=2.7, 12.8 Hz, 1H), 2.15 (tdd, J=2.7, 6.0, 13.8 Hz, 1H), 1.78 (m, 1H), 1.54 (s, 3H), 1.33 (d, J=6.7 Hz, 3H); m/z=407 (M+1).

From the column, the fractions containing compound T15 were combined and concentrated. The crude was purified by flash chromatography (C18, eluting with 0% to 80% MeCN in water) to give compound T15 (7 mg, 0.3% yield) as a white foamy solid. $^1$H NMR (400 MHz, CDCl$_3$) δ 8.79 (m, 2H), 8.38 (m, 2H), 7.62 (m, 2H), 7.53 (m, 3H), 5.32 (s, 1H), 2.94 (m, 2H), 2.29 (m 2H), 1.99 (m, 1H), 1.61 (tdd, J=6.2, 12.3, 18.6 Hz, 1H), 1.39 (s, 3H), 1.34 (d, J=7.0 Hz, 3H); m/z=423 (M+1).

T16: A solution of compound T14 (100 mg, 0.25 mmol) and hydrido(dimethylphosphinous acid-kP)[hydrogen bis(dimethylphosphinito-kP)]platinum (II) (10 mg, 0.023 mmol) in aq. 90% EtOH/water (2.75 mL) was heated at reflux for 16 h. The mixture was concentrated. The residue was purified by flash chromatography (silica gel, 0 to 50% acetone in CH$_2$Cl$_2$) to give compound T16 (46 mg, 44% yield) as a light yellow foamy solid. $^1$H NMR (400 MHz, CDCl$_3$) δ 9.51 (s, 1H), 8.77 (m, 2H), 8.49 (br s, 1H), 8.42 (m, 2H), 7.60 (m, 2H), 7.52 (m, 3H), 5.69 (br s, 1H), 2.96 (m, 2H), 2.64 (m, 1H), 2.24 (dt, J=2.7, 12.7 Hz, 1H), 2.10 (m, 1H), 1.77 (ddt, J=7.0, 10.6, 13.4 Hz, 1H), 1.52 (s, 3H), 1.32 (d, J=6.7 Hz, 3H); m/z=425 (M+1).

Compound 35: A solution of compound 31 (2.16 g, 5.89 mmol) and aq. 3 N HCl (20 mL, 60 mmol) in MeOH (10 mL) and THF (10 mL) was stirred at room temperature under nitrogen overnight. The sample was concentrated, cooled, basified with aq. 10% NH$_4$OH (50 mL) then extracted with CHCl$_3$ (50 mL). The organic extract was washed with brine (50 mL), dried with MgSO$_4$, filtered and concentrated to give compound 35 (1.80 g, 95% yield) as light yellow solid, which was used directly in the next step without purification. m/z=324 (M+1).

Compound 36: To a stirring solution at room temperature under nitrogen of compound 35 (1.67 g, 5.16 mmol) and ethyl formate (21 mL, 260 mmol) in THF (25 mL) was added sodium methoxide (30 wt. % solution in methanol, 4.8 mL, 25.6 mmol). After stirring for 16 h, the solution was concentrated then partitioned between aq. sat. KH$_2$PO$_4$ (100 mL) and CHCl$_3$ (100 mL). The organic extract was washed with brine (100 mL), dried with MgSO$_4$, filtered and concentrated to give compound 36 (2.09 g) as orange-yellow foamy solid, which was used in the next reaction without purification. m/z=352 (M+1).

Compound 37: A mixture under nitrogen of compound 36 (all from the last step), acetic acid (3 mL, 52.4 mmol) and hydroxylamine hydrochloride (540 mg, 7.77 mmol) in EtOH (25 mL) was heated at 60° C. for 2 h then stirred at room temperature overnight. The solution was concentrated, cooled, carefully basified with aq. sat. NaHCO$_3$ (100 mL) and extracted with CHCl$_3$ (100 mL). The organic extract was washed with brine (100 mL), dried with MgSO$_4$, filtered, and concentrated. The residue was purified by chromatography (silica gel, eluting with 5% MeOH in CHCl$_3$) to give compound 37 (1.29 g, 72% from compound 35) as tan foamy solid. m/z=349 (M+1).

Compound 38: To a stirring solution at room temperature under nitrogen of compound 37 (1.29 g, 3.69 mmol) in methanol (37 mL) was added sodium methoxide (30 wt. % solution in methanol, 3.5 mL, 18.7 mmol). The sample was stirred at room temperature overnight, and concentrated. The residue was partitioned between aq. sat. KH$_2$PO$_4$ (100 mL) and CHCl$_3$ (100 mL). The aqueous phase was back extracted with 20% MeOH in CHCl$_3$ (100 mL). The combined organic extract was dried with MgSO$_4$, filtered and concentrated to give compound 38 (1.03 g, 80% yield) as an off-white solid. m/z=349 (M+1).

T17: To a stirring solution at 0° C. under nitrogen of compound 38 (1.03 g, 2.95 mmol) in DMF (10 mL) was added dropwise a solution of 1,3-dibromo-5,5-dimethylhydantoin (420 mg, 1.47 mmol) in DMF (3 mL). After stirring at 0° C. for 30 min, pyridine (2.4 mL, 29.7 mmol) was added. The ice-bath was removed. The sample was heated at 60° C. for 4 h, cooled, and concentrated. The residue was partitioned between aq. sat. KH$_2$PO$_4$ (50 mL) and 20% MeOH in CHCl$_3$ (50 mL). The organic extract was dried with MgSO$_4$, filtered and concentrated to give compound T17 (1.19 g, quantitative yield) as tan foamy solid. $^1$H NMR (400 MHz, CDCl$_3$) δ 13.33 (br s, 1H), 8.87 (m, 2H), 8.80 (s, 1H), 8.18 (m, 2H), 2.92 (m, 1H), 2.62 (m, 2H), 2.20 (m, 1H), 2.12 (dt, J=2.6, 12.7 Hz, 1H), 1.76 (qdd, J=6.6, 12.9, 19.5 Hz, 1H), 1.48 (s, 3H), 1.33 (d, J=6.7 Hz, 3H); m/z=347 (M+1).

T18: To a stirring solution at room temperature under nitrogen of compound T17 (1.19 g, 2.95 mmol), pyridine (0.84 mL, 10.38 mmol) and 4-dimethylaminopyridine (50 mg) in CH$_2$Cl$_2$ (30 mL) was added dropwise a solution of p-toluenesulfonyl chloride (980 mg, 5.14 mmol) in CH$_2$Cl$_2$ (10 mL). After stirring for 2 days, the sample was concentrated then partitioned between aq. sat. KH$_2$PO$_4$ (50 mL) and CHCl$_3$ (50 mL). The organic extract was washed with brine (50 mL), dried with MgSO$_4$, filtered and concentrated. The residue was purified by flash chromatography (silica gel, eluting with 100% EtOAc then 5% MeOH in EtOAc) to give compound T18 (341 mg, 23% yield) and recover compound T17 (507 mg, 49% yield) as tan solid. T18: NMR (400 MHz, CDCl$_3$) δ 8.84 (s, 1H), 8.77 (m, 2H), 8.01 (m, 4H), 7.43 (m, 2H), 3.07 (ddd, J=1.1, 6.8, 18.9 Hz, 1H), 2.84 (ddd, J=7.6, 11.2, 18.9 Hz, 1H), 2.59 (m, 1H), 2.51 (s, 3H), 2.16 (m, 2H), 1.80 (m, 1H), 1.48 (s, 3H), 1.33 (d, J=6.7 Hz, 3H); m/z=501 (M+1).

Compound 39: Compound 8 (2.5 g, 10.5 mmol) was taken up in THF (100 mL). Benzaldehyde (1.15 g, 10.8 mmol) and sodium methoxide (30 wt. % in methanol, 7.5 g, 41.7 mmol) were added. The mixture was stirred overnight at room temperature. The reaction mixture was neutralized with aq. KH$_2$PO$_4$, and extracted with ethyl acetate. The organic extract was dried with MgSO$_4$ and concentrated to give compound 39 (3.4 g, quantitative yield) as an oil. m/z=327 (M+1).

Compound 40: Compound 39 (3.4 g, 10.4 mmol) was taken up in EtOH (50 mL). Thiourea (6.3 g, 82.8 mmol) and potassium t-butoxide (1.18 g, 10.5 mmol) were added. The reaction mixture was heated at reflux for 16 h, cooled and concentrated. Water (50 mL) was added. The mixture was neutralized with aq. 3 N HCl. The precipitate was collected by filtration, washed with water, and dried under vacuum to give compound 40 (3.8 g, 94% yield) as an off-white solid. m/z=385 (M+1).

Compound 41a: Compound 40 (800 mg, 2.08 mmol) was taken up in 1,4-dioxane (10 mL). Copper(I) thiophene-2-carboxylate (1.2 g, 6.29 mmol), tetrakis(triphenylphosphine) palladium (120 mg, 0.10 mmol) and phenylboronic acid (380 mg, 3.11 mmol) were added. The mixture was bubbled with nitrogen for 10 min, stirred at 100° C. for 16 h, and cooled to room temperature. The reaction mixture was filtered. The filtrate was concentrated. The residue was purified by flash chromatography (silica gel, eluting with 0% to 20% EtOAc in hexanes) to give compound 41a (250 mg, 28% yield) as an oil. m/z=427 (M+1).

Compound 42a: Compound 41a (250 mg, 0.59 mmol) was taken up in THF (6 mL), and aq. 3 N HCl (3 mL, 9.0 mmol) was added. The mixture was stirred overnight at room temperature, and concentrated. The residue was neutralized with aq. sat. NaHCO$_3$, and extracted with EtOAc. The organic extract was washed with water, dried with MgSO$_4$, and concentrated to give compound 42a (220 mg, 98% yield) as a foamy solid. m/z=383 (M+1).

Compound 43a: Compound 42a (220 mg, 0.57 mmol) was taken up in ethyl formate (15 mL, 186.6 mmol). Sodium methoxide (30 wt. % in MeOH, 420 mg, 2.3 mmol) was added. After the reaction mixture was stirred overnight at room temperature, it was neutralized with aq. KH$_2$PO$_4$, and extracted with EtOAc. The organic extract was dried with MgSO$_4$ and concentrated to give compound 43a (240 mg, quantitative yield) as a foamy solid. m/z=411 (M+1).

Compound 44a: Compound 43a (240 mg, 0.57 mmol) was dissolved in EtOH (15 mL). Hydroxylamine hydrochloride (82 mg, 1.18 mmol) was added. The reaction mixture was stirred overnight at 50° C., cooled to room temperature, and concentrated. The residue was taken up in EtOAc, and washed with aq. NaHCO$_3$. The organic extract was dried with MgSO$_4$, and concentrated to give compound 44a (220 mg, 92% yield) as a foamy solid. m/z=408 (M+1).

Compound 45a: Compound 44a (220 mg, 0.54 mmol) was dissolved in THF (5 mL), and sodium methoxide (30 wt. % in MeOH, 390 mg, 2.2 mmol) was added. After reaction mixture was stirred at room temperature overnight, it was neutralized with aq. sat. KH$_2$PO$_4$, and extracted with EtOAc. The organic extract was washed with brine, dried with MgSO$_4$, and concentrated to give compound 45a (220 mg, quantitative yield) as a foamy solid. m/z=408 (M+1).

T19: Compound 45a (220 mg, 0.54 mmol) was dissolved in dry DMF (2 mL), and the solution was cooled to 0° C. Bromine (95 mg, 0.59 mmol) in CH$_2$Cl$_2$ (1 mL) was added, and the reaction was stirred at 0° C. for 2 h. Pyridine (2 mL, 24.8 mmol) was added. The reaction was allowed to warm to room temperature, and stirred at 50° C. for 16 h. The mixture was concentrated. The crude residue was purified by flash chromatography (silica gel, eluting with 0% to 30% EtOAc in hexanes) to give compound T19 (90 mg, 41% yield) as a foamy solid. $^1$H NMR (400 MHz, CDCl$_3$) δ 9.09 (s, 1H), 8.54 (m, 2H), 7.61 (m, 2H), 7.51 (m, 6H), 2.95 (m, 2H), 2.62 (qd, J=6.7, 13.3 Hz, 1H), 2.26 (dt, J=2.7, 12.8 Hz, 1H), 2.13 (m, 1H), 1.77 (ddt, J=7.0, 10.6, 13.3 Hz, 1H), 1.55 (s, 3H), 1.33 (d, J=6.7 Hz, 3H); m/z=406 (M+1).

Compound 41b: Compound 40 (800 mg, 2.08 mmol) was taken up in 1,4-dioxane (10 mL). Copper(I) thiophene-2-carboxylate (1.2 g, 6.29 mmol), tetrakis(triphenylphosphine)-palladium (120 mg, 0.10 mmol) and 4-(trifloromethyl)phenylboronic acid (590 mg, 3.11 mmol) were added. The mixture was bubbled with nitrogen for 10 min, stirred at 100° C. for 16 h, and cooled to room temperature. The reaction mixture was filtered. The filtrate was concentrated. The residue was purified by flash chromatography (silica gel, 0 to 20% EtOAc in hexanes) to give compound 41b (290 mg, 28% yield) as a white solid. m/z=495 (M+1).

Compound 42b: Compound 41b (290 mg, 0.58 mmol) was taken up in THF (4 mL), and aq. 3 N HCl (2 mL, 6.0 mmol) was added. The mixture was stirred overnight at room temperature then concentrated. The residue was neutralized with aq. sat. NaHCO$_3$, and extracted with EtOAc. The organic extract was washed with water, dried with MgSO$_4$, and concentrated to give compound 42b (265 mg, quantitative yield) as a foamy solid. m/z=451 (M+1).

Compound 43b: Compound 42b (265 mg, 0.58 mmol) was taken up in ethyl formate (15 mL, 186.6 mmol). Sodium methoxide (30 wt. % in MeOH, 425 mg, 2.4 mmol) was added. After reaction mixture was stirred at room temperature overnight, it was neutralized with aq. sat. KH$_2$PO$_4$, and extracted with EtOAc. The organic extract was dried with MgSO$_4$ and concentrated to give compound 43b (280 mg, quantitative yield) as a foamy solid. m/z=479 (M+1).

Compound 44b: Compound 43b (280 mg, 0.58 mmol) was dissolved in EtOH (15 mL). Hydroxylamine hydrochloride (82 mg, 1.18 mmol) was added. The reaction mixture was stirred overnight at 50° C., cooled to room temperature, and concentrated. The residue was taken up in EtOAc, then washed with aq. NaHCO$_3$. The organic extract was dried with MgSO$_4$, and concentrated to give compound 44b (270 mg, 97% yield) as a foamy solid. m/z=476 (M+1).

Compound 45b: Compound 44b (270 mg, 0.57 mmol) was dissolved in THF (5 mL), and sodium methoxide (30 wt. % in MeOH, 400 mg, 2.2 mmol) was added. After reaction mixture was stirred at room temperature overnight, it was neutralized with aq. sat. KH$_2$PO$_4$, and extracted with EtOAc. The organic extract was washed with brine, then dried with MgSO$_4$, and concentrated to give compound 45b (270 mg, quantitative yield) as a foamy solid. m/z=476 (M+1).

T20: Compound 45b (270 mg, 0.57 mmol) was dissolved in dry DMF (2 mL), and the solution was cooled to 0° C. Bromine (100 mg, 0.63 mmol) in CH$_2$Cl$_2$ (1 mL) was added, and the reaction was stirred at 0° C. for 2 h. Pyridine (2 mL, 24.8 mmol) was added, and the reaction was allowed to warm to room temperature, and stirred at 50° C. for 16 h.

The reaction mixture was concentrated. The crude residue was purified by flash chromatography (silica gel, eluting with 0% to 30% EtOAc in hexanes) to give compound T20 (105 mg, 39% yield) as a foamy solid. $^1$H NMR (400 MHz, CDCl$_3$) δ 9.04 (s, 1H), 8.65 (d, J=7.9 Hz, 2H), 7.76 (d, J=8.3 Hz, 2H), 7.61 (m, 2H), 7.53 (m, 3H), 2.98 (m, 2H), 2.63 (qd, J=6.7, 13.3 Hz, 1H), 2.27 (dt, J=2.6, 12.7 Hz, 1H), 2.15 (m, 1H), 1.79 (m, 1H), 1.55 (s, 3H), 1.33 (d, J=6.8 Hz, 3H); m/z=474 (M+1).

Compound 46: To a stirring solution at 0° C. under nitrogen of T17 (1.39 g, 4.01 mmol) and uinolonemine (2.8 mL, 20.1 mmol) in CH$_2$Cl$_2$ (80 mL) was added dropwise a solution of trifluoromethanesulfonic anhydride in CH$_2$Cl$_2$ (1.0 M, 6 mL, 6.0 mmol). The sample was stirred at 0° C. for 2.5 h, concentrated then partitioned between aq. sat. KH$_2$PO$_4$ (100 mL) and EtOAc (100 mL). The organic extract was washed with brine (100 mL), dried with MgSO$_4$, filtered, and concentrated. The residue was purified by flash chromatography (silica gel, eluting with 50% EtOAc in hexanes) to give compound 46 (905 mg, 47% yield) as a tan solid. m/z=479 (M+1).

T21: In a sealable vial, a mixture of compound 46 (195 mg, 0.408 mmol), 4-(hydroxymethyl)phenylboronic acid (124 mg, 0.82 mmol) and potassium carbonate (170 mg, 1.23 mmol) in 1,4-dioxane (8 mL) was degassed. 1,1'-[bis(diphenylphosphino)-ferrocene]palladium (II) dichloride (30 mg, 0.041 mmol) was added, and the mixture was degassed again. The vial was sealed and heated at 90° C. for 48 h. The dark sample was cooled and concentrated. The residue was partitioned between aq. sat. KH$_2$PO$_4$ (50 mL) and EtOAc (50 mL). The organic extract was washed with brine (50 mL), dried with MgSO$_4$, filtered, and concentrated. The residue was purified by flash chromatography (silica gel, eluting with 100% EtOAc) to give partially purified product, which was purified again by flash chromatography (silica gel, eluting with 5% MeOH in CHCl$_3$) to give compound T21 (20 mg, 11% yield) as an orange solid. $^1$H NMR (400 MHz, CDCl$_3$) δ 9.02 (s, 1H), 8.80 (m, 2H), 8.37 (m, 2H), 7.62 (m, 2H), 7.54 (m, 2H), 4.82 (s, 2H), 3.00 (m, 2H), 2.63 (qd, J=6.7, 13.1 Hz, 1H), 2.26 (m, 1H), 2.15 (m, 1H), 1.78 (ddt, J=7.1, 10.5, 13.3 Hz, 1H), 1.43 (s, 3H), 1.33 (d, J=6.8 Hz, 3H); m/z=437 (M+1).

Compound 47a: Compound 39 (370 mg, 1.13 mmol) was taken up in EtOH (10 mL). Formamidine acetate (240 mg, 2.30 mmol) and potassium t-butoxide (380 mg, 3.39 mmol) were added. The reaction mixture was heated at reflux for 16 h, cooled and concentrated. The residue was mixed with water (20 mL), and neutralized with aq. 3 N HCl. The precipitate was collected by filtration, washed with water, and dried under vacuum to give compound 47a (305 mg, 76% yield) as a solid. m/z=353 (M+1).

Compound 48a: Compound 47a (305 mg, 0.87 mmol) was taken up in CH$_2$Cl$_2$ (10 mL). Manganese (IV) oxide (88%, 400 mg, 4.05 mmol) was added. The mixture was stirred overnight at room temperature, and filtered. The filtrate was concentrated to give compound 48a (260 mg, 86% yield) as a solid. m/z=351 (M+1).

Compound 49a: Compound 48a (400 mg, 1.14 mmol) was taken up in THF (4 mL), and 3 N HCl (2 mL, 6.0 mmol) was added. The mixture was stirred overnight at room temperature and concentrated. The residue was neutralized with aq. sat. NaHCO$_3$, and extracted with EtOAc. The organic extract was washed with water, then dried with MgSO$_4$, and concentrated to give compound 49a (350 mg, quantitative yield) as a foamy solid. m/z=307 (M+1).

Compound 50a: Compound 49a (350 mg, 1.14 mmol) was taken up in ethyl formate (15 mL, 186.6 mmol). Sodium methoxide (30 wt. % in methanol, 800 mg, 4.44 mmol) was added. After the mixture was stirred overnight at room temperature, it was neutralized with aq. KH$_2$PO$_4$, and extracted with EtOAc. The organic extract was dried with MgSO$_4$ and concentrated to give compound 50a (380 mg, 99% yield) as a foamy solid. m/z=335 (M+1).

Compound 51a: Compound 50a (380 mg, 1.14 mmol) was dissolved in EtOH (15 mL).

Hydroxylamine hydrochloride (140 mg, 2.01 mmol) was added. The reaction mixture was stirred overnight at 50° C., cooled room temperature, and concentrated. The residue was taken up in EtOAc, and washed with aq. NaHCO$_3$. The organic extract was dried with MgSO$_4$, and concentrated to give compound 51a (340 mg, 90% yield) as a foamy solid. m/z=332 (M+1).

Compound 52a: Compound 51a (340 mg, 1.03 mmol) was dissolved in THF (5 mL), and sodium methoxide (30 wt. % in MeOH, 800 mg, 4.44 mmol) was added. After the reaction mixture was stirred at room temperature overnight, it was neutralized with aq. sat. KH$_2$PO$_4$, and extracted with EtOAc. The organic extract was washed with brine, then dried with MgSO$_4$, and concentrated to give compound 52a (340 mg, quantitative yield) as a foamy solid. m/z=332 (M+1).

T22: Compound 52a (340 mg, 1.03 mmol) was dissolved in dry DMF (2 mL), and the solution was cooled to 0° C. Bromine (180 mg, 1.13 mmol) in CH$_2$Cl$_2$ (1 mL) was added, and the reaction stirred at 0° C. for 2 h. Pyridine (2 mL, 24.8 mmol) was added. The reaction was allowed to warm to room temperature, and stirred at 50° C. for 16 h. The reaction mixture was concentrated. The crude residue was purified by flash chromatography (silica gel, eluting with 0% to 35% EtOAc in hexanes) to give compound T22 (150 mg, 44% yield) as a foamy solid. NMR (400 MHz, CDCl$_3$) δ 9.12 (s, 1H), 8.91 (s, 1H), 7.49 (m, 5H), 2.93 (m, 2H), 2.59 (qd, J=6.7, 13.4 Hz, 1H), 2.21 (dt, J=2.7, 12.8 Hz, 1H), 2.10 (m, 1H), 1.74 (m, 1H), 1.48 (s, 3H), 1.30 (d, J=6.7 Hz, 3H); m/z=330 (M+1).

Compound 47b: Compound 39 (780 mg, 2.39 mmol) was taken up in EtOH (10 mL). Cyclohexanecarboximidamide HCl salt (650 mg, 4.00 mmol) and potassium t-butoxide (560 mg, 4.99 mmol) were added. The reaction mixture was heated at reflux for 16 h, cooled and concentrated. The residue was mixed with water (20 mL), neutralized with aq. 3 N HCl, and extracted with EtOAc. The organic extract was washed with brine, then dried with MgSO$_4$, and concentrated to give compound 47b (1.05 g, quantitative yield) as an oil. m/z=435 (M+1).

Compound 48b: Compound 47b (1.05 g, 2.42 mmol) was taken up in CH$_2$Cl$_2$ (20 mL). Manganese (IV) oxide (88%, 600 mg, 6.07 mmol) was added. The mixture was stirred for 3 days at room temperature, and filtered. The filtrate was concentrated to give compound 48b (900 mg, 86% yield) as a solid. m/z=433 (M+1).

Compound 49b: Compound 48b (900 mg, 2.08 mmol) was taken up in THF (6 mL), and aq. 3 N HCl (3 mL, 9.0 mmol) was added. The mixture was stirred overnight at room temperature, and concentrated. The residue was neutralized with aq. sat. NaHCO$_3$, and extracted with EtOAc. The organic extract was washed with water, then dried with MgSO$_4$, and concentrated to give compound 49b (700 mg, 86% yield) as a foamy solid. m/z=389 (M+1).

Compound 50b: Compound 49b (700 mg, 1.8 mmol) was taken up in ethyl formate (15 mL, 187.5 mmol). Sodium methoxide (30 wt. % in methanol, 1300 mg, 7.2 mmol) was added. The mixture was stirred overnight at room temperature. The reaction mixture was neutralized with aq. KH$_2$PO$_4$, and extracted with ethyl acetate. The organic extract was dried with MgSO$_4$ and concentrated to give a foam compound 50b (745 mg, quantitative yield). m/z=417 (M+1).

Compound 51b: Compound 50b (745 mg, 1.80 mmol) was dissolved in EtOH (20 mL). Hydroxylamine hydrochloride (245 mg, 3.52 mmol) was added. The reaction mixture was stirred overnight at 50° C., cooled to room temperature, and concentrated. The residue was taken up in EtOAc, and washed with aq. NaHCO$_3$. The organic extract was dried with MgSO$_4$, and concentrated to give compound 51b (650 mg, 88% yield) as a foamy solid. m/z=414 (M+1).

Compound 52b: Compound 51b (650 mg, 1.57 mmol) was dissolved in THF (5 mL), and sodium methoxide (30 wt. % in MeOH, 1100 mg, 6.11 mmol) was added. After the reaction mixture was stirred at room temperature overnight, it was neutralized with aq. sat. KH$_2$PO$_4$, and extracted with EtOAc. The organic extract was washed with brine, then dried with MgSO$_4$, and concentrated. The crude residue was purified by flash chromatography (silica gel, eluting with 0% to 30% EtOAc in hexanes) to give compound 52b (350 mg, 54% yield) as a foamy solid. m/z=414 (M+1).

T23: Compound 52b (350 mg, 0.84 mmol) was dissolved in dry DMF (2 mL), and the solution was cooled to 0° C. Bromine (150 mg, 0.94 mmol) in CH$_2$Cl$_2$ (1 mL) was added, and the reaction stirred at 0° C. for 2 h. Pyridine (2 ml, 24.8 mmol) was added. The reaction was allowed to warm to room temperature, and stirred at 50° C. for 16 h. The reaction mixture was concentrated. The crude residue was purified by flash chromatography (silica gel, eluting with 0% to 30% EtOAc in hexanes) to give compound T23 (150 mg, 43% yield) as a foamy solid. $^1$H NMR (400 MHz, CDCl$_3$) δ 8.96 (s, 1H), 7.47 (m, 5H), 2.88 (m, 3H), 2.58 (qd, J=6.7, 13.4 Hz, 1H), 2.19 (dt, J=2.7, 12.8 Hz, 1H), 2.05 (m, 3H), 1.87 (m, 2H), 1.73 (m, 4H), 1.46 (s, 3H), 1.39 (m, 3H), 1.29 (d, J=6.7 Hz, 3H); m/z=412 (M+1).

Compound 53: To a stirring solution at 0° C. under nitrogen of compound 31 (1.00 g, 2.72 mmol) and uinolonemine (1.9 mL, 13.6 mmol) in CH$_2$Cl$_2$ (27 mL) was added dropwise a solution of trifluoromethanesulfonic anhydride in CH$_2$Cl$_2$ (1.0 M, 4 mL, 4.0 mmol). The sample was stirred at 0° C. for 45 min, and concentrated. The residue was partitioned between aq. sat. KH$_2$PO$_4$ (100 mL) and EtOAc (100 mL). The organic extract was washed with brine (100 mL), dried with MgSO$_4$, filtered, and concentrated. The residue was purified by flash chromatography (silica gel, eluting with 50% EtOAc in hexanes) to give compound 53 (322 mg, 24% yield) as a tan solid. m/z=500 (M+1).

Compound 54: In a sealable vial, a mixture of compound 53 (257 mg, 0.514 mmol), 4-(trifluoromethyl)phenylboronic acid (147 mg, 0.774 mmol) and potassium phosphate (330 mg, 1.55 mmol) in DME (10 mL) was degassed. Tetrakis(triphenylphosphine)palladium(O) (59 mg, 0.051 mmol) was added, and the mixture was degassed again. The vial was sealed and heated at 90° C. for 16 h. The dark sample was cooled, and concentrated. The residue was partitioned between aq. sat. KH$_2$PO$_4$ (50 mL) and EtOAc (50 mL). The organic extract was washed with brine (50 mL), dried with MgSO$_4$, filtered, and concentrated. The residue was purified by flash chromatography (silica gel, eluting with 50% EtOAc in hexanes) to give compound 54 (106 mg, 41% yield) as a tan foamy solid. m/z=496 (M+1).

Compound 55: A solution of compound 54 (106 mg, 0.214 mmol) and aq. 3 N HCl (0.7 mL, 2.1 mmol) in MeOH (20 mL) was stirred at room temperature under nitrogen overnight. The sample was concentrated, cooled, basified with aq. 10% NH$_4$OH (25 mL) then extracted with CHCl$_3$ (2×25 mL). The combined organic extract was washed with brine (25 mL), dried with MgSO$_4$, filtered and concentrated to give compound 55 (95 mg, 98% yield) as a tan foamy solid, which was used directly in the next step without purification. m/z=452 (M+1).

Compound 56: To a stirring solution at room temperature under nitrogen of compound 55 (95 mg, 0.21 mmol) in ethyl formate (2.0 mL, 24.8 mmol) was added sodium methoxide (30 wt. % solution in MeOH, 0.20 mL, 1.07 mmol). After 16 h, the solution was concentrated, and then partitioned between aq. sat. KH$_2$PO$_4$ (10 mL) and CHCl$_3$ (10 mL). The organic extract was washed with brine (10 mL), dried with MgSO$_4$, filtered and concentrated to give compound 56 (112 mg) as a yellow oil, which was used in the next reaction without purification. m/z=480 (M+1).

Compound 57: A mixture under nitrogen of compound 56 (all from the last step), and hydroxylamine hydrochloride (37 mg, 0.53 mmol) in EtOH (2 mL) was heated at 60° C. for 2 h, and then stirred at room temperature overnight. The solution was concentrated, cooled, carefully basified with aq. sat. NaHCO$_3$ (25 mL) and extracted with CHCl$_3$ (25 mL). The organic extract was washed with brine (25 mL), dried with MgSO$_4$, filtered, and concentrated to give compound 57 (98 mg, 98% yield from compound 55) as a tan foamy solid, which was used in the next reaction without purification. m/z=477 (M+1).

Compound 58: To a stirring solution at room temperature under nitrogen of compound 57 (98 mg, 0.206 mmol) in MeOH (5 mL) was added sodium methoxide (30 wt. % solution in methanol, 0.20 mL, 1.10 mmol). The sample was stirred at room temperature overnight, and concentrated. The residue was partitioned between aq. sat. KH$_2$PO$_4$ (25 mL) and CHCl$_3$ (25 mL). The organic extract was washed with brine (25 mL), dried with MgSO$_4$, filtered, and concentrated. The crude product was purified by flash chromatography (silica gel, eluting with 50% EtOAc in hexanes) to give compound 58 (46 mg, 47% yield) as a yellow oil. m/z=477 (M+1).

T24: To a stirring solution at 0° C. under nitrogen of compound 58 (42 mg, 0.088 mmol) in DMF (3 mL) was added dropwise a solution of 1,3-dibromo-5,5-dimethylhydantoin (13 mg, 0.045 mmol) in DMF (1 mL). After the mixture was stirred at 0° C. for 30 min, pyridine (0.10 mL, 1.24 mmol) was added. The ice-bath was removed. The sample was heated at 60° C. for 4 h, cooled, and concentrated. The residue was partitioned between aq. sat. KH$_2$PO$_4$ (25 mL) and EtOAc (25 mL). The organic extract was washed with brine (25 mL), dried with MgSO$_4$, filtered, and concentrated. The crude product was purified by flash chromatography (silica gel, eluting with 50% EtOAc in hexanes) to give compound T24 (14 mg, 33% yield) as a tan solid. $^1$H NMR (400 MHz, CDCl$_3$) δ 9.01 (s, 1H), 8.81 (d, J=5.2 Hz, 2H), 8.35 (m, 2H), 7.80 (d, J=7.7 Hz, 2H), 7.73 (d, J=7.7 Hz, 2H), 2.96 (m, 2H), 2.64 (qd, J=6.7, 13.4 Hz, 1H), 2.27 (dt, J=2.7, 12.8 Hz, 1H), 2.17 (m, 1H), 1.80 (m, 1H), 1.56 (s, 3H), 1.34 (d, J=6.7 Hz, 3H); m/z=475 (M+1).

Compound 60: In a sealable vial, a suspension of compound 31 (1.31 g, 3.56 mmol) and phosphorus (V) oxychloride (3.3 mL, 35.4 mmol) in toluene (7 mL) was flushed with nitrogen. The vial was sealed and heated at 100° C. for 1 h. The solution was cooled and slowly poured into a stirring suspension of NaHCO$_3$ (15 g, 178 mmol) in water (100 mL). The sample was stirred at room temperature for 20 min, and then extracted with EtOAc (2×100 mL). The organic extract was washed with brine (200 mL), dried with MgSO$_4$, filtered, concentrated. The residue was purified by flash chromatography (silica gel, eluting with 100% EtOAc) to give a mixture of compound 59 and 60 (714 mg) as off-white solid. m/z=386 (59, M+1) and 342 (60, M+1).

A solution of the above mixture of compound 59 and 60 (714 mg) and aq. 3 N HCl (5.5 mL, 16.5 mmol) in MeOH (10 mL) and THF (10 mL) was stirred at room temperature under nitrogen overnight. The sample was concentrated, cooled, basified with aq. 10% $NH_4OH$ to pH 9-10, and then extracted with $CHCl_3$ (2×50 mL). The combined organic extract was washed with brine (50 mL), dried with $MgSO_4$, filtered and concentrated to give compound 60 (616 mg, 50% yield from compound 31) as a light yellow solid. m/z=342 (M+1).

Compound 61a: In a sealable vial, a mixture of compound 60 (243 mg, 0.711 mmol), 3-pyridinylboronic acid (130 mg, 1.06 mmol) and potassium phosphate (450 mg, 2.12 mmol) in 1,4-dioxane (7 mL) was degassed. Tetrakis(triphenylphosphine)palladium(O) (82 mg, 0.071 mmol) was added, and the mixture was degassed again. The vial was sealed and heated at 90° C. for 48 h. The dark sample was cooled, concentrated, and then partitioned between aq. sat. $KH_2PO_4$ (25 mL) and $CHCl_3$ (25 mL). The organic extract was washed with brine (25 mL), dried with $MgSO_4$, filtered, and concentrated. The residue was purified by flash chromatography (silica gel, eluting with 5% MeOH in EtOAc) to give compound 61a (257 mg, 94% yield) as a dark yellow oil. m/z=385 (M+1).

Compound 62a: To a stirring solution at room temperature under nitrogen of compound 61a (257 mg, 0.668 mmol) in ethyl formate (4.5 mL, 55.9 mmol) was added sodium methoxide (30 wt. % solution in MeOH, 0.63 mL, 3.36 mmol). After 16 h, the solution was concentrated, and then partitioned between aq. sat. $KH_2PO_4$ (25 mL) and $CHCl_3$ (25 mL). The organic extract was washed with brine (25 mL), dried with $MgSO_4$, filtered and concentrated to give compound 62a (276 mg, quantitative yield) as a tan foamy solid, which was used in the next reaction without purification. m/z=413 (M+1).

Compound 63a: A mixture under nitrogen of compound 62a (276 mg, 0.668 mmol) and hydroxylamine hydrochloride (230 mg, 3.31 mmol) in EtOH (20 mL) was heated at 60° C. for 2 h, and then stirred at room temperature overnight. The solution was concentrated, cooled, and carefully basified with aq. sat. $NaHCO_3$ (100 mL). The mixture was extracted with $CHCl_3$ (25 mL). The organic extract was washed with brine (25 mL), dried with $MgSO_4$, filtered, and concentrated. The crude product was purified by column and chromatography (silica gel, eluting with 100% EtOAc) to give compound 63a (134 mg, 49% yield) as an off-white solid. m/z=410 (M+1).

Compound 64a: To a stirring solution at room temperature under nitrogen of compound 63a (134 mg, 0.327 mmol) in methanol (5 mL) and THF (5 mL) was added sodium methoxide (30 wt. % solution in MeOH, 0.31 mL, 1.65 mmol). The sample was stirred at room temperature overnight, and concentrated. The residue was partitioned between aq. sat. $KH_2PO_4$ (25 mL) and $CHCl_3$ (25 mL). The organic extract was washed with brine (25 mL), dried with $MgSO_4$, filtered and concentrated to give compound 64a (198 mg) as a yellow oil, which was used in the next reaction without purification. m/z=410 (M+1).

T25: To a stirring solution at 0° C. under nitrogen of compound 64a (all from the last step) in DMF (7 mL) was added dropwise a solution of 1,3-dibromo-5,5-dimethylhydantoin (47 mg, 0.164 mmol) in DMF (3 mL). After stirring at 0° C. for 30 min, pyridine (0.26 mL, 3.21 mmol) was added. The ice-bath was removed. The sample was heated at 60° C. for 4 h, cooled, and concentrated. The residue was partitioned between aq. sat. $KH_2PO_4$ (50 mL) and $CHCl_3$ (50 mL). The organic extract was washed with brine (50 mL), dried with $MgSO_4$, filtered, and concentrated. The crude product was purified by flash chromatography (silica gel, eluting with 5% MeOH in $CHCl_3$) to give compound T25 (68 mg, 51% yield from compound 63a) as off-white solid. $^1$H NMR (400 MHz, $CDCl_3$) δ 9.00 (s, 1H), 8.90 (dd, J=0.9, 2.3 Hz, 1H), 8.82 (m, 2H), 8.77 (dd, J=1.7, 4.9 Hz, 1H), 8.36 (m, 2H), 7.98 (ddd, J=1.7, 2.3, 7.9 Hz, 1H), 7.49 (ddd, J=0.9, 4.9, 7.9 Hz, 1H), 3.02 (m, 2H), 2.64 (qd, J=6.7, 13.4 Hz, 1H), 2.28 (dt, J=2.7, 12.7 Hz, 1H), 2.18 (ddd, J=2.8, 6.1, 12.0 Hz, 1H), 1.82 (ddt, J=7.0, 10.3, 13.5 Hz, 1H), 1.56 (s, 3H), 1.34 (d, J=6.7 Hz, 3H); m/z=408 (M+1).

Compound 61b: In a sealable vial, a mixture of compound 60 (327 mg, 0.956 mmol), 3-(trifluoromethyl)phenylboronic acid (360 mg, 1.90 mmol) and potassium phosphate (610 mg, 2.87 mmol) in DME (6 mL) and DMF (3 mL) was degassed. Tetrakis(triphenylphosphine)-palladium(O) (110 mg, 0.095 mmol) was added, and the mixture was degassed again. The vial was sealed and heated at 90° C. for 48 h. The dark sample was cooled, concentrated, and then partitioned between aq. sat. $KH_2PO_4$ (25 mL) and $CHCl_3$ (25 mL). The organic extract was washed with brine (25 mL), dried with $MgSO_4$, filtered, and concentrated. The residue was purified by flash chromatography (silica gel, eluting with 75% EtOAc in hexanes) to give compound 61b (556 mg) as a dark yellow oil. m/z=452 (M+1).

Compound 62b: To a stirring solution at room temperature under nitrogen of compound 61b (all from the last step) in ethyl formate (10 mL, 123 mmol) was added sodium methoxide (30 wt. % solution in MeOH, 0.90 mL, 4.80 mmol). After 16 h, the solution was concentrated. The residue was partitioned between aq. sat. $KH_2PO_4$ (25 mL) and $CHCl_3$ (25 mL). The organic extract was washed with brine (25 mL), dried with $MgSO_4$, filtered and concentrated to give compound 62b (567 mg) as a yellow-orange foamy solid, which was used in the next reaction without purification. m/z=480 (M+1).

Compound 63b: A mixture under nitrogen of compound 62b (all from the last step) and hydroxylamine hydrochloride (170 mg, 2.45 mmol) in EtOH (20 mL) was heated at 60° C. for 2 h, and then stirred at room temperature overnight. The solution was concentrated, cooled, carefully basified with aq. sat. $NaHCO_3$ (25 mL). The mixture was extracted with $CHCl_3$ (25 mL). The organic extract was washed with brine (25 mL), dried with $MgSO_4$, filtered and concentrated to give compound 63b (512 mg) as a tan foamy solid, which was used in the next reaction without purification. m/z=477 (M+1).

Compound 64b: To a stirring solution at room temperature under nitrogen of compound 63b (all from the last step) in MeOH (25 mL) was added sodium methoxide (30 wt. % solution in methanol, 0.90 mL, 4.80 mmol). The sample was stirred at room temperature overnight, and concentrated. The residue was partitioned between aq. sat. $KH_2PO_4$ (25 mL) and $CHCl_3$ (25 mL). The organic extract was washed with brine (25 mL), dried with $MgSO_4$, filtered and concentrated to give compound 64b (468 mg) as a yellow-orange foamy solid, which was used in the next reaction without purification. m/z=477 (M+1).

T26: To a stirring solution at 0° C. under nitrogen of compound 64b (all from the last step) in DMF (6 mL) was added dropwise a solution of 1,3-dibromo-5,5-dimethylhydantoin (137 mg, 0.479 mmol) in DMF (3 mL). After stirring at 0° C. for 30 min, pyridine (0.77 mL, 9.52 mmol) was added. The ice-bath was removed. The sample was heated at 60° C. for 4 h, cooled, and concentrated. The residue was partitioned between aq. sat. KH$_2$PO$_4$ (50 mL) and CHCl$_3$ (50 mL). The organic extract was washed with brine (50 mL), dried with MgSO$_4$, filtered, and concentrated. The residue was purified by flash chromatography (silica gel, eluting with 75% EtOAc in hexanes) to give partially purified product, which was purified again by flash chromatography (silica gel, eluting with 50% EtOAc in hexanes) to give compound T26 (26 mg, 6% yield from compound 60) as a light yellow foamy solid. $^1$H NMR (400 MHz, CDCl$_3$) δ 9.01 (s, 1H), 8.81 (m, 2H), 8.36 (m, 2H), 7.87 (m, 1H), 7.80 (m, 2H), 7.68 (t, J=7.8 Hz, 1H), 2.95 (m, 2H), 2.64 (qd, J=6.7, 13.4 Hz, 1H), 2.28 (dt, J=2.8, 12.8 Hz, 1H), 2.18 (m, 1H), 1.80 (ddt, J=6.8, 10.8, 13.4 Hz, 1H), 1.55 (s, 3H), 1.34 (d, J=6.7 Hz, 3H); m/z=475 (M+1).

Compound 61c: In a sealable vial, a mixture of compound 60 (200 mg, 0.585 mmol), 4-methylphenylboronic acid (160 mg, 1.17 mmol) and potassium phosphate (370 mg, 1.74 mmol) in 1,4-dioxane (6 mL) was degassed. Tetrakis(triphenylphosphine)palladium(O) (68 mg, 0.059 mmol) was added, and the mixture was degassed again. The vial was sealed and heated at 90° C. for 16 h. The dark sample was cooled, and concentrated. The residue was partitioned between aq. sat. KH$_2$PO$_4$ (50 mL) and EtOAc (50 mL). The organic extract was washed with brine (50 mL), dried with MgSO$_4$, filtered, and concentrated. The crude product was purified by flash chromatography (silica gel, eluting with 50% EtOAc in hexanes) to give compound 6k (273 mg) as a light yellow oil. m/z=398 (M+1).

Compound 62c: To a stirring solution at room temperature under nitrogen of compound 6k (all from the last step) in ethyl formate (10 mL, 123 mmol) was added sodium methoxide (30 wt. % solution in methanol, 0.65 mL, 3.46 mmol). After 16 h, the solution was concentrated. The residue was partitioned between aq. sat. KH$_2$PO$_4$ (50 mL) and CHCl$_3$ (50 mL). The organic extract was washed with brine (50 mL), dried with MgSO$_4$, filtered and concentrated to give compound 62c (269 mg) as a tan foamy solid, which was used in the next reaction without purification. m/z=426 (M+1).

Compound 63c: A mixture under nitrogen of compound 62c (all from the last step) and hydroxylamine hydrochloride (100 mg, 1.44 mmol) in EtOH (20 mL) was heated at 60° C. for 2 h, and then stirred at room temperature overnight. The solution was concentrated, cooled, and carefully basified with sat. NaHCO$_3$ (50 mL). The mixture was extracted with CHCl$_3$ (50 mL). The organic extract was washed with brine (50 mL), dried with MgSO$_4$, filtered and concentrated to give compound 63c (257 mg) as a tan foamy solid, which was used in the next reaction without purification. m/z=423 (M+1).

Compound 64c: To a stirring solution at room temperature under nitrogen of compound 63c (all from the last step) in MeOH (20 mL) was added sodium methoxide (30 wt. % solution in MeOH, 0.57 mL, 3.04 mmol). The sample was stirred at room temperature overnight, and concentrated. The residue was partitioned between aq. sat. KH$_2$PO$_4$ (50 mL) and EtOAc (50 mL). The organic extract was washed with brine (50 mL), dried with MgSO$_4$, filtered and concentrated to give compound 64c (209 mg, 84% yield from compound 60) as tan foamy solid, which was used in the next reaction without purification. m/z=423 (M+1).

T27: To a stirring solution at 0° C. under nitrogen of compound 64c (209 mg, 0.495 mmol) in DMF (6 mL) was added dropwise a solution of 1,3-dibromo-5,5-dimethylhydantoin (71 mg, 0.248 mmol) in DMF (3 mL). After stirring at 0° C. for 30 min, pyridine (0.40 mL, 4.96 mmol) was added. The ice-bath was removed. The sample was heated at 60° C. for 4 h, cooled, and concentrated. The residue was partitioned between aq. sat. KH$_2$PO$_4$ (50 mL) and EtOAc (50 mL). The organic extract was washed with brine (50 mL), dried with MgSO$_4$, filtered, and concentrated. The crude product was purified by flash chromatography (silica gel, eluting with 50% EtOAc in hexanes) to give compound T27 (84 mg, 40% yield) as a light yellow solid. $^1$H NMR (400 MHz, CDCl$_3$) δ 9.02 (s, 1H), 8.79 (m, 2H), 8.37 (m, 2H), 7.52 (d, J=8.4 Hz, 2H), 7.33 (d, J=7.9 Hz, 2H), 3.00 (m, 2H), 2.62 (qd, J=6.7, 13.4 Hz, 1H), 2.46 (s, 3H), 2.26 (dt, J=2.7, 12.8 Hz, 1H), 2.15 (ddd, J=3.2, 6.3, 14.0 Hz, 1H), 1.77 (ddt, J=7.3, 10.3, 13.3 Hz, 1H), 1.54 (s, 3H), 1.33 (d, J=6.7 Hz, 3H); m/z=421 (M+1).

Compound 61d: In a sealable vial, a mixture of compound 60 (200 mg, 0.585 mmol), 4-chlorophenylboronic acid (180 mg, 1.15 mmol) and potassium phosphate (370 mg, 1.74 mmol) in 1,4-dioxane (6 mL) was degassed. Tetrakis(triphenylphosphine)palladium(O) (68 mg, 0.059 mmol) was added, and the mixture was degassed again. The vial was sealed and heated at 90° C. for 16 h. The dark sample was cooled, and concentrated. The residue was partitioned between aq. sat. KH$_2$PO$_4$ (25 mL) and EtOAc (25 mL). The organic extract was washed with brine (25 mL), dried with MgSO$_4$, filtered, and concentrated. The residue was purified by flash chromatography (silica gel, eluting with 50% EtOAc in hexanes) to give compound 61d (224 mg, 92% yield) as a tan foamy solid. m/z=418 (M+1).

Compound 62d: To a stirring solution at room temperature under nitrogen of compound 61d (224 mg, 0.536 mmol) in ethyl formate (10 mL, 123 mmol) was added sodium methoxide (30 wt. % solution in MeOH, 0.50 mL, 2.66 mmol). After 16 h, the solution was concentrated. The residue was partitioned between aq. sat. KH$_2$PO$_4$ (50 mL) and CHCl$_3$ (50 mL). The organic extract was washed with brine (50 mL), dried with MgSO$_4$, filtered and concentrated to give compound 62d (288 mg) as yellow oil, which was used in the next reaction without purification. m/z=446 (M+1).

Compound 63d: A mixture under nitrogen of compound 62d (all from the last step) and hydroxylamine hydrochloride (100 mg, 1.44 mmol) in EtOH (20 mL) was heated at 60° C. for 2 h, and then stirred at room temperature overnight. The solution was concentrated, cooled, and carefully basified with aq. sat. NaHCO$_3$ (50 mL). The mixture was extracted with CHCl$_3$ (50 mL). The organic extract was washed with brine (50 mL), dried with MgSO$_4$, filtered and concentrated to give compound 63d (235 mg, 99% yield from compound 61d) as a light yellow foamy solid, which was used in the next reaction without purification. m/z=443 (M+1).

Compound 64d: To a stirring solution at room temperature under nitrogen of compound 63d (235 mg, 0.530 mmol) in MeOH (20 mL) was added sodium methoxide (30 wt. % solution in MeOH, 0.50 mL, 2.66 mmol). The sample was stirred at room temperature overnight, and concentrated. The residue was partitioned between aq. sat. KH$_2$PO$_4$ (50 mL) and EtOAc (50 mL). The organic extract was washed with brine (50 mL), dried with MgSO$_4$, filtered, and concentrated. The residue was purified by flash chromatography (silica gel, eluting with 75% EtOAc in hexanes) to give compound 64d (130 mg, 55% yield) as a light yellow solid. m/z=443 (M+1).

T28: To a stirring solution at 0° C. under nitrogen of compound 64d (130 mg, 0.293 mmol) in DMF (6 mL) was added dropwise a solution of 1,3-dibromo-5,5-dimethylhydantoin (42 mg, 0.146 mmol) in DMF (3 mL). After stirring the mixture at 0° C. for 30 min, pyridine (0.25 mL, 3.09 mmol) was added. The ice-bath was removed. The sample was heated at 60° C. for 4 h, cooled, and concentrated. The residue was partitioned between aq. sat. $KH_2PO_4$ (50 mL) and EtOAc (50 mL). The organic extract was washed with brine (50 mL), dried with $MgSO_4$, filtered, and concentrated. The crude product was purified by flash chromatography (silica gel, eluting with 50% EtOAc in hexanes), and then washed with $Et_2O$ to give compound T28 (40 mg, 31% yield) as an off-white solid. $^1$H NMR (400 MHz, $CDCl_3$) δ 9.00 (s, 1H), 8.81 (m, 2H), 8.35 (m, 2H), 7.57 (m, 2H), 7.51 (m, 2H), 2.99 (m, 2H), 2.63 (qd, J=6.7, 13.4 Hz, 1H), 2.26 (dt, J=2.7, 12.8 Hz, 1H), 2.16 (tdd, J=2.7, 6.0, 14.0 Hz, 1H), 1.79 (ddt, J=7.1, 10.4, 13.3 Hz, 1H), 1.54 (s, 3H), 1.33 (d, J=6.7 Hz, 3H); m/z=441 (M+1).

Compound 61e: In a sealable vial, a mixture of compound 60 (200 mg, 0.585 mmol), 4-pyridinylboronic acid (140 mg, 1.14 mmol) and potassium phosphate (370 mg, 1.74 mmol) in 1,4-dioxane (6 mL) was degassed. Tetrakis(triphenylphosphine)palladium(O) (68 mg, 0.059 mmol) was added, and the mixture was degassed again. The vial was sealed and heated at 90° C. for 16 h. The dark sample was cooled, and concentrated. The residue was partitioned between aq. sat. $KH_2PO_4$ (25 mL) and EtOAc (25 mL). The organic extract was washed with brine (25 mL), dried with $MgSO_4$, filtered, and concentrated. The crude product was purified by flash chromatography (silica gel, eluting with 0% to 5% MeOH in EtOAc) to give compound 61e (90 mg, 40% yield) as a white foamy solid. m/z=385 (M+1).

Compound 62e: To a stirring solution at room temperature under nitrogen of compound 61e (90 mg, 0.234 mmol) in ethyl formate (10 mL, 123 mmol) was added sodium methoxide (30 wt. % solution in MeOH, 0.22 mL, 1.17 mmol). After 16 h, the solution was concentrated. The residue was partitioned between aq. sat. $KH_2PO_4$ (50 mL) and $CHCl_3$ (50 mL). The organic extract was washed with brine (50 mL), dried with $MgSO_4$, filtered and concentrated to give compound 62e (102 mg) as a tan foamy solid, which was used in the next reaction without purification. m/z=413 (M+1).

Compound 63e: A mixture under nitrogen of compound 62e (all from the last step) and hydroxylamine hydrochloride (41 mg, 0.59 mmol) in EtOH (25 mL) was heated at 60° C. for 2 h, and then stirred at room temperature overnight. The solution was concentrated, cooled, and carefully basified with aq. sat. $NaHCO_3$ (50 mL). The mixture was extracted with $CHCl_3$ (50 mL). The organic extract was washed with brine (50 mL), dried with $MgSO_4$, filtered and concentrated to give compound 63e (72 mg, 75% yield from compound 61e) as a tan foamy solid, which was used in the next reaction without purification. m/z=410 (M+1).

Compound 64e: To a stirring solution at room temperature under nitrogen of compound 63e (72 mg, 0.176 mmol) in MeOH (20 mL) was added sodium methoxide (30 wt. % solution in MeOH, 0.17 mL, 0.91 mmol). The sample was stirred at room temperature overnight, and concentrated. The residue was partitioned between aq. sat. $KH_2PO_4$ (50 mL) and EtOAc (50 mL). The organic extract was washed with brine (50 mL), dried with $MgSO_4$, filtered and concentrated to give compound 64e (58 mg, 80% yield) as a tan foamy solid. m/z=410 (M+1).

T29: To a stirring solution at 0° C. under nitrogen of compound 64e (58 mg, 0.142 mmol) in DMF (5 mL) was added dropwise a solution of 1,3-dibromo-5,5-dimethylhydantoin (20 mg, 0.070 mmol) in DMF (1 mL). After stirring the mixture at 0° C. for 30 min, pyridine (0.11 mL, 1.36 mmol) was added. The ice-bath was removed. The sample was heated at 60° C. for 4 h, cooled, and concentrated. The residue was partitioned between aq. sat. $KH_2PO_4$ (50 mL) and EtOAc (50 mL). The organic extract was washed with brine (50 mL), dried with $MgSO_4$, filtered, and concentrated. The crude product was purified by flash chromatography (silica gel, eluting with 5% MeOH in $CHCl_3$) to give compound T29 (13 mg, 22% yield) as a yellow solid. $^1$H NMR (400 MHz, $CDCl_3$) δ 8.99 (s, 1H), 8.82 (m, 4H), 8.35 (m, 2H), 7.51 (m, 2H), 2.97 (m, 2H), 2.64 (qd, J=6.8, 13.4 Hz, 1H), 2.27 (dt, J=2.7, 12.8 Hz, 1H), 2.19 (m, 1H), 1.82 (m, 1H), 1.55 (s, 3H), 1.34 (d, J=6.8 Hz, 3H); m/z=408 (M+1).

Compound 61f: In a sealable vial, a mixture of compound 60 (200 mg, 0.585 mmol), 4-methoxyphenylboronic acid (180 mg, 1.18 mmol) and potassium phosphate (370 mg, 1.74 mmol) in 1,4-dioxane (6 mL) was degassed. Tetrakis (triphenylphosphine)palladium(O) (68 mg, 0.059 mmol) was added, and the mixture was degassed again. The vial was sealed and heated at 90° C. for 16 h. The dark sample was cooled, and concentrated. The residue was partitioned between aq. sat. $KH_2PO_4$ (50 mL) and EtOAc (50 mL). The organic extract was washed with brine (50 mL), dried with $MgSO_4$, filtered, and concentrated. The crude product was purified by flash chromatography (silica gel, eluting with 50% to 75% EtOAc in hexanes) to give compound 61f (249 mg) as a light yellow oil. m/z=414 (M+1).

Compound 62f: To a stirring solution at room temperature under nitrogen of compound 61f (all from the last step) in ethyl formate (10 mL, 123 mmol) was added sodium methoxide (30 wt. % solution in MeOH, 0.56 mL, 2.98 mmol). After 16 h, the solution was concentrated. The residue was partitioned between aq. sat. $KH_2PO_4$ (50 mL) and EtOAc (50 mL). The organic extract was washed with brine (50 mL), dried with $MgSO_4$, filtered and concentrated to give compound 62f (253 mg, 98% yield from compound 60) as a tan foamy solid, which was used in the next reaction without purification. m/z=442 (M+1).

Compound 63f: A mixture under nitrogen of compound 62f (253 mg, 0.573 mmol) and hydroxylamine hydrochloride (100 mg, 1.44 mmol) in EtOH (20 mL) was heated at 60° C. for 2 h, and then stirred at room temperature overnight. The solution was concentrated, cooled, and carefully basified with aq. sat. $NaHCO_3$ (50 mL). The mixture was extracted with $CHCl_3$ (50 mL). The organic extract was washed with brine (50 mL), dried with $MgSO_4$, filtered and concentrated to give compound 63f (268 mg) as tan foamy solid, which was used in the next reaction without purification. m/z=439 (M+1).

Compound 64f: To a stirring solution at room temperature under nitrogen of compound 63f (all from the last step) in MeOH (20 mL) was added sodium methoxide (30 wt. % solution in methanol, 0.57 mL, 3.04 mmol). The sample was stirred at room temperature overnight, and concentrated. The residue was partitioned between aq. sat. $KH_2PO_4$ (50 mL) and EtOAc (50 mL). The organic extract was washed with brine (50 mL), dried with $MgSO_4$, filtered, and concentrated. The crude product was purified by flash chromatography (silica gel, eluting with 50% EtOAc in hexanes) to give compound 64f (158 mg, 62% yield from compound 62l) as light a yellow oil. m/z=439 (M+1).

T30: To a stirring solution at 0° C. under nitrogen of compound 64f (158 mg, 0.360 mmol) in DMF (5 mL) was added dropwise a solution of 1,3-dibromo-5,5-dimethylhydantoin (52 mg, 0.182 mmol) in DMF (1 mL). After stirring the mixture at 0° C. for 30 min, pyridine (0.30 mL, 3.71 mmol) was added. The ice-bath was removed. The sample was heated at 60° C. for 4 h, cooled, and concentrated. The residue was partitioned between aq. sat. $KH_2PO_4$ (25 mL) and EtOAc (25 mL). The organic extract was washed with brine (25 mL), dried with $MgSO_4$, filtered, and concentrated. The crude product was purified by flash chromatography (silica gel, eluting with 50% EtOAc in hexanes) to give compound T30 (54 mg, 34% yield) as a light yellow foamy solid. $^1H$ NMR (400 MHz, $CDCl_3$) δ 9.02 (s, 1H), 8.80 (m, 2H), 8.37 (m, 2H), 7.63 (m, 2H), 7.04 (m, 2H), 3.90 (s, 3H), 3.04 (m, 2H), 2.63 (qd, J=6.7, 13.3 Hz, 1H), 2.27 (dt, J=2.7, 12.8 Hz, 1H), 2.16 (m, 1H), 1.79 (m, 1H), 1.53 (s, 3H), 1.33 (d, J=6.8 Hz, 3H); m/z=437 (M+1).

Compound 61g: In a sealable vial, a mixture of compound 60 (200 mg, 0.585 mmol), 3,4-dichlorophenylboronic acid (130 mg, 0.68 mmol) and potassium phosphate (370 mg, 1.74 mmol) in 1,4-dioxane (6 mL) was degassed. Tetrakis(triphenylphosphine)palladium(O) (68 mg, 0.059 mmol) was added, and the mixture was degassed again. The vial was sealed and heated at 90° C. for 16 h. The dark sample was cooled, and concentrated. The residue was partitioned between aq. sat. $KH_2PO_4$ (50 mL) and EtOAc (50 mL). The organic extract was washed with brine (50 mL), dried with $MgSO_4$, filtered, and concentrated. The residue was purified by flash chromatography (silica gel, eluting with 50% EtOAc in hexanes) to give compound 61g (206 mg, 78% yield) as a white foamy solid. m/z=452 (M+1).

Compound 62g: To a stirring solution at room temperature under nitrogen of compound 61g (206 mg, 0.455 mmol) in ethyl formate (10 mL, 123 mmol) was added sodium methoxide (30 wt. % solution in MeOH, 0.43 mL, 2.29 mmol). After 16 h, the solution was concentrated. The residue was partitioned between aq. sat. $KH_2PO_4$ (50 mL) and EtOAc (50 mL). The organic extract was washed with brine (50 mL), dried with $MgSO_4$, filtered and concentrated to give compound 62g (234 mg) as yellow oil, which was used in the next reaction without purification. m/z=480 (M+1).

Compound 63g: A mixture under nitrogen of compound 62g (all from the last step) and hydroxylamine hydrochloride (85 mg, 1.22 mmol) in EtOH (20 mL) was heated at 60° C. for 2 h, and then stirred at room temperature overnight. The solution was concentrated, cooled, and carefully basified with aq. sat. $NaHCO_3$ (50 mL). The mixture was extracted with EtOAc (50 mL). The organic extract was washed with brine (50 mL), dried with $MgSO_4$, filtered and concentrated to give compound 63g (200 mg, 92% yield from compound 61g) as a light yellow foamy solid, which was used in the next reaction without purification. m/z=477 (M+1).

Compound 64g: To a stirring solution at room temperature under nitrogen of compound 63g (200 mg, 0.419 mmol) in MeOH (10 mL) and THF (10 mL) was added sodium methoxide (30 wt. % solution in MeOH, 0.39 mL, 2.08 mmol). The sample was stirred at room temperature overnight, and concentrated. The residue was partitioned between aq. sat. $KH_2PO_4$ (50 mL) and EtOAc (50 mL). The organic extract was washed with brine (50 mL), dried with $MgSO_4$, filtered, and concentrated. The crude product was purified by flash chromatography (silica gel, eluting with 50% EtOAc in hexanes) to give compound 64g (128 mg, 64% yield) as a light yellow foamy solid. m/z=477 (M+1).

T31: To a stirring solution at 0° C. under nitrogen of compound 64g (128 mg, 0.268 mmol) in DMF (5 mL) was added dropwise a solution of 1,3-dibromo-5,5-dimethylhydantoin (38 mg, 0.133 mmol) in DMF (1 mL). After stirring the mixture at 0° C. for 30 min, pyridine (0.22 mL, 2.72 mmol) was added. The ice-bath was removed. The sample was heated at 60° C. for 4 h, cooled, and concentrated. The residue was partitioned between aq. sat. $KH_2PO_4$ (25 mL) and EtOAc (25 mL). The organic extract was washed with brine (25 mL), dried with $MgSO_4$, filtered, and concentrated. The crude product was purified by flash chromatography (silica gel, eluting with 50% EtOAc in hexanes) to give compound T31 (74 mg, 58% yield) as a light yellow solid. $^1H$ NMR (400 MHz, $CDCl_3$) δ 8.99 (s, 1H), 8.82 (m, 2H), 8.35 (m, 2H), 7.72 (d, J=2.0 Hz, 1H), 7.61 (d, J=8.4 Hz, 1H), 7.46 (dd, J=2.1, 8.3 Hz, 1H), 2.97 (m, 2H), 2.63 (qd, J=6.7, 13.3 Hz, 1H), 2.23 (m, 2H), 1.80 (ddt, J=7.2, 10.4, 13.3 Hz, 1H), 1.54 (s, 3H), 1.34 (d, J=6.7 Hz, 3H); m/z=475 (M+1).

Compound 65 and 66: Compound 12 (1120 mg, 3.75 mmol) was taken up in 1,4-dioxane (20 mL). Potassium carbonate (770 mg, 5.58 mmol), [1,1'-bis (diphenylphosphino)-ferrocene]dichloropalladium (II) (270 mg, 0.37 mmol) and phenylboronic acid (456 mg, 3.73 mmol) were added. After sparged with nitrogen for 10 min, the mixture was heated at 90° C. for 16 h, cooled, and filtered. The filtrate was concentrated. The residue was purified by flash chromatography (silica gel, eluting with 0% to 30% EtOAc in hexanes) to give compound 65 (830 mg, 65% yield) and compound 66 (220 mg, 17% yield) as foamy solid. Compound 65: m/z=341 (M+1). Compound 66: m/z=341 (M+1).

Compound 67: Compound 65 (830 mg, 2.43 mmol) was taken up in 1,4-dioxane/DMF (3:1, 10 mL). Potassium carbonate (550 mg, 3.99 mmol), [1,1'-bis (diphenylphosphino)-ferrocene]dichloropalladium(II) (190 mg, 0.26 mmol) and quinolin-4-ylboronic acid (450 mg, 2.60 mmol) were added. After sparged with nitrogen for 10 min, the mixture was heated at 100° C. for 16 h, cooled, and filtered. The filtrate was concentrated. The residue was purified by flash chromatography (silica gel, 0 to 30% EtOAc in hexanes) to give compound 67 (160 mg, 15% yield) as a foamy solid. m/z=434 (M+1).

Compound 68: To a stirring mixture of compound 67 (160 mg, 0.37 mmol) in ethyl formate (15 mL, 186.5 mmol) was added sodium methoxide (30 wt. % in MeOH, 300 mg, 1.67 mmol) at room temperature. After overnight stirring, the mixture was neutralized with aq. $KH_2PO_4$, and extracted with EtOAc. The organic extract was dried with $MgSO_4$ and concentrated to give compound 68 (170 mg, quantitative yield) as a foamy solid. m/z=462 (M+1).

Compound 69: Compound 68 (170 mg, 0.37 mmol) was dissolved in EtOH (15 mL). Hydroxylamine hydrochloride (55 mg, 0.79 mmol) was added. The reaction mixture was stirred overnight at 50° C., cooled to room temperature, and concentrated. The residue was taken up in EtOAc, and washed with aq. $NaHCO_3$. The organic extract was dried with $MgSO_4$, and concentrated to give compound 69 (165 mg, 98% yield) as a foamy solid. m/z=459 (M+1).

Compound 70: Compound 69 (165 mg, 0.36 mmol) was dissolved in THF (5 mL), and sodium methoxide (30 wt. % in MeOH, 300 mg, 1.67 mmol) was added at room temperature. After stirring overnight, the reaction mixture was neutralized by the addition of aq. sat. $KH_2PO_4$, and extracted with EtOAc. The organic extract was washed with brine, dried with $MgSO_4$, and concentrated to give compound 70 (165 mg, quantitative yield) as a foamy solid. m/z=459 (M+1).

T32: Compound 70 (165 mg, 0.36 mmol) was dissolved in dry DMF (2 mL), and the solution was cooled to 0° C. Bromine (62 mg, 0.39 mmol) in $CH_2Cl_2$ (1 ml) was added, and the reaction was stirred at 0° C. for 2 h. Pyridine (2 ml, 24.8 mmol) was added. The reaction was allowed to warm to room temperature, and heated at 50° C. for 16 h. The mixture was concentrated. The residue was purified by flash chromatography (silica gel, eluting with 0% to 50% EtOAc in hexanes) to give compound T32 (45 mg, 27% yield) as a foamy solid. $^1$H NMR (400 MHz, CDCl$_3$) δ 9.09 (d, J=4.4 Hz, 1H), 8.95 (s, 1H), 8.74 (dd, J=1.4, 8.7 Hz, 1H), 8.22 (dd, J=0.8, 8.8 Hz, 1H), 8.03 (d, J=4.4 Hz, 1H), 7.78 (ddd, J=1.4, 6.8, 8.4 Hz, 1H), 7.63 (m, 3H), 7.53 (m, 3H), 3.05 (m, 2H), 2.64 (td, J=6.7, 13.4 Hz, 1H), 2.32 (dt, J=2.7, 12.8 Hz, 1H), 2.19 (tdd, J=2.9, 6.1, 12.2 Hz, 1H), 1.84 (m, 1H), 1.59 (s, 3H), 1.35 (d, J=6.7 Hz, 3H); m/z=457 (M+1).

Compound 71: Compound 65 (450 mg, 1.32 mmol) was taken up in 1,4-dioxane/DMF (3:1, 10 mL). Potassium carbonate (550 mg, 3.99 mmol), [1,1'-bis (diphenylphosphino)-ferrocene]dichloropalladium (II) (100 mg, 0.14 mmol) and 2-methoxypyridine-4-boronic acid (400 mg, 2.62 mmol) were added. After sparged with nitrogen for 10 min, the mixture was heated at 100° C. for 16 h, cooled, and filtered. The filtrate was concentrated. The residue was purified by flash chromatography (silica gel, 0 to 50% EtOAc in hexanes) to give compound 71 (510 mg, 93% yield) as a foamy solid. m/z=414 (M+1).

Compound 72: To a stirring mixture of compound 71 (510 mg, 1.23 mmol) in ethyl formate (15 mL, 186.5 mmol) was added sodium methoxide (30 wt. % in MeOH, 900 mg, 5.00 mmol) at room temperature. After overnight stirring, the mixture was neutralized with aq. KH$_2$PO$_4$, and extracted with EtOAc. The organic extract was dried with MgSO$_4$ and concentrated to give compound 72 (545 mg, quantitative yield) as a foamy solid. m/z=442 (M+1).

Compound 73: Compound 72 (545 mg, 1.23 mmol) was dissolved in EtOH (15 mL). Hydroxylamine hydrochloride (175 mg, 2.52 mmol) was added. The reaction mixture was stirred overnight at 50° C., cooled to room temperature, and concentrated. The residue was taken up in EtOAc, and washed with aq. NaHCO$_3$. The organic extract was dried with MgSO$_4$, and concentrated to give compound 73 (540 mg, 99% yield) as a foamy solid. m/z=439 (M+1).

Compound 74: Compound 73 (540 mg, 1.23 mmol) was dissolved in THF (5 mL), and sodium methoxide (30 wt. % in MeOH, 900 mg, 5.00 mmol) was added at room temperature. After stirring overnight, the reaction mixture was neutralized by the addition of aq. sat. KH$_2$PO$_4$, and extracted with EtOAc. The organic extract was washed with brine, dried with MgSO$_4$, and concentrated to give compound 74 (410 mg, 76% yield) as a foamy solid. m/z=439 (M+1).

T33: Compound 74 (410 mg, 0.93 mmol) was dissolved in dry DMF (2 mL), and the solution was cooled to 0° C. Bromine (165 mg, 1.03 mmol) in CH$_2$Cl$_2$ (1 ml) was added, and the reaction was stirred at 0° C. for 2 h. Pyridine (2 ml, 24.8 mmol) was added. The reaction was allowed to warm to room temperature, and heated at 50° C. for 16 h. The mixture was concentrated. The residue was purified by flash chromatography (silica gel, eluting with 0% to 50% EtOAc in hexanes) to give compound T33 (150 mg, 37% yield) as a foamy solid. $^1$H NMR (400 MHz, CDCl$_3$) δ 9.00 (s, 1H), 8.33 (dd, J=0.7, 5.4 Hz, 1H), 7.95 (dd, J=1.4, 5.4 Hz, 1H), 7.85 (dd, J=0.7, 1.5 Hz, 1H), 7.60 (m, 2H), 7.52 (m, 3H), 4.02 (s, 3H), 2.99 (m, 2H), 2.62 (qd, J=6.7, 13.3 Hz, 1H), 2.26 (dt, J=2.7, 12.8 Hz, 1H), 2.14 (tdd, J=2.7, 6.2, 13.9 Hz, 1H), 1.77 (ddt, J=7.0, 10.6, 13.4 Hz, 1H), 1.53 (s, 3H), 1.32 (d, J=6.7 Hz, 3H); m/z=437 (M+1).

Compound 75: Compound 8 (5.04 g, 21.2 mmol) was taken up in CH$_2$Cl$_2$ (200 mL) and magnesium bromide diethyletherate (13.08 g, 50.6 mmol) was added followed by and N,N-diisopropylethylamine (10.8 mL, 62.0 mmol) at room temperature. The mixture was stirred for 30 min, and benzoyl chloride (3.3 mL, 28.4 mmol) was added. The mixture was stirred overnight at room temperature, and then washed with aq. sat. KH$_2$PO$_4$ (100 mL), aq. sat. NaHCO$_3$ (100 mL), and brine. The organic extract was dried over MgSO$_4$, concentrated, and dried under vacuum. The crude product was triturated with hexanes, and the solid was collected by filtration and dried to give of compound 75 (6.91 g, 95% yield) as a tan solid. m/z=343 (M+1).

Compound 76: Compound 75 (1.907 g, 5.57 mmol) and guanidine carbonate (1.20 g, 13.32 mmol) were mixed in EtOH (50 mL), and sodium methoxide (5.4 M solution in MeOH, 2.2 mL, 11.88 mmol) was added. The mixture was heated at reflux overnight, then cooled and concentrated. The residue was partitioned between EtOAc (200 mL) and aq. sat. NaHCO$_3$ (100 mL). The organic extract was washed with brine (50 mL), dried over MgSO$_4$, and concentrated. The residue was purified by flash chromatography (silica gel, eluting with 40% EtOAc in hexanes) to give compound 76 (744 mg, 37% yield) as a light yellow foam. m/z=366 (M+1).

Compound 77: Compound 76 (681 mg, 1.86 mmol) was taken up in MeOH (20 mL) and aq. 1 N HCl (6 mL) was added. The solution was stirred overnight and then concentrated. The residue was partitioned between EtOAc (200 mL) and aq. sat. NaHCO$_3$. The organic extract was washed with brine (30 mL), dried over MgSO$_4$, and concentrated to give compound 77 as a clear glass, which was used directly in the next step. m/z=322 (M+1).

Compound 78 and 79: Compound 77 (all from the last step) was taken up in ethyl formate (20 mL) and sodium methoxide (5.4 M solution in MeOH, 1 mL, 5.4 mmol) was added. The solution was stirred overnight at room temperature, and then partitioned between EtOAc (150 mL) and aq. sat. KH$_2$PO$_4$ (40 mL). The organic extract was dried over MgSO$_4$ and concentrated to give a mixture of compound 78 and compound 79 (0.63 g) as a waxy glass. m/z=350 (M+1, compound 78), 378 (M+1, compound 79).

Compound 80: Compound 78 and compound 79 (0.62 g) were mixed with hydroxylamine hydrochloride (0.376 g, 5.41 mmol) in EtOH (40 mL) and water (2 mL). The mixture was stirred at room temperature overnight, and concentrated. The residue was partitioned between EtOAc (200 mL) and aq. sat. NaHCO$_3$ (50 mL). The organic layer was separated, washed with brine (30 mL), dried over MgSO$_4$, and concentrated to give compound 80 (0.485 g, 75% yield from compound 76) as a foam. m/z=347 (M+1).

Compound 81: Compound 80 (0.485 g, 1.40 mmol) was mixed in THF (30 mL) and MeOH (1 mL). Sodium methoxide (5.4 M solution in MeOH, 1 mL, 5.4 mmol) was added. The solution was stirred overnight at room temperature, and then partitioned between EtOAc (200 mL) and aq. sat. KH$_2$PO$_4$ (100 mL). The organic layer was separated, dried over MgSO$_4$, concentrated, and dried under vacuum to give compound 81 (0.498 g, quantitative yield).

T34: Compound 81 (0.49 g, 1.41 mmol) was taken up in DMF (4 mL) and cooled in an ice bath. 1,3-dibromo-5,5-dimethylhydantoin (0.227 g, 0.79 mmol) was added and the solution was stirred 1 h at 0° C. Pyridine (1 mL, 12.4 mmol) was added and the solution was heated at 65° C. for 3 h and then concentrated. The residue was partitioned between EtOAc (200 mL) and aq. sat. KH$_2$PO$_4$ (50 mL). The organic layer was washed with aq. sat. NaHCO$_3$ (50 mL), brine (50 mL), dried over MgSO$_4$, and concentrated. The residue was purified by flash chromatography (silica gel, eluting with 50% EtOAc in hexanes) to give impure T34 (152 mg), which was purified again by flash chromatography (silica gel, eluting with 10% EtOAc in CH$_2$Cl$_2$) to give compound T34 (18.8 mg, 4% yield) as a yellow foam. $^1$H NMR (400 MHz, CDCl$_3$) δ 8.85 (s, 1H), 7.46 (m, 5H), 4.99 (br s, 2H), 2.70

(m, 2H), 2.53 (td, J=6.7, 13.4 Hz, 1H), 2.14 (dt, J=2.7, 12.8 Hz, 1H), 2.02 (m, 1H), 1.67 (m, 1H), 1.44 (s, 3H), 1.28 (d, J=6.7 Hz, 3H); m/z=345 (M+1).

T35: A mixture of T34 (48 mg, 0.14 mmol), pyridine (0.1 mL, 1.24 mmol), and cyclohexanecarbonyl chloride (48 mg, 0.33 mmol) in $CH_2Cl_2$ (2 mL) was stirred at room temperature overnight. The mixture was concentrated and EtOAc was added. The insoluble material was filtered off, and the filtrate was concentrated. The residue was purified by flash chromatography (silica gel, eluting with 5% EtOAc in $CH_2Cl_2$) to give impure T35, which was taken up in EtOAc, and washed with aq. sat. $NaHCO_3$ and brine. The organic extract was dried over $MgSO_4$, filtered and concentrated. The residue was purified twice by flash chromatography (silica gel, eluting with 5% EtOAc in $CH_2Cl_2$) to give compound T35 (14.8 mg, 23% yield) as a yellow foam. $^1H$ NMR (400 MHz, $CDCl_3$) δ 8.85 (s, 1H), 7.92 (br s, 1H), 7.49 (m, 5H), 2.86 (m, 2H), 2.56 (td, J=6.7, 13.3 Hz, 1H), 2.19 (dt, J=2.7, 12.8 Hz, 1H), 2.13-1.25 (m, 13H), 1.49 (s, 3H), 1.30 (d, J=6.7 Hz, 3H); m/z=455 (M+1).

Compound 82: To a stirring solution at room temperature under nitrogen of compound 8 (2.50 g, 10.49 mmol) and N,N-diisopropylethylamine (5.5 mL, 31.6 mmol) in $CH_2Cl_2$ (52 mL) was added in one portion magnesium bromide diethyl etherate (6.8 g, 26.3 mmol). The suspension was stirred for 30 min, then a solution of phenylacetyl chloride (1.5 mL, 11.3 mmol) in $CH_2Cl_2$ (10 mL) was added dropwise. The sample was stirred at room temperature under nitrogen overnight, and concentrated. The residue was mixed with aq. sat. $KH_2PO_4$ (100 mL) and EtOAc (100 mL), and filtered through a pad of Celite® to remove insoluble material. The layers of the filtrate were separated. The organic extract was washed with brine (100 mL), dried over $MgSO_4$, filtered and concentrated to give crude compound 82 (4.15 g, quantitative yield), which was used directly in the next step without purification. m/z=357 (M+1).

Compound 83: A mixture of compound 82 (2.08 g, assuming 5.25 mmol), 4-amidinopyridine hydrochloride (1.00 g, 6.34 mmol) and potassium carbonate (1.74 g, 12.59 mmol) in EtOH (5 mL) was stirred at room temperature under nitrogen for 5 days. The sample was concentrated, and the residue was partitioned between aq. sat. $KH_2PO_4$ (100 mL) and EtOAc (100 mL). The organic extract was washed with brine (100 mL), dried over $MgSO_4$, filtered, and concentrated. The crude product was purified by flash chromatography (silica gel, eluting with 50% EtOAc in hexanes) to give impure compound 83 (1.92 g, 83% yield from compound 8) as a yellow oil, which was used directly in the next step without purification. m/z=442 (M+1).

Compound 84: A solution of compound 83 (1.92 g, 4.34 mmol) and aq. 3 N HCl (14.5 mL, 43.5 mmol) in MeOH (50 mL) was stirred at room temperature under nitrogen overnight. The sample was concentrated, cooled, and basified with aq. 10% $NH_4OH$ solution (50 mL). The mixture was extracted with $CHCl_3$ (2×25 mL). The combined organic extract was washed with brine (10 mL), dried over $MgSO_4$, filtered, and concentrated. The residue was purified by flash chromatography (silica gel, eluting with 50% EtOAc in hexanes) to give compound 84 (69 mg, 4% yield) as a yellow oil. m/z=398 (M+1).

Compound 85: To a stirring solution at room temperature under nitrogen of compound 84 (69 mg, 0.17 mmol) in ethyl formate (10 mL, 124 mmol) was added sodium methoxide (30 wt. % solution in MeOH, 0.16 mL, 0.85 mmol). After 16 h, the solution was concentrated, and the residue was partitioned between aq. sat. $KH_2PO_4$ (25 mL) and EtOAc (25 mL). The organic extract was washed with brine (25 mL), dried over $MgSO_4$, filtered and concentrated to give compound 85 (73 mg, quantitative yield) as a yellow oil, which was used in the next reaction without purification. m/z=426 (M+1).

Compound 86: A mixture under nitrogen of compound 85 (73 mg, 0.17 mmol), and hydroxylamine hydrochloride (30 mg, 0.43 mmol) in EtOH (20 mL) was heated at 60° C. for 2 h, and then stirred at room temperature overnight. The mixture was concentrated, cooled, carefully basified with aq. sat. $NaHCO_3$ (25 mL), and extracted with EtOAc (25 mL). The organic extract was washed with brine (25 mL), dried over $MgSO_4$, filtered, and concentrated to give compound 86 (67 mg, 93%) as a yellow oil, which was used in the next reaction without purification. m/z=423 (M+1).

Compound 87: To a stirring solution at room temperature under nitrogen of compound 86 (67 mg, 0.16 mmol) in MeOH (10 mL) was added sodium methoxide (30 wt. % solution in MeOH, 0.15 mL, 0.80 mmol). The mixture was stirred at room temperature overnight, and concentrated. The residue was partitioned between aq. sat. $KH_2PO_4$ (25 mL) and EtOAc (25 mL). The organic extract was washed with brine (25 mL) dried over $MgSO_4$, filtered and concentrated to give compound 87 (62 mg, 92%) as a yellow foamy solid, which was used in the next reaction without purification. m/z=423 (M+1).

T36: To a stirring solution at 0° C. under nitrogen of compound 87 (62 mg, 0.15 mmol) in DMF (5 mL) was added dropwise a solution of 1,3-dibromo-5,5-dimethylhydantoin (21 mg, 0.073 mmol) in DMF (1 mL). After stirring the mixture at 0° C. for 30 min, pyridine (0.12 mL, 1.49 mmol) was added. The ice-bath was removed. The mixture was heated at 60° C. for 4 h, cooled, and concentrated. The residue was partitioned between aq. sat. $KH_2PO_4$ (25 mL) and EtOAc (25 mL). The organic extract was washed with brine (25 mL), dried over $MgSO_4$, filtered, and concentrated. The crude product was purified by flash chromatography (silica gel, eluting with 50% EtOAc in hexanes) to give compound T36 (13 mg, 21%) as a light yellow foamy solid. $^1H$ NMR (400 MHz, $CDCl_3$) δ 8.96 (s, 1H), 8.81 (m, 2H), 8.35 (m, 2H), 7.28 (m, 5H), 4.20 (s, 2H), 2.99 (dd, J=5.2, 16.0 Hz, 1H), 2.76 (ddd, J=7.4, 11.1, 18.3 Hz, 1H), 2.58 (qd, 6.8, 13.3 Hz, 1H), 2.13 (m, 2H), 1.79 (dq, J=6.6, 13.1 Hz, 1H), 1.47 (s, 3H), 1.30 (d, J=6.7 Hz, 3H); m/z=421 (M+1).

Compound 88: Compound 8 (10 g, 42.0 mmol) was taken up in EtOH (150 mL). 2-Fluorobenzaldehyde (4.9 mL, 46.2 mmol) and potassium fluoride on aluminum oxide (5.5 mmol/g, 11.5 g, 63.0 mmol) were added. The mixture was stirred overnight at room temperature. The reaction mixture was diluted with $CH_2Cl_2$ and filtered. The filtrate was concentrated, mixed with hexanes. The product was precipitated, filtered and dried under vacuum to give an off-white solid compound 88 (10.8 g, 74% yield). m/z=345 (M+1).

Compound 89 ($MnO_2$): Compound 88 (4.4 g, 12.8 mmol) was taken up in EtOH (100 mL). 4-Quinolinecarboximidamide hydrochloride (4 g, 19.3 mmol) and $K_2CO_3$ (5.35 g, 38.7 mmol) were added. The reaction mixture was heated to reflux for 16 h. The reaction mixture was concentrated and mixed with water (50 mL), neutralized with aq. $KH_2PO_4$, and extracted with ethyl acetate. The organic extract was dried with $MgSO_4$ and concentrated. The crude product was taken up in $CH_2Cl_2$ (25 mL). Manganese (IV) oxide (88%, 10 g, 101.2 mmol) was added. The mixture was stirred overnight at room temperature. The reaction mixture was filtered and concentrated. The crude residue was purified by flash chromatography (silica gel, eluted with 0 to 35%

EtOAc in hexanes) to give compound 89 (6.1 g, 96% yield) as a white foamy solid. m/z=496 (M+1).

Compound 89 (DDQ): Compound 88 (1.10 g, 3.19 mmol), 4-quinolinecarboximidamide hydrochloride (1.00 g, 4.82 mmol) and $K_2CO_3$ (1.33 g, 9.62 mmol) in EtOH (25 mL) were heated at reflux under nitrogen for 16 h. The reaction mixture was concentrated, neutralized with aq. 10% $NaH_2PO_4$, and extracted with EtOAc. The organic extract was dried with $Na_2SO_4$, and concentrated to give the crude product as a dark green foamy solid. The crude product was dissolved in $CH_2Cl_2$ (21 mL). DDQ (796 mg, 3.51 mmol) was added. The reaction was stirred at room temperature for 1 h. Aq. sat. $NaHCO_3$ was added. The mixture was stirred for 5 min, and filtered through a pad of Celite®. The filtrate was extracted with $CH_2Cl_2$. The organic extract was washed with aq. sat. $NaHCO_3$, dried with $Na_2SO_4$, and concentrated. The residue was purified by flash chromatography (silica gel, eluted with 0 to 60% EtOAc in hexanes) to give compound 89 (1.43 g, 90% yield) as a white foamy solid. m/z=496 (M+1).

Compound 90: Compound 89 (6.1 g, 12.3 mmol) was taken up in THF (50 mL). Aq. 3 N HCl (25 mL, 75 mmol) was added. The mixture was stirred overnight at room temperature. After concentrated, the residue was neutralized with aq. sat. $NaHCO_3$, and extracted with EtOAc. The organic extract was washed with water, dried with $MgSO_4$, and concentrated to give compound 90 (5.4 g, 97% yield) as a white foamy solid. m/z=452 (M+1).

Compound 91: Compound 90 (1.828 g, 4.0 mmol) was dissolved in ethyl formate (9.8 mL, 121.9 mmol) and cooled to 0° C. Sodium methoxide (25 wt. % in methanol, 9.4 mL, 41.1 mmol) was added. The mixture was stirred at room temperature for 2 h, and cooled to 0° C. Aq. HCl (6 N, 7.5 mL, 45.0 mmol) was added. The pH of the reaction mixture is ~2 (pH paper). EtOH (40 mL) and hydroxylamine hydrochloride (425 mg, 6.1 mmol) were added sequentially. The mixture was heated at 55° C. (oil bath) for 16 h. The reaction mixture was concentrated. EtOAc (50 mL) and aq. sat. $NaHCO_3$ (50 mL) were added. The organic extract was separated. The aqueous phase was extracted with EtOAc (20 mL). The combined organic extract was dried with $Na_2SO_4$ and concentrated. The residue was purified by flash chromatography (silica gel, eluted with 0% to 60% EtOAc in hexanes) to give compound 91 (1.660 g, 86% yield) as a white foamy solid. m/z=477 (M+1).

Compound 92 (T186): Compound 91 (1.656 g, 3.5 mmol) was dissolved in MeOH (35 mL). Sodium methoxide (25 wt. % in methanol, 1.2 mL, 5.2 mmol) was added. The reaction mixture was stirred at 55° C. for 1.5 h. The reaction was cooled to 0° C., and neutralized by adding aq. 10% $NaH_2PO_4$ (9.4 mL). MeOH was removed by evaporation. EtOAc (50 mL) and water (25 mL) were added. The organic extract was separated. The aqueous phase was extracted with EtOAc (20 mL). The combined organic extract was dried with $Na_2SO_4$ and concentrated. The residue was purified by flash chromatography (silica gel, eluted with 0% to 80% EtOAc in hexanes) to give compound 92 (T186) (1.570 g, 95% yield) as an off-white foamy solid. m/z=477 (M+1); mixture of isomers; the major isomer $^1$H NMR (400 MHz, $CDCl_3$) δ 9.05 (d, J=4.5 Hz, 1H), 8.75 (m, 1H), 8.20 (m, 1H), 8.00 (d, J=4.5 Hz, 1H), 7.76 (m, 1H), 7.62 (m, 1H), 7.49 (m, 2H), 7.32 (m, 1H), 7.22 (m, 1H), 3.90 (dd, J=13.8, 5.7 Hz, 1H), 3.53 (dd, J=13.6, 5.7 Hz, 1H), 2.85 (m, 2H), 2.59 (m, 1H), 2.32 (t, J=13.7 Hz, 1H), 2.07 (m, 1H), 1.95 (td, J=12.4, 2.6 Hz, 1H), 1.75 (m, 1H), 1.59 (s, 3H), 1.21 (d, J=6.4 Hz, 3H).

T37 (Method A): Compound 92 (1.364 g, 2.8 mmol) was dissolved in anhydrous DMF (7 mL), and the solution was cooled to 0° C. 1,3-dibromo-5,5-dimethylhydantoin (409 mg, 1.4 mmol) in DMF (7 mL) was added. The reaction was stirred at 0° C. for 1 h. Pyridine (0.70 mL, 8.7 mmol) was added. The reaction was heated at 55° C. (oil bath) for 3 h, and cooled to room temperature. $CH_2Cl_2$ (50 mL) was added. The mixture was washed with water (4×40 mL). The organic extract was dried with $Na_2SO_4$, and concentrated. The residual pyridine was removed by azeotropic evaporation with toluene (30 mL). The residue was purified by flash chromatography (silica gel, eluted with 0% to 80% EtOAc in hexanes) to give compound T37 (1.190 g, 88% yield) as a light yellow foamy solid. $^1$H NMR (400 MHz, $CDCl_3$) δ 9.09 (d, J=4.5 Hz, 1H), 8.95 (s, 1H), 8.71 (dd, J=1.4, 8.5 Hz, 1H), 8.22 (br d, J=8.4 Hz, 1H), 8.02 (d, J=4.5 Hz, 1H), 7.78 (ddd, J=1.4, 6.9, 8.4 Hz, 1H), 7.64 (ddd, J=1.4, 6.8, 8.4 Hz, 1H), 7.50 (m, 2H), 7.33 (dt, J=1.1, 7.5 Hz, 1H), 7.22 (m, 1H), 2.89 (m, 2H), 2.64 (qd, J=6.7, 13.4 Hz, 1H), 2.31 (dt, J=2.8, 12.8 Hz, 1H), 2.17 (m, 1H), 1.85 (ddd, J=10.3, 15.5, 18.3 Hz, 1H), 1.60 (s, 3H), 1.34 (d, J=6.7 Hz, 3H); m/z=475 (M+1).

T37 and T38 (Method B): Compound 92 (5.2 g, 10.91 mmol) was dissolved in dry DMF (10 mL), and the solution was cooled to 0° C. Bromine (1.92 g, 12.03 mmol) in $CH_2Cl_2$ (2 mL) was added. The reaction was stirred at 0° C. for 2 h, and pyridine (5 mL, 61.96 mmol) was added. The reaction was heated at 50° C. for 4 h, and then concentrated. The residue was mixed with aq. $NaHCO_3$ (30 mL) and EtOAc (10 mL) and stirred for 1 h. The precipitated solid was collected by filtration and washed with water. The solid was dissolved in $CH_2Cl_2$, dried with $MgSO_4$, filtered, and concentrated. The crude product was mixed with EtOAc (60 mL), and heated at reflux overnight. The mixture was cooled; the precipitated solid was collected by filtration; and dried under vacuum give compound T37 (3.1 g, 60% yield) as an off-white solid. m/z=475 (M+1). The filtrate was purified by flash chromatography for three times (silica gel, 0 to 35% EtOAc in hexanes) to give compound T38 (35 mg, 0.7% yield) as a foam. T38: $^1$H NMR (400 MHz, $CDCl_3$) δ 9.09 (d, J=4.5 Hz, 1H), 8.70 (dd, J=0.8, 8.4 Hz, 1H), 8.65 (s, 1H), 8.23 (br d, J=8.8 Hz, 1H), 8.02 (d, J=4.4 Hz, 1H), 7.79 (ddd, J=1.4, 6.8, 8.4 Hz, 1H), 7.65 (ddd, J=1.3, 6.8, 8.3 Hz, 1H), 7.53 (m, 2H), 7.34 (dt, J=1.1, 7.5 Hz, 1H), 7.24 (m, 1H), 3.19 (ddd, J=3.1, 5.0, 13.8 Hz, 1H), 2.98 (m, 2H), 2.70 (m, 1H), 2.08 (s, 3H), 1.89 (s, 3H); m/z=473 (M+1).

Compound 93: Compound 9 (860 mg, 2.90 mmol) was taken up in EtOH (10 mL). Quinoline-4-carboximidamide hydrochloride (1 g, 4.81 mmol) and potassium carbonate (800 mg, 5.80) were added. The reaction mixture was stirred at room temperature for 3 days, and concentrated. The residue was mixed with water (20 mL) and EtOAc (100 mL), heated at 65° C. for 30 min, and cooled to room temperature. The mixture was extracted with EtOAc. The organic extract was dried over $MgSO_4$, filtered and concentrated. The residue was purified by flash chromatography (silica gel, eluting with 0% to 100% EtOAc in hexanes) to give compound 93 (360 mg, 30% yield) as an off-white solid. m/z=418 (M+1).

Compound 94 and 95: Compound 93 (345 mg, 0.83 mmol) was taken up in toluene (2 mL). Phosphorus (V) oxychloride (1.3 g, 8.48 mmol) was added. The mixture was heated in Biotage® Initiator™ microwave synthesizer at 100° C. for 30 min, cooled, and poured into ice. The mixture was extracted with EtOAc. The organic extract was washed with aq. $NaHCO_3$, dried with $MgSO_4$, and concentrated. The residue was purified by flash chromatography (silica gel, eluting with 0% to 50% EtOAc in hexanes) to give a mixture of compound 94 and compound 95 (300 mg) as an off-white solid. m/z=436 (compound 94, M+1) and 392 (compound 95, M+1).

Compound 96a and 97a: A mixture of compound 94 and compound 95 (300 mg) was taken up in 1,4-dioxane (6 mL). Potassium carbonate (290 mg, 2.10 mmol), [1,1'-bis(diphenylphosphino)ferrocene]dichloropalladium(II) (55 mg, 0.075 mmol) and 3-fluorophenylboronic acid (190 mg, 1.36 mmol) were added. After sparged with nitrogen for 10 min, the mixture was heated at 90° C. for 16 h, cooled, and filtered. The filtrate was concentrated. The residue was purified by flash chromatography (silica gel, eluting with 0% to 30% EtOAc in hexanes) to give a mixture of compound 96a and 97a (300 mg) as a foam. m/z=496 (compound 96a, M+1) and 452 (compound 97a, M+1).

Compound 97a: A mixture of compound 96a and 97a (300 mg) was taken up in THF (6 mL), and aq. 3 N HCl (3 mL, 9.0 mmol) was added. The mixture was stirred overnight at room temperature, and concentrated. The residue was neutralized with aq. sat. NaHCO$_3$, and extracted with EtOAc. The organic extract was washed with water, dried with MgSO$_4$, and concentrated to give compound 97a (270 mg, 72% yield from compound 93) as a foam. m/z=452 (M+1).

Compound 98a: Compound 97a (270 mg, 0.60 mmol) was taken up in ethyl formate (15 mL, 186.5 mmol). Sodium methoxide (30 wt. % in methanol, 250 mg, 1.39 mmol) was added. After stirring overnight at room temperature, the reaction mixture was neutralized with aq. KH$_2$PO$_4$, and extracted with EtOAc. The organic extract was dried with MgSO$_4$ and concentrated to give compound 98a (290 mg, quantitative yield) as a foam. m/z=480 (M+1).

Compound 99a: Compound 98a (290 mg, 0.60 mmol) was dissolved in EtOH (15 mL). Hydroxylamine hydrochloride (100 mg, 1.44 mmol) was added. The reaction mixture was stirred overnight at 50° C. After cooling to room temperature, the reaction mixture was concentrated. The residue was taken up in EtOAc, and washed with aq. NaHCO$_3$. The organic extract was dried with MgSO$_4$, and concentrated to give compound 99a (290 mg, quantitative yield) as a foam. m/z=477 (M+1).

Compound 100a: Compound 99a (290 mg, 0.60 mmol) was dissolved in THF (5 mL), and sodium methoxide (30 wt. % in methanol, 250 mg, 1.39 mmol) was added. The reaction mixture was stirred at room temperature overnight, and neutralized by the addition of aq. sat. KH$_2$PO$_4$. The mixture was extracted with EtOAc. The organic extract was washed with brine, dried with MgSO$_4$, and concentrated to give compound 100a (290 mg, quantitative yield) as a foam. m/z=477 (M+1).

T39: Compound 100a (290 mg, 0.60 mmol) was dissolved in dry DMF (2 mL), and the solution was cooled to 0° C. Bromine (110 mg, 0.69 mmol) in CH$_2$Cl$_2$ (1 mL) was added. The reaction was stirred at 0° C. for 2 h. Pyridine (2 ml, 24.8 mmol) was added. The reaction was allowed to warm to room temperature, stirred at 50° C. for 16 h, and concentrated. The residue was purified by flash chromatography (silica gel, eluting with 0% to 35% EtOAc in hexanes) to give compound T39 (80 mg, 28% yield) as a foam. $^1$H NMR (400 MHz, CDCl$_3$) δ 9.09 (d, J=4.4 Hz, 1H), 8.93 (s, 1H), 8.71 (dd, J=1.4, 8.7 Hz, 1H), 8.23 (dd, J=1.5, 8.8 Hz, 1H), 8.02 (d, J=4.4 Hz, 1H), 7.78 (ddd, J=1.4, 6.8, 8.4 Hz, 1H), 7.64 (dd, J=1.4, 6.8, 8.4 Hz, 1H), 7.51 (dt, J=5.7, 8.0 Hz, 1H), 7.41 (td, J=1.3, 7.7 Hz, 1H), 7.35 (ddd, J=1.5, 2.6, 9.4 Hz, 1H), 7.22 (ddt, J=1.0, 2.6, 8.3 Hz, 1H), 3.04 (m, 2H), 2.65 (qd, J=6.7, 13.4 Hz, 1H), 2.31 (dt, J=2.7, 12.8 Hz, 1H), 2.21 (tdd, J=2.9, 6.0, 14.0 Hz, 1H), 1.85 (m, 1H), 1.59 (s, 3H), 1.35 (d, J=6.7 Hz, 3H); m/z=475 (M+1).

Compound 96b and 97b: A mixture of compound 94 and compound 95 (300 mg) was taken up in 1,4-dioxane (6 mL). Potassium carbonate (290 mg, 2.10 mmol), [1,1'-bis(diphenylphosphino)ferrocene]dichloropalladium(II) (55 mg, 0.075 mmol) and 4-fluorophenylboronic acid (190 mg, 1.36 mmol) were added. After sparged with nitrogen for 10 min, the mixture was heated at 90° C. for 16 h, cooled, and filtered. The filtrate was concentrated. The residue was purified by flash chromatography (silica gel, 0 to 30% EtOAc in hexanes) to give a mixture of compound 96b and 97b (340 mg) as a foam. m/z=496 (compound 96b, M+1) and 452 (compound 97b, M+1).

Compound 97b: A mixture of compound 96b and 97b (340 mg) was taken up in THF (6 mL), and aq. 3 N HCl (3 mL, 9.0 mmol) was added. The mixture was stirred overnight at room temperature, and concentrated. The residue was neutralized with aq. sat. NaHCO$_3$, and extracted with EtOAc. The organic extract was washed with water, dried with MgSO$_4$, and concentrated to give compound 97b (310 mg, 83% yield from compound 93) as a foam. m/z=452 (M+1).

Compound 98b: Compound 97b (310 mg, 0.69 mmol) was taken up in ethyl formate (15 mL, 186.5 mmol). Sodium methoxide (30 wt. % in methanol, 400 mg, 2.22 mmol) was added. After stirring overnight at room temperature, the reaction mixture was neutralized with aq. KH$_2$PO$_4$, and extracted with EtOAc. The organic extract was dried with MgSO$_4$ and concentrated to give compound 98b (330 mg, quantitative yield). m/z=480 (M+1).

Compound 99b: Compound 98b (330 mg, 0.69 mmol) was dissolved in EtOH (15 mL). Hydroxylamine hydrochloride (100 mg, 1.44 mmol) was added. The reaction mixture was stirred overnight at 50° C. After cooling to room temperature, the reaction mixture was concentrated. The residue was taken up in EtOAc, and washed with aq. NaHCO$_3$. The organic extract was dried with MgSO$_4$, and concentrated to give compound 99b (330 mg, quantitative yield) as a foam. m/z=477 (M+1).

Compound 100b: Compound 99b (330 mg, 0.69 mmol) was dissolved in THF (5 mL), and sodium methoxide (30 wt. % in methanol, 400 mg, 2.22 mmol) was added. The reaction mixture was stirred at room temperature overnight, and neutralized by the addition of aq. sat. KH$_2$PO$_4$. The mixture was extracted with EtOAc. The organic extract was washed with brine, then dried with MgSO$_4$, and concentrated to give compound 100b (330 mg, quantitative yield) as a foam. m/z=477 (M+1).

T40: Compound 100b (330 mg, 0.69 mmol) was dissolved in dry DMF (2 mL), and the solution was cooled to 0° C. Bromine (110 mg, 0.69 mmol) in CH$_2$Cl$_2$ (1 mL) was added, and the reaction stirred at 0° C. for 2 h. Pyridine (2 ml, 24.8 mmol) was added, and the reaction was allowed to warm to room temperature, stirred at 50° C. for 16 h, and concentrated. The residue was purified by flash chromatography (silica gel, eluting with 0% to 30% EtOAc in hexanes) to give compound T40 (55 mg, 17% yield) as a foam. $^1$H NMR (400 MHz, CDCl$_3$) δ 9.09 (d, J=4.4 Hz, 1H), 8.94 (s, 1H), 8.71 (dd, J=1.3, 8.6 Hz, 1H), 8.23 (d, J=0.8, 8.4 Hz, 1H), 8.02 (d, J=4.5 Hz, 1H), 7.78 (ddd, J=1.4, 6.8, 8.4 Hz, 1H), 7.65 (m, 3H), 7.23 (m, 2H), 3.05 (m, 2H), 2.65 (qd, J=6.7, 13.4 Hz, 1H), 2.31 (dt, J=2.7, 12.8 Hz, 1H), 2.21 (tdd, J=3.2, 6.3, 14.1 Hz, 1H), 1.84 (ddt, J=7.3, 10.4, 13.4 Hz, 1H), 1.59 (s, 3H), 1.36 (d, J=6.7 Hz, 3H); m/z=475 (M+1).

Compound 101 and 102: A mixture of compound 94 and compound 95 (300 mg) was taken up in THF (4 mL). A solution of sodium hydride (60% dispersion in mineral oil, 115 mg, 2.88 mmol), and 2-propanol (1 g, 16.6 mmol) in THF (5 mL) was added. The mixture was stirred at room temperature for 1 h, and concentrated. The residue was neutralized with aq. $KH_2PO_4$, and extracted with EtOAc. The organic extract was dried with $MgSO_4$ and concentrated to give a mixture of compound 101 and 102 (300 mg). m/z=460 (compound 101, M+1) and 416 (compound 102, M+1).

Compound 102: A mixture of compound 101 and 102 (300 mg) was taken up in THF (6 mL), and aq. 3 N HCl (3 mL, 9.0 mmol) was added. The mixture was stirred overnight at room temperature, and concentrated. The residue was neutralized with aq. sat. $NaHCO_3$, and extracted with EtOAc. The organic extract was washed with water, then dried with $MgSO_4$, and concentrated to give compound 102 (270 mg, 78% yield from compound 93) as a foam. m/z=416 (M+1).

Compound 103: Compound 102 (270 mg, 0.65 mmol) was taken up in ethyl formate (15 mL, 186.5 mmol). Sodium methoxide (30 wt. % in methanol, 250 mg, 1.39 mmol) was added. After stirring overnight at room temperature, the reaction mixture was neutralized with aq. $KH_2PO_4$, and extracted with EtOAc. The organic extract was dried with $MgSO_4$ and concentrated to give compound 103 (290 mg, quantitative yield) as a foam. m/z=444 (M+1).

Compound 104: Compound 103 (290 mg, 0.65 mmol) was dissolved in EtOH (15 mL). Hydroxylamine hydrochloride (100 mg, 1.44 mmol) was added. The reaction mixture was stirred overnight at 50° C., cooled to room temperature, and concentrated. The residue was taken up in EtOAc, and washed with aq. $NaHCO_3$. The organic extract was dried with $MgSO_4$, and concentrated to give compound 104 (290 mg, quantitative yield) as a foam. m/z=441 (M+1).

Compound 105: Compound 104 (290 mg, 0.65 mmol) was dissolved in THF (5 mL), and sodium methoxide (30 wt. % in methanol, 250 mg, 1.39 mmol) was added. After stirring at room temperature overnight, the reaction mixture was neutralized by the addition of aq. sat. $KH_2PO_4$, and extracted with EtOAc. The organic extract was washed with brine, then dried with $MgSO_4$, and concentrated to give compound 105 (260 mg, 91% yield) as a foam. m/z=441 (M+1).

T41: Compound 105 (260 mg, 0.59 mmol) was dissolved in dry DMF (2 mL), and the solution was cooled to 0° C. Bromine (110 mg, 0.69 mmol) in $CH_2Cl_2$ (1 ml) was added, and the reaction stirred at 0° C. for 2 h. Pyridine (2 ml, 24.8 mmol) was added. The reaction was allowed to warm to room temperature, stirred at 50° C. for 16 h, and concentrated. The residue was purified by flash chromatography (silica gel, eluting with 0% to 35% EtOAc in hexanes) to give compound T41 (25 mg, 10% yield) as a foam. $^1$H NMR (400 MHz, $CDCl_3$) δ 9.07 (d, J=4.5 Hz, 1H), 8.39 (s, 1H), 8.76 (d, J=8.5 Hz, 1H), 8.22 (d, J=8.5 Hz, 1H), 7.96 (d, J=4.5 Hz, 1H), 7.77 (t, J=7.2 Hz, 1H), 7.62 (t, J=7.6 Hz, 1H), 5.53 (septet, J=6.2 Hz, 1H), 2.92 (dd, J=6.7, 18.8 Hz, 1H), 2.66 (m, 2H), 2.20 (m, 2H), 1.82 (m, 1H), 1.52 (s, 3H), 1.44 (d, J=6.3 Hz, 3H), 1.42 (d, J=6.3 Hz, 3H), 1.34 (d, J=6.7 Hz, 3H); m/z=439 (M+1).

Compound 106 and 107: A mixture of compound 94 and compound 95 (410 mg, 0.94 mmol) was taken up in 1,4-dioxane (6 mL). Potassium carbonate (400 mg, 2.99 mmol), [1,1'-bis(diphenylphosphino)ferrocene]dichloropalladium (II) (70 mg, 0.095 mmol) and 4,4,5,5-tetramethyl-2-(prop-1-en-2-yl)-1,3,2-dioxaborolane (320 mg, 1.90 mmol) were added. After sparged with nitrogen for 10 min, the mixture was heated at 90° C. for 16 h, cooled, and filtered. The filtrate was concentrated. The residue was purified by flash chromatography (silica gel, eluting with 0% to 30% EtOAc in hexanes) to give a mixture of compound 106 and 107 (410 mg, quantitative yield) as a foam. m/z=442 (compound 106, M+1) and 398 (compound 107, M+1).

Compound 108 and 109: A mixture of compound 106 and 107 (410 mg, 0.93 mmol) and 10% palladium on carbon (35 mg) in THF (15 mL) was hydrogenated at atmospheric pressure for 16 h at room temperature. The reaction mixture was filtered through a Celite® pad. The filtrate was concentrated to give a mixture of compound 108 and 109 (410 mg, quantitative yield) as a foam. m/z=444 (compound 108, M+1) and 400 (compound 109, M+1).

Compound 109: A mixture of compound 108 and 109 (410 mg, 0.93 mmol) was taken up in THF (6 mL), and aq. 3 N HCl (3 mL, 9.0 mmol) was added. The mixture was stirred overnight at room temperature, and concentrated. The residue was neutralized with aq. sat. $NaHCO_3$, and extracted with EtOAc. The organic extract was washed with water, then dried with $MgSO_4$, and concentrated to give compound 109 (270 mg, 72% yield) as a foam. m/z=400 (M+1).

Compound 110: Compound 109 (270 mg, 0.67 mmol) was taken up in ethyl formate (15 mL, 186.5 mmol). Sodium methoxide (30 wt. % in methanol, 400 mg, 2.22 mmol) was added. After stirring overnight at room temperature, the reaction mixture was neutralized with aq. $KH_2PO_4$, and extracted with EtOAc. The organic extract was dried with $MgSO_4$ and concentrated to give compound 110 (290 mg, quantitative yield) as a foam. m/z=428 (M+1).

Compound 111: Compound 110 (290 mg, 0.67 mmol) was dissolved in EtOH (15 mL). Hydroxylamine hydrochloride (100 mg, 1.44 mmol) was added. The reaction mixture was stirred overnight at 50° C., cooled to room temperature, and concentrated. The residue was taken up in EtOAc, and washed with aq. $NaHCO_3$. The organic extract was dried with $MgSO_4$, and concentrated to give compound 111 (275 mg, 95% yield) as a foam. m/z=425 (M+1).

Compound 112: Compound 111 (275 mg, 0.65 mmol) was dissolved in THF (5 mL), and sodium methoxide (30 wt. % in methanol, 400 mg, 2.22 mmol) was added. After stirring at room temperature overnight, the reaction mixture was neutralized by the addition of aq. sat. $KH_2PO_4$, and extracted with EtOAc. The organic extract was washed with brine, then dried with $MgSO_4$, and concentrated to give compound 112 (250 mg, 91% yield) as a foam. m/z=425 (M+1).

T42: Compound 112 (250 mg, 0.59 mmol) was dissolved in dry DMF (2 mL), and the solution was cooled to 0° C. Bromine (105 mg, 0.66 mmol) in $CH_2Cl_2$ (1 ml) was added, and the reaction stirred at 0° C. for 2 h. Pyridine (2 ml, 24.8 mmol) was added. The reaction was allowed to warm to room temperature, stirred at 50° C. for 16 h, and concentrated. The residue was purified by flash chromatography (silica gel, eluting with 0% to 50% EtOAc in hexanes) to give compound T42 (45 mg, 18% yield) as a foam. $^1$H NMR (400 MHz, $CDCl_3$) δ 9.10 (d, J=4.5 Hz, 1H), 8.94 (s, 1H), 8.83 (d, J=1.4, 8.8 Hz, 1H), 8.22 (dd, J=1.2, 8.6 Hz, 1H), 8.05 (d, J=4.5 Hz, 1H), 7.78 (ddd, J=1.4, 6.8, 8.4 Hz, 1H), 7.63 (ddd, J=1.4, 6.8, 8.2 Hz, 1H), 3.32 (septet, J=6.7 Hz, 1H), 3.11 (dd, J=6.7, 18.2 Hz, 1H), 2.94 (ddd, J=7.4, 11.1, 18.2 Hz, 1H), 2.63 (qd, J=6.7, 13.3 Hz, 1H), 2.23 (m, 2H), 1.89 (m, 1H), 1.54 (s, 3H), 1.40 (d, J=6.6 Hz, 3H), 1.36 (d, J=6.8 Hz, 3H), 1.33 (d, J=6.6 Hz, 3H); m/z=423 (M+1).

Compound 113: In a sealable vial, a mixture of compound 65 (175 mg, 0.513 mmol), 2-methylpyridine-4-boronic acid (105 mg, 0.767 mmol) and potassium carbonate (210 mg, 1.52 mmol) in 1,4-dioxane (6 mL) and DMF (2 mL) was degassed. [1,1'-bis(diphenylphosphino)ferrocene]dichloropalladium (II) (38 mg, 0.052 mmol) was added, and the mixture was degassed again. The vial was sealed and heated at 90° C. for 16 h. The dark mixture was cooled, diluted with EtOAc (50 mL), stirred for 30 min, and filtered through a pad of Celite®. The filtrate was washed with aq. sat. $KH_2PO_4$ (50 mL) and brine (50 mL). The organic extract was dried over $MgSO_4$, filtered, and concentrated. The residue was purified by flash chromatography (silica gel, eluting with 50% EtOAc in hexanes) to give compound 113 (154 mg, 75% yield) as a tan foamy solid. m/z=398 (M+1).

Compound 114: To a stirring solution at room temperature under nitrogen of compound 113 (154 mg, 0.387 mmol) in ethyl formate (10 mL, 124 mmol) was added sodium methoxide (30 wt. % solution in MeOH, 0.36 mL, 1.92 mmol). After stirring for 16 h, the solution was concentrated. The residue was partitioned between aq. sat. $KH_2PO_4$ (25 mL) and EtOAc (25 mL). The organic extract was washed with brine (25 mL), dried over $MgSO_4$, filtered and concentrated to give compound 114 (162 mg, 98% yield) as a tan foamy solid, which was used in the next reaction without purification. m/z=426 (M+1).

Compound 115: A mixture under nitrogen of compound 114 (162 mg, 0.381 mmol) and hydroxylamine hydrochloride (67 mg, 0.964 mmol) in EtOH (20 mL) was heated at 60° C. for 2 h, and then stirred at room temperature overnight. The solution was concentrated, cooled, carefully basified with aq. sat. $NaHCO_3$ (25 mL) and extracted with EtOAc (25 mL). The organic extract was washed with brine (25 mL), dried over $MgSO_4$, filtered and concentrated to give compound 115 (156 mg, 97% yield) as a tan foamy solid, which was used in the next reaction without purification. m/z=423 (M+1).

Compound 116: To a stirring solution at room temperature under nitrogen of compound 115 (156 mg, 0.369 mmol) in MeOH (20 mL) was added sodium methoxide (30 wt. % solution in MeOH, 0.35 mL, 1.86 mmol). The mixture was stirred at room temperature overnight, and concentrated. The residue was partitioned between aq. sat. $KH_2PO_4$ (25 mL) and EtOAc (25 mL). The organic extract was washed with brine (25 mL), dried over $MgSO_4$, filtered, and concentrated. The residue was purified by flash chromatography (silica gel, eluting with 50% EtOAc in hexanes) to give compound 116 (104 mg, 67% yield) as an off-white foamy solid. m/z=423 (M+1).

T43: To a stirring solution at 0° C. under nitrogen of compound 116 (104 mg, 0.245 mmol) in DMF (5 mL) was added dropwise a solution of 1,3-dibromo-5,5-dimethylhydantoin (35 mg, 0.122 mmol) in DMF (1 mL). After stirring at 0° C. for 30 min, pyridine (0.20 mL, 2.48 mmol) was added. The ice-bath was removed. The mixture was heated at 60° C. for 4 h, cooled, and concentrated. The residue was partitioned between aq. sat. $KH_2PO_4$ (25 mL) and EtOAc (25 mL). The organic extract was washed with brine (25 mL), dried over $MgSO_4$, filtered, and concentrated. The residue was purified by flash chromatography (silica gel, eluting with 50% EtOAc in hexanes) to give compound T43 (28 mg, 27% yield) as a light yellow foamy solid. $^1$H NMR (400 MHz, $CDCl_3$) δ 9.03 (s, 1H), 8.67 (d, J=5.2, 1H), 8.22 (s, 1H), 8.17 (d, J=5.2 Hz, 1H), 7.60 (m, 2H), 7.53 (m, 3H), 2.99 (m, 2H), 2.70 (s, 3H), 2.63 (qd, J=6.8, 13.4 Hz, 1H), 2.27 (dt, J=2.7, 12.8 Hz, 1H), 2.15 (m, 1H), 1.79 (m, 1H), 1.54 (s, 3H), 1.33 (d, J=6.7 Hz, 3H); m/z=421 (M+1).

Compound 117: In a sealable vial, a mixture of compound 65 (403 mg, 1.18 mmol), N-Boc-1,2,3,6-tetrahydropyridine-4-boronic acid pinacol ester (550 mg, 1.78 mmol) and potassium phosphate (750 mg, 3.53 mmol) in 1,4-dioxane (12 mL) was degassed. Tetrakis(triphenylphosphine)palladium(O) (140 mg, 0.12 mmol) was added, and the mixture was degassed again. The vial was sealed and heated at 90° C. overnight. The mixture was cooled, diluted with EtOAc (50 mL), stirred for 30 min, and filtered through a pad of Celite®. The filtrated was washed with aq. sat. $KH_2PO_4$ (50 mL) and brine (50 mL). The organic extract was dried with $MgSO_4$, filtered, and concentrated. The residue was purified by flash chromatography (silica gel, eluting with 5% EtOAc in $CH_2Cl_2$) to give compound 117 (724 mg) as a yellow foamy solid, which was used in the next reaction without additional purification. m/z=488 (M+1).

Compound 118: A mixture of compound 117 (all from the last step) and 10% palladium on carbon (70 mg) in EtOAc (25 mL) was hydrogenated (balloon pressure) at room temperature overnight. Additional amount of 10% palladium on carbon (100 mg) was added, and the mixture was hydrogenated (balloon pressure) at room temperature for another overnight. The mixture was filtered, and the filtrate was concentrated. The residue was purified by flash chromatography (silica gel, eluting with 25% EtOAc in hexanes) to give compound 118 (334 mg, 58% yield from compound 65) as an off-white solid. m/z=490 (M+1).

Compound 119: To a stirring solution at room temperature under nitrogen of compound 118 (334 mg, 0.68 mmol) in ethyl formate (10 mL, 124 mmol) was added sodium methoxide (30 wt. % solution in MeOH, 0.64 mL, 3.41 mmol). After stirring for 16 h, the solution was concentrated. The residue was partitioned between aq. sat. $KH_2PO_4$ (25 mL) and EtOAc (25 mL). The organic extract was washed with brine (25 mL), dried over $MgSO_4$, filtered and concentrated to give compound 119 (356 mg, quantitative yield) as an off-white foamy solid, which was used in the next reaction without purification. m/z=518 (M+1).

Compound 120: A mixture under nitrogen of compound 119 (356 mg, 0.68 mmol) and hydroxylamine hydrochloride (71 mg, 1.02 mmol) in EtOH (20 mL) was heated at 60° C. for 2 h, and stirred at room temperature overnight. The solution was concentrated, cooled, carefully basified with aq. sat. $NaHCO_3$ (25 mL) and extracted with EtOAc (25 mL). The organic extract was washed with brine (25 mL), dried over $MgSO_4$, filtered and concentrated to give compound 120 (305 mg, 87% yield) as a tan foamy solid, which was used in the next reaction without purification. m/z=515 (M+1).

Compound 121: To a stirring solution at room temperature under nitrogen of compound 120 (305 mg, 0.59 mmol) in MeOH (20 mL) was added sodium methoxide (30 wt. % solution in MeOH, 0.56 mL, 2.98 mmol). The mixture was stirred at room temperature overnight, and concentrated. The residue was partitioned between aq. sat. $KH_2PO_4$ (25 mL) and EtOAc (25 mL). The organic extract was washed with brine (25 mL), dried over $MgSO_4$, filtered, and concentrated. The residue was purified by flash chromatography (silica gel, eluting with 50% EtOAc in hexanes) to give compound 121 (273 mg, 89% yield) as a tan foamy solid. m/z=515 (M+1).

T44: To a stirring solution at 0° C. under nitrogen of compound 121 (273 mg, 0.53 mmol) in DMF (8 mL) was added dropwise a solution of 1,3-dibromo-5,5-dimethylhydantoin (76 mg, 0.26 mmol) in DMF (2 mL). After stirring the mixture at 0° C. for 30 min, pyridine (0.43 mL, 5.32 mmol) was added. The ice-bath was removed. The mixture was heated at 60° C. for 4 h, cooled, and concentrated. The residue was partitioned between aq. sat. $KH_2PO_4$ (25 mL) and EtOAc (25 mL). The organic extract was washed with brine (25 mL), dried over $MgSO_4$, filtered, and concentrated. The residue was purified by flash chromatography (silica gel, eluting with 50% EtOAc in hexanes) to give compound T44 (164 mg, 60% yield) as a light yellow solid. $^1$H NMR (400 MHz, CDCl$_3$) δ 8.91 (s, 1H), 7.48 (m, 5H), 4.24 (br s, 2H), 3.07 (tt, J=3.6, 11.6 Hz, 1H), 2.89 (m, 4H), 2.58 (m, 1H), 2.19 (dt, J=2.8, 12.8 Hz, 1H), 2.07 (m, 3H), 1.88 (m, 2H), 1.72 (m, 1H), 1.49 (s, 9H), 1.46 (s, 3H), 1.30 (d, J=7.2 Hz, 3H); m/z=457 (M-C$_4$H$_7$).

T45: A solution of T44 (140 mg, 0.27 mmol) in CH$_2$Cl$_2$ (20 mL) at room temperature under nitrogen was treated with hydrogen chloride (4 N solution in 1,4-dioxane, 0.70 mL, 2.8 mmol). The mixture was stirred for 4 h and concentrated to a gummy solid, which was triturated with Et$_2$O, filtered and vacuum dried to give compound T45 (101 mg, 83% yield) as an off-white solid. $^1$H NMR (400 MHz, CDCl$_3$) δ 9.77 (br s, 1H), 9.49 (br s, 1H), 8.86 (s, 1H), 7.47 (m, 5H), 3.59 (m, 2H), 3.19 (m, 3H), 2.89 (m, 2H), 2.57 (m, 1H), 2.44 (m, 4H), 2.20 (br t, J=12.0 Hz, 1H), 2.09 (m, 1H), 1.72 (m, 1H), 1.46 (s, 3H), 1.29 (d, J=6.4 Hz, 3H); m/z=413 (M+1).

T46: A mixture of T45 (48 mg, 0.11 mmol) and sodium acetate (88 mg, 1.07 mmol) in acetic anhydride (1 mL, 10.58 mmol) was stirred at room temperature under nitrogen for 48 h. The mixture was concentrated. The residue was purified by flash chromatography (silica gel, eluting with 100% EtOAc) to give compound T46 (34 mg, 69% yield) as an off-white foamy solid. T46 is a 1:1 mixture of amide isomers. $^1$H NMR (400 MHz, CDCl$_3$) δ [8.90 (s), 8.88 (s), 1:1, 1H], 7.48 (m, 5H), 4.75 (br d, J=14.3 Hz, 1H), 3.97 (br t, J=13.0 Hz, 1H), 3.22 (m, 2H), 2.82 (m, 3H), 2.58 (m, 1H), [2.17 (s), 2.15 (s), 1:1, 3H], 1.94 (m, 7H), 1.46 (s, 3H), 1.30 (d, J=6.7 Hz, 3H); m/z=455 (M+1).

Compound 122: In a sealable vial, a mixture of compound 65 (287 mg, 0.842 mmol), tert-butyl 3-(4,4,5,5-tetramethyl-1,3,2-dioxaborolan-2-yl)-5,6-dihydropyridine-1(2H)-carboxylate (260 mg, 0.841 mmol) and potassium phosphate (750 mg, 3.53 mmol) in 1,4-dioxane (10 mL) was degassed. [1,1'-bis(diphenylphosphino)ferrocene]dichloropalladium (II) (62 mg, 0.085 mmol) was added, and the mixture degassed again. The vial was sealed and heated at 90° C. overnight. The mixture was cooled, diluted with EtOAc (50 mL), stirred for 30 min, and then filtered through a pad of Celite®. The filtrate was washed with aq. sat. KH$_2$PO$_4$ (50 mL) and brine (50 mL). The organic extract was dried over MgSO$_4$, filtered, and concentrated. The residue was purified by flash chromatography (silica gel, eluting with 10% EtOAc in CH$_2$Cl$_2$) to give compound 122 (220 mg, 54% yield) as an off-white foamy solid. m/z=488 (M+1).

Compound 123: To a stirring solution at room temperature under nitrogen of compound 122 (220 mg, 0.451 mmol) in ethyl formate (10 mL, 124 mmol) was added sodium methoxide (30 wt. % solution in MeOH, 0.42 mL, 2.24 mmol). After stirring for 16 h, the solution was concentrated. The residue was partitioned between aq. sat. KH$_2$PO$_4$ (25 mL) and EtOAc (25 mL). The organic extract was washed with brine (25 mL), dried over MgSO$_4$, filtered and concentrated to give compound 123 (250 mg) as a yellow oil, which was used in the next reaction without purification. m/z=516 (M+1).

Compound 124: A mixture under nitrogen of compound 123 (all from the last step) and hydroxylamine hydrochloride (47 mg, 0.676 mmol) in EtOH (20 mL) was heated at 60° C. for 2 h, and stirred at room temperature overnight. The solution was concentrated, cooled, carefully basified with aq. sat. NaHCO$_3$ (25 mL) and extracted with EtOAc (25 mL). The organic extract was washed with brine (25 mL), dried over MgSO$_4$, filtered and concentrated to give compound 124 (181 mg, 78% from compound 122) as a tan foamy solid, which was used in the next reaction without purification. m/z=513 (M+1).

Compound 125: To a stirring solution at room temperature under nitrogen of compound 124 (181 mg, 0.353 mmol) in MeOH (20 mL) was added sodium methoxide (30 wt. % solution in MeOH, 0.33 mL, 1.76 mmol). The mixture was stirred at room temperature overnight, and concentrated. The residue was partitioned between aq. sat. KH$_2$PO$_4$ (25 mL) and EtOAc (25 mL). The organic extract was washed with brine (25 mL), dried over MgSO$_4$, filtered and concentrated to give compound 125 (139 mg, 77% yield) as a yellow foamy solid, which was used in the next reaction without purification. m/z=513 (M+1).

T47: To a stirring solution at 0° C. under nitrogen of compound 125 (139 mg, 0.271 mmol) in DMF (8 mL) was added dropwise a solution of 1,3-dibromo-5,5-dimethylhydantoin (51 mg, 0.178 mmol) in DMF (2 mL). After stirring at 0° C. for 30 min, pyridine (0.29 mL, 3.59 mmol) was added. The ice-bath was removed. The mixture was heated at 60° C. for 4 h, cooled, and concentrated. The residue was partitioned between aq. sat. KH$_2$PO$_4$ (25 mL) and EtOAc (25 mL). The organic extract was washed with brine (25 mL), dried over MgSO$_4$, filtered, and concentrated. The residue was purified by flash chromatography (silica gel, eluting with 25% EtOAc in hexanes) to give compound T47 (55 mg, 40% yield) as light a yellow foamy solid. $^1$H NMR (400 MHz, CDCl$_3$) δ 8.90 (s, 1H), 7.49 (m, 6H), 4.54 (m, 1H), 3.60 (m, 2H), 2.92 (m, 2H), 2.58 (qd, J=6.7, 13.3 Hz, 1H), 2.42 (m, 2H), 2.20 (dt, J=2.6, 12.8 Hz, 1H), 2.08 (m, 2H), 1.72 (m, 1H), 1.51 (s, 9H), 1.46 (s, 3H), 1.30 (d, J=6.7 Hz, 3H); m/z=511 (M+1).

T48: A solution of T47 (42 mg, 0.082 mmol) in CH$_2$Cl$_2$ (10 mL) at room temperature under nitrogen was treated with hydrogen chloride (4 N solution in 1,4-dioxane, 0.40 mL, 1.60 mmol). The mixture was stirred for 16 h and concentrated to a gummy solid, which was triturated with Et$_2$O, filtered and vacuum dried to give compound T48 (37 mg, quantitative yield) as an off-white solid. $^1$H NMR (400 MHz, CDCl$_3$) δ $^1$H NMR (400 MHz, CDCl$_3$) δ10.21 (br s, 1H), 10.13 (br s, 1H), 8.84 (s, 1H), 7.57 (m, 1H), 7.48 (m, 5H), 4.36 (m, 2H), 3.41 (m, 2H), 2.89 (m, 4H), 2.59 (qd, J=6.6, 13.3 Hz, 1H), 2.21 (t, J=12.6 Hz, 1H), 2.07 (m, 1H), 1.71 (m, 1H), 1.46 (s, 3H), 1.31 (d, J=6.7 Hz, 3H); m/z=411 (M+1).

T49: A mixture of T48 (32 mg, 0.071 mmol) and sodium acetate (60 mg, 0.73 mmol) in acetic anhydride (1 mL, 10.58 mmol) was stirred at room temperature under nitrogen for 48 h. The mixture was concentrated, and the residue was purified by flash chromatography (silica gel, eluting with 100% EtOAc) to give compound T49 (11 mg, 34% yield) as a light yellow foamy solid. T49 is a 1:1 mixture of amide isomers. $^1$H NMR (400 MHz, CDCl$_3$) δ [8.91 (s), 8.88 (s), 1:1, 1H], 7.50 (m, 6H), [4.78 (dd, J=2.6, 18.6 Hz), 4.62 (dd, J=2.6, 18.6 Hz), 1:1, 1H], 4.54 (m, 1H), 3.79 (m, 1H), 3.62 (m, 1H), 2.91 (m, 2H), 2.58 (m, 1H), 2.46 (m, 2H), [2.22 (s), 2.19 (s), 1:1, 3H], 2.14 (m, 2H), 1.73 (m, 1H), 1.48 (s, 3H), [1.31 (d, J=6.7 Hz), 1.30 (d, J=6.7 Hz), 1:1, 3H]; m/z=453 (M+1).

Compound 126: In a pressure vessel, a mixture of compound 8 (5.00 g, 20.98 mmol), 4-fluorobenzaldehyde (6.7 mL, 62.4 mmol) and potassium fluoride on aluminum oxide (5.5 mmol/g, 7.6 g, 41.8 mmol) in 2-propanol (42 mL) was flushed with nitrogen, and sealed. After heated at 60° C. for 4 h, and stirred at room temperature overnight, the mixture was filtered through a pad of Celite®. The filtrate was concentrated. The residue was partitioned between aq. sat.

KH$_2$PO$_4$ (100 mL) and EtOAc (100 mL). The organic extract was washed with brine (100 mL), dried over MgSO$_4$, filtered, and concentrated. The residue was purified by flash chromatography (silica gel, eluting with 20% EtOAc in hexanes) to give compound 126 (6.28 g, 87% yield) as a light yellow solid. m/z=345 (M+1).

Compound 127: A mixture of compound 126 (7.34 g, 21.31 mmol), 2-methyl-4-pyridinecarboximidamide hydrochloride (Bolli, et al., 2003) (5.50 g, 32.04 mmol) and potassium carbonate (7.4 g, 53.5 mmol) in EtOH (43 mL) was refluxed under nitrogen for 48 h. The mixture was cooled to room temperature, filtered through a pad of Celite® and the solid was washed with EtOH (100 mL). The combined filtrate and wash was concentrated. The residue was partitioned between aq. sat. KH$_2$PO$_4$ (100 mL) and CHCl$_3$ (100 mL). The organic extract was washed with brine (100 mL), dried over MgSO$_4$, filtered, and concentrated to give the crude dihydropyrimidine (12.38 g) as a bright yellow solid. m/z=462 (M+1).

A mixture of the crude dihydropyrimidine (12.38 g) and manganese (IV) oxide (88%, 9.26 g, 93.73 mmol) in CH$_2$Cl$_2$ (100 mL) was stirred at room temperature under nitrogen overnight. The mixture was filtered through a pad of Celite®. The filtrate was concentrated and the residue was purified by flash chromatography (silica gel, eluting with 20% to 50% EtOAc in hexanes) to give compound 127 (8.72 g, 89% yield) as a gummy light yellow foamy solid. m/z=460 (M+1).

Compound 128: A solution of compound 127 (8.72 g, 18.98 mmol) in MeOH (63 mL) was treated with aq. 3 N HCl solution (63 mL, 189 mmol). After stirring at room temperature under nitrogen overnight, the mixture was concentrated, cooled, basified with concentrated ammonium hydroxide to pH ~9-10, and then extracted with CHCl$_3$ (100 mL). The organic extract was washed with brine (100 mL), dried over MgSO$_4$, filtered and concentrated to give compound 128 (8.57 g, quantitative yield) as a light yellow foamy solid. m/z=416 (M+1).

Compound 129: To a stirring solution at 0° C. (under a drying tube) of compound 128 (all from the last step) in ethyl formate (80 mL) was added dropwise sodium methoxide (30 wt. % solution in MeOH, 17.6 mL, 94.8 mmol). After addition, the ice-bath was removed and the mixture was stirred at room temperature overnight. The resultant orange-brown suspension was concentrated, and the residue was partitioned between aq. sat. KH$_2$PO$_4$ (150 mL) and EtOAc (100 mL). The organic extract was washed with brine (100 mL), dried over MgSO$_4$, filtered and concentrated to give compound 129 (8.26 g, 98% yield) as an orange-pink foamy solid. m/z=444 (M+1).

Compound 130: To a stirring solution at room temperature under nitrogen of compound 129 (8.26 g, 18.64 mmol) and acetic acid (10.7 mL, 186.9 mmol) in EtOH (93 mL) was added hydroxylamine hydrochloride (1.94 g, 27.92 mmol). The mixture was heated at 60° C. for 4 h, and then stirred at room temperature overnight. After concentration, the residue was partitioned between aq. 10% NH$_4$OH (100 mL) and CHCl$_3$ (100 mL). The organic extract was washed with brine (100 mL), dried over MgSO$_4$, filtered and concentrated to give compound 130 (9.23 g, quantitative yield) as a brown foamy solid. m/z=441 (M+1).

Compound 131 (T187): A mixture of compound 130 (all from the last step) and potassium carbonate (5.5 g, 39.8 mmol) in MeOH (79 mL) was stirred at room temperature under nitrogen overnight. The mixture was concentrated, and the residue was partitioned between Et$_2$O (50 mL) and water (50 mL). The basic aqueous extract was cooled, acidified with aq. sat. KH$_2$PO$_4$ (150 mL), and then extracted with EtOAc (2×100 mL). The combined organic extract was washed with brine (100 mL), dried over MgSO$_4$, filtered, and concentrated. The residue was purified by flash chromatography (silica gel, eluting with 50% EtOAc in hexanes) to give compound 131 (T187) (5.63 g, 68% yield) as a yellow foamy solid. m/z=441 (M+1); mixture of isomers; the major isomer $^1$H NMR (400 MHz, CDCl$_3$) δ 8.64 (dd, J=5.2, 0.9 Hz, 1H), 8.16 (s, 1H), 8.12 (ddd, J=5.3, 1.7, 0.7 Hz, 1H), 7.61 (m, 2H), 7.20 (m, 2H), 3.92 (dd, J=13.6, 5.6 Hz, 1H), 3.59 (dd, J=13.6, 5.7 Hz, 1H), 2.93 (m, 2H), 2.68 (s, 3H), 2.60 (dq, J=12.8, 6.4 Hz, 1H), 2.26 (t, J=13.7 Hz, 1H), 2.07 (m, 1H), 1.89 (td, J=12.5, 2.6 Hz, 1H), 1.68 (m, 1H), 1.53 (s, 3H), 1.20 (d, J=6.4 Hz, 3H).

T50: To a stirring solution at 0° C. under nitrogen of compound 131 (5.56 g, 12.62 mmol) in degassed DMF (50 mL) was added dropwise a solution of 1,3-dibromo-5,5-dimethylhydantoin (1.98 g, 6.92 mmol) in degassed DMF (10 mL). After stirring at 0° C. for 30 min, pyridine (10.2 mL, 126.4 mmol) was added. The ice-bath was removed. The mixture was heated at 60° C. for 4 h, cooled, and concentrated. The residue was partitioned between aq. sat. KH$_2$PO$_4$ (200 mL) and CHCl$_3$ (200 mL). The organic extract was washed with brine (200 mL), dried over MgSO$_4$, filtered, and concentrated. The residue was purified by flash chromatography (silica gel, eluting with 50% to 100% EtOAc in hexanes) to give partially purified product. The sample was suspended in degassed EtOH (100 mL), stirred at room temperature for 30 min, and then concentrated to dryness. This process was repeated twice. In the third time, the mixture was concentrated to 25 mL, cooled and filtered. The solid was washed with cold degassed EtOH, and vacuum dried to give compound T50 (3.25 g, 59% yield) as a light yellow solid. $^1$H NMR (400 MHz, CDCl$_3$) δ 9.01 (s, 1H), 8.68 (d, J=5.1 Hz, 1H), 8.20 (s, 1H), 8.15 (dd, J=1.6, 5.2 Hz, 1H), 7.63 (m, 2H), 7.22 (m, 2H), 2.97 (m, 2H), 2.71 (s, 3H), 2.63 (qd, J=6.7, 13.4 Hz, 1H), 2.26 (dt, J=2.7, 12.8 Hz, 1H), 2.16 (tdd, J=2.6, 5.8, 13.6 Hz, 1H), 1.79 (m, 1H), 1.54 (s, 3H), 1.33 (d, J=6.7 Hz, 3H); m/z=439 (M+1).

Compound 132: In a sealable vial, a mixture of compound 9 (2.61 g, 8.81 mmol), 2-methyl-4-pyridinecarboximidamide hydrochloride (1.80 g, 10.49 mmol) and potassium carbonate (2.9 g, 21.0 mmol) in EtOH (9 mL) was flushed with nitrogen, sealed and stirred at room temperature for 5 days. The mixture was concentrated. The residue was diluted with EtOAc (150 mL) and water (50 mL) and heated at 65° C. until all solid was in solution (15 min). The layers were separated. The organic extract was washed with aq. sat. KH$_2$PO$_4$ (50 mL) and brine (50 mL), dried over MgSO$_4$, filtered, and concentrated. The crude product was purified by flash chromatography (silica gel, eluting with 0% to 5% MeOH in EtOAc) to give compound 132 (2.00 g, 60% yield) as a light yellow solid. m/z=382 (M+1).

Compound 133: In a microwave vessel, a mixture of compound 132 (1.00 g, 2.62 mmol) and phosphorus (V) oxychloride (2.4 mL, 25.4 mmol) in toluene (10 mL) was flushed with nitrogen. The vial was sealed, and heated in Biotage® microwave synthesizer at 100° C. for 1 h. The mixture was cooled to room temperature, and then carefully poured into a stirring solution of NaHCO$_3$ (11 g, 131 mmol) in water (100 mL). After stirring for 30 min, the mixture was extracted with EtOAc (2×100 mL). The combined organic extract was washed with brine (50 mL), dried over MgSO$_4$, filtered and concentrated to give a mixture of ketone and ketal (1.14 g). The sample was mixed with aq. 3 N HCl (8.7 mL, 26.1 mmol) in MeOH (20 mL), and stirred at room temperature overnight. The mixture was concentrated, cooled, basified with aq. 10% NH₄OH, and then extracted with CHCl₃ (50 mL). The organic extract was washed with brine (50 mL), dried over MgSO₄, filtered, and concentrated. The crude product was purified by flash chromatography (silica gel, eluting with 75% EtOAc in hexanes) to give compound 133 (0.81 g, 87% yield) as a light yellow solid. m/z=356 (M+1).

Compound 134: In a sealable vial, a mixture of compound 133 (0.37 g, 1.04 mmol), 2-fluorophenylboronic acid (0.22 g, 1.56 mmol), potassium phosphate (0.66 g, 3.11 mmol) and tetrakis(triphenylphosphine)palladium(O) (0.12 g, 0.10 mmol) in 1,4-dioxane (10 mL) was degassed with nitrogen. The vial was sealed, and heated at 90° C. for 16 h. The mixture was cooled, and then partitioned between aq. 1 N NaOH solution (50 mL) and EtOAc (50 mL). The organic extract was washed with brine (50 mL), dried over MgSO₄, filtered, and concentrated. The crude product was purified by flash chromatography (silica gel, eluting with 50% EtOAc in hexanes) to give compound 134 (0.47 g, quantitative yield) as a light yellow oil. m/z=416 (M+1).

Compound 135: To a stirring solution at room temperature of compound 134 (all from the last step) in ethyl formate (10 mL, 124 mmol) was added sodium methoxide (30 wt. % solution in MeOH, 0.97 mL, 5.17 mmol). The mixture was stirred for 2 h, and then partitioned between EtOAc (50 mL) and aq. sat. KH₂PO₄ (50 mL). The organic extract was washed with brine (50 mL), dried over MgSO₄, filtered and concentrated to give compound 135 (0.41 g, 89% yield) as a yellow oil. m/z=444 (M+1).

Compound 136: To a solution of compound 135 (0.41 g, 0.92 mmol) in EtOH (20 mL) was added acetic acid (0.53 mL, 9.26 mmol) and hydroxylamine hydrochloride (0.10 g, 1.44 mmol). The mixture was heated at 60° C. under nitrogen for 2 h, and stirred at room temperature overnight. The mixture was concentrated, and the residue was partitioned between aq. sat. NaHCO₃ (50 mL) and EtOAc (50 mL). The organic extract was washed with brine (50 mL), dried over MgSO₄, filtered and concentrated to give compound 136 (0.38 g, 93% yield) as a yellow foamy solid. m/z=441 (M+1).

Compound 137: To a solution of compound 136 (0.34 g, 0.77 mmol) in MeOH (20 mL) was added sodium methoxide (30 wt. % solution in MeOH, 0.72 mL, 3.84 mmol). The mixture was stirred at room temperature under nitrogen for 16 h, and concentrated. The residue was partitioned between aq. sat. KH₂PO₄ (50 mL) and EtOAc (50 mL). The organic extract was washed with brine (50 mL), dried over MgSO₄, filtered, and concentrated. The crude product was purified by flash chromatography (silica gel, eluting with 100% EtOAc) to give compound 137 (0.24 g, 71% yield) as a light yellow foamy solid. m/z=441 (M+1).

T51: To a stirring solution at 0° C. under nitrogen of compound 137 (0.24 g, 0.54 mmol) in degassed DMF (8 mL) was added dropwise a solution of 1,3-dibromo-5,5-dimethylhydantoin (0.077 g, 0.27 mmol) in DMF (2 mL). After stirring the mixture for 30 min, pyridine (0.44 mL, 5.44 mmol) was added. The ice-bath was removed. The mixture was heated at 60° C. for 4 h, cooled, and concentrated. The residue was partitioned between aq. sat. KH₂PO₄ (50 mL) and EtOAc (50 mL). The organic extract was washed with brine (50 mL), dried over MgSO₄, filtered, and concentrated. The crude product was purified by flash chromatography (silica gel, eluting with 50% EtOAc in hexanes) to give compound T51 (0.13 g, 55% yield) as a light yellow foamy solid. ¹H NMR (400 MHz, CDCl₃) δ 9.03 (s, 1H), 8.67 (d, J=4.8 Hz, 1H), 8.19 (br s, 1H), 8.15 (dd, J=1.2, 4.2 Hz, 1H), 7.52 (m, 1H), 7.45 (dt, J=2.0, 7.6 Hz, 1H), 7.35 (tt, J=1.2, 7.6, 1H), 7.22 (br t, J=8.8 Hz, 1H), 2.81 (m, 2H), 2.70 (s, 3H), 2.62 (m, 1H), 2.26 (dt, J=2.8, 12.8 Hz, 1H), 2.13 (m, 1H), 1.82 (m, 1H), 1.55 (s, 3H), 1.32 (d, J=6.8 Hz, 3H); m/z=439 (M+1).

Compound 138: In a pressure vessel, a mixture of compound 8 (2.50 g, 10.49 mmol), 2,4-difluorobenzaldehyde (1.72 mL, 15.72 mmol) and potassium fluoride (40 wt. % on alumina, 3.0 g, 20.65 mmol) in 2-propanol (21 mL) was flushed with nitrogen. The vial was sealed, heated at 60° C. for 4 h, and stirred at room temperature overnight. The mixture was filtered through a pad of Celite®, and the filtrate was concentrated. The residue was partitioned between aq. sat. KH₂PO₄ solution (50 mL) and EtOAc (50 mL). The organic extract was washed with brine (50 mL), dried over MgSO₄, filtered and concentrated. The crude product was triturated with hexanes (50 mL), filtered and vacuum dried to give compound 138 (1.93 g, 51% yield) as a light yellow solid. m/z=363 (M+1, 100%).

Compound 139: Step 1. A mixture of compound 138 (2.22 g, 6.12 mmol), 4-quinolinecarboximidamide hydrochloride (1.91 g, 9.20 mmol) and potassium carbonate (2.5 g, 18.4 mmol) in EtOH (61 mL) was refluxed under nitrogen for 48 h. The mixture was cooled to room temperature, filtered through a pad of Celite® and the solid was washed with EtOH (100 mL). The combined filtrate and wash was concentrated, and the residue was partitioned between aq. sat. KH₂PO₄ (50 mL) and EtOAc (50 mL). The organic extract was washed brine (50 mL), dried over MgSO₄, filtered and concentrated to give crude dihydropyrimidine (3.0 g) as a bright yellow foamy solid. m/z=516 (M+1).

A mixture of the crude dihydropyrimidine (3.0 g) and manganese (IV) oxide (88%, 3.0 g, 30.4 mmol) in CH₂Cl₂ (60 mL) was stirred at room temperature under nitrogen overnight. The mixture was filtered through a pad of Celite®, and the filtrate was concentrated. The crude product was purified by flash chromatography (silica gel, eluting with 50% EtOAc in hexanes) to give compound 139 (2.39 g, 76% yield) as a light yellow foamy solid. m/z 514 (M+1).

Compound 140: A solution of compound 139 (2.39 g, 4.65 mmol) in MeOH (47 mL) was treated with aq. 3 N HCl (16 mL, 48 mmol). The mixture was stirred at room temperature under nitrogen overnight and concentrated. The residue was cooled, basified with concentrated ammonium hydroxide to pH~9-10, and then extracted with CHCl₃ (50 mL). The organic extract was washed with brine (50 mL), dried over MgSO₄, filtered and concentrated to give compound 140 (2.38 g, quantitative yield) as a light yellow foamy solid. m/z=470 (M+1).

Compound 141: To a stirring solution at 0° C. (under a drying tube) of compound 140 (all from the last step) in ethyl formate (20 mL) was added dropwise sodium methoxide (30 wt. % solution in MeOH, 2.6 mL, 13.9 mmol). After addition, the ice-bath was removed. The mixture was stirred at room temperature for 2 h, and concentrated. The residue was partitioned between aq. sat. KH₂PO₄ (50 mL) and EtOAc (50 mL). The organic extract was washed with brine (50 mL), dried over MgSO₄, filtered and concentrated to give compound 141 (2.69 g, quantitative yield) as a dark yellow oil. m/z=498 (M+1).

Compound 142: To a stirring solution at room temperature under nitrogen of compound 141 (all from the last step) and acetic acid (2.7 mL, 47.2 mmol) in EtOH (46 mL) was added hydroxylamine hydrochloride (0.49 g, 7.05 mmol). The mixture was heated at 60° C. for 4 h, stirred at room temperature overnight, and concentrated. The residue was carefully partitioned between aq. sat. NaHCO₃ (50 mL) and EtOAc (50 mL). The organic extract was washed with brine (50 mL), dried over MgSO$_4$, filtered and concentrated to give compound 142 (2.21 g, 96% yield) as an orange-dark yellow foamy solid. m/z=495 (M+1).

Compound 143: A mixture of compound 142 (2.21 g, 4.47 mmol) and potassium carbonate (3.1 g, 22.4 mmol) in MeOH (45 mL) was stirred at room temperature under nitrogen overnight, and concentrated. The residue was partitioned between EtOAc (50 mL) and aq. sat. KH$_2$PO$_4$ (50 mL). The organic extract was washed with brine (50 mL), dried over MgSO$_4$, filtered, and concentrated. The crude product was purified by flash chromatography (silica gel, eluting with 50% EtOAc in hexanes) to give compound 143 (1.54 g, 69% yield) as a yellow foamy solid. m/z=495 (M+1).

T52: To a stirring solution at 0° C. under nitrogen of compound 143 (1.54 g, 3.11 mmol) in degassed DMF (10 mL) was added dropwise a solution of 1,3-dibromo-5,5-dimethylhydantoin (0.49 g, 1.71 mmol) in degassed DMF (2 mL). After stirring at 0° C. for 30 min, pyridine (2.5 mL, 31.0 mmol) was added. The ice-bath was removed. The sample was heated at 60° C. for 4 h, cooled, and concentrated. The residue was partitioned between aq. sat. KH$_2$PO$_4$ (50 mL) and EtOAc (50 mL). The organic extract was washed with brine (50 mL), dried over MgSO$_4$, filtered, and concentrated. The crude product was purified by flash chromatography (silica gel, eluting with 50% EtOAc in hexanes) to give partially purified product. The sample was dissolved into CH$_2$Cl$_2$ (20 mL). Degassed EtOH (20 mL) was added. The mixture was concentrated to remove most of the CH$_2$Cl$_2$, and cooled. The precipitate was collected by filtration, and vacuum dried to give compound T52 (0.73 g, 48% yield) as a light yellow solid. $^1$H NMR (400 MHz, CDCl$_3$) δ 9.09 (d, J=4.4 Hz, 1H), 8.93 (s, 1H), 8.68 (dd, J=0.8, 8.6 Hz, 1H), 8.22 (dd, J=0.8, 8.6 Hz, 1H), 8.01 (d, J=4.4 Hz, 1H), 7.78 (ddd, J=1.4, 6.8, 8.4 Hz, 1H), 7.64 (ddd, J=1.4, 6.8, 8.4 Hz, 1H), 7.49 (dt, J=6.3, 8.4 Hz, 1H), 7.08 (m, 1H), 7.00 (ddd, J=2.5, 8.7, 10.2 Hz, 1H), 2.87 (m, 2H), 2.64 (qd, J=6.7, 13.4 Hz, 1H), 2.31 (dt, J=2.7, 12.7 Hz, 1H), 2.19 (m, 1H), 1.87 (m, 1H), 1.60 (s, 3H), 1.35 (d, J=6.7 Hz, 3H); m/z=493 (M+1).

Compound 144: Compound 88 (1.08 g, 3.14 mmol), 2-chloropyridine-4-carboximidamide hydrochloride (900 mg, 4.69 mmol) and K$_2$CO$_3$ (1.30 g, 9.42 mmol) in EtOH (15 mL) were heated in a Biotage® microwave synthesizer at 120° C. for 3 h. After the reaction was cooled to room temperature, MTBE was added. The mixture was washed with water. The organic extract was dried with Na$_2$SO$_4$, and concentrated. The residue was purified by flash chromatography (silica gel, eluting with 0% to 50% EtOAc in hexanes) to give the product (914 mg, 61% yield) as a yellow foamy solid. The product (903 mg, 1.88 mmol) was dissolved in CH$_2$Cl$_2$ (18 mL). DDQ (510 mg, 2.25 mmol) was added. The reaction was stirred at room temperature for 1 h. MTBE and Aq. sat. NaHCO$_3$ were added, and the mixture was stirred for 5 min. The product was extracted with MTBE. The combined organic extract was washed with aq. sat. NaHCO$_3$, and water, dried with Na$_2$SO$_4$, and concentrated. The residue was purified by flash chromatography (silica gel, eluting with 0% to 20% EtOAc in hexanes) to give compound 144 (832 g, 92% yield) as a white foamy solid. m/z=480 (M+1).

Compound 145: A mixture of compound 144 (300 mg, 0.63 mmol), cyclopropylboronic acid (90 mg, 1.05 mmol), potassium phosphate (660 mg, 3.11 mmol), tricyclohexylphosphine (54 mg, 0.19 mmol), palladium acetate (24 mg, 0.11 mmol), toluene (4 mL) and water (0.2 mL) in a vial was sparged with nitrogen for 5 min. The vial was sealed, and heated in a Biotage® microwave synthesizer at 130° C. for 4 h. After the reaction was cooled to room temperature, EtOAc was added. The mixture was washed with water. The aqueous phase was extracted with EtOAc. The combined organic extract was dried with Na$_2$SO$_4$, and concentrated. The residue was purified by flash chromatography (silica gel, eluting with 0% to 30% EtOAc in hexanes) to give the compound 145 (254 mg, 84% yield) as a white solid. m/z=486 (M+1).

Compound 146: Compound 145 (306 mg, 0.63 mmol) was taken up in THF (2.1 mL) and MeOH (2.1 mL). Aq. 3 N HCl (2.1 mL, 6.3 mmol) was added. The mixture was stirred overnight at room temperature. After concentrated, the residue was neutralized with aq. sat. NaHCO$_3$ to pH ~8, and extracted with EtOAc. The organic extract was dried with Na$_2$SO$_4$, and concentrated to give compound 146 (296 mg) as a white foamy solid. m/z=442 (M+1).

Compound 147: Compound 146 (all from above) was dissolved in ethyl formate (1.6 mL) and cooled to 0° C. Sodium methoxide (25 wt. % in methanol, 2.3 mL, 9.96 mmol) was added. The mixture was stirred at room temperature for 2 h, and cooled to 0° C. Aq. 6 N HCl (1.7 mL, 10.2 mmol), EtOH (6.6 mL) and hydroxylamine hydrochloride (71 mg, 1.02 mmol) were added sequentially. The mixture was heated at 55° C. (oil bath) for overnight, and concentrated. EtOAc was added. The mixture was washed with water. The aqueous phase was treated with aq. sat. NaHCO$_3$, and extracted with EtOAc. The combined organic extract was dried with Na$_2$SO$_4$ and concentrated. The residue was purified by flash chromatography (silica gel, eluting with 0% to 40% EtOAc in hexanes) to give compound 147 (242 mg, 82% yield from compound 145) as a white foamy solid. m/z=467 (M+1).

Compound 148: Compound 147 (240 mg, 0.52 mmol) was dissolved in MeOH (2.6 mL). Sodium methoxide (25 wt. % in methanol, 0.18 mL, 0.78 mmol) was added. The reaction mixture was stirred at 55° C. for 2 h, and cooled to 0° C. Aq. 10% NaH$_2$PO$_4$ was added. The mixture was extracted with EtOAc. The organic extract was dried with Na$_2$SO$_4$ and concentrated. The residue was purified by flash chromatography (silica gel, eluting with 0% to 50% EtOAc in hexanes) to give compound 148 (224 mg, 93% yield) as a white foamy solid. m/z=467 (M+1).

T53: Compound 148 (224 mg, 0.48 mmol) was dissolved in anhydrous DMF (2 mL), and the solution was cooled to 0° C. 1,3-dibromo-5,5-dimethylhydantoin (72 mg, 0.25 mmol) in DMF (0.5 mL) was added. The reaction was stirred at 0° C. for 1.5 h. Pyridine (120 µL, 1.49 mmol) was added. The reaction was heated at 55° C. (oil bath) for 2.5 h, and cooled to room temperature. EtOAc was added. The mixture was washed with water, aq. sat. NaHCO$_3$, and aq. 10% Na$_2$SO$_3$. The organic extract was dried with Na$_2$SO$_4$, and concentrated. The residual pyridine was removed by azeotropic evaporation with toluene. The residue was purified by flash chromatography (silica gel, eluting with 0% to 40% EtOAc in hexanes) to give partially purified product, which was purified again by flash chromatography (silica gel, eluting with 0% to 25% acetone in hexanes) to give compound T53 (167 mg, 75% yield) as a white foamy solid. $^1$H NMR (400 MHz, CDCl$_3$) δ 9.03 (s, 1H), 8.61 (d, J=4.8 Hz, 1H), 8.20 (dd, J=0.9, 1.7 Hz, 1H), 8.07 (dd, J=1.6, 5.2 Hz, 1H), 7.51 (m, 1H), 7.45 (dt, J=2.0, 7.2 Hz, 1H), 7.34 (br t, J=7.6 Hz, 1H), 7.21 (br t, J=9.2 Hz, 1H), 2.82 (m, 2H), 2.62 (qd, J=6.7, 13.4 Hz, 1H), 2.24 (m, 2H), 2.12 (m, 1H), 1.80 (m, 1H), 1.55 (s, 3H), 1.32 (d, J=6.7 Hz, 3H), 1.12 (m, 2H), 1.04 (m, 2H); m/z=465 (M+1).

Compound 149: A mixture of compound 88 (3.50 g, 10.16 mmol), thiourea (850 mg, 11.18 mmol) and potassium t-butoxide (1.15 g, 10.27 mmol) in EtOH (14 mL) was heated in a Biotage® microwave synthesizer at 120° C. for 1 h. After the reaction mixture was cooled to room temperature, MTBE was added. The mixture was washed with water. The organic extract was dried with $Na_2SO_4$, filtered and concentrated. The residue was purified by flash chromatography (silica gel, eluting with 0% to 50% EtOAc in hexanes) to give compound 149 (3.25 g, 79% yield) as a white foam. m/z=403 (M+1).

Compound 150: To a solution of compound 149 (5.40 g, 13.42 mmol) in $CH_2Cl_2$ (135 mL) was added DDQ (4.70 g, 20.70 mmol). After stirring at room temperature for 30 min, the mixture was diluted with MTBE, and washed with aq. sat. $NaHCO_3$. The organic extract was dried with $Na_2SO_4$, filtered and concentrated. The residue was purified by flash chromatography (silica gel, eluting with 0% to 30% EtOAc in hexanes) to give compound 150 (3.90 g, 72% yield) as a white foam. m/z=799 (M+1).

Compound 151: To a solution of compound 150 (3.90 g, 4.88 mmol) in THF (12 mL) and EtOH (48 mL) were added iodomethane (3.04 mL, 48.85 mmol) and sodium borohydride (1.50 g, 39.65 mmol) sequentially at 0° C. After stirring the mixture at room temperature for 1 h, additional amount of sodium borohydride (0.50 g, 13.21 mmol) was added. The mixture was stirred at room temperature for another 45 min, and then partitioned between EtOAc and aq. 10% $Na_2SO_3$. The organic extract was washed with brine, dried with $Na_2SO_4$, filtered and concentrated. The residue was purified by flash chromatography (silica gel, eluting with 0% to 40% EtOAc in hexanes) to give compound 151 (3.50 g, 86% yield) as a white foam. m/z=415 (M+1).

Compound 152a: A mixture of compound 151 (414 mg, 1.00 mmol), copper(I) thiophene-2-carboxylate (570 mg, 3.00 mmol), 2-(trifluoromethyl)pyridine-4-boronic acid (381 mg, 2.00 mmol) and THF (10 mL) in a pressure bottle was sparged with nitrogen for 5 min. Tetrakis(triphenylphosphine)palladium(O) (58 mg, 0.05 mmol) was added, and the nitrogen sparging was continued for another 2 min. The bottle was sealed, and heated at 100° C. for 14 h. After the reaction was cooled to room temperature, EtOAc was added. The mixture was filtered through a plug of Celite®, and eluted with EtOAc. The filtrate was washed with aq. 1 N NaOH and water. The organic extract was dried with $Na_2SO_4$, and concentrated. The residue was purified by flash chromatography (silica gel, eluting with 0% to 35% EtOAc in hexanes) to give the compound 152a (273 mg, 53% yield) as a white foamy solid. m/z=514 (M+1).

Compound 153a: Compound 152a (271 mg, 0.53 mmol) was taken up in THF (1.75 mL) and MeOH (1.75 mL). Aq. 3 N HCl (1.75 mL, 52.5 mmol) was added. The mixture was stirred overnight at room temperature. After concentrated, aq. sat. $NaHCO_3$ was added. The mixture was extracted with EtOAc. The organic extract was dried with $Na_2SO_4$, and concentrated to give compound 153a (248 mg, quantitative yield) as a light yellow foamy solid. m/z=470 (M+1).

Compound 154a: Compound 153a (246 mg, 0.52 mmol) was dissolved in ethyl formate (1.3 mL) and cooled to 0° C. Sodium methoxide (25 wt. % in methanol, 1.8 mL, 7.79 mmol) was added. The mixture was stirred at room temperature for 2 h, and cooled to 0° C. Aq. 6 N HCl (1.3 mL, 7.8 mmol), EtOH (5.2 mL) and hydroxylamine hydrochloride (55 mg, 0.79 mmol) were added sequentially. The mixture was heated at 55° C. (oil bath) for overnight, and concentrated. Aq. sat. $NaHCO_3$ was added. The mixture was extracted with EtOAc. The combined organic extract was dried with $Na_2SO_4$ and concentrated. The residue was purified by flash chromatography (silica gel, eluting with 0% to 40% EtOAc in hexanes) to give compound 154a (140 mg, 54% yield) as a yellow foamy solid. m/z=495 (M+1).

Compound 155a: Compound 154a (137 mg, 0.28 mmol) was dissolved in MeOH (1.4 mL). Sodium methoxide (25 wt. % in methanol, 96 µL, 0.42 mmol) was added. The reaction mixture was stirred at 55° C. for 2 h, and cooled to 0° C. Aq. 10% $NaH_2PO_4$ was added. The mixture was extracted with EtOAc. The organic extract was dried with $Na_2SO_4$ and concentrated. The residue was purified by flash chromatography (silica gel, eluting with 0% to 40% EtOAc in hexanes) to give compound 155a (117 mg, 85% yield) as a white foamy solid. m/z=495 (M+1).

T54: Compound 155a (117 mg, 0.24 mmol) was dissolved in anhydrous DMF (0.8 mL), and the solution was cooled to 0° C. 1,3-dibromo-5,5-dimethylhydantoin (34 mg, 0.12 mmol) in DMF (0.4 mL) was added. The reaction was stirred at 0° C. for 1 h. Pyridine (58 µL, 0.72 mmol) was added. The reaction was heated at 55° C. (oil bath) for 2.5 h, and cooled to room temperature. $CH_2Cl_2$ was added. The mixture was washed with water. The organic extract was dried with $Na_2SO_4$, and concentrated. The residual pyridine was removed by azeotropic evaporation with toluene. The residue was purified by flash chromatography (silica gel, eluting with 0% to 30% acetone in hexanes) to give compound T54 (107 mg, 91% yield) as a white foamy solid. $^1$H NMR (400 MHz, $CDCl_3$) δ 8.97 (s, 1H), 8.92 (d, J=5.1 Hz, 1H), 8.70 (dd, J=0.8, 1.2 Hz, 1H), 8.57 (dd, J=1.5, 5.1 Hz, 1H), 7.54 (m, 1H), 7.45 (dt, J=1.9, 7.4 Hz, 1H), 7.36 (dt, J=1.1, 7.5 Hz, 1H), 7.23 (m, 1H), 2.85 (m, 2H), 2.63 (td, J=6.7, 13.4 Hz, 1H), 2.27 (dt, J=2.7, 12.8 Hz, 1H), 2.16 (m, 1H), 1.81 (dq, J=7.1, 13.1 Hz, 1H), 1.55 (s, 3H), 1.33 (d, J=6.8 Hz, 3H); m/z=493 (M+1).

Compound 152b: A mixture of compound 151 (414.5 mg, 1.00 mmol), copper(I) thiophene-2-carboxylate (570 mg, 2.99 mmol), 3-picoline-4-boronic acid (274 mg, 2.00 mmol) and THF (10 mL) in a pressure bottle was sparged with nitrogen for 5 min. Tetrakis(triphenylphosphine)palladium (O) (58 mg, 0.05 mmol) was added, and the nitrogen sparging was continued for another 2 min. The bottle was sealed, and heated at 100° C. for 14 h. After the reaction was cooled to room temperature, EtOAc was added. The mixture was filtered through a plug of Celite®, and eluted with EtOAc. The filtrate was washed with aq. 1 N NaOH and water. The organic extract was dried with $Na_2SO_4$, filtered and concentrated. The residue was purified by flash chromatography (silica gel, eluting with 0% to 35% EtOAc in hexanes) to give the compound 152b (50 mg, 11% yield) as a white foam. m/z=460 (M+1). The starting material compound 151 (340 mg, 82% yield) was also recovered after the flash chromatography.

Compound 153b: To a solution of Compound 152b (115 mg, 0.25 mmol) in MeOH (0.8 mL) and THF (0.8 mL) was added aq. 3 N HCl (0.8 mL, 2.4 mmol). The reaction mixture was stirred for 4 h at room temperature, and concentrated. The residue was neutralized with aq. sat. $NaHCO_3$, and extracted with EtOAc. The organic extract was washed with water, dried over $Na_2SO_4$, filtered and concentrated to give compound 153b (100 mg, 96% yield) as a white foam. m/z=416 (M+1).

Compound 154b: Compound 153b (100 mg, 0.24 mmol) was dissolved in ethyl formate (0.6 mL, 7.46 mmol) and cooled to 0° C. Sodium methoxide (25 wt. % solution in MeOH, 0.823 mL, 3.56 mmol) was added. The mixture was stirred at room temperature for 2 h, and then cooled to 0° C. Aq. 6 N HCl (0.6 mL, 3.6 mmol) was added to adjust the reaction mixture to pH 2. EtOH (4 mL) and hydroxylamine hydrochloride (27 mg, 0.39 mmol) were added sequentially. The mixture was heated at 55° C. for 16 h, cooled and concentrated. The residue was partitioned between EtOAc and aq. sat. NaHCO$_3$. The organic extract was dried with Na$_2$SO$_4$, filtered and concentrated. The residue was purified by flash chromatography (silica gel, eluting with 0% to 50% acetone in hexanes) to give compound 154b (54 mg, 51% yield) as a white foam. m/z=441 (M+1).

Compound 155b (T55): To a solution of compound 154b (54 mg, 0.12 mmol) in MeOH (0.6 mL) was added sodium methoxide (25 wt. % solution in MeOH, 0.07 mL, 0.30 mmol). The reaction mixture was stirred at 55° C. for 2 h, cooled to 0° C., and then neutralized by adding aq. 10% NaH$_2$PO$_4$. MeOH was removed by evaporation. The residue was partitioned between EtOAc and water. The organic phase was separated, and the aqueous phase was extracted with EtOAc. The combined organic extracts were dried with Na$_2$SO$_4$, filtered and concentrated. The residue was purified by flash chromatography (silica gel, eluting with 0% to 40% acetone in hexanes) to give compound 155b (24 mg, 44% yield) as a pale yellow foam. $^1$H NMR (400 MHz, CDCl$_3$) δ 8.57 (m, 2H), 7.87 (m, 1H), 7.47 (m, 2H), 7.30 (dt, J=1.1, 7.5 Hz, 1H), 7.20 (m, 1H), 3.89 (dd, J=5.7, 13.8 Hz, 1H), 3.47 (dd, J=5.7, 13.7 Hz, 1H), 2.80 (m, 2H), 2.63 (s, 3H), 2.60 (m, 1H), 2.26 (t, J=13.7 Hz, 1H), 2.04 (m, 1H), 1.91 (dt, J=2.7, 12.5 Hz, 1H), 1.70 (dq, J=7.6, 13.1 Hz, 1H), 1.54 (s, 3H), 1.20 (d, J=6.5 Hz, 3H); m/z=441 (M+1).

T56: Compound 155b (23 mg, 0.052 mmol) was dissolved in dry DMF (0.6 mL) and cooled to 0° C. 1,3-dibromo-5,5-dimethylhydantoin (7.5 mg, 0.026 mmol) in DMF (0.3 mL) was added. After the reaction mixture was stirred at 0° C. for 1 h, pyridine (0.012 mL, 0.15 mmol) was added. The reaction was heated at 55° C. for 3 h, and cooled to room temperature. CH$_2$Cl$_2$ (10 mL) was added. The mixture was washed with water (4×10 mL). The organic extract was dried with Na$_2$SO$_4$, filtered and concentrated. The residual pyridine was removed by azeotropic evaporation with toluene (10 mL). The residue was purified by flash chromatography (silica gel, eluting with 0% to 40% acetone in hexanes) to give compound T56 (14 mg, 61% yield) as a light yellow solid. $^1$H NMR (400 MHz, CDCl$_3$) δ 8.90 (s, 1H), 8.60 (m, 2H), 7.88 (d, J=5.1 Hz, 1H), 7.50 (m, 1H), 7.43 (dt, J=1.8, 7.4 Hz, 1H), 7.32 (dt, J=1.1, 7.5 Hz, 1H), 7.21 (m, 1H), 2.83 (m, 2H), 2.65 (s, 3H), 2.61 (m, 1H), 2.27 (dt, J=2.8, 12.8 Hz, 1H), 2.14 (m, 1H), 1.81 (m, 1H), 1.55 (s, 3H), 1.32 (d, J=6.7 Hz, 3H); m/z=439 (M+1).

Compound 152c: A mixture of compound 151 (275 mg, 0.664 mmol), 3-fluoropyridine-4-boronic acid hydrate (214.4 mg, 1.349 mmol), copper(I)-thiophene-2-carboxylate (382.2 mg, 2.004 mmol), tetrakis(triphenylphosphine)palladium(O) (39.3 mg, 0.034 mmol) and THF (5 mL) was sparged with N$_2$ for 3 min. The tube was sealed and heated to 100° C. for 17 h. The resultant mixture was diluted with EtOAc (10 mL), filtered through a plug of Celite®, and eluted with EtOAc (75 mL) and CH$_2$Cl$_2$ (25 mL). The combined eluent was concentrated. The resultant residue was purified by flash chromatography (silica gel, eluting with 0% to 85% EtOAc in hexanes) to give compound 152c (237 mg, 70% purity) as an off-white solid. m/z=464 (M+1).

Compound 153c: A suspension of impure compound 152c (237 mg), aq. 3 N HCl (4.8 mL, 14.4 mmol), MeOH (4.8 mL) and THF (2.4 mmol) was stirred at room temperature for 5 h. The mixture was diluted with saturated NaHCO$_3$ (25 mL), and extracted with EtOAc (200 mL, then 25 mL). The combined organic extracts were washed with brine (25 mL), dried over Na$_2$SO$_4$, filtered and concentrated. The resultant residue was purified by flash chromatography (silica gel, eluting with 0% to 75% EtOAc in hexanes) to give compound 153c (175 mg, 63% yield from 151) as a white foam solid. m/z=420 (M+1).

Compound 154c: A solution of sodium methoxide (25 wt. % in MeOH, 1 mL, 4.37 mmol) was added to a 0° C. solution of compound 153c (175 mg, 0.417 mmol) in ethyl formate (4 mL, 49.73 mmol). The mixture was stirred at 0° C. for 15 min, warmed to room temperature for an additional 1.5 h. The mixture was cooled to 0° C.; acidified with aq. 6 N HCl (0.73 mL, 4.38 mmol); hydroxylamine hydrochloride (47.3 mg, 0.681 mmol) and EtOH (10 mL) were added and the reaction was heated to 55° C. for 20 h. The mixture was concentrated to 4 mL; diluted with EtOAc (100 mL); washed with aq. sat. NaHCO$_3$ (25 mL) and brine (25 mL); dried over Na$_2$SO$_4$, filtered and concentrated. The resultant residue was purified by flash chromatography (silica gel, eluting with 0% to 75% EtOAc in hexanes) to give compound 154c (168.5 mg, 91% yield) as a white foam solid. m/z=445 (M+1).

Compound 155c: A solution of sodium methoxide (25% in MeOH, 0.13 mL, 0.57 mmol) was added to a room temperature mixture of compound 154c (168 mg, 0.378 mmol) in MeOH (1.9 mL). The mixture was stirred at room temperature for 1.25 h, diluted with aq. 10% NaH$_2$PO$_4$ (10 mL), and extracted with MTBE (75 mL) and EtOAc (25 mL). The combined organic extracts were dried over Na$_2$SO$_4$, filtered and concentrated. The resultant residue was purified by flash chromatography (silica gel, eluting with 0% to 75% EtOAc in hexanes) to give compound 155c (150 mg, 89% yield) as a white foam solid. m/z=445 (M+1).

T57: A solution of 1,3-dibromo-5,5-dimethylhydantoin (46.9 mg, 0.164 mmol) in DMF (1.4 mL) was added to a 0° C. solution of compound 155c (144.5 mg, 0.325 mmol) in DMF (3.6 mL). After 1.5 h, pyridine (0.08 mL, 0.99 mmol) was added and the reaction was heated to 55° C. for 2 h. The mixture was diluted with EtOAc (100 mL); washed with aq. sat. NaHCO$_3$ (25 mL), aq. 10% Na$_2$SO$_3$ (10 mL) and brine (10 mL). The organic extract was dried over Na$_2$SO$_4$, filtered, concentrated and azeotroped with toluene. The resultant residue was purified by flash chromatography (silica gel, eluting with 0% to 60% EtOAc in hexanes) to give compound T57 (98.2 mg, 68% yield) as a white foam solid. $^1$H NMR (400 MHz, CDCl$_3$) δ 8.95 (s, 1H), 8.65 (d, J=2.9 Hz, 1H), 8.56 (d, J=4.9 Hz, 1H), 8.06 (dd, J=5.0, 6.6 Hz, 1H), 7.51 (m, 1H), 7.44 (dt, J=2.0, 7.6 Hz, 1H), 7.33 (dt, J=1.1, 7.5 Hz, 1H), 7.21 (ddd, J=1.0, 8.4, 9.6 Hz, 1H), 2.84 (m, 2H), 2.62 (qd, J=6.7, 13.4 Hz, 1H), 2.26 (dt, J=2.8, 12.8 Hz, 1H), 2.13 (m, 1H), 1.81 (m, 1H), 1.54 (s, 3H), 1.32 (d, J=6.7 Hz, 3H); m/z=443 (M+1).

Compound 152d: A mixture of compound 151 (419.4 mg, 1.012 mmol), (3-methyl-5-pyridyl)boronic acid (281 mg, 2.052 mmol), copper(I)-thiophene-2-carboxylate (583 mg, 3.057 mmol), tetrakis(triphenylphosphine)palladium(O) (87.9 mg, 0.0761 mmol) and THF (10 mL) was sparged with nitrogen for 3 min. The tube was sealed and heated to 100° C. for 17 h. After cooled to room temperature, the resultant mixture was filtered through a plug of Celite®, eluted with EtOAc (40 mL), CH$_2$Cl$_2$ (40 mL) and acetone (40 mL); and concentrated. The resultant residue was purified by flash chromatography (silica gel, eluting with 0% to 75% EtOAc in hexanes) to give compound 152d (131.3 mg, 28% yield) as a white solid. m/z=460 (M+1).

Compound 153d: A suspension of compound 152d (197.5 mg, 0.430), aq. 3 N HCl (5 mL, 15 mmol), MeOH (5 mL) and THF (2.5 mmol) was stirred at room temperature for 5 h. The mixture was diluted with aq. sat. NaHCO$_3$ (25 mL), and extracted with EtOAc (200 ml, then 25 mL). The combined organic fractions were washed with brine (25 mL), dried over Na$_2$SO$_4$, filtered and concentrated. The resultant residue was purified by flash chromatography (silica gel, eluting with 0% to 60% EtOAc in hexanes) to give compound 153d (165 mg, 92% yield) as a white solid. m/z=416 (M+1).

Compound 154d: A solution of sodium methoxide (25 wt. % in MeOH, 0.91 mL, 3.98 mmol) was added to a 0° C. solution of compound 153d (165 mg, 0.395 mmol) in ethyl formate (6 mL, 74.60 mmol). The mixture was stirred at 0° C. for 15 min, warmed to room temperature for an additional 2 h. The mixture was cooled to 0° C.; acidified with aq. 6 N HCl (0.67 mL, 4.02 mmol); hydroxylamine hydrochloride (46.4 mg, 0.668 mmol) and EtOH (10 mL) were added and reaction was heated to 55° C. for 3 h. The mixture was diluted with aq. 10% NaH$_2$PO$_4$ (10 mL), and extracted with MTBE (75 mL) and EtOAc (25 mL). The combined organic extracts were dried over Na$_2$SO$_4$, filtered and concentrated. The resultant residue was purified by flash chromatography (silica gel, eluting with 0% to 70% EtOAc in hexanes) to give compound 154d (146.4 mg, 84% yield) as a white solid. m/z=441 (M+1).

Compound 155d: A solution of sodium methoxide (25 wt. % in MeOH, 0.12 mL, 0.53 mmol) was added to a room temperature mixture of compound 154d (146 mg, 0.332 mmol) in MeOH (1.7 mL). The mixture was stirred at room temperature for 1.5 h, diluted with aq. 10% NaH$_2$PO$_4$ (25 mL), and extracted with MTBE (75 mL) and EtOAc (25 mL). The combined organic extracts were dried over Na$_2$SO$_4$, filtered and concentrated. The resultant residue was purified by flash chromatography (silica gel, eluting with 0% to 80% EtOAc in hexanes) to give compound 155d (85.9 mg, 59% yield) as a white foam solid. m/z=441 (M+1).

T58: A solution of 1,3-dibromo-5,5-dimethylhydantoin (27.9 mg, 0.0976 mmol) in DMF (1.0 mL) was added to a 0° C. solution of compound 155d (85.9 mg, 0.195 mmol) in DMF (2.0 mL). After 2 h, pyridine (0.05 mL, 0.62 mmol) was added and the reaction was heated to 55° C. for 2 h. The mixture was diluted with EtOAc (125 mL); washed with aq. sat. NaHCO$_3$ (25 mL), aq. 10% Na$_2$SO$_3$ (25 mL) and brine (25 mL); dried over Na$_2$SO$_4$; filtered and concentrated. The resultant residue was purified by flash chromatography (silica gel, eluting with 0% to 80% EtOAc in hexanes) to give T58 (64.7 mg, 76% yield) as a white foam solid. $^1$H NMR (400 MHz, CDCl$_3$) δ 9.49 (d, J=2.0 Hz, 1H), 9.02 (s, 1H), 8.56 (d, J=1.6 Hz, 1H), 8.53 (m, 1H), 7.51 (m, 1H), 7.45 (dt, J=1.2, 7.6 Hz, 1H), 7.33 (dt, J=1.1, 7.5 Hz, 1H), 7.21 (ddd, J=1.0, 8.4, 9.5 Hz, 1H), 2.80 (m, 2H), 2.62 (qd, J=6.7, 13.4 Hz, 1H), 2.47 (s, 3H), 2.26 (dt, J=2.7, 12.7 Hz, 1H), 2.12 (m, 1H), 1.79 (m, 1H), 1.55 (s, 3H), 1.32 (d, J=6.7 Hz, 3H); m/z=439 (M+1).

Compound 152e: A mixture of compound 151 (419.4 mg, 1.012 mmol), 3-quinolineboronic acid (343.6 mg, 1.986 mmol), copper(I)-thiophene-2-carboxylate (571.8 mg, 2.998 mmol), tetrakis(triphenylphosphine)palladium(O) (87.9 mg, 0.0761 mmol) and THF (10 mL) was sparged with N$_2$ for 2 min. The tube was sealed and heated to 100° C. for 17 h. After cooled to room temperature, the resultant mixture was filtered through a plug of Celite®; eluted with EtOAc (25 mL), CH$_2$Cl$_2$ (25 mL) and acetone (25 mL); and concentrated. The resultant material was diluted with EtOAc (150 mL); washed with aq. sat. NaHCO$_3$ (2×30 mL) and brine (25 mL); dried over Na$_2$SO$_4$; filtered and concentrated. The resultant residue was purified by flash chromatography (silica gel, eluting with 0% to 70% EtOAc in hexanes) to give compound 152e (204.4 mg, 41% yield) as an off-white solid. m/z=496 (M+1).

Compound 153e: A suspension of compound 152e (204.4 mg, 0.412 mmol), aq. 3 N HCl (5 mL, 15.0 mmol), MeOH (5 mL) and THF (2.5 mmol) was stirred at room temperature for 4 h. The mixture was diluted with aq. sat. NaHCO$_3$ (30 mL), and extracted with EtOAc (150 mL, then 50 mL). The combined organic fractions were washed with brine (25 mL), dried over Na$_2$SO$_4$, filtered and concentrated. The resultant residue was purified by flash chromatography (silica gel, eluting with 0% to 60% EtOAc in hexanes) to give compound 153e (182.1 mg, 98% yield) as a white foam solid. m/z=452 (M+1).

Compound 154e: A solution of sodium methoxide (25 wt. % in MeOH, 0.92 mL, 4.02 mmol) was added to a 0° C. solution of compound 153e (182.1 mg, 0.401 mmol) in ethyl formate (6.1 mL, 75.84 mmol). The mixture was stirred at 0° C. for 5 min, warmed to room temperature for an additional 1 h. The mixture was cooled to 0° C.; acidified with aq. 6 N HCl (0.67 mL, 4.02 mmol); hydroxylamine hydrochloride (44.8 mg, 0.645 mmol) and EtOH (10.2 mL) were added and reaction was heated to 55° C. overnight. The mixture was diluted with aq. sat. NaHCO$_3$ (25 mL) and extracted with EtOAc (75 mL, then 25 mL). The combined organic fractions were washed with brine (25 mL); dried over Na$_2$SO$_4$; filtered and concentrated. The resultant residue was purified by flash chromatography (silica gel, eluting with 0% to 70% EtOAc in hexanes) to give compound 154e (163.2 mg, 85% yield) as a white foam solid. m/z=477 (M+1).

Compound 155e: A solution of sodium methoxide (25 wt. % in MeOH, 0.20 mL, 0.88 mmol) was added to a room temperature mixture of compound 154e (163 mg, 0.342 mmol) in MeOH (6.8 mL). The mixture was stirred at 55° C. for 2 h, diluted with aq. 10% NaH$_2$PO$_4$ (30 mL), and extracted with MTBE (100 mL) and EtOAc (50 mL). The combined organic fractions were dried over Na$_2$SO$_4$, filtered and concentrated. The resultant residue was purified by flash chromatography (silica gel, eluting with 0% to 75% EtOAc in hexanes) to give compound 155e (126.3 mg, 77% yield) as a white solid. m/z=477 (M+1).

T59: A solution of 1,3-dibromo-5,5-dimethylhydantoin (14.8 mg, 0.0518 mmol) in DMF (1.0 mL) was added to a 0° C. solution of compound 155e (48.8 mg, 0.102 mmol) in DMF (3.0 mL). After 1 h, pyridine (0.04 mL, 0.50 mmol) was added and the reaction was heated to 55° C. for 2 h. The mixture was diluted with EtOAc (125 mL); washed with aq. sat. NaHCO$_3$ (25 mL), aq. 10% Na$_2$SO$_3$ (25 mL) and brine (25 mL); dried over Na$_2$SO$_4$; filtered and concentrated. The resultant residue was purified by flash chromatography (silica gel, eluting with 0% to 75% EtOAc in hexanes) to give T59 (34.3 mg, 71% yield) as an off-white foam solid. $^1$H NMR (400 MHz, CDCl$_3$) δ 9.99 (d, J=2.2 Hz, 1H), 9.24 (d, J=1.6 Hz, 1H), 9.09 (s, 1H), 8.19 (d, J=8.5 Hz, 1H), 8.02 (dd, J=1.4, 8.2 Hz, 1H), 7.79 (ddd, J=1.5, 6.9, 8.4 Hz, 1H), 7.62 (ddd, J=1.2, 6.9, 8.1 Hz, 1H), 7.52 (m, 2H), 7.36 (dt, J=1.1, 7.5 Hz, 1H), 7.23 (m, 1H), 2.83 (m, 2H), 2.64 (qd, J=6.7, 13.4 Hz, 1H), 2.29 (dt, J=2.8, 12.8 Hz, 1H), 2.14 (m, 1H), 1.82 (m, 1H), 1.59 (s, 3H), 1.34 (d, J=6.7 Hz, 3H); m/z=475.2 (M+1).

Compound 152f: A mixture of compound 151 (418.5 mg, 1.010 mmol), uinolone-6-boronic acid (344.5 mg, 1.992 mmol), copper(I)-thiophene-2-carboxylate (574.7 mg, 3.014 mmol), tetrakis(triphenylphosphine)palladium(O) (86.9 mg, 0.0752 mmol) and THF (10 mL) was sparged with nitrogen for 3 min. The tube was sealed and heated to 100° C. for 21 h. After cooled to room temperature, the resultant mixture was filtered through a plug of Celite®; eluted with EtOAc (40 mL), CH$_2$Cl$_2$ (40 mL) and acetone (40 mL); and concentrated. The resultant material was diluted with EtOAc (100 mL); washed with aq. sat. NaHCO$_3$ (2×25 mL); dried over Na$_2$SO$_4$; filtered and concentrated. The resultant residue was purified by flash chromatography (silica gel, eluting with 0% to 80% EtOAc in hexanes) to give compound 152f (155.6 mg, 31% yield) as a white foam solid. m/z=496.2 (M+1).

Compound 153f: A suspension of compound 152f (156 mg, 0.314 mmol), aq. 3 N HCl (5 mL, 15.0 mmol), MeOH (5 mL) and THF (2.5 mmol) was stirred at room temperature for 1 h. The mixture was diluted with EtOAc (100 mL); washed with aq. sat. NaHCO$_3$ (25 mL) and brine (25 mL); dried over Na$_2$SO$_4$, filtered and concentrated. The resultant residue was purified by flash chromatography (silica gel, eluting with 0% to 70% EtOAc in hexanes) to give compound 153f (134.4 mg, 95% yield) as a white foam solid. m/z=452.2 (M+1).

Compound 154f: A solution of sodium methoxide (25 wt. % in MeOH, 0.68 mL, 2.97 mmol) was added to a 0° C. solution of compound 153f (134.4 mg, 0.296 mmol) in ethyl formate (6.5 mL, 80.82 mmol). The mixture was stirred at 0° C. for 5 min, warmed to room temperature for an additional 2 h. The mixture was cooled to 0° C.; acidified with aq. 6 N HCl (0.50 mL, 3.0 mmol); hydroxylamine hydrochloride (30.9 mg, 0.445 mmol) and EtOH (7.5 mL) were added and reaction was heated to 55° C. overnight. The mixture was diluted with aq. sat. NaHCO$_3$ (50 mL) and extracted with EtOAc (75 mL, then 25 mL). The combined organic fractions were washed with brine (25 mL); dried over Na$_2$SO$_4$, filtered and concentrated. The resultant residue was purified by flash chromatography (silica gel, eluting with 0% to 75% EtOAc in hexanes) to give compound 154f (122 mg, 86% yield) as a white foam solid. m/z=477.2 (M+1).

Compound 155f: A solution of sodium methoxide (25 wt. % in MeOH, 0.15 mL, 0.66 mmol) was added to a room temperature mixture of compound 154f (122 mg, 0.256 mmol) in MeOH (5.1 mL). The mixture was stirred at 55° C. for 2 h, diluted with aq. 10% NaH$_2$PO$_4$ (50 mL), and extracted with MTBE (100 mL) and EtOAc (25 mL). The combined organic fractions were washed with brine (25 mL), dried over Na$_2$SO$_4$, filtered and concentrated. The resultant residue was purified by flash chromatography (silica gel, eluting with 0% to 80% EtOAc in hexanes) to give compound 155f (51.4 mg, 42% yield) as a white solid. m/z=477.2 (M+1).

T60: A solution of 1,3-dibromo-5,5-dimethylhydantoin (15.8 mg, 0.0553 mmol) in DMF (1.0 mL) was added to a 0° C. solution of compound 155f (51.4 mg, 0.108 mmol) in DMF (3.0 mL). After 2 h, pyridine (0.05 mL, 0.62 mmol) was added and the reaction was heated to 55° C. for 2 h. The mixture was diluted with EtOAc (125 mL); washed with aq. sat. NaHCO$_3$ (25 mL), aq. 10% Na$_2$SO$_3$ (25 mL), water (25 mL) and brine (25 mL); dried over Na$_2$SO$_4$; filtered and concentrated. The resultant residue was purified by flash chromatography (silica gel, eluting with 0% to 60% EtOAc in hexanes) to give T60 (34.8 mg, 68% yield) as an off-white foam solid. $^1$H NMR (400 MHz, CDCl$_3$) δ 9.13 (s, 1H), 9.01 (d, J=1.9 Hz, 1H), 8.98 (dd, J=1.8, 4.3 Hz, 1H), 8.87 (dd, J=2.0, 8.9 Hz, 1H), 8.36 (m, 1H), 8.23 (d, J=8.9 Hz, 1H), 7.50 (m, 3H), 7.35 (dt, J=1.1, 7.5 Hz, 1H), 7.23 (m, 1H), 2.82 (m, 2H), 2.64 (qd, J=6.7, 13.3 Hz, 1H), 2.29 (dt, J=2.7, 12.8 Hz, 1H), 2.13 (m, 1H), 1.81 (m, 1H), 1.59 (s, 3H), 1.34 (d, J=6.7 Hz, 3H); m/z=475.2 (M+1).

Compound 152g: A mixture of compound 151 (418.6 mg, 1.010 mmol), N-(4-(4,4,5,5-tetramethyl-1,3,2-dioxaborolan-2-yl)uinolon-2-yl)acetamide (524.6 mg, 2.001 mmol), copper(I)-thiophene-2-carboxylate (575.6 mg, 3.018 mmol), tetrakis(triphenylphosphine)palladium(O) (89.5 mg, 0.0774 mmol) and THF (10 mL) was sparged with nitrogen for 3 min. The tube was sealed and heated to 100° C. for 18 h. After cooled to room temperature, the resultant mixture was filtered through a plug of Celite®; eluted with EtOAc (25 mL), CH$_2$Cl$_2$ (25 mL) and acetone (25 mL); and concentrated. The resultant material was diluted with EtOAc (150 mL); washed with aq. sat. NaHCO$_3$ (2×35 mL); dried over Na$_2$SO$_4$; filtered and concentrated. The resultant residue was purified by flash chromatography (silica gel, eluting with 0% to 70% EtOAc in hexanes) to give compound 152g (74.9 mg, 15% yield) as a glassy solid. m/z=503.2 (M+1).

Compound 153g: A suspension of compound 152g (74.9 mg, 0.149 mmol), aq. 3 N HCl (2.4 mL, 7.2 mmol), MeOH (2.4 mL) and THF (1.2 mmol) was stirred at room temperature for 4 h, concentrated and loaded directly onto silica, and purified by flash chromatography (silica gel, eluting with 0% to 100% EtOAc in hexanes) to give compound 153g (40.3 mg, 59% yield) as a white solid. m/z=459.2 (M+1).

Compound 154g: A solution of sodium methoxide (25 wt. % in MeOH, 0.20 mL, 0.87 mmol) was added to a 0° C. solution of compound 153g (40.3 mg, 0.0879 mmol) in ethyl formate (4 mL, 49.73 mmol). The mixture was stirred at 0° C. for 5 min, warmed to room temperature for an additional 3 h. The mixture was cooled to 0° C.; acidified with aq. 6 N HCl (0.15 mL, 0.90 mmol); hydroxylamine hydrochloride (9.4 mg, 0.135 mmol) and EtOH (2.3 mL) were added and reaction was heated to 55° C. overnight. The mixture was diluted with aq. sat. NaHCO$_3$ (25 mL) and extracted with EtOAc (2×50 mL). The combined organic fractions were washed with brine (25 mL); dried over Na$_2$SO$_4$, filtered and concentrated. The resultant residue was purified by flash chromatography (silica gel, eluting with 0% to 100% EtOAc in hexanes) to give compound 154g (32.7 mg, 77% yield) as a white solid. m/z=484.2 (M+1).

Compound 155g: A solution of sodium methoxide (25 wt. % in MeOH, 0.04 mL, 0.18 mmol) was added to a room temperature mixture of compound 154g (32.7 mg, 0.0676 mmol) in MeOH (1.4 mL). The mixture was stirred at 55° C. for 1 h, diluted with aq. 10% NaH$_2$PO$_4$ (10 mL), and extracted with MTBE (50 mL) and EtOAc (25 mL). The combined organic fractions were washed with brine (10 mL), dried over Na$_2$SO$_4$, filtered and concentrated. The resultant residue was purified by flash chromatography (silica gel, eluting with 0% to 100% EtOAc in hexanes) to give compound 155g (34.7 mg, quantitative yield) which was used as-is in subsequent reaction.

T61: A solution of 1,3-dibromo-5,5-dimethylhydantoin (4.5 mg, 0.016 mmol) in DMF (0.6 mL) was added to a 0° C. solution of compound 155g (15.1 mg, 0.0312 mmol) in DMF (1.0 mL). After 2 h, pyridine (15 µL, 0.19 mmol) was added and the reaction was heated to 55° C. for 2 h. The mixture was diluted with EtOAc (75 mL); washed with aq. sat. NaHCO$_3$ (10 mL), aq. 10% Na$_2$SO$_3$ (10 mL) and brine (10 mL); dried over Na$_2$SO$_4$; filtered and concentrated. The resultant residue was purified by flash chromatography (silica gel, eluting with 0% to 100% EtOAc in hexanes) to give T61 (9.1 mg, 61% yield) as a white solid. $^1$H NMR (400 MHz, CDCl$_3$) δ 9.16 (br s, 1H), 9.00 (s, 1H), 8.42 (d, J=5.2 Hz, 1H), 8.35 (br s, 1H), 8.08 (dd, J=1.5, 5.2 Hz, 1H), 7.48 (m, 2H), 7.32 (dt, J=1.1, 7.5 Hz, 1H), 7.19 (ddd, J=1.0, 8.4, 9.6 Hz, 1H), 2.82 (m, 2H), 2.62 (qd, J=6.7, 13.4 Hz, 1H), 2.25 (s, 3H), 2.25 (m, 1H), 2.12 (m, 1H), 1.80 (m, 1H), 1.55 (s, 3H), 1.32 (d, J=6.7 Hz, 3H); m/z=482.2 (M+1).

Compound 152h: A mixture of compound 151 (424.2 mg, 1.023 mmol), 8-quinolinylboronic acid (230.5 mg, 1.333 mmol), copper(I)-thiophene-2-carboxylate (574 mg, 3.01 mmol), tetrakis(triphenylphosphine)palladium(O) (86.6 mg, 0.0749 mmol) and THF (10 mL) was sparged with nitrogen for 5 min. The tube was sealed and heated to 100° C. overnight. After cooled to room temperature, the resultant mixture was filtered through a plug of Celite®, eluted with EtOAc (40 mL), $CH_2Cl_2$ (40 mL) and acetone (40 mL); and concentrated. The resultant residue was dissolved in EtOAc (100 mL), washed with aq. sat. $NaHCO_3$ (2×25 mL), dried over $Na_2SO_4$, filtered and concentrated. The resultant residue was purified by flash chromatography (silica gel, eluting with 0% to 100% EtOAc in hexanes) to give compound 152h (75.5 mg, 15% yield) as a white solid. m/z=496.2 (M+1).

Compound 153h: A suspension of compound 152h (75.5 mg, 0.152 mmol), aq. 3 N HCl (2 mL, 6 mmol), MeOH (2 mL) and THF (1 mmol) was stirred at room temperature for 3 h. The mixture was diluted with aq. sat. $NaHCO_3$ (10 mL), and extracted with EtOAc (50 ml, then 20 mL). The combined organic fractions were washed with brine (10 mL), dried over $Na_2SO_4$, filtered and concentrated. The resultant crude compound 153h (66.6 mg) was used without further purification.

Compound 154h: A solution of sodium methoxide (25 wt. % in MeOH, 0.34 mL, 1.49 mmol) was added to a 0° C. solution of compound 153h (66.6 mg, ≤0.147 mmol) in ethyl formate (2.2 mL, 27.35 mmol). The mixture was stirred at 0° C. for 5 min, warmed to room temperature for an additional 3 h. The mixture was cooled to 0° C.; acidified with aq. 6 N HCl (0.25 mL, 1.5 mmol); hydroxylamine hydrochloride (18.3 mg, 0.263 mmol) and EtOH (3.7 mL) were added and reaction was heated to 55° C. overnight. The mixture was diluted with aq. 10% $NaH_2PO_4$ (10 mL), and extracted with MTBE (75 mL) and EtOAc (25 mL). The combined organic fractions were dried over $Na_2SO_4$, filtered and concentrated. The resultant residue was purified by flash chromatography (silica gel, eluting with 0% to 100% EtOAc in hexanes) to give compound 154h (57.2 mg, 79% yield from compound 152h) as a white solid. m/z=477.2 (M+1).

Compound 155h: A solution of sodium methoxide (25 wt. % in MeOH, 0.05 mL, 0.22 mmol) was added to a room temperature mixture of compound 154h (57.2 mg, 0.120 mmol) in MeOH (2 mL). The mixture was stirred at room temperature for 2 h, diluted with EtOAc (100 mL), washed with aq. 10% $NaH_2PO_4$ (25 mL), dried over $Na_2SO_4$, filtered and concentrated. The resultant residue was purified by flash chromatography (silica gel, eluting with 0% to 100% EtOAc in hexanes) to give compound 155h (48.3 mg, 84% yield) as a glassy solid. m/z=477.2 (M+1).

T62: A solution of 1,3-dibromo-5,5-dimethylhydantoin (14.5 mg, 0.0507 mmol) in DMF (1.0 mL) was added to a 0° C. solution of compound 155h (48.3 mg, 0.101 mmol) in DMF (3.0 mL). After 1 h, pyridine (0.05 mL, 0.62 mmol) was added and the reaction was heated to 55° C. for 3 h. The mixture was diluted with EtOAc (100 mL); washed with aq. sat. $NaHCO_3$ (25 mL), aq. 10% $Na_2SO_3$ (25 mL) and brine (25 mL); dried over $Na_2SO_4$; filtered and concentrated. The resultant residue was purified by flash chromatography (silica gel, eluting with 0% to 100% EtOAc in hexanes) to give T62 (31.5 mg, 65% yield) as a yellow foam solid. $^1$H NMR (400 MHz, $CDCl_3$) δ 10.17 (dd, J=0.8, 1.2 Hz, 1H), 8.98 (s, 1H), 8.58 (d, J=5.7 Hz, 1H), 8.30 (dd, J=1.2, 7.2 Hz, 1H), 7.97 (d, J=8.0 Hz, 1H), 7.84 (dd, J=7.2, 8.0 Hz, 1H), 7.74 (dd, J=0.8, 5.5 Hz, 1H), 7.50 (m, 2H), 7.32 (dt, J=1.1, 7.6 Hz, 1H), 7.21 (m, 1H), 2.88 (m, 2H), 2.64 (qd, J=6.8, 13.5 Hz, 1H), 2.31 (dt, J=2.8, 12.9 Hz, 1H), 2.16 (m, 1H), 1.87 (m, 1H), 1.62 (s, 3H), 1.34 (d, J=6.7 Hz, 3H); m/z=475.2 (M+1).

Compound 157: A mixture of compound 156 (500 mg, 2.56 mmol), bis(pinacolato)diboron (712 mg, 2.80 mmol), potassium acetate (626 mg, 6.38 mmol), [1,1'-bis(diphenylphosphino)ferrocene]dichloropalladium(II) (98 mg, 0.013 mmol) and 1,4-dioxane (6 mL) in a vial was sparged with $N_2$ for 5 min. The vial was sealed, and heated at 125° C. for 2 h. After the reaction was cooled to room temperature, EtOAc was added. The mixture was filtered through a plug of Celite®, and eluted with EtOAc and water. The organic phase of the filtrate was separated, washed with aq. sat. $NaHCO_3$, dried with $Na_2SO_4$, and concentrated. The residue was purified by flash chromatography (silica gel, eluting with 0% to 35% acetone in hexanes) to give compound 157 (475 mg, 64% yield) as a white solid. m/z=206 (M-$C_6H_9$).

Compound 158: A mixture of compound 151 (231 mg, 0.56 mmol), copper(I) thiophene-2-carboxylate (320 mg, 1.68 mmol), compound 157 (200 mg, 0.70 mmol) and THF (5 mL) in a pressure bottle was sparged with $N_2$ for 5 min. Tetrakis(triphenylphosphine)palladium(O) (32 mg, 0.028 mmol) was added. The $N_2$ sparging was continued for another 2 min. The bottle was sealed, and heated at 100° C. for 14 h. After the reaction was cooled to room temperature, EtOAc was added. The mixture was filtered through a plug of Celite®, and eluted with EtOAc. The filtrate was washed with aq. 1 N NaOH and water. The organic extract was dried with $Na_2SO_4$, and concentrated. The residue was purified by flash chromatography (silica gel, eluting with 0% to 40% EtOAc in hexanes) to give the compound 158 (65 mg, 22% yield) as a white foamy solid. m/z=528 (M+1).

Compound 159: Compound 158 (64 mg, 0.12 mmol) was taken up in MeOH (0.8 mL). Aq. 3 N HCl (0.4 mL, 1.2 mmol) was added. The mixture was stirred for 4 h at room temperature. After concentrated, aq. sat. $NaHCO_3$ was added. The mixture was extracted with EtOAc. The organic extract was dried with $Na_2SO_4$, and concentrated to give compound 159 (60 mg, quantitative yield) as a light yellow foamy solid. m/z=484 (M+1).

Compound 160: Compound 159 (57 mg, 0.12 mmol) was dissolved in ethyl formate (0.28 mL) and cooled to 0° C. Sodium methoxide (25 wt. % in methanol, 0.41 mL, 1.77 mmol) was added. The mixture was stirred at room temperature for 2 h, and cooled to 0° C. Aq. 6 N HCl (0.3 mL, 1.8 mmol), EtOH (1.2 mL) and hydroxylamine hydrochloride (13 mg, 0.18 mmol) were added sequentially. The mixture was heated at 55° C. (oil bath) for 6 h, and concentrated. Aq. sat. $NaHCO_3$ was added. The mixture was extracted with EtOAc. The combined organic extract was dried with $Na_2SO_4$ and concentrated. The residue was purified by flash chromatography (silica gel, eluting with 0% to 60% EtOAc in hexanes) to give compound 160 (46 mg, 77% yield) as a white foamy solid. m/z=509 (M+1).

Compound 161: Compound 160 (46 mg, 0.090 mmol) was dissolved in MeOH (0.9 mL). Potassium carbonate (38 mg, 0.28 mmol) was added. The reaction mixture was stirred at room temperature for 16 h. Aq. 10% $NaH_2PO_4$ was added. The mixture was extracted with EtOAc. The organic extract was dried with $Na_2SO_4$ and concentrated. The residue was purified by flash chromatography (silica gel, eluting with 0% to 50% EtOAc in hexanes) to give compound 161 (39 mg, 85% yield) as a white foamy solid. m/z=509 (M+1).

T63: Compound 161 (39 mg, 0.077 mmol) was dissolved in benzene (1 mL). DDQ (20 mg, 0.088 mmol) was added. The mixture was heated at 85° C. for 1 h, and cooled to rt.

$CH_2Cl_2$ and aq. sat. $NaHCO_3$ were added. The mixture was stirred for 5 min, and extracted with $CH_2Cl_2$. The combined organic extract was washed with aq. sat. $NaHCO_3$, dried with $Na_2SO_4$, and concentrated. The residue was purified by flash chromatography (silica gel, eluting with 0% to 50% EtOAc in hexanes) to give compound T63 (15 mg, 38% yield) as a white foamy solid. $^1$H NMR (400 MHz, $CDCl_3$) δ 8.93 (s, 1H), 8.38 (td, J=1.1, 8.5 Hz, 1H), 7.94 (s, 1H), 7.47 (m, 4H), 7.33 (dt, J=1.1, 7.5 Hz, 1H), 7.24 (m, 1H), 2.90 (s, 3H), 2.88 (m, 2H), 2.64 (qd, J=6.7, 13.3 Hz, 1H), 2.31 (dt, J=2.8, 12.8 Hz, 1H), 2.17 (m, 1H), 1.87 (m, 1H), 1.60 (s, 3H), 1.34 (d, J=6.7 Hz, 3H); m/z=507 (M+1).

Compound 162: A mixture of compound 144 (161 mg, 0.33 mmol), morpholine (59 μL, 0.68 mmol), Xphos (19 mg, 0.040 mmol), tris(dibenzylideneacetone)dipalladium(O) (12 mg, 0.013 mmol), sodium tert-butoxide (48 mg, 0.50 mmol) and toluene (1 mL) in a vail was sparged with nitrogen for 5 min. The vial was sealed, and heated in a Biotage® microwave synthesizer at 100° C. for 2 h. After the reaction was cooled to room temperature, EtOAc was added. The mixture was washed with water. The organic extract was dried with $Na_2SO_4$, and concentrated. The residue was purified by flash chromatography (silica gel, eluting with 0% to 50% EtOAc in hexanes) to give the compound 162 (125 mg, 70% yield) as a light brown foamy solid. m/z=531 (M+1).

Compound 163: Compound 162 (439 mg, 0.83 mmol) was taken up in THF (2.8 mL) and MeOH (2.8 mL). Aq. 3 N HCl (2.8 mL, 8.4 mmol) was added. The mixture was stirred overnight at room temperature. After concentrated, aq. sat. $NaHCO_3$ was added. The mixture was extracted with EtOAc. The organic extract was dried with $Na_2SO_4$, and concentrated to give compound 163 (387 mg, 96% yield) as a light brown foamy solid. m/z=487 (M+1).

Compound 164: Compound 163 (385 mg, 0.79 mmol) was dissolved in ethyl formate (1.9 mL) and cooled to 0° C. Sodium methoxide (25 wt. % in methanol, 2.7 mL, 11.7 mmol) was added. The mixture was stirred at room temperature for 2 h, and cooled to 0° C. Aq. 6 N HCl (2.0 mL, 12.0 mmol), EtOH (11.9 mL) and hydroxylamine hydrochloride (84 mg, 1.21 mmol) were added sequentially. The mixture was heated at 55° C. (oil bath) for overnight, and concentrated. Aq. sat. $NaHCO_3$ was added. The mixture was extracted with EtOAc. The combined organic extract was dried with $Na_2SO_4$ and concentrated. The residue was purified by flash chromatography (silica gel, eluting with 0% to 50% EtOAc in hexanes) to give compound 164 (309 mg, 76% yield) as a yellow foamy solid. m/z=512 (M+1).

Compound 165: Compound 164 (306 mg, 0.60 mmol) was dissolved in MeOH (3 mL). Sodium methoxide (25 wt. % in methanol, 0.21 mL, 0.90 mmol) was added. The reaction mixture was stirred at 55° C. for 2 h, and cooled to 0° C. Aq. 10% $NaH_2PO_4$ was added. The mixture was extracted with EtOAc. The organic extract was dried with $Na_2SO_4$ and concentrated. The residue was purified by flash chromatography (silica gel, eluting with 0% to 50% EtOAc in hexanes) to give compound 165 (273 mg, 89% yield) as a yellow foamy solid. m/z=512 (M+1).

T64: Compound 165 (128 mg, 0.25 mmol) was dissolved in benzene (2.5 mL). DDQ (60 mg, 0.26 mmol) was added. The mixture was heated at reflux for 1 h, and cooled to rt. $CH_2Cl_2$ and aq. sat. $NaHCO_3$ were added. The mixture was extracted with $CH_2Cl_2$. The combined organic extract was washed with water and brine, dried with $Na_2SO_4$, and concentrated. The residue was purified by flash chromatography (silica gel, eluting with 0% to 20% EtOAc in $CH_2Cl_2$) to give compound T64 (98 mg, 77% yield) as a yellow foamy solid. $^1$H NMR (400 MHz, $CDCl_3$) δ 8.99 (s, 1H), 8.37 (dd, J=0.7, 5.3 Hz, 1H), 7.72 (dd, J=1.2, 5.2 Hz, 1H), 7.69 (t, J=0.8 Hz, 1H), 7.51 (m, 1H), 7.44 (dt, J=1.9, 7.4 Hz, 1H), 7.33 (dt, J=1.1, 7.5 Hz, 1H), 7.21 (ddd, J=1.0, 8.3, 9.6 Hz, 1H), 3.86 (dd, J=4.0, 5.8 Hz, 4H), 3.62 (dd, J=3.8, 6.0 Hz, 4H), 2.80 (m, 2H), 2.62 (qd, J=6.7, 13.4 Hz, 1H), 2.25 (dt, J=2.7, 12.8 Hz, 1H), 2.11 (m, 1H), 1.79 (dq, J=7.1, 12.9 Hz, 1H), 1.54 (s, 3H), 1.32 (d, J=6.7 Hz, 3H); m/z=510 (M+1).

Compound 166: A mixture of compound 144 (166 mg, 0.35 mmol), phenylboronic acid (55 mg, 0.45 mmol), potassium carbonate (239 mg, 1.73 mmol), toluene (2 mL), EtOH (1 mL) and water (1 mL) in a vail was sparged with nitrogen for 5 min. Tetrakis(triphenylphosphine)palladium(O) (12 mg, 0.010 mmol) was added. The nitrogen sparging was continued for another 2 min. The vial was sealed, and heated in a Biotage® microwave synthesizer at 100° C. for 2 h. After the reaction was cooled to room temperature, EtOAc was added. The mixture was washed with water. The organic extract was dried with $Na_2SO_4$, and concentrated. The residue was purified by flash chromatography (silica gel, eluting with 0% to 25% EtOAc in hexanes) to give the compound 166 (180 mg, quantitative yield) as a white foamy solid. m/z=522 (M+1).

Compound 167: Compound 166 (210 mg, 0.40 mmol) was taken up in THF (1.4 mL) and MeOH (1.4 mL). Aq. 3 N HCl (1.4 mL, 8.4 mmol) was added. The mixture was stirred overnight at room temperature. After concentrated, aq. sat. $NaHCO_3$ was added. The mixture was extracted with EtOAc. The organic extract was dried with $Na_2SO_4$, and concentrated to give compound 167 (189 mg, 98% yield) as a yellow foamy solid. m/z=478 (M+1).

Compound 168: Compound 167 (187 mg, 0.39 mmol) was dissolved in ethyl formate (945 μL) and cooled to 0° C. Sodium methoxide (25 wt. % in methanol, 1.4 mL, 6.06 mmol) was added. The mixture was stirred at room temperature for 2 h, and cooled to 0° C. Aq. 6 N HCl (0.98 mL, 5.88 mmol), EtOH (4 mL) and hydroxylamine hydrochloride (42 mg, 0.60 mmol) were added sequentially. The mixture was heated at 55° C. (oil bath) for overnight, and concentrated. Aq. sat. $NaHCO_3$ was added. The mixture was extracted with EtOAc. The combined organic extract was dried with $Na_2SO_4$ and concentrated. The residue was purified by flash chromatography (silica gel, eluting with 0% to 25% EtOAc in hexanes) to give compound 168 (132 mg, 67% yield) as a yellow foamy solid. m/z=503 (M+1).

Compound 169: Compound 168 (130 mg, 0.26 mmol) was dissolved in MeOH (1.3 mL). Sodium methoxide (25 wt. % in methanol, 90 μL, 0.39 mmol) was added. The reaction mixture was stirred at 55° C. for 2 h, and cooled to 0° C. Aq. 10% $NaH_2PO_4$ was added. The mixture was extracted with EtOAc. The organic extract was dried with $Na_2SO_4$ and concentrated. The residue was purified by flash chromatography (silica gel, eluting with 0% to 50% EtOAc in hexanes) to give compound 169 (112 mg, 86% yield) as a white foamy solid. m/z=503 (M+1).

T65: Compound 169 (82 mg, 0.16 mmol) was dissolved in anhydrous DMF (0.4 mL), and the solution was cooled to 0° C. 1,3-dibromo-5,5-dimethylhydantoin (23 mg, 0.080 mmol) in DMF (0.4 mL) was added. The reaction was stirred at 0° C. for 2 h. Pyridine (40 μL, 0.50 mmol) was added. The reaction was heated at 55° C. (oil bath) for 3 h, and cooled to room temperature. $CH_2Cl_2$ was added. The mixture was washed with water. The organic extract was dried with $Na_2SO_4$, and concentrated. The residual pyridine was removed by azeotropic evaporation with toluene. The residue was purified by flash chromatography (silica gel, eluting with 0% to 30% acetone in hexanes) to give compound T65 (63 mg, 76% yield) as a white foamy solid. $^1$H NMR (400 MHz, CDCl$_3$) δ 9.03 (s, 1H), 8.88 (dd, J=0.8, 5.1 Hz, 1H), 8.76 (dd, J=0.9, 1.5 Hz, 1H), 8.30 (dd, J=1.6, 5.1 Hz, 1H), 8.11 (m, 2H), 7.50 (m, 5H), 7.35 (dt, J=1.1, 7.5 Hz, 1H), 7.23 (m, 1H), 2.83 (m, 2H), 2.63 (td, J=6.7, 13.3 Hz, 1H), 2.28 (dt, J=2.7, 12.8 Hz, 1H), 2.14 (m, 1H), 1.81 (m, 1H), 1.58 (s, 3H), 1.33 (d, J=6.7 Hz, 3H); m/z=501 (M+1).

Compound 170a: A mixture of compound 88 (1.30 g, 3.77 mmol), 4-isoquinolinecarboximidamide hydrochloride (1.21 g, 5.81 mmol) and potassium carbonate (1.56 g, 11.28 mmol) in EtOH (38 mL) was refluxed under nitrogen overnight. The mixture was cooled, and concentrated. The residue was partitioned between EtOAc (50 mL) and aq. sat. KH$_2$PO$_4$ (50 mL). The organic extract was washed with brine (50 mL), dried over MgSO$_4$, filtered and concentrated to give the dihydropyrimidine. The crude product was dissolved in CH$_2$Cl$_2$ (50 mL), and treated with manganese dioxide (88%, 1.63 g, 16.50 mmol). After stirring at room temperature overnight, the mixture was filtered. The filtrate was concentrated, and the residue was purified by flash chromatography (silica gel, eluting with 100% EtOAc) to give compound 170a (0.70 g, 38% yield) as a light yellow foamy solid. m/z=496 (M+1).

Compound 171a: A solution of compound 170a (0.70 g, 1.42 mmol) and aq. 3 N HCl (4.7 mL, 14.1 mmol) in MeOH (15 mL) was stirred at room temperature overnight. The mixture was concentrated, cooled, basified with aq. 10% NH$_4$OH, and then extracted with CHCl$_3$ (50 mL). The organic extract was washed with brine (50 mL), dried over MgSO$_4$, filtered and concentrated to give compound 171a (0.63 g, 98% yield) as an off-white foamy solid. m/z=452 (M+1).

Compound 172a: To a stirring solution at room temperature of compound 171a (0.63 g, 1.40 mmol) in ethyl formate (10 mL, 124 mmol) was added sodium methoxide (30 wt. % solution in MeOH, 0.80 mL, 4.26 mmol). The mixture was stirred for 2 h, and then partitioned between EtOAc (50 mL) and aq. sat. KH$_2$PO$_4$ (50 mL). The organic extract was washed with brine (50 mL), dried over MgSO$_4$, filtered and concentrated to give compound 172a (0.60 g, 88% yield) as a light brown foamy solid. m/z=480 (M+1).

Compound 173a: To a solution of compound 172a (0.60 g, 1.25 mmol) in EtOH (25 mL) was added acetic acid (0.70 mL, 12.23 mmol) and hydroxylamine hydrochloride (0.13 g, 1.87 mmol). The mixture was heated at 60° C. under nitrogen for 2 h, stirred at room temperature overnight, and concentrated. The residue was partitioned between aq. sat. NaHCO$_3$ (50 mL) and EtOAc (50 mL). The organic extract was washed with brine (50 mL), dried over MgSO$_4$, filtered and concentrated to give compound 173a (0.57 g, 96% yield) as a tan foamy solid. m/z=477 (M+1).

Compound 174a: A mixture of compound 173a (0.57 g, 1.20 mmol) and potassium carbonate (0.83 g, 6.00 mmol) in MeOH (12 mL) was stirred at room temperature under nitrogen for 16 h. The mixture was filtered, and the filtrate was concentrated. The residue was carefully partitioned between aq. sat. KH$_2$PO$_4$ (50 mL) and EtOAc (50 mL). The organic extract was washed with brine (50 mL), dried over MgSO$_4$, filtered and concentrated. The residue was purified by flash chromatography (silica gel, eluting with 50% EtOAc in hexanes) to give compound 174a (0.37 g, 65% yield) as a light yellow foamy solid. m/z=477 (M+1).

T66: To a stirring solution at 0° C. under nitrogen of compound 174a (0.37 g, 0.78 mmol) in degassed DMF (8 mL) was added dropwise a solution of 1,3-dibromo-5,5-dimethylhydantoin (0.12 g, 0.42 mmol) in DMF (2 mL). After stirring the mixture for 30 min, pyridine (0.6 mL, 7.44 mmol) was added. The ice-bath was removed. The mixture was heated at 60° C. for 4 h, cooled, and concentrated. The residue was partitioned between aq. sat. KH$_2$PO$_4$ (50 mL) and EtOAc (50 mL). The organic extract was washed with brine (50 mL), dried over MgSO$_4$, filtered, and concentrated. The residue was purified by flash chromatography (silica gel, eluting with 70% EtOAc in hexanes) to give compound T66 (0.13 g, 35% yield) as a light yellow foamy solid. $^1$H NMR (400 MHz, CDCl$_3$) δ 9.36 (s, 1H), 9.22 (s, 1H), 8.98 (s, 1H), 8.79 (ddd, J=0.8, 1.6, 8.8 Hz, 1H), 8.08 (d, J=8.2 Hz, 1H), 7.81 (ddd, J=1.4, 6.9, 8.6 Hz, 1H), 7.68 (ddd, J=1.1, 6.9, 8.1 Hz, 1H), 7.50 (m, 2H), 7.33 (dt, J=1.1, 7.5 Hz, 1H), 7.23 (m, 1H), 2.88 (m, 2H), 2.64 (qd, J=6.7, 13.4 Hz, 1H), 2.31 (dt, J=2.8, 12.8 Hz, 1H), 2.17 (m, 1H), 1.86 (m, 1H), 1.60 (s, 3H), 1.34 (d, J=6.8 Hz, 3H); m/z=475 (M+1).

Compound 170b: A mixture of compound 88 (1.30 g, 3.77 mmol), impure pyrazolo[1,5-a]pyridine-3-carboximidamide hydrochloride (<5.78 mmol) and potassium carbonate (1.56 g, 11.28 mmol) in EtOH (38 mL) was refluxed under nitrogen overnight. The mixture was cooled, and concentrated. The residue was partitioned between EtOAc (50 mL) and aq. sat. KH$_2$PO$_4$ (50 mL). The organic extract was washed with brine (50 mL), dried over MgSO$_4$, filtered and concentrated to give the dihydropyrimidine. The crude product was dissolved in CH$_2$Cl$_2$ (50 mL), and treated with manganese dioxide (88%, 1.7 g, 17.2 mmol). After stirring at room temperature overnight, the mixture was filtered. The filtrate was concentrated, and the residue was purified by flash chromatography (silica gel, eluting with 50% EtOAc in hexanes) to give compound 170b (0.15 g, 8% yield) as a tan foamy solid. m/z=485 (M+1).

Compound 171b: A solution of compound 170b (0.15 g, 0.31 mmol) and aq. 3 N HCl (1.0 mL, 3.0 mmol) in MeOH (1 mL) was stirred at room temperature overnight. The mixture was concentrated, cooled, basified with aq. 10% NH$_4$OH, and then extracted with CHCl$_3$ (25 mL). The organic extract was washed with brine (25 mL), dried over MgSO$_4$, filtered and concentrated to give compound 171b (0.13 g, 96% yield) as a tan foamy solid. m/z=441 (M+1).

Compound 172b: To a stirring solution at room temperature of compound 171b (0.13 g, 0.30 mmol) in ethyl formate (10 mL, 124 mmol) was added sodium methoxide (30 wt. % solution in MeOH, 0.28 mL, 1.49 mmol). The mixture was stirred for 2 h, and then partitioned between EtOAc (25 mL) and aq. sat. KH$_2$PO$_4$ (25 mL). The organic extract was washed with brine (25 mL), dried over MgSO$_4$, filtered and concentrated to give compound 172b (0.11 g, 80% yield) as a tan foamy solid. m/z=469 (M+1).

Compound 173b: To a solution of compound 172b (0.11 g, 0.23 mmol) in EtOH (10 mL) was added acetic acid (0.15 mL, 2.62 mmol) and hydroxylamine hydrochloride (0.025 g, 0.36 mmol). The mixture was heated at 60° C. under nitrogen for 2 h, stirred at room temperature overnight, and concentrated. The residue was partitioned between aq. sat. NaHCO$_3$ (25 mL) and EtOAc (25 mL). The organic extract was washed with brine (25 mL), dried over MgSO$_4$, filtered and concentrated to give compound 173b (0.10 g, 91% yield) as a tan foamy solid. m/z=466 (M+1).

Compound 174b: A mixture of compound 173b (0.10 g, 0.21 mmol) and potassium carbonate (0.15 g, 1.08 mmol) in MeOH (10 mL) was stirred at room temperature under nitrogen for 16 h. After filtration, the filtrate was concentrated. The residue was carefully partitioned between aq. sat. KH$_2$PO$_4$ (25 mL) and EtOAc (25 mL). The organic extract was washed with brine (25 mL), dried over MgSO$_4$, filtered and concentrated. The crude product was purified by flash chromatography (silica gel, eluting with 70% EtOAc in hexanes) to give compound 174b (0.073 g, 73% yield) as a tan foamy solid. m/z=466 (M+1).

T67: To a stirring solution at 0° C. under nitrogen of compound 174b (0.073 g, 0.16 mmol) in degassed DMF (5 mL) was added dropwise a solution of 1,3-dibromo-5,5-dimethylhydantoin (0.025 g, 0.087 mmol) in DMF (1 mL). After stirring the mixture for 30 min, pyridine (0.13 mL, 1.61 mmol) was added. The ice-bath was removed. The mixture was heated at 60° C. for 4 h, cooled, and concentrated. The residue was partitioned between aq. sat. $KH_2PO_4$ (25 mL) and EtOAc (25 mL). The organic extract was washed with brine (25 mL), dried over $MgSO_4$, filtered, and concentrated. The crude product was purified by flash chromatography (silica gel, eluting with 50% EtOAc in hexanes) to give compound T67 (0.031 g, 42% yield) as a yellow foamy solid. $^1$H NMR (400 MHz, $CDCl_3$) δ 9.03 (s, 1H), 8.79 (s, 1H), 8.56 (td, J=1.1, 6.9 Hz, 1H), 8.50 (td, J=1.3, 9.0 Hz, 1H), 7.49 (m, 2H), 7.35 (m, 2H), 7.21 (ddd, J=1.0, 8.3, 9.5 Hz, 1H), 6.92 (dt, J=1.4, 6.9 Hz, 1H), 2.76 (m, 2H), 2.62 (qd, J=6.7, 13.4 Hz, 1H), 2.26 (dt, J=2.7, 12.8 Hz, 1H), 2.08 (m, 1H), 1.77 (tdd, J=7.0, 13.0, 19.3 Hz, 1H), 1.57 (s, 3H), 1.32 (d, J=6.7 Hz, 3H); m/z=464 (M+1).

Compound 170c: A mixture of compound 88 (1.50 g, 4.36 mmol), 8-methyl-4-quinolinecarboximidamide hydrochloride (1.21 g, 5.46 mmol) and potassium carbonate (1.81 g, 13.10 mmol) in EtOH (30 mL) was refluxed under nitrogen overnight. The mixture was cooled, and concentrated. The residue was partitioned between EtOAc (50 mL) and aq. sat. $KH_2PO_4$ (50 mL). The organic extract was washed with brine (50 mL), dried over $MgSO_4$, filtered and concentrated to give the dihydropyrimidine. The crude product was dissolved in $CH_2Cl_2$ (100 mL), treated with manganese dioxide (88%, 2.0 g, 20.2 mmol) and stirred at room temperature overnight. After filtration, the filtrate was concentrated. The crude product was purified by flash chromatography (silica gel, eluting with 25% EtOAc in hexanes) to give compound 170c (1.49 g, 67% yield) as light a yellow foamy solid. m/z=510 (M+1).

Compound 171c: A solution of compound 170c (1.49 g, 2.92 mmol) and aq. 3 N HCl (10 mL, 30 mmol) in MeOH (30 mL) was stirred at room temperature overnight. After concentration, the mixture was cooled, basified with aq. 10% $NH_4OH$, and then extracted with $CHCl_3$ (50 mL). The organic extract was washed with brine (50 mL), dried over $MgSO_4$, filtered and concentrated to give compound 171c (1.44 g, quantitative yield) as a light yellow foamy solid. m/z=466 (M+1).

Compound 172c: To a stirring solution at room temperature of compound 171c (all from the last step) in ethyl formate (12 mL, 148 mmol) was added sodium methoxide (30 wt. % solution in MeOH, 1.6 mL, 8.64 mmol). The mixture was stirred for 2 h, and then partitioned between EtOAc (50 mL) and aq. sat. $KH_2PO_4$ (50 mL). The organic extract was washed with brine (50 mL), dried over $MgSO_4$, filtered and concentrated to give compound 172c (1.34 g, 92% yield) as a tan foamy solid. m/z=494 (M+1).

Compound 173c: To a solution of compound 172c (1.34 g, 2.71 mmol) in EtOH (25 mL) was added acetic acid (1.6 mL, 27.9 mmol) and hydroxylamine hydrochloride (0.28 g, 4.03 mmol). The mixture was heated at 60° C. under nitrogen for 2 h, stirred at room temperature overnight, and concentrated. The residue was partitioned between aq. sat. $NaHCO_3$ (50 mL) and EtOAc (50 mL). The organic extract was washed with brine (50 mL), dried over $MgSO_4$, filtered and concentrated to give compound 173c (1.31 g, 98% yield) as a tan foamy solid. m/z=491 (M+1).

Compound 174c: A mixture of compound 173c (1.31 g, 2.67 mmol) and potassium carbonate (1.84 g, 13.31 mmol) in MeOH (27 mL) was stirred at room temperature under nitrogen for 16 h. After filtration, the filtrate was concentrated. The residue was carefully partitioned between aq. sat. $KH_2PO_4$ (50 mL) and EtOAc (50 mL). The organic extract was washed with brine (50 mL), dried over $MgSO_4$, filtered and concentrated. The crude product was purified by flash chromatography (silica gel, eluting with 50% EtOAc in hexanes) to give compound 174c (0.94 g, 72% yield) as a light yellow foamy solid. m/z=491 (M+1).

T68: To a stirring solution at 0° C. under nitrogen of compound 174c (0.94 g, 1.91 mmol) in degassed DMF (10 mL) was added dropwise a solution of 1,3-dibromo-5,5-dimethylhydantoin (0.30 g, 1.05 mmol) in DMF (2 mL). After stirring the mixture for 30 min, pyridine (1.5 mL, 18.5 mmol) was added. The ice-bath was removed. The mixture was heated at 60° C. for 4 h, cooled, and concentrated. The residue was partitioned between aq. sat. $KH_2PO_4$ (50 mL) and EtOAc (50 mL). The organic extract was washed with brine (50 mL), dried over $MgSO_4$, filtered, and concentrated. The crude product was purified by flash chromatography (silica gel, eluting with 50% EtOAc in hexanes) to give compound T68 (0.30 g, 32% yield) as a light yellow solid. $^1$H NMR (400 MHz, $CDCl_3$) δ 9.11 (d, J=4.5 Hz, 1H), 8.94 (s, 1H), 8.48 (m, 1H), 7.97 (d, J=4.4 Hz, 1H), 7.63 (td, J=1.3, 7.0 Hz, 1H), 7.49 (m, 3H), 7.32 (dt, J=1.1, 7.6 Hz, 1H), 7.23 (m, 1H), 2.89 (m, 2H), 2.88 (s, 3H), 2.63 (td, J=6.7, 13.4 Hz, 1H), 2.31 (dt, J=2.7, 12.8 Hz, 1H), 2.17 (m, 1H), 1.85 (m, 1H), 1.59 (s, 3H), 1.34 (d, J=6.7 Hz, 3H); m/z=489 (M+1).

Compound 170d: A mixture of compound 1 (1.50 g, 4.36 mmol), 2-methyl-4-quinolinecarboximidamide hydrochloride (1.21 g, 5.46 mmol) and potassium carbonate (1.81 g, 13.10 mmol) in EtOH (30 mL) was refluxed under nitrogen overnight. The mixture was cooled, and concentrated. The residue was partitioned between EtOAc (50 mL) and aq. sat. $KH_2PO_4$ (50 mL). The organic extract was washed with brine (50 mL), dried over $MgSO_4$, filtered and concentrated to give the dihydropyrimidine. The crude product was dissolved into $CH_2Cl_2$ (100 mL), and treated with manganese dioxide (88%, 2.0 g, 20.2 mmol). The mixture was stirred at room temperature overnight, filtered, and concentrated. The crude product was purified by flash chromatography (silica gel, eluting with 50% EtOAc in hexanes) to give compound 170d (1.44 g, 65% yield) as a light yellow foamy solid. m/z=510 (M+1).

Compound 171d: A solution of compound 170d (1.44 g, 2.83 mmol) and aq. 3 N HCl (9.5 mL, 28.5 mmol) in MeOH (28 mL) was stirred at room temperature overnight, and concentrated. The residue was cooled, basified with aq. 10% $NH_4OH$, and then extracted with $CHCl_3$ (50 mL). The organic extract was washed with brine (50 mL), dried over $MgSO_4$, filtered and concentrated to give compound 171d (1.41 g, quantitative yield) as a light yellow foamy solid. m/z=466 (M+1).

Compound 172d: To a stirring solution at room temperature of compound 171d (all from the last step) in ethyl formate (12 mL, 148 mmol) was added sodium methoxide (30 wt. % solution in MeOH, 1.6 mL, 8.64 mmol). The mixture was stirred for 2 h, and then partitioned between EtOAc (50 mL) and aq. sat. $KH_2PO_4$ (50 mL). The organic extract was washed with brine (50 mL), dried over $MgSO_4$, filtered and concentrated to give compound 172d (1.34 g, 95% yield) as a dark yellow foamy solid. m/z=494 (M+1).

Compound 173d: To a solution of compound 172d (1.34 g, 2.71 mmol) in EtOH (25 mL) was added acetic acid (1.6 mL, 27.9 mmol) and hydroxylamine hydrochloride (0.28 g, 4.03 mmol). The mixture was heated at 60° C. under nitrogen for 2 h, stirred at room temperature overnight, concentrated. The residue was partitioned between aq. sat. NaHCO$_3$ (50 mL) and EtOAc (50 mL). The organic extract was washed with brine (50 mL), dried over MgSO$_4$, filtered and concentrated to give compound 173d (1.28 g, 96% yield) as an orange foamy solid. m/z=491 (M+1).

Compound 174d: A mixture of compound 173d (1.28 g, 2.62 mmol) and potassium carbonate (1.81 g, 13.10 mmol) in MeOH (26 mL) was stirred at room temperature under nitrogen for 16 h. The mixture was filtered, and the filtrate was concentrated. The residue was carefully partitioned between aq. sat. KH$_2$PO$_4$ (50 mL) and EtOAc (50 mL). The organic extract was washed with brine (50 mL), dried over MgSO$_4$, filtered and concentrated. The crude product was purified by flash chromatography (silica gel, eluting with 50% EtOAc in hexanes) to give compound 174d (0.80 g, 63% yield) as a light yellow foamy solid. m/z=491 (M+1).

T69: To a stirring solution at 0° C. under nitrogen of compound 174d (0.80 g, 1.64 mmol) in degassed DMF (8 mL) was added dropwise a solution of 1,3-dibromo-5,5-dimethylhydantoin (0.26 g, 0.91 mmol) in DMF (2 mL). After stirring the mixture for 30 min, pyridine (1.3 mL, 16.1 mmol) was added. The ice-bath was removed. The mixture was heated at 60° C. for 4 h, cooled, and concentrated. The residue was partitioned between aq. sat. KH$_2$PO$_4$ (50 mL) and EtOAc (50 mL). The organic extract was washed with brine (50 mL), dried over MgSO$_4$, filtered, and concentrated. The crude product was purified by flash chromatography (silica gel, eluting with 75% EtOAc in hexanes), and then crystallized from EtOH to give compound T69 (0.14 g, 18% yield) as an off-white solid. $^1$H NMR (400 MHz, CDCl$_3$) δ 8.95 (s, 1H), 8.57 (dd, J=1.4, 8.6 Hz, 1H), 8.12 (ddd, J=0.8, 1.2, 8.4 Hz, 1H), 7.86 (s, 1H), 7.73 (ddd, J=1.5, 6.8, 8.4 Hz, 1H), 7.52 (m, 3H), 7.33 (dt, J=1.0, 7.5 Hz, 1H), 7.23 (m, 1H), 2.88 (m, 2H), 2.85 (s, 3H), 2.64 (qd, J=6.7, 13.4 Hz, 1H), 2.31 (dt, J=2.7, 12.8 Hz, 1H), 2.17 (m, 1H), 1.86 (m, 1H), 1.60 (s, 3H), 1.34 (d, J=6.7 Hz, 3H); m/z=489 (M+1).

Compound 170e: A mixture of compound 88 (1.51 g, 4.38 mmol), impure 2,4-dimethyl-5-thiazolecarboximidamide hydrochloride (<6.58 mmol) and potassium carbonate (3.0 g, 21.7 mmol) in EtOH (44 mL) was refluxed under nitrogen overnight. The mixture was cooled, and concentrated. The residue was partitioned between EtOAc (50 mL) and aq. sat. KH$_2$PO$_4$ (50 mL). The organic extract was washed with brine (50 mL), dried over MgSO$_4$, filtered and concentrated to give the dihydropyrimidine. The crude product was dissolved into CH$_2$Cl$_2$ (100 mL), and treated with manganese dioxide (88%, 2.0 g, 20.2 mmol). The mixture was stirred at room temperature overnight, and filtered. The filtrate was concentrated. The crude product was purified by flash chromatography (silica gel, eluting with 25% EtOAc in hexanes) to give compound 170e (1.12 g, 53% yield) as a light yellow solid. m/z=480 (M+1).

Compound 171e: A solution of compound 170e (1.12 g, 2.33 mmol) and aq. 3 N HCl (8 mL, 24 mmol) in MeOH (23 mL) was stirred at room temperature overnight, and concentrated. The residue was cooled, basified with aq. 10% NH$_4$OH, and then extracted with CHCl$_3$ (50 mL). The organic extract was washed with brine (50 mL), dried over MgSO$_4$, filtered and concentrated to give compound 171e (1.01 g, quantitative yield) as a light yellow foamy solid. m/z=436 (M+1).

Compound 172e: To a stirring solution at room temperature of compound 171e (1.01 g, 2.33 mmol) in ethyl formate (10 mL, 124 mmol) was added sodium methoxide (30 wt. % solution in MeOH, 1.3 mL, 7.02 mmol). The mixture was stirred for 2 h, and then partitioned between EtOAc (50 mL) and aq. sat. KH$_2$PO$_4$ (50 mL). The organic extract was washed with brine (50 mL), dried over MgSO$_4$, filtered and concentrated to give compound 172e (1.11 g, quantitative yield) as a dark yellow foamy solid. m/z=464 (M+1).

Compound 173e: To a solution of compound 172e (all from the last step) in EtOH (25 mL) was added acetic acid (1.4 mL, 24.4 mmol) and hydroxylamine hydrochloride (0.25 g, 3.60 mmol). The mixture was heated at 60° C. under nitrogen for 2 h, stirred at room temperature overnight, and concentrated. The residue was partitioned between aq. sat. NaHCO$_3$ (50 mL) and EtOAc (50 mL). The organic extract was washed with brine (50 mL), dried over MgSO$_4$, filtered and concentrated to give compound 173e (1.08 g, quantitative yield) as a brown foamy solid. m/z=461 (M+1).

Compound 174e. A mixture of compound 173e (1.08 g, 2.33 mmol) and potassium carbonate (1.62 g, 11.72 mmol) in MeOH (25 mL) was stirred at room temperature under nitrogen for 16 h. The mixture was filtered, and the filtrate was concentrated. The residue was carefully partitioned between aq. sat. KH$_2$PO$_4$ (50 mL) and EtOAc (50 mL). The organic extract was washed with brine (50 mL), dried over MgSO$_4$, filtered and concentrated. The crude product was purified by flash chromatography (silica gel, eluting with 50% EtOAc in hexanes) to give compound 174e (0.72 g, 67% yield) as a light yellow foamy solid. m/z=461 (M+1).

T70: To a stirring solution at 0° C. under nitrogen of compound 174e (0.72 g, 1.57 mmol) in degassed DMF (8 mL) was added dropwise a solution of 1,3-dibromo-5,5-dimethylhydantoin (0.25 g, 0.87 mmol) in DMF (2 mL). After stirring the mixture for 30 min, pyridine (1.3 mL, 16.1 mmol) was added. The ice-bath was removed. The mixture was heated at 60° C. for 4 h, cooled, and concentrated. The residue was partitioned between aq. sat. KH$_2$PO$_4$ (50 mL) and EtOAc (50 mL). The organic extract was washed with brine (50 mL), dried over MgSO$_4$, filtered, and concentrated. The crude product was purified by flash chromatography repeatedly (silica gel, eluting with 50% EtOAc in hexanes) to give compound T70 (0.21 g, 29% yield) as a light yellow foamy solid. $^1$H NMR (400 MHz, CDCl$_3$) δ 8.85 (s, 1H), 7.49 (m, 1H), 7.41 (dt, J=1.2, 7.6 Hz, 1H), 7.30 (dt, J=1.1, 7.5 Hz, 1H), 7.19 (ddd, J=1.0, 8.4, 9.6 Hz, 1H), 2.86 (s, 3H), 2.75 (m, 2H), 2.70 (s, 3H), 2.59 (qd, J=6.7, 13.4 Hz, 1H), 2.22 (dt, J=2.3, 12.8 Hz, 1H), 2.09 (m, 1H), 1.75 (dq, J=7.1, 13.0 Hz, 1H), 1.50 (s, 3H), 1.31 (d, J=6.7 Hz, 3H); m/z=459 (M+1).

Compound 170f: A mixture of compound 88 (1.45 g, 4.21 mmol), 5-methyl-1,2,4-oxadiazole-3-carboximidamide hydrochloride (0.86 g, 5.29 mmol) and potassium carbonate (1.74 g, 12.59 mmol) in EtOH (30 mL) was refluxed under nitrogen overnight. The mixture was cooled and concentrated. The residue was partitioned between EtOAc (50 mL) and aq. sat. KH$_2$PO$_4$ (50 mL). The organic extract was washed with brine (50 mL), dried over MgSO$_4$, filtered and concentrated to give the dihydropyrimidine. The crude product was dissolved in CH$_2$Cl$_2$ (100 mL), and treated with manganese dioxide (88%, 2.0 g, 20.2 mmol). The mixture was stirred at room temperature overnight, and filtered. The filtrate was concentrated, and the crude product was purified by flash chromatography (silica gel, eluting with 50% EtOAc in hexanes) to give compound 170f (0.64 g, 34% yield) as an off-white solid. m/z=451 (M+1).

Compound 171f: A solution of compound 170f (0.64 g, 1.42 mmol) and aq. 3 N HCl (5 mL, 15 mmol) in MeOH (14 mL) was stirred at room temperature overnight, and concentrated. The residue was cooled, basified with aq. 10% NH$_4$OH, and then extracted with CHCl$_3$ (50 mL). The organic extract was washed with brine (50 mL), dried over MgSO$_4$, filtered and concentrated to give compound 171f (0.62 g, quantitative yield) as a light yellow foamy solid. m/z=407 (M+1).

Compound 172f: To a stirring solution at room temperature of compound 171f (all from the last step) in ethyl formate (10 mL, 124 mmol) was added sodium methoxide (30 wt. % solution in MeOH, 0.8 mL, 4.32 mmol). The mixture was stirred for 2 h, and then partitioned between EtOAc (50 mL) and aq. sat. KH$_2$PO$_4$ (50 mL). The organic extract was washed with brine (50 mL), dried over MgSO$_4$, filtered and concentrated to give compound 172f (0.63 g, quantitative yield) as a bright yellow foamy solid. m/z=435 (M+1).

Compound 173f: To a solution of compound 172f (all from the last step) in EtOH (20 mL) was added acetic acid (0.8 mL, 14.1 mmol) and hydroxylamine hydrochloride (0.15 g, 2.16 mmol). The mixture was heated at 60° C. under nitrogen for 2 h, stirred at room temperature overnight, and concentrated. The residue was partitioned between aq. sat. NaHCO$_3$ (50 mL) and EtOAc (50 mL). The organic extract was washed with brine (50 mL), dried over MgSO$_4$, filtered, and concentrated. The crude product was purified by flash chromatography (silica gel, eluting with 50% EtOAc in hexanes) to give compound 173f (0.33 g, 55% yield) as a yellow foamy solid. m/z=432 (M+1).

Compound 174f: A mixture of compound 173f (0.33 g, 0.76 mmol) and potassium carbonate (0.32 g, 2.32 mmol) in MeOH (20 mL) was stirred at room temperature under nitrogen for 16 h. The mixture was filtered, and the filtrate was concentrated. The residue was carefully partitioned between aq. sat. KH$_2$PO$_4$ (50 mL) and EtOAc (50 mL). The organic extract was washed with brine (50 mL), dried over MgSO$_4$, filtered and concentrated. The crude product was purified by flash chromatography (silica gel, eluting with 75% EtOAc in hexanes, and then 5% MeOH in CHCl$_3$) to give compound 174f (0.080 g, 24% yield) as a light yellow foamy solid. m/z=432 (M+1).

T71: To a stirring solution at 0° C. under nitrogen of compound 174f (0.080 g, 0.18 mmol) in degassed DMF (2 mL) was added 1,3-dibromo-5,5-dimethylhydantoin (0.029 g, 0.10 mmol). After stirring the mixture for 30 min, pyridine (0.15 mL, 1.85 mmol) was added. The ice-bath was removed. The mixture was heated at 60° C. for 4 h, cooled, and concentrated. The residue was partitioned between aq. sat. KH$_2$PO$_4$ (50 mL) and EtOAc (50 mL). The organic extract was washed with brine (50 mL), dried over MgSO$_4$, filtered, and concentrated. The crude product was purified by flash chromatography (silica gel, eluting with 75% EtOAc in hexanes) to give compound T71 (0.045 g, 56% yield) as a light yellow foamy solid. $^1$H NMR (400 MHz, CDCl$_3$) δ 9.03 (s, 1H), 7.47 (m, 2H), 7.29 (dt, J=1.2, 7.7 Hz, 1H), 7.17 (dd, J=8.5, 9.9 Hz, 1H), 2.86 (m, 2H), 2.75 (s, 3H), 2.61 (qd, J=6.7, 13.3 Hz, 1H), 2.26 (m, 1H), 2.14 (m, 1H), 1.83 (m, 1H), 1.57 (s, 3H), 1.32 (d, J=6.7 Hz, 3H); m/z=430 (M+1).

Compound 170g: Compound 88 (850 mg, 2.45 mmol) was taken up in EtOH (20 mL). 1-Methyl-1H-pyrrolo[2,3-b]pyridine-3-carboximidamide hydrochloride (2.1 g, 10 mmol) and potassium carbonate (2.8 g, 20.2 mmol) were added. The reaction mixture was heated at reflux for 16 h, cooled and concentrated. Water (50 mL) was added. The mixture was neutralized with aq. KH$_2$PO$_4$, and extracted with EtOAc. The organic extract was dried with MgSO$_4$ and concentrated to give the dihydropyrimidine. The crude product was taken up in CH$_2$Cl$_2$ (20 mL), and treated with manganese dioxide (88%, 1.3 g, 13.3 mmol). The mixture was stirred overnight at room temperature, and filtered. The filtrate was concentrated. The crude product was purified by flash chromatography (silica gel, eluting with 0% to 35% EtOAc in hexanes) to give compound 170g (1.05 g, 84% yield) as a foam. m/z=499 (M+1).

Compound 171g: Compound 170g (1.05 g, 2.11 mmol) was taken up in THF (10 mL), and aq. 3 N HCl (5 mL, 15 mmol) was added. The mixture was stirred overnight at room temperature, and concentrated. The residue was neutralized with aq. sat. NaHCO$_3$, and extracted with EtOAc. The organic extract was washed with water, dried with MgSO$_4$, filtered, and concentrated to give compound 171g (0.95 g, 99% yield) as a foam. m/z=455 (M+1).

Compound 172g: Compound 171g (0.95 g, 2.09 mmol) was taken up in ethyl formate (15 mL, 186 mmol). Sodium methoxide (30 wt. % in MeOH, 0.75 g, 4.17 mmol) was added. After stirring for 2 h at room temperature, the mixture was neutralized with aq. KH$_2$PO$_4$, and extracted with EtOAc. The organic extract was dried with MgSO$_4$, filtered, and concentrated to give compound 172g (0.96 g, 95% yield) as a foam. m/z=483 (M+1).

Compound 173g: Compound 172g (0.96 g, 1.99 mmol) was dissolved in EtOH (15 mL). Hydroxylamine hydrochloride (1.4 g, 20 mmol) and acetic acid (1.2 g, 20 mmol) were added. The reaction mixture was stirred overnight at 50° C., cooled, and concentrated. The residue was taken up in EtOAc, and washed with aq. NaHCO$_3$. The organic extract was dried with MgSO$_4$, filtered, and concentrated to give compound 173g (0.83 g, 87% yield) as a foam. m/z=480 (M+1).

Compound 174g: Compound 173g (830 mg, 1.73 mmol) was dissolved in MeOH (10 mL). K$_2$CO$_3$ (1.2 g, 8.68 mmol) was added. After stirring at room temperature overnight, the reaction mixture was neutralized by the addition of aq. sat. KH$_2$PO$_4$, and extracted with EtOAc. The organic extract was washed with brine, dried with MgSO$_4$, filtered, and concentrated. The residue was purified by flash chromatography (silica gel, eluting with 0% to 35% EtOAc in hexanes) to give compound 174g (410 mg, 49% yield) as a foam. m/z=480 (M+1).

T72: Compound 174g (410 mg, 0.85 mmol) was dissolved in dry DMF (4 mL), and the solution was cooled to 0° C. 1,3-dibromo-5,5-dimethylhydantoin (135 mg, 0.47 mmol) in DMF (1 mL) was added. After stirring the mixture at 0° C. for 2 h, pyridine (3 mL, 37.2 mmol) was added. The mixture was heated at 60° C. for 4 h, cooled to room temperature, and partitioned between aq. NaHCO$_3$ and EtOAc. The organic extract was dried with MgSO$_4$, filtered and concentrated. The residue was purified by flash chromatography (silica gel, eluting with 0% to 35% EtOAc in hexanes) to give compound T72 (105 mg, 26% yield) as a foam. $^1$H NMR (400 MHz, CDCl$_3$) δ 9.05 (s, 1H), 8.78 (dd, J=1.7, 7.9 Hz, 1H), 8.41 (dd, J=1.6, 4.7 Hz, 1H), 8.25 (s, 1H), 7.50 (m, 2H), 7.33 (dt, J=1.1, 7.5 Hz, 1H), 7.22 (m, 2H), 4.00 (s, 3H), 2.75 (m, 2H), 2.62 (qd, J=6.7, 13.4 Hz, 1H), 2.26 (dt, J=2.7, 12.8 Hz, 1H), 2.08 (m, 1H), 1.77 (m, 1H), 1.57 (s, 3H), 1.32 (d, J=6.7 Hz, 3H); m/z=478 (M+1).

Compound 170h: Compound 88 (1 g, 2.90 mmol) was taken up in EtOH (20 mL). 6-Methylquinoline-4-carboximidamide hydrochloride (820 mg, 3.70 mmol) and potassium carbonate (1.1 g, 7.96 mmol) were added. The reaction mixture was heated at reflux for 16 h, cooled and concentrated. Water (50 mL) was added. The mixture was neutralized with aq. KH$_2$PO$_4$, and extracted with EtOAc. The organic extract was dried with MgSO$_4$ and concentrated to give the dihydropyrimidine. The crude product was taken up in CH$_2$Cl$_2$ (20 mL), and treated with manganese dioxide (88%, 1.35 g, 13.66 mmol). The mixture was stirred overnight at room temperature, and filtered. The filtrate was concentrated. The crude product was purified by flash chromatography (silica gel, eluting with 0% to 35% EtOAc in hexanes) to give compound 170h (660 mg, 45% yield) as a foam. m/z=510 (M+1).

Compound 171h: Compound 170h (660 mg, 1.30 mmol) was taken up in THF (10 mL), and aq. 3 N HCl (5 mL, 15 mmol) was added. The mixture was stirred overnight at room temperature, and concentrated. The residue was neutralized with aq. sat. NaHCO$_3$, and extracted with EtOAc. The organic extract was washed with water, dried with MgSO$_4$, filtered, and concentrated to give compound 171h (0.61 g, quantitative yield) as a foam. m/z=466 (M+1).

Compound 172h: Compound 171h (0.61 g, 1.30 mmol) was taken up in ethyl formate (15 mL, 186 mmol). Sodium methoxide (30 wt. % in MeOH, 0.47 g, 2.61 mmol) was added. After stirring for 2 h at room temperature, the mixture was neutralized with aq. KH$_2$PO$_4$, and extracted with EtOAc. The organic extract was dried with MgSO$_4$, filtered, and concentrated to give compound 172h (0.59 g, 92% yield) as a foam. m/z=494 (M+1).

Compound 173h Compound 172h (0.59 g, 1.20 mmol) was dissolved in EtOH (15 mL). Hydroxylamine hydrochloride (0.83 g, 11.94 mmol) and acetic acid (0.72 g, 12 mmol) were added. The reaction mixture was stirred overnight at 50° C., cooled, and concentrated. The residue was taken up in EtOAc, and washed with aq. NaHCO$_3$. The organic extract was dried with MgSO$_4$, filtered, and concentrated to give compound 173h (0.57 g, 97% yield) as a foam. m/z=491 (M+1).

Compound 174h Compound 173h (570 mg, 1.16 mmol) was dissolved in MeOH (10 mL). potassium carbonate (0.8 g, 5.79 mmol) was added. After stirring at room temperature overnight, the reaction mixture was neutralized by the addition of aq. sat. KH$_2$PO$_4$, and extracted with EtOAc. The organic extract was washed with brine, dried with MgSO$_4$, filtered, and concentrated. The residue was purified by flash chromatography (silica gel, eluting with 0% to 35% EtOAc in hexanes) to give compound 174h (400 mg, 70% yield) as a foam. m/z=491 (M+1).

T73: Compound 174h (400 mg, 0.82 mmol) was dissolved in dry DMF (4 mL), and the solution was cooled to 0° C. 1,3-dibromo-5,5-dimethylhydantoin (130 mg, 0.45 mmol) in DMF (1 mL) was added. After stirring the mixture at 0° C. for 2 h, pyridine (3 mL, 37.2 mmol) was added. The mixture was heated at 60° C. for 4 h, cooled to room temperature, and partitioned between aq. NaHCO$_3$ and EtOAc. The organic extract was dried with MgSO$_4$, filtered and concentrated. The residue was purified by flash chromatography (silica gel, eluting with 0% to 35% EtOAc in hexanes) to give compound T73 (250 mg, 62% yield) as a foam. $^1$H NMR (400 MHz, CDCl$_3$) δ 9.00 (d, J=4.5 Hz, 1H), 8.99 (s, 1H), 8.49 (m, 1H), 8.11 (d, J=8.6 Hz, 1H), 7.97 (d, J=4.5 Hz, 1H), 7.61 (dd, J=2.0, 8.6 Hz, 1H), 7.50 (m, 2H), 7.33 (dt, J=1.1, 7.6 Hz, 1H), 7.23 (m, 1H), 2.91 (m, 2H), 2.64 (qd, J=6.7, 13.4 Hz, 1H), 2.58 (s, 3H), 2.33 (dt, J=2.7, 12.8 Hz, 1H), 2.18 (m, 1H), 1.86 (m, 1H), 1.59 (s, 3H), 1.35 (d, J=6.7 Hz, 3H); m/z=489 (M+1).

Compound 170i: Compound 88 (0.7 g, 2.03 mmol) was taken up in EtOH (20 mL). 4-Quinazolinecarboximidamide hydrochloride (1.6 g, 7.67 mmol) and potassium carbonate (2.1 g, 15.19 mmol) were added. The reaction mixture was heated at reflux for 16 h, cooled and concentrated. Water (50 mL) was added. The mixture was neutralized with aq. KH$_2$PO$_4$, and extracted with EtOAc. The organic extract was dried with MgSO$_4$ and concentrated to give the dihydropyrimidine. The crude product was taken up in CH$_2$Cl$_2$ (20 mL), and treated with manganese dioxide (88%, 2.0 g, 20.24 mmol). The mixture was stirred overnight at room temperature, and filtered. The filtrate was concentrated. The crude product was purified by flash chromatography (silica gel, eluting with 0% to 35% EtOAc in hexanes) to give compound 170i (130 mg, 13% yield) as a foam. m/z=497 (M+1).

Compound 171l: Compound 170i (130 mg, 0.26 mmol) was taken up in THF (6 mL), and aq. 3 N HCl (3 mL, 9.0 mmol) was added. The mixture was stirred overnight at room temperature, and concentrated. The residue was neutralized with aq. sat. NaHCO$_3$, and extracted with EtOAc. The organic extract was washed with water, dried with MgSO$_4$, filtered, and concentrated to give compound 171l (120 mg, quantitative yield) as a foam. m/z=453 (M+1).

Compound 172i: Compound 171l (0.12 g, 0.26 mmol) was taken up in ethyl formate (10 mL, 124 mmol). Sodium methoxide (30 wt. % in MeOH, 0.10 g, 0.56 mmol) was added. After stirring for 2 h at room temperature, the mixture was neutralized with aq. KH$_2$PO$_4$, and extracted with EtOAc. The organic extract was dried with MgSO$_4$, filtered, and concentrated to give compound 172i (0.12 g, 94% yield) as a foam. m/z=481 (M+1).

Compound 173i: Compound 172i (0.12 g, 0.25 mmol) was dissolved in EtOH (15 mL). Hydroxylamine hydrochloride (175 mg, 2.52 mmol) and acetic acid (150 mg, 2.50 mmol) were added. The reaction mixture was stirred overnight at 50° C., cooled, and concentrated. The residue was taken up in EtOAc, and washed with aq. NaHCO$_3$. The organic extract was dried with MgSO$_4$, filtered, and concentrated to give compound 173i (0.11 g, 92% yield) as a foam. m/z=478 (M+1).

Compound 174i: Compound 173i (110 mg, 0.23 mmol) was dissolved in MeOH (10 mL). Potassium carbonate (160 mg, 1.15 mmol) was added. After stirring at room temperature overnight, the reaction mixture was neutralized by the addition of aq. sat. KH$_2$PO$_4$, and extracted with EtOAc. The organic extract was washed with brine, dried with MgSO$_4$, filtered, and concentrated. The residue was purified by flash chromatography (silica gel, eluting with 0% to 35% EtOAc in hexanes) to give compound 174i (60 mg, 55% yield) as a foam. m/z=478 (M+1).

T74: Compound 174i (60 mg, 0.13 mmol) was dissolved in dry DMF (2 mL), and the solution was cooled to 0° C. 1,3-dibromo-5,5-dimethylhydantoin (20 mg, 0.070 mmol) in DMF (1 mL) was added. After stirring the mixture at 0° C. for 2 h, pyridine (1 mL, 12.4 mmol) was added. The mixture was heated at 60° C. for 4 h, cooled to room temperature, and partitioned between aq. NaHCO$_3$ and EtOAc. The organic extract was dried with MgSO$_4$, filtered and concentrated. The residue was purified by flash chromatography (silica gel, eluting with 0% to 35% EtOAc in hexanes) to give compound T74 (20 mg, 33% yield). $^1$H NMR (400 MHz, CDCl$_3$) δ 9.53 (s, 1H), 8.91 (s, 1H), 8.40 (ddd, J=0.8, 1.6, 8.3 Hz, 1H), 8.18 (td, J=0.8, 8.6 Hz, 1H), 7.98 (ddd, J=1.4, 6.9, 8.5 Hz, 1H), 7.72 (ddd, J=1.3, 6.9, 8.3 Hz, 1H), 7.49 (m, 2H), 7.31 (dt, J=1.1, 7.5 Hz, 1H), 7.21 (m, 1H), 2.94 (m, 2H), 2.64 (qd, J=6.7, 13.4 Hz, 1H), 2.32 (dt, J=2.8, 12.8 Hz, 1H), 2.18 (tdd, J=3.0, 6.2, 13.8 Hz, 1H), 1.87 (m, 1H), 1.60 (s, 3H), 1.34 (d, J=6.7 Hz, 3H); m/z=476 (M+1).

Compound 170j: Compound 88 (0.65 g, 1.88 mmol) was taken up in EtOH (20 mL). 1-Isoquinolinecarboximidamide hydrochloride (790 mg, 3.80 mmol) and potassium carbonate (1.2 g, 8.68 mmol) were added. The reaction mixture was heated at reflux for 16 h, cooled and concentrated. Water (50 mL) was added. The mixture was neutralized with aq. KH$_2$PO$_4$, and extracted with EtOAc. The organic extract was dried with MgSO$_4$ and concentrated to give the dihydropyrimidine. The crude product was taken up in CH$_2$Cl$_2$ (20 mL), and treated with manganese dioxide (88%, 1.1 g, 11.14 mmol). The mixture was stirred overnight at room temperature, and filtered. The filtrate was concentrated. The crude product was purified by flash chromatography (silica gel, eluting with 0% to 35% EtOAc in hexanes) to give compound 170j (190 mg, 20% yield) as a foam. m/z=496 (M+1).

Compound 171j: Compound 170j (190 mg, 0.38 mmol) was taken up in THF (6 mL), and aq. 3 N HCl (3 mL, 9.0 mmol) was added. The mixture was stirred overnight at room temperature, and concentrated. The residue was neutralized with aq. sat. NaHCO$_3$, and extracted with EtOAc. The organic extract was washed with water, then dried with MgSO$_4$, filtered, and concentrated to give compound 171j (175 mg, quantitative yield) as a foam. m/z=452 (M+1).

Compound 172j: Compound 171j (175 mg, 0.38 mmol) was taken up in ethyl formate (10 mL, 124 mmol). Sodium methoxide (30 wt. % in MeOH, 0.15 g, 0.83 mmol) was added. After stirring for 2 h at room temperature, the mixture was neutralized with aq. KH$_2$PO$_4$, and extracted with EtOAc. The organic extract was dried with MgSO$_4$, filtered, and concentrated to give compound 172j (0.18 g, 98% yield) as a foam. m/z=480 (M+1).

Compound 173j: Compound 172j (0.18 g, 0.38 mmol) was dissolved in EtOH (15 mL). Hydroxylamine hydrochloride (260 mg, 3.74 mmol) and acetic acid (225 mg, 3.75 mmol) were added. The reaction mixture was stirred overnight at 50° C., cooled, and concentrated. The residue was taken up in EtOAc, and washed with aq. NaHCO$_3$. The organic extract was dried with MgSO$_4$, filtered, and concentrated to give compound 173j (0.17 g, 94% yield) as a foam. m/z=477 (M+1).

Compound 174j: Compound 173j (170 mg, 0.36 mmol) was dissolved in MeOH (10 mL). Potassium carbonate (250 mg, 1.81 mmol) was added. After stirring at room temperature overnight, the reaction mixture was neutralized by the addition of aq. sat. KH$_2$PO$_4$, and extracted with EtOAc. The organic extract was washed with brine, dried with MgSO$_4$, filtered, and concentrated. The residue was purified by flash chromatography (silica gel, eluting with 0% to 35% EtOAc in hexanes) to give compound 174j (110 mg, 65% yield) as a foam. m/z=477 (M+1).

T75: Compound 174j (330 mg, 0.69 mmol) was dissolved in dry DMF (4 mL), and the solution was cooled to 0° C. 1,3-dibromo-5,5-dimethylhydantoin (110 mg, 0.38 mmol) in DMF (1 mL) was added. After stirring the mixture at 0° C. for 2 h, pyridine (2 mL, 24.8 mmol) was added. The mixture was heated at 60° C. for 4 h, cooled to room temperature, and partitioned between aq. NaHCO$_3$ and EtOAc. The organic extract was dried with MgSO$_4$, filtered and concentrated. The residue was purified by flash chromatography (silica gel, eluting with 0% to 35% EtOAc in hexanes) to give compound T75 (165 mg, 50% yield) as a foam. $^1$H NMR (400 MHz, CDCl$_3$) δ 8.96 (s, 1H), 8.72 (d, J=5.6 Hz, 1H), 8.30 (qd, J=1.0, 8.5 Hz, 1H), 7.94 (td, J=0.9, 8.3 Hz, 1H), 7.81 (dd, J=0.9, 5.7 Hz, 1H), 7.74 (ddd, J=1.2, 6.9, 8.2 Hz, 1H), 7.64 (ddd, J=1.3, 6.9, 8.4 Hz, 1H), 7.47 (m, 2H), 7.28 (m, 1H), 7.19 (ddd, J=1.0, 8.3, 9.5 Hz, 1H), 2.91 (m, 2H), 2.63 (qd, J=6.7, 13.3 Hz, 1H), 2.32 (dt, J=2.7, 12.8 Hz, 1H), 2.16 (m, 1H), 1.87 (m, 1H), 1.58 (s, 3H), 1.34 (d, J=6.7 Hz, 3H); m/z=475 (M+1).

Compound 170k: A mixture of compound 88 (1.01 g, 2.95 mmol), 7-fluoro-4-quinolinecarboximidamide hydrochloride (1.0 g, 4.43 mmol), and potassium carbonate (1.22 g, 8.85 mmol) in EtOH (25 mL) was heated at reflux for 44 h. The reaction mixture was concentrated and the residue was partitioned between aq. sat. KH$_2$PO$_4$ and CH$_2$Cl$_2$. The organic extract was washed with brine, dried over MgSO$_4$, filtered and concentrated to give the crude dihydropyrimidine as a yellow glass. The crude product was dissolved in CH$_2$Cl$_2$ (15 mL) and the solution was treated with manganese dioxide (88%, 2.27 g, 23.01 mmol). The reaction mixture was stirred under nitrogen at room temperature for 22 h, and filtered through Celite®. The filtrate was concentrated, and the residue was purified by flash chromatography (silica gel, eluting with 40% EtOAc in hexanes) to give compound 170k (1.16 g, 77% yield) as a white glass. m/z=514 (M+1).

Compound 171k: A solution of compound 170k (1.13 g, 2.20 mmol) in THF (15 mL) was treated with aq. 3 N HCl (7.3 ml, 21.9 mmol) and the reaction mixture was stirred at room temperature for 18 h. The solvent was removed in vacuo, and the residue was cooled to 0° C., neutralized cautiously with aq. sat. NaHCO$_3$, and extracted with EtOAc. The organic extract was washed with water and brine, dried over MgSO$_4$, filtered, and concentrated to a give compound 171k (1.03 g, quantitative yield) as a white glass. m/z=470 (M+1).

Compound 172k: A solution of compound 171k (1.03 g, 2.19 mmol) in ethyl formate (15 mL, 186 mmol) was cooled to 0° C. and treated dropwise with sodium methoxide (5.4 M solution in MeOH, 2.04 mL, 11.02 mmol). The cold bath was removed and the reaction mixture was stirred at room temperature for 18 h. The solvent was removed in vacuo, and the residue was partitioned between EtOAc and aq. sat. KH$_2$PO$_4$. The organic extract was washed with brine, dried over MgSO$_4$, filtered, and concentrated to give compound 172k (1.03 g, 94% yield) as an off-white glass. m/z=498 (M+1).

Compound 173k: A solution of compound 172k (1.03 g, 2.07 mmol) in glacial acetic acid (1.19 mL, 20.7 mmol) and EtOH (10 mL) was treated with hydroxylamine hydrochloride (216 mg, 3.11 mmol). The reaction mixture was stirred under nitrogen at 60° C. for 4 h and at room temperature for 18 h. The solvent was removed in vacuo, and the residue was cautiously partitioned between aq. 10% NH$_4$OH and CH$_2$Cl$_2$. The organic extract was washed with brine, dried over MgSO$_4$, filtered and concentrated to give compound 173k (942 mg, 92% yield) as a pale yellow glass. m/z=495 (M+1).

Compound 174k: A mixture of compound 173k (942 mg, 1.90 mmol) and potassium carbonate (525 mg, 3.80 mmol) in MeOH (10 mL) was stirred under nitrogen at room temperature for 17 h. The reaction mixture was concentrated, and the residue was partitioned between water and Et$_2$O. The aqueous phase was cooled in an ice-water bath and acidified with aq. sat. KH$_2$PO$_4$. The acidified aqueous mixture was extracted with EtOAc (2×50 ml), and the combined organic extracts were washed with brine, dried over MgSO$_4$, filtered and concentrated. The residue was purified by flash chromatography (silica gel, eluting with 50% EtOAc in hexanes) to give compound 174k (646 mg, 69% yield) as a white glass. m/z=495 (M+1).

T76: A solution of compound 174k (646 mg, 1.31 mmol) in degassed DMF (10 mL) was cooled to 0° C., and treated dropwise with a solution of 1,3-dibromo-5,5-dimethylhydantoin (206 mg, 0.72 mmol) in degassed DMF (3 mL). After stirring at 0° C. for 30 min, anhydrous pyridine (1.06 mL, 13.13 mmol) was added. The cold bath was removed, and the reaction mixture was heated at 60° C. under an argon atmosphere for 4 h. Upon cooling to room temperature, the reaction mixture was partitioned between EtOAc and aq. sat.

KH₂PO₄. The organic extract was washed with brine, dried over MgSO₄, filtered and concentrated. The residue was purified by flash chromatography (silica gel, eluting with 50% EtOAc in hexanes) to give compound T76 (401 mg, 62% yield) as a light yellow glass. ¹H NMR (400 MHz, CDCl₃) δ 9.09 (d, J=4.5 Hz, 1H), 8.93 (s, 1H), 8.79 (dd, J=6.1, 9.4 Hz, 1H), 8.02 (d, J=4.5 Hz, 1H), 7.84 (dd, J=2.7, 9.9 Hz, 1H), 7.47 (m, 3H), 7.33 (dt, J=1.0, 7.5 Hz, 1H), 7.24 (m, 1H), 2.90 (m, 2H), 2.64 (qd, J=6.7, 13.4 Hz, 1H), 2.31 (dt, J=2.7, 12.8 Hz, 1H), 2.18 (m, 1H), 1.87 (m, 1H), 1.60 (s, 3H), 1.34 (d, J=6.7 Hz, 3H); m/z=493 (M+1).

Compound 170l: A mixture of compound 88 (285 mg, 0.83 mmol), 8-fluoro-4-quinolinecarboximidamide hydrochloride (280 mg, 1.24 mmol), and potassium carbonate (343 mg, 2.48 mmol) in EtOH (20 mL) was heated at reflux for 66 h. The reaction mixture was concentrated, and the residue was partitioned between aq. sat. KH₂PO₄ and CH₂Cl₂. The organic extract was washed with brine, dried over MgSO₄, filtered and concentrated to give the crude dihydropyrimidine as a yellow glass. The crude product was dissolved in CH₂Cl₂ (15 mL) and the solution was treated with manganese dioxide (88%, 625 mg, 6.33 mmol). The reaction mixture was stirred under nitrogen at room temperature for 23 h and filtered through Celite®. The filtrate was concentrated and the residue was purified by flash chromatography (silica gel, eluting with 40% EtOAc in hexanes) to give compound 170l (316 mg, 74% yield) as a white glass. m/z=514 (M+1).

Compound 171l: A solution of compound 170l (316 mg, 0.62 mmol) in THF (15 mL) was treated with aq. 3 N HCl (2.05 mL, 6.15 mmol) and the reaction mixture was stirred at room temperature for 24 h. The solvent was removed in vacuo, and the residue was cooled to 0° C., neutralized cautiously with aq. sat. NaHCO₃, and extracted with EtOAc. The organic extract was washed with water and brine, dried over MgSO₄, filtered and concentrated to give compound 171l (276 mg, 95% yield) as a white glass. m/z=470 (M+1).

Compound 172l: A solution of compound 171l (477 mg, 1.02 mmol) in ethyl formate (15 mL, 186 mmol) was cooled to 0° C. and treated dropwise with sodium methoxide (5.4 M solution in MeOH, 0.94 mL, 5.08 mmol). The cold bath was removed and the reaction mixture was stirred at room temperature for 18 h. The solvent was removed in vacuo, and the residue was partitioned between EtOAc and aq. sat. KH₂PO₄. The organic extract was washed with brine, dried over MgSO₄, filtered and concentrated to give compound 172l (495 mg, 98% yield) as a yellow glass. m/z=498 (M+1).

Compound 173l: A solution of compound 172l (490 mg, 0.99 mmol) in glacial acetic acid (0.57 mL, 9.85 mmol) and EtOH (10 mL) was treated with hydroxylamine hydrochloride (103 mg, 1.48 mmol). The reaction mixture was stirred under nitrogen at 60° C. for 4 h and at room temperature for 19 h. The solvent was removed in vacuo, and the residue was cautiously partitioned between aq. 10% NH₄OH and CH₂Cl₂. The organic extract was washed with brine, dried over MgSO₄, filtered and concentrated to give compound 173l (567 mg) as an orange glass. m/z=495 (M+1).

Compound 174l: A mixture of compound 173l (all from the last step) and potassium carbonate (272 mg, 1.97 mmol) in MeOH (10 mL) was stirred under nitrogen at room temperature for 22 h. The reaction mixture was concentrated and the residue was partitioned between water and Et₂O. The aqueous phase was cooled in an ice-water bath and acidified with aq. sat. KH₂PO₄. The acidified aqueous mixture was extracted with EtOAc (2×50 ml) and the combined organic extracts were washed with brine, dried over MgSO₄, filtered and concentrated. The residue was purified by flash chromatography, eluting with 50% EtOAc in hexanes) to give compound 174l (300 mg, 62% yield) as a clear glass. m/z=495 (M+1).

T77: A solution of compound 174l (300 mg, 0.606 mmol) in degassed DMF (10 mL) was cooled to 0° C., and treated dropwise with a solution of 1,3-dibromo-5,5-dimethylhydantoin (95 mg, 0.332 mmol) in degassed DMF (2 mL). After stirring the mixture at 0° C. for 30 min, anhydrous pyridine (0.49 mL, 6.07 mmol) was added. The cold bath was removed, and the reaction mixture was heated at 60° C. under an argon atmosphere for 4 h. Upon cooling to room temperature, the reaction mixture was partitioned between EtOAc and aq. sat. KH₂PO₄. The organic extract was washed with brine, dried over MgSO₄, filtered and concentrated. The residue was purified by flash chromatography (silica gel, eluting with 50% EtOAc in hexanes) to give compound T77 (210 mg, 70% yield) as a clear glass. ¹H NMR (400 MHz, CDCl₃) δ 9.14 (d, J=4.4 Hz, 1H), 8.92 (s, 1H), 8.52 (td, J=1.1, 8.6 Hz, 1H), 8.11 (d, J=4.4 Hz, 1H), 7.52 (m, 4H), 7.33 (dt, J=1.1, 7.5 Hz, 1H), 7.24 (m, 1H), 2.91 (m, 2H), 2.64 (qd, J=6.7, 13.4 Hz, 1H), 2.31 (dt, J=2.8, 12.8 Hz, 1H), 2.18 (m, 1H), 1.86 (m, 1H), 1.60 (s, 3H), 1.34 (d, J=6.7 Hz, 3H); m/z=493 (M+1).

Compound 170m: A mixture of compound 88 (1.06 g, 3.08 mmol), 6-methyl-4-pyrimidinecarboximidamide hydrochloride (800 mg, 4.63 mmol), and potassium carbonate (1.28 g, 9.26 mmol) in EtOH (40 mL) was heated at reflux for 96 h, cooled and concentrated. The residue was partitioned between aq. sat. KH₂PO₄ and CH₂Cl₂. The organic extract was washed with brine, dried over MgSO₄, filtered and concentrated to give the dihydropyrimidine as a yellow glass. The crude product was dissolved in CH₂Cl₂ (20 mL) and the solution was treated with manganese dioxide (88%, 2.38 g, 24.10 mmol). The reaction mixture was stirred under nitrogen at room temperature for 22 h and filtered through Celite®. The filtrate was concentrated and the residue was purified by flash chromatography (silica gel, eluting with 30% to 100% EtOAc in hexanes) to give compound 170m (518 mg, 36% yield) as a glass. m/z=461 (M+1).

Compound 171m: A solution of compound 170m (514 mg, 1.12 mmol) in THF (20 mL) was treated with aq. 3 N HCl (3.73 ml, 11.19 mmol). The reaction mixture was stirred at room temperature for 16 h, and concentrated. The residue was cooled to 0° C., neutralized cautiously with aq. NaHCO₃, and extracted with EtOAc. The organic extract was washed with water, brine, dried over MgSO₄, filtered and concentrated. The residue was purified by flash chromatography (silica gel, eluting with 65% to 100% EtOAc in hexanes) to give compound 171m (264 mg, 57% yield) as a clear glass. m/z=417 (M+1).

Compound 172m: A solution of compound 171m (264 mg, 0.633 mmol) in ethyl formate (10 mL, 124 mmol) was cooled to 0° C. and treated dropwise with sodium methoxide (5.4 M solution in MeOH, 0.59 ml, 3.19 mmol). The cold bath was removed and the reaction mixture was stirred at room temperature for 14 h. The solvent was removed in vacuo and the residue was partitioned between EtOAc and aq. sat. KH₂PO₄. The organic extract was washed with brine, dried over MgSO₄, filtered and concentrated give compound 172m (274 mg, 97% yield) as an orange glass. m/z=445 (M+1).

Compound 173m: A solution of compound 172m (270 mg, 0.607 mmol) in glacial acetic acid (0.36 mL, 6.30 mmol) and EtOH (10 mL) was treated with hydroxylamine hydrochloride (66 mg, 0.950 mmol). The reaction mixture was stirred under nitrogen at 60° C. for 4 h and at room temperature for 24 h. The solvent was removed in vacuo and the residue was cautiously partitioned between aq. 10% NH$_4$OH and CH$_2$Cl$_2$. The organic extract was washed with brine, dried over MgSO$_4$, filtered and concentrated to give compound 173m (267 mg, quantitative yield) as an orange-brown glass. m/z=442 (M+1).

Compound 174m: A mixture of compound 173m (267 mg, 0.605 mmol) and potassium carbonate (167 mg, 1.21 mmol) in MeOH (10 mL) was stirred under nitrogen at room temperature for 16 h. The reaction mixture was concentrated and the residue was partitioned between water and Et$_2$O. The aqueous phase was cooled in an ice-water bath and acidified with aq. sat. KH$_2$PO$_4$. The acidified aqueous mixture was extracted with EtOAc (2×50 ml). The combined organic extracts were washed with brine, dried over MgSO$_4$, filtered and concentrated. The residue was purified by flash chromatography (silica gel, eluting with 100% EtOAc) to give compound 174m (126 mg, 47% yield) as a yellow glass. m/z=442 (M+1).

T78: A solution of compound 174m (126 mg, 0.285 mmol) in degassed DMF (5 mL) was cooled to 0° C., and treated dropwise with a solution of 1,3-dibromo-5,5-dimethylhydantoin (45 mg, 0.156 mmol) in degassed DMF (2 mL). After stirring the mixture at 0° C. for 30 min, anhydrous pyridine (0.23 mL, 2.85 mmol) was added. The cold bath was removed, and the reaction mixture was heated at 60° C. under an argon atmosphere for 4 h. Upon cooling to room temperature, the reaction mixture was partitioned between EtOAc and aq. sat. KH$_2$PO$_4$. The organic extract was washed with brine, dried over MgSO$_4$, filtered and concentrated. The residue was purified by flash chromatography (silica gel, eluting with 100% EtOAc) to give compound T78 as a yellow glass (83 mg, 66% yield). $^1$H NMR (400 MHz, CDCl$_3$) δ 9.34 (d, J=1.3 Hz, 1H), 9.05 (s, 1H), 8.33 (dd, J=0.8, 1.2 Hz, 1H), 7.48 (m, 2H), 7.31 (dt, J=1.0, 7.5 HZ, 1H), 7.19 (ddd, J=1.0, 8.4, 9.5 Hz, 1H), 2.85 (m, 2H), 2.73 (s, 3H), 2.63 (qd, J=6.7, 13.4 Hz, 1H), 2.28 (dt, J=2.7, 12.7 Hz, 1H), 2.13 (m, 1H), 1.82 (m, 1H), 1.57 (s, 3H), 1.33 (d, J=6.7 Hz, 3H); m/z=440 (M+1).

Compound 170n: A mixture of compound 88 (701 mg, 2.03 mmol), 4-pyridazinecarboximidamide hydrochloride (484 mg, 3.05 mmol), and potassium carbonate (842 mg, 6.09 mmol) in EtOH (30 mL) was heated at reflux for 67 h. The reaction mixture was concentrated and the residue was partitioned between aq. sat. KH$_2$PO$_4$ and EtOAc. The organic extract was washed with brine, dried over MgSO$_4$, filtered and concentrated to give the dihydropyrimidine as a dark orange glass. The crude product was dissolved in CH$_2$Cl$_2$ (20 mL) and the solution was treated with manganese dioxide (88%, 1.56 g, 15.79 mmol). The reaction mixture was stirred under nitrogen at room temperature for 26 h and filtered through Celite®. The filtrate was concentrated and the residue was purified by flash chromatography (silica gel, eluting with 100% EtOAc) to give compound 170n as an oil which crystallized upon standing (276 mg, 30% yield). m/z=447 (M+1).

Compound 171n: A solution of compound 170n (273 mg, 0.611 mmol) in THF (20 mL) was treated with aq. 3 N HCl (2.04 ml, 6.12 mmol) and the reaction mixture was stirred at room temperature for 17 h, and concentrated. The residue was cooled to 0° C., neutralized cautiously with aq. sat. NaHCO$_3$, and extracted with EtOAc. The organic extract was washed with water, brine, dried over MgSO$_4$, filtered and concentrated to give compound 171n (256 mg, quantitative yield) as a glass. m/z=403 (M+1).

Compound 172n: A solution of compound 171n (245 mg, 0.609 mmol) in ethyl formate (8 mL, 99.5 mmol) was cooled to 0° C. and treated dropwise with sodium methoxide (5.4 M solution in MeOH, 0.56 ml, 3.02 mmol). The cold bath was removed and the reaction mixture was stirred at room temperature for 18 h. The solvent was removed in vacuo and the residue was partitioned between EtOAc and aq. sat. KH$_2$PO$_4$. The organic extract was washed with brine, dried over MgSO$_4$, filtered and concentrated to give compound 172n (258 mg, 98% yield) as an orange glass. m/z=431 (M+1).

Compound 173n: A solution of compound 172n (258 mg, 0.599 mmol) in glacial acetic acid (0.35 mL, 5.99 mmol) and EtOH (5 mL) was treated with hydroxylamine hydrochloride (62 mg, 0.892 mmol). The reaction mixture was stirred under nitrogen at 60° C. for 4 h and at room temperature for 21 h. The solvent was removed in vacuo and the residue was cautiously partitioned between aq. 10% NH$_4$OH and CH$_2$Cl$_2$. The organic extract was washed with brine, dried over MgSO$_4$, filtered and concentrated to give compound 173n (236 mg, 92% yield) as an orange glass. m/z=428 (M+1).

Compound 174n: A mixture of compound 173n (236 mg, 0.552 mmol) and potassium carbonate (153 mg, 1.10 mmol) in MeOH (10 mL) was stirred under nitrogen at room temperature for 21 h. The reaction mixture was concentrated and the residue was partitioned between water and Et$_2$O. The aqueous phase was cooled in an ice-water bath and acidified with aq. sat. KH$_2$PO$_4$. The acidified aqueous mixture was extracted with EtOAc (2×30 mL). The combined organic extracts were washed with brine, dried over MgSO$_4$, filtered and concentrated. The residue was purified by flash chromatography (silica gel, eluting with 100% EtOAc) to give compound 174n (164 mg, 69% yield) as a clear glass. m/z=428 (M+1).

T79: A solution of compound 174n (164 mg, 0.384 mmol) in degassed DMF (5 mL) was cooled to 0° C., and treated dropwise with a solution of 1,3-dibromo-5,5-dimethylhydantoin (60 mg, 0.210 mmol) in degassed DMF (2 mL). After stirring the mixture at 0° C. for 30 min, anhydrous pyridine (0.31 mL, 3.84 mmol) was added. The cold bath was removed, and the reaction mixture was heated at 60° C. under an argon atmosphere for 4 h. Upon cooling to room temperature, the reaction mixture was partitioned between EtOAc and aq. sat. KH$_2$PO$_4$. The organic extract was washed with brine, dried over MgSO$_4$, filtered and concentrated. The residue was purified by flash chromatography (silica gel, eluting with 80% EtOAc in hexanes) to give compound T79 (115 mg, 70% yield) as a yellow oil which crystallized upon standing. $^1$H NMR (400 MHz, CDCl$_3$) δ 10.19 (dd, J=1.3, 2.3 Hz, 1H), 9.40 (dd, J=1.3, 5.3 Hz, 1H), 8.96 (s, 1H), 8.47 (dd, J=2.3, 5.3 Hz, 1H), 7.55 (m, 1H), 7.44 (dt, J=2.0, 7.4 Hz, 1H), 7.35 (dt, J=1.1, 7.5 Hz, 1H), 7.24 (m, 1H), 2.84 (m, 2H), 2.63 (qd, J=6.7, 13.4 Hz, 1H), 2.27 (dt, J=2.8, 12.8 Hz, 1H), 2.15 (m, 1H), 1.81 (ddt, J=7.2, 10.5, 13.2 Hz, 1H), 1.56 (s, 3H), 1.33 (d, J=6.7 Hz, 3H); m/z=426 (M+1).

Compound 175: Compound 88 (172 mg, 0.50 mmol), 6,7-dihydro-5H-cyclopenta[b]pyridine-4-carboximidamide hydrochloride (176 mg, 0.82 mmol) and K$_2$CO$_3$ (207 mg, 1.50 mmol) in EtOH (2.5 mL) were heated in a Biotage® microwave synthesizer at 120° C. for 11 h. After the reaction was cooled to room temperature, EtOAc was added. The mixture was washed with water. The organic extract was dried with Na$_2$SO$_4$, and concentrated. The residue was purified by flash chromatography (silica gel, eluting with 0% to 90% acetone in hexanes) to give the partially purified product (210 mg) as a yellow foamy solid. m/z=488. The product (210 mg, 0.43 mmol) was dissolved in CH$_2$Cl$_2$ (4 mL). DDQ (107 mg, 0.47 mmol) was added. The reaction was stirred at room temperature for 1 h. Aq. sat. NaHCO$_3$ was added, and the mixture was extracted with CH$_2$Cl$_2$. The combined organic extract was washed with aq. sat. NaHCO$_3$, dried with Na$_2$SO$_4$, and concentrated. The residue was purified by flash chromatography (silica gel, eluting with 0% to 50% acetone in hexanes) to give compound 175 (159 g, 66% yield from compound 98) as a white foamy solid. m/z=486 (M+1).

Compound 176: Compound 175 (157 mg, 0.32 mmol) was taken up in THF (1.1 mL) and MeOH (1.1 mL). Aq. 3 N HCl (1.1 mL, 3.3 mmol) was added. The mixture was stirred overnight at room temperature. Aq. sat. NaHCO$_3$ was added, and the mixture was extracted with EtOAc. The organic extract was washed with water, dried with Na$_2$SO$_4$, and concentrated to give compound 176 (146 mg) as a light brown foamy solid. m/z=442 (M+1).

Compound 177: Compound 176 (all from above) was dissolved in ethyl formate (0.8 mL) and cooled to 0° C. Sodium methoxide (25 wt. % in methanol, 1.14 mL, 4.94 mmol) was added. The mixture was stirred at room temperature for 1 h, and cooled to 0° C. Aq. 6 N HCl (0.82 mL, 4.92 mmol), EtOH (3.3 mL) and hydroxylamine hydrochloride (35 mg, 0.50 mmol) were added sequentially. The mixture was heated at 55° C. (oil bath) for 4 h, and concentrated. Aq. sat. NaHCO$_3$ was added, and the mixture was extracted with EtOAc. The organic extract was washed with water, dried with Na$_2$SO$_4$ and concentrated. The residue was purified by flash chromatography (silica gel, eluting with 0% to 50% acetone in hexanes) to give compound 177 (102 mg, 68% yield from compound 175) as a white foamy solid. m/z=467 (M+1).

Compound 178: Compound 177 (100 mg, 0.21 mmol) was dissolved in MeOH (2.1 mL). Potassium carbonate (89 mg, 0.64 mmol) was added. The reaction mixture was stirred at room temperature for overnight. Aq. 10% NaH$_2$PO$_4$ was added. The mixture was extracted with EtOAc. The organic extract was dried with Na$_2$SO$_4$ and concentrated. The residue was purified by flash chromatography (silica gel, eluting with 0% to 50% acetone in hexanes) to give compound 178 (100 mg, quantitative yield) as a white foamy solid. m/z=467 (M+1).

T80: Compound 178 (100 mg, 0.21 mmol) was dissolved in anhydrous DMF (1 mL), and the solution was cooled to 0° C. 1,3-dibromo-5,5-dimethylhydantoin (31 mg, 0.11 mmol) was added. The reaction was stirred at 0° C. for 1 h. Pyridine (52 µL, 0.64 mmol) was added. The reaction was heated at 55° C. (oil bath) for 2 h, and cooled to room temperature. CH$_2$Cl$_2$ was added. The mixture was washed with water. The organic extract was dried with Na$_2$SO$_4$, and concentrated. The residual pyridine was removed by azeotropic evaporation with toluene. The residue was purified by flash chromatography (silica gel, eluting with 0% to 50% acetone in hexanes) to give compound T80 (56 mg, 56% yield) as an off-white foamy solid. $^1$H NMR (400 MHz, CDCl$_3$) δ 8.94 (s, 1H), 8.51 (td, J=0.9, 5.3 Hz, 1H), 8.00 (td, J=0.8, 5.3 Hz, 1H), 7.51 (m, 1H), 7.45 (dt, J=2.0, 7.2 Hz, 1H), 7.33 (dt, J=1.1, 7.5 Hz, 1H), 7.21 (ddd, J=1.0, 8.3, 9.6 Hz, 1H), 3.47 (t, J=7.5 Hz, 2H), 3.12 (t, J=7.8 Hz, 2H), 2.84 (m, 2H), 2.62 (qd, J=6.7, 13.4 Hz, 1H), 2.22 (m, 4H), 1.80 (m, 1H), 1.55 (s, 3H), 1.33 (d, J=6.7 Hz, 3H); m/z=465 (M+1).

Compound 179 and 180: A mixture of compound 12 (1.203 g, 4.00 mmol), 2-fluorophenylboronic acid (559 mg, 4.02 mmol), sodium carbonate (1.28 g, 12.1 mmol), 1,4-dioxane (15 mL) and water (5 mL) in a pressure bottle was sparged with nitrogen for 5 min. [1,1'-Bis(diphenylphosphino)ferrocene]dichloropalladium (II) (294 mg, 0.40 mmol) was added. The nitrogen sparging was continued for another 2 min. The bottle was sealed, and heated at 100° C. for 1 h. After the reaction was cooled to room temperature, EtOAc was added. The mixture was filtered through a plug of Celite®, and eluted with EtOAc. The filtrate was washed with water. The organic extract was dried with Na$_2$SO$_4$, and concentrated. The residue was purified by flash chromatography (silica gel, eluting with 0% to 30% EtOAc in hexanes) to give compound 179 (675 mg, 47% yield) as a white solid. m/z=359 (M+1). From the column, also get compound 180 (135 mg, 8% yield) as a white foamy solid. m/z=419 (M+1).

Compound 181: Compound 180 (135 mg, 0.32 mmol) was dissolved in ethyl formate (0.78 mL) and cooled to 0° C. Sodium methoxide (25 wt. % in methanol, 1.1 mL, 4.76 mmol) was added. The mixture was stirred at room temperature for 1 h, and cooled to 0° C. Aq. 6 N HCl (0.79 mL, 4.74 mmol), EtOH (3.2 mL) and hydroxylamine hydrochloride (34 mg, 0.49 mmol) were added sequentially. The mixture was heated at 55° C. (oil bath) for 16 h, and concentrated. Aq. sat. NaHCO$_3$ was added. The mixture was extracted with EtOAc. The combined organic extract was dried with Na$_2$SO$_4$ and concentrated. The residue was purified by flash chromatography (silica gel, eluting with 0% to 30% EtOAc in hexanes) to give compound 181 (71 mg, 50% yield) as a white foamy solid. m/z=444 (M+1).

Compound 182: Compound 181 (70 mg, 0.16 mmol) was dissolved in MeOH (1.6 mL). Potassium carbonate (65 mg, 0.47 mmol) was added. The reaction mixture was stirred at room temperature for 16 h. EtOAc and aq. 10% NaH$_2$PO$_4$ were added. The mixture was extracted with EtOAc. The organic extract was dried with Na$_2$SO$_4$ and concentrated. The residue was purified by flash chromatography (silica gel, eluting with 0% to 35% EtOAc in hexanes) to give compound 182 (67 mg, 96% yield) as a white foamy solid. m/z=444 (M+1).

T81: Compound 182 (67 mg, 0.15 mmol) was dissolved in anhydrous DMF (0.75 mL), and the solution was cooled to 0° C. 1,3-dibromo-5,5-dimethylhydantoin (22 mg, 0.077 mmol) was added. The reaction was stirred at 0° C. for 1 h. Pyridine (37 µL, 0.46 mmol) was added. The reaction was heated at 55° C. (oil bath) for 2 h, and cooled to room temperature. CH$_2$Cl$_2$ was added. The mixture was washed with water. The organic extract was dried with Na$_2$SO$_4$, and concentrated. The residual pyridine was removed by azeotropic evaporation with toluene. The residue was purified by flash chromatography (silica gel, eluting with 0% to 30% acetone in hexanes) to give compound T81 (18 mg, 27% yield) as a white foamy solid. $^1$H NMR (400 MHz, CDCl$_3$) δ 9.01 (s, 1H), 8.11 (dt, J=1.9, 7.8, 1H), 7.47 (m, 3H), 7.24 (m, 4H), 2.81 (m, 2H), 2.61 (qd, J=6.7, 13.4 Hz, 1H), 2.26 (dt, J=2.7, 12.8 Hz, 1H), 2.11 (m, 1H), 1.80 (m, 1H), 1.54 (s, 3H), 1.32 (d, J=6.7 Hz, 3H); m/z=442 (M+1).

Compound 184: To a solution of compound 183 (290 mg, 1.41 mmol) in MeCN (7 mL) was added tetrabutylammonium fluoride trihydrate (887 mg, 2.82 mmol) at room temperature. After stirring for 2 h, the reaction mixture was concentrated. The residue was dissolved in 1/1 CH$_2$Cl$_2$/toluene, and was purified by flash chromatography (silica gel, eluting with 0% to 10% acetone in hexanes) to give compound 184 (72 mg, 35% yield) as a colorless oil.

Compound 185: A mixture of compound 184 (70 mg, 0.48 mmol), bis(pinacolato)diboron (244 mg, 0.96 mmol), potassium acetate (141 mg, 1.44 mmol), [1,1'-bis(diphenylphosphino)ferrocene]dichloropalladium(II) (18 mg, 0.025 mmol) and 1,4-dioxane (1.5 mL) in a vial was sparged with nitrogen for 5 min. The vial was sealed, and heated at 130° C. for 2 h. After the reaction was cooled to room temperature, EtOAc was added. The mixture was filtered through a plug of Celite®, and eluted with EtOAc. The filtrate was concentrated. The residue was purified by flash chromatography (silica gel, eluting with 0% to 50% acetone in hexanes) to give partially purified compound 185 (103 mg) as a viscous oil, which was used in the next step without further purification. m/z=156 (M-$C_6H_9$).

Compound 187a: A mixture of 4-chloro-6-fluoro-2-methyl-quinoline (186a, 250 mg, 1.28 mmol), bis(pinacolato)diboron (357 mg, 1.41 mmol), potassium acetate (314 mg, 3.20 mmol), [1,1'-bis(diphenylphosphino)ferrocene]dichloropalladium(II) (47 mg, 0.064 mmol) and 1,4-dioxane (3 mL) in a vial was sparged with nitrogen for 5 min. The vial was sealed, and heated at 125° C. for 5 h. After the reaction was cooled to room temperature, EtOAc and water were added. The mixture was filtered through a plug of Celite®, and eluted with EtOAc. The filtrate was washed with aq. sat. $NaHCO_3$. The organic extract was dried with $Na_2SO_4$, filtered and concentrated. The residue was purified by flash chromatography (silica gel, eluting with 0% to 30% acetone in hexanes) to give compound 187a (140 mg, 38% yield) as a tan solid. m/z=206 (M-$C_6H_9$).

Compound 187b: A mixture of 4-chloro-6-fluoro-quinoline (186b, 463 mg, 2.55 mmol), bis(pinacolato)diboron (712 mg, 2.80 mmol), potassium acetate (626 mg, 6.38 mmol), [1,1'-bis(diphenylphosphino)ferrocene]dichloropalladium(II) (98 mg, 0.13 mmol) and 1,4-dioxane (6 mL) in a vial was sparged with $N_2$ for 5 min. The vial was sealed, and heated at 125° C. for 2 h. After the reaction was cooled to room temperature, EtOAc was added. The mixture was filtered through a plug of Celite®, and eluted with EtOAc. The filtrate was concentrated. The residue was purified by flash chromatography (silica gel, eluting with 0% to 60% EtOAc in hexanes) to give partially purified product, which was purified again by flash chromatography (silica gel, eluting with 0% to 30% acetone in hexanes) to give compound 187b (131 mg, 19% yield) as a white solid.

Compound 187c: A mixture of 4-chloro-6,8-difluoro-quinoline (186c, 508 mg, 2.55 mmol), bis(pinacolato)diboron (712 mg, 2.80 mmol), potassium acetate (626 mg, 6.38 mmol), [1,1'-bis(diphenylphosphino)ferrocene]dichloropalladium(II) (98 mg, 0.13 mmol) and 1,4-dioxane (6 mL) in a vial was sparged with $N_2$ for 5 min. The vial was sealed, and heated at 125° C. for 2 h. After the reaction was cooled to room temperature, EtOAc was added. The mixture was filtered through a plug of Celite®, and eluted with EtOAc. The filtrate was concentrated. The residue was purified by flash chromatography (silica gel, eluting with 0% to 100% EtOAc in hexanes) to give compound 187c (442 mg, 60% yield) as a white solid.

Compound 188a: A mixture of compound 179 (550 mg, 1.53 mmol), 2-(hydroxymethyl)pyridine-4-boronic acid (351 mg, 2.29 mmol), sodium carbonate (487 mg, 4.59 mmol), 1,4-dioxane (6 mL) and water (2 mL) in a vial was sparged with nitrogen for 5 min. [1,1'-Bis(diphenylphosphino)ferrocene]dichloropalladium(II) (112 mg, 0.15 mmol) was added. The nitrogen sparging was continued for another 2 min. The vial was sealed, and heated in a Biotage® microwave synthesizer at 110° C. for 2 h. After the reaction was cooled to room temperature, EtOAc and water were added. The mixture was filtered through a plug of Celite®, and eluted with EtOAc. The filtrate was washed with water. The aqueous wash was extracted with EtOAc. The combined organic extracts were dried with $Na_2SO_4$, and concentrated. The residue was purified by flash chromatography (silica gel, eluting with 0% to 60% acetone in hexanes) to give compound 188a (213 mg, 32% yield) as a light brown foamy solid. m/z=432 (M+1).

Compound 189a: Compound 188a (211 mg, 0.49 mmol) was dissolved in ethyl formate (1.2 mL) and cooled to 0° C. Sodium methoxide (25 wt. % in methanol, 1.7 mL, 7.36 mmol) was added. The mixture was stirred at room temperature for 1 h, and cooled to 0° C. Aq. 6 N HCl (1.23 mL, 7.38 mmol), EtOH (4.8 mL) and hydroxylamine hydrochloride (52 mg, 0.75 mmol) were added sequentially. The mixture was heated at 55° C. (oil bath) for 16 h, and concentrated. Aq. sat. $NaHCO_3$ was added. The mixture was extracted with EtOAc. The combined organic extract was dried with $Na_2SO_4$ and concentrated. The residue was purified by flash chromatography (silica gel, eluting with 0% to 50% acetone in hexanes) to give compound 189a (165 mg, 74% yield) as a light yellow foamy solid. m/z=457 (M+1).

Compound 190a: Compound 189a (62 mg, 0.14 mmol) was dissolved in MeOH (1.4 mL). Sodium methoxide (25 wt. % in methanol, 47 µL, 0.20 mmol) was added. The reaction mixture was stirred at 55° C. for 1 h, and cooled to 0° C. Aq. 10% $NaH_2PO_4$ was added. The mixture was extracted with EtOAc. The organic extract was dried with $Na_2SO_4$ and concentrated. The residue was purified by flash chromatography (silica gel, eluting with 0% to 40% acetone in hexanes) to give compound 190a (56 mg, 90% yield) as a white foamy solid. m/z=457 (M+1).

T82: Compound 190a (55 mg, 0.12 mmol) was dissolved in benzene (1.2 mL). DDQ (30 mg, 0.13 mmol) was added. The mixture was heated at 85° C. for 30 min, and cooled to rt. $CH_2Cl_2$ and aq.

sat. $NaHCO_3$ were added. The mixture was extracted with $CH_2Cl_2$. The combined organic extract was dried with $Na_2SO_4$, and concentrated. The residue was purified by flash chromatography (silica gel, eluting with 0% to 50% acetone in hexanes) to give compound T82 (36 mg, 66% yield) as a brown foamy solid. $^1$H NMR (400 MHz, $CDCl_3$) δ 9.01 (s, 1H), 8.74 (m, 1H), 8.28 (m, 2H), 7.52 (dddd, J=1.9, 5.3, 7.3, 8.4 Hz, 1H), 7.45 (dt, J=1.9, 7.4 Hz, 1H), 7.34 (dt, J=1.1, 7.5 Hz, 1H), 7.22 (ddd, J=1.0, 8.4, 9.6 Hz, 1H), 4.91 (s, 2H), 3.81 (br s, 1H), 2.83 (m, 2H), 2.63 (m, 1H), 2.26 (dt, J=2.8, 12.8 Hz, 1H), 2.13 (m, 1H), 1.81 (m, 1H), 1.55 (s, 3H), 1.33 (d, J=6.8 Hz, 3H); m/z=455 (M+1).

Compound 188b: A mixture of compound 179 (100 mg, 0.28 mmol), compound 185 (partially purified, 100 mg), sodium carbonate (89 mg, 0.84 mmol), [1,1'-bis(diphenylphosphino)ferrocene]dichloropalladium(II) (20 mg, 0.027 mmol), 1,4-dioxane (1 mL) and water (0.3 mL) in a vial was sparged with nitrogen for 5 min. The vial was sealed, and heated in a Biotage® microwave synthesizer at 120° C. for 2 h. After the reaction was cooled to room temperature, EtOAc was added. The mixture was filtered through a plug of Celite®, and eluted with EtOAc. The filtrate was washed with water. The organic extract was dried with $Na_2SO_4$, and concentrated. The residue was purified by flash chromatography (silica gel, eluting with 0% to 50% EtOAc in hexanes) to give compound 188b (46 mg, 38% yield) as a viscous oil. m/z=434 (M+1).

Compound 189b: Compound 188b (46 mg, 0.11 mmol) was dissolved in ethyl formate (0.26 mL) and cooled to 0° C. Sodium methoxide (25 wt. % in methanol, 0.36 mL, 1.55 mmol) was added. The mixture was stirred at room temperature for 1 h, and cooled to 0° C. Aq. 6 N HCl (0.26 mL, 1.56 mmol), EtOH (1 mL) and hydroxylamine hydrochloride (12 mg, 0.17 mmol) were added sequentially. The mixture was heated at 55° C. (oil bath) for overnight, and concentrated. Aq. sat. $NaHCO_3$ was added. The mixture was extracted with EtOAc. The combined organic extract was dried with Na$_2$SO$_4$ and concentrated. The residue was purified by flash chromatography (silica gel, eluting with 0% to 50% EtOAc in hexanes) to give compound 189b (30 mg, 62% yield) as a white foamy solid. m/z=459 (M+1).

Compound 190b: Compound 189b (28 mg, 0.061 mmol) was dissolved in MeOH (0.6 mL). Sodium methoxide (25 wt. % in methanol, 22 µL, 0.095 mmol) was added. The reaction mixture was stirred at 55° C. for 1 h, and cooled to 0° C. Aq. 10% NaH$_2$PO$_4$ was added. The mixture was extracted with EtOAc. The organic extract was dried with Na$_2$SO$_4$ and concentrated. The residue was purified by flash chromatography (silica gel, eluting with 0% to 50% EtOAc in hexanes) to give compound 190b (23 mg, 82% yield) as a white foamy solid. m/z=459 (M+1).

T83: Compound 190b (23 mg, 0.050 mmol) was dissolved in benzene (0.5 mL). DDQ (12 mg, 0.053 mmol) was added. The mixture was heated at 85° C. for 30 min, and cooled to rt. CH$_2$Cl$_2$ and aq. sat. NaHCO$_3$ were added. The mixture was stirred until a by-phase solution was obtained, and extracted with CH$_2$Cl$_2$. The combined organic extract was washed with aq. sat. NaHCO$_3$, dried with Na$_2$SO$_4$, and concentrated. The residue was purified by flash chromatography (silica gel, eluting with 0% to 40% acetone in hexanes) to give compound T83 (19 mg, 83% yield) as a white foamy solid. $^1$H NMR (400 MHz, CDCl$_3$) δ 9.01 (s, 1H), 8.77 (d, J=5.1 Hz, 1H), 8.48 (s, 1H), 8.32 (m, 1H), 7.53 (dddd, J=1.9, 5.3, 7.2, 8.3 Hz, 1H), 7.45 (dt, J=1.9, 7.4 Hz, 1H), 7.34 (dt, J=1.1, 7.5 Hz, 1H), 7.22 (ddd, J=1.0, 8.4, 9.6 Hz, 1H), 5.61 (d, J=46.3 Hz, 2H), 2.83 (m, 2H), 2.63 (qd, J=6.7, 13.4 Hz, 1H), 2.27 (dt, J=2.7, 12.8 Hz, 1H), 2.13 (m, 1H), 1.81 (m, 1H), 1.56 (s, 3H), 1.33 (d, J=6.7 Hz, 3H); m/z=457 (M+1).

Compound 188c: A mixture of compound 179 (150 mg, 0.42 mmol), uinolone-5-boronic acid (108 mg, 0.62 mmol), sodium carbonate (133 mg, 1.25 mmol), [1,1'-bis(diphenylphosphino)ferrocene]dichloropalladium(II) (31 mg, 0.042 mmol), 1,4-dioxane (1.5 mL) and water (0.5 mL) in a vial was sparged with nitrogen for 5 min. The vial was sealed, and heated in a Biotage® microwave synthesizer at 110° C. for 2 h. After the reaction was cooled to room temperature, EtOAc was added. The mixture was washed with water. The aqueous wash was extracted with EtOAc. The combined organic extract was dried with Na$_2$SO$_4$, and concentrated. The residue was purified by flash chromatography (silica gel, eluting with 0% to 60% EtOAc in hexanes) to give compound 188c (192 mg, quantitative yield) as a white solid. m/z=452 (M+1).

Compound 189c: Compound 188c (192 mg, 0.42 mmol) was dissolved in ethyl formate (1.0 mL) and cooled to 0° C. Sodium methoxide (25 wt. % in methanol, 1.5 mL, 6.50 mmol) was added. The mixture was stirred at room temperature for 1 h. THF (0.5 mL) was added. The mixture was stirred for another 1 h, and additional amount of THF (0.5 mL) was added. The mixture was stirred for another 2 h, and cooled to 0° C. Aq. 6 N HCl (1.08 mL, 6.48 mmol), EtOH (4 mL) and hydroxylamine hydrochloride (45 mg, 0.65 mmol) were added sequentially. The mixture was heated at 55° C. (oil bath) for overnight, and concentrated. Aq. sat. NaHCO$_3$ was added. The mixture was extracted with EtOAc. The combined organic extract was dried with Na$_2$SO$_4$ and concentrated. The residue was purified by flash chromatography (silica gel, eluting with 0% to 35% acetone in hexanes) to give compound 189c (160 mg, 79% yield) as a white foamy solid. m/z=477 (M+1).

Compound 190c: Compound 189c (157 mg, 0.33 mmol) was dissolved in MeOH (3.3 mL). Sodium methoxide (25 wt. % in methanol, 0.12 mL, 0.52 mmol) was added. The reaction mixture was stirred at 55° C. for 1 h, and cooled to 0° C. Aq. 10% NaH$_2$PO$_4$ was added. The mixture was extracted with EtOAc. The organic extract was dried with Na$_2$SO$_4$ and concentrated. The residue was purified by flash chromatography (silica gel, eluting with 0% to 35% acetone in hexanes) to give compound 190c (150 mg, 96% yield) as a white foamy solid. m/z=477 (M+1).

T84: Compound 190c (150 mg, 0.32 mmol) was dissolved in benzene (3.2 mL). DDQ (75 mg, 0.33 mmol) was added. The mixture was heated at reflux for 1 h, and cooled to rt. CH$_2$Cl$_2$ and aq. sat. NaHCO$_3$ were added. The mixture was stirred for 10 min, and extracted with CH$_2$Cl$_2$. The combined organic extract was washed with aq. sat. NaHCO$_3$, dried with Na$_2$SO$_4$, and concentrated. The residue was purified by flash chromatography (silica gel, eluting with 0% to 35% acetone in hexanes) to give compound T84 (122 mg, 81% yield) as a light yellow foamy solid. $^1$H NMR (400 MHz, CDCl$_3$) δ 9.17 (ddd, J=0.9, 1.8, 8.7 Hz, 1H), 8.98 (s, 1H), 8.97 (dd, J=1.7, 4.4 Hz, 1H), 8.31 (dd, J=1.3, 7.3 Hz, 1H), 8.27 (td, J=1.1, 8.5 Hz, 1H), 7.86 (dd, J=7.3, 8.4 Hz, 1H), 7.49 (m, 3H), 7.32 (dt, J=1.1, 7.6 Hz, 1H), 7.23 (m, 1H), 2.87 (m, 2H), 2.63 (qd, J=6.7, 13.5 Hz, 1H), 2.31 (dt, J=2.7, 12.8 Hz, 1H), 2.17 (m, 1H), 1.85 (m, 1H), 1.60 (s, 3H), 1.34 (d, J=6.7 Hz, 3H); m/z=475 (M+1).

Compound 188d: A mixture of compound 179 (157 mg, 0.437 mmol), compound 187a (138 mg, 0.481 mmol), sodium carbonate (139 mg, 1.311 mmol), 1,4-dioxane (1.5 mL) and water (0.5 mL) was sparged with nitrogen for 10 min. [1,1'-Bis (diphenylphosphino)ferrocene]dichloropalladium (II) (36.2 mg, 0.050 mmol) was added and the nitrogen sparging was continued for another 10 min. The reaction vial was sealed and heated to 110° C. in a Biotage® microwave synthesizer for 2 h. The mixture was cooled to room temperature, filtered through a plug of Celite®, and eluted with EtOAc. The filtrate was concentrated. The residue was purified by flash chromatography (silica gel, eluting with 0% to 50% EtOAc in hexanes) to give compound 188d (220 mg, quantitative yield) as a white foam. m/z=484.2 (M+1).

Compound 189d: Compound 188d (220 mg, 0.437 mmol) was dissolved in ethyl formate (1.1 mL, 13.65 mmol) and cooled to 0° C. Sodium methoxide (25 wt. % in MeOH, 1.6 mL, 6.99 mmol) was added. The mixture was stirred at room temperature for 2 h, and then cooled to 0° C. Aq. 6 N HCl (1.1 mL, 6.6 mmol), EtOH (4 mL) and hydroxylamine hydrochloride (47.4 mg, 0.682 mmol) were added sequentially. The mixture was heated at 55° C. for 16 h, and concentrated. The residue was diluted with aq. sat. NaHCO$_3$, and the mixture was extracted twice with EtOAc. The combined organic extracts were dried with Na$_2$SO$_4$, filtered and concentrated. The residue was purified by flash chromatography (silica gel, eluting with 0% to 50% acetone in hexanes) to give compound 189d (170 mg, 76% yield) as a yellow foam. m/z=509.2 (M+1).

Compound 190d: To a solution of compound 189d (170 mg, 0.334 mmol) in MeOH (4 mL) was added sodium methoxide (25 wt. % solution in MeOH, 0.115 mL, 0.503 mmol). The reaction mixture was stirred at 55° C. for 2 h, cooled to 0° C., and neutralized by adding aq. 10% NaH$_2$PO$_4$ (4 mL). MeOH was removed by evaporation. The residue was diluted with water, and the mixture was extracted twice with EtOAc. The combined organic extracts were dried with Na$_2$SO$_4$, filtered and concentrated. The residue was purified by flash chromatography (silica gel, eluting with 0% to 30% acetone in hexanes) to give compound 190d (130 mg, 76% yield) as an off-white foamy solid. m/z=509.2 (M+1).

T85: A mixture of compound 190d (130 mg, 0.256 mmol), DDQ (70.0 mg, 0.307 mmol) and benzene (3 mL) was stirred at reflux for 2 h. The reaction mixture was cooled to room temperature and concentrated. The residue was purified by flash chromatography (silica gel, eluting with 0% to 60% acetone in hexanes) to give compound T85 (50 mg, 39% yield) as a white solid. $^1$H NMR (400 MHz, CDCl$_3$) δ 8.93 (s, 1H), 8.37 (dd, J=2.9, 10.9 Hz, 1H), 8.11 (dd, J=5.6, 9.3 Hz, 1H), 7.95 (s, 1H), 7.50 (m, 3H), 7.34 (dt, J=1.0, 7.5 Hz, 1H), 7.25 (m, 1H), 2.87 (m, 2H), 2.85 (s, 3H), 2.65 (qd, J=6.6, 13.4 Hz, 1H), 2.31 (dt, J=2.7, 12.8 Hz, 1H), 2.17 (m, 1H), 1.86 (m, 1H), 1.61 (s, 3H), 1.34 (d, J=6.7 Hz, 3H); m/z=507.2 (M+1).

Compound 191: A mixture of compound 179 (150 mg, 0.42 mmol), isoquinoline-5-boronic acid (108 mg, 0.62 mmol), sodium carbonate (133 mg, 1.25 mmol), [1,1'-bis (diphenylphosphino)ferrocene]dichloropalladium(II) (31 mg, 0.042 mmol), 1,4-dioxane (1.5 mL) and water (0.5 mL) in a vial was sparged with nitrogen for 5 min. The vial was sealed, and heated in a Biotage® microwave synthesizer at 110° C. for 2 h. After the reaction was cooled to room temperature, EtOAc was added. The mixture was washed with water. The aqueous wash was extracted with EtOAc. The combined organic extract was dried with Na$_2$SO$_4$, and concentrated. The residue was purified by flash chromatography (silica gel, eluting with 0% to 60% acetone in hexanes) to give compound 191 (89 mg, 47% yield) as a brown foamy solid. m/z=452 (M+1).

Compound 192: Compound 191 (87 mg, 0.19 mmol) was dissolved in ethyl formate (0.46 mL) and cooled to 0° C. Sodium methoxide (25 wt. % in methanol, 0.67 mL, 2.90 mmol) was added. The mixture was stirred at room temperature for 1 h, and cooled to 0° C. Aq. 6 N HCl (0.48 mL, 2.88 mmol), EtOH (2 mL) and hydroxylamine hydrochloride (20 mg, 0.29 mmol) were added sequentially. The mixture was heated at 55° C. (oil bath) for overnight, and concentrated. Aq. sat. NaHCO$_3$ was added. The mixture was extracted with EtOAc. The combined organic extract was dried with Na$_2$SO$_4$ and concentrated. The residue was purified by flash chromatography (silica gel, eluting with 0% to 30% acetone in hexanes) to give compound 192 (75 mg, 82% yield) as a white foamy solid. m/z=477 (M+1).

Compound 193: Compound 192 (73 mg, 0.15 mmol) was dissolved in MeOH (1.5 mL). Potassium carbonate (63 mg, 0.46 mmol) was added. The reaction mixture was stirred at room temperature for overnight. EtOAc and aq. 10% NaH$_2$PO$_4$ were added. The mixture was extracted with EtOAc. The organic extract was dried with Na$_2$SO$_4$ and concentrated. The residue was purified by flash chromatography (silica gel, eluting with 0% to 60% acetone in hexanes) to give compound 193 (66 mg, 90% yield) as a white foamy solid. m/z=477 (M+1).

T86: Compound 193 (65 mg, 0.14 mmol) was dissolved in benzene (1.4 mL). DDQ (33 mg, 0.15 mmol) was added. The mixture was heated at 85° C. for 1 h, and cooled to rt. CH$_2$Cl$_2$ and aq. sat. NaHCO$_3$ were added. The mixture was stirred for 10 min, and extracted with CH$_2$Cl$_2$. The combined organic extract was washed with aq. sat. NaHCO$_3$, dried with Na$_2$SO$_4$, and concentrated. The residue was purified by flash chromatography (silica gel, eluting with 0% to 60% acetone in hexanes) to give compound T86 (37 mg, 57% yield) as a light yellow foamy solid. $^1$H NMR (400 MHz, CDCl$_3$) δ 9.34 (s, 1H), 8.99 (s, 1H), 8.67 (td, J=0.9, 6.0 Hz, 1H), 8.61 (d, J=6.1 Hz, 1H), 8.51 (td, J=0.9, 7.3 Hz, 1H), 8.14 (dd, J=1.1, 8.3 Hz, 1H), 7.78 (dd, J=7.3, 8.1 Hz, 1H), 7.51 (m, 2H), 7.33 (tt, J=0.8, 7.6 Hz, 1H), 7.23 (m, 1H), 2.87 (m, 2H), 2.64 (m, 1H), 2.31 (dt, J=2.7, 12.8 Hz, 1H), 2.17 (m, 1H), 1.85 (m, 1H), 1.61 (s, 3H), 1.34 (d, J=6.7 Hz, 3H); m/z=475 (M+1).

Compound 194a: A mixture of compound 179 (258 mg, 0.72 mmol), 3,5-dimethylisoxazole-4-boronic acid (152 mg, 1.08 mmol), sodium carbonate (229 mg, 2.16 mmol), 1,4-dioxane (2.7 mL) and water (0.9 mL) in a vial was sparged with nitrogen for 5 min. [1,1'-Bis(diphenylphosphino)ferrocene]dichloropalladium(II) (53 mg, 0.073 mmol) was added. The nitrogen sparging was continued for another 2 min. The vial was sealed, and heated in a Biotage® microwave synthesizer at 110° C. for 2 h. After the reaction was cooled to room temperature, EtOAc was added. The mixture was filtered through a plug of Celite®, and eluted with EtOAc. The filtrate was concentrated. The residue was purified by flash chromatography (silica gel, eluting with 0% to 30% EtOAc in hexanes) to give compound 194a (279 mg, 92% yield) as a white foamy solid. m/z=420 (M+1).

Compound 195a: Compound 194a (277 mg, 0.66 mmol) was dissolved in ethyl formate (1.6 mL) and cooled to 0° C. Sodium methoxide (25 wt. % in methanol, 2.3 mL, 9.96 mmol) was added. The mixture was stirred at room temperature for 1.5 h, and cooled to 0° C. Aq. 6 N HCl (1.7 mL, 10.2 mmol), EtOH (6.6 mL) and hydroxylamine hydrochloride (70 mg, 1.01 mmol) were added sequentially. The mixture was heated at 55° C. (oil bath) for 4 h, and concentrated. Aq. sat. NaHCO$_3$ was added. The mixture was extracted with EtOAc. The combined organic extract was dried with Na$_2$SO$_4$ and concentrated. The residue was purified by flash chromatography (silica gel, eluting with 0% to 50% EtOAc in hexanes) to give compound 195a (250 mg, 85% yield) as a white foamy solid. m/z=445 (M+1).

Compound 196a: Compound 195a (247 mg, 0.56 mmol) was dissolved in MeOH (5.5 mL). Sodium methoxide (25 wt. % in methanol, 0.19 mL, 0.82 mmol) was added. The reaction mixture was stirred at 55° C. for 2 h, and cooled to 0° C. Aq. 10% NaH$_2$PO$_4$ was added. The mixture was extracted with EtOAc. The organic extract was dried with Na$_2$SO$_4$ and concentrated. The residue was purified by flash chromatography (silica gel, eluting with 0% to 30% EtOAc in hexanes) to give compound 196a (217 mg, 88% yield) as a white foamy solid. m/z=445 (M+1).

T87: Compound 196a (217 mg, 0.49 mmol) was dissolved in anhydrous DMF (1.2 mL), and the solution was cooled to 0° C. 1,3-dibromo-5,5-dimethylhydantoin (34 mg, 0.12 mmol) in DMF (1.2 mL) was added. The reaction was stirred at 0° C. for 1.5 h. Pyridine (0.12 mL, 1.49 mmol) was added. The reaction was heated at 55° C. (oil bath) for 3 h, and cooled to room temperature. CH$_2$Cl$_2$ was added. The mixture was washed with water. The organic extract was dried with Na$_2$SO$_4$, and concentrated. The residual pyridine was removed by azeotropic evaporation with toluene. The residue was purified by flash chromatography (silica gel, eluting with 0% to 30% acetone in hexanes) to give compound T87 (177 mg, 82% yield) as a white solid. $^1$H NMR (400 MHz, CDCl$_3$) δ 8.81 (s, 1H), 7.50 (m, 1H), 7.40 (dt, J=1.9, 7.4 Hz, 1H), 7.30 (dt, J=1.1, 7.5 Hz, 1H), 7.20 (ddd, J=1.0, 8.4, 9.7 Hz, 1H), 2.79 (s, 3H), 2.78 (m, 2H), 2.63 (s, 3H), 2.60 (m, 1H), 2.24 (dt, J=2.8, 12.8 Hz, 1H), 2.10 (m, 1H), 1.76 (dq, J=7.3, 13.1 Hz, 1H), 1.52 (s, 3H), 1.32 (d, J=6.8 Hz, 3H); m/z=443 (M+1).

Compound 194b: A mixture of compound 179 (150 mg, 0.42 mmol), 2-methylpyridine-5-boronic acid (86 mg, 0.63 mmol), sodium carbonate (133 mg, 1.25 mmol), 1,4-dioxane (1.5 mL) and water (0.5 mL) in a vial was sparged with nitrogen for 5 min. [1,1'-Bis(diphenylphosphino)ferrocene] dichloropalladium(II) (31 mg, 0.042 mmol) was added. The nitrogen sparging was continued for another 2 min. The vial was sealed, and heated in a Biotage® microwave synthesizer at 110° C. for 2 h. After the reaction was cooled to room temperature, EtOAc was added. The mixture was filtered through a plug of Celite®, and eluted with EtOAc. The filtrate was concentrated. The residue was purified by flash chromatography (silica gel, eluting with 0% to 60% EtOAc in hexanes) to give compound 194b (132 mg, 76% yield) as a pink foamy solid. m/z=416 (M+1).

Compound 195b: Compound 194b (130 mg, 0.31 mmol) was dissolved in ethyl formate (0.75 mL) and cooled to 0° C. Sodium methoxide (25 wt. % in methanol, 1.1 mL, 4.76 mmol) was added. The mixture was stirred at room temperature for 1 h, and cooled to 0° C. Aq. 6 N HCl (0.8 mL, 4.8 mmol), EtOH (1.6 mL) and hydroxylamine hydrochloride (33 mg, 0.47 mmol) were added sequentially. The mixture was heated at 55° C. (oil bath) for 6 h, and concentrated. Aq. sat. NaHCO$_3$ was added. The mixture was extracted with EtOAc. The combined organic extract was dried with Na$_2$SO$_4$ and concentrated. The residue was purified by flash chromatography (silica gel, eluting with 0% to 35% acetone in hexanes) to give compound 195b (102 mg, 74% yield) as a light yellow foamy solid. m/z=441 (M+1).

Compound 196b: Compound 195b (100 mg, 0.23 mmol) was dissolved in MeOH (2.2 mL). Sodium methoxide (25 wt. % in methanol, 0.1 mL, 0.43 mmol) was added. The reaction mixture was stirred at 55° C. for 1 h, and cooled to 0° C. Aq. 10% NaH$_2$PO$_4$ was added. The mixture was extracted with EtOAc. The organic extract was dried with Na$_2$SO$_4$ and concentrated. The residue was purified by flash chromatography (silica gel, eluting with 0% to 60% EtOAc in hexanes) to give compound 196b (96 mg, 96% yield) as a white foamy solid. m/z=441 (M+1).

T88: Compound 196b (96 mg, 0.22 mmol) was dissolved in anhydrous DMF (0.55 mL), and the solution was cooled to 0° C. 1,3-dibromo-5,5-dimethylhydantoin (31 mg, 0.11 mmol) in DMF (0.55 mL) was added. The reaction was stirred at 0° C. for 1 h. Pyridine (53 µL, 0.66 mmol) was added. The reaction was heated at 55° C. (oil bath) for 3 h, and cooled to room temperature. CH$_2$Cl$_2$ was added. The mixture was washed with water. The organic extract was dried with Na$_2$SO$_4$, and concentrated. The residual pyridine was removed by azeotropic evaporation with toluene. The residue was purified by flash chromatography (silica gel, eluting with 0% to 35% acetone in hexanes) to give compound T88 (71 mg, 74% yield) as an off-white foamy solid. $^1$H NMR (400 MHz, CDCl$_3$) δ 9.55 (d, J=2.3 Hz, 1H), 9.01 (s, 1H), 8.62 (dd, J=2.3, 8.1 Hz, 1H), 7.50 (m, 1H), 7.44 (dt, J=1.9, 7.4 Hz, 1H), 7.32 (dt, J=1.0, 7.5 Hz, 1H), 7.28 (d, J=8.1 Hz, 1H), 7.20 (ddd, J=1.0, 8.4, 9.6 Hz, 1H), 2.81 (m, 2H), 2.66 (s, 3H), 2.61 (m, 1H), 2.25 (dt, J=2.7, 12.7 Hz, 1H), 2.11 (m, 1H), 1.79 (m, 1H), 1.54 (s, 3H), 1.32 (d, J=6.8 Hz, 3H); m/z=439 (M+1).

Compound 194c: A mixture of compound 179 (150 mg, 0.42 mmol), compound 187b (125 mg, 0.45 mmol), sodium carbonate (133 mg, 1.25 mmol), [1,1'-bis(diphenylphosphino)ferrocene]dichloropalladium(II) (15 mg, 0.021 mmol), 1,4-dioxane (1.5 mL) and water (0.5 mL) in a vial was sparged with N$_2$ for 5 min. The vial was sealed, and heated in a Biotage® microwave synthesizer at 110° C. for 2 h. After the reaction was cooled to room temperature, EtOAc was added. The mixture was washed with water. The aqueous wash was extracted with EtOAc. The combined organic extract was dried with Na$_2$SO$_4$, and concentrated. The residue was purified by flash chromatography (silica gel, eluting with 0% to 50% EtOAc in hexanes) to give compound 194c (162 mg, 83% yield) as a white foamy solid. m/z=470 (M+1).

Compound 195c: Compound 194c (160 mg, 0.34 mmol) was dissolved in ethyl formate (0.82 mL) and cooled to 0° C. Sodium methoxide (25 wt. % in methanol, 0.79 mL, 3.42 mmol) was added. The mixture was stirred at room temperature for 1.5 h, and cooled to 0° C. Aq. 6 N HCl (0.57 mL, 3.42 mmol), EtOH (3.4 mL) and hydroxylamine hydrochloride (36 mg, 0.52 mmol) were added sequentially. The mixture was heated at 55° C. (oil bath) for overnight, and concentrated. Aq. sat. NaHCO$_3$ was added. The mixture was extracted with EtOAc. The combined organic extract was dried with Na$_2$SO$_4$ and concentrated. The residue was purified by flash chromatography (silica gel, eluting with 0% to 40% EtOAc in hexanes) to give compound 195c (133 mg, 79% yield) as a white foamy solid. m/z=495 (M+1).

Compound 196c: Compound 195c (131 mg, 0.27 mmol) was dissolved in MeOH (2.6 mL) and THF (0.5 mL). Sodium methoxide (25 wt. % in methanol, 92 µL, 0.40 mmol) was added. The reaction mixture was stirred at 55° C. for 1 h, and cooled to room temperature. Aq. 10% NaH$_2$PO$_4$ were added. The mixture was extracted with EtOAc. The organic extract was dried with Na$_2$SO$_4$ and concentrated. The residue was purified by flash chromatography (silica gel, eluting with 0% to 50% EtOAc in hexanes) to give compound 196c (113 mg, 86% yield) as a white foamy solid. m/z=495 (M+1).

T89: Compound 196c (112 mg, 0.23 mmol) was dissolved in anhydrous DMF (0.55 mL), and the solution was cooled to 0° C. 1,3-dibromo-5,5-dimethylhydantoin (32 mg, 0.11 mmol) in DMF (0.55 mL) was added. The reaction was stirred at 0° C. for 1 h. Pyridine (55 µL, 0.68 mmol) was added. The reaction was heated at 55° C. (oil bath) for 2.5 h, and cooled to room temperature. CH$_2$Cl$_2$ was added. The mixture was washed with water. The organic extract was dried with Na$_2$SO$_4$, and concentrated. The residual pyridine was removed by azeotropic evaporation with toluene. The residue was purified by flash chromatography (silica gel, eluting with 0% to 50% EtOAc in hexanes) to give compound T89 (73 mg, 65% yield) as an white foamy solid. $^1$H NMR (400 MHz, CDCl$_3$) δ 9.06 (d, J=4.5 Hz, 1H), 8.94 (s, 1H), 8.51 (dd, J=2.9, 11.0 Hz, 1H), 8.22 (dd, J=5.7, 9.2 Hz, 1H), 8.12 (d, J=4.6 Hz, 1H), 7.52 (m, 3H), 7.34 (dt, J=1.1, 7.6 Hz, 1H), 7.24 (m, 1H), 2.90 (m, 2H), 2.65 (qd, J=6.7, 13.4 Hz, 1H), 2.31 (dt, J=2.7, 12.8 Hz, 1H), 2.18 (m, 1H), 1.86 (m, 1H), 1.61 (s, 3H), 1.34 (d, J=6.7 Hz, 3H); m/z=493 (M+1).

Compound 194d: A mixture of compound 179 (150 mg, 0.42 mmol), compound 187c (182 mg, 0.63 mmol), sodium carbonate (133 mg, 1.25 mmol), [1,1'-bis(diphenylphosphino)ferrocene]dichloropalladium (H) (15 mg, 0.021 mmol), 1,4-dioxane (1.5 mL) and water (0.5 mL) in a vial was sparged with N$_2$ for 5 min. The vial was sealed, and heated in a Biotage® microwave synthesizer at 110° C. for 2 h. After the reaction was cooled to room temperature, EtOAc was added. The mixture was washed with water. The aqueous wash was extracted with EtOAc. The combined organic extract was dried with Na$_2$SO$_4$, and concentrated. The residue was purified by flash chromatography (silica gel, eluting with 0% to 40% EtOAc in hexanes) to give partially purified compound 194d (225 mg, quantitative yield) as a white foamy solid, which was used in the next step without further purification. m/z=488 (M+1).

Compound 195d: Compound 194d (222 mg, 0.46 mmol) was dissolved in ethyl formate (1.1 mL) and cooled to 0° C. Sodium methoxide (25 wt. % in methanol, 1.6 mL, 6.93 mmol) was added. The mixture was stirred at room temperature for 1.5 h, and cooled to 0° C. Aq. 6 N HCl (1.2 mL, 7.2 mmol), EtOH (4.5 mL) and hydroxylamine hydrochloride (48 mg, 0.69 mmol) were added sequentially. The mixture was heated at 55° C. (oil bath) for overnight, and concentrated. Aq. sat. NaHCO$_3$ was added. The mixture was extracted with EtOAc. The combined organic extract was dried with Na$_2$SO$_4$ and concentrated. The residue was purified by flash chromatography (silica gel, eluting with 0% to 40% EtOAc in hexanes) to give compound 195d (130 mg, 56% yield) as a light yellow foamy solid. m/z=513 (M+1).

Compound 196d: Compound 195d (128 mg, 0.25 mmol) was dissolved in MeOH (2.5 mL). Sodium methoxide (25 wt. % in methanol, 86 µL, 0.37 mmol) was added. The reaction mixture was stirred at 55° C. for 1 h, and cooled to room temperature. Aq. 10% NaH$_2$PO$_4$ were added. The mixture was extracted with EtOAc. The organic extract was dried with Na$_2$SO$_4$ and concentrated. The residue was purified by flash chromatography (silica gel, eluting with 0% to 50% EtOAc in hexanes) to give compound 196d (103 mg, 80% yield) as a white foamy solid. m/z=513 (M+1).

T90: Compound 196d (103 mg, 0.20 mmol) was dissolved in anhydrous DMF (0.5 mL), and the solution was cooled to 0° C. 1,3-dibromo-5,5-dimethylhydantoin (29 mg, 0.10 mmol) in DMF (0.5 mL) was added. The reaction was stirred at 0° C. for 1 h. Pyridine (49 µL, 0.61 mmol) was added. The reaction was heated at 55° C. (oil bath) for 2.5 h, and cooled to room temperature. CH$_2$Cl$_2$ was added. The mixture was washed with water. The organic extract was dried with Na$_2$SO$_4$, and concentrated. The residual pyridine was removed by azeotropic evaporation with toluene. The residue was purified by flash chromatography (silica gel, eluting with 0% to 50% EtOAc in hexanes) to give compound T90 (74 mg, 72% yield) as an white foamy solid. $^1$H NMR (400 MHz, CDCl$_3$) δ 9.10 (d, J=4.5 Hz, 1H), 8.91 (s, 1H), 8.38 (ddd, J=1.7, 2.7, 10.9 Hz, 1H), 8.21 (d, J=4.4 Hz, 1H), 7.53 (m, 1H), 7.47 (dt, J=1.8, 7.4 Hz, 1H), 7.32 (m, 3H), 2.90 (m, 2H), 2.65 (qd, J=6.7, 13.3 Hz, 1H), 2.31 (dt, J=2.7, 12.8 Hz, 1H), 2.18 (m, 1H), 1.85 (m, 1H), 1.61 (s, 3H), 1.34 (d, J=6.7 Hz, 3H); m/z=511 (M+1).

Compound 197: To a solution of compound 179 (150 mg, 0.42 mmol) in methylpyrrolidone (0.6 mL) was added 1-methylpiperazine (200 µL, 1.80 mmol). The mixture was heated at 100° C. for 2 h, and cooled to room temperature. EtOAc was added. The mixture was washed with water. The organic extract was dried with Na$_2$SO$_4$ and concentrated. The residue was purified by flash chromatography (silica gel, eluting with 0% to 10% MeOH in CH$_2$Cl$_2$) to give compound 197 (157 mg, 89% yield) as an off-white foamy solid. m/z=423 (M+1).

Compound 198: Compound 197 (210 mg, 0.50 mmol) was dissolved in ethyl formate (1.2 mL) and cooled to 0° C. Sodium methoxide (25 wt. % in methanol, 1.7 mL, 7.36 mmol) was added. The mixture was stirred at 0° C. for 1 h, at room temperature for 4 h, and cooled to 0° C. Aq. 6 N HCl (1.25 mL, 7.50 mmol), EtOH (5 mL) and hydroxylamine hydrochloride (53 mg, 0.76 mmol) were added sequentially. The mixture was heated at 55° C. (oil bath) for overnight, and concentrated. Aq. sat. NaHCO$_3$ was added. The mixture was extracted with EtOAc. The combined organic extract was dried with Na$_2$SO$_4$ and concentrated. The residue was purified by flash chromatography (silica gel, eluting with 0% to 15% MeOH in CH$_2$Cl$_2$) to give compound 198 (192 mg, 86% yield) as a yellow foamy solid. m/z=448 (M+1).

Compound 199: Compound 198 (188 mg, 0.42 mmol) was dissolved in MeOH (4 mL). Potassium carbonate (174 mg, 1.26 mmol) was added. The reaction mixture was stirred at room temperature for overnight. Aq. 10% NaH$_2$PO$_4$ was added. The mixture was extracted with EtOAc. The organic extract was dried with Na$_2$SO$_4$ and concentrated. The residue was purified by flash chromatography (silica gel, eluting with 0% to 20% MeOH in CH$_2$Cl$_2$) to give compound 199 (176 mg, 94% yield) as a yellow foamy solid. m/z=448 (M+1).

T91: Compound 199 (175 mg, 0.39 mmol) was dissolved in benzene (4 mL). DDQ (97 mg, 0.43 mmol) was added. The mixture was heated at 85° C. for 1 h, and cooled to rt. CH$_2$Cl$_2$ and aq. sat. NaHCO$_3$ were added. The mixture was stirred for 10 min, and extracted with CH$_2$Cl$_2$. The combined organic extract was washed with aq. sat. NaHCO$_3$, dried with Na$_2$SO$_4$, and concentrated. The residue was purified by flash chromatography (silica gel, eluting with 0% to 60% acetone in CH$_2$Cl$_2$) to give compound T91 (119 mg, 68% yield) as a light yellow foamy solid. $^1$H NMR (400 MHz, CDCl$_3$) δ 8.84 (s, 1H), 7.41 (dddd, J=1.9, 5.2, 7.2, 8.2 Hz, 1H), 7.33 (dt, J=1.9, 7.4 Hz, 1H), 7.24 (dt, J=1.2, 7.5 Hz, 1H), 7.13 (ddd, J=1.1, 8.3, 9.6 Hz, 1H), 3.87 (t, J=5.1 Hz, 4H), 2.52 (m, 7H), 2.36 (s, 3H), 2.13 (dt, J=2.7, 12.8 Hz, 1H), 1.99 (m, 1H), 1.66 (m, 1H), 1.44 (s, 3H), 1.27 (d, J=6.7 Hz, 3H); m/z=446 (M+1).

Compound 200: A mixture of compound 88 (900 mg, 2.61 mmol), N-amidinomorpholine hydro-bromide (823 mg, 3.92 mmol), and potassium carbonate (1.08 g, 7.81 mmol) in EtOH (50 mL) was heated at reflux for 70 h. The reaction mixture was concentrated and the residue was partitioned between aq. sat. KH$_2$PO$_4$ and EtOAc. The organic extract was washed with brine, dried over MgSO$_4$, filtered and concentrated to give the dihydropyrimidine as a yellow glass. The crude product was dissolved in CH$_2$Cl$_2$ (20 mL) and the solution was treated with manganese dioxide (88%, 2.01 g, 20.36 mmol). The reaction mixture was stirred under nitrogen at room temperature for 24 h and filtered through Celite®. The filtrate was concentrated and the residue was purified by flash chromatography (silica gel, eluting with 30% EtOAc in hexanes) to give compound 200 (749 mg, 63% yield) as a clear viscous oil. m/z=454 (M+1).

Compound 201: A solution of compound 200 (745 mg, 1.64 mmol) in THF (30 mL) was treated with aq. 3 N HCl (5.47 mL, 16.4 mmol) and the reaction mixture was stirred at room temperature for 17 h. The solvent was removed in vacuo and the residue was cooled to 0° C., neutralized cautiously with aq. sat. NaHCO$_3$, and extracted with EtOAc. The organic extract was washed with water, brine, dried over MgSO$_4$, filtered and concentrated to give compound 201 (565 mg, 84% yield) as an oil. m/z=410 (M+1).

Compound 202: A solution of compound 201 (564 mg, 1.38 mmol) in ethyl formate (18 ml, 224 mmol) was cooled to 0° C. and treated dropwise with sodium methoxide (5.4 M solution in MeOH, 1.28 ml, 6.91 mmol). The cold bath was removed and the reaction mixture was stirred at room temperature for 18 h. The solvent was removed in vacuo and the residue was partitioned between EtOAc and aq. sat. KH$_2$PO$_4$. The organic extract was washed with brine, dried over MgSO$_4$, filtered and concentrated to give compound 202 (604 mg, quantitative yield) as an orange oil. m/z=438 (M+1).

Compound 203: A solution of compound 202 (604 mg, 1.38 mmol) in glacial acetic acid (0.80 mL, 13.8 mmol) and EtOH (12 mL) was treated with hydroxylamine hydrochloride (144 mg, 2.07 mmol). The reaction mixture was stirred under nitrogen at 60° C. for 4 h and at room temperature for 22 h. The solvent was removed in vacuo and the residue was cautiously partitioned between aq. 10% NH$_4$OH and EtOAc. The organic extract was washed with brine, dried over MgSO₄, filtered and concentrated to give compound 203 (541 mg, 90% yield) as a light brown glass. m/z=435 (M+1).

Compound 204: A mixture of compound 203 (541 mg, 1.25 mmol) and potassium carbonate (346 mg, 2.50 mmol) in MeOH (20 mL) was stirred under nitrogen at room temperature for 21 h. The reaction mixture was concentrated and the residue was partitioned between water and Et₂O. The aqueous phase was cooled in an ice-water bath and acidified with aq. sat. KH₂PO₄. The acidified aqueous mixture was extracted with EtOAc (2×40 ml) and the combined organic extracts were washed with brine, dried over MgSO₄, filtered and concentrated. The residue was purified by flash chromatography (silica gel, eluting with 40% EtOAc in hexanes) to give compound 204 (383 mg, 71% yield) as a clear glass. m/z=435 (M+1).

T92: A solution of compound 204 (327 mg, 0.752 mmol) in anhydrous DMF (5 mL) was cooled to 0° C., and was treated dropwise with a solution of 1,3-dibromo-5,5-dimethylhydantoin (118 mg, 0.413 mmol) in anhydrous DMF (2 mL). After stirring the mixture at 0° C. for 30 min, anhydrous pyridine (0.61 ml, 7.56 mmol) was added. The cold bath was removed, and the reaction mixture was heated at 60° C. under an argon atmosphere for 4 h. Upon cooling to room temperature, the reaction mixture was partitioned between EtOAc and aq. sat. KH₂PO₄. The organic extract was washed with brine, dried over MgSO₄, filtered and concentrated. The residue was purified by flash chromatography (silica gel, eluting with 30% EtOAc in hexanes) to give partially purified product, which was purified again by flash chromatography (silica gel, eluting with 0% to 3% EtOAc in CH₂Cl₂) to give compound T92 (160 mg, 49% yield) as a glass. $^1$H NMR (400 MHz, CDCl₃) δ 8.82 (s, 1H), 7.42 (ddd, J=1.9, 5.2, 7.2, 8.4 Hz, 1H), 7.32 (dt, J=1.9, 7.4 Hz, 1H), 7.24 (m, 1H), 7.14 (ddd, J=1.0, 8.4, 9.6 Hz, 1H), 3.82 (m, 8H), 2.55 (m, 3H), 2.14 (dt, J=2.8, 12.8 Hz, 1H), 2.00 (m, 1H), 1.67 (dq, J=7.4, 13.2 Hz, 1H), 1.44 (s, 3H), 1.27 (d, J=6.8 Hz, 3H); m/z=433 (M+1).

Compound 205: A mixture of compound 95 (245 mg, 0.63 mmol), cyclopropylboronic acid (90 mg, 1.05 mmol), potassium phosphate (660 mg, 3.11 mmol), tricyclohexylphosphine (54 mg, 0.19 mmol), palladium acetate (24 mg, 0.11 mmol), toluene (4 mL) and water (0.2 mL) in a vial was sparged with N₂ for 3 min. The vial was sealed, and heated in a Biotage® microwave synthesizer at 130° C. for 4 h. After the reaction was cooled to room temperature, the mixture was filtered through a plug of Celite®, and eluted with EtOAc. The filtrate was concentrated. The residue was purified by flash chromatography (silica gel, eluting with 0% to 35% acetone in hexanes) to give the compound 205 (123 mg, 49% yield) as a white solid. m/z=398 (M+1).

Compound 206: Compound 205 (121 mg, 0.30 mmol) was dissolved in ethyl formate (0.73 mL) and cooled to 0° C. Sodium methoxide (25 wt. % in methanol, 1.05 mL, 4.55 mmol) was added. The mixture was stirred at room temperature for 6 h, and cooled to 0° C. Aq. 6 N HCl (0.76 mL, 4.56 mmol), EtOH (3 mL) and hydroxylamine hydrochloride (43 mg, 0.62 mmol) were added sequentially. The mixture was heated overnight at 55° C. (oil bath), and concentrated. Aq. sat. NaHCO₃ was added, and the mixture was extracted with EtOAc. The organic extract dried with Na₂SO₄ and concentrated. The residue was purified by flash chromatography (silica gel, eluting with 0% to 40% acetone in hexanes) to give compound 206 (72 mg, 56% yield) as a white foamy solid. m/z=423 (M+1).

Compound 207: Compound 206 (72 mg, 0.17 mmol) was dissolved in MeOH (1.7 mL). Sodium methoxide (25 wt. % in methanol, 60 μL, 0.26 mmol) was added. The reaction mixture was stirred at 55° C. for 1 h, and cooled to room temperature. Aq. 10% NaH₂PO₄ were added. The mixture was extracted with EtOAc. The organic extract was dried with Na₂SO₄ and concentrated. The residue was purified by flash chromatography (silica gel, eluting with 0% to 50% acetone in hexanes) to give compound 207 (54 mg, 75% yield) as a white foamy solid. m/z=423 (M+1).

T93: Compound 207 (54 mg, 0.13 mmol) was dissolved in anhydrous DMF (0.6 mL), and the solution was cooled to 0° C. 1,3-dibromo-5,5-dimethylhydantoin (18 mg, 0.063 mmol) was added. The reaction was stirred at 0° C. for 1 h. Pyridine (31 μL, 0.38 mmol) was added. The reaction was heated at 55° C. (oil bath) for 5 h, and cooled to room temperature. CH₂Cl₂ was added. The mixture was washed with water. The organic extract was dried with Na₂SO₄, and concentrated. The residual pyridine was removed by azeotropic evaporation with toluene. The residue was purified by flash chromatography (silica gel, eluting with 0% to 40% acetone in hexanes) to give compound T93 (35 mg, 65% yield) as a white solid. $^1$H NMR (400 MHz, CDCl₃) δ 9.06 (d, J=4.4 Hz, 1H), 8.91 (s, 1H), 8.67 (dd, J=1.2, 8.8 Hz, 1H), 8.20 (dd, J=0.8, 8.4 Hz, 1H), 7.94 (d, J=4.5 Hz, 1H), 7.76 (ddd, J=1.5, 6.8, 8.4 Hz, 1H), 7.61 (ddd, J=1.4, 6.8, 8.4 Hz, 1H), 3.22 (ddd, J=1.2, 6.8, 17.9 Hz, 1H), 3.03 (ddd, J=7.7, 11.2, 18.3 Hz, 1H), 2.63 (qd, J=6.7, 13.4 Hz, 1H), 2.30 (m, 1H), 2.22 (dt, J=2.7, 12.8 Hz, 1H), 2.15 (m, 1H), 1.91 (ddt, J=6.8, 11.4, 13.3 Hz, 1H), 1.54 (s, 3H), 1.36 (d, J=6.8 Hz, 3H), 1.35 (m, 2H), 1.17 (m, 2H); m/z=421.2 (M+1).

Compound 94: Compound 93 (1 g, 2.40 mmol) was taken up in toluene (10 mL). Phosphorus (V) oxychloride (4 g, 26.09 mmol) was added. The mixture was heated in Biotage® Initiator™ microwave synthesizer at 100° C. for 60 min, cooled, and poured into ice. After sitting for 10 min, the mixture was extracted with EtOAc. The organic extract was washed with aq. NaHCO₃, dried with MgSO₄, filtered and concentrated. The crude product was mixed in benzene (100 mL), and treated with ethylene glycol (1 g, 16.11 mmol) and p-toluenesulfonic acid monohydrate (60 mg, 0.32 mmol). The mixture was refluxed for 16 h with a Dean-Stark trap, cooled to room temperature, and washed with water. The organic extract was dried over MgSO₄, and concentrated. The residue was purified by flash chromatography (silica gel, eluting with 0% to 35% EtOAc in hexanes) to give compound 94 (550 mg, 53% yield) as a light color solid. m/z=436 (M+1).

Compound 208: A mixture of compound 94 (550 mg, 1.26 mmol) was taken up in THF (10 mL). Cyclobutanol (200 mg, 2.77 mmol) and NaH (60% dispersion in mineral oil, 120 mg, 3.00 mmol) were added. The reaction was stirred at 60° C. for 16 h, cooled, and concentrated. The residue was neutralized by the addition of aq. sat. KH₂PO₄, and extracted with EtOAc. The organic extract was washed with brine, dried with MgSO₄, filtered, and concentrated. The crude product was purified by flash chromatography (silica gel, eluting with 0% to 35% EtOAc in hexanes) to give compound 208 (500 mg, 84% yield) as a white solid. m/z=472 (M+1).

Compound 209: A mixture of compound 208 (500 mg, 1.06 mmol) was taken up in THF (10 mL), and aq. 3 N HCl (5 mL, 15.0 mmol) was added. The mixture was stirred overnight at room temperature, and concentrated. The residue was neutralized with aq. sat. NaHCO₃, and extracted with EtOAc. The organic extract was washed with water, dried with MgSO₄, filtered, and concentrated to give compound 209 (450 mg, 99% yield) as a white solid. m/z=428 (M+1).

Compound 210: Compound 209 (450 mg, 1.05 mmol) was taken up in ethyl formate (15 mL, 186 mmol). Sodium methoxide (30 wt. % in MeOH, 200 mg, 1.11 mmol) was added. After stirring at room temperature for 2 h, the reaction mixture was neutralized with aq. $KH_2PO_4$, and extracted with EtOAc. The organic extract was dried with $MgSO_4$, filtered, and concentrated to give compound 210 (430 mg, 90% yield) as a foam. m/z=456 (M+1).

Compound 211: Compound 210 (430 mg, 0.94 mmol) was dissolved in EtOH (15 mL). Hydroxylamine hydrochloride (660 mg, 9.50 mmol) and acetic acid (550 mg, 9.15 mmol) were added. The reaction mixture was stirred overnight at 50° C., cooled, and concentrated. The residue was taken up in EtOAc, and washed with aq. $NaHCO_3$. The organic extract was dried with $MgSO_4$, filtered, and concentrated to give compound 211 (425 mg, 99% yield) as a foam. m/z=453 (M+1).

Compound 212: Compound 211 (425 mg, 0.94 mmol) was dissolved in MeOH (10 mL). Potassium carbonate (650 mg, 4.70 mmol) was added. After stirring at room temperature overnight, the reaction mixture was neutralized by the addition of aq. sat. $KH_2PO_4$, and extracted with EtOAc. The organic extract was washed with brine, dried with $MgSO_4$, filtered, and concentrated. The residue was purified by flash chromatography (silica gel, eluting with 0% to 35% EtOAc in hexanes) to give compound 212 (235 mg, 55% yield) as a foam. m/z=453 (M+1).

T94: Compound 212 (235 mg, 0.52 mmol) was dissolved in dry DMF (2 mL), and the solution was cooled to 0° C. 1,3-dibromo-5,5-dimethylhydantoin (82 mg, 0.29 mmol) in DMF (1 mL) was added. The reaction stirred at 0° C. for 2 h, and pyridine (2 mL, 24.8 mmol) was added. The reaction was heated at 60° C. for 4 h, cooled, and concentrated. The residue was purified by flash chromatography (silica gel, eluting with 0% to 35% EtOAc in hexanes) to give compound T94 (115 mg, 49% yield) as a foam. $^1$H NMR (400 MHz, $CDCl_3$) δ 9.07 (d, J=4.4 Hz, 1H), 8.88 (s, 1H), 8.76 (m, 1H), 8.21 (m, 1H), 7.95 (d, J=4.5 Hz, 1H), 7.77 (ddd, J=1.5, 6.8, 8.4 Hz, 1H), 7.62 (ddd, J=1.4, 6.8, 8.3 Hz, 1H), 5.34 (m, 1H), 2.96 (ddd, J=1.1, 6.8, 18.8 Hz, 1H), 2.72 (ddd, J=7.6, 11.3, 18.9 Hz, 1H), 2.61 (td, J=6.7, 12.8 Hz, 1H), 2.56 (m, 2H), 2.22 (m, 4H), 1.80 (m, 3H), 1.51 (s, 3H), 1.35 (d, J=6.8 Hz, 3H); m/z=451 (M+1).

Compound 213: To a suspension of sodium hydride (60% dispersion in mineral oil, 37 mg, 0.93 mmol) in THF (1 mL) was added cyclobutanemethanol (86 μL, 0.91 mmol) at room temperature. A solution of compound 94 (200 mg, 0.46 mmol) in THF (3.5 mL) was added at room temperature. The mixture was stirred at room temperature for 30 min, at 50° C. for 2 h, and cooled to room temperature. Aq. sat. $NaHCO_3$ was added. The mixture was extracted with EtOAc. The organic extract was dried with $Na_2SO_4$, and concentrated. The residue was purified by flash chromatography (silica gel, eluting with 0% to 50% EtOAc in hexanes) to give compound 213 (203 mg, 91% yield).

Compound 214: To a stirring solution of compound 213 (203 mg, 0.42 mmol) in MeOH (1.5 mL) and THF (1.5 mL) was added aq. 3 N HCl (1.4 mL, 4.2 mmol) at room temperature. The reaction was stirred at room temperature for 2 h, and concentrated. The residue was neutralized with aq. sat. $NaHCO_3$, and extracted with EtOAc. The organic extract was washed with water, dried with $Na_2SO_4$, and concentrated to give compound 214 (193 mg, quantitative yield) as a white solid, which was used in the next step without further purification. m/z=442 (M+1).

Compound 215: Compound 214 (193 mg, 0.42 mmol) in ethyl formate (1.9 mL, 23.62 mmol) was cooled to 0° C. Sodium methoxide (25 wt. % in methanol, 2.7 mL, 11.69 mmol) was added. The mixture was stirred at room temperature for 30 min. THF (0.5 mL) was added. After stirring for another 1.5 h, additional amount of THF (0.5 mL) was added. The reaction was stirred for another 1 h, and cooled to 0° C. Aq. 6 N HCl (2.0 mL, 12 mmol), EtOH (8 mL) and hydroxylamine hydrochloride (84 mg, 1.21 mmol) were added sequentially. The mixture was heated overnight at 55° C. (oil bath), and concentrated. Aq. sat. $NaHCO_3$ was added, and the mixture was extracted with EtOAc. The organic extract dried with $Na_2SO_4$ and concentrated. The residue was purified by flash chromatography (silica gel, eluting with 0% to 60% EtOAc in hexanes) to give compound 215 (145 mg, 71% yield) as a white foamy solid. m/z=467 (M+1).

Compound 216: Compound 215 (143 mg, 0.31 mmol) was dissolved in MeOH (3 mL). Potassium carbonate (123 mg, 0.89 mmol) was added. The reaction mixture was stirred at room temperature for 16 h. Aq. 10% $NaH_2PO_4$ was added. The mixture was extracted with EtOAc. The organic extract was dried with $Na_2SO_4$ and concentrated. The residue was purified by flash chromatography (silica gel, eluting with 0% to 60% EtOAc in hexanes) to give compound 216 (122 mg, 85% yield) as a white foamy solid. m/z=467 (M+1).

T95: Compound 216 (121 mg, 0.26 mmol) was dissolved in anhydrous DMF (1.3 mL), and the solution was cooled to 0° C. 1,3-dibromo-5,5-dimethylhydantoin (37 mg, 0.13 mmol) was added. The reaction was stirred at 0° C. for 1 h, and at room temperature for 1 h. Pyridine (63 μL, 0.78 mmol) was added. The reaction was heated at 55° C. (oil bath) for 3 h, and cooled to room temperature. $CH_2Cl_2$ was added. The mixture was washed with water. The organic extract was dried with $Na_2SO_4$, and concentrated. The residual pyridine was removed by azeotropic evaporation with toluene. The residue was purified by flash chromatography (silica gel, eluting with 0% to 40% acetone in hexanes) to give compound T95 (87 mg, 72% yield) as a white solid. $^1$H NMR (400 MHz, $CDCl_3$) δ 9.08 (d, J=4.5 Hz, 1H), 8.88 (s, 1H), 8.77 (ddd, J=0.6, 1.5, 8.6 Hz, 1H), 8.22 (td, J=1.0, 8.4 Hz, 1H), 7.98 (d, J=4.5 Hz, 1H), 7.78 (ddd, J=1.5, 6.8, 8.4 Hz, 1H), 7.63 (ddd, J=1.4, 6.8, 8.3 Hz, 1H), 4.49 (m, 1H), 4.45 (dd, J=6.5, 10.8 Hz, 1H), 2.96 (ddd, J=1.0, 6.6, 18.7 Hz, 1H), 2.78 (m, 2H), 2.61 (qd, J=6.7, 13.4 Hz, 1H), 2.17 (m, 4H), 1.92 (m, 5H), 1.52 (s, 3H), 1.35 (d, J=6.7 Hz, 3H); m/z=465 (M+1).

Compound 217a: To a suspension of sodium hydride (60% dispersion in mineral oil, 37 mg, 0.93 mmol) in THF (1 mL) was added cyclohexanol (0.097 mL, 0.92 mmol) at room temperature. The mixture was stirred for 10 min, and added at 0° C. to a solution of compound 94 (200 mg, 0.46 mmol) in THF (3.6 mL). The mixture was stirred at room temperature for 30 min, at 50° C. for 2 h, and cooled to room temperature. Aq. sat. $NaHCO_3$ was added. The mixture was extracted with EtOAc. The organic extract was dried with $Na_2SO_4$, filtered and concentrated. The residue was purified by flash chromatography (silica gel, eluting with 0% to 40% EtOAc in hexanes) to give compound 217a (208 mg, 90% yield) as a white foam.

Compound 218a: To a stirring solution of 217a (208 mg, 0.416 mmol) in MeOH (1.5 mL) and THF (1.5 mL) was added aq. 3 N HCl (1.5 mL, 4.5 mmol) at room temperature. The reaction was stirred at room temperature for 2 h, and concentrated. The residue was neutralized with aq. sat. $NaHCO_3$, and extracted with EtOAc. The organic extract was washed with water, dried with $Na_2SO_4$, filtered and concentrated to give compound 218a (200 mg, quantitative yield) as a white foam. m/z=456.2 (M+1).

Compound 219a: Compound 218a (200 mg, 0.416 mmol) was dissolved in ethyl formate (1.06 mL, 13.16 mmol) and cooled to 0° C. Sodium methoxide (25 wt. % in methanol, 1.5 mL, 6.56 mmol) was added. The mixture was stirred at room temperature for 2 h and then cooled to 0° C. Aq. 6 N HCl (1.09 mL, 6.54 mmol), EtOH (2 mL) and hydroxylamine hydrochloride (46 mg, 0.66 mmol) were added sequentially. The mixture was heated at 55° C. for 16 h, cooled to room temperature, and concentrated. Aq. sat. NaHCO$_3$ was added, and the mixture was extracted twice with EtOAc. The combined organic extracts were dried over Na$_2$SO$_4$, filtered and concentrated. The residue was purified by flash chromatography (silica gel, eluting with 0% to 30% EtOAc in hexanes) to give compound 219a (88 mg, 44% yield) as a pale yellow foam.

Compound 220a: To a solution of Compound 219a (88 mg, 0.18 mmol) in MeOH (1 mL) was added sodium methoxide (25 wt. % solution in MeOH, 0.063 mL, 0.27 mmol) at room temperature. The reaction mixture was stirred at 55° C. for 2 h, cooled to 0° C., and neutralized with aq. 10% NaH$_2$PO$_4$ mL). MeOH was removed by evaporation. The residue was diluted with water, and the mixture was extracted twice with EtOAc. The combined organic extracts were dried with Na$_2$SO$_4$ filtered and concentrated. The residue was purified by flash chromatography (silica gel, eluting with 0% to 40% EtOAc in hexanes) to give compound 220a (42 mg, 48% yield) as an off-white foamy solid. m/z=481.2 (M+1).

T96: Compound 220a (42 mg, 0.087 mmol) was dissolved in anhydrous DMF (0.5 mL), and the solution was cooled to 0° C. 1,3-dibromo-5,5-dimethylhydantoin (12.5 mg, 0.043 mmol) in DMF (0.5 mL) was added. The reaction mixture was stirred at 0° C. for 1 h, and pyridine (0.021 mL, 0.262 mmol) was added. The reaction mixture was heated at 55° C. for 3 h, and then cooled to room temperature. CH$_2$Cl$_2$ was added, and the mixture was washed with water. The organic layer was dried with Na$_2$SO$_4$, filtered and concentrated. The residual pyridine was removed by azeotropic evaporation with toluene. The residue was purified by flash chromatography (silica gel, eluting with 0% to 40% EtOAc in hexanes) to give compound T96 (20 mg, 48% yield) as a white foamy solid. $^1$H NMR (400 MHz, CDCl$_3$) δ 9.08 (d, J=4.5 Hz, 1H), 8.89 (s, 1H), 8.81 (m, 1H), 8.21 (m, 1H), 7.99 (d, J=4.4 Hz, 1H), 7.77 (ddd, J=1.4, 6.7, 8.4 Hz, 1H), 7.62 (ddd, J=1.3, 6.8, 8.3 Hz, 1H), 5.32 (tt, J=3.8, 8.4 Hz, 1H), 2.94 (dd, J=6.7, 18.6 Hz, 1H), 2.72 (ddd, J=7.5, 11.2, 18.8 Hz, 1H), 2.61 (qd, J=6.7, 13.3 Hz, 1H), 2.19 (m, 2H), 2.02 (m, 2H), 1.83 (m, 3H), 1.55 (m, 6H), 1.52 (s, 3H), 1.34 (d, J=6.7 Hz, 3H); m/z=479.2 (M+1).

Compound 217b: To a suspension of sodium hydride (60% dispersion in mineral oil, 37 mg, 0.93 mmol) in THF (1 mL) was added cyclopentanol (0.084 mL, 0.92 mmol) at room temperature. The mixture was stirred for 10 min, and added at 0° C. to a solution of compound 94 (200 mg, 0.46 mmol) in THF (3.6 mL). The mixture was stirred at room temperature for 30 min, at 50° C. for 2 h, and cooled to room temperature. Aq. sat. NaHCO$_3$ was added. The mixture was extracted with EtOAc. The organic extract was dried with Na$_2$SO$_4$, filtered and concentrated. The residue was purified by flash chromatography (silica gel, eluting with 0% to 40% EtOAc in hexanes) to give compound 217b (160 mg, 72% yield) as a white foam.

Compound 218b: To a stirring solution of 217b (160 mg, 0.329 mmol) in MeOH (1.0 mL) and THF (1.0 mL) was added aq. 3 N HCl (1.1 mL, 3.3 mmol) at room temperature. The reaction was stirred at room temperature for 2 h, and concentrated. The residue was neutralized with aq. sat. NaHCO$_3$, and extracted with EtOAc. The organic extract was washed with water, dried with Na$_2$SO$_4$, filtered and concentrated to give compound 218b (150 mg, quantitative yield) as a white foam. m/z=442.2 (M+1).

Compound 219b: Compound 218b (150 mg, 0.329 mmol) was dissolved in ethyl formate (0.82 mL, 10.2 mmol) and cooled to 0° C. Sodium methoxide (25 wt. % in methanol, 1.2 mL, 5.24 mmol) was added. The mixture was stirred at room temperature for 2 h and then cooled to 0° C. Aq. 6 N HCl (0.85 mL, 5.10 mmol), EtOH (2 mL) and hydroxylamine hydrochloride (35.4 mg, 0.51 mmol) were added sequentially. The mixture was heated at 55° C. for 16 h, cooled to room temperature, and concentrated. Aq. sat. NaHCO$_3$ was added, and the mixture was extracted twice with EtOAc. The combined organic extracts were dried over Na$_2$SO$_4$, filtered and concentrated. The residue was purified by flash chromatography (silica gel, eluting with 0% to 40% EtOAc in hexanes) to give compound 219b (100 mg, 65% yield) as a white foam. m/z=467.2 (M+1).

Compound 220b: To a solution of Compound 219b (100 mg, 0.214 mmol) in MeOH (2 mL) was added sodium methoxide (25 wt. % in MeOH, 0.074 mL, 0.323 mmol) at room temperature. The reaction mixture was stirred at 55° C. for 2 h, cooled to 0° C., and neutralized with aq. 10% NaH$_2$PO$_4$ (4 mL). MeOH was removed by evaporation. The residue was diluted with water, and the mixture was extracted twice with EtOAc. The combined organic extracts were dried with Na$_2$SO$_4$ filtered and concentrated. The residue was purified by flash chromatography (silica gel, eluting with 0% to 40% EtOAc in hexanes) to give compound 220b (88 mg, 88% yield) as an off-white foamy solid. m/z=467.2 (M+1).

T97: Compound 220b (87 mg, 0.186 mmol) was dissolved in anhydrous DMF (1.0 mL), and the solution was cooled to 0° C. 1,3-dibromo-5,5-dimethylhydantoin (26.6 mg, 0.093 mmol) in DMF (0.5 mL) was added. The reaction was stirred at 0° C. for 1 h, and pyridine (0.045 mL, 0.56 mmol) was added. The reaction mixture was heated at 55° C. for 3 h, and then cooled to room temperature. CH$_2$Cl$_2$ was added. The mixture was washed with water. The organic extract was dried with Na$_2$SO$_4$, filtered and concentrated. The residual pyridine was removed by azeotropic evaporation with toluene (10 mL). The residue was purified by flash chromatography (silica gel, eluting with 0% to 40% EtOAc in hexanes) to give compound T97 (55 mg, 64% yield) as a white foamy solid. $^1$H NMR (400 MHz, CDCl$_3$) δ 9.07 (d, J=4.4 Hz, 1H), 8.89 (s, 1H), 8.81 (ddd, J=0.6, 1.4, 8.6 Hz, 1H), 8.21 (ddd, J=0.7, 1.4, 8.5 Hz, 1H), 7.98 (d, J=4.5 Hz, 1H), 7.77 (ddd, J=1.5, 6.8, 8.4 Hz, 1H), 7.62 (ddd, J=1.4, 6.8, 8.3 Hz, 1H), 5.63 (tt, J=2.7, 6.1 Hz, 1H), 2.90 (dd, J=6.4, 18.8 Hz, 1H), 2.66 (m, 2H), 1.97 (m, 11H), 1.52 (s, 3H), 1.34 (d, J=6.7 Hz, 3H); m/z=465.2 (M+1).

Compound 221a and 221b: A mixture of compound 94 (600 mg, 1.37 mmol) was taken up in DMF (5 mL). Methanesulfonamide (660 mg, 6.94 mmol) and NaH (60% dispersion in mineral oil, 170 mg, 4.25 mmol) were added. The reaction was stirred at 80° C. for 16 h, cooled and concentrated. The residue was neutralized by the addition of aq. sat. KH$_2$PO$_4$, and extracted with EtOAc. The organic extract was washed with brine, dried with MgSO$_4$, filtered, and concentrated. The crude product was purified by flash chromatography (silica gel, eluting with 0% to 35% EtOAc in hexanes) to give compound 221a (250 mg, 37% yield) and 221b (225 mg, 37% yield) as foamy solid. m/z=495 (compound 221a, M+1). m/z=445 (compound 221b, M+1).

Compound 222a: Compound 221a (250 mg, 0.51 mmol) was taken up in THF (6 mL), and aq. 3 N HCl (3 mL, 9.0 mmol) was added. The mixture was stirred overnight at room temperature, and concentrated. The residue was neutralized with aq. sat. NaHCO$_3$, and extracted with EtOAc. The organic extract was washed with water, dried with MgSO$_4$, filtered and concentrated to give compound 222a (180 mg, 79% yield) as a foam. m/z=451 (M+1).

Compound 223a: Compound 222a (180 mg, 0.40 mmol) was taken up in ethyl formate (10 mL, 124 mmol). Sodium methoxide (30 wt. % in MeOH, 150 mg, 0.83 mmol) was added. After stirring at room temperature for 2 h, the reaction mixture was neutralized with aq. KH$_2$PO$_4$, and extracted with EtOAc. The organic extract was dried with MgSO$_4$, filtered, and concentrated to give compound 223a (175 mg, 92% yield) as a foam. m/z=479 (M+1).

Compound 224a: Compound 223a (175 mg, 0.37 mmol) was dissolved in EtOH (15 mL). Hydroxylamine hydrochloride (255 mg, 3.67 mmol) and acetic acid (220 mg, 3.66 mmol) were added. The reaction mixture was stirred overnight at 50° C., cooled, and concentrated. The residue was taken up in EtOAc, and washed with aq. NaHCO$_3$. The organic extract was dried with MgSO$_4$, filtered, and concentrated to give compound 224a (130 mg, 75% yield) as a foam. m/z=476 (M+1).

Compound 225a: Compound 224a (130 mg, 0.27 mmol) was dissolved in MeOH (10 mL). Potassium carbonate (230 mg, 1.66 mmol) was added. After stirring at room temperature overnight, the reaction mixture was neutralized by the addition of aq. sat. KH$_2$PO$_4$, and extracted with EtOAc. The organic extract was washed with brine, dried with MgSO$_4$, filtered, and concentrated. The residue was purified by flash chromatography (silica gel, eluting with 0% to 35% EtOAc in hexanes) to give compound 225a (110 mg, 85% yield) as a foam. m/z=476 (M+1).

T98: Compound 225a (110 mg, 0.23 mmol) was dissolved in dry DMF (2 mL), and the solution was cooled to 0° C. 1,3-dibromo-5,5-dimethylhydantoin (37 mg, 0.13 mmol) in DMF (1 mL) was added. The reaction stirred at 0° C. for 2 h, and pyridine (2 mL, 24.8 mmol) was added. The reaction was heated at 60° C. for 4 h, cooled, and concentrated. The residue was purified by flash chromatography (silica gel, eluting with 0% to 35% EtOAc in hexanes) to give compound T98 (45 mg, 41% yield) as a foam. $^1$H NMR (400 MHz, CDCl$_3$) δ 9.11 (d, J=4.4 Hz, 1H), 8.85 (m, 2H), 8.23 (d, J=8.5 Hz, 1H), 8.00 (m, 1H), 7.80 (dd, J=6.8, 8.6 Hz, 1H), 7.68 (dd, J=6.9, 8.5 Hz, 1H), 3.44 (br s, 3H), 2.83 (dd, J=6.7, 17.7 Hz, 1H), 2.65 (m, 2H), 2.28 (dd, J=7.6, 14.1 Hz, 1H), 2.19 (t, J=12.9 Hz, 1H), 1.88 (m, 1H), 1.54 (s, 3H), 1.36 (d, J=6.7 Hz, 3H); m/z=474 (M+1).

Compound 222b: Compound 221b (225 mg, 0.51 mmol) was taken up in THF (6 mL), and aq. 3 N HCl (3 mL, 9.0 mmol) was added. The mixture was stirred overnight at room temperature, and concentrated. The residue was neutralized with aq. saturated NaHCO$_3$, and extracted with EtOAc. The organic extract was washed with water, dried with MgSO$_4$, filtered and concentrated to give compound 222b (205 mg, quantitative yield) as a foam. m/z=401 (M+1).

Compound 223b: Compound 222b (205 mg, 0.51 mmol) was taken up in ethyl formate (10 mL, 124 mmol). Sodium methoxide (30 wt. % in MeOH, 210 mg, 1.17 mmol) was added. After stirring at room temperature for 2 h, the reaction mixture was neutralized with aq. KH$_2$PO$_4$, and extracted with EtOAc. The organic extract was dried with MgSO$_4$, filtered, and concentrated to give compound 223b (220 mg, quantitative yield) as a foam. m/z=429 (M+1).

Compound 224b: Compound 223b (220 mg, 0.51 mmol) was dissolved in EtOH (15 mL). Hydroxylamine hydrochloride (360 mg, 5.18 mmol) and acetic acid (310 mg, 5.16 mmol) were added. The reaction mixture was stirred overnight at 50° C., cooled, and concentrated. The residue was taken up in EtOAc, and washed with aq. NaHCO$_3$. The organic extract was dried with MgSO$_4$, filtered, and concentrated to give compound 224b (200 mg, 92% yield) as a foam. m/z=426 (M+1).

Compound 225b: Compound 224b (200 mg, 0.47 mmol) was dissolved in MeOH (10 mL). Potassium carbonate (390 mg, 2.82 mmol) was added. After stirring at room temperature overnight, the reaction mixture was neutralized by the addition of aq. sat. KH$_2$PO$_4$, and extracted with EtOAc. The organic extract was washed with brine, dried with MgSO$_4$, filtered, and concentrated. The residue was purified by flash chromatography (silica gel, eluting with 0% to 35% EtOAc in hexanes) to give compound 225b (140 mg, 70% yield) as a foam. m/z=426 (M+1).

T99: Compound 225b (140 mg, 0.33 mmol) was dissolved in dry DMF (2 mL), and the solution was cooled to 0° C. 1,3-Dibromo-5,5-dimethylhydantoin (52 mg, 0.18 mmol) in DMF (1 mL) was added. The reaction stirred at 0° C. for 2 h, and pyridine (2 mL, 24.8 mmol) was added. The reaction was heated at 60° C. for 4 h, cooled, and concentrated. The residue was purified by flash chromatography (silica gel, eluting with 0% to 35% EtOAc in hexanes) to give compound T99 (45 mg, 32% yield) as a foam. $^1$H NMR (400 MHz, CDCl$_3$) δ 9.06 (d, J=4.5 Hz, 1H), 8.87 (s, 1H), 8.82 (m, 1H), 8.20 (m, 1H), 7.99 (d, J=4.5 Hz, 1H), 7.75 (ddd, J=1.4, 6.8, 8.4 Hz, 1H), 7.60 (ddd, J=1.3, 6.8, 8.4 Hz, 1H), 3.16 (s, 6H), 2.91 (m, 2H), 2.61 (qd, J=6.7, 13.3 Hz, 1H), 2.22 (m, 2H), 1.77 (m, 1H), 1.51 (s, 3H), 1.34 (d, J=6.7 Hz, 3H); m/z=424 (M+1).

Compound 226a: A mixture of compound 94 (300 mg, 0.69 mmol), 3,5-dimethylisoxazole-4-boronic acid (145.4 mg, 1.03 mmol), sodium carbonate (219 mg, 2.06 mmol), 1,4-dioxane (2.7 mL) and water (0.9 mL) was sparged with nitrogen for 10 min. [1,1'-bis(diphenylphosphino)ferrocene]dichloropalladium(II) (50 mg, 0.069 mmol) was added and nitrogen sparging was continued for another 10 min. The reaction vial was sealed and heated to 110° C. in a Biotage® microwave synthesizer for 2 h. The mixture was cooled to room temperature, filtered through a plug of Celite®, and eluted with EtOAc. The filtrate was concentrated, and the residue was purified by flash chromatography (silica gel, eluting with 0% to 50% EtOAc in hexanes) to give compound 226a (290 mg, 85% yield) as a white foam. m/z=497.2 (M+1).

Compound 227a: To a mixture of compound 226a (290 mg, 0.584 mmol) in MeOH (1.9 mL) and THF (1.9 mL) was added aq. 3 N HCl (1.9 mL, 5.7 mmol) at room temperature. After stirring for 2 h, the mixture was concentrated. The residue was neutralized with aq. sat. NaHCO$_3$, and extracted with EtOAc. The organic extract was washed with water, dried with Na$_2$SO$_4$, filtered and concentrated to give compound 227a (240 mg, 91% yield) as a white solid. m/z=453.2 (M+1).

Compound 228a: Compound 227a (240 mg, 0.530 mmol) was dissolved in ethyl formate (1.3 mL, 16.2 mmol) and cooled to 0° C. Sodium methoxide (25 wt. % in MeOH, 1.8 mL, 7.87 mmol) was added The mixture was stirred at room temperature for 2 h, and then cooled to 0° C. Aq. 6 N HCl (1.3 mL, 7.8 mmol), EtOH (2 mL) and hydroxylamine hydrochloride (55 mg, 0.79 mmol) were added sequentially. The mixture was heated at 55° C. for 16 h, and concentrated. The residue was diluted with aq. sat. NaHCO$_3$, and the mixture was extracted twice with EtOAc. The combined organic extracts were dried with Na$_2$SO$_4$, filtered and concentrated. The residue was purified by flash chromatography (silica gel, eluting with 0% to 40% EtOAc in hexanes) to give compound 228a (220 mg, 87% yield) as a white foam. m/z=478.2 (M+1).

Compound 229a: To a solution of Compound 228a (220 mg, 0.46 mmol) in MeOH (4 mL) was added sodium methoxide (25 wt. % solution in MeOH, 0.16 mL, 0.70 mmol). The reaction mixture was stirred at 55° C. for 1.5 h, cooled to 0° C., and neutralized by adding aq. 10% $NaH_2PO_4$. MeOH was removed by evaporation. The residue was diluted with water, and the mixture was extracted twice with EtOAc. The combined organic extract was dried with $Na_2SO_4$ and filtered and concentrated. The residue was purified by flash chromatography (silica gel, eluting with 0% to 60% EtOAc in hexanes) to give compound 229a (160 mg, 73% yield) as an off-white solid. m/z=478.2 (M+1).

T100: Compound 229a (160 mg, 0.335 mmol) was dissolved in anhydrous DMF (2 mL), and the solution was cooled to 0° C. 1,3-dibromo-5,5-dimethylhydantoin (47.9 mg, 0.168 mmol) in DMF (1.3 mL) was added. The reaction was stirred at 0° C. for 1 h, and pyridine (0.081 mL, 1.0 mmol) was added. The mixture was heated at 55° C. for 3 h, and then cooled to room temperature. $CH_2Cl_2$ was added. The mixture was washed with water. The organic extract was dried with $Na_2SO_4$, filtered and concentrated. The residual pyridine was removed by azeotropic evaporation with toluene. The residue was purified by flash chromatography (silica gel, eluting with 0% to 70% acetone in hexanes) to give compound T100 (20 mg, 13% yield) as a light yellow solid. $^1$H NMR (400 MHz, $CDCl_3$) δ 9.11 (d, J=4.5 Hz, 1H), 8.91 (s, 1H), 8.71 (m, 1H), 8.26 (m, 1H), 8.03 (d, J=4.5 Hz, 1H), 7.80 (ddd, J=1.4, 6.8, 8.3 Hz, 1H), 7.65 (ddd, J=1.3, 6.8, 8.3 Hz, 1H), 2.82 (m, 2H), 2.66 (qd, J=6.6, 13.3 Hz, 1H), 2.42 (s, 3H), 2.29 (s, 3H), 2.27 (m, 2H), 1.89 (m, 1H), 1.48 (s, 3H), 1.36 (d, J=6.8 Hz, 3H); m/z=476.2 (M+1).

Compound 226b: A mixture of compound 94 (300 mg, 0.69 mmol), 4-(benzyl(methyl)carbamoyl)phenylboronic acid (278 mg, 1.03 mmol), sodium carbonate (219 mg, 2.06 mmol), 1,4-dioxane (3.3 mL) and water (1.1 mL) was sparged with nitrogen for 10 min. [1,1'-Bis(diphenylphosphino)ferrocene]dichloropalladium(II) (50 mg, 0.069 mmol) was added and nitrogen sparging was continued for another 10 min. The reaction vial was sealed and heated to 110° C. in a Biotage® microwave synthesizer for 2 h. The mixture was cooled to room temperature, filtered through a plug of Celite®, and eluted with EtOAc. The filtrate was concentrated, and the residue was purified by flash chromatography (silica gel, eluting with 0% to 60% EtOAc in hexanes) to give compound 226b (416 mg, 97% yield) as a light yellow foam. m/z=625.3 (M+1).

Compound 227b: To a solution of compound 226b (416 mg, 0.665 mmol) in MeOH (2.2 mL) and THF (2.2 mL) was added aq. 3 N HCl (2.2 mL, 6.6 mmol) at room temperature. After stirring for 2 h, the mixture was concentrated. The residue was neutralized with aq. sat. $NaHCO_3$, and extracted with EtOAc. The organic extract was washed with water, dried with $Na_2SO_4$, filtered and concentrated to give compound 227b (359 mg, 93% yield) as a yellow foam. m/z=581.3 (M+1).

Compound 228b: Compound 227b (355 mg, 0.611 mmol) was dissolved in ethyl formate (1.5 mL, 18.6 mmol) and cooled to 0° C. Sodium methoxide (25 wt. % in MeOH, 2.1 mL, 9.17 mmol) was added. The mixture was stirred at room temperature for 2 h, and then cooled to 0° C. Aq. 6 N HCl (1.53 mL, 9.2 mmol), EtOH (9 mL), and hydroxylamine hydrochloride (63.7 mg, 0.92 mmol) were added sequentially. The mixture was heated at 55° C. for 16 h, and concentrated. The residue was diluted with aq. sat. $NaHCO_3$, and the mixture was extracted twice with EtOAc. The combined organic extracts were dried with $Na_2SO_4$, filtered and concentrated. The residue was purified by flash chromatography (silica gel, eluting with 0% to 60% EtOAc in hexanes) to give compound 228b (183 mg, 49% yield) as a white foam. m/z=606.3 (M+1).

Compound 229b: To a solution of compound 228b (183 mg, 0.302 mmol) in MeOH (4 mL) was added sodium methoxide (25 wt. % solution in MeOH, 0.105 mL, 0.458 mmol). The reaction mixture was stirred at 55° C. for 1.5 h, cooled to 0° C., and neutralized by adding aq. 10% $NaH_2PO_4$. MeOH was removed by evaporation. The residue was diluted with water, and the mixture was extracted twice with EtOAc. The combined organic extracts were dried with $Na_2SO_4$, filtered and concentrated. The residue was purified by flash chromatography (silica gel, eluting with 0% to 60% EtOAc in hexanes) to give compound 229b (140 mg, 76% yield) as an off-white solid. m/z=606.2 (M+1).

T101: Compound 229b (140 mg, 0.231 mmol) was dissolved in dry DMF (2 mL), and the solution was cooled to 0° C. 1,3-dibromo-5,5-dimethylhydantoin (33 mg, 0.115 mmol) in DMF (1 mL) was added. The reaction mixture was stirred at 0° C. for 1 h, and pyridine (0.056 mL, 0.693 mmol) was added. The mixture was heated at 55° C. for 3 h, and then cooled to room temperature. $CH_2Cl_2$ was added. The mixture was washed with water. The organic extract was dried with $Na_2SO_4$, filtered and concentrated. The residual pyridine was removed by azeotropic evaporation with toluene (10 mL). The residue was purified by flash chromatography (silica gel, eluted with 0% to 20% acetone in hexanes) to give compound T101 (110 mg, 79% yield) as a light yellow solid. T101 is a 1:1 mixture of amide isomers. $^1$H NMR (400 MHz, $CDCl_3$) δ 9.07 (m, 1H), 8.93 (m, 1H), 8.68 (m, 1H), 8.22 (d, J=8.6 Hz, 1H), 8.00 (m, 1H), 7.77 (t, J=7.8 Hz, 1H), 7.63 (m, 5H), 7.36 (m, 4H), 7.18 (d, J=7.0 Hz, 1H), [4.79 (s), 4.56 (s), 1:1, 2H], [3.07 (s), 2.91 (s), 1:1, 3H], 3.02 (m, 2H), 2.64 (m, 1H), 2.24 (m, 2H), 1.84 (m, 1H), 1.59 (s, 3H), 1.35 (d, J=6.7 Hz, 3H); m/z=604.2 (M+1).

Compound 230a: A mixture of compound 94 (250 mg, 0.573 mmol), 2-furanboronic acid (96.3 mg, 0.86 mmol), sodium carbonate (182 mg, 1.72 mmol), 1,4-dioxane (3 mL) and water (1 mL) was sparged with nitrogen for 10 min. [1,1'-Bis(diphenylphosphino)ferrocene]dichloropalladium (II) (42 mg, 0.057 mmol) was added and nitrogen sparging was continued for another 10 min. The reaction vial was sealed and heated to 110° C. in a Biotage® microwave synthesizer for 2 h. The mixture was cooled to room temperature, filtered through a plug of Celite®, and eluted with EtOAc. The filtrate was concentrated. The residue was purified by flash chromatography (silica gel, eluting with, 0% to 60% EtOAc in hexanes) to give compound 230a (226 mg, 84% yield) as a white foam. m/z=468.2 (M+1).

Compound 231a: To a solution of compound 230a (226 mg, 0.483 mmol) in MeOH (1.6 mL) and THF (1.6 mL) was added aq. 3 N HCl (1.6 mL, 4.8 mmol) at room temperature. The mixture was stirred 2 h at room temperature, and concentrated. The residue was neutralized with aq. sat. $NaHCO_3$, and extracted with EtOAc. The organic extract was washed with water, dried with $Na_2SO_4$, filtered and concentrated to give compound 231a (190 mg, 93% yield) as a yellow foam. m/z=424.2 (M+1).

Compound 232a: Compound 231a (190 mg, 0.449 mmol) was dissolved in ethyl formate (1.1 mL, 13.7 mmol) and cooled to 0° C. Sodium methoxide (25 wt. % in MeOH, 1.5 mL, 6.56 mmol) was added. The mixture was stirred at room temperature for 2 h, and then cooled to 0° C. Aq. 6 N HCl (1.1 mL, 6.6 mmol), EtOH (6 mL) and hydroxylamine hydrochloride (46.8 mg, 0.67 mmol) were added sequentially. The mixture was heated at 55° C. for 16 h, and concentrated. The residue was diluted with aq. sat. NaHCO$_3$, and the mixture was extracted twice with EtOAc. The combined organic extracts were dried with Na$_2$SO$_4$, filtered and concentrated. The residue was purified by flash chromatography (silica gel, eluting with 0% to 20% acetone in hexanes) to give compound 232a (171 mg, 85% yield) as a white foam. m/z=449.2 (M+1).

Compound 233a: To a solution of Compound 232a (171 mg, 0.381 mmol) in MeOH (4 mL) was added sodium methoxide (25 wt. % solution in MeOH, 0.13 mL, 0.57 mmol). The reaction mixture was stirred at 55° C. for 1.5 h, cooled to 0° C., and neutralized by adding aq. 10% NaH$_2$PO$_4$. MeOH was removed by evaporation. The residue was diluted with water, and the mixture was extracted twice with EtOAc. The combined organic extracts were dried with Na$_2$SO$_4$, filtered and concentrated. The residue was purified by flash chromatography (silica gel, eluting with 0% to 60% EtOAc in hexanes) to give compound 233a (110 mg, 64% yield) as an off-white foam. m/z=449.2 (M+1).

T102: A mixture of compound 233a (90 mg, 0.201 mmol), DDQ (55 mg, 0.241 mmol) and benzene (2 mL) was stirred at reflux for 3 h. The reaction mixture was cooled to room temperature and then concentrated. The residue was purified by flash chromatography (silica gel, eluting with 0% to 60% EtOAc in hexanes) to give compound T102 (67 mg, 75% yield) as a white solid. $^1$H NMR (400 MHz, CDCl$_3$) δ 9.10 (d, J=4.5 Hz, 1H), 8.94 (s, 1H), 8.78 (m, 1H), 8.23 (m, 1H), 8.05 (d, J=4.5 Hz, 1H), 7.79 (ddd, J=1.4, 6.8, 8.3 Hz, 1H), 7.73 (td, J=0.7, 1.6 Hz, 1H), 7.64 (ddd, J=1.3, 6.8, 8.3 Hz, 1H), 7.45 (td, J=0.8, 3.6 Hz, 1H), 6.65 (ddd, J=0.6, 1.8, 3.6 Hz, 1H), 3.49 (dd, J=6.5, 18.9 Hz, 1H), 3.28 (ddd, J=7.4, 11.2, 18.8 Hz, 1H), 2.64 (qd, J=6.7, 13.5 Hz, 1H), 2.28 (m, 2H), 1.92 (dq, J=6.4, 13.1 Hz, 1H), 1.58 (s, 3H), 1.37 (d, J=6.7 Hz, 3H); m/z=447.1 (M+1).

Compound 230b: A mixture of compound 94 (216 mg, 0.496 mmol), 2-benzofuranboronic acid (120.4 mg, 0.74 mmol), sodium carbonate (158 mg, 1.49 mmol)), 1,4-dioxane (3 mL) and water (1 mL) was sparged with nitrogen for 10 min. [1,1'-Bis(diphenylphosphino)ferrocene]dichloropalladium(II) (36.2 mg, 0.049 mmol) was added and nitrogen sparging was continued for another 10 min. The reaction vial was sealed and heated to 110° C. in a Biotage® microwave synthesizer for 2 h. The mixture was cooled to room temperature, filtered through a plug of Celite®, and eluted with EtOAc. The filtrate was concentrated. The residue was purified by flash chromatography (silica gel, eluting with 0% to 50% EtOAc in hexanes) to give compound 230b (230 mg, 90% yield) as a white foam. m/z=518.2 (M+1).

Compound 231b: To a solution of compound 230b (230 mg, 0.444 mmol) in MeOH (2 mL) and THF (2 mL) was added aq. 3 N HCl (2 mL, 6 mmol). The mixture was stirred for 2 h at room temperature, and concentrated. The residue was neutralized with aq. sat. NaHCO$_3$, and extracted with EtOAc. The organic extract was washed with water, dried with Na$_2$SO$_4$, filtered and concentrated to give compound 231b (195 mg, 93% yield) as a yellow foam. m/z=474.2 (M+1).

Compound 232b: Compound 231b (195 mg, 0.412 mmol) was dissolved in ethyl formate (0.99 mL, 12.32 mmol) and cooled to 0° C. Sodium methoxide (25 wt. % in MeOH, 1.4 mL, 6.12 mmol) was added. The mixture was stirred at room temperature for 2 h, and then cooled to 0° C. Aq. 6 N HCl (1.1 mL, 6.6 mmol), EtOH (6 mL) and hydroxylamine hydrochloride (42.9 mg, 0.617 mmol) were added sequentially. The mixture was heated at 55° C. for 16 h, and concentrated. The residue was diluted with aq. sat. NaHCO$_3$, and the mixture was extracted twice with EtOAc. The combined organic extracts were dried with Na$_2$SO$_4$, filtered and concentrated. The residue was purified by flash chromatography (silica gel, eluting with 0% to 50% acetone in hexanes) to give compound 232b (136 mg, 66% yield) as a white foam. m/z=499.2 (M+1).

Compound 233b: To a solution of Compound 232b (130 mg, 0.261 mmol) in MeOH (4 mL) was added sodium methoxide (25 wt. % solution in MeOH, 0.089 mL, 0.39 mmol). The reaction mixture was stirred at 55° C. for 1.5 h, cooled to 0° C., and neutralized by adding aq. 10% NaH$_2$PO$_4$. MeOH was removed by evaporation. The residue was diluted with water, and the mixture was extracted twice with EtOAc. The combined organic extracts were dried with Na$_2$SO$_4$, filtered and concentrated. The residue was purified by flash chromatography (silica gel, eluting with 0% to 60% EtOAc in hexanes) to give compound 233b (93 mg, 71% yield) as an off-white foam. m/z=499.2 (M+1).

T103: A mixture of compound 233b (93 mg, 0.186 mmol), DDQ (50.8 mg, 0.224 mmol) and benzene (2 mL) was stirred at reflux for 3 h. The reaction mixture was cooled to room temperature then concentrated. The residue was purified by flash chromatography (silica gel, eluting with 0% to 60% acetone in hexanes) to give compound T103 (38 mg, 41% yield) as a white solid. $^1$H NMR (400 MHz, CDCl$_3$) δ 9.13 (d, J=4.5 Hz, 1H), 8.95 (s, 1H), 8.82 (m, 1H), 8.26 (m, 1H), 8.09 (d, J=4.4 Hz, 1H), 7.81 (m, 2H), 7.73 (d, J=7.6 Hz, 1H), 7.68 (ddd, J=1.4, 6.8, 8.4 Hz, 1H), 7.62 (d, J=8.3 Hz, 1H), 7.45 (ddd, J=1.3, 7.1, 8.4 Hz, 1H), 7.35 (t, J=7.6 Hz, 1H), 3.68 (dd, J=6.5, 18.9 Hz, 1H), 3.46 (ddd, J=7.7, 11.2, 18.9 Hz, 1H), 2.67 (qd, J=6.7, 13.3 Hz, 1H), 2.32 (m, 2H), 1.98 (m, 1H), 1.61 (s, 3H), 1.40 (d, J=6.7 Hz, 3H); m/z=497.2 (M+1).

Compound 234: A mixture of compound 94 (250 mg, 0.57 mmol), 5-methyl-2-furanboronic acid pinacol ester (0.17 mL, 0.86 mmol) and sodium carbonate (182 mg, 1.72 mmol) was sparged with nitrogen for 6 min. [1,1'-bis(diphenylphosphino)ferrocene]dichloropalladium(II) (42 mg, 0.057 mmol) was added and mixture was held under nitrogen stream for 1 min. The reaction vial was sealed and heated to 110° C. in Biotage® microwave synthesizer for 2 h. The mixture was cooled to room temperature, filtered through a plug of Celite®, and eluted with EtOAc. The filtrate was concentrated, and the residue was purified by flash chromatography (silica gel, eluting with 0% to 60% EtOAc in hexanes) to give compound 234 (345 mg) as a white foam. m/z=482.2 (M+1).

Compound 235: To a mixture of compound 234 (345 mg, 0.57 mmol) in MeOH (2.2 mL) and THF (2.2 mL) was added aq. 3 N HCl (2.2 mL, 6.6 mmol) at room temperature. After stirring for 3 h, the mixture was concentrated. The residue was neutralized with aq. sat. NaHCO$_3$, and extracted with EtOAc. The organic extract was washed with brine, dried with NaSO$_4$, filtered and concentrated to give compound 235 (207 mg, 82% yield from compound 94). m/z=438.2 (M+1).

Compound 236: Compound 235 (206 mg, 0.47 mmol) was dissolved in ethyl formate (1.6 mL, 19.8 mmol) and cooled to 0° C. Sodium methoxide (25 wt. % in MeOH, 1.6 mL, 7.05 mmol) was added. The mixture was stirred at room temperature for 2 h. Aq. 6 N HCl (1.2 mL, 7.2 mmol), EtOH (3 mL) and hydroxylamine hydrochloride (49 mg, 0.71 mmol) were added sequentially. The mixture was heated to 55° C. for 3 h, and concentrated. The residue was diluted with aq. sat. NaHCO$_3$ and the mixture was extracted twice with EtOAc. The combined organic extracts were washed with brine, dried with Na$_2$SO$_4$, filtered and concentrated. The residue was purified by flash chromatography (silica gel, eluting with 0% to 65% acetone in hexanes) to give compound 236 (107 mg, 49% yield). m/z=463.2 (M+1).

Compound 237: To a solution of compound 236 (107 mg, 0.23 mmol) in MeOH (3.3 mL) was added sodium methoxide (25 wt. % solution in MeOH, 0.08 mL, 0.35 mmol). The reaction mixture was stirred at 55° C. for 2 h, cooled to 0° C., and neutralized by adding aq. 10% NaH$_2$PO$_4$. The mixture was extracted with EtOAc. The organic extract was dried with Na$_2$SO$_4$, filtered and concentrated. The residue was purified by flash chromatography (silica gel, eluting with 0% to 65% acetone in hexanes) to give compound 237 (76 mg, 71% yield) as an off-white solid. m/z=463.2 (M+1).

T104: Compound 237 (76 mg, 0.17 mmol) was dissolved in anhydrous DMF (1.8 mL), and the solution was cooled to 0° C. 1,3-dibromo-5,5-dimethylhydantoin (24.5 mg, 0.086 mmol) in DMF (0.7 mL) was added. The reaction was stirred at 0° C. for 1.5 h, and pyridine (0.041 mL, 0.51 mmol) was added. The mixture was heated at 55° C. for 2.5 h and then cooled to room temperature. EtOAc (100 mL) was added. The mixture was washed with aq. sat. NaHCO$_3$ (10 mL), aq. 10% Na$_2$SO$_3$ (10 mL) and brine (10 mL). The organic extract was dried with Na$_2$SO$_4$, filtered and concentrated. The residual pyridine was removed by azeotropic evaporation with toluene. The residue was purified by flash chromatography (silica gel, eluting with 0% to 65% acetone in hexanes) to give compound T104 (42 mg, 56% yield) as a yellow solid. $^1$H NMR (400 MHz, CDCl$_3$) δ 9.09 (d, J=4.5 Hz, 1H), 8.94 (s, 1H), 8.81 (dd, J=1.4, 8.6 Hz, 1H), 8.22 (d, J=8.8 Hz, 1H), 8.05 (d, J=4.4 Hz, 1H), 7.77 (ddd, J=1.5, 6.8, 8.4 Hz, 1H), 7.63 (ddd, J=1.4, 6.8, 8.4 Hz, 1H), 7.36 (d, J=3.4 Hz, 1H), 6.26 (m, 1H), 3.45 (dd, J=6.2, 19.0 Hz, 1H), 3.22 (ddd, J=7.7, 11.2, 18.7 Hz, 1H), 2.62 (m, 1H), 2.47 (s, 3H), 2.29 (m, 2H), 1.92 (m, 1H), 1.56 (s, 3H), 1.37 (d, J=6.7 Hz, 3H); m/z=461.2 (M+1).

Compound 238: A mixture of compound 94 (510 mg, 1.17 mmol), zinc cyanide (206 mg, 1.85 mmol) and tetrakis (triphenylphosphine)palladium(O) (135 mg, 0.12 mmol) were weighed in a vial. The vial was sealed, and kept under vacuum. N,N-Dimethylacetamide (sparged with N$_2$ for 5 min, 5 mL) was added. The vial was filled with argon, heated at 120° C. for 3 h, and cooled to room temperature. EtOAc was added. The mixture was filtered through a plug of Celite®, and eluted with EtOAc. The filtrate was washed with water. The organic extract was dried with Na$_2$SO$_4$, and concentrated. The residue was purified by flash chromatography (silica gel, eluting with 0% to 60% EtOAc in hexanes) to give compound 238 (433 mg, 87% yield) as a white foamy solid. m/z=427 (M+1).

Compound 239: To a suspension of compound 238 (100 mg, 0.23 mmol) in water (1.25 mL) was added aq. H$_2$SO$_4$ (prepared by diluting conc. H$_2$SO$_4$ (1.25 mL, 22.5 mmol) with water (0.63 mL) at room temperature. The mixture was heated overnight at 100° C., cooled to room temperature, and poured into ice (30 g). The mixture was adjusted to pH~8 using aq. 1 N NaOH, and extracted with EtOAc. The aqueous phase was treated with NaH$_2$PO$_4$ to adjust pH~5, and extracted with EtOAc. The organic extract was dried with Na$_2$SO$_4$, and concentrated to give compound 239 (90 mg, 96% yield) as a brown solid. m/z=402 (M+1).

Compound 240: Compound 239 (88 mg, 0.22 mmol) in ethyl formate (0.53 mL) was cooled to 0° C. Sodium methoxide (25 wt. % in methanol, 0.76 mL, 3.29 mmol) was added. The mixture was stirred at room temperature for 30 min. THF (0.5 mL) was added. The reaction was stirred for another 1 h, and cooled to 0° C. Aq. 6 N HCl (0.55 mL, 3.30 mmol), EtOH (2.2 mL) and hydroxylamine hydrochloride (23 mg, 0.33 mmol) were added sequentially. The mixture was heated overnight at 55° C. (oil bath), and concentrated. CH$_2$Cl$_2$ and water were added. The mixture was extracted repeatedly with EtOAc. The combined organic extract dried with Na$_2$SO$_4$ and concentrated. The residue was purified by flash chromatography (C18, eluting with 0% to 50% MeCN in water) to give compound 240 (51 mg, 55% yield) as a yellow foamy solid. m/z=427 (M+1).

Compound 241: To a mixture of compound 240 (50 mg, 0.12 mmol) in CH$_2$Cl$_2$ (1.2 mL) was added oxalyl chloride (24 μL, 0.30 mmol) and DMF (1 drop) sequentially at 0° C. The reaction was stirred at room temperature for 4 h, and concentrated. The crude acid chloride was dissolved in in CH$_2$Cl$_2$ (1.2 mL), and cooled to 0° C. Triethylamine (65 μL, 0.47 mmol) and acetamide oxime (13 mg, 0.18 mmol) were added sequentially. After the reaction was stirred at room temperature for 1 h, EtOAc was added. The mixture was washed with water. The organic extract was dried with Na$_2$SO$_4$, and concentrated. The residue was purified by flash chromatography (silica gel, eluting with 0% to 65% acetone in hexanes) to give compound 241 (25 mg, 44% yield) as a yellow foamy solid. m/z=483 (M+1).

Compound 242: Compound 241 (25 mg, 0.052 mmol) in toluene (5 mL) was heated at reflux with Dean-Stark apparatus for 4 h, and cooled to room temperature. The mixture was purified by flash chromatography (silica gel, eluting with 0% to 50% acetone in hexanes) to give compound 242 (21 mg, 44% yield) as a white foamy solid. m/z=465 (M+1).

Compound 243: Compound 242 (20 mg, 0.043 mmol) was dissolved in MeOH (0.5 mL). Potassium carbonate (18 mg, 0.13 mmol) was added. The reaction mixture was stirred at room temperature for 16 h. Aq. 10% NaH$_2$PO$_4$ was added. The mixture was extracted with EtOAc. The organic extract was dried with Na$_2$SO$_4$ and concentrated. The residue was purified by flash chromatography (silica gel, eluting with 0% to 50% acetone in hexanes) to give compound 243 (15 mg, 75% yield) as a white foamy solid. m/z=465 (M+1).

T105: Compound 243 (15 mg, 0.032 mmol) was dissolved in benzene (1 mL). DDQ (8 mg, 0.035 mmol) was added. The mixture was heated at 85° C. for 1 h, and cooled to room temperature. CH$_2$Cl$_2$ and aq. sat. NaHCO$_3$ were added. The mixture was stirred at room temperature for 10 min, and extracted with CH$_2$Cl$_2$. The combined organic extract was washed with aq. sat. NaHCO$_3$, dried with Na$_2$SO$_4$, and concentrated. The residue was purified by flash chromatography (silica gel, eluting with 0% to 50% acetone in hexanes) to give compound T105 (11 mg, 73% yield) as a light yellow solid. $^1$H NMR (400 MHz, CDCl$_3$) δ 9.13 (d, J=4.5 Hz, 1H), 8.90 (s, 1H), 8.82 (m, 1H), 8.25 (m, 1H), 8.12 (d, J=4.4 Hz, 1H), 7.81 (ddd, J=1.4, 6.8, 8.4 Hz, 1H), 7.69 (ddd, J=1.4, 6.8, 8.3 Hz, 1H), 3.67 (dd, J=6.1, 19.7 Hz, 1H), 3.38 (ddd, J=7.8, 11.1, 19.5 Hz, 1H), 2.65 (m, 1H), 2.58 (s, 3H), 2.31 (m, 2H), 1.95 (m, 1H), 1.61 (s, 3H), 1.38 (d, J=6.8 Hz, 3H); m/z=463 (M+1).

Compound 244: A mixture of hydroxylamine hydrochloride (66 mg, 0.94 mmol) and NaHCO$_3$ (79 mg, 0.94 mmol) in EtOH (1 mL) was heated at reflux for 1 h, and cooled to 0° C. Compound 238 (200 mg, 0.47 mmol) and EtOH (0.5 mL) were added, and the mixture was stirred at room temperature for 5 h. EtOAc and water were added. The mixture was extracted with EtOAc. The combined organic extract was dried with Na$_2$SO$_4$ and concentrated to give compound 244 (198 mg, 92% yield) as a white solid. m/z=460 (M+1).

Compound 246: To a mixture of compound 244 (196 mg, 0.43 mmol) in AcOH (1 mL) was added acetic anhydride (60 μL, 0.64 mmol) at room temperature. The mixture was stirred at room temperature for 20 min, heated at 100° C. for 16 h, and cooled to room temperature. Toluene was added, and the mixture was concentrated to dryness to give a mixture of compound 245 and 246. The mixture was dissolved in MeOH (2.8 mL). Aq. 3 N HCl (1.4 mL, 4.2 mmol) was added. The reaction was stirred at room temperature for 4 h. Aq. sat. NaHCO$_3$ was added, and the mixture was extracted with EtOAc. The organic extract was dried with Na$_2$SO$_4$, and concentrated. The residue was purified by flash chromatography (silica gel, eluting with 0% to 100% EtOAc in hexanes) to give compound 246 (159 mg, 85% yield) as a light yellow foamy solid. m/z=440 (M+1).

Compound 247: Compound 246 (155 mg, 0.35 mmol) in ethyl formate (0.85 mL) was cooled to 0° C. Sodium methoxide (25 wt. % in methanol, 0.81 mL, 3.51 mmol) was added. The mixture was stirred at room temperature for 2 h, and cooled to 0° C. Aq. 6 N HCl (0.58 mL, 3.48 mmol), EtOH (3.5 mL) and hydroxylamine hydrochloride (37 mg, 0.53 mmol) were added sequentially. The mixture was heated at 55° C. (oil bath) for 6 h, and concentrated. Aq. sat. NaHCO$_3$ was added, and the mixture was extracted with EtOAc. The organic extract dried with Na$_2$SO$_4$ and concentrated. The residue was purified by flash chromatography (silica gel, eluting with 0% to 100% EtOAc in hexanes) to give compound 247 (67 mg, 41% yield) as a yellow foamy solid. m/z=465 (M+1).

Compound 248: Compound 247 (67 mg, 0.14 mmol) was dissolved in MeOH (1.4 mL). Potassium carbonate (60 mg, 0.43 mmol) was added. The reaction mixture was stirred at room temperature for 16 h. Aq. 10% NaH$_2$PO$_4$ was added. The mixture was extracted with EtOAc. The organic extract was dried with Na$_2$SO$_4$ and concentrated. The residue was purified by flash chromatography (silica gel, eluting with 0% to 100% EtOAc in hexanes) to give compound 248 (53 mg, 79% yield) as a yellow foamy solid. m/z=465 (M+1).

T106: Compound 248 (53 mg, 0.11 mmol) was dissolved in benzene (1.1 mL). DDQ (29 mg, 0.12 mmol) was added. The mixture was heated at 85° C. for 1 h, and cooled to room temperature. CH$_2$Cl$_2$ and aq. sat. NaHCO$_3$ were added. The mixture was stirred at room temperature for 5 min, and extracted with CH$_2$Cl$_2$. The combined organic extract was washed with aq. sat. NaHCO$_3$, dried with Na$_2$SO$_4$, and concentrated. The residue was purified by flash chromatography (silica gel, eluting with 0% to 100% EtOAc in hexanes) to give partially purified product, which was purified again by flash chromatography (silica gel, eluting with 0% to 10% MeOH in CH$_2$Cl$_2$) compound T106 (28 mg, 53% yield) as a light yellow solid. $^1$H NMR (400 MHz, CDCl$_3$) δ 9.10 (d, J=4.6 Hz, 1H), 8.91 (s, 1H), 8.69 (dd, J=1.3, 8.6 Hz, 1H), 8.23 (m, 1H), 8.04 (d, J=4.5 Hz, 1H), 7.79 (ddd, J=1.4, 6.8, 8.5 Hz, 1H), 7.66 (ddd, J=1.4, 6.8, 8.3 Hz, 1H), 3.51 (m, 1H), 3.29 (ddd, J=7.6, 11.1, 19.2 Hz, 1H), 2.75 (s, 3H), 2.65 (qd, J=6.7, 13.4 Hz, 1H), 2.31 (m, 2H), 1.92 (m, 1H), 1.60 (s, 3H), 1.37 (d, J=6.7 Hz, 3H); m/z=463 (M+1).

Compound 249: A mixture of compound 94 (250 mg, 0.573 mmol) in 1,4-dioxane (3 mL) was sparged with N$_2$ for 10 min. 2-(Tri-n-butylstannyl)thiazole (0.144 mL, 0.459 mmol) and tetrakis(triphenylphosphine)palladium(O) (26.5 mg, 0.023 mmol) were added sequentially, and nitrogen sparging was continued for another 10 min. The reaction mixture was refluxed for 8 h, cooled to room temperature, and concentrated. The residue diluted with EtOAc, and treated with aq. 10% KF (10 mL). The mixture was stirred at room temperature for 30 minutes, and filtered. The filtrate was washed with water. The organic extract was dried over Na$_2$SO$_4$, filtered and concentrated. The residue was purified by flash chromatography (silica gel, eluting with 0% to 60% acetone in hexanes) to give compound 249 (168 mg, 60% yield) as a white foam. m/z=485.2 (M+1).

Compound 250: To a solution of compound 249 (168 mg, 0.346 mmol) in MeOH (2 mL) and THF (2 mL) was added aq. 3 N HCl (2 mL, 6 mmol) at room temperature. The reaction mixture was stirred for 2 h, and concentrated. The residue was neutralized with aq. sat. NaHCO$_3$, and extracted with EtOAc. The organic extract was washed with water, dried with Na$_2$SO$_4$, filtered and concentrated. The residue was purified by flash chromatography (silica gel, eluting with 0% to 60% acetone in hexanes) to give compound 250 (112 mg, 73% yield) as a yellow solid. m/z=441.1 (M+1).

Compound 251: Compound 250 (112 mg, 0.254 mmol) was dissolved in ethyl formate (0.613 mL, 7.62 mmol) and cooled to 0° C. Sodium methoxide (25 wt. % in MeOH, 0.872 ml, 3.81 mmol) was added. The mixture was stirred at room temperature for 2 h, and then cooled to 0° C. Aq. 6 N HCl (0.64 mL, 3.84 mmol), EtOH (4 mL) and hydroxylamine hydrochloride (27 mg, 0.389 mmol) were added sequentially. The mixture was heated at 55° C. for 16 h, and concentrated. The residue was diluted with aq. sat. NaHCO$_3$, and the mixture was extracted twice with EtOAc. The combined organic extracts were dried with Na$_2$SO$_4$, filtered and concentrated. The residue was purified by flash chromatography (silica gel, eluting with 0% to 50% acetone in hexanes) to give compound 251 (50 mg, 42% yield) as a yellow foam. m/z=466.1 (M+1).

Compound 252: To a solution of Compound 251 (50 mg, 0.107 mmol) in MeOH (1 mL) was added potassium carbonate (22.2 mg, 0.161 mmol). The reaction mixture was stirred at room temperature for 4 h, cooled to 0° C., and neutralized by adding aq. 10% NaH$_2$PO$_4$. MeOH was removed by evaporation. The residue was diluted with water, and the mixture was extracted twice with EtOAc. The combined organic extracts were dried with Na$_2$SO$_4$, filtered and concentrated. The residue was purified by flash chromatography (silica gel, eluting with 0% to 40% acetone in hexanes) to give compound 252 (20 mg, 40% yield) as an off-white foam. m/z=466.1 (M+1).

T107: A mixture of compound 252 (20 mg, 0.043 mmol), DDQ (11.7 mg, 0.051 mmol) and benzene (1 mL) was stirred at reflux for 3 h. The reaction mixture was cooled to room temperature and concentrated. The residue was purified by flash chromatography (silica gel, eluting with 0% to 60% EtOAc in hexanes) to give compound T107 (5.4 mg, 27% yield) as a white solid. $^1$H NMR (400 MHz, CDCl$_3$) δ 9.10 (d, J=4.4 Hz, 1H), 9.02 (s, 1H), 8.93 (s, 1H), 8.80 (dd, J=1.3, 8.8 Hz, 1H), 8.55 (s, 1H), 8.25 (m, 1H), 8.08 (d, J=4.4 Hz, 1H), 7.81 (ddd, J=1.4, 6.8, 8.4 Hz, 1H), 7.67 (ddd, J=1.4, 6.8, 8.4 Hz, 1H), 3.33 (ddd, J=1.4, 6.9, 17.8 Hz, 1H), 3.20 (ddd, J=7.5, 10.9, 18.0 Hz, 1H), 2.67 (qd, J=6.7, 13.4 Hz, 1H), 2.41 (m, 1H), 2.33 (dt, J=2.7, 12.7 Hz, 1H), 2.01 (m, 1H), 1.60 (s, 3H), 1.39 (d, J=6.7 Hz, 3H); m/z=464.1 (M+1).

Compound 253: In a sealable vial, a mixture of compound 9 (assume 16.78 mmol), 2-methyl-4-quinolinecarboximidamide hydrochloride (3.90 g, 17.59 mmol) and potassium carbonate (4.86 g, 35.16 mmol) in EtOH (17 mL) was flushed with nitrogen. The vial was sealed and heated at 40° C. for 2 days. The mixture was concentrated, and the residue was diluted with EtOAc (150 mL) and water (50 mL), and heated at 65° C. until all solid was in solution (~1.5 h). The layers were separated, and the organic extract was washed with aq. sat. KH$_2$PO$_4$ (50 mL) and brine (50 mL), dried over MgSO$_4$, filtered, concentrated. The residue was purified by flash chromatography (silica gel, eluting with 5% MeOH in CHCl$_3$) to give compound 253 (5.35 g, 74% yield) as an orange foamy solid. m/z=432 (M+1).

Compound 254: In a microwave vessel, a mixture of compound 253 (1.78 g, 4.12 mmol) and phosphorus (V) oxychloride (3.8 mL, 40.7 mmol) in toluene (12 mL) was flushed with nitrogen. The vial was sealed and heated in Biotage® microwave synthesizer at 100° C. for 1 h. The mixture was cooled to room temperature, and carefully poured into a stirring suspension of NaHCO$_3$ (17 g, 205 mmol) in water (100 mL). After stirring for 30 min, the mixture was extracted with EtOAc (200 mL). The organic extract was washed with brine (100 mL), dried over MgSO$_4$, filtered and concentrated to give a mixture of ketal and ketone (1.70 g) as dark yellow foamy solid. The crude product was dissolved in benzene (50 mL), and treated with ethylene glycol (2.3 mL, 41.2 mmol) and p-toluenesulfonic acid monohydrate (0.078 g, 0.41 mmol). The mixture was refluxed with Dean-Stark trap for 4 h, cooled, and partitioned between aq. sat. NaHCO$_3$ (50 mL) and EtOAc (50 mL). The organic extract was washed with brine (50 mL), dried over MgSO$_4$, filtered, concentrated. The residue was purified by flash chromatography (silica gel, eluting with 50% EtOAc in hexanes) to give compound 254 (1.56 g, 84% yield) as an off-white foamy solid. m/z=450 (M+1).

Compound 255a: In a sealable vial, a mixture of compound 254 (0.40 g, 0.89 mmol), 3-fluorophenylboronic acid (0.19 g, 1.36 mmol), potassium phosphate (0.57 g, 2.68 mmol) and tetrakis(triphenylphosphine)palladium(O) (0.10 g, 0.088 mmol) in 1,4-dioxane (9 mL) was degassed with nitrogen. The vial was sealed and heated at 90° C. for 16 h. After cooling to room temperature, the mixture partitioned between aq. 1N NaOH (50 mL) and EtOAc (50 mL). The organic extract was washed with brine (50 mL), dried over MgSO$_4$, filtered, concentrated. The residue was purified by flash chromatography (silica gel, eluting with 50% EtOAc in hexanes) to give compound 255a (0.40 g, 88% yield) as a light yellow foamy solid. m/z=510 (M+1).

Compound 256a: A solution of compound 255a (0.40 g, 0.79 mmol) and aq. 3 N HCl (5 mL, 15 mmol) in MeOH (10 mL) was stirred at room temperature overnight, and concentrated. The residue was cooled, basified with aq. 10% NH$_4$OH, and extracted with CHCl$_3$ (50 mL). The organic extract was washed with brine (50 mL), dried over MgSO$_4$, filtered and concentrated to give compound 256a (0.32 g, 88% yield) as a light yellow foamy solid. m/z=466 (M+1).

Compound 257a: To a stirring solution at room temperature of compound 256a (0.32 g, 0.68 mmol) in ethyl formate (10 mL, 124 mmol) was added sodium methoxide (30 wt. % solution in MeOH, 0.37 mL, 2.05 mmol). The mixture was stirred for 2 h, and then partitioned between EtOAc (50 mL) and aq. sat. KH$_2$PO$_4$ (50 mL). The organic extract was washed with brine (50 mL), dried over MgSO$_4$, filtered and concentrated to give compound 257a (0.29 g, 85% yield) as yellow orange foamy solid. m/z=494 (M+1).

Compound 258a: To a solution of compound 257a (0.29 g, 0.59 mmol) in EtOH (10 mL) was added acetic acid (0.34 mL, 5.93 mmol) and hydroxylamine hydrochloride (0.062 g, 0.89 mmol). The mixture was stirred at 60° C. under nitrogen for 2 h, at room temperature overnight, and concentrated. The residue was partitioned between aq. sat. NaHCO$_3$ (50 mL) and EtOAc (50 mL). The organic extract was washed with brine (50 mL), dried over MgSO$_4$, filtered and concentrated to give compound 258a (0.27 g, 94% yield) as a yellow-orange foamy solid. m/z=491 (M+1).

Compound 259a: A solution of compound 258a (0.27 g, 0.55 mmol) in MeOH (6 mL) was treated with potassium carbonate (0.38 g, 2.75 mmol). The mixture was stirred at room temperature under nitrogen for 16 h, and concentrated. The residue was partitioned between aq. sat. KH$_2$PO$_4$ (50 mL) and EtOAc (50 mL). The organic extract was washed with brine, dried over MgSO$_4$, filtered, concentrated. The residue was purified by flash chromatography (silica gel, eluting with 50% EtOAc in hexanes) to give compound 259a (0.18 g, 67% yield) as a light yellow foamy solid. m/z=491 (M+1).

T108: To a stirring solution at 0° C. under nitrogen of compound 259a (0.18 g, 0.37 mmol) in degassed DMF (5 mL) was added dropwise a solution of 1,3-dibromo-5,5-dimethylhydantoin (0.057 g, 0.20 mmol) in DMF (2 mL). After stirring the mixture for 30 min, pyridine (0.30 mL, 3.72 mmol) was added. The ice-bath was removed, and the mixture was heated at 60° C. for 4 h, cooled, and concentrated. The residue was partitioned between aq. sat. KH$_2$PO$_4$ (50 mL) and EtOAc (50 mL). The organic extract was washed with brine (50 mL), dried over MgSO$_4$, filtered, concentrated. The residue was purified by flash chromatography (silica gel, eluting with 50% EtOAc in hexanes) to give compound T108 (0.069 g, 39% yield) as a light yellow solid. $^1$H NMR (400 MHz, CDCl$_3$) δ 8.93 (s, 1H), 8.58 (dd, J=0.8, 8.4, 1H), 8.13 (dd, J=0.4, 8.4 Hz, 1H), 7.87 (s, 1H), 7.74 (ddd, J=1.4, 6.8, 8.4 Hz, 1H), 7.57 (ddd, J=1.3, 6.8, 8.3 Hz, 1H), 7.51 (dt, J=5.6, 8.0 Hz, 1H), 7.40 (td, J=1.2, 7.7 Hz, 1H), 7.34 (ddd, J=1.6, 2.6, 9.3 Hz, 1H), 7.22 (ddt, J=1.0, 2.6, 8.3 Hz, 1H), 3.03 (m, 2H), 2.86 (s, 3H), 2.65 (qd, J=6.7, 13.4 Hz, 1H), 2.31 (dt, J=2.7, 12.8 Hz, 1H), 2.21 (tdd, J=2.8, 5.8, 12.2 Hz, 1H), 1.84 (ddt, J=7.4, 10.1, 13.5 Hz, 1H), 1.59 (s, 3H), 1.35 (d, J=6.7 Hz, 3H); m/z=489 (M+1).

Compound 255b: In a sealable vial, a mixture of compound 254 (0.40 g, 0.89 mmol), 4-fluorophenylboronic acid (0.19 g, 1.36 mmol), potassium phosphate (0.57 g, 2.69 mmol) and tetrakis(triphenylphosphine)palladium(O) (0.10 g, 0.088 mmol) in 1,4-dioxane (9 mL) was degassed with nitrogen. The vial was sealed and heated at 90° C. for 16 h. The mixture was cooled and partitioned between aq. 1 N NaOH (50 mL) and EtOAc (50 mL). The organic extract was washed with brine (50 mL), dried over MgSO$_4$, filtered, and concentrated. The residue was purified by flash chromatography (silica gel, eluting with 50% EtOAc in hexanes) to give compound 255b (0.39 g, 86% yield) as a light yellow foamy solid. m/z=510 (M+1).

Compound 256b: A solution of compound 255b (0.39 g, 0.77 mmol) and aq. 3 N HCl (2.6 mL, 7.8 mmol) in MeOH (8 mL) was stirred at room temperature overnight, and concentrated. The residue was cooled, basified with aq. 10% NH$_4$OH, and extracted with CHCl$_3$ (50 mL). The organic extract was washed with brine (50 mL), dried over MgSO$_4$, filtered, and concentrated to give compound 256b (0.35 g, 98% yield) as a light yellow foamy solid. m/z=466 (M+1).

Compound 257b: To a stirring solution at room temperature of compound 256b (0.35 g, 0.75 mmol) in ethyl formate (10 mL, 124 mmol) was added sodium methoxide (30 wt. % solution in MeOH, 0.41 g, 2.28 mmol). The mixture was stirred for 2 h and concentrated. The residue was partitioned between EtOAc (50 mL) and aq. sat. KH$_2$PO$_4$ (50 mL). The organic extract was washed with brine (50 mL), dried over MgSO$_4$, filtered and concentrated to give compound 257b (0.31 g, 83% yield) as an orange foamy solid. m/z=494 (M+1).

Compound 258b: A solution of compound 257b (310 mg, 0.627 mmol) in glacial acetic acid (0.36 ml, 6.28 mmol) and EtOH (10 mL) was treated with hydroxylamine hydrochloride (65 mg, 0.935 mmol). The reaction mixture was stirred under nitrogen at 60° C. for 4 h and at room temperature for 24 h. The solvent was removed in vacuo and the residue was cautiously partitioned between aq. 10% NH$_4$OH and EtOAc. The organic extract was washed with brine, dried over MgSO$_4$, filtered and concentrated to give compound 258b (357 mg) as a yellow glass. m/z=491 (M+1).

Compound 259b: A mixture of compound 258b (all from the last step) and potassium carbonate (201 mg, 1.45 mmol) in MeOH (10 mL) was stirred under nitrogen at room temperature for 16 h. The reaction mixture was concentrated and the residue was partitioned between water and Et$_2$O. The aqueous phase was cooled in an ice-water bath and acidified with aq. sat. KH$_2$PO$_4$. The acidified aqueous mixture was extracted with EtOAc (2×50 mL). The combined organic extracts were washed with brine, dried over MgSO$_4$, filtered and concentrated. The residue was purified by flash chromatography (silica gel, eluting with 50% EtOAc in hexanes) to give compound 259b (167 mg, 54% yield from compound 257b) as a white glass. m/z=491 (M+1).

T109: A solution of compound 259b (167 mg, 0.34 mmol) in degassed DMF (5 mL), was cooled to 0° C., and was treated dropwise with a solution of 1,3-dibromo-5,5-dimethylhydantoin (53 mg, 0.185 mmol) in degassed DMF (2 mL). After stirring the mixture at 0° C. for 30 min, anhydrous pyridine (0.27 mL, 3.35 mmol) was added. The cold bath was removed, and the reaction mixture was heated at 60° C. under an argon atmosphere for 4 h. Upon cooling to room temperature, the reaction mixture was partitioned between EtOAc and aq. sat. KH$_2$PO$_4$. The organic extract was washed with brine, dried over MgSO$_4$, filtered and concentrated. The residue was purified by flash chromatography (silica gel, eluting with 50% EtOAc in hexanes) to give compound T109 (90 mg, 54% yield) as a white amorphous solid. $^1$H NMR (400 MHz, CDCl$_3$) δ 8.93 (s, 1H), 8.58 (dd, J=1.4, 8.6 Hz, 1H), 8.13 (ddd, J=0.6, 1.3, 8.5 Hz, 1H), 7.86 (s, 1H), 7.74 (ddd, J=1.4, 6.8, 8.4 Hz, 1H), 7.65 (m, 2H), 7.56 (ddd, J=1.3, 6.9, 8.4 Hz, 1H), 7.22 (m, 2H), 3.03 (m, 2H), 2.86 (s, 3H), 2.64 (qd, J=6.7, 13.4 Hz, 1H), 2.31 (dt, J=2.7, 12.8 Hz, 1H), 2.20 (tdd, J=2.8, 5.9, 13.7 Hz, 1H), 1.84 (ddt, J=7.2, 10.2, 13.5 Hz, 1H), 1.59 (s, 3H), 1.35 (d, J=6.7 Hz, 3H); m/z=489 (M+1).

Compound 260a: Sodium hydride (60% dispersion in mineral oil, 0.066 g, 1.65 mmol) was added portionwise to a stirring solution of cyclobutanol (0.12 g, 1.66 mmol) in THF (10 mL) at room temperature over 10 min. The mixture was stirred for 1 h, and was treated with compound 254 (0.50 g, 1.11 mmol). The mixture was heated at 60° C. under nitrogen overnight, cooled to room temperature, and quenched with aq. sat. KH$_2$PO$_4$ (50 mL). The solvent was evaporated in vacuo and the residue was extracted with EtOAc (50 mL). The organic extract was washed with brine (100 mL), dried over MgSO$_4$, filtered, and concentrated. The residue was purified by flash chromatography (silica gel, eluting with 50% EtOAc in hexanes) to give compound 260a (0.54 g, quantitative yield) as an off-white foamy solid. m/z=486 (M+1).

Compound 261a: A solution of compound 260a (0.54 g, assume 1.11 mmol) and aq. 3 N HCl (3.7 mL, 11.1 mmol) in MeOH (11 mL) was stirred at room temperature overnight. The mixture was concentrated, cooled, basified with aq. 10% NH$_4$OH and extracted with CHCl$_3$ (50 mL). The organic extract was washed with brine (50 mL), dried over MgSO$_4$, filtered and concentrated to give compound 261a (0.52 g) as an off-white foamy solid. m/z=442 (M+1).

Compound 262a: To a stirring solution at room temperature of compound 261a (all from the last step) in ethyl formate (10 mL, 124 mmol) was added sodium methoxide (30 wt. % solution in MeOH, 0.61 mL, 3.39 mmol). The mixture was stirred for 2 h and partitioned between EtOAc (50 mL) and aq. sat. KH$_2$PO$_4$ (50 mL). The organic extract was washed with brine (50 mL), dried over MgSO$_4$, filtered and concentrated to give compound 262a (0.51 g, 98% yield from compound 260a) as an orange foamy solid. m/z=470 (M+1).

Compound 263a: To a solution of compound 262a (0.51 g, 1.08 mmol) in EtOH (10 mL) was added acetic acid (0.62 mL, 10.83 mmol) and hydroxylamine hydrochloride (0.12 g, 1.73 mmol). The mixture was stirred at 60° C. under N$_2$ for 2 h, at room temperature overnight, and concentrated. The residue was partitioned between aq. sat. NaHCO$_3$ (50 mL) and EtOAc (50 mL). The organic extract was washed with brine (50 mL), dried over MgSO$_4$, filtered and concentrated to give compound 263a (0.47 g, 93% yield) as a yellow-orange foamy solid. m/z=467 (M+1).

Compound 264a: A solution of compound 263a (0.47 g, 1.01 mmol) in MeOH (10 mL) was treated with potassium carbonate (0.71 g, 5.14 mmol). The sample was stirred at room temperature under nitrogen for 16 h, and concentrated. The residue was partitioned between aq. sat. KH$_2$PO$_4$ (50 mL) and EtOAc (50 mL). The organic extract was washed with brine (50 mL), dried over MgSO$_4$, filtered, and concentrated. The residue was purified by flash chromatography (silica gel, eluting with 50% EtOAc in hexanes) to give compound 264a (0.33 g, 70% yield) as a light yellow foamy solid. m/z=467 (M+1).

T110: To a stirring solution at 0° C. under nitrogen of compound 264a (0.33 g, 0.71 mmol) in degassed DMF (5 mL) was added dropwise a solution of 1,3-dibromo-5,5-dimethylhydantoin (0.11 g, 0.38 mmol) in DMF (2 mL). After stirring the mixture for 30 min, pyridine (0.57 mL, 7.06 mmol) was added. The ice-bath was removed, and the mixture was heated at 60° C. for 4 h, cooled and concentrated. The residue was partitioned between aq. sat. KH$_2$PO$_4$ (50 mL) and EtOAc (50 mL). The organic extract was washed with brine (50 mL), dried over MgSO$_4$, filtered, and concentrated. The residue was purified by flash chromatography (silica gel, eluting with 50% EtOAc in hexanes) to give compound T110 (0.11 g, 33% yield) as a light yellow foamy solid. $^1$H NMR (400 MHz, CDCl$_3$) δ 8.89 (s, 1H), 8.61 (dd, J=0.8, 8.8 Hz, 1H), 8.12 (dd, J=0.8, 8.4 Hz, 1H), 7.79 (s, 1H), 7.73 (ddd, J=1.5, 6.8, 8.4 Hz, 1H), 7.54 (ddd, J=1.3, 6.8, 8.4 Hz, 1H), 5.34 (m, 1H), 2.95 (ddd, J=0.8, 6.8, 18.8 Hz, 1H), 2.86 (s, 3H), 2.72 (ddd, J=7.6, 11.5, 18.8 Hz, 1H), 2.60 (qd, J=6.9, 13.8 Hz, 1H), 2.52 (m, 2H), 2.22 (m, 4H), 1.80 (m, 3H), 1.51 (s, 3H), 1.35 (d, J=6.7 Hz, 3H); m/z=465 (M+1).

Compound 260b: Compound 254 (800 mg, 1.78 mmol) was taken up in THF (10 mL). Cyclopentanol (600 mg, 6.97 mmol) and sodium hydride (60% dispersion in mineral oil, 280 mg, 7.00 mmol) were added. The mixture was stirred at 60° C. for 16 h, cooled, and concentrated. The residue was neutralized by the addition of aq. sat. KH$_2$PO$_4$, and extracted with EtOAc. The organic extract was washed with brine, dried over MgSO$_4$, filtered and concentrated. The residue was purified by flash chromatography (silica gel, eluting with 0% to 35% EtOAc in hexanes) to give compound 260b (850 mg, 95% yield) as a foam. m/z=500 (M+1).

Compound 261b: A mixture of compound 260b (850 mg, 1.70 mmol) was taken up in THF (10 mL), and aq. 3 N HCl (5 mL, 15 mmol) was added. The mixture was stirred overnight at room temperature, and concentrated. The residue was neutralized with aq. sat. NaHCO$_3$, and extracted with EtOAc. The organic extract was washed with water, then dried over MgSO₄, filtered and concentrated to give compound 261b (775 mg, quantitative yield) as a foam. m/z=456 (M+1).

Compound 262b: Compound 261b (775 mg, 1.70 mmol) was taken up in ethyl formate (15 mL, 186.5 mmol). Sodium methoxide (30 wt. % in methanol, 600 mg, 3.33 mmol) was added. After stirring at room temperature for 2 h, the mixture was neutralized with aq. KH₂PO₄, and extracted with EtOAc. The organic extract was dried over MgSO₄, filtered and concentrated to give compound 262b (825 mg, quantitative yield) as a foam. m/z=484 (M+1).

Compound 263b: Compound 262b (825 mg, 1.70 mmol) was dissolved in EtOH (15 mL). Hydroxylamine hydrochloride (1.2 g, 17.26 mmol) and AcOH (1 g, 16.65 mmol) were added. The mixture was stirred overnight at 50° C., cooled to room temperature, and concentrated. The residue was taken up in EtOAc, and washed with aq. NaHCO₃. The organic extract was dried over MgSO₄, filtered and concentrated to give compound 263b (820 mg, quantitative yield) as a foam. m/z=481 (M+1).

Compound 264b: Compound 263b (820 mg, 1.70 mmol) was dissolved in MeOH (10 mL). Potassium carbonate (1.2 g, 8.68 mmol) was added. The mixture was stirred at room temperature overnight, neutralized by the addition of aq. sat. KH₂PO₄, and extracted with EtOAc. The organic extract was washed with brine, dried over MgSO₄, filtered and concentrated. The residue was purified by flash chromatography (silica gel, eluting with 0% to 35% EtOAc in hexanes) to give compound 264b (570 mg, 70% yield) as a foam. m/z=481 (M+1).

T111: Compound 264b (570 mg, 1.19 mmol) was dissolved in dry DMF (2 mL), and the solution was cooled to 0° C. Bromine (210 mg, 1.31 mmol) in CH₂Cl₂ (1 mL) was added. The mixture was stirred at 0° C. for 2 h, and pyridine (2 mL, 24.8 mmol) was added. The ice-bath was removed. The reaction mixture heated at 60° C. for 4 h, cooled and concentrated. The residue was purified by flash chromatography (silica gel, eluting with 0% to 35% EtOAc in hexanes) to give compound T111 (75 mg, 13% yield) as a foam. $^{1}$H NMR (400 MHz, CDCl₃) δ 8.90 (s, 1H), 8.66 (dd, J=1.3, 8.7 Hz, 1H), 8.12 (m, 1H), 7.82 (s, 1H), 7.72 (ddd, J=1.4, 6.8, 8.3 Hz, 1H), 7.54 (ddd, J=1.3, 6.7, 8.3 Hz, 1H), 5.62 (tt, J=2.7, 6.1 Hz, 1H), 2.90 (m, 1H), 2.86 (s, 3H), 2.65 (m, 2H), 2.18 (m, 2H), 1.81 (m, 9H), 1.51 (s, 3H), 1.34 (d, J=6.7 Hz, 3H); m/z=479 (M+1).

Compound 265: Compound 9 (1.1 g, 3.71 mmol) was taken up in EtOH (15 mL). Quinazoline-4-carboximidamide hydrochloride (0.6 g, 2.88 mmol) and potassium carbonate (1 g, 7.24) were added. The reaction mixture was stirred at 40° C. for 2 days, cooled, and concentrated. The residue was treated with water (20 mL) and EtOAc (100 mL), and heated at 65° C. for 30 min. After cooling to room temperature, the mixture was extracted with EtOAc. The organic extract was dried over MgSO₄, filtered and concentrated. The residue was purified by flash chromatography (silica gel, eluting with 0% to 100% EtOAc in hexanes) to give compound 265 (1.05 g, 68% yield) as an off-white solid. m/z=419 (M+1).

Compound 266: Compound 265 (1.05 g, 2.51 mmol) was taken up in toluene (8 mL). Phosphorus (V) oxychloride (4 g, 26.09 mmol) was added. The mixture was heated in Biotage® Initiator™ microwave synthesizer at 100° C. for 60 min, cooled, and poured into ice. After sitting for 10 min, the mixture was extracted with EtOAc. The organic extract was washed with aq. NaHCO₃, dried with MgSO₄, filtered and concentrated. The residue was purified by flash chromatography (silica gel, eluting with 0% to 35% EtOAc in hexanes) to give a mixture of ketal and ketone (600 mg). The mixture was mixed in benzene (100 mL), and treated with ethylene glycol (1 g, 16.11 mmol) and p-toluenesulfonic acid monohydrate (60 mg, 0.32 mmol). The mixture was refluxed for 16 h with a Dean-Stark trap, cooled to room temperature, and washed with water. The organic extract was dried over MgSO₄, filtered and concentrated. The residue was purified by flash chromatography (silica gel, eluting with 0% to 35% EtOAc in hexanes) to give compound 266 (300 mg, 27% yield) as a light color solid. m/z=437 (M+1).

Compound 267: Compound 266 (300 mg, 0.69 mmol) was taken up in THF (10 mL). Cyclobutanol (75 mg, 1.04 mmol) and NaH (60% dispersion in mineral oil, 45 mg, 1.13 mmol) were added. The reaction mixture was stirred at 60° C. for 16 h, cooled, and concentrated. The residue was neutralized by the addition of aq. sat. KH₂PO₄, and extracted with EtOAc. The organic extract was washed with brine, dried with MgSO₄, filtered and concentrated. The residue was purified by flash chromatography (silica gel, eluting with 0% to 35% EtOAc in hexanes) to give compound 267 (300 mg, 92% yield) as a foam. m/z=473 (M+1).

Compound 268: A mixture of compound 267 (300 mg, 0.63 mmol) was taken up in THF (6 mL), and aq. 3N HCl (3 mL, 9.0 mmol) was added. The mixture was stirred overnight at room temperature and concentrated. The residue was neutralized with aq. sat. NaHCO₃, and extracted with EtOAc. The organic extract was washed with water, dried with MgSO₄, filtered, and concentrated to give compound 268 (220 mg, 81% yield) as a white solid. m/z=429 (M+1).

Compound 269: Compound 268 (200 mg, 0.47 mmol) was taken up in ethyl formate (15 mL, 186 mmol). Sodium methoxide (30 wt. % solution in MeOH, 170 mg, 0.94 mmol) was added. The mixture was stirred at room temperature for 2 h, neutralized with aq. KH₂PO₄, and extracted with EtOAc. The organic extract was dried with MgSO₄, filtered and concentrated to give compound 269 (215 mg, quantitative yield) as a foam. m/z=457 (M+1).

Compound 270: Compound 269 (215 mg, 0.47 mmol) was dissolved in EtOH (15 mL). Hydroxylamine hydrochloride (335 mg, 4.82 mmol) and acetic acid (280 mg, 4.66 mmol) were added. The reaction mixture was stirred overnight at 50° C., cooled, and concentrated. The residue was taken up in EtOAc and washed with aq. NaHCO₃. The organic extract was dried with MgSO₄, filtered and concentrated to give compound 270 (210 mg, quantitative yield) as a foam. m/z=454 (M+1).

Compound 271: Compound 270 (210 mg, 0.46 mmol) was dissolved in MeOH (10 mL). Potassium carbonate (310 mg, 2.24 mmol) was added. The reaction mixture was stirred at room temperature overnight, neutralized by the addition of aq. sat. KH₂PO₄, and extracted with EtOAc. The organic extract was washed with brine, dried over MgSO₄, filtered and concentrated. The residue was purified by flash chromatography (silica gel, eluting with 0% to 35% EtOAc in hexanes) to give compound 271 (70 mg, 33% yield) as a foam. m/z=454 (M+1).

T112: Compound 271 (70 mg, 0.15 mmol) was dissolved in dry DMF (2 mL), and the solution was cooled to 0° C. 1,3-Dibromo-5,5-dimethylhydantoin (25 mg, 0.087 mmol) in DMF (1 mL) was added. The reaction stirred at 0° C. for 2 h, and pyridine (2 mL, 24.8 mmol) was added. The mixture was heated at 60° C. for 4 h, cooled and concentrated. The residue was purified by flash chromatography (silica gel, eluting with 0% to 35% EtOAc in hexanes) to give compound T112 (45 mg, 65% yield) as a foam. $^{1}$H NMR (400 MHz, CDCl₃) δ 9.50 (s, 1H), 8.85 (s, 1H), 8.30 (ddd, J=0.7, 1.5, 8.5 Hz, 1H), 8.17 (td, J=0.9, 8.6 Hz, 1H), 7.97 (ddd, J=1.4, 6.9, 8.5 Hz, 1H), 7.67 (ddd, J=1.2, 6.9, 8.3 Hz, 1H), 5.37 (m, 1H), 2.97 (ddd, J=0.9, 6.7, 19.0 Hz, 1H), 2.74 (ddd, J=7.6, 11.3, 18.8 Hz, 1H), 2.60 (qd, J=6.7, 13.3 Hz, 1H), 2.47 (m, 2H), 2.20 (m, 4H), 1.84 (m, 2H), 1.65 (m, 1H), 1.50 (s, 3H), 1.34 (d, J=6.7 Hz, 3H); m/z=452 (M+1).

Compound 272a: Compound 266 (760 mg, 1.74 mmol) was taken up in 1,4-dioxane (8 mL). Potassium carbonate (725 mg, 5.24 mmol), [1,1'-bis(diphenylphosphino)ferrocene]-dichloropalladium(II) (200 mg, 0.27 mmol) and 3-fluorophenylboronic acid (365 mg, 2.61 mmol) were added. The mixture was sparged with nitrogen for 10 min, and stirred at 90° C. for 16 h. Upon cooling to room temperature, the mixture was filtered, and the filtrate was concentrated. The residue was purified by flash chromatography (silica gel, eluting with 0% to 35% EtOAc in hexanes) to give compound 272a (510 mg, 59% yield) as a foam. m/z=497 (M+1).

Compound 273a: Compound 272a (510 mg, 1.02 mmol) was taken up in THF (10 mL), and aq. 3 N HCl (5 mL, 15.0 mmol) was added. The mixture was stirred overnight at room temperature, and concentrated. The residue was neutralized with aq. sat. NaHCO$_3$, and extracted with EtOAc. The organic extract was washed with water, dried over MgSO$_4$, filtered and concentrated to give compound 273a (460 mg, 99% yield) as a foam. m/z=453 (M+1).

Compound 274a: Compound 273a (460 mg, 1.01 mmol) was taken up in ethyl formate (15 mL, 186 mmol). Sodium methoxide (30 wt. % in methanol, 200 mg, 1.11 mmol) was added. The mixture was stirred at room temperature for 2 h, neutralized with aq. KH$_2$PO$_4$, and extracted with EtOAc. The organic extract was dried with MgSO$_4$, filtered and concentrated to give compound 274a (490 mg, quantitative yield) as a foam. m/z=481 (M+1).

Compound 275a: Compound 274a (490 mg, 1.01 mmol) was dissolved in EtOH (15 mL). Hydroxylamine hydrochloride (710 mg, 10.22 mmol) and acetic acid (615 mg, 10.12 mmol) were added. The reaction mixture was stirred overnight at 50° C., cooled and concentrated. The residue was taken up in EtOAc and washed with aq. NaHCO$_3$. The organic extract was dried over MgSO$_4$, filtered and concentrated to give compound 275a (440 mg, 91% yield) as a foam. m/z=478 (M+1).

Compound 276a: Compound 275a (440 mg, 0.92 mmol) was dissolved in MeOH (10 mL). Potassium carbonate (650 mg, 4.69 mmol) was added. The reaction mixture was stirred at room temperature overnight, neutralized by the addition of aq. sat. KH$_2$PO$_4$, and extracted with EtOAc. The organic extract was washed with brine, dried over MgSO$_4$, filtered and concentrated. The residue was purified by flash chromatography (silica gel, eluting with 0% to 35% EtOAc in hexanes) to give compound 276a (270 mg, 61% yield) as a foam. m/z=478 (M+1).

T113: Compound 276a (270 mg, 0.57 mmol) was dissolved in dry DMF (2 mL), and the solution was cooled to 0° C. 1,3-Dibromo-5,5-dimethylhydantoin (90 mg, 0.31 mmol) in DMF (1 mL) was added, and the reaction stirred at 0° C. for 2 h. Pyridine (2 mL, 24.8 mmol) was added, and the reaction was heated at 60° C. for 4 h. Upon cooling to room temperature, the mixture was concentrated. The residue was purified by flash chromatography (silica gel, eluting with 0% to 35% EtOAc in hexanes) to give compound T113 (115 mg, 43% yield) as a foam. $^1$H NMR (400 MHz, CDCl$_3$) δ 9.53 (s, 1H), 8.89 (s, 1H), 8.37 (ddd, J=0.6, 1.4, 8.5 Hz, 1H), 8.19 (td, J=0.9, 8.4 Hz, 1H), 7.99 (ddd, J=1.4, 6.9, 8.4 Hz, 1H), 7.72 (ddd, J=1.2, 6.9, 8.3 Hz, 1H), 7.49 (dt, J=5.6, 8.0 Hz, 1H), 7.39 (ddd, J=1.1, 1.6, 7.7 Hz, 1H), 7.33 (ddd, J=1.5, 2.5, 9.2 Hz, 1H), 7.20 (ddt, J=1.1, 2.6, 8.4 Hz, 1H), 3.06 (m, 2H), 2.64 (qd, J=6.7, 13.3 Hz, 1H), 2.32 (dt, J=2.7, 12.7 Hz, 1H), 2.22 (tdd, J=3.2, 5.9, 13.6 Hz, 1H), 1.87 (m, 1H), 1.59 (s, 3H), 1.35 (d, J=6.7 Hz, 3H); m/z=476 (M+1).

Compound 272b: Compound 266 (780 mg, 1.79 mmol) was taken up in 1,4-dioxane (8 mL). Potassium carbonate (740 mg, 5.35 mmol), [1,1'-bis(diphenylphosphino)ferrocene]-dichloropalladium(II) (210 mg, 0.29 mmol) and 4-fluorophenylboronic acid (375 mg, 2.68 mmol) were added. The mixture was sparged with nitrogen for 10 min and stirred at 90° C. for 16 h. Upon cooling to room temperature, the mixture was filtered, and the filtrate was concentrated. The residue was purified by flash chromatography (silica gel, eluting with 0% to 35% EtOAc in hexanes) to give compound 272b (650 mg, 73% yield) as a foam. m/z=497 (M+1).

Compound 273b: Compound 272b (650 mg, 1.31 mmol) was taken up in THF (10 mL), and aq. 3 N HCl (5 mL, 15.0 mmol) was added. The mixture was stirred overnight at room temperature and concentrated. The residue was neutralized with aq. sat. NaHCO$_3$ and extracted with EtOAc. The organic extract was washed with water, dried over MgSO$_4$, filtered and concentrated to give compound 273b (595 mg, quantitative yield) as a foam. m/z=453 (M+1).

Compound 274b: Compound 273b (595 mg, 1.31 mmol) was taken up in ethyl formate (15 mL, 186 mmol). Sodium methoxide (30 wt. % in methanol, 230 mg, 1.28 mmol) was added. The mixture was stirred at room temperature for 2 h, neutralized with aq. KH$_2$PO$_4$, and extracted with EtOAc. The organic extract was dried over MgSO$_4$, filtered and concentrated to give compound 274b (620 mg, 98% yield) as a foam. m/z=481 (M+1).

Compound 275b: Compound 274b (620 mg, 1.29 mmol) was dissolved in EtOH (15 mL). Hydroxylamine hydrochloride (900 mg, 12.95 mmol) and acetic acid (780 mg, 12.98 mmol) were added. The reaction mixture was stirred overnight at 50° C., cooled and concentrated. The residue was taken up in EtOAc and washed with aq. NaHCO$_3$. The organic extract was dried over MgSO$_4$, filtered and concentrated to give compound 275b (540 mg, 88% yield) as a foam. m/z=478 (M+1).

Compound 276b: Compound 275b (540 mg, 1.13 mmol) was dissolved in MeOH (10 mL). Potassium carbonate (650 mg, 4.70 mmol) was added. The reaction mixture was stirred at room temperature overnight, neutralized by the addition of aq. sat. KH$_2$PO$_4$, and extracted with EtOAc. The organic extract was washed with brine, dried over MgSO$_4$, filtered and concentrated. The residue was purified by flash chromatography (silica gel, eluting with 0% to 35% EtOAc in hexanes) to give compound 276b (290 mg, 54% yield) as a foam. m/z=478 (M+1).

T114: Compound 276b (290 mg, 0.61 mmol) was dissolved in dry DMF (2 mL), and the solution was cooled to 0° C. 1,3-Dibromo-5,5-dimethylhydantoin (96 mg, 0.34 mmol) in DMF (1 mL) was added, and the mixture was stirred at 0° C. for 2 h. Pyridine (2 ml, 24.8 mmol) was added. The reaction was heated at 60° C. for 4 h, cooled and concentrated. The residue was purified by flash chromatography (silica gel, eluting with 0% to 35% EtOAc in hexanes) to give compound T114 (125 mg, 43% yield) as a foam. $^1$H NMR (400 MHz, CDCl$_3$) δ 9.53 (s, 1H), 8.89 (s, 1H), 8.37 (ddd, J=0.6, 1.4, 8.5 Hz, 1H), 8.19 (td, J=0.9, 8.5 Hz, 1H), 7.99 (ddd, J=1.4, 6.9, 8.5 Hz, 1H), 7.71 (ddd, J=1.2, 6.9, 8.3 Hz, 1H), 7.63 (m, 2H), 3.07 (m, 2H), 2.64 (qd, J=6.7, 13.4 Hz, 1H), 2.32 (dt, J=2.8, 12.8 Hz, 1H), 2.22 (tdd, J=3.1, 6.0, 13.8 Hz, 1H), 1.86 (m, 1H), 1.59 (s, 3H), 1.35 (d, J=6.7 Hz, 3H); m/z=476 (M+1).

Compound 277: A mixture of compound 170d (0.99 g, 1.94 mmol) and selenium dioxide (0.44 g, 3.96 mmol) in 1,4-dioxane (20 mL) was heated at 100° C. under nitrogen for 1 h. The mixture was cooled to room temperature and filtered through a pad of Celite®. The filtrate was concentrated, and the residue was purified by flash chromatography (silica gel, eluting with 50% EtOAc in hexanes) to give compound 277 (0.87 g, 85% yield) as a light yellow foamy solid. m/z=524 (M+1).

Compound 278: A solution of compound 277 (0.46 g, 0.88 mmol) in EtOH (10 mL) was treated with NaBH$_4$ (0.033 g, 0.87 mmol). The mixture was stirred at room temperature under nitrogen for 16 h and concentrated. The residue was partitioned between aq. sat. KH$_2$PO$_4$ (50 mL) and EtOAc (50 mL). The organic extract was washed with brine (50 mL), dried over MgSO$_4$, filtered and concentrated to give compound 278 (0.45 g, 98% yield) as an off-white foamy solid. m/z=526 (M+1).

Compound 279: To a solution at 0° C. of compound 278 (0.45 g, 0.86 mmol) in CH$_2$Cl$_2$ (9 mL) was added a solution of (diethylamino)sulfur trifluoride (0.28 g, 1.74 mmol) in CH$_2$Cl$_2$ (2 mL). The resultant blue solution was stirred at 0° C. for 2 h and then partitioned between aq. sat. NaHCO$_3$ (50 mL) and EtOAc (50 mL). The organic extract was washed with brine (50 mL), dried over MgSO$_4$, filtered, and concentrated. The residue was purified by flash chromatography (silica gel, eluting with 50% EtOAc in hexanes) to give compound 279 (0.27 g, 60% yield) as light yellow foamy solid. m/z=528 (M+1).

Compound 280: A solution of compound 279 (0.27 g, 0.51 mmol) and aq. 3 N HCl (1.7 mL, 5.1 mmol) in MeOH (5 mL) was stirred at room temperature overnight. The mixture was concentrated, cooled, basified with aq. 10% NH$_4$OH, and extracted with CHCl$_3$ (50 mL). The organic extract was washed with brine (50 mL), dried over MgSO$_4$, filtered and concentrated to give compound 280 (0.25 g, quantitative yield) as a light yellow foamy solid. m/z=484 (M+1).

Compound 281: A solution at room temperature of compound 280 (0.25 g, 0.51 mmol) in ethyl formate (10 mL, 124 mmol) was treated with sodium methoxide (30 wt. % in methanol, 0.30 mL, 1.60 mmol). The mixture was stirred for 2 h and then partitioned between EtOAc (50 mL) and aq. sat. KH$_2$PO$_4$ (50 mL). The organic extract was washed with brine (50 mL), dried over MgSO$_4$, filtered and concentrated to give compound 281 (0.25 g, 95% yield) as an orange foamy solid. m/z=512 (M+1).

Compound 282: A solution of compound 281 (0.25 g, 0.48 mmol) and acetic acid (0.28 mL, 4.89 mmol) in EtOH (5 mL) was treated with hydroxylamine hydrochloride (0.051 g, 0.73 mmol). The mixture was stirred at 60° C. under nitrogen for 2 h at room temperature overnight and concentrated. The residue was partitioned between aq. sat. NaHCO$_3$ (50 mL) and EtOAc (50 mL). The organic extract was washed with brine (50 mL), dried over MgSO$_4$, filtered, and concentrated to give compound 282 (0.23 g, 92% yield) as an orange-brown foamy solid. m/z=509 (M+1).

Compound 283: A mixture of compound 282 (0.23 g, 0.45 mmol) and potassium carbonate (0.31 g, 2.24 mmol) in MeOH (5 mL) was stirred at room temperature under nitrogen for 16 h and then filtered. The filtrate was concentrated, and the residue was carefully partitioned between aq. sat. KH$_2$PO$_4$ (50 mL) and EtOAc (50 mL). The organic extract was washed with brine (50 mL), dried over MgSO$_4$, filtered, and concentrated. The residue was purified by flash chromatography (silica gel, eluting with 50% EtOAc in hexanes) to give compound 283 (0.14 g, 61% yield) as a light yellow foamy solid. m/z=509 (M+1).

T115: To a stirring solution at 0° C. under nitrogen of compound 283 (0.14 g, 0.28 mmol) in degassed DMF (5 mL) was added 1,3-dibromo-5,5-dimethylhydantoin (0.043 g, 0.15 mmol). After stirring the mixture for 30 min, pyridine (0.22 mL, 2.72 mmol) was added. The ice-bath was removed, and the mixture was heated at 60° C. for 4 h. Upon cooling to room temperature, the mixture was concentrated, and the residue was partitioned between aq. sat. KH$_2$PO$_4$ (50 mL) and EtOAc (50 mL). The organic extract was washed with brine (50 mL), dried over MgSO$_4$, filtered, and concentrated. The residue was purified by flash chromatography (silica gel, eluting with 50% EtOAc in hexanes) to give compound T115 (0.071 g, 51% yield) as a light yellow foamy solid. $^1$H NMR (400 MHz, CDCl$_3$) δ 8.93 (s, 1H), 8.64 (dd, J=0.8, 8.4 Hz, 1H), 8.16 (m, 2H), 7.79 (ddd, J=1.4, 6.8, 8.5 Hz, 1H), 7.64 (ddd, J=1.3, 6.8, 8.3 Hz, 1H), 7.50 (m, 2H), 7.33 (dt, J=1.1, 7.5 Hz, 1H), 7.24 (m, 1H), 5.75 (d, J=46.9 Hz, 2H), 2.90 (m, 2H), 2.64 (qd, J=6.7, 13.4 Hz, 1H), 2.32 (dt, J=2.7, 12.8 Hz, 1H), 2.18 (m, 1H), 1.86 (m, 1H), 1.61 (s, 3H), 1.34 (d, J=6.7 Hz, 3H); m/z=507 (M+1).

Compound 284: A solution of compound 278 (0.815 g, 1.55 mmol) and aq. 3 N HCl (5.2 mL, 15.6 mmol) in MeOH (15 mL) was stirred at room temperature overnight. The mixture was concentrated; the residue was carefully partitioned between aq. sat. NaHCO$_3$ (50 mL) and EtOAc (50 mL). The organic extract was washed with brine (50 mL), dried over MgSO$_4$, filtered and concentrated to give compound 284 (0.69 g, 92% yield) as a light yellow foamy solid. m/z=482 (M+1).

Compound 285: To a stirring solution at room temperature of compound 284 (0.69 g, 1.43 mmol) in ethyl formate (10 mL, 124 mmol) was added sodium methoxide (30 wt. % solution in MeOH, 0.81 mL, 4.32 mmol). The mixture was stirred for 2 h and concentrated. The residue was partitioned between EtOAc (50 mL) and aq. sat. KH$_2$PO$_4$ (50 mL). The organic extract was washed with brine (50 mL), dried over MgSO$_4$, filtered and concentrated to give compound 285 (0.707 g, 97% yield) as an orange foamy solid. m/z=510 (M+1).

Compound 286: A solution of compound 285 (0.707 g, 1.39 mmol) and acetic acid (0.80 mL, 13.99 mmol) in EtOH (25 mL) was treated with hydroxylamine hydrochloride (0.14 g, 2.01 mmol). The mixture was stirred at 60° C. under nitrogen for 2 h then at room temperature overnight. The mixture was concentrated; the residue was partitioned between aq. sat. NaHCO$_3$ solution (50 mL) and EtOAc (50 mL). The organic extract was washed with brine (50 mL), dried over MgSO$_4$, filtered, and concentrated. The residue was purified by flash chromatography (silica gel, eluting with 50% EtOAc in hexanes) to give compound 286 (0.43 g, 61% yield) as an orange foamy solid. m/z=507 (M+1).

Compound 287: A mixture of compound 286 (0.43 g, 0.85 mmol) and potassium carbonate (0.62 g, 4.49 mmol) in MeOH (20 mL) was stirred at room temperature under nitrogen overnight. The mixture was concentrated; the residue was carefully partitioned between aq. sat. KH$_2$PO$_4$ (50 mL) and EtOAc (50 mL). The organic extract was washed with brine (50 mL), dried over MgSO$_4$, filtered, and concentrated. The residue was purified by flash chromatography (silica gel, eluting with 75% EtOAc in hexanes) to give compound 287 (0.30 g, 70% yield) as a yellow foamy solid. m/z=507 (M+1).

T116: To a stirring solution at 0° C. under nitrogen of compound 287 (0.30 g, 0.59 mmol) in benzene (10 mL) was added in one portion DDQ (0.15 g, 0.66 mmol). The reaction was heated at 80° C. for 0.5 h. The mixture was cooled and concentrated. The residue was partitioned between aq. sat.

Na₂CO₃ (50 mL) and EtOAc (50 mL). The organic extract was washed with brine (50 mL), dried over MgSO₄, filtered and concentrated. The residue was purified by flash chromatography (silica gel, eluting with 25% to 75% EtOAc in hexanes) to give compound T116 (0.047 g, 16% yield) as a light yellow foamy solid. $^1$H NMR (400 MHz, CDCl₃) δ 10.31 (s, 1H), 8.91 (s, 1H), 8.73 (dd, J=1.3, 8.6 Hz, 1H), 8.59 (s, 1H), 8.37 (m, 1H), 7.88 (ddd, J=1.4, 6.8, 8.4 Hz, 1H), 7.78 (ddd, J=1.4, 6.8, 8.4 Hz, 1H), 7.51 (m, 2H), 7.34 (dt, J=1.1, 7.5 Hz, 1H), 7.24 (m, 1H), 2.91 (m, 2H), 2.65 (qd, J=6.7, 13.3 Hz, 1H), 2.32 (dt, J=2.8, 12.8 Hz, 1H), 2.19 (m, 1H), 1.87 (m, 1H), 1.61 (s, 3H), 1.34 (d, J=6.7 Hz, 3H); m/z=503 (M+1).

Impure compound 288 (0.075 g) was also obtained as a dark yellow solid from the column. The sample was purified again by flash chromatography (silica gel, eluting with 5% MeOH in CHCl₃) to give compound 288 (0.028 g, 9% yield from compound 287) as a light yellow foamy solid which was still impure. m/z=505 (M+1).

T117: A mixture of compound 288 (0.028 g, 0.055 mmol) and sodium acetate (50 mg, 0.61 mmol) in acetic anhydride (2 mL) was stirred at room temperature overnight. The mixture was concentrated and purified by flash chromatography (silica gel, eluting with 50% EtOAc in hexanes) to give T117 (0.015 g, 50% yield) as a light yellow foamy solid. $^1$H NMR (400 MHz, CDCl₃) δ 8.93 (s, 1H), 8.64 (dd, J=1.4, 8.7 Hz, 1H), 8.19 (d, J=8.4 Hz, 1H), 8.05 (s, 1H), 7.78 (ddd, J=1.4, 6.8, 8.4 Hz, 1H), 7.63 (ddd, J=1.3, 6.8, 8.4 Hz, 1H), 7.50 (m, 2H), 7.33 (dt, J=1.1, 7.5 Hz, 1H), 7.24 (m, 1H), 5.48 (s, 2H), 2.91 (m, 2H), 2.65 (qd, J=6.7, 13.3 Hz, 1H), 2.31 (dt, J=2.7, 12.8 Hz, 1H), 2.21 (s, 3H), 2.19 (m, 1H), 1.87 (m, 1H), 1.60 (s, 3H), 1.34 (d, J=6.7 Hz, 3H); m/z=547 (M+1).

Compound 289: To a stirring solution of compound 4 (30.37 g, assume 145.2 mmol) and pyridinium p-toluenesulfonate (3.60 g, 14.32 mmol) in CH₂Cl₂ (400 mL) was added dropwise 3,4-dihydro-2H-pyran (14.6 mL, 160.0 mmol) at room temperature under nitrogen. The mixture was stirred overnight and concentrated. The residue was partitioned between EtOAc (400 mL) and aq. sat. NaHCO₃ (400 mL). The organic extract was washed with aq. sat. KH₂PO₄ (400 mL), brine (400 mL), dried over MgSO₄, filtered, and concentrated. The residue was purified by flash chromatography (silica gel, eluting with 20% EtOAc in hexanes) to give compound 289 (26.86 g, 66% yield) as a viscous colorless oil. m/z=279 (M+1).

Compound 290: To a stirring solution at room temperature under nitrogen of compound 289 (10.16 g, 36.49 mmol) in benzene (145 mL) was added portionwise potassium tert-butoxide (4.09 g, 36.45 mmol) over 30 min. After addition, the resulting dark suspension was heated at 60° C. for 30 min, cooled to 0° C., and treated with dropwise addition of iodomethane (6.8 mL, 109.2 mmol). The mixture was slowly allowed to warm to room temperature overnight and quenched with aq. sat. KH₂PO₄ (200 mL). The organic extract was washed with brine (200 mL), dried over MgSO₄, filtered, and concentrated. The residue was purified by flash chromatography (silica gel, eluting with 10% EtOAc in hexanes) to give compound 290 (8.60 g, 80% yield) as a viscous light yellow oil. m/z=293 (M+1).

Compound 291: A solution of compound 290 (10.63 g, 36.35 mmol) and pyridinium p-toluenesulfonate (0.91 g, 3.62 mmol) in EtOH (100 mL) was refluxed under nitrogen overnight. The mixture was cooled, and concentrated. The residue was partitioned between aq. 1 N HCl (50 mL) and EtOAc (50 mL). The organic extract was washed with aq. sat. NaHCO₃ and brine, dried over MgSO₄, filtered, and concentrated. The residue was purified by flash chromatography (silica gel, eluting with 25% EtOAc in hexanes) to give compound 291 (6.32 g, 83% yield) as a white waxy solid. m/z=209 (M+1).

Compound 292: A solution of compound 291 (6.32 g, 30.34 mmol), ethylene glycol (17 mL, 305 mmol) and p-toluenesulfonic acid monohydrate (0.58 g, 3.05 mmol) in benzene (100 mL) was refluxed with Dean-Stark conditions trap overnight. The mixture was cooled, and concentrated. The residue was partitioned between EtOAc (50 mL) and aq. sat. NaHCO₃ (50 mL). The organic extract was washed with brine (50 mL), dried over MgSO₄, filtered, and concentrated. The residue was purified by flash chromatography (silica gel, eluting with 20% EtOAc in hexanes) to give compound 292 (7.68 g, quantitative yield) as a yellow waxy solid. m/z=253 (M+1).

Compound 293: A mixture of compound 292 (1.39 g, 5.51 mmol) and 20 wt. % palladium hydroxide on carbon (0.30 g) in MeOH (60 mL) was hydrogenated (1 atm) at room temperature for 7 days. The catalyst was removed by filtration, and the filtrate was concentrated to give a mixture of ketal and ketone (1.42 g). The mixture was dissolved in benzene (100 mL), and treated with ethylene glycol (3.1 mL, 55.6 mmol) and p-toluenesulfonic acid monohydrate (0.11 g, 0.58 mmol). The mixture was refluxed with Dean-Stark trap for 4 h, and then cooled, and concentrated. The residue was partitioned between EtOAc (50 mL) and aq. sat. NaHCO₃ (50 mL). The organic extract was washed with brine (50 mL), dried over MgSO₄, filtered, concentrated. The residue was purified by flash chromatography (silica gel, eluting with 20% EtOAc in hexanes) to give compound 293 (0.92 g, 66% yield) as a gummy white solid. m/z=237 (M-OH).

Compound 294: Compound 293 (0.92 g, 3.62 mmol) in CH₂Cl₂ (50 mL) was treated with MgSO₄ (0.44 g, 3.66 mmol) and pyridinium dichromate (6.82 g, 18.13 mmol). After stirring the mixture at room temperature under nitrogen for 16 h, additional amount of pyridinium dichromate (3.41 g, 9.06 mmol) was added. The mixture was stirred for a second night and concentrated. The residue was diluted with Et₂O (50 mL), stirred at room temperature for 2 h, and filtered through a pad of Celite®. The filtrate was concentrated to give compound 294 (0.81 g, 88% yield) as an off-white gummy solid. m/z=253 (M+1).

Compound 295: A solution of compound 294 (0.61 g, 2.43 mmol), 2-fluorobenzaldehyde (0.33 g, 2.66 mmol) and potassium fluoride (40 wt. % on alumina, 0.53 g, 3.65 mmol) in EtOH (8 mL) was stirred at room temperature under nitrogen overnight. The mixture was filtered through a pad of Celite®, and the filtrate was concentrated. The residue was partitioned between aq. sat. KH₂PO₄ (100 mL) and EtOAc (100 mL). The organic extract was washed with brine (100 mL), dried over MgSO₄, filtered, and concentrated. The residue was purified by flash chromatography (silica gel, eluting with 5% EtOAc in CH₂Cl₂) to give compound 295 (0.59 g, 68% yield) as a light yellow waxy solid. m/z=359 (M+1).

Compound 296a: A mixture of compound 295 (0.59 g, 1.65 mmol), 4-quinolinecarboximidamide hydrochloride (0.51 g, 2.46 mmol) and potassium carbonate (0.68 g, 4.92 mmol) in EtOH (16 mL) was refluxed under nitrogen overnight. The mixture was cooled, and concentrated. The residue was partitioned between EtOAc (50 mL) and aq. sat. KH₂PO₄ (50 mL). The organic extract was washed with brine (50 mL), dried over MgSO₄, filtered and concentrated to give the dihydropyrimidine. The crude product was dissolved in CH₂Cl₂ (50 mL), and treated with manganese dioxide (88%, 0.81 g, 8.20 mmol). The mixture was stirred at room temperature overnight and filtered. The filtrate was concentrated, and the residue was purified by flash chromatography (silica gel, eluting with 50% EtOAc in hexanes) to give compound 296a (0.62 g, 74% yield) as a light yellow foamy solid. m/z=510 (M+1).

Compound 297a: A solution of compound 296a (0.62 g, 1.22 mmol) and aq. 3 N HCl (2.0 mL, 6.0 mmol) in MeOH (12 mL) was stirred at room temperature overnight, and concentrated. The residue was cooled, basified with aq. 10% $NH_4OH$, and extracted with $CHCl_3$ (50 mL). The organic extract was washed with brine (50 mL), dried over $MgSO_4$, filtered and concentrated to give compound 297a (0.60 g, quantitative yield) as an off-white foamy solid. m/z=466 (M+1).

Compound 298a: A solution of compound 297a (all from the last step) in ethyl formate (10 mL, 124 mmol) was treated with sodium methoxide (30 wt. % solution in methanol, 0.70 mL, 3.73 mmol) at room temperature under nitrogen. The mixture was stirred for 2 h, and then partitioned between EtOAc (50 mL) and aq. sat. $KH_2PO_4$ solution (50 mL). The organic extract was washed with brine (50 mL), dried over $MgSO_4$, filtered and concentrated to give compound 298a (0.58 g, 96% yield) as a tan foamy solid. m/z=494 (M+1).

Compound 299a: To a solution of compound 298a (0.58 g, 1.17 mmol) in EtOH (12 mL) was added acetic acid (0.70 mL, 12.23 mmol) and hydroxylamine hydrochloride (0.13 g, 1.87 mmol). The mixture was stirred at 60° C. under nitrogen for 2 h, at room temperature overnight, and concentrated. The residue was partitioned between aq. sat. $NaHCO_3$ (50 mL) and EtOAc (50 mL). The organic extract was washed with brine (50 mL), dried over $MgSO_4$, filtered and concentrated to give compound 299a (0.56 g, 97% yield) as light yellow foamy solid. m/z=491 (M+1).

Compound 300a: A mixture of compound 299a (0.56 g, 1.14 mmol) and potassium carbonate (0.79 g, 5.72 mmol) in MeOH (11 mL) was stirred at room temperature under nitrogen for 16 h. After filtration, the filtrate was concentrated, and the residue was carefully partitioned between aq. sat. $KH_2PO_4$ (50 mL) and EtOAc (50 mL). The organic extract was washed with brine (50 mL), dried over $MgSO_4$, filtered and concentrated. The residue was purified by flash chromatography (silica gel, eluting with 50% EtOAc in hexanes) to give compound 300a (0.41 g, 73% yield) as a light yellow foamy solid. m/z=491 (M+1).

T118: To a stirring solution at 0° C. under nitrogen of compound 300a (0.41 g, 0.84 mmol) in degassed DMF (5 mL) was added dropwise a solution of 1,3-dibromo-5,5-dimethylhydantoin (0.13 g, 0.45 mmol) in DMF (2 mL). After stirring the mixture for 30 min, pyridine (0.7 mL, 8.67 mmol) was added. The ice-bath was removed. The mixture was heated at 60° C. for 4 h, cooled, and concentrated. The residue was partitioned between aq. sat. $KH_2PO_4$ (50 mL) and EtOAc (50 mL). The organic extract was washed with brine (50 mL), dried over $MgSO_4$, filtered, and concentrated. The residue was purified by flash chromatography (silica gel, eluting with 50% EtOAc in hexanes) to give compound T118 (0.22 g, 54% yield) as a light yellow foamy solid. $^1$H NMR (400 MHz, $CDCl_3$) δ 9.08 (d, J=4.5 Hz, 1H), 8.93 (s, 1H), 8.69 (dd, J=0.8, 8.4 Hz, 1H), 8.21 (dd, J=0.4, 8.4 Hz, 1H), 8.01 (d, J=4.6 Hz, 1H), 7.77 (ddd, J=1.2, 6.6, 7.9 Hz, 1H), 7.63 (tdd, J=1.0, 6.8, 7.8 Hz, 1H), 7.50 (m, 2H), 7.33 (dt, J=1.0, 7.5 Hz, 1H), 7.24 (m, 1H), 2.91 (dd, J=4.7, 8.6 Hz, 2H), 2.39 (dd, J=2.9, 12.2 Hz, 1H), 2.02 (m, 2H), 1.65 (s, 3H), 1.34 (s, 3H), 1.28 (s, 3H); m/z=489 (M+1).

Compound 296b: A mixture of compound 295 (0.54 g, 1.51 mmol), 2-methyl-4-quinolinecarboximidamide hydrochloride (0.42 g, 1.89 mmol) and potassium carbonate (0.63 g, 4.56 mmol) in EtOH (5 mL) was refluxed under nitrogen overnight. The mixture was cooled and concentrated. The residue was partitioned between EtOAc (50 mL) and aq. sat. $KH_2PO_4$ (50 mL). The organic extract was washed with brine (50 mL), dried over $MgSO_4$, filtered and concentrated to give the dihydropyrimidine. The crude product was dissolved into $CH_2Cl_2$ (50 mL) and treated with manganese dioxide (88%, 0.75 g, 7.59 mmol). The mixture was stirred at room temperature overnight and filtered. The filtrate was concentrated, and the residue was purified by flash chromatography (silica gel, eluting with 50% EtOAc in hexanes) to give compound 296b (0.62 g, 78% yield) as a light yellow foamy solid. m/z=524 (M+1).

Compound 297b: A solution of compound 296b (0.24 g, 0.45 mmol) and aq. 3 N HCl (1.5 mL, 4.5 mmol) in MeOH (10 mL) was stirred at room temperature overnight and concentrated. The residue was cooled, basified with aq. 10% $NH_4OH$, and extracted with $CHCl_3$ (50 mL). The organic extract was washed with brine (50 mL), dried over $MgSO_4$, filtered and concentrated to give compound 297b (0.22 g, quantitative yield) as an off-white foamy solid. m/z=480 (M+1).

Compound 298b: A solution of compound 297b (0.22 g, 0.45 mmol) in ethyl formate (10 mL, 124 mmol) was treated with sodium methoxide (30 wt. % solution in methanol, 0.26 mL, 1.39 mmol) at room temperature under nitrogen. The mixture was stirred for 2 h and then partitioned between EtOAc (50 mL) and aq. sat. $KH_2PO_4$ (50 mL). The organic extract was washed with brine (50 mL), dried over $MgSO_4$, filtered and concentrated to give compound 298b (0.20 g, 86% yield) as a yellow foamy solid. m/z=508 (M+1).

Compound 299b: To a solution of compound 298b (0.20 g, 0.39 mmol) in EtOH (40 mL) was added acetic acid (0.23 mL, 4.02 mmol) and hydroxylamine hydrochloride (0.042 g, 0.60 mmol). The mixture was stirred at 60° C. under nitrogen for 2 h at room temperature overnight and concentrated. The residue was partitioned between aq. sat. $NaHCO_3$ (50 mL) and EtOAc (50 mL). The organic extract was washed with brine (50 mL), dried over $MgSO_4$, filtered and concentrated to give compound 299b (0.18 g, 91% yield) as a tan foamy solid. m/z=505 (M+1).

Compound 300b: A mixture of compound 299b (0.18 g, 0.36 mmol) and potassium carbonate (0.24 g, 1.74 mmol) in MeOH (10 mL) was stirred at room temperature under nitrogen for 16 h. After filtration, the filtrate was concentrated. The residue was carefully partitioned between aq. sat. $KH_2PO_4$ (50 mL) and EtOAc (50 mL). The organic extract was washed with brine (50 mL), dried over $MgSO_4$, filtered and concentrated. The residue was purified by flash chromatography (silica gel, eluting with 30% to 50% EtOAc in hexanes) to give compound 300b (0.088 g, 49% yield) as a light yellow foamy solid. m/z=505 (M+1).

T119: To a stirring solution at 0° C. under nitrogen of compound 300b (0.088 g, 0.17 mmol) in degassed DMF (5 mL) was added dropwise a solution of 1,3-dibromo-5,5-dimethylhydantoin (0.027 g, 0.094 mmol) in DMF (1 mL). After stirring the mixture for 30 min, pyridine (0.14 mL, 1.73 mmol) was added. The ice-bath was removed. The mixture was heated at 60° C. for 4 h, cooled and concentrated. The residue was partitioned between aq. sat. $KH_2PO_4$ (50 mL) and EtOAc (50 mL). The organic extract was washed with brine (50 mL), dried over $MgSO_4$, filtered, and concentrated. The residue was purified by flash chromatography (silica gel, eluting with 10% EtOAc in $CH_2Cl_2$) to give compound T119 (0.031 g, 36% yield) as a light yellow foamy solid. $^1$H NMR (400 MHz, $CDCl_3$) δ 8.93 (s, 1H), 8.57 (d, J=8.6 Hz, 1H), 8.12 (d, J=8.4 Hz, 1H), 7.86 (s, 1H), 7.73 (ddd, J=1.4, 6.8, 8.4 Hz, 1H), 7.51 (m, 3H), 7.33 (dt, J=1.1, 7.5 Hz, 1H), 7.25 (m, 1H), 2.90 (dd, J=4.6, 8.4 Hz, 2H), 2.85 (s, 3H), 2.39 (dd, J=2.8, 12.1 Hz, 1H), 2.03 (m, 2H), 1.65 (s, 3H), 1.34 (s, 3H), 1.29 (s, 3H); m/z=503 (M+1).

Compound 301: A mixture of compound 260b (0.90 g, 1.80 mmol) and selenium dioxide (0.40 g, 3.60 mmol) in 1,4-dioxane (18 mL) was heated at 100° C. under nitrogen for 1 h. The mixture was cooled to room temperature and filtered through a pad of Celite®. The filtrate was concentrated to give compound 301 (0.92 g, 99% yield) as an off-white solid. m/z=514 (M+1).

Compound 302: A solution of compound 301 (0.92 g, 1.79 mmol) in EtOH (18 mL) was treated with NaBH$_4$ (0.068 g, 1.79 mmol) at room temperature. After stirring under nitrogen for 1 h, the mixture was concentrated, and the residue was partitioned between aq. sat. KH$_2$PO$_4$ (50 mL) and EtOAc (50 mL). The organic extract was washed with brine (50 mL), dried over MgSO$_4$, filtered, and concentrated to give compound 302 (0.92 g, quantitative yield) as a tan foamy solid. m/z=516 (M+1).

Compound 303: To a solution of compound 302 (0.92 g, 1.78 mmol) in CH$_2$Cl$_2$ (20 mL) was added a solution of diethylaminosulfur trifluoride (0.58 g, 3.60 mmol) in CH$_2$Cl$_2$ (2 mL) at 0° C. The resultant blue solution was stirred at 0° C. for 2 h and then partitioned between aq. sat. NaHCO$_3$ (50 mL) and EtOAc (50 mL). The organic extract was washed with brine (50 mL), dried over MgSO$_4$, filtered, and concentrated. The residue was purified by flash chromatography (silica gel, eluting with 20% EtOAc in hexanes) to give compound 303 (0.47 g, 51% yield) as a light yellow foamy solid. m/z=518 (M+1).

Compound 304: A solution of compound 303 (0.47 g, 0.91 mmol) and aq. 3 N HCl (1.5 mL, 4.5 mmol) in MeOH (45 mL) was stirred at room temperature overnight and concentrated. The residue was cooled, basified with aq. 10% NH$_4$OH, and extracted with CHCl$_3$ (50 mL). The organic extract was washed with brine (50 mL), dried over MgSO$_4$, filtered and concentrated to give compound 304 (0.43 g, quantitative yield) as a tan foamy solid. m/z=474 (M+1).

Compound 305: A solution of compound 304 (0.43 g, 0.91 mmol) in ethyl formate (10 mL, 124 mmol) was treated with sodium methoxide (30 wt. % solution in MeOH, 0.51 mL, 2.72 mmol) at room temperature. The mixture was stirred for 2 h and then partitioned between EtOAc (50 mL) and aq. sat. KH$_2$PO$_4$ (50 mL). The organic extract was washed with brine (50 mL), dried over MgSO$_4$, filtered and concentrated to give compound 305 (0.47 g) as a dark yellow oil. m/z=502 (M+1).

Compound 306: A solution of compound 305 (all from the last step) and acetic acid (0.51 mL, 8.92 mmol) in EtOH (25 mL) was treated with hydroxylamine hydrochloride (0.10 g, 1.44 mmol). The mixture was stirred at 60° C. under nitrogen for 2 h at room temperature overnight and concentrated. The residue was partitioned between aq. sat. NaHCO$_3$ (50 mL) and EtOAc (50 mL). The organic extract was washed with brine (50 mL), dried over MgSO$_4$, filtered, and concentrated to give compound 306 (0.40 g, 88% yield) as an orange-brown foamy solid. m/z=499 (M+1).

Compound 307: A mixture of compound 306 (0.40 g, 0.80 mmol) and potassium carbonate (0.56 g, 4.05 mmol) in MeOH (8 mL) was stirred at room temperature under nitrogen for 16 h. After filtration, the filtrate was concentrated. The residue was carefully partitioned between aq. sat. KH$_2$PO$_4$ (50 mL) and EtOAc (50 mL). The organic extract was washed with brine (50 mL), dried over MgSO$_4$, filtered, and concentrated. The residue was purified by flash chromatography (silica gel, eluting with 25% EtOAc in hexanes) to give compound 307 (0.23 g, 58% yield) as light yellow foamy solid. m/z=499 (M+1).

T120: To a stirring solution of compound 307 (0.23 g, 0.46 mmol) in degassed DMF (5 mL) was added dropwise a solution of 1,3-dibromo-5,5-dimethylhydantoin (0.071 g, 0.25 mmol) in DMF (2 mL) at 0° C. under nitrogen. After stirring the mixture for 30 min, pyridine (0.37 mL, 4.59 mmol) was added. The ice-bath was removed. The mixture was heated at 60° C. for 4 h, cooled, and concentrated. The residue was partitioned between aq. sat. KH$_2$PO$_4$ (50 mL) and EtOAc (50 mL). The organic extract was washed with brine (50 mL), dried over MgSO$_4$, filtered, and concentrated. The residue was purified by flash chromatography (silica gel, eluting with 30% EtOAc in hexanes) to give compound T120 (0.12 g, 52% yield) as a light yellow solid. $^1$H NMR (400 MHz, CDCl$_3$) δ 8.87 (s, 1H), 8.74 (dd, J=0.8, 8.6 Hz, 1H), 8.16 (d, J=8.4 Hz, 1H), 8.13 (d, J=1.1 Hz, 1H), 7.78 (ddd, J=1.4, 6.8, 8.4 Hz, 1H), 7.62 (ddd, J=1.3, 6.8, 8.4 Hz, 1H), 5.73 (d, J=46.8 Hz, 2H), 5.63 (tt, J=2.7, 6.1 Hz, 1H), 2.91 (dd, J=6.3, 18.9 Hz, 1H), 2.66 (m, 2H), 2.18 (m, 2H), 2.03 (m, 2H), 1.86 (m, 5H), 1.68 (m, 2H), 1.52 (s, 3H), 1.34 (d, J=6.7 Hz, 3H); m/z=497 (M+1).

Compound 308: Compound 9 (1.25 g, 4.22 mmol) was taken up in EtOH (15 mL). 8-fluoroquinoline-4-carboximidamide hydrochloride (0.95 g, 4.21 mmol) and potassium carbonate (1.2 g, 8.68 mmol) were added. The reaction mixture was stirred at 40° C. for 2 days, cooled and concentrated. The residue was mixed with water (20 mL) and EtOAc (100 mL) and heated at 65° C. for 30 min. After cooled to room temperature, the organic extract was dried over MgSO$_4$, filtered and concentrated. The residue was purified by flash chromatography (silica gel, eluting with 0% to 100% EtOAc in hexanes) to give compound 308 (1.6 g, 87% yield) as an off-white solid. m/z=436 (M+1).

Compound 309: To a solution of compound 308 (1.25 g, 2.87 mmol) in toluene (8 mL) was added phosphorus (V) oxychloride (4.4 g, 28.70 mmol) at room temperature. The mixture was heated in Biotage® Initiator™ microwave synthesizer at 100° C. for 60 min, cooled to room temperature, and poured into ice. The mixture was stirred for 30 min and extracted with EtOAc. The organic extract was washed with aq. NaHCO$_3$, dried over MgSO$_4$, filtered and concentrated to give a mixture of ketal and ketone. The crude product was mixed in benzene (100 mL) and treated with ethylene glycol (1.8 g, 29.00 mmol) and p-toluenesulfonic acid monohydrate (100 mg, 0.52 mmol). The mixture was refluxed for 16 h with a Dean-Stark trap, cooled to room temperature, and washed with water. The organic extract was dried over MgSO$_4$, filtered and concentrated. The residue was purified by flash chromatography (silica gel, eluting with 0% to 35% EtOAc in hexanes) to give compound 309 (950 mg, 73% yield) as a light color solid. m/z=454 (M+1).

Compound 310: Compound 309 (950 mg, 2.09 mmol) was taken up in THF (10 mL). Cyclopentanol (1 g, 11.61 mmol) and sodium hydride (60% dispersion in mineral oil (400 mg, 10 mmol) were added. The mixture was stirred at 60° C. for 16 h, cooled, and concentrated. The residue was neutralized by the addition of aq. sat. KH$_2$PO$_4$ and extracted with EtOAc. The organic extract was washed with brine, dried over MgSO$_4$, filtered and concentrated. The residue was purified by flash chromatography (silica gel, eluting with 0% to 35% EtOAc in hexanes) to give compound 310 (420 mg, 40% yield) as a light color solid. m/z=504 (M+1).

Compound 311: A mixture of compound 310 (420 mg, 0.83 mmol) was taken up in THF (10 mL), and aq. 3 N HCl (5 mL, 15 mmol) was added. The mixture was stirred overnight at room temperature and concentrated. The residue was neutralized with aq. sat. NaHCO$_3$ and extracted with EtOAc. The organic extract was washed with water, dried over MgSO$_4$, filtered and concentrated to give compound 311 (385 mg, quantitative yield) as a foam. m/z=460 (M+1).

Compound 312: To a mixture of compound 311 (385 mg, 0.83 mmol) in ethyl formate (15 mL, 186.5 mmol) was added sodium methoxide (30 wt. % in methanol, 160 mg, 0.89 mmol). The mixture was stirred at room temperature for 2 h, neutralized with aq. KH$_2$PO$_4$, and extracted with EtOAc. The organic extract was dried over MgSO$_4$, filtered and concentrated to give compound 312 (405 mg, quantitative yield) as a foam. m/z=488 (M+1).

Compound 313: Compound 312 (405 mg, 0.83 mmol) was dissolved in EtOH (15 mL). Hydroxylamine hydrochloride (570 mg, 8.20 mmol) and AcOH (500 mg, 8.32 mmol) were added. The reaction mixture was stirred overnight at 50° C., cooled to room temperature, and concentrated. The residue was taken up in EtOAc and washed with aq. NaHCO$_3$. The organic extract was dried over MgSO$_4$, filtered and concentrated to give compound 313 (350 mg, 87% yield) as a foam. m/z=485 (M+1).

Compound 314: Compound 313 (350 mg, 0.72 mmol) was dissolved in MeOH (10 mL). Potassium carbonate (500 mg, 3.62 mmol) was added. After stirring at room temperature overnight, the reaction mixture was neutralized by the addition of aq. sat. KH$_2$PO$_4$ and extracted with EtOAc. The organic extract was washed with brine, dried over MgSO$_4$, filtered and concentrated. The residue was purified by flash chromatography (silica gel, eluting with 0% to 35% EtOAc in hexanes) to give compound 314 (250 mg, 71% yield) as a foam. m/z=485 (M+1).

T121: Compound 314 (250 mg, 0.51 mmol) was dissolved in dry DMF (2 mL), and the solution was cooled to 0° C. Bromine (91 mg, 0.57 mmol) in CH$_2$Cl$_2$ (1 mL) was added. The reaction was stirred at 0° C. for 2 h, and pyridine (2 mL, 24.8 mmol) was added. The ice-bath was removed. The reaction mixture heated at 60° C. for 4 h, cooled and concentrated. The residue was purified by flash chromatography (silica gel, eluting with 0% to 35% EtOAc in hexanes) to give compound T121 (155 mg, 62% yield) as a foam. $^1$H NMR (400 MHz, CDCl$_3$) δ 9.13 (d, J=4.4 Hz, 1H), 8.86 (s, 1H), 8.61 (td, J=1.1, 8.6 Hz, 1H), 8.06 (d, J=4.4 Hz, 1H), 7.56 (ddd, J=5.3, 7.7, 8.6 Hz, 1H), 7.47 (ddd, J=1.3, 7.7, 10.3 Hz, 1H), 5.61 (tt, J=2.7, 6.1 Hz, 1H), 2.91 (ddd, J=1.1, 6.8, 18.8 Hz, 1H), 2.66 (m, 2H), 2.18 (m, 2H), 1.83 (m, 9H), 1.51 (s, 3H), 1.34 (d, J=6.8 Hz, 3H); m/z=483 (M+1).

Compound 315: A mixture of compound 296b (0.36 g, 0.69 mmol) and selenium dioxide (0.15 g, 1.35 mmol) in 1,4-dioxane (10 mL) was heated at 100° C. under nitrogen for 15 min. The mixture was cooled to room temperature and filtered through a pad of Celite®. The filtrate was concentrated, and the residue was purified by flash chromatography (silica gel, eluting with 25% EtOAc in hexanes) to give compound 315 (0.32 g, 87% yield) as an off-white foamy solid. m/z=538 (M+1).

Compound 316: A solution of compound 315 (0.32 g, 0.60 mmol) in EtOH (50 mL) was treated with NaBH$_4$ (0.023 g, 0.61 mmol) at room temperature. After stirring under nitrogen for 1 h, the mixture was cooled to 0° C., quenched with aq. sat. KH$_2$PO$_4$ (50 mL), and concentrated. The residue was extracted with EtOAc (50 mL). The organic extract was washed with brine (50 mL), dried over MgSO$_4$, filtered and concentrated to give compound 316 (0.28 g, 87% yield) as a light yellow foamy solid. m/z=540 (M+1).

Compound 317: To a solution of compound 316 (0.28 g, 0.52 mmol) in CH$_2$Cl$_2$ (5 mL) was added a solution of diethylaminosulfur trifluoride (0.17 g, 1.05 mmol) in CH$_2$Cl$_2$ (1 mL) at 0° C. The resultant blue solution was stirred at 0° C. for 2 h and partitioned between aq. sat. NaHCO$_3$ (50 mL) and EtOAc (50 mL). The organic extract was washed with brine (50 mL), dried over MgSO$_4$, filtered, and concentrated. The residue was purified by flash chromatography (silica gel, eluting with 30% EtOAc in hexanes) to give compound 317 (0.16 g, 57% yield) as an off-white foamy solid. m/z=542 (M+1).

Compound 318: A solution of compound 317 (0.16 g, 0.30 mmol) and aq. 3 N HCl (1 mL, 3 mmol) in MeOH (10 mL) was stirred at room temperature overnight and concentrated. The residue was cooled, basified with aq. 10% NH$_4$OH, and extracted with CHCl$_3$ (50 mL). The organic extract was washed with brine (50 mL), dried over MgSO$_4$, filtered and concentrated to give compound 318 (0.15 g, quantitative yield) as a yellow oil. m/z=498 (M+1).

Compound 319: A solution of compound 318 (0.15 g, 0.30 mmol) in ethyl formate (10 mL, 124 mmol) was treated with sodium methoxide (30 wt. % solution in MeOH, 0.16 mL, 0.86 mmol) at room temperature. After stirring for 2 h, the mixture was partitioned between EtOAc (50 mL) and aq. sat. KH$_2$PO$_4$ (50 mL). The organic extract was washed with brine (50 mL), dried over MgSO$_4$, filtered and concentrated to give compound 319 (0.14 g, 88% yield) as an orange foamy solid. m/z=526 (M+1).

Compound 320: A solution of compound 319 (0.14 g, 0.26 mmol) and acetic acid (0.15 mL, 2.62 mmol) in EtOH (20 mL) was treated with hydroxylamine hydrochloride (0.027 g, 0.39 mmol). The mixture was stirred at 60° C. under nitrogen for 2 h at room temperature overnight and concentrated. The residue was partitioned between aq. sat. NaHCO$_3$ (50 mL) and EtOAc (50 mL). The organic extract was washed with brine (50 mL), dried over MgSO$_4$, filtered, and concentrated to give compound 320 (0.13 g, 93% yield) as an orange foamy solid. m/z=523 (M+1).

Compound 321: A mixture of compound 320 (0.13 g, 0.25 mmol) and potassium carbonate (0.17 g, 1.23 mmol) in MeOH (5 mL) was stirred at room temperature under nitrogen for 16 h. After filtration, the filtrate was concentrated. The residue was carefully partitioned between aq. sat. KH$_2$PO$_4$ (50 mL) and EtOAc (50 mL). The organic extract was washed with brine (50 mL), dried over MgSO$_4$, filtered and concentrated to give compound 321 (0.11 g, 85% yield) as light yellow foamy solid. m/z=523 (M+1).

T122: To a stirring solution of compound 321 (0.11 g, 0.21 mmol) in degassed DMF (5 mL) was added dropwise a solution of 1,3-dibromo-5,5-dimethylhydantoin (0.034 g, 0.12 mmol) in DMF (1 mL) at 0° C. under nitrogen. After stirring the mixture for 30 min, pyridine (0.17 mL, 2.11 mmol) was added. The ice-bath was removed. The mixture was heated at 60° C. for 4 h, cooled, and concentrated. The residue was partitioned between aq. sat. KH$_2$PO$_4$ (50 mL) and EtOAc (50 mL). The organic extract was washed with brine (50 mL), dried over MgSO$_4$, filtered, and concentrated. The residue was purified by flash chromatography (silica gel, eluting with 25% EtOAc in hexanes) to give T122 (0.057 g, 52% yield) as a light yellow foamy solid. $^1$H NMR (400 MHz, CDCl$_3$) δ 8.92 (s, 1H), 8.63 (dd, J=0.8, 8.4 Hz, 1H), 8.16 (m, 2H), 7.79 (ddd, J=1.4, 6.8, 8.4 Hz, 1H), 7.64 (ddd, J=1.6, 6.8, 8.3 Hz, 1H), 7.50 (m, 2H), 7.33 (dt, J=1.1, 7.5 Hz, 1H), 7.23 (m, 1H), 5.75 (d, J=46.8 Hz, 2H), 2.92 (dd, J=4.7, 8.5 Hz, 2H), 2.40 (dd, J=2.8, 12.1 Hz, 1H), 2.01 (m, 2H), 1.66 (s, 3H), 1.34 (s, 3H), 1.29 (s, 3H); m/z=521 (M+1).

Compound 322: A solution of compound 277 (530 mg, 1.01 mmol) in anhydrous THF (15 ml) was cooled to 0° C. under nitrogen. Methylmagnesium bromide (3.0 M solution in Et$_2$O, 0.67 mL, 2.01 mmol) was added dropwise. The reaction mixture was stirred at room temperature for 4 h and poured into aq. sat. NH$_4$Cl. The aqueous mixture was extracted with EtOAc (2×50 mL) and the combined organic extracts were dried over MgSO$_4$, filtered, and concentrated. The residue was purified by flash chromatography (silica gel, eluting with 50% EtOAc in hexanes) to give compound 322 (432 mg, 79% yield) as a yellow glass. m/z=540 (M+1).

Compound 323: A solution of compound 322 (432 mg, 0.80 mmol) in CH$_2$Cl$_2$ (20 mL) was treated with manganese dioxide (88%, 395 mg, 4.00 mmol) at room temperature. After stirring under nitrogen for 24 h, the mixture was filtered through a pad of Celite® and the filtrate was concentrated. The residue was purified by flash chromatography (silica gel, eluting with 20% EtOAc in hexanes) to give compound 323 (388 mg, 90% yield) as a clear, viscous oil. m/z=538 (M+1).

Compound 324: To suspension of methyltriphenylphosphonium bromide (1.38 g, 3.86 mmol) in anhydrous THF (30 mL) under nitrogen was added portionwise with stirring potassium t-butoxide (434 mg, 3.87 mmol) at 0° C. After addition was complete, the mixture was stirred at room temperature for 2 h and cooled to 0° C. again. A solution of compound 323 (520 mg, 0.967 mmol) in anhydrous THF (10 mL) was added dropwise and the reaction mixture was stirred at room temperature for 21 h. The mixture was diluted with water and extracted with EtOAc (2×60 mL). The combined organic extracts were washed with brine, dried over MgSO$_4$, filtered, and concentrated. The residue was purified by flash chromatography (silica gel, eluting with 10% EtOAc in hexanes) to give compound 324 (478 mg, 92% yield) as a viscous oil. m/z=536 (M+1).

Compound 325: A solution of compound 324 (477 mg, 0.890 mmol) in MeOH (15 mL) and EtOAc (15 mL) was treated with 10% Pd/C (50 mg) and the reaction mixture was stirred under 1 atm hydrogen at room temperature for 22 h. The catalyst was removed by filtered through a pad of Celite® and the filtrate was concentrated. The residue was purified by flash chromatography (silica gel, eluting with 20% EtOAc in hexanes) to give compound 325 (333 mg, 70% yield) as a white glass. m/z=538 (M+1).

Compound 326: A solution of compound 325 (403 mg, 0.749 mmol) in THF (25 mL) was treated with aq. 3 N HCl (2.50 mL, 7.50 mmol) and the reaction mixture was stirred at room temperature for 16 h. The solvent was removed in vacuo and the residue was cooled to 0° C., neutralized cautiously with aq. sat. NaHCO$_3$, and extracted with EtOAc. The organic extract was washed with water, brine, dried over MgSO$_4$, filtered and concentrated to give compound 326 (370 mg, quantitative yield) as a clear, viscous oil. m/z=494 (M+1).

Compound 327: A solution of compound 326 (390 g, 0.790 mmol) in ethyl formate (12 mL, 149 mmol) was cooled to 0° C. and treated dropwise with sodium methoxide (5.4 M solution in MeOH, 0.73 ml, 3.94 mmol). The cold bath was removed and the reaction mixture was stirred at room temperature for 18 h. The solvent was removed in vacuo and the residue was partitioned between EtOAc and aq. sat. KH$_2$PO$_4$. The organic extract was washed with brine, dried over MgSO$_4$, filtered and concentrated to give compound 327 (384 mg, 93% yield) as a yellow glass. m/z=522 (M+1).

Compound 328: A solution of compound 327 (382 mg, 0.732 mmol) in glacial acetic acid (0.43 mL, 7.52 mmol) and EtOH (7 mL) was treated with hydroxylamine hydrochloride (76 mg, 1.09 mmol). The reaction mixture was stirred under nitrogen at 60° C. for 4 h and at room temperature for 20 h. The solvent was removed in vacuo and the residue was cautiously partitioned between aq. 10% NH$_4$OH and EtOAc. The organic phase was washed with brine, dried over MgSO$_4$, filtered and concentrated to give a pale yellow glass (351 mg), which was trituration with MeOH to give compound 328 (237 mg, 62% yield) as a light yellow crystalline solid. m/z=519 (M+1).

Compound 329: A suspension of compound 328 (237 mg, 0.456 mmol) and potassium carbonate (187 mg, 1.35 mmol) in MeOH (15 mL) was stirred under nitrogen at room temperature for 19 h and heated at 50° C. for 1 h. The reaction mixture was concentrated and the residue was partitioned between water and Et$_2$O. The aqueous phase was cooled in an ice-water bath and neutralized with aq. sat. KH$_2$PO$_4$. The neutralized aqueous mixture was extracted with EtOAc (2×30 mL) and the combined organic extracts were washed brine, dried over MgSO$_4$, filtered and concentrated. The residue was purified by flash chromatography (silica gel, eluting with 40% EtOAc in hexanes) to give compound 329 (176 mg, 74% yield) as a white glass. m/z=519 (M+1).

T123: A solution of compound 329 (176 mg, 0.339 mmol) in anhydrous DMF (4 mL) was cooled to 0° C. under nitrogen, and treated dropwise with a solution of 1,3-dibromo-5,5-dimethylhydantoin (53 mg, 0.185 mmol) in anhydrous DMF (1 mL). After stirring at 0° C. for 45 min, anhydrous pyridine (0.27 mL, 3.39 mmol) was added. The cold bath was removed, and the reaction mixture was heated at 60° C. for 4 h. Upon cooling to room temperature, the reaction mixture was partitioned between EtOAc and aq. sat. KH$_2$PO$_4$. The organic phase was washed with brine, dried over MgSO$_4$, filtered and concentrated. The residue was purified by flash chromatography (silica gel, eluting with 40% EtOAc in hexanes) to give compound T123 (126 mg, 72% yield) as an off-white glass. $^1$H NMR (400 MHz, CDCl$_3$) δ 8.93 (s, 1H), 8.51 (dd, J=1.3, 8.6 Hz, 1H), 8.15 (dd, J=0.8, 8.4 Hz, 1H), 7.86 (s, 1H), 7.72 (ddd, J=1.4, 6.8, 8.4 Hz, 1H), 7.52 (m, 3H), 7.33 (dt, J=1.1, 7.6 Hz, 1H), 7.23 (m, 1H), 3.36 (hept, J=7.0 Hz, 1H), 2.89 (m, 2H), 2.64 (qd, J=6.7, 13.4 Hz, 1H), 2.31 (dt, J=2.8, 12.8 Hz, 1H), 2.18 (m, 1H), 1.86 (m, 1H), 1.60 (s, 3H), 1.46 (d, J=6.9 Hz, 6H), 1.34 (d, J=6.7 Hz, 3H); m/z=517 (M+1).

Compound 330: A solution of compound 90 (605 mg, 1.34 mmol) and 2-iodoxybenzoic acid (1.50 g, 5.36 mmol) in DMSO (10 mL) was heated at 65° C. under nitrogen for 26 h. The reaction mixture was diluted with water (200 mL) and extracted with EtOAc (3×50 mL). The combined organic extracts were washed with brine, dried over MgSO$_4$, filtered, and concentrated. The residue was purified by flash chromatography (silica gel, eluting with 50% EtOAc in hexanes) to give compound 330 (437 mg, 73% yield) as a clear glass. m/z=450 (M+1).

Compound 331: To a stirring suspension of potassium hydride (30% dispersion in mineral oil, 280 mg, 2.09 mmol) in anhydrous THF (10 mL) under nitrogen at 0° C. was added dropwise a solution of compound 330 (316 mg, 0.703 mmol) in anhydrous THF (10 mL). After stirring the mixture for 30 min at 0° C., allyl bromide (0.61 mL, 7.05 mmol) was added. The mixture was stirred at 0° C. for another 3 h, quenched with aq. sat. NH₄Cl and extracted with EtOAc. The organic extract was dried over MgSO₄, filtered, and concentrated. The residue was purified by flash chromatography (silica gel, eluting with 30% EtOAc in hexanes) to give compound 331 (152 mg, 44% yield) as a light yellow glass. m/z=490 (M+1).

Compound 332: A mixture of compound 331 (152 mg, 0.310 mmol) and 10% palladium on carbon (~50 mg) in MeOH (15 mL) was stirred under 1 atm hydrogen at room temperature for 24 h. The catalyst was filtered off through a plug of Celite®, and the filtrate was concentrated. The residue was purified by flash chromatography (silica gel, eluting with 30% EtOAc in hexanes) to give compound 332 (116 mg, 76% yield) as a clear glass. m/z=494 (M+1).

Compound 333: A solution of compound 332 (115 mg, 0.232 mmol) in ethyl formate (10 mL, 124 mmol) was cooled to 0° C. and treated dropwise with sodium methoxide (5.4 M solution in MeOH, 0.21 mL, 1.13 mmol). The cold bath was removed and the reaction mixture was stirred at room temperature for 16 h. The solvent was removed in vacuo and the residue was partitioned between EtOAc and aq. sat. KH₂PO₄. The organic phase was washed with brine, dried over MgSO₄, filtered and concentrated to give compound 333 (114 mg, 94% yield) as an off-white glass which was used in the subsequent step without further purification. m/z=522 (M+1).

Compound 334: A solution of compound 333 (113 mg, 0.218 mmol) in glacial acetic acid (0.13 mL, 2.27 mmol) and EtOH (10 mL) was treated with hydroxylamine hydrochloride (23 mg, 0.331 mmol). The reaction mixture was stirred under nitrogen at 60° C. for 4 h and at room temperature for 24 h. The solvent was removed in vacuo and the residue was cautiously partitioned between aq. 10% NH₄OH and EtOAc. The organic phase was washed with brine, dried over MgSO₄, filtered and concentrated to give compound 334 (101 mg, 90% yield) as a glass, which was used in the subsequent step without further purification. m/z=519 (M+1).

Compound 335: A mixture of compound 334 (100 mg, 0.192 mmol) and potassium carbonate (53 mg, 0.383 mmol) in MeOH (10 mL) was stirred under nitrogen at room temperature for 17 h followed by heated at 50° C. for 4 h. The reaction mixture was concentrated and the residue was partitioned between water and Et₂O. The aqueous phase was cooled in an ice-water bath, acidified with aq. sat. KH₂PO₄, and extracted with EtOAc (2×25 mL). The combined organic extracts were washed with brine, dried over MgSO₄, filtered and concentrated. The residue was purified by flash chromatography (silica gel, eluting with 40% EtOAc in hexanes) to give compound 335 (54 mg, 54% yield) as a white glass. m/z=519 (M+1).

T124: A solution of compound 335 (53 mg, 0.102 mmol) in anhydrous DMF (2 mL) was cooled to 0° C. under nitrogen and treated dropwise with a solution of 1,3-dibromo-5,5-dimethylhydantoin (16 mg, 0.056 mmol) in anhydrous DMF (1 mL). After stirring the mixture at 0° C. for 30 min, anhydrous pyridine (0.082 mL, 1.02 mmol) was added. The cold bath was removed, and the reaction mixture was heated at 60° C. for 4 h. Upon cooling to room temperature, the reaction mixture was partitioned between EtOAc and aq. sat. KH₂PO₄. The organic phase was washed with brine, dried over MgSO₄, filtered and concentrated. The residue was purified by flash chromatography (silica gel, eluting with 40% EtOAc in hexanes) to give compound T124 (41 mg, 78% yield) as an off-white glass. ¹H NMR (400 MHz, CDCl₃) δ 9.09 (dd, J=0.9, 4.5 Hz, 1H), 8.90 (s, 1H), 8.70 (d, J=8.6 Hz, 1H), 8.22 (d, J=8.4 Hz, 1H), 8.01 (d, J=4.4 Hz, 1H), 7.78 (ddd, J=1.2, 7.0, 8.4 Hz, 1H), 7.64 (dt, J=1.2, 7.5 Hz, 1H), 7.50 (m, 2H), 7.33 (tt, J=1.0, 7.6 Hz, 1H), 7.24 (m, 1H), 2.90 (t, J=6.6 Hz, 2H), 2.61 (m, 1H), 1.94 (m, 3H), 1.65 (s, 3H), 1.33 (m, 2H), 1.26 (s, 3H), 1.08 (m, 1H), 0.89 (t, J=7.1 Hz, 3H); m/z=517 (M+1).

Compound 336: Compound 146 (435 mg, 0.98 mmol) was dissolved in ethyl formate (2.4 mL, 29.84 mmol) and cooled to 0° C. Sodium methoxide (25 wt. % solution in MeOH, 3.4 mL, 14.86 mmol) was added. The mixture was stirred at room temperature for 4 h; diluted with water; adjusted to pH~7 using aq. 1 N HCl; and extracted with EtOAc. The organic extract was washed with water and brine, dried with Na₂SO₄, filtered and concentrated to give compound 336 (460 mg, 99% yield) as a pinkish foam, which was used in the subsequent step without further purification. m/z=470.2 (M+1).

Compound 337: To a solution of compound 336 (200 mg, 0.43 mmol) and N-methylaniline (0.102 mL, 0.94 mmol) in CH₂Cl₂ (2 mL) at room temperature was added magnesium sulfate (205 mg, 1.70 mmol). The reaction mixture was stirred at room temperature for 1 h, treated with p-toluenesulfonic acid monohydrate (8.1 mg, 0.042 mmol), and stirred at room temperature for another 48 h. The mixture was filtered through a plug of Celite® and eluted with CH₂Cl₂. The filtrate was concentrated, and the residue was purified by flash chromatography (silica gel, eluting with 0% to 50% EtOAc in CH₂Cl₂) to give compound 337 (120 mg, 50% yield) as a pale yellow foam. m/z=559.3 (M+1).

Compound 338: To a solution of potassium tert-butoxide (71.7 mg, 0.64 mmol) in THF (1 mL) under argon was added a solution of compound 337 (119 mg, 0.21 mmol) in THF (1 mL) at 0° C. The mixture was stirred at 0° C. for 10 min and treated with iodomethane (0.04 mL, 0.64 mmol). After stirring at 0° C. for another 2 h, the reaction mixture was quenched by adding aq. sat. NH₄Cl (3 mL) and was extracted with EtOAc. The organic extract was dried over Na₂SO₄, filtered and concentrated. The residue was purified by flash chromatography (silica gel, eluting with 0% to 80% EtOAc in hexanes) to give compound 338 (93 mg, 76% yield) as a pale yellow foam. m/z=573.2 (M+1).

Compound 339: To a solution of compound 338 (90 mg, 0.157 mmol) in EtOH (1.6 mL) was added 1 N aq. HCl (0.32 mL, 0.32 mmol) and hydroxylamine hydrochloride (16.4 mg, 0.236 mmol) sequentially at room temperature. The mixture was heated at 55° C. for 3 h and concentrated. The residue was diluted with aq. sat. NaHCO₃ and extracted twice with EtOAc. The combined organic extracts were dried with Na₂SO₄, filtered and concentrated. The residue was purified by flash chromatography (silica gel, eluting with 0% to 50% EtOAc in hexanes) to give compound 339 (43 mg, 57% yield) as a white foam. m/z=481.2 (M+1).

Compound 340: To a solution of compound 339 (40 mg, 0.083 mmol) in MeOH (0.8 mL) was added sodium methoxide (25 wt. % solution in MeOH, 0.03 mL, 0.13 mmol). The reaction mixture was stirred at 55° C. for 2 h, cooled to 0° C., and then neutralized by adding aq. 10% NaH₂PO₄. The mixture was diluted with water and extracted twice with EtOAc. The combined organic extracts were dried with Na₂SO₄, filtered and concentrated to give compound 340 (38 mg, 95% yield) as a clear film, which was used in the subsequent step without further purification. m/z=481.2 (M+1).

T125: Compound 340 (38 mg, 0.079 mmol) was dissolved in dry DMF (0.5 mL), and the solution was cooled to 0° C. 1,3-dibromo-5,5-dimethylhydantoin (11.3 mg, 0.040 mmol) in DMF (0.3 mL) was added. The reaction mixture was stirred at 0° C. for 2 h, and pyridine (0.019 mL, 0.24 mmol) was added. The mixture was heated at 55° C. for 4 h and cooled to room temperature. EtOAc was added. The mixture was washed with water. The organic extract was dried with Na$_2$SO$_4$, filtered and concentrated. The residual pyridine was removed by azeotropic evaporation with toluene (10 mL). The residue was purified by flash chromatography (silica gel, eluting with 0% to 30% acetone in hexanes) to give compound T125 (24 mg, 63% yield) as a white solid. $^1$H NMR (400 MHz, CDCl$_3$) δ 9.01 (s, 1H), 8.60 (dd, J=0.8, 5.2 Hz, 1H), 8.19 (s, 1H), 8.06 (dd, J=1.6, 5.2 Hz, 1H), 7.52 (m, 1H), 7.45 (dt, J=1.9, 7.4 Hz, 1H), 7.34 (dt, J=1.1, 7.5 Hz, 1H), 7.22 (ddd, J=1.0, 8.4, 9.5 Hz, 1H), 2.84 (m, 2H), 2.34 (dd, J=2.7, 12.3 Hz, 1H), 2.21 (tt, J=4.9, 8.1 Hz, 1H), 1.97 (m, 2H), 1.60 (s, 3H), 1.32 (s, 3H), 1.27 (s, 3H), 1.12 (m, 2H), 1.04 (m, 2H); m/z=479.2 (M+1).

Compound 341: To a mixture of compound 90 (500 mg, 1.11 mmol) and ethyl formate (2.65 mL, 32.95 mmol) was added sodium methoxide (25 wt. % solution in MeOH, 2.55 mL, 11.14 mmol) under nitrogen at 0° C. The mixture was stirred at room temperature for 1 h and cooled to 0° C. Aq. 6 N HCl (1.86 mL, 11.10 mmol) and EtOAc were added. The mixture was washed with aq. 10% NaH$_2$PO$_4$. The organic extract was dried with Na$_2$SO$_4$, filtered and concentrated to give compound 341 (550 mg, quantitative yield) as a light yellow foam, which was used in the subsequent step without further purification. m/z=480.2 (M+1).

Compound 342: A mixture of compound 341 (550 mg, 1.11 mmol) and N-methylaniline (0.126 mL, 1.16 mmol) in benzene was heated at reflux with Dean-Stark trap for 16 h. The solvent was removed by distillation. The resultant crude oil was heated at 110° C. for another 3 h; cooled to room temperature; and purified by flash chromatography (silica gel, eluting with 0% to 80% EtOAc in hexanes) to give compound 342 (315 mg, 50% yield) as a yellow foam. m/z=569.2 (M+1).

Compound 343: To a solution of potassium tert-butoxide (62 mg, 0.55 mmol) in THF (0.9 mL) under argon was added a solution of compound 342 (105 mg, 0.18 mmol) in THF (1.3 mL) at 0° C. The mixture was stirred at 0° C. for 10 min and treated with iodoethane (0.045 mL, 0.56 mmol). After stirring at 0° C. for another 1 h, the reaction mixture was quenched by adding aq. sat. NH$_4$Cl and was extracted with EtOAc. The organic extract was dried over Na$_2$SO$_4$, filtered and concentrated to give crude compound 343 (112 mg) as a dark green foam, which was used in the subsequent step without further purification. m/z=597.3 (M+1).

Compound 344: To a solution of compound 343 (112 mg, <0.18 mmol) in EtOH (1.8 mL) was added 1 N aq. HCl (0.37 mL, 0.37 mmol) and hydroxylamine hydrochloride (20 mg, 0.29 mmol) sequentially at room temperature. The mixture was heated at 55° C. for 18 h; cooled to room temperature; diluted with aq. sat. NaHCO$_3$; and extracted twice with EtOAc. The combined organic extracts were dried with Na$_2$SO$_4$, filtered and concentrated. The residue was purified by flash chromatography (silica gel, eluting with 0% to 85% EtOAc in hexanes) to give compound 344 (20 mg, 22% yield from compound 342) as a brown glass. m/z=505.2 (M+1).

Compound 345: To a solution of compound 344 (20 mg, 0.040 mmol) in MeOH (0.4 mL) was added sodium methoxide (25 wt. % solution in MeOH, 0.014 mL, 0.061 mmol). The reaction mixture was stirred at 55° C. for 1.5 h; cooled to room temperature; diluted with aq. 10% NaH$_2$PO$_4$; and extracted twice with EtOAc. The combined organic extracts were dried with Na$_2$SO$_4$, filtered and concentrated to give compound 345 (17.5 mg, 88% yield) as a yellow foam, which was used in the subsequent step without further purification. m/z=505.2 (M+1).

T126: Compound 345 (17.5 mg, 0.035 mmol) was dissolved in dry DMF (0.2 mL), and the solution was cooled to 0° C. 1,3-dibromo-5,5-dimethylhydantoin (5 mg, 0.017 mmol) was added. The reaction mixture was stirred at 0° C. for 1 h, and pyridine (0.009 mL, 0.11 mmol) was added. The mixture was heated at 55° C. for 3 h; cooled to room temperature; diluted with CH$_2$Cl$_2$; and washed with water. The organic extract was dried with Na$_2$SO$_4$, filtered and concentrated. The residual pyridine was removed by azeotropic evaporation with toluene (10 mL). The residue was purified by flash chromatography (silica gel, eluting with 0% to 80% EtOAc in hexanes) to give compound T126 (10 mg, 57% yield) as a yellow foam. $^1$H NMR (400 MHz, CDCl$_3$) δ 9.09 (d, J=4.5 Hz, 1H), 8.90 (s, 1H), 8.71 (dd, J=1.4, 8.6 Hz, 1H), 8.22 (d, J=8.4 Hz, 1H), 8.01 (d, J=4.5 Hz, 1H), 7.78 (ddd, J=1.4, 6.8, 8.4 Hz, 1H), 7.64 (ddd, J=1.4, 6.8, 8.4 Hz, 1H), 7.51 (m, 2H), 7.34 (t, J=7.6 Hz, 1H), 7.24 (m, 1H), 2.90 (t, J=6.6 Hz, 2H), 2.61 (dd, J=5.4, 9.5 Hz, 1H), 2.00 (m, 3H), 1.65 (s, 3H), 1.61 (m, 1H), 1.27 (s, 3H), 0.83 (t, J=7.4 Hz, 3H); m/z=503.2 (M+1).

Compound 346: To a mixture of compound 172l (1 g, 2.01 mmol) and 3 Å molecular sieve (500 mg) in CH$_2$Cl$_2$ (10 mL) was added N-methylaniline (0.5 g, 4.67 mmol). The mixture was stirred for 2 days at room temperature and was purified by flash chromatography (silica gel, eluting with 0% to 50% EtOAc in hexanes) to give compound 346 (610 mg, 52% yield) as a foam. m/z=587 (M+1).

Compound 347: To a solution of compound 346 (610 mg, 1.04 mmol) in THF (15 mL) at 0° C. was added t-BuOK (350 mg, 3.12 mmol). The mixture was stirred for 15 min; treated with iodomethane (450 mg, 3.17 mmol); and stirred for another 3 h. The reaction mixture was neutralized with aq. KH$_2$PO$_4$ and extracted with EtOAc. The organic extract was dried with MgSO$_4$, filtered and concentrated to give impure compound 347 (620 mg, quantitative yield) as a foam, which was used in the next step without purification. m/z=601 (M+1).

Compound 348: Compound 347 (620 mg, 1.04 mmol) was dissolved in EtOH (15 mL). Hydroxylamine hydrochloride (120 mg, 1.73 mmol) and aq. 1 N HCl (2.1 mL, 2.1 mmol) were added. The reaction mixture was stirred at 50° C. for 4 h; cooled to room temperature; and concentrated. The residue was taken up in EtOAc and washed with aq. NaHCO$_3$. The organic extract was dried with MgSO$_4$, filtered and concentrated. The residue was purified flash chromatography (silica gel, eluting with 0% to 35% EtOAc in hexanes) to give partially purified compound 348 (130 mg, 25% yield) as a foam. m/z=509 (M+1).

Compound 349: To a solution of compound 348 (130 mg, 0.26 mmol) in MeOH (10 mL) was added potassium carbonate (180 mg, 1.30 mmol). The reaction mixture was stirred at room temperature overnight; neutralized by adding aq. sat. KH$_2$PO$_4$; and extracted with EtOAc. The organic extract was washed with brine, dried with MgSO$_4$, filtered and concentrated. The residue was purified by flash chromatography (silica gel, eluting with 0% to 35% EtOAc in hexanes) to give partially purified compound 349 (100 mg, 77% yield) as a foam. m/z=509 (M+1).

T127 and T128: Compound 349 (100 mg, 0.20 mmol) was dissolved in dry DMF (2 mL), and the solution was cooled to 0° C. 1,3-dibromo-5,5-dimethylhydantoin (30 mg, 0.10 mmol) in DMF (0.5 mL) was added. The reaction mixture was stirred at 0° C. for 2 h, and pyridine (1 mL, 12.4 mmol) was added. The mixture was stirred at 60° C. for 4 h and concentrated. The residue was purified by flash chromatography (silica gel, eluting with 0 to 35% EtOAc in hexanes) to give compound T127 (30 mg, 30% yield) and T128 (25 mg, 25% yield) as foamy solid. T127: $^1$H NMR (400 MHz, CDCl$_3$) δ 9.14 (d, J=4.4 Hz, 1H), 8.91 (s, 1H), 8.51 (d, J=8.6 Hz, 1H), 8.10 (d, J=4.4 Hz, 1H), 7.51 (m, 4H), 7.33 (dt, J=1.1, 7.5 Hz, 1H), 7.24 (m, 1H), 2.91 (dd, J=4.7, 8.6 Hz, 2H), 2.39 (dd, J=2.8, 12.2 Hz, 1H), 2.03 (m, 2H), 1.65 (s, 3H), 1.34 (s, 3H), 1.28 (s, 3H); m/z=507 (M+1). T128: $^1$H NMR (400 MHz, CDCl$_3$) δ 9.15 (d, J=4.4 Hz, 1H), 8.63 (s, 1H), 8.51 (d, J=8.8 Hz, 1H), 8.11 (d, J=4.4 Hz, 1H), 7.54 (m, 4H), 7.34 (dt, J=1.1, 7.5 Hz, 1H), 7.24 (m, 1H), 3.19 (ddd, J=3.2, 5.2, 13.8 Hz, 1H), 3.00 (m, 2H), 2.70 (dt, J=6.9, 12.7 Hz, 1H), 2.08 (s, 3H), 1.89 (s, 3H); m/z=491 (M+1).

T129: To a solution of T76 (100 mg, 0.203 mmol) in MeCN (5 mL) at room temperature was added in one portion hydrogen peroxide (30 wt. % solution in water, 0.14 mL, 1.37 mmol). The reaction mixture was stirred at room temperature for 4 h and partitioned between EtOAc and water. The organic extract was washed with brine, dried over MgSO$_4$, filtered, and concentrated. The residue was purified by flash chromatography (silica gel, eluting with 30% EtOAc in hexanes) to give compound T129 (82 mg, 79% yield) as a white glass. $^1$H NMR (400 MHz, CDCl$_3$) δ 9.07 (d, J=4.5 Hz, 1H), 8.78 (dd, J=6.1, 9.4 Hz, 1H), 8.01 (d, J=4.5 Hz, 1H), 7.83 (dd, J=2.7, 9.8 Hz, 1H), 7.50 (m, 2H), 7.42 (ddd, J=2.7, 8.0, 9.4 Hz, 1H), 7.33 (dt, J=1.1, 7.5 Hz, 1H), 7.24 (m, 1H), 5.23 (s, 1H), 2.87 (m, 2H), 2.34 (m, 1H), 2.25 (m, 1H), 2.01 (m, 1H), 1.68 (dq, J=6.2, 12.4 Hz, 1H), 1.44 (s, 3H), 1.35 (d, J=6.9 Hz, 3H); m/z=509 (M+1).

T130: To a solution of T53 (100 mg, 0.215 mmol) in MeCN (5 mL) at room temperature was added in one portion hydrogen peroxide (30 wt. % solution in water, 0.15 mL, 1.47 mmol). The reaction mixture was stirred at room temperature for 5 h and partitioned between EtOAc and water. The organic extract was washed with brine, dried over MgSO$_4$, filtered, and concentrated. The residue was purified by flash chromatography (silica gel, eluting with 20% to 40% EtOAc in hexanes) to give compound T130 (89 mg, 86% yield) as a white glass. $^1$H NMR (400 MHz, CDCl$_3$) δ 8.59 (td, J=0.8, 5.2 Hz, 1H), 8.18 (s, 1H), 8.06 (ddd, J=0.6, 1.7, 5.1 Hz, 1H), 7.52 (m, 1H), 7.46 (dt, J=1.8, 7.4 Hz, 1H), 7.33 (tt, J=0.9, 7.4 Hz, 1H), 7.21 (t, J=9.2 Hz, 1H), 5.33 (s, 1H), 2.84 (ddd, J=6.9, 11.7, 18.4 Hz, 1H), 2.72 (dd, J=5.8, 18.1 Hz, 1H), 2.24 (m, 3H), 1.96 (dd, J=6.7, 13.7 Hz, 1H), 1.64 (m, 1H), 1.39 (s, 3H), 1.33 (d, J=6.7 Hz, 3H), 1.12 (m, 2H), 1.03 (m, 2H); m/z=481 (M+1).

T131: To a solution of T66 (156 mg, 0.329 mmol) in MeCN (5 mL) at room temperature was added hydrogen peroxide (30 wt. % solution in water, 0.17 mL, 1.66 mmol). The reaction mixture was stirred at room temperature for 1 h and partitioned between EtOAc (50 mL) and aq. sat. KH$_2$PO$_4$ (50 mL). The organic extract was washed with brine (50 mL), dried over MgSO$_4$, filtered, and concentrated. The residue was purified by flash chromatography (silica gel, eluting with 50% EtOAc in hexanes) to give compound T131 (96 mg, 59% yield) as a light yellow foamy solid. $^1$H NMR (400 MHz, CDCl$_3$) δ 9.35 (s, 1H), 9.20 (s, 1H), 8.78 (m, 1H), 8.07 (d, J=8.1 Hz, 1H), 7.80 (ddd, J=1.3, 6.9, 8.6 Hz, 1H), 7.67 (ddd, J=1.1, 6.9, 8.1 Hz, 1H), 7.51 (m, 2H), 7.33 (dt, J=1.1, 7.6 Hz, 1H), 7.23 (m, 1H), 5.28 (s, 1H), 2.89 (ddd, J=6.8, 11.5, 18.3 Hz, 1H), 2.79 (dd, J=5.9, 18.0 Hz, 1H), 2.28 (m, 2H), 2.00 (m, 1H), 1.68 (dq, J=6.4, 12.7 Hz, 1H), 1.45 (s, 3H), 1.35 (d, J=7.0 Hz, 3H); m/z=491 (M+1).

T132: To a solution of T37 (100 mg, 0.210 mmol) in MeCN (5 mL) at room temperature was added hydrogen peroxide (30 wt. % solution in water, 135 mg, 1.19 mmol). The reaction mixture was stirred at room temperature for 2 h and diluted with water. The mixture was extracted with EtOAc (2×15 mL). The organic extract was dried over MgSO$_4$, filtered, and concentrated. The residue was purified by flash chromatography (silica gel, eluting with 0% to 35% EtOAc in hexanes) to give compound T132 (25 mg, 24% yield) as a foam. $^1$H NMR (400 MHz, CDCl$_3$) δ 9.08 (d, J=4.5 Hz, 1H), 8.70 (dd, J=1.1, 8.1 Hz, 1H), 8.21 (dd, J=0.4, 8.4 Hz, 1H), 8.01 (d, J=4.5 Hz, 1H), 7.77 (ddd, J=1.4, 6.8, 8.4 Hz, 1H), 7.63 (ddd, J=1.3, 6.8, 8.4 Hz, 1H), 7.51 (m, 2H), 7.33 (dt, J=1.1, 7.5 Hz, 1H), 7.24 (m, 1H), 5.25 (s, 1H), 2.91 (ddd, J=7.1, 11.6, 18.4 Hz, 1H), 2.80 (dd, J=6.0, 18.1 Hz, 1H), 2.31 (m, 2H), 2.02 (m, 1H), 1.69 (m, 1H), 1.44 (s, 3H), 1.35 (d, J=7.0 Hz, 3H); m/z=491 (M+1).

T133: To a solution of T118 (95 mg, 0.194 mmol) in MeCN (5 mL) at room temperature was added hydrogen peroxide (30 wt. % solution in water, 0.11 g, 0.97 mmol). The reaction mixture was stirred at room temperature for 2 h and partitioned between EtOAc (50 mL) and aq. sat. KH$_2$PO$_4$ (50 mL). The organic extract was washed with brine (50 mL), dried over MgSO$_4$, filtered, and concentrated. The residue was purified by flash chromatography (silica gel, eluting with 50% EtOAc in hexanes) to give compound to give T133 (74 mg, 76% yield) as an off-white foamy solid. $^1$H NMR (400 MHz, CDCl$_3$) δ 9.07 (dd, J=1.3, 4.4 Hz, 1H), 8.68 (d, J=8.8 Hz, 1H), 8.21 (d, J=8.4 Hz, 1H), 8.00 (dd, J=1.3, 4.5 Hz, 1H), 7.77 (tdd, J=1.5, 6.9, 8.4 Hz, 1H), 7.62 (tdd, J=1.4, 6.8, 8.3 Hz, 1H), 7.51 (m, 2H), 7.33 (tt, J=1.2, 7.3 Hz, 1H), 7.24 (m, 1H), 5.24 (s, 1H), 2.85 (m, 2H), 2.59 (m, 1H), 1.91 (m, 1H), 1.78 (td, J=6.3, 12.6 Hz, 1H), 1.47 (s, 3H), 1.29 (s, 3H), 1.21 (s, 3H); m/z=505 (M+1).

T134: To a solution of compound 14d (238 mg, 0.71 mmol) in THF (3.5 mL) was added lithium bis(trimethylsilyl)amide solution (1 M in THF, 1.1 mL, 1.1 mmol) at −78° C. After the mixture was stirred at −78° C. for 10 min, phenylselenyl chloride (202 mg, 1.05 mmol) in THF (3.5 mL) was added. The mixture was stirred at −78° C. for an additional 1.5 h. Aq. sat. NH$_4$Cl was added. The mixture was extracted with EtOAc. The organic extract was dried with Na$_2$SO$_4$, and concentrated. The residue was purified by flash chromatography to give partially purified product. The product was dissolved in EtOAc (10 mL) and THF (3 mL). Hydrogen peroxide (30 wt. % solution in water, 0.35 mL, 3.43 mmol) was added at room temperature. The reaction was stirred for 1 h. Aq. 10% Na$_2$SO$_3$ was added. The mixture was extracted with EtOAc. The organic extract was washed with water, dried with Na$_2$SO$_4$, filtered and concentrated. The residue was purified by flash chromatography (silica gel, eluting with 0% to 50% EtOAc in hexanes) to give compound T134 (60 mg, 25% yield) as a white solid. $^1$H NMR (400 MHz, CDCl$_3$) δ 8.76 (m, 2H), 8.33 (m, 2H), 8.21 (d, J=10.1 Hz, 1H), 6.07 (d, J=10.1 Hz, 1H), 4.12 (s, 3H), 2.88 (ddd, J=1.1, 6.8, 16.8 Hz, 1H), 2.65 (m, 1H), 2.50 (m, 1H), 2.12 (m, 2H), 1.76 (m, 1H), 1.40 (s, 3H), 1.28 (d, J=6.8 Hz, 3H); m/z=336.2 (M+1).

T135: To a solution of compound T134 (59 mg, 0.18 mmol) in THF (1.2 mL) was added freshly prepared LDA (1 M solution in THF, 0.21 mL, 0.21 mmol). The mixture was stirred at 0° C. for 1 h; cooled to −78° C.; treated with HMPA (30 μL, 0.17 mmol) and methyl cyanoformate (17 μL, 0.21 mmol); and stirred at −78° C. for 1 h. The reaction was quenched by adding aq. sat. NH$_4$Cl. The mixture was stirred for 5 min at room temperature and extracted with EtOAc. The organic extract was washed with water, dried with Na$_2$SO$_4$, filtered and concentrated. The residue was purified by flash chromatography (silica gel, eluting with 0% to 20% acetone in hexanes) to give T135 (20 mg, 29% yield) as a white solid. $^1$H NMR (400 MHz, CDCl$_3$) δ

8.77 (m, 2H), 8.32 (m, 2H), 8.28 (d, J=10.3 Hz, 1H), 6.17 (d, J=10.3 Hz, 1H), 4.12 (s, 3H), 3.73 (s, 3H), 3.02 (dd, J=2.2, 13.0 Hz, 1H)), 2.87 (ddd, J=1.1, 6.9, 18.5 Hz, 1H), 2.66 (ddd, J=7.8, 11.1, 18.8 Hz, 1H), 2.00 (m, 1H), 1.70 (m, 1H), 1.60 (s, 3H), 1.49 (s, 3H); m/z=394.1 (M+1).

Compound 350: To a solution of potassium tert-butoxide (240.9 mg, 2.14 mmol) in THF (3 mL) under argon was added a solution of compound 337 (400 mg, 0.72 mmol) in THF (4 mL) at 0° C. The mixture was stirred at 0° C. for 10 min and treated with allylbromide (0.19 mL, 2.20 mmol). After stirring at 0° C. for another 2 h, the reaction mixture was quenched by adding aq. sat. NH$_4$Cl (10 mL) and was extracted with EtOAc. The organic extract was dried over Na$_2$SO$_4$, filtered and concentrated. The residue was purified by flash chromatography (silica gel, eluting with 0% to 40% acetone in hexanes) to give compound 350 (300 mg, 70% yield) as a pale yellow foam. m/z=599.3(M+1).

Compound 351: To a solution of compound 350 (300 mg, 0.50 mmol) in EtOH (5.0 mL) was added aq. 1 N HCl (1.0 mL, 1.0 mmol) and hydroxylamine hydrochloride (52.2 mg, 0.75 mmol) sequentially at room temperature. The mixture was heated at 55° C. for 4 h, and concentrated. The residue was diluted with aq. sat. NaHCO$_3$ and extracted twice with EtOAc. The combined organic extracts were dried with Na$_2$SO$_4$, filtered and concentrated. The residue was purified by flash chromatography (silica gel, eluting with 0% to 40% EtOAc in hexanes) to give compound 351 (160 mg, 63% yield) as a white foam. m/z=507.2 (M+1).

Compound 352: To a solution of compound 351 (70 mg, 0.138 mmol) in THF (1.38 mL) was added 9-BBN (0.5 M solution in THF, 1.38 mL, 0.69 mmol) at room temperature. The reaction mixture was stirred at room temperature for 2 h and then cooled to 0° C. Water (70 µL), aq. 3N NaOH (0.39 mL, 1.17 mmol) and 30% aq. hydrogen peroxide (0.39 mL, 3.82 mmol) were added sequentially. The reaction mixture was stirred at room temperature for 1 h, and then diluted with EtOAc. The mixture was washed with water and aq. 10% Na$_2$SO$_3$. The organic extract was dried over Na$_2$SO$_4$, filtered and concentrated. The residue was purified by flash chromatography (silica gel, eluting with 0% to 40% acetone in hexanes) to give compound 352 (60 mg, 82% yield) as a white foam. m/z=525.2 (M+1).

Compound 353: To a solution of compound 352 (65 mg, 0.124 mmol) in MeOH (1.2 mL) was added sodium methoxide (25 wt. % solution in MeOH, 42 µL, 0.186 mmol). The reaction mixture was stirred at 55° C. for 2 h, cooled to 0° C., and then neutralized by adding aq. 10% NaH$_2$PO$_4$. The mixture was diluted with water and extracted twice with EtOAc. The combined organic extracts were dried with Na$_2$SO$_4$, filtered and concentrated to give compound 353 (50 mg, 77% yield) as a clear film, which was used in the subsequent step without further purification. m/z=525.2 (M+1).

T136: A mixture of compound 353 (50 mg, 0.095 mmol), DDQ (23.8 mg, 0.105 mmol) and benzene (0.95 mL) was stirred at reflux for 2 h, and cooled to room temperature. The mixture was diluted with CH$_2$Cl$_2$ and washed with water and aq. sat. NaHCO$_3$. The combined aqueous washes were extracted with EtOAc. The combined organic extracts were dried with Na$_2$SO$_4$, filtered and concentrated. The residue was purified by flash chromatography (silica gel, eluting with 0% to 30% acetone in hexanes) to give compound T136 (19 mg, 38% yield) as a white foam. T136 is contaminated with 24% of the corresponding 1,2-epoxide. $^1$H NMR (400 MHz, CDCl$_3$) 8.99 (s, 1H), 8.60 (d, J=5.2 Hz, 1H), 8.19 (br s, 1H), 8.06 (dd, J=1.6, 5.2 Hz, 1H), 7.52 (m, 1H), 7.45 (dt, J=1.6, 7.6 Hz, 1H), 7.34 (dt, J=0.8, 7.6 Hz, 1H), 7.22 (br t, J=9.2 Hz, 1H), 3.60 (m, 2H), 2.82 (m, 2H), 2.54 (dd, J=3.2, 11.2 Hz, 1H), 1.61 (s, 3H), 1.40-2.05 (m, 7H), 1.28 (s, 3H), 1.11 (m, 2H), 1.04 (m, 2H); m/z=523.2 (M+1).

Compound 354: To a solution of compound 351 (75 mg, 0.148 mmol) in MeOH (1.6 mL) was added potassium carbonate (33.4 mg, 0.242 mmol). The reaction mixture was stirred at room temperature for 4 h, cooled to 0° C., and neutralized by adding aq. 10% NaH$_2$PO$_4$. MeOH was removed by evaporation. The residue was diluted with water, and the mixture was extracted twice with EtOAc. The combined organic extracts were dried with Na$_2$SO$_4$, filtered and concentrated. The residue was purified by flash chromatography (silica gel, eluting with 0% to 40% acetone in hexanes) to give compound 354 (60 mg, 80% yield) as an off-white foam. m/z=507.2 (M+1).

Compound 355: To a solution of compound 354 (60 mg, 0.118 mmol) in EtOAc (2.4 mL) was added 10% palladium on carbon (20 mg). The reaction mixture was stirred under hydrogen (1 atm) at room temperature for 2 h. The catalyst was removed by filtration through a pad of Celite® and the filtrate was concentrated. The residue was purified by flash chromatography (silica gel, eluting with 0% to 35% acetone in hexanes) to give compound 355 (40 mg, 66% yield) as a white solid. m/z=509.2 (M+1).

T137: A solution of compound 355 (40 mg, 0.079 mmol) in anhydrous DMF (0.4 mL) was cooled to 0° C. under nitrogen and treated dropwise with a solution of 1,3-dibromo-5,5-dimethylhydantoin (11.2 mg, 0.039 mmol) in anhydrous DMF (0.4 mL). After stirring the reaction at 0° C. for 2 h, anhydrous pyridine (19 µL, 0.236 mmol) was added. The cold bath was removed, and the reaction mixture was heated at 55° C. for 2 h. Upon cooling to room temperature, the reaction mixture was partitioned between EtOAc and aq. sat. KH$_2$PO$_4$. The organic phase was washed with brine, dried over MgSO$_4$, filtered and concentrated. The residue was purified by flash chromatography (silica gel, eluting with 0% to 40% acetone in hexanes) to give compound T137 (18.9 mg, 47% yield) as an off-white solid. $^1$H NMR (400 MHz, CDCl$_3$) 8.97 (s, 1H), 8.60 (dd, J=1.2, 5.2 Hz, 1H), 8.19 (dd, J=0.8, 1.6 Hz, 1H), 8.06 (dd, J=2.0, 5.2 Hz, 1H), 7.52 (m, 1H), 7.45 (dt, J=1.6, 7.6 Hz, 1H), 7.34 (dt, J=1.2, 7.6 Hz, 1H), 7.22 (ddd, J=0.8, 8.0, 9.2 Hz, 1H), 2.82 (m, 2H), 2.54 (dd, J=4.0, 10.8 Hz, 1H), 2.21 (m, 1H), 1.90 (m, 3H), 1.59 (s, 3H), 1.54 (m, 1H), 1.30 (m, 2H), 1.25 (s, 3H), 1.22 (m, 2H), 1.04 (m, 2H), 0.87 (t, J=7.2 Hz, 3H); m/z=507.2 (M+1).

Compound 356: Compound 94 (216 mg, 0.50 mmol) was taken up in pyrrolidine (0.319 mL, 3.88 mmol). The reaction was stirred at reflux for 16 h, cooled, and concentrated. The crude residue was purified by flash chromatography (silica gel, eluting with 0% to 10% MeOH in CH$_2$Cl$_2$) to give compound 356 (241 mg, quantitative yield) as an orange oil. m/z=471 (M+1).

Compound 357: Compound 356 (241 mg, 0.50 mmol) was taken up in THF (2.3 mL) and MeOH (2.3 mL). Aq. 3 N HCl (2.3 mL, 6.9 mmol) was added. The mixture was stirred for 3 h at room temperature and concentrated. The residue was neutralized with aq. sat. NaHCO$_3$ and extracted with EtOAc. The organic extract was dried with Na$_2$SO$_4$, filtered, and concentrated to give compound 357 (141 mg, 66% yield) as a yellow solid. m/z=427 (M+1).

Compound 358: Compound 357 (141 mg, 0.33 mmol) was taken up in ethyl formate (0.81 mL, 10.07 mmol). Sodium methoxide (25 wt. % in MeOH, 1.14 mL, 4.97 mmol) was added. After stirring at room temperature overnight, EtOH (4.8 mL), aq. 6 N HCl (0.83 mL, 4.98 mmol), and hydroxylamine hydrochloride (35 mg, 0.50 mmol) were added to the reaction mixture. The reaction was stirred at 55° C. for 6 h, cooled, and concentrated. The residue was diluted with EtOAc, neutralized with aq. sat. KHCO$_3$, and then extracted with EtOAc. The combined organic extract was washed with brine and concentrated. The crude residue was purified by flash chromatography (silica gel, eluting with 0% to 60% acetone in hexanes) to give compound 358 (118 mg, 79% yield) as a yellow foam. m/z=452 (M+1).

Compound 359: Compound 358 (118 mg, 0.26 mmol) was dissolved in MeOH (2.61 mL). Sodium methoxide (25 wt. % in MeOH, 90 µL, 0.39 mmol) was added. After stirring at room temperature for 3 h, the reaction mixture was neutralized with aq. sat. KH$_2$PO$_4$, and extracted with EtOAc. The organic extract was washed with brine, dried with Na$_2$SO$_4$, filtered, and concentrated to give compound 359 (100 mg, 85% yield) as a yellow foam. m/z=452 (M+1).

T138: Compound 359 (100 mg, 0.22 mmol) was dissolved in dry DMF (2.45 mL), and the solution was cooled to 0° C. 1,3-dibromo-5,5-dimethylhydantoin (32.3 mg, 0.11 mmol) in DMF (0.95 mL) was added. The reaction was stirred at 0° C. for 1 h, and pyridine (53 µL, 0.66 mmol) was added. The reaction was heated at 55° C. for 3 h and cooled to room temperature. The reaction mixture was diluted with EtOAc and washed with aq. sat. NaHCO$_3$, aq. sat. Na$_2$SO$_3$, and brine. The organic extract was dried with Na$_2$SO$_4$, filtered and concentrated. The crude residue was purified by flash chromatography (silica gel, eluting with 0% to 85% EtOAc in hexanes) to give compound T138 (54.4 mg, 55% yield) as an orange tinted solid. $^1$H NMR (400 MHz, CDCl$_3$) δ 9.04 (d, J=4.8 Hz, 1H), 8.90 (s, 1H), 8.86 (dd, J=0.8, 8.8 Hz, 1H), 8.18 (dd, J=1.2, 7.8 Hz, 1H), 7.98 (d, J=4.8 Hz, 1H), 7.74 (ddd, J=1.2, 6.8, 8.4 Hz, 1H), 7.59 (ddd, J=1.2, 6.4, 8.0 Hz, 1H), 3.83 (m, 2H), 3.74 (m, 2H), 3.07 (m, 2H), 2.59 (dq, J=13.4, 6.7 Hz, 1H), 2.18 (m, 2H), 2.04 (m, 2H), 1.91 (m, 2H), 1.77 (m, 1H), 1.51 (s, 3H), 1.33 (d, J=6.8 Hz, 3H); m/z=450 (M+1).

Compound 360: To a solution of compound 179 (150 mg, 0.42 mmol) in methylpyrrolidone (0.6 mL) was added 1-acetylpiperazine (268 mg, 2.09 mmol). The mixture was heated at 100° C. for 2 h and cooled to room temperature. EtOAc was added. The mixture was washed with water. The organic extract was dried with Na$_2$SO$_4$ and concentrated. The residue was purified by flash chromatography (silica gel, eluting with 0% to 80% EtOAc in hexanes) to give compound 360 (183 mg, 97% yield) as a white foamy solid. m/z=451 (M+1).

Compound 361: Compound 360 (180 mg, 0.40 mmol) was dissolved in ethyl formate (0.96 mL, 11.94 mmol) and cooled to 0° C. Sodium methoxide (25 wt. % in methanol, 1.38 mL, 6.03 mmol) was added. The mixture was stirred at room temperature for 2 h, and cooled to 0° C. Aq. 6 N HCl (1.0 mL, 6.0 mmol), EtOH (4 mL) and hydroxylamine hydrochloride (42 mg, 0.60 mmol) were added sequentially. The mixture was heated at 55° C. (oil bath) overnight and concentrated. Aq. sat. NaHCO$_3$ was added. The mixture was extracted with EtOAc. The combined organic extract was dried with Na$_2$SO$_4$ and concentrated. The residue was purified by flash chromatography (silica gel, eluting with 0% to 100% EtOAc in hexanes) to give compound 361 (151 mg, 79% yield) as a light yellow foamy solid. m/z=476 (M+1).

Compound 362: Compound 361 (147 mg, 0.31 mmol) was dissolved in MeOH (3 mL). Sodium methoxide (25 wt. % in methanol, 0.11 mL, 0.48 mmol) was added at room temperature. The reaction mixture was stirred at 55° C. for 2 h and cooled to room temperature. Aq. 10% NaH$_2$PO$_4$ was added. The mixture was extracted with EtOAc. The organic extract was dried with Na$_2$SO$_4$ and concentrated. The residue was purified by flash chromatography (silica gel, eluting with 0% to 100% EtOAc in hexanes) to give compound 362 (130 mg, 88% yield) as a light yellow foamy solid. m/z=476 (M+1).

T139: Compound 362 (130 mg, 0.27 mmol) was dissolved in anhydrous DMF (0.7 mL), and the solution was cooled to 0° C. 1,3-dibromo-5,5-dimethylhydantoin (39 mg, 0.14 mmol) in DMF (0.7 mL) was added. The reaction was stirred at 0° C. for 1 h. Pyridine (66 µL, 0.82 mmol) was added. The reaction was heated at 55° C. (oil bath) for 4 h, and cooled to room temperature. EtOAc was added. The mixture was washed with 4 times with water. The organic extract was dried with Na$_2$SO$_4$, and concentrated. The residual pyridine was removed by azeotropic evaporation with toluene (10 mL). The residue was purified by flash chromatography (silica gel, eluting with 0% to 100% EtOAc in hexanes) to give compound T139 (75 mg, 58% yield) as a light yellow foamy solid. $^1$H NMR (400 MHz, CDCl$_3$) δ 8.80 (s, 1H), 7.43 (m, 1H), 7.32 (dt, J=2.0, 6.8 Hz, 1H), 7.25 (m, 1H), 7.14 (br t, J=8.4 Hz, 1H), 3.89 (m, 2H), 3.84 (m, 2H), 3.72 (m, 2H), 3.58 (m, 2H), 2.56 (m, 3H), 2.17 (s, 3H), 2.13 (m, 1H), 2.00 (m, 1H), 1.67 (m, 1H), 1.45 (s, 3H), 1.27 (d, J=6.7 Hz, 3H); m/z=474 (M+1).

Compound 363: Compound 88 (1.08 g, 3.14 mmol), 6-chloropyridine-3-carboximidamide hydrochloride (900 mg, 4.69 mmol) and K$_2$CO$_3$ (1.30 g, 9.42 mmol) in EtOH (15 mL) were heated in a Biotage® microwave synthesizer at 120° C. for 3 h. After the reaction was cooled to room temperature, EtOAc was added. The mixture was washed with water. The organic extract was dried with Na$_2$SO$_4$ and concentrated. The crude product was dissolved in CH$_2$Cl$_2$ (31 mL) and treated with DDQ (713 mg, 3.14 mmol). After the reaction was stirred at room temperature for 1 h, aq. sat. NaHCO$_3$ was added. The mixture was stirred at room temperature for 10 min; filtered through a pad of Celite®; and eluted with CH$_2$Cl$_2$. The organic phase of the filtrate was separated. The aqueous phase was extracted with CH$_2$Cl$_2$. The combined organic extract was dried with Na$_2$SO$_4$ and filtered and concentrated. The residue was purified by flash chromatography (silica gel, eluting with 0% to 5% EtOAc in CH$_2$Cl$_2$) to give compound 363 (902 g, 60% yield) as a white foamy solid. m/z=480 (M+1).

Compound 364: A mixture of compound 363 (150 mg, 0.31 mmol), cyclopropylboronic acid (45 mg, 0.52 mmol), potassium phosphate (330 mg, 1.56 mmol), tricyclohexylphosphine (27 mg, 0.096 mmol), palladium acetate (12 mg, 0.054 mmol), toluene (2 mL) and water (0.1 mL) in a vial was sparged with nitrogen for 5 min. The vial was sealed and heated in a Biotage® microwave synthesizer at 130° C. for 4 h. After the reaction was cooled to room temperature, EtOAc was added. The mixture was washed with water. The aqueous phase was extracted with EtOAc. The combined organic extract was dried with Na$_2$SO$_4$, filtered and concentrated. The residue was purified by flash chromatography (silica gel, eluting with 0% to 40% EtOAc in hexanes) to give the compound 364 (135 mg, 89% yield) as a white foamy solid. m/z=486 (M+1).

Compound 365: Compound 364 (135 mg, 0.28 mmol) in MeOH (1.8 mL) was treated with aq. 3 N HCl (0.92 mL, 2.76 mmol). The mixture was stirred for 2 h at room temperature and concentrated. The residue was neutralized with aq. sat. NaHCO$_3$ and extracted with EtOAc. The organic extract was dried with Na$_2$SO$_4$, filtered and concentrated to give compound 365 (123 mg, quantitative yield) as a white foamy solid. m/z=442 (M+1).

Compound 366: Compound 365 (123 mg, 0.28 mmol) was dissolved in ethyl formate (0.67 mL, 8.33 mmol) and cooled to 0° C. Sodium methoxide (25 wt. % in methanol, 0.63 mL, 2.75 mmol) was added. After stirring at room temperature for 15 min, the mixture turned into a semi-solid. Ethyl formate (0.67 mL, 8.33 mmol) was added. The mixture was stirred for another 45 min at room temperature, and cooled to 0° C. Aq. 6 N HCl (0.46 mL, 2.76 mmol), EtOH (2.7 mL) and hydroxylamine hydrochloride (30 mg, 0.43 mmol) were added sequentially. The mixture was heated at 55° C. (oil bath) for 3 h and concentrated. The residue was diluted with aq. sat. $NaHCO_3$ and extracted twice with EtOAc. The combined organic extract was dried with $Na_2SO_4$ and concentrated. The residue was purified by flash chromatography (silica gel, eluting with 0% to 40% EtOAc in hexanes) to give compound 366 (113 mg, 87% yield) as a white foamy solid. m/z=467 (M+1).

Compound 367: Compound 366 (110 mg, 0.24 mmol) was dissolved in MeOH (2.4 mL). Sodium methoxide (25 wt. % in methanol, 0.11 mL, 0.48 mmol) was added. The reaction mixture was stirred at 55° C. for 2 h, and cooled to room temperature. Aq. 10% $NaH_2PO_4$ was added. The mixture was extracted twice with EtOAc. The combined organic extract was dried with $Na_2SO_4$, filtered and concentrated. The residue was purified by flash chromatography (silica gel, eluting with 0% to 40% EtOAc in hexanes) to give compound 367 (103 mg, 94% yield) as a white foamy solid. m/z=467 (M+1).

T140: Compound 367 (103 mg, 0.22 mmol) was dissolved in anhydrous DMF (0.6 mL), and the solution was cooled to 0° C. 1,3-dibromo-5,5-dimethylhydantoin (32 mg, 0.11 mmol) in DMF (0.5 mL) was added. After the reaction was stirred at 0° C. for 1 h, pyridine (54 µL, 0.67 mmol) was added. The reaction was heated at 55° C. (oil bath) for 4 h and cooled to room temperature. EtOAc was added. The mixture was washed 4 times with water. The organic extract was dried with $Na_2SO_4$ and concentrated. The residual pyridine was removed by azeotropic evaporation with toluene (10 mL). The residue was purified by flash chromatography (silica gel, eluting with 0% to 40% EtOAc in hexanes) to give compound T140 (81 mg, 79% yield) as a white foamy solid. $^1$H NMR (400 MHz, $CDCl_3$) δ 9.53 (d, J=2.4 Hz, 1H), 9.00 (s, 1H), 8.55 (dd, J=2.0, 8.0 Hz, 1H), 7.50 (m, 1H), 7.43 (td, J=7.4, 1.8 Hz, 1H), 7.31 (td, J=7.5, 1.1 Hz, 1H), 7.26 (m, 1H), 7.19 (ddd, J=9.6, 8.3, 1.0 Hz, 1H), 2.79 (m, 2H), 2.60 (dq, J=13.4, 6.7 Hz, 1H), 2.24 (td, J=12.8, 2.7 Hz, 1H), 2.12 (m, 2H), 1.78 (m, 1H), 1.53 (s, 3H), 1.31 (d, J=6.7 Hz, 3H), 1.14 (m, 2H), 1.07 (m, 2H); m/z=465 (M+1).

Compound 368: A mixture of compound 363 (166 mg, 0.35 mmol), phenylboronic acid (55 mg, 0.45 mmol), potassium carbonate (239 mg, 1.73 mmol), tetrakis(triphenylphosphine)palladium(O) (12 mg, 0.010 mmol), toluene (2 mL), EtOH (1 mL) and water (1 mL) in a vail was sparged with nitrogen for 5 min. The vial was sealed and heated in a Biotage® microwave synthesizer at 110° C. for 1 h. After the reaction was cooled to room temperature, EtOAc was added. The mixture was washed with water. The organic extract was dried with $Na_2SO_4$ and concentrated. The residue was purified by flash chromatography (silica gel, eluting with 0% to 35% EtOAc in hexanes) to give the compound 368 (148 mg, 82% yield) as a white foamy solid. m/z=522 (M+1).

Compound 369: Compound 368 (144 mg, 0.28 mmol) was taken up in THF (1.8 mL) and MeOH (1.8 mL). Aq. 3 N HCl (0.92 mL, 2.76 mmol) was added. The mixture was stirred for 3 h at room temperature and concentrated. The residue was neutralized with aq. sat. $NaHCO_3$ and extracted twice with EtOAc. The combined organic extract was dried with $Na_2SO_4$, filtered and concentrated to give compound 369 (138 mg, quantitative yield) as a white foamy solid. m/z=478 (M+1).

Compound 370: Compound 369 (138 mg, 0.28 mmol) was dissolved in ethyl formate (0.67 mL, 8.33 mmol) and cooled to 0° C. Sodium methoxide (25 wt. % in methanol, 0.63 mL, 2.75 mmol) was added. The mixture was stirred at room temperature for 2 h, and cooled to 0° C. Aq. 6 N HCl (0.46 mL, 2.76 mmol), EtOH (2.8 mL) and hydroxylamine hydrochloride (29 mg, 0.42 mmol) were added sequentially. The mixture was heated at 55° C. (oil bath) for 14 h and concentrated. Aq. sat. $NaHCO_3$ was added. The mixture was extracted twice with EtOAc. The combined organic extract was dried with $Na_2SO_4$ and concentrated. The residue was purified by flash chromatography (silica gel, eluting with 0% to 40% EtOAc in hexanes) to give compound 370 (115 mg, 82% yield) as a white foamy solid. m/z=503 (M+1).

Compound 371: Compound 370 (112 mg, 0.22 mmol) was dissolved in MeOH (2.2 mL). Sodium methoxide (25 wt. % in methanol, 0.10 mL, 0.44 mmol) was added. The reaction mixture was stirred at 55° C. for 1 h, and cooled to room temperature. Aq. 10% $NaH_2PO_4$ was added. The mixture was extracted with EtOAc. The organic extract was dried with $Na_2SO_4$, filtered and concentrated. The residue was purified by flash chromatography (silica gel, eluting with 0% to 50% EtOAc in hexanes) to give compound 371 (101 mg, 90% yield) as a white foamy solid. m/z=503 (M+1).

T141: Compound 371 (100 mg, 0.20 mmol) was dissolved in anhydrous DMF (0.5 mL), and the solution was cooled to 0° C. 1,3-dibromo-5,5-dimethylhydantoin (28 mg, 0.098 mmol) in DMF (0.5 mL) was added. The reaction was stirred at 0° C. for 1 h. Pyridine (48 µL, 0.59 mmol) was added. The reaction was heated at 55° C. (oil bath) for 1.5 h and cooled to room temperature. EtOAc was added. The mixture was washed 4 times with water. The organic extract was dried with $Na_2SO_4$, filtered and concentrated. The residual pyridine was removed by azeotropic evaporation with toluene (10 mL). The residue was purified by flash chromatography (silica gel, eluting with 0% to 40% EtOAc in hexanes) to give compound T141 (72 mg, 72% yield) as a light yellow foamy solid. $^1$H NMR (400 MHz, $CDCl_3$) δ 9.77 (dd, J=2.2, 0.8 Hz, 1H), 9.04 (s, 1H), 8.79 (dd, J=8.3, 2.2 Hz, 1H), 8.11 (m, 2H), 7.88 (dd, J=8.3, 0.9 Hz, 1H), 7.50 (m, 5H), 7.34 (td, J=7.5, 1.1 Hz, 1H), 7.22 (ddd, J=0.8, 8.4, 9.6 Hz, 1H), 2.84 (m, 2H), 2.61 (dq, J=13.4, 6.7 Hz, 1H), 2.26 (td, J=12.8, 2.8 Hz, 1H), 2.12 (m, 1H), 1.80 (m, 1H), 1.56 (s, 3H), 1.32 (d, J=6.7 Hz, 3H); m/z=501 (M+1).

Compound 372: A mixture of compound 363 (382 mg, 0.80 mmol), potassium vinyltrifluoroborate (214 mg, 1.60 mmol), potassium phosphate (296 mg, 1.40 mmol), tricyclohexylphosphine (11 mg, 0.039 mmol), tris(dibenzylideneacetone)dipalladium (15 mg, 0.016 mmol) were weighed in a vial and put under vacuum. Degassed 1,4-dioxane (7.5 mL) and water (1.5 mL) were added. The mixture was sparged with nitrogen for 2 min and heated in a Biotage® microwave synthesizer at 140° C. for 30 min. The reaction mixture was cooled to room temperature, filtered through a pad of Celite® and eluted with EtOAc. The filtrate was concentrated, and residue was diluted with toluene and concentrated again. The residue was purified by flash chromatography (silica gel, eluting with 0% to 40% EtOAc in hexanes) to give the compound 372 (240 mg, 64% yield) as a white foamy solid. m/z=472 (M+1).

Compound 373: Compound 372 (300 mg, 0.64 mmol) in MeOH (2.1 mL) and THF (2.1 mL) was treated with aq. 3 N HCl (2.1 mL, 6.3 mmol). The mixture was stirred for 2 h at room temperature and concentrated. The residue was neutralized with aq. sat. NaHCO$_3$ and extracted twice with EtOAc. The combined organic extract was dried with Na$_2$SO$_4$, filtered and concentrated to give compound 373 (260 mg, 96% yield) as a white foamy solid. m/z=428 (M+1).

Compound 374: Compound 373 (257 mg, 0.60 mmol) was dissolved in ethyl formate (1.5 mL, 18.64 mmol) and cooled to 0° C. Sodium methoxide (25 wt. % in methanol, 1.4 mL, 6.12 mmol) was added. The mixture was stirred for 1 h at room temperature, and cooled to 0° C. Aq. 6 N HCl (1.02 mL, 6.12 mmol), EtOH (6 mL) and hydroxylamine hydrochloride (63 mg, 0.91 mmol) were added sequentially. The mixture was heated at 55° C. (oil bath) for 3 h, and concentrated. The residue was diluted with aq. sat. NaHCO$_3$ and extracted twice with EtOAc. The combined organic extract was dried with Na$_2$SO$_4$ and concentrated. The residue was purified by flash chromatography (silica gel, eluting with 0% to 40% EtOAc in hexanes) to give compound 374 (49 mg, 18% yield) as a light yellow foamy solid. m/z=453 (M+1).

Compound 375: A mixture of compound 374 (46 mg, 0.10 mmol), sodium methanesulfinate (52 mg, 0.51 mmol), EtOH (0.64 mL) and acetic acid (58 µL, 1.01 mmol) was heated at 60° C. under nitrogen for 2 h. After cooled to room temperature, the mixture was diluted with toluene and EtOAc and washed with water. The organic extract was dried with Na$_2$SO$_4$, filtered and concentrated. The residue was purified by flash chromatography (silica gel, eluting with 0% to 60% acetone in hexanes) to give compound 375 (48 mg, 89% yield) as a white foamy solid. m/z=533 (M+1).

Compound 376: Compound 375 (46 mg, 0.086 mmol) was dissolved in MeOH (0.86 mL). Potassium carbonate (48 mg, 0.35 mmol) was added. After stirring the mixture at room temperature overnight, aq. 10% NaH$_2$PO$_4$ was added. The mixture was extracted twice with EtOAc. The combined organic extract was dried with Na$_2$SO$_4$, filtered and concentrated. The residue was purified by flash chromatography (silica gel, eluting with 0% to 60% acetone in hexanes) to give compound 376 (31 mg, 67% yield) as a white foamy solid. m/z=533 (M+1).

T142: Compound 376 (30 mg, 0.056 mmol) was dissolved in anhydrous DMF (0.15 mL), and the solution was cooled to 0° C. 1,3-dibromo-5,5-dimethylhydantoin (8 mg, 0.028 mmol) in DMF (0.15 mL) was added. After the reaction was stirred at 0° C. for 1 h, pyridine (14 µL, 0.17 mmol) was added. The reaction was heated at 55° C. (oil bath) for 2 h and cooled to room temperature. EtOAc was added. The mixture was washed 4 times with water. The organic extract was dried with Na$_2$SO$_4$, filtered and concentrated. The residual pyridine was removed by azeotropic evaporation with toluene (10 mL). The residue was purified by flash chromatography (silica gel, eluting with 0% to 60% acetone in hexanes) to give compound T142 (22 mg, 74% yield) as a white foamy solid. $^1$H NMR (400 MHz, CDCl$_3$) δ 9.61 (dd, J=2.3, 0.8 Hz, 1H), 8.99 (s, 1H), 8.70 (dd, J=8.1, 2.2 Hz, 1H), 7.51 (m, 1H), 7.44 (td, J=7.4, 1.9 Hz, 1H), 7.38 (d, J=8.2 Hz, 1H), 7.33 (td, J=7.5, 1.1 Hz, 1H), 7.21 (ddd, J=9.7, 8.3, 1.0 Hz, 1H), 3.65 (m, 2H), 3.44 (m, 2H), 2.89 (s, 3H), 2.82 (m, 2H), 2.61 (m, 1H), 2.25 (td, J=12.8, 2.8 Hz, 1H), 2.11 (m, 1H), 1.80 (m, 1H), 1.54 (s, 3H), 1.32 (d, J=6.7 Hz, 3H); m/z=531 (M+1).

Compound 377: A mixture of compound 88 (6.34 g, 18.41 mmol), 2-methyl-4-pyridinecarboximidamide hydrochloride (4.74 g, 27.62 mmol) and potassium carbonate (6.4 g, 46.3 mmol) in EtOH (40 mL) was heated at 80° C. under nitrogen. After 48 h, the mixture was filtered; the filtrate was concentrated; and the residue was partitioned between aq. sat. KH$_2$PO$_4$ solution (100 mL) and EtOAc (100 mL). The organic extract was washed with brine (100 mL), dried over MgSO$_4$, filtered and concentrated. The crude product was dissolved in CH$_2$Cl$_2$ (100 mL) and treated with manganese (IV) oxide (88%, 9.1 g, 92.1 mmol). The mixture was stirred at room temperature overnight and filtered. The filtrate was concentrated, and the residue was purified by flash chromatography (silica gel, eluting with 50% EtOAc in hexanes) to give compound 377 (6.09 g, 72% yield) as a light yellow foamy solid. m/z=460 (M+1).

Compound 378: A solution of compound 377 (1.70 g, 3.70 mmol) at room temperature under nitrogen in CH$_2$Cl$_2$ (20 mL) was treated with portionwise addition (over 10 min) of solid 3-chloroperoxybenzoic acid 77%, 0.91 g, 4.06 mmol). After stirring for 1 h, the solution was washed with aq. 1 N NaOH (50 mL). The organic extract was washed with brine (100 mL), dried over MgSO$_4$, filtered and concentrated to give compound 378 (1.88 g, quantitative yield) as a light yellow foamy solid. m/z=476 (M+1).

Compound 379: A mixture of compound 378 (1.88 g, 3.70 mmol) in acetic anhydride (20 mL) was heated at 80° C. under nitrogen overnight. The resultant dark brown solution was cooled, concentrated and very carefully partitioned between aq. sat. NaHCO$_3$ (100 mL) and EtOAc (100 mL). The organic extract was washed with brine (100 mL), dried over MgSO$_4$, filtered, and concentrated. The residue was purified by flash chromatography (silica gel, eluting with 50% EtOAc in hexanes) to give compound 379 (1.08 g, 56% yield) as a light yellow foamy solid. m/z=518 (M+1).

Compound 380: A mixture of compound 379 (1.08 g, 2.09 mmol) and potassium carbonate (1.44 g, 10.42 mmol) in MeOH (20 mL) was stirred at room temperature under nitrogen for 1 h. The mixture was filtered through a pad of Celite®; the filtrate was concentrated; and the residue was carefully partitioned between aq. sat. KH$_2$PO$_4$ (50 mL) and EtOAc (50 mL). The organic extract was washed with brine (50 mL), dried over MgSO$_4$, filtered and concentrated to give compound 380 (0.91 g, 92% yield) as yellow solid. m/z=476 (M+1).

Compound 381: To a stirring solution at 0° C. under nitrogen of compound 380 (0.45 g, 0.95 mmol), triethylamine (0.17 mL, 1.22 mmol) and catalytic amount of 4-dimethylaminopyridine in CH$_2$Cl$_2$ (10 mL) was added dropwise a solution of methanesulfonyl chloride (0.13 g, 1.13 mmol) in CH$_2$Cl$_2$ (2 mL). After stirring for 4 h at 0° C., the mixture was washed aq. sat. KH$_2$PO$_4$ (25 mL). The organic extract was washed with brine (25 mL), dried over MgSO$_4$, filtered and concentrated to give crude compound 381 (0.47 g, 90% yield) as a light yellow-green foamy solid, which was used immediately in the next reaction without purification. m/z=554 (M+1).

Compound 382: A solution of crude compound 381 (0.47 g, 0.85 mmol) and sodium methanesulfinate (0.12 g, 1.18 mmol) in DMF (8 mL) was stirred at room temperature under nitrogen overnight. The mixture was partitioned between aq. sat. KH$_2$PO$_4$ (100 mL) and EtOAc (100 mL). The organic extract was washed with brine (100 mL), dried over MgSO$_4$, filtered, and concentrated. The residue was purified by flash chromatography (silica gel, eluting with 50% EtOAc in hexanes) to give compound 382 (0.23 g, 49% yield) as a light yellow foamy solid. m/z=538 (M+1).

Compound 383: A solution of compound 382 (0.23 g, 0.43 mmol) in MeOH (10 mL) was treated with aq. 3 N HCl (1.4 mL, 4.2 mmol). After stirring at room temperature under nitrogen overnight, the mixture was concentrated. The residue was neutralized with aq. sat. NaHCO$_3$ (50 mL) and extracted with CHCl$_3$ (50 mL). The organic extract was washed with brine (50 mL), dried over MgSO$_4$, filtered and concentrated to give compound 383 (0.20 g, 95% yield) as a light yellow foamy solid. m/z=494 (M+1).

Compound 384: To a stirring solution at 0° C. (under a drying tube) of compound 383 (0.17 g, 0.34 mmol) in ethyl formate (10 mL) was added dropwise sodium methoxide (30 wt. % in MeOH, 0.19 g, 1.06 mmol). After addition, the ice-bath was removed and the mixture was stirred at room temperature for 2 h. The resultant yellow suspension was partitioned between aq. sat. KH$_2$PO$_4$ (50 mL) and EtOAc (50 mL). The organic extract was washed with brine (50 mL), dried over MgSO$_4$, filtered and concentrated to give impure compound 384 (0.17 g) as a bright yellow foamy solid, which was used in the next step without further purification. m/z=522 (M+1).

Compound 385: To a stirring solution at room temperature under nitrogen of crude compound 384 (0.17 g, 0.34 mmol) and acetic acid (0.20 mL, 3.49 mmol) in EtOH (20 mL) was added hydroxylamine hydrochloride (36 mg, 0.52 mmol). The mixture was stirred at 60° C. for 2 h and at room temperature overnight. The mixture was concentrated, and the residue was carefully partitioned between aq. sat. NaHCO$_3$ (50 mL) and EtOAc (50 mL). The organic extract was washed with brine (50 mL), dried over MgSO$_4$, filtered, and concentrated. The residue was purified by flash chromatography (silica gel, eluting with 5% MeOH in CHCl$_3$) to give compound 385 (77 mg, 43% yield from compound 383) as a yellow foamy oil. m/z=519 (M+1).

Compound 386: A mixture of compound 385 (77 mg, 0.15 mmol) and potassium carbonate (0.10 g, 0.72 mmol) in MeOH (15 mL) was stirred at room temperature under nitrogen overnight. The mixture was concentrated, and the residue was partitioned between EtOAc (25 mL) and aq. sat. KH$_2$PO$_4$ (25 mL). The organic extract was washed with brine (25 mL), dried over MgSO$_4$, filtered and concentrated to give compound 386 (60 mg, 78% yield) as a light yellow foamy solid. m/z=519 (M+1).

T143: To a stirring solution at 0° C. under nitrogen of compound 386 (60 mg, 0.12 mmol) in degassed DMF (2 mL) was added in one portion 1,3-dibromo-5,5-dimethylhydantoin (18 mg, 0.063 mmol). After stirring at 0° C. for 30 min, pyridine (0.10 mL, 1.24 mmol) was added. The ice-bath was removed; the mixture was heated at 60° C. for 4 h; cooled and concentrated. The residue was partitioned between aq. sat. KH$_2$PO$_4$ (25 mL) and EtOAc (25 mL). The organic extract was washed with brine (25 mL), dried over MgSO$_4$, filtered, and concentrated. The residue was purified by flash chromatography (silica gel, eluting with 75% EtOAc in hexanes). The product obtained was dissolved into EtOAc (5 mL) and washed with water (2×5 mL). The organic extract was dried over MgSO$_4$, filtered, concentrated and vacuum dried to give compound T143 (26 mg, 43% yield) as a light yellow solid. $^1$H NMR (400 MHz, CDCl$_3$) δ 8.99 (s, 1H), 8.79 (d, J=5.2 Hz, 1H), 8.49 (br s, 1H), 8.39 (dd, J=5.2, 1.6 Hz, 1H), 7.53 (m, 1H), 7.44 (td, J=7.4, 1.9 Hz, 1H), 7.34 (td, J=7.5, 1.1 Hz, 1H), 7.22 (ddd, J=9.7, 8.4, 1.1 Hz, 1H), 4.56 (s, 2H), 3.00 (s, 3H), 2.84 (m, 2H), 2.63 (dq, J=13.4, 6.7 Hz, 1H), 2.26 (td, J=12.8, 2.7 Hz, 1H), 2.13 (m, 1H), 1.80 (m, 1H), 1.55 (s, 3H), 1.33 (d, J=6.7 Hz, 3H); m/z=517 (M+1).

Compound 387: A mixture of compound 380 (3.25 g, 6.83 mmol) and manganese (IV) oxide (88%, 7.0 g, 70.85 mmol) in CH$_2$Cl$_2$ (150 mL) was stirred at room temperature under nitrogen for 2 days. The mixture was filtered through a pad of Celite®, and the filtrate was concentrated. The residue was purified by flash chromatography (silica gel, eluting with 30% EtOAc in hexanes) to give compound 387 (2.05 g, 63% yield) as light yellow solid. m/z=474 (M+1).

Compound 388: To a suspension of methyltriphenylphosphonium bromide (765 mg, 2.14 mmol) in anhydrous THF (16 mL) at 0° C. under nitrogen was added portionwise with stirring potassium t-butoxide (240 mg, 2.14 mmol). After the addition was complete, the mixture was stirred at room temperature for 2 h; cooled to 0° C.; and treated dropwise with a solution of compound 387 (254 mg, 0.536 mmol) in anhydrous THF (5.0 mL). After the addition was complete, the reaction mixture was stirred at room temperature for 19 h; diluted with water; and extracted with EtOAc (2×60 mL). The combined organic extracts were washed with brine, dried over MgSO$_4$, filtered, and concentrated. The residue was purified by flash chromatography (silica gel, eluting with 20% EtOAc in hexanes) to give compound 388 (201 mg, 79% yield) as a white glass. m/z=472 (M+1).

Compound 389: A solution of compound 388 (195 mg, 0.413 mmol) in THF (15 mL) was treated with aq. 3.0 N HCl (1.38 mL, 4.14 mmol). After the reaction mixture was stirred at room temperature for 23 h, the solvent was removed in vacuo. The residue was cooled to 0° C.; neutralized cautiously with aq. sat. NaHCO$_3$; and extracted with EtOAc. The organic extract was washed with brine, dried over MgSO$_4$, filtered and concentrated to give compound 389 (178 mg, quantitative yield) as a yellow glass. m/z=428 (M+1).

Compound 390: A solution of compound 389 (176 mg, 0.411 mmol) in ethyl formate (10 mL) was cooled to 0° C. and treated dropwise with sodium methoxide (5.4 M solution in MeOH, 0.38 mL, 2.05 mmol). The cold bath was removed and the reaction mixture was stirred at room temperature for 20 h. The solvent was removed in vacuo and the residue was partitioned between EtOAc and aq. sat. KH$_2$PO$_4$. The organic phase was washed with brine, dried over MgSO$_4$, filtered and concentrated to give compound 390 (168 mg, 90% yield) as an off-white glass. m/z=456 (M+1).

Compound 391: A solution of compound 390 (168 mg, 0.368 mmol) in glacial acetic acid (0.22 mL, 3.85 mmol) and EtOH (6 mL) was treated with hydroxylamine hydrochloride (38 mg, 0.546 mmol). The reaction mixture was stirred under nitrogen at 60° C. for 4 h and at room temperature for 19 h. The solvent was removed in vacuo and the residue was cautiously partitioned between aq. 10% NH$_4$OH and EtOAc. The organic phase was washed with brine, dried over MgSO$_4$, filtered and concentrated to give compound 391 (153 mg, 92% yield) as an orange glass. m/z=453 (M+1).

Compound 392: A solution of compound 391 (153 mg, 0.338 mmol) in EtOH (10 mL) was treated with sodium methanesulfinate (345 mg, 3.38 mmol) and glacial acetic acid (0.20 mL, 3.50 mmol). After the reaction mixture was stirred under nitrogen at 60° C. for 4 h, the solvent was removed in vacuo. The residue was partitioned between aq. 10% NH$_4$OH and EtOAc. The organic phase was washed with brine, dried over MgSO$_4$, filtered, and concentrated. The residue was purified by flash chromatography (silica gel, eluting with 60% EtOAc in hexanes) to give compound 392 as an off-white glass (66 mg, 37% yield). m/z=533 (M+1).

Compound 393: A suspension of compound 392 (63 mg, 0.118 mmol) and potassium carbonate (33 mg, 0.236 mmol) in MeOH (5 mL) was stirred under nitrogen at room temperature for 23 h. The reaction mixture was concentrated and the residue was partitioned between EtOAc and aq. sat. KH$_2$PO$_4$. The organic phase was washed with brine, dried over MgSO$_4$, filtered and concentrated to give compound 393 (50 mg, 79% yield) as a light yellow glass. m/z=533 (M+1).

T144: A solution of compound 393 (50 mg, 0.093 mmol) in anhydrous DMF (2 mL) was cooled to 0° C. under nitrogen and treated dropwise with a solution of 1,3-dibromo-5,5-dimethylhydantoin (14.6 mg, 0.051 mmol) in anhydrous DMF (1 mL). After stirring at 0° C. for 30 min, anhydrous pyridine (75 µL, 0.93 mmol) was added. The cold bath was removed, and the reaction mixture was heated at 60° C. for 4 h. Upon cooling to room temperature, the reaction mixture was partitioned between EtOAc and aq. sat. KH$_2$PO$_4$. The organic phase was washed with brine, dried over MgSO$_4$, filtered and concentrated. The residue was purified by flash chromatography (silica gel, eluting with 80% EtOAc in hexanes) to give compound T144 (39 mg, 79% yield) as a light yellow glass. $^1$H NMR (400 MHz, CDCl$_3$) δ 9.00 (s, 1H), 8.72 (d, J=5.2 Hz, 1H), 8.28 (br s, 1H), 8.24 (dd, J=5.2, 1.6 Hz, 1H), 7.53 (m, 1H), 7.45 (td, J=7.4, 1.9 Hz, 1H), 7.35 (td, J=7.5, 1.1 Hz, 1H), 7.22 (ddd, J=9.7, 8.4, 1.1 Hz, 1H), 3.64 (m, 2H), 3.48 (m, 2H), 2.90 (s, 3H), 2.82 (m, 2H), 2.62 (m, 1H), 2.26 (td, J=12.8, 2.8 Hz, 1H), 2.13 (m, 1H), 1.81 (m, 1H), 1.56 (s, 3H), 1.33 (d, J=6.7 Hz, 3H); m/z=531 (M+1).

Compound 395: To a mixture of compound 394 (2.00 g, 11.22 mmol) in ethylene glycol (56 mL) was added p-toluenesulfonic acid monohydrate (2.13 g, 11.20 mmol) at room temperature. The mixture was stirred at room temperature for 35 min and then poured into a mixture of NaHCO$_3$ (5 g) and ice (100 g). After stirring at ambient temperature for 20 min, the mixture was extracted with EtOAc (4×50 mL). The combined organic extracts were washed with brine, dried with Na$_2$SO$_4$, filtered and concentrated. The residue was purified by flash chromatography (silica gel, eluting with 0% to 50% EtOAc in hexanes) to give compound 395 (2.12 g, 85% yield) as a viscous oil. m/z=223.1 (M+1).

Compound 396: A solution of compound 395 (1.00 g, 4.50 mmol) and water (146 µL, 8.11 mmol) in tetrahydrofuran (15 mL) was added dropwise to a stirring solution of lithium (109 mg, 15.71 mmol) in liquid ammonia (50 mL) at −78° C. under nitrogen. After addition, the cold bath was removed; the mixture was stirred at ambient temperature for 10 min; and cooled to −78° C. Allyl bromide (3.9 mL, 45.07 mmol) was added. The mixture was stirred at −78° C. for 1 h; the cold bath was removed; and ammonia was evaporated at ambient temperature. The residue was partitioned between EtOAc and aq. 10% NaH$_2$PO$_4$. The organic extract was separated, and the aqueous phase was extracted twice with EtOAc. The combined organic extracts were washed with water, dried with Na$_2$SO$_4$, filtered and concentrated. The residue was purified by flash chromatography (silica gel, eluting with 0% to 35% EtOAc in hexanes) to give compound 396 (1.06 g, 89% yield) as a viscous oil. m/z=265.1 (M+1).

Compound 397 and 398: A solution of compound 396 (1.06 g, 4.01 mmol) in EtOH (20 mL) was treated with NaBH$_4$ (76 mg, 2.01 mmol) at 0° C. After the mixture was stirred at 0° C. for 1 h, additional amount of NaBH$_4$ (20 mg, 0.53 mmol) was added, and the mixture was stirred for another 30 min. Aq. 3 N HCl (16.4 mL, 49.2 mmol) was added. The mixture was stirred at room temperature for 72 h and concentrated. The residue was extracted with EtOAc (2×20 mL). The combined organic extracts were dried with Na$_2$SO$_4$, filtered and concentrated. The residue was purified by flash chromatography (silica gel, eluting with 0% to 40% EtOAc in hexanes) to give compound 397 (402 mg, 45% yield) and compound 398 (474 mg, 53% yield) as white solid.

Compound 399: Compound 398 (471 mg, 2.11 mmol) was taken up in EtOH (8.5 mL). 2-Fluorobenzaldehyde (246 µL, 2.33 mmol) and potassium fluoride on aluminum oxide (5.5 mmol/g, 579 mg, 3.18 mmol) were added sequentially. The mixture was stirred at room temperature for 20 h; filtered through a pad of Celite®; and eluted with EtOAc. The filtrate was washed with water; dried with Na$_2$SO$_4$; filtered and concentrated. The residue was purified by flash chromatography (silica gel, eluting with 0% to 40% EtOAc in hexanes) to give compound 399 (560 mg, 80% yield) as a viscous oil. m/z=329.1 (M+1).

Compound 400: Compound 399 (180 mg, 0.55 mmol) was taken up in EtOH (5.5 mL). 2-Cyclopropyl-4-carboximidamide pyridine hydrochloride (163 mg, 0.82 mmol) and K$_2$CO$_3$ (227 mg, 1.64 mmol) were added. The reaction mixture was refluxed overnight and concentrated. The residue was partitioned between EtOAc and water. The organic extract was separated, and the aqueous phase was extracted twice with EtOAc. The combined organic extracts were washed with water; dried with Na$_2$SO$_4$; filtered and concentrated. The residue was purified by flash chromatography (silica gel, eluting with 0% to 80% acetone in hexanes) to give the product (180 mg) as a yellow glass. The compound was taken up in CH$_2$Cl$_2$ (3.7 mL). Manganese (IV) oxide (88%, 286 mg, 2.89 mmol) was added. The mixture was stirred overnight at room temperature and purified by flash chromatography (silica gel, eluted with 0% to 50% EtOAc in hexanes) to give compound 400 (145 mg, 56% yield) as a white foamy solid. m/z=470.2 (M+1).

Compound 401: To a solution of compound 400 (140 mg, 0.30 mmol) in CH$_2$Cl$_2$ (3 mL) was added Dess-Martin periodinane (190 mg, 0.45 mmol) at room temperature. After the reaction was stirred for 2 h at room temperature, aq. 10% Na$_2$SO$_3$ and aq. sat. NaHCO$_3$ were added. The mixture was extracted three times with CH$_2$Cl$_2$. The combined organic extracts were dried with Na$_2$SO$_4$, filtered and concentrated. The residue was purified by flash chromatography (silica gel, eluting with 0% to 40% EtOAc in hexanes) to give compound 401 (125 mg, 89% yield) as a white foamy solid. m/z=468.2 (M+1).

Compound 402: Compound 401 (125 mg, 0.27 mmol) was dissolved in ethyl formate (0.65 mL, 8.08 mmol) and cooled to 0° C. Sodium methoxide (25 wt. % in methanol, 0.61 mL, 2.67 mmol) was added. The mixture was stirred at room temperature for 2 h, and cooled to 0° C. Aq. 6 N HCl (0.45 mL, 2.70 mmol), EtOH (2.7 mL) and hydroxylamine hydrochloride (28 mg, 0.40 mmol) were added sequentially. The mixture was heated at 55° C. (oil bath) for 16 h, and concentrated. Aq. sat. NaHCO$_3$ was added. The mixture was extracted twice with EtOAc. The combined organic extract was dried with Na$_2$SO$_4$, filtered and concentrated. The residue was purified by flash chromatography (silica gel, eluting with 0% to 40% EtOAc in hexanes) to give compound 402 (113 mg, 86% yield) as a white foamy solid. m/z=493.2 (M+1).

Compound 403: Compound 402 (111 mg, 0.23 mmol) was dissolved in MeOH (2.4 mL). Sodium methoxide (25 wt. % in methanol, 110 µL, 0.48 mmol) was added at room temperature. The reaction mixture was stirred at 55° C. for 1 h and cooled to 0° C. Aq. 10% NaH$_2$PO$_4$ was added. The mixture was extracted twice with EtOAc. The combined organic extracts were dried with Na$_2$SO$_4$, filtered and concentrated. The residue was purified by flash chromatography (silica gel, eluting with 0% to 50% EtOAc in hexanes) to give compound 403 (107 mg, 96% yield) as a white foamy solid. m/z=493.2 (M+1).

T145: To a solution of compound 403 (23 mg, 0.047 mmol) in toluene (1 mL) was added DDQ (12 mg, 0.053 mmol). The mixture was heated at 85° C. for 1 h; cooled to room temperature; and purified by flash chromatography (silica gel, eluting with 0% to 50% EtOAc in hexanes) to give compound T145 (14 mg, 61% yield) as a light yellow foamy solid. $^1$H NMR (400 MHz, CDCl$_3$) δ 9.03 (s, 1H), 8.60 (dd, J=0.8, 5.2 Hz, 1H), 8.19 (dd, J=0.8, 1.6 Hz, 1H), 8.06 (dd, J=1.6, 5.1 Hz, 1H), 7.52 (ddt, J=1.9, 5.3, 7.9 Hz, 1H), 7.45 (dt, J=1.9, 7.4 Hz, 1H), 7.33 (dt, J=1.1, 7.5 Hz, 1H), 7.22 (m, 1H), 5.64 (m, 1H), 5.12 (m, 2H), 3.04 (m, 1H), 2.77 (dd, J=4.3, 8.7 Hz, 2H), 2.69 (td, J=4.2, 13.1 Hz, 1H), 2.48 (m, 2H), 2.19 (m, 2H), 1.78 (m, 1H), 1.55 (s, 3H), 1.12 (m, 2H), 1.05 (m, 2H); m/z=491.2 (M+1).

Compound 404: Compound 403 (85 mg, 0.17 mmol) and 10% palladium on carbon (20 mg) in EtOAc (5 mL) was hydrogenated (balloon pressure) at room temperature for 1.5 h. The mixture was filtered through a pad of Celite® and was eluted with EtOAc. The filtrate was concentrated. The residue was purified by flash chromatography (silica gel, eluting with 0% to 45% EtOAc in hexanes) to give compound 404 (68 mg, 80% yield) as a white foamy solid. m/z=495.2 (M+1).

T146: Compound 404 (68 mg, 0.14 mmol) was dissolved in dry DMF (0.3 mL), and the solution was cooled to 0° C. 1,3-dibromo-5,5-dimethylhydantoin (20 mg, 0.070 mmol) in DMF (0.4 mL) was added. After stirring the mixture at 0° C. for 1 h, pyridine (34 μL, 0.42 mmol) was added. The mixture was heated at 55° C. for 2 h and cooled to room temperature. The mixture was diluted with EtOAc and washed three times with water. The organic extract was dried with Na$_2$SO$_4$, filtered and concentrated. The residual pyridine was removed by azeotropic evaporation with toluene. The crude product was purified by flash chromatography (silica gel, eluting with 0% to 40% EtOAc in hexanes) to give partially purified product, which was purified again by flash chromatography (silica gel, eluting with 0% to 30% acetone in hexanes) to give compound T146 (41 mg, 60% yield) as a white foamy solid. $^1$H NMR (400 MHz, CDCl$_3$) δ 9.00 (s, 1H), 8.60 (dd, J=0.8, 5.2 Hz, 1H), 8.20 (dd, J=0.8, 1.6 Hz, 1H), 8.07 (dd, J=1.6, 5.2 Hz, 1H), 7.52 (dddd, J=1.9, 5.3, 7.2, 8.3 Hz, 1H), 7.45 (dt, J=1.8, 7.4 Hz, 1H), 7.34 (dt, J=1.1, 7.5 Hz, 1H), 7.21 (ddd, J=1.0, 8.3, 9.6 Hz, 1H), 2.81 (m, 2H), 2.60 (ddd, J=3.2, 4.9, 13.1 Hz, 1H), 2.46 (dt, J=2.5, 12.8 Hz, 1H), 2.21 (tt, J=4.8, 8.1 Hz, 1H), 2.09 (m, 2H), 1.81 (m, 1H), 1.69 (m, 1H), 1.53 (s, 3H), 1.34 (m, 1H), 1.20 (m, 1H), 1.12 (m, 2H), 1.04 (m, 2H), 0.93 (t, J=7.2 Hz, 3H); m/z=493.2 (M+1).

Compound 406: To a solution of compound 405 (6.52 g, 34.64 mmol) in MeCN (60 mL) was added triethylamine (9.64 mL, 69.29 mmol) and ethyl vinyl ketone (5.18 mL, 52.03 mmol) at room temperature. The mixture was heated at 75° C. for 22 h and concentrated. The residue was dissolved in MeCN (2×100 mL) and concentrated. The crude product was dried under vacuum and then dissolved in DMSO (20 mL). Pyridinium p-toluenesulfonate (8.71 g, 34.66 mmol) and D-phenylalanine (5.72 g, 34.63 mmol) were added at room temperature. The mixture was heated at 45° C. for 74 h and cooled to room temperature. MTBE (80 mL), aq. sat. NH$_4$Cl (40 mL) and water (40 mL) were added. The mixture was stirred for 5 min. The organic phase was separated. The aqueous phase was extracted with MTBE (2×40 mL). The combined organic extracts were washed with water (3×40 mL), dried with Na$_2$SO$_4$, filtered and concentrated. The residue was purified by flash chromatography (silica gel, eluting with 0% to 30% EtOAc in hexanes) to give compound 406 (6.13 g, 70% yield) as a yellow oil. m/z=255.1 (M+1).

Compound 407: To a solution of compound 406 (4.255 g, 16.73 mmol) was added NaBH$_4$ (210 mg, 5.55 mmol) at 0° C. After the mixture was stirred at 0° C. for 1 h, additional amount of NaBH$_4$ (30 mg, 0.79 mmol) was added, and the mixture was stirred for another 30 min. Aq. 10% NaH$_2$PO$_4$ was added. The mixture was stirred for 5 min and concentrated. The residue was extracted twice with EtOAc. The combined organic extracts were dried with Na$_2$SO$_4$, filtered and concentrated. The residue was purified by flash chromatography (silica gel, eluting with 0% to 50% EtOAc in hexanes) to give compound 407 (3.330 g, 78% yield, 79% ee) as a white solid. Compound 407 was dissolved in MTBE (30 mL) at 50° C. and treated with hexanes (30 mL). The mixture was cooled to room temperature and then kept at 4° C. for 16 h. The precipitated solid was collected by filtration; washed with hexanes/MTBE (2/1 v/v); and dried under vacuum to give compound 407 (1.758 g, 41% yield, 99% ee) as a white solid. m/z=257.1 (M+1).

Compound 408: Compound 407 (1.003 mg, 3.92 mmol), 10% palladium on carbon (200 mg) in pyridine (2 mL) and THF (8 mL) was hydrogenated (balloon pressure) at room temperature for 16 h. The mixture was filtered through a pad of Celite® and was eluted with EtOAc. The filtrate was concentrated. The residual pyridine was removed by azeotropic evaporation with toluene (2×50 mL). The crude product was dissolved in EtOH (8 mL). Aq. 3 N HCl (3 mL, 9 mmol) was added. The mixture was stirred at room temperature for 2 h and concentrated. The residue was partitioned between EtOAc and water. The organic phase was separated. The aqueous phase was extracted with EtOAc. The combined organic extracts were washed with water, dried with Na$_2$SO$_4$, filtered and concentrated. The residue was purified by flash chromatography (silica gel, eluting with 0% to 50% EtOAc in hexanes) to give compound 408 (938 mg, 93% yield) as a viscous oil. m/z=241.1 (M−17).

Compound 409: A mixture of compound 408 (935 mg, 3.62 mmol), ethylene glycol (1.01 mL, 18.11 mmol), p-toluenesulfonic acid monohydrate (69 mg, 0.36 mmol) in toluene (20 mL) was refluxed with Dean-Stark trap for 3 h. After cooled to room temperature, the mixture was washed with aq. sat. NaHCO$_3$ and water. The aqueous washes were extracted twice with EtOAc. The combined organic extracts were washed with water, dried with Na$_2$SO$_4$, filtered and concentrated to give compound 409 (1.20 g) as a viscous oil. m/z=285.2 (M−17).

Compound 410: Sodium phosphate dibasic (21 mg, 0.15 mmol) and sodium tungstate dihydrate (12 mg, 0.036 mmol) were dissolved in aq. 30% H$_2$O$_2$ (0.43 mL, 4.21 mmol) to give a yellow solution. The solution was added dropwise to a solution of compound 409 (1.20 g, 3.62 mmol) in N,N-dimethylacetamide (7 mL) at 60° C. The mixture was heated at 90° C. for 3 h and cooled to room temperature. EtOAc was added. The mixture was washed with water. The organic extract was dried over Na$_2$SO$_4$, filtered and concentrated to give the crude product as a white solid. The crude product was recrystallized from MTBE/hexanes to give compound 410 (837 mg, 77% yield from compound 408) as a white solid. The mother liquor was concentrated, and the residue was purified by flash chromatography (silica gel, eluting with 0% to 30% EtOAc in hexanes) to give the 2 crop of compound 410 (150 mg, 14% yield from compound 408) as a viscous oil. m/z=301.1 (M+1).

Compound 411: Compound 410 (450 mg, 1.50 mmol) was taken up in EtOH (6 mL). 2-Fluorobenzaldehyde (190 µL, 1.80 mmol) and potassium fluoride on aluminum oxide (5.5 mmol/g, 409 mg, 2.25 mmol) were added sequentially. After the mixture was stirred at room temperature for 1 h, THF (1.5 mL) was added. The mixture was continued stirring for another 60 h; diluted with EtOAc; filtered through a pad of silica gel; and eluted with EtOAc. The filtrate was concentrated. The residue was purified by flash chromatography (silica gel, eluting with 0% to 40% EtOAc in hexanes) to give compound 411 (480 mg, 79% yield) as a white solid. m/z=407.2 (M+1).

Compound 412a: Compound 411 (150 mg, 0.37 mmol) was taken up in EtOH (3.7 mL). 2-Cyclopropyl-4-carboximidamide pyridine hydrochloride (110 mg, 0.56 mmol) and $K_2CO_3$ (153 mg, 1.11 mmol) were added. The reaction mixture was refluxed for 18 h; cooled to room temperature; diluted with EtOAc; and washed with water. The organic extract was separated, and the aqueous phase was extracted with EtOAc. The combined organic extracts were dried with $Na_2SO_4$; filtered and concentrated. The crude compound was taken up in $CH_2Cl_2$ (3.7 mL). DDQ (84 mg, 0.37 mmol) was added. The mixture was stirred at room temperature for 1 h; diluted with MTBE (30 mL) and aq. sat. $NaHCO_3$ (30 mL); and stirred for 15 min. The organic phase was separated; washed with sat. aq. $NaHCO_3$; dried with $Na_2SO_4$; filtered and concentrated. The residue was purified by flash chromatography (silica gel, eluted with 0% to 40% EtOAc in hexanes) to give compound 412a (40 mg, 20% yield) as a white foamy solid. m/z=548.3 (M+1).

Compound 413a: A solution of compound 412a (39 mg, 0.071 mmol) in MeOH (0.7 mL) and THF (0.35 mL) was treated with aq. 3 N HCl solution (0.24 mL, 0.72 mmol). After stirring at room temperature overnight, the mixture was partitioned between EtOAc and sat. aq. $NaHCO_3$. The organic extract was separated, and the aqueous phase was extracted twice with EtOAc. The combined organic extracts were dried over $Na_2SO_4$, filtered and concentrated to give compound 413a (35 mg, 97% yield) as a white foamy solid. m/z=504.3 (M+1).

Compound 414a: Compound 413a (35 mg, 0.069 mmol) was dissolved in ethyl formate (0.17 mL, 2.11 mmol) and cooled to 0° C. Sodium methoxide (25 wt. % in methanol, 0.16 mL, 0.70 mmol) was added. The mixture was stirred at room temperature for 2 h and cooled to 0° C. Aq. 6 N HCl (0.12 mL, 0.72 mmol), EtOH (0.7 mL) and hydroxylamine hydrochloride (8 mg, 0.12 mmol) were added sequentially. The mixture was heated at 55° C. (oil bath) for 14 h and concentrated. Aq. sat. $NaHCO_3$ was added. The mixture was extracted twice with EtOAc. The combined organic extracts were dried with $Na_2SO_4$, filtered and concentrated. The residue was purified by flash chromatography (silica gel, eluting with 0% to 50% EtOAc in hexanes) to give compound 414a (28 mg, 76% yield) as a yellow foamy solid. m/z=529.2 (M+1).

Compound 415a: Compound 414a (26 mg, 0.049 mmol) was dissolved in MeOH (0.5 mL). Sodium methoxide (25 wt. % in methanol, 24 µL, 0.10 mmol) was added at room temperature. The reaction mixture was stirred at 55° C. for 1 h and cooled to room temperature. Aq. 10% $NaH_2PO_4$ (10 mL) was added. The mixture was extracted with EtOAc (2×15 mL). The combined organic extracts were dried with $Na_2SO_4$, filtered and concentrated. The residue was purified by flash chromatography (silica gel, eluting with 0% to 50% EtOAc in hexanes) to give compound 415a (23 mg, 88% yield) as a light yellow foamy solid. m/z=529.2 (M+1).

T147: Compound 415a (23 mg, 0.044 mmol) was dissolved in dry DMF (0.22 mL), and the solution was cooled to 0° C. 1,3-dibromo-5,5-dimethylhydantoin (6.2 mg, 0.022 mmol) in DMF (0.1 mL) was added. After stirring the mixture at 0° C. for 1 h, pyridine (11 µL, 0.14 mmol) was added. The mixture was heated at 55° C. for 2.5 h and cooled to room temperature. The mixture was diluted with EtOAc (20 mL) and washed with water (3×10 mL). The organic extract was dried with $Na_2SO_4$, filtered and concentrated. The residual pyridine was removed by azeotropic evaporation with toluene. The crude product was purified by flash chromatography (silica gel, eluting with 0% to 30% acetone in hexanes) to give compound T147 (18 mg, 78% yield) as a light yellow foamy solid. $^1$H NMR (400 MHz, $CDCl_3$) δ 9.07 (s, 1H), 8.54 (dd, J=0.8, 5.2 Hz, 1H), 8.11 (m, 1H), 7.98 (dd, J=1.6, 5.2 Hz, 1H), 7.55 (m, 2H), 7.36 (m, 4H), 7.26 (m, 1H), 6.89 (m, 2H), 2.93 (m, 2H), 2.50 (dd, J=6.4, 12.9 Hz, 1H), 2.43 (dt, J=2.5, 12.7 Hz, 1H), 2.14 (tt, J=4.9, 8.2 Hz, 1H), 1.93 (m, 1H), 1.63 (m, 1H), 1.19 (d, J=6.3 Hz, 3H), 1.07 (m, 2H), 1.00 (m, 2H); m/z=527.2 (M+1).

Compound 412b: Compound 411 (150 mg, 0.37 mmol) was taken up in EtOH (3.7 mL). 4-Quinolinecarboximidamide hydrochloride (115 mg, 0.55 mmol) and $K_2CO_3$ (153 mg, 1.11 mmol) were added. The reaction mixture was refluxed for 18 h; cooled to room temperature; diluted with EtOAc; and washed with water. The organic extract was separated, and the aqueous phase was extracted with EtOAc. The combined organic extracts were dried with $Na_2SO_4$; filtered and concentrated. The crude compound was taken up in $CH_2Cl_2$ (3.7 mL). DDQ (84 mg, 0.37 mmol) was added. The mixture was stirred at room temperature for 1 h; diluted with MTBE (30 mL) and aq. sat. $NaHCO_3$ (30 mL); and stirred for 15 min. The organic phase was separated; washed with sat. aq. $NaHCO_3$; dried with $Na_2SO_4$; filtered and concentrated. The residue was purified by flash chromatography (silica gel, eluted with 0% to 50% EtOAc in hexanes) to give compound 412b (71 mg, 35% yield). m/z=558.2 (M+1).

Compound 413b: A solution of compound 412b (69 mg, 0.12 mmol) in MeOH (1.2 mL) and THF (0.6 mL) was treated with aq. 3 N HCl solution (0.41 mL, 1.23 mmol). After stirring at room temperature overnight, the mixture was partitioned between EtOAc and sat. aq. $NaHCO_3$. The organic extract was separated, and the aqueous phase was extracted twice with EtOAc. The combined organic extracts were dried over $Na_2SO_4$, filtered and concentrated. The residue was purified by flash chromatography (silica gel, eluted with 0% to 70% EtOAc in hexanes) to give compound 413b (56 mg, 88% yield). m/z=514.2 (M+1).

Compound 414b: Compound 413b (56 mg, 0.11 mmol) was dissolved in ethyl formate (0.26 mL, 3.23 mmol) and cooled to 0° C. Sodium methoxide (25 wt. % in methanol, 0.25 mL, 1.09 mmol) was added. The mixture was stirred at room temperature for 2 h and cooled to 0° C. Aq. 6 N HCl (0.18 mL, 1.08 mmol), EtOH (1.1 mL) and hydroxylamine hydrochloride (12 mg, 0.17 mmol) were added sequentially. The mixture was heated at 55° C. (oil bath) for 14 h and concentrated. Aq. sat. $NaHCO_3$ was added. The mixture was extracted twice with EtOAc. The combined organic extracts were dried with $Na_2SO_4$, filtered and concentrated. The residue was purified by flash chromatography (silica gel, eluting with 0% to 70% EtOAc in hexanes) to give compound 414b (41 mg, 70% yield) as a light yellow foamy solid. m/z=539.2 (M+1).

Compound 415b: Compound 414b (41 mg, 0.076 mmol) was dissolved in MeOH (0.8 mL). Sodium methoxide (25 wt. % in methanol, 37 µL, 0.16 mmol) was added at room temperature. The reaction mixture was stirred at 55° C. for 1 h, and cooled to room temperature. Aq. 10% NaH$_2$PO$_4$ (10 mL) was added. The mixture was extracted with EtOAc (2×15 mL). The combined organic extracts were dried with Na$_2$SO$_4$, filtered and concentrated. The residue was purified by flash chromatography (silica gel, eluting with 0% to 40% acetone in hexanes) to give compound 415b (27 mg, 66% yield) as a white foamy solid. m/z=539.2 (M+1).

T148: Compound 415b (27 mg, 0.050 mmol) was dissolved in dry DMF (0.25 mL), and the solution was cooled to 0° C. 1,3-dibromo-5,5-dimethylhydantoin (7.2 mg, 0.025 mmol) in DMF (0.1 mL) was added. After stirring the mixture at 0° C. for 1 h, pyridine (12 µL, 0.15 mmol) was added. The mixture was heated at 55° C. for 2.5 h and cooled to room temperature. The mixture was diluted with EtOAc (20 mL) and washed with water (3×10 mL). The organic extract was dried with Na$_2$SO$_4$, filtered and concentrated. The residual pyridine was removed by azeotropic evaporation with toluene. The crude product was purified by flash chromatography (silica gel, eluting with 0% to 35% acetone in hexanes) to give compound T148 (23 mg, 85% yield) as a light yellow foamy solid. $^1$H NMR (400 MHz, CDCl$_3$) δ 9.02 (d, J=4.8 Hz, 1H), 8.97 (s, 1H), 8.48 (dd, J=0.8, 8.4 Hz, 1H), 8.16 (dd, J=0.8, 8.0 Hz, 1H), 7.96 (d, J=4.8 Hz, 1H), 7.71 (ddd, J=8.4, 6.9, 1.4 Hz, 1H), 7.62-7.51 (m, 2H), 7.48 (ddd, J=8.4, 6.9, 1.3 Hz, 1H), 7.43-7.26 (m, 5H), 6.97-6.89 (m, 2H), 3.05-2.93 (m, 2H), 2.58-2.43 (m, 2H), 1.98 (m, 1H), 1.68 (m, 1H), 1.21 (d, J=6.0 Hz, 3H); m/z=537.2 (M+1).

Compound 416: Compound 188c (430 mg, 0.95 mmol) was taken up in ethyl formate (2.29 mL, 28.5 mmol). Sodium methoxide (25 wt. % in MeOH, 3.27 mL, 14.28 mmol) was added. After stirring at room temperature for 4 h, the reaction mixture was neutralized with aq. sat. KH$_2$PO$_4$ and extracted with EtOAc. The organic extract was washed with brine, dried with Na$_2$SO$_4$, filtered, and concentrated to give compound 416 (430 mg, 94% yield) as a yellow foam. m/z=480.2 (M+1).

Compound 417: Compound 416 (430 mg, 0.90 mmol) was taken up in CH$_2$Cl$_2$ (4.5 mL). MgSO$_4$ (431.8 mg, 3.59 mmol), p-toluenesulfonic acid monohydrate (17.1 mg, 0.09 mmol) and N-methylaniline (0.214 mL, 1.97 mmol) were added. The reaction mixture was stirred at room temperature for 17 h under nitrogen atmosphere, filtered and concentrated. The residue was purified by flash chromatography (silica gel, eluting with 0% to 50% EtOAc in hexanes) to give compound 417 (327 mg, 64% yield) as a yellow foam. m/z=569.2 (M+1).

Compound 418: To a solution of potassium tert-butoxide (71 mg, 0.63 mmol) in THF (1 mL) under argon was added a solution of compound 416 (120 mg, 0.21 mmol) in THF (1 mL) at 0° C. The mixture was stirred at 0° C. for 10 min and treated with methyl iodide (39 µL, 0.63 mmol). After stirring at 0° C. for another 2 h, the reaction mixture was quenched by adding aq. sat. NH$_4$Cl (10 mL) and was extracted with EtOAc. The organic extract was dried over Na$_2$SO$_4$, filtered and concentrated. The residue was purified by flash chromatography (silica gel, eluting with 0% to 50% EtOAc in hexanes) to give compound 418 (71 mg, 58% yield) as a pale yellow foam. m/z=583.3(M+1).

Compound 419: To a solution of compound 418 (70 mg, 0.12 mmol) in EtOH (1.2 mL) was added aq. 1 N HCl (0.24 mL, 0.24 mmol) and hydroxylamine hydrochloride (12.5 mg, 0.18 mmol) sequentially at room temperature. The mixture was heated at 55° C. for 4 h and concentrated. The residue was diluted with aq. sat. NaHCO$_3$ and extracted twice with EtOAc. The combined organic extracts were dried with Na$_2$SO$_4$, filtered and concentrated. The residue was purified by flash chromatography (silica gel, eluting with 0% to 60% EtOAc in hexanes) to give compound 419 (44 mg, 74% yield) as a white foam. m/z=491.2 (M+1).

Compound 420: To a solution of compound 419 (44 mg, 0.090 mmol) in MeOH (0.89 mL) was added sodium methoxide (25 wt. % solution in MeOH, 30.8 µL, 0.134 mmol). The reaction mixture was stirred at 55° C. for 2 h, cooled to 0° C., and then neutralized by adding aq. 10% NaH$_2$PO$_4$. The mixture was diluted with water and extracted twice with EtOAc. The combined organic extracts were dried with Na$_2$SO$_4$, filtered and concentrated to give compound 420 (40 mg, 91% yield) as a pale yellow solid, which was used in the subsequent step without further purification. m/z=491.2 (M+1).

T149: A solution of compound 420 (40 mg, 0.082 mmol) in anhydrous DMF (0.5 mL) was cooled to 0° C. under nitrogen and treated dropwise with a solution of 1,3-dibromo-5,5-dimethylhydantoin (11.6 mg, 0.041 mmol) in anhydrous DMF (0.3 mL). After stirring at 0° C. for 2 h, anhydrous pyridine (19.8 µL, 0.25 mmol) was added. The cold bath was removed, and the reaction mixture was heated at 55° C. for 2 h. Upon cooling to room temperature, the reaction mixture was partitioned between EtOAc and aq. sat. KH$_2$PO$_4$. The organic phase was washed with brine, dried over MgSO$_4$, filtered and concentrated. The residue was purified by flash chromatography (silica gel, eluting with 0% to 40% acetone in hexanes) to give partially pure product, which was purified again by flash chromatography (silica gel, eluting with 0% to 30% EtOAc in CH$_2$Cl$_2$) to give T149 (13.0 mg, 33% yield) as a yellow foam. $^1$H NMR (400 MHz, CDCl$_3$) δ 9.16 (m, 1H), 8.97 (d, J=3.8 Hz, 1H), 8.96 (s, 1H), 8.30 (dd, J=1.3, 7.3 Hz, 1H), 8.27 (m, 1H), 7.86 (dd, J=7.3, 8.5 Hz, 1H), 7.49 (m, 3H), 7.32 (dt, J=1.1, 7.5 Hz, 1H), 7.23 (m, 1H), 2.89 (m, 2H), 2.39 (dd, J=2.9, 12.1 Hz, 1H), 2.01 (m, 2H), 1.65 (s, 3H), 1.33 (s, 3H), 1.28 (s, 3H); m/z=489.2 (M+1).

Compound 421: A solution of compound 387 (1.09 g, 2.30 mmol) and methyl (triphenylphosphoranylidene)acetate (1.16 g, 3.47 mmol) in benzene (25 mL) was heated at 80° C. under nitrogen. After 2 h, the solution was cooled and concentrated. The residue was purified by flash chromatography (silica gel, eluting with 30% EtOAc in hexanes) to give compound 421 (1.36 g) as a light yellow foamy solid. m/z=530 (M+1). $^1$H NMR spectrum indicates compound 421 is a (95:5) mixture of (E:Z) isomers.

Compound 422: A solution of compound 421 (1.36 g, 2.30 mmol) in EtOAc (25 mL) was treated with 10% palladium on carbon (0.5 g). The mixture was hydrogenated (balloon pressure) at room temperature for 16 h. The catalyst was removed by filtration, and the filtrate was concentrated to give compound 422 (1.23 g, quantitative yield from compound 420) as a light yellow foamy solid. m/z=532 (M+1).

Compound 423: A solution of compound 422 (1.23 g, 2.31 mmol) in MeOH (25 mL) was treated with aq. 3 N HCl (4.0 mL, 12.0 mmol). After stirring at room temperature under nitrogen overnight, the mixture was concentrated. Sat. aq. NaHCO$_3$ solution (50 mL) was added, and the mixture was extracted with EtOAc (50 mL). The organic extract was washed with brine (50 mL), dried over MgSO$_4$, filtered and concentrated to give compound 423 (1.00 g, 89% yield) as a light yellow foamy solid. m/z=488 (M+1).

Compound 424: To a stirring solution at 0° C. (under a drying tube) of compound 423 (1.00 g, 2.06 mmol) in ethyl formate (10 mL, 124.33 mmol) was added dropwise sodium methoxide (30 wt. % solution in methanol, 2.0 mL, 10.7 mmol). After addition, the ice-bath was removed and the mixture was stirred at room temperature for 16 h. The resultant yellow suspension was partitioned between sat. aq. KH$_2$PO$_4$ (50 mL) and EtOAc (50 mL). The organic extract was washed with brine (50 mL), dried over MgSO$_4$, filtered and concentrated to give compound 424 (1.10 g, quantitative yield) as a light yellow foamy solid. m/z=530 (M+1).

Compound 425: To a stirring solution of compound 424 (1.10 g, 2.06 mmol) and acetic acid (1.2 mL, 21.0 mmol) in EtOH (20 mL) was added hydroxylamine hydrochloride (0.22 g, 3.17 mmol) at room temperature under nitrogen. The mixture was stirred at 60° C. for 2 h and then at room temperature overnight. After concentration, the residue was carefully partitioned between sat. aq. NaHCO$_3$ solution (50 mL) and EtOAc (50 mL). The organic extract was washed with brine (50 mL), dried over MgSO$_4$, filtered and concentrated to give compound 425 (1.06 g, 98% yield) as a yellow foamy oil. m/z=527 (M+1).

Compound 426: A mixture of compound 425 (1.06 g, 2.01 mmol) and potassium carbonate (1.44 g, 10.42 mmol) in MeOH (20 mL) was stirred at room temperature under nitrogen overnight. The mixture was filtered, and the filtrate was concentrated. The residue was partitioned between EtOAc (50 mL) and sat. aq. KH$_2$PO$_4$ solution (50 mL). The organic extract was washed with brine (25 mL), dried over MgSO$_4$, filtered and concentrated to give compound 426 (1.04 g, quantitative yield) as a dark brown foamy solid. m/z=499 (M+1).

T150: To a stirring solution of compound 426 (1.04 g, 2.01 mmol) at 0° C. under nitrogen in degassed DMF (10 mL) was added dropwise a solution of 1,3-dibromo-5,5-dimethylhydantoin (0.33 g, 1.15 mmol) in DMF (2 mL). After stirring at 0° C. for 30 min, pyridine (1.7 mL, 21.0 mmol) was added. The ice-bath was removed; the mixture was heated at 60° C. for 4 h; cooled, and concentrated. The residue was partitioned between sat. aq. KH$_2$PO$_4$ (50 mL) and EtOAc (50 mL). The organic extract was washed with brine (50 mL), dried over MgSO$_4$, filtered, and concentrated. The residue was purified by flash chromatography (silica gel, eluting with 5% MeOH in CHCl$_3$) to give compound T150 (0.61 g, 61% yield) as light yellow foamy solid. $^1$H NMR (400 MHz, CDCl$_3$) δ 8.98 (s, 1H), 8.67 (dd, J=0.8, 5.4 Hz, 1H), 8.37 (dd, J=1.6, 5.4 Hz, 1H), 8.34 (br s, 1H), 7.54 (m, 1H), 7.44 (dt, J=1.9, 7.4 Hz, 1H), 7.35 (dt, J=1.1, 7.5 Hz, 1H), 7.23 (ddd, J=1.2, 8.5, 9.6 Hz, 1H), 3.33 (m, 2H), 2.91 (m, 2H), 2.86 (m, 2H), 2.63 (qd, J=6.7, 13.5 Hz, 1H), 2.27 (dt, J=2.7, 12.8 Hz, 1H), 2.14 (m, 1H), 1.81 (m, 1H), 1.56 (s, 3H), 1.33 (d, J=6.7 Hz, 3H); m/z=497 (M+1).

T151: A solution of compound T150 (77 mg, 0.16 mmol) and aq. 1 N HCl (0.23 mL, 0.23 mmol) in EtOH (10 mL) was heated at 50° C. under nitrogen. After 16 h, the solution was cooled, and concentrated. The residue was carefully partitioned between aq. NaHCO$_3$ (25 mL) and EtOAc (25 mL). The organic extract was washed with brine (25 mL), dried over MgSO$_4$, filtered, and concentrated. The residue was purified by flash chromatography (silica gel, eluting with 50% EtOAc in hexanes) to give compound T151 (28 mg, 34% yield) as an off-white foamy solid. $^1$H NMR (400 MHz, CDCl$_3$) δ 9.01 (s, 1H), 8.70 (dd, J=0.8, 5.5 Hz, 1H), 8.22 (m, 1H), 8.17 (dd, J=1.6, 5.1 Hz, 1H), 7.52 (m, 1H), 7.44 (dt, J=1.8, 7.4 Hz, 1H), 7.34 (dt, J=1.0, 7.5 Hz, 1H), 7.21 (ddd, J=1.0, 8.3, 9.6 Hz, 1H), 4.14 (q, J=7.2 Hz, 2H), 3.25 (t, J=7.5 Hz, 2H), 2.87 (t, J=7.6 Hz, 2H), 2.81 (m, 2H), 2.62 (qd, J=6.7, 13.4 Hz, 1H), 2.26 (dt, J=2.7, 12.8 Hz, 1H), 2.12 (dd, J=6.7, 13.8 Hz, 1H), 1.79 (qd, J=7.0, 12.7 Hz, 1H), 1.55 (s, 3H), 1.32 (d, J=6.7 Hz, 3H), 1.23 (t, J=7.2 Hz, 3H); m/z=547 (M+Na).

T152: A solution of compound T150 (68 mg, 0.14 mmol), dimethylamine hydrochloride (14 mg, 0.17 mmol) and HATU (62 mg, 0.16 mmol) in CH$_2$Cl$_2$ (5 mL) at 0° C. under nitrogen was treated with dropwise addition of a solution of N,N-diisopropylethylamine (54 mg, 0.42 mmol) in CH$_2$Cl$_2$ (1 mL). The reaction was allowed to slowly warm to room temperature overnight and then concentrated. The residue was partitioned between aq. KH$_2$PO$_4$ (25 mL) and EtOAc (25 mL). The organic extract was washed with brine (25 mL), dried over MgSO$_4$, filtered, and concentrated. The residue was purified by flash chromatography (silica gel, eluting with 2% MeOH in CHCl$_3$) to give compound T152 (31 mg, 43% yield) as light yellow foamy solid. $^1$H NMR (400 MHz, CDCl$_3$) δ 9.01 (s, 1H), 8.69 (dd, J=0.8, 1.6 Hz, 1H), 8.26 (dd, J=0.8, 1.6 Hz, 1H), 8.15 (dd, J=1.6, 5.2 Hz, 1H), 7.51 (m, 1H), 7.45 (dt, J=1.9, 7.4 Hz, 1H), 7.34 (dt, J=1.1, 7.5 Hz, 1H), 7.21 (ddd, J=1.0, 8.4, 9.7 Hz, 1H), 3.27 (t, J=7.5 Hz, 2H), 3.04 (s, 3H), 2.94 (s, 3H), 2.86 (m, 4H), 2.62 (qd, J=6.7, 13.4 Hz, 1H), 2.26 (dt, J=6.7, 13.4 Hz, 1H), 2.12 (m, 1H), 1.81 (m, 1H), 1.55 (s, 3H), 1.33 (d, J=6.7 Hz, 3H); m/z=524 (M+1).

Compound 427: A solution of compound 391 (350 mg, 0.773 mmol) in EtOH (25 mL) was treated with sodium ethylsulfonate (897 mg, 7.73 mmol) and glacial acetic acid (0.45 mL, 7.86 mmol). The reaction mixture was stirred under nitrogen at 60° C. for 6 h and the solvent was removed in vacuo. The residue was partitioned between aq. 10% NH$_4$OH and EtOAc. The organic phase was washed with brine, dried over MgSO$_4$, filtered, and concentrated. The residue was purified by flash chromatography (silica gel, eluting with EtOAc) to give compound 427 (123 mg, 29% yield) as an orange glass. m/z=547 (M+1).

Compound 428: A mixture of compound 427 (123 mg, 0.225 mmol) and potassium carbonate (62 mg, 0.450 mmol) in MeOH (10 mL) was stirred under nitrogen at room temperature for 26 h. The reaction mixture was concentrated and the residue was partitioned between EtOAc and aq. sat. KH$_2$PO$_4$. The organic phase was washed with brine, dried over MgSO$_4$, filtered and concentrated give compound 428 (112 mg, 91% yield) as an orange glass, which was used without further purification.

T153: A solution of compound 428 (110 mg, 0.201 mmol) in anhydrous DMF (4 mL) cooled to 0° C. under nitrogen, was treated dropwise with a solution of 1,3-dibromo-5,5-dimethylhydantoin (32 mg, 0.111 mmol) in anhydrous DMF (2 mL). After stirring at 0° C. for 30 min, anhydrous pyridine (0.16 mL, 1.98 mmol) was added. The cold bath was removed, and the reaction mixture was heated at 60° C. for 4 h. Upon cooling to room temperature, the reaction mixture was partitioned between EtOAc and aq. sat. KH$_2$PO$_4$. The organic phase was washed with brine, dried over MgSO$_4$, filtered and concentrated. The residue was purified by flash chromatography (silica gel, eluting with 20% EtOAc in hexanes) to give impure compound T153 (69 mg) as an orange glass. The product was taken up in EtOAc and washed five times with water to remove residual 5,5-dimethylhydantoin. The organic phase was dried over MgSO$_4$, filtered and concentrated to give compound T153 (44 mg, 40% yield) as an orange glass. $^1$H NMR (400 MHz, CDCl$_3$) δ 9.00 (s, 1H), 8.72 (dd, J=0.8, 5.1 Hz, 1H), 8.28 (m, 1H), 8.24 (dd, J=1.6, 5.1 Hz, 1H), 7.53 (m, 1H), 7.45 (dt, J=1.9, 7.4 Hz, 1H), 7.35 (dt, J=1.1, 7.5 Hz, 1H), 7.22 (ddd, J=1.1, 8.4, 9.6 Hz, 1H), 3.58 (m, 2H), 3.46 (m, 2H), 2.99 (q, J=7.5 Hz, 2H), 2.83 (m, 2H), 2.63 (qd, J=6.7, 13.4 Hz, 1H), 2.26 (dt, J=2.7, 12.8 Hz, 1H), 2.13 (m, 1H), 1.81 (m, 1H), 1.56 (s, 3H), 1.42 (t, J=7.5 Hz, 3H), 1.33 (d, J=6.7 Hz, 3H); m/z=545 (M+1).

Compound 429: To a stirring solution of compound 136 (0.61 g, 1.39 mmol) in $CH_2Cl_2$ (15 mL) at room temperature under nitrogen was added portionwise 3-chloroperoxybenzoic acid 77%, 0.34 g, 1.52 mmol) over 10 min. After 1 h, the solution was washed with aq. 1 N NaOH solution (25 mL) and brine (25 mL). The organic extract was dried over $MgSO_4$, filtered and concentrated to give compound 429 (0.61 g, 96% yield) as a light yellow foamy solid, which was used without further purification. m/z=457 (M+1).

Compound 430: To a solution of compound 429 (0.61 g, 1.34 mmol) in $CH_2Cl_2$ (20 mL) was added trifluoroacetic anhydride (1.0 mL, 7.2 mmol) dropwise. After stirring at room temperature for 16 h, the solution was concentrated. The residue was mixed with sat. aq. $NaHCO_3$ (50 mL) and EtOAc (50 mL). The mixture was stirred for 1 h. The organic layer were separated; washed with brine (50 mL); dried over $MgSO_4$; filtered and concentrated. The residue was purified by flash chromatography (silica gel, eluting with EtOAc) to give compound 430 (0.34 g, 56% yield) as a yellow-orange foamy solid. m/z=457 (M+1, 100%).

Compound 431: To a stirring solution of compound 430 (0.34 g, 0.74 mmol), triethylamine (0.13 mL, 0.93 mmol) and catalytic amount of 4-dimethylaminopyridine in $CH_2Cl_2$ (10 mL) at 0° C. under nitrogen was added dropwise a solution of methanesulfonyl chloride (0.10 g, 0.87 mmol) in $CH_2Cl_2$ (2 mL). After stirring at 0° C. 15 min, the mixture was washed aq. sat. $KH_2PO_4$ (25 mL) and brine (25 mL). The organic extract was dried over $MgSO_4$, filtered and concentrated to give compound 431 (0.32 g, 81% yield) as a light yellow-green foamy solid, which was used in the next reaction immediately. m/z=535 (M+1).

Compound 432: A solution of compound 431 (0.32 g, 0.60 mmol) and sodium ethylsulfinate (77 mg, 0.66 mmol) in DMF (6 mL) was stirred at room temperature under nitrogen overnight. The mixture was partitioned between aq. sat. $KH_2PO_4$ (50 mL) and EtOAc (50 mL). The organic extract was washed with brine (50 mL), dried over $MgSO_4$, filtered and concentrated to give compound 432 (0.28 g, 88% yield) as a tan foamy solid. m/z=533 (M+1).

Compound 433: A mixture of compound 432 (0.28 g, 0.53 mmol) and potassium carbonate (0.37 g, 2.68 mmol) in MeOH (5 mL) was stirred at room temperature under nitrogen overnight. The mixture was concentrated, and the residue was partitioned between EtOAc (25 mL) and aq. sat. $KH_2PO_4$ solution (25 mL). The organic extract was washed with brine (25 mL), dried over $MgSO_4$, filtered, and concentrated. The residue was purified by flash chromatography (silica gel, eluting with 70% EtOAc in hexanes) to give compound 433 (0.21 g, 75% yield) as a light yellow foamy solid. m/z=533 (M+1).

T154: To a stirring solution of compound 433 (0.21 g, 0.39 mmol) in degassed DMF (5 mL) at 0° C. under nitrogen was added dropwise a solution of 1,3-dibromo-5,5-dimethylhydantoin (63 mg, 0.22 mmol) in DMF (1 mL). After stirring at 0° C. for 30 min, pyridine (0.33 mL, 4.08 mmol) was added. The ice-bath was removed. The mixture was heated at 60° C. for 4 h, cooled, and concentrated. The residue was partitioned between aq. sat. $KH_2PO_4$ (25 mL) and EtOAc (25 mL). The organic extract was washed with brine (25 mL), dried over $MgSO_4$, filtered, and concentrated. The residue was purified by flash chromatography (silica gel, eluting with 75% EtOAc in hexanes) to give partially purified product, which was purified again by flash chromatography (silica gel, eluting with 2% MeOH in $CHCl_3$) to give compound T154 (44 mg, 21% yield) as an off-white solid. $^1$H NMR (400 MHz, $CDCl_3$) δ 8.99 (s, 1H), 8.78 (dd, J=0.8, 5.2 Hz, 1H), 8.49 (dd, J=0.9, 1.6 Hz, 1H), 8.37 (dd, J=1.6, 5.2 Hz, 1H), 7.53 (m, 1H), 7.45 (dt, J=1.9, 7.4 Hz, 1H), 7.34 (dt, J=1.1, 7.5 Hz, 1H), 7.21 (m, 1H), 4.53 (s, 2H), 3.77 (q, J=7.4 Hz, 2H), 2.84 (m, 2H), 2.63 (qd, J=6.7, 13.4 Hz, 1H), 2.26 (dt, J=2.7, 12.8 Hz, 1H), 2.13 (m, 1H), 1.80 (qd, J=7.1, 12.9 Hz, 1H), 1.55 (s, 3H), 1.45 (t, J=7.5 Hz, 3H), 1.33 (d, J=6.7 Hz, 3H); m/z=531 (M+1).

Compound 434: Compound 434 was synthesized using the reported procedure (Bradshaw, et al., 2009). The compound was checked by chiral HPLC, and the optical purity is 94% ee. m/z=205 (M+1).

Compound 435: A solution of sodium borohydride (16 mg, 0.42 mmol) in EtOH (5 mL) was added to a 0° C. solution of compound 434 (350 mg, 1.71 mmol) in EtOH (10 mL). The reaction was stirred at 0° C. for 1 h and quenched with acetic acid (210 mg, 3.50 mmol). The reaction mixture was warmed to room temperature and concentrated. The residue was purified by flash chromatography (silica gel, eluting with 0% to 30% EtOAc in hexanes) to give compound 435 (250 mg, 71% yield) as an oil. m/z=207 (M+1).

Compound 436: Liquid ammonia (50 mL) was condensed in a two-necked flask at −78° C. Lithium wire (250 mg, 36.02 mmol) was added in small portions. After the lithium wire was dissolved, a solution of compound 435 (3.7 g, 17.94 mmol) and t-BuOH (1.33 g, 17.94 mmol) in THF (10 mL) was added dropwise. After the reaction mixture was stirred at −78° C. for 1 h, ammonium chloride (25 g) was added and the ammonia was evaporated. The residue was diluted with water, and the mixture was extracted EtOAc (2×100 mL). The combined organic extracts were concentrated. The residue was purified by column chromatography (silica gel, eluting with 0% to 30% EtOAc in hexanes) to give compound 436 (2.05 g, 55% yield) as an oil. m/z=209 (M+1).

Compound 437: A mixture of compound 436 (2.8 g, 13.4 mmol) and 10% palladium on carbon (100 mg) in EtOAc (35 mL) was hydrogenated at atmospheric pressure for 2 h at room temperature. The catalyst was removed by filtered through a Celite® pad. The filtrate was concentrated to give compound 437 (2.81 g, quantitative yield) as an oil. m/z=211 (M+1).

Compound 438: A solution of compound 437 (2.81 g, 13.38 mmol), ethylene glycol (8.2 g, 132.1 mmol) and p-toluenesulfonic acid monohydrate (300 mg, 1.57 mmol) in benzene (100 mL) was refluxed with a Dean-Stark trap for 16 h. The reaction mixture was cooled, washed with water, and concentrated. The residue was purified by column chromatography (silica gel, eluting with 0% to 30% EtOAc in hexanes) to give compound 438 (3.4 g, quantitative yield) as an oil. m/z=255 (M+1).

Compound 439: To a stirring mixture of compound 438 (3.4 g, 13.4 mmol) and $MgSO_4$ (1 g, 8.31 mmol) in $CH_2Cl_2$ (150 mL) was added pyridinium dichromate (10.5 g, 27.9 mmol) at room temperature. The reaction mixture was stirred overnight at room temperature; filtered through a silica gel pad; and eluted with $CH_2Cl_2$. The filtrate was concentrated to give compound 439 (3.4 g, quantitative yield) as an oil. m/z=253 (M+1).

Compound 440: Compound 439 (3.1 g, 12.28 mmol) was taken up in EtOH (50 mL). 2-Fluorobenzaldehyde (1.7 g, 13.7 mmol) and potassium fluoride on aluminum oxide (40 wt. %, 3.8 g, 26.16 mmol) were added. After stirring overnight at room temperature, the reaction mixture was diluted with $CH_2Cl_2$ and filtered. The filtrate was concentrated, and the residue was purified by column chromatography (silica gel, eluting with 0% to 30% EtOAc in hexanes) to give compound 440 (3.6 g, 82% yield) as an oil. m/z=359 (M+1).

Compound 441a: Compound 440 (500 mg, 1.39 mmol) was taken up in EtOH (20 mL). 2-(Fluoromethyl)-4-carboximidamide pyridine hydrochloride (320 mg, 1.68 mmol) and potassium carbonate (425 mg, 3.1 mmol) were added. The reaction mixture was heated to reflux for 4 days; concentrated; mixed with water (50 mL); neutralized with aq. $KH_2PO_4$ (aq); and extracted with EtOAc. The organic extract was dried with $MgSO_4$, filtered and concentrated. The crude product was taken up in $CH_2Cl_2$ (25 mL). Manganese dioxide (88%, 1 g, 10 mmol) was added. The mixture was stirred overnight at room temperature; filtered; and concentrated. The residue was purified by column chromatography (silica gel, eluting with 0 to 35% EtOAc in hexanes) to give compound 441a (275 mg, 40% yield) as a foam. m/z=492 (M+1).

Compound 442a: Compound 441a (275 mg, 0.56 mmol) was taken up in THF (5 mL), and aq. 3 N HCl (3 mL, 9 mmol) was added. The mixture was stirred overnight at room temperature and concentrated. The residue was neutralized with aq. sat. $NaHCO_3$ and extracted with EtOAc. The organic extract was washed with water, dried with $MgSO_4$, filtered and concentrated to give compound 442a (250 mg, quantitative yield) as a foam. m/z=448 (M+1).

Compound 443a: Compound 442a (0.25 g, 0.56 mmol) was taken up in ethyl formate (10 mL, 124.3 mmol). Sodium methoxide (30 wt. % in MeOH, 1.1 g, 6.1 mmol) was added. After stirring for 2 h at room temperature, the reaction mixture was neutralized with aq. 12 N HCl (0.6 mL, 7.2 mmol). EtOH (10 mL) and hydroxylamine hydrochloride (120 mg, 1.73 mmol) were added. The mixture was heated at 50° C. overnight and concentrated. The residue was taken up in EtOAc, and the mixture was washed with aq. $NaHCO_3$. The organic extract was dried with $MgSO_4$, filtered and concentrated. The residue was purified by column chromatography (silica gel, eluting with 0 to 35% EtOAc in hexanes) to give compound 443a (250 mg, 94% yield) as a foam. m/z=473 (M+1).

Compound 444a: Compound 443a (250 mg, 0.53 mmol) was dissolved in MeOH (10 mL). Potassium carbonate (365 mg, 2.65 mmol) was added. After stirring at room temperature overnight, the reaction mixture was neutralized by addition of aq. sat. $KH_2PO_4$ and extracted with EtOAc. The organic extract was washed with brine, dried with $MgSO_4$, filtered and concentrated. The residue was purified by column chromatography (silica gel, eluting with 0% to 35% EtOAc in hexanes) to give compound 444a (170 mg, 68% yield) as a foam. m/z=473 (M+1).

T155: Compound 444a (170 mg, 0.36 mmol) was dissolved in dry DMF (4 mL), and the solution was cooled to 0° C. 1,3-Dibromo-5,5-dimethylhydantoin (60 mg, 0.21 mmol) in DMF (1 mL) was added. The reaction mixture was stirred at 0° C. for 2 h. Pyridine (3 mL, 37.18 mmol) was added. The mixture was stirred at 60° C. for 4 h; cooled to room temperature; and then partitioned between EtOAc and aq. $NaHCO_3$. The organic extract was dried with $MgSO_4$, filtered and concentrated. The residue was purified by column chromatography (silica gel, eluting with 0% to 35% EtOAc in hexanes) to give compound T155 (60 mg, 35% yield) as a foam. $^1$H NMR (400 MHz, $CDCl_3$) δ 9.11 (s, 1H), 8.77 (dd, J=0.9, 5.2 Hz, 1H), 8.46 (m, 1H), 8.31 (td, J=1.0, 5.2 Hz, 1H), 7.52 (dddd, J=1.9, 5.3, 7.2, 8.3 Hz, 1H), 7.44 (dt, J=1.9, 7.4 Hz, 1H), 7.34 (dt, J=1.1, 7.5 Hz, 1H), 7.22 (ddd, J=1.0, 8.3, 9.6 Hz, 1H), 5.60 (d, J=46.9 Hz, 2H), 2.85 (dd, J=5.0, 8.8 Hz, 1H), 2.71 (m, 2H), 2.58 (tt, J=4.3, 13.2 Hz, 1H), 1.89 (m, 4H), 1.50 (m, 2H), 0.88 (t, J=7.2 Hz, 3H); m/z=471 (M+1).

Compound 441b: Compound 440 (400 mg, 1.11 mmol) was taken up in EtOH (20 mL). 4-Quinolinecarboximidamide hydrochloride (300 mg, 1.44 mmol) and potassium carbonate (400 mg, 2.90 mmol) were added. The reaction mixture was heated to reflux for 2 days and concentrated. The residue was mixed with water (50 mL). The mixture was neutralized with aq. $KH_2PO_4$ and extracted with EtOAc. The organic extract was dried with $MgSO_4$, filtered and concentrated. The crude product was taken up in $CH_2Cl_2$ (25 mL). Manganese dioxide (88%, 1 g, 10 mmol) was added. The mixture was stirred overnight at room temperature and filtered. The filtrate was concentrated, and the residue was purified by column chromatography (silica gel, eluting with 0% to 35% EtOAc in hexanes) to give compound 441b (350 mg, 62% yield) as a foam. m/z=510 (M+1).

Compound 442b: Compound 441b (350 mg, 0.68 mmol) was taken up in THF (5 mL), and aq. 3 N HCl (3 mL, 9 mmol) was added. The mixture was stirred overnight at room temperature, and concentrated. The residue was neutralized with aq. sat. $NaHCO_3$ and extracted with EtOAc. The organic extract was washed with water, dried with $MgSO_4$, filtered and concentrated to give compound 442b (310 g, 97% yield) as a foam. m/z=466 (M+1).

Compound 443b: Compound 442b (0.31 g, 0.67 mmol) was taken up in ethyl formate (10 mL, 124.3 mmol). Sodium methoxide (30 wt. % in MeOH, 1.28 g, 7.11 mmol) was added. After stirring for 2 h at room temperature, the reaction mixture was neutralized with aq. 12 N HCl (0.7 mL, 8.4 mmol). EtOH (10 mL) and hydroxylamine hydrochloride (150 mg, 2.16 mmol) were added. The mixture was heated at 50° C. overnight and concentrated. The residue was taken up in EtOAc and then washed with aq. $NaHCO_3$. The organic extract was dried with $MgSO_4$, filtered and concentrated. The residue was purified by column chromatography (silica gel, eluting with 0% to 35% EtOAc in hexanes) to give compound 443b (290 mg, 88% yield) as a foam. m/z=491 (M+1).

Compound 444b: Compound 443b (290 mg, 0.59 mmol) was dissolved in MeOH (10 mL). Potassium carbonate (410 mg, 2.95 mmol) was added. After stirring at room temperature overnight, the reaction mixture was neutralized by addition of aq. sat. $KH_2PO_4$, and extracted with EtOAc. The organic extract was washed with brine, dried with $MgSO_4$, filtered and concentrated. The residue was purified by column chromatography (silica gel, eluting with 0% to 35% EtOAc in hexanes) to give compound 444b (180 mg, 62% yield) as a foam. m/z=491 (M+1).

T156: Compound 444b (180 mg, 0.36 mmol) was dissolved in dry DMF (4 mL), and the solution was cooled to 0° C. 1,3-Dibromo-5,5-dimethylhydantoin (60 mg, 0.21 mmol) in DMF (1 mL) was added. The reaction mixture was stirred at 0° C. for 2 h. Pyridine (3 mL, 37.18 mmol) was added. The reaction mixture was stirred at 60° C. for 4 h; cooled to room temperature; mixed with aq. $NaHCO_3$; and extracted with EtOAc. The organic extract was dried with $MgSO_4$, filtered and concentrated. The residue was purified by column chromatography (silica gel, eluting with 0% to 35% EtOAc in hexanes) to give compound T156 (90 mg, 50% yield) as a foam. $^1$H NMR (400 MHz, $CDCl_3$) δ 9.10 (d, J=4.5 Hz, 1H), 9.08 (s, 1H), 8.74 (ddd, J=0.7, 1.5, 8.5 Hz, 1H), 8.22 (ddd, J=0.6, 1.4, 8.5 Hz, 1H), 8.03 (d, J=4.5 Hz, 1H), 7.77 (ddd, J=1.4, 6.8, 8.4 Hz, 1H), 7.63 (ddd, J=1.4, 6.8, 8.4 Hz, 1H), 7.50 (m, 2H), 7.33 (dt, J=1.1, 7.5 Hz, 1H), 7.24 (m, 1H), 2.81 (m, 4H), 2.62 (tdd, J=4.2, 8.7, 13.0 Hz, 1H), 2.07 (m, 1H), 1.92 (m, 3H), 1.49 (m, 2H), 0.91 (t, J=7.2 Hz, 3H); m/z=489 (M+1).

Compound 445: Compound 342 (1.1298 g, 1.99 mmol) was dissolved in THF (9.94 mL) and cooled to 0° C. Potassium tert-butoxide (0.669 g, 5.96 mmol) in THF (9.94 mL) was added. The reaction was stirred for 10 min at 0° C. Allyl bromide (0.52 mL, 6.01 mmol) was then added, and the reaction was stirred under argon for 2 h at 0° C. The reaction mixture was neutralized with aq. sat. $NH_4Cl$ and extracted twice with EtOAc. The organic extract was dried over $Na_2SO_4$, filtered and concentrated. The residue was purified by flash chromatography (silica gel, eluting with 0% to 90% EtOAc in hexanes) to give compound 445 (0.7978 g, 66% yield) as a dark orange viscous oil. m/z=609.2 (M+1).

Compound 446: Compound 445 (0.7978 g, 1.31 mmol) was dissolved in EtOH (13.6 mL). Hydroxylamine hydrochloride (0.136 g, 1.96 mmol) and aq. 1 N HCl (2.7 mL, 2.7 mmol) were added. The reaction mixture was stirred for 3.5 h at 55° C.; cooled; neutralized with aq. sat. $K_2CO_3$; and extracted with twice EtOAc. The combined organic extracts were washed with brine and concentrated. The residue was purified by flash chromatography (silica gel, eluting with 0% to 80% EtOAc in hexanes) to give compound 446 (0.5582 g, 82% yield) as a reddish-brown foam. m/z=517.2 (M+1).

Compound 447: Compound 446 (0.5582 g, 1.08 mmol) was dissolved in dry $CH_2Cl_2$ (5.25 mL) and purged with argon for 7 min. Triisobutylaluminium (1M in hexanes, 5.52 mL, 5.52 mmol) was added. After the mixture was stirred at room temperature for 45 min, diiodomethane (0.33 mL, 4.11 mmol) was added dropwise, and the reaction vessel was covered in aluminum foil. After the reaction was stirred for 6 h, aq. 8% NaOH (15 mL) was added at 0° C., and the mixture was stirred for another 45 min. The crude mixture was extracted three times with $CH_2Cl_2$. The combined organic extracts were washed with brine, dried over $Na_2SO_4$, filtered and concentrated to give the crude product contained a mixture of compound 446 and 447. The crude product and 4-methylmorpholine N-oxide (0.34 g, 2.90 mmol) was dissolved in acetone (2.9 mL) and $H_2O$ (0.97 mL). The solution was cooled to 0° C., and osmium tetroxide (2.5 wt. % in t-butanol, 97 µL, 0.008 mmol) was added. The reaction mixture was stirred at ambient temperature under nitrogen for 16 h and then quenched by addition of aq. sat. $Na_2SO_3$. The mixture was filtered, and the solid was washed with acetone. The filtrate was extracted with EtOAc. The organic extract was dried over $Na_2SO_4$, filtered and concentrated. The residue was purified by flash chromatography (silica gel, eluting with 0% to 75% acetone in hexanes) to give compound 447 (36.4 mg, 6% yield) as a yellow viscous oil. m/z=531 (M+1).

Compound 448: Compound 447 (36.4 mg, 0.069 mmol) was dissolved in MeOH (0.695 mL). Sodium methoxide (25 wt. % in MeOH, 0.524 mL, 2.29 mmol) was added under nitrogen. After stirring at 55° C. for 2.5 h, the reaction mixture was neutralized with aq. sat. $KH_2PO_4$ and extracted with EtOAc. The organic extract was washed with $H_2O$ and brine; dried with $Na_2SO_4$; filtered; and concentrated to give compound 448 (34.4 mg, 95% yield) as a yellow solid.

T157: Compound 448 (34.4 mg, 0.065 mmol) was dissolved in dry DMF (0.72 mL), and the solution was cooled to 0° C. under nitrogen. 1,3-dibromo-5,5-dimethylhydantoin (10 mg, 0.035 mmol) in DMF (0.28 mL) was added, and the mixture was stirred at 0° C. for 2 h. Pyridine (16 µL, 0.20 mmol) was added. The reaction mixture was heated to 55° C. for 2.5 h, and then cooled to room temperature. The reaction mixture was diluted with EtOAc and washed with $H_2O$, aq. sat. $NaHCO_3$, aq. sat. $Na_2SO_3$, and brine. The organic extract was dried with $Na_2SO_4$, filtered and concentrated. The residue was purified by flash chromatography (silica gel, eluting with 0% to 60% EtOAc in hexanes) to give compound T157 (24.6 mg, 72% yield) as a white solid. $^1$H NMR (400 MHz, $CDCl_3$) δ 9.09 (d, J=4.5 Hz, 1H), 8.91 (s, 1H), 8.72 (d, J=8.6 Hz, 1H), 8.22 (d, J=8.5 Hz, 1H), 8.02 (d, J=4.5 Hz, 1H), 7.78 (t, J=7.7 Hz, 1H), 7.64 (t, J=7.8 Hz, 1H), 7.51 (m, 2H), 7.34 (t, J=7.5 Hz, 1H), 7.25 (m, 1H), 2.96 (m, 2H), 1.65 (s, 3H), 1.58 (m, 6H), 1.25 (s, 3H), 0.87 (m, 2H), 0.49 (m, 2H); m/z=529.2 (M+1).

Compound 449a: Compound 399 (180 mg, 0.55 mmol) was taken up in EtOH (5.5 mL). 4-quinolinecarboximidamide hydrochloride (171 mg, 0.82 mmol) and $K_2CO_3$ (227 mg, 1.64 mmol) were added. The reaction mixture was refluxed for 40 h and concentrated. The residue was partitioned between EtOAc (20 mL) and water (20 mL). The organic extract was separated, and the aqueous phase was extracted with EtOAc (2×20 mL). The combined organic extracts were dried with $Na_2SO_4$, filtered and concentrated. The crude product was taken up in $CH_2Cl_2$ (5.5 mL). Manganese (IV) oxide (88%, 434 mg, 4.39 mmol) was added. The mixture was stirred overnight at room temperature and purified by flash chromatography (silica gel, eluted with 0% to 100% EtOAc in hexanes) to give compound 449a (143 mg, 54% yield) as a pink foamy solid. m/z=480.2 (M+1).

Compound 450a: To a solution of compound 449a (141 mg, 0.29 mmol) in $CH_2Cl_2$ (3 mL) was added Dess-Martin periodinane (187 mg, 0.44 mmol) at room temperature. After the reaction was stirred for 2 h at room temperature, aq. 10% $Na_2SO_3$ (15 mL) was added. The mixture was stirred for 5 min, and extracted MTBE (30 mL). The organic extract was washed with aq. sat. $NaHCO_3$ (2×15 mL). The organic extract was dried with $Na_2SO_4$, filtered and concentrated. The residue was purified by flash chromatography (silica gel, eluting with 0% to 60% EtOAc in hexanes) to give compound 450a (126 mg, 89% yield) as a white foamy solid. m/z=478.2 (M+1).

Compound 451a: Compound 450a (124 mg, 0.26 mmol) and 10% palladium on carbon (40 mg) in EtOAc (5 mL) was hydrogenated (balloon pressure) at room temperature for 2.5 h. The mixture was filtered through a pad of silica gel and was eluted with EtOAc. The filtrate was concentrated. The residue was purified by flash chromatography (silica gel, eluting with 0% to 60% EtOAc in hexanes) to give compound 451a (114 mg, 92% yield) as a white foamy solid. m/z=480.2 (M+1).

Compound 452a: To a mixture of compound 451a (62 mg, 0.13 mmol) in ethyl formate (0.31 mL, 3.85 mmol) was added sodium methoxide (25 wt. % in MeOH, 0.30 mL, 1.31 mmol) at 0° C. The mixture was stirred at room temperature for 1.5 h and cooled to 0° C. again. Aq. 6 N HCl (0.22 mL, 1.32 mmol), EtOH (1.3 mL) and hydroxylamine hydrochloride (14 mg, 0.20 mmol) were added sequentially. The mixture was stirred at 55° C. (oil bath) for 2 h and at room temperature for 60 h. After concentration, the residue was diluted with EtOAc and washed with aq. sat. $NaHCO_3$. The organic extract was dried with $Na_2SO_4$, filtered and concentrated. The residue was purified by flash chromatography (silica gel, eluting with 0% to 60% EtOAc in hexanes) to give compound 452a (54 mg, 83% yield) as a white foamy solid. m/z=505.2 (M+1).

Compound 453a: To a mixture of compound 452a (52 mg, 0.10 mmol) in MeOH (1 mL) was added sodium methoxide (25 wt. % in MeOH, 47 µL, 0.21 mmol) at room temperature. The mixture was heated at 55° C. for 1 h and cooled to room temperature. Aq. 10% $NaH_2PO_4$ (15 mL) was added, and the mixture was extracted with EtOAc (2×20 mL). The combined organic extracts were dried with Na$_2$SO$_4$, filtered and concentrated. The residue was purified by flash chromatography (silica gel, eluting with 0% to 60% EtOAc in hexanes) to give compound 453a (48 mg, 92% yield) as a white foamy solid. m/z=505.2 (M+1).

T158: To a solution of compound 453a (48 mg, 0.095 mmol) in DMF (0.5 mL) was added a solution of 1,3-dibromo-5,5-dimethylhydantoin (14 mg, 0.049 mmol) in DMF (0.2 mL). After the mixture was stirred at 0° C. for 1 h, pyridine (23 µL, 0.29 mmol) was added. The mixture was heated at 55° C. for 1.5 h and cooled to room temperature. EtOAc (25 mL) was added, and the mixture was washed with water (3×15 mL). The organic extract was dried with Na$_2$SO$_4$, filtered and concentrated. The residue was purified by flash chromatography (silica gel, eluting with 0% to 60% EtOAc in hexanes) to give compound T158 (33 mg, 69% yield) as a white foamy solid. $^1$H NMR (400 MHz, CDCl$_3$) δ 9.09 (d, J=4.4 Hz, 1H), 8.93 (s, 1H), 8.70 (ddd, J=8.6, 1.5, 0.6 Hz, 1H), 8.22 (ddd, J=8.5, 1.3, 0.6 Hz, 1H), 8.01 (d, J=4.4 Hz, 1H), 7.78 (ddd, J=8.4, 6.8, 1.4 Hz, 1H), 7.64 (ddd, J=8.4, 6.8, 1.3 Hz, 1H), 7.51 (m, 2H), 7.33 (td, J=7.6, 1.1 Hz, 1H), 7.23 (m, 1H), 2.90 (m, 2H), 2.62 (ddd, J=13.1, 4.8, 3.1 Hz, 1H), 2.51 (td, J=12.7, 2.5 Hz, 1H), 2.12 (m, 2H), 1.85 (m, 1H), 1.71 (m, 1H), 1.58 (s, 3H), 1.35 (m, 1H), 1.25 (m, 1H), 0.95 (t, J=7.2 Hz, 3H); m/z=503.2 (M+1).

Compound 449b: Compound 399 (180 mg, 0.55 mmol) was taken up in EtOH (5.5 mL). 5-quinolinecarboximidamide hydrochloride (171 mg, 0.82 mmol) and K$_2$CO$_3$ (227 mg, 1.64 mmol) were added. The reaction mixture was refluxed for 40 h and concentrated. The residue was partitioned between EtOAc (20 mL) and water (20 mL). The organic extract was separated, and the aqueous phase was extracted with EtOAc (2×20 mL). The combined organic extracts were dried with Na$_2$SO$_4$, filtered and concentrated. The crude product was taken up in CH$_2$Cl$_2$ (5.5 mL). Manganese (IV) oxide (88%, 434 mg, 4.39 mmol) was added. The mixture was stirred overnight at room temperature and purified by flash chromatography (silica gel, eluted with 0% to 100% EtOAc in hexanes) to give compound 449b (96 mg, 37% yield) as a light yellow foamy solid. m/z=480.2 (M+1).

Compound 450b: To a solution of compound 449b (94 mg, 0.20 mmol) in CH$_2$Cl$_2$ (2 mL) was added Dess-Martin periodinane (125 mg, 0.29 mmol) at room temperature. After the reaction was stirred for 2 h at room temperature, aq. 10% Na$_2$SO$_3$ (15 mL) was added. The mixture was stirred for 5 min and extracted MTBE (30 mL). The organic extract was washed with aq. sat. NaHCO$_3$ (2×15 mL). The organic extract was dried with Na$_2$SO$_4$, filtered and concentrated. The residue was purified by flash chromatography (silica gel, eluting with 0% to 60% EtOAc in hexanes) to give compound 450b (78 mg, 83% yield) as a white foamy solid. m/z=478.2 (M+1).

Compound 451b: Compound 450b (76 mg, 0.16 mmol) and 10% palladium on carbon (25 mg) in EtOAc (5 mL) was hydrogenated (balloon pressure) at room temperature for 2.5 h. The mixture was filtered through a pad of silica gel and was eluted with EtOAc. The filtrate was concentrated. The residue was purified by flash chromatography (silica gel, eluting with 0% to 70% EtOAc in hexanes) to give compound 451b (60 mg, 79% yield) as a white foamy solid. m/z=480.2 (M+1).

Compound 452b: To a mixture of compound 451b (58 mg, 0.12 mmol) in ethyl formate (0.29 mL, 3.60 mmol) was added sodium methoxide (25 wt. % in MeOH, 0.28 mL, 1.22 mmol) at 0° C. After stirring the mixture for 5 min at room temperature, addition amount of ethyl formate (0.29 mL, 3.60 mmol) was added. The mixture was stirred at room temperature for another 1.5 h, and cooled to 0° C. again. Aq. 6 N HCl (0.20 mL, 1.20 mmol), EtOH (1.2 mL) and hydroxylamine hydrochloride (13 mg, 0.19 mmol) were added sequentially. The mixture was stirred at 55° C. (oil bath) for 2 h and at room temperature for 60 h. After concentration, the residue was diluted with EtOAc and washed with aq. sat. NaHCO$_3$. The organic extract was dried with Na$_2$SO$_4$, filtered and concentrated. The residue was purified by flash chromatography (silica gel, eluting with 0% to 60% EtOAc in hexanes) to give compound 452b (57 mg, 93% yield) as a white foamy solid. m/z=505.2 (M+1).

Compound 453b: To a mixture of compound 452b (55 mg, 0.11 mmol) in MeOH (1 mL) was added sodium methoxide (25 wt. % in MeOH, 50 µL, 0.22 mmol) at room temperature. The mixture was heated at 55° C. for 1 h and cooled to room temperature. Aq. 10% NaH$_2$PO$_4$ (15 mL) was added, and the mixture was extracted with EtOAc (2×20 mL). The combined organic extracts were dried with Na$_2$SO$_4$, filtered and concentrated. The residue was purified by flash chromatography (silica gel, eluting with 0% to 60% EtOAc in hexanes) to give compound 453b (52 mg, 95% yield) as a white foamy solid. m/z=505.2 (M+1).

T159: To a solution of compound 453b (52 mg, 0.103 mmol) in DMF (0.5 mL) was added a solution of 1,3-dibromo-5,5-dimethylhydantoin (15 mg, 0.052 mmol) in DMF (0.2 mL). After the mixture was stirred at 0° C. for 1 h, pyridine (25 µL, 0.31 mmol) was added. The mixture was heated at 55° C. for 1.5 h and cooled to room temperature. EtOAc (25 mL) was added, and the mixture was washed with water (3×15 mL). The organic extract was dried with Na$_2$SO$_4$, filtered and concentrated. The residue was purified by flash chromatography (silica gel, eluting with 0% to 60% EtOAc in hexanes) to give compound T159 (31 mg, 60% yield) as a white solid. $^1$H NMR (400 MHz, CDCl$_3$) δ 9.17 (ddt, J=8.8, 1.6, 0.7 Hz, 1H), 8.97 (dd, J=1.6, 4.4 Hz, 1H), 8.96 (s, 1H), 8.29 (m, 2H), 7.86 (dd, J=3.2, 4.4 Hz, 1H), 7.49 (m, 3H), 7.32 (tt, J=7.5, 0.8 Hz, 1H), 7.22 (m, 1H), 2.88 (m, 2H), 2.62 (ddd, J=13.2, 4.9, 3.2 Hz, 1H), 2.50 (td, J=12.8, 2.5 Hz, 1H), 2.11 (m, 2H), 1.85 (m, 1H), 1.70 (m, 1H), 1.58 (s, 3H), 1.36 (m, 1H), 1.23 (m, 1H), 0.94 (t, J=7.2 Hz, 3H); m/z=503.2 (M+1).

Compound 454a and 455a: A mixture of compound 94 and compound 95 (300 mg, 0.69 mmol) was taken up in 1,4-dioxane (6 mL). Potassium carbonate (290 mg, 2.10 mmol), [1,1'-bis(diphenylphosphino)ferrocene]dichloropalladium(II) (55 mg, 0.075 mmol) and 3-isopropylphenylboronic acid (225 mg, 1.37 mmol) were added. The reaction mixture was bubbled with nitrogen for 10 min; stirred at 90° C. for 16 h; cooled to room temperature and filtered. The filtrate was concentrated. The residue was purified by column chromatography (silica gel, eluting with 0% to 30% EtOAc in hexanes) to give a mixture of compound 454a and 455a (270 mg, 79% yield) as a foam. m/z=520 (454a, M+1) and 476 (455a, M+1).

Compound 455a: A mixture of compound 454a and 455a (270 mg, 0.52 mmol) was taken up in THF (6 mL), and aq. 3 N HCl (3 mL, 9.0 mmol) was added. The mixture was stirred overnight at room temperature and concentrated. The residue was neutralized with aq. sat. NaHCO$_3$ and extracted with EtOAc. The organic extract was washed with water; dried with MgSO$_4$; filtered and concentrated to give compound 455a (250 mg, quantitative yield) as a foam. m/z=476 (M+1).

Compound 456a: Compound 455a (0.25 g, 0.53 mmol) was taken up in ethyl formate (10 mL, 124.3 mmol). Sodium methoxide (30 wt. % in MeOH, 1.1 g, 6.11 mmol) was added. After stirring for 2 h at room temperature, the reaction mixture was neutralized with aq. 12 N HCl (0.6 mL, 7.2 mmol). EtOH (10 mL) and hydroxylamine hydrochloride (120 mg, 1.72 mmol) were then added. The mixture was heated at 55° C. overnight. After concentration, the residue was taken up in EtOAc and washed with aq. NaHCO$_3$. The organic extract was dried with MgSO$_4$, filtered and concentrated. The residue was purified by column chromatography (silica gel, eluting with 0% to 35% EtOAc in hexanes) to give compound 456a (270 mg, quantitative yield) as a foam. m/z=501 (M+1).

Compound 457a: Compound 456a (270 mg, 0.54 mmol) was dissolved in MeOH (10 mL). Potassium carbonate (400 mg, 2.89 mmol) was added. After stirring at room temperature overnight, the reaction mixture was neutralized by addition of aq. sat. KH$_2$PO$_4$ and extracted with EtOAc. The organic extract was washed with brine; dried with MgSO$_4$; filtered and concentrated. The residue was purified by column chromatography (silica gel, eluting with 0% to 35% EtOAc in hexanes) to give compound 457a (190 mg, 70% yield) as a foam. m/z=501 (M+1).

T160: Compound 457a (190 mg, 0.38 mmol) was dissolved in dry DMF (4 mL), and the solution was cooled to 0° C. 1,3-Dibromo-5,5-dimethylhydantoin (60 mg, 0.21 mmol) in DMF (1 mL) was added. The reaction was stirred at 0° C. for 2 h, and pyridine (3 mL, 37.18 mmol) was added. The reaction mixture was stirred at 60° C. for 4 h, cooled to room temperature, and partitioned between aq. NaHCO$_3$ and EtOAc. The organic extract was dried with MgSO$_4$, filtered and concentrated. The residue was purified by column chromatography (silica gel, eluting with 0% to 35% EtOAc in hexanes) to give T160 (105 mg, 55% yield) as a foam. $^1$H NMR (400 MHz, CDCl$_3$) δ 9.09 (d, J=4.4 Hz, 1H), 8.96 (s, 1H), 8.78 (ddd, J=8.6, 1.5, 0.7 Hz, 1H), 8.22 (ddd, J=8.5, 1.3, 0.6 Hz, 1H), 8.05 (d, J=4.4 Hz, 1H), 7.78 (ddd, J=8.4, 6.8, 1.4 Hz, 1H), 7.64 (ddd, J=8.4, 6.9, 1.4 Hz, 1H), 7.45 (m, 3H), 7.37 (dtd, J=6.3, 1.8, 0.9 Hz, 1H), 3.03 (m, 3H), 2.64 (dq, J=13.4, 6.7 Hz, 1H), 2.32 (td, J=12.8, 2.7 Hz, 1H), 2.19 (ddd, J=14.2, 6.2, 3.3 Hz, 1H), 1.83 (m, 1H), 1.59 (s, 3H), 1.35 (d, J=6.7 Hz, 3H), 1.31 (d, J=6.9 Hz, 3H), 1.31 (d, J=6.9 Hz, 3H); m/z=499 (M+1).

Compound 454b and 455b: A mixture of compound 94 and compound 95 (350 mg, 0.80 mmol) was taken up in 1,4-dioxane (6 mL). Potassium carbonate (345 mg, 2.50 mmol), [1,1'-bis(diphenylphosphino)ferrocene]dichloropalladium(II) (75 mg, 0.10 mmol) and 4-isopropylphenylboronic acid (270 mg, 1.65 mmol) were added. The reaction mixture was bubbled with nitrogen for 10 min; stirred at 90° C. for 16 h; cooled to room temperature and filtered. The filtrate was concentrated. The residue was purified by column chromatography (silica gel, eluting with 0% to 30% EtOAc in hexanes) to give a mixture of compound 454b and 455b (360 mg, 86% yield) as a foam. m/z=520 (454b, M+1) and 476 (455b, M+1).

Compound 455b: A mixture of compound 454b and 455b (360 mg, 0.69 mmol) was taken up in THF (6 mL), and aq. 3 N HCl (3 mL, 9 mmol) was added. The mixture was stirred overnight at room temperature and concentrated. The residue was neutralized with aq. sat. NaHCO$_3$ and extracted with EtOAc. The organic extract was washed with water; dried with MgSO$_4$; filtered and concentrated to give compound 455b (330 mg, quantitative yield) as a foam. m/z=476 (M+1).

Compound 456b: Compound 455b (0.33 g, 0.69 mmol) was taken up in ethyl formate (10 mL, 124.3 mmol). Sodium methoxide (30 wt. % in MeOH, 1.3 g, 7.21 mmol) was added. After stirring at for 2 h at room temperature, the mixture was neutralized with aq. 12 N HCl (0.7 mL, 8.40 mmol). EtOH (10 mL) and hydroxylamine hydrochloride (120 mg, 1.73 mmol) were then added. The mixture was heated at 55° C. overnight and concentrated. The residue was taken up in EtOAc and washed with aq. NaHCO$_3$. The organic extract was dried with MgSO$_4$, filtered and concentrated. The residue was purified by column chromatography (silica gel, eluting with 0% to 35% EtOAc in hexanes) to give compound 456b (350 mg, quantitative yield) as a foam. m/z=501 (M+1).

Compound 457b: Compound 456b (350 mg, 0.70 mmol) was dissolved in MeOH (10 mL). Potassium carbonate (485 mg, 3.51 mmol) was added. After stirring at room temperature overnight, the reaction mixture was neutralized by addition of aq. sat. KH$_2$PO$_4$ and extracted with EtOAc. The organic extract was washed with brine; dried with MgSO$_4$; filtered and concentrated. The residue was purified by column chromatography (silica gel, eluting with 0% to 35% EtOAc in hexanes) to give compound 457b (195 mg, 56% yield) as a foam. m/z=501 (M+1).

T161: Compound 457b (105 mg, 0.21 mmol) was dissolved in dry DMF (3 mL), and the solution was cooled to 0° C. 1,3-Dibromo-5,5-dimethylhydantoin (35 mg, 0.12 mmol) in DMF (1 mL) was added. The reaction was stirred at 0° C. for 2 h, and pyridine (3 ml, 37.18 mmol) was added. The reaction mixture was stirred at 60° C. for 4 h, cooled to room temperature, and partitioned between aq. NaHCO$_3$ and EtOAc. The organic extract was dried with MgSO$_4$, filtered and concentrated. The residue was purified by column chromatography (silica gel, eluting with 0% to 35% EtOAc in hexanes) to give compound T161 (50 mg, 48% yield) as a foam. $^1$H NMR (400 MHz, CDCl$_3$) δ 9.08 (d, J=4.4 Hz, 1H), 8.95 (s, 1H), 8.74 (ddd, J=8.6, 1.5, 0.6 Hz, 1H), 8.22 (dd, J=0.8, 8.4 Hz, 1H), 8.03 (d, J=4.4 Hz, 1H), 7.77 (ddd, J=8.4, 6.8, 1.4 Hz, 1H), 7.64 (ddd, J=8.3, 6.8, 1.4 Hz, 1H), 7.58 (m, 2H), 7.37 (m, 2H), 3.09 (m, 2H), 2.99 (m, 1H), 2.64 (dq, J=13.3, 6.7 Hz, 1H), 2.31 (td, J=12.8, 2.7 Hz, 1H), 2.19 (m, 1H), 1.84 (m, 1H), 1.58 (s, 3H), 1.35 (d, J=6.7 Hz, 3H), 1.30 (d, J=6.9 Hz, 6H); m/z=499 (M+1).

Compound 454c and 455c: A mixture of compound 94 and compound 95 (300 mg, 0.69 mmol) was taken up in 1,4-dioxane (6 mL). Potassium carbonate (290 mg, 2.10 mmol), [1,1'-bis(diphenylphosphino)ferrocene]dichloropalladium (H) (55 mg, 0.075 mmol) and 3-biphenylboronic acid (275 mg, 1.39 mmol) were added. The reaction mixture was bubbled with nitrogen for 10 min; stirred at 90° C. for 16 h; cooled to room temperature and filtered. The filtrate was concentrated. The residue was purified by column chromatography (silica gel, eluting with 0% to 30% EtOAc in hexanes) to give a mixture of compound 454c and 455c (280 mg, 73% yield) as a foam. m/z=554 (454c, M+1) and 510 (455c, M+1).

Compound 455c: A mixture of compound 454c and 455c (280 mg, 0.51 mmol) was taken up in THF (6 mL), and aq. 3 N HCl (3 mL, 9.0 mmol) was added. The mixture was stirred overnight at room temperature and then concentrated. The residue was neutralized with aq. sat. NaHCO$_3$ and extracted with EtOAc. The organic extract was washed with water; dried with MgSO$_4$; filtered and concentrated to give compound 455c (265 mg, quantitative yield) as a foam. m/z=510 (M+1).

Compound 456c: Compound 455c (250 mg, 0.49 mmol) was taken up in ethyl formate (10 mL, 124.3 mmol). Sodium methoxide (30 wt. % in MeOH, 1 g, 5.55 mmol) was added. After stirring for 2 h at room temperature, the reaction mixture was neutralized with aq. 12 N HCl (0.55 mL, 6.60 mmol). EtOH (10 mL) and hydroxylamine hydrochloride (110 mg, 1.58 mmol) were then added. The mixture was heated at 55° C. overnight and concentrated. The residue was taken up in EtOAc and washed with aq. NaHCO$_3$. The organic extract was dried with MgSO$_4$, filtered and concentrated. The residue was purified by column chromatography (silica gel, eluting with 0% to 35% EtOAc in hexanes) to give compound 456c (250 mg, 95% yield) as a foam. m/z=535 (M+1).

Compound 457c: Compound 456c (250 mg, 0.47 mmol) was dissolved in MeOH (10 mL). Potassium carbonate (325 mg, 2.35 mmol) was added. After stirring at room temperature overnight, the reaction was neutralized by addition of aq. sat. KH$_2$PO$_4$ and extracted with EtOAc. The organic extract was washed with brine; dried with MgSO$_4$; filtered and concentrated. The residue was purified by column chromatography (silica gel, eluting with 0% to 35% EtOAc in hexanes) to give compound 457c (195 mg, 78% yield) as a foam. m/z=535 (M+1).

T162: Compound 457c (195 mg, 0.36 mmol) was dissolved in dry DMF (4 mL), and the solution was cooled to 0° C. 1,3-Dibromo-5,5-dimethylhydantoin (60 mg, 0.21 mmol) in DMF (1 mL) was added. The reaction was stirred at 0° C. for 2 h, and pyridine (3 ml, 37.18 mmol) was added. The reaction mixture was stirred at 60° C. for 4 h, cooled to room temperature, and partitioned between aq. NaHCO$_3$ and EtOAc. The organic extract was dried with MgSO$_4$, filtered and concentrated. The residue was purified by column chromatography (silica gel, eluting with 0% to 35% EtOAc in hexanes) to give compound T162 (100 mg, 51% yield) as a foam. $^1$H NMR (400 MHz, CDCl$_3$) δ 9.09 (d, J=4.4 Hz, 1H), 8.96 (s, 1H), 8.77 (ddd, J=8.6, 1.5, 0.6 Hz, 1H), 8.23 (ddd, J=8.4, 1.4, 0.6 Hz, 1H), 8.06 (d, J=4.5 Hz, 1H), 7.83 (m, 1H), 7.78 (ddd, J=8.4, 6.8, 1.4 Hz, 1H), 7.74 (m, 1H), 7.62 (m, 5H), 7.47 (m, 2H), 7.40 (m, 1H), 3.10 (m, 2H), 2.65 (dq, J=13.3, 6.7 Hz, 1H), 2.33 (td, J=12.8, 2.7 Hz, 1H), 2.19 (m, 1H), 1.85 (m, 1H), 1.60 (s, 3H), 1.35 (d, J=6.7 Hz, 3H); m/z=533 (M+1).

Compound 454d and 455d: A mixture of compound 94 and compound 95 (350 mg, 0.80 mmol) was taken up in 1,4-dioxane (6 mL). Potassium carbonate (345 mg, 2.50 mmol), [1,1'-bis(diphenylphosphino)ferrocene]dichloropalladium (H) (75 mg, 0.10 mmol) and 4-biphenylboronic acid (325 mg, 1.64 mmol) were added. The reaction mixture was bubbled with nitrogen for 10 min; stirred at 90° C. for 16 h; cooled to room temperature and filtered. The filtrate was concentrated. The residue was purified by column chromatography (silica gel, eluting with 0% to 30% EtOAc in hexanes) to give a mixture of compound 454d and 455d (290 mg, 65% yield) as a foam. m/z=554 (454d, M+1) and 510 (455d, M+1).

Compound 455d: A mixture of compound 454d and 455d (290 mg, 0.52 mmol) was taken up in THF (6 mL), and aq. 3 N HCl (3 mL, 9.0 mmol) was added. The mixture was stirred overnight at room temperature and concentrated. The residue was neutralized with aq. sat. NaHCO$_3$ and extracted with EtOAc. The organic extract was washed with water; dried with MgSO$_4$; filtered and concentrated to give compound 455d (275 mg, quantitative yield) as a foam. m/z=510 (M+1).

Compound 456d: Compound 455d (275 mg, 0.54 mmol) was taken up in ethyl formate (10 mL, 124.3 mmol). Sodium methoxide (30 wt. % in methanol, 1.1 g, 6.11 mmol) was added. After stirring for 2 h at room temperature, the reaction mixture was neutralized with aq. 12 N HCl (0.6 mL, 7.2 mmol). EtOH (10 mL) and hydroxylamine hydrochloride (120 mg, 1.73 mmol) were then added. The mixture was heated at 55° C. overnight and concentrated. The residue was taken up in EtOAc and washed with aq. NaHCO$_3$. The organic extract was dried with MgSO$_4$, filtered and concentrated. The residue was purified by column chromatography (silica gel, eluting with 0% to 35% EtOAc in hexanes) to give compound 456d (260 mg, 90% yield) as a foam. m/z=535 (M+1).

Compound 457d: Compound 456d (260 mg, 0.49 mmol) was dissolved in MeOH (10 mL). Potassium carbonate (350 mg, 2.53 mmol) was added. After stirring at room temperature overnight, the reaction was neutralized by addition of aq. sat. KH$_2$PO$_4$ and extracted with EtOAc. The organic extract was washed with brine; dried with MgSO$_4$; filtered and concentrated. The residue was purified by column chromatography (silica gel, eluting with 0% to 35% EtOAc in hexanes) to give compound 457d (200 mg, 77% yield) as a foam. m/z=535 (M+1).

T163: Compound 457d (200 mg, 0.37 mmol) was dissolved in dry DMF (4 mL), and the solution was cooled to 0° C. 1,3-Dibromo-5,5-dimethylhydantoin (60 mg, 0.21 mmol) in DMF (1 mL) was added.

The reaction was stirred at 0° C. for 2 h, and pyridine (3 ml, 37.18 mmol) was added. The reaction mixture was stirred at 60° C. for 4 h, cooled to room temperature, and partitioned between aq. NaHCO$_3$ and EtOAc. The organic extract was dried with MgSO$_4$, filtered and concentrated. The residue was purified by column chromatography (silica gel, eluting with 0% to 35% EtOAc in hexanes) to give compound T163 (125 mg, 63% yield) as a foam. $^1$H NMR (400 MHz, CDCl$_3$) δ 9.10 (d, J=4.5 Hz, 1H), 8.96 (s, 1H), 8.76 (ddd, J=8.5, 1.5, 0.6 Hz, 1H), 8.23 (ddd, J=8.5, 1.4, 0.6 Hz, 1H), 8.05 (d, J=4.5 Hz, 1H), 7.76 (m, 5H), 7.65 (m, 3H), 7.49 (m, 2H), 7.42 (m, 1H), 3.13 (m, 2H), 2.65 (dt, J=13.4, 6.7 Hz, 1H), 2.34 (td, J=12.8, 2.7 Hz, 1H), 2.22 (m, 1H), 1.85 (m, 1H), 1.61 (s, 3H), 1.36 (d, J=6.7 Hz, 3H); m/z=533 (M+1).

Compound 460: Compound 460 was synthesized from compound 458 using the reported procedure (Bradshaw, et al., 2009). A 50 mL round bottom flask equipped with a magnetic stirbar was charged with compound 458 (7.50 g, 29.96 mmol), catalyst 459 (802 mg, 1.50 mmol) and benzoic acid (36 mg, 0.29 mmol). The flask was sealed and the reaction mixture was stirred at room temperature for 5 days. The dark brown mixture purified by flash chromatography (silica gel 60, eluting with 30% EtOAc in hexanes), and the obtained product was recrystallized from hexanes to give compound 460 (3.97 g, 57% yield, 99% ee) as a grayish-white solid. m/z=233 (M+1).

Compound 461: To a solution of compound 460 (3.87 g, 16.65 mmol) in EtOH (80 mL) at 0° C. under nitrogen with vigorous stirring was added sodium borohydride (189 mg, 5.00 mmol) portionwise over approximately 30 min. The reaction mixture was stirred at 0° C. for 2 h and quenched by dropwise addition of glacial acetic acid (1.94 mL, 33.92 mmol). The ice bath was removed; the reaction mixture was stirred at room temperature for 2 h; and the solvent was removed in vacuo. The residue was partitioned between EtOAc and water. The organic phase was cautiously washed with aq. sat. NaHCO$_3$ and brine; dried with MgSO$_4$; filtered and concentrated. The residue was purified by column chromatography (silica gel, eluting with 50% EtOAc in hexanes) to give compound 461 (4.00 g, quantitative yield) as an oil. m/z=235 (M+1).

Compound 462: Liquid ammonia (20 mL) was condensed into a 100 mL round bottom flask at −78° C. Lithium wire (300 mg, 43.22 mmol) was added portionwise with stirring and all metal was dissolved within 30 min. A solution of compound 461 (3.90 g, 16.64 mmol) in THF (10 mL) and t-butanol (1.23 g, 16.59 mmol) was added dropwise. Five minutes after addition was complete, the reaction mixture turned green in color and more lithium wire (143 mg, 20.60 mmol) was added to maintain the blue color. The reaction mixture was stirred at −78° C. for 30 min and quenched by portionwise addition of ammonium chloride (658 mg, 12.30 mmol). The ammonia was allowed to evaporate and the residue was partitioned between EtOAc and water. The organic extract was separated, and the aqueous layer was extracted with EtOAc. The combined organic extracts were dried with MgSO$_4$, filtered, and concentrated. The residue was purified by column chromatography (silica gel, eluting with 30% to 50% EtOAc in hexanes) to give compound 462 (2.27 g, 58% yield) as a clear oil. m/z=237 (M+1).

Compound 463: A mixture of compound 462 (333 mg, 1.41 mmol) and 10% palladium on carbon (25 mg) in EtOAc (10 mL) was hydrogenated under hydrogen (1 atm) for 3 h at room temperature. The catalyst was removed by filtered through a pad of Celite®. The filtrate was concentrated to give compound 463 (308 mg, 92% yield) as a clear, viscous oil, which was used without further purification. m/z=239 (M+1).

Compound 464: A solution of compound 463 (308 mg, 1.29 mmol), ethylene glycol (0.72 mL, 12.90 mmol) and p-toluenesulfonic acid monohydrate (25 mg, 0.13 mmol) in benzene (15 mL) was refluxed with a Dean-Stark trap for 2 h. The mixture was cooled and concentrated. The residue was taken up in EtOAc, and washed with aq. sat. NaHCO$_3$, aq. sat. KH$_2$PO$_4$ and brine. The organic extract was dried over Na$_2$SO$_4$, filtered, and concentrated to give compound 464 (364 mg, quantitative yield) as a yellow oil, which was used without further purification. m/z=283 (M+1).

Compound 465: A solution of compound 464 (367 mg, 1.29 mmol) in dichloromethane (15 mL) under nitrogen was treated with magnesium sulfate (155 mg, 1.29 mmol) and pyridinium dichromate (727 mg, 1.93 mmol). The reaction mixture was stirred at room temperature for 17 h and concentrated. The residue was taken up in diethyl ether and stirred at room temperature for 1 h. The mixture was filtered through a pad of Celite®, and the filtrate was concentrated to give compound 465 (327 mg, 90% yield) as a yellow, viscous oil, which was used without further purification. m/z=281 (M+1).

Compound 466: A solution of compound 465 (165 mg, 0.588 mmol) in isopropanol (10 mL) was treated with 2-fluorobenzaldehyde (0.19 mL, 1.80 mmol) and potassium fluoride on alumina (40 wt %, 171 mg, 1.18 mmol). The reaction mixture was stirred at room temperature for 16 h; filtered through a plug of magnesium sulfate; and eluted with CH$_2$Cl$_2$. The filtrate was concentrated. The residue was purified by column chromatography (silica gel, eluting with 0% to 3% EtOAc in CH$_2$Cl$_2$) to give compound 466 (137 mg, 60% yield) as a clear oil. m/z=387 (M+1).

Compound 467: A solution of compound 466 (134 mg, 0.346 mmol), 4-quinolinecarboximidamide hydrochloride (108 mg, 0.520 mmol) and potassium carbonate (143 mg, 1.03 mmol) in EtOH (10 mL) was heated at reflux for 5 days. The reaction mixture was concentrated, and the residue was partitioned between EtOAc and aq. sat. KH$_2$PO$_4$. The organic phase was washed with brine; dried with Na$_2$SO$_4$; filtered and concentrated. The crude dihydropyrimidine was taken up in CH$_2$Cl$_2$ (10 mL) and treated with manganese (IV) oxide (88%, 266 mg, 2.69 mmol). The reaction mixture was stirred under nitrogen at room temperature for 16 h, and filtered through a pad of Celite®. The filtrate was concentrated. The residue was purified by column chromatography (silica gel, eluting with 50% EtOAc in hexanes) to give compound 467 (131 mg, 70% yield) as a clear glass. m/z=538 (M+1).

Compound 468: A solution of compound 467 (130 mg, 0.241 mmol) in THF (10 mL) was treated with aq. 3 N HCl (0.80 mL, 2.40 mmol). The reaction mixture was stirred at room temperature for 24 h; heated at 50° C. for 2 h; and concentrated. The residue was cooled to 0° C. and was cautiously treated with aq. sat. NaHCO$_3$ until neutralized. The mixture was extracted with EtOAc. The organic extract was washed with water and brine; dried with Na$_2$SO$_4$; filtered and concentrated to give compound 468 (104 mg, 87% yield) as a clear glass, which was used without further purification. m/z=494 (M+1).

Compound 469: A mixture of compound 468 (104 mg, 0.210 mmol) in ethyl formate (5.0 mL, 62.16 mmol) was treated dropwise with sodium methoxide (5.4 M solution in MeOH, 0.39 mL, 2.10 mmol) at 0° C. The reaction mixture was stirred at room temperature for 2 h; cooled to 0° C.; and treated with aq. 6 N HCl (0.39 mL, 2.34 mmol). EtOH (15 mL) and hydroxylamine hydrochloride (22 mg, 0.317 mmol) were added sequentially. The reaction mixture was heated at 55° C. for 5 h and concentrated. The residue was partitioned between EtOAc and aq. sat. NaHCO$_3$. The organic extract was separated, and the aqueous layer was extracted with EtOAc. The combined organic extracts were dried with Na$_2$SO$_4$, filtered, and concentrated to give compound 469 (104 mg, 95% yield) as an orange glass, which was used without further purification. m/z=519 (M+1).

Compound 470: A mixture of compound 469 (100 mg, 0.193 mmol) and potassium carbonate (53 mg, 0.383 mmol) in MeOH (10 mL) was stirred under nitrogen at room temperature for 24 h. The solvent was removed in vacuo and the residue was partitioned between EtOAc and aq. sat. KH$_2$PO$_4$. The organic phase was washed with brine, dried with MgSO$_4$, filtered, and concentrated. The residue was purified by column chromatography (silica gel, eluting with 40% EtOAc in hexanes) to give compound 470 (51 mg, 51% yield) as an off-white powder. m/z=519 (M+1).

T164: A solution of compound 470 (50 mg, 0.096 mmol) in anhydrous DMF (3.0 mL), was treated dropwise with a solution of 1,3-dibromo-5,5-dimethylhydantoin (15 mg, 0.052 mmol) in anhydrous DMF (1.0 mL) at 0° C. under nitrogen. After the mixture was stirred at 0° C. for 30 min, anhydrous pyridine (0.077 mL, 0.95 mmol) was added. The cold bath was removed, and the reaction mixture was heated at 60° C. for 4 h. Upon cooling, the reaction mixture was partitioned between EtOAc and aq. sat. KH$_2$PO$_4$. The organic phase was separated, and the aqueous phase was extracted with EtOAc. The combined organic extracts were washed with brine; dried with Na$_2$SO$_4$; filtered and concentrated. The residue was purified by column chromatography (silica gel, eluting with 50% EtOAc in hexanes) to give compound T164 (30 mg, 60% yield) gave a yellow glass. $^1$H NMR (400 MHz, CDCl$_3$) δ 9.09 (d, J=4.5 Hz, 1H), 9.04 (s, 1H), 8.73 (ddd, J=8.6, 1.5, 0.7 Hz, 1H), 8.22 (ddd, J=8.4, 1.4, 0.6 Hz, 1H), 8.00 (d, J=4.4 Hz, 1H), 7.78 (ddd, J=8.4, 6.8, 1.4 Hz, 1H), 7.62 (ddd, J=8.3, 6.8, 1.3 Hz, 1H), 7.51 (m, 2H), 7.33 (td, J=7.6, 1.1 Hz, 1H), 7.23 (m, 1H), 2.78 (m, 5H), 1.97 (m, 4H), 1.44 (m, 2H), 1.32 (m, 1H), 0.88 (d, J=6.7 Hz, 3H), 0.84 (d, J=6.2 Hz, 3H); m/z=517 (M+1).

Compound 471: A solution of compound 466 (401 mg, 1.04 mmol, (2-fluoromethyl)-isonicotinamidine hydrochloride (293 mg, 1.54 mmol), and potassium carbonate (427 mg, 3.09 mmol) in EtOH (25 mL) was heated at reflux for 4 days. The reaction mixture was concentrated and the residue was partitioned between EtOAc and sat. aq.

KH$_2$PO$_4$. The organic phase was washed with sat. aq. NaCl; dried with Na$_2$SO$_4$; filtered and concentrated. The crude dihydropyrimidine was taken up in CH$_2$Cl$_2$ (20 mL) and treated with manganese (IV) oxide (88% pure, 793 mg, 8.03 mmol). The reaction mixture was stirred under nitrogen at room temperature for 24 h. The reagent was filtered through a pad of Celite® and the filtrate was concentrated. The residue was purified by column chromatography (silica gel, eluting with 40% EtOAc in hexanes) to give compound 471 (99 mg, 18% yield) as a clear glass. m/z=520 (M+1).

Compound 472: A solution of compound 471 (168 mg, 0.323 mmol) in THF (20 mL) was treated with 3.0 N aq. HCl (1.08 mL, 3.24 mmol). The reaction mixture was stirred at room temperature for 21 h followed by heating at 50° C. for 3 h; and then concentrated. The residue was cooled to 0° C., and cautiously treated with sat. aq. NaHCO$_3$ until neutralized. The mixture was extracted with EtOAc. The organic extract was washed with water, and sat. aq. NaCl; dried with Na$_2$SO$_4$; filtered, and concentrated to give compound 472 (162 mg, quantitative yield) as a yellow glass. m/z=476 (M+1).

Compound 473: A mixture compound 472 (160 mg, 0.336 mmol) in ethyl formate (7.0 mL, 87.03 mmol) at 0° C. was treated dropwise with sodium methoxide solution (5.4 M in methanol, 0.62 mL, 3.35 mmol). The reaction mixture was stirred at room temperature for 2 h, and then cooled to 0° C. The mixture was treated with 6.0 N aq. HCl (0.63 mL, 3.78 mmol) to adjust to pH~2. EtOH (20 mL) and hydroxylamine hydrochloride (35 mg, 0.504 mmol) were added sequentially. The reaction mixture was heated at 55° C. for 4 h and concentrated. The residue was partitioned between EtOAc and sat. aq. NaHCO$_3$. The aqueous layer was extracted with EtOAc. The combined organic layers were dried with Na$_2$SO$_4$; filtered; and concentrated to give compound 473 (154 mg, 92% yield) as an orange glass. m/z=501 (M+1).

Compound 474: A mixture of compound 473 (154 mg, 0.307 mmol) and potassium carbonate (85 mg, 0.614 mmol) in MeOH (10 mL) was stirred under nitrogen at room temperature for 24 h. The solvent was removed in vacuo and the residue was partitioned between EtOAc and sat. aq. KH$_2$PO$_4$. The organic phase was washed with sat. aq. NaCl; dried with MgSO$_4$; filtered; and concentrated. The residue was purified by column chromatography (silica gel, eluting with 50% EtOAc in hexanes) to give compound 474 (58 mg, 38% yield) as a yellow glass. m/z=501 (M+1).

T165: A solution of compound 474 (58 mg, 0.115 mmol) in anhydrous DMF (3.0 mL) was cooled to 0° C. under nitrogen. The solution was treated dropwise with a solution of 1,3-dibromo-5,5-dimethylhydantoin (18 mg, 0.063 mmol) in anhydrous DMF (1.0 mL). After stirring at 0° C. for 30 min, anhydrous pyridine (0.093 mL, 1.15 mmol) was added. The cold bath was removed, and the reaction mixture was heated at 60° C. for 4 h. Upon cooling, the reaction mixture was partitioned between EtOAc and sat. aq. KH$_2$PO$_4$. The aqueous phase was extracted with EtOAc. The combined organic phases were washed with sat. aq. NaCl; dried with Na$_2$SO$_4$; filtered; and concentrated. The residue was purified by column chromatography (silica gel, eluting with 40% EtOAc in hexanes) to give compound T165 (24 mg, 42% yield) as a yellow glass. m/z=499 (M+1); $^1$H NMR (400 MHz, CDCl$_3$) δ 9.09 (s, 1H), 8.78 (d, J=5.2 Hz, 1H), 8.47 (d, J=1.5 Hz, 1H), 8.30 (dd, J=1.3, 5.0 Hz, 1H), 7.53 (m, 1H), 7.45 (dt, J=1.8, 7.4 Hz, 1H), 7.35 (dt, J=1.1, 7.5 Hz, 1H), 7.21 (m, 1H), 5.61 (d, J=46.8 Hz, 2H), 2.74 (m, 5H), 2.01 (m, 2H), 1.84 (m, 2H), 1.34 (m, 3H), 0.84 (d, J=6.2 Hz, 3H), 0.78 (d, J=6.1 Hz, 3H).

Compound 475: To a solution of compound 342 (300 mg, 0.527 mmol) in anhydrous THF (3 mL) at 0° C. under nitrogen was added dropwise a solution of potassium-t-butoxide (177 mg, 1.58 mmol) in anhydrous THF (5 mL). The mixture was stirred at 0° C. for 15 min and 3-chloro-2-methylpropene (0.52 mL, 5.31 mmol) was added dropwise. The reaction mixture was stirred at 0° C. for an additional 2 h, and then allowed to warm to room temperature over 2 h. The reaction was quenched with sat. aq. NH$_4$Cl, and the mixture was extracted with EtOAc (2×50 mL). The combined organic extracts were dried with Na$_2$SO$_4$; filtered; and concentrated. The residue was purified by column chromatography (silica gel, eluting with 40% EtOAc in hexanes) to give compound 475 (140 mg, 43% yield) as a yellow glass. m/z=623 (M+1).

Compound 476: A solution of compound 475 (284 mg, 0.456 mmol) in EtOH (8 mL) was treated with 1.0 N aq. HCl (0.912 mL, 0.912 mmol) and hydroxylamine hydrochloride (48 mg, 0.691 mmol). The reaction mixture was stirred at 60° C. for 4 h and at room temperature for 20 h. The solvent was removed in vacuo and the residue was partitioned between EtOAc and 10% aq. NH$_4$OH. The organic phase was washed with sat. aq. NaCl; dried with Na$_2$SO$_4$; filtered; and concentrated. The residue was purified by column chromatography (silica gel, eluting with 50% EtOAc in hexanes) to give compound 476 (192 mg, 79% yield) as a yellow glass. m/z=531 (M+1).

Compound 477: A mixture of compound 476 (192 mg, 0.361 mmol) and potassium carbonate (100 mg, 0.723 mmol) in MeOH (15 mL) was stirred at room temperature for 26 h. The reaction mixture was concentrated and the residue was partitioned between water and diethyl ether. The aqueous phase was cooled in an ice-water bath and neutralized with sat. aq. KH$_2$PO$_4$. The mixture was extracted with EtOAc (2×25 mL). The combined organic extracts were washed with sat. aq. NaCl; dried with Na$_2$SO$_4$; filtered and concentrated to give compound 477 (101 mg, 53% yield) as a white glass. m/z=531 (M+1).

T166: A solution of compound 477 (100 mg, 0.188 mmol) in anhydrous toluene (10 mL) was treated with DDQ (55 mg, 0.242 mmol). The reaction mixture was stirred at room temperature for 1 h and concentrated. The residue was purified by column chromatography (silica gel, eluting with 40% EtOAc in hexanes) to give compound T166 (53 mg, 53% yield) as a glass. m/z=529 (M+1); $^1$H NMR (400 MHz, CDCl$_3$) δ 9.09 (d, J=4.5 Hz, 1H), 8.93 (s, 1H), 8.71 (ddd, J=0.7, 1.4, 8.5 Hz, 1H), 8.22 (td, J=0.9, 8.6 Hz, 1H), 8.01 (d, J=4.5 Hz, 1H), 7.78 (ddd, J=1.4, 6.9, 8.4 Hz, 1H), 7.64 (ddd, J=1.3, 6.9, 8.3 Hz, 1H), 7.50 (m, 2H), 7.34 (dt, J=1.1, 7.5 Hz, 1H), 7.23 (m, 1H), 4.88 (s, 1H), 4.75 (s, 1H), 2.89 (d, J=13.9 Hz, 1H), 2.83 (m, 2H), 2.58 (dd, J=2.2, 12.0 Hz, 1H), 2.40 (d, J=13.9 Hz, 1H), 2.17 (s, 3H), 1.95 (m, 2H), 1.66 (s, 3H), 1.28 (s, 3H).

Compound 478: Compound 440 (2.56 g, 7.14 mmol) was taken up in EtOH (15 mL). 2-cyclopropylisonicotinimidamide hydrochloride (1.6 g, 8.09 mmol) and potassium carbonate (2.5 g, 18.09 mmol) were added. The reaction mixture was heated to reflux for 5 days, and then concentrated. The residue was mixed with water (50 mL), and neutralized with aq. KH$_2$PO$_4$. The mixture was extracted with CHCl$_3$. The organic extract was dried with MgSO$_4$; filtered and concentrated. The crude product was taken up in CH$_2$Cl$_2$ (200 mL), and manganese (IV) oxide (88%, 3.5 g, 35.43 mmol) was added. The mixture was stirred overnight at room temperature; and filtered. The filtrate was concentrated. The crude residue was purified by column chromatography (silica gel, eluting with 0% to 35% EtOAc in hexanes) to give compound 478 (1.48 g, 41% yield) as a foam. m/z=500 (M+1).

Compound 479: Compound 478 (1.48 g, 2.96 mmol) was taken up in THF (30 mL), and 3 N aq. HCl (10 mL) was added. The mixture was stirred overnight at room temperature; and then concentrated. The residue was neutralized with 10% aq. NH$_4$OH, and extracted with CHCl$_3$. The organic extract was washed with water; dried with MgSO$_4$; filtered and concentrated to give compound 479 (1.36 g, quantitative yield) as a foam. m/z=456 (M+1).

Compound 480: Compound 479 (275 mg, 0.60 mmol) was taken up in ethyl formate (10 mL, 124.33 mmol). Sodium methoxide solution (30 wt. % in MeOH, 1.2 g, 6.66 mmol) was added. After stirring for 2 h at room temperature, the reaction mixture was treated with 12 N aq. HCl (0.6 mL, 7.20 mmol), EtOH (10 mL) and hydroxylamine hydrochloride (120 mg, 1.7 mmol) sequentially. The mixture was heated at 50° C. overnight, and then concentrated. The residue was taken up in EtOAc, and then washed with aq. NaHCO$_3$. The organic extract was dried with MgSO$_4$; filtered and concentrated. The residue was purified by column chromatography (silica gel, eluting with 0% to 35% EtOAc in hexanes) to give compound 480 (260 mg, 90% yield) as a foam. m/z=481 (M+1).

Compound 481: Compound 480 (260 mg, 0.54 mmol) was dissolved in MeOH (10 mL). K$_2$CO$_3$ (380 mg, 2.75 mmol) was added. After stirring at room temperature overnight, the reaction mixture was neutralized by addition of sat. aq. KH$_2$PO$_4$, and extracted with EtOAc. The organic extract was washed with brine; dried with MgSO$_4$; filtered and concentrated. The residue was purified by column chromatography (silica gel, eluting with 0% to 35% EtOAc in hexanes) to give compound 481 (165 mg, 63% yield) as a foam. m/z=481 (M+1).

T167: Compound 481 (165 mg, 0.34 mmol) was dissolved in dry DMF (4 mL), and the solution was cooled to 0° C. 1,3-Dibromo-5,5-dimethylhydantoin (55 mg, 0.19 mmol) in DMF (1 mL) was added. The reaction was stirred at 0° C. for 2 h. Pyridine (3 mL, 37.09 mmol) was added. The reaction mixture was stirred at 60° C. for 4 h, and cooled to room temperature. The reaction was partitioned between aq. NaHCO$_3$ and extracted with EtOAc. The organic extract was dried with MgSO$_4$; filtered and concentrated. The residue was purified by column chromatography (silica gel, eluting with 0% to 35% EtOAc in hexanes) to give compound T167 (60 mg, 37% yield) as a yellow foam. m/z=479 (M+1); $^1$H NMR (400 MHz, CDCl$_3$) δ 9.14 (s, 1H), 8.61 (d, J=5.2 Hz, 1H), 8.18 (t, J=1.2 Hz, 1H), 8.06 (dd, J 1.6, 5.2 Hz, 1H), 7.52 (ddt, J=1.9, 5.2, 7.9 Hz, 1H), 7.44 (dt, J=1.9, 7.4 Hz, 1H), 7.34 (dt, J=1.0, 7.5 Hz, 1H), 7.21 (ddd, J=1.0, 8.3, 9.6 Hz, 1H), 2.84 (dd, J=5.0, 8.8 Hz, 2H), 2.70 (m, 2H), 2.57 (tt, J 4.2, 13.3 Hz, 1H), 2.21 (tt, J=4.8, 8.1 Hz, 1H), 1.89 (m, 5H), 1.49 (m, 1H), 1.12 (m, 2H), 1.05 (m, 2H), 0.88 (t, J=7.2 Hz, 3H).

Compound 482: Compound 479 (1.35 g, 2.97 mmol) was taken up in ethyl formate (20 mL, 248.65 mmol). Sodium methoxide solution (30 wt. % in MeOH, 5.3 g, 29.43 mmol) was added. After stirring at room temperature for 4 h, the reaction mixture was neutralized with aq. KH$_2$PO$_4$, and extracted with EtOAc. The organic extract was dried with MgSO$_4$; filtered; and concentrated to give compound 482 (1.43 g, quantitative yield) as a foam. m/z=484 (M+1).

Compound 483: To a mixture of compound 482 (1 g, 2.07 mmol) and 3 Å molecular sieves (500 mg) in CH$_2$Cl$_2$ (15 mL) was added N-methylaniline (0.66 g, 6.16 mmol) and p-toluenesulfonic acid monohydrate (38 mg, 0.20 mmol). After stirring at room temperature for 2 days, the reaction mixture was purified by column chromatography (silica gel, eluting with 0% to 50% EtOAc in hexanes) to give compound 483 (0.93 g, 78% yield) as a foam. m/z=573 (M+1).

Compound 484: Compound 483 (780 mg, 1.36 mmol) was taken up in THF (15 mL) at 0° C. Lithium diisopropylamide (1.5 M in cyclohexane, 1.1 mL, 1.65 mmol) was added. After the mixture was stirred for 1 h, allyl bromide (500 mg, 4.13 mmol) was added dropwise. The mixture was stirred for another 3 h; neutralized with aq. KH$_2$PO$_4$; and extracted with EtOAc. The organic extract was dried with MgSO$_4$; filtered and concentrated. The residue was purified by column chromatography (silica gel, eluting with 0% to 50% EtOAc in hexanes) to give compound 484 (230 mg, 28% yield) as a foam. m/z=613 (M+1).

Compound 485: Compound 484 (290 mg, 0.47 mmol) was taken up in EtOH (15 mL). Hydroxylamine hydrochloride (70 mg, 1.01 mmol) and 1 N aq. HCl (1 mL, 1.0 mmol) were added. The reaction mixture was stirred at 55° C. for 16 h. After cooling to room temperature, the reaction mixture was concentrated. The residue was taken up in EtOAc, and then washed with aq. NaHCO$_3$. The organic extract was dried with MgSO$_4$, filtered and concentrated. The residue was purified by column chromatography (silica gel, eluting with 0% to 50% EtOAc in hexanes) to give compound 485 (110 mg, 45% yield) as a foam. m/z=521 (M+1).

Compound 486: Compound 485 (110 mg, 0.21 mmol) was taken up in MeOH (10 mL). K$_2$CO$_3$ (150 mg, 1.09 mmol) was added. The reaction mixture was stirred at room temperature overnight; neutralized by addition of sat. aq. KH$_2$PO$_4$; and extracted with EtOAc. The organic extract was dried with MgSO$_4$; filtered and concentrated. The residue was purified by column chromatography (silica gel, eluting with 0% to 50% EtOAc in hexanes) to give compound 486 (110 mg, quantitative yield). m/z=521 (M+1).

Compound 487: Compound 486 (110 mg, 0.21 mmol) was hydrogenated at atmospheric pressure in EtOAc (10 mL) over 10% palladium on carbon (35 mg) for 16 h at room temperature. The reaction mixture was filtered through a Celite® pad. The filtrate was concentrated to give compound 487 (110 mg, quantitative yield) as a foam. m/z=523 (M+1).

T168: Compound 487 (110 mg, 0.21 mmol) was taken up in dry DMF (2 mL), and cooled to 0° C. 1,3-Dibromo-5,5-dimethylhydantoin (35 mg, 0.12 mmol) in DMF (0.5 mL) was added. The reaction was stirred at 0° C. for 2 h, and then pyridine (1 mL, 12.36 mmol) was added. The mixture was stirred at 60° C. for 4 h, and then concentrated. The crude residue was purified by column chromatography (silica gel, eluting with 0% to 50% EtOAc in hexanes) to give compound T168 (55 mg, 50% yield) as a light yellow foam. m/z=521 (M+1); $^1$H NMR (400 MHz, CDCl$_3$) δ 9.12 (s, 1H), 8.61 (d, J=5.1 Hz, 1H), 8.18 (t, J=1.1 Hz, 1H), 8.05 (dd, J=1.6, 5.2 Hz, 1H), 7.49 (m, 2H), 7.34 (dt, J=1.0, 7.5 Hz, 1H), 7.22 (m, 1H), 2.84 (m, 2H), 2.70 (ddd, J=3.3, 5.1, 13.0 Hz, 1H), 2.40 (dt, J=3.5, 12.9 Hz, 1H), 2.21 (ddd, J=4.8, 8.3, 13.1 Hz, 1H), 2.05 (m, 1H), 1.88 (m, 3H), 1.65 (m, 1H), 1.19 (m, 9H), 0.91 (t, J=7.3 Hz, 3H), 0.86 (t, J=7.3 Hz, 3H).

Compound 488: To a solution of compound 483 (300 mg, 0.52 mmol) was in THF (15 mL) at 0° C. was added lithium diisopropylamide (1.5 M in cyclohexane, 0.42 mL, 0.63 mmol). The mixture was stirred for 1 h, and then iodomethane (250 mg, 1.76 mmol) was added dropwise. The mixture was stirred for another 3 h; neutralized with aq. KH$_2$PO$_4$; and extracted with EtOAc. The organic extract was dried with MgSO$_4$, filtered and concentrated. The residue was purified by column chromatography (silica gel, eluting with 0% to 50% EtOAc in hexanes) to give compound 488 (280 mg, 91% yield) as a foam. m/z=587 (M+1).

Compound 489: Compound 488 (280 mg, 0.48 mmol) was taken up in EtOH (15 mL). Hydroxylamine hydrochloride (70 mg, 1.01 mmol) and 1 N aq. HCl (1 mL, 1 mmol) were added. The reaction mixture was stirred at 55° C. for 16 h. After cooling to room temperature, the reaction mixture was concentrated. The residue was taken up in EtOAc, and then washed with aq. NaHCO$_3$. The organic extract was dried with MgSO$_4$, filtered and concentrated. The residue was purified by column chromatography (silica gel, eluting with 0% to 50% EtOAc in hexanes) to give compound 489 (180 mg, 76% yield) as a foam. m/z=495 (M+1).

Compound 490: Compound 489 (180 mg, 0.36 mmol) was taken up in MeOH (10 mL). K$_2$CO$_3$ (250 mg, 1.81 mmol) was added. The reaction mixture was stirred at room temperature overnight; neutralized by addition of sat. aq. KH$_2$PO$_4$; and extracted with EtOAc. The organic extract was dried with MgSO$_4$, filtered and concentrated. The residue was purified by column chromatography (silica gel, eluting with 0% to 50% EtOAc in hexanes) to give compound 490 (175 mg, 97% yield). m/z=495 (M+1).

T169: Compound 490 (175 mg, 0.35 mmol) was taken up in dry DMF (2 mL), and cooled to 0° C. 1,3-Dibromo-5,5-dimethylhydantoin (56 mg, 0.196 mmol) in DMF (0.5 mL) was added. The reaction stirred at 0° C. for 2 h, and then pyridine (1 mL, 12.36 mmol) was added. The mixture was stirred at 60° C. for 4 h, and concentrated. The crude residue was purified by column chromatography (silica gel, eluting with 0% to 50% EtOAc in hexanes) to give T169 (140 mg, 80% yield) as a light yellow foam. m/z=493 (M+1); $^1$H NMR (400 MHz, CDCl$_3$) δ 9.14 (s, 1H), 8.61 (dd, J=0.7, 5.2 Hz, 1H), 8.18 (s, 1H), 8.06 (dd, J=1.6, 5.2 Hz, 1H), 7.52 (m, 1H), 7.45 (dt, J=1.9, 7.4 Hz, 1H), 7.34 (dt, J=1.0, 7.5 Hz, 1H), 7.22 (ddd, J=1.0, 8.3, 9.6 Hz, 1H), 2.84 (m, 2H), 2.72 (qd, J=6.7, 13.4 Hz, 1H), 2.20 (m, 2H), 2.09 (tdd, J=3.5, 7.3, 14.1 Hz, 1H), 1.90 (m, 3H), 1.47 (m, 2H), 1.30 (d, J=6.7 Hz, 3H), 1.09 (m, 4H), 0.87 (t, J=7.3 Hz, 3H).

Compound 491 was synthesis using the same procedure as reported for the synthesis of its enantiomer (WO 2012/083306A2).

Compound 492: Compound 491 (1 g, 4.46 mmol) was taken up in EtOH (15 mL). 2-Fluorobenzaldehyde (0.61 g, 4.92 mmol) and KF/Al$_2$O$_3$ (40 wt. %, 1 g, 6.89 mmol) were added. The mixture was stirred overnight at room temperature; diluted with CH$_2$Cl$_2$; and filtered. The filtrate was concentrated, and the residue was mixed with hexanes. The precipitated product was collected by filtration and dried under vacuo to give compound 492 (1.4 g, 95% yield) as an off-white solid. m/z=331 (M+1).

Compound 493a: Compound 492 (430 mg, 1.30 mmol) was taken up in EtOH (20 mL). Quinoline-4-carboximidamide HCl salt (310 mg, 1.49 mmol) and potassium carbonate (400 mg, 2.89 mmol) were added. The reaction mixture was heated at reflux for 2 days, and then concentrated. The residue was mixed with water (50 mL); neutralized with aq. KH$_2$PO$_4$; and extracted with EtOAc. The organic extract was dried with MgSO$_4$, filtered and concentrated. The crude product was taken up in CH$_2$Cl$_2$ (20 mL). Manganese (IV) oxide (88%, 1.2 g, 12.15 mmol) was added. The mixture was stirred overnight at room temperature, and filtered. The filtrate was concentrated. The crude residue was purified by column chromatography (silica gel, eluting with 0% to 50% EtOAc in hexanes) to give compound 493a (290 mg, 46% yield) as a foam. m/z=482 (M+1).

Compound 494a: Compound 493a (290 mg, 0.60 mmol) was taken up in THF (5 mL), and 3 N aq. HCl (3 mL) was added. The mixture was stirred overnight at room temperature, and then concentrated. The residue was neutralized with sat. aq. NaHCO$_3$, and the mixture was extracted with EtOAc. The organic extract was washed with water; dried with MgSO$_4$; filtered and concentrated to give compound 494a as (250 mg, 95% yield) a foam. m/z=438 (M+1).

Compound 495a: Compound 494a (240 mg, 0.55 mmol) was taken up in ethyl formate (5 mL, 62.16 mmol). Sodium methoxide solution (30 wt. % in MeOH, 1 g, 5.55 mmol) was added. The mixture was stirred for 2 h at room temperature; neutralized with aq. KH$_2$PO$_4$; and extracted with EtOAc. The organic extract was dried with MgSO$_4$, filtered and concentrated to give compound 495a (250 mg, 98% yield) as a foam. m/z=466 (M+1).

Compound 496a: Compound 495a (250 mg, 0.54 mmol) was taken up in EtOH. Hydroxylamine hydrochloride (100 mg, 1.44 mmol) and 12 N aq. HCl (2 drops) were added. The reaction mixture was stirred overnight at 55° C.; cooled to room temperature; and concentrated. The residue was taken up in EtOAc, and then washed with aq. NaHCO$_3$. The organic extract was dried with MgSO$_4$, filtered and concentrated to give compound 496a (250 mg, quantitative yield) as a foam. m/z=463 (M+1).

Compound 497a: Compound 496a (250 mg, 0.54 mmol) was taken up in MeOH. K$_2$CO$_3$ (0.4 g, 2.89 mmol) was added. The reaction mixture was stirred at room temperature overnight; neutralized by addition of sat. aq. KH$_2$PO$_4$; and extracted with EtOAc. The organic extract was washed with brine; dried with MgSO$_4$; filtered and concentrated. The crude residue was purified by column chromatography (silica gel, eluting with 0% to 50% EtOAc in hexanes) to give compound 497a (210 mg, 84% yield) as a foam. m/z=463 (M+1).

T170: Compound 497a (210 mg, 0.45 mmol) was taken up in dry DMF (2 mL), and cooled to 0° C. 1,3-Dibromo-5,5-dimethylhydantoin (75 mg, 0.26 mmol) in DMF (1 mL) was added. The reaction stirred at 0° C. for 2 h, and then pyridine (1 ml, 12.36 mmol) was added. The reaction mixture was stirred at 60° C. for 4 h; cooled to room temperature; and partitioned between aq. NaHCO$_3$ and EtOAc. The organic extract was dried with MgSO$_4$, filtered and concentrated. The residue was purified by column chromatography (silica gel, eluting with 0% to 50% EtOAc in hexanes) to give compound T170 (150 mg, 72% yield) as an off-white foam. m/z=461 (M+1); $^1$H NMR (400 MHz, CDCl$_3$) δ 9.09 (d, J=4.4 Hz, 1H), 8.78 (ddd, J=0.6, 1.4, 8.6 Hz, 1H), 8.59 (s, 1H), 8.22 (m, 1H), 8.07 (d, J=4.4 Hz, 1H), 7.80 (m, 2H), 7.65 (ddd, J=1.4, 6.8, 8.4 Hz, 1H), 7.56 (dddd, J=1.8, 5.2, 7.2, 8.3 Hz, 1H), 7.36 (dt, J=1.1, 7.6 Hz, 1H), 7.28 (m, 1H), 3.10 (ddd, J=3.5, 12.2, 15.8 Hz, 1H), 2.96 (m, 2H), 2.53 (dt, J=6.3, 12.8 Hz, 1H), 1.56 (s, 3H), 1.36 (d, J=6.8 Hz, 3H).

Compound 493b: Compound 492 (500 mg, 1.51 mmol) was taken up in EtOH (20 mL). 2-(Fluoromethyl) isonicotinimidamide HCl salt (435 mg, 2.29 mmol) and potassium carbonate (550 mg, 3.98 mmol) were added. The reaction mixture was heated at reflux for 4 days, and then concentrated. The residue was mixed with water (50 mL); neutralized with aq. KH$_2$PO$_4$; and extracted with EtOAc. The organic extract was dried with MgSO$_4$, filtered and concentrated. The crude product was taken up in CH$_2$Cl$_2$ (20 mL). Manganese (IV) oxide 2 (88%, 1.5 g, 15.18 mmol) was added. The mixture was stirred overnight at room temperature, and then filtered. The filtrate was concentrated. The crude residue was purified by column chromatography (silica gel, eluting with 0% to 50% EtOAc in hexanes) to give compound 493b (260 mg, 37% yield) as a foam. m/z=464 (M+1).

Compound 494b: Compound 493b (260 mg, 0.56 mmol) was taken up in THF (5 mL). 3 N aq. HCl (3 mL) was added. The mixture was stirred overnight at room temperature, and then concentrated. The residue was neutralized with sat. aq. NaHCO$_3$, and extracted with EtOAc. The organic extract was washed with water; dried with MgSO$_4$; filtered and concentrated to give compound 494b (240 mg, quantitative yield) as a foam. m/z=420 (M+1).

Compound 495b: Compound 494b (240 mg, 0.56 mmol) was taken up in ethyl formate (5 mL, 62.16 mmol). Sodium methoxide solution (30 wt. % in MeOH, 1 g, 5.55 mmol) was added. The mixture was stirred for 2 h at room temperature; neutralized with aq. KH$_2$PO$_4$; and extracted with EtOAc. The organic extract was dried with MgSO$_4$, filtered and concentrated to give compound 495b as (250 mg, quantitative yield) a foam. m/z=448 (M+1).

Compound 496b: Compound 495b (250 mg, 0.56 mmol) was taken up in EtOH (15 mL). Hydroxylamine hydrochloride (100 mg, 1.44 mmol) and 12 N aq. HCl (2 drops) were added. The reaction mixture was stirred overnight at 55° C.; cooled to room temperature; and concentrated. The residue was taken up in EtOAc, and washed with aq. NaHCO$_3$. The organic extract was dried with MgSO$_4$, filtered and concentrated to give compound 496b (230 mg, 92% yield) as a foam. m/z=445 (M+1).

Compound 497b: Compound 496b (230 mg, 0.52 mmol) was taken up in MeOH (10 mL). K$_2$CO$_3$ (0.4 g, 2.89 mmol) was added. The reaction mixture was stirred at room temperature overnight; neutralized by addition of sat. aq. KH$_2$PO$_4$; and extracted with EtOAc. The organic extract was washed with brine; dried with MgSO$_4$; filtered and concentrated. The crude residue was purified by column chromatography (silica gel, eluting with 0% to 50% EtOAc in hexanes) to give compound 497b (200 mg, 87% yield) as a foam. m/z=445 (M+1).

T171: Compound 497b (190 mg, 0.43 mmol) was taken up in dry DMF (2 mL), and cooled to 0° C. 1,3-Dibromo-5,5-dimethylhydantoin (68 mg, 0.24 mmol) in DMF (1 mL) was added. The reaction stirred at 0° C. for 2 h. Pyridine (1 ml, 12.36 mmol) was added. The reaction mixture was stirred at 60° C. for 4 h, and then partitioned between aq. NaHCO$_3$ and EtOAc. The organic extract was dried with MgSO$_4$, filtered and concentrated. The residue was purified by column chromatography (silica gel, eluting with 0% to 50% EtOAc in hexanes) to give T171 (103 mg, 54% yield) as a white foam. m/z=443 (M+1); $^1$H NMR (400 MHz, CDCl$_3$) δ 8.76 (d, J=5.1 Hz, 1H), 8.62 (s, 1H), 8.56 (d, J=1.5 Hz, 1H), 8.37 (td, J=1.0, 5.2 Hz, 1H), 7.84 (dt, J=1.8, 7.5 Hz, 1H), 7.57 (dddd, J=1.8, 5.2, 7.2, 8.5 Hz, 1H), 7.39 (dt, J=1.1, 7.6 Hz, 1H), 7.25 (m, 1H), 5.62 (d, J=46.8 Hz, 2H), 3.04 (ddd, J=3.6, 12.2, 15.8 Hz, 1H), 2.91 (m, 2H), 2.45 (dt, J=6.3, 12.8 Hz, 1H), 1.51 (s, 3H), 1.33 (d, J=6.7 Hz, 3H).

Compound 493c: Compound 492 (500 mg, 1.51 mmol) was taken up in EtOH (20 mL). 2-Methyl-8-fluoro-quinoline-4-carboximidamide HCl salt (550 mg, 2.29 mmol) and potassium carbonate (550 mg, 3.98 mmol) were added. The reaction mixture was heated at reflux for 5 days, and then concentrated. The residue was mixed with water (50 mL); neutralized with aq. KH$_2$PO$_4$; and extracted with EtOAc. The organic extract was dried with MgSO$_4$, filtered and concentrated. The crude product was taken up in CH$_2$Cl$_2$ (20 mL). Manganese (IV) oxide (88%, 1.5 g, 15.18 mmol) was added. The mixture was stirred overnight at room temperature, and then filtered. The filtrated was concentrated. The crude residue was purified by column chromatography (silica gel, eluting with 0% to 50% EtOAc in hexanes) to give compound 493c (560 mg, 72% yield) as a foam. m/z=514 (M+1).

Compound 494c: Compound 493c (0.56 g, 1.09 mmol) was taken up in THF (5 mL), and 3 N aq. HCl (3 mL) was added. The mixture was stirred overnight at room temperature, and then concentrated. The residue was neutralized with saturated aq. NaHCO$_3$, and extracted with EtOAc. The organic extract was washed with water; dried with MgSO$_4$; filtered and concentrated to give compound 494c (515 mg, quantitative yield) as a foam. m/z=470 (M+1).

Compound 495c: Compound 494c (515 mg, 1.09 mmol) was taken up in ethyl formate (10 mL, 124.32 mmol). Sodium methoxide solution (30 wt. % in MeOH, 2 g, 11.11 mmol) was added. The mixture was stirred for 2 h at room temperature; neutralized with aq. KH$_2$PO$_4$; and extracted with EtOAc. The organic extract was dried with MgSO$_4$, filtered and concentrated to give compound 495c (545 mg, quantitative yield) as a foam. m/z=498 (M+1).

Compound 496c: Compound 495c (545 mg, 1.09 mmol) was taken up in EtOH (20 mL). Hydroxylamine hydrochloride (0.16 g, 2.30 mmol) and 12 N aq. HCl (3 drops) were added. The reaction mixture was stirred overnight at 55° C.; cooled to room temperature; and concentrated. The residue was taken up in EtOAc, and then washed with aq. NaHCO$_3$. The organic extract was dried with MgSO$_4$, filtered and concentrated to give compound 496c (0.53 g, 98% yield) as a foam. m/z=495 (M+1).

Compound 497c: Compound 496c (530 mg, 1.07 mmol) was taken up in MeOH (20 mL). K$_2$CO$_3$ (0.75 g, 5.42 mmol) was added. The reaction mixture was stirred at room temperature overnight; neutralized by addition of saturated KH$_2$PO$_4$; and extracted with EtOAc. The organic extract was washed with brine; dried with MgSO$_4$; filtered and concentrated. The crude residue was purified by column chromatography (silica gel, eluting with 0% to 50% EtOAc in hexanes) to give compound 497c (360 mg, 68% yield) as a foam. m/z=495 (M+1).

T172: Compound 497c (350 mg, 0.71 mmol) was taken up in dry DMF (4 mL), and cooled to 0° C. 1,3-Dibromo-5,5-dimethylhydantoin (112 mg, 0.39 mmol) in DMF (1 mL) was added. After the reaction stirred at 0° C. for 2 h, pyridine (1 ml, 12.36 mmol) was added. The reaction mixture was stirred at 60° C. for 4 h, and then partitioned between aq. NaHCO$_3$ and EtOAc. The organic extract was dried with MgSO$_4$, filtered and concentrated. The residue was purified by column chromatography (silica gel, eluting with 0% to 50% EtOAc in hexanes) to give compound T172 (170 mg, 49% yield) as an off-white foam. m/z=493 (M+1); $^1$H NMR (400 MHz, CDCl$_3$) δ 8.59 (s, 1H), 8.49 (td, J=1.2, 8.2 Hz, 1H), 8.01 (s, 1H), 7.80 (dt, J=1.8, 7.6 Hz, 1H), 7.57 (dddd, J=1.8, 5.2, 7.2, 8.3 Hz, 1H), 7.47 (m, 2H), 7.37 (dt, J=1.1, 7.6 Hz, 1H), 7.28 (m, 1H), 3.09 (ddd, J=3.5, 12.2, 15.7 Hz, 1H), 2.96 (m, 2H), 2.91 (s, 3H), 2.53 (dt, J=6.5, 12.8 Hz, 1H), 1.56 (s, 3H), 1.36 (d, J=6.8 Hz, 3H).

Compound 493d: Compound 492 (500 mg, 1.51 mmol) was taken up in EtOH (20 mL). 5-Quinoline carboximidamide HCl salt (400 mg, 1.93 mmol) and potassium carbonate (550 mg, 3.98 mmol) were added. The reaction mixture was heated at reflux for 5 days, and then concentrated. The residue was mixed with water (50 mL); neutralized with aq. KH$_2$PO$_4$; and extracted with EtOAc. The organic extract was dried with MgSO$_4$, filtered and concentrated. The crude product was taken up in CH$_2$Cl$_2$ (20 mL). Manganese (IV) oxide (88%, 1.5 g, 15 mmol) was added. The mixture was stirred overnight at room temperature, and then filtered. The filtrate was concentrated. The crude residue was purified by column chromatography (silica gel, eluting with 0% to 50% EtOAc in hexanes) to give compound 493d (500 mg, 69% yield) as a foam. m/z=482 (M+1).

Compound 494d: Compound 493d (500 mg, 1.04 mmol) was taken up in THF (5 mL), and 3 N aq. HCl (3 mL) was added. The mixture was stirred overnight at room temperature, and then concentrated. The residue was neutralized with sat. aq. $NaHCO_3$; and extracted with EtOAc. The organic extract was washed with water; dried with $MgSO_4$; filtered and concentrated to give compound 494d (455 mg, quantitative yield) as a foam. m/z=438 (M+1).

Compound 495d: Compound 494d (455 mg, 1.04 mmol) was taken up in ethyl formate (10 mL, 124.33 mmol). Sodium methoxide solution (30 wt. % in MeOH, 1.9 g, 10.55 mmol) was added. The mixture was stirred for 2 h at room temperature; neutralized with aq. $KH_2PO_4$; and extracted with EtOAc. The organic extract was dried with $MgSO_4$, filtered and concentrated to give compound 495d (480 mg, 99% yield) as a foam. m/z=466 (M+1).

Compound 496d: Compound 495d (480 mg, 1.03 mmol) was taken up in EtOH (20 mL). Hydroxylamine hydrochloride (145 mg, 2.09 mmol) and 12 N aq. HCl (3 drops) were added. The reaction mixture was stirred overnight at 55° C.; cooled to room temperature; and concentrated. The residue was taken up in EtOAc, and washed with aq. $NaHCO_3$. The organic extract was dried with $MgSO_4$, filtered and concentrated to give compound 496d (0.47 g, 98% yield) as a foam. m/z=463 (M+1).

Compound 497d: Compound 496d (470 mg, 1.02 mmol) was taken up in MeOH (20 mL). $K_2CO_3$ (700 mg, 5.07 mmol) was added. The reaction mixture was stirred at room temperature overnight; neutralized by addition of sat. aq. $KH_2PO_4$; and extracted with EtOAc. The organic extract was washed with brine; dried with $MgSO_4$; filtered and concentrated. The crude residue was purified by column chromatography (silica gel, eluting with 0% to 50% EtOAc in hexanes) to give compound 497d (300 mg, 64% yield) as a foam. m/z=463 (M+1).

T173: Compound 497d (300 mg, 0.65 mmol) was taken up in dry DMF (4 mL), and cooled to 0° C. 1,3-Dibromo-5,5-dimethylhydantoin (105 mg, 0.37 mmol) in DMF (1 mL) was added. After the reaction stirred at 0° C. for 2 h, pyridine (1 ml, 12.36 mmol) was added. The reaction mixture was stirred at 60° C. for 4 h, and then partitioned between aq. $NaHCO_3$ and EtOAc. The organic extract was dried with $MgSO_4$, filtered and concentrated. The residue was purified by column chromatography (silica gel, eluting with 0% to 50% EtOAc in hexanes) to give compound T173 (225 mg, 75% yield) as an off-white foam. m/z=461 (M+1); $^1H$ NMR (400 MHz, $CDCl_3$) δ 9.26 (d, J=8.4 Hz, 1H), 8.98 (dd, J=1.7, 4.2 Hz, 1H), 8.60 (s, 1H), 8.38 (dd, J=1.2, 7.3 Hz, 1H), 8.28 (dd, J=1.1, 8.5 Hz, 1H), 7.86 (dd, J=7.3, 8.4 Hz, 1H), 7.81 (dt, J=1.8, 7.6 Hz, 1H), 7.56 (m, 1H), 7.51 (dd, J=4.2, 8.8 Hz, 1H), 7.36 (dt, J=1.1, 7.6 Hz, 1H), 7.26 (m, 1H), 3.08 (ddd, J=3.4, 12.2, 15.6 Hz, 1H), 2.95 (m, 2H), 2.52 (dt, J=6.5, 12.9 Hz, 1H), 1.55 (s, 3H), 1.35 (d, J=6.7 Hz, 3H).

Compound 493e: Compound 492 (500 mg, 1.51 mmol) was taken up in EtOH (20 mL). 2-(Cyclopropyl)isonicotinimidamide HCl salt (380 mg, 1.92 mmol) and potassium carbonate (550 mg, 3.98 mmol) were added. The reaction mixture was heated at reflux for 5 days, and then concentrated. The residue was mixed with water (50 mL); neutralized with aq. $KH_2PO_4$; and extracted with EtOAc. The organic extract was dried with $MgSO_4$, filtered and concentrated. The crude product was taken up in $CH_2Cl_2$ (20 mL). Manganese (IV) oxide (88%, 1.5 g, 15.18 mmol) was added. The mixture was stirred overnight at room temperature, and then filtered. The filtrated was concentrated. The crude residue was purified by column chromatography (silica gel, eluting with 0% to 50% EtOAc in hexanes) to give compound 493e (370 mg, 52% yield) as a foam. m/z=472 (M+1).

Compound 494e: Compound 493e (370 mg, 0.78 mmol) was taken up in THF (5 mL), and 3 N aq. HCl (3 mL) was added. The mixture was stirred overnight at room temperature, and then concentrated. The residue was neutralized with sat. aq. $NaHCO_3$, and extracted with EtOAc. The organic extract was washed with water; dried with $MgSO_4$; filtered and concentrated to give compound 494e (340 mg, quantitative yield) as a foam. m/z=428 (M+1).

Compound 495e: Compound 494e (340 mg, 0.78 mmol) was taken up in ethyl formate (10 mL, 124.33 mmol). Sodium methoxide solution (30 wt. % in MeOH, 1.5 g, 8.33 mmol) was added. The mixture was stirred for 2 h at room temperature; neutralized with aq. $KH_2PO_4$; and extracted with EtOAc. The organic extract was dried with $MgSO_4$, filtered and concentrated to give compound 495e (355 mg, quantitative yield) as a foam. m/z=456 (M+1).

Compound 496e: Compound 495e (355 mg, 0.78 mmol) was taken up in EtOH (15 mL). Hydroxylamine hydrochloride (120 mg, 1.73 mmol) and 12 N aq. HCl (3 drops) were added. The reaction mixture was stirred overnight at 55° C.; cooled to room temperature; and concentrated. The residue was taken up in EtOAc, and then washed with aq. $NaHCO_3$. The organic extract was dried with $MgSO_4$, filtered and concentrated to give compound 496e (350 mg, 99% yield) as a foam. m/z=453 (M+1).

Compound 497e: Compound 496e (350 mg, 0.77 mmol) was taken up in MeOH (15 mL). $K_2CO_3$ (600 mg, 4.34 mmol) was added. The reaction mixture was stirred at room temperature overnight; neutralized by addition of sat. aq. $KH_2PO_4$; and extracted with EtOAc. The organic extract was washed with brine; dried with $MgSO_4$; filtered and concentrated. The crude residue was purified by column chromatography (silica gel, eluting with 0% to 50% EtOAc in hexanes) to give compound 497e (320 mg, 91% yield) as a foam. m/z=453 (M+1).

T174: Compound 497e (320 mg, 0.71 mmol) was taken up in dry DMF (4 mL), and cooled to 0° C. 1,3-Dibromo-5,5-dimethylhydantoin (115 mg, 0.40 mmol) in DMF (1 mL) was added. After the reaction was stirred at 0° C. for 2 h, pyridine (1 mL, 12.36 mmol) was added. The reaction mixture was stirred at 60° C. for 4 h, and then partitioned between aq. $NaHCO_3$ and EtOAc. The organic extract was dried with $MgSO_4$, filtered and concentrated. The residue was purified by column chromatography (silica gel, eluting with 0% to 50% EtOAc in hexanes) to give compound T174 (140 mg, 44% yield) as a light yellow foam. m/z=451 (M+1); $^1H$ NMR (400 MHz, $CDCl_3$) δ 8.61 (m, 2H), 8.25 (m, 1H), 8.13 (dd, J=1.6, 5.1 Hz, 1H), 7.84 (dt, J=1.9, 7.6 Hz, 1H), 7.56 (m, 1H), 7.38 (dt, J=1.1, 7.6 Hz, 1H), 7.25 (m, 1H), 3.03 (ddd, J=3.6, 12.2, 15.8 Hz, 1H), 2.90 (m, 2H), 2.45 (dt, J=6.3, 12.7 Hz, 1H), 2.21 (tt, J=4.9, 8.1 Hz, 1H), 1.50 (s, 3H), 1.33 (d, J=6.8 Hz, 3H), 1.10 (m, 4H).

Compound 498: A mixture of compound 3 (1.00 g, 5.20 mmol), and 5% Pd/C (100 mg) in 95% aq. EtOH was hydrogenated (hydrogen balloon) at room temperature for 3-4 h. The starting material was completely consumed. The mixture was filtered through a pad of Celite®, and the Celite® pad was eluted with EtOAc. The filtrate was concentrated. The residue was purified by column chromatography (silica gel, eluting with 0% to 40% EtOAc in hexanes) to give compound 498 (521 mg, 52% yield) as a white solid.

m/z=195.1 (M+1) Compound 499: To a mixture of compound 498 (3.00 g, 15.44 mmol) and ethylene glycol (2.22 g, 35.77 mmol) 2-ethyl-2-methyl-1,3-dioxolane (15 mL) was added p-toluenesulfonic acid monohydrate (505 mg, 2.66 mmol) at 15° C. The reaction was stirred at 15° C. for 2 h, and then concentrated. The residue was diluted with EtOAc (300 mL), and washed with 10% aq. $NaHCO_3$ (100 mL). The organic extract was dried with $Na_2SO_4$; filtered and concentrated. The residue was purified by column chromatography (silica gel, eluting with 5% EtOAc in petroleum ether) to give compound 499 (3.20 g, 13.43 mmol, 87% yield) as a white solid. m/z=239.1 (M+1)

Compound 500: Compound 499 (2 g, 8.39 mmol) was taken up in EtOH (35 mL). 2-Fluorobenzaldehyde (1.2 g, 9.67 mmol) and $KF/Al_2O_3$ (40 wt. %, 2 g, 13.77 mmol) were added. The mixture was stirred overnight at room temperature; diluted with $CH_2Cl_2$; and filtered. The filtrate was concentrated, and the residue was mixed with hexanes. The precipitated solid was collected by filtration, and dried under vacuum to give compound 500 (2.75 g, 95% yield) as an off-white solid. m/z=345 (M+1).

Compound 501: Compound 500 (0.6 g, 1.74 mmol) was taken up in EtOH (20 mL). 4-Quinolinecarboximidamide hydrochloride (455 mg, 2.2 mmol) and potassium carbonate (0.6 g, 4.34 mmol) were added. The reaction mixture was heated to reflux for 3 days. The reaction mixture was mixed with water (20 mL); neutralized with aq. $KH_2PO_4$; and extracted with EtOAc. The organic extract was dried with $MgSO_4$ and concentrated. The crude product was taken up in $CH_2Cl_2$ (25 mL). $MnO_2$ (88%, 1.5 g, 15.18 mmol) was added. The mixture was stirred overnight at room temperature, and then filtered. The filtrate was concentrated. The residue was purified by column chromatography (silica gel, eluting with 0% to 35% EtOAc in hexanes) to give compound 501 (0.45 g, 52% yield) as a foam. m/z=496 (M+1).

Compound 502: Compound 501 (0.45 g, 0.91 mmol) was taken up in THF (55 mL). 3 N aq. HCl (3 mL) was added. The mixture was stirred overnight at room temperature, and concentrated. The residue was neutralized with sat. aq. $NaHCO_3$, and extracted with EtOAc. The organic extract was dried with $MgSO_4$, filtered and concentrated to give compound 502 (0.41 g, quantitative yield) as a foam. m/z=452 (M+1).

Compound 503: Compound 502 (0.41 g, 0.91 mmol) was taken up in ethyl formate (10 mL, 124.32 mmol). Sodium methoxide solution (30 wt. % in MeOH, 1.8 g, 10.00 mmol) was added. After stirring overnight at room temperature, the reaction mixture was neutralized with aq. $KH_2PO_4$, and extracted with EtOAc. The organic extract was dried with $MgSO_4$, filtered and concentrated to give compound 503 (435 mg, quantitative yield) as a foam. m/z=480 (M+1).

Compound 504: Compound 503 (435 mg, 0.91 mmol) was taken up in EtOH (15 mL). Hydroxylamine hydrochloride (0.15 g, 2.16 mmol) and 12 N aq. HCl (2 drops) were added. The reaction mixture was stirred overnight at 55° C. After cooling to room temperature, the reaction mixture was concentrated. The residue was taken up in EtOAc, and washed with aq. $NaHCO_3$. The organic extract was dried with $MgSO_4$, filtered and concentrated to give compound 504 (0.3 g, 69% yield) as a foam. m/z=477 (M+1).

Compounds 505 and 506: Compound 504 (0.71 g, 1.49 mmol) was taken up in MeOH (15 mL). $K_2CO_3$ (1.03 g, 7.45 mmol) was added. After stirring at room temperature overnight, the reaction was neutralized by addition of sat. aq. $KH_2PO_4$, and extracted with EtOAc. The organic extract was dried with $MgSO_4$, filtered and concentrated. The crude residue was purified by column chromatography (silica gel, eluting with 0% to 35% EtOAc in hexanes) to give compound 505 (0.43 g, 61% yield) and compound 506 (0.1 g, 14% yield) as foamy solids. m/z=477 (M+1).

T175: Compound 505 (0.43 g, 0.90 mmol) was taken up in dry DMF (4 mL), and cooled to 0° C. 1,3-Dibromo-5,5-dimethylhydantoin (145 mg, 0.51 mmol) in DMF (1 mL) was added. The reaction was stirred at 0° C. for 2 h. Pyridine (1 mL, 12.36 mmol) was then added, and the mixture was stirred at 60° C. for 4 h. After cooled to room temperature, the mixture was partitioned between aq. $NaHCO_3$ and EtOAc. The organic extract was dried with $MgSO_4$, filtered and concentrated. The residue was purified by column chromatography (silica gel, eluting with 0% to 35% EtOAc in hexanes) to give compound T175 (195 mg, 45% yield) as a yellow foam. m/z=475 (M+1); $^1H$ NMR (400 MHz, $CDCl_3$) δ 9.07 (d, J=4.5, 1H), 8.67 (dd, J=1.4, 8.6 Hz, 1H), 8.21 (m, 2H), 7.98 (d, J=4.5 Hz, 1H), 7.77 (ddd, J=1.4, 6.8, 8.4 Hz, 1H), 7.65 (ddd, J=1.4, 6.8, 8.7 Hz, 1H), 7.52 (m, 2H), 7.34 (dt, J=1.1, 7.6 Hz, 1H), 7.23 (m, 1H), 2.87 (ddd, J=6.1, 12.3, 18.4 Hz, 1H), 2.69 (m, 1H), 2.58 (qd, J=6.6, 13.2 Hz, 1H), 2.29 (td, J=3.4, 12.9 Hz, 1H), 2.15 (m, 2H), 1.80 (s, 3H), 1.31 (d, J=6.6 Hz, 3H).

T176: Compound 506 (0.1 g, 0.21 mmol) was taken up in dry DMF (2 mL), and cooled to 0° C. 1,3-Dibromo-5,5-dimethylhydantoin (35 mg, 0.12 mmol) in DMF (1 mL) was added. The reaction was stirred at 0° C. for 2 h, and then pyridine (1 mL, 12.36 mmol) was added. The reaction mixture was stirred at 60° C. for 4 h; cooled to room temperature; and partitioned between aq. $NaHCO_3$ and EtOAc. The organic extract was dried with $MgSO_4$, filtered and concentrated. The residue was purified by column chromatography (silica gel, eluting with 0% to 35% EtOAc in hexanes) to give compound T176 as (17 mg, 17% yield) as an off-white foam. m/z=475 (M+1); $^1H$ NMR (400 MHz, $CDCl_3$) δ 9.09 (d, J=4.5 Hz, 1H), 8.75 (ddd, J=0.6, 1.5, 8.6 Hz, 1H), 8.22 (m, 1H), 8.03 (d, J=4.5 Hz, 1H), 7.78 (m, 2H), 7.64 (ddd, J=1.3, 6.8, 8.3 Hz, 1H), 7.54 (m, 2H), 7.34 (dt, J=1.1, 7.5 Hz, 1H), 7.24 (m, 1H), 3.22 (m, 1H), 2.91 (m, 1H), 2.69 (ddd, J=2.4, 4.3, 17.5 Hz, 1H), 2.44 (m, 1H), 2.03 (m, 1H), 2.02 (s, 3H), 1.32 (d, J=6.7 Hz, 3H), 1.26 (m, 1H).

Compound 507: A mixture of compound 380 (1.78 g, 3.74 mmol) and manganese (IV) oxide (88%, 3.7 g, 37.45 mmol) in $CH_2Cl_2$ (100 mL) was stirred at room temperature under $N_2$ for 16 h. The mixture was filtered through a pad of Celite®. The filtrate was concentrated, and the residue was purified by column chromatography (silica gel, eluting with 50% EtOAc in hexanes) to give compound 507 (1.13 g, 63% yield) as a light yellow solid. m/z=474 (M+1).

Compound 508: A solution of compound 507 (1.13 g, 2.39 mmol) and methyl (triphenylphosphoranylidene)acetate (1.20 g, 3.48 mmol) in benzene (25 mL) was stirred at room temperature under $N_2$ overnight. The mixture was concentrated, and the residue was purified by column chromatography (silica gel, eluting with 50% EtOAc in hexanes) to give compound 508 (1.26 g, 99% yield) as a light yellow foamy solid. m/z=530 (M+1).

Compound 509: A mixture of compound 508 (1.26 g, 2.38 mmol) and 10% palladium on carbon (0.13 g) in EtOAc (50 mL) was hydrogenated (balloon pressure) at room temperature for 16 h. The mixture was filtered, and the filtrate was concentrated to give compound 509 (1.17 g, 93% yield) as a light yellow foamy solid. m/z=532 (M+1).

Compound 510: A solution of compound 509 (1.17 g, 2.20 mmol) and 3 N aq. HCl (7.3 mL, 21.9 mmol) in THF (50 mL) was stirred at room temperature under $N_2$ overnight. The mixture was concentrated. The residue was cooled, and adjusted to pH~6 by adding sat. aq. $NaHCO_3$ (30 mL) and sat. aq. KH$_2$PO$_4$ (50 mL) sequentially. The mixture was extracted with EtOAc (50 mL). The organic extract was washed with sat. aq. NaCl (50 mL); dried with MgSO$_4$; filtered and concentrated to give compound 510 (1.09 g) as a yellow foamy solid. Compound 510 is a mixture of carboxylic acid (R=H) and methyl ester (R=Me) in 93/7 ratio. m/z=474 (R=H, M+1) and 488 (R=Me, M+1).

Compound 511: A solution of compound 510 (1.09 g, ≤2.20 mmol) in ethyl formate (20 mL, 248.65 mmol) was treated with and sodium ethoxide (21 wt. % in EtOH, 4.1 mL, 10.98 mmol). The mixture was stirred at room temperature under N$_2$ overnight, and then concentrated. The residue was partitioned between EtOAc (50 mL) and sat. aq. KH$_2$PO$_4$ solution (50 mL). The organic extract was washed with sat. aq. NaCl (50 mL); dried with MgSO$_4$; filtered and concentrated to give compound 511 (1.06 g, 96% yield from 509) as a tan solid. m/z=502 (M+1).

Compound 512: A solution of compound 511 (1.06 g, 2.11 mmol), acetic acid (1.26 mL, 22.01 mmol) and hydroxylamine hydrochloride (0.23 g, 3.31 mmol) in EtOH (25 mL) was stirred at 60° C. for 2 h then at room temperature overnight. The mixture was concentrated, and the residue was carefully partitioned between sat. aq. NaHCO$_3$ (25 mL) and EtOAc (25 mL). The organic extract was washed with sat. aq. NaCl (25 mL); dried with MgSO$_4$; filtered and concentrated to give compound 512 (1.08 g, 97% yield) as a brown foamy solid. m/z=527 (M+1).

Compound 513: To a stirring solution at 0° C. under N$_2$ of ammonium chloride (53 mg, 0.99 mmol) in toluene (2 mL) was added dropwise trimethylaluminum (1.0 M in heptane, 1.0 mL, 1.0 mmol). After addition, the ice-bath was removed, and the mixture was stirred at room temperature for 3 h. A solution of compound 512 (0.17 g, 0.32 mmol) in toluene (2 mL) was then added dropwise. The mixture was stirred for 72 h; cooled; and quenched with dropwise addition of MeOH (20 mL). The mixture was concentrated, and the residue was partitioned between sat. aq. Rochelle's salt (25 mL) and EtOAc (25 mL). The organic extract was washed with sat. aq. NaCl (25 mL); dried with MgSO$_4$; filtered; and concentrated. The residue was purified by column chromatography (silica gel, eluting with 5% MeOH in CHCl$_3$) to give compound 513 (86 mg, 54% yield) as a yellow oil. m/z=498 (M+1).

Compound 514: A mixture of compound 513 (0.31 g, 0.62 mmol) and potassium carbonate (0.43 g, 3.11 mmol) in MeOH (20 mL) was stirred at room temperature under N$_2$ overnight. The mixture was concentrated, and the residue was carefully partitioned between sat. aq. KH$_2$PO$_4$ (25 mL) and EtOAc (25 mL). The organic extract was washed with sat. aq. NaCl (25 mL); dried with MgSO$_4$; filtered; and concentrated. The residue was purified by column chromatography (silica gel, eluting with 5% MeOH in CHCl$_3$) to give compound 514 (0.22 g, 71% yield) as a yellow foamy solid. m/z=498 (M+1).

T177: To a stirring solution at 0° C. under N$_2$ of compound 514 (0.19 g, 0.38 mmol) in degassed DMF (4 mL) was added dropwise a solution of 1,3-dibromo-5,5-dimethylhydantoin (54 mg, 0.19 mmol) in degassed DMF (1 mL). The mixture was stirred at 0° C. for 30 min. Pyridine (0.31 mL, 3.83 mmol) was added. The mixture was heated at 60° C. for 4 h, and then concentrated. The residue was partitioned between sat. aq. KH$_2$PO$_4$ (25 mL) and EtOAc (25 mL). The organic extract was washed with sat. aq. NaCl (25 mL); dried with MgSO$_4$; filtered; and concentrated. The residue was purified by column chromatography (silica gel, eluting with 10% MeOH in CHCl$_3$) to give compound T177 (83 mg, 44% yield) as a tan foamy solid. m/z=496 (M+1);

$^1$H NMR (400 MHz, CDCl$_3$) δ 9.01 (s, 1H), 8.69 (dd, J=0.8, 5.2 Hz, 1H), 8.25 (t, J=1.1 Hz, 1H), 8.20 (dd, J=1.6, 5.2 Hz, 1H), 7.52 (dddd, J=1.9, 5.3, 7.2, 8.4 Hz, 1H), 7.45 (dt, J=1.1, 7.5 Hz, 1H), 7.34 (dt, J=1.1, 7.5 Hz, 1H), 7.21 (ddd, J=1.0, 8.3, 9.7 Hz, 1H), 6.39 (br s, 1H), 5.37 (br s, 1H), 3.28 (t, J=7.1 Hz, 2H), 2.81 (m, 4H), 2.63 (qd, J=6.7, 13.4 Hz, 1H), 2.26 (dt, J=2.7, 12.7 Hz, 1H), 2.12 (m, 1H), 1.82 (m, 1H), 1.55 (s, 3H), 1.32 (d, J=6.7 Hz, 3H).

Compound 515: A solution of compound 381 (1.28 g, assume 2.31 mmol) in CH$_3$CN (10 mL) was treated with 18-Crown-6 (0.90 g, 3.41 mmol) followed by potassium cyanide (0.19 g, 2.92 mmol). The mixture was heated at 50° C. under N$_2$ overnight; cooled; and then partitioned between 1 N aq. NaOH (50 mL) and EtOAc (50 mL). The organic extract was washed with sat. aq. NaCl (50 mL); dried with MgSO$_4$; filtered; and concentrated. The residue was purified by column chromatography (silica gel, eluting with 50% EtOAc in hexanes) to give compound 515 (0.92 g, 82% yield) as an orange-yellow solid. m/z=485 (M+1).

Compound 516: A suspension of compound 515 (0.92 g, 1.90 mmol) in ammonia (7 N in MeOH, 50 mL) was treated with W2 Raney nickel [1.5 g, washed with MeOH (50 mL)]. The mixture was hydrogenated (balloon pressure) at room temperature for 16 h, and filtered. The filtrate was concentrated to give compound 516 (0.82 g, 88% yield) as a tan foamy solid. m/z=489 (M+1).

Compound 517: A suspension of compound 516 (0.82 g, 1.68 mmol) and sodium acetate (1.38 g, 16.82 mmol) in acetic anhydride (10 mL, 105.78 mmol) was stirred at room temperature under N$_2$ overnight, and then concentrated. The residue was carefully partitioned between sat. aq. NaHCO$_3$ (50 mL) and EtOAc (50 mL). The organic extract was washed with sat. aq. NaCl (50 mL); dried with MgSO$_4$; filtered; and concentrated. The residue was purified by column chromatography (silica gel, eluting with 2.5% MeOH in CHCl$_3$) to give compound 517 (0.89 g, quantitative yield) as a light yellow foamy solid. m/z=531 (M+1).

Compound 518: A solution of compound 517 (0.89 g, 1.68 mmol) and 3 N aq. HCl (6 mL, 18 mmol) in THF (20 mL) was stirred at room temperature under N$_2$ overnight. The mixture was concentrated; cooled; carefully basified with sat. aq. NaHCO$_3$ (50 mL); and extracted with EtOAc (50 mL). The organic extract was washed with sat. aq. NaCl (50 mL); dried with MgSO$_4$; filtered; and concentrated to give compound 518 (0.68 g, 83% yield) as a light yellow foamy solid. m/z=487 (M+1).

Compound 519: In a sealable vial, a solution of compound 518 (0.68 g, 1.40 mmol) in N,N-dimethylformamide dimethylacetal (10 mL, 75.28 mmol) was flushed with N$_2$. The vial was sealed. The mixture was heated at 100° C. for 4 days; cooled; and concentrated to give compound 519 (0.96 g) as a brown foamy solid. m/z=542 (M+1).

Compound 520: A solution of compound 519 (0.96 g, ≤1.40 mmol), acetic acid (0.80 mL, 13.97 mmol) and hydroxylamine hydrochloride (0.14 g, 2.01 mmol) in EtOH (20 mL) was stirred at 60° C. for 2 h, and then at room temperature overnight. The mixture was concentrated, and the residue was carefully partitioned between sat. aq. NaHCO$_3$ (50 mL) and EtOAc (50 mL). The organic extract was washed with sat. aq. NaCl (50 mL); dried with MgSO$_4$; filtered; and concentrated. The residue was purified by column chromatography (silica gel, eluting with 5% MeOH in CHCl$_3$) to give compound 520 (0.42 g, 59% yield from 518) as a dark yellow foamy solid. m/z=512 (M+1).

Compound 521: A mixture of compound 520 (0.42 g, 0.82 mmol) and potassium carbonate (0.57 g, 4.12 mmol) in MeOH (20 mL) was stirred at room temperature under N$_2$ overnight. The mixture was concentrated, and the residue was carefully partitioned between sat. aq. $KH_2PO_4$ (50 mL) and EtOAc (50 mL). The organic extract was washed with sat. aq. NaCl (50 mL); dried with $MgSO_4$; filtered; and concentrated. The residue was purified by column chromatography (silica gel, eluting with 5% MeOH in $CHCl_3$) to give compound 521 (0.26 g, 62% yield) as a yellow foamy solid. m/z=512 (M+1).

T178: To a stirring solution at 0° C. under $N_2$ of compound 521 (0.26 g, 0.51 mmol) in degassed DMF (4 mL) was added dropwise a solution of 1,3-dibromo-5,5-dimethylhydantoin (89 mg, 0.31 mmol) in degassed DMF (1 mL). The mixture was stirred at 0° C. for 30 min. Pyridine (0.42 mL, 5.19 mmol) was added. The mixture was heated at 60° C. for 4 h, and then concentrated. The residue was partitioned between sat. aq. $KH_2PO_4$ (25 mL) and EtOAc (25 mL). The organic extract was washed with sat. aq. NaCl (25 mL); dried with $MgSO_4$; filtered; and concentrated. The residue was purified by column chromatography (silica gel, eluting with 5% MeOH in $CHCl_3$) to give partially purified product, which was purified again by column chromatography (silica gel, eluting with MeOH/EtOAc/$CH_2Cl_2$ in 1/4/4 ratio) to give compound T178 (53 mg, 20% yield) as a light yellow foamy solid. m/z=510 (M+1); $^1$H NMR (400 MHz, $CDCl_3$) δ 9.01 (s, 1H), 8.71 (dd, J=0.8, 5.1 Hz, 1H), 8.22 (m, 2H), 7.52 (m, 1H), 7.44 (dt, J=1.9, 7.4 Hz, 1H), 7.34 (dt, J=1.0, 7.5 Hz, 1H), 7.22 (ddd, J=1.1, 8.3, 9.7 Hz, 1H), 6.52 (br s, 1H), 3.73 (q, J=6.1 Hz, 2H), 3.13 (dd, J=5.5, 7.1 Hz, 2H), 2.82 (m, 2H), 2.63 (qd, J=6.7, 13.4 Hz, 1H), 2.26 (dt, J=2.7, 12.8 Hz, 1H), 2.13 (m, 1H), 1.97 (s, 3H), 1.82 (m, 1H), 1.55 (s, 3H), 1.33 (d, J 6.7 Hz, 3H).

Compound 522: In a sealable vial, a mixture of 3-bromoisonicotinimidamide hydrochloride (1.00 g, 4.23 mmol), compound 88 (1.75 g, 5.08 mmol) and potassium carbonate (1.75 g, 12.66 mmol) in EtOH (10 mL) was stirred at room temperature under $N_2$ for 2 h. The vial was sealed. The mixture was heated at 80° C. overnight; cooled; and filtered. The filtrate was concentrated, and the residue was partitioned between sat. aq. $KH_2PO_4$ (50 mL) and EtOAc (50 mL). The organic extract was washed with sat. aq. NaCl (50 mL); dried with $MgSO_4$; filtered; and concentrated to give the dihydropyrimidine (2.48 g) as a yellow foamy solid. A mixture of the dihydropyrimidine (2.48 g) and manganese (IV) oxide (88%, 2.1 g, 21.26 mmol) in $CH_2Cl_2$ (50 mL) was stirred at room temperature under $N_2$ for 16 h. The mixture was filtered through a pad of Celite®, and the filtrate was concentrated. The residue was purified by column chromatography (silica gel, eluting with 50% EtOAc in hexanes) to give compound 522 (1.35 g, 51% yield) as a light yellow solid. m/z=524/526 (M+1).

Compound 523: In a sealable vial, a mixture of compound 522 (0.40 g, 0.76 mmol), phenylboronic acid (0.18 g, 1.48 mmol), potassium phosphate (0.48 g, 2.26 mmol), 1,4-dioxane (6.4 mL) and DMF (1.6 mL) was degassed. The mixture was treated with tetrakis(triphenylphosphine)palladium (O) (88 mg, 0.076 mmol), and degassed again. The vial was sealed and heated at 100° C. for 16 h. The mixture was cooled to room temperature; diluted with EtOAc (50 mL); and washed with 1 N aq. NaOH (50 mL). The organic extract was washed with sat. aq. $KH_2PO_4$ (50 mL) and sat. aq. NaCl (50 mL); dried with $MgSO_4$; filtered; and concentrated. The residue was purified by column chromatography (silica gel, eluting with 50% EtOAc in hexanes) to give compound 523 (0.48 g, quantitative yield) as a light yellow foamy solid. m/z=522 (M+1).

Compound 524: A solution of compound 523 (0.48 g, ≤0.76 mmol) and 3 N aq. HCl (2.5 mL, 7.5 mmol) in MeOH (50 mL) was stirred at room temperature under $N_2$ for 16 h. The mixture was concentrated. The residue was cooled, and basified with 10% aq. $NH_4OH$ to pH 9-10. The mixture was extracted with $CHCl_3$ (50 mL). The organic extract was washed with sat. aq. NaCl (50 mL); dried with $MgSO_4$; filtered and concentrated to give compound 524 (0.42 g, quantitative yield) as an off-white foamy solid. m/z=478 (M+1).

Compound 525: A solution of compound 524 (0.42 g, ≤0.76 mmol) in ethyl formate (20 mL, 248.65 mmol) was treated with and sodium methoxide (30 wt. % in MeOH, 0.75 mL, 4.04 mmol). The mixture was stirred at room temperature under $N_2$ overnight, and concentrated. The residue was partitioned between EtOAc (50 mL) and sat. aq. $KH_2PO_4$ (50 mL). The organic extract was washed with sat. aq. NaCl (50 mL); dried with $MgSO_4$; filtered; and concentrated to give compound 525 (0.42 g, quantitative yield) as a yellow foamy solid. m/z=506 (M+1).

Compound 526: A solution of compound 525 (0.42 g, ≤0.76 mmol), acetic acid (0.45 mL, 7.86 mmol) and hydroxylamine hydrochloride (80 mg, 1.15 mmol) in EtOH (20 mL) was stirred at 60° C. for 2 h, and then at room temperature overnight. The mixture was concentrated, and the residue was partitioned between sat. aq. $NaHCO_3$ (25 mL) and EtOAc (25 mL). The organic extract was washed with sat. aq. NaCl (25 mL); dried with $MgSO_4$; filtered and concentrated to give compound 526 (0.39 g, quantitative yield) as a tan foamy solid. m/z=503 (M+1).

Compound 527: A mixture of compound 526 (0.39 g, ≤0.76 mmol) and potassium carbonate (0.52 g, 3.76 mmol) in MeOH (20 mL) was stirred at room temperature under $N_2$ overnight. The mixture was concentrated, and the residue was carefully partitioned between sat. aq. $KH_2PO_4$ (25 mL) and EtOAc (25 mL). The organic extract was washed with sat. aq. NaCl (25 mL); dried with $MgSO_4$; filtered; and concentrated to give compound 527 (0.38 g, quantitative yield) as a tan foamy solid. m/z=503 (M+1).

T179: To a stirring solution at 0° C. under $N_2$ of compound 527 (0.38 g, 0.76 mmol) in degassed DMF (5 mL) was added dropwise a solution of 1,3-dibromo-5,5-dimethylhydantoin (0.11 g, 0.39 mmol) in degassed DMF (2 mL). The mixture was stirred at 0° C. for 30 min. Pyridine (0.61 mL, 7.54 mmol) was added. The mixture was heated at 60° C. for 4 h, and then concentrated. The residue was partitioned between sat. aq. $KH_2PO_4$ (25 mL) and EtOAc (25 mL). The organic extract was washed with sat. aq. NaCl (25 mL); dried with $MgSO_4$; filtered; and concentrated. The residue was purified by column chromatography (silica gel, eluting with 50% EtOAc in hexanes) to give compound T179 (0.20 g, 53% yield) as a light yellow foamy solid. m/z=501 (M+1); $^1$H NMR (400 MHz, $CDCl_3$) δ 8.75 (d, J=5.1 Hz, 1H), 8.73 (m, 1H), 7.96 (dd, J=0.7, 5.1 Hz, 1H), 7.61 (s, 1H), 7.46 (m, 4H), 7.31 (m, 2H), 7.21 (m, 3H), 2.81 (ddd, J=7.0 Hz, 11.2, 18.3 Hz, 1H), 2.71 (dd, J=6.3, 18.2 Hz, 1H), 2.45 (td, J=6.7, 13.4 Hz, 1H), 2.07 (m, 2H), 1.67 (dq, J=6.7, 12.9 Hz, 1H), 1.25 (d, J=7.0 Hz, 3H), 1.17 (s, 3H).

Compound 528: In a sealable vial, a mixture of compound 522 (0.40 g, 0.76 mmol), potassium cyclopropyltrifluoroborate (0.34 g, 2.30 mmol), potassium phosphate (0.48 g, 2.26 mmol), RuPhos (35 mg, 0.075 mmol), toluene (6.4 mL) and water (1.6 mL) was degassed. Palladium (II) acetate (8 mg, 0.036 mmol) was added. The mixture was degassed again. The vial was sealed and heated at 100° C. for 16 h. After cooled to room temperature, the mixture was diluted with EtOAc (50 mL), and washed with sat. aq. $KH_2PO_4$ solution (50 mL). The organic extract was washed with sat. aq. NaCl solution (50 mL); dried with $MgSO_4$; filtered; and concentrated. The residue was purified by column chromatography (silica gel, eluting with 50% EtOAc in hexanes) to give compound 528 (0.18 g, 49% yield) as a yellow solid. m/z=486 (M+1).

Compound 529: A solution of compound 528 (0.18 g, 0.37 mmol) and 3 N aq. HCl (1.25 mL, 3.75 mmol) in MeOH (20 mL) was stirred at room temperature under $N_2$ for 16 h. The mixture was concentrated. The residue was cooled, and basified with 10% aq. $NH_4OH$ solution to pH 9-10. The mixture was extracted with $CHCl_3$ (25 mL). The organic extract was washed with sat. aq. NaCl solution (25 mL); dried with $MgSO_4$; filtered; and concentrated to give compound 529 (0.20 g, quantitative yield) as a light orange foamy solid. m/z=442 (M+1).

Compound 530: A solution of compound 529 (0.20 g, ≤0.37 mmol) in ethyl formate (10 mL, 124.33 mmol) was treated with and sodium methoxide (30 wt. % solution in MeOH, 0.35 mL, 1.89 mmol). The mixture was stirred at room temperature under $N_2$ overnight, and then concentrated. The residue was partitioned between EtOAc (25 mL) and sat. aq. $KH_2PO_4$ solution (25 mL). The organic extract was washed with sat. aq. NaCl solution (25 mL); dried with $MgSO_4$; filtered and concentrated to give compound 530 (0.17 g, 98% yield) as a tan foamy solid. m/z=470 (M+1).

Compound 531: A solution of compound 530 (0.17 g, 0.36 mmol), acetic acid (0.21 mL, 3.67 mmol) and hydroxylamine hydrochloride (39 mg, 0.56 mmol) in EtOH (10 mL) was stirred at 60° C. for 2 h, and then at room temperature overnight. The mixture was concentrated, and the residue was partitioned between sat. aq. $NaHCO_3$ solution (25 mL) and EtOAc (25 mL). The organic extract was washed with sat. aq. NaCl solution (25 mL); dried with $MgSO_4$; filtered and concentrated to give compound 531 (0.16 g, 95% yield) as a tan foamy solid. m/z=467 (M+1).

Compound 532: A mixture of compound 531 (0.16 g, 0.34 mmol) and potassium carbonate (0.24 g, 1.74 mmol) in MeOH (20 mL) was stirred at room temperature under $N_2$ overnight. The sample was concentrated, and the residue was partitioned between sat. aq. $KH_2PO_4$ solution (25 mL) and EtOAc (25 mL). The organic extract was washed with sat. aq. NaCl solution (25 mL); dried with $MgSO_4$; filtered and concentrated to give compound 532 (0.15 g, 94% yield) as a tan foamy solid. m/z=467 (M+1).

T180: To a stirring solution at 0° C. under $N_2$ of compound 532 (0.15 g, 0.32 mmol) in degassed DMF (3 mL) was added dropwise a solution of 1,3-dibromo-5,5-dimethylhydantoin (46 mg, 0.16 mmol) in degassed DMF (1 mL). The mixture was stirred at 0° C. for 30 min. Pyridine (0.26 mL, 3.21 mmol) was added. The mixture was heated at 60° C. for 4 h, and then concentrated. The residue was partitioned between sat. aq. $KH_2PO_4$ (25 mL) and EtOAc (25 mL). The organic extract was washed with sat. aq. NaCl (25 mL); dried with $MgSO_4$; filtered; and concentrated. The residue was purified by column chromatography (silica gel, eluting with 50% EtOAc in hexanes) to give compound T180 (46 mg, 31% yield) as an off-white solid. m/z=465 (M+1); $^1$H NMR (400 MHz, $CDCl_3$) δ 8.91 (s, 1H), 8.57 (d, J=5.0 Hz, 1H), 8.47 (s, 1H), 7.70 (d, J=5.0 Hz, 1H), 7.50 (dddd, J=1.9, 5.3, 7.3, 8.4 Hz, 1H), 7.41 (dt, J=1.9, 7.4 Hz, 1H), 7.30 (dt, J=1.1, 7.5 Hz, 1H), 7.20 (ddd, J=1.0, 8.4, 9.7 Hz, 1H), 2.85 (m, 2H), 2.62 (qd, J=6.7, 13.4 Hz, 1H), 2.50 (tt, J=5.5, 8.6 Hz, 1H), 2.28 (dt, J=2.7, 12.8 Hz, 1H), 2.14 (m, 1H), 1.83 (m, 1H), 1.54 (s, 3H), 1.32 (d, J=6.7 Hz, 3H), 0.93 (m, 2H), 0.73 (m, 2H).

Compound 533: To a stirring solution of potassium tert-butoxide (72.3 mg, 0.644 mmol) in THF (0.7 mL) a 0° C. under argon was added a solution of compound 337 (120 mg, 0.215 mmol) in THF (1.5 mL). After the reaction mixture was stirred at 0° C. for 10 min, ethyl iodide (0.052 mL, 0.647 mmol) was added. The reaction mixture was stirred at 0° C. for 1 h, and then quenched with sat. aq. $NH_4Cl$. The mixture was extracted with EtOAc. The organic extract was dried over $Na_2SO_4$, filtered and concentrated. The residue was purified by column chromatography (silica gel, eluting with 0% to 60% EtOAc in hexanes) to give compound 533 (80 mg, 63% yield) as a pale yellow foam. m/z=587.3 (M+1).

Compound 534: To a stirring solution of compound 533 (80 mg, 0.136 mmol) in EtOH (1.4 mL) was added 1 N aq. HCl solution (0.273 mL, 0.273 mmol) and hydroxylamine hydrochloride (14.2 mg, 0.204 mmol). The reaction mixture was stirred at 60° C. for 3 h. After cooled to room temperature, the mixture was diluted with sat. aq. $NaHCO_3$ solution (10 mL), and extracted with EtOAc. The organic extract was dried over $Na_2SO_4$, filtered and concentrated. The residue was purified by column chromatography (silica gel, eluting with 0% to 40% acetone in hexanes) to give compound 534 (25 mg, 37% yield) as a pale yellow foam. m/z=495.2 (M+1).

Compound 535: A mixture of compound 534 (25 mg, 0.051 mmol) and potassium carbonate (10.5 mg, 0.076 mmol) in MeOH (0.5 mL) was stirred at room temperature under $N_2$ for 16 h, and then filtered. The filtrate was concentrated, and the residue was diluted with EtOAc (10 mL). The mixture was washed with 1 N aq. HCl solution (10 mL). The organic extract was dried over $Na_2SO_4$, filtered and concentrated to give crude compound 535 (23 mg, 92% yield) as a light yellow foamy solid. m/z=495.2 (M+1).

T181: To a stirring solution of compound 535 (23 mg, 0.047 mmol) at 0° C. under $N_2$ in degassed DMF (0.7 mL) was added dropwise a solution of 1,3-dibromo-5,5-dimethylhydantoin (6.7 mg, 0.023 mmol) in DMF (0.7 mL). The mixture was stirred at 0° C. for 1 h. Pyridine (0.011 mL, 0.136 mmol) was added. The mixture was heated at 55° C. overnight; cooled to room temperature; and partitioned between water (10 mL) and EtOAc (10 mL). The organic extract was washed with sat. aq. NaCl (10 mL); dried with $Na_2SO_4$; filtered; and concentrated. The residue was purified multiple times by column chromatography (silica gel, eluting with 40% EtOAc in hexanes) to give compound T181 (15 mg, 65% yield) as an off-white foamy solid. m/z=493.2 (M+1); $^1$H NMR (400 MHz, $CDCl_3$) δ 8.97 (s, 1H), 8.60 (m, 1H), 8.19 (m, 1H), 8.06 (dd, J=1.6, 5.2 Hz, 1H), 7.49 (m, 2H), 7.34 (dt, J=1.1, 7.5 Hz, 1H), 7.22 (ddd, J=1.0, 8.3, 9.7 Hz, 1H), 2.81 (m, 2H), 2.55 (dd, J=4.4, 10.2 Hz, 1H), 2.21 (tt, J=4.6, 7.6 Hz, 1H), 1.97 (m, 3H), 1.60 (s, 3H), 1.56 (m, 1H), 1.25 (s, 3H), 1.12 (m, 2H), 1.05 (m, 2H), 0.80 (t, J=7.4 Hz, 3H).

Compound 536: To a solution of compound 3 (50 g, 260.08 mmol) in ethylene glycol (200 mL, 3.59 mol) was added p-toluenesulfonic acid monohydrate (15 g, 78.86 mmol). The mixture was stirred at 15° C. for 40 h. The mixture was partitioned between EtOAc (800 mL) and 10% aq. $NaHCO_3$ (100 mL). The organic layer was dried with $Na_2SO_4$; filtered; and concentrated under reduced pressure. The residue was purified by column chromatography (silica gel, eluting with 6/1 petroleum ether/EtOAc) to give compound 536 (41 g, 67% yield) as a colorless oil. m/z=237.2 (M+1).

Compound 537: Liquid ammonia (100 g, 5.87 mol) was condensed in the reaction flask at −78° C. Lithium wire (2.50 g, 360.23 mmol) was added. The mixture was stirred until a dark blue solution was obtained. A solution of compound 536 (20.5 g, 86.75 mmol) and water (1.50 g, 83.26 mmol) in THF (100 mL) was then added. The reaction was stirred at −30° C. for 1 h, and then quenched with the addition of aq ammonium chloride. The mixture was warmed to 20° C. to let ammonia evaporate, and then extracted with EtOAc (500 mL). The organic extract was washed with water (100 mL); dried with $Na_2SO_4$; filtered; and concentrated. The residue was purified by column chromatography (silica gel, eluting with 10/1 petroleum ether/EtOAc) to give compound 537 (14 g, 68% yield) as a colorless oil. m/z=239 (M+1).

Compound 538: To a solution of compound 537 (26 g, 109.10 mmol) in $Et_2O$ (300 mL) was added lithium aluminum hydride (1.24 g, 32.67 mmol) at −78° C. The reaction mixture was stirred at −78° C. for 1 h, and then quenched by carefully added 10% aq. $NH_4Cl$ (20 mL). The mixture was diluted with EtOAc (500 mL), and washed with water (200 mL). The organic extract was dried with $Na_2SO_4$; filtered; and concentrated to give compound 538 (6/1 mixtures of epimers, 23 g, 88% yield) as a colorless oil. m/z=223.2 (M-OH).

Compound 539: To a solution of compound 538 (23 g, 95.70 mmol) in $CH_2Cl_2$ (300 mL) was added benzoyl chloride (25.41 g, 180.77 mmol) and pyridine (25 mL, 309.10 mmol) at 15° C., and stirred for 16 h. The mixture was diluted with EtOAc (800 mL), and washed with water (200 mL). The organic layer was dried with $Na_2SO_4$; filtered; and concentrated. The residue was purified by column chromatography (silica gel, eluting with 15/1 petroleum ether/EtOAc) to give partially purified compound 539 (38 g) as a colorless oil, which was used in the next step without further purification. m/z=345 (M+1).

Compound 540: To a solution of compound 539 (38 g, ≤95.70 mmol) in EtOH (200 mL) was added 3 N aq. HCl (100 mL, 300 mmol). After stirring at 20° C. for 1 h, the mixture was diluted with EtOAc (500 mL), and washed with water (100 mL). The organic layer was dried with $Na_2SO_4$; filtered; and concentrated. The residue was purified by column chromatography (silica gel, eluting with 15/1 petroleum ether/EtOAc) to give a mixture of compound 540 and 541 (30 g). The product was dissolved in petroleum ether (100 mL) at 40° C., cooled to 20° C., and kept for 1 h. The precipitated solid was collected by filtration, and dried in vacuo to compound 540 (19.2 g, 67% yield from 538) as a white solid. m/z=179 (M-OBz).

Compound 542: To a solution of compound 540 (17.2 g, 57.26 mmol) in $Et_2O$ (600 mL) was added boron trifluoride diethyl etherate (49.45 g, 348.41 mmol) and ethyl diazoacetate (38.15 g, 334.35 mmol) sequentially at 0° C. under $N_2$. The reaction mixture was stirred at 25° C. for 16 h; cooled to 0° C.; and quenched with 10% aq. $NaHCO_3$ (100 mL). The organic layer was dried with $Na_2SO_4$; filtered; and concentrated. The residue was purified by column chromatography (silica gel, eluting with 30/1 petroleum ether/EtOAc) to give partially purified compound 542 (22 g), which was triturated with a mixture of petroleum ether (100 mL) and EtOAc (3 mL) at 15° C. for 1 h. The solid was collected by filtration; washed with petroleum ether (10 mL); and dried in vacuo to give compound 542 (13.4 g, 61% yield) as a white solid. The mother liquor was concentrated under reduced pressure. The residue (6.5 g) was dissolved in petroleum ether (20 mL) and stirred at −30° C. for 1 h. The precipitated solid was collected by filtration and dried in vacuo to the $2^{nd}$ crop of compound 542 (1.7 g, 8% yield) as a white solid. m/z=387 (M+1).

Compound 543: A mixture of compound 542 (10 g, 25.87 mmol), lithium iodide (15 g, 112.07 mmol) and water (5 g, 277.54 mmol) in 2,4,6-collidine (50 mL) was stirred at 150° C. for 2 h under $N_2$. After cooled to room temperature, the mixture was diluted with EtOAc (500 mL), and washed with water (300 mL). The organic layer was dried with $Na_2SO_4$; filtered; and concentrated. The residue was purified by column chromatography (silica gel, eluting with 20/1 petroleum ether/EtOAc) to give compound 543 (8.1 g, 97% yield) as a yellow solid. m/z=193 (M-OBz).

Compound 544: To a solution of compound 543 (8.1 g, 25.76 mmol) in EtOH (200 mL) was added 2 M aq. NaOH (30 mL, 60 mmol). The mixture was stirred at 15° C. for 16 h, and then concentrated. The residue was extracted with EtOAc (500 mL). The organic extract was washed with 1 N aq. HCl (100 mL) and 10% aq. $NaHCO_3$ (100 mL); dried with $Na_2SO_4$; filtered; and concentrated. The residue was purified by column chromatography (silica gel, eluting with 6/1 petroleum ether/EtOAc) to give compound 544 (4.8 g, 89% yield) as a white solid. m/z=193 (M-OH).

Compound 545: To a solution of compound 544 (1.7 g, 8.08 mmol) in $CH_2Cl_2$ (16 mL) under $N_2$ at room temperature was added N,N-diisopropylethylamine (4.22 mL, 24.23 mmol) and methoxymethyl chloride (1.23 mL, 16.19 mmol) sequentially. After stirring at room temperature for 4 h, the reaction mixture was treated with 1 N aq. HCl (20 mL). The organic phase was separated, and washed with 1 N aq. HCl (2×20 mL). The combined aqueous washes were extracted with EtOAc (2×20 mL). The combined organic extracts were dried with $Na_2SO_4$; filtered; and concentrated to give compound 545 (2.0 g, 97% yield) as a white solid. m/z=193 (M-OMOM).

Compound 546: To a solution of compound 545 (712 mg, 2.80 mmol) in t-BuOH (5 mL) at room temperature was added benzaldehyde (512 mg, 5.04 mmol). The mixture was stirred at room temperature for 5 min, and then treated with potassium tert-butoxide (393 mg, 3.50 mmol). The flask neck was rinsed with t-BuOH (2 mL). The reaction mixture was refluxed for 20 h, and then cooled to room temperature. The mixture was diluted with MTBE (40 mL), and washed with water (3×20 mL). The combined aqueous washes were extracted with MTBE (20 mL). The combined organic extracts were dried with $Na_2SO_4$; filtered; and concentrated. The residue was purified by column chromatography (silica gel, eluting with 0% to 30% EtOAc in hexanes) to give compound 546 (290 mg, 30% yield) as a yellow semisolid. m/z=343.2 (M+1).

Compound 547a: Potassium tert-butoxide (138 mg, 1.23 mmol) and 2-methylisonicotinimidamide hydrochloride (105 mg, 0.61 mmol) were weighed in a microwave vial. Compound 546 (contains 32 mol % compound 545, 140 mg, 0.30 mmol) in 1,4-dioxane (2.8 mL) was added. The mixture was heated in the Biotage microwave at 200° C. for 1 h. After cooled to room temperature, the mixture was partitioned between EtOAc (40 mL) and water (40 mL). The organic extract was separated, and washed with water (20 mL). The combined aqueous washes were extracted with EtOAc (2×30 mL). The combined organic extracts were dried with $Na_2SO_4$; filtered; and concentrated. The residue was purified by column chromatography (silica gel, eluting with 0% to 100% EtOAc in hexanes) to give compound 547a (65 mg, 47% yield) as a white foam. m/z=458.3 (M+1).

Compound 548a: To a solution of compound 547a (132 mg, 0.29 mmol) in THF (1.3 mL) was added water (0.4 mL) and 12 N aq. HCl (0.15 mL, 1.80 mmol) sequentially at room temperature. After the mixture was stirred for 16 h at room temperature, MTBE (40 mL) and 1 N aq. NaOH (2 mL) were added. The mixture was washed with sat. aq. $NaHCO_3$ (20 mL). The aqueous wash was extracted with EtOAc (3×15 mL). The combined organic extracts were dried with $Na_2SO_4$; filtered; and concentrated. The residue was purified by column chromatography (silica gel, eluting with 0% to 60% acetone in hexanes) to give compound 548a (103 mg, 86% yield) as a white foam. m/z=414.2 (M+1).

Compound 549a: To a solution of compound 548a (100 mg, 0.24 mmol) in CH$_2$Cl$_2$ (2.5 mL) was added Dess-Martin periodinane (210 mg, 0.50 mmol) at room temperature. After the reaction was stirred for 7 h at room temperature, aq. 10% Na$_2$SO$_3$ (10 mL) was added. After stirring at room temperature for 5 min, the mixture was extracted with CH$_2$Cl$_2$ (3×15 mL). The combined organic extracts were washed with aq. sat. NaHCO$_3$ (15 mL); dried with Na$_2$SO$_4$; filtered; and concentrated. The residue was purified by column chromatography (silica gel, eluting with 0% to 60% acetone in hexanes) to give compound 549a (96 mg, 96% yield) as a white foam. m/z=412.2 (M+1).

Compound 550a: To a stirring solution of compound 549a (94 mg, 0.23 mmol) in ethyl formate (0.55 mL, 6.84 mmol) was added sodium methoxide (25 wt. % in methanol, 0.52 mL, 2.27 mmol) at 0° C. The mixture was stirred at room temperature for 1 h, and cooled to 0° C. 12 N aq. HCl (0.21 mL, 2.52 mmol), EtOH (1.8 mL), and hydroxylamine hydrochloride (24 mg, 0.35 mmol) were added sequentially. The mixture was heated at 55° C. for 5 h, and was concentrated. Sat. aq. NaHCO$_3$ (10 mL) was added. The mixture was extracted with CH$_2$Cl$_2$ (3×20 mL). The combined organic extract was dried with Na$_2$SO$_4$, filtered and concentrated. The residue was purified by flash chromatography (silica gel, eluting with 0% to 100% EtOAc in hexanes) to give compound 550a (80 mg, 80% yield) as a white foamy solid. m/z=437.2 (M+1).

Compound 551a: Compound 550a (75 mg, 0.17 mmol) was dissolved in MeOH (1.7 mL). Sodium methoxide (25 wt. % in methanol, 0.080 mL, 0.35 mmol) was added. The reaction mixture was stirred at 55° C. for 2 h, and cooled to room temperature. MTBE (10 mL) and 10% aq. NaH$_2$PO$_4$ (10 mL) were added. The mixture was extracted with EtOAc (20 mL). The combined organic extract was washed with water; dried with Na$_2$SO$_4$; filtered and concentrated. The residue was purified by flash chromatography (silica gel, eluting with 0% to 100% EtOAc in hexanes) to give compound 551a (69 mg, 92% yield) as a white foamy solid. m/z=437.2 (M+1).

T182: Compound 551a (68 mg, 0.16 mmol) was dissolved in anhydrous DMF (0.38 mL), and the solution was cooled to 0° C. 1,3-dibromo-5,5-dimethylhydantoin (23 mg, 0.080 mmol) in DMF (0.4 mL) was added. The reaction was stirred at 0° C. for 1 h. Pyridine (0.038 mL, 0.47 mmol) was added. The reaction was heated at 55° C. for 2.5 h, and cooled to room temperature. EtOAc (20 mL) was added. The mixture was washed with water (3×15 mL). The organic extract was dried with Na$_2$SO$_4$, filtered and concentrated. The residual pyridine was removed by azeotropic evaporation with toluene on rotary evaporator. The residue was purified by flash chromatography (silica gel, eluting with 0% to 70% EtOAc in hexanes) to give compound T182 (58 mg, 85% yield) as a white foamy solid. m/z=435.2 (M+1); $^1$H NMR (400 MHz, CDCl$_3$) δ 8.67 (dd, J=5.2, 0.8 Hz, 1H), 8.59 (s, 1H), 8.16 (m, 1H), 8.09 (ddd, J=5.2, 1.6, 0.7 Hz, 1H), 7.65-7.57 (m, 2H), 7.56-7.47 (m, 3H), 3.10 (m, 1H), 2.98 (m, 1H), 2.68 (s, 3H), 2.50 (dq, J=13.1, 6.6 Hz, 1H), 2.36 (td, J=11.9, 3.5 Hz, 1H), 2.23 (m, 1H), 1.97-1.81 (m, 2H), 1.77 (s, 3H), 1.60 (m, 1H), 1.29 (d, J=6.5 Hz, 3H).

Compound 547b: Potassium tert-butoxide (157 mg, 1.40 mmol) and quinoline-5-carboximidamide hydrochloride (146 mg, 0.70 mmol) were weighed in a microwave vial. Compound 546 (contains 42 mol % compound 545, 160 mg, 0.30 mmol) in 1,4-dioxane (3.2 mL) was added. The mixture was heated in the Biotage microwave at 200° C. for 1 h. After cooled to room temperature, the mixture was partitioned between EtOAc (15 mL) and water (15 mL). The organic extract was separated, and washed with water (15 mL). The combined aqueous washes were extracted with EtOAc (2×10 mL). The combined organic extracts were dried with Na$_2$SO$_4$; filtered; and concentrated. The residue was purified by column chromatography (silica gel, eluting with 0% to 50% EtOAc in hexanes) to give partially purified compound 547b (90% pure, 45 mg, 27% yield) as a white foam. m/z=494.2 (M+1), which was used in the next step without further purification.

Compound 548b: To a solution of compound 547b (90% pure, 106 mg, 0.19 mmol) in THF (1.1 mL) was added water (0.2 mL) and 12 N aq. HCl (0.19 mL, 2.28 mmol) sequentially at room temperature. After the mixture was stirred for 7 h at room temperature, MTBE (20 mL) and 1 N aq. NaOH (2.4 mL) were added. The mixture was diluted with sat. aq. NaHCO$_3$ (20 mL), and extracted with CH$_2$Cl$_2$ (3×20 mL). The combined organic extracts were dried with Na$_2$SO$_4$; filtered; and concentrated. The residue was purified by column chromatography (silica gel, eluting with 0% to 100% EtOAc in hexanes) to give compound 548b (73 mg, 84% yield) as a white foam. m/z=450.2 (M+1).

Compound 549b: To a solution of compound 548b (73 mg, 0.16 mmol) in CH$_2$Cl$_2$ (1.6 mL) was added Dess-Martin periodinane (138 mg, 0.33 mmol) at room temperature. After the reaction was stirred for 5 h at room temperature, additional amount of Dess-Martin periodinane (69 mg, 0.16 mmol) was added. The reaction was stirred at room temperature for an additional 2 h, and was quenched with 10% aq. Na$_2$SO$_3$ (10 mL) and 10% aq. NaHCO$_3$ (10 mL). After stirring at room temperature for 5 min, the mixture was extracted with CH$_2$Cl$_2$ (3×20 mL). The combined organic extracts were dried with Na$_2$SO$_4$; filtered; and concentrated. The residue was purified by column chromatography (silica gel, eluting with 0% to 70% EtOAc in hexanes) to give compound 549b (59 mg, 81% yield) as a white foam. m/z=448.2 (M+1).

Compound 550b: To a stirring solution of compound 549b (57 mg, 0.13 mmol) in ethyl formate (0.31 mL, 3.85 mmol) was added sodium methoxide (25 wt. % in methanol, 0.29 mL, 1.27 mmol) at 0° C. The mixture was stirred at room temperature for 1 h, and cooled to 0° C. 12 N aq. HCl (0.12 mL, 1.44 mmol), EtOH (1.2 mL), and hydroxylamine hydrochloride (14 mg, 0.20 mmol) were added sequentially. The mixture was heated at 55° C. for 5 h, and was concentrated. The residue was partitioned between EtOAc (20 mL) and sat. aq. NaHCO$_3$ (20 mL). The aqueous phase was separated, and extracted with EtOAc (2×10 mL). The combined organic extract was dried with Na$_2$SO$_4$, filtered and concentrated. The residue was purified by flash chromatography (silica gel, eluting with 0% to 70% EtOAc in hexanes) to give compound 550b (49 mg, 81% yield) as a white foamy solid. m/z=473.2 (M+1).

Compound 551b: Compound 550b (48 mg, 0.10 mmol) was dissolved in MeOH (1.0 mL). Sodium methoxide (25 wt. % in methanol, 0.047 mL, 0.21 mmol) was added. The reaction mixture was stirred at 55° C. for 1 h, and cooled to room temperature. The mixture was partitioned between CH$_2$Cl$_2$ (20 mL) and 10% aq. NaH$_2$PO$_4$ (10 mL). The aqueous phase was separated, and extracted with CH$_2$Cl$_2$ (2×20 mL). The combined organic extract was washed with water; dried with Na$_2$SO$_4$; filtered and concentrated. The residue was purified by flash chromatography (silica gel, eluting with 0% to 80% EtOAc in hexanes) to give compound 551b (39 mg, 81% yield) as a white foamy solid. m/z=473.2 (M+1).

T183: Compound 551b (38 mg, 0.080 mmol) was dissolved in anhydrous DMF (0.2 mL), and the solution was cooled to 0° C. 1,3-dibromo-5,5-dimethylhydantoin (11.5 mg, 0.040 mmol) in DMF (0.2 mL) was added. The reaction was stirred at 0° C. for 1 h. Pyridine (0.032 mL, 0.40 mmol) was added. The reaction was heated at 55° C. for 2 h, and cooled to room temperature. EtOAc (20 mL) was added. The mixture was washed with water (3×20 mL). The organic extract was dried with $Na_2SO_4$, filtered and concentrated. The residue was purified by flash chromatography (silica gel, eluting with 0% to 80% EtOAc in hexanes) to give compound T183 (28 mg, 74% yield) as a white foamy solid. m/z=471.2 (M+1); $^1$H NMR (400 MHz, $CDCl_3$) δ 9.33 (ddd, J=8.7, 1.7, 0.8 Hz, 1H), 8.97 (dd, J=4.2, 1.7 Hz, 1H), 8.62 (s, 1H), 8.39 (dd, J=7.3, 1.3 Hz, 1H), 8.25 (dt, J=8.4, 1.1 Hz, 1H), 7.84 (dd, J=8.4, 7.3 Hz, 1H), 7.66-7.58 (m, 2H), 7.57-7.49 (m, 4H), 3.14 (m, 1H), 3.02 (m, 1H), 2.51 (dq, J=12.8, 6.4 Hz, 1H), 2.41 (td, J=11.9, 3.4 Hz, 1H), 2.28 (m, 1H), 2.03-1.83 (m, 2H), 1.80 (s, 3H), 1.66 (m, 1H), 1.31 (d, J=6.4 Hz, 3H).

T184: A mixture of compound T50 (140 mg, 0.319 mmol), hydrido(dimethylphosphinous acid-kP)[hydrogen bis(dimethylphosphinito-kP)]platinum (H) (13.1 mg, 0.031 mmol), EtOH (3 mL) and water (3 mL) was refluxed open to the air for 4 h. The catalyst was removed by filtering through a pad of Celite®. The filtrate was concentrated. The residue was purified by flash chromatography (silica gel, eluting with 0% to 100% EtOAc in hexanes) to compound T184 (86 mg, 59% yield) as a white solid. m/z=457.1 (M+1); $^1$H NMR (400 MHz, $CDCl_3$) δ 9.48 (s, 1H), 8.65 (dd, J=5.2, 0.9 Hz, 1H), 8.50 (d, J=4.5 Hz, 1H), 8.25-8.20 (m, 2H), 7.65-7.58 (m, 2H), 7.24-7.17 (m, 2H), 5.72 (d, J=4.6 Hz, 1H), 3.07-2.88 (m, 2H), 2.68 (s, 3H), 2.66 (m, 1H), 2.24 (td, J=12.7, 2.6 Hz, 1H), 2.10 (m, 1H), 1.78 (m, 1H), 1.51 (s, 3H), 1.32 (d, J=6.7 Hz, 3H).

T185: A mixture of compound 131 (91 mg 0.207 mmol), hydrido(dimethylphosphinous acid-kP)[hydrogen bis(dimethylphosphinito-kP)]platinum (II) (8.5 mg, 0.020 mmol), EtOH (2 mL) and water (2 mL) was refluxed open to the air for 4 h. The catalyst was removed by filtering through a pad of celite. The filtrate was concentrated. The residue was purified by flash chromatography (silica gel, eluting with 0% to 100% EtOAc in hexanes) to give partially purified product, which was triturated with EtOAc at reflux for 5 min, and then cooled to room temperature. The solid was collected by filtration, and dried in vacuo to give compound T185 (20 mg, 21% yield) as a white solid. m/z=459.2 (M+1); $^1$H NMR (400 MHz, $CDCl_3$) δ 8.63 (dd, J=5.2, 0.8 Hz, 1H), 8.17 (m, 1H), 8.13 (ddd, J=5.2, 1.6, 0.7 Hz, 1H), 7.68-7.61 (m, 2H), 7.24-7.16 (m, 2H), 5.36 (bs, 3H), 3.04 (d, J=14.8 Hz, 1H), 2.98-2.78 (m, 2H), 2.67 (s, 3H), 2.37 (dd, J=14.4, 2.5 Hz, 1H), 2.30 (m, 1H), 2.06 (m, 1H), 1.68 (ddd, J=11.7, 10.7, 2.2 Hz, 1H), 1.49 (qd, J=12.5, 5.4 Hz, 1H), 1.32 (d, J=6.8 Hz, 3H), 1.29 (s, 3H).

Example 2: Biological Activity Methods and Materials

A. AREc32 Luciferase Reporter Assay

The AREc32 luciferase reporter assay allows for quantitative assessment of the endogenous activity of the Nrf2 transcription factor in cultured mammalian cells. AREc32 cells are derived from MCF-7 human breast carcinoma cells that were stably transfected with a reporter construct that contains the firefly luciferase gene located downstream of eight copies of the rat GSTA2 antioxidant response element (ARE) sequence (Wang et al., 2006; CXR Biosciences). Active NRF2 binds to the ARE sequences and increases expression of the firefly luciferase gene. To assess the NRF2-activating potential of the test compounds, AREc32 cells were plated in black 96-well plates at a density of 20,000 cells per well in triplicate in DMEM+10% FBS+0.8 mg/mL Geneticin and incubated at 37° C. with 5% $CO_2$ in a humidified atmosphere. The next day, cells were treated with DMSO (vehicle) or test compound (concentration ranges of 0.4-200 nM or 2-1000 nM) for 19 hours. Luciferase activity was determined using the ONE-Glo Luciferase assay (Promega). The luminescence signal was measured on a BMG Pherastar microplate reader. The mean luminescence value from test compound-treated wells was normalized to that from DMSO-treated wells and was represented as fold-induction. Data were analyzed using GraphPad Prism version 6.00 for Windows, GraphPad Software, La Jolla California USA. A non-linear regression curve with log (agonist) vs. response using a variable slope was used to fit the data. Where applicable, a maximum threshold value of 50-fold over DMSO was set. $EC_{2x}$ values were interpolated from the curve. $EC_{2x}$ corresponds to the concentration of test compound required to increase GST ARE Luciferase reporter activity by 2-fold.

B. RORγ Assay and Cell Viability

The RORγ assay system was purchased from Indigo Biosciences. This nuclear receptor assay utilizes a human cell line that has been engineered to express a hybrid form of the Human RAR-related Orphan Receptor Gamma (RORγ) at high levels. The N-terminal DNA binding domain (DBD) of the native RORγ receptor was substituted with the yeast GAL4-DBD to generate the GAL4-RORγ hybrid nuclear receptor. The reporter cell line is transfected with a plasmid that encodes the beetle luciferase gene under the control of the GAL4 upstream activating sequence (UAS). GAL4 binds to the UAS and increases transcription of downstream target genes. The GAL4-RORγ hybrid is constitutively active; therefore, the principle application of this reporter assay system is to screen test compounds to quantify inverse-agonist activities against human RORγ. To assess the RORγ inverse-agonist activity of the test compounds, reporter cells were plated in white 96-well plates in triplicate and were treated with DMSO (vehicle) or test compound (concentration ranges of 0.4-200 nM or 2-1000 nM) at 37° C. with 5% $CO_2$ in a humidified atmosphere for 23 hours. After this incubation, luciferin was added to the wells and luciferase activity was determined by measuring the luminescence signal using a BMG Pherastar microplate reader. Viability was determined using the Live Cell Multiplex Assay (Indigo Biosciences). Values from test compound samples were normalized to those from DMSO-treated samples. Data were analyzed using GraphPad Prism version 6.00 for Windows (GraphPad Software, La Jolla California USA). A non-linear regression analysis with log (inhibitor) vs. normalized response using a variable slope was applied to fit the data and determine the $IC_{50}$ values for inhibition of RORγ and cell viability.

C. IL-17 Release from Differentiated Primary Human T-Cells and Cell Viability Primary human cryopreserved CD4+ T Cells (Lonza, donor #0000402103) were plated in Lymphocyte Growth Medium-3 (LGM-3, Lonza) according to the manufacturer's recommendations, and allowed to recover for approximately 3 hours at 37° C. with 5% $CO_2$ in a humidified atmosphere. After the recovery step, cells were collected by centrifugation and re-plated in 96-well plates at a density of ~140,000 cells per well in LGM-3 medium that contained DMSO (vehicle) or test compound (2-500 nM or 4-1000 nM concentration range). Triplicate wells were plated for each test condition. DMSO (final concentration ≤0.1%) was used as the vehicle Immediately after plating, CD4+ T cells were activated by adding Dynabeads Human T-Activator CD3/CD28 (Life Technologies; bead-to-cell ratio of 1:2.5) and differentiated into Th17 cells by adding a mixture of the following cytokines: transforming growth factor-β (TGF-β, 5 ng/mL), IL-6 (20 ng/mL), IL-23 (20 ng/mL), and IL-1β (10 ng/mL). Undifferentiated control cells received only cytokine IL-2 (50 ng/mL). All human recombinant cytokines were purchased from R&D Systems. Following a 46-hour incubation at 37° C. with 5% $CO_2$ in a humidified atmosphere, the plates were centrifuged for 3 minutes at 250× g, and half of the supernatant was transferred to a new plate to be used in the IL-17A assay (see below). Cell viability was assessed in the original plate using the CyQuant Direct Assay (Life Technologies). CyQuant values from test compound samples were normalized to those from DMSO-treated samples. The concentration of IL-17A in the supernatant was measured using the Homogeneous Time-Resolved Fluorescence (HTRF) assay (Cisbio Bioassays) according to the manufacturer's protocol. The assay was performed at room temperature in low volume, solid white 384-well plates (Greiner Bio-One). Samples and standards (serially-diluted human recombinant IL-17A (0 to 5,000 pg/mL concentration range; Cisbio Bioassays) were incubated with the anti-human IL-17A antibody conjugate for 16 hours and fluorescence was measured using a Pherastar FS microplate reader (BMG Labtech) in the HTRF mode (excitation at 337 nm and emission at 665 nm and 620 nm). IL-17A concentrations were assessed in duplicate aliquots of supernatant from each well resulting in a total of six readings per test condition. The 665 nm/620 nm signal ratio was calculated and the concentration of IL-17A in each sample was determined by interpolation from the standard curve. IL-17A values from test compound samples were normalized to those from DMSO-treated samples. Data were analyzed using GraphPad Prism version 6.00 for Windows (GraphPad Software, La Jolla California USA). A non-linear regression analysis with log (inhibitor) vs. normalized response using a variable slope was applied to fit the data and determine the $IC_{50}$ values for inhibition of IL-17A levels and cell viability.

TABLE 1

Compound Activity in hIL17 inhibition, $ROR_\gamma$ inhibition, and NRF2 Activation Assays

| Compound ID | Compound | $ROR_\gamma$ $IC_{50}$ (nM) | hIL17 $IC_{50}$ (nM) | NRF2 ARE 2× (nM) |
|---|---|---|---|---|
| T1 | | 603 | N/A | 487 |
| T2 | | 120 | N/A | 247 |
| T3 | | 124 | N/A | 232 |

TABLE 1-continued

Compound Activity in hIL17 inhibition, ROR_γ inhibition, and NRF2 Activation Assays

| Compound ID | Compound | ROR_γ IC$_{50}$ (nM) | hIL17 IC$_{50}$ (nM) | NRF2 ARE 2× (nM) |
|---|---|---|---|---|
| T4 | | 142 | N/A | 449 |
| T5 | | 178 | N/A | 365 |
| T6 | | 152 | N/A | 341 |
| T7 | | 176 | N/A | 388 |

TABLE 1-continued

Compound Activity in hIL17 inhibition, ROR$_\gamma$ inhibition, and NRF2 Activation Assays

| Compound ID | Compound | ROR$_\gamma$ IC$_{50}$ (nM) | hIL17 IC$_{50}$ (nM) | NRF2 ARE 2× (nM) |
|---|---|---|---|---|
| T8 | | 299 | 185 | 534 |
| T9 | | 114 | 67 | 510 |
| T10 | | N/A | N/A | N/A |
| T11 | | >2000 | N/A | 2438 |

TABLE 1-continued

Compound Activity in hIL17 inhibition, ROR$_\gamma$ inhibition, and NRF2 Activation Assays

| Compound ID | Compound | ROR$_\gamma$ IC$_{50}$ (nM) | hIL17 IC$_{50}$ (nM) | NRF2 ARE 2× (nM) |
|---|---|---|---|---|
| T12 | | N/A | N/A | N/A |
| T13 | | 748 | 476 | >2000 |
| T14 | | 71 | 84 | 281 |
| T15 | | 117 | N/A | 738 |

TABLE 1-continued

Compound Activity in hIL17 inhibition, ROR$_\gamma$ inhibition, and NRF2 Activation Assays

| Compound ID | Compound | ROR$_\gamma$ IC$_{50}$ (nM) | hIL17 IC$_{50}$ (nM) | NRF2 ARE 2× (nM) |
|---|---|---|---|---|
| T16 | | 305 | 223 | 1000 |
| T17 | | >2000 | N/A | 839 |
| T18 | | 100 | N/A | 381 |
| T19 | | 143 | N/A | 741 |

TABLE 1-continued
Compound Activity in hIL17 inhibition, RORγ inhibition, and NRF2 Activation Assays
| Compound ID | Compound | RORγ IC50 (nM) | hIL17 IC50 (nM) | NRF2 ARE 2× (nM) |
|---|---|---|---|---|
| T20 | 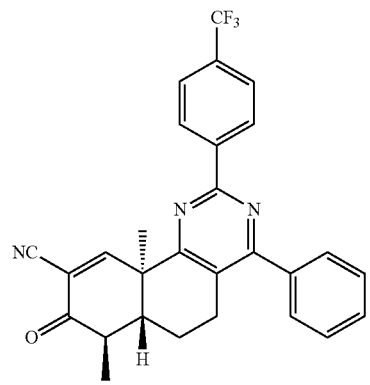 [SMILES: C[C@H]1C(=O)C(C#N)=C[C@@]2(C)c3nc(-c4ccc(C(F)(F)F)cc4)nc(-c4ccccc4)c3CC[C@H]12] | 425 | N/A | 608 |
| T21 | 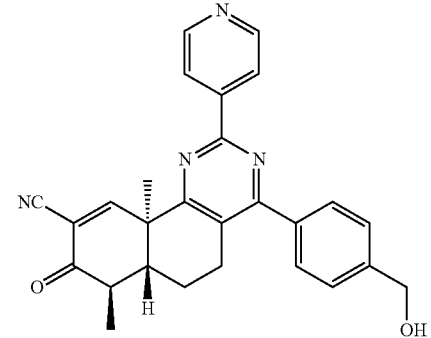 [SMILES: C[C@H]1C(=O)C(C#N)=C[C@@]2(C)c3nc(-c4ccncc4)nc(-c4ccc(CO)cc4)c3CC[C@H]12] | 233 | N/A | 443 |
| T22 | 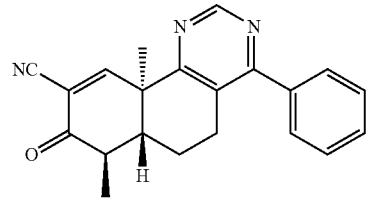 [SMILES: C[C@H]1C(=O)C(C#N)=C[C@@]2(C)c3ncnc(-c4ccccc4)c3CC[C@H]12] | 608 | N/A | 90 |
| T23 | 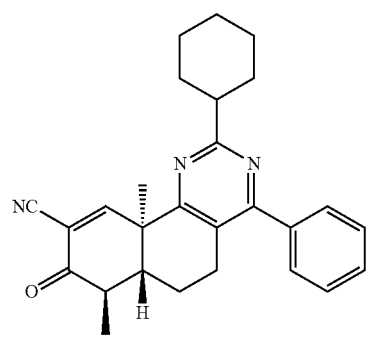 [SMILES: C[C@H]1C(=O)C(C#N)=C[C@@]2(C)c3nc(C4CCCCC4)nc(-c4ccccc4)c3CC[C@H]12] | 255 | 40 | 144 |

TABLE 1-continued

Compound Activity in hIL17 inhibition, ROR$_\gamma$ inhibition, and NRF2 Activation Assays

| Compound ID | Compound | ROR$_\gamma$ IC$_{50}$ (nM) | hIL17 IC$_{50}$ (nM) | NRF2 ARE 2× (nM) |
|---|---|---|---|---|
| T24 | | 399 | N/A | 171 |
| T25 | | 278 | N/A | 449 |
| T26 | | 220 | N/A | 267 |
| T27 | | 145 | N/A | 181 |

TABLE 1-continued

Compound Activity in hIL17 inhibition, ROR$_\gamma$ inhibition, and NRF2 Activation Assays

| Compound ID | Compound | ROR$_\gamma$ IC$_{50}$ (nM) | hIL17 IC$_{50}$ (nM) | NRF2 ARE 2× (nM) |
|---|---|---|---|---|
| T28 | | 190 | N/A | 141 |
| T29 | | 337 | N/A | 484 |
| T30 | | 165 | N/A | 136 |
| T31 | | 228 | N/A | 186 |

TABLE 1-continued

Compound Activity in hIL17 inhibition, ROR$_\gamma$ inhibition, and NRF2 Activation Assays

| Compound ID | Compound | ROR$_\gamma$ IC$_{50}$ (nM) | hIL17 IC$_{50}$ (nM) | NRF2 ARE 2× (nM) |
|---|---|---|---|---|
| T32 | (structure) | 54 | 68 | 272 |
| T33 | (structure) | 126 | 40 | 480 |
| T34 | (structure) | 482 | N/A | 469 |
| T35 | (structure) | 287 | N/A | 575 |

TABLE 1-continued

Compound Activity in hIL17 inhibition, RORγ inhibition, and NRF2 Activation Assays

| Compound ID | Compound | RORγ IC50 (nM) | hIL17 IC50 (nM) | NRF2 ARE 2× (nM) |
|---|---|---|---|---|
| T36 | | 161 | 125 | 484 |
| T37 | | 52 | 32 | 351 |
| T38 | | 504 | 374 | >2000 |
| T39 | | 87 | 63 | 427 |

TABLE 1-continued

Compound Activity in hIL17 inhibition, ROR$_\gamma$ inhibition, and NRF2 Activation Assays

| Compound ID | Compound | ROR$_\gamma$ IC$_{50}$ (nM) | hIL17 IC$_{50}$ (nM) | NRF2 ARE 2× (nM) |
|---|---|---|---|---|
| T40 | | 67 | 63 | 273 |
| T41 | | 69 | 64 | 528 |
| T42 | | 88 | 165 | 513 |
| T43 | | 40 | 39 | 278 |

TABLE 1-continued

Compound Activity in hIL17 inhibition, ROR$_\gamma$ inhibition, and NRF2 Activation Assays

| Compound ID | Compound | ROR$_\gamma$ IC$_{50}$ (nM) | hIL17 IC$_{50}$ (nM) | NRF2 ARE 2× (nM) |
|---|---|---|---|---|
| T44 | | 85 | 60 | 596 |
| T45 | | 723 | 1057 | >2000 |
| T46 | | 116 | 177 | 735 |
| T47 | | 238 | 38 | 622 |

TABLE 1-continued

Compound Activity in hIL17 inhibition, ROR$_\gamma$ inhibition, and NRF2 Activation Assays

| Compound ID | Compound | ROR$_\gamma$ IC$_{50}$ (nM) | hIL17 IC$_{50}$ (nM) | NRF2 ARE 2× (nM) |
|---|---|---|---|---|
| T48 | | 171 | 225 | 460 |
| T49 | | 121 | 181 | 491 |
| T50 | | 49 | 40 | 256 |
| T51 | | 50 | 47 | 364 |

TABLE 1-continued

Compound Activity in hIL17 inhibition, ROR$_\gamma$ inhibition, and NRF2 Activation Assays

| Compound ID | Compound | ROR$_\gamma$ IC$_{50}$ (nM) | hIL17 IC$_{50}$ (nM) | NRF2 ARE 2× (nM) |
|---|---|---|---|---|
| T52 | | 50 | 35 | 272 |
| T53 | | 69 | 33 | 380 |
| T54 | | 89 | 31 | 483 |
| T55 | | 1117 | 590 | >2000 |

TABLE 1-continued

Compound Activity in hIL17 inhibition, ROR$_\gamma$ inhibition, and NRF2 Activation Assays

| Compound ID | Compound | ROR$_\gamma$ IC$_{50}$ (nM) | hIL17 IC$_{50}$ (nM) | NRF2 ARE 2× (nM) |
|---|---|---|---|---|
| T56 | | 51 | 47 | 193 |
| T57 | | 113 | 77 | 419 |
| T58 | | 91 | 69 | 155 |
| T59 | | 155 | 34 | 311 |

TABLE 1-continued

Compound Activity in hIL17 inhibition, ROR$_\gamma$ inhibition, and NRF2 Activation Assays

| Compound ID | Compound | ROR$_\gamma$ IC$_{50}$ (nM) | hIL17 IC$_{50}$ (nM) | NRF2 ARE 2× (nM) |
|---|---|---|---|---|
| T60 | | 195 | N/A | 380 |
| T61 | | 112 | 60 | 461 |
| T62 | | 130 | 39 | 401 |
| T63 | | 42 | 21 | 259 |

TABLE 1-continued

Compound Activity in hIL17 inhibition, ROR$_\gamma$ inhibition, and NRF2 Activation Assays

| Compound ID | Compound | ROR$_\gamma$ IC$_{50}$ (nM) | hIL17 IC$_{50}$ (nM) | NRF2 ARE 2× (nM) |
|---|---|---|---|---|
| T64 | | 114 | 35 | 425 |
| T65 | | 129 | 29 | 463 |
| T66 | | 64 | 39 | 190 |
| T67 | | 108 | 63 | 208 |

TABLE 1-continued

Compound Activity in hIL17 inhibition, ROR$_\gamma$ inhibition, and NRF2 Activation Assays

| Compound ID | Compound | ROR$_\gamma$ IC$_{50}$ (nM) | hIL17 IC$_{50}$ (nM) | NRF2 ARE 2× (nM) |
|---|---|---|---|---|
| T68 | | 121 | 31 | 253 |
| T69 | | 49 | 20 | 227 |
| T70 | | 153 | 61 | 391 |
| T71 | | 229 | 198 | 780 |

TABLE 1-continued

Compound Activity in hIL17 inhibition, ROR$_\gamma$ inhibition, and NRF2 Activation Assays

| Compound ID | Compound | ROR$_\gamma$ IC$_{50}$ (nM) | hIL17 IC$_{50}$ (nM) | NRF2 ARE 2× (nM) |
|---|---|---|---|---|
| T72 | | 135 | N/A | 374 |
| T73 | | 141 | 69 | 407 |
| T74 | | 57 | 49 | 507 |
| T75 | | 82 | 42 | 552 |

TABLE 1-continued

Compound Activity in hIL17 inhibition, ROR$_\gamma$ inhibition, and NRF2 Activation Assays

| Compound ID | Compound | ROR$_\gamma$ IC$_{50}$ (nM) | hIL17 IC$_{50}$ (nM) | NRF2 ARE 2× (nM) |
|---|---|---|---|---|
| T76 | | 82 | 35 | 315 |
| T77 | | 82 | 31 | 264 |
| T78 | | 184 | 89 | 629 |
| T79 | | 77 | 143 | 109 |

TABLE 1-continued

Compound Activity in hIL17 inhibition, ROR$_\gamma$ inhibition, and NRF2 Activation Assays

| Compound ID | Compound | ROR$_\gamma$ IC$_{50}$ (nM) | hIL17 IC$_{50}$ (nM) | NRF2 ARE 2× (nM) |
|---|---|---|---|---|
| T80 | | 82 | 58 | 312 |
| T81 | | 247 | N/A | 705 |
| T82 | | 169 | N/A | 480 |
| T83 | | 72 | 35 | 484 |

TABLE 1-continued
Compound Activity in hIL17 inhibition, ROR$_\gamma$ inhibition, and NRF2 Activation Assays
| Compound ID | Compound | ROR$_\gamma$ IC$_{50}$ (nM) | hIL17 IC$_{50}$ (nM) | NRF2 ARE 2× (nM) |
|---|---|---|---|---|
| T84 | 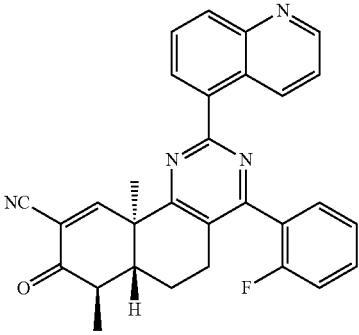 [SMILES: C[C@H]1C(=O)C(C#N)=C[C@@]2(C)c3nc(-c4cccc5ncccc45)nc(-c4ccccc4F)c3CC[C@H]12] | 73 | 36 | 321 |
| T85 | 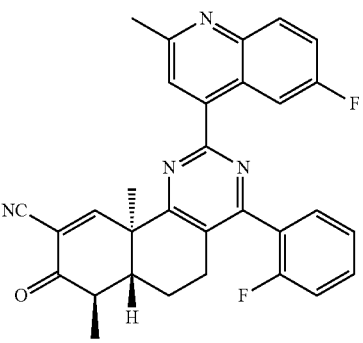 [SMILES: Cc1cc(-c2nc(-c3ccccc3F)c3c(n2)[C@]2(C)C=C(C#N)C(=O)[C@H](C)[C@H]2CC3)c2cc(F)ccc2n1] | 88 | 38 | 307 |
| T86 | 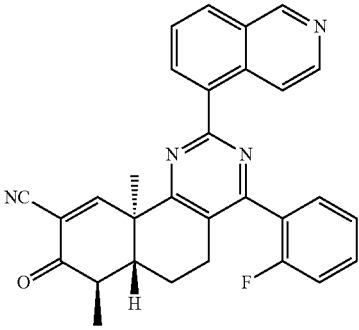 [SMILES: C[C@H]1C(=O)C(C#N)=C[C@@]2(C)c3nc(-c4cccc5cnccc45)nc(-c4ccccc4F)c3CC[C@H]12] | 112 | 33 | 276 |
| T87 | 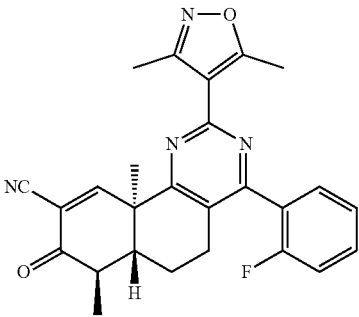 [SMILES: Cc1noc(C)c1-c1nc(-c2ccccc2F)c2c(n1)[C@]1(C)C=C(C#N)C(=O)[C@H](C)[C@H]1CC2] | 88 | 109 | 245 |

TABLE 1-continued

Compound Activity in hIL17 inhibition, ROR$_\gamma$ inhibition, and NRF2 Activation Assays

| Compound ID | Compound | ROR$_\gamma$ IC$_{50}$ (nM) | hIL17 IC$_{50}$ (nM) | NRF2 ARE 2× (nM) |
|---|---|---|---|---|
| T88 | | 99 | N/A | 177 |
| T89 | | 87 | 62 | 274 |
| T90 | | 90 | 37 | 301 |
| T91 | | 323 | 265 | 552 |

TABLE 1-continued

Compound Activity in hIL17 inhibition, ROR$_\gamma$ inhibition, and NRF2 Activation Assays

| Compound ID | Compound | ROR$_\gamma$ IC$_{50}$ (nM) | hIL17 IC$_{50}$ (nM) | NRF2 ARE 2× (nM) |
|---|---|---|---|---|
| T92 | | 164 | 97 | 491 |
| T93 | | 67 | 101 | 283 |
| T94 | | 52 | 58 | 321 |
| T95 | | 61 | 68 | 430 |

TABLE 1-continued
Compound Activity in hIL17 inhibition, ROR$_\gamma$ inhibition, and NRF2 Activation Assays
| Compound ID | Compound | ROR$_\gamma$ IC$_{50}$ (nM) | hIL17 IC$_{50}$ (nM) | NRF2 ARE 2× (nM) |
|---|---|---|---|---|
| T96 | 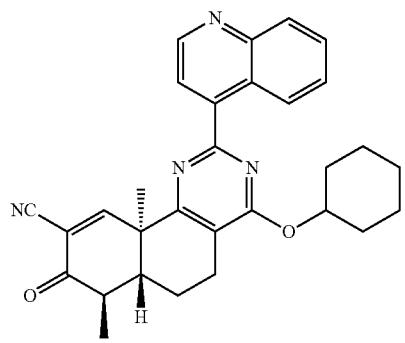 [SMILES: C[C@H]1C(=O)C(C#N)=C[C@@]2(C)c3nc(-c4ccnc5ccccc45)nc(OC4CCCCC4)c3CC[C@H]12] | 135 | 58 | 492 |
| T97 | 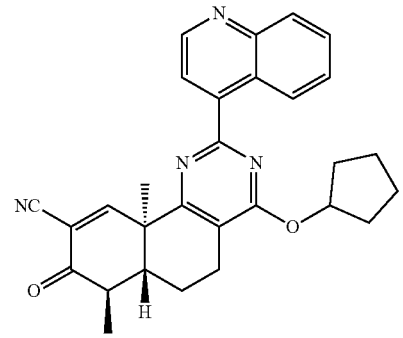 [SMILES: C[C@H]1C(=O)C(C#N)=C[C@@]2(C)c3nc(-c4ccnc5ccccc45)nc(OC4CCCC4)c3CC[C@H]12] | 80 | 35 | 330 |
| T98 | 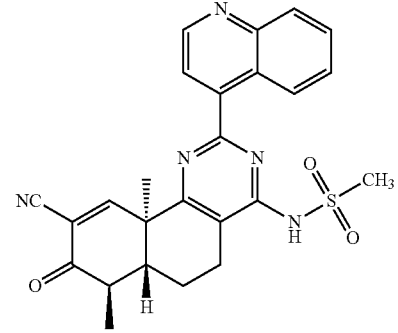 [SMILES: C[C@H]1C(=O)C(C#N)=C[C@@]2(C)c3nc(-c4ccnc5ccccc45)nc(NS(C)(=O)=O)c3CC[C@H]12] | >2000 | >1000 | >2000 |
| T99 | 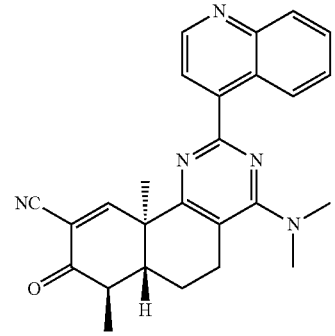 [SMILES: C[C@H]1C(=O)C(C#N)=C[C@@]2(C)c3nc(-c4ccnc5ccccc45)nc(N(C)C)c3CC[C@H]12] | 194 | 189 | 508 |

TABLE 1-continued

Compound Activity in hIL17 inhibition, ROR$_\gamma$ inhibition, and NRF2 Activation Assays

| Compound ID | Compound | ROR$_\gamma$ IC$_{50}$ (nM) | hIL17 IC$_{50}$ (nM) | NRF2 ARE 2× (nM) |
|---|---|---|---|---|
| T100 | | 212 | 178 | 865 |
| T101 | | 117 | 200 | 295 |
| T102 | | 59 | 153 | 287 |
| T103 | | 144 | 38 | 277 |

TABLE 1-continued

Compound Activity in hIL17 inhibition, ROR$_\gamma$ inhibition, and NRF2 Activation Assays

| Compound ID | Compound | ROR$_\gamma$ IC$_{50}$ (nM) | hIL17 IC$_{50}$ (nM) | NRF2 ARE 2× (nM) |
|---|---|---|---|---|
| T104 | | 92 | 86 | 293 |
| T105 | | 44 | 65 | 292 |
| T106 | | 98 | 173 | 139 |
| T107 | | 101 | 170 | 284 |

TABLE 1-continued

Compound Activity in hIL17 inhibition, ROR$_\gamma$ inhibition, and NRF2 Activation Assays

| Compound ID | Compound | ROR$_\gamma$ IC$_{50}$ (nM) | hIL17 IC$_{50}$ (nM) | NRF2 ARE 2× (nM) |
|---|---|---|---|---|
| T108 | | 97 | 21 | 225 |
| T109 | | 80 | 18 | 251 |
| T110 | | 82 | 37 | 317 |
| T111 | | 60 | 19 | 317 |

TABLE 1-continued
Compound Activity in hIL17 inhibition, ROR$_\gamma$ inhibition, and NRF2 Activation Assays
| Compound ID | Compound | ROR$_\gamma$ IC$_{50}$ (nM) | hIL17 IC$_{50}$ (nM) | NRF2 ARE 2× (nM) |
|---|---|---|---|---|
| T112 | 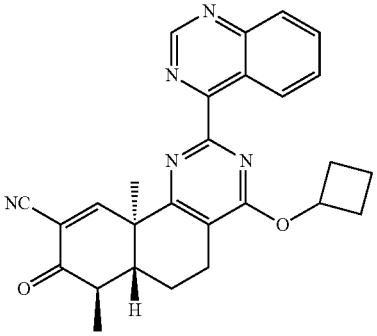 [SMILES: C[C@H]1C(=O)C(C#N)=C[C@@]2(C)c3nc(-c4ncnc5ccccc45)nc(OC4CCC4)c3CC[C@H]12] | 87 | 85 | 559 |
| T113 | 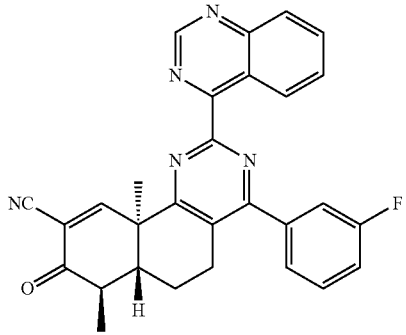 [SMILES: C[C@H]1C(=O)C(C#N)=C[C@@]2(C)c3nc(-c4ncnc5ccccc45)nc(-c4cccc(F)c4)c3CC[C@H]12] | 91 | 48 | 734 |
| T114 | 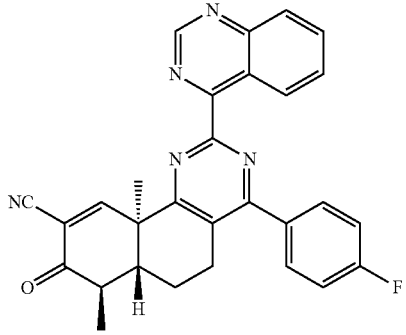 [SMILES: C[C@H]1C(=O)C(C#N)=C[C@@]2(C)c3nc(-c4ncnc5ccccc45)nc(-c4ccc(F)cc4)c3CC[C@H]12] | 89 | 46 | 484 |
| T115 | 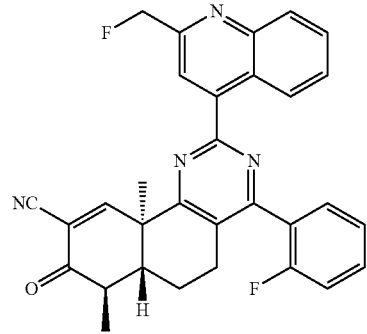 [SMILES: C[C@H]1C(=O)C(C#N)=C[C@@]2(C)c3nc(-c4cc(CF)nc5ccccc45)nc(-c4ccccc4F)c3CC[C@H]12] | 58 | 14 | 260 |

TABLE 1-continued

Compound Activity in hIL17 inhibition, ROR$_\gamma$ inhibition, and NRF2 Activation Assays

| Compound ID | Compound | ROR$_\gamma$ IC$_{50}$ (nM) | hIL17 IC$_{50}$ (nM) | NRF2 ARE 2× (nM) |
|---|---|---|---|---|
| T116 | | 97 | 65 | 303 |
| T117 | | 73 | 58 | 232 |
| T118 | | 71 | 28 | 395 |
| T119 | | 70 | 37 | 351 |

TABLE 1-continued

Compound Activity in hIL17 inhibition, ROR$_\gamma$ inhibition, and NRF2 Activation Assays

| Compound ID | Compound | ROR$_\gamma$ IC$_{50}$ (nM) | hIL17 IC$_{50}$ (nM) | NRF2 ARE 2× (nM) |
|---|---|---|---|---|
| T120 | | 51 | 29 | 334 |
| T121 | | 73 | 36 | 390 |
| T122 | | 60 | 31 | 402 |
| T123 | | 55 | 20 | 371 |

TABLE 1-continued

Compound Activity in hIL17 inhibition, ROR$_\gamma$ inhibition, and NRF2 Activation Assays

| Compound ID | Compound | ROR$_\gamma$ IC$_{50}$ (nM) | hIL17 IC$_{50}$ (nM) | NRF2 ARE 2× (nM) |
|---|---|---|---|---|
| T124 | | 65 | 22 | 220 |
| T125 | | 117 | 27 | 549 |
| T126 | | 56 | 36 | 280 |
| T127 | | 60 | 36 | 343 |

TABLE 1-continued

Compound Activity in hIL17 inhibition, ROR<sub>γ</sub> inhibition, and NRF2 Activation Assays

| Compound ID | Compound | ROR<sub>γ</sub> IC$_{50}$ (nM) | hIL17 IC$_{50}$ (nM) | NRF2 ARE 2× (nM) |
|---|---|---|---|---|
| T128 | | 238 | N/A | 1385 |
| T129 | | 394 | N/A | 697 |
| T130 | | 183 | N/A | 692 |
| T131 | | N/A | N/A | N/A |

TABLE 1-continued

Compound Activity in hIL17 inhibition, ROR$_\gamma$ inhibition, and NRF2 Activation Assays

| Compound ID | Compound | ROR$_\gamma$ IC$_{50}$ (nM) | hIL17 IC$_{50}$ (nM) | NRF2 ARE 2× (nM) |
|---|---|---|---|---|
| T132 | | 113 | 74 | 437 |
| T133 | | 162 | N/A | 1199 |
| T134 | | 881 | N/A | 3137 |
| T135 | | 2048 | N/A | >2000 |

TABLE 1-continued
Compound Activity in hIL17 inhibition, ROR$_\gamma$ inhibition, and NRF2 Activation Assays
| Compound ID | Compound | ROR$_\gamma$ IC$_{50}$ (nM) | hIL17 IC$_{50}$ (nM) | NRF2 ARE 2× (nM) |
|---|---|---|---|---|
| T136 | 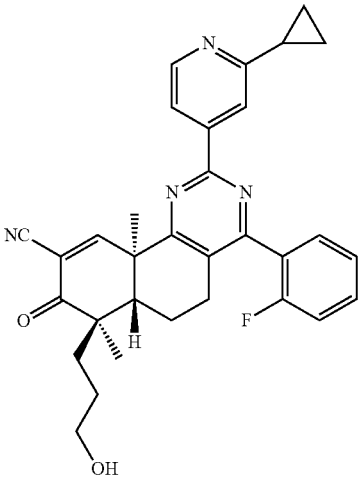 [SMILES: C[C@]1(CCCO)C(=O)C(C#N)=C[C@@]2(C)c3nc(-c4ccnc(C5CC5)c4)nc(-c4ccccc4F)c3CC[C@H]12] | 132 | 25 | 518 |
| T137 | 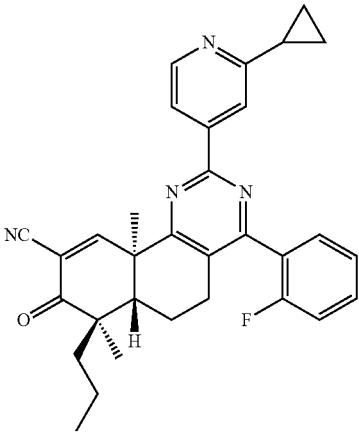 [SMILES: CCC[C@@]1(C)C(=O)C(C#N)=C[C@@]2(C)c3nc(-c4ccnc(C5CC5)c4)nc(-c4ccccc4F)c3CC[C@H]12] | 114 | 9 | 274 |
| T138 | 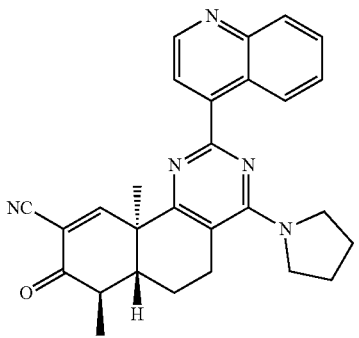 [SMILES: C[C@H]1C(=O)C(C#N)=C[C@@]2(C)c3nc(-c4ccnc5ccccc45)nc(N4CCCC4)c3CC[C@H]12] | 108 | 167 | 641 |

TABLE 1-continued
Compound Activity in hIL17 inhibition, RORγ inhibition, and NRF2 Activation Assays
| Compound ID | Compound | RORγ IC50 (nM) | hIL17 IC50 (nM) | NRF2 ARE 2× (nM) |
|---|---|---|---|---|
| T139 | 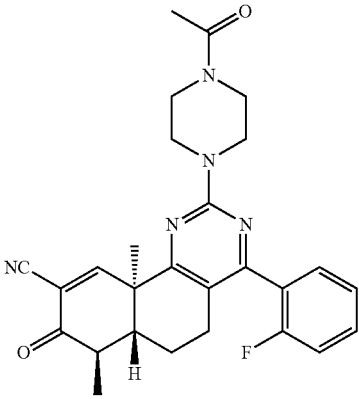 [SMILES: CC(=O)N1CCN(c2nc(-c3ccccc3F)c3c(n2)[C@]2(C)C=C(C#N)C(=O)[C@H](C)[C@H]2CC3)CC1] | 162 | 104 | 222 |
| T140 | 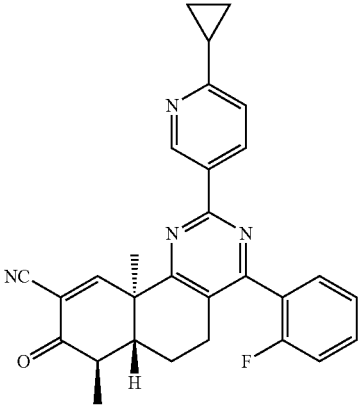 [SMILES: C[C@H]1C(=O)C(C#N)=C[C@@]2(C)c3nc(-c4ccc(C5CC5)nc4)nc(-c4ccccc4F)c3CC[C@H]12] | 179 | 26 | 451 |
| T141 | 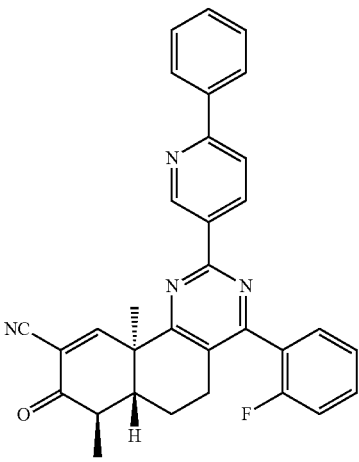 [SMILES: C[C@H]1C(=O)C(C#N)=C[C@@]2(C)c3nc(-c4ccc(-c5ccccc5)nc4)nc(-c4ccccc4F)c3CC[C@H]12] | 236 | 22 | 557 |

TABLE 1-continued

Compound Activity in hIL17 inhibition, ROR$_\gamma$ inhibition, and NRF2 Activation Assays

| Compound ID | Compound | ROR$_\gamma$ IC$_{50}$ (nM) | hIL17 IC$_{50}$ (nM) | NRF2 ARE 2× (nM) |
|---|---|---|---|---|
| T142 | | 143 | 77 | 217 |
| T143 | | 210 | 94 | 538 |
| T144 | | 117 | 72 | 299 |

TABLE 1-continued
Compound Activity in hIL17 inhibition, ROR$_\gamma$ inhibition, and NRF2 Activation Assays
| Compound ID | Compound | ROR$_\gamma$ IC$_{50}$ (nM) | hIL17 IC$_{50}$ (nM) | NRF2 ARE 2× (nM) |
|---|---|---|---|---|
| T145 | 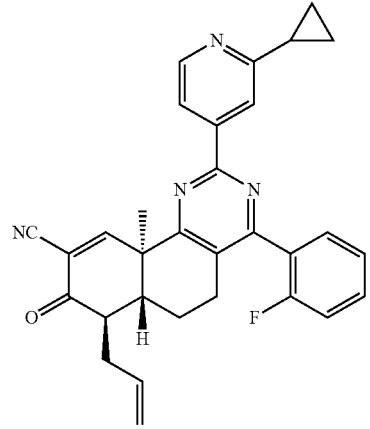 [SMILES: C=CC[C@H]1C(=O)C(C#N)=C[C@@]2(C)c3nc(-c4ccnc(C5CC5)c4)nc(-c4ccccc4F)c3CC[C@H]12] | 44 | 15 | 337 |
| T146 | 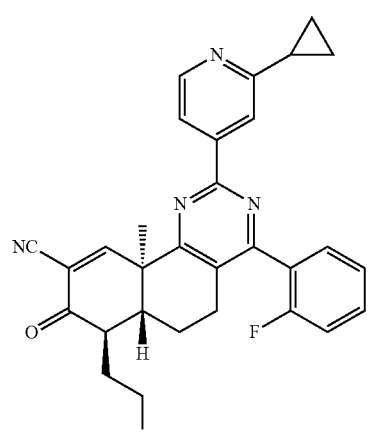 | 49 | 10 | 447 |
| T147 | 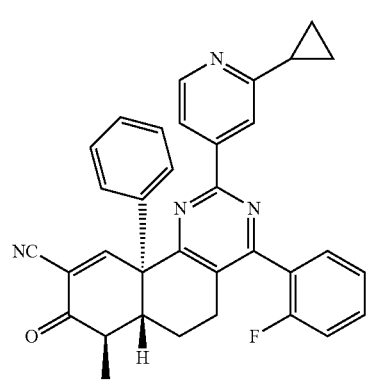 [SMILES: C[C@H]1C(=O)C(C#N)=C[C@@]2(c3ccccc3)c3nc(-c4ccnc(C5CC5)c4)nc(-c4ccccc4F)c3CC[C@H]12] | 287 | 54 | >2000 |

TABLE 1-continued

Compound Activity in hIL17 inhibition, ROR$_\gamma$ inhibition, and NRF2 Activation Assays

| Compound ID | Compound | ROR$_\gamma$ IC$_{50}$ (nM) | hIL17 IC$_{50}$ (nM) | NRF2 ARE 2× (nM) |
|---|---|---|---|---|
| T148 | | 259 | 77 | 1758 |
| T149 | | 45 | 14 | 330 |
| T150 | | >2000 | N/A | >2000 |
| T151 | | 100 | 54 | 1111 |

US 12,195,443 B2
TABLE 1-continued
Compound Activity in hIL17 inhibition, ROR$_\gamma$ inhibition, and NRF2 Activation Assays
| Compound ID | Compound | ROR$_\gamma$ IC$_{50}$ (nM) | hIL17 IC$_{50}$ (nM) | NRF2 ARE 2× (nM) |
|---|---|---|---|---|
| T152 | 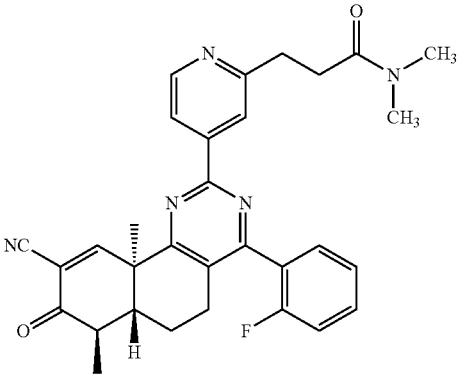 [SMILES: C[C@H]1C(=O)C(C#N)=C[C@@]2(C)c3nc(-c4ccnc(CCC(=O)N(C)C)c4)nc(-c4ccccc4F)c3CC[C@H]12] | 81 | 46 | 323 |
| T153 | 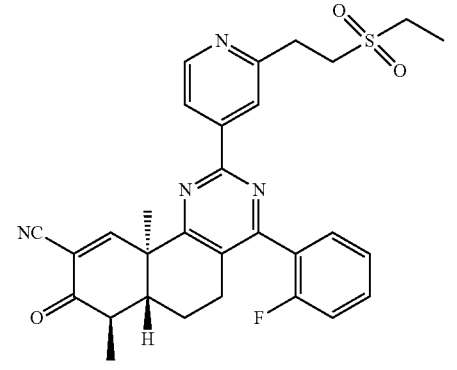 [SMILES: CCS(=O)(=O)CCc1cc(-c2nc(-c3ccccc3F)c3c(n2)[C@]2(C)C=C(C#N)C(=O)[C@H](C)[C@H]2CC3)ccn1] | 102 | 52 | 282 |
| T154 | 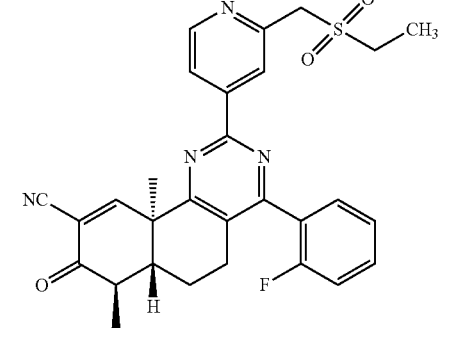 | 119 | 65 | 469 |
| T155 | 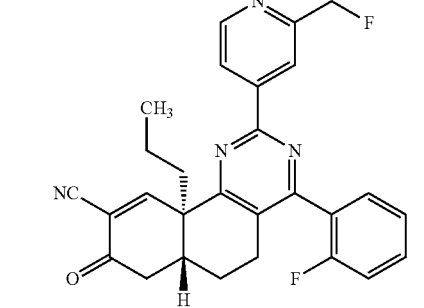 | 100 | 71 | 267 |

TABLE 1-continued
Compound Activity in hIL17 inhibition, ROR$_\gamma$ inhibition, and NRF2 Activation Assays
| Compound ID | Compound | ROR$_\gamma$ IC$_{50}$ (nM) | hIL17 IC$_{50}$ (nM) | NRF2 ARE 2× (nM) |
|---|---|---|---|---|
| T156 | 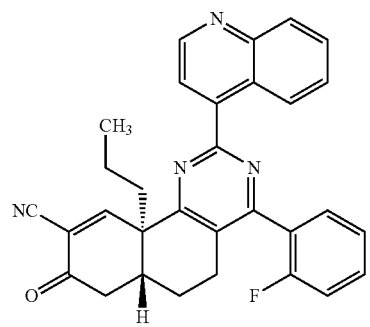 [SMILES: CCC[C@@]12C=C(C#N)C(=O)C[C@H]1CCc1c(-c3ccccc3F)nc(-c3ccnc4ccccc34)nc12] | 112 | 54 | 333 |
| T157 | 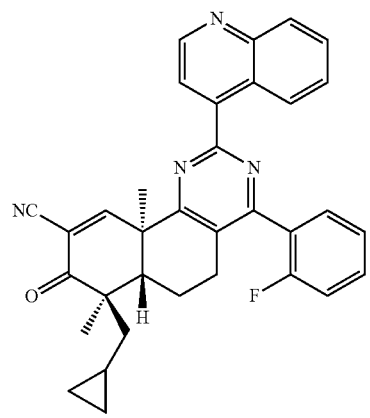 [SMILES: C[C@]1(CC2CC2)C(=O)C(C#N)=C[C@@]2(C)c3nc(-c4ccnc5ccccc45)nc(-c4ccccc4F)c3CC[C@H]12] | 83 | 23 | 304 |
| T158 | 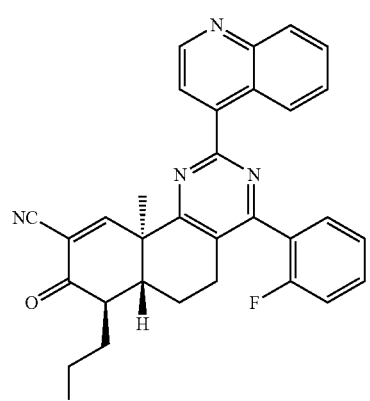 | 36 | 16 | 316 |

TABLE 1-continued

Compound Activity in hIL17 inhibition, ROR$_\gamma$ inhibition, and NRF2 Activation Assays

| Compound ID | Compound | ROR$_\gamma$ IC$_{50}$ (nM) | hIL17 IC$_{50}$ (nM) | NRF2 ARE 2× (nM) |
|---|---|---|---|---|
| T159 | | 32 | 22 | 337 |
| T160 | | 95 | 22 | 418 |
| T161 | | 134 | N/A | 158 |
| T162 | | 129 | 50 | 601 |

TABLE 1-continued

Compound Activity in hIL17 inhibition, ROR$_\gamma$ inhibition, and NRF2 Activation Assays

| Compound ID | Compound | ROR$_\gamma$ IC$_{50}$ (nM) | hIL17 IC$_{50}$ (nM) | NRF2 ARE 2× (nM) |
|---|---|---|---|---|
| T163 | | 179 | N/A | 312 |
| T164 | | 201 | 352 | 1059 |
| T165 | | 274 | 65 | 863 |
| T166 | | 141 | 31 | 878 |

TABLE 1-continued

Compound Activity in hIL17 inhibition, ROR$_\gamma$ inhibition, and NRF2 Activation Assays

| Compound ID | Compound | ROR$_\gamma$ IC$_{50}$ (nM) | hIL17 IC$_{50}$ (nM) | NRF2 ARE 2× (nM) |
|---|---|---|---|---|
| T167 | | 251 | 106 | 493 |
| T168 | | 156 | 32 | 1239 |
| T169 | | 118 | 35 | 540 |
| T170 | | 245 | 147 | 1222 |

TABLE 1-continued

Compound Activity in hIL17 inhibition, ROR$_\gamma$ inhibition, and NRF2 Activation Assays

| Compound ID | Compound | ROR$_\gamma$ IC$_{50}$ (nM) | hIL17 IC$_{50}$ (nM) | NRF2 ARE 2× (nM) |
|---|---|---|---|---|
| T171 | | 263 | 120 | 1474 |
| T172 | | 189 | N/A | 998 |
| T173 | | 717 | N/A | >2000 |
| T174 | | 190 | N/A | >2000 |

TABLE 1-continued

Compound Activity in hIL17 inhibition, ROR$_\gamma$ inhibition, and NRF2 Activation Assays

| Compound ID | Compound | ROR$_\gamma$ IC$_{50}$ (nM) | hIL17 IC$_{50}$ (nM) | NRF2 ARE 2× (nM) |
|---|---|---|---|---|
| T175 | | 484 | 329 | >2000 |
| T176 | | 834 | 455 | >2000 |
| T177 | | 151 | N/A | 491 |
| T178 | | 113 | 130 | 444 |

TABLE 1-continued

Compound Activity in hIL17 inhibition, ROR$_\gamma$ inhibition, and NRF2 Activation Assays

| Compound ID | Compound | ROR$_\gamma$ IC$_{50}$ (nM) | hIL17 IC$_{50}$ (nM) | NRF2 ARE 2× (nM) |
|---|---|---|---|---|
| T179 | | 115 | 27 | 649 |
| T180 | | 61 | 21 | 494 |
| T181 | | 158 | N/A | 518 |
| T182 | | 37 | 44 | 892 |

TABLE 1-continued

Compound Activity in hIL17 inhibition, ROR$_\gamma$ inhibition, and NRF2 Activation Assays

| Compound ID | Compound | ROR$_\gamma$ IC$_{50}$ (nM) | hIL17 IC$_{50}$ (nM) | NRF2 ARE 2× (nM) |
|---|---|---|---|---|
| T183 | | 94 | 70 | 1868 |
| T184 | | 293 | N/A | 1832 |
| T185 | | >2000 | N/A | >2000 |
| T186 | | 382 | 195 | >2000 |

TABLE 1-continued

Compound Activity in hIL17 inhibition, ROR$_\gamma$ inhibition, and NRF2 Activation Assays

| Compound ID | Compound | ROR$_\gamma$ IC$_{50}$ (nM) | hIL17 IC$_{50}$ (nM) | NRF2 ARE 2× (nM) |
|---|---|---|---|---|
| T187 | 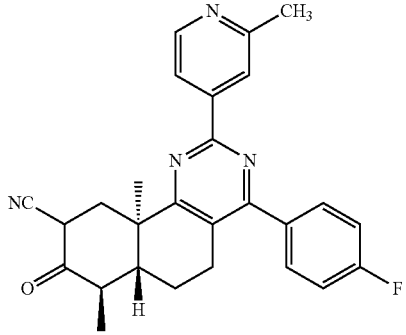 | 277 | N/A | >2000 |

All of the compounds, compositions, and methods disclosed and claimed herein can be made and executed without undue experimentation in light of the present disclosure. While the disclosure may have focused on several embodiments or may have been described in terms of preferred embodiments, it will be apparent to those of skill in the art that variations and modifications may be applied to the compounds, compositions, and methods without departing from the spirit, scope, and concept of the invention. All variations and modifications apparent to those skilled in the art are deemed to be within the spirit, scope, and concept of the invention as defined by the appended claims.

REFERENCES

The following references to the extent that they provide exemplary procedural or other details supplementary to those set forth herein, are specifically incorporated herein by reference.

Anderson, *Practical Process Research & Development A Guide for Organic Chemists*, 2 ed., Academic Press, New York, 2012.
Bolli, et al., *Bioorg. & Med. Chem. Lett.*, 13:955-959, 2003.
Bradshaw, et al., *Advanced Synthesis and Catalysts*, 351: 2482-2490, 2009.
Bronner, et al., *Expert Opin. Ther. Pat.*, 2016, Published Online Ahead of Print
Fujiwara, et al., *J. Immunol.*, 193(5):2565-73, 2014.
Gaffen, et al., *Nature Reviews Immunology*, 14(9):585-600, 2014.
Garigipati, *Tetrahedron Letters*, 31(14):1969-1972, 1990.
*Handbook of Pharmaceutical Salts: Properties, and Use*, Stahl and Wermuth Eds., Verlag Helvetica Chimica Acta, 2002.
Lu et al., *J. Clin. Invest.*, 121(10):4015-29, 2011.
Miosse and Kolls, *Nature Reviews*, 11(10):763-776, 2012.
Reagan-Shaw et al., *FASEB J.*, 22(3):659-661, 2008.
Smith, *March's Advanced Organic Chemistry: Reactions, Mechanisms, and Structure*, 7$^{th}$ Ed., Wiley, 2013.
Waite and Skokos, *International Journal of Inflammation*, 2012:1-10, 2011.
Yang, et al., *Trends in Pharmacological Sciences*, 35(10): 493-500, 2014.
Zhang, et al., *Acta Pharmacologica Sinica*, 36:71-87, 2015.

What is claimed is:

1. A compound of the formula:

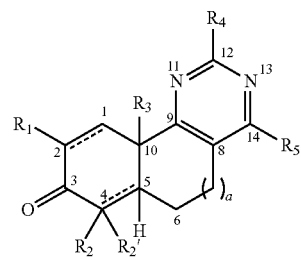

(X)

wherein:
  the bond between carbon atoms 1 and 2 is a single bond, an epoxidized double bond, or a double bond;
  the bond between carbon atoms 4 and 5 is a single bond or a double bond;
  a is 0, 1, or 2;
  $R_1$ is cyano, heteroaryl (c≤8), substituted heteroaryl (c≤8), —CF$_3$, or —C(O)R$_a$; wherein:
    $R_a$ is hydroxy, amino, or alkoxy (C≤8), alkylamino (c≤8), dialkylamino (c≤8), alkylsulfonylamino (c≤8), or a substituted version of any of these groups;
  $R_2$ is hydrogen, alkyl (c≤12), cycloalkyl (C≤12), alkenyl (c≤12), alkynyl (c≤12), or a substituted version of the last four groups, or -alkanediyl (c≤8)-cycloalkyl (c≤12) or a substituted version of this group;
  $R_2'$ is absent, hydrogen, alkyl (c≤12), cycloalkyl (c≤12), alkenyl (c≤12), alkynyl (c≤12), or a substituted version of the last four groups, provided that when the bond between carbon atoms 4 and 5 is a double bond then $R_2'$ is absent;
  $R_3$ is alkyl (c≤12), aryl (c≤12), aralkyl (c≤12), or a substituted version of any of these groups;
  $R_4$ is cycloalkyl (c≤18), substituted cycloalkyl (c≤18), heteroaryl (c≤18), substituted heteroaryl (c≤18), heterocycloalkyl (<18), substituted heterocycloalkyl (c≤18), or

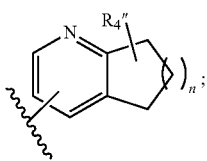

wherein:
n is 0, 1, 2, 3, or 4; and
R$_4$" is —H, —OH, —F, —Cl, —Br, —I, —NH$_2$, —NO$_2$, —CN, —SH, —S(O)$_2$OH, or —S(O)$_2$NH$_2$, or alkyl (C≤8), cycloalkyl (c≤8), aryl (c≤8), heteroaryl (c≤8), heterocycloalkyl (c≤8), acyl (c≤8), amido (C≤8), alkoxy (C≤8), acyloxy (C≤8), alkylamino (C≤8), dialkylamino (C≤8), —C(O)-alkoxy (c≤8), —C(O)-alkylamino (C≤8), —C(O)-dialkyl-amino (c≤8), alkylsulfonyl (c≤8), arylsulfonyl (c≤8), alkoxysulfonyl (c≤8), or a substituted version of any of these groups; or —X$_2$—(CH$_2$)$_p$—R$_4$";

wherein:
X$_2$ is arenediyl (c≤12), substituted arenediyl (c≤12), heterocycloalkanediyl (c≤12), substituted heterocycloalkanediyl (c≤12), heteroarenediyl (C≤12), or substituted heteroarenediyl (C≤12),
p is 0, 1, 2, 3, or 4; and
R$_4$" is alkyl (c≤8), cycloalkyl (c≤8), aryl (c≤8), heteroaryl (c≤8), heterocycloalkyl (c≤8), acyl (c≤8), alkoxy (C≤8), acyloxy (C≤8), —C(O)-alkoxy (c≤8), —C(O)-alkylamino (C≤8), —C(O)-dialkyl-amino (C≤8), alkylsulfonyl (c≤8), arylsulfonyl (c≤8), alkoxysulfonyl (c≤8), or a substituted version of any of these groups; and
R$_5$ is cycloalkoxy (C≤12), aryl (c≤12), heteroaryl (c≤12), or a substituted version of any of these groups, or

—OY$_1$-A$_1$;

wherein:
Y$_1$ is alkanediyl (c≤8) or substituted alkanediyl (c≤8); and
A$_1$ is cycloalkyl (c≤8) or substituted cycloalkyl (c≤8);
provided that when carbon atoms 4 and 5 are joined by a double bond, then R$_2$' and the hydrogen atom at carbon atom 5 are absent;
or a pharmaceutically acceptable salt thereof.

2. The compound of claim 1, wherein the bond between carbon atom 1 and carbon atom 2 is a double bond.

3. The compound of claim 1, wherein the bond between carbon atom 4 and carbon atom 5 is a single bond.

4. The compound of claim 1, wherein a is 1.

5. The compound of claim 1, wherein R$_1$ is cyano.

6. The compound of claim 1, wherein R$_2$ is alkyl (c≤12) or substituted alkyl (C≤12).

7. The compound of claim 6, wherein R$_2$ is methyl, ethyl, propyl, or 3-hydroxypropyl.

8. The compound of claim 1, wherein R$_2$' is hydrogen, alkyl (c≤12), or substituted alkyl (c≤12).

9. The compound of claim 1, wherein R$_3$ is alkyl (c≤12) or substituted alkyl (c≤12).

10. The compound of claim 9, wherein R$_3$ is methyl.

11. The compound of claim 1, wherein R$_4$ is heteroaryl (c≤18) or substituted heteroaryl (c≤18).

12. The compound of claim 11, wherein R$_4$ is a heteroaryl (c≤12) or a substituted heteroaryl (c≤12) group wherein at least one of the heteroatoms in the aromatic ring is a nitrogen atom.

13. The compound of claim 11, wherein R$_4$ is heteroaryl (c≤18).

14. The compound of claim 13, wherein R$_4$ is 3-pyridinyl, 4-pyridinyl, 4-(2-cyclopropyl)-pyridinyl, 5-(2-cyclopropyl)-pyridinyl, 4-(2-morpholino)-pyridinyl, 4-(2-phenyl)-pyridinyl, 3-(5-methyl)-pyridinyl, 3-(6-methyl)-pyridinyl, 4-(2-methyl)-pyridinyl, 4-(3-methyl)-pyridinyl, 3-pyrazolo [1,5-a] pyridinyl, 3-(N-methyl)-pyrrolo [2,3-b] pyridinyl, 5-isoquinolinyl, 2-isoquinolinyl, 1-isoquinolinyl, 4-(3-phenyl)-pyridinyl, 5-(2-phenyl)-pyridinyl, 4-(3,5-dimethyl)-isoxazolyl, 3-(4-methyl)-pyridinyl, 4-(6-methyl)-pyrimidinyl, 6-(4-methyl)-pyrimidinyl, 4-pyridazinyl, 2-quinazolinyl, 4-quinazolinyl, 2-quinolinyl, 3-quinolinyl, 4-quinolinyl, 5-quinolinyl, 6-quinolinyl, 8-quinolinyl, 4-isoquinolinyl, 3-(8-methyl)-quinolinyl, 3-(1-methyl)-quinolinyl, 4-(2-methyl)-quinolinyl, 4-(2-isopropyl)-quinolinyl, 4-(6-methyl)-quinolinyl, 4-(7-methyl)-quinolinyl, 4-(8-methyl)-quinolinyl, 2-(N-methyl)-indolyl, 5-(2,4-dimethyl)-thiazolyl, or 3-(5-methyl)-oxadizolyl.

15. The compound of claim 11, wherein R$_4$ is substituted heteroaryl (c≤18).

16. The compound of claim 15, wherein R$_4$ is 4-(2-trifluoromethyl)-pyridinyl, 4-(3-fluoro)-pyridinyl, 4-(2-methoxy)-pyridinyl, 4-(2-hydroxymethyl)-pyridinyl, 4-(2-acetylamino)-pyridinyl, 4-(2-fluoromethyl)-pyridinyl, 4-(2-acetamidylethyl)-pyridinyl, 4-(2-fluoromethyl)-quinolinyl, 4-(2-acetoxymethyl)-quinolinyl, 4-(2-formyl)-quinolinyl, 4-(6-fluoro)-quinolinyl, 4-(7-fluoro)-quinolinyl, 4-(8-fluoro)-quinolinyl, 4-(6,8-difluoro)-quinolinyl, 4-(6-fluoro-2-methyl)-quinolinyl, or 4-(8-fluoro-2-methyl)-quinolinyl.

17. The compound of claim 1, wherein R$_4$ is —X$_2$—(CH$_2$)$_p$—R$_4$";
wherein:
X$_2$ is arenediyl (c≤12), substituted arenediyl (c≤12), heterocycloalkanediyl (C≤12), substituted heterocycloalkanediyl (C≤12), heteroarenediyl (c≤12), or substituted heteroarenediyl (C≤12);
p is 0, 1, 2, 3, or 4; and
R$_4$" is alkyl (c≤8), cycloalkyl (c≤8), aryl (c≤8), heteroaryl (c≤8), heterocycloalkyl (c≤8), acyl (c≤8), alkoxy (C=8), acyloxy (c≤8), —C(O)-alkoxy (c≤8), —C(O)-alkylamino (c≤8), —C(O)-dialkylamino (c≤8), alkylsulfonyl (c≤8), arylsulfonyl (c≤8), alkoxysulfonyl (c≤8), or a substituted version of any of these groups.

18. The compound of claim 17, wherein X$_2$ is heteroarenediyl (c≤12) or substituted heteroarenediyl (C≤12).

19. The compound of claim 17, wherein R$_4$" is cycloalkyl (c≤8) or substituted cycloalkyl (c≤8).

20. The compound of claim 19, wherein R$_4$" is cycloalkyl (c≤8).

21. The compound of claim 20, wherein R$_4$" is cyclopropyl.

22. The compound of claim 1, wherein R$_5$ is aryl (c≤12) or substituted aryl (c≤12).

23. The compound of claim 22, wherein R$_5$ is aryl (c≤12).

24. The compound of claim 23, wherein R$_5$ is phenyl, 4-methylphenyl, 3-isopropylphenyl, 4-isopropylphenyl, 1,3-biphenyl, or 1,4-biphenyl.

25. The compound of claim 22, wherein R$_5$ is substituted aryl (c≤12), wherein one or more hydrogen atoms has been replaced with one or more fluorine atoms.

26. The compound of claim 22, wherein $R_5$ is substituted aryl (c≤12).

27. The compound of claim 26, wherein $R_5$ is 2-fluorophenyl, 3-fluorophenyl, 4-fluorophenyl, 2,4-difluorophenyl, 4-hydroxymethylphenyl, 3-trifluoromethylphenyl, 4-trifluoromethylphenyl, 4-methoxyphenyl, 4-chlorophenyl, or 3,4-dichlorophenyl.

28. The compound of claim 1, wherein $R_5$ is cycloalkoxy (C≤12) or substituted cycloalkoxy (C≤12).

29. The compound of claim 28, wherein $R_5$ is cyclobutyloxy, cyclopentyloxy, or cyclohexyloxy.

30. The compound of claim 1, wherein $R_5$ is heteroaryl (c≤12) or substituted heteroaryl (c≤12).

31. The compound of claim 12, wherein the compound is further defined as:

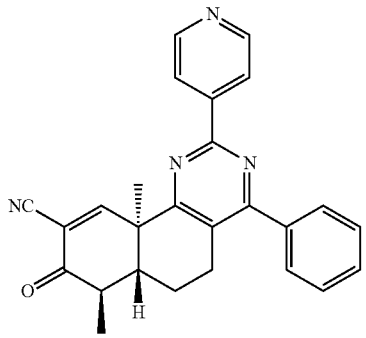

,

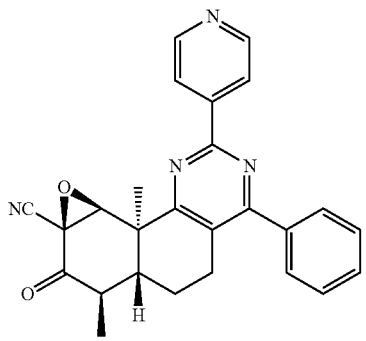

,

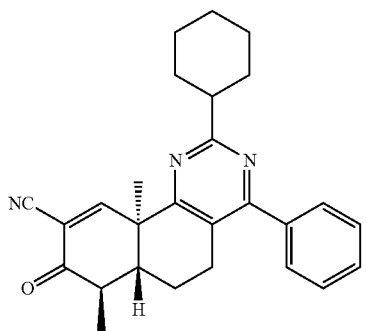

,

-continued

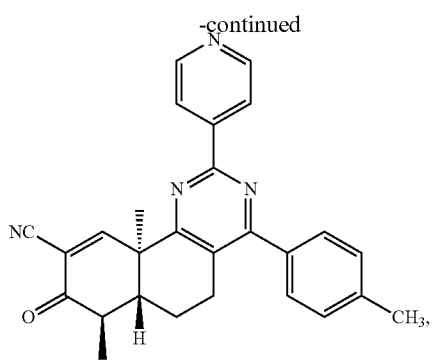

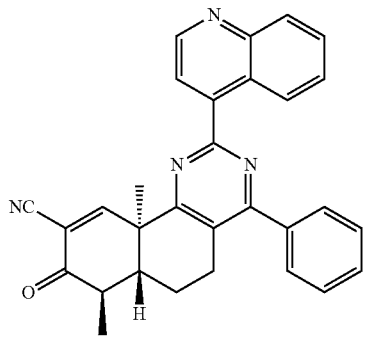

,

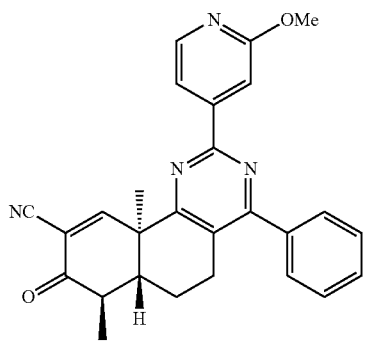

,

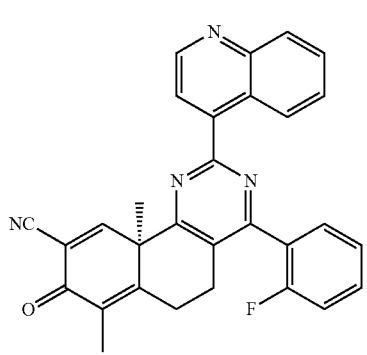

,

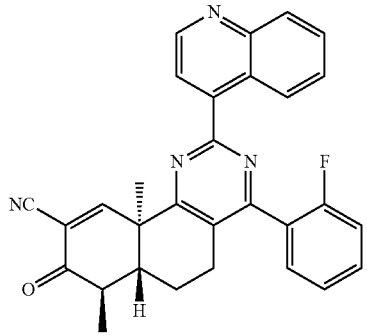 [SMILES: C[C@@H]1C(=O)C(C#N)=C[C@@]2(C)c3nc(-c4ccnc5ccccc45)nc(-c4ccccc4F)c3CC[C@@H]12]

,

599
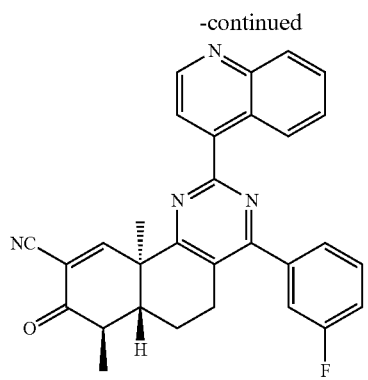
,
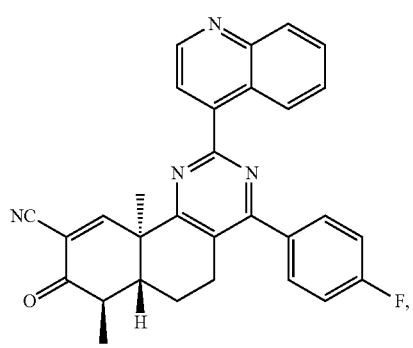
,
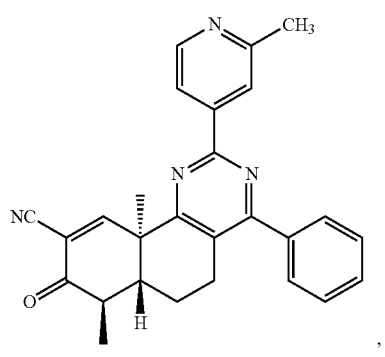
,
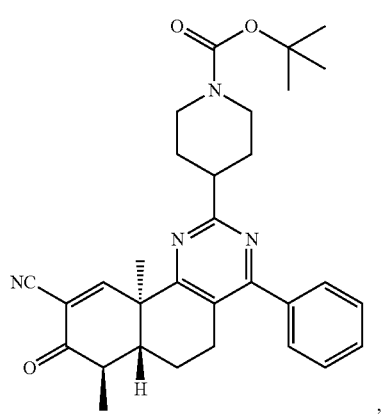
,
600
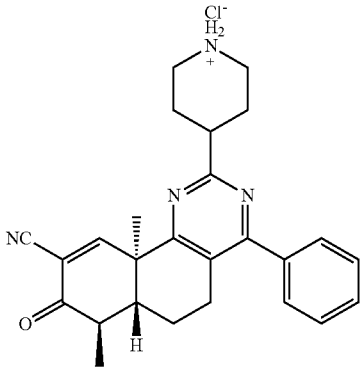
,
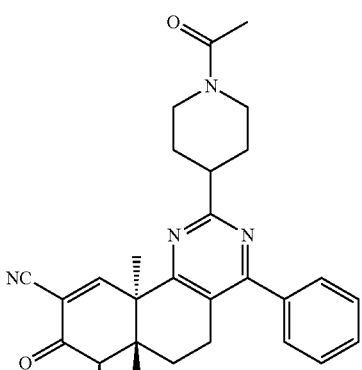
,
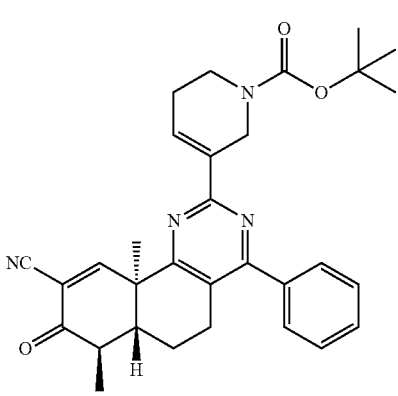
,
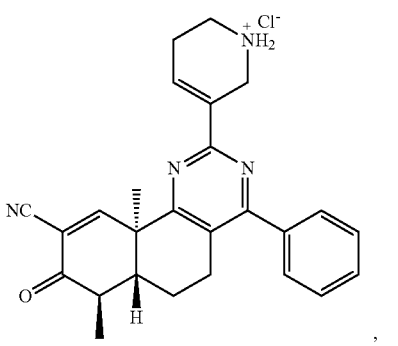
, 601
-continued
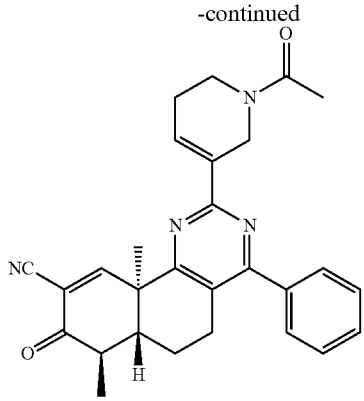
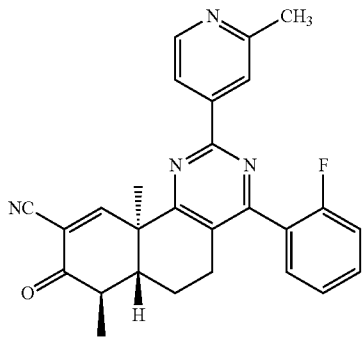
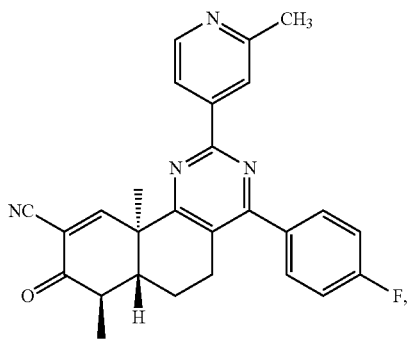
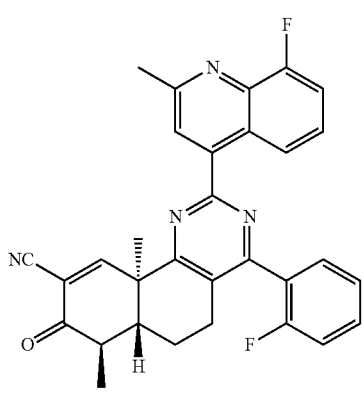
602
-continued
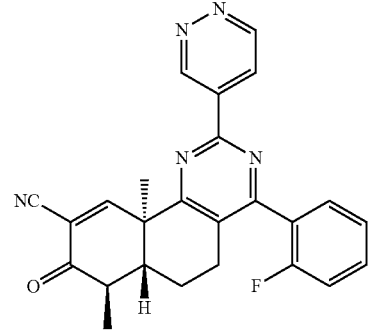
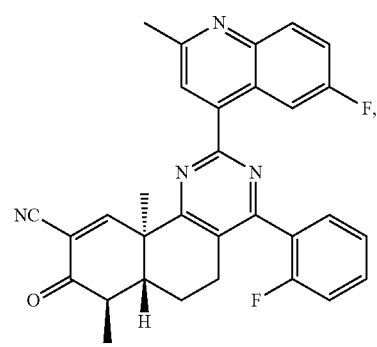
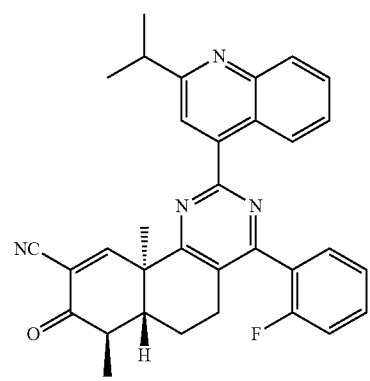
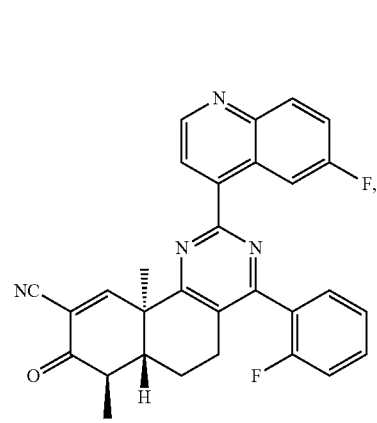

603
-continued
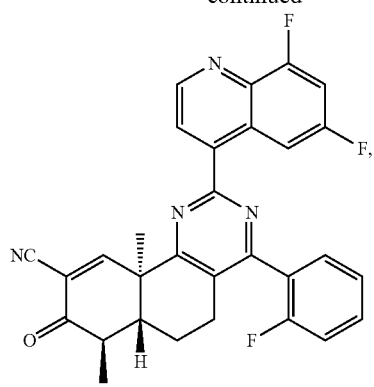
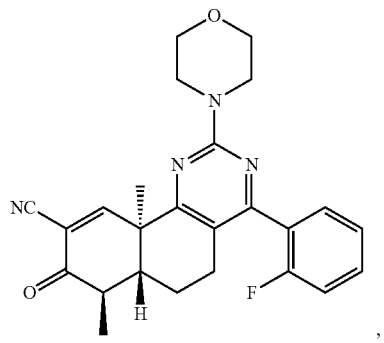
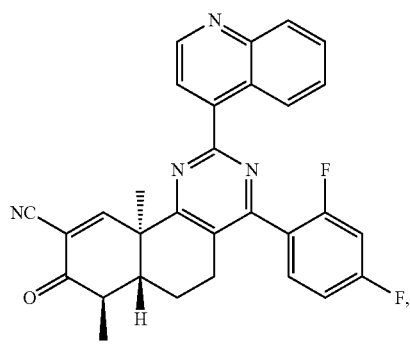
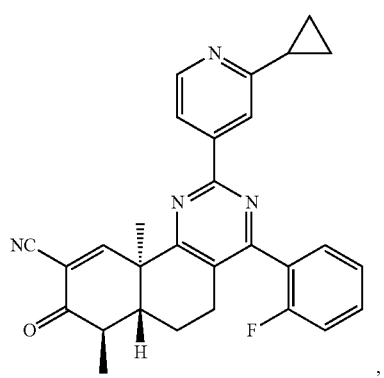
604
-continued
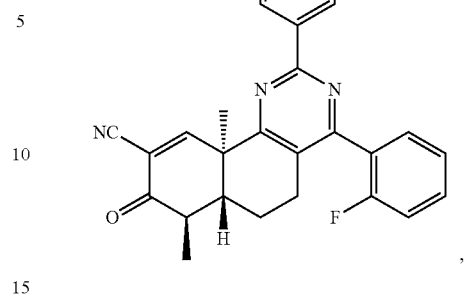
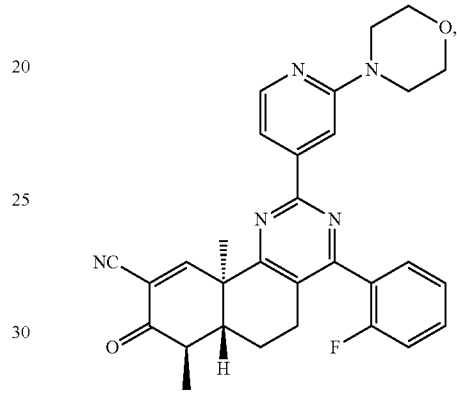
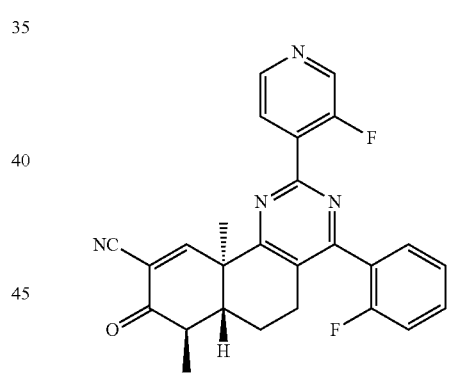
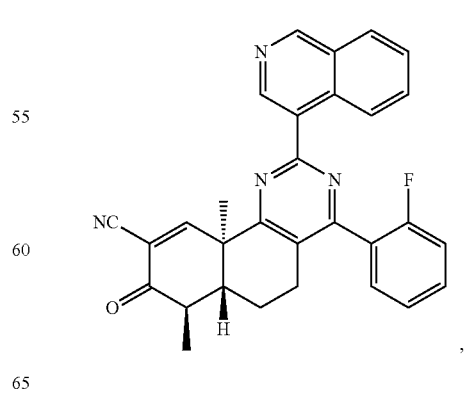

605
-continued
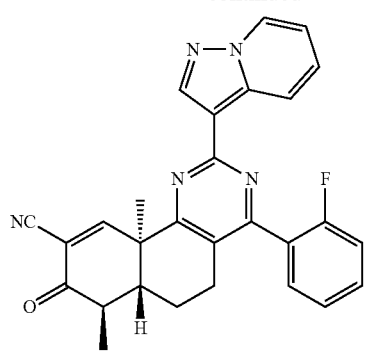
,
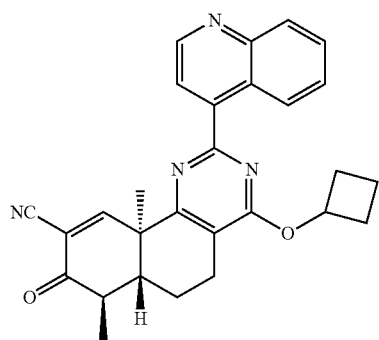
,
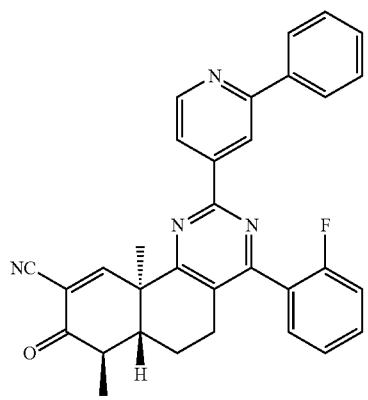
,
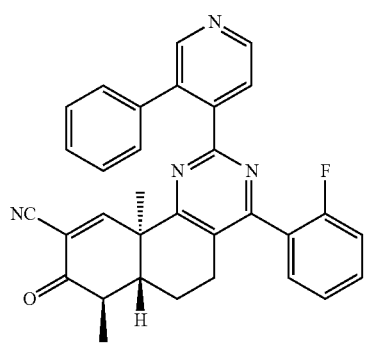
,
606
-continued
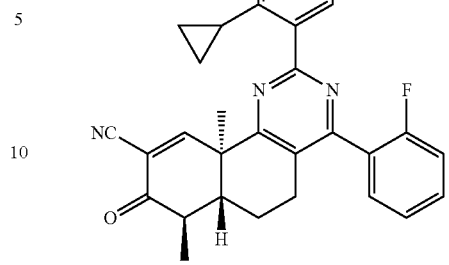
,
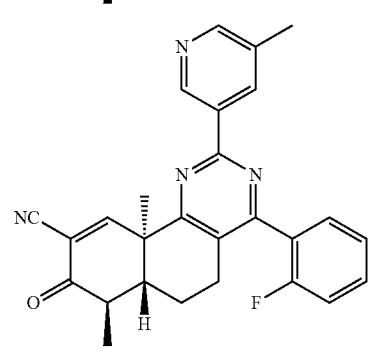
,
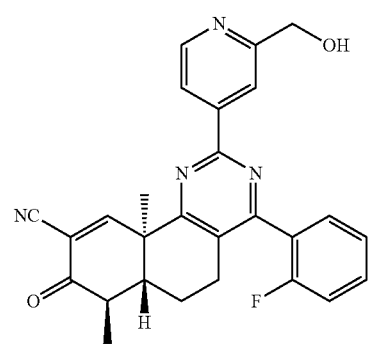
,
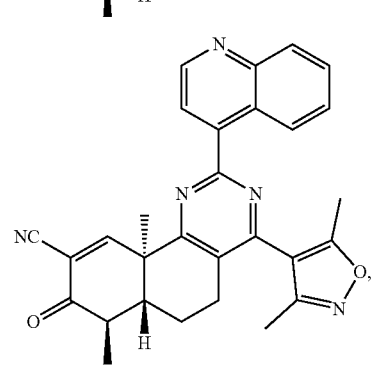
,
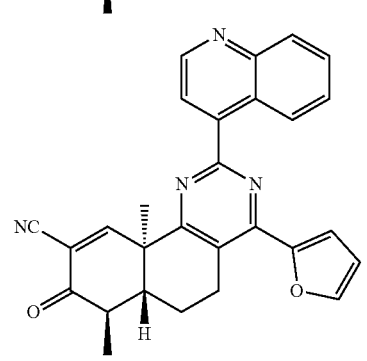
, 607
-continued
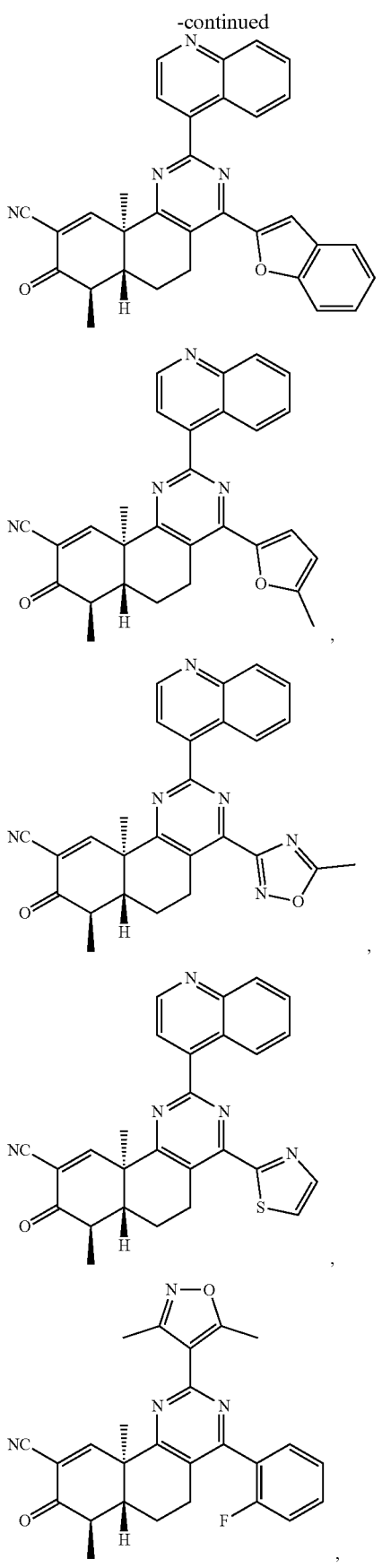
608
-continued
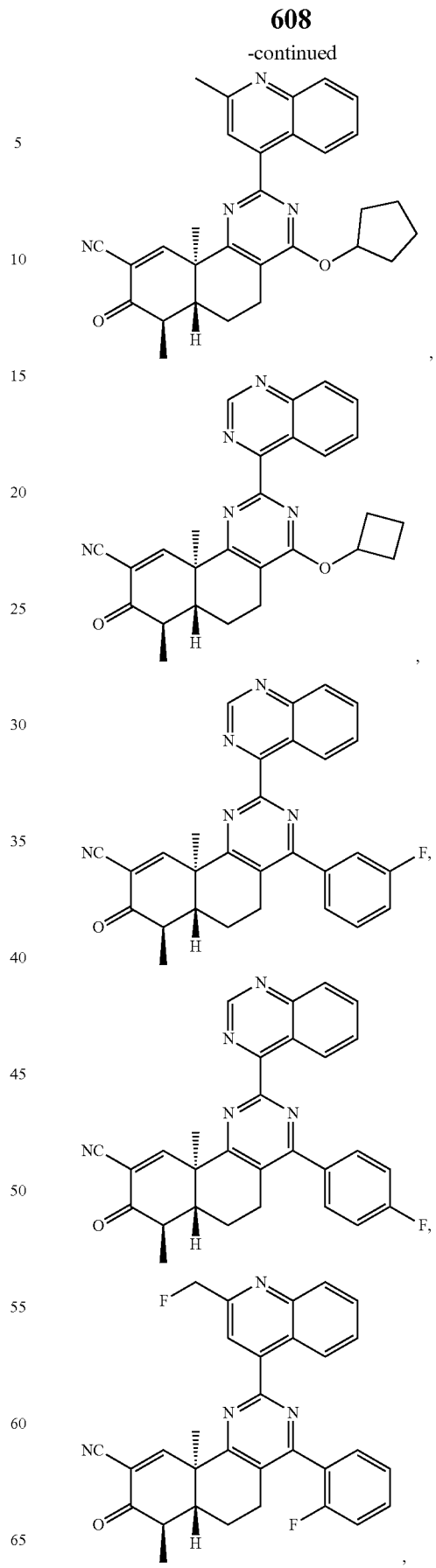

609
-continued
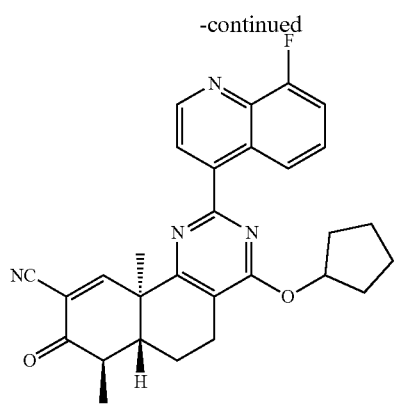
,
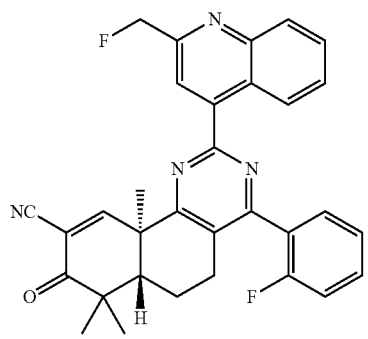
,
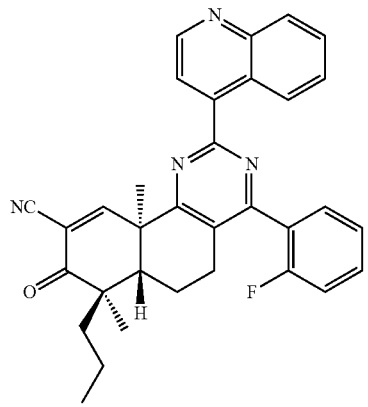
,
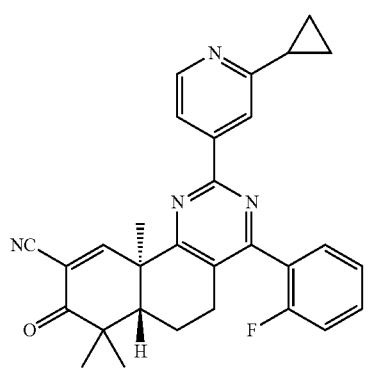
,
610
-continued
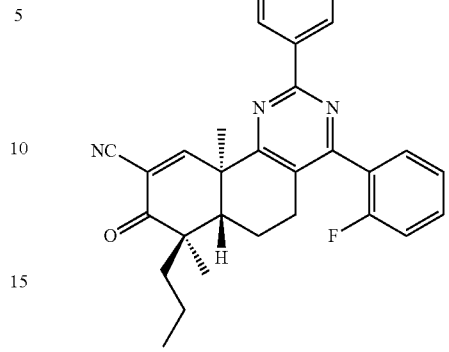
,
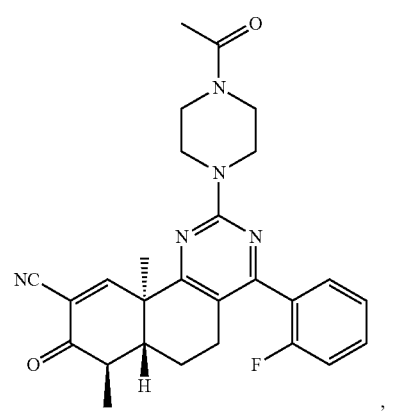
,
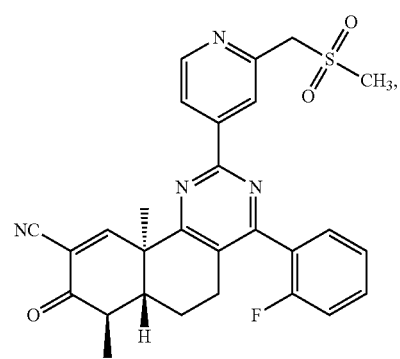
,
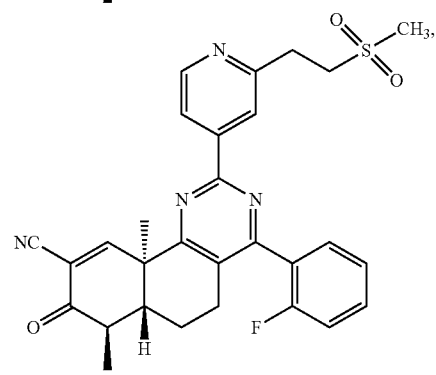
, 611
-continued
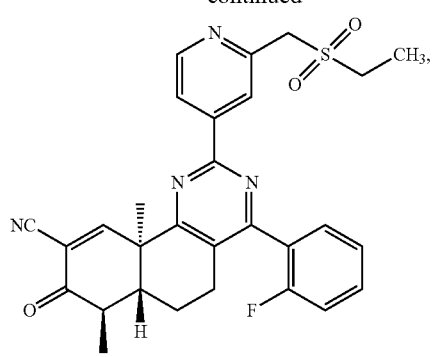
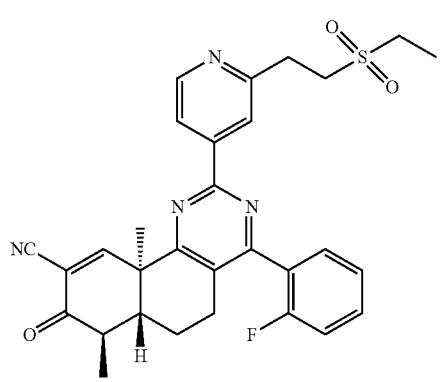
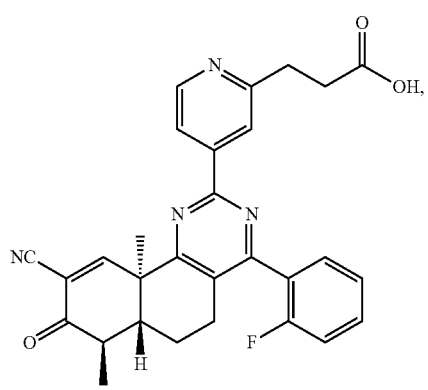 [SMILES: C[C@H]1C(=O)C(C#N)=C[C@@]2(C)c3nc(-c4ccnc(CCC(N)=O)c4)nc(-c4ccccc4F)c3CC[C@H]12]
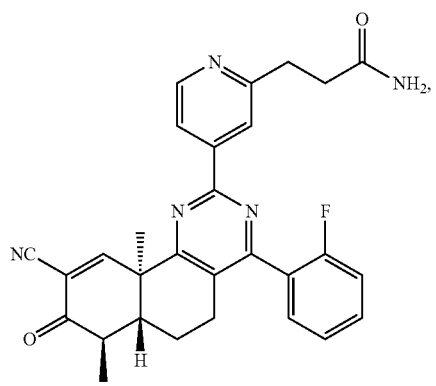
612
-continued
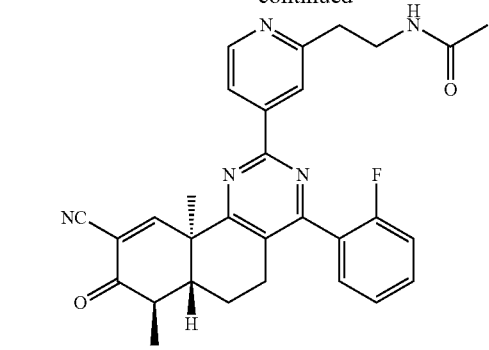
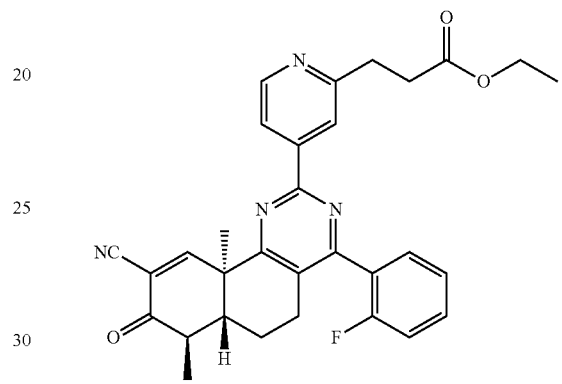
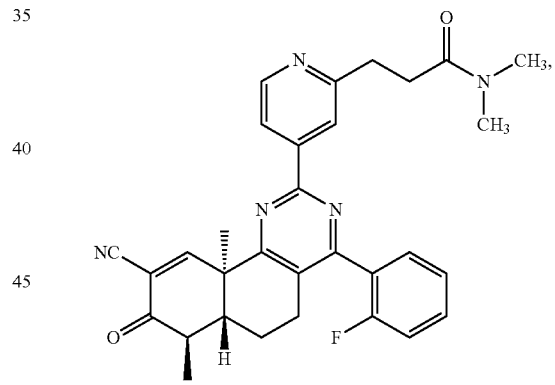
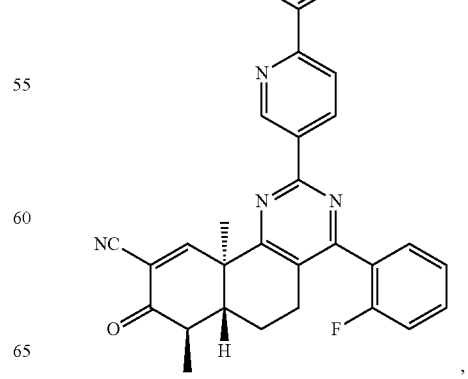

613
-continued
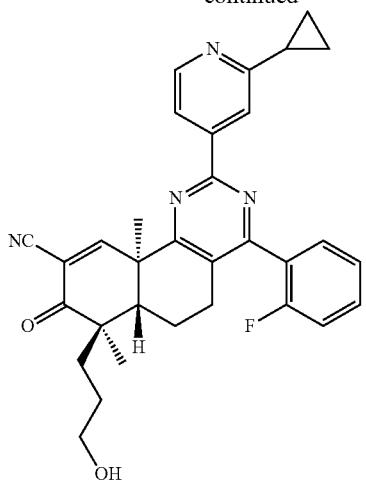
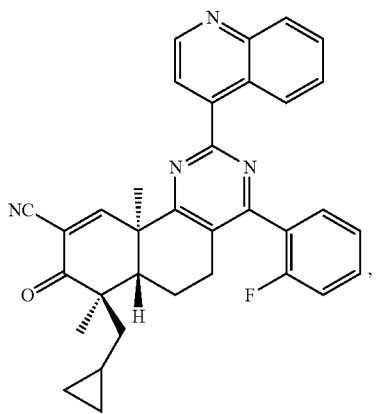
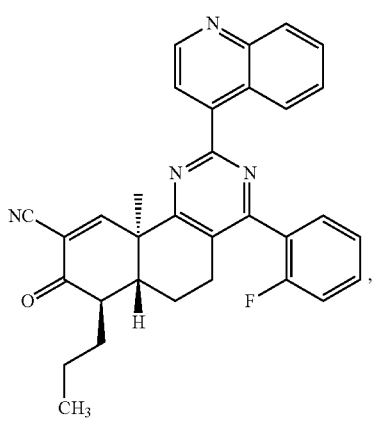
614
-continued
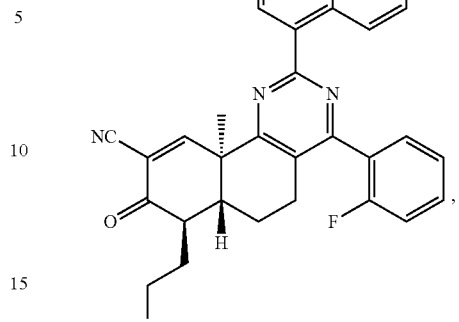
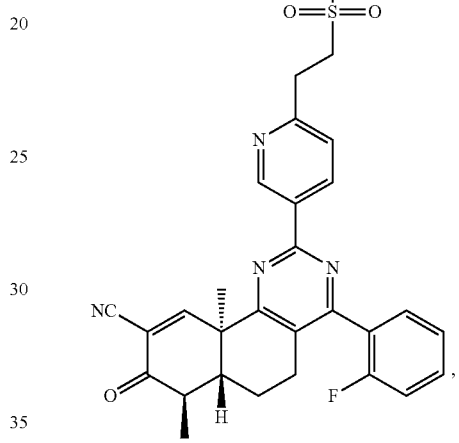

615
-continued
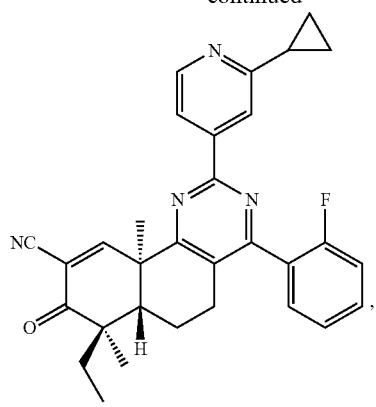
,
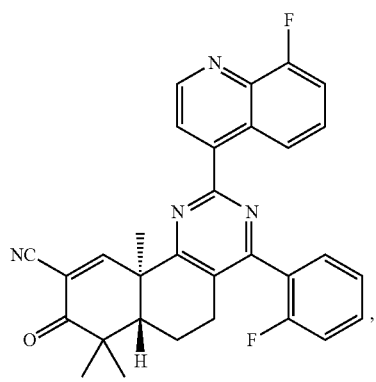
,
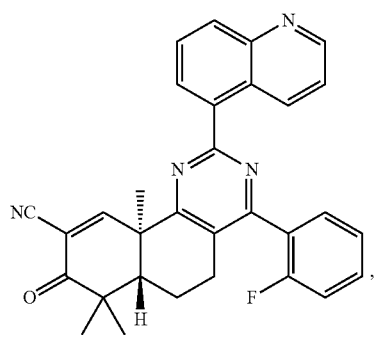
,
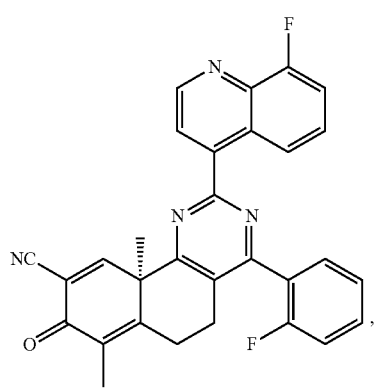
,
616
-continued
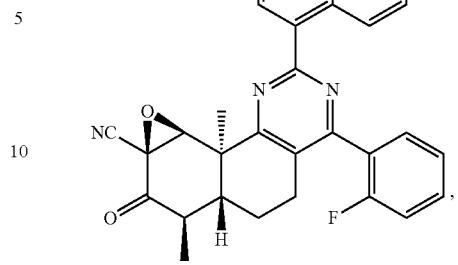
,
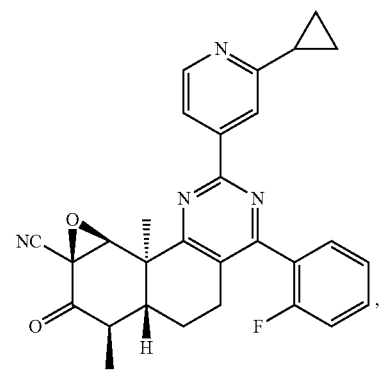
,
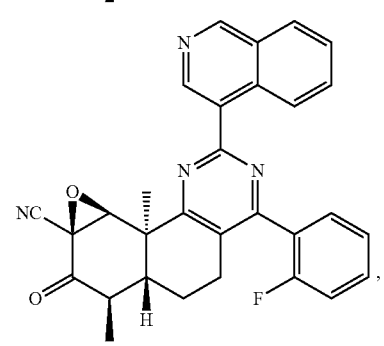
,
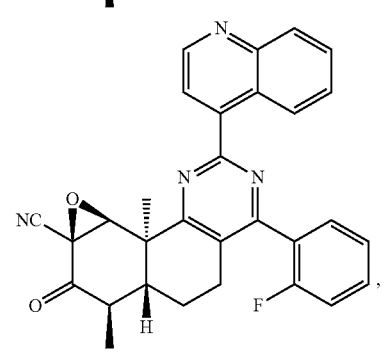
,
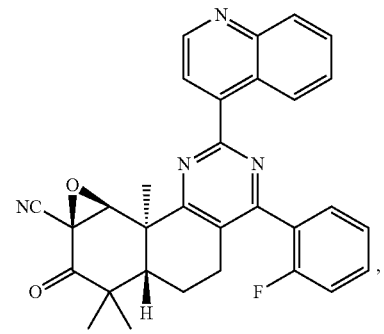
, 617
-continued
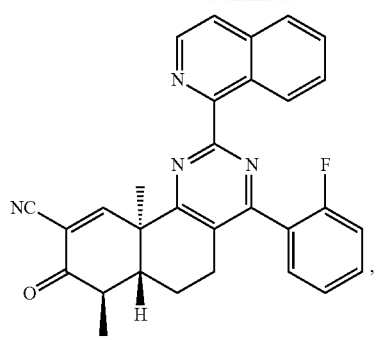
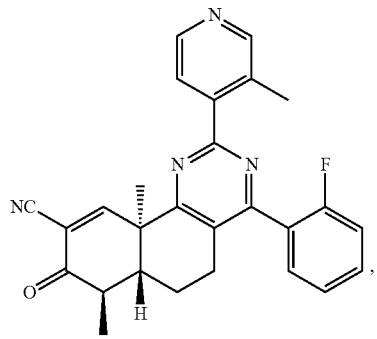
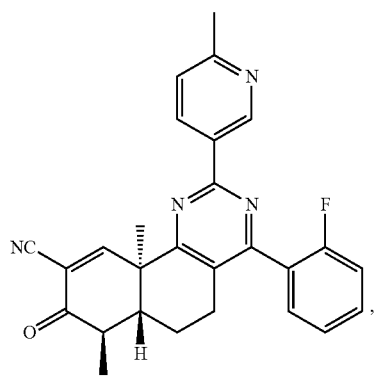
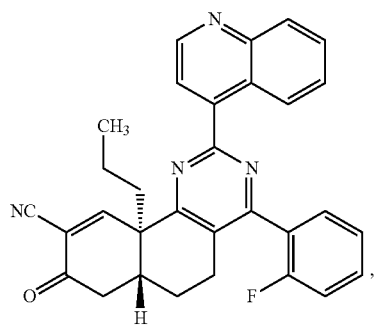
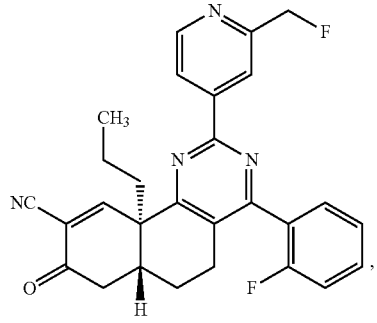
618
-continued
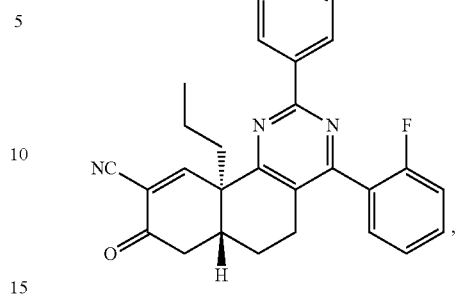
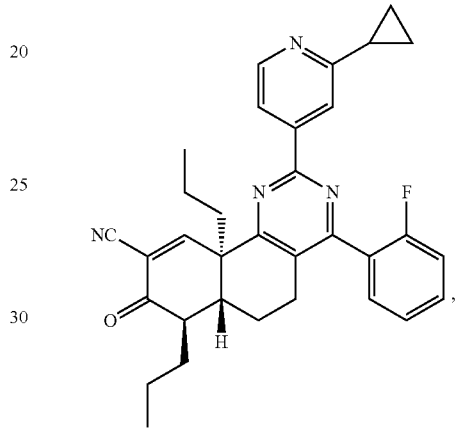
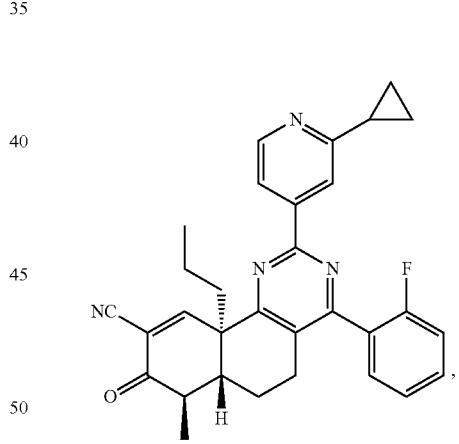
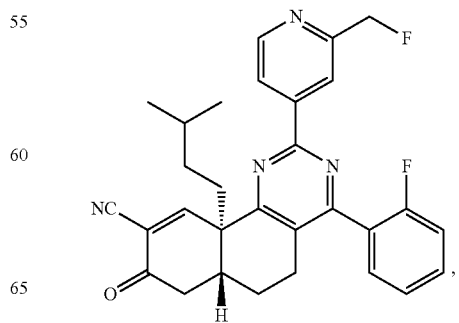

619
-continued
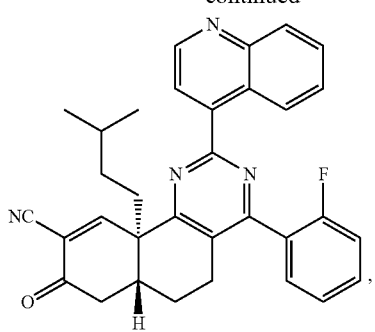
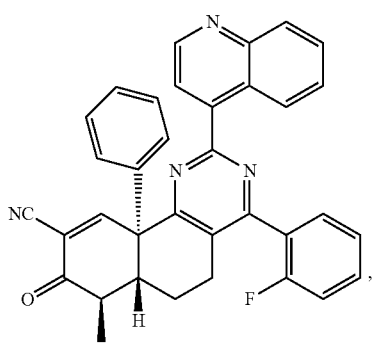
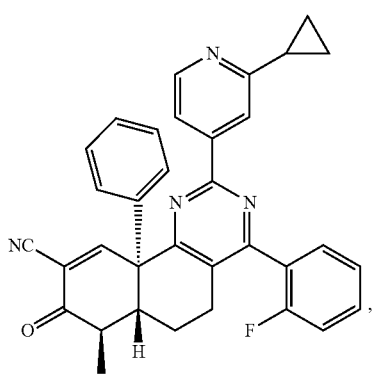
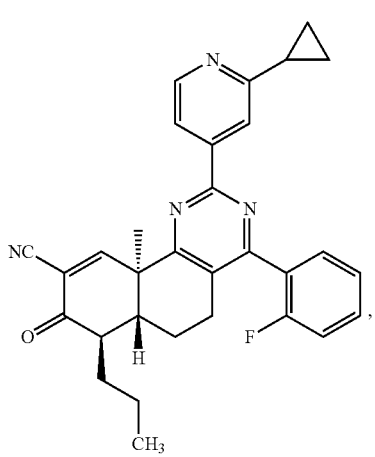
620
-continued
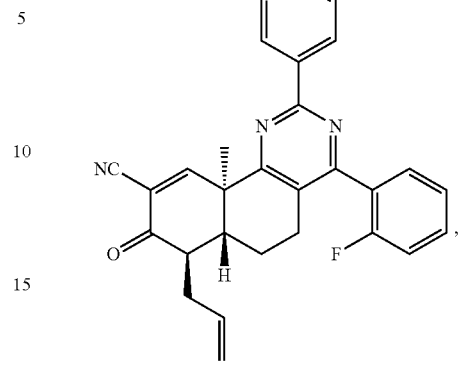
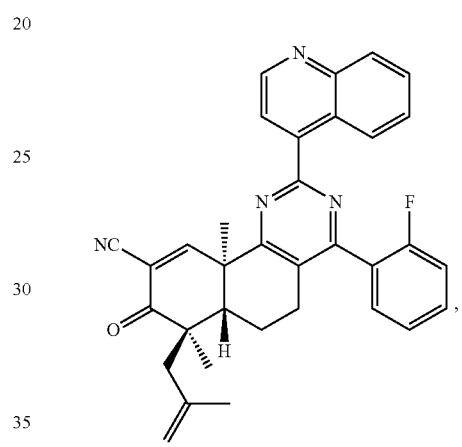
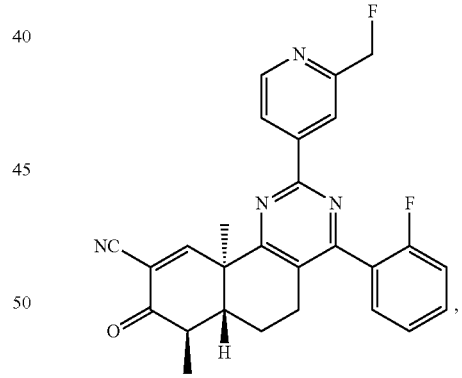
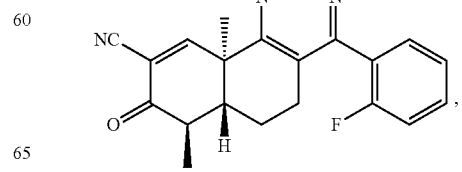

621
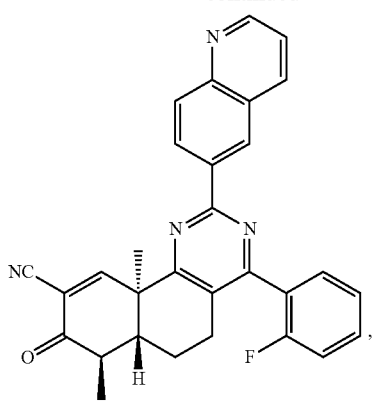
,
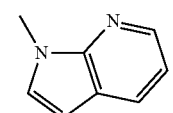
,
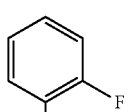
,
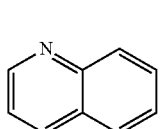
,
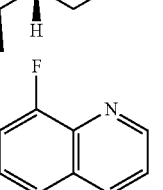
622
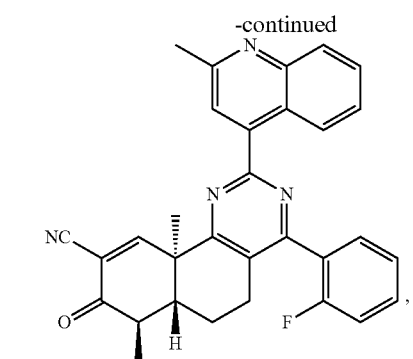
,
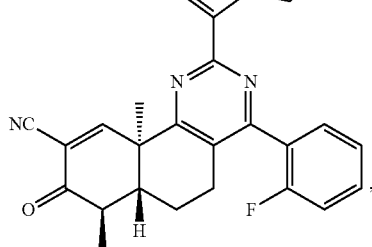
,
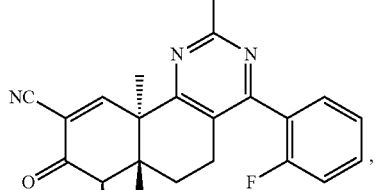
,
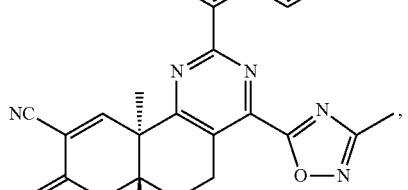
,
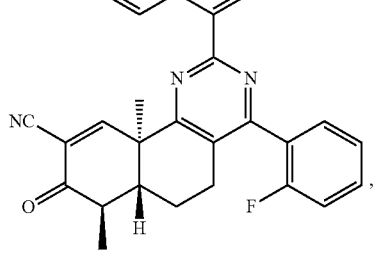
, 623
-continued
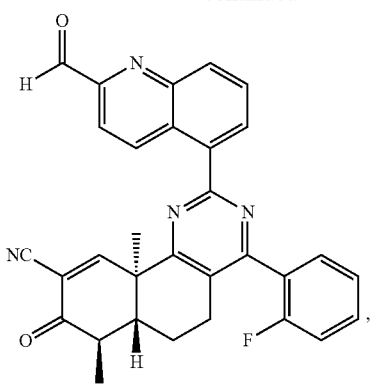
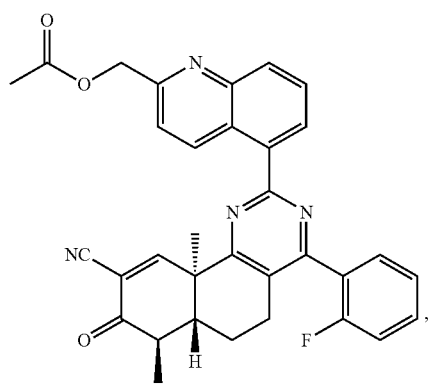
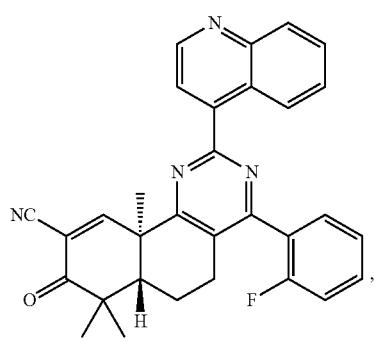
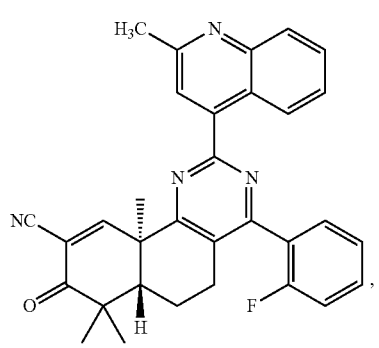
624
-continued
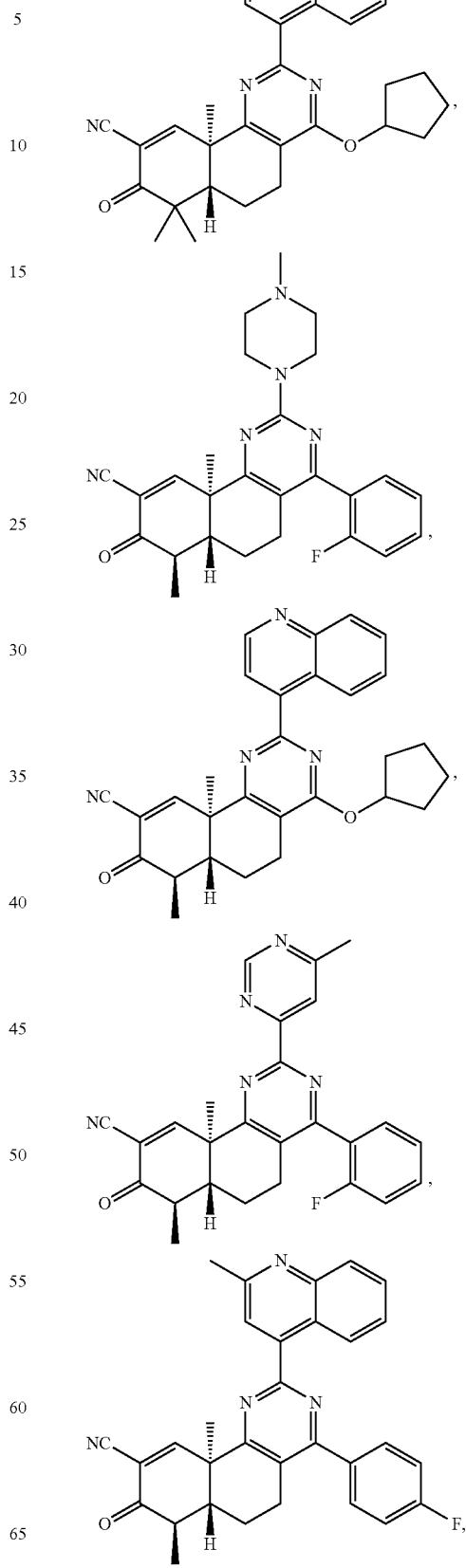

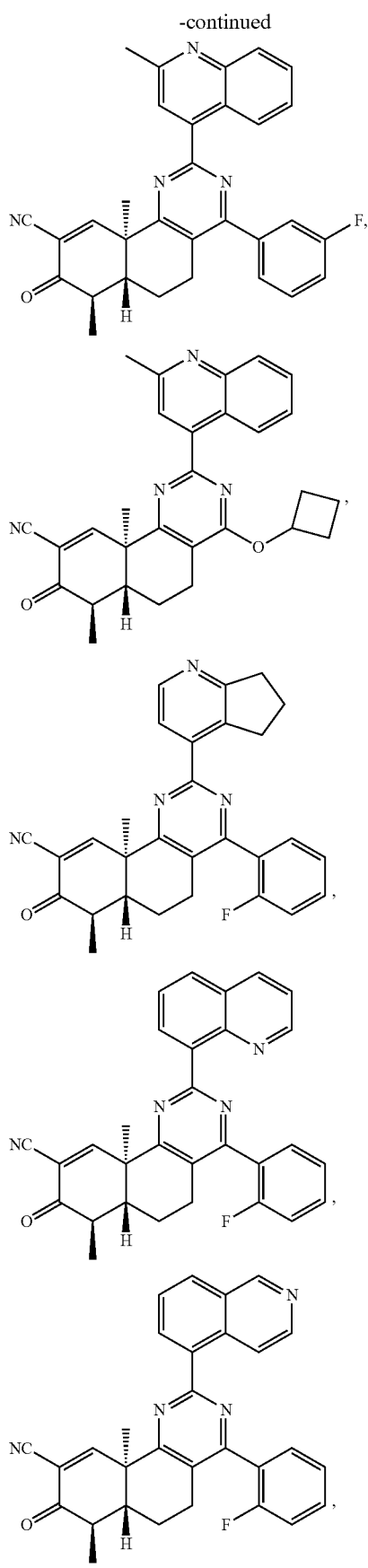
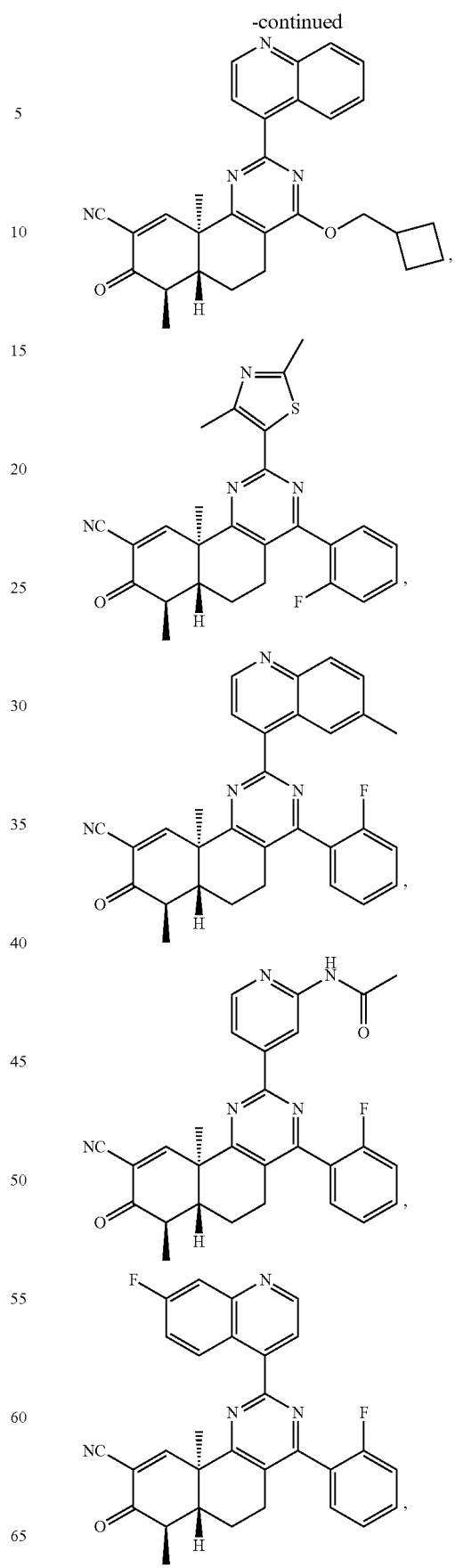

627
-continued
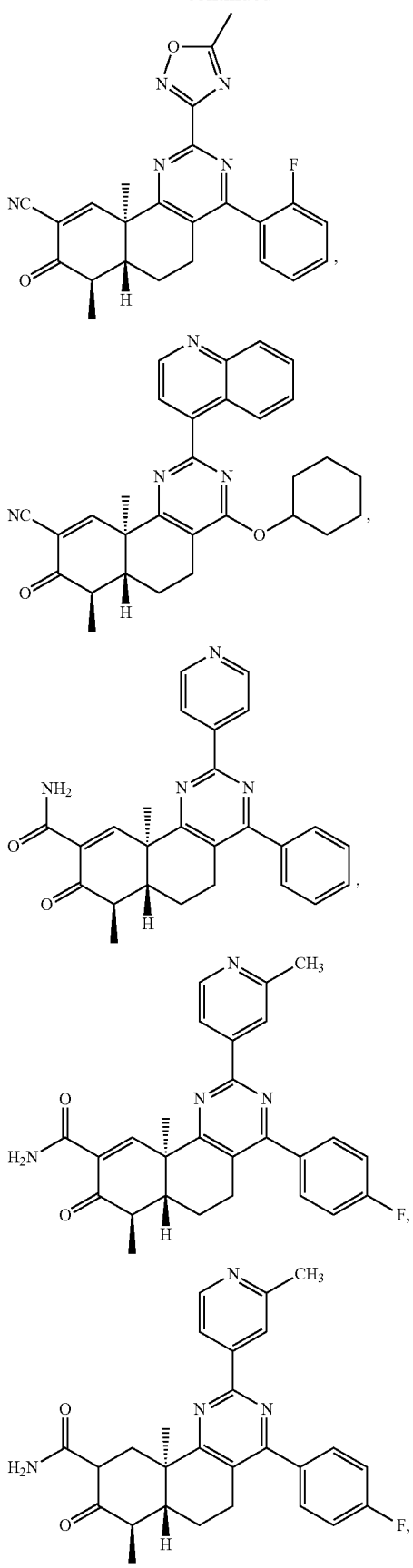
628
-continued
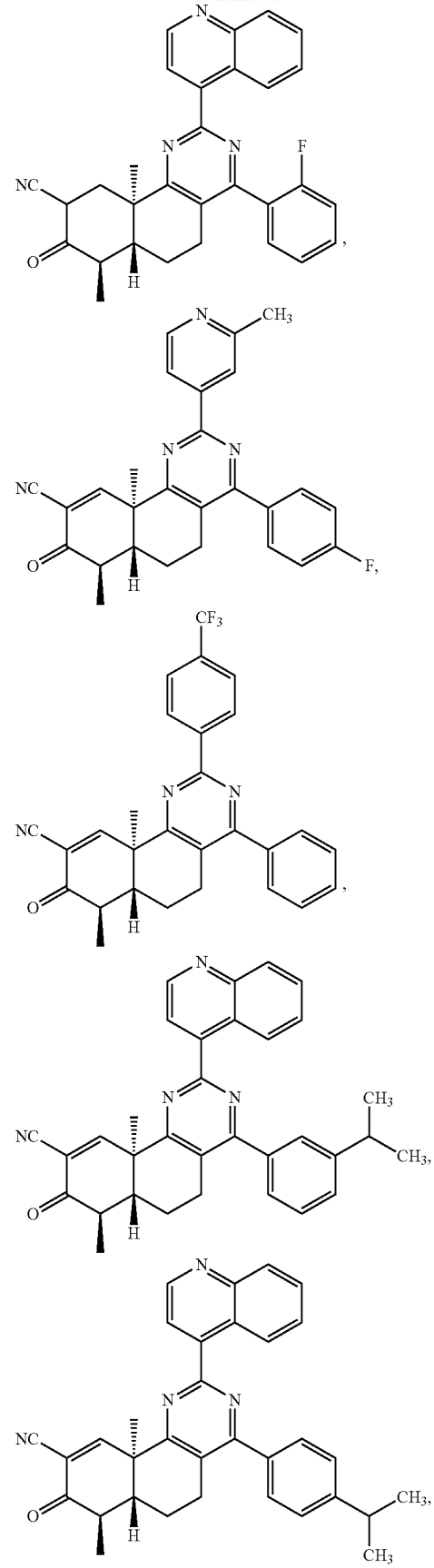

629
-continued
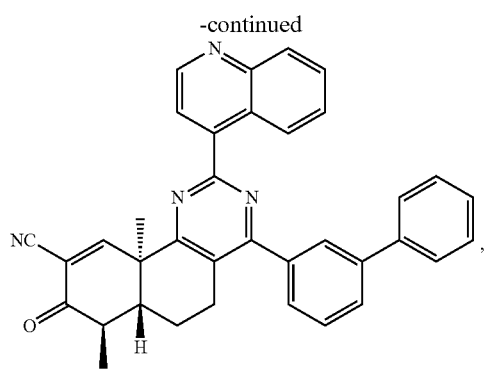
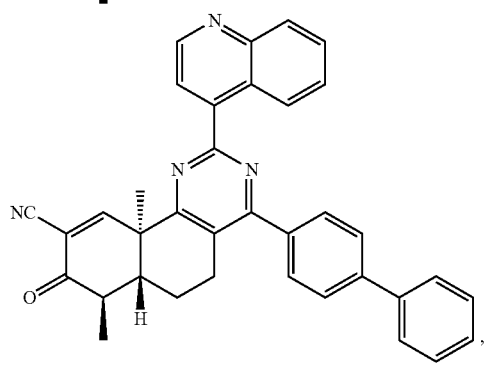
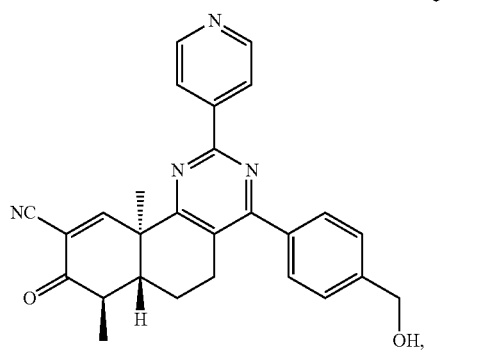
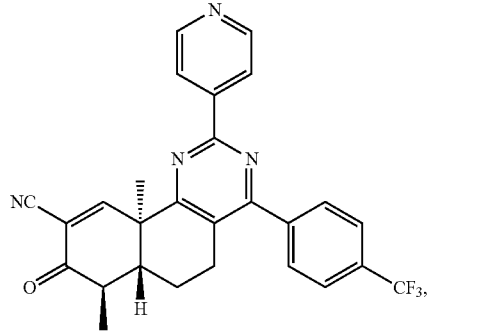
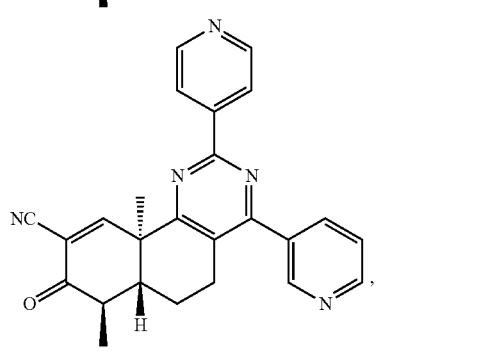
630
-continued
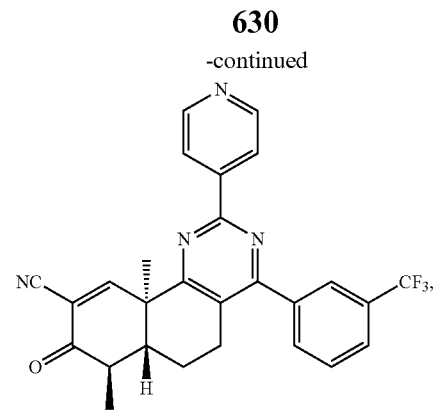
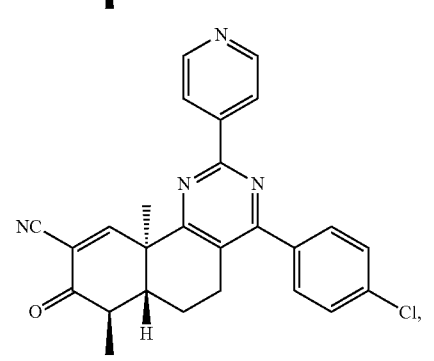
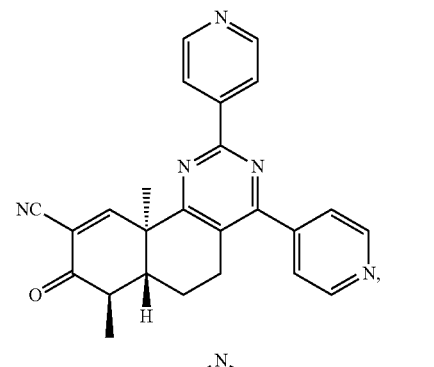
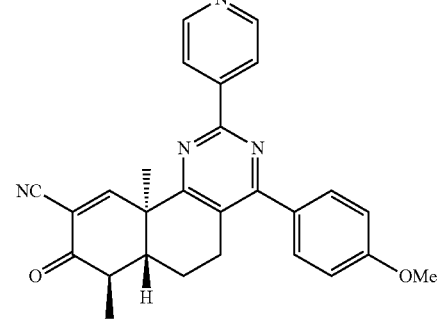
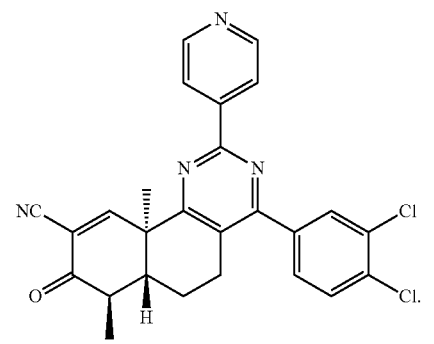

631
-continued

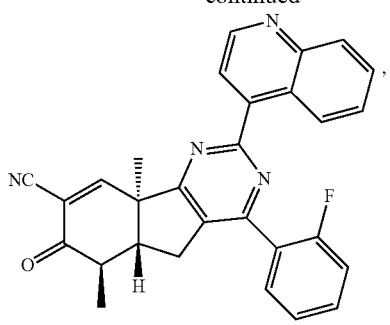

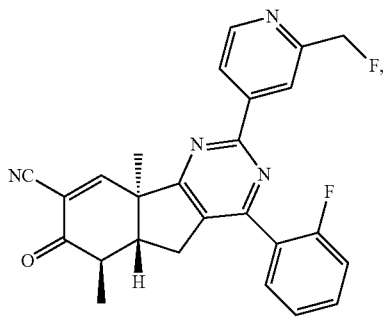

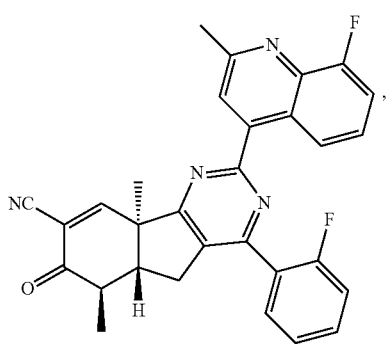

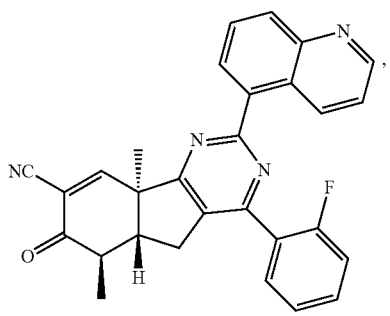

632
-continued

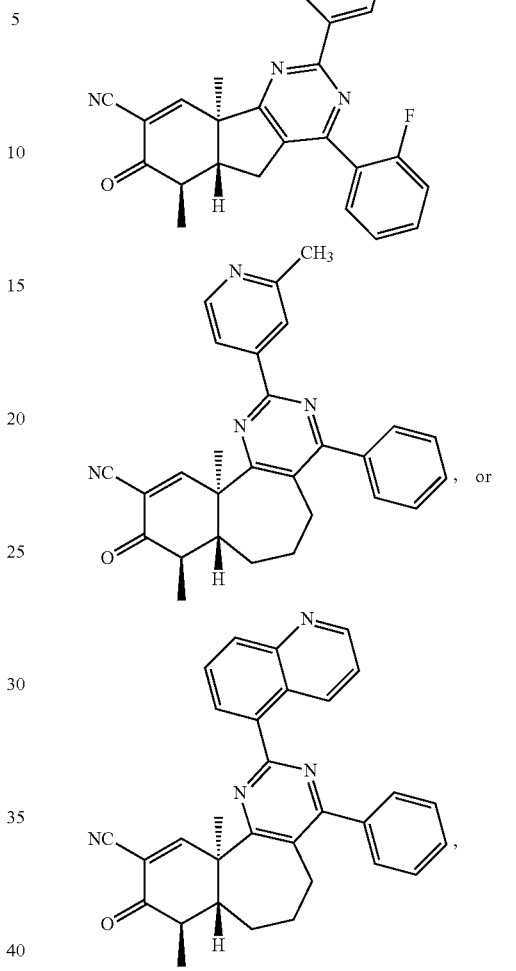

or a pharmaceutically acceptable salt thereof.

32. A pharmaceutical composition comprising:
 (A) a compound of claim 1; and
 (B) an excipient.

33. The pharmaceutical composition of claim 32, wherein the pharmaceutical composition is formulated for oral administration, administration via injection, or topical administration.

34. The pharmaceutical composition of claim 33, wherein the pharmaceutical composition is formulated for intraarterial administration, intramuscular administration, intraperitoneal administration, or intravenous administration.

35. The pharmaceutical composition of claim 33, wherein the pharmaceutical composition is formulated for topical administration to the skin or to the eye.

* * * * *